US012617783B2

(12) United States Patent
Wang et al.

(10) Patent No.: US 12,617,783 B2
(45) Date of Patent: May 5, 2026

(54) HETEROCYCLIC GLP-1R AGONISTS

(71) Applicant: BIOMEA FUSION, INC., Redwood City, CA (US)

(72) Inventors: Xiaodong Wang, Millbrae, CA (US); Thorsten A. Kirschberg, San Carlos, CA (US); Johannes H. Voigt, San Carlos, CA (US); Thomas Butler, Redwood City, CA (US); Ravindra B. Upasani, San Jose, CA (US); Yongli Su, Foster City, CA (US); Thu Phan, Fremont, CA (US); James T. Palmer, Warrandyte (AU); Neil Howard Squires, San Francisco, CA (US); Yeyu Cao, Foster City, CA (US); Solomon B. Ungashe, Sunnyvale, CA (US); Nan-Horng Lin, Vernon Hills, IL (US); Mini Balakrishnan, San Mateo, CA (US); Petr Jansa, Foster City, CA (US); Satish Goud Pappali, Sunnyvale, CA (US)

(73) Assignee: BIOMEA FUSION, INC., Redwood City, CA (US)

( * ) Notice: Subject to any disclaimer, the term of this patent is extended or adjusted under 35 U.S.C. 154(b) by 0 days.

(21) Appl. No.: 19/094,187

(22) Filed: Mar. 28, 2025

(65) Prior Publication Data

US 2025/0304572 A1 Oct. 2, 2025

Related U.S. Application Data

(60) Provisional application No. 63/768,592, filed on Mar. 7, 2025, provisional application No. 63/760,318, filed on Feb. 19, 2025, provisional application No. 63/720,442, filed on Nov. 14, 2024, provisional application No. 63/706,540, filed on Oct. 11, 2024, provisional application No. 63/689,349, filed on Aug. 30, 2024, provisional application No. 63/672,080, filed on Jul. 16, 2024, provisional application No. 63/635,840, filed on Apr. 18, 2024, provisional application No. 63/571,826, filed on Mar. 29, 2024.

(51) Int. Cl.

| | |
|---|---|
| *C07D 451/00* | (2006.01) |
| *A61K 31/437* | (2006.01) |
| *A61K 31/439* | (2006.01) |
| *A61K 31/46* | (2006.01) |
| *A61K 31/4709* | (2006.01) |
| *A61K 31/496* | (2006.01) |
| *A61K 31/502* | (2006.01) |
| *A61K 31/5377* | (2006.01) |
| *A61K 31/5386* | (2006.01) |
| *A61K 31/541* | (2006.01) |
| *A61K 31/55* | (2006.01) |
| *A61K 31/551* | (2006.01) |
| *A61K 31/675* | (2006.01) |
| *C07D 471/04* | (2006.01) |
| *C07D 471/18* | (2006.01) |
| *C07D 487/04* | (2006.01) |
| *C07D 498/18* | (2006.01) |
| *C07D 519/00* | (2006.01) |
| *C07F 9/6561* | (2006.01) |

(52) U.S. Cl.

CPC .......... *C07D 451/00* (2013.01); *A61K 31/437* (2013.01); *A61K 31/439* (2013.01); *A61K 31/46* (2013.01); *A61K 31/4709* (2013.01); *A61K 31/496* (2013.01); *A61K 31/502* (2013.01); *A61K 31/5377* (2013.01); *A61K 31/5386* (2013.01); *A61K 31/541* (2013.01); *A61K 31/55* (2013.01); *A61K 31/551* (2013.01); *A61K 31/675* (2013.01); *C07D 471/04* (2013.01); *C07D 471/18* (2013.01); *C07D 487/04* (2013.01); *C07D 498/18* (2013.01); *C07D 519/00* (2013.01); *C07F 9/6561* (2013.01)

(58) Field of Classification Search

None

See application file for complete search history.

(56) References Cited

U.S. PATENT DOCUMENTS

| | | | |
|---|---|---|---|
| 10,858,356 | B2 | 12/2020 | Hitoshi et al. |
| 11,584,751 | B1 | 2/2023 | Ren |
| 12,234,236 | B1 | 2/2025 | Liang et al. |
| 2019/0225604 | A1 | 7/2019 | Hitoshi et al. |
| 2021/0017176 | A1 | 1/2021 | Hitoshi et al. |
| 2025/0195481 | A1 | 6/2025 | Nie et al. |

FOREIGN PATENT DOCUMENTS

| | | | |
|---|---|---|---|
| AU | 2021 311 567 | A1 | 2/2023 |
| CN | 116003403 | A | 4/2023 |
| CN | 117069743 | A | 11/2023 |

(Continued)

OTHER PUBLICATIONS

International Search Report for International PCT Application No. PCT/US2025/022166 3 pages, mailed Jul. 24, 2025.

*Primary Examiner* — Jeffrey S Lundgren
*Assistant Examiner* — Eric Tran
(74) *Attorney, Agent, or Firm* — SQUIRE PATTON BOGGS (US)

(57) ABSTRACT

Disclosed herein are heterocyclic compounds that activate GLP-1R pathways. Also disclosed are pharmaceutical compositions that include the compounds. Methods of using the GLP-1R agonists are disclosed, alone or in combination with other therapeutic agents, for the treatment of diabetes, obesity, and other diseases or conditions dependent on GLP-1R pathways.

20 Claims, 14 Drawing Sheets

(56) References Cited

FOREIGN PATENT DOCUMENTS

| | | | | | |
|---|---|---|---|---|---|
| CN | 117964617 | A | | 5/2024 | |
| CN | 119019428 | A | | 11/2024 | |
| CN | 119176808 | A | | 12/2024 | |
| CN | 119285580 | A | | 1/2025 | |
| CN | 119306743 | A | | 1/2025 | |
| CN | 119528907 | A | * | 2/2025 | ................ A61P 3/04 |
| JP | 2019-99571 | A | | 6/2019 | |
| KR | 20250102249 | A | | 7/2025 | |
| WO | WO 2021/155841 | A1 | | 8/2021 | |
| WO | WO 2023/016546 | A1 | | 2/2023 | |
| WO | WO 2023/169456 | A1 | | 9/2023 | |
| WO | WO-2024153070 | A1 | * | 7/2024 | ............. A61K 45/06 |
| WO | WO 2024/169952 | A1 | | 8/2024 | |
| WO | WO 2025/002250 | A1 | | 1/2025 | |
| WO | WO 2025002326 | A1 | | 1/2025 | |
| WO | WO 2025006921 | A1 | | 1/2025 | |
| WO | WO 2025011664 | A1 | | 1/2025 | |
| WO | WO 2025026436 | A1 | | 2/2025 | |
| WO | WO 2025045208 | A1 | | 3/2025 | |
| WO | WO 2025097835 | A1 | | 5/2025 | |
| WO | WO 2025103443 | A1 | | 5/2025 | |
| WO | WO 2025108361 | A1 | | 5/2025 | |
| WO | WO 2025131043 | A1 | | 6/2025 | |
| WO | WO 2025140532 | A1 | | 7/2025 | |
| WO | WO 2025140533 | A1 | | 7/2025 | |
| WO | WO 2025148997 | A1 | | 7/2025 | |
| WO | WO 2025/162065 | A1 | | 8/2025 | |

* cited by examiner

Absolute Configuration Structure

ORTEP structure

Picture of crystals

Absolute configuration structure

HETEROCYCLIC GLP-1R AGONISTS

CROSS-REFERENCE

This application claims the benefit of U.S. provisional application Nos. 63/768,592, filed Mar. 7, 2025, 63/760,318, filed Feb. 19, 2025, 63/720,442, filed Nov. 14, 2024, 63/706,540, filed Oct. 11, 2024, 63/689,349, filed Aug. 30, 2024, 63/672,080, filed Jul. 16, 2024, 63/635,840, filed Apr. 18, 2024, and 63/571,826, filed Mar. 29, 2024, the contents of which are hereby incorporated in their entireties.

FIELD

Described herein are compounds, methods of making such compounds, pharmaceutical compositions, and medicaments containing such compounds, and methods of using such compounds and compositions to activate GLP-1R.

BACKGROUND

Diabetes is a chronic condition and a major public health concern due to its high prevalence and health risks (Sakran N. et al, BMC Endocrine Disorders, 2022, 22, 9). The condition is primarily manifested by the high levels of glucose in blood, that occurs when body cannot produce enough insulin, effectively use available insulin or both. Pancreatic β cells are primarily responsible for the production of insulin. In diabetic patients, high levels of glucose can cause serious damage to many organs over time. There are two common forms of diabetes: Type 1 and Type 2. Type 1 diabetes (TID) conditions are the result of body's immune system destroying β cells. Type 2 diabetes (T2D), on the other hand, develops when the body does not produce enough insulin or develops a resistance to insulin. Patients with T2D have been shown to have significantly higher risks of coronary related diseases in addition to many other life-threatening diseases. Obesity is also a highly prevalent chronic condition and is associated with the development of many diseases including stroke, heart disease, hypertension, and some cancers (Del Prato S. Obesity Rev. 2022, 23). Importantly, obesity has been found to correlate directly with T2D and insulin resistance.

Incretin hormones modulate glucose metabolism by stimulating the release of insulin by pancreatic β cells. One of the incretin hormones, glucagon-like-peptide-1 (GLP-1) exerts its effects to induce glucose-stimulated insulin secretion and lower glucose through its receptor (Seino Y. et al. J. Diabet. Inv., 2010, 1 (1/2), 8-23). GLP-1 is a thirty-one amino acid hormone which is secreted from intestinal L-cells. GLP-1 binds to GLP-1 receptor (GLP-1R), a GPCR, which is particularly expressed in pancreatic β cells and other metabolically relevant tissues. GLP-1 undergoes rapid proteolytic digestion by dipeptidyl peptidase-4 (DPP-4) and has a relatively short half-life of few minutes. Binding of GLP-1 to its receptor activates a cascade of signaling pathways including activation of adenylate cyclase and an increase of cyclic adenosine monophosphate (cAMP) in β cells, which then lead to stimulation of insulin. Additionally, GLP-1 has anti-apoptotic function in pancreatic β cells, and it can enhance β cell proliferation and delay gastric emptying. GLP-1 can also stimulate the proliferation of β cells, which happens through activation of RAF/MEK/ERK and PI3K pathways. Both anti-apoptotic and proliferative effects of GLP-1 can have clinical implication for the treatment of patients with diabetes and obesity.

Diabetes and obesity together represent one of the most preventable causes of premature complications including death. Various pharmacological approaches have been developed to treat diabetes. One of such approaches has been the application of GLP-1R agonists, which increase the secretion of insulin through binding to GLP-1R on pancreatic β cells. Currently marketed agonists are peptides and are primarily administered via subcutaneous injection. These peptide GLP-1 agonists often suffer from inconvenient dosing regimen and poor bioavailability. Currently, there is no approved small molecule GLP-1 agonist to treat diabetes or other metabolic diseases. Therefore, GLP-1 small molecule agonist that can be easily administered may be useful to treat wide ranges diseases and conditions including diabetes and obesity.

SUMMARY

In one aspect, described herein are agonists of GLP-1R. Also described herein are specific heterocyclic agonists of GLP-1R.

In another aspect, described herein are methods for synthesizing such agonists, methods for using such agonists in the treatment of diseases (including diseases wherein agonists of GLP-1R provides therapeutic benefit to a patient having the disease). Further described are pharmaceutical compositions that include agonists of GLP-1R. Specifically, described herein are compounds and methods of use thereof to activate GLP-1R.

In another aspect, provided herein is a compound according to Formula (L-I) having the structure:

N-I

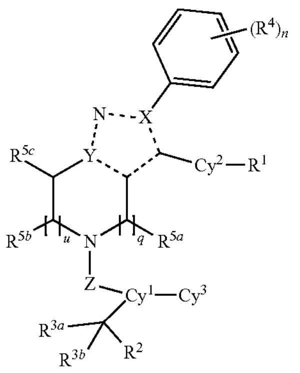

or a stereoisomer or a pharmaceutically acceptable salt thereof, wherein each of dotted bond is independently a single or a double bond;

Z is substituted or unsubstituted $C_1$-$C_4$ alkylene, —C(O)—, —S(O)—, $S(O)_2$, or —$C(R^{3c})(R^{3d})$—;

$Cy^1$ is substituted or unsubstituted 5,6-fused heteroaryl or 6,6-fused heteroaryl;

$Cy^2$ is substituted or unsubstituted heteroaryl; or -$Cy^2$-$R^1$ is —C(O)—$NR^{6a}$—$(CH_2)_m$—$R^1$; wherein $R^{6a}$ is H, or substituted or unsubstituted alkyl; and m is 0, 1, 2, or 3;

$Cy^3$ is substituted or unsubstituted cycloalkyl, substituted or unsubstituted heterocycloalkyl, substituted or unsubstituted aryl, or substituted or unsubstituted heteroaryl;

$R^1$ is substituted or unsubstituted aryl or heteroaryl;

$R^2$ is CN, substituted or unsubstituted heterocycloalkyl, or substituted or unsubstituted heteroaryl;

each $R^{3a}$ and $R^{3b}$ is independently H, or substituted or unsubstituted alkyl; or $R^{3a}$ and $R^{3b}$ form an oxo; or $R^{3a}$ and $R^{3b}$ are joined together to form substituted or unsubstituted cycloalkyl or heterocycloalkyl ring;

each $R^{3c}$ and $R^{3d}$ is independently H, or substituted or unsubstituted alkyl;

each $R^4$ is independently H, halo, CN, substituted or unsubstituted alkyl, substituted or unsubstituted alkoxy, alkylsulfonyl, arylsulfonyl, alkylsulfinyl, or arylsulfinyl; and n is 1, 2, 3, 4, or 5;

each $R^{5a}$, $R^{5b}$ and $R^{5c}$ is independently H, or substituted or unsubstituted alkyl;

or $R^{5a}$ and $R^{5b}$ or $R^{5a}$ and $R^{5c}$ are joined together to form a heterocycloalkyl;

q is 1, 2, or 3; provided that when q is 2 or 3, only one $R^{5a}$ is other than H;

u is 1, 2, or 3; provided that when u is 2 or 3, only one $R^{5b}$ is other than H;

and wherein the substitution on each alkyl is independently selected from halo, CN, hydroxy, and alkoxy; the substitution on each alkoxy is independently selected from halo, CN, and substituted or unsubstituted alkyl; the substitution on each cycloalkyl is independently selected from halo, CN, hydroxy, substituted or unsubstituted alkyl, and substituted or unsubstituted alkoxy; the substitution on each heterocycloalkyl is independently selected from halo, CN, hydroxy, substituted or unsubstituted alkyl, and substituted or unsubstituted alkoxy; the substitution on each aryl is independently 1-3 groups independently selected from halo, haloalkyl, amino, dialkylamino, amido, CN, hydroxy, substituted or unsubstituted alkyl, and substituted or unsubstituted alkoxy; the substitution on each heteroaryl is independently 1-3 groups independently selected from halo, haloalkyl, amino, dialkylamino, amido, CN, hydroxy, substituted or unsubstituted alkyl, substituted or unsubstituted alkoxy, and oxo;

provided that when $Cy^2$ is

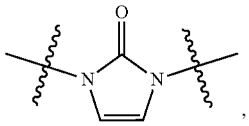 [SMILES: *n1ccn(*)c1=O]

, q is 1, u is 1, X is N, and Y is C; then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl;

or ii) $R^{5a}$ and $R^{5b}$ or $R^{5a}$ and $R^{5c}$ are joined together to form a heterocycloalkyl.

In some embodiments, provided herein is a compound according to Formula (N-II) having the structure:

N-II

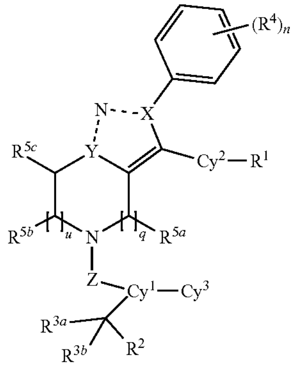

or a stereoisomer or a pharmaceutically acceptable salt thereof; wherein one of X and Y is N, and the other is C; one of dotted bonds is a double bond, and the other is a single bond.

In some embodiments, provided herein is a compound according to Formula (N-III) having the structure:

N-III

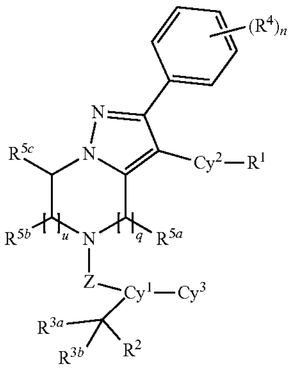

or a stereoisomer or a pharmaceutically acceptable salt thereof.

In some embodiments, provided herein is a compound according to Formula (N-III) having the structure:

N-IV

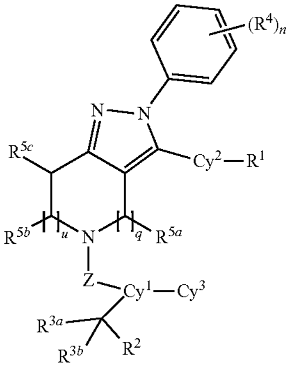

or a stereoisomer or a pharmaceutically acceptable salt thereof.

In some embodiments, provided herein is a compound according to Formula (L-I) having the structure:

L-I

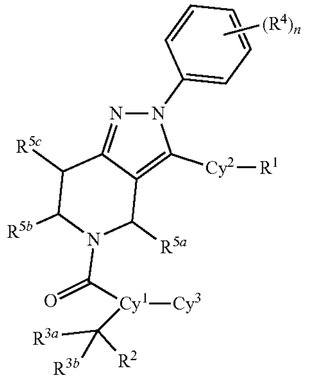

or a stereoisomer or a pharmaceutically acceptable salt thereof, wherein $Cy^1$ is substituted or unsubstituted 5,6-fused or 6,6-fused heteroaryl;

$Cy^2$ is substituted or unsubstituted heteroaryl; or —$Cy^2$-$R^1$ is —C(O)—$NR^{6a}$—$(CH_2)_m$—$R^1$; and wherein $R^{6a}$ is H, or substituted or unsubstituted alkyl; and m is 0, 1, 2, or 3;

$Cy^3$ is substituted or unsubstituted cycloalkyl, substituted or unsubstituted heterocycloalkyl, substituted or unsubstituted aryl, or substituted or unsubstituted heteroaryl;

$R^1$ is substituted or unsubstituted aryl or heteroaryl;

$R^2$ is CN, or substituted or unsubstituted heteroaryl;

each $R^{3a}$ and $R^{3b}$ is independently H, or substituted or unsubstituted alkyl; or $R^{3a}$ and $R^{3b}$ form an oxo; or $R^{3a}$ and $R^{3b}$ are joined together to form substituted or unsubstituted cycloalkyl or heterocycloalkyl ring;

each $R^4$ is independently H, halo, CN, substituted or unsubstituted alkyl, substituted or unsubstituted alkoxy, alkylsulfonyl, arylsulfonyl, alkylsulfinyl, or arylsulfinyl; and n is 1, 2, 3, 4, or 5;

each $R^{5a}$, $R^{5b}$ and $R^{5c}$ is independently H, or substituted or unsubstituted alkyl;

or $R^{5a}$ and $R^{5b}$ or $R^{5a}$ and $R^{5c}$ are joined together to form a heterocycloalkyl;

and wherein the substitution on each alkyl is independently selected from halo, CN, hydroxy, and alkoxy; the substitution on each alkoxy is independently selected from halo, CN, and substituted or unsubstituted alkyl; the substitution on each cycloalkyl is independently selected from halo, CN, hydroxy, substituted or unsubstituted alkyl, and substituted or unsubstituted alkoxy; the substitution on each heterocycloalkyl is independently selected from halo, CN, hydroxy, substituted or unsubstituted alkyl, and substituted or unsubstituted alkoxy; the substitution on each aryl is independently 1-3 groups independently selected from halo, haloalkyl, amino, dialkylamino, amido, CN, hydroxy, substituted or unsubstituted alkyl, and substituted or unsubstituted alkoxy; the substitution on each heteroaryl is independently 1-3 groups independently selected from halo, haloalkyl, amino, dialkylamino, amido, CN, hydroxy, substituted or unsubstituted alkyl, substituted or unsubstituted alkoxy, and oxo;

provided that when $Cy^2$ is

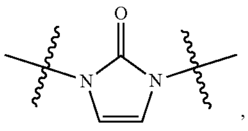 [SMILES: *n1ccn(*)c1=O]

, then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl, or ii) $R^{5a}$ and $R^{5b}$ or $R^{5a}$ and $R^{5c}$ are joined together to form a heterocycloalkyl.

In some embodiments, provided herein is a compound according to Formula (I) having the structure:

I

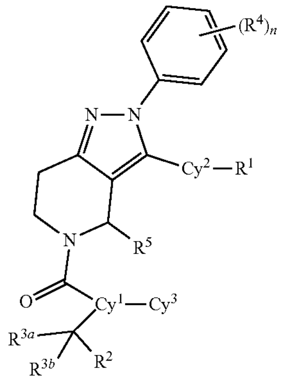

or a stereoisomer or a pharmaceutically acceptable salt thereof, wherein $Cy^1$ is substituted or unsubstituted 5,6-fused or 6,6-fused heteroaryl;

$Cy^2$ is substituted or unsubstituted heteroaryl; or -$Cy^2$-$R^1$ is —C(O)—$NR^{6a}$—$(CH_2)_m$—$R^1$; and wherein $R^{6a}$ is H, or substituted or unsubstituted alkyl; and m is 0, 1, 2, or 3;

$Cy^3$ is substituted or unsubstituted cycloalkyl, substituted or unsubstituted heterocycloalkyl, substituted or unsubstituted aryl, or substituted or unsubstituted heteroaryl;

$R^1$ is substituted or unsubstituted aryl or heteroaryl;

$R^2$ is CN, or substituted or unsubstituted heteroaryl;

each $R^{3a}$ and $R^{3b}$ is independently H, or substituted or unsubstituted alkyl; or $R^{3a}$ and $R^{3b}$ form an oxo; or $R^{3a}$ and $R^{3b}$ are joined together to form substituted or unsubstituted cycloalkyl or heterocycloalkyl ring;

each $R^4$ is independently H, halo, CN, substituted or unsubstituted alkyl, substituted or unsubstituted alkoxy, alkylsulfonyl, arylsulfonyl, alkylsulfinyl, or arylsulfinyl; and n is 1, 2, 3, 4, or 5;

$R^5$ is H, or substituted or unsubstituted alkyl;

and wherein the substitution on each alkyl is independently selected from halo, CN, hydroxy, and alkoxy; the substitution on each alkoxy is independently selected from halo, CN, and substituted or unsubstituted alkyl; the substitution on each cycloalkyl is independently selected from halo, CN, hydroxy, substituted or unsubstituted alkyl, and substituted or unsubstituted alkoxy; the substitution on each heterocycloalkyl is independently selected from halo, CN, hydroxy, substituted or unsubstituted alkyl, and substituted or unsubstituted alkoxy; the substitution on each aryl is independently 1-3 groups independently selected from halo, haloalkyl, amino, dialkylamino, amido, CN, hydroxy, substituted or unsubstituted alkyl, and substituted or unsubstituted alkoxy; the substitution on each heteroaryl is independently 1-3 groups independently selected from halo, haloalkyl, amino, dialkylamino, amido, CN, hydroxy, substituted or unsubstituted alkyl, substituted or unsubstituted alkoxy, and oxo;

provided that when $Cy^2$ is

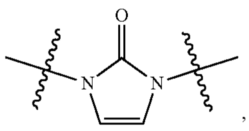 [SMILES: *n1ccn(*)c1=O]

, then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl, or ii) $R^{5a}$ and $R^{5b}$ or $R^{5a}$ and $R^{5c}$ are joined together to form a heterocycloalkyl.

In particular embodiments, the compound is according to formula (L-IIa) or (L-IIb):

L-IIa

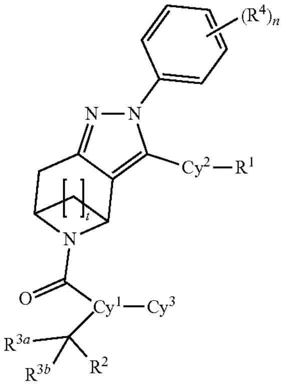

or

L-IIb

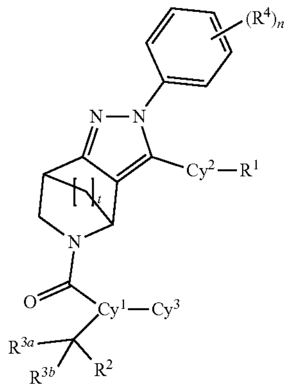

or a stereoisomer or a pharmaceutically acceptable salt thereof, wherein t is 1, 2, or 3.

In particular embodiments, the compound is according to formula (IIa) or (IIb):

IIa

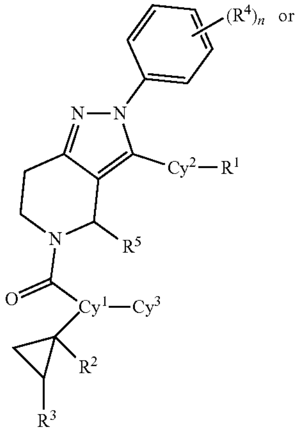

or

IIb

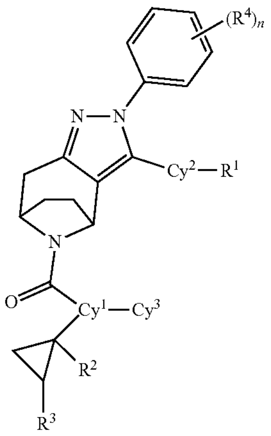

or a stereoisomer or a pharmaceutically acceptable salt thereof;

provided that when $Cy^2$ is

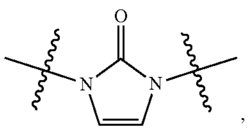

, then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl, or ii) the compound is according to formula (IIb).

In more particular embodiments, the compound is according to formula (IIc):

IIc
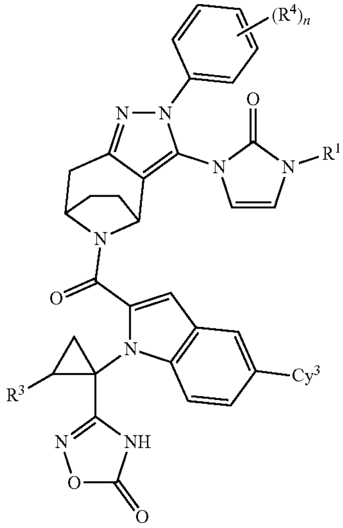
or a stereoisomer or a pharmaceutically acceptable salt thereof.
In more particular embodiments, the compound is according to formula (L-VIIIa), (L-VIIIb), (L-VIIIc), or (L-VIIId):
L-VIIIa
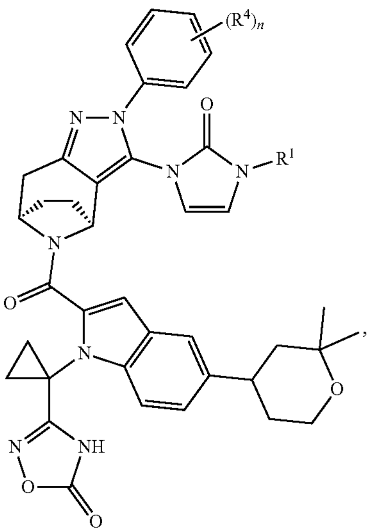
-continued
L-VIIIb
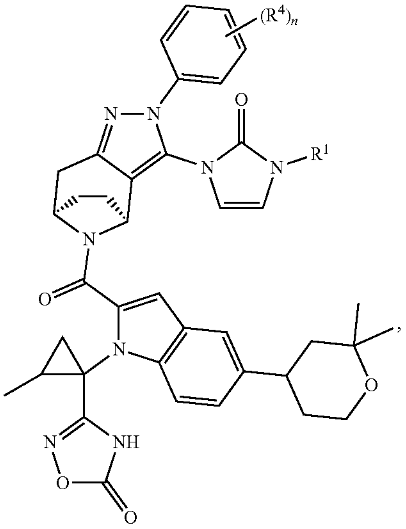
L-VIIIc
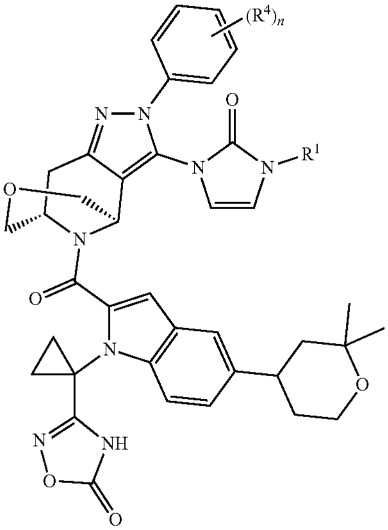
or
L-VIIId
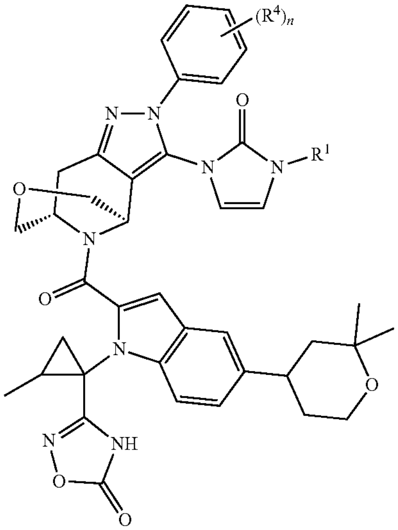
or a stereoisomer or a pharmaceutically acceptable salt thereof.

In more particular embodiments, the compound is according to formula (M-VIIa), (M-VIIb), (M-VIIc), or (M-VIId):

M-VIIa

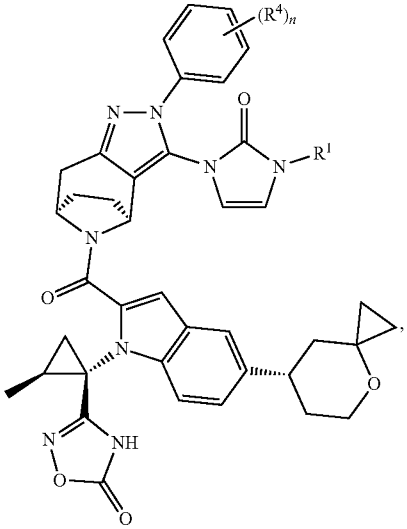

M-VIIb

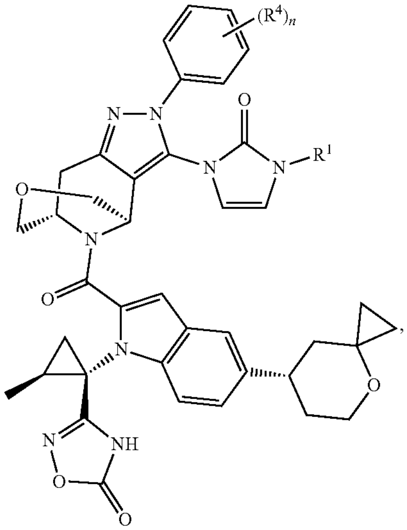

M-VIIc

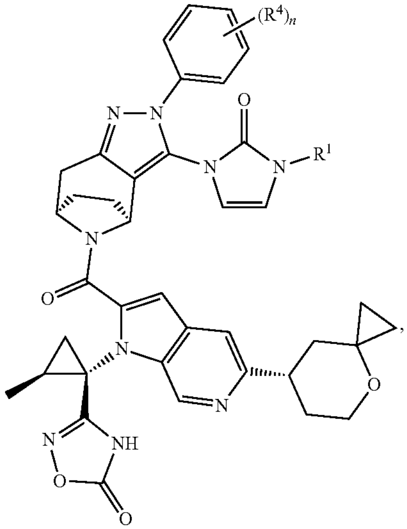

-continued

M-VIId

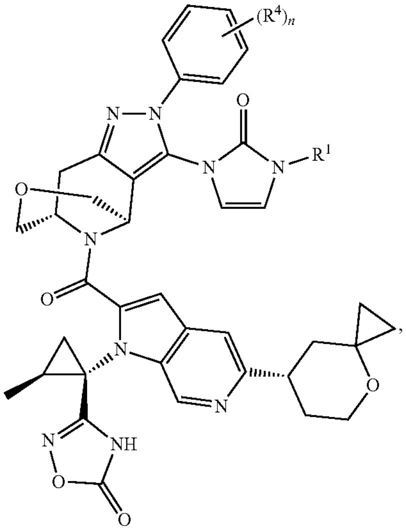

a pharmaceutically acceptable salt thereof.

In most particular embodiments, the compound is according to formula Q-IIa or Q-IIIb Q-IIa

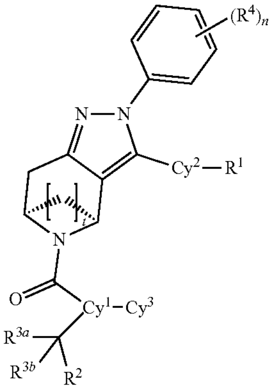

or

Q-IIIb

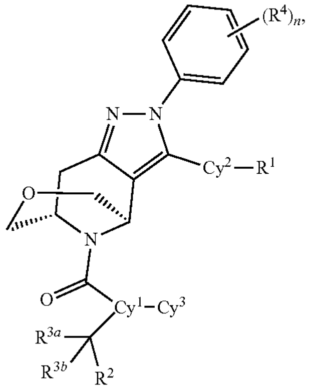

and t is 1, 2, or 3; or a pharmaceutically acceptable salt thereof.

In the most particular embodiment, the compound is according to formula M-VIIa. In another most particular embodiment, the compound is according to formula M-VIIb.

In some embodiments, provided herein are methods for preventing, treating or ameliorating in a mammal a disease or condition that is causally related to the modulation of GLP-1R in vivo, which comprises administering to the mammal an effective disease-treating or condition-treating amount of a compound according to Formula (I). In some embodiments, the disease or condition is metabolic diseases, an autoimmune disease, a heteroimmune disease, an inflammatory disease, a proliferative disease, or a bone disease.

In some embodiments, provided herein are pharmaceutical compositions comprising a therapeutically effective amount of a compound of Formula (I) and a pharmaceutically acceptable excipient. In some embodiments, the pharmaceutical composition comprising the compound of Formula (I) is formulated for a route of administration selected from oral administration, parenteral administration, buccal administration, nasal administration, topical administration, or rectal administration. In some embodiments, provided herein are methods for treating a disease or condition comprising administering to a patient in need a therapeutically effective amount of a compound of Formula (I). In some embodiments, provided herein is a method for treating metabolic diseases, an autoimmune disease or condition comprising administering to a patient in need a therapeutically effective amount of a compound of Formula (I). In some embodiments, provided herein is a method for treating a heteroimmune disease or condition comprising administering to a patient in need a therapeutically effective amount of a compound of Formula (I). In some embodiments, provided herein is a method for treating an inflammatory disease or condition comprising administering to a patient in need a therapeutically effective amount of a compound of Formula (I). In some embodiments provided herein is a method for treating a proliferative disease comprising administering to a patient in need a therapeutically effective amount of a compound of Formula (I).

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

In some embodiments, provided herein are pharmaceutical compositions, which include a therapeutically effective amount of at least one of any of the compounds herein, or a pharmaceutically acceptable salt, pharmaceutically active metabolite, pharmaceutically acceptable prodrug, or pharmaceutically acceptable solvate. In certain embodiments, compositions provided herein further include a pharmaceutically acceptable diluent, excipient and/or binder.

Pharmaceutical compositions formulated for administration by an appropriate route and means containing effective concentrations of one or more of the compounds provided herein, or pharmaceutically effective derivatives thereof, that deliver amounts effective for the treatment, prevention, or amelioration of one or more symptoms of diseases, disorders or conditions that are modulated or otherwise affected by GLP-1R activity, or in which GLP-1R activity is implicated, are provided. The effective amounts and concentrations are effective for ameliorating any of the symptoms of any of the diseases, disorders or conditions disclosed herein.

In certain embodiments, provided herein is a pharmaceutical composition containing: i) a physiologically acceptable carrier, diluent, and/or excipient; and ii) one or more compounds provided herein.

In some embodiments, provided herein are methods for treating a patient by administering a compound provided herein. In some embodiments, provided herein is a method of activating the GLP-1R, or of treating a disease, disorder, or condition, which would benefit from activation of GLP-1R, in a patient, which includes administering to the patient a therapeutically effective amount of at least one of any of the compounds herein, or pharmaceutically acceptable salt, pharmaceutically active metabolite, pharmaceutically acceptable prodrug, or pharmaceutically acceptable solvate.

In some embodiments, provided herein is the use of a compound disclosed herein for activating GLP-1R or for the treatment of a disease, disorder, or condition, which would benefit from activation of GLP-1R.

In some embodiments, compounds provided herein are administered to a human.

In some embodiments, compounds provided herein are orally administered.

In some embodiments, compounds provided herein are used for the formulation of a medicament for the activation of GLP-1R. In some embodiments, compounds provided herein are used for the formulation of a medicament for the activation of GLP-1R.

Articles of manufacture including packaging material, a compound or composition or pharmaceutically acceptable derivative thereof provided herein, which is effective for activation of GLP-1R, within the packaging material, and a label that indicates that the compound or composition, or pharmaceutically acceptable salt, pharmaceutically active metabolite, pharmaceutically acceptable prodrug, or pharmaceutically acceptable solvate thereof, is used for activation of GLP-1R, are provided.

In certain embodiments, provided herein is a pharmaceutical composition containing: i) a physiologically acceptable carrier, diluent, and/or excipient; and ii) one or more compounds provided herein.

In some embodiments, compounds provided herein are administered to a human.

In some embodiments, compounds provided herein are orally administered.

In any of the aforementioned embodiments are some embodiments in which administration is enteral, parenteral, or both, and wherein (a) an effective amount of a provided compound is systemically administered to the mammal; (b) an effective amount of a provided compound is administered orally to the mammal; (c) an effective amount of a provided compound is intravenously administered to the mammal; (d) an effective amount of a provided compound is administered by inhalation; (e) an effective amount of a provided compound is administered by nasal administration; or (f) an effective amount of a provided compound is administered by injection to the mammal; (g) an effective amount of a provided compound is administered topically (dermal) to the mammal; (h) an effective amount of a provided compound is administered by ophthalmic administration; or (i) an effective amount of a provided compound is administered rectally to the mammal.

In any of the aforementioned embodiments are some embodiments comprising single administrations of an effective amount of a provided compound including some embodiments in which (i) a provided compound is administered once; (ii) a provided compound is administered to the mammal multiple times over the span of one day; (iii) continually; or (iv) continuously.

In any of the aforementioned embodiments are some embodiments comprising multiple administrations of an effective amount of a provided compound, including some embodiments in which (i) a provided compound is administered in a single dose; (ii) the time between multiple administrations is every 6 hours; (iii) a provided compound is administered to the mammal every 8 hours. In some embodiments, the method comprises a drug holiday, wherein the administration of the compound is temporarily suspended, or the dose of the compound being administered is temporarily reduced; at the end of the drug holiday, dosing of the compound is resumed. The length of the drug holiday can vary from 2 days to 1 year.

In some embodiments, the compounds of Formula (I) are agonists of GLP-1Ractivity. In certain embodiments, such inhibitors have an $EC_{50}$ below 10 μM in enzyme assay. In some embodiments, GLP-1R agonists has an $EC_{50}$ of less than 1 μM, and in some embodiments, less than 0.25 μM.

Other objects, features, and advantages of the methods and compositions described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

DETAILED DESCRIPTION OF THE PREFERRED EMBODIMENTS

Certain Terminology

Figure 1A:
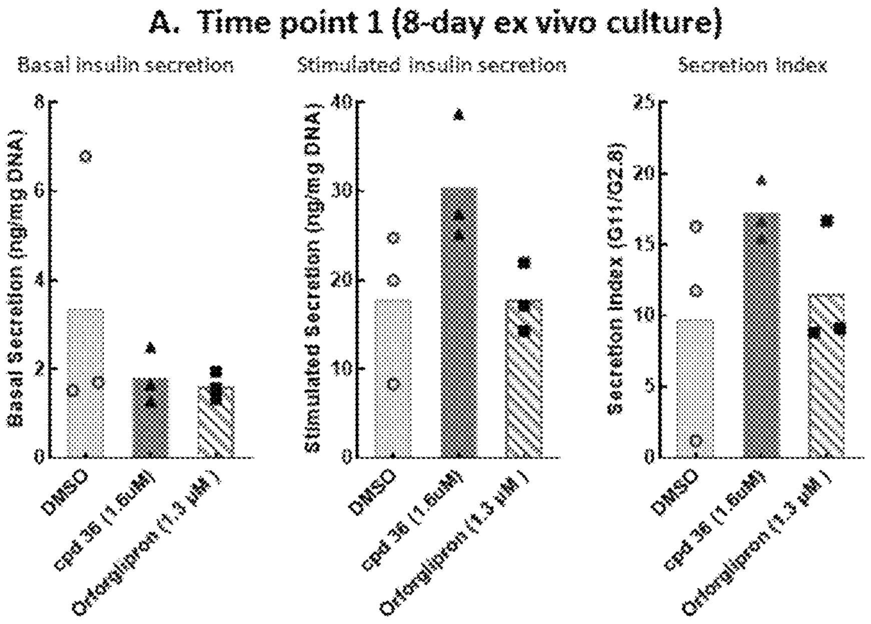
FIG. 1A and FIG. 1B show Compound 36 increases the responsiveness of Type 2 diabetic donor islets to glucose stimulation. Islets from a Type 2 diabetic donor were cultured ex vivo for 8 days (FIG. 1A) or 12 days (FIG. 1B) were assayed for GSIS in the presence of compound 36 (cpd 36), orforglipron or DMSO. Basal insulin secretion, stimulated insulin secretion and secretion index were measured.

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. Use of the term "including" as well as other forms, such as "include", "includes," and "included," is not limiting. Definition of standard chemistry terms may be found in reference works, including Carey and Sundberg "Advanced Organic Chemistry $4^{TH}$ Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection). Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

All publications and patents mentioned herein are incorporated herein by reference in their entirety for the purpose of describing and disclosing, for example, the constructs and methodologies that are described in the publications, which might be used in connection with the methods, compositions and compounds described herein. The publications discussed herein are provided solely for their disclosure prior to the filing date of the present application. Nothing herein is to be construed as an admission that the inventors described herein are not entitled to antedate such disclosure by virtue of prior invention or for any other reason.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$alkyl). In some embodiments, an alkyl comprises five to fifteen carbon atoms (e.g., $C_5$-$C_{15}$ alkyl). In certain embodiments, an alkyl comprises five to eight carbon atoms (e.g., $C_5$-$C_8$alkyl). The alkyl is attached to the rest of the molecule by a single bond, for example, methyl (Me), ethyl (Et), n-propyl (n-pr), 1-methylethyl (iso-propyl or i-Pr), n-butyl (n-Bu), n-pentyl, 1,1-dimethylethyl (t-butyl, or t-Bu), 3-methylhexyl, 2-methylhexyl, and the like. Unless stated otherwise specifically in the specification, an alkyl group is optionally substituted as defined and described below and herein.

The alkyl group could also be a "lower alkyl" having 1 to 6 carbon atoms.

As used herein, $C_1$-$C_x$ includes $C_1$-$C_2$, $C_1$-$C_3$ . . . $C_1$-$C_x$.

"Alkenyl" refers to a straight or branched hydrocarbon chain radical group consisting solely of carbon and hydrogen atoms, containing at least one double bond, and having from two to twelve carbon atoms. In certain embodiments, an alkenyl comprises two to eight carbon atoms. In some embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted as defined and described below and herein.

"Alkynyl" refers to a straight or branched hydrocarbon chain radical group consisting solely of carbon and hydrogen atoms, containing at least one triple bond, having from two to twelve carbon atoms. In certain embodiments, an alkynyl comprises two to eight carbon atoms. In some embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted as defined and described below and herein.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain. Unless stated otherwise specifically in the specification, an alkylene chain is optionally substituted as defined and described below and herein.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, for example, ethenylene, propenylene, n-butenylene, and the like. The alkenylene chain is attached to the rest of the molecule through a double bond or a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain is optionally substituted as defined and described below and herein. "Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. Aryl groups include, but are not limited to, groups such as phenyl (Ph), fluorenyl, and naphthyl. Unless stated otherwise specifically in the specification, the term "aryl" or the prefix "ar-" (such as in "aralkyl") is meant to include aryl radicals optionally substituted as defined and described below and herein.

"Aralkyl" refers to a radical of the formula-$R^c$-aryl where $R^c$ is an alkylene chain as defined above, for example, benzyl, diphenylmethyl and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula-$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula-$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl or cycloalkyl" refers to a stable non-aromatic monocyclic, polycyclic, bridged, spiro hydrocarbon radical consisting solely of carbon and hydrogen atoms, which includes fused or bridged ring systems, having from three to fifteen carbon atoms. In certain embodiments, a carbocyclyl comprises three to ten carbon atoms. In some embodiments, a carbocyclyl comprises five to seven carbon atoms. The carbocyclyl is attached to the rest of the molecule by a single bond. Carbocyclyl is optionally saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted as defined and described below and herein. "Halo" or "halogen" refers to bromo, chloro, fluoro or iodo substituents.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In some embodiments in which two or more hydrogen atoms are replaced with halogen atoms, the halogen atoms are not all the same as one another.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical is optionally substituted as defined above for an alkyl group.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three to 14 ring atoms, such as three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, monocyclics, bicyclics, bridged, spiro, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

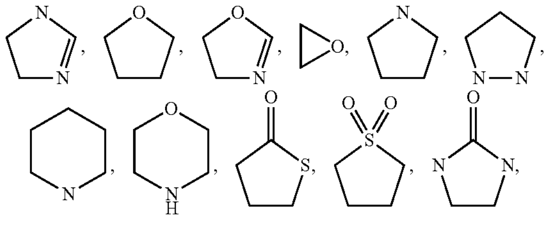

-continued

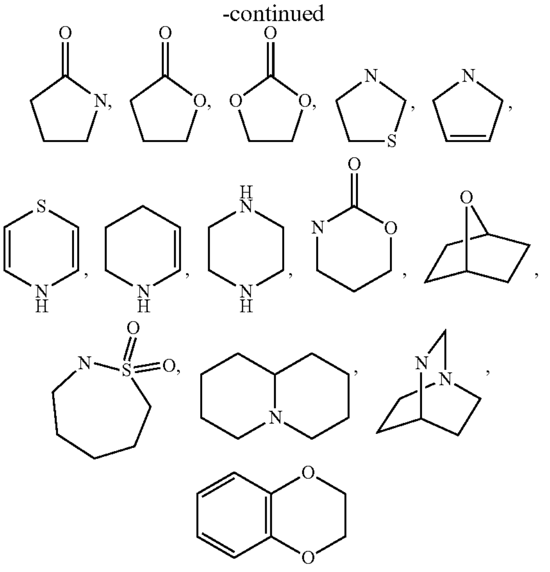

and the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) T-electron system in accordance with the Hückel theory. Heteroaryl includes fused or bridged ring systems. In some embodiments, heteroaryl rings have five, six, seven, eight, nine, or more than nine ring atoms. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl- 1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted as defined and described below and herein.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula-$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Sulfanyl" refers to the —S— radical.

"Sulfinyl" refers to the —S(═O)— radical.

"Sulfonyl" refers to the —S(═O)$_2$— radical.

"Amino" refers to the —$NH_2$ radical.

"Cyano" refers to the —CN radical.

"Nitro" refers to the —$NO_2$ radical.

"Oxa" refers to the —O— radical.

"Oxo" refers to the ═O radical.

"Imino" refers to the ═NH radical.

"Thioxo" refers to the ═S radical.

An "alkoxy" group refers to a (alkyl)O— group, where alkyl is as defined herein.

An "aryloxy" group refers to an (aryl)O— group, where aryl is as defined herein.

"Carbocyclylalkyl" means an alkyl radical, as defined herein, substituted with a carbocyclyl group. "Cycloalkylalkyl" means an alkyl radical, as defined herein, substituted with a cycloalkyl group. Non-limiting cycloalkylalkyl groups include cyclopropylmethyl, cyclobutylmethyl, cyclopentylmethyl, cyclohexylmethyl, and the like.

As used herein, the terms "heteroalkyl" "heteroalkenyl" and "heteroalkynyl" include optionally substituted alkyl, alkenyl and alkynyl radicals in which one or more skeletal chain atoms is a heteroatom, e.g., oxygen, nitrogen, sulfur, silicon, phosphorus or combinations thereof. The heteroatom(s) may be placed at any interior position of the heteroalkyl group or at the position at which the heteroalkyl group is attached to the remainder of the molecule. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH═CH—O—$CH_3$, —Si($CH_3$)$_3$, —$CH_2$—CH═N—$OCH_3$, and —CH—CH—N($CH_3$)—$CH_3$. In addition, up to two heteroatoms may be consecutive, such as, by way of example, —$CH_2$—NH—$OCH_3$ and —$CH_2$—O—Si($CH_3$)$_3$.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

The term "bond," "direct bond" or "single bond" refers to a chemical bond between two atoms, or two moieties when the atoms joined by the bond are considered to be part of larger substructure.

An "isocyanato" group refers to a —NCO group.

An "isothiocyanato" group refers to a —NCS group.

The term "moiety" refers to a specific segment or functional group of a molecule. Chemical moieties are often recognized chemical entities embedded in or appended to a molecule.

A "thioalkoxy" or "alkylthio" group refers to a —S-alkyl group.

A "alkylthioalkyl" group refers to an alkyl group substituted with a —S-alkyl group.

As used herein, the term "acyloxy" refers to a group of formula RC(═O)O—.

"Carboxy" means a —C(O) OH radical.

As used herein, the term "acetyl" refers to a group of formula —C(═O) $CH_3$.

"Acyl" refers to the group —C(O) R.

As used herein, the term "trihalomethanesulfonyl" refers to a group of formula $X_3$CS(═O)$_2$— where X is a halogen.

"Cyanoalkyl" means an alkyl radical, as defined herein, substituted with at least one cyano group.

As used herein, the term "N-sulfonamido" or "sulfonylamino" refers to a group of formula RS(═O)$_2$NH—.

As used herein, the term "O-carbamyl" refers to a group of formula —OC(═O)$NR_2$.

As used herein, the term "N-carbamyl" refers to a group of formula ROC(═O)NH—.

As used herein, the term "O-thiocarbamyl" refers to a group of formula —OC(═S)$NR_2$.

As used herein, "N-thiocarbamyl" refers to a group of formula ROC(═S)NH—.

As used herein, the term "C-amido" refers to a group of formula —C(═O)$NR_2$.

"Aminocarbonyl" refers to a —$CONH_2$ radical.

As used herein, the term "N-amido" refers to a group of formula RC(═O)NH—.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl.

"Alkoxyalkyl" refers to an alkyl radical, as defined herein, substituted with an alkoxy group, as defined herein.

An "alkenyloxy" group refers to a (alkenyl)O— group, where alkenyl is as defined herein.

The term "alkylamine" refers to the —N(alkyl)$_x$H$_y$ group, where x and y are selected from among x=1, y=1 and x=2, y=0. When x=2, the alkyl groups, taken together with the N atom to which they are attached, can optionally form a cyclic ring system.

"Alkylaminoalkyl" refers to an alkyl radical, as defined herein, substituted with an alkylamine, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters are known to those of skill in the art and can readily be found in reference sources such as Greene and Wuts, Protective Groups in Organic Synthesis, 3$^{rd}$ Ed., John Wiley & Sons, New York, NY, 1999, which is incorporated herein by reference in its entirety.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "fused" refers to structures in which two or more rings share one or more bonds.

As described herein, compounds provided herein may be "optionally substituted". In general, the term "substituted," whether preceded by the term "optionally" or not, means that one or more hydrogens of a designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents provided herein are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^{\circ}$; —$(CH_2)_{0-4}OR^{\circ}$; —$O(CH_2)_{0-4}R^{\circ}$, —O—$(CH_2)_{0-4}C(O)OR^{\circ}$; —$(CH_2)_{0-4}CH(OR^{\circ})_2$; —$(CH_2)_{0-4}SR^{\circ}$; —$(CH_2)_{0-4}Ph$, which may be substituted with $R^{\circ}$; —$(CH_2)_{0-4}O(CH_2)_{0-1}Ph$ which may be substituted with $R^{\circ}$; —CH═CHPh, which may be substituted with $R^{\circ}$; —$(CH_2)_{0-4}O(CH_2)_{0-1}$-pyridyl which may be substituted with $R^{\circ}$; —$NO_2$; —CN; —$N_3$; —$(CH_2)_{0-4}N(R^{\circ})_2$; —$(CH_2)_{0-4}N(R^{\circ})C(O)R^{\circ}$; —$N(R^{\circ})C(S)R^{\circ}$; —$(CH_2)_{0-4}N(R^{\circ})C(O)NR^{\circ}_2$; —$N(R^{\circ})C(S)NR^{\circ}_2$; —$(CH_2)_{0-4}N(R^{\circ})C(O)OR^{\circ}$; —$N(R^{\circ})N(R^{\circ})C(O)R^{\circ}$; —$N(R^{\circ})N(R^{\circ})C(O)NR^{\circ}_2$; —$N(R^{\circ})N(R^{\circ})C(O)OR^{\circ}$; —$(CH_2)_{0-4}C(O)R^{\circ}$; —$C(S)R^{\circ}$; —$(CH_2)_{0-4}C(O)OR^{\circ}$; —$(CH_2)_{0-4}C(O)SR^{\circ}$; —$(CH_2)_{0-4}C(O)OSiR^{\circ}_3$; —$(CH_2)_{0-4}OC(O)R^{\circ}$; —$OC(O)(CH_2)_{0-4}SR$—, —$SC(S)SR^{\circ}$; —$(CH_2)_{0-4}SC(O)R^{\circ}$; —$(CH_2)_{0-4}C(O)NR^{\circ}_2$; —$C(S)NR^{\circ}_2$; —$C(S)SR^{\circ}$; —$(CH_2)_{0-4}OC(O)NR^{\circ}_2$; —$C(O)N(OR^{\circ})R^{\circ}$; —$C(O)C(O)R^{\circ}$; —$C(O)CH_2C(O)R^{\circ}$; —$C(NOR^{\circ})R^{\circ}$; —$(CH_2)_{0-4}SSR^{\circ}$; —$(CH_2)_{0-4}S(O)_2R^{\circ}$; —$(CH_2)_{0-4}S(O)_2OR^{\circ}$; —$(CH_2)_{0-4}OS(O)_2R^{\circ}$; —$S(O)_2NR^{\circ}_2$; —$(CH_2)_{0-4}S(O)R^{\circ}$; —$N(R^{\circ})S(O)_2NR^{\circ}_2$; —$N(R^{\circ})S(O)_2R^{\circ}$; —$N(OR^{\circ})R^{\circ}$; —$C(NH)NR^{\circ}_2$; —$P(O)_2R^{\circ}$; —$P(O)R^{\circ}_2$; —$OP(O)R^{\circ}_2$; —$OP(O)(OR^{\circ})_2$; $SiR^{\circ}_3$; —($C_{1-4}$ straight or branched alkylene)O—$N(R^{\circ})_2$; or —($C_{1-4}$ straight or branched alkylene)C(O)O—$N(R^{\circ})_2$, wherein each $R^{\circ}$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^{\circ}$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^{\circ}$ (or the ring formed by taking two independent occurrences of $R^{\circ}$ together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)$C(O)OR^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^{\circ}$ include ═O and ═S.

Suitable divalent substituents on a saturated carbon atom of an "optionally substituted" group include the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}O$—, or —$S(C(R^*_2))_{2-3}S$—, wherein each independent occurrence of $R^*$ is selected from hydrogen, $C_1$-6 aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —C(O)$R^\dagger$, —C(O)O$R^\dagger$, —C(O)C(O)$R^\dagger$, —C(O)$CH_2$C(O)$R^\dagger$, —$S(O)_2R^\dagger$, —$S(O)_2NR^\dagger_2$, —C(S)$NR^\dagger_2$, —C(NH)$NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of Rt, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —C(O)$OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "nucleophile" or "nucleophilic" refers to an electron rich compound, or moiety thereof.

The term "electrophile", or "electrophilic" refers to an electron poor or electron deficient molecule, or moiety thereof. Examples of electrophiles include, but in no way are limited to, Michael acceptor moieties.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

"Bioavailability" refers to the percentage of the weight of compounds disclosed herein, such as, compounds of any of Formula (I) dosed that is delivered into the general circulation of the animal or human being studied. The total exposure ($AUC_{(0-\infty)}$) of a drug when administered intravenously is usually defined as 100% bioavailable (F %). "Oral bioavailability" refers to the extent to which compounds disclosed herein, such as, compounds of any of Formula (I) are absorbed into the general circulation when the pharmaceutical composition is taken orally as compared to intravenous injection.

"Blood plasma concentration" refers to the concentration of compounds disclosed herein, such as, compounds of any of Formula (I) in the plasma component of blood of a subject. It is understood that the plasma concentration of compounds of any of Formula (I) may vary significantly between subjects, due to variability with respect to metabolism and/or possible interactions with other therapeutic agents. In accordance with some embodiments disclosed herein, the blood plasma concentration of the compounds of any of Formula (I) may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of a compound of any of Formula (I) may vary from subject to subject.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of the compound of any of Formula (I), age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 43% identical, about 90% identical, or about 95% identical over a specified region. Such percentages to describe the "percent identity" of two or more sequences. The identity of a sequence can exist over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 43% identical, about 90% identical, or about 95% identical over a specified region. The identity can exist over a region that is at least about 75-100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 43% identical, about 90% identical, or about 95% identical over a specified region. The identity can exist over a region that is at least about 75-100 nucleic acids in length, over a region that is about 50 nucleic acids in length, or, where not specified, across the entire sequence of a polynucleotide sequence.

The term "isolated," as used herein, refers to separating and removing a component of interest from components not of interest. Isolated substances can be in either a dry or semi-dry state, or in solution, including but not limited to an aqueous solution. The isolated component can be in a homogeneous state, or the isolated component can be a part of a pharmaceutical composition that comprises additional pharmaceutically acceptable carriers and/or excipients. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes, such as, oxidation reactions) by which a particular substance is changed by an organism. Thus, enzymes may produce specific structural alterations to a compound. For example, cytochrome P450 catalyzes a variety of oxidative and reductive reactions while uridine diphosphate glucuronyl transferases catalyze the transfer of an activated glucuronic-acid molecule to aromatic alcohols, aliphatic alcohols, carboxylic acids, amines and free sulfhydryl groups. Further information on metabolism may be obtained from The Pharmacological Basis of Therapeutics, 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

As used herein, the term "modulator" refers to a compound that alters an activity of a molecule. For example, a modulator can cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "prophylactically effective amount," as used herein, refers that amount of a composition applied to a patient that will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "prophylactically effective amount," as used herein, refers that amount of a composition applied to a patient that will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

As used herein, the term "selective binding compound" refers to a compound that selectively binds to any portion of one or more target proteins.

As used herein, the term "selectively binds" refers to the ability of the agonists to selective binding to a target protein, such as, for example, GLP-IR, with greater affinity than it binds to a non-target protein. In certain embodiments, specific binding refers to binding to a target with an affinity that is at least 10, 50, 100, 250, 500, 1000 or more times greater than the affinity for a non-target.

As used herein, the term "selective modulator" refers to a compound that selectively modulates a target activity relative to a non-target activity. In certain embodiments, specific modulator refers to modulating a target activity at least 10, 50, 100, 250, 500, 1000 times more than a non-target activity.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 43%, about 90%, about 95%, about 96%, about 97%, about 98%, about 99% or greater.

The term "subject" or "patient" as used herein, refers to an animal which is the object of treatment, observation, or experiment. By way of example only, a subject may be, but is not limited to, a mammal including, but not limited to, a human.

As used herein, the term "target protein" refers to a molecule or a portion of a protein capable of being bound by a selective binding compound. In certain embodiments, a target protein is GLP-1R.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the $EC_{50}$ refers to an amount, concentration, or dosage of a particular test compound that achieves a 50% activation of a maximal response, such as activation of GLP-1R, in an assay that measures such response.

As used herein, $EC_{50}$ refers to a dosage, concentration, or amount of a particular test compound that elicits a dose-dependent response at 50% of maximal expression of a particular response that is induced, provoked, or potentiated by the particular test compound.

Methods described herein include administering to a subject in need a composition containing a therapeutically effective amount of one or more GLP-1R agonists described herein.

Compounds

In one aspect, described herein are activators of GLP-1R.

In the following description of GLP-1R agonists suitable for use in the methods described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

GLP-1R agonists can be used for the manufacture of a medicament for treating any of the foregoing conditions (e.g., autoimmune diseases, inflammatory diseases, allergy disorders, B-cell proliferative disorders, Myeloid cell proliferative disorder, Lymphoid cell proliferative disorder, or thromboembolic disorders).

In some embodiments, the GLP-1R agonists used for the methods described herein activates GLP-1R activity with an in vitro $EC_{50}$ of less than about 10 μM (e.g., less than about 1 μM, less than about 0.5 μM, less than about 0.4 μM, less than about 0.3 μM, less than about 0.1 μM, less than about 0.08 μM, less than about 0.06 μM, less than about 0.05 μM, less than about 0.04 μM, less than about 0.03 μM, less than about 0.02 μM, less than about 0.01 μM, less than about 0.008 μM, less than about 0.006 μM, less than about 0.005 μM, less than about 0.004 μM, less than about 0.003 μM, less than about 0.002 μM, less than about 0.001 μM, less than about 0.00099 μM, less than about 0.00098 μM, less than about 0.00097 μM, less than about 0.00096 μM, less than about 0.00095 μM, less than about 0.00094 μM, less than about 0.00093 μM, less than about 0.00092 μM, or less than about 0.00090 μM).

Also described herein are methods for synthesizing such agonists, methods for using such agonists in the treatment of diseases (including diseases wherein activation of GLP-1R provides therapeutic benefit to a patient having the disease). Further described are pharmaceutical compositions that include a GLP-1R agonists.

Generally, a reversible or irreversible GLP-1R agonists used in the methods described herein is identified or characterized in an in vitro assay, e.g., an acellular biochemical assay or a cellular functional assay. Such assays are useful to determine an in vitro $EC_{50}$ for a reversible or irreversible GLP-1R agonists.

Described herein are compounds of any of Formula (I) or (L-I). Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided. In some embodiments, when compounds disclosed herein contain an oxidizable nitrogen atom, the nitrogen atom can be converted to an N-oxide by methods well known in the art. In certain embodiments, isomers and chemically protected forms of compounds having a structure represented by any of formulas described herein are also provided.

In some embodiments, provided herein are GLP-1R agonists according to compounds of any of formulas described herein.

In another aspect, provided herein is a compound according to Formula (L-I) having the structure:

N-I

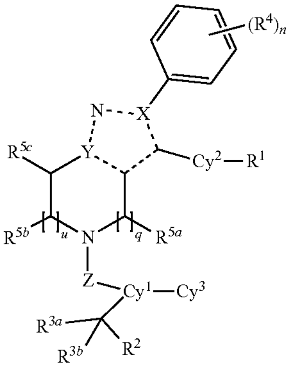

or a stereoisomer or a pharmaceutically acceptable salt thereof, wherein each of dotted bond is independently a single or a double bond;

Z is substituted or unsubstituted $C_1$-$C_4$ alkylene, —C(O)—, —S(O)—, $S(O)_2$, or —$C(R^{3c})(R^{3d})$—;

$Cy^1$ is substituted or unsubstituted 5,6-fused heteroaryl or 6,6-fused heteroaryl;

$Cy^2$ is substituted or unsubstituted heteroaryl; or -$Cy^2$-$R^1$ is —C(O)—$NR^{6a}$—$(CH_2)_m$—$R^1$; wherein $R^{6a}$ is H, or substituted or unsubstituted alkyl; and m is 0, 1, 2, or 3;

$Cy^3$ is substituted or unsubstituted cycloalkyl, substituted or unsubstituted heterocycloalkyl, substituted or unsubstituted aryl, or substituted or unsubstituted heteroaryl;

$R^1$ is substituted or unsubstituted aryl or heteroaryl;

$R^2$ is CN, substituted or unsubstituted heterocycloalkyl, or substituted or unsubstituted heteroaryl;

each $R^{3a}$ and $R^{3b}$ is independently H, or substituted or unsubstituted alkyl; or $R^{3a}$ and $R^{3b}$ form an oxo; or $R^{3a}$ and $R^{3b}$ are joined together to form substituted or unsubstituted cycloalkyl or heterocycloalkyl ring;

each $R^{3c}$ and $R^{3d}$ is independently H, or substituted or unsubstituted alkyl;

each $R^4$ is independently H, halo, CN, substituted or unsubstituted alkyl, substituted or unsubstituted alkoxy, alkylsulfonyl, arylsulfonyl, alkylsulfinyl, or arylsulfinyl; and n is 1, 2, 3, 4, or 5;

each $R^{5a}$, $R^{5b}$ and $R^{5c}$ is independently H, or substituted or unsubstituted alkyl;

or $R^{5a}$ and $R^{5b}$ or $R^{5a}$ and $R^{5c}$ are joined together to form a heterocycloalkyl;

q is 1, 2, or 3; provided that when q is 2 or 3, only one $R^{5a}$ is other than H;

u is 1, 2, or 3; provided that when u is 2 or 3, only one $R^{5b}$ is other than H;

and wherein the substitution on each alkyl is independently selected from halo, CN, hydroxy, and alkoxy; the substitution on each alkoxy is independently selected from halo, CN, and substituted or unsubstituted alkyl; the substitution on each cycloalkyl is independently selected from halo, CN, hydroxy, substituted or unsubstituted alkyl, and substituted or unsubstituted alkoxy; the substitution on each heterocycloalkyl is independently selected from halo, CN, hydroxy, substituted or unsubstituted alkyl, and substituted or unsubstituted alkoxy; the substitution on each aryl is independently 1-3 groups independently selected from halo, haloalkyl, amino, dialkylamino, amido, CN, hydroxy, substituted or unsubstituted alkyl, and substituted or unsubstituted alkoxy; the substitution on each heteroaryl is independently 1-3 groups independently selected from halo, haloalkyl, amino, dialkylamino, amido, CN, hydroxy, substituted or unsubstituted alkyl, substituted or unsubstituted alkoxy, and oxo;

provided that when $Cy^2$ is

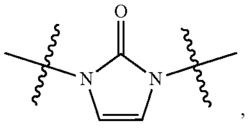 [SMILES: *n1ccn(*)c1=O]

, q is 1, u is 1, X is N, and Y is C; then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl;

or ii) $R^{5a}$ and $R^{5b}$ or $R^{5a}$ and $R^{5c}$ are joined together to form a heterocycloalkyl;

or the compound is any of the compounds listed in Table 1;

In certain embodiments, the compound according to formula (N-II):

N-II

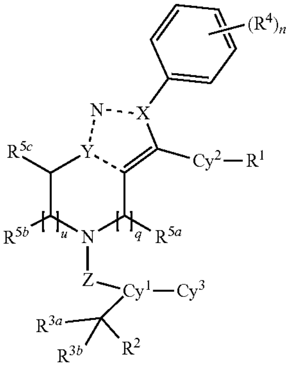

or a stereoisomer or a pharmaceutically acceptable salt thereof; wherein one of X and Y is N, and the other is C; one of dotted bonds is a double bond, and the other is a single bond.

In certain embodiments, X is N and Y is C.

In certain embodiments, Y is N and X is C.

In certain embodiments, the compound according to formula (N-III):

N-III

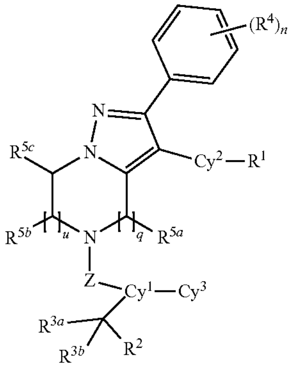

or a stereoisomer or a pharmaceutically acceptable salt thereof.

In certain embodiments, the compound according to formula (N-IV):

N-IV

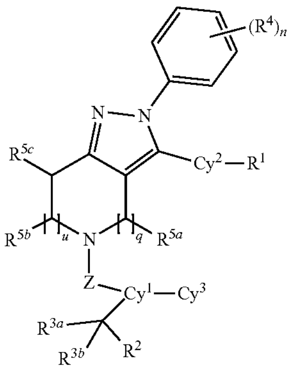

or a stereoisomer or a pharmaceutically acceptable salt thereof.

In certain embodiments, q is 1, and u is 2.

In certain embodiments, q is 2, and u is 1 or 2.

In certain embodiments, q is 1, and u is 1.

In certain embodiments, the compound according to formula (N-V):

N-V

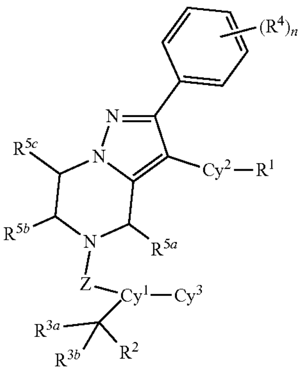

or a stereoisomer or a pharmaceutically acceptable salt thereof.

In certain embodiments, the compound according to formula (N-VI):

N-VI

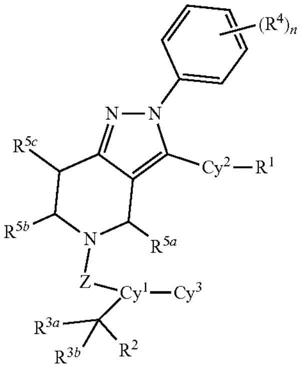

or a stereoisomer or a pharmaceutically acceptable salt thereof.

In certain embodiments, Z is —C(O)—, or —C($R^{3c}$)($R^{3d}$)—.

In certain embodiments, Z is —$CH_2$—.

In certain embodiments, Z is —C(O)—.

In certain embodiments, Z is —S(O)—, $S(O)_2$,

In certain embodiments, the compound according to formula (N-VII):

N-VII

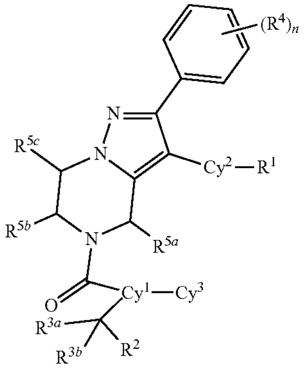

or a stereoisomer or a pharmaceutically acceptable salt thereof.

In certain embodiments, the compound according to formula (L-I):

L-I

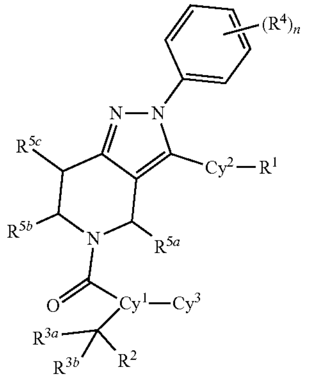

or a stereoisomer or a pharmaceutically acceptable salt thereof, wherein $Cy^1$ is substituted or unsubstituted 5,6-fused heteroaryl or 6,6-fused heteroaryl;

$Cy^2$ is substituted or unsubstituted heteroaryl; or $-Cy^2-R^1$ is $-C(O)-NR^{6a}-(CH_2)_m-R^1$; and wherein $R^{6a}$ is H, or substituted or unsubstituted alkyl; and m is 0, 1, 2, or 3;

$Cy^3$ is substituted or unsubstituted cycloalkyl, substituted or unsubstituted heterocycloalkyl, substituted or unsubstituted aryl, or substituted or unsubstituted heteroaryl;

$R^1$ is substituted or unsubstituted aryl or heteroaryl;

$R^2$ is CN, or substituted or unsubstituted heteroaryl;

each $R^{3a}$ and $R^{3b}$ is independently H, or substituted or unsubstituted alkyl; or $R^{3a}$ and $R^{3b}$ form an oxo; or $R^{3a}$ and $R^{3b}$ are joined together to form substituted or unsubstituted cycloalkyl or heterocycloalkyl ring;

each $R^4$ is independently H, halo, CN, substituted or unsubstituted alkyl, substituted or unsubstituted alkoxy, alkylsulfonyl, arylsulfonyl, alkylsulfinyl, or arylsulfinyl; and n is 1, 2, 3, 4, or 5;

each $R^{5a}$, $R^{5b}$ and $R^{5c}$ is independently H, or substituted or unsubstituted alkyl;

or $R^{5a}$ and $R^{5b}$ or $R^{5a}$ and $R^{5c}$ are joined together to form a heterocycloalkyl;

and wherein the substitution on each alkyl is independently selected from halo, CN, hydroxy, and alkoxy; the substitution on each alkoxy is independently selected from halo, CN, and substituted or unsubstituted alkyl; the substitution on each cycloalkyl is independently selected from halo, CN, hydroxy, substituted or unsubstituted alkyl, and substituted or unsubstituted alkoxy; the substitution on each heterocycloalkyl is independently selected from halo, CN, hydroxy, substituted or unsubstituted alkyl, and substituted or unsubstituted alkoxy; the substitution on each aryl is independently 1-3 groups independently selected from halo, haloalkyl, amino, dialkylamino, amido, CN, hydroxy, substituted or unsubstituted alkyl, and substituted or unsubstituted alkoxy; the substitution on each heteroaryl is independently 1-3 groups independently selected from halo, haloalkyl, amino, dialkylamino, amido, CN, hydroxy, substituted or unsubstituted alkyl, substituted or unsubstituted alkoxy, and oxo;

provided that when $Cy^2$ is

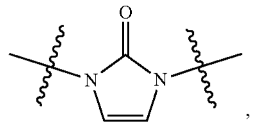 [SMILES: *n1ccn(*)c1=O]

, then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl;

or ii) $R^{5a}$ and $R^{5b}$ or $R^{5a}$ and $R^{5c}$ are joined together to form a heterocycloalkyl.

In certain embodiments, one of $R^{5a}$ and $R^{5b}$ is substituted or unsubstituted alkyl, and the other is H; and wherein the substitution on each alkyl is independently selected from halo, CN, and alkoxy.

In certain embodiments, each of $R^{5a}$ and $R^{5b}$ is substituted or unsubstituted alkyl; and wherein the substitution on each alkyl is independently selected from halo, CN, and alkoxy.

In certain embodiments, $R^{5b}$ is H; and $R^{5a}$ is $R^5$, and $R^5$ is H or substituted or unsubstituted alkyl; and wherein the substitution on each alkyl is independently selected from halo, CN, and alkoxy.

In certain embodiments, the compounds provided herein have favorable stereochemistry. In certain embodiments of compounds of Formula N-I, N-II, N-III, or N-IV, $R^{5a}$ and $R^{5b}$ are taken together with the bridgehead carbons to which they are attached to form a heterocycloalkyl, where $R^{5a}$ and $R^{5b}$ proceed into the plane or away from the reader, as depicted in Formula N-I, N-II, N-III, or N-IV. In certain embodiments of compounds of Formula N-IV, $R^{5a}$ and $R^{5c}$ are taken together with the bridgehead carbons to which they are attached to form a heterocycloalkyl, where $R^{5a}$ and $R^{5c}$ proceed into the plane or away from the reader, as depicted in Formula N-I, N-II, N-III, or N-IV. In certain embodiments of the bridged heterocycloalkyl, where the heterocycloalkyl formed by $R^{5a}$ and $R^{5b}$ has only one heteroatom, the bridgehead carbon linked to $R^{5a}$ is in the (S)-configuration, and the bridgehead carbon linked to $R^{5b}$ is in the (R)-configuration. In certain embodiments of the bridged heterocycloalkyl, where the heterocycloalkyl formed by $R^{5a}$ and $R^{5b}$ has more than one heteroatom, the bridging atoms proceed into the plane or away from the reader, as depicted in Formula N-I, N-II, N-III, or N-IV. In certain embodiments of the bridged heterocycloalkyl, where the heterocycloalkyl formed by $R^{5a}$ and $R^{5c}$ has only one heteroatom, the bridgehead carbon linked to $R^{5a}$ is in the (S)-configuration, and the bridgehead carbon linked to $R^{5a}$ is in the (R)-configuration. In certain embodiments of the bridged heterocycloalkyl, where the heterocycloalkyl formed by $R^{5a}$ and $R^{5c}$ has more than one heteroatom, the bridging atoms proceed into the plane or away from the reader, as depicted in Formula N-I, N-II, N-III, or N-IV.

In certain embodiments, the compound is according to formula (I):

I

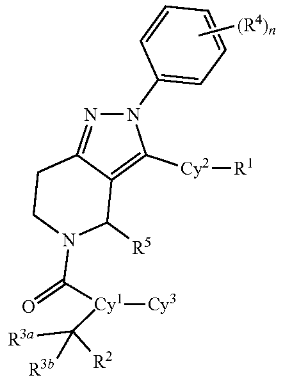

or a stereoisomer or a pharmaceutically acceptable salt thereof, wherein $Cy^1$ is substituted or unsubstituted 5,6-fused or 6,6-fused heteroaryl;

$Cy^2$ is substituted or unsubstituted heteroaryl; or $-Cy^2-R^1$ is $-C(O)-NR^{6a}-(CH_2)_m-R^1$; and wherein $R^{6a}$ is H, or substituted or unsubstituted alkyl; and m is 0, 1, 2, or 3;

$Cy^3$ is substituted or unsubstituted cycloalkyl, substituted or unsubstituted heterocycloalkyl, substituted or unsubstituted aryl, or substituted or unsubstituted heteroaryl;

$R^1$ is substituted or unsubstituted aryl or heteroaryl;

$R^2$ is CN, or substituted or unsubstituted heteroaryl each $R^{3a}$ and $R^{3b}$ is independently H, or substituted or unsubstituted alkyl; or $R^{3a}$ and $R^{3b}$ form an oxo; or $R^{3a}$ and $R^{3b}$ are joined together to form substituted or unsubstituted cycloalkyl or heterocycloalkyl ring;

each $R^4$ is independently H, halo, CN, substituted or unsubstituted alkyl, substituted or unsubstituted alkoxy, alkylsulfonyl, arylsulfonyl, alkylsulfinyl, or arylsulfinyl; and n is 1, 2, 3, 4, or 5;

$R^5$ is H, or substituted or unsubstituted alkyl;

and wherein the substitution on each alkyl is independently selected from halo, CN, hydroxy, and alkoxy; the substitution on each alkoxy is independently selected from halo, CN, and substituted or unsubstituted alkyl; the substitution on each cycloalkyl is independently selected from halo, CN, hydroxy, substituted or unsubstituted alkyl, and substituted or unsubstituted alkoxy; the substitution on each heterocycloalkyl is independently selected from halo, CN, hydroxy, substituted or unsubstituted alkyl, and substituted or unsubstituted alkoxy; the substitution on each aryl is independently 1-3 groups independently selected from halo, haloalkyl, amino, dialkylamino, amido, CN, hydroxy, substituted or unsubstituted alkyl, and substituted or unsubstituted alkoxy; the substitution on each heteroaryl is independently 1-3 groups independently selected from halo, haloalkyl, amino, dialkylamino, amido, CN, hydroxy, substituted or unsubstituted alkyl, substituted or unsubstituted alkoxy, and oxo;

provided that when $Cy^2$ is

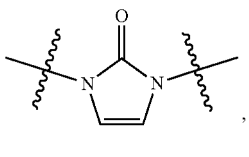

, then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl, or ii) $R^{5a}$ and $R^{5b}$ or $R^{5a}$ and $R^{5c}$ are joined together to form a heterocycloalkyl.

In certain embodiments, $R^{5a}$ and $R^{5b}$ are joined together to form a heterocycloalkyl.

In certain embodiments, $R^{5a}$ and $R^{5c}$ are joined together to form a heterocycloalkyl.

In certain embodiments, the compound is according to formula (L-IIa) or (L-IIb):

L-IIa

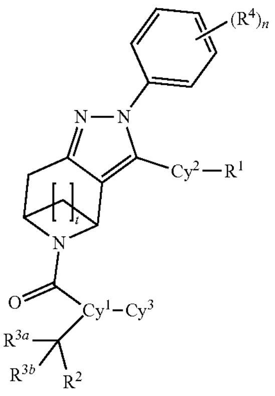

or

L-IIb

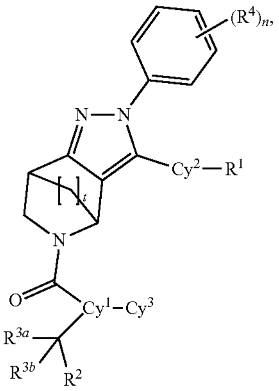

or a stereoisomer or a pharmaceutically acceptable salt thereof, wherein t is 1, 2, or 3.

In certain embodiments, the compound is according to formula (Q-IIa) or (Q-IIb):

Q-IIa

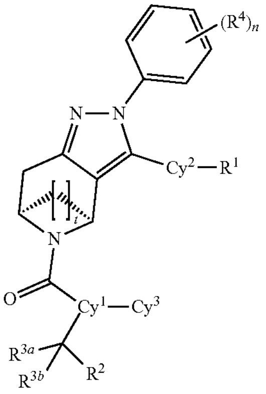

or

Q-IIb

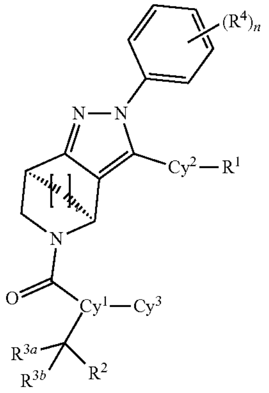

or a stereoisomer or a pharmaceutically acceptable salt thereof, wherein t is 1, 2, or 3.

In certain embodiments, tis 1, or 2.

In certain embodiments, t is 3.

In certain embodiments, the compound is according to formula (L-IIIa), (L-IIIb), or (L-IIIc):

L-IIIa

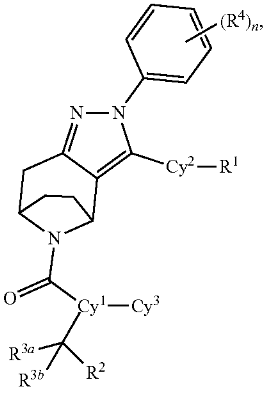

-continued

L-IIIb

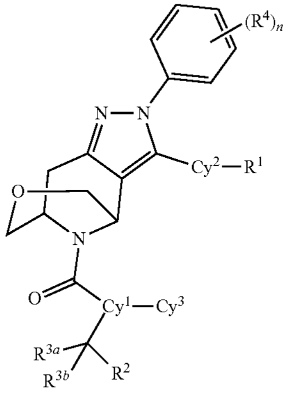

or

L-IIIc

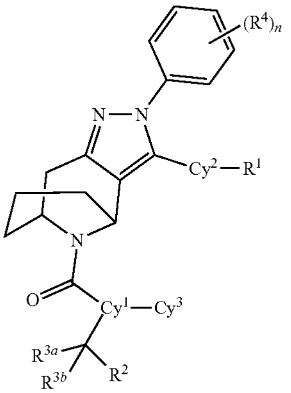

or a stereoisomer or a pharmaceutically acceptable salt thereof.

In certain embodiments, the compound is according to formula (Q-IIIa), (Q-IIIb), or (Q-IIIc):

Q-IIIa

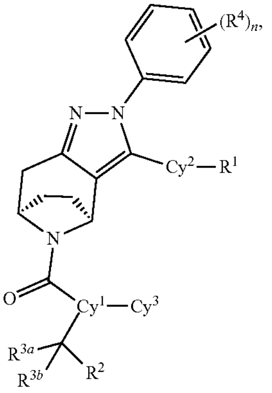

-continued

Q-IIIb

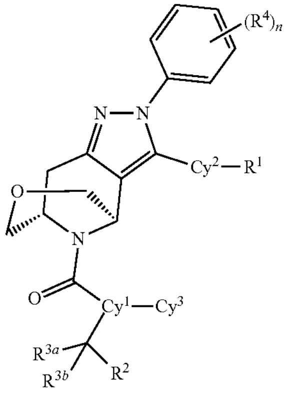

or

Q-IIIc

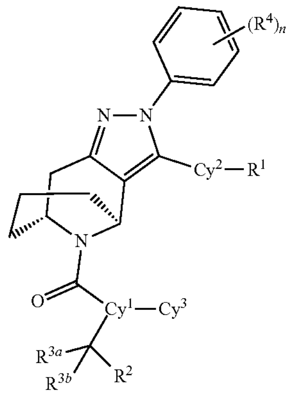

or a stereoisomer or a pharmaceutically acceptable salt thereof.

In certain embodiments, $Cy^2$ is

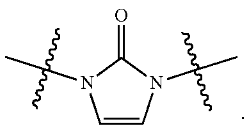 [SMILES: *n1ccn(*)c1=O]

.

In certain embodiments, the compound is according to formula (L-IVa), (L-IVb), or (L-IVc):

L-IVa

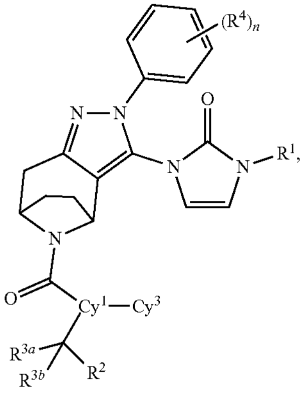

-continued

L-IVb

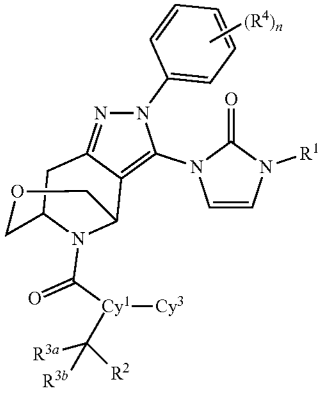

or

L-IVc

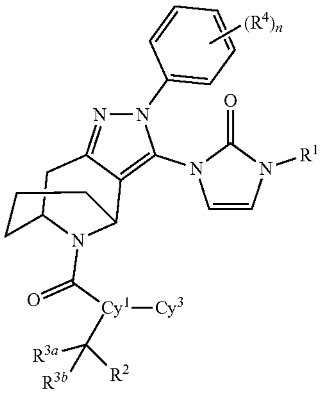

or a stereoisomer or a pharmaceutically acceptable salt thereof.

In certain embodiments, the compound is according to formula (Q-IVa), (Q-IVb), or (Q-IVc):

Q-IVa

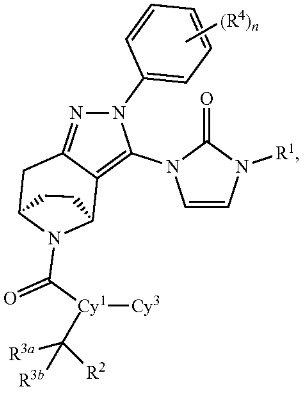

-continued

Q-IVb

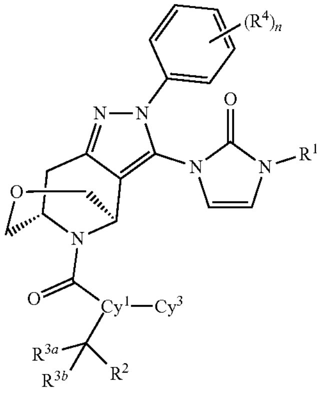

or

Q-IVc

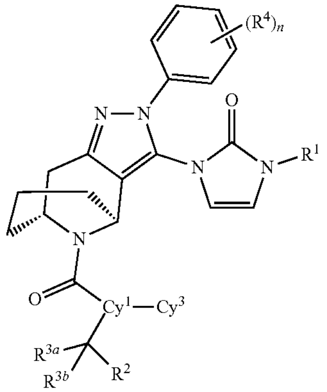

or a stereoisomer or a pharmaceutically acceptable salt thereof.

In certain embodiments, $R^{3a}$ and $R^{3b}$ form an oxo.

In certain embodiments, $R^{3a}$ and $R^{3b}$ are joined together to form cycloalkyl or heterocycloalkyl.

In certain embodiments, $R^{3a}$ and $R^{3b}$ are joined together to form cyclopropyl, cyclobutyl, cyclopentyl or cyclohexyl.

In certain embodiments, $R^{3a}$ and $R^{3b}$ are joined together to form azetidinyl, tetrahydro furanyl, or tetrahydropyranyl.

In certain embodiments, the compound is according to formula (IIa), (IIb) or (IIc), or (IId); or Q-IIb', Q-IIc' or Q-IId':

IIa

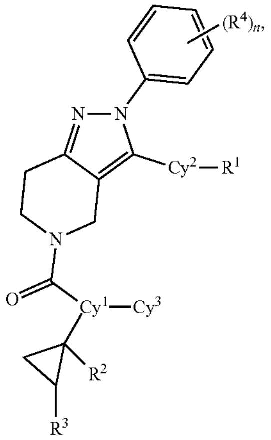

-continued

IIb

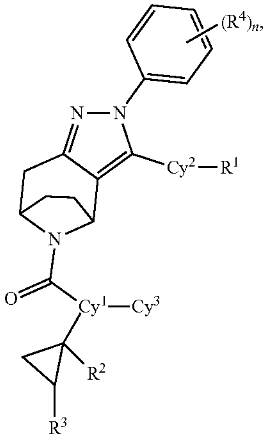

IIc

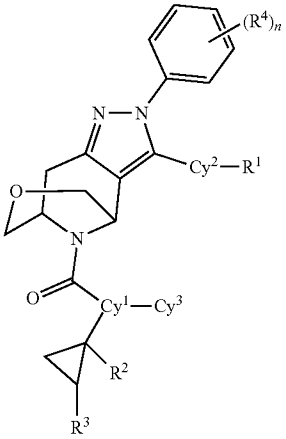

or

IId

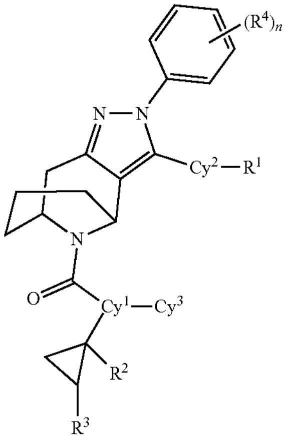

or

-continued

Q-IIb'

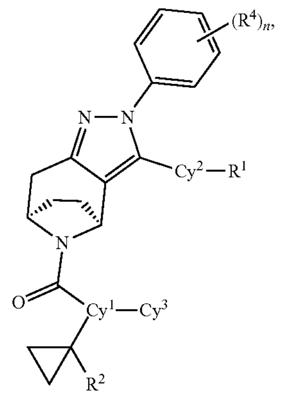

Q-IIc'

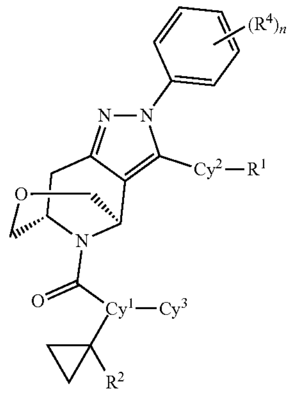

or

Q-IId'

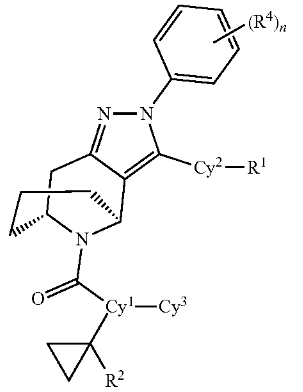

or a stereoisomer or a pharmaceutically acceptable salt thereof, wherein $R^3$ is H, or substituted or unsubstituted alkyl;

provided that when $Cy^2$ is

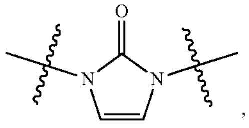 [SMILES: *n1ccn(*)c1=O]

, then i) $Cy^1$ is substituted or unsubstituted 6,6-fused heteroaryl, substituted or unsubstituted 5,5-fused heteroaryl, substituted or unsubstituted 5,6-fused heteroaryl, or substituted or unsubstituted 6,5-fused heteroaryl, or ii) the compound is according to formula IIb.

In certain embodiments, $R^2$ is substituted or unsubstituted heteroaryl; and the substitution is selected from alkyl, halo, CN, and oxo.

In certain embodiments, $R^2$ is substituted or unsubstituted tetrazolyl, triazolyl, or oxadiazolyl; and the substitution is selected from alkyl, halo, CN, and oxo. In certain embodiments, $R^2$ is substituted or unsubstituted heterocycloalkyl.

In certain embodiments, $R^2$ is

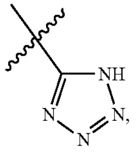

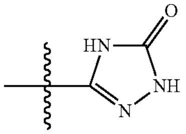

or

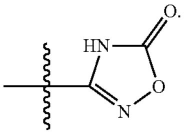

In certain embodiments, $R^2$ is

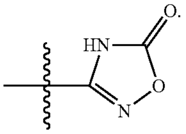 [SMILES: *c1noc(=O)[nH]1]

In certain embodiments, $R^2$ is

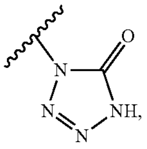

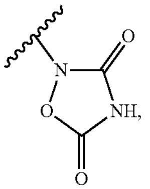

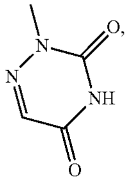

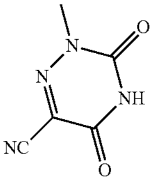

or

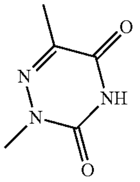

In certain embodiments, the compound is according to formula (IId), (IIe), or (IIf); or Q-IIe', Q-IIf or Q-IIg':

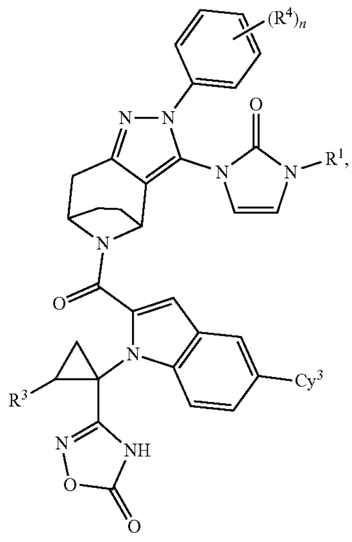
IId
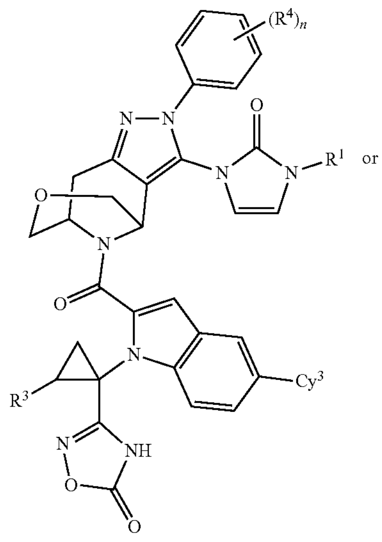
IIe
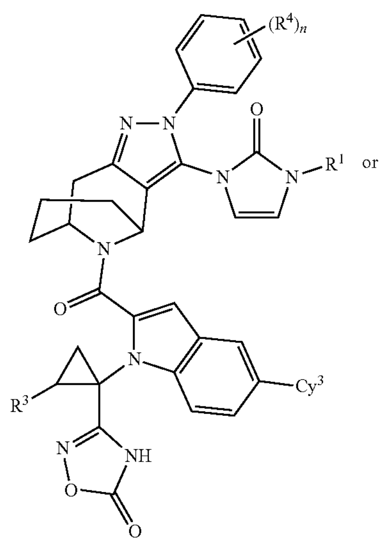
IIf
-continued
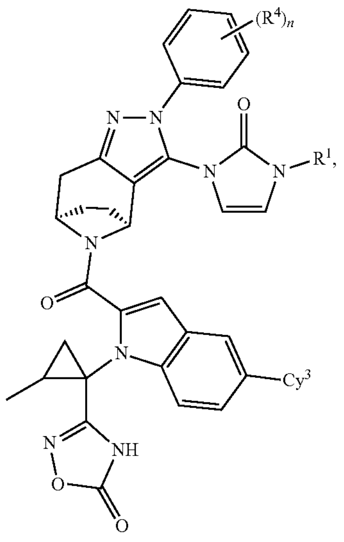
Q-IIe′
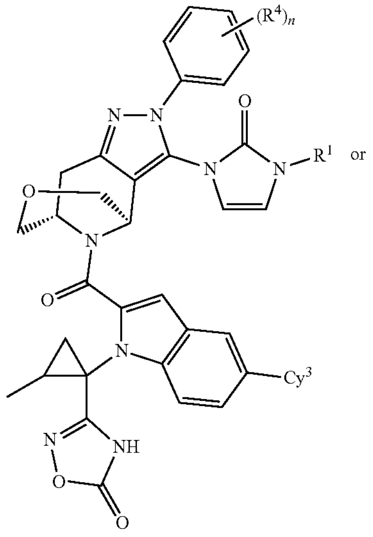
Q-IIf′
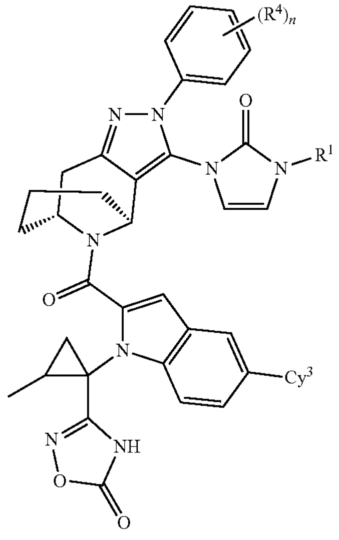
Q-IIg′ or a stereoisomer or a pharmaceutically acceptable salt thereof.

In certain embodiments, $Cy^3$ is substituted or unsubstituted cycloalkyl; and the substitution is 1-3 groups independently selected from alkyl and halo.

In certain embodiments, $Cy^3$ is substituted or unsubstituted cycloalkyl; and the substitution is 1-3 groups independently selected from Me, Cl, and F.

In certain embodiments, $Cy^3$ is substituted or unsubstituted heterocycloalkyl; and the substitution is 1-3 groups independently selected from alkyl.

In certain embodiments, $Cy^3$ is substituted or unsubstituted tetrahydrofuranyl or tetrahydropyranyl; and the substitution is 1-3 groups independently selected from alkyl.

In certain embodiments, $Cy^3$ is substituted or unsubstituted tetrahydropyranyl; and the substitution is 1-3 groups independently selected from alkyl.

In certain embodiments, $Cy^3$ is

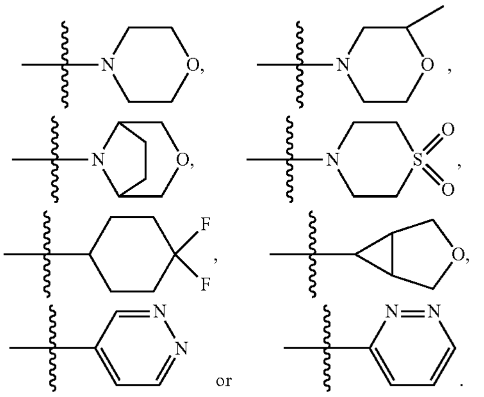

or

In certain embodiments, $Cy^3$ is

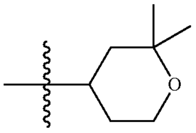

or

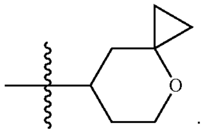

In certain embodiments, $Cy^3$ is substituted or unsubstituted aryl; and the substitution is 1-3 groups independently selected from alkyl, alkoxy, CN, and halo.

In certain embodiments, $Cy^3$ is substituted or unsubstituted heteroaryl; and the substitution is 1-3 groups independently selected from alkyl, alkoxy, CN, and halo.

In certain embodiments, $Cy^3$ is substituted with $-L^1-N(R^7)-CH=CH_2$, or $-L^1-N(R^7)-C\equiv CH-Me$; $L^1$ is a single bond, or $C_1$-$C_4$ alkylene; and $R^7$ is H or substituted or unsubstituted alkyl.

In certain embodiments, $Cy^3$ is substituted with $-L^1-N(R^7)-CH=CH_2$, or $-L^1-N(R^7)-C\equiv CH-Me$; $L^1$ is a single bond, $-CH_2-$, or $-CH_2-CH_2-$; and $R^7$ is H, or Me.

In certain embodiments, $R^{5a}$ is H.

In certain embodiments, $R^{5a}$ is Me, Et, or i-Pr.

In certain embodiments, $R^{5a}$ is Me, or Et.

In certain embodiments, the compound is according to formula (IIIa), (IIIb), (IIIc), or (IIId); or Q-IIIe', Q-IIIf', or Q-IIIg':

IIIa

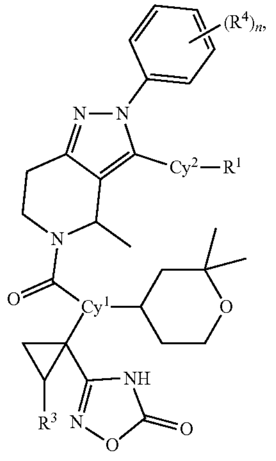

IIIb

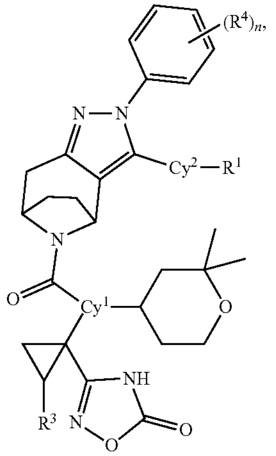

IIIc

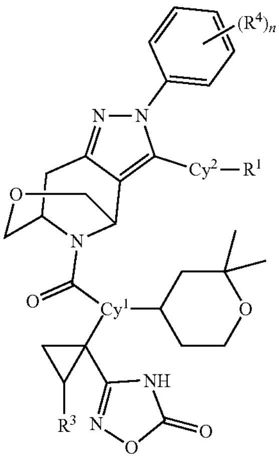

or

-continued

IIId

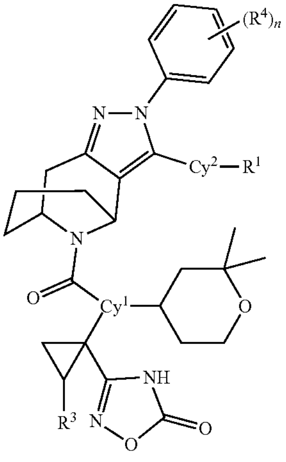

Q-IIIe'

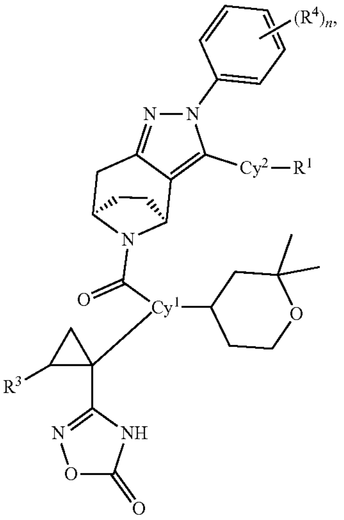

Q-IIIf'

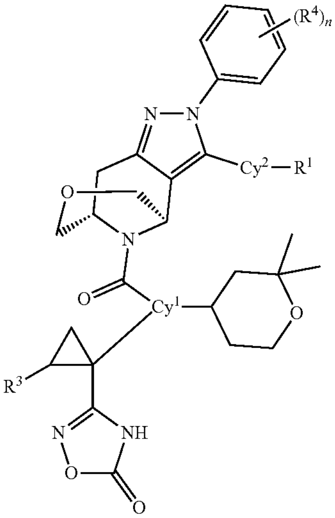

or

-continued

Q-IIIg'

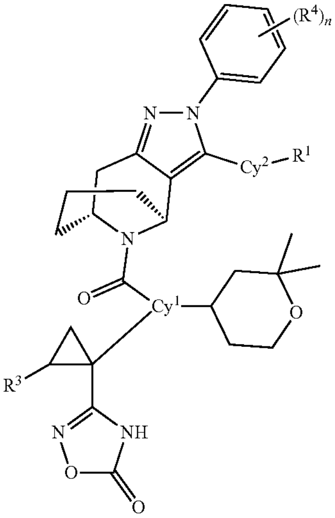

or a stereoisomer or a pharmaceutically acceptable salt thereof.

In certain embodiments, $Cy^2$ is —C(O)—$NR^{6a}$—$(CH_2)_m$—.

In certain embodiments, $R^{6a}$ is H, Me, Et, or i-Pr.

In certain embodiments, $R^{6a}$ is H.

In certain embodiments, m is 0 or 1.

In certain embodiments, m is 0.

In certain embodiments, $Cy^2$ is substituted or unsubstituted 5 membered heteroaryl; and the substitution is selected from alkyl, halo, CN, and oxo.

In certain embodiments, $Cy^2$ is

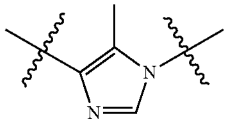,
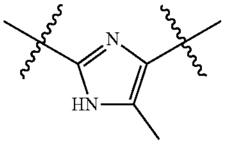,
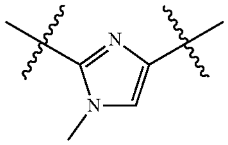,
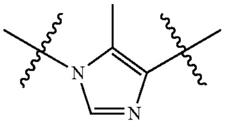,
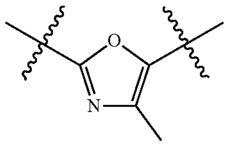,
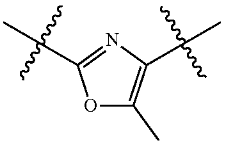,
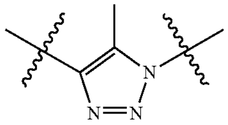,
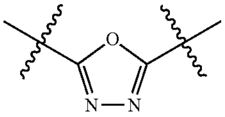,
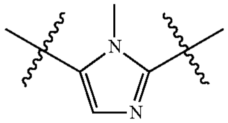,
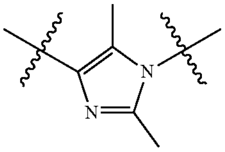, -continued

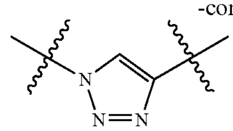
,
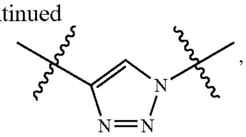
,
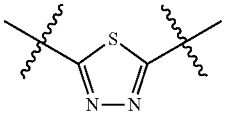
,
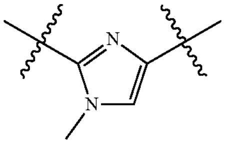
or
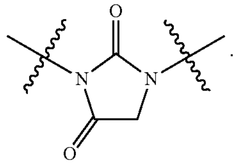

In certain embodiments, $Cy^2$ is

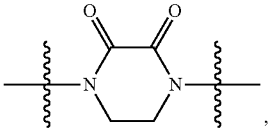
,
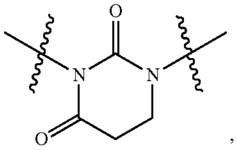
,
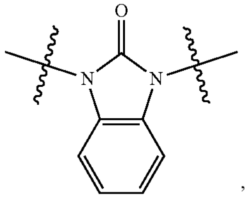
,
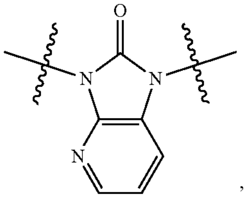
,
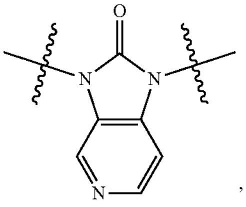
,
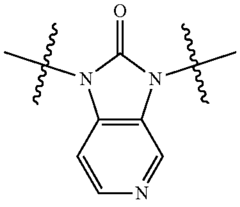
or
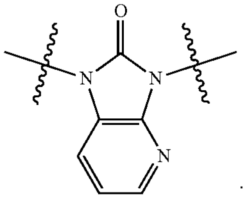

In certain embodiments, $Cy^1$ is substituted or unsubstituted 5,6-fused or 6,6-fused heteroaryl; and the substitution is selected from 1-3 groups independently selected from alkyl, CN, and halo.

In certain embodiments, $Cy^2$ is

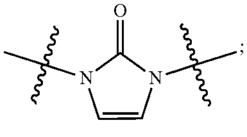 [SMILES: *n1ccn(*)c1=O]
;

and $Cy^1$ is substituted or unsubstituted 6,6-fused heteroaryl; wherein the substitution is selected from 1-3 groups independently selected from alkyl, CN, and halo.

In certain embodiments, the compound is according to formula (IIb) or (IIIb); and $Cy^2$ is

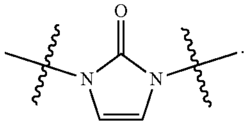 [SMILES: *n1ccn(*)c1=O]

In certain embodiments, the compound is according to formula (L-Va), (L-Vb), or (L-Vc):

L-Va

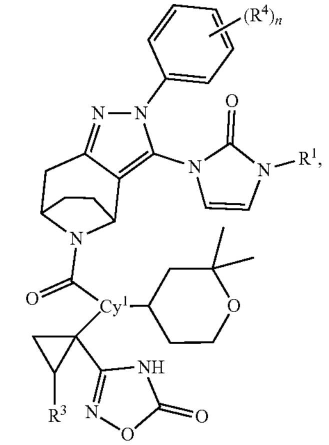

L-Vb

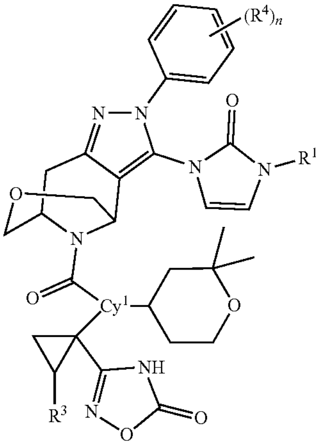
or

-continued
L-Vc
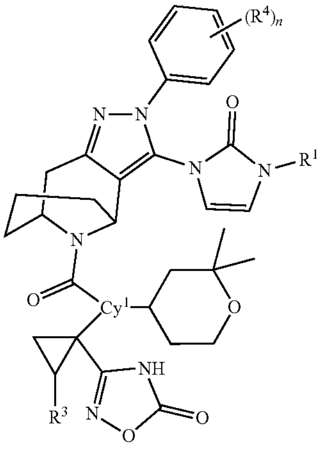
or a stereoisomer or a pharmaceutically acceptable salt thereof; and $Cy^1$ as in claim 1.
In certain embodiments, the compound is according to formula (IVa), (IVb), (IVc), or (IVd); or Q-IVa, Q-IVb, or Q-IVc:
IVa
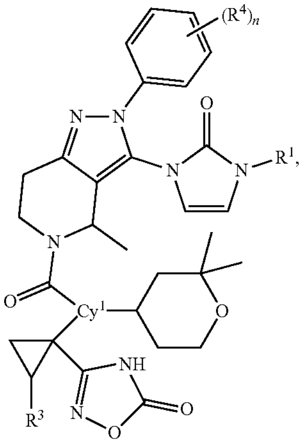
IVb
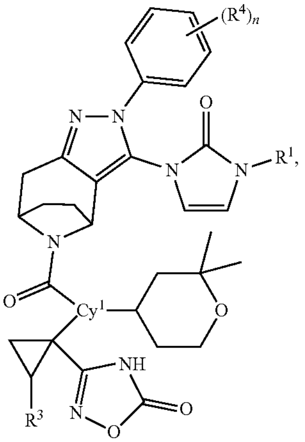
-continued
IVc
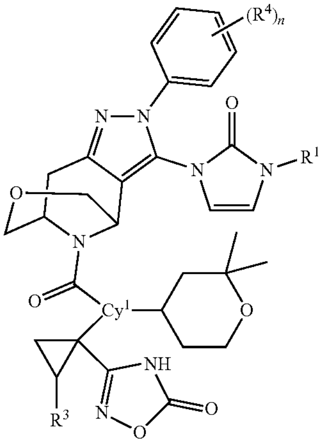
or
IVd
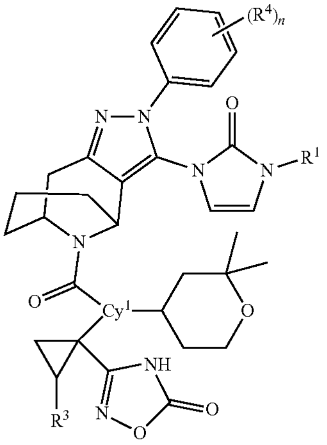
or
Q-IVb
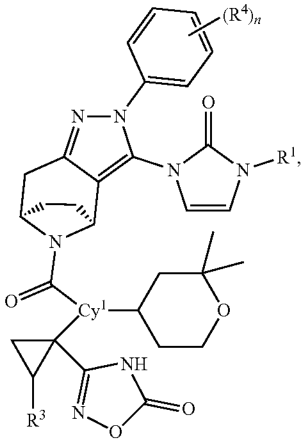

-continued

Q-IVc

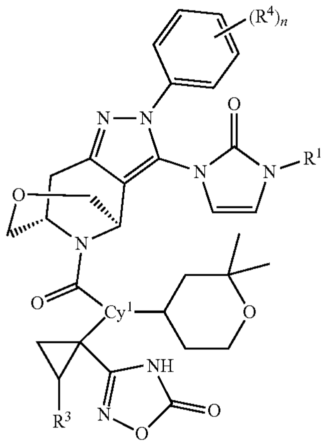

or

Q-IVd

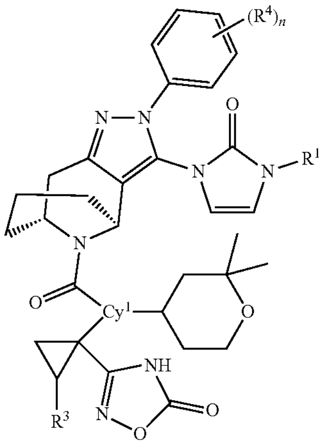

or a stereoisomer or a pharmaceutically acceptable salt thereof; wherein $Cy^1$ is substituted or unsubstituted

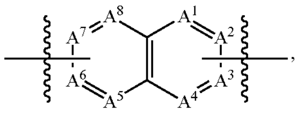

,

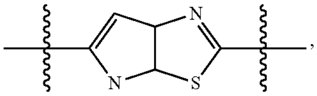

,

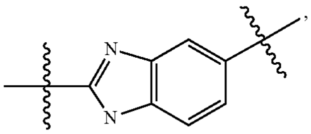

,

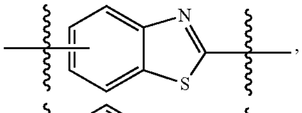

,

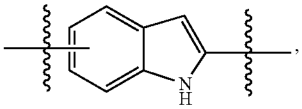

,

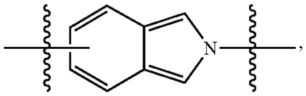

,

-continued

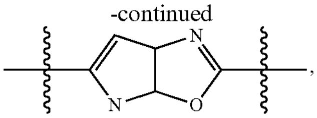

,

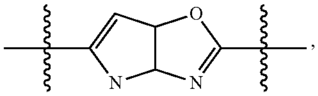

, or

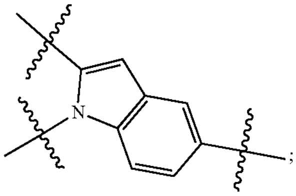

;

and each $A^1$, $A^2$, $A^3$, $A^4$, $A^5$, $A^6$, $A^7$, and $A^8$ is independently CH, or N; provided no more than 3 of $A^1$-$A^8$ are N at the same time; wherein the substitution is selected from 1-3 groups independently selected from alkyl, CN, alkoxy, and halo.

In certain embodiments, the substitution is selected from Me, Et, CN, OMe, OEt, F, or Cl. In particular embodiments, the substitution is F. In a more particular embodiments, $Cy^1$ is unsubstituted.

In certain embodiments, one of $A^1$-$A^8$ is N; and the rest are CH.

In certain embodiments, two of $A^1$-$A^8$ is N; and the rest are CH.

In certain embodiments, $Cy^1$ is substituted or unsubstituted quinolinyl or isoquinolinyl.

In certain embodiments, $Cy^1$ is substituted or unsubstituted

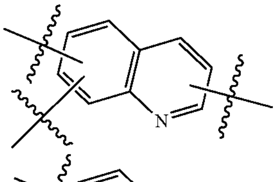

or

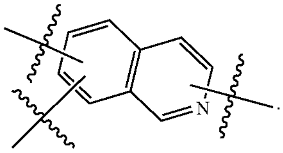

.

In certain embodiments, $Cy^1$ is substituted or unsubstituted

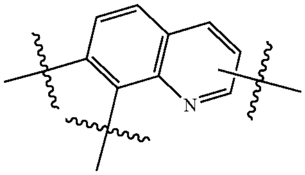

or

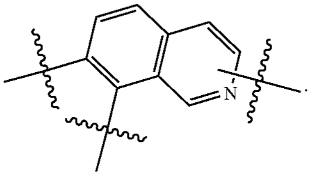

.

In certain embodiments, the compound is according to formula (Va), (Vb), or (Vc):

Va

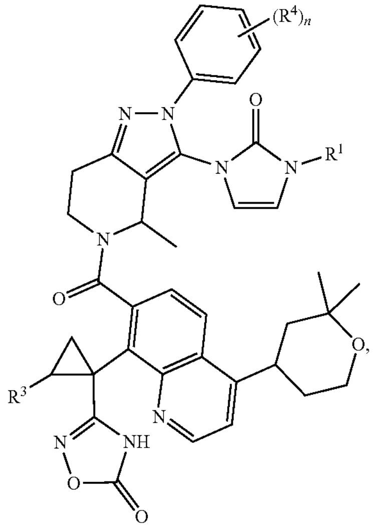

Vb

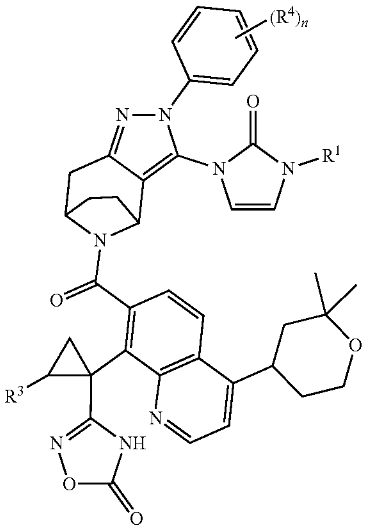

or

-continued

Vc

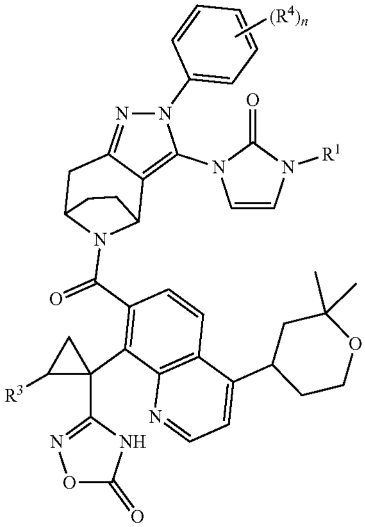

or a stereoisomer or a pharmaceutically acceptable salt thereof.

In certain embodiments, $Cy^1$ is substituted or unsubstituted

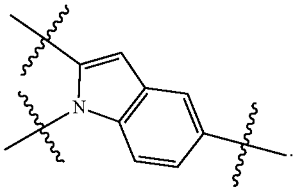 [SMILES: *c1ccc2c(c1)cc(*)n2*]

In certain embodiments, $Cy^1$ is substituted or unsubstituted

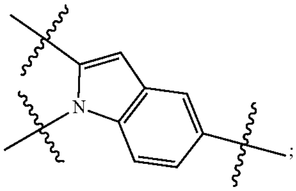 [SMILES: *c1ccc2c(c1)cc(*)n2*]

and the substitution is selected from Me, Et, CN, OMe, OEt, F, or Cl. In particular embodiments, the substitution is F. In a more particular embodiments, $Cy^1$ is unsubstituted.

In certain embodiments, $Cy^1$ is

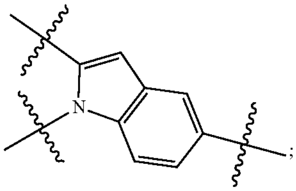 [SMILES: *c1ccc2c(c1)cc(*)n2*]

and $Cy^2$ is
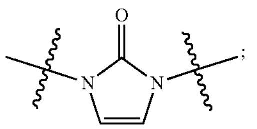 [SMILES: *n1ccn(*)c1=O]
and the compound is according to formula (L-VIa), (L-VIb), or (L-VIc):
L-VIa
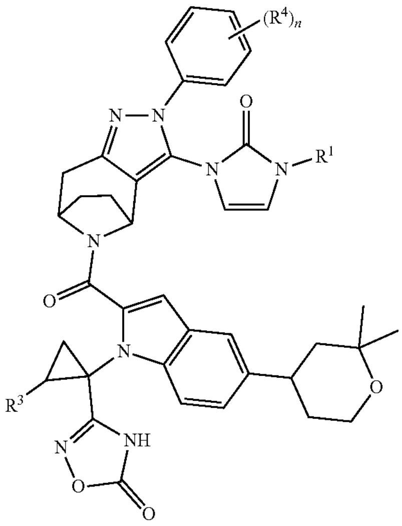
or
L-VIb
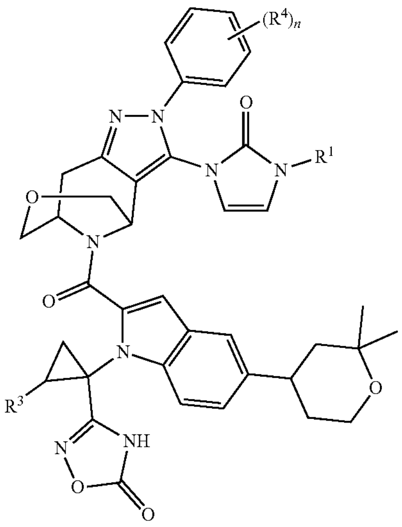
or
-continued
L-VIc
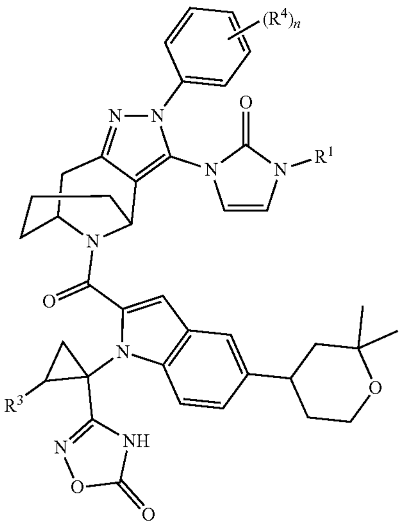
or a stereoisomer or a pharmaceutically acceptable salt thereof.
In certain embodiments, $Cy^1$ is
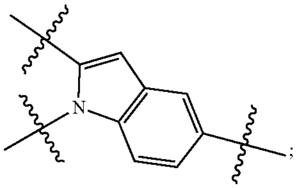 [SMILES: *c1ccc2c(c1)cc(*)n2*]
and $Cy^2$ is other than
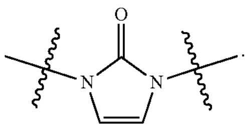 [SMILES: *n1ccn(*)c1=O]
In certain embodiments, the compound is according to formula (VIa), (VIb), (VIc), or (VId):

-continued
VIa
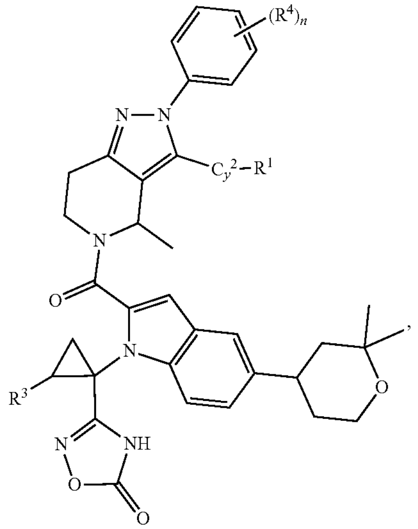
,
VIb
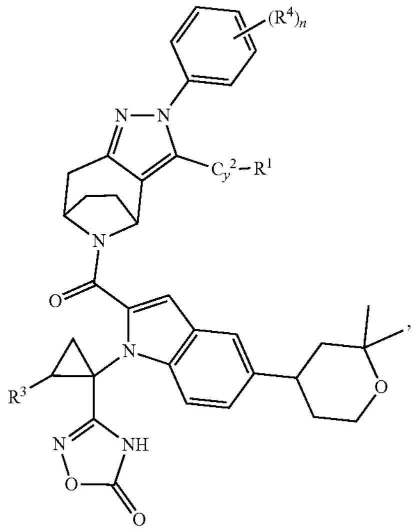
,
VIc
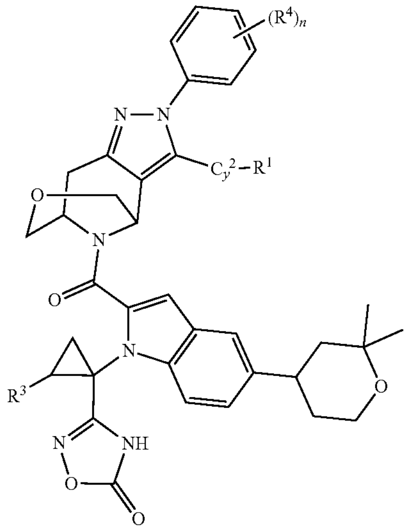
or
VId
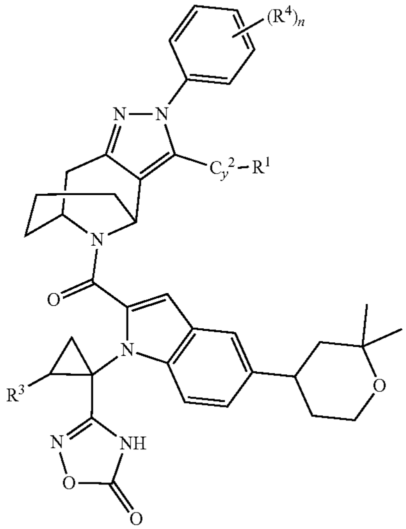
or a stereoisomer or a pharmaceutically acceptable salt thereof; and wherein $Cy^2$ is
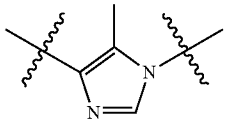, 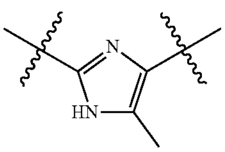,
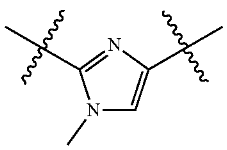, 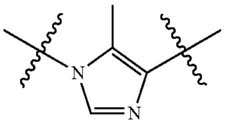,
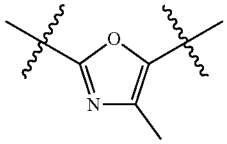, 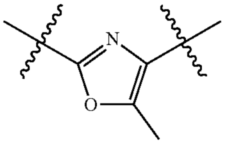,
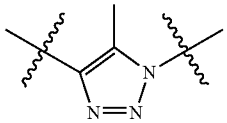, 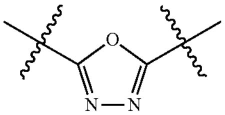,
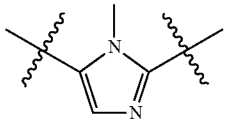, 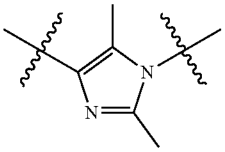,
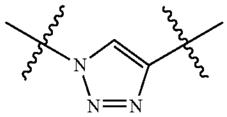, 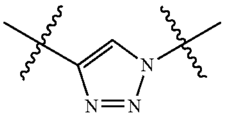,
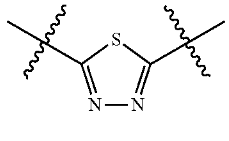, 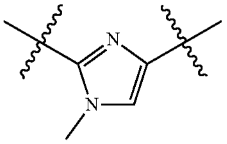 or -continued

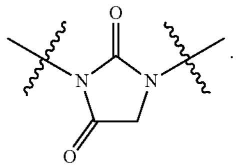

In certain embodiments, $Cy^2$ is —C(O)—NH—, or —C(O)—NH—$CH_2$—.

In certain embodiments, $R^3$ is H.

In certain embodiments, $R^3$ is alkyl.

In certain embodiments, $R^3$ is H, Me, or Et.

In certain embodiments, the compound is according to formula (L-VIIa), (L-VIIb), (L-VIIc), or (L-VIId):

L-VIIa

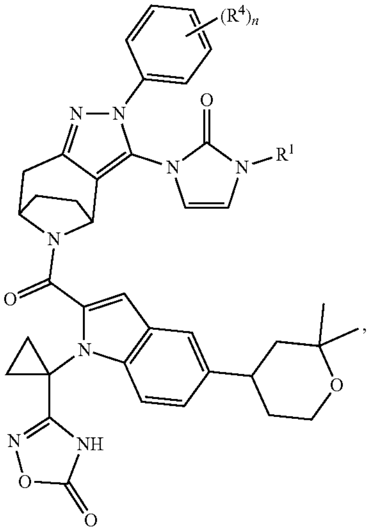

L-VIIb

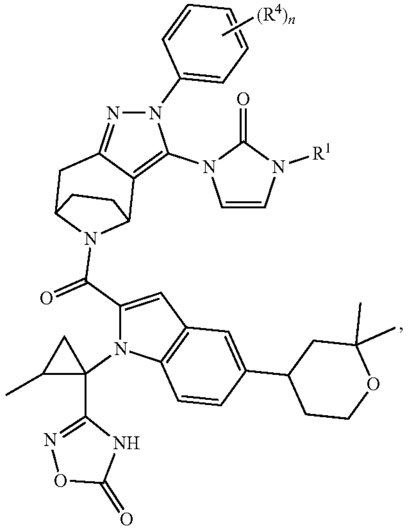

-continued

L-VIIc

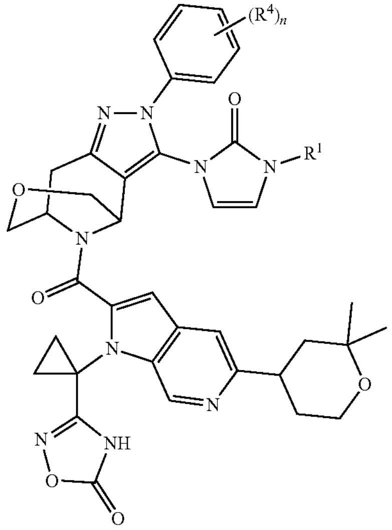

or

L-VIId

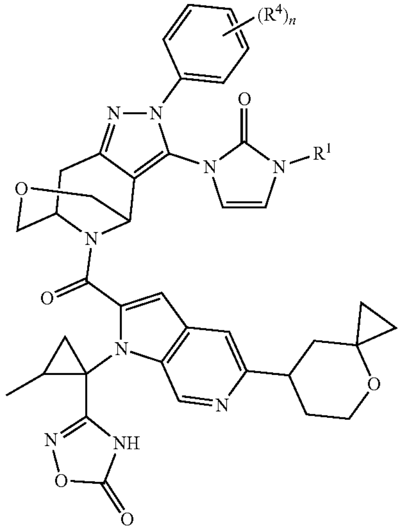

or a stereoisomer or a pharmaceutically acceptable salt thereof.

In certain embodiments, the compound is according to formula (L-VIIIa), (L-VIIIb), (L-VIIIc), or (L-VIIId):

-continued
L-VIIIa
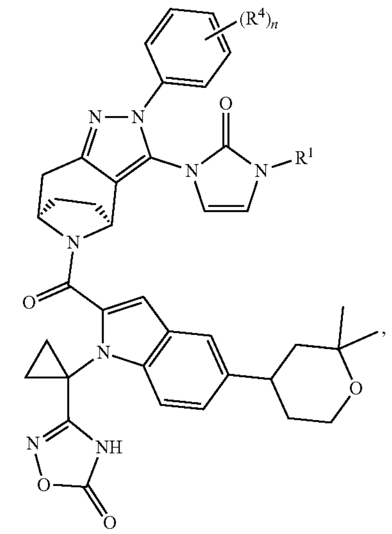
L-VIIIb
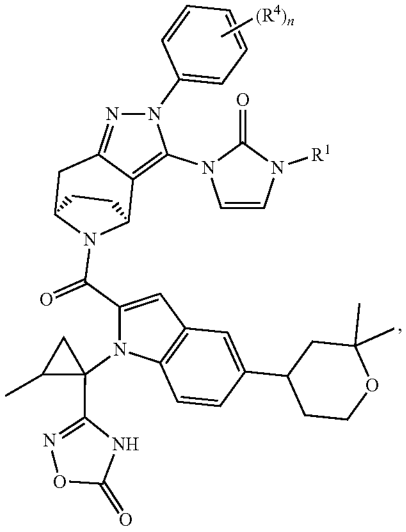
L-VIIIc
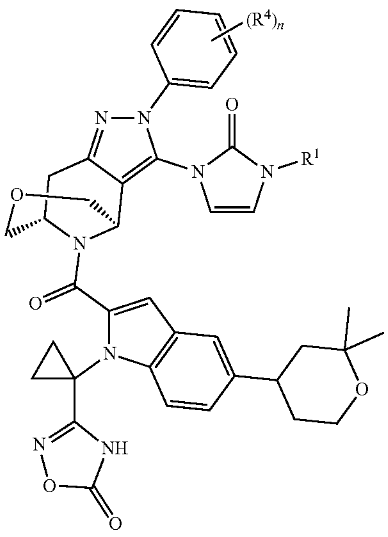
or
L-VIIId
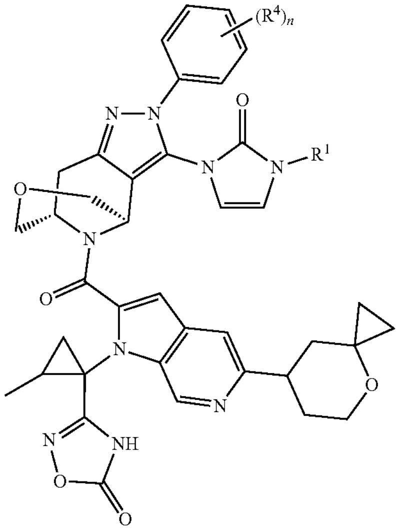
or a stereoisomer or a pharmaceutically acceptable salt thereof.
In certain embodiments, the compound is according to formula (M-IIa) or (M-IIb):
M-IIa
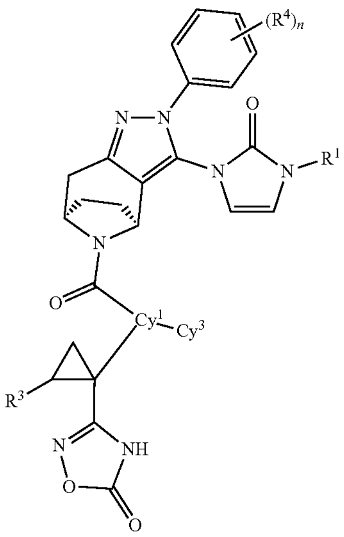
or -continued
M-IIb
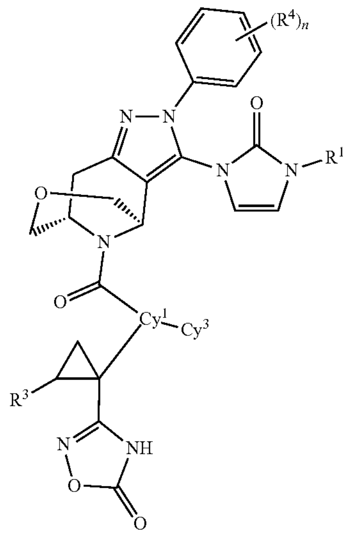
or a stereoisomer or a pharmaceutically acceptable salt thereof.
In certain embodiments, $Cy^1$ is
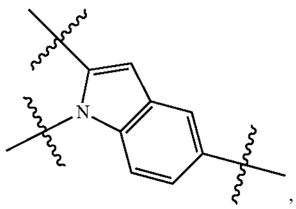
,
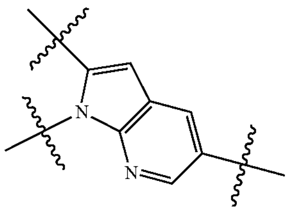
or
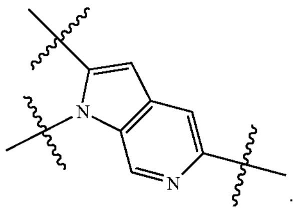
.
In certain embodiments, the compound is according to formula (M-IIIa), (M-IIIb), (M-IIIc), (M-IIId), (M-IIIe), or (M-IIIf):
M-IIIa
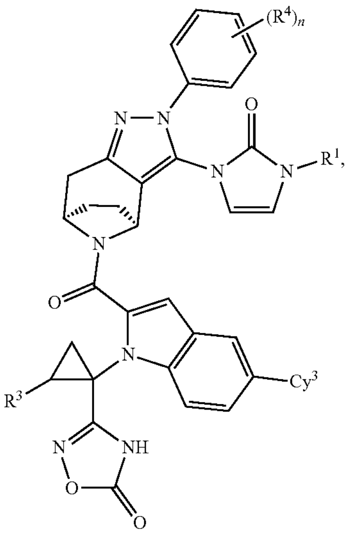
M-IIIb
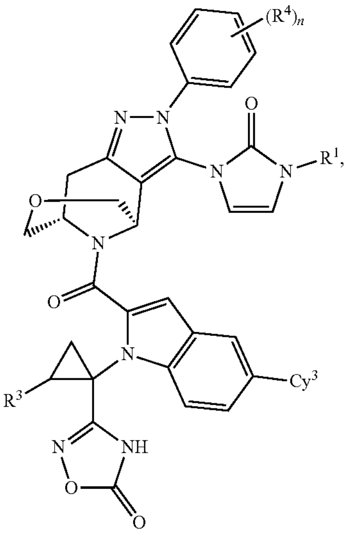
M-IIIc
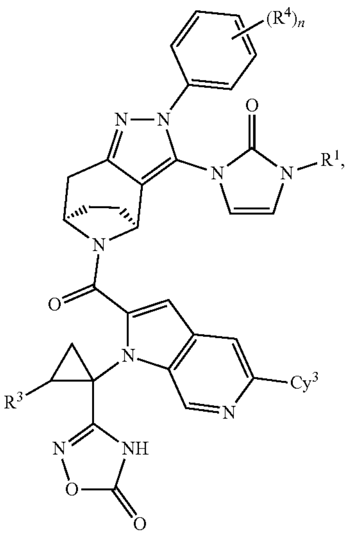

-continued
M-IIId
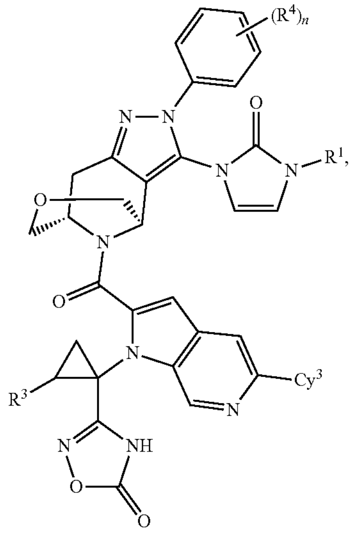
M-IIIe
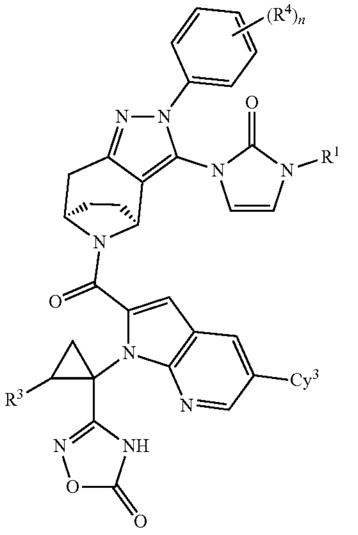
or
M-IIIf
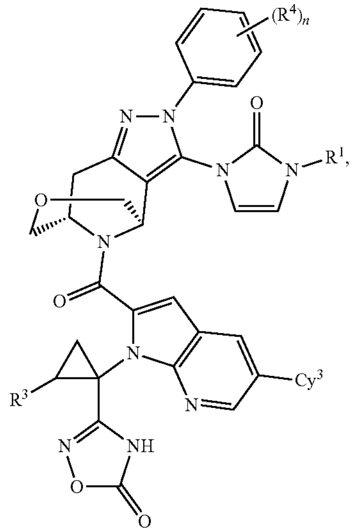
or a stereoisomer or a pharmaceutically acceptable salt thereof.
In certain embodiments, the compound is according to formula (M-IVa), (M-IVb), (M-IVc), (M-IVd), (M-IVe), or (M-IVf):
M-IVa
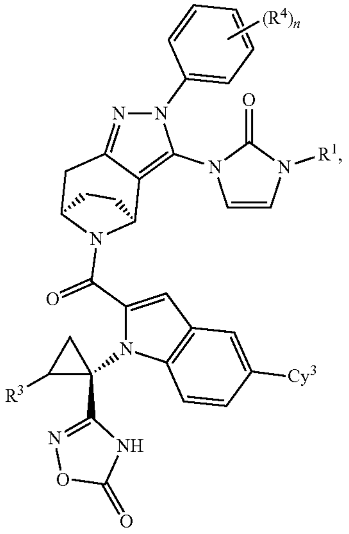
M-IVb
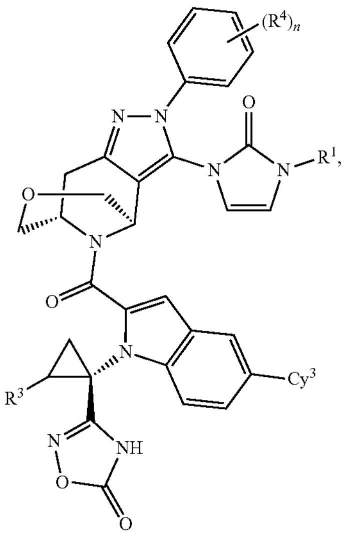

-continued
M-IVc
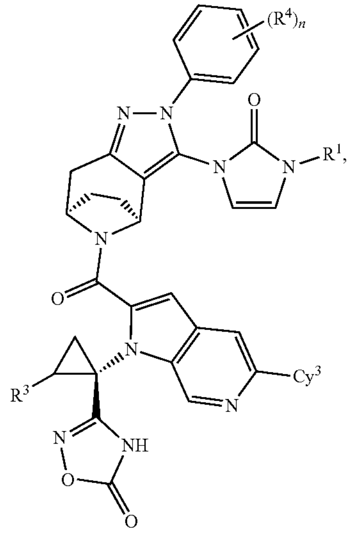
M-IVd
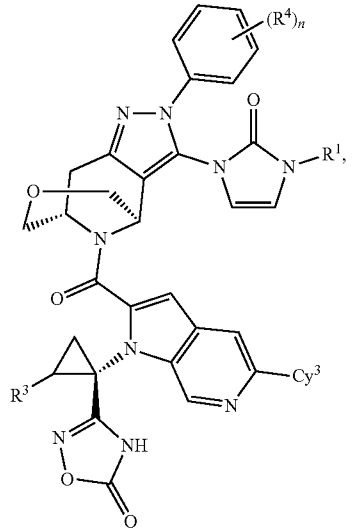
M-IVe
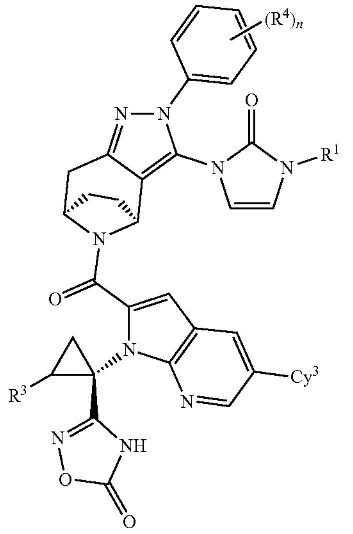
or
-continued
M-IVf
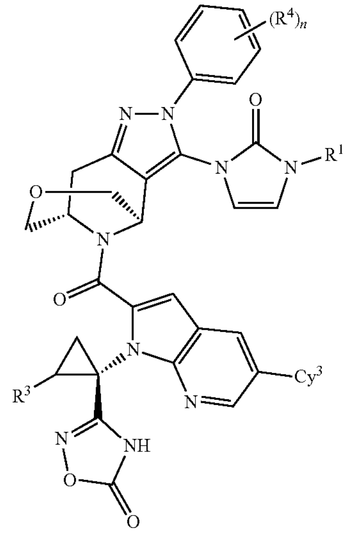
or a stereoisomer or a pharmaceutically acceptable salt thereof.
In certain embodiments, $R^3$ is H.
In certain embodiments, $R^3$ is alkyl.
In certain embodiments, $R^3$ is H, Me, or Et.
In certain embodiments, the compound is according to formula (M-Va), (M-Vb), (M-Vc), (M-Vd), (M-Ve), or (M-Vf):
M-Va
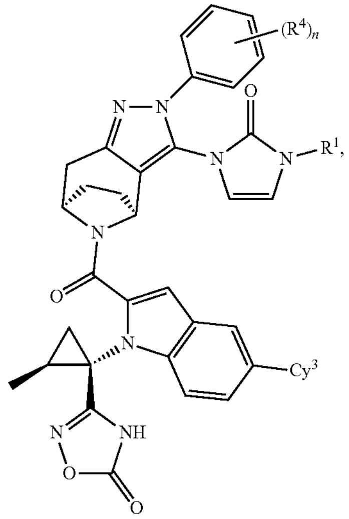

-continued
M-Vb
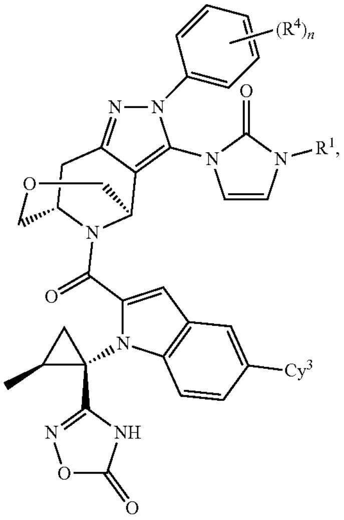
M-Vc
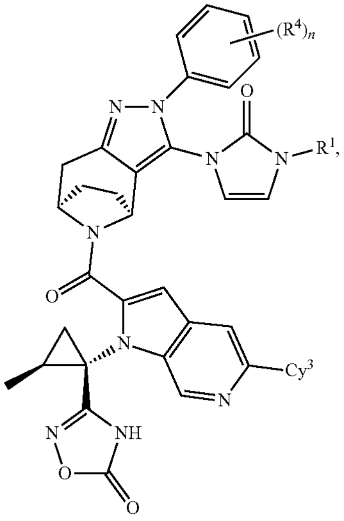
M-Vd
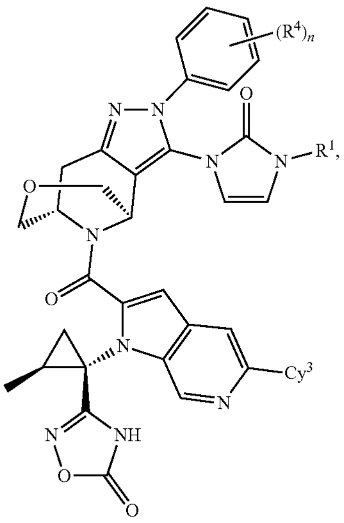
-continued
M-Ve
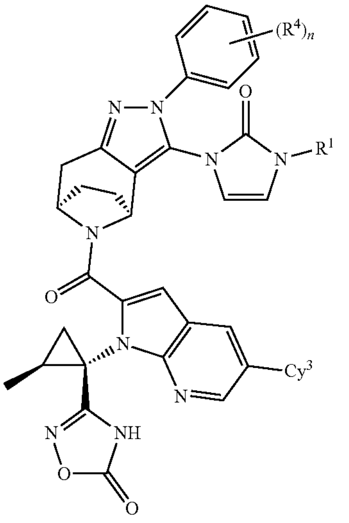
or
M-Vf
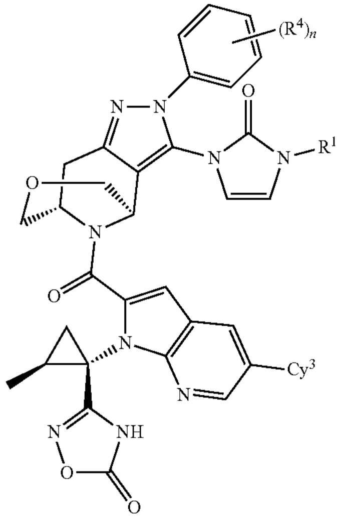
or a stereoisomer or a pharmaceutically acceptable salt thereof.
In certain embodiments, the compound is according to formula (M-Vg), or (M-Vh), M-Vg
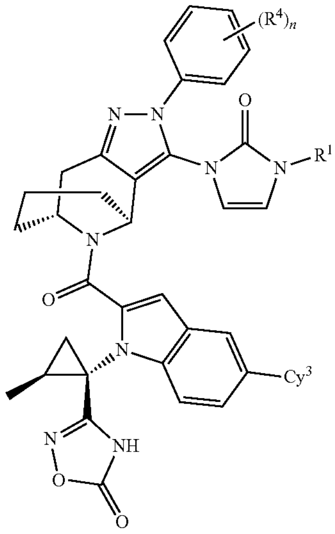
or
M-Vh
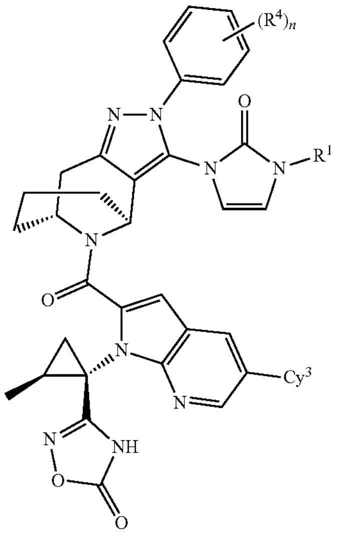
or a stereoisomer or a pharmaceutically acceptable salt thereof.
In certain embodiments, $Cy^3$ is
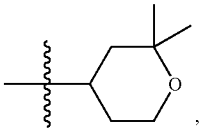
,
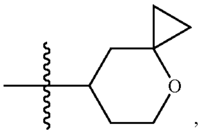
,
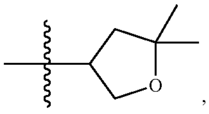
,
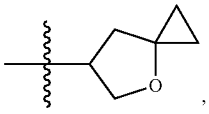
,
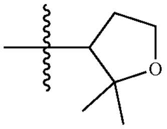
or
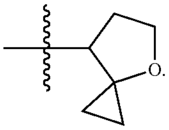
In certain embodiments, $Cy^3$ is
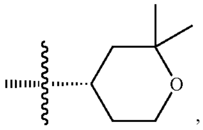
,
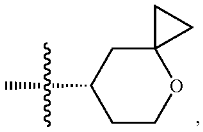
,
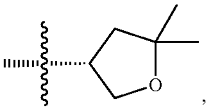
,
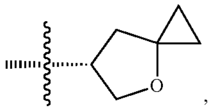
,
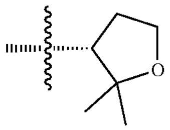
or
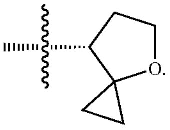
In certain embodiments, the compound is according to formula (M-VIa), (M-VIb), (M-VIc), (M-VId), (M-VIe), or (M-VIf):
M-VIa
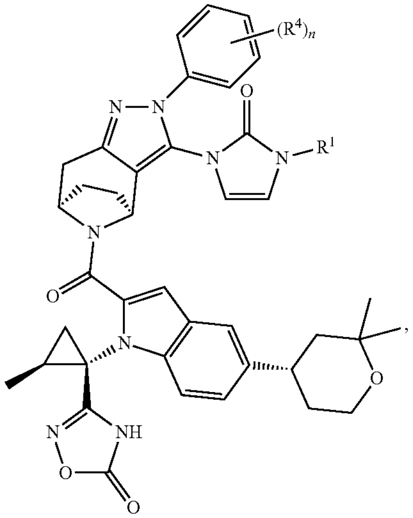
M-VIb
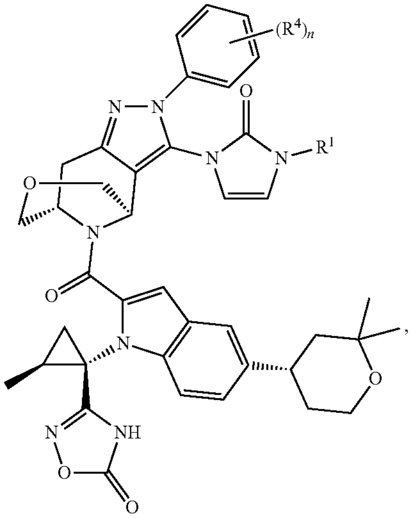

-continued
M-VIc
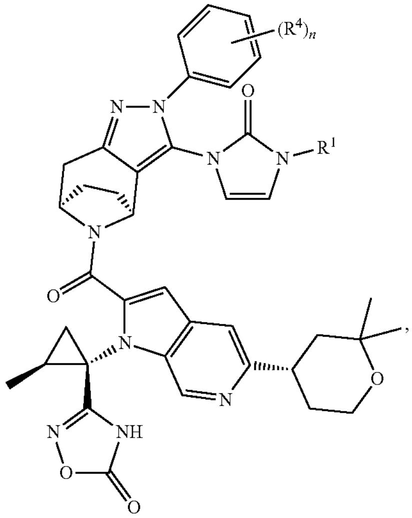
,
M-VId
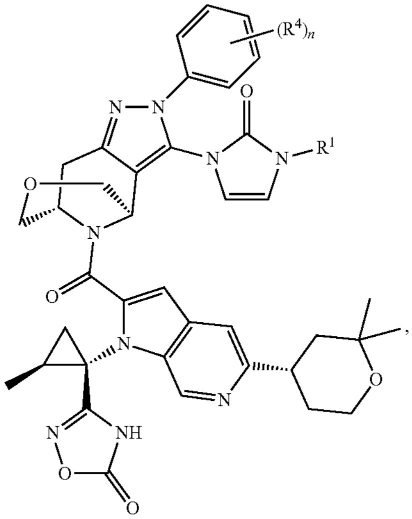
,
M-VIe
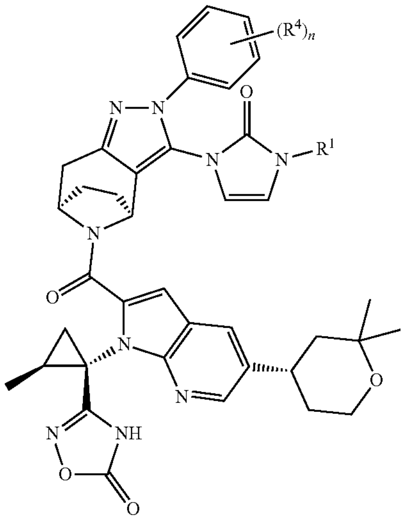
or
-continued
M-VIf
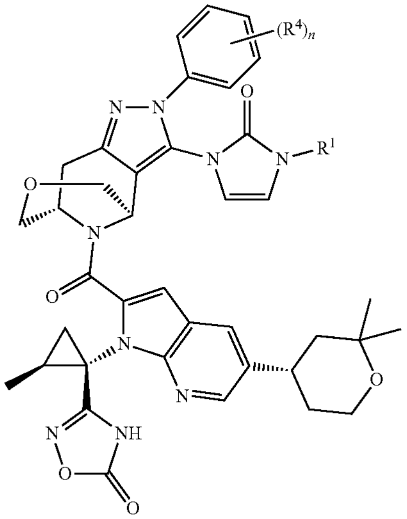
or a stereoisomer or a pharmaceutically acceptable salt thereof.
In certain embodiments, the compound is according to formula (M-VIg), (M-VIh), or (M-VIj):
M-VIg
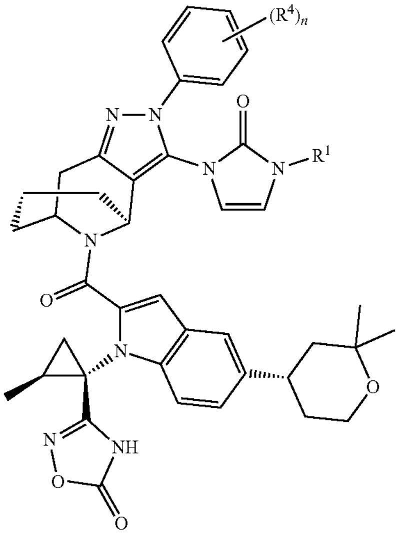
, -continued
M-VIh
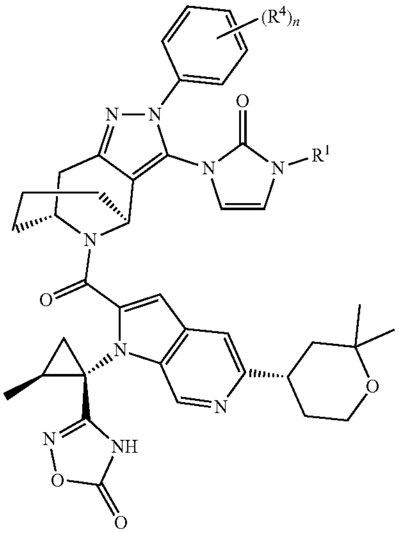
or
M-VIj
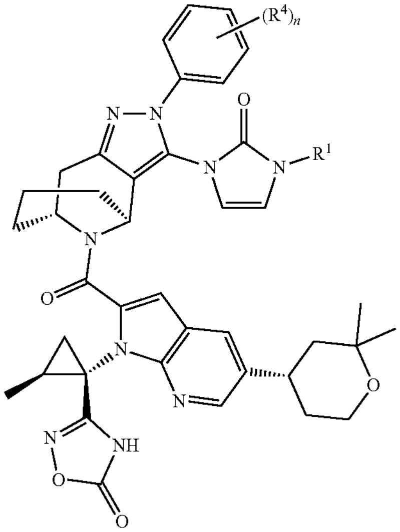
or a stereoisomer or a pharmaceutically acceptable salt thereof.
In certain embodiments, the compound is according to formula (M-VIIa), (M-VIIb), (M-VIIc), (M-VIId), (M-VIIe), or (M-VIIf):
M-VIIa
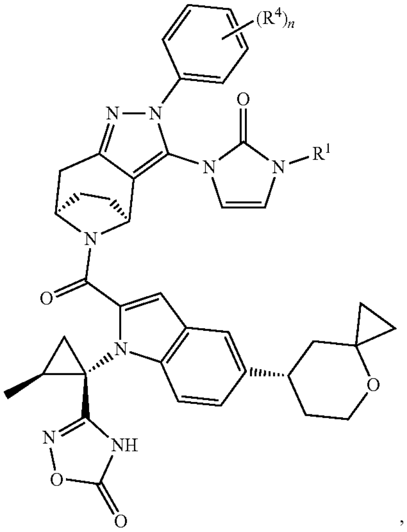
,
M-VIIb
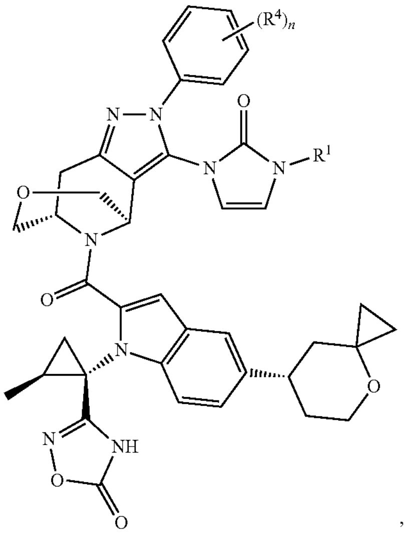
,
M-VIIc
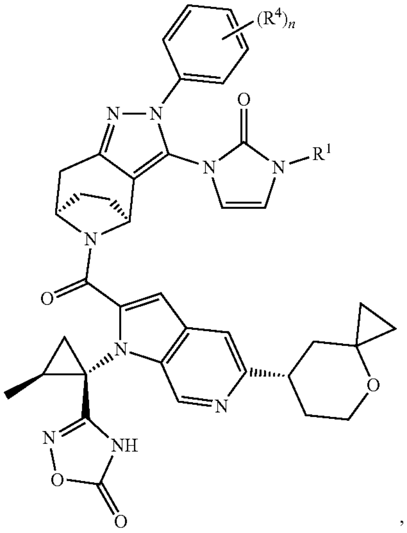
, -continued
M-VIId
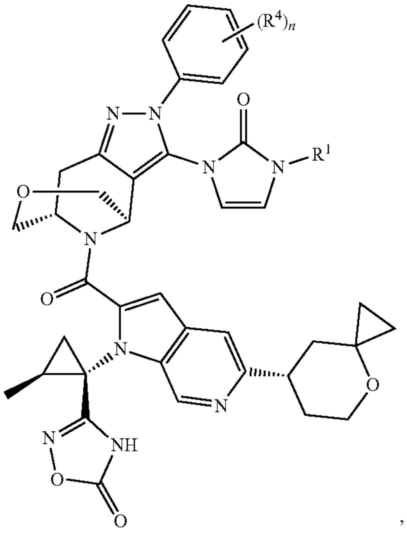
,
M-VIIe
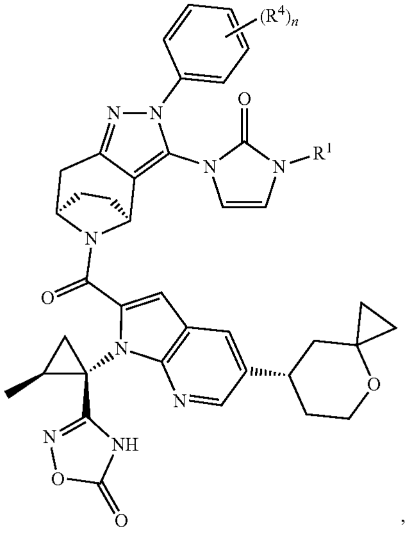
,
M-VIIf
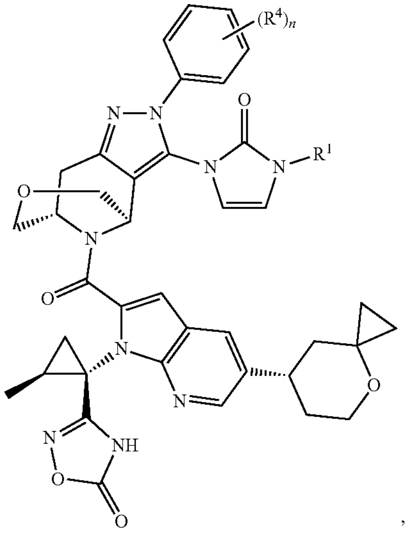
,
or a stereoisomer or a pharmaceutically acceptable salt thereof.
In certain embodiments, the compound is according to formula (M-VIIg), (M-VIIh), or (M-VIIj):
M-VIIg
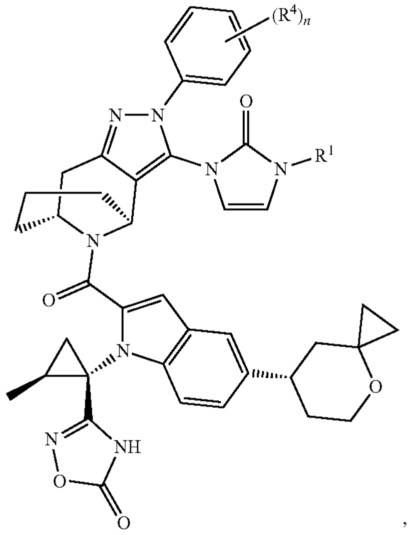
,
M-VIIh
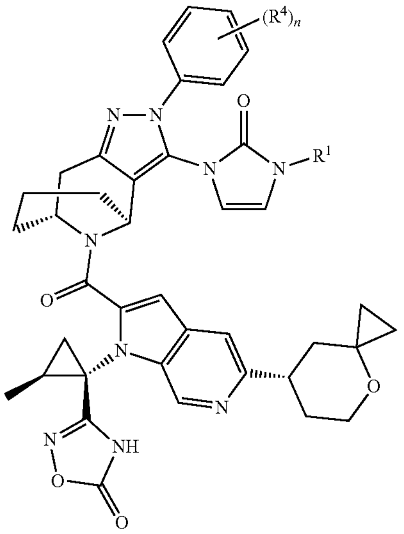
or -continued M-VIIj

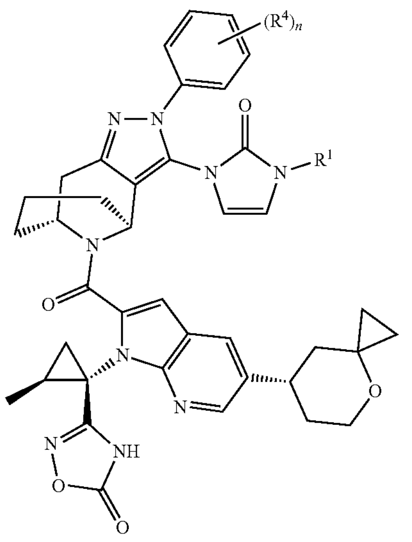

or a stereoisomer or a pharmaceutically acceptable salt thereof.

In certain embodiments, $R^1$ is substituted or unsubstituted aryl or heteroaryl; wherein the substitution is 1-3 groups independently selected from substituted or unsubstituted alkyl, CN, substituted or unsubstituted alkoxy, substituted or unsubstituted amido, —S(O)(=NH)—$R^{1a}$, and halo; and wherein the substitution on alkyl is selected from halo, CN, and alkoxy; and wherein the substitution on each alkoxy is independently selected from halo, CN, and alkyl; and wherein the substitution on amido is selected from alkyl, aryl, and heteroaryl; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1.

In certain embodiments, $R^1$ is substituted or unsubstituted aryl; wherein the substitution is 1-3 groups independently selected from substituted or unsubstituted alkyl, CN, substituted or unsubstituted alkoxy, amido, S(O)(=NH)—$R^{1a}$, and halo; and wherein the substitution on alkyl is selected from halo, CN, and alkoxy; and wherein the substitution on each alkoxy is independently selected from halo, CN, and alkyl; and wherein the substitution on amido is selected from alkyl, aryl, and heteroaryl; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1.

In certain embodiments, $R^1$ is substituted or unsubstituted phenyl; the substitution is selected from 1-3 groups independently selected from substituted or unsubstituted alkyl, CN, substituted or unsubstituted alkoxy, substituted or unsubstituted amido, S(O)(=NH)—$R^{1a}$, —P(O)($R^{1a}$)$_2$, and halo; and wherein the substitution on alkyl is selected from halo, CN, and alkoxy; and wherein the substitution on each alkoxy is independently selected from halo, CN, and alkyl; and wherein the substitution on amido is selected from alkyl, aryl, and heteroaryl; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1.

In certain embodiments, $R^1$ is substituted or unsubstituted phenyl; the substitution is 1-3 groups independently selected from Me, Et, i-Pr, $CF_3$, OMe, $OCF_3$, OMe, OEt, F, Cl, Br, I, —S(O)(=NH)—$R^{1a}$; —($CH_2$)t-N(Me)-C(O)—CH=$CH_2$; —P(O)($R^{1a}$)$_2$, —NHMe, or C(O)$NH_2$; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1; and t is 0, 1, 2, or 3.

In certain embodiments, $R^1$ is substituted or unsubstituted heteroaryl; the substitution is 1-3 groups independently selected from substituted or unsubstituted alkyl, CN, substituted or unsubstituted alkoxy, amido, S(O)(=NH)—$R^{1a}$, and halo; and wherein the substitution on alkyl is selected from halo, CN, and alkoxy; and wherein the substitution on each alkoxy is independently selected from halo, CN, and alkyl; and wherein the substitution on amido is selected from alkyl, aryl, and heteroaryl; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1.

In certain embodiments, $R^1$ is substituted or unsubstituted pyridyl, pyrimidinyl, quinolinyl, isoquinolinyl, indolyl, or indazolyl; the substitution is 1-3 groups independently selected from substituted or unsubstituted alkyl, CN, substituted or unsubstituted alkoxy, substituted or unsubstituted amido, —S(O)(=NH)—$R^{1a}$, and halo; and wherein the substitution on alkyl is selected from halo, CN, and alkoxy; and wherein the substitution on each alkoxy is independently selected from halo, CN, and alkyl; and wherein the substitution on amido is selected from alkyl, aryl, and heteroaryl; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1.

In certain embodiments, $R^1$ is substituted or unsubstituted indazolyl; the substitution 1-3 groups independently selected from Me, Et, i-Pr, $CF_3$, OMe, $OCF_3$, OMe, OEt, F, Cl, Br, I, —S(O)(=NH)—$R^{1a}$; —($CH_2$)t-N(Me)-C(O)—CH=$CH_2$; or C(O)$NH_2$; and $R^{1a}$ is substituted or unsubstituted alkyl, substituted or unsubstituted cycloalkyl, substituted or unsubstituted aryl, or substituted or unsubstituted heteroaryl; and the substitution on each of alkyl, cycloalkyl, aryl, and heteroaryl are as in claim 1; and t is 0, 1, 2, or 3.

In certain embodiments, $R^1$ is substituted or unsubstituted

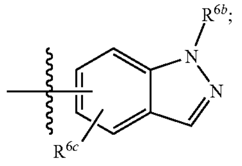

the substitution is 1-3 groups independently selected from Me, Et, i-Pr, $CF_3$, OMe, $OCF_3$, OMe, OEt, F, Cl, Br, I, or C(O)$NH_2$; and wherein $R^{6b}$ is H, substituted or unsubstituted alkyl, or substituted or unsubstituted cycloalkyl; and $R^{6c}$ is substituted or unsubstituted alkyl, or halo; and wherein the substitution on alkyl is selected from halo, CN, and alkoxy; and wherein the substitution on each alkoxy is independently selected from halo, CN, and alkyl.

In certain embodiments, $R^1$ is substituted or unsubstituted

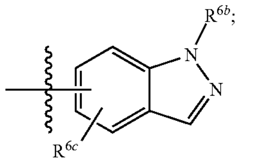

and the substitution is 1-3 groups independently selected from Me, Et, i-Pr, $CF_3$, OMe, $OCF_3$, OMe, OEt, F, Cl, Br, I, or $C(O)NH_2$; wherein $R^{6b}$ is H, Me, cyclopropyl, $—CH_2CH_2\text{-}Cy^4$; and $R^{6c}$ is Me, F, or Cl; and $Cy^4$ is heterocycloalkyl.

In certain embodiments, $R^1$ is substituted or unsubstituted

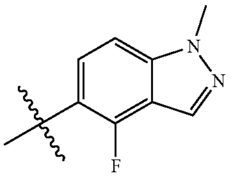

or

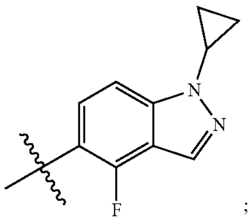

;

the substitution is 1-3 groups independently selected from Me, Et, i-Pr, $CF_3$, OMe, $OCF_3$, OMe, OEt, F, Cl, Br, I, or $C(O)NH_2$.

In certain embodiments, $R^1$ is

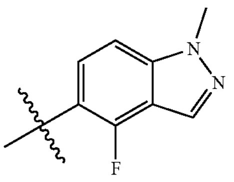

or

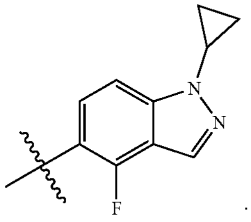

.

In certain embodiments, n is 1, 2, or 3; and each $R^4$ is independently H, halo, CN, substituted or unsubstituted alkyl, substituted or unsubstituted alkoxy, alkylsulfonyl, arylsulfonyl, alkylsulfinyl, or arylsulfinyl; and wherein the substitution on alkyl is selected from halo, CN, and alkoxy; and wherein the substitution on each alkoxy is independently selected from halo, CN, and alkyl.

In certain embodiments, n is 1, 2, or 3; and each $R^4$ is independently halo, CN, substituted or unsubstituted alkyl, and substituted or unsubstituted cycloalkyl; and wherein the substitution on alkyl is selected from halo, CN, and alkoxy; and wherein the substitution on cycloalkyl is selected from halo, CN, and alkyl.

In certain embodiments, n is 1, 2, or 3; and each $R^4$ is independently F, Cl, CN, Me, Et, i-Pr, cyclopropyl, or $CF_3$.

In certain embodiments,

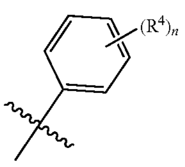

is

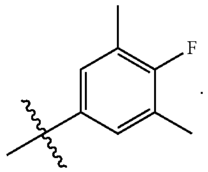

.

In certain embodiments, the compound is according to formula (M-VIIIa), (M-VIIIb), (M-VIIIc), (M-VIIId), (M-VIIIe), or (M-VIIIf):

M-VIIIa

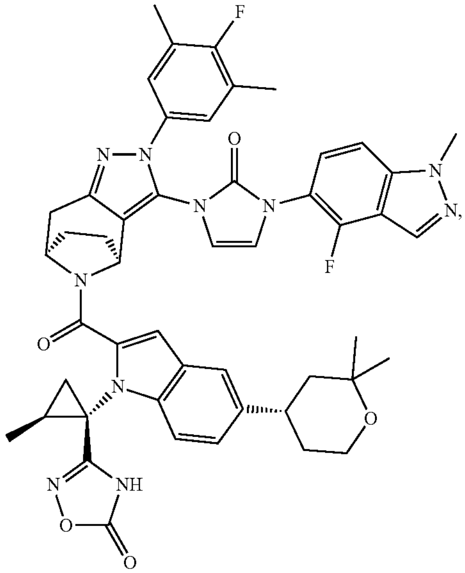

M-VIIIb

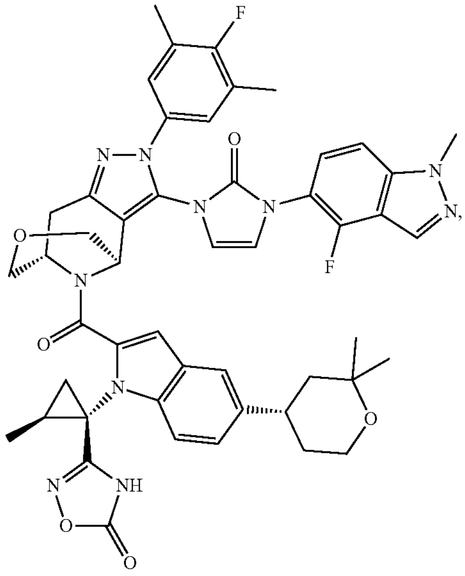

-continued
M-VIIIc
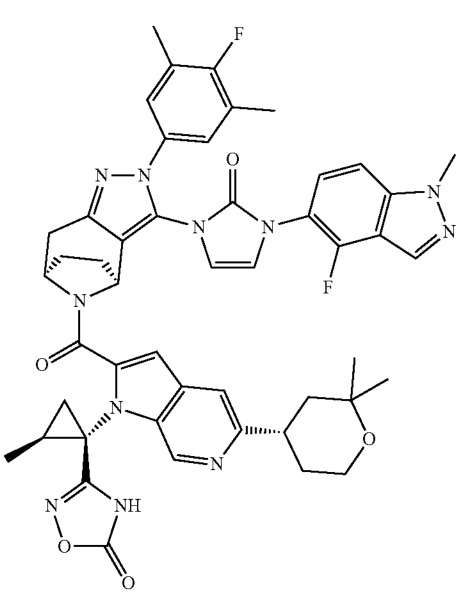
or
M-VIIId
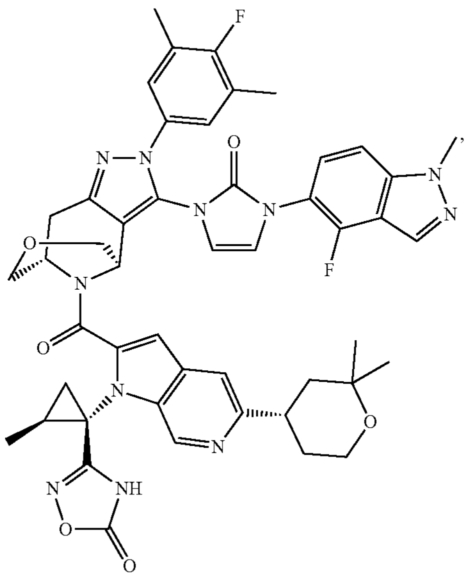
-continued
M-VIIIe
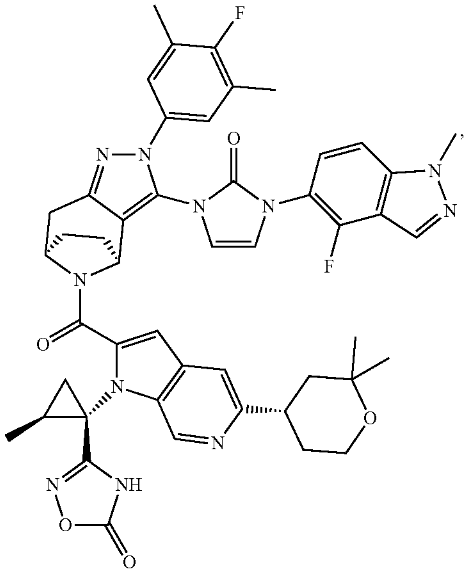
M-VIIIf
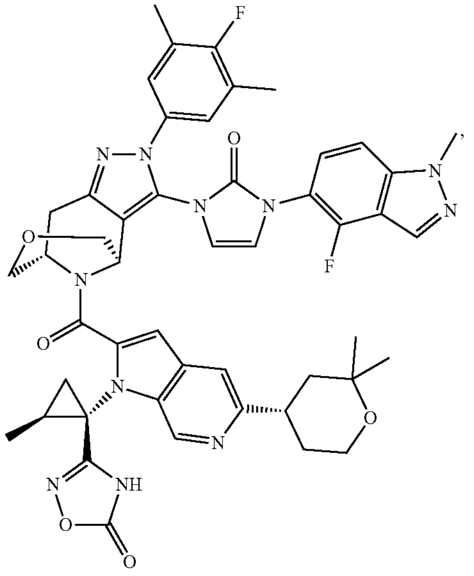
a pharmaceutically acceptable salt thereof.
In certain embodiments, the compound is according to formula (M-VIIIg), (M-VIIIh), or (M-VIIIj):

M-VIIIg
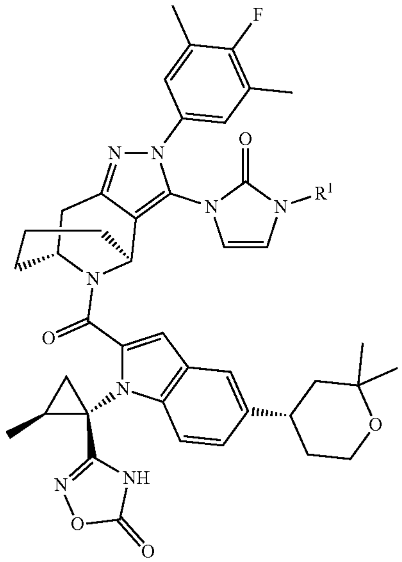
,
-continued
M-VIIIj
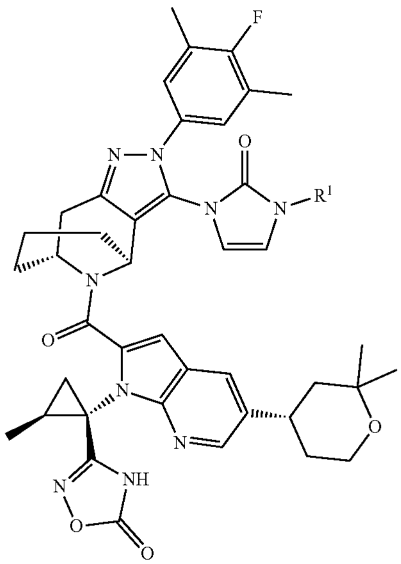
,
or a stereoisomer or a pharmaceutically acceptable salt thereof.
In certain embodiments, the compound is according to formula (M-VIIIg'), (M-VIIIh'), or (M-VIIIj'):
M-VIIIh
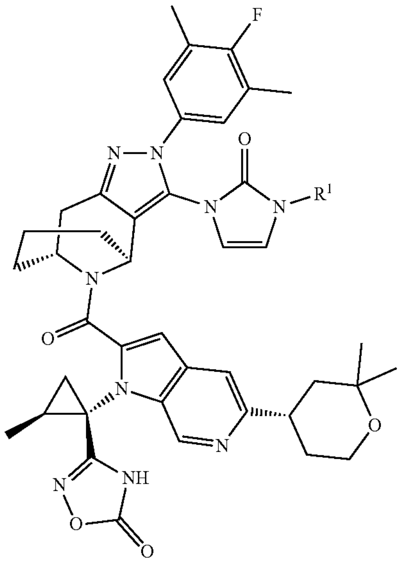
or
M-VIIIg′
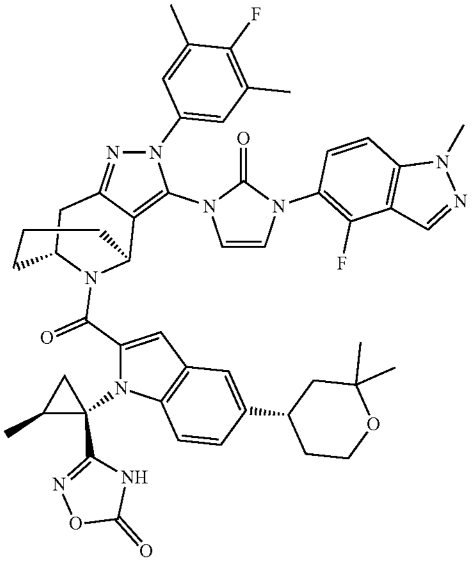
, -continued
M-VIIIh'
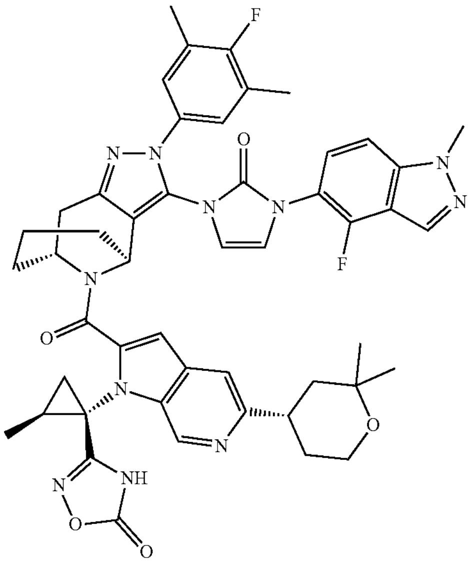
or
M-VIIIj'
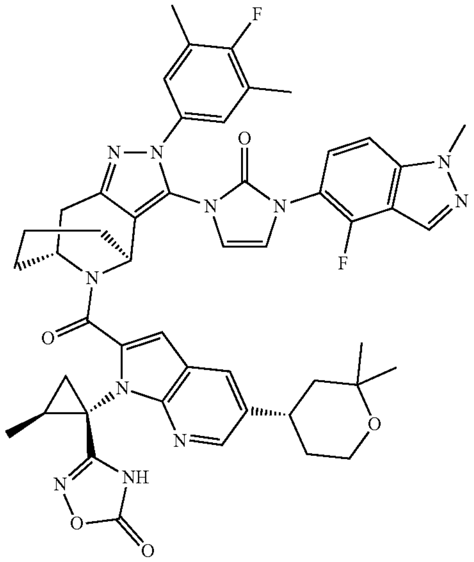
,
or a stereoisomer or a pharmaceutically acceptable salt thereof.
In certain embodiments, the compound is according to formula (M-IXa), (M-IXb), (M-IXc), (M-IXd), (M-IXIe), or (M-IXf):
M-IXa
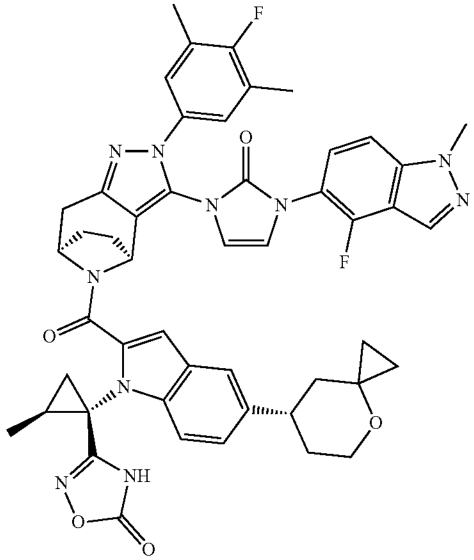
,
M-IXb
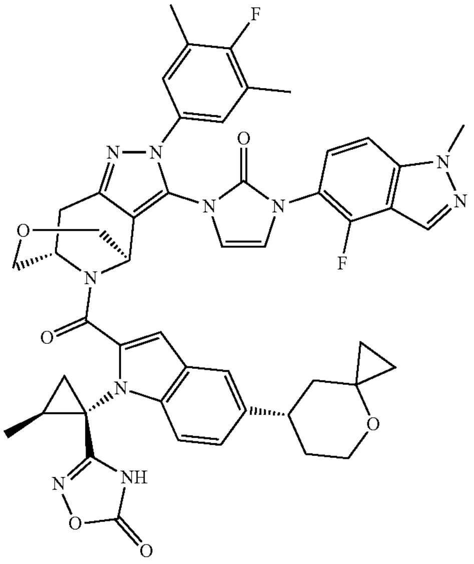
, -continued
M-IXc
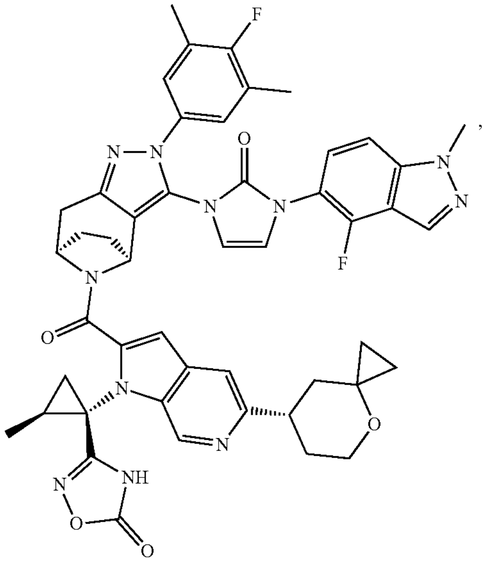
M-IXd
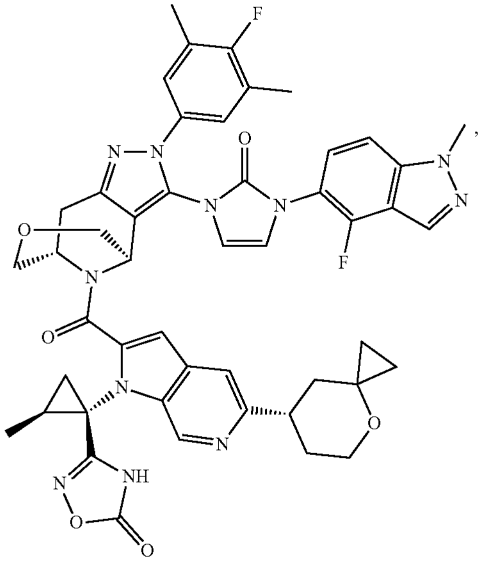
-continued
M-IXe
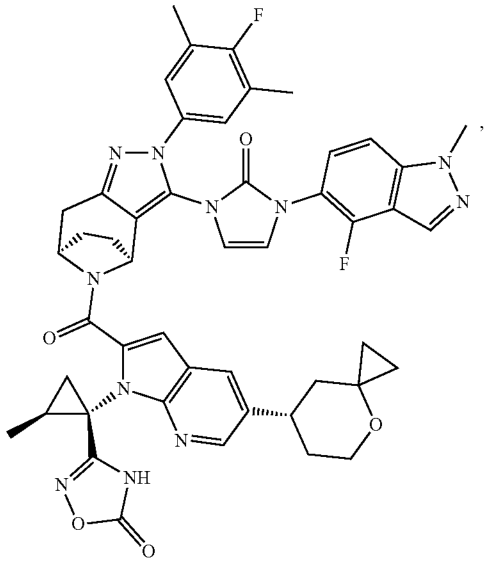
M-IXf
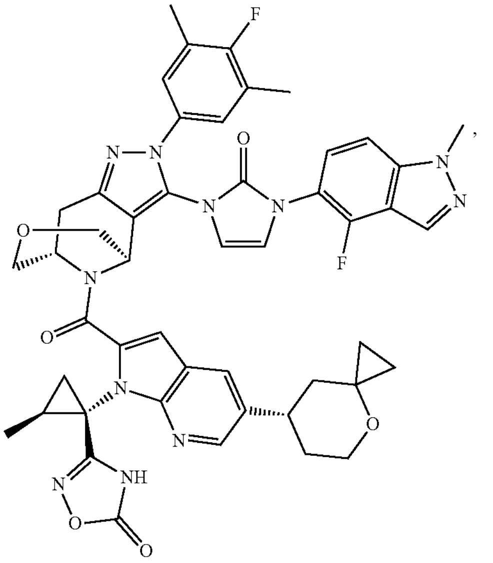
a pharmaceutically acceptable salt thereof.
In certain embodiments, the compound is according to formula (M-IXg), (M-IXh), or (M-IXj):

M-IXg
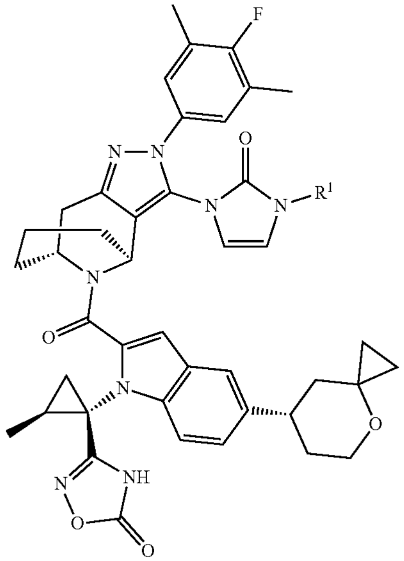
,
M-IXh
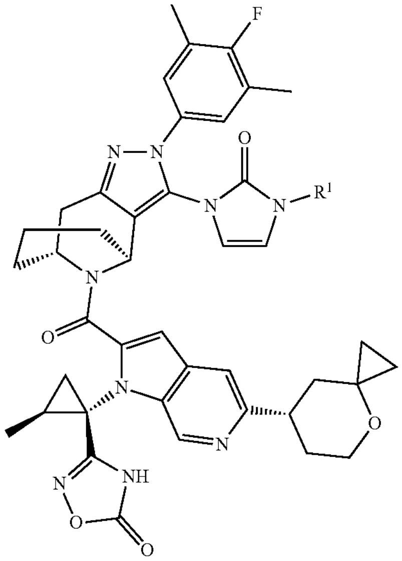
or
M-IXj
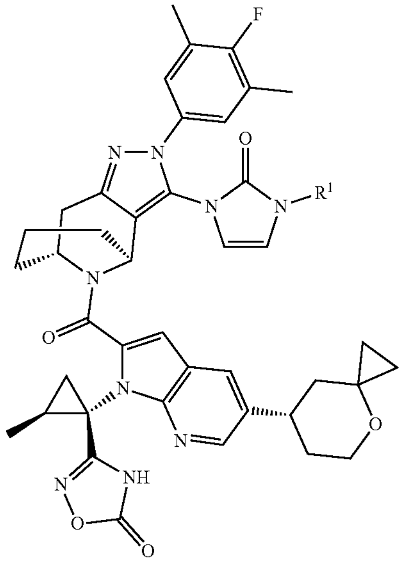
,
or a stereoisomer or a pharmaceutically acceptable salt thereof.
In certain embodiments, the compound is according to formula (M-IXg'), (M-IXh'), or (M-IXj'):
M-IXg'
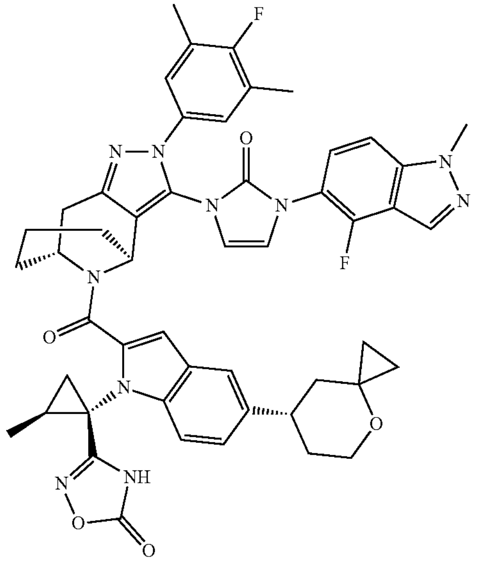
,
M-IXh'
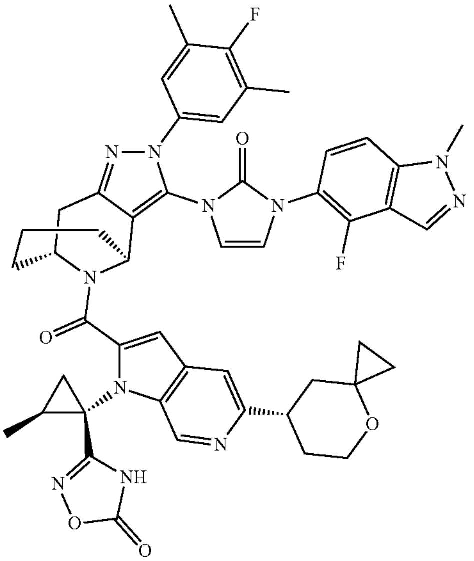
or -continued M-IXj'

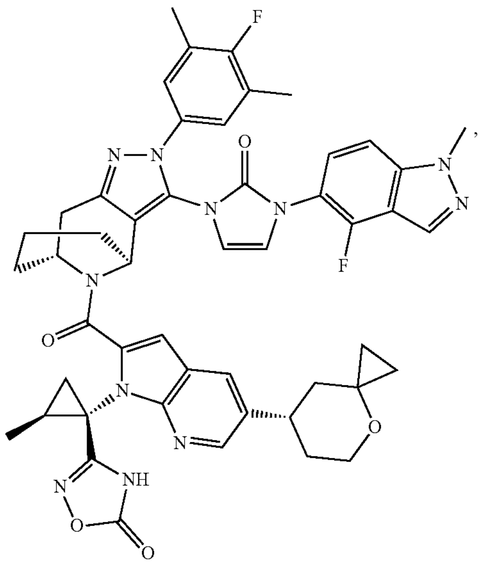

or a stereoisomer or a pharmaceutically acceptable salt thereof.

In certain embodiments, the compound is any one of compounds listed in Table 1. Throughout, chemical names are provided from standard chemistry software packages (Dotmatics, ChemDraw). Table 1 below includes Dotmatics names while the Examples include ChemDraw names. Structures are also provided for many compounds. Those of skill will recognize that minor discrepancies in names can accurately apply to the same structure. Where necessary and appropriate, the depicted chemical structures are preferred.

In certain embodiments, the compound is any one of compounds listed below:

| ID | Compound Name |
|---|---|
| 1 | 3-[(1S,2S)-1-[5-[(4S)-2,2-dimethyltetrahydropyran-4-yl]-2-[(4S)-2-(4-fluoro-3,5-dimethyl-phenyl)-3-[4-(4-fluoro-1-methyl-indazol-5-yl)triazol-1-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 5 | 3-[(1S,2S)-1-[5-[(4S)-2,2-dimethyltetrahydropyran-4-yl]-2-[(4S)-2-(4-fluoro-3,5-dimethyl-phenyl)-3-[5-(4-fluoro-1-methyl-indazol-5-yl)-1,3,4-oxadiazol-2-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 8 | 3-[(1S,2S)-1-[5-[(4S)-2,2-dimethyltetrahydropyran-4-yl]-2-[(4S)-2-(4-fluoro-3,5-dimethyl-phenyl)-4-methyl-3-[1-(1-methylindazol-5-yl)triazol-4-yl]-6,7-dihydro-4H-pyrazolo[4,3-c]pyridine-5-carbonyl]indol-1-yl]-2-methyl-cyclopropyl]-4H-1,2,4-oxadiazol-5-one |
| 9 | 3-[(1S,2S)-1-[5-[(4S)-2,2-dimethyltetrahydropyran-4-yl]-2-[(4S)-2-(4-fluoro-3,5-dimethyl-phenyl)-3-[5-(4-fluoro-1-methyl-indazol-5-yl)-1,3,4-thiadiazol-2-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 11 | 3-[(1S,2S)-1-[5-[(4S)-2,2-dimethyltetrahydropyran-4-yl]-2-[(4S)-2-(4-fluoro-3,5-dimethyl-phenyl)-3-[2-(4-fluoro-1-methyl-indazol-5-yl)-3-methyl-imidazol-4-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 12 | 3-[(1S,2S)-1-[5-[(4S)-2,2-dimethyltetrahydropyran-4-yl]-2-[(4S)-2-(4-fluoro-3,5-dimethyl-phenyl)-3-[1-(4-fluoro-1-methyl-indazol-5-yl)-2-methyl-imidazol-4-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 13 | 3-[(1S,2S)-1-[5-[(4S)-2,2-dimethyltetrahydropyran-4-yl]-2-[(4S)-2-(4-fluoro-3,5-dimethyl-phenyl)-3-[1-(4-fluoro-1-methyl-indazol-5-yl)triazol-4-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 14 | 3-[(1S,2S)-1-[5-[(4S)-2,2-dimethyltetrahydropyran-4-yl]-2-[(4S)-2-(4-fluoro-3,5-dimethyl-phenyl)-4-methyl-3-[5-methyl-4-(1-methylindazol-5-yl)imidazol-1-yl]-6,7-dihydro-4H-pyrazolo[4,3-c]pyridine-5-carbonyl]indol-1-yl]-2-methyl-cyclopropyl]-4H-1,2,4-oxadiazol-5-one |
| 15 | 3-[(1S,2S)-1-[5-[(4S)-2,2-dimethyltetrahydropyran-4-yl]-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 16 | 3-[(1S,2S)-1-[5-[(4S)-2,2-dimethyltetrahydropyran-4-yl]-2-[(4S)-2-(4-fluoro-3,5-dimethyl-phenyl)-3-[4-(4-fluoro-1-methyl-indazol-5-yl)-5-methyl-oxazol-2-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 17 | 3-[1-[5-[(4S)-2,2-dimethyltetrahydropyran-4-yl]-2-[(4S)-2-(4-fluoro-3,5-dimethyl-phenyl)-4-methyl-3-[5-methyl-4-(1-methylindazol-5-yl)imidazol-1-yl]-6,7-dihydro-4H-pyrazolo[4,3-c]pyridine-5-carbonyl]indol-1-yl]cyclopropyl]-4H-1,2,4-oxadiazol-5-one |
| 18 | 3-[(1S,2S)-1-[5-[(4S)-2,2-dimethyltetrahydropyran-4-yl]-2-[(4S)-2-(4-fluoro-3,5-dimethyl-phenyl)-3-[5-(4-fluoro-1-methyl-indazol-5-yl)-4-methyl-oxazol-2-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |

-continued

| ID | Compound Name |
|---|---|
| 20 | 3-[(1S,2S)-1-[5-[(4S)-2,2-dimethyltetrahydropyran-4-yl]-2-[(4S)-2-(4-fluoro-3,5-dimethyl-phenyl)-3-[4-(4-fluoro-1-methyl-indazol-5-yl)-5-methyl-imidazol-1-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 21 | 3-[(1S,2S)-1-[5-[(4S)-2,2-dimethyltetrahydropyran-4-yl]-2-[(4S)-2-(4-fluoro-3,5-dimethyl-phenyl)-3-[4-(4-fluoro-1-methyl-indazol-5-yl)-1-methyl-imidazol-2-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 22 | 3-[1-[5-(2,2-dimethylmorpholin-4-yl)-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indol-1-yl]cyclopropyl]-4H-1,2,4-oxadiazol-5-one |
| 23 | 3-[(4S)-5-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-2-(4-fluoro-3,5-dimethyl-phenyl)-4-methyl-6,7-dihydro-4H-pyrazolo[4,3-c]pyridin-3-yl]-1-(4-fluoro-1-methyl-indazol-5-yl)imidazolidine-2,4-dione |
| 24 | 3-[(1S,2S)-1-[5-[(4S)-2,2-dimethyltetrahydropyran-4-yl]-2-[(4S)-2-(4-fluoro-3,5-dimethyl-phenyl)-3-[4-(4-fluoro-1-methyl-indazol-5-yl)-5-methyl-1H-imidazol-2-yl]-4-methyl-6,7-dihydro-4H-pyrazolo[4,3-c]pyridine-5-carbonyl]indol-1-yl]-2-methyl-cyclopropyl]-4H-1,2,4-oxadiazol-5-one |
| 26 | 3-[1-[7-[(4S)-2,2-dimethyltetrahydropyran-4-yl]-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indolizin-3-yl]cyclopropyl]-4H-1,2,4-oxadiazol-5-one |
| 27 | 3-[1-[2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]-5-morpholino-indol-1-yl]cyclopropyl]-4H-1,2,4-oxadiazol-5-one |
| 28 | 1-[(4S)-5-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-2-(4-fluoro-3,5-dimethyl-phenyl)-4-methyl-6,7-dihydro-4H-pyrazolo[4,3-c]pyridin-3-yl]-4-(4-fluoro-1-methyl-indazol-5-yl)piperazine-2,3-dione |
| 30 | 3-[1-[5-[(4S)-2,2-dimethyltetrahydropyran-4-yl]-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indol-1-yl]cyclopropyl]-4H-1,2,4-oxadiazol-5-one |
| 31 | 3-[(4S)-5-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-2-(4-fluoro-3,5-dimethyl-phenyl)-4-methyl-6,7-dihydro-4H-pyrazolo[4,3-c]pyridin-3-yl]-1-(4-fluoro-1-methyl-indazol-5-yl)-5-methyl-imidazolidine-2,4-dione |
| 32 | 3-[(1S,2S)-1-[5-[(4S)-2,2-dimethyltetrahydropyran-4-yl]-2-[4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 35 | 3-[(1S,2S)-1-[5-[(4S)-2,2-dimethyltetrahydropyran-4-yl]-2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 36 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 37 | 3-[(4S)-5-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-2-(4-fluoro-3,5-dimethyl-phenyl)-4-methyl-6,7-dihydro-4H-pyrazolo[4,3-c]pyridin-3-yl]-1-(4-fluoro-1-methyl-indazol-5-yl)-5,5-dimethyl-imidazolidine-2,4-dione |
| 105 | 3-[1-[5-(4,4-difluorocyclohexen-1-yl)-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indol-1-yl]cyclopropyl]-4H-1,2,4-oxadiazol-5-one |
| 106 | 3-[1-[5-(4,4-difluorocyclohexyl)-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indol-1-yl]cyclopropyl]-4H-1,2,4-oxadiazol-5-one |
| 107 | 3-[1-[2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]-5-(3-oxa-8-azabicyclo[3.2.1]octan-8-yl)indol-1-yl]cyclopropyl]-4H-1,2,4-oxadiazol-5-one |
| 108 | 3-[1-[5-(1,1-dioxo-1,4-thiazinan-4-yl)-2-[(4S)-2-(4-fluoro-3,5-dimethyl-phenyl)-3-[1-(4-fluoro-1-methyl-indazol-5-yl)-5-methyl-imidazol-4-yl]-4-methyl-6,7-dihydro-4H-pyrazolo[4,3-c]pyridine-5-carbonyl]indol-1-yl]cyclopropyl]-4H-1,2,4-oxadiazol-5-one |
| 109 | 2-fluoro-4-[3-[(4S)-2-(4-fluoro-3,5-dimethyl-phenyl)-4-methyl-5-[2-[1-(5-oxo-4H-1,2,4-oxadiazol-3-yl)cyclopropyl]-7-tetrahydropyran-4-yl-quinoline-3-carbonyl]-6,7-dihydro-4H-pyrazolo[4,3-c]pyridin-3-yl]-2-oxo-imidazol-1-yl]benzamide |
| 113 | 3-[1-[7-[(4S)-2-(4-fluoro-3,5-dimethyl-phenyl)-3-[3-(4-fluoro-1-methyl-indazol-5-yl)-2-oxo-imidazol-1-yl]-4-methyl-6,7-dihydro-4H-pyrazolo[4,3-c]pyridine-5-carbonyl]-3-tetrahydropyran-4-yl-8-quinolyl]cyclopropyl]-4H-1,2,4-oxadiazol-5-one |
| 114 | 3-[1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]cyclopropyl]-4H-1,2,4-oxadiazol-5-one |
| 115 | 3-[5-[(4S)-2,2-dimethyltetrahydropyran-4-yl]-2-[(4S)-2-(4-fluoro-3,5-dimethyl-phenyl)-3-[3-(4-fluoro-1-methyl-indazol-5-yl)-2-oxo-imidazol-1-yl]-4-methyl-6,7-dihydro-4H-pyrazolo[4,3-c]pyridine-5-carbonyl]indole-1-carbonyl]-4H-1,2,4-oxadiazol-5-one |

-continued

| ID | Compound Name |
|---|---|
| 116 | 3-[(1S,2S)-1-[5-[(4S)-2,2-dimethyltetrahydropyran-4-yl]-2-[4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 117 | 4-[3-[(1S,8R)-11-[5-[(4S)-2,2-dimethyltetrahydropyran-4-yl]-1-[1-(5-oxo-4H-1,2,4-oxadiazol-3-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-2-oxo-imidazol-1-yl]-2-fluoro-benzamide |
| 118 | 1-[(1S,8R)-11-[5-[(4S)-2,2-dimethyltetrahydropyran-4-yl]-1-[1-(1H-tetrazol-5-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-3-(4-fluoro-1-methyl-indazol-5-yl)imidazol-2-one |
| 119 | 3-[1-[2-[(1S,8R)-3-(3-cinnolin-6-yl-2-oxo-imidazol-1-yl)-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]cyclopropyl]-4H-1,2,4-oxadiazol-5-one |
| 120 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 121 | 3-[(1S,2S)-1-[5-[(4S)-2,2-dimethyltetrahydropyran-4-yl]-2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 122 | 3-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indole-1-carbonyl]-4H-1,2,4-oxadiazol-5-one |
| 123 | 3-[1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-benzimidazol-5-yl)-2-oxo-imidazol-1-yl]-4,5,11-triazatricyclo[6.2.1.02,6]undeca-2,5-diene-11-carbonyl]indol-1-yl]cyclopropyl]-4H-1,2,4-oxadiazol-5-one |
| 124 | 3-[1-[5-[(4S)-2,2-dimethyltetrahydropyran-4-yl]-2-[(1S,8R)-4-(4-fluoro-3,5-dimethyl-phenyl)-3-(2-oxo-3-phthalazin-6-yl-imidazol-1-yl)-4,5,11-triazatricyclo[6.2.1.02,6]undeca-2,5-diene-11-carbonyl]indol-1-yl]cyclopropyl]-4H-1,2,4-oxadiazol-5-one |
| 125 | 3-[3-[(1S,8R)-11-[5-[(4S)-2,2-dimethyltetrahydropyran-4-yl]-1-[1-(5-oxo-4H-1,2,4-oxadiazol-3-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-2-oxo-imidazol-1-yl]-2-fluoro-benzamide |
| 126 | 3-[1-[7-(2,2-dimethyltetrahydropyran-4-yl)-3-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-2-quinolyl]cyclopropyl]-4H-1,2,4-oxadiazol-5-one |
| 127 | 3-[(1S,2S)-1-[5-[(4S)-2,2-dimethyltetrahydropyran-4-yl]-2-[(1S,8R)-4-(4-fluoro-3,5-dimethyl-phenyl)-3-(2-oxo-3-phthalazin-6-yl-imidazol-1-yl)-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 128 | 1-[(1S,8R)-11-[5-[(4S)-2,2-dimethyltetrahydropyran-4-yl]-1-[(1S,2S)-2-methyl-1-(1H-tetrazol-5-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-3-(4-fluoro-1-methyl-indazol-5-yl)imidazol-2-one |
| 129 | 3-[1-[2-(2,2-dimethyltetrahydropyran-4-yl)-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-1,3-benzothiazol-6-yl]cyclopropyl]-4H-1,2,4-oxadiazol-5-one |
| 130 | 3-[1-[5-(2,2-dimethyltetrahydropyran-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]benzimidazol-1-yl]cyclopropyl]-4H-1,2,4-oxadiazol-5-one |
| 131 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-[4-fluoro-2-(2-morpholinoethyl)indazol-5-yl]-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 132 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-[4-fluoro-1-(2-morpholinoethyl)indazol-5-yl]-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 133 | 3-[1-[2-(2,2-dimethyltetrahydropyran-4-yl)-6-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-1,3-benzothiazol-5-yl]cyclopropyl]-4H-1,2,4-oxadiazol-5-one |
| 134 | 3-[1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]cyclobutyl]-4H-1,2,4-oxadiazol-5-one |
| 135 | 3-[1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-(2-methyl-5-oxa-2-azaspiro[3.5]nonan-8-yl)indol-1-yl]cyclopropyl]-4H-1,2,4-oxadiazol-5-one |
| 136 | 3-[1-[5-(2,5-dioxaspiro[3.5]nonan-8-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]cyclopropyl]-4H-1,2,4-oxadiazol-5-one |
| 137 | trans-(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropanecarbonitrile |

-continued

| ID | Compound Name |
|---|---|
| 138 | cis-(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropanecarboxamide |
| 139 | 3-[(1S,2S)-1-[2-(2,2-dimethyltetrahydropyran-4-yl)-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-d]thiazol-4-yl]-2-methyl-cyclopropyl]-4H-1,2,4-oxadiazol-5-one |
| 140 | 3-[1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-1-methyl-ethyl]-4H-1,2,4-oxadiazol-5-one |
| 201 | cis-(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-N-methylsulfonyl-cyclopropanecarboxamide |
| 202 | 3-[1-[2-(2,2-dimethyltetrahydropyran-4-yl)-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-d]thiazol-4-yl]-2-methyl-cyclopropyl]-4H-1,2,4-oxadiazol-5-one |
| 203 | 3-[(1S,2S)-1-[2-[(1S,8R)-3-[3-[4-diethylphosphoryl-3-(methylamino)phenyl]-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]-2-methyl-cyclopropyl]-4H-1,2,4-oxadiazol-5-one |
| 204 | cis-(1S,2S)-N-cyclopropylsulfonyl-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropanecarboxamide |
| 205 | cis-(1S,2S)-N-(dimethylsulfamoyl)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropanecarboxamide |
| 206 | 3-[(1S,2S)-1-[2-[(4S)-2,2-dimethyltetrahydropyran-4-yl]-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-d]thiazol-4-yl]-2-methyl-cyclopropyl]-4H-1,2,4-oxadiazol-5-one |
| 207 | 3-[(1S,2S)-1-[2-[(4R)-2,2-dimethyltetrahydropyran-4-yl]-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-d]thiazol-4-yl]-2-methyl-cyclopropyl]-4H-1,2,4-oxadiazol-5-one |
| 208 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-tetrahydropyran-4-yl-indol-1-yl]-2-methyl-cyclopropyl]-4H-1,2,4-oxadiazol-5-one |
| 209 | 3-[(1S,2S)-1-[5-(2,2-dimethyltetrahydropyran-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-c]pyridin-1-yl]-2-methyl-cyclopropyl]-4H-1,2,4-oxadiazol-5-one |
| 210 | 3-[(1S,2S)-1-[5-(2,2-dimethyltetrahydropyran-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-b]pyridin-1-yl]-2-methyl-cyclopropyl]-4H-1,2,4-oxadiazol-5-one |
| 211 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-c]pyridin-1-yl]-2-methyl-cyclopropyl]-4H-1,2,4-oxadiazol-5-one |
| 212 | 3-[(1S,2S)-1-[5-[(4R)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-c]pyridin-1-yl]-2-methyl-cyclopropyl]-4H-1,2,4-oxadiazol-5-one |
| 213 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-(4-oxaspiro[2.5]octan-7-yl)indol-1-yl]-2-methyl-cyclopropyl]-4H-1,2,4-oxadiazol-5-one |
| 214 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 215 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 216 | 3-[(1S,2S)-1-[2-[(1S,8R)-3-[3-[4-diethylphosphoryl-3-(methylamino)phenyl]-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-tetrahydropyran-4-yl-indol-1-yl]-2-methyl-cyclopropyl]-4H-1,2,4-oxadiazol-5-one |
| 217 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-b]pyridin-1-yl]-2-methyl-cyclopropyl]-4H-1,2,4-oxadiazol-5-one |
| 218 | 3-[(1S,2S)-1-[5-[(4R)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11- |

-continued

| ID | Compound Name |
|---|---|
| | triazatricyclo[6.2.1.02,6]undeca-2,5-diene-11-carbonyl]pyrrolo[3,2-b]pyridin-1-yl]-2-methyl-cyclopropyl]-4H-1,2,4-oxadiazol-5-one |
| 219 | 3-[(1S,2S)-1-[5-(2-ethyl-3-methyl-4-pyridyl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 220 | 3-[(1S,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]-5-(4-oxaspiro[2.5]octan-7-yl)indol-1-yl]-2-methyl-cyclopropyl]-4H-1,2,4-oxadiazol-5-one |
| 221 | 3-[(1S,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]-5-tetrahydropyran-4-yl-indol-1-yl]-2-methyl-cyclopropyl]-4H-1,2,4-oxadiazol-5-one |
| 222 | 3-[(1S,2S)-1-[2-[(1R,8S)-3-[3-(4-chloro-1-methyl-indazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-[(4S)-2,2-dimethyltetrahydropyran-4-yl]indol-1-yl]-2-methyl-cyclopropyl]-4H-1,2,4-oxadiazol-5-one |
| 223 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-methoxyphenyl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 224 | 3-[(1S,2S)-1-[2-[(1R,8S)-3-[3-(4,7-difluoro-1-methyl-indazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-[(4S)-2,2-dimethyltetrahydropyran-4-yl]indol-1-yl]-2-methyl-cyclopropyl]-4H-1,2,4-oxadiazol-5-one |
| 225 | 3-[(1S,2S)-1-[5-[(4S)-2,2-dimethyltetrahydropyran-4-yl]-2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]pyrrolo[2,3-c]pyridin-1-yl]-2-methyl-cyclopropyl]-4H-1,2,4-oxadiazol-5-one |
| 226 | 3-[(1S,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]-5-[(7S)-4-oxaspiro[2.5]octan-7-yl]indol-1-yl]-2-methyl-cyclopropyl]-4H-1,2,4-oxadiazol-5-one |
| 227 | 3-[(1S,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]-5-[(7R)-4-oxaspiro[2.5]octan-7-yl]indol-1-yl]-2-methyl-cyclopropyl]-4H-1,2,4-oxadiazol-5-one |
| 228 | 3-[(1S,2S)-1-[2-[(1R,8S)-3-[3-(1,4-dimethylindazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-[(4S)-2,2-dimethyltetrahydropyran-4-yl]indol-1-yl]-2-methyl-cyclopropyl]-4H-1,2,4-oxadiazol-5-one |
| 229 | 3-[(1S,2S)-1-[5-(2,2-dimethylmorpholin-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 230 | 3-[(1S,2S)-1-[2-[(1R,8S)-3-[3-(4-chloro-1-methyl-indazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-(4-oxaspiro[2.5]octan-7-yl)indol-1-yl]-2-methyl-cyclopropyl]-4H-1,2,4-oxadiazol-5-one |
| 231 | 3-[(1S,2S)-1-[5-(2,2-dimethyltetrahydropyran-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-4-oxo-pyrrolo[3,2-c]pyridin-1-yl]-2-methyl-cyclopropyl]-4H-1,2,4-oxadiazol-5-one |
| 232 | 3-[(1S,2S)-1-[4-(2,2-dimethyltetrahydropyran-4-yl)oxy-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-c]pyridin-1-yl]-2-methyl-cyclopropyl]-4H-1,2,4-oxadiazol-5-one |
| 233 | 3-[(1S,8R)-11-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-1-(4-fluoro-1-methyl-indazol-5-yl)imidazolidine-2,4-dione |
| 234 | 3-[(1R,8S)-11-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-1-(4-fluoro-1-methyl-indazol-5-yl)imidazolidine-2,4-dione |
| 235 | 3-[(1S,2S)-1-[2-[(1S,8R)-3-[3-(4,7-difluoro-1-methyl-indazol-5-yl)-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]-2-methyl-cyclopropyl]-4H-1,2,4-oxadiazol-5-one |
| 236 | 3-[(1S,2S)-1-[2-[(1S,8R)-3-[3-(4,7-difluoro-1-methyl-indazol-5-yl)-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]pyrrolo[2,3-c]pyridin-1-yl]-2-methyl-cyclopropyl]-4H-1,2,4-oxadiazol-5-one |
| 237 | 3-[(1R,2S)-1-[3-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-7-tetrahydropyran-4-yl-2-quinolyl]-2-methyl-cyclopropyl]-4H-1,2,4-oxadiazol-5-one |

-continued

| ID | Compound Name |
|---|---|
| 238 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-4-oxo-pyrrolo[3,2-c]pyridin-1-yl]-2-methyl-cyclopropyl]-4H-1,2,4-oxadiazol-5-one |
| 239 | 3-[(1S,2S)-1-[5-[(4R)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-4-oxo-pyrrolo[3,2-c]pyridin-1-yl]-2-methyl-cyclopropyl]-4H-1,2,4-oxadiazol-5-one |
| 240 | cis-(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-N,N,2-trimethyl-cyclopropanecarboxamide |
| 241 | N-[[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]methyl]-2-hydroxy-acetamide |
| 242 | 3-[(1S,2S)-1-[2-[(1R,8S)-3-[3-(4,7-difluoro-1-methyl-indazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-(4-oxaspiro[2.5]octan-7-yl)indol-1-yl]-2-methyl-cyclopropyl]-4H-1,2,4-oxadiazol-5-one |
| 243 | N-[[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]methyl]acetamide |
| 244 | cis-(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-N,2-dimethyl-cyclopropanecarboxamide |
| 245 | 3-[(1S,2S)-1-[2-(2,2-dimethyltetrahydropyran-4-yl)-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-d]thiazol-4-yl]-2-methyl-cyclopropyl]-4H-1,2,4-oxadiazol-5-one |
| 246 | cis-(1S,2S)-N-cyclopropyl-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropanecarboxamide |
| 301 | 3-[(1S,2S)-1-[2-(2,2-dimethyltetrahydropyran-4-yl)-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-d]oxazol-4-yl]-2-methyl-cyclopropyl]-4H-1,2,4-oxadiazol-5-one |
| 302 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(1-methylindazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 303 | 3-[(1S,2S)-1-[4-[(4S)-2,2-dimethyltetrahydropyran-4-yl]oxy-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-c]pyridin-1-yl]-2-methyl-cyclopropyl]-4H-1,2,4-oxadiazol-5-one |
| 304 | 3-[(1S,2S)-1-[4-[(4R)-2,2-dimethyltetrahydropyran-4-yl]oxy-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[3,2-c]pyridin-1-yl]-2-methyl-cyclopropyl]-4H-1,2,4-oxadiazol-5-one |
| 305 | 3-[(1S,2S)-1-[2-[(1S,8R)-3-[3-(1,4-dimethylindazol-5-yl)-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]-2-methyl-cyclopropyl]-4H-1,2,4-oxadiazol-5-one |
| 306 | 3-[(1S,2S)-1-[2-[(4S)-2,2-dimethyltetrahydropyran-4-yl]-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-d]thiazol-4-yl]-2-methyl-cyclopropyl]-4H-1,2,4-oxadiazol-5-one |
| 307 | 3-[(1S,2S)-1-[2-[(4R)-2,2-dimethyltetrahydropyran-4-yl]-5-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-d]thiazol-4-yl]-2-methyl-cyclopropyl]-4H-1,2,4-oxadiazol-5-one |
| 308 | 3-[(1S,2S)-1-[2-[(1S,8R)-3-[3-(4-chloro-1-methyl-indazol-5-yl)-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]-2-methyl-cyclopropyl]-4H-1,2,4-oxadiazol-5-one |
| 309 | 3-[(1S,2S)-1-[2-[(1S,8R)-3-[3-[2-(difluoromethyl)-4-fluoro-indazol-5-yl]-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]-2-methyl-cyclopropyl]-4H-1,2,4-oxadiazol-5-one |
| 310 | 3-[(1S,2S)-1-[2-[(1S,8R)-3-[3-[1-(difluoromethyl)-4-fluoro-indazol-5-yl]-2-oxo-imidazol-1-yl]-4-(4-fluoro-3,5-dimethyl-phenyl)-4,5,11-triazatricyclo[6.2.1.02,6]undeca-2,5-diene-11-carbonyl]-5-[(4S)-2,2-dimethyltetrahydropyran-4-yl]indol-1-yl]-2-methyl-cyclopropyl]-4H-1,2,4-oxadiazol-5-one |
| 311 | 3-[(1S,2S)-1-[5-(2,2-dimethyltetrahydropyran-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11- |

-continued

| ID | Compound Name |
|---|---|
| | triazatricyclo[6.2.1.02,6]undeca-2,5-diene-11-carbonyl]pyrrolo[2,3-b]pyridin-1-yl]-2-methyl-cyclopropyl]-4H-1,2,4-oxadiazol-5-one |
| 312 | 3-[(1S,2S)-1-[5-[(4R)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-b]pyridin-1-yl]-2-methyl-cyclopropyl]-4H-1,2,4-oxadiazol-5-one |
| 313 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]pyrrolo[2,3-b]pyridin-1-yl]-2-methyl-cyclopropyl]-4H-1,2,4-oxadiazol-5-one |
| 318 | 3-[(1R,2S)-1-[7-[(4S)-2,2-dimethyltetrahydropyran-4-yl]-3-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-2-quinolyl]-2-methyl-cyclopropyl]-4H-1,2,4-oxadiazol-5-one |
| 319 | 3-[(1R,2S)-1-[7-[(4R)-2,2-dimethyltetrahydropyran-4-yl]-3-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-2-quinolyl]-2-methyl-cyclopropyl]-4H-1,2,4-oxadiazol-5-one |
| 323 | 3-[(1S,2S)-1-[2-[(1S,8R)-4-(4-fluoro-3,5-dimethyl-phenyl)-3-[3-(1-methylindazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 324 | 3-[(1S,2S)-1-[5-(2,2-dimethyltetrahydropyran-4-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-6-oxo-pyrrolo[3,2-c]pyridin-1-yl]-2-methyl-cyclopropyl]-4H-1,2,4-oxadiazol-5-one |
| 325 | N-[[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-1-[(1S,2S)-2-methyl-1-(5-oxo-4H-1,2,4-oxadiazol-3-yl)cyclopropyl]indol-5-yl]methyl]-N-methyl-but-2-ynamide |
| 406 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1H-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 410 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(5-fluorophthalazin-6-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 411 | 3-[(1S,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 412 | 4-[3-[(1S,8R)-11-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,11-triazatricyclo[6.2.1.02,6]undeca-2,5-dien-3-yl]-2-oxo-imidazol-1-yl]-2-fluoro-benzamide |
| 413 | 3-[(1S,2S)-1-[5-(2,2-dimethyltetrahydrofuran-3-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 414 | 3-[(1S,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 415 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-(5-oxaspiro[3.5]nonan-8-yl)indol-1-yl]-2-methyl-cyclopropyl]-4H-1,2,4-oxadiazol-5-one |
| 416 | 3-[(1S,2S)-1-[5-[(4S)-2,2-dimethyltetrahydropyran-4-yl]-2-[2-(4-fluoro-3,5-dimethyl-phenyl)-3-[3-(4-fluoro-1-methyl-indazol-5-yl)-2-oxo-imidazol-1-yl]-4,6,7,8-tetrahydropyrazolo[4,3-c]azepine-5-carbonyl]indol-1-yl]-2-methyl-cyclopropyl]-4H-1,2,4-oxadiazol-5-one |
| 417 | 3-[(1S,2S)-1-[5-[(4S)-2,2-dimethyltetrahydropyran-4-yl]-2-[[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-dien-11-yl]methyl]indol-1-yl]-2-methyl-cyclopropyl]-4H-1,2,4-oxadiazol-5-one |
| 418 | 3-[(1S,2S)-1-[5-(5,5-dimethyltetrahydrofuran-3-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 419 | 3-[(1S,2S)-1-[5-[(3R)-2,2-dimethyltetrahydrofuran-3-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 420 | 3-[(1S,2S)-1-[5-[(3S)-2,2-dimethyltetrahydrofuran-3-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 421 | 3-[(1S,2S)-1-[5-[(4S)-2,2-dimethyltetrahydropyran-4-yl]-2-[2-(4-fluoro-3,5-dimethyl-phenyl)-3-[3-(4-fluoro-1-methyl-indazol-5-yl)-2-oxo-imidazol-1-yl]-4,5,7,8-tetrahydropyrazolo[3,4-d]azepine-6-carbonyl]indol-1-yl]-2-methyl-cyclopropyl]-4H-1,2,4-oxadiazol-5-one |
| 422 | 3-[3-[(1S,8R)-11-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,11- |

-continued

| ID | Compound Name |
|---|---|
| | triazatricyclo[6.2.1.02,6]undeca-2,5-dien-3-yl]-2-oxo-imidazol-1-yl]-2-fluoro-benzamide |
| 423 | 3-[(1S,2S)-1-[5-[(3S)-5,5-dimethyltetrahydrofuran-3-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 424 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(8R)-5-oxaspiro[3.5]nonan-8-yl]indol-1-yl]-2-methyl-cyclopropyl]-4H-1,2,4-oxadiazol-5-one |
| 425 | 3-[(1S,2S)-1-[5-[(3R)-5,5-dimethyltetrahydrofuran-3-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 426 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(8S)-5-oxaspiro[3.5]nonan-8-yl]indol-1-yl]-2-methyl-cyclopropyl]-4H-1,2,4-oxadiazol-5-one |
| 427 | 3-[(1S,2S)-1-[5-[(4S)-2,2-dimethyltetrahydropyran-4-yl]-2-[4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 428 | 3-[(1S,2S)-1-[5-[(4S)-2,2-dimethyltetrahydropyran-4-yl]-2-[(1S,8R)-3-[3-[4-(ethylsulfonimidoyl)-2-fluoro-phenyl]-2-oxo-imidazol-1-yl]-4-(4-fluoro-3,5-dimethyl-phenyl)-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 429 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-2-oxo-pyrazolo[1,5-a]pyridin-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 430 | 3-[(1S,2S)-1-[5-[(4S)-2,2-dimethyltetrahydropyran-4-yl]-2-[(1R,8S)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 431 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-2-methoxy-pyrazolo[1,5-a]pyridin-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 432 | 3-[(1S,2S)-1-[5-[(4S)-2,2-dimethyltetrahydropyran-4-yl]-2-[[2-(4-fluoro-3,5-dimethyl-phenyl)-3-[3-(4-fluoro-1-methyl-indazol-5-yl)-2-oxo-imidazol-1-yl]-4,6,7,8-tetrahydropyrazolo[4,3-c]azepin-5-yl]methyl]indol-1-yl]-2-methyl-cyclopropyl]-4H-1,2,4-oxadiazol-5-one |
| 433 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 434 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-ethyl-cyclopropyl]-4H-1,2,4-oxadiazol-5-one |
| 435 | 3-[(1R,2R)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-ethyl-cyclopropyl]-4H-1,2,4-oxadiazol-5-one |
| 436 | 3-[(1S,2S)-1-[2-[(1S,8R)-4-(4-fluoro-3,5-dimethyl-phenyl)-3-[3-(4-fluoro-1H-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 437 | 3-[(1S,2S)-1-[2-[(1S,8R)-4-(4-fluoro-3,5-dimethyl-phenyl)-3-[3-(5-fluorophthalazin-6-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 501 | 3-[(1S,2S)-1-[2-[3-[3-[4-diethylphosphoryl-3-(methylamino)phenyl]-2-oxo-imidazol-1-yl]-2-(4-fluoro-3,5-dimethyl-phenyl)-4,6,7,8-tetrahydropyrazolo[4,3-c]azepine-5-carbonyl]-5-[(4S)-2,2-dimethyltetrahydropyran-4-yl]indol-1-yl]-2-methyl-cyclopropyl]-4H-1,2,4-oxadiazol-5-one |
| 502 | 3-[(1S,2S)-1-[2-[2-(4-fluoro-3,5-dimethyl-phenyl)-3-[3-(4-fluoro-1-methyl-indazol-5-yl)-2-oxo-imidazol-1-yl]-4,6,7,8-tetrahydropyrazolo[4,3-c]azepine-5-carbonyl]-5-tetrahydropyran-4-yl-indol-1-yl]-2-methyl-cyclopropyl]-4H-1,2,4-oxadiazol-5-one |
| 503 | 3-[(1S,2S)-1-[5-(2,2-dimethyltetrahydropyran-4-yl)-2-[[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-dien-11-yl]sulfonyl]indol-1-yl]-2-methyl-cyclopropyl]-4H-1,2,4-oxadiazol-5-one |
| 504 | 3-[(1R,2S)-1-[5-(2,2-dimethyltetrahydropyran-4-yl)-2-[[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-dien-11-yl]sulfonyl]indol-1-yl]-2-methyl-cyclopropyl]-4H-1,2,4-oxadiazol-5-one |
| 505 | 3-[(1S,2S)-1-[5-[(4S)-2,2-dimethyltetrahydropyran-4-yl]-2-[2-(4-fluoro-3,5-dimethyl-phenyl)-3-[3-(4-fluoro-1H-indazol-5-yl)-2-oxo-imidazol-1-yl]-4,6,7,8-tetrahydropyrazolo[4,3-c]azepine-5-carbonyl]indol-1-yl]-2-methyl-cyclopropyl]-4H-1,2,4-oxadiazol-5-one |
| 506 | 3-[(1S,2S)-1-[2-[3-[3-[4-diethylphosphoryl-3-(methylamino)phenyl]-2-oxo-imidazol-1-yl]-2-(4-fluoro-3,5-dimethyl-phenyl)-4,6,7,8-tetrahydropyrazolo[4,3-c]azepine-5-carbonyl]-5-tetrahydropyran-4-yl-indol-1-yl]-2-methyl-cyclopropyl]-4H-1,2,4-oxadiazol-5-one |
| 507 | 3-[(1S,2S)-1-[5-[(4S)-2,2-dimethyltetrahydropyran-4-yl]-2-[(7S)-7-fluoro-4-(4-fluoro-3,5-dimethyl-phenyl)-3-[3-(4-fluoro-1-methyl-indazol-5-yl)-2-oxo-imidazol-1-yl]-4,5,11- |

-continued

| ID | Compound Name |
|---|---|
| | triazatricyclo[6.2.1.02,6]undeca-2,5-diene-11-carbonyl]indol-1-yl]-2-methyl-cyclopropyl]-4H-1,2,4-oxadiazol-5-one |
| 508 | 3-[(1S,2S)-1-[5-(2,2-dimethyltetrahydropyran-4-yl)-2-[[2-(4-fluoro-3,5-dimethyl-phenyl)-3-[3-(4-fluoro-1-methyl-indazol-5-yl)-2-oxo-imidazol-1-yl]-4,6,7,8-tetrahydropyrazolo[4,3-c]azepin-5-yl]sulfonyl]indol-1-yl]-2-methyl-cyclopropyl]-4H-1,2,4-oxadiazol-5-one |
| 509 | 3-[(1S,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]-5-[(7S)-4-oxaspiro[2.5]octan-7-yl]indol-1-yl]-2-methyl-cyclopropyl]-4H-1,2,4-oxadiazol-5-one |
| 510 | 3-[(1S,2S)-1-[5-(3,3-dimethyl-6-oxo-2H-pyridin-1-yl)-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 511 | 3-[(1S,2S)-1-[5-[(4S)-2,2-dimethyltetrahydropyran-4-yl]-2-[(7R)-7-fluoro-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 512 | 3-[(1S,2S)-1-[5-[(4S)-2,2-dimethyltetrahydropyran-4-yl]-2-[(1S,7R,8R)-7-fluoro-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 513 | 3-[(1S,2S)-1-[5-[(4S)-2,2-dimethyltetrahydropyran-4-yl]-2-[(1R,7S,8S)-7-fluoro-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 514 | 3-[(1S,2S)-1-[5-[(4S)-2,2-dimethyltetrahydropyran-4-yl]-2-[(1R,7R,8S)-7-fluoro-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 515 | 3-[(1S,2S)-1-[5-[(4S)-2,2-dimethyltetrahydropyran-4-yl]-2-[(1S,7S,8R)-7-fluoro-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 516 | 3-[(1R,2R)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 517 | 3-[(1R,2R)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 518 | 3-[(1S,2S)-1-[5-[(4S)-2,2-dimethyltetrahydropyran-4-yl]-2-[(4S)-2-(4-fluoro-3,5-dimethyl-phenyl)-3-[3-(4-fluoro-1-methyl-indazol-5-yl)-2-oxo-imidazol-1-yl]-4-methyl-4,6,7,8-tetrahydropyrazolo[4,3-c]azepine-5-carbonyl]indol-1-yl]-2-methyl-cyclopropyl]-4H-1,2,4-oxadiazol-5-one |
| 519 | 3-[(1R,2R)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 520 | 3-[(1R,2R)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 521 | 3-[(1S,2S)-1-[5-[(4S)-2,2-dimethyltetrahydropyran-4-yl]-2-[2-(4-fluoro-3,5-dimethyl-phenyl)-3-[3-(5-fluorophthalazin-6-yl)-2-oxo-imidazol-1-yl]-4,6,7,8-tetrahydropyrazolo[4,3-c]azepine-5-carbonyl]indol-1-yl]-2-methyl-cyclopropyl]-4H-1,2,4-oxadiazol-5-one |
| 522 | 3-[(1S,2S)-1-[5-[(4S)-2,2-dimethyltetrahydropyran-4-yl]-2-[4-(4-fluoro-3,5-dimethyl-phenyl)-3-[3-(4-fluoro-1-methyl-indazol-5-yl)-2-oxo-imidazol-1-yl]-4,5,12-triazatricyclo[7.2.1.02,6]dodeca-2,5-diene-12-carbonyl]indol-1-yl]-2-methyl-cyclopropyl]-4H-1,2,4-oxadiazol-5-one |
| 523 | 3-[(1S,2S)-1-[5-[(4S)-2,2-dimethyltetrahydropyran-4-yl]-2-[(1S,9R)-4-(4-fluoro-3,5-dimethyl-phenyl)-3-[3-(4-fluoro-1-methyl-indazol-5-yl)-2-oxo-imidazol-1-yl]-4,5,12-triazatricyclo[7.2.1.02,6]dodeca-2,5-diene-12-carbonyl]indol-1-yl]-2-methyl-cyclopropyl]-4H-1,2,4-oxadiazol-5-one |
| 524 | 3-[(1S,2S)-1-[5-[(4S)-2,2-dimethyltetrahydropyran-4-yl]-2-[(1R,9S)-4-(4-fluoro-3,5-dimethyl-phenyl)-3-[3-(4-fluoro-1-methyl-indazol-5-yl)-2-oxo-imidazol-1-yl]-4,5,12-triazatricyclo[7.2.1.02,6]dodeca-2,5-diene-12-carbonyl]indol-1-yl]-2-methyl-cyclopropyl]-4H-1,2,4-oxadiazol-5-one |
| 525 | 3-[(1S,2S)-1-[5-[(4S)-2,2-dimethyltetrahydropyran-4-yl]-2-[[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-dien-11-yl]sulfonyl]indol-1-yl]-2-methyl-cyclopropyl]-4H-1,2,4-oxadiazol-5-one |
| 526 | 3-[(1S,2S)-1-[2-[[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-dien-12-yl]sulfonyl]-5-tetrahydropyran-4-yl-indol-1-yl]-2-methyl-cyclopropyl]-4H-1,2,4-oxadiazol-5-one |
| 527 | 3-[(2S)-1-[5-[(4S)-2,2-dimethyltetrahydropyran-4-yl]-2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]indol-1-yl]-2-methyl-cyclopropyl]-4H-1,2,4-oxadiazol-5-one |
| 528 | 3-[(1R,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5- |

-continued

| ID | Compound Name |
|---|---|
| | [(7S)-4-oxaspiro[2.5]octan-7-yl]indol-1-yl]-2-methyl-cyclopropyl]-4H-1,2,4-oxadiazol-5-one |
| 529 | 3-[(1R,2S)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 530 | 3-[(1R,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 531 | 3-[(1R,2S)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 532 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-3-methyl-indol-1-yl]-2-methyl-cyclopropyl]-4H-1,2,4-oxadiazol-5-one |
| 533 | 3-[(1S,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-tetrahydropyran-4-yl-indol-1-yl]-2-methyl-cyclopropyl]-4H-1,2,4-oxadiazol-5-one |
| 534 | 3-[(1R,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-tetrahydropyran-4-yl-indol-1-yl]-2-methyl-cyclopropyl]-4H-1,2,4-oxadiazol-5-one |
| 535 | 3-[(1S,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-(4-oxa-7-azaspiro[2.5]octan-7-yl)indol-1-yl]-2-methyl-cyclopropyl]-4H-1,2,4-oxadiazol-5-one |
| 536 | 3-[(1S,2S)-1-[5-[(4S)-2,2-dimethyltetrahydropyran-4-yl]-2-[[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-dien-12-yl]sulfonyl]indol-1-yl]-2-methyl-cyclopropyl]-4H-1,2,4-oxadiazol-5-one |
| 537 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]-3-methyl-indol-1-yl]-2-methyl-cyclopropyl]-4H-1,2,4-oxadiazol-5-one |
| 538 | 3-[(1R,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-(4-oxa-7-azaspiro[2.5]octan-7-yl)indol-1-yl]-2-methyl-cyclopropyl]-4H-1,2,4-oxadiazol-5-one |
| 539 | 3-[(1S,2R)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 540 | 3-[(1S,2R)-1-[2-[(1R,8S)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 541 | 3-[(1S,2R)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7R)-4-oxaspiro[2.5]octan-7-yl]indol-1-yl]-2-methyl-cyclopropyl]-4H-1,2,4-oxadiazol-5-one |
| 542 | 3-[(1S,2R)-1-[2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]-5-[(7S)-4-oxaspiro[2.5]octan-7-yl]indol-1-yl]-2-methyl-cyclopropyl]-4H-1,2,4-oxadiazol-5-one |
| 543 | 2-chloro-N-cyclopropyl-4-[3-[(1S,8R)-12-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,12-triazatricyclo[6.3.1.02,6]dodeca-2,5-dien-3-yl]-2-oxo-imidazol-1-yl]-N-methyl-benzamide |
| 544 | 2-[4-[3-[(1S,8R)-12-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-luoro-3,5-dimethyl-phenyl)-f4,5,12-triazatricyclo[6.3.1.02,6]dodeca-2,5-dien-3-yl]-2-oxo-imidazol-1-yl]phenyl]-N-methyl-acetamide |
| 545 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(l'-methyl-2'-oxo-spiro[cyclopropane-1,3'-indoline]-6'-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 546 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-[4-(methylsulfonylmethyl)phenyl]-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 547 | N-cyclopropyl-4-[3-[(1S,8R)-12-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,12-triazatricyclo[6.3.1.02,6]dodeca-2,5-dien-3-yl]-2-oxo-imidazol-1-yl]-2,3-difluoro-N-methyl-benzamide |
| 601 | 3-[(1S,2S)-1-[5-[(4S)-2,2-dimethyltetrahydropyran-4-yl]-2-[(6S)-2-(4-fluoro-3,5-dimethyl-phenyl)-3-[3-(4-fluoro-1-methyl-indazol-5-yl)-2-oxo-imidazol-1-yl]-6-methyl-4,6,7,8-tetrahydropyrazolo[4,3-c]azepine-5-carbonyl]indol-1-yl]-2-methyl-cyclopropyl]-4H-1,2,4-oxadiazol-5-one |
| 602 | 3-[(1S,2S)-1-[5-[(4S)-2,2-dimethyltetrahydropyran-4-yl]-2-[[(1S,8R)-4-(4-fluoro-3,5-dimethyl-phenyl)-3-[3-(8-fluoro-7-isoquinolyl)-2-oxo-imidazol-1-yl]-4,5,12-triazatricyclo[6.3.1.02,6]dodeca-2,5-dien-12-yl]sulfonyl]indol-1-yl]-2-methyl-cyclopropyl]-4H-1,2,4-oxadiazol-5-one |
| 603 | 3-[(1R,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5- |

-continued

| ID | Compound Name |
|---|---|
| | [(7R)-4-oxaspiro[2.5]octan-7-yl]indol-1-yl]-2-methyl-cyclopropyl]-4H-1,2,4-oxadiazol-5-one |
| 604 | 3-[(1S,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-[(7R)-4-oxaspiro[2.5]octan-7-yl]indol-1-yl]-2-methyl-cyclopropyl]-4H-1,2,4-oxadiazol-5-one |
| 605 | 3-[(1R,2S)-1-[5-[(4S)-2,2-dimethyltetrahydropyran-4-yl]-2-[[(1S,8R)-4-(4-fluoro-3,5-dimethyl-phenyl)-3-[3-(8-fluoro-7-isoquinolyl)-2-oxo-imidazol-1-yl]-4,5,12-triazatricyclo[6.3.1.02,6]dodeca-2,5-dien-12-yl]sulfonyl]indol-1-yl]-2-methyl-cyclopropyl]-4H-1,2,4-oxadiazol-5-one |
| 606 | 3-[(1S,2S)-1-[2-[(4S)-2-(4-fluoro-3,5-dimethyl-phenyl)-3-[3-(4-fluoro-1-methyl-indazol-5-yl)-2-oxo-imidazol-1-yl]-4-methyl-4,6,7,8-tetrahydropyrazolo[4,3-c]azepine-5-carbonyl]-5-[(7S)-4-oxaspiro[2.5]octan-7-yl]indol-1-yl]-2-methyl-cyclopropyl]-4H-1,2,4-oxadiazol-5-one |
| 607 | 3-[(1S,2S)-1-[2-[(4S)-2-(4-fluoro-3,5-dimethyl-phenyl)-3-[3-(4-fluoro-1-methyl-indazol-5-yl)-2-oxo-imidazol-1-yl]-4-methyl-4,6,7,8-tetrahydropyrazolo[4,3-c]azepine-5-carbonyl]-5-tetrahydropyran-4-yl-indol-1-yl]-2-methyl-cyclopropyl]-4H-1,2,4-oxadiazol-5-one |
| 608 | 3-[(1S,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-[(7S)-4-oxaspiro[2.5]octan-7-yl]indol-1-yl]-2-methyl-cyclopropyl]-4H-1,2,4-oxadiazol-5-one |
| 609 | 3-[(1R,2S)-1-[2-[[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-dien-12-yl]sulfonyl]-5-[(7S)-4-oxaspiro [2.5]octan-7-yl]indol-1-yl]-2-methyl-cyclopropyl]-4H-1,2,4-oxadiazol-5-one |
| 610 | 3-[(1S,2S)-1-[2-[(1S,8R)-4-(4-fluoro-3,5-dimethyl-phenyl)-3-[3-(8-fluoro-7-isoquinolyl)-2-oxo-imidazol-1-yl]-4,5,12-triazatricyclo[6.3.1.02,6]dodeca-2,5-diene-12-carbonyl]-5-[(7S)-4-oxaspiro[2.5]octan-7-yl]indol-1-yl]-2-methyl-cyclopropyl]-4H-1,2,4-oxadiazol-5-one |
| 611 | 2-[4-[3-[(1S,8R)-12-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,12-triazatricyclo[6.3.1.02,6]dodeca-2,5-dien-3-yl]-2-oxo-imidazol-1-yl]-2-fluoro-phenyl]-N-methyl-acetamide |
| 612 | N-[2-chloro-4-[3-[(1S,8R)-12-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,12-triazatricyclo[6.3.1.02,6]dodeca-2,5-dien-3-yl]-2-oxo-imidazol-1-yl]phenyl]-N-methyl-cyclopropanecarboxamide |
| 613 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4-methyl-1,2,4-oxadiazol-5-one |
| 614 | 3-[(1S,2S)-1-[2-[(1S,8R)-4-(4-fluoro-3,5-dimethyl-phenyl)-3-[3-(5-fluoro-6-isoquinolyl)-2-oxo-imidazol-1-yl]-4,5,12-triazatricyclo[6.3.1.02,6]dodeca-2,5-diene-12-carbonyl]-5-[(7S)-4-oxaspiro[2.5]octan-7-yl]indol-1-yl]-2-methyl-cyclopropyl]-4H-1,2,4-oxadiazol-5-one |
| 615 | 3-[(1S,2S)-1-[5-(2,2-dimethyltetrahydropyran-4-yl)-7-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 616 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-1,4-dihydro-1,2,4-triazol-5-one |
| 617 | 3-[(1S,2S)-1-[2-[(1R,8S)-3-[3-(1-cyclopropyl-4-fluoro-indazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-[(4S)-2,2-dimethyltetrahydropyran-4-yl]indol-1-yl]-2-methyl-cyclopropyl]-4H-1,2,4-oxadiazol-5-one |
| 618 | 3-[(1S,2S)-1-[5-(2,2-dimethyltetrahydropyran-4-yl)-7-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 619 | 3-[(1S,2S)-1-[5-(2,2-dimethyltetrahydropyran-4-yl)-7-fluoro-2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 701 | 3-[(1S,2S)-1-[5-[(4S)-2,2-dimethyltetrahydropyran-4-yl]-7-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 702 | 3-[(1S,2S)-1-[5-[(4S)-2,2-dimethyltetrahydropyran-4-yl]-2-[(4S)-2-(4-fluoro-3,5-dimethyl-phenyl)-3-[3-(4-fluoro-1-methyl-indazol-5-yl)-2-oxo-imidazol-1-yl]-4-methyl-4,6,7,8-tetrahydropyrazolo[1,5-a][1,4]diazepine-5-carbonyl]indol-1-yl]-2-methyl-cyclopropyl]-4H-1,2,4-oxadiazol-5-one |
| 703 | 3-[(1S,2S)-1-[5-[(4S)-2,2-dimethyltetrahydropyran-4-yl]-2-[(4R)-2-(4-fluoro-3,5-dimethyl-phenyl)-3-[3-(4-fluoro-1-methyl-indazol-5-yl)-2-oxo-imidazol-1-yl]-4-methyl-4,6,7,8-tetrahydropyrazolo[1,5-a][1,4]diazepine-5-carbonyl]indol-1-yl]-2-methyl-cyclopropyl]-4H-1,2,4-oxadiazol-5-one |
| 704 | 3-[(1S,2S)-1-[5-[(4S)-2,2-dimethyltetrahydropyran-4-yl]-2-[(1R,8S)-4-(4-fluoro-3,5-dimethyl-phenyl)-3-[3-(1'-methyl-2'-oxo-spiro[cyclopropane-1,3'-indoline]-6'-yl)-2-oxo-imidazol-1-yl]-4,5,12-triazatricyclo[6.3.1.02,6]dodeca-2,5-diene-12-arbonyl]indol-1-yl]-2-methyl-ccyclopropyl]-4H-1,2,4-oxadiazol-5-one |
| 705 | 3-[(1S,2S)-1-[5-[(4R)-2,2-dimethyltetrahydropyran-4-yl]-7-fluoro-2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]indol-1-yl]-2-methyl-cyclopropyl]-4H-1,2,4-oxadiazol-5-one |

-continued

| ID | Compound Name |
|---|---|
| 706 | 3-[(1S,2S)-1-[5-[(4S)-2,2-dimethyltetrahydropyran-4-yl]-7-fluoro-2-[(1R,8S)-4-(4-fluoro-3,5-dimethyl-phenyl)-3-[3-(4-fluoro-1-methyl-indazol-5-yl)-2-oxo-imidazol-1-yl]-10-oxa-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 707 | 3-[(1S,2S)-1-[5-[(4R)-2,2-dimethyltetrahydropyran-4-yl]-7-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 708 | 3-[(1S,2S)-1-[5-(2,2-dimethyltetrahydropyran-4-yl)-3-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 709 | 3-[(1S,2S)-1-[5-[(4R)-2,2-dimethyltetrahydropyran-4-yl]-7-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 710 | 6-[3-[(1S,8R)-12-[5-[(4S)-2,2-dimethyltetrahydropyran-4-yl]-1-[(1S,2S)-2-methyl-1-(5-oxo-4H-1,2,4-oxadiazol-3-yl)cyclopropyl]indole-2-carbonyl]-4-(4-fluoro-3,5-dimethyl-phenyl)-4,5,12-triazatricyclo[6.3.1.02,6]dodeca-2,5-dien-3-yl]-2-oxo-imidazol-1-yl]-1-methyl-indoline-2,3-dione |
| 711 | 3-[(1S,2S)-1-[5-[(4S)-2,2-dimethyltetrahydropyran-4-yl]-7-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 712 | 3-[(1S,2S)-1-[5-[(4S)-2,2-dimethyltetrahydropyran-4-yl]-3-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 713 | 3-[(1S,2S)-1-[5-[(4R)-2,2-dimethyltetrahydropyran-4-yl]-3-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |
| 714 | 3-[(1S,2S)-1-[5-[(4S)-2,2-dimethyltetrahydropyran-4-yl]-2-[(1S,8R)-4-(4-fluoro-3,5-dimethyl-phenyl)-3-[3-(1'-methyl-2'-oxo-spiro[cyclopropane-1,3'-indoline]-5'-yl)-2-oxo-imidazol-1-yl]-4,5,12-triazatricyclo[6.3.1.02,6]dodeca-2,5-diene-12-carbonyl]indol-1-yl]-2-methyl-cyclopropyl]-4H-1,2,4-oxadiazol-5-one |
| 715 | 3-[(1S,2S)-1-[2-[(1R,8S)-3-[3-(1-cyclopropyl-4-fluoro-indazol-5-yl)-2-oxo-imidazol-1-yl]-4-(4-fluoro-3,5-dimethyl-phenyl)-10-oxa-4,5,12-triazatricyclo[6.3.1.02,6]dodeca-2,5-diene-12-carbonyl]-5-tetrahydropyran-4-yl-indol-1-yl]-2-methyl-cyclopropyl]-4H-1,2,4-oxadiazol-5-one |
| 716 | 3-[(1S,2S)-1-[5-(2,2-dimethyltetrahydropyran-4-yl)-6-fluoro-2-[(1S,8R)-4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.02,6]undeca-2,5-diene-11-carbonyl]indol-1-yl]-2-methyl-cyclopropyl]-4H-1,2,4-oxadiazol-5-one |

In certain embodiments, the compound is any one of compounds listed below:

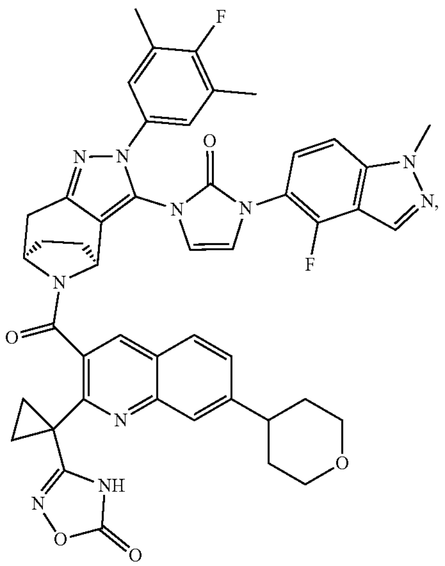

-continued

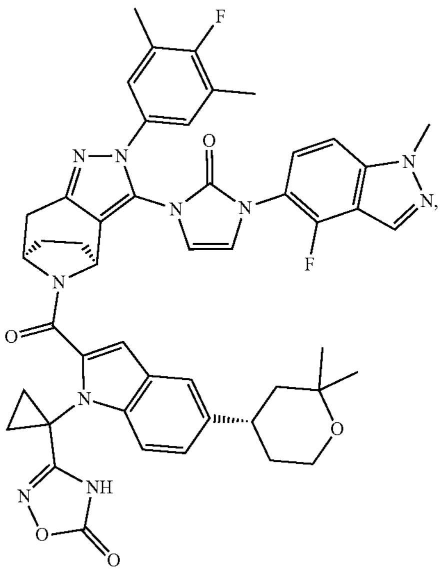

-continued
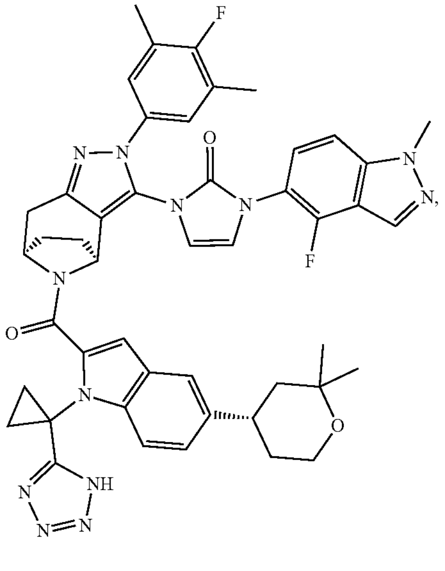
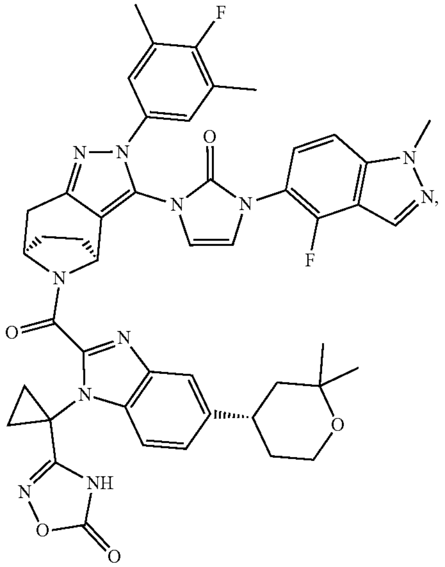
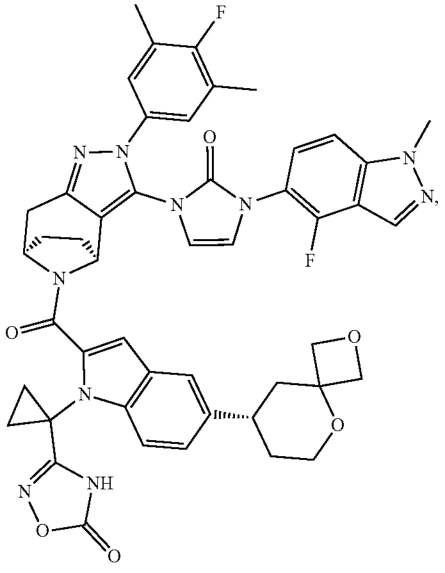
-continued
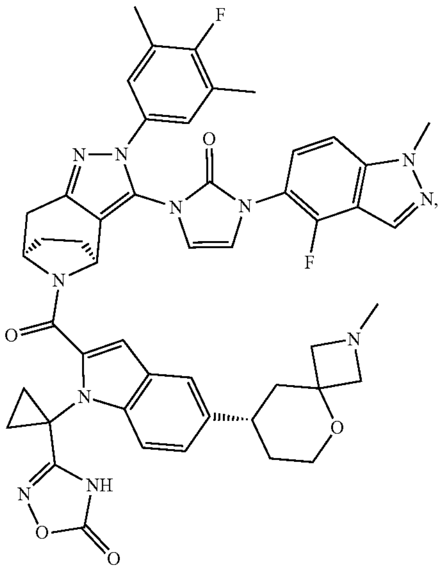
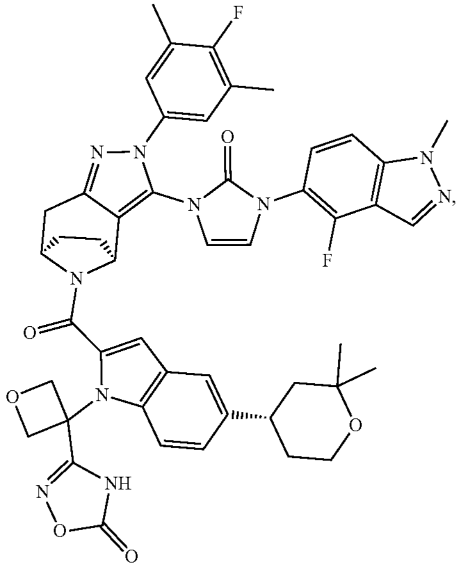
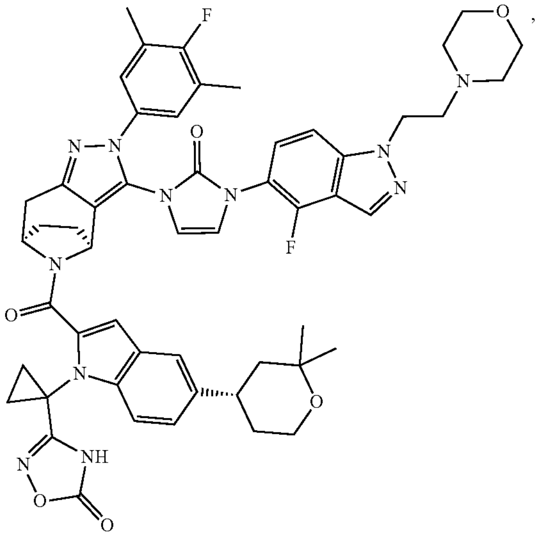

-continued
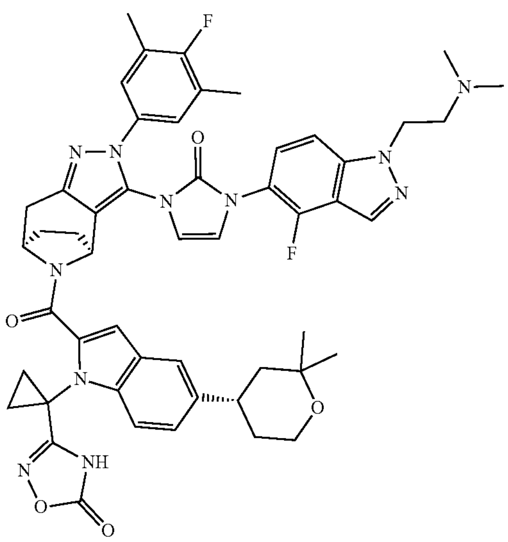
,
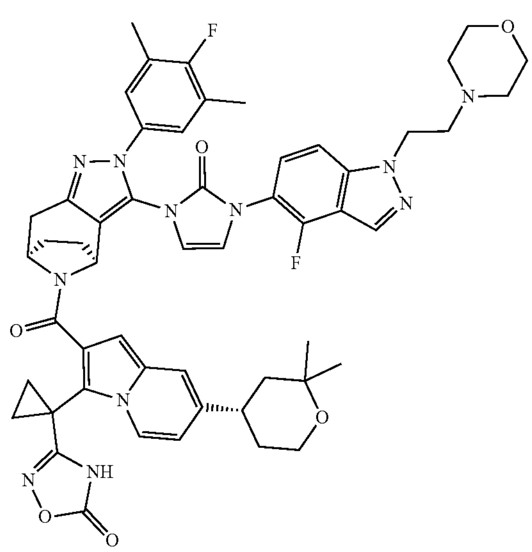
,
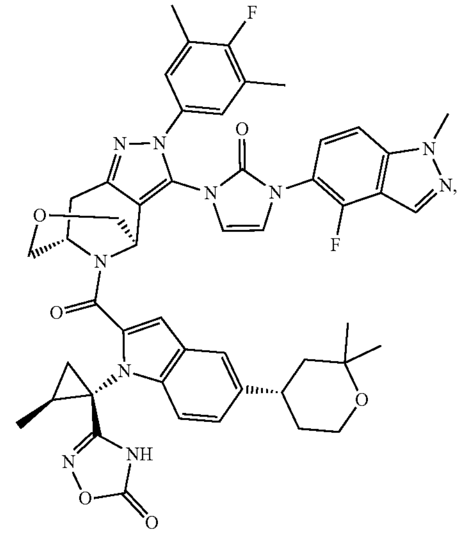
-continued
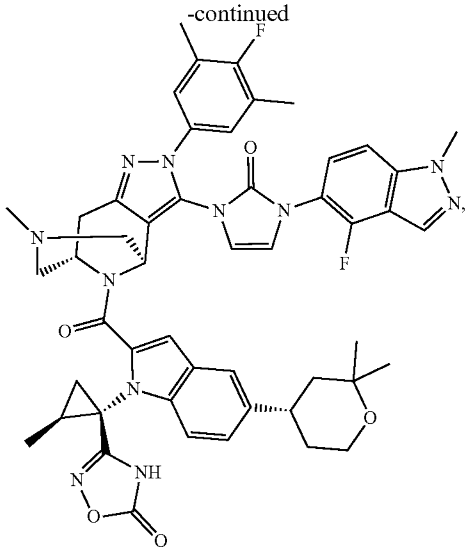
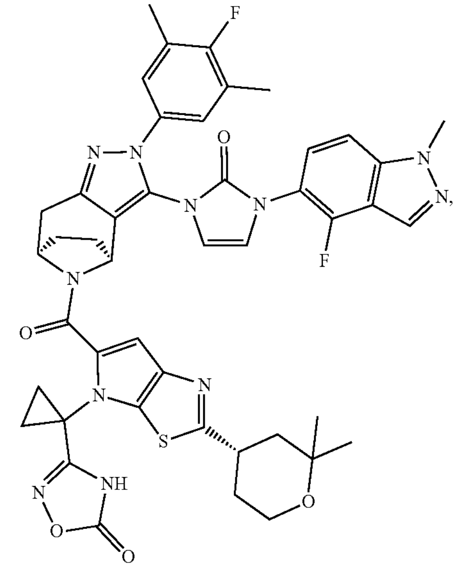
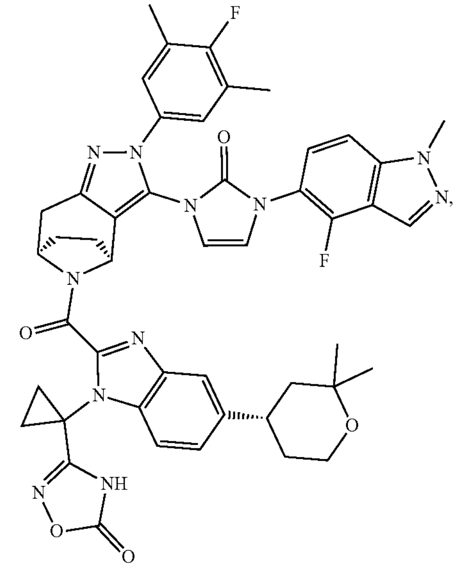

-continued
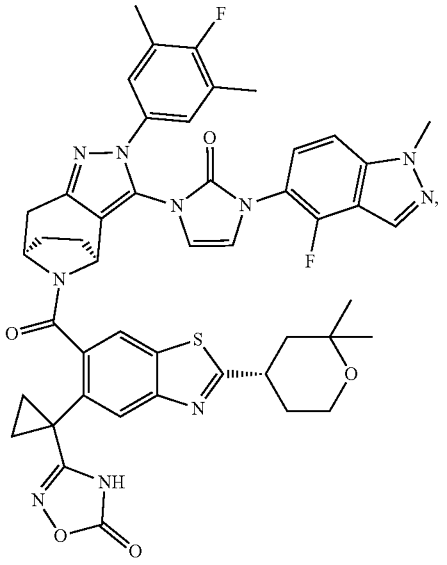
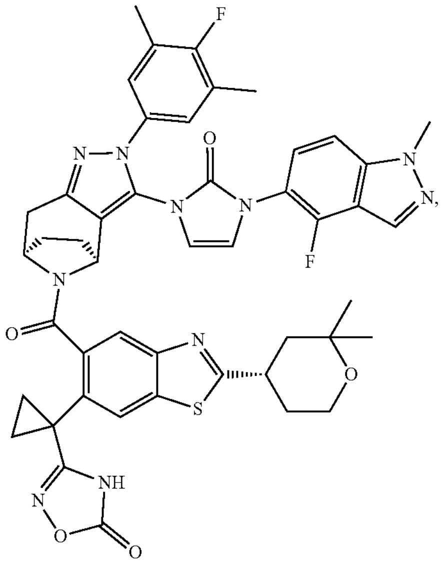
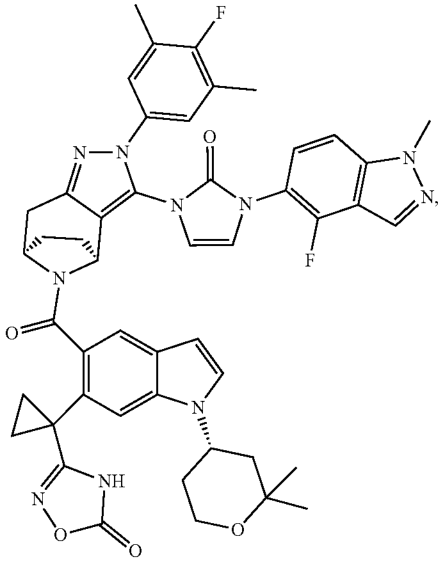
-continued
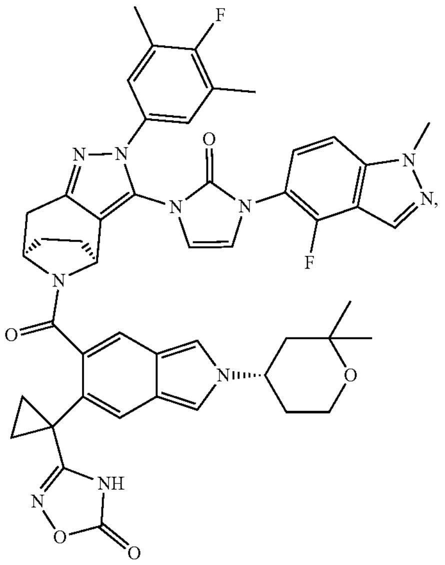
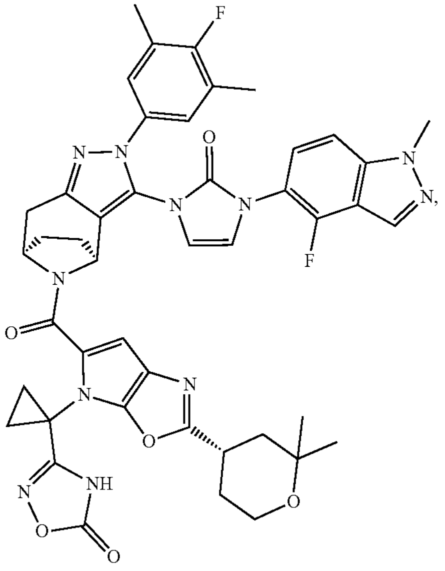
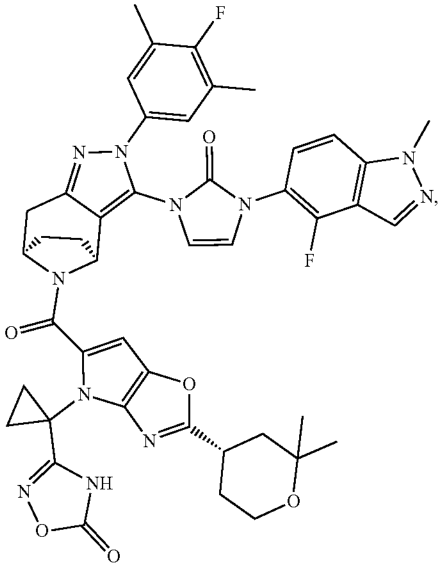

-continued
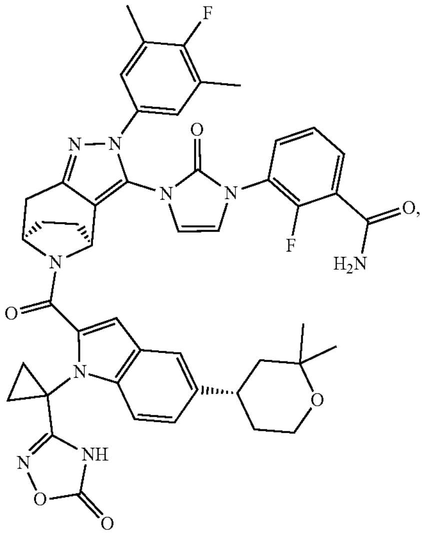
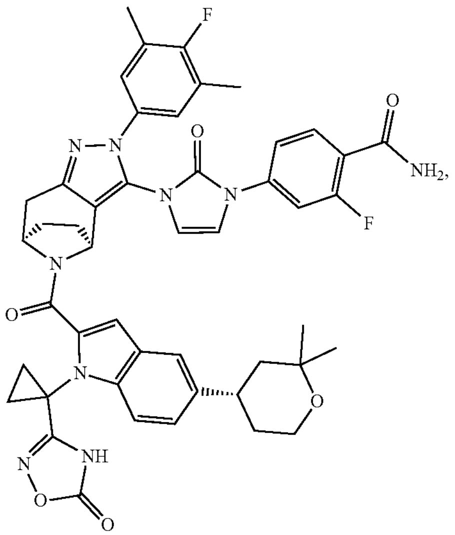
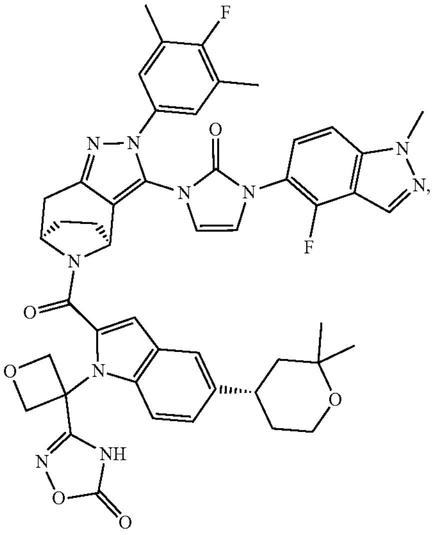
-continued
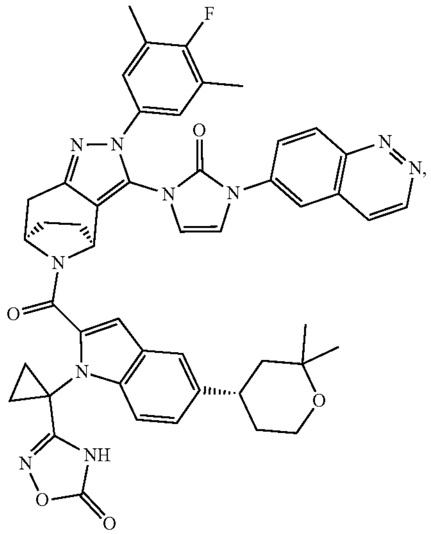
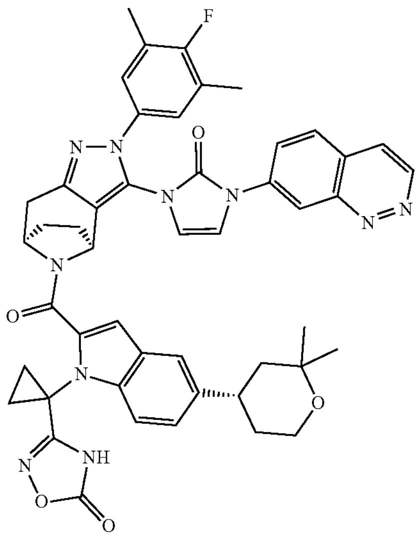
,
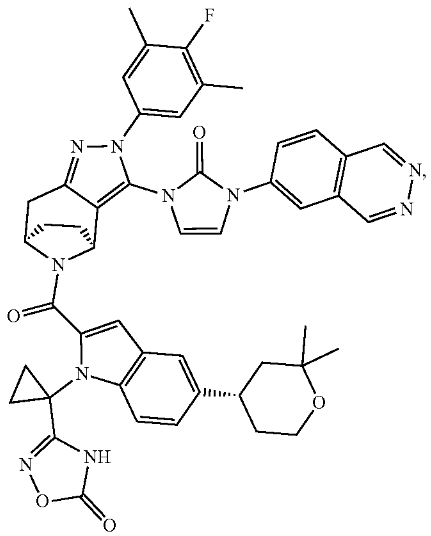

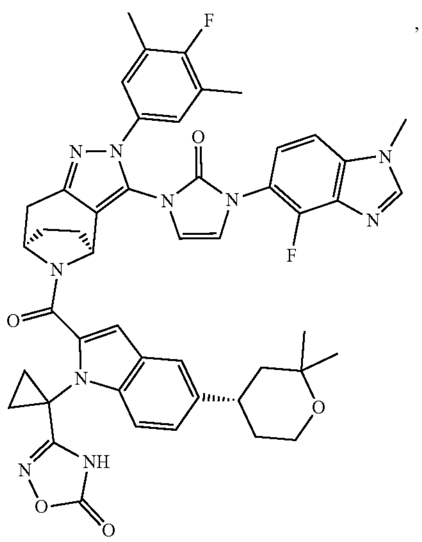
,
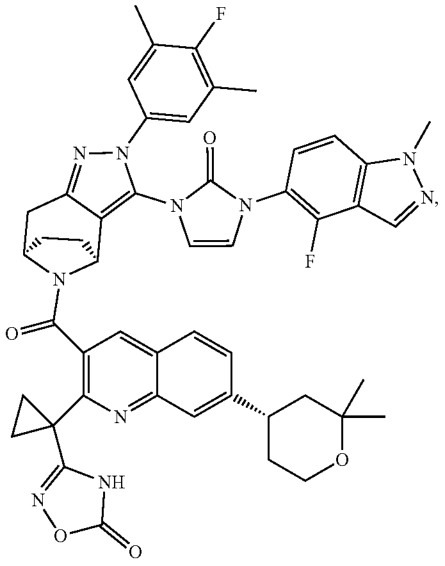
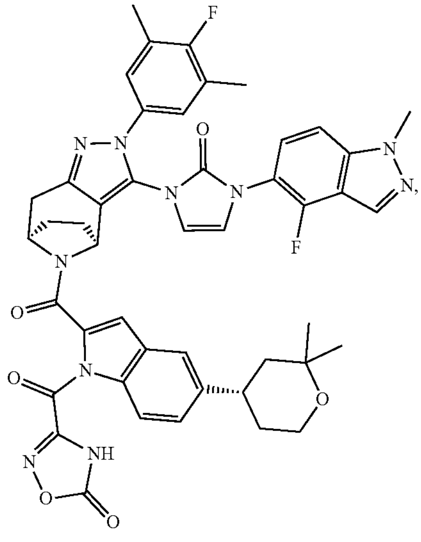
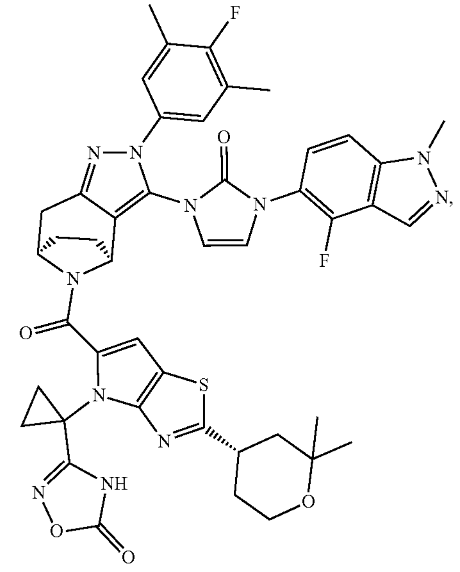
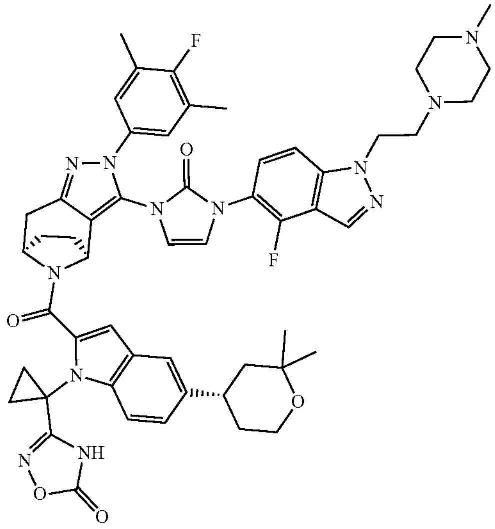
,
or
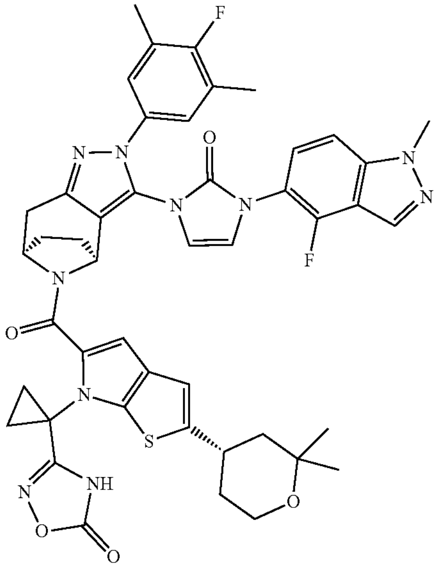 [SMILES: Cc1cc(-n2nc3c(c2-n2ccn(-c4ccc5c(cnn5C)c4F)c2=O)[C@@H]2CC[C@H](C3)N2C(=O)c2cc3sc([C@H]4CCOC(C)(C)C4)cc3n2C2(c3noc(=O)[nH]3)CC2)cc(C)c1F]

-continued

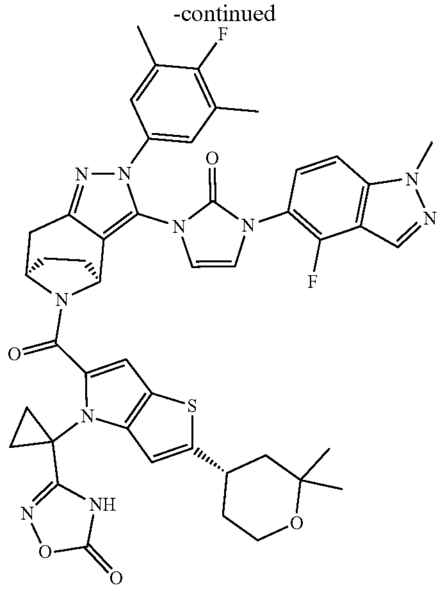

In certain embodiments, the compound is any one of compounds listed in Table 1; and wherein the ID is 114-140, 201-246, 301-313, 323-325, 406-437, 501-547, 601-619, or 701-708.

In certain embodiments, the compound is any one of compounds listed in Table 1; and wherein the ID is selected from a group of 23, 36, 116, 118, 121, 127, 128, 201, 203, 204, 208, 209, 211, 213, 214, 216, 219-226, 302, 311, 313, 323, 406, 410, 427-429, 433, 436-437, 503, 518, 121, 214, 226, 302, 323, 36, 428, 429, 433, 509, 518, 525, 606, 607, 610, 612, 614, 617, 221, 225, 311, 314, 406, 410, 436, 437, and 611. In certain embodiments, the compound is any one of compounds listed in Table 1; and wherein the ID is selected from a group of 121, 214, 226, 302, 323, 36, 428, 429, 433, 509, 518, 525, 606, 607, 610, 612, 614, and 617. In certain embodiments, the compound is any one of compounds listed in Table 1; and wherein the ID is selected from a group of 221, 225, 311, 314, 406, 410, 436, 437, and 611.

In certain embodiments, with respect to the compounds depicted above, the cyclopropyl ring is substituted with Me.

Embodiments of the compounds of Formula (I) display improved potency against GLP-IR with $EC_{50}$ values of as low as less than 1 nM or less than 0.1 nM, and/or high occupancy of active site of GLP-1R (e.g., more than 50%, 70% or 90% occupancy) at low dosages of below 5 mg/kg (e.g., at or below 3 mg/kg) when administered in vivo (e.g., in rats).

Embodiments of the compounds of Formula (I) display improved potency against GLP-1R with $EC_{50}$ values of as low as less than 1 nM or less than 0.1 nM, and/or high occupancy of active site of GLP-1R (e.g., more than 50%, 70% or 90% occupancy) at low dosages of below 5 mg/kg (e.g., at or below 3 mg/kg) when administered in vivo (e.g., in rats).

In some embodiments, provided herein is a pharmaceutical composition comprising a compound according to formula (I).

In some embodiments, provided herein is a pharmaceutical composition comprising a therapeutically effective amount of a compound of formula (I), and a pharmaceutically acceptable excipient.

In some embodiments, the pharmaceutical composition is formulated for a route of administration selected from oral administration, parenteral administration, buccal administration, nasal administration, topical administration, or rectal administration.

In some embodiments, provided herein are methods for treating an autoimmune disease or condition comprising administering to a patient in need the pharmaceutical composition provided herein.

In some embodiments, provided herein the immune disorder is selected from Type 1 Diabetes In some embodiments, provided herein the disease is selected from Type 2 Diabetes.

In some embodiments, immune disease is selected from inflammatory diseases such as psoriasis, irritable bowel diseases or Ulcerative colitis.

In some embodiments, provided herein are methods for treating an inflammatory disease or condition comprising administering to a patient in need the pharmaceutical composition provided herein.

In some embodiments, provided herein are methods for treating a heteroimmune disease or condition comprising administering to a patient in need the pharmaceutical composition provided herein.

In some embodiments, provided herein the autoimmune disease is selected from rheumatoid arthritis or lupus.

In some embodiments, provided herein provided herein are methods for treating a cancer comprising administering to a patient in need the pharmaceutical composition provided herein.

In some embodiments, the disease is cancer cachexia, which is a syndrome of anorexia, wasting, asthenia.

In some embodiments, provided herein are methods for treating osteoporosis or bone resorption disorders comprising administering to a patient in need the pharmaceutical composition provided herein.

In some embodiments, provided herein are methods for treating lupus comprising administering to a subject in need thereof a composition containing a therapeutically effective amount of a compound of formula (I) that is GLP-1R agonists.

In some embodiments, provided herein is a pharmaceutical composition comprising a pharmaceutically acceptable carrier and a pharmaceutically effective amount of a compound according to any one of the formulas described herein. In some embodiments, the compound is according to any one of Formula (I).

In some embodiments, the pharmaceutical composition is formulated for a route of administration selected from oral administration, parenteral administration, buccal administration, nasal administration, topical administration, or rectal administration.

In some embodiments, the carrier is a parenteral carrier.

In some embodiments, the carrier is an oral carrier.

In some embodiments, the carrier is a topical carrier.

Any combination of the groups described above for the various variables is contemplated herein. It is understood that substituents and substitution patterns on the compounds provided herein can be selected by one of ordinary skill in the art to provide compounds that are chemically stable and that can be synthesized by techniques known in the art, as well as those set forth herein.

Further representative embodiments of compounds of Formula (I), include compounds listed in Table 1, or a pharmaceutically acceptable salt, solvate, hydrate, or stereoisomer thereof.

Throughout the specification, groups and substituents thereof can be chosen by one skilled in the field to provide stable moieties and compounds.

In some embodiments, the compounds of Formula (I) GLP-1R agonists. In some embodiments, the compounds of Formula (I) are used to treat patients suffering from GLP-1R-dependent or GLP-1R mediated conditions or diseases, including, but not limited to, autoimmune diseases, heteroimmune diseases, inflammatory diseases, proliferative diseases, and bone diseases.

In some embodiments, the compounds of Formula (I) activate GLP-1R. In some embodiments, the compounds of Formula (I) are used to treat patients suffering from GLP-1R-dependent or GLP-1R-mediated conditions or diseases, including, but not limited to, autoimmune diseases, heteroimmune diseases, inflammatory diseases, proliferative diseases, and bone diseases.

Preparation of Compounds

Compounds of any of Formula (I) may be synthesized using standard synthetic reactions known to those of skill in the art or using methods known in the art. The reactions can be employed in a linear sequence to provide the compounds, or they may be used to synthesize fragments which are subsequently joined by the methods known in the art. Exemplary methods are provided in the Examples herein.

Described herein are compounds that activates GLP-1R, and processes for their preparation. Also described herein are pharmaceutically acceptable salts, pharmaceutically acceptable solvates, pharmaceutically active metabolites, and pharmaceutically acceptable prodrugs of such compounds. Pharmaceutical compositions that include at least one such compound or a pharmaceutically acceptable salt, pharmaceutically acceptable solvate, pharmaceutically active metabolite or pharmaceutically acceptable prodrug of such compound, are provided.

The starting material used for the synthesis of the compounds described herein may be synthesized or can be obtained from commercial sources, such as, but not limited to, Aldrich Chemical Co. (Milwaukee, Wisconsin), Bachem (Torrance, California), or Sigma Chemical Co. (St. Louis, Mo.). The compounds described herein, and other related compounds having different substituents can be synthesized using techniques and materials known to those of skill in the art, such as described, for example, in March, Advanced Organic Chemistry $4^{th}$ Ed., (Wiley 1992); Carey and Sundberg, Advanced Organic Chemistry $4^{th}$ Ed., Vols. A and B (Plenum 2000, 2001); Green and Wuts, Protective Groups in Organic Synthesis $3^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989). (all of which are incorporated by reference in their entirety). Additional methods for the synthesis of compounds described herein may be found in International Patent Publication No. WO 01/01982901, Arnold et al. Bioorganic & Medicinal Chemistry Letters 10 (2000) 2167-2170; Burchat et al. Bioorganic & Medicinal Chemistry Letters 12 (2002) 1687-1690. General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography, and the like. Such materials may be characterized using conventional means, including physical constants and spectral data.

Compounds described herein may be prepared as a single isomer or a mixture of isomers.

In some embodiments, representative compounds of Formula (I) are prepared according to synthetic schemes depicted herein.

In certain embodiments, compounds of Formula (I) are prepared according to the methods described herein.

Further Forms of Compounds

Compounds disclosed herein have a structure of Formula (I). It is understood that when reference is made to compounds described herein, it is meant to include compounds of any of Formula (I) as well as to all of the specific compounds that fall within the scope of these generic formulae, unless otherwise indicated.

Compounds described herein may possess one or more stereocenters and each center may exist in the R or S configuration. Compounds presented herein include all diastereomeric, enantiomeric, and epimeric forms as well as the appropriate mixtures thereof. Stereoisomers may be obtained, if desired, by methods known in the art as, for example, the separation of stereoisomers by chiral chromatographic columns.

Diastereomeric mixtures can be separated into their individual diastereomers on the basis of their physical chemical differences by methods known, for example, by chromatography and/or fractional crystallization. In some embodiments, enantiomers can be separated by chiral chromatographic columns. In some embodiments, enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

Methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, compounds described herein can exist in unsolvated as well as solvated forms with pharmaceutically acceptable solvents such as water, ethanol, and the like. Solvated forms of compounds presented herein are also considered to be disclosed herein.

Compounds of any of Formula (I) in unoxidized form can be prepared from N-oxides of compounds of any of Formula (I) by treating with a reducing agent, such as, but not limited to, sulfur, sulfur dioxide, triphenyl phosphine, lithium borohydride, sodium borohydride, phosphorus trichloride, tribromide, or the like in a suitable inert organic solvent, such as, but not limited to, acetonitrile, ethanol, aqueous dioxane, or the like at 0 to 80° C.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound. To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound. (see, for example, Nogrady (1943) Medicinal Chemistry A Biochemical Approach, Oxford University Press, New York, pages 388-392; Silverman (1992), The Organic Chemistry of Drug Design and Drug Action, Academic Press, Inc., San Diego, pages 352-401, Saulnier et al., (1994), Bioorganic and Medicinal Chemistry Letters, Vol. 4, p. 1943).

Prodrug forms of the herein described compounds, wherein the prodrug is metabolized in vivo to produce a derivative as set forth herein are included within the scope of the claims. In some cases, some of the herein-described compounds may be a prodrug for another derivative or active compound.

Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. Prodrugs may be designed as reversible drug derivatives, for use as modifiers to enhance drug transport to site-specific tissues. In some embodiments, the design of a prodrug increases the effective water solubility. See, e.g., Fedorak et al., Am. J. Physiol., 269: G210-218 (1995); McLoed et al., Gastroenterol, 106:405-413 (1994); Hochhaus et al., Biomed. Chrom., 6:241-244 (1992); J. Larsen and H. Bundgaard, Int. J. Pharmaceutics, 37, 87 (1987); J. Larsen et al., Int. J. Pharmaceutics, 47, 103 (1988); Sinkula et al., J. Pharm. Sci., 64:181-210 (1975); T. Higuchi and V. Stella, Pro-drugs as Novel Delivery Systems, Vol. 14 of the A.C.S. Symposium Series; and Edward B. Roche, Bioreversible Carriers in Drug Design, American Pharmaceutical Association and Pergamon Press, 1987, all incorporated herein in their entirety.

Sites on the aromatic ring portion of compounds of any of Formula (I) can be susceptible to various metabolic reactions, therefore incorporation of appropriate substituents on the aromatic ring structures, such as, by way of example only, halogens can reduce, minimize or eliminate this metabolic pathway.

Compounds described herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

In additional or some embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid such as hydrochloric acid, hydrobromic acid, sulfuric acid, nitric acid, phosphoric acid, metaphosphoric acid, and the like; or with an organic acid such as acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion (e.g. lithium, sodium, potassium), an alkaline earth ion (e.g. magnesium, or calcium), or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

The salts are recovered by using at least one of the following techniques: filtration, precipitation with a non-solvent followed by filtration, evaporation of the solvent, or, in the case of aqueous solutions, lyophilization.

It should be understood that a reference to a pharmaceutically acceptable salt includes the solvent addition forms or crystal forms thereof, particularly solvates or polymorphs. Solvates contain either stoichiometric or non-stoichiometric amounts of a solvent and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

It should be understood that a reference to a salt includes the solvent addition forms or crystal forms thereof, particularly solvates or polymorphs. Solvates contain either stoichiometric or non-stoichiometric amounts of a solvent and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

Compounds described herein may be in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of the pharmaceutically acceptable salts, polymorphs, and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Throughout the specification, groups and substituents thereof can be chosen by one skilled in the field to provide stable moieties and compounds.

Pharmaceutical Composition/Formulation

Pharmaceutical compositions may be formulated in a conventional manner using one or more physiologically acceptable carriers including excipients and auxiliaries which facilitate processing of the active compounds into preparations which can be used pharmaceutically. Proper formulation is dependent upon the route of administration chosen. Any of the well-known techniques, carriers, and excipients may be used as suitable and as understood in the art. A summary of pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety.

A pharmaceutical composition, as used herein, refers to a mixture of a compound described herein, such as, for example, compounds of any of Formula (I) with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. Preferably, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some embodiments, compositions may also include one or more salts in an amount required to bring osmolality of the composition into an acceptable range. Such salts include those having sodium, potassium or ammonium cations, and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein and a co-agent, are both administered to a patient simultaneously in the form of a single entity or dosage. The term "non-fixed combination" means that the active ingredients, e.g. a compound described herein and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The pharmaceutical compositions described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical compositions described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

The pharmaceutical compositions will include at least one compound described herein, such as, for example, a compound of any of Formula (I) as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite, and tocopherol. In certain embodiments, antioxidants enhance chemical stability where required.

In certain embodiments, compositions provided herein may also include one or more preservatives to modulate microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of any of Formula (I) and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Erosion facilitators" include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruity, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or 1 of blood serum, absorbed into the bloodstream after administration. As used herein, measurable plasma concentrations are typically measured in ng/ml or μg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium docusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

Dosage Forms

The compositions described herein can be formulated for administration to a subject via any conventional means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of any of Formula (I) can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In some embodiments, the pharmaceutical composition is in the form of a powder. In some embodiments, the pharmaceutical composition is in the form of a tablet, including but not limited to, a fast-melt tablet. Additionally, pharmaceutical compositions described herein may be administered as a single capsule or in multiple capsule dosage form. In some embodiments, the pharmaceutical composition is administered in two, or three, or four, capsules or tablets.

In some embodiments, solid dosage forms, e.g., tablets, effervescent tablets, and capsules, are prepared by mixing particles of a compound of any of Formula (I) with one or more pharmaceutical excipients to form a bulk blend composition. When referring to these bulk blend compositions as homogeneous, it is meant that the particles of the compound of any of Formula (I) are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1944). Other methods include, e.g., spray drying, pan coating, melt granulation, granulation, fluidized bed spray drying or coating (e.g., wurster coating), tangential coating, top spraying, tableting, extruding and the like.

The pharmaceutical solid dosage forms described herein can include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In some embodiments, using standard coating procedures, such as those described in Remington's Pharmaceutical Sciences, 20th Edition (2000), a film coating is provided around the formulation of the compound of any of Formula (I). In some embodiments, some or all of the particles of the compound of any of Formula (I) are coated. In some embodiments, some or all of the particles of the compound of any of Formula (I), are microencapsulated. In still some embodiments, the particles of the compound of any of Formula (I) are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound of any of Formula (I) from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat- 603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

The term "non water-soluble diluent" represents compounds typically used in the formulation of pharmaceuticals, such as calcium phosphate, calcium sulfate, starches, modified starches and microcrystalline cellulose, and microcellulose (e.g., having a density of about 0.45 $g/cm^3$, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms described herein. The amounts of such additives can be readily determined by one skilled in the art, according to the particular properties desired.

In some embodiments, one or more layers of the pharmaceutical composition are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In some embodiments, the compressed tablets will include a film surrounding the final compressed tablet. In some embodiments, the film coating can provide a delayed release of the compound of any of Formula (I) from the formulation. In some embodiments, the film coating aids in patient compliance (e.g., Opadry® coatings or sugar coating). Film coatings including Opadry® typically range from about 1% to about 3% of the tablet weight. In some embodiments, the compressed tablets include one or more excipients.

A capsule may be prepared, for example, by placing the bulk blend of the formulation of the compound of any of Formula (I), described above, inside of a capsule. In some embodiments, the formulations (non-aqueous suspensions and solutions) are placed in a soft gelatin capsule. In some embodiments, the formulations are placed in standard gelatin capsules or non-gelatin capsules such as capsules comprising HPMC. In some embodiments, the formulation is placed in a sprinkle capsule, wherein the capsule may be swallowed whole, or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound of any of Formula (I) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In some embodiments, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of any of Formula (I) which sufficiently isolate the compound of any of Formula (I) from other non-compatible excipients. Materials compatible with compounds of any of Formula (I) are those that delay the release of the compounds of any of Formula (I), in vivo.

Exemplary microencapsulation materials useful for delaying the release of the formulations including compounds described herein, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP423, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In some embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In some embodiments, the microencapsulating material useful for delaying the release of the pharmaceutical compositions is from the USP or the National Formulary (NF). In some embodiments, the microencapsulation material is Klucel. In some embodiments, the microencapsulation material is methocel.

Microencapsulated compounds of any of Formula (I) may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In some embodiments, the particles of compounds of any of Formula (I) are microencapsulated prior to being formulated into one of the above forms. In still some embodiments, some or most of the particles are coated prior to being further formulated by using standard coating procedures, such as those described in Remington's Pharmaceutical Sciences, 20th Edition (2000).

In some embodiments, the solid dosage formulations of the compounds of any of Formula (I) are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

In some embodiments, a powder including the formulations with a compound of any of Formula (I), described herein, may be formulated to include one or more pharmaceutical excipients and flavors. Such a powder may be prepared, for example, by mixing the formulation and optional pharmaceutical excipients to form a bulk blend composition. Additional embodiments also include a suspending agent and/or a wetting agent. This bulk blend is uniformly subdivided into unit dosage packaging or multi-dosage packaging units.

In still some embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid, and/or tartaric acid. When salts of the compositions described herein are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In some embodiments, the formulations described herein, which include a compound of Formula (I), are solid dispersions. Methods of producing such solid dispersions are known in the art and include, but are not limited to, for example, U.S. Pat. Nos. 4,343,789, 5,340,591, 5,456,923, 5,700,443, 5,723,269, and U.S. Pub. Appl 2004/0013734, each of which is specifically incorporated by reference. In some embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions are known in the art and include, but are not limited to, for example, U.S. Pat. Nos. 4,151,273, 5,281,420, and 6,041,518, each of which is specifically incorporated by reference.

The pharmaceutical solid oral dosage forms including formulations described herein, which include a compound of any of Formula (I) can be further formulated to provide a controlled release of the compound of Formula (I). Controlled release refers to the release of the compound of any of Formula (I) from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term “delayed release” as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the methods and compositions described herein to achieve delivery to the lower gastrointestinal tract. In some embodiments the polymers described herein are anionic carboxylic polymers. In some embodiments, the polymers and compatible mixtures thereof, and some of their properties, include, but are not limited to:

Shellac, also called purified lac, a refined product obtained from the resinous secretion of an insect. This coating dissolves in media of pH>7;

Acrylic polymers. The performance of acrylic polymers (primarily their solubility in biological fluids) can vary based on the degree and type of substitution. Examples of suitable acrylic polymers include methacrylic acid copolymers and ammonium methacrylate copolymers. The Eudragit series E, L, S, RL, RS, and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine.

Cellulose Derivatives. Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP psuedolatex with particles <1 μm. Other components in Aquateric can include pluronics, Tweens, and acetylated monoglycerides. Other suitable cellulose derivatives include: cellulose acetate trimellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions.

Poly Vinyl Acetate Phthalate (PVAP). PVAP dissolves in pH>5, and it is much less permeable to water vapor and gastric fluids.

In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the intestinal tract is reached.

Colorants, detackifiers, surfactants, antifoaming agents, lubricants (e.g., carnauba wax or PEG) may be added to the coatings besides plasticizers to solubilize or disperse the coating material, and to improve coating performance and the coated product.

In some embodiments, the formulations described herein, which include a compound of Formula (I), are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of any of Formula (I) may be administered using a variety of pulsatile formulations known in the art. For example, such formulations include, but are not limited to, those described in U.S. Pat. Nos. 5,011,692, 5,017,381, 5,229,135, and 5,420,329, each of which is specifically incorporated by reference. Other pulsatile release dosage forms suitable for use with the present formulations include, but are not limited to, for example, U.S. Pat. Nos. 4,871,549, 5,260,068, 5,260,069, 5,508,040, 5,567,441 and 5,417,242, all of which are specifically incorporated by reference. In some embodiments, the controlled release dosage form is pulsatile release solid oral dosage form including at least two groups of particles, (i.e. multiparticulate) each containing the formulation described herein. The first group of particles provides a substantially immediate dose of the compound of any of Formula (I) upon ingestion by a mammal. The first group of particles can be either uncoated or include a coating and/or sealant. The second group of particles includes coated particles, which includes from about 2% to about 75%, from about 2.5% to about 70%, or from about 40% to about 70%, by weight of the total dose of the compound of any of Formula (I) in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of any of Formula (I).

Many other types of controlled release systems known to those of ordinary skill in the art and are suitable for use with the formulations described herein. Examples of such delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. See, e.g., Liberman et al., Pharmaceutical Dosage Forms, 2 Ed., Vol. 1, pp. 209-214 (1990); Singh et al., Encyclopedia of Pharmaceutical Technology, $2^{nd}$ Ed., pp. 751-753 (2002); U.S. Pat. Nos. 4,327,725, 4,624,428, 4,968,509, 5,461,140, 5,456,923, 5,516,527, 5,622,721, 5,644,105, 5,700,410, 5,977,175, 6,465,014, and 6,932,941, each of which is specifically incorporated by reference.

In some embodiments, pharmaceutical compositions are provided that include particles of the compounds of any of Formula (I), described herein and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, $2^{nd}$ Ed., pp. 754-757 (2002). In addition to the particles of compound of Formula (I), the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline agonist.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In some embodiments, an aqueous suspension can be re-suspended into a homogenous suspension by physical agitation lasting less than 1 minute. In some embodiments, an aqueous suspension can be re-suspended into a homogenous suspension by physical agitation lasting less than 45 seconds. In yet some embodiments, an aqueous suspension can be re-suspended into a homogenous suspension by physical agitation lasting less than 30 seconds. In still some embodiments, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In some embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC- SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethylcellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions described herein are known in the art and include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, *eucalyptus*, eugenol, fructose, fruit punch, ginger, glycyrrhetinate, *glycyrrhiza* (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, *stevia*, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-*eucalyptus*, orange-cream, vanilla-mint, and mixtures thereof. In some embodiments, the aqueous liquid dispersion can comprise a sweetening agent or flavoring agent in a concentration ranging from about 0.001% to about 1.0% the volume of the aqueous dispersion. In some embodiments, the aqueous liquid dispersion can comprise a sweetening agent or flavoring agent in a concentration ranging from about 0.005% to about 0.5% the volume of the aqueous dispersion. In yet some embodiments, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium docusate, cholesterol, cholesterol esters, taurocholic acid, phosphatidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical compositions described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms are known in the art and include, but are not limited to, for example, U.S. Pat. Nos. 5,438,401, 6,667,048, and 6,960,563, each of which is specifically incorporated by reference.

It is to be appreciated that there is overlap between the above-listed additives used in the aqueous dispersions or suspensions described herein, since a given additive is often classified differently by different practitioners in the field or is commonly used for any of several different functions. Thus, the above-listed additives should be taken as merely exemplary, and not limiting, of the types of additives that can be included in formulations described herein. The amounts of such additives can be readily determined by one skilled in the art, according to the particular properties desired.

Intranasal Formulations

Intranasal formulations are known in the art and are described in, for example, U.S. Pat. Nos. 4,476,116, 5,116,817, and 6,391,452, each of which is specifically incorporated by reference. Formulations that include a compound of any of Formula (I) which are prepared according to these and other techniques well-known in the art are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. The nasal dosage form should be isotonic with nasal secretions.

For administration by inhalation, the compounds of any of Formula (I), described herein may be in a form as an aerosol, a mist or a powder. Pharmaceutical compositions described herein are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal Formulations

Buccal formulations that include compounds of any of Formula (I) may be administered using a variety of formulations known in the art. For example, such formulations include, but are not limited to, U.S. Pat. Nos. 4,229,447, 4,596,795, 4,755,344, and 5,739,136, each of which is specifically incorporated by reference. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of any of Formula (I), is provided essentially throughout. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of any of Formula (I), and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal Formulations

Transdermal formulations described herein may be administered using a variety of devices which have been described in the art. For example, such devices include, but are not limited to, U.S. Pat. Nos. 3,598,122, 3,598,123, 3,710,795, 3,731,641, 3,742,951, 3,814,097, 3,921,636, 3,972,995, 3,993,072, 3,993,073, 3,996,934, 4,031,894, 4,060,042, 4,069,307, 4,077,407, 4,201,211, 4,230,105, 4,292,299, 4,292,303, 5,336,168, 5,665,378, 5,417,280, 5,449,090, 6,923,941, 6,929,801 and 6,946,144, each of which is specifically incorporated by reference in its entirety.

The transdermal dosage forms described herein may incorporate certain pharmaceutically acceptable excipients which are conventional in the art. In some embodiments, the transdermal formulations described herein include at least three components: (1) a formulation of a compound of any of Formula (I); (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In some embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of any of Formula (I). The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Injectable Formulations

Formulations that include a compound of any of Formula (I), suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations may include aqueous or nonaqueous solutions, preferably with physiologically compatible buffers or excipients. Such excipients are generally known in the art.

Parenteral injections may involve bolus injection or continuous infusion. Formulations for injection may be presented in unit dosage form, e.g., in ampoules or in multidose containers, with an added preservative. The pharmaceutical composition described herein may be in a form suitable for parenteral injection as a sterile suspensions, solutions, or emulsions in oily or aqueous vehicles, and may contain formulatory agents such as suspending, stabilizing and/or dispersing agents. Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

Formulations

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams, or ointments. Such pharmaceutical compounds can contain solubilizers, stabilizers, tonicity enhancing agents, buffers, and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Dosing and Treatment Regimens

The compounds described herein can be used in the preparation of medicaments for the activate GLP-1R or a homolog thereof, or for the treatment of diseases or conditions that would benefit, at least in part, from activation of GLP-1R or a homolog thereof. In addition, a method for treating any of the diseases or conditions described herein in a subject in need of such treatment, involves administration of pharmaceutical compositions containing at least one compound of any of Formula (I), described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician. It is considered well within the skill of the art for one to determine such therapeutically effective amounts by routine experimentation (including, but not limited to, a dose escalation clinical trial).

In prophylactic applications, compositions containing the compounds described herein are administered to a patient susceptible to or otherwise at risk of a particular disease, disorder, or condition. Such an amount is defined to be a "prophylactically effective amount or dose." In this use, the precise amounts also depend on the patient's state of health, weight, and the like. It is considered well within the skill of the art for one to determine such prophylactically effective amounts by routine experimentation (e.g., a dose escalation clinical trial). When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status docs improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 43%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, or from about 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Methods of Treatment

In certain embodiments, provided herein are methods of treating or preventing a disease or condition by administering to a subject in need thereof an effective amount of a compound provided herein to treat or prevent the disease or condition. The disease or condition can be any deemed suitable for treatment or prevention with a compound describe herein by a practitioner of skill. In certain embodiments, the disease or condition is selected from autoimmune diseases and conditions, heteroimmune diseases and conditions, inflammatory diseases and conditions, and proliferative diseases and conditions, and bone diseases and conditions.

The compounds presented here would modulate the functions of GLP-1R and would be useful to treat disease or conditions associated with these three receptors.

T2D occurs when there is not sufficient insulin or resistance. TID is an autoimmune disease where body makes little or no insulin. GLP-1 agonists play key role in insulin secretion and balanced metabolism after food intake.

In certain embodiments, provided herein are methods of treating Obesity, which is a chronic condition and can result in life-threatening diseases.

In certain embodiments, provided herein are methods of treating metabolic disorders which can be any disease that can arise from abnormal metabolism of meal.

In certain embodiments, provided herein are methods of treating nonalcoholic fatty liver diseases NAFLD.

In certain embodiments, provided herein are methods of treating nonalcoholic steatohepatitis NASH.

The agonists reported here may be useful for various neurogenerative disorders such as Alzheimer's, Dementia, cognitive dysfunction, Huntington disease, Perkinson's disease.

In certain embodiments, provided herein are methods of treating depression.

In certain embodiments, provided herein are methods of treating stroke.

In certain embodiments, provided herein are methods of treating learning disability.

In certain embodiments, provided herein are methods of treating asthma.

In certain embodiment, disease associated with mutant GLP-1R.

The autoimmune disease or condition can be any autoimmune disease or condition known to the person of skill or deemed suitable by the practitioner of skill. In certain embodiments, the autoimmune disease or condition is selected from Long COVID, Acquired hemophilia, Antiphospholipid syndrome, Anticardiolipin antibody syndrome, Hughes syndrome, Aplastic anemia, Autoimmune lymphoproliferative syndrome, Autoimmune neutropenia, Autoimmune thrombocytopenia purpura, Immune thrombocytopenia, Cold agglutinin disease, Eosinophilic esophagitis, Essential mixed cryoglobulinemia, Evans syndrome, IgG4-related diseases, Hyper-IgG4 disease, Systemic IgG4-related plasmacytic syndrome, Paroxysmal nocturnal hemoglobinuria, Pure red cell aplasia, Warm autoimmune hemolytic anemia, Autoimmune hemolytic anemia, Autoimmune enteropathy, Autoimmune Gastritis, Celiac disease, Adult form of celiac disease, Acquired celiac disease, Crohn's disease, Microscopic colitis, Pernicious anemia, Ulcerative colitis, Addison's disease, Autoimmune adrenalitis, Anti-Sperm Antibodies, Autoimmune oophoritis, Autoimmune orchitis, Autoimmune pancreatitis, Autoimmune polyendocrine syndrome type 1, Autoimmune polyendocrinopathy-candidiasis-ectodermal dystrophy, Polyglandular autoimmune syndrome 1, Whitaker Syndrome, Autoimmune polyendocrine syndrome type 2, Polyglandular autoimmune syndrome 2, Autoimmune polyendocrine syndrome type 3, Polyglandular autoimmune syndrome 3, Autoimmune thyroiditis, Hashimoto's thyroiditis, Diabetes mellitus type 1, Endometriosis, Graves' disease, Autoimmune thyrotoxicosis, Sjogren's disease, Anti-Glomerular Basement Membrane nephritis, Goodpasture disease, Antisynthetase syndrome, Autoimmune hepatitis, Autoimmune myocarditis, Acute rheumatic myocarditis, Cryptogenic organizing pneumonia, Idiopathic pulmonary fibrosis, IgA nephropathy, Interstitial cystitis, Lupus nephritis, SLE glomerulonephritis syndrome, Post-myocardial infarction syndrome, Post-cardiotomy syndrome, Post-pericardiotomy pericarditis, Subacute bacterial endocarditis, Dressler's syndrome, Primary biliary cholangitis, Primary biliary cirrhosis, Primary idiopathic dilated cardiomyopathy, Primary sclerosing cholangitis, Acute disseminated encephalomyelitis, Acute hemorrhagic encephalomyelitis, Acute hemorrhagic leukoencephalitis, Acute necrotizing hemorrhagic leukoencephalitis, Nonvasculitic autoimmune meningoencephalitis, Hurst's disease, Perivenous encephalomyelitis, Weston-Hurst syndrome, Anti-n-methyl-D-aspartate receptor encephalitis, Autoimmune encephalitis, Autoimmune inner ear disease, Meniere's disease, Autoimmune retinopathy, Autoimmune uveitis, Bickerstaff's encephalitis, Chronic inflammatory demyelinating polyneuropathy, Relapsing polyneuropathy, Chronic inflammatory demyelinating polyneuritis, Chronic inflammatory demyelinating polyradiculoneuropathy, Miller-Fisher syndrome, Cogan syndrome, Encephalopathy Associated with Autoimmune Thyroid Disease, Hashimoto's encephalopathy, Steroid-responsive encephalopathy associated with autoimmune thyroiditis, Episcleritis, Graves' ophthalmopathy, Guillain-Barre syndrome, Acute motor axonal neuropathy, Progressive inflammatory neuropathy, Intermediate uveitis, Pars planitis, Peripheral Uveitis, Lambert-Eaton myasthenic syndrome, Ligneous conjunctivitis, Mooren's ulcer, Multiple sclerosis, Balo concentric sclerosis, Primary progressive multiple sclerosis, Relapsing-remitting multiple sclerosis, Schilders disease, Disseminated sclerosis, Encephalomyelitis disseminata, Myelin oligodendrocyte glycoprotein disease, Narcolepsy with cataplexy, Neuromyelitis optica, Devic's disease, Neuromyotonia, Isaacs' syndrome, Opsoclonus myoclonus syndrome, Paraneoplastic cerebellar degeneration, Pediatric autoimmune neuropsychiatric disorder associated with *streptococcus*, Restless leg syndrome, Retinocochleocerebral vasculopathy, Susac's syndrome, Rheumatic chorea, Sydenham chorea, Scleritis, Stiff person syndrome, Stiff man syndrome, Sympathetic ophthalmia, Sympathetic uveitis, Tolosa-Hunt syndrome, Transverse myelitis, Alopecia, Alopecia areata, Alopecia Totalis, Alopecia Universalis, Autoimmune progesterone dermatitis, Autoimmune urticaria, Bullous pemphigoid, Cicatricial pemphigoid, Ocular cicatricial pemphigoid, Benign Mucosal Pemphigoid, Cutaneous lupus erythematosus, Chronic discoid lupus erythematosus, Discoid lupus erythematosus, Discoid lupus erythematosus of eyelid, Discoid lupus erythematosus of oral mucosa, Lupus erythematosus tumidus, Subacute cutancous lupus erythematosus, Dermatitis herpetiformis, Epidermolysis bullosa acquisita, Erythema nodosum, Gestational pemphigoid, Herpes gestationis, Hidradenitis suppurativa, Lichen planus, Lichen sclerosus, Linear IgA disease, Morphea, Localized Scleroderma, Pemphigus vulgaris, Pityriasis lichenoides et varioliformis acuta, Mucha-Habermann disease, Psoriasis, Guttate psoriasis, Pyoderma gangrenosum, Systemic scleroderma, CREST syndrome, Vitiligo, Adiposis dolorosa, Dercum's disease, Adult-onset Still's disease, Ankylosing Spondylitis, Chronic Lyme disease, Complex regional pain syndrome, Amplified musculoskeletal pain syndrome, Reflex neurovascular dystrophy, Reflex sympathetic dystrophy, Dermatomyositis, Enthesitis-related arthritis, Eosinophilic fasciitis, Shulman's syndrome, Felty syndrome, Fibromyalgia, Inclusion body myositis, Juvenile Arthritis, Juvenile idiopathic arthritis, Juvenile rheumatoid arthritis, Juvenile dermatomyositis, Mixed connective tissue disease, Myalgic encephalomyelitis, Chronic fatigue syndrome, Myasthenia gravis, Myositis, Palindromic rheumatism, Hench-Rosenberg syndrome, Parry Romberg syndrome, POEMS syndrome, Polymyositis, Psoriatic arthritis, Reactive arthritis, Reiter's syndrome, Relapsing polychondritis, Chronic Atrophic polychondritis, Generalized chondromalacia, Meyenburg-Altherr-Uehlinger syndrome, Systemic chondromalacia, Retroperitoneal fibrosis, Rheumatic fever, Rheumatoid arthritis, Sarcoidosis, Schnitzler syndrome, Secondary Raynaud's phenomenon, Systemic Lupus Erythematosus, Lupus, Undifferentiated connective tissue disease, Anti-neutrophil cytoplasmic antibody-associated vasculitis, Eosinophilic granulomatosis with polyangiitis, Granulomatosis with polyangiitis, Churg-Strauss syndrome, Wegener's granulomatosis, Autoimmune Angioedema, Behcet's disease, Hughes-Stovin syndrome, Giant cell arteritis, Cranial arteritis, Temporal Arteritis, Kawasaki's disease, Lymph node syndrome, Mucocutaneous lymph node syndrome, Leukocytoclastic vasculitis, Urticarial vasculitis, Lupus vasculitis, Microscopic polyangiitis, Microscopic polyarteritis, Moyamoya-disease, Polyarteritis nodosa, Kussmaul-Maier disease, Panarteritis nodosa, Periarteritis nodosa, Polymyalgia rheumatica, Purpura rheumatica, Immunoglobulin A vasculitis, Anaphylactoid purpura, Henoch-Schonlein Purpura, Rheumatoid vasculitis, Angioneurotic edema, and Takayasu arteritis.

The heteroimmune disease or condition can be any heteroimmune disease or condition known to the person of skill or deemed suitable by the practitioner of skill. In certain embodiments, the heterommune disease or condition is selected from graft versus host disease, transplantation, transfusion, anaphylaxis, allergy, type I hypersensitivity, allergic conjunctivitis, allergic rhinitis, and atopic dermatitis.

The inflammatory disease or condition can be any inflammatory disease or condition known to the person of skill or deemed suitable by the practitioner of skill. In certain embodiments, the inflammatory disease or condition is selected from CNS inflammatory diseases or conditions, Encephalitis, Myelitis, Meningitis, Arachnoiditis, PNS inflammatory diseases or conditions, Neuritis, eye inflammatory diseases or conditions, Dacryoadenitis, Scleritis, Episcleritis, Keratitis, Retinitis, Chorioretinitis, Blepharitis, Conjunctivitis, Uveitis, ear inflammatory diseases or conditions, Otitis externa, Otitis media, Labyrinthitis, Mastoiditis, Cardiovascular inflammatory diseases or conditions, Carditis, Endocarditis, Myocarditis, Pericarditis, Vasculitis, Arteritis, Phlebitis, Capillaritis, Respiratory system inflammatory diseases or conditions, Sinusitis, Rhinitis, Pharyngitis, Laryngitis, Tracheitis, Bronchitis, Bronchiolitis, Pneumonitis, Pleuritis, Mediastinitis, Digestion system inflammatory diseases or conditions, Mouth inflammatory diseases or conditions, Stomatitis, Gingivitis, Gingivostomatitis, Glossitis, Tonsillitis, Sialadenitis/Parotitis, Cheilitis, Pulpitis, Gnathitis, Gastrointestinal tract inflammatory diseases or conditions, Esophagitis, Gastritis, Gastroenteritis, Enteritis, Colitis, Enterocolitis, Duodenitis, Ileitis, Caecitis, Appendicitis, Proctitis, Accessory digestive organs inflammatory diseases or conditions, Hepatitis, Ascending cholangitis, Cholecystitis, Pancreatitis, Peritonitis, Integumentary system inflammatory diseases or conditions, Dermatitis, Folliculitis, Cellulitis, Hidradenitis, Musculoskeletal system inflammatory diseases or conditions, Arthritis, Dermatomyositis, soft tissue inflammatory diseases or conditions, Myositis, Synovitis/Tenosynovitis, Bursitis, Enthesitis, Fasciitis, Capsulitis, Epicondylitis, Tendinitis, Panniculitis, steochondritis: Osteitis/Osteomyelitis, Spondylitis, Periostitis, Chondritis, Urinary system inflammatory diseases or conditions, Nephritis, Glomerulonephritis, Pyelonephritis, Ureteritis, Cystitis, Urethritis, Reproductive system inflammatory diseases or conditions, ophoritis, Salpingitis, Endometritis, Parametritis, Cervicitis, Vaginitis, Vulvitis, Mastitis, Orchitis, Epididymitis, Prostatitis, Seminal vesiculitis, Balanitis, Posthitis, Balanoposthitis, Chorioamnionitis, Funisitis, Omphalitis, Endocrine system inflammatory diseases or conditions, Insulitis, Hypophysitis, Thyroiditis, Parathyroiditis, Adrenalitis, Lymphatic system inflammatory diseases or conditions, Lymphangitis, and Lymphadenitis.

Combination Treatments

The GLP-1R agonist compositions described herein can also be used in combination with other well-known therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

In certain instances, it may be appropriate to administer at least one GLP-1R agonist described herein in combination with another therapeutic agent. By way of example only, if one of the side effects experienced by a patient upon receiving one of the GLP-1R agonists described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis of the attending physicians and their judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the skilled physician after evaluation of the disease being treated and the condition of the patient.

It is known to those of skill in the art that therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease or condition being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound of Formula (I), described herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life, and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. The compounds and compositions can be administered to a subject during or as soon as possible after the onset of the symptoms. The administration of the compounds can be initiated within the first 48 hours of the onset of the symptoms, within the first 6 hours of the onset of the symptoms, or within 3 hours of the onset of the symptoms. The initial administration can be via any route practical, such as, for example, an intravenous injection, a bolus injection, infusion over 5 minutes to about 5 hours, a pill, a capsule, transdermal patch, buccal delivery, and the like, or combination thereof. A compound should be administered as soon as is practicable after the onset of a disease or condition is detected or suspected, and for a length of time necessary for the treatment of the disease, such as, for example, from about 1 month to about 3 months. The length of treatment can vary for each subject, and the length can be determined using the known criteria. For example, the compound or a formulation containing the compound can be administered for at least 2 weeks, between about 1 month to about 5 years, or from about 1 month to about 3 years.

Exemplary Therapeutic Agents for Use in Combination with a GLP-IR Agonists

Where the subject is suffering from or at risk of suffering from an autoimmune disease or an inflammatory disease, a GLP-1R agonists can be used in with one or more of second therapeutic agents in any combination.

A GLP-1R agonist can be used in with one or more of second therapeutic agents in any combination. In certain embodiments, the second agent is an alpha-glucosidase agonists. In certain embodiments, the second agent is miglitol or acarbose. In certain embodiments, the second agent is an amylin analog. In certain embodiments, the second agent is pramlintide. In certain embodiments, the second agent is dipeptidyl peptidase 4 inhibitor. In certain embodiments, the second agent is selected from sitagliptin, linagliptin, saxagliptin, and alogliptin. In certain embodiments, the second agent is an incretin mimetic. In certain embodiments, the second agent is selected from liraglutide, semaglutine, dulaglutide, tirzepatide, exenatide, albiglutide, and lixisenatide. In certain embodiments, the second agent is insulin. In certain embodiments, the second agent is selected from insulin, insulin degludec, insulin glargine, insulin detemir, insulin lispro, insulin isophane, insulin aspart, insulin glulisine, and insulin zinc. In certain embodiments, the second agent is a meglitinide. In certain embodiments, the second agent is selected from repaglinide and nateglinide. In certain embodiments, the second agent is teplizumab. In certain embodiments, the second agent is a non-sulfonylurea. In certain embodiments, the second agent is metformin. In certain embodiments, the second agent is an SGLT-2 inhibitor. In certain embodiments, the second agent is empagliflozin, canagliflozin, dapagliflozin, ertugliflozin, or bexagliflozin. In certain embodiments, the second agent is a sulfonylurea. In certain embodiments, the second agent is glimepiride, glipizide, tolazamide, tolbutamide, glyburide, or chlorpropamide. In certain embodiments, the second agent is a thiazolidinedione. In certain embodiments, the second agent is pioglitazone or rosiglitazone.

Kits/Articles of Manufacture

For use in the therapeutic applications described herein, kits and articles of manufacture are also described herein. Such kits can include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. The containers can be formed from a variety of materials such as glass or plastic.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease, disorder, or condition that would benefit by GLP-1R agonists, or in which GLP-IR is a mediator or contributor to the symptoms or cause.

For example, the container(s) can include one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically may include one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

In certain embodiments, the pharmaceutical compositions can be presented in a pack or dispenser device which can contain one or more unit dosage forms containing a compound provided herein. The pack can for example contain metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions containing a compound provided herein formulated in a compatible pharmaceutical carrier can also be prepared, placed in an appropriate container, and labeled for treatment of an indicated condition.

EXAMPLES

| Abbreviation | Term |
|---|---|
| aq = | aqueous |
| Boc = | tert-butyloxycarbonyl |
| t-BuOH = | tertiary butanol |
| DCE = | 1,2-dichloroethane |
| DCM = | dichloromethane |
| DIAD = | diisopropyl azodicarboxylate |
| DIEA or DIPEA = | N,N-diisopropylethylamine |
| DMAP = | dimethylaminopyridine |
| DMF = | dimethylformamide |
| DMSO = | dimethylsulfoxide |
| ESI = | electron spray ionization |
| EA = | ethyl acetate |
| g = | gram |
| HCl = | hydrogen chloride |
| HPLC = | high performance liquid chromatography |
| hr = | hour |
| $^1H$ NMR = | proton nuclear magnetic resonance |
| IPA = | isopropyl alcohol |
| KOAc = | potassium acetate |
| LC-MS = | liquid chromatography mass spectroscopy |
| M = | molar |
| MeCN = | acetonitrile |
| MeOH = | methanol |
| mg = | milligram |
| min = | minute |
| ml = | milliliter |
| mM = | millimolar |
| mmol = | millimole |
| m.p. = | melting point |
| MS = | mass spectrometry |
| m/z = | mass-to-charge ratio |
| N = | normal |
| NIS = | N-iodosuccinimide |
| nM = | nanomolar |
| nm = | nanometer |
| $Pd(dppf)Cl_2$ = | [1,1'-Bis(diphenylphosphino)ferrocene]dichloropalladium(II) |
| PE = | petroleum ether |
| PyBOP = | benzotriazol-1-yl-oxytripyrrolidinophosphonium hexafluorophosphate |
| quant. = | quantitative |
| RP = | reverse phase |
| rt or r.t. = | room temperature |
| Sat. = | saturated |
| TEA = | triethylamine |
| TFA = | trifluoroacetic acid |
| μL = | microliter |
| μM = | Micromolar |

Intermediates

Intermediate 1-1

5-ethynyl-4-fluoro-1-methyl-1H-indazole

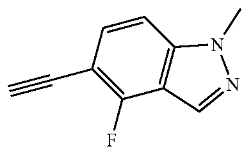

Step 1: 4-fluoro-1-methyl-5-((trimethylsilyl) ethynyl)-1H-indazole

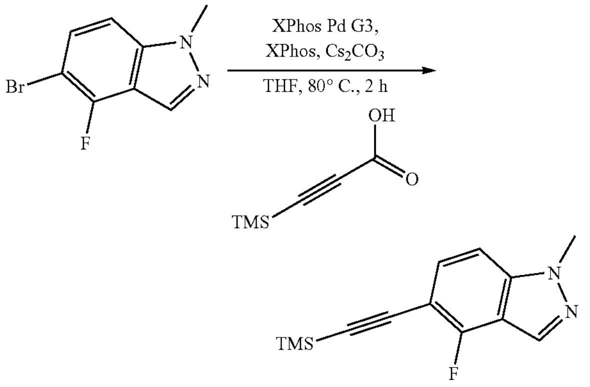

To a solution of 5-bromo-4-fluoro-1-methyl-1H-indazole (300 mg, 1.31 mmol, 1 eq) and 3-(trimethylsilyl) propiolic acid (558.85 mg, 3.93 mmol, 3 eq) in THF (6 mL) was added $Cs_2CO_3$ (853.49 mg, 2.62 mmol, 2 eq), XPhos (124.88 mg, 261.95 μmol, 0.2 eq) and XPhos Pd G3 (110.87 mg, 130.98 μmol, 0.1 eq). The mixture was stirred at 80° C. for 2 hours under $N_2$ atmosphere. LCMS indicated the reaction was completed. The reaction mixture was poured into saturated EDTA solution (20 mL) and EtOAc (30 mL) and stirred for 1 hour, and then extracted with EtOAc (30 mL*2). The organic layers were combined and washed with water (25 mL*2), saturated brine (25 mL*2), dried over $Na_2SO_4$, filtered, concentrated under reduced pressure. The residue was purified by column chromatography ($SiO_2$, Petroleum ether/Ethyl acetate=100/1 to 5/1) to afford 4-fluoro-1-methyl-5-((trimethylsilyl) ethynyl)-1H-indazole (275 mg, 1.12 mmol, 42.61% yield). LC-MS (ES+, m/z): 247.2 [(M+H)$^+$]; Rt=0.616 min.

Step 2: 5-ethynyl-4-fluoro-1-methyl-1H-indazole

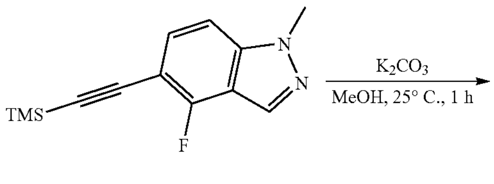

-continued

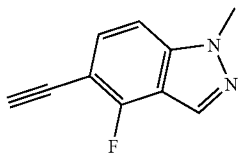

To a solution of 4-fluoro-1-methyl-5-((trimethylsilyl)ethynyl)-1H-indazole (275 mg, 1.12 mmol, 1 eq) in MeOH (6 mL) was added $K_2CO_3$ (308.55 mg, 2.23 mmol, 2 eq). The mixture was stirred at 25° C. for 1 hour. LCMS indicated the reaction was completed. The reaction mixture was diluted with $H_2O$ (15 mL) and extracted with EtOH (25 mL*3). The organic layers were combined, washed with water (25 mL*2), saturated brine (20 mL*2), dried over $Na_2SO_4$, filtered, concentrated under reduced pressure to afford 5-ethynyl-4-fluoro-1-methyl-1H-indazole (190 mg, crude). LC-MS (ES+, m/z): 175.2 [(M+H)$^+$]; Rt=0.456 min.

Scheme Intermediate 3-1

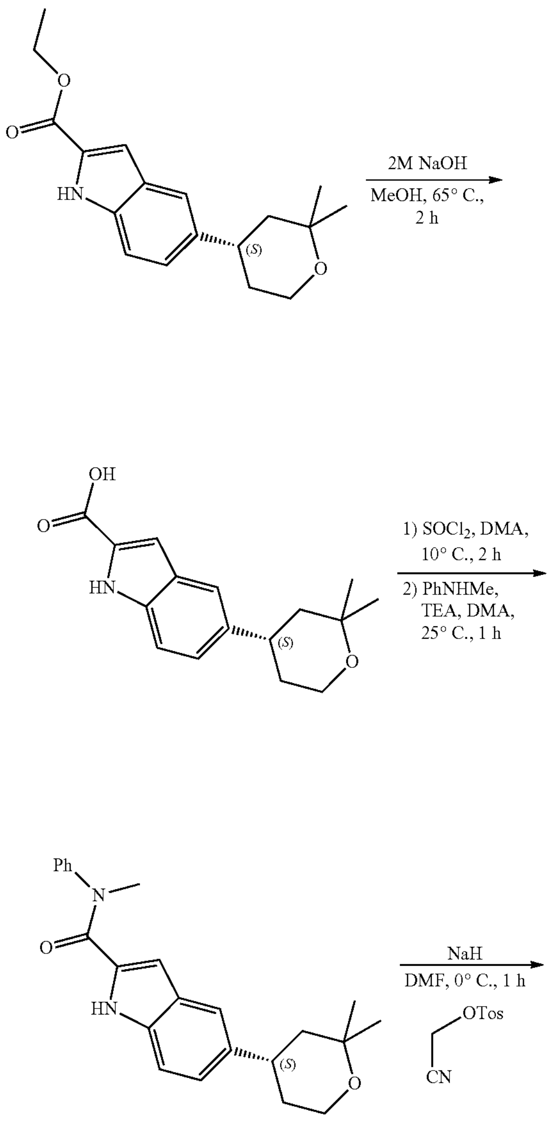

-continued

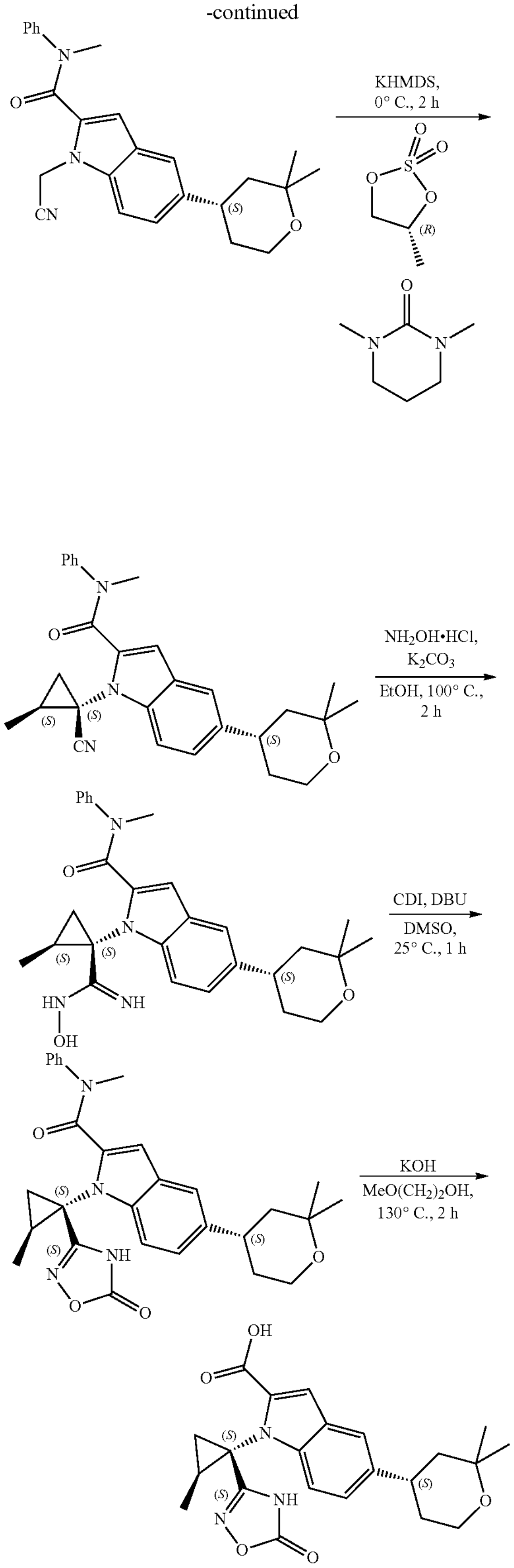

Intermediate 3-1

5-((S)-2,2-dimethyltetrahydro-2H-pyran-4-yl)-1-((1S,2S)-2-methyl-1-(5-oxo-4,5-dihydro-1, 2, 4-oxadiazol-3-yl)cyclopropyl)-1H-indole-2-carboxylic acid

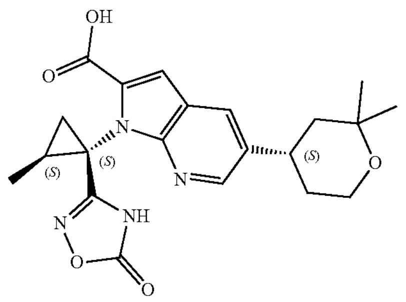

Step 1: (S)-5-(2, 2-dimethyltetrahydro-2H-pyran-4-yl)-1H-indole-2-carboxylic acid

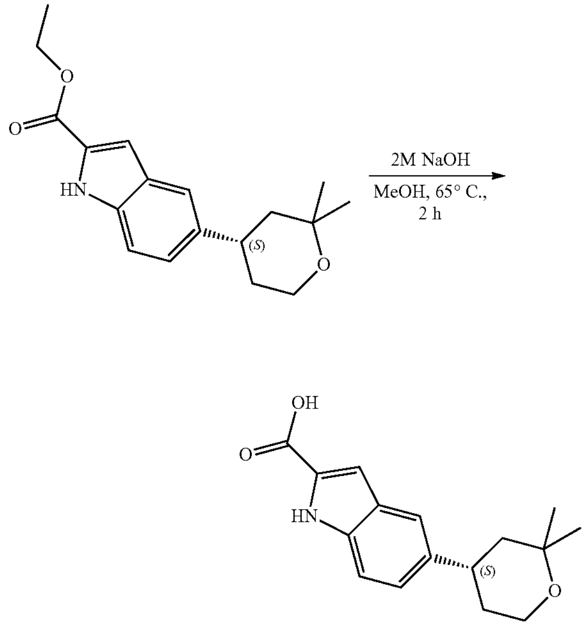

To a solution of ethyl(S)-5-(2, 2-dimethyltetrahydro-2H-pyran-4-yl)-1H-indole-2-carboxylate (5 g, 16.59 mmol, 1 eq) in MeOH (75 mL), NaOH (2 M, 18.33 mL, 2.21 eq) was added dropwise, the mixture was stirred at 65° C. for 2 hours. LCMS showed reaction was completed. The reaction solution was cooled to 15° C., was added to water (35 mL) and adjusted to pH=1 with 5N hydrochloric acid (7.5 mL). The precipitated solid was collected by filtration. The obtained solid was washed with water (60 mL) and dried under reduced pressure to give(S)-5-(2, 2-dimethyltetrahydro-2H-pyran-4-yl)-1H-indole-2-carboxylic acid (3.9 g, crude). LC-MS (ES+, m/z): 274.3 [(M+H)$^+$]; Rt=0.430 min.

Step 2: (S)-5-(2, 2-dimethyltetravhydro-2H-pyran-4-yl)-N-methyl-N-phenyl-1H-indole-2-carboxamide

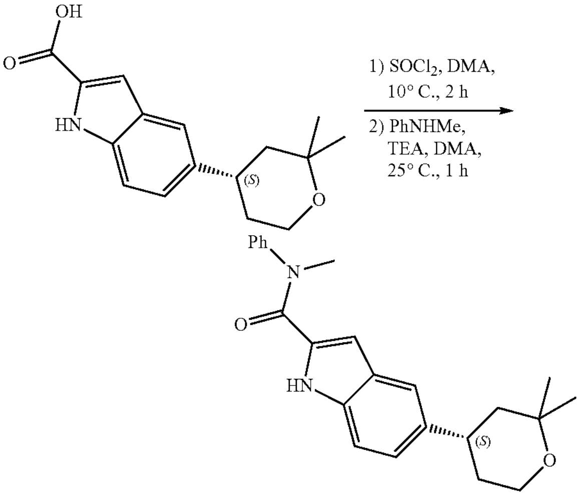

To a solution of(S)-5-(2, 2-dimethyltetrahydro-2H-pyran-4-yl)-1H-indole-2-carboxylic acid (3.9 g, 14.27 mmol, 1 eq) in DMA (40 mL), $SOCl_2$ (2.04 g, 17.12 mmol, 1.24 mL, 1.2 eq) was added dropwise at 10° C. After stirring for 2 hours, PhNHMe (1.83 g, 17.12 mmol, 1.86 mL, 1.2 eq) and TEA (3.47 g, 34.24 mmol, 4.77 mL, 2.4 eq) were added dropwise at 10° C. The mixture was stirred at 25° C. for 1 hour. LCMS showed reaction was completed. The reaction mixture was added dropwise to $NaHCO_3$ (60 mL), and the precipitated solid was collected by filtration. The obtained solid was washed with water (150 mL) and dried under reduced pressure to give(S)-5-(2, 2-dimethyltetrahydro-2H-pyran-4-yl)-N-methyl-N-phenyl-1H-indole-2-carboxamide (3.9 g, crude). LC-MS (ES+, m/z): 363.2 [(M+H)$^+$]; Rt=0.554 min.

Step 3: (S)-1-(cyanomethyl)-5-(2, 2-dimethyltetrahydro-2H-pyran-4-yl)-N-methyl-N-phenyl-1H-indole-2-carboxamide

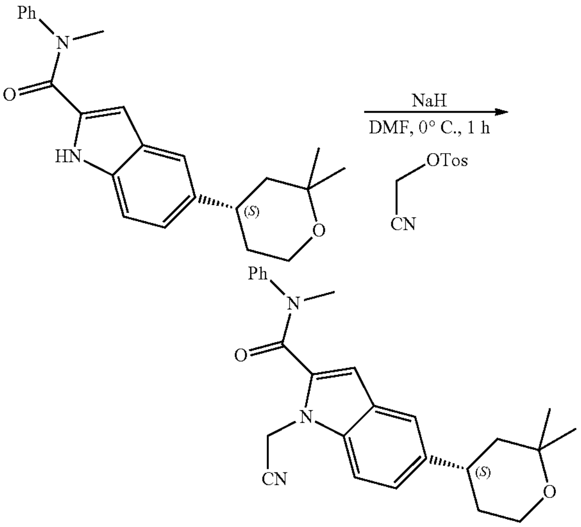

To a solution of(S)-5-(2, 2-dimethyltetrahydro-2H-pyran-4-yl)-N-methyl-N-phenyl-1H-indole-2-carboxamide (3.9 g, 10.76 mmol, 1 eq) in DMF (40 mL) was added NaH (1.29 g, 32.28 mmol, 60% purity, 3 eq) at 0° C. under $N_2$, the mixture was stirred for 0.5 hour, and then cyanomethyl 4-methylbenzenesulfonate (4.55 g, 21.52 mmol, 2 eq) was added. The mixture was stirred at 0° C. for 0.5 hour under $N_2$. LCMS indicated the reaction was completed. The mixture was added dropwise to $H_2O$ (100 mL) and then extracted with DCM (100 mL*2). The organic layers were combined, washed with water (150 mL*2), saturated brine (150 mL), dried over $Na_2SO_4$, filtered, and concentrated to give crude product. The crude product was purified by chromatography on silica gel (Petroleum ether: Ethyl acetate=100/1 to 1/5) to give(S)-1-(cyanomethyl)-5-(2, 2-dimethyltetrahydro-2H-pyran-4-yl)-N-methyl-N-phenyl-1H-indole-2-carboxamide (3.75 g, 9.34 mmol, 86.81% yield). LC-MS (ES+, m/z): 402.3 [$(M+H)^+$]; Rt=0.542 min.

Step 4: 1-((1S,2S)-1-cyano-2-methylcyclopropyl)-5-((S)-2, 2-dimethyltetrahydro-2H-pyran-4-yl)-N-methyl-N-phenyl-1H-indole-2-carboxamide

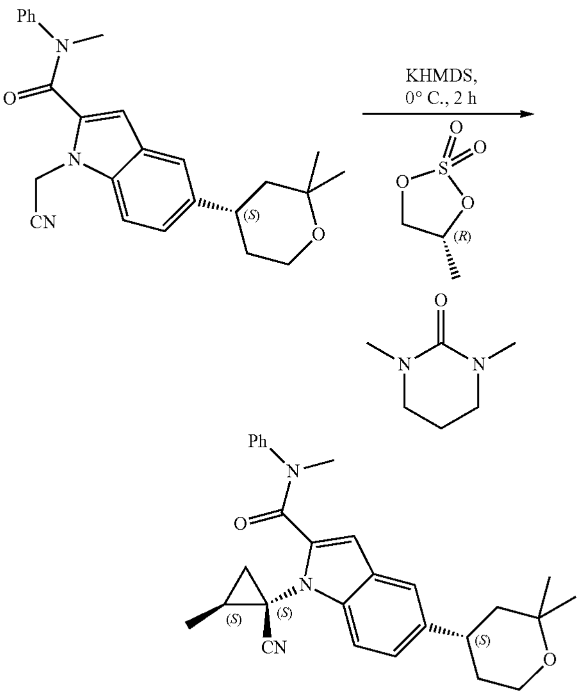

To a solution of(S)-1-(cyanomethyl)-5-(2, 2-dimethyltetrahydro-2H-pyran-4-yl)-N-methyl-N-phenyl-1H-indole-2-carboxamide (2.7 g, 6.72 mmol, 1 eq) and (R)-4-methyl-1, 3, 2-dioxathiolane 2, 2-dioxide (2.79 g, 20.17 mmol, 3 eq) in 1, 3-dimethyltetrahydropyrimidin-2 (1H)-one (20 mL), KHMDS (1 M, 26.90 mL, 4 eq) was added dropwise at 0° C. under $N_2$. The mixture was stirred at 0° C. for 2 hours. LCMS showed reaction was completed. The mixture was added dropwise to saturated $NH_4Cl$ (100 mL), and then extracted with EtOAc (100 mL*3). The organic layers were combined, washed with water (150 mL*2), saturated brine (200 mL), dried over $Na_2SO_4$, filtered, and concentrated to give crude product. The crude product was purified by chromatography on silica gel (Petroleum ether: Ethyl acetate=100/1 to 1/3). The residue was purified by prep-TLC ($SiO_2$, Petroleum ether: Ethyl acetate=1:1) to give 1-((1S, 2S)-1-cyano-2-methylcyclopropyl)-5-((S)-2, 2-dimethyltetrahydro-2H-pyran-4-yl)-N-methyl-N-phenyl-1H-indole-2-carboxamide (2 g, 4.46 mmol, 66.27% yield). LC-MS (ES+, m/z): 442.4 [$(M+H)^+$]; Rt=0.577 min.

Step 5: 5-((S)-2, 2-dimethyltetrahydro-2H-pyran-4-yl)-1-((1S,2S)-1-(N-hydroxycarbamimidoyl)-2-methylcyclopropyl)-N-methyl-N-phenyl-1H-indole-2-carboxamide

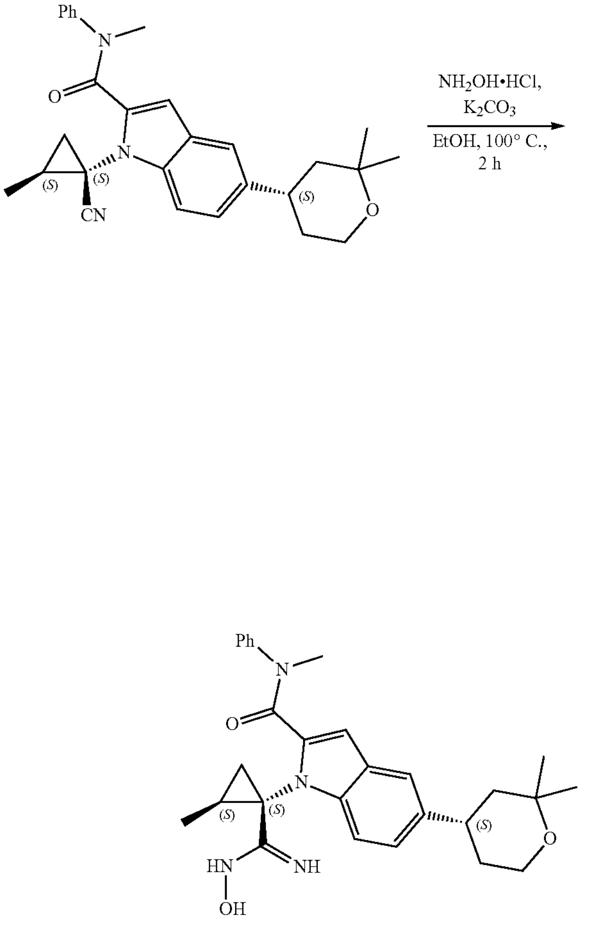

To a solution of 1-((1S,2S)-1-cyano-2-methylcyclopropyl)-5-((S)-2, 2-dimethyltetrahydro-2H-pyran-4-yl)-N-methyl-N-phenyl-1H-indole-2-carboxamide (2 g, 4.53 mmol, 1 eq) and $K_2CO_3$ (3.44 g, 24.91 mmol, 5.5 eq) in EtOH (20 mL) was added $NH_2OH \cdot HCl$ (1.57 g, 22.65 mmol, 5 eq). The mixture was stirred at 100° C. for 2 hours. LCMS indicated the reaction was completed. The mixture was added dropwise to $H_2O$ (50 mL), and then extracted with EtOAc (50 mL*3). The organic layers were combined, washed with water (100 mL*2), saturated brine (100 mL), dried over $Na_2SO_4$, filtered, and concentrated to give 5-((S)-2, 2-dimethyltetrahydro-2H-pyran-4-yl)-1-((1S,2S)-1-(N-hydroxycarbamimidoyl)-2-methylcyclopropyl)-N-methyl-N-phenyl-1H-indole-2-carboxamide (2.1 g, crude). LC-MS (ES+, m/z): 475.4 [$(M+H)^+$]; Rt=0.432 min.

Step 6: 5-((S)-2, 2-dimethyltetrahydro-2H-pyran-4-yl)-N-methyl-1-((1S,2S)-2-methyl-1-(5-oxo-4, 5-dihydro-1, 2, 4-oxadiazol-3-yl)cyclopropyl)-N-phenyl-1H-indole-2-carboxamide

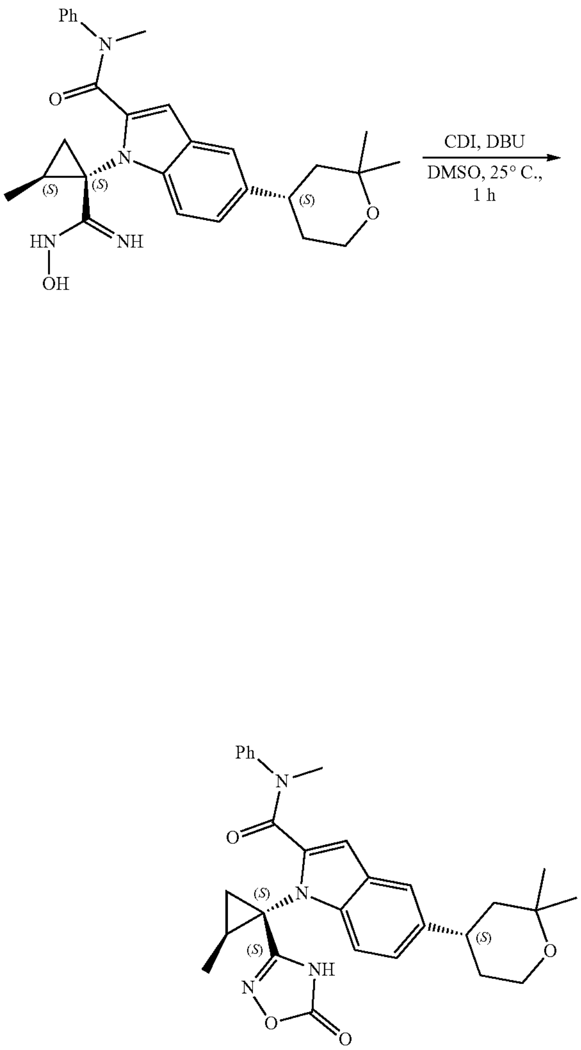

To a solution of 5-((S)-2, 2-dimethyltetrahydro-2H-pyran-4-yl)-1-((1S,2S)-1-(N-hydroxycarbamimidoyl)-2-methylcyclopropyl)-N-methyl-N-phenyl-1H-indole-2-carboxamide (2.1 g, 4.42 mmol, 1 eq) in DMSO (21 mL) was added DBU (1.68 g, 11.06 mmol, 1.67 mL, 2.5 eq) and CDI (1.43 g, 8.85 mmol, 2 eq). The mixture was stirred at 25° C. for 1 hour. LCMS indicated the reaction was completed. The mixture was added to $H_2O$ (50 mL), and then extracted with EtOAc (50 mL*3). The organic layers were combined, washed with water (100 mL*2), saturated brine (100 mL), dried over $Na_2SO_4$, filtered, and concentrated to give crude product. The residue was purified by column chromatography ($SiO_2$, Petroleum ether/Ethyl acetate=100/1 to 1/3) to give 5-((S)-2, 2-dimethyltetrahydro-2H-pyran-4-yl)-N-methyl-1-((1S,2S)-2-methyl-1-(5-oxo-4,5-dihydro-1, 2, 4-oxadiazol-3-yl)cyclopropyl)-N-phenyl-1H-indole-2-carboxamide (2 g, 3.80 mmol, 85.78% yield). LC-MS (ES+, m/z): 501.2 [$(M+H)^+$]; Rt=0.612 min.

Step 7: 5-((S)-2, 2-dimethyltetrahydro-2H-pyran-4-yl)-1-((1S,2S)-2-methyl-1-(5-oxo-4,5-dihydro-1, 2, 4-oxadiazol-3-yl)cyclopropyl)-1H-indole-2-carboxylic acid

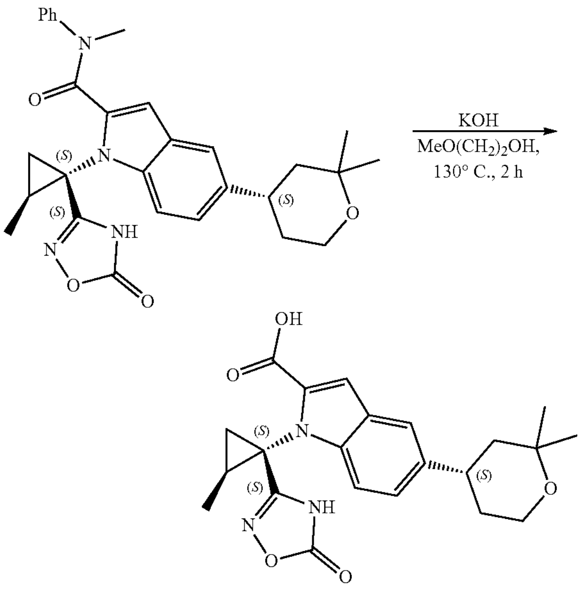

To a solution of 5-((S)-2, 2-dimethyltetrahydro-2H-pyran-4-yl)-N-methyl-1-((1S,2S)-2-methyl-1-(5-oxo-4,5-dihydro-1, 2, 4-oxadiazol-3-yl)cyclopropyl)-N-phenyl-1H-indole-2-carboxamide (2 g, 4.00 mmol, 1 eq) in 2-methoxyethanol (10 mL) was added KOH (2.24 g, 39.95 mmol, 10 eq). The mixture was stirred at 130° C. for 2 hours. LCMS indicated the reaction was completed. The reaction mixture was adjusted to pH=4 with 1N HCl, and then filtered. The obtained solid was washed with water (30 mL) and dried under reduced pressure to give 5-((S)-2, 2-dimethyltetrahydro-2H-pyran-4-yl)-1-((1S,2S)-2-methyl-1-(5-oxo-4,5-dihydro-1, 2, 4-oxadiazol-3-yl)cyclopropyl)-1H-indole-2-carboxylic acid (1 g, crude), which was used directly for the next step without further purification. $^1H$ NMR (400 MHz, DMSO-$d_6$) δ=13.35-12.14 (m, 1H), 7.57-7.46 (m, 1H), 7.40-7.04 (m, 4H), 3.71 (br d, J=6.0 Hz, 2H), 3.02 (dtd, J=4.2, 8.3, 12.2 Hz, 1H), 2.03-1.37 (m, 8H), 1.36-1.09 (m, 8H). LC-MS (ES+, m/z): 412.3 [$(M+H)^+$]; Rt=0.475 min.

Step 8: 5-((S)-2, 2-dimethyltetrahydro-2H-pyran-4-yl)-1-((1S,2S)-2-methyl-1-(5-oxo-4,5-dihydro-1, 2, 4-oxadiazol-3-yl)cyclopropyl)-1H-indole-2-carboxylic acid

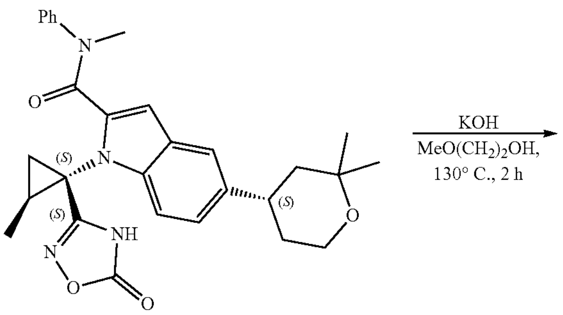

-continued

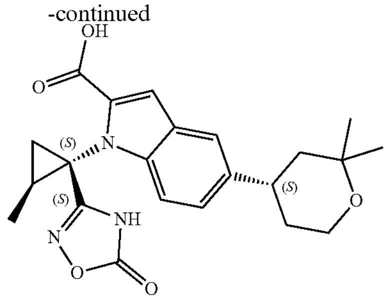

To a solution of 5-((S)-2, 2-dimethyltetrahydro-2H-pyran-4-yl)-N-methyl-1-((1S,2S)-2-methyl-1-(5-oxo-4,5-dihydro-1, 2, 4-oxadiazol-3-yl)cyclopropyl)-N-phenyl-1H-indole-2-carboxamide (2 g, 4.00 mmol, 1 eq) in 2-methoxyethanol (10 mL) was added KOH (2.24 g, 39.95 mmol, 10 eq). The mixture was stirred at 130° C. for 2 hours. LCMS indicated the reaction was completed. The reaction mixture was adjusted to pH-4 with 1N HCl, and then filtered. The obtained solid was washed with water (30 mL) and dried under reduced pressure to give 5-((S)-2, 2-dimethyltetrahydro-2H-pyran-4-yl)-1-((1S,2S)-2-methyl-1-(5-oxo-4,5-dihydro-1, 2, 4-oxadiazol-3-yl)cyclopropyl)-1H-indole-2-carboxylic acid (1 g, crude). 1H NMR (400 MHz, DMSO-$d_6$) δ=13.35-12.14 (m, 1H), 7.57-7.46 (m, 1H), 7.40-7.04 (m, 4H), 3.71 (br d, J=6.0 Hz, 2H), 3.02 (dtd, J=4.2, 8.3, 12.2 Hz, 1H), 2.03-1.37 (m, 8H), 1.36-1.09 (m, 8H). LC-MS (ES+, m/z): 412.3 [$(M+H)^+$]; Rt=0.475 min.

Intermediate 5-1

4-fluoro-1-methyl-1H-indazole-5-carboxylic acid

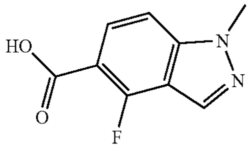

Step 1: methyl 4-fluoro-1-methyl-1H-indazole-5-carboxylate

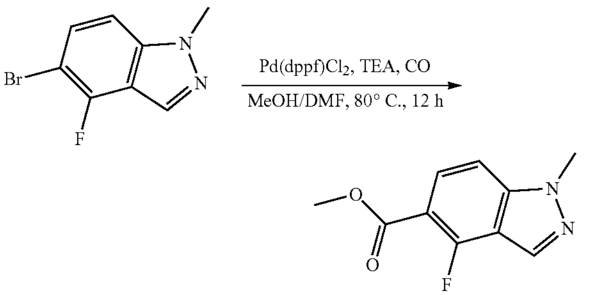

To a solution of 5-bromo-4-fluoro-1-methyl-1H-indazole (500 mg, 2.18 mmol, 1 eq) in MeOH (15 mL) and DMF (5 mL) was added $Pd(dppf)Cl_2$ (159.73 mg, 218.29 μmol, 0.1 eq) and TEA (2.21 g, 21.83 mmol, 10 eq). The mixture was stirred at 80° C. for 12 hours under CO of 15 psi. LCMS indicated the reaction was completed. The crude was added to sat. EDTA (30 mL) and EtOAc (50 mL) and stirred for 1 hour, extracted with EtOAc (50 mL*5). The combined layers were washed with water (30 mL), saturated brine (30 mL), filtered and concentrated. The crude product was purified by chromatography on silica gel (PE:EtOAc=1:1) to afford methyl 4-fluoro-1-methyl-1H-indazole-5-carboxylate (320 mg, 1.54 mmol, 70.41% yield). LC-MS (ES+, m/z): 209.1 [$(M+H)^+$]. Rt=0.407 min.

Step 2: 4-fluoro-1H-indazole-5-carboxylic acid

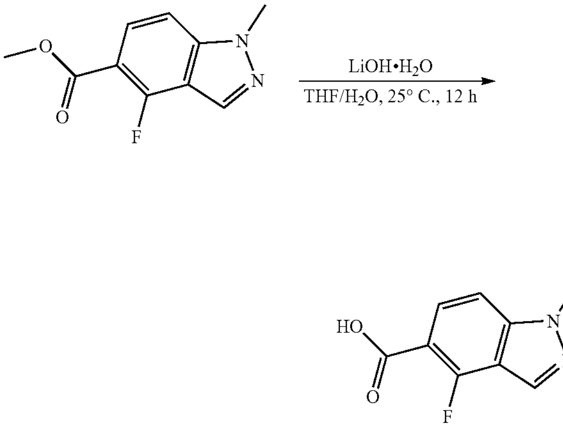

To a solution of methyl 4-fluoro-1-methyl-1H-indazole-5-carboxylate (120 mg, 576.40 μmol, 1 eq) in MeOH (0.4 mL), THF (1.2 mL) and $H_2O$ (0.4 mL) was added $LiOH \cdot H_2O$ (48.38 mg, 1.15 mmol, 2 eq). The mixture was stirred at 25° C. for 12 hours. LCMS indicated the reaction was completed. The crude was adjusted to pH=2 with 6N (HCl) (1 mL) and filtered to give 4-fluoro-1-methyl-1H-indazole-5-carboxylic acid (85 mg, crude). LC-MS (ES+, m/z): 195.1 [$(M+H)^+$]. Rt=0.320 min.

Intermediate 8-1 tert-butyl (S)-3-ethynyl-2-(4-fluoro-3,5-dimethylphenyl)-4-methyl-2,4,6,7-tetrahydro-5H-pyrazolo[4,3-c]pyridine-5-carboxylate

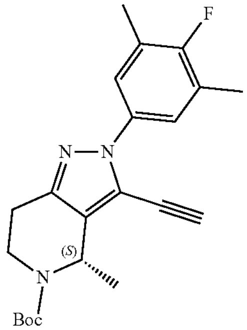

Step 1: tert-butyl (S)-2-(4-fluoro-3,5-dimethylphenyl)-4-methyl-3-((trimethylsilyl) ethynyl)-2,4,6,7-tetrahydro-5H-pyrazolo[4,3-c]pyridine-5-carboxylate

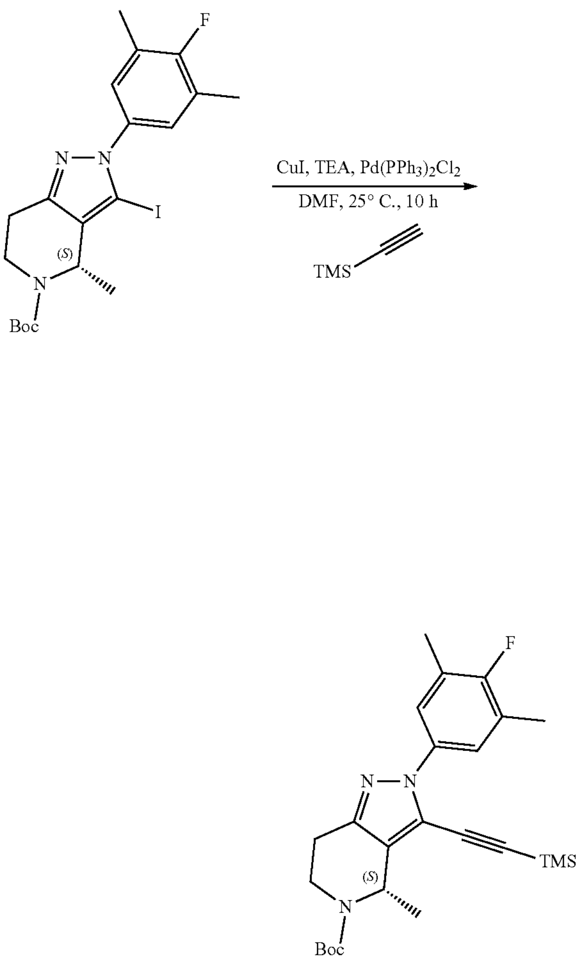

To a solution of tert-butyl (S)-2-(4-fluoro-3,5-dimethylphenyl)-3-iodo-4-methyl-2,4,6,7-tetrahydro-5H-pyrazolo [4,3-c]pyridine-5-carboxylate (500 mg, 1.03 mmol, 1 eq) and ethynyltrimethylsilane (607.12 mg, 6.18 mmol, 856.30 μL, 6 eq) in DMF (6 mL) was added TEA (312.74 mg, 3.09 mmol, 430.18 μL, 3 eq), $Pd(PPh_3)_2Cl_2$ (72.31 mg, 103.02 μmol, 0.1 eq) and CuI (39.24 mg, 206.04 μmol, 0.2 eq). The mixture was stirred at 25° C. for 10 hours under $N_2$ atmosphere. LCMS indicated the reaction was completed. The reaction mixture was poured into saturated EDTA solution (20 mL) and EtOAc (30 mL) and stirred for 1 hour, and then extracted with EtOAc (30 mL*2). The organic layers were combined and washed with water (25 mL*2), saturated brine (25 mL*2), dried over $Na_2SO_4$, filtered, concentrated under reduced pressure. The residue was purified by column chromatography ($SiO_2$, Petroleum ether/Ethyl acetate=0/1 to 20/1) to afford tert-butyl (S)-2-(4-fluoro-3,5-dimethylphenyl)-4-methyl-3-((trimethylsilyl) ethynyl)-2, 4,6,7-tetrahydro-5H-pyrazolo[4,3-c]pyridine-5-carboxylate (370 mg, 812.05 μmol, 78.82% yield). LC-MS (ES+, m/z): 456.3 [$(M+H)^+$]; Rt=0.827 min.

Step 2: tert-butyl (S)-3-ethynyl-2-(4-fluoro-3,5-dimethylphenyl)-4-methyl-2,4,6,7-tetrahydro-5H-pyrazolo[4,3-c]pyridine-5-carboxylate

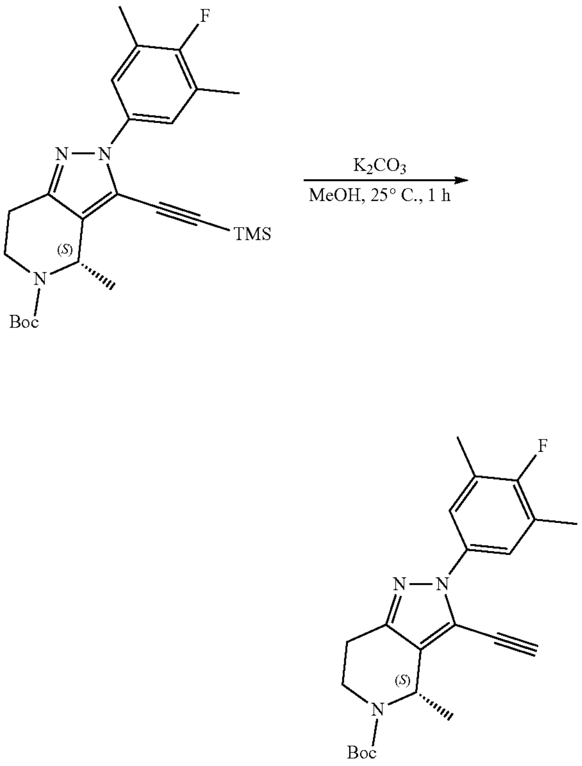

To a solution of tert-butyl (S)-2-(4-fluoro-3,5-dimethylphenyl)-4-methyl-3-((trimethylsilyl) ethynyl)-2,4,6,7-tetrahydro-5H-pyrazolo[4,3-c]pyridine-5-carboxylate (370 mg, 812.05 μmol, 1 eq) in MeOH (8 mL) was added $K_2CO_3$ (224.46 mg, 1.62 mmol, 2 eq). The mixture was stirred at 25° C. for 1 hour. LCMS indicated the reaction was completed. The reaction mixture was diluted with $H_2O$ (20 mL) and extracted with EtOAc (30 mL*3). The organic layers were combined, washed with water (25 mL*2), saturated brine (25 mL*2), dried over $Na_2SO_4$, filtered, concentrated under reduced pressure to afford tert-butyl (S)-3-ethynyl-2-(4-fluoro-3,5-dimethylphenyl)-4-methyl-2,4,6,7-tetrahydro-5H-pyrazolo[4,3-c]pyridine-5-carboxylate (300 mg, crude). LC-MS (ES+, m/z): 384.3 [$(M+H)^+$]; Rt=0.667 min.

Intermediate 10-1

4-fluoro-1-methyl-1H-indazol-5-amine

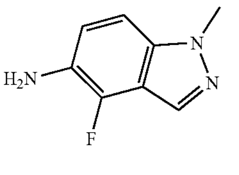

Step 1: tert-butyl (4-fluoro-1-methyl-1H-indazol-5-yl) carbamate

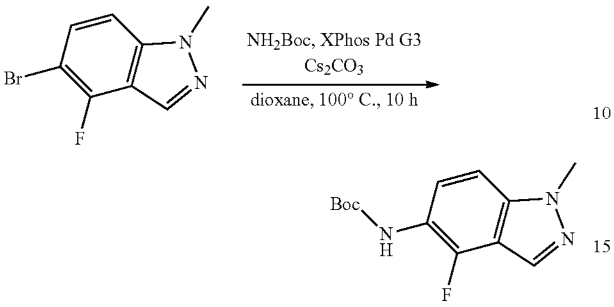

To a solution of 5-bromo-4-fluoro-1-methyl-1H-indazole (5 g, 21.83 mmol, 1 eq) and tert-butyl carbamate (3.84 g, 32.74 mmol, 1.5 eq) in dioxane (50 mL) was added XPhos Pd G3 (3.70 g, 4.37 mmol, 0.2 eq) and $Cs_2CO_3$ (14.22 g, 43.66 mmol, 2 eq). The mixture was stirred at 100° C. for 10 hours under $N_2$ atmosphere. LCMS indicated the reaction was completed. The residue was poured into saturated EDTA (150 mL) and ethyl acetate (150 mL), stirred for 1 hour. The aqueous phase was extracted with ethyl acetate (150 mL*2). The combined organic phase was washed with saturated brine (100 mL), dried with anhydrous $Na_2SO_4$, filtered, and concentrated in vacuum. The residue was purified by column chromatography ($SiO_2$, Petroleum ether/Ethyl acetate=1/0 to 30/1) to afford tert-butyl (4-fluoro-1-methyl-1H-indazol-5-yl) carbamate (4 g, 15.08 mmol, 69.07% yield). LC-MS (ES+, m/z): 266.1 [$(M+H)^+$]; Rt=1.615 min.

Step 2: 4-fluoro-1-methyl-1H-indazol-5-amine

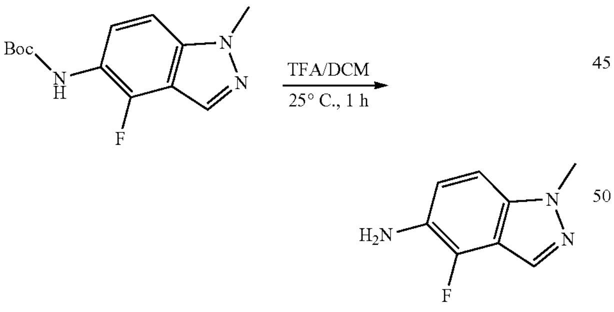

To a solution of tert-butyl (4-fluoro-1-methyl-1H-indazol-5-yl) carbamate (400 mg, 1.51 mmol, 1 eq) in DCM (4 mL) was added TFA (2 mL), the mixture was stirred for 1 hour at 25° C. LCMS showed reaction was completed. The reaction mixture was quenched by addition saturated $Na_2CO_3$ solution (100 mL) at 0° C., extracted with DCM (50 mL*3). The combined organic layers were washed with saturated brine (50 mL), dried over anhydrous $Na_2SO_4$, filtered, and concentrated under reduced pressure to give 4-fluoro-1-methyl-1H-indazol-5-amine (150 mg, crude). LC-MS (ES+, m/z): 166.2 [$(M+H)^+$]; Rt=0.156 min.

Intermediate 13-1

(S)-tert-butyl 2-(4-fluoro-3,5-dimethylphenyl)-4-methyl-3-(4,4,5,5-tetramethyl-1,3,2-dioxaborolan-2-yl)-6,7-dihydro-2H-pyrazolo[4,3-c]pyridine-5 (4H)-carboxylate

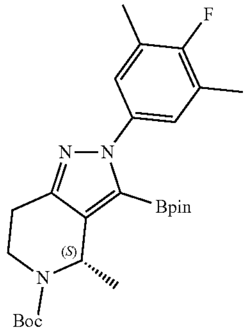

Step 1: (S)-tert-butyl 3-bromo-2-(4-fluoro-3,5-dimethylphenyl)-4-methyl-6,7-dihydro-2H-pyrazolo[4,3-c]pyridine-5 (4H)-carboxylate

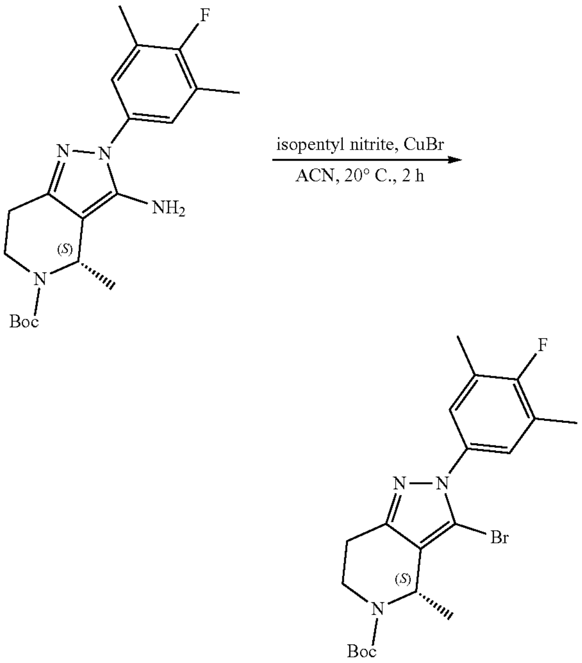

To a solution of(S)-tert-butyl 3-amino-2-(4-fluoro-3,5-dimethylphenyl)-4-methyl-6,7-dihydro-2H-pyrazolo[4,3-c] pyridine-5 (4H)-carboxylate (6 g, 16.02 mmol, 1 eq) in ACN (120 mL) was added isopentyl nitrite (6.57 g, 56.08 mmol, 3.5 eq) and CuBr (45.97 g, 320.47 mmol, 20 eq). The mixture was stirred at 20° C. for 2 hours. LCMS indicated the reaction was completed. The mixture was poured into water (200 mL) and extracted with ethyl acetate (200 mL*2). The organic layers were combined and washed with water (100 mL*2), saturated brine (100 mL*2), dried over $Na_2SO_4$, filtered, concentrated under reduced pressure. The residue was purified by prep-HPLC (column: Phenomenex luna C18250*150 mm*15 um; mobile phase: [$H_2O$ (0.1% TFA)-ACN]; gradient: 70%-100% B over 15.0 min) to afford(S)-tert-butyl 3-bromo-2-(4-fluoro-3,5-dimethylphenyl)-4-methyl-6,7-dihydro-2H-pyrazolo[4,3-c]pyridine-5 (4H)-carboxylate (4.2 g, 9.58 mmol, 59.80% yield). LC-MS (ES+, m/z): 438.0 [$(M+H)^+$]. Rt=0.702 min.

Step 2: (S)-tert-butyl 2-(4-fluoro-3,5-dimethylphenyl)-4-methyl-3-(4,4,5,5-tetramethyl-1,3,2-dioxaborolan-2-yl)-6,7-dihydro-2H-pyrazolo[4,3-c]pyridine-5 (4H)-carboxylate

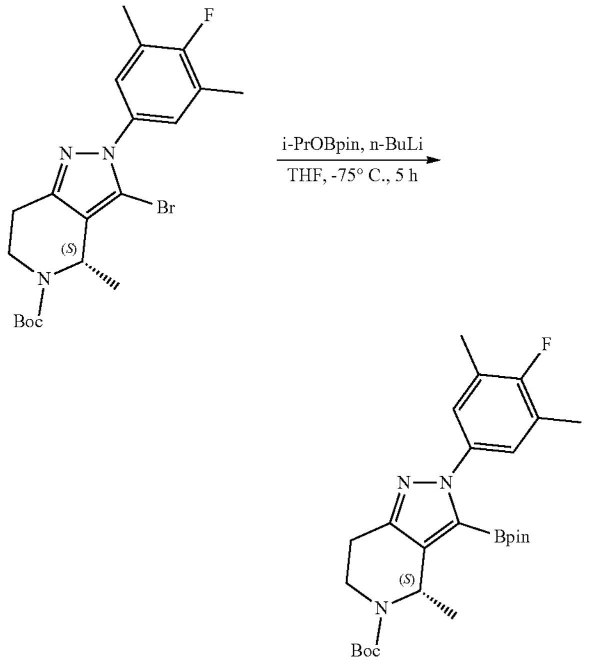

To a solution of(S)-tert-butyl 3-bromo-2-(4-fluoro-3,5-dimethylphenyl)-4-methyl-6,7-dihydro-2H-pyrazolo[4,3-c] pyridine-5 (4H)-carboxylate (3.7 g, 8.44 mmol, 1 eq) in THF (80 mL) was added n-BuLi (2.5 M, 1.1 eq) dropwise at −75° C. The mixture was stirred at −75° C. for 1 hour. 2-isopropoxy-4,4,5,5-tetramethyl-1,3,2-dioxaborolane (4.71 g, 25.32 mmol, 3 eq) was then added at −75° C. The reaction mixture was stirred at −75° C. for 4 hours. LCMS indicated the reaction was completed. The reaction mixture was quenched by addition saturated $NH_4Cl$ solution (100 mL) at 0° C., extracted with ethyl acetate (100 mL*3). The combined organic layers were washed with saturated brine (50 mL), dried over anhydrous $Na_2SO_4$, filtered, and concentrated under reduced pressure to give a residue. The residue was purified by prep-HPLC (column: Phenomenex luna C18 (250*70 mm, 15 um); mobile phase: [$H_2O$ (0.1% TFA)-ACN]; gradient: 75%-100% B over 23.0 min) to afford(S)-tert-butyl 2-(4-fluoro-3,5-dimethylphenyl)-4-methyl-3-(4,4,5,5-tetramethyl-1,3,2-dioxaborolan-2-yl)-6,7-dihydro-2H-pyrazolo[4,3-c]pyridine-5 (4H)-carboxylate (2 g, 4.12 mmol, 48.81% yield). LC-MS (ES+, m/z): 486.3 [$(M+H)^+$]. Rt=0.727 min.

Intermediate 13-2

4-fluoro-1-methyl-5-(4, 4, 5, 5-tetramethyl-1, 3, 2-dioxaborolan-2-yl)-1H-indazole

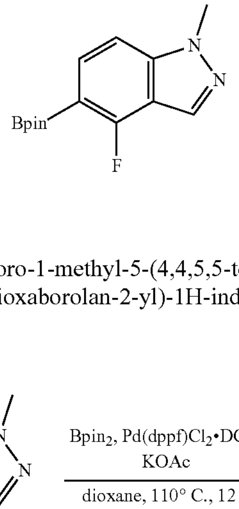

Step 1: 4-fluoro-1-methyl-5-(4,4,5,5-tetramethyl-1,3,2-dioxaborolan-2-yl)-1H-indazole

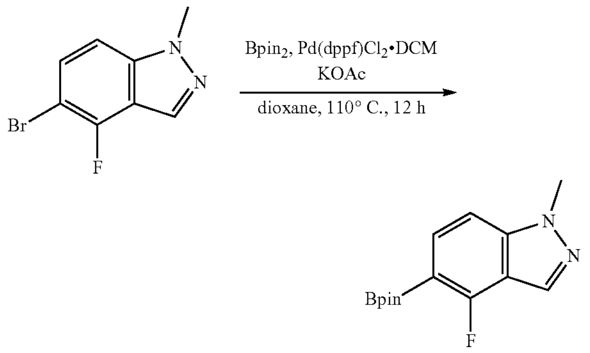

To a solution of 5-bromo-4-fluoro-1-methyl-indazole (6 g, 26.20 mmol, 1 eq) and 4,4,5,5-tetramethyl-2-(4,4,5,5-tetramethyl-1,3,2-dioxaborolan-2-yl)-1,3,2-dioxaborolane (13.30 g, 52.39 mmol, 2 eq) in dioxane (60 mL) was added KOAc (7.71 g, 78.59 mmol, 3 eq) and $Pd(dppf)Cl_2 \cdot DCM$ (2.14 g, 2.62 mmol, 0.1 eq). The mixture was stirred at 110° C. for 12 hours under $N_2$. LCMS showed the reaction was completed. The residue was poured into saturated EDTA (150 mL) and ethyl acetate (150 mL) and stirred for 1 hour. The aqueous phase was extracted with ethyl acetate (150 mL*2). The combined organic phase was washed with saturated brine (100 mL), dried with anhydrous $Na_2SO_4$, filtered, and concentrated in vacuum. The residue was purified by prep-HPLC (FA condition column: Phenomenex luna C18 250*150 mm*15 um; mobile phase: [$H_2O$-ACN]; gradient: 25%-70% B over 30.0 min) to give 4-fluoro-1-methyl-5-(4,4,5,5-tetramethyl-1,3,2-dioxaborolan-2-yl) indazole (3.8 g, 13.76 mmol, 52.54% yield). 1H NMR (400 MHz, DMSO-$d_6$) δ=8.15 (s, 1H), 7.59-7.54 (m, 1H), 7.49-7.45 (m, 1H), 4.07 (s, 3H), 1.32-1.30 (m, 12H). LC-MS (ES+, m/z): 277.3 [$(M+H)^+$]. Rt=0.536 min.

Intermediate 14-1

2-bromo-1-(1-methyl-1H-indazol-5-yl) propan-1-one

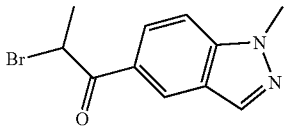

Step 1: 1-(1-methyl-1H-indazol-5-yl) propan-1-one

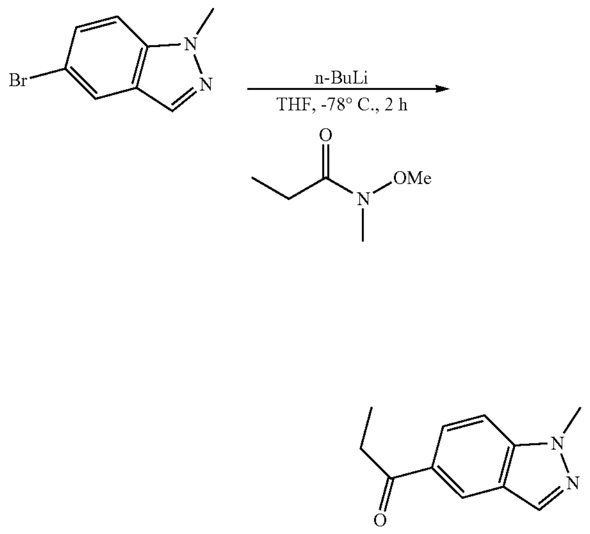

To a solution of 5-bromo-1-methyl-1H-indazole (3 g, 14.21 mmol, 1 eq) in THF (20 mL) was added n-BuLi (2.5 M, 11.37 mL, 2 eq) dropwise at −78° C. The mixture was stirred at −78° C. for 0.5 hour. N-methoxy-N-methylpropionamide (3.33 g, 28.43 mmol, 2 eq) as solution in THF (10 mL) was then added dropwise. The mixture was stirred at −78° C. for 1.5 hours. LCMS showed the reaction was completed. The residue was poured into saturated $NH_4Cl$ solution (400 mL) and extracted with ethyl acetate (200 mL*3). The combined organic phase was washed with saturated brine (250 mL), dried with anhydrous $Na_2SO_4$, filtered, and concentrated in vacuum. The residue was purified by column chromatography ($SiO_2$, Petroleum ether/Ethyl acetate=100/1 to 20/1) to give 1-(1-methyl-1H-indazol-5-yl) propan-1-one (1.77 g, 9.31 mmol, 65.50% yield). LC-MS (ES+, m/z): 189.1 [$(M+H)^+$]; Rt=0.403 min.

Step 2: 2-bromo-1-(1-methyl-1H-indazol-5-yl) propan-1-one

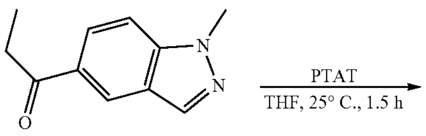

-continued

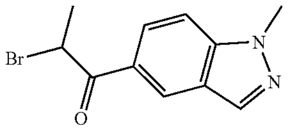

To a solution of 1-(1-methyl-1H-indazol-5-yl) propan-1-one (1 g, 5.31 mmol, 1 eq) in THF (10 mL) was added PTAT (2.60 g, 6.91 mmol, 1.3 eq). The mixture was stirred at 25° C. for 1.5 hours. LCMS showed the reaction was completed. The residue was poured into water (100 mL) and extracted with DCM (50 mL*3). The combined organic phase was washed with saturated brine (75 mL), dried over $Na_2SO_4$, filtered, and concentrated in vacuum. The residue was purified by column chromatography ($SiO_2$, Petroleum ether/ethyl acetate=1/0 to 3/1) to give 2-bromo-1-(1-methyl-1H-indazol-5-yl) propan-1-one (1.2 g, 4.45 mmol, 83.80% yield). LC-MS (ES+, m/z): 267.0 [$(M+H)^+$]; Rt=0.460 min.

Intermediate 15-2

(S)-tert-butyl 2-(4-fluoro-3,5-dimethylphenyl)-4-methyl-3-(4,4,5,5-tetramethyl-1,3,2-dioxaborolan-2-yl)-6,7-dihydro-2H-pyrazolo[4,3-c]pyridine-5 (4H)-carboxylate

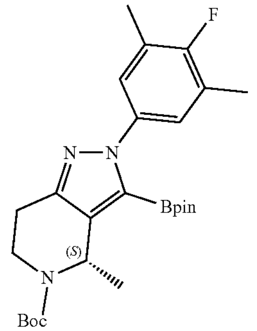

Step 1: (S)-tert-butyl 3-bromo-2-(4-fluoro-3,5-dimethylphenyl)-4-methyl-6,7-dihydro-2H-pyrazolo[4,3-c]pyridine-5 (4H)-carboxylate

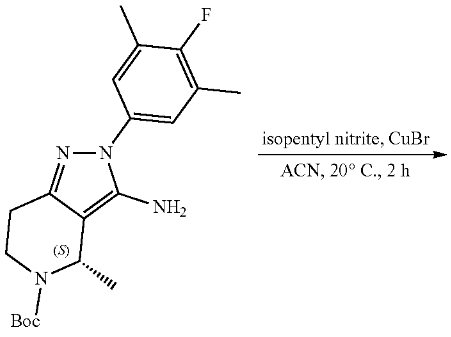

-continued

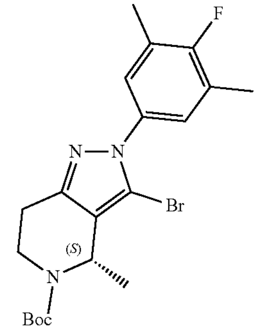

To a solution of(S)-tert-butyl 3-amino-2-(4-fluoro-3,5-dimethylphenyl)-4-methyl-6,7-dihydro-2H-pyrazolo[4,3-c] pyridine-5 (4H)-carboxylate (6 g, 16.02 mmol, 1 eq) in ACN (120 mL) was added isopentyl nitrite (6.57 g, 56.08 mmol, 3.5 eq) and CuBr (45.97 g, 320.47 mmol, 20 eq). The mixture was stirred at 20° C. for 2 hours. LCMS indicated the reaction was completed. The mixture was concentrated. The residue was purified by prep-HPLC (column: Phenomenex luna C18250*150 mm*15 um; mobile phase: [$H_2O$ (0.1% TFA)-ACN]; gradient: 70%-100% B over 15.0 min) to afford(S)-tert-butyl 3-bromo-2-(4-fluoro-3,5-dimethylphenyl)-4-methyl-6,7-dihydro-2H-pyrazolo[4,3-c]pyridine-5 (4H)-carboxylate (4.2 g, 9.58 mmol, 59.80% yield). LC-MS (ES+, m/z): 438.0 [$(M+H)^+$]. Rt=0.702 min.

Step 2: (S)-tert-butyl 2-(4-fluoro-3,5-dimethylphenyl)-4-methyl-3-(4,4,5,5-tetramethyl-1,3,2-dioxaborolan-2-yl)-6,7-dihydro-2H-pyrazolo[4,3-c]pyridine-5 (4H)-carboxylate

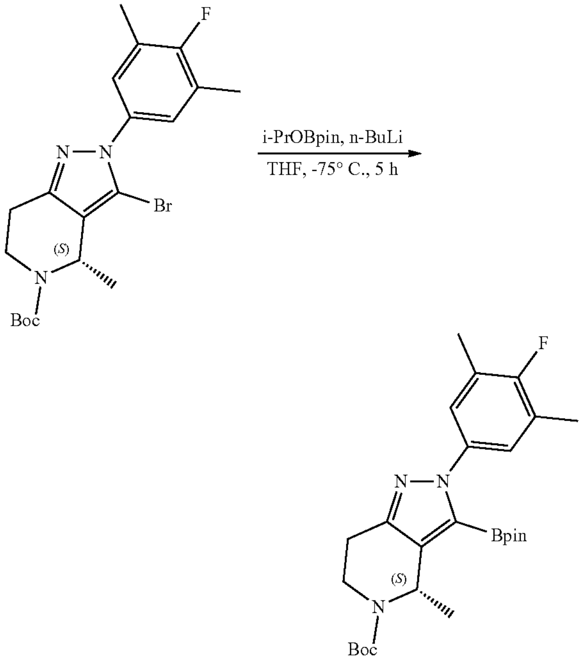

To a solution of(S)-tert-butyl 3-bromo-2-(4-fluoro-3,5-dimethylphenyl)-4-methyl-6,7-dihydro-2H-pyrazolo[4,3-c] pyridine-5 (4H)-carboxylate (3.7 g, 8.44 mmol, 1 eq) in THF (80 mL) was added n-BuLi (2.5 M, 1.1 eq) dropwise at −75° C. The mixture was stirred for 1 hour at −75° C., i-PrOBpin (4.71 g, 25.32 mmol, 3 eq) was then added at −75° C. The reaction mixture was stirred at −75° C. for 4 hours. LCMS indicated the reaction was completed. The reaction mixture was quenched by addition saturated $NH_4Cl$ solution (100 mL) at 0° C., extracted with ethyl acetate (100 mL*3). The combined organic layers were washed with saturated brine (50 mL), dried over anhydrous $Na_2SO_4$, filtered, and concentrated under reduced pressure to give a residue. The residue was purified by prep-HPLC (column: Phenomenex luna C18 (250*70 mm, 15 um); mobile phase: [$H_2O$ (0.1% TFA)-ACN]; gradient: 75%-100% B over 23.0 min) to afford(S)-tert-butyl 2-(4-fluoro-3,5-dimethylphenyl)-4-methyl-3-(4,4,5,5-tetramethyl-1,3,2-dioxaborolan-2-yl)-6,7-dihydro-2H-pyrazolo[4,3-c]pyridine-5 (4H)-carboxylate (2 g, 4.12 mmol, 48.81% yield). LC-MS (ES+, m/z): 486.3 [$(M+H)^+$]. Rt=0.727 min.

Scheme I-16

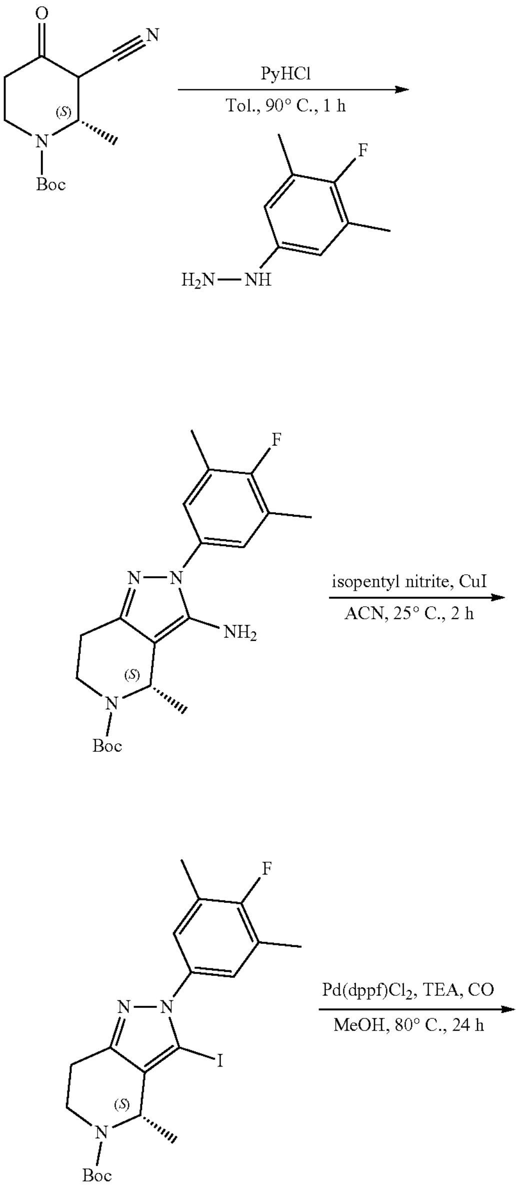

-continued

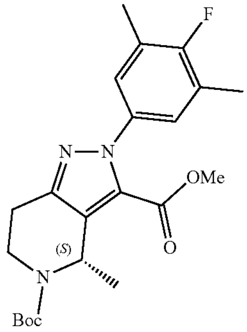

Intermediate 16-1

5-(tert-butyl)$_3$-methyl(S)-2-(4-fluoro-3, 5-dimethylphenyl)-4-methyl-2, 4, 6, 7-tetrahydro-5H-pyrazolo [4, 3-c]pyridine-3, 5-dicarboxylate

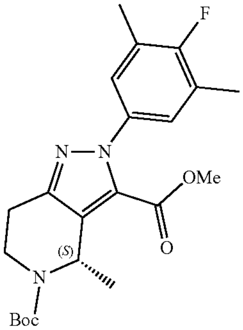

Step 1: tert-butyl (S)-3-amino-2-(4-fluoro-3,5-dimethylphenyl)-4-methyl-2,4,6,7-tetrahydro-5H-pyrazolo[4,3-c]pyridine-5-carboxylate

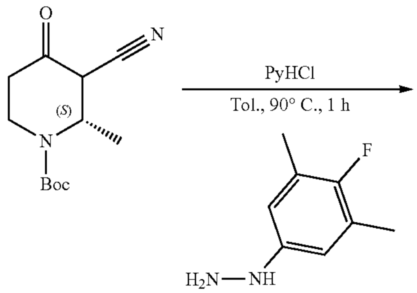

-continued

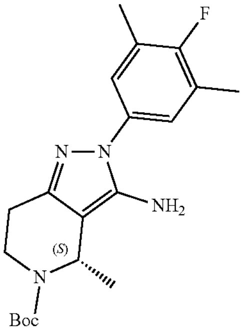

A mixture of tert-butyl (2S)-3-cyano-2-methyl-4-oxopiperidine-1-carboxylate (30 g, 125.90 mmol, 1 eq), (4-fluoro-3,5-dimethylphenyl) hydrazine (19.41 g, 125.90 mmol, 1 eq), pyridine hydrochloride (1.45 g, 12.59 mmol, 0.1 eq) and Tol. (200 mL) was heated to 90° C. for 1 hour. LCMS indicated the reaction was completed. The mixture was adjusted to pH-7 with saturated $NaHCO_3$ (500 mL) and extracted with ethyl acetate (1000 mL*2). The combined organic layers were combined and washed with $H_2O$ (850 mL), saturated brine (850 mL), filtered, and concentrated. The crude product was purified by chromatography on silica gel (Petroleum ether:ethyl acetate=5:1) to give tert-butyl (S)-3-amino-2-(4-fluoro-3,5-dimethylphenyl)-4-methyl-2,4,6,7-tetrahydro-5H-pyrazolo[4,3-c]pyridine-5-carboxylate (33 g, 88.13 mmol, 70.00% yield) as yellow solid. $^1H$ NMR (400 MHz, DMSO-$d_6$) δ=7.24 (d, J=6.5 Hz, 2H), 5.23 (br s, 2H), 5.16-4.95 (m, 1H), 4.26-4.01 (m, 1H), 3.18-2.88 (m, 1H), 2.49-2.38 (m, 2H), 2.26 (d, J=1.6 Hz, 6H), 1.54-1.38 (m, 9H), 1.32-1.16 (m, 3H). LC-MS (ES+, m/z): 375.2 $[(M+H)^+]$; Rt=0.446 min.

Step 2: tert-butyl (S)-2-(4-fluoro-3, 5-dimethylphenyl)-3-iodo-4-methyl-2, 4, 6, 7-tetrahydro-5H-pyrazolo [4, 3-c]pyridine-5-carboxylate

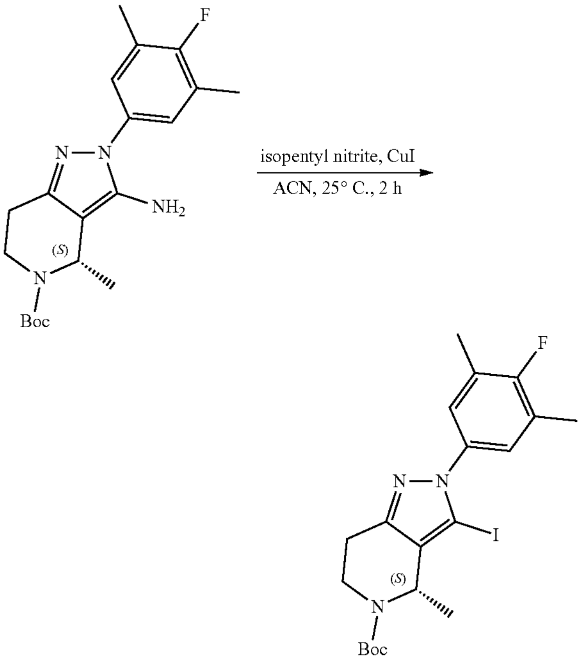

To a solution of tert-butyl (S)-3-amino-2-(4-fluoro-3,5-dimethylphenyl)-4-methyl-2,4,6,7-tetrahydro-5H-pyrazolo[4,3-c]pyridine-5-carboxylate (4 g, 10.68 mmol, 1 eq) in ACN (80 mL) was added isopentyl nitrite (4.38 g, 37.39 mmol, 5.03 mL, 3.5 eq) and CuI (10.17 g, 53.41 mmol, 5 eq). The mixture was stirred at 25° C. for 2 hours. LCMS indicated the reaction was completed. The mixture was poured into water (200 mL) and extracted with ethyl acetate (200 mL*2). The organic layers were combined and washed with water (150 mL*2), saturated brine (150 mL*2), dried over $Na_2SO_4$, filtered, concentrated under reduced pressure. The residue was purified by prep-HPLC (column: Phenomenex luna C18 (250*70 mm, 15 um); mobile phase: [$H_2O$ (0.1% TFA)-ACN]; gradient: 70%-100% B over 20.0 min) to afford tert-butyl (S)-2-(4-fluoro-3,5-dimethylphenyl)-3-iodo-4-methyl-2,4,6,7-tetrahydro-5H-pyrazolo[4,3-c]pyridine-5-carboxylate (2.7 g, 5.56 mmol, 52.08% yield). LC-MS (ES+, m/z): 486.2 [$(M+H)^+$]. Rt=0.679 min.

Step 3: 5-(tert-butyl)$_3$-methyl(S)-2-(4-fluoro-3, 5-dimethylphenyl)-4-methyl-2, 4, 6, 7-tetrahydro-5H-pyrazolo[4, 3-c]pyridine-3, 5-dicarboxylate

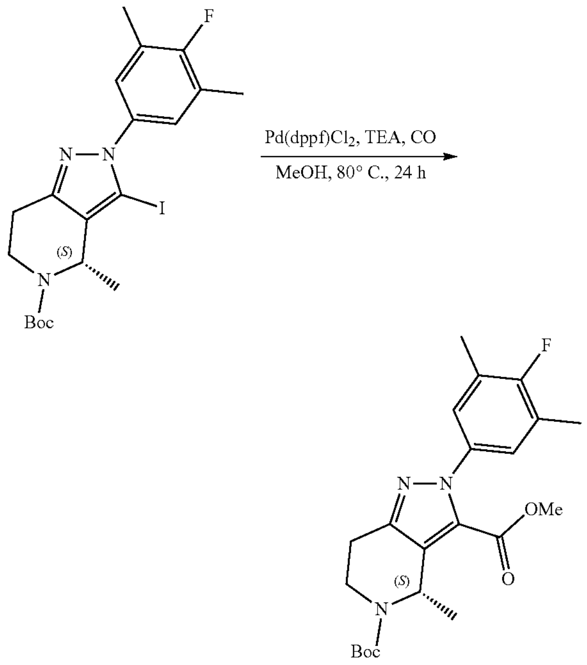

To a solution of tert-butyl (S)-2-(4-fluoro-3,5-dimethylphenyl)-3-iodo-4-methyl-2,4,6,7-tetrahydro-5H-pyrazolo[4,3-c]pyridine-5-carboxylate (1 g, 2.06 mmol, 1 eq) in MeOH (60 mL) and DMF (30 mL) was added Pd(dppf)$Cl_2$ (150.76 mg, 206.04 μmol, 0.1 eq) and TEA (2.08 g, 20.60 mmol, 10 eq). The mixture was stirred at 80° C. for 24 hours under CO (50 psi). LCMS indicated the reaction was completed. The crude was added to saturated EDTA (80 mL) and ethyl acetate (80 mL), stirred for 1 hour and extracted with ethyl acetate (80 mL*3). The combined layers were washed with water (80 mL), saturated brine (80 mL), filtered and concentrated. The crude product was purified by chromatography on silica gel (Petroleum ether/ethyl acetate=4:1) to afford 5-(tert-butyl)$_3$-methyl(S)-2-(4-fluoro-3,5-dimethylphenyl)-4-methyl-2,4,6,7-tetrahydro-5H-pyrazolo[4,3-c]pyridine-3,5-dicarboxylate (600 mg, 1.44 mmol, 69.75% yield). LC-MS (ES+, m/z): 418.1 [$(M+H)^+$]. Rt=0.645 min.

Intermediate 16-2

2-bromo-1-(4-fluoro-1-methyl-1H-indazol-5-yl) propan-1-one

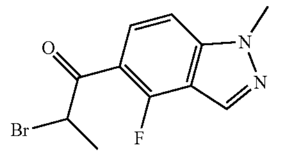 [SMILES: CC(Br)C(=O)c1ccc2c(cnn2C)c1F]

Step 1: 1-(4-fluoro-1-methyl-1H-indazol-5-yl) propan-1-one

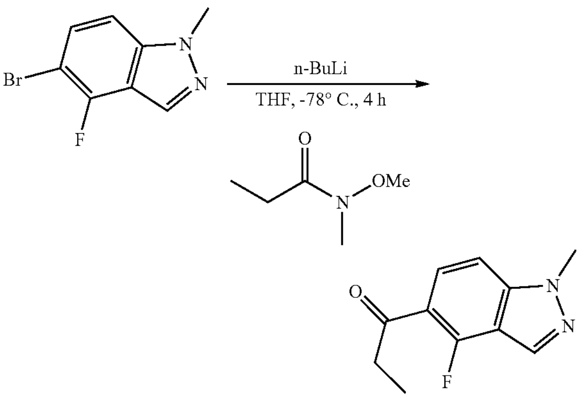

To a solution of 5-bromo-4-fluoro-1-methyl-1H-indazole (5 g, 21.83 mmol, 1 eq) and N-methoxy-N-methylpropionamide (3.32 g, 28.38 mmol, 1.3 eq) in THF (50 mL) was added n-BuLi (2.5 M, 10.48 mL, 1.2 eq) dropwise at −78° C. under $N_2$. The mixture was stirred at −78° C. for 4 hours under $N_2$. LCMS showed reaction was completed. The mixture was added to saturated $NH_4Cl$ (100 mL) and then extracted with ethyl acetate (100 mL*2). The organic layers were combined, washed with water (150 mL), saturated brine (150 mL), dried over $Na_2SO_4$, filtered, and concentrated to give crude product. The residue was purified by column chromatography ($SiO_2$, Petroleum ether/ethyl acetate=3/1 to 1/1) to give 1-(4-fluoro-1-methyl-1H-indazol-5-yl) propan-1-one (2.75 g, 11.60 mmol, 53.15% yield). LC-MS (ES+, m/z): 207.2 [$(M+H)^+$]; Rt=0.460 min.

Step 2: 2-bromo-1-(4-fluoro-1-methyl-1H-indazol-5-yl) propan-1-one

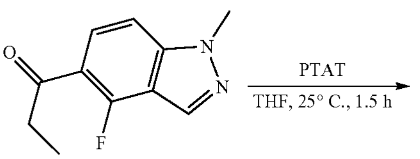

-continued

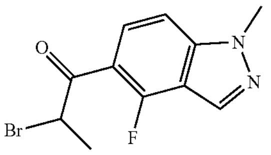

To a solution of 1-(4-fluoro-1-methyl-1H-indazol-5-yl) propan-1-one (1.8 g, 8.73 mmol, 1 eq) in THF (36 mL) was added PTAT (4.27 g, 11.35 mmol, 1.3 eq). The mixture was stirred at 25° C. for 1.5 hours. LCMS showed reaction was completed. The mixture was added to $H_2O$ (50 mL), and then extracted with ethyl acetate (50 mL*3). The organic layers were combined, washed with water (100 mL), saturated brine (100 mL), dried over $Na_2SO_4$, filtered, and concentrated to give crude product. The residue was purified by column chromatography ($SiO_2$, Petroleum ether/ethyl acetate=10/1 to 3/1) to give 2-bromo-1-(4-fluoro-1-methyl-1H-indazol-5-yl) propan-1-one (2.2 g, 7.38 mmol, 84.60% yield). LC-MS (ES+, m/z): 285.0 [$(M+H)^+$]; Rt=0.511 min.

Scheme Intermediate 19-1

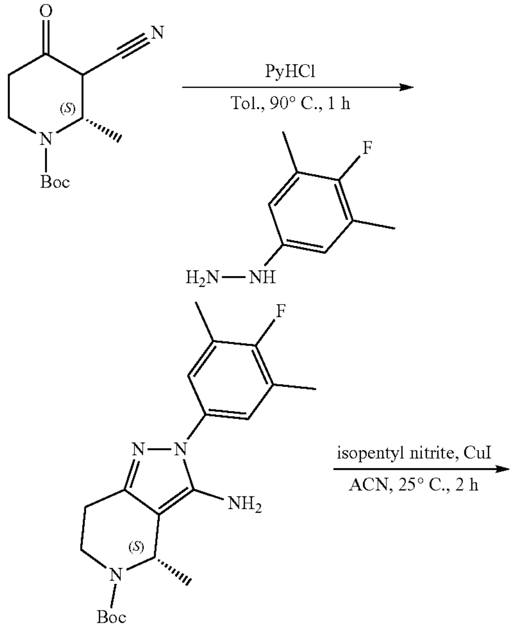

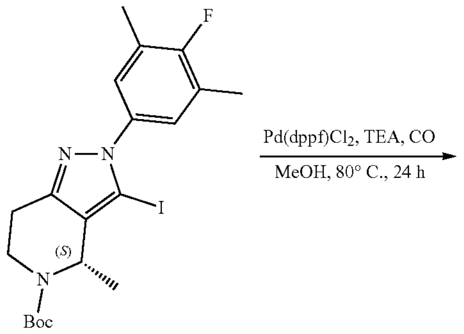

-continued

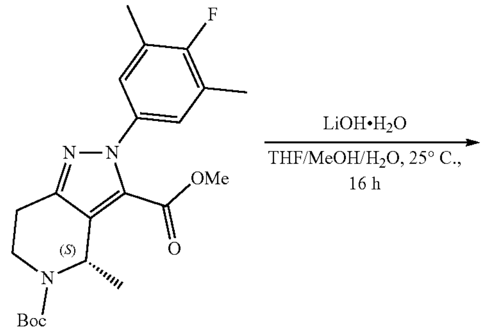

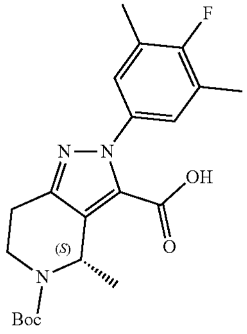

Intermediate 19-1

(S)-5-(tert-butoxycarbonyl)-2-(4-fluoro-3,5-dimethylphenyl)-4-methyl-4,5,6,7-tetrahydro-2H-pyrazolo [4,3-c]pyridine-3-carboxylic acid

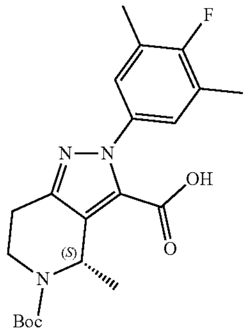

Step 1: tert-butyl (S)-3-amino-2-(4-fluoro-3,5-dimethylphenyl)-4-methyl-2,4,6,7-tetrahydro-5H-pyrazolo[4,3-c]pyridine-5-carboxylate

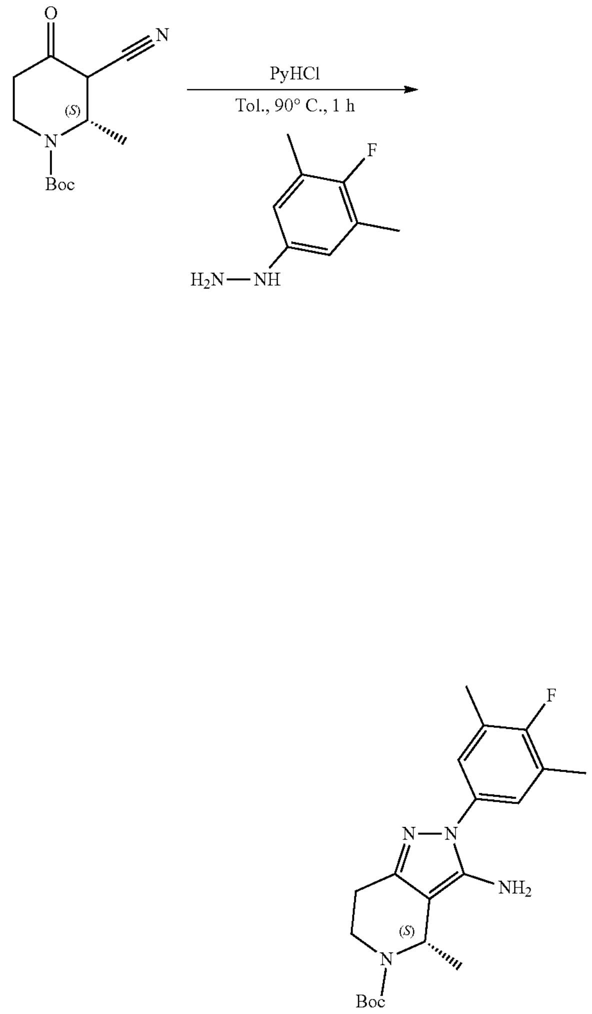

A mixture of tert-butyl (2S)-3-cyano-2-methyl-4-oxopiperidine-1-carboxylate (30 g, 125.90 mmol, 1 eq), (4-fluoro-3,5-dimethylphenyl) hydrazine (19.41 g, 125.90 mmol, 1 eq), pyridine hydrochloride (1.45 g, 12.59 mmol, 0.1 eq) in Tol. (200 mL) was heated to 90° C. for 1 hour. LCMS indicated the reaction was completed. The mixture was adjusted to pH=7 with saturated $NaHCO_3$ (500 mL) and extracted with ethyl acetate (1000 mL*2). The combined organic layers were combined and washed with $H_2O$ (850 mL), saturated brine (850 mL), filtered, and concentrated. The crude product was purified by chromatography on silica gel (Petroleum ether:ethyl acetate-5:1) to give tert-butyl (S)-3-amino-2-(4-fluoro-3,5-dimethylphenyl)-4-methyl-2,4,6,7-tetrahydro-5H-pyrazolo[4,3-c]pyridine-5-carboxylate (33 g, 88.13 mmol, 70.00% yield). $^1H$ NMR (400 MHz, DMSO-$d_6$) δ=7.24 (d, J=6.5 Hz, 2H), 5.23 (br s, 2H), 5.16-4.95 (m, 1H), 4.26-4.01 (m, 1H), 3.18-2.88 (m, 1H), 2.49-2.38 (m, 2H), 2.26 (d, J=1.6 Hz, 6H), 1.54-1.38 (m, 9H), 1.32-1.16 (m, 3H); LC-MS (ES+, m/z): 375.2 [$(M+H)^+$]; Rt=0.446 min.

Step 2: tert-butyl (S)-2-(4-fluoro-3, 5-dimethylphenyl)-3-iodo-4-methyl-2, 4, 6, 7-tetrahydro-5H-pyrazolo [4, 3-c]pyridine-5-carboxylate

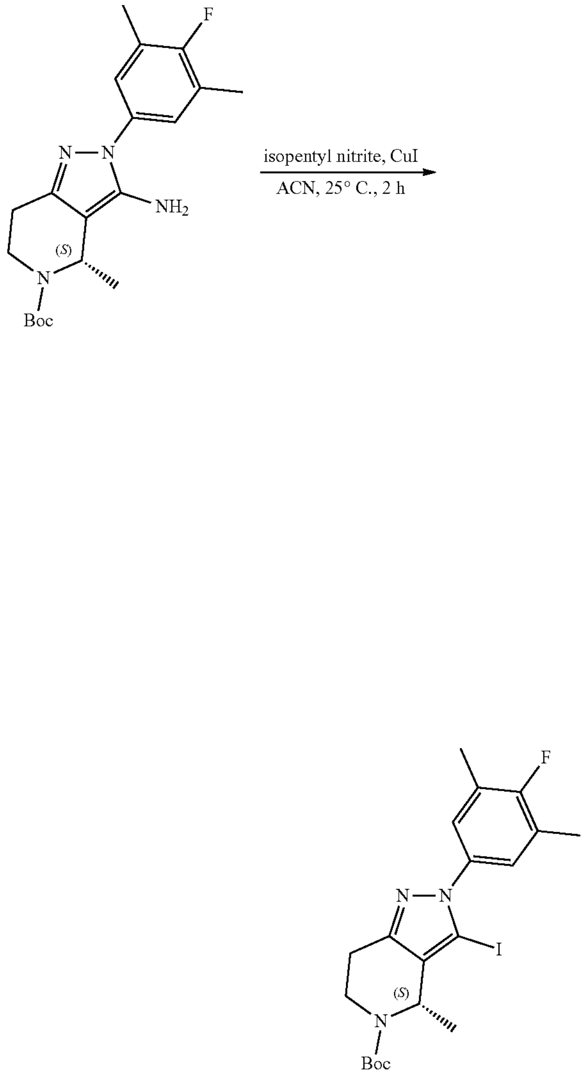

To a solution of tert-butyl (S)-3-amino-2-(4-fluoro-3,5-dimethylphenyl)-4-methyl-2,4,6,7-tetrahydro-5H-pyrazolo [4,3-c]pyridine-5-carboxylate (4 g, 10.68 mmol, 1 eq) in ACN (80 mL) was added isopentyl nitrite (4.38 g, 37.39 mmol, 5.03 mL, 3.5 eq) and CuI (10.17 g, 53.41 mmol, 5 eq). The mixture was stirred at 25° C. for 2 hours. LCMS indicated the reaction was completed. The mixture was poured into water (200 mL) and extracted with ethyl acetate (200 mL*2). The organic layers were combined and washed with water (150 mL*2), saturated brine (150 mL*2), dried over $Na_2SO_4$, filtered, concentrated under reduced pressure. The residue was purified by prep-HPLC (column: Phenomenex luna C18 (250*70 mm, 15 um); mobile phase: [$H_2O$ (0.1% TFA)-ACN]; gradient: 70%-100% B over 20.0 min) to afford tert-butyl (S)-2-(4-fluoro-3,5-dimethylphenyl)-3-iodo-4-methyl-2,4,6,7-tetrahydro-5H-pyrazolo[4,3-c]pyridine-5-carboxylate (2.7 g, 5.56 mmol, 52.08% yield). LC-MS (ES+, m/z): 486.2 [$(M+H)^+$]. Rt=0.679 min.

Step 3: 5-(tert-butyl)$_3$-methyl(S)-2-(4-fluoro-3, 5-dimethylphenyl)-4-methyl-2, 4, 6, 7-tetrahydro-5H-pyrazolo[4, 3-c]pyridine-3, 5-dicarboxylate

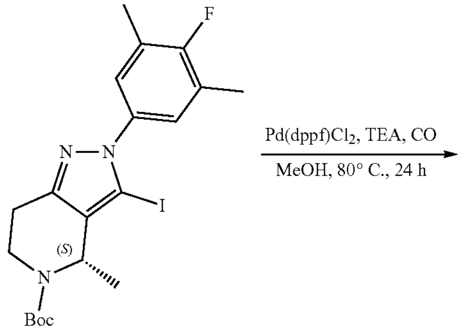

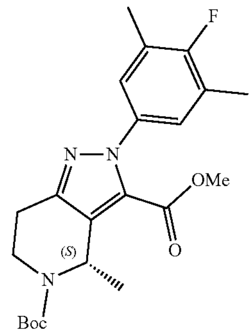

To a solution of tert-butyl (S)-2-(4-fluoro-3,5-dimethylphenyl)-3-iodo-4-methyl-2,4,6,7-tetrahydro-5H-pyrazolo[4,3-c]pyridine-5-carboxylate (1 g, 2.06 mmol, 1 eq) in MeOH (60 mL) and DMF (30 mL) was added Pd(dppf)$Cl_2$ (150.76 mg, 206.04 μmol, 0.1 eq) and TEA (2.08 g, 20.60 mmol, 10 eq). The mixture was stirred at 80° C. for 24 hours under CO (50 psi). LCMS indicated the reaction was completed. The crude was added to saturated EDTA (80 mL) and ethyl acetate (80 mL), stirred for 1 hour and extracted with ethyl acetate (80 mL*3). The combined layers were washed with water (80 mL), saturated brine (80 mL), filtered and concentrated. The crude product was purified by chromatography on silica gel (Petroleum ether/ethyl acetate=4:1) to afford 5-(tert-butyl)$_3$-methyl(S)-2-(4-fluoro-3,5-dimethylphenyl)-4-methyl-2,4,6,7-tetrahydro-5H-pyrazolo[4,3-c]pyridine-3,5-dicarboxylate (600 mg, 1.44 mmol, 69.75% yield). LC-MS (ES+, m/z): 418.1 [$(M+H)^+$]. Rt=0.645 min.

Step 4: (S)-5-(tert-butoxycarbonyl)-2-(4-fluoro-3, 5-dimethylphenyl)-4-methyl-4, 5, 6, 7-tetrahydro-2H-pyrazolo[4, 3-c]pyridine-3-carboxylic acid

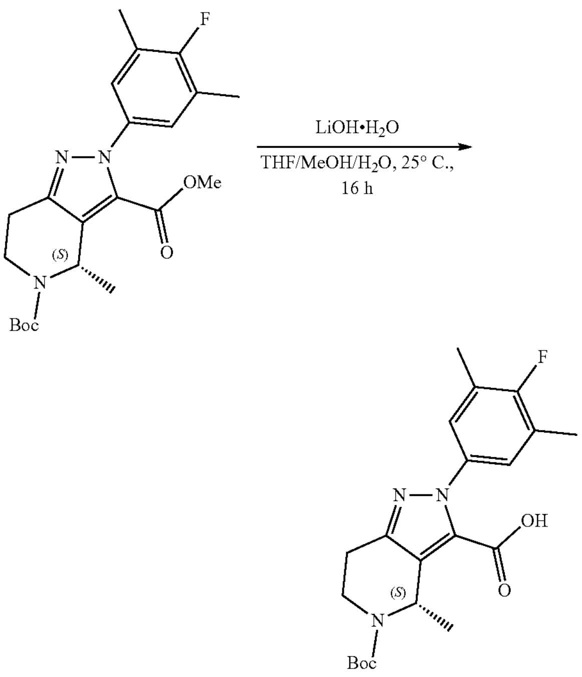

To a solution of 5-(tert-butyl)$_3$-methyl(S)-2-(4-fluoro-3, 5-dimethylphenyl)-4-methyl-2, 4, 6, 7-tetrahydro-5H-pyrazolo[4, 3-c]pyridine-3, 5-dicarboxylate (800 mg, 1.92 mmol, 1 eq) in THF (4 mL), MeOH (2 mL) and $H_2O$ (2 mL) was added LiOH·$H_2O$ (241.24 mg, 5.75 mmol, 3 eq). The mixture was stirred at 25° C. for 16 hours. LCMS showed reaction was completed. The mixture was concentrated to give crude product. And then the residue was dissolved in water (20 mL), adjusted to pH-4 with HCl (2 M) and then extracted with ethyl acetate (50 mL*3). The organic layers were combined, washed with water (50 mL), saturated brine (50 mL), dried over $Na_2SO_4$, filtered and concentrated to give(S)-5-(tert-butoxycarbonyl)-2-(4-fluoro-3, 5-dimethylphenyl)-4-methyl-4, 5, 6, 7-tetrahydro-2H-pyrazolo[4, 3-c]pyridine-3-carboxylic acid (800 mg, crude). LC-MS (ES+, m/z): 404.3 [$(M+H)^+$]; Rt=0.539 min.

Intermediate 20-1

2-bromo-1-(1-methyl-1H-indazol-5-yl) propan-1-one

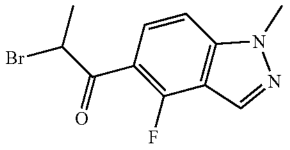 [SMILES: CC(Br)C(=O)c1ccc2c(cnn2C)c1F]

Step 1: 1-(4-fluoro-1-methyl-1H-indazol-5-yl) propan-1-one

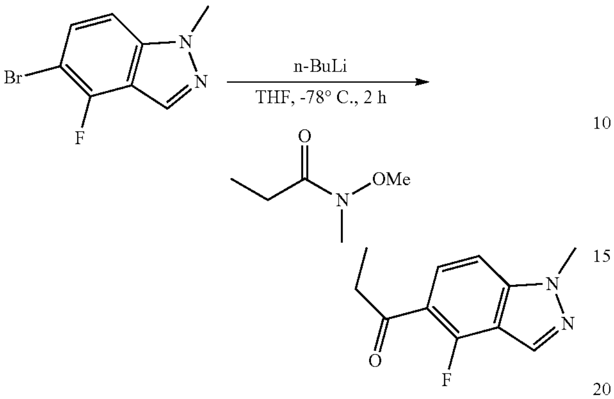

To a solution of 5-bromo-4-fluoro-1-methyl-1H-indazole (3 g, 13.10 mmol, 1 eq) in THF (20 mL) was added n-BuLi (2.5 M, 10.48 mL, 2 eq) at −78° C. The mixture was stirred at −78° C. for 0.5 hour. To it was then added N-methoxy-N-methylpropionamide (3.07 g, 26.20 mmol, 2 eq) as a solution in THF (10 mL). The mixture was stirred at −78° C. for 1.5 hours. LCMS showed the reaction was completed. The residue was poured into saturated $NH_4Cl$ solution (400 mL) and extracted with ethyl acetate (200 mL*3). The combined organic phase was washed with saturated brine (250 mL), dried with anhydrous $Na_2SO_4$, filtered, and concentrated in vacuum. The residue was purified by column chromatography ($SiO_2$, Petroleum ether/ethyl acetate=100/1 to 20/1) to give 1-(4-fluoro-1-methyl-1H-indazol-5-yl) propan-1-one (1.1 g, 4.36 mmol, 33.31% yield). LC-MS (ES+, m/z): 207.1 [(M+H)$^+$]; Rt=0.444 min.

Step 2: 2-bromo-1-(4-fluoro-1-methyl-1H-indazol-5-yl) propan-1-one

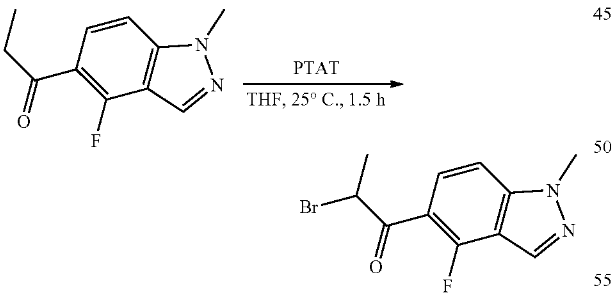

To a solution of 1-(4-fluoro-1-methyl-1H-indazol-5-yl) propan-1-one (1 g, 4.85 mmol, 1 eq) in THF (10 mL) was added PTAT (2.37 g, 6.30 mmol, 1.3 eq). The mixture was stirred at 25° C. for 1.5 hours. LCMS showed the reaction was completed. The residue was poured into water (50 mL) and extracted with DCM (25 mL*3). The combined organic phase was washed with saturated brine (30 mL), dried with anhydrous $Na_2SO_4$, filtered, and concentrated in vacuum. The residue was purified by prep-TLC ($SiO_2$, Petroleum ether:ethyl acetate=3:1) to give 2-bromo-1-(4-fluoro-1-methyl-1H-indazol-5-yl) propan-1-one (1.1 g, 3.09 mmol, 63.73% yield). LC-MS (ES+, m/z): 285.0 [(M+H)$^+$]; Rt=0.495 min.

Intermediate 21-1

2-bromo-1-(4-fluoro-1-methyl-1H-indazol-5-yl) ethan-1-one

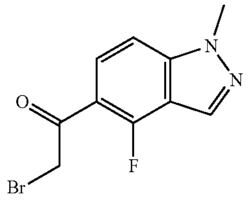

Step 1: 1-(4-fluoro-1-methyl-1H-indazol-5-yl) ethan-1-one

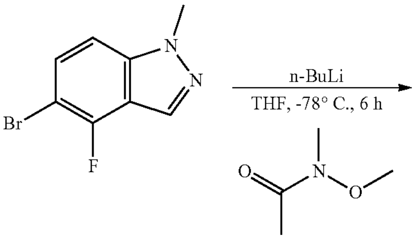

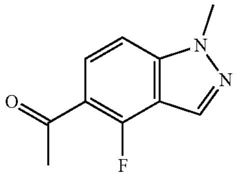

To a solution of 5-bromo-4-fluoro-1-methyl-1H-indazole (2 g, 8.73 mmol, 1 eq) and N-methoxy-N-methylacetamide (1.80 g, 17.46 mmol, 1.86 mL, 2 eq) in THF (20 mL) was added n-BuLi (2.5 M, 4.19 mL, 1.2 eq) dropwise at −78° C. under $N_2$. The mixture was stirred at −78° C. for 6 hours under $N_2$. LCMS showed reaction was completed. The mixture was added to saturated $NH_4Cl$ (50 mL) and then extracted with ethyl acetate (50 mL*3). The organic layers were combined, washed with water (100 mL), saturated brine (100 mL), dried over $Na_2SO_4$, filtered, and concentrated to give crude product. The residue was purified by column chromatography ($SiO_2$, Petroleum ether/ethyl acetate=7/1 to 3/1) to give 1-(4-fluoro-1-methyl-1H-indazol-5-yl) ethan-1-one (1.2 g, 6.24 mmol, 71.51% yield). LC-MS (ES+, m/z): 193.1 [(M+H)$^+$]; Rt=0.418 min.

Step 2: 2-bromo-1-(4-fluoro-1-methyl-1H-indazol-5-yl) ethan-1-one

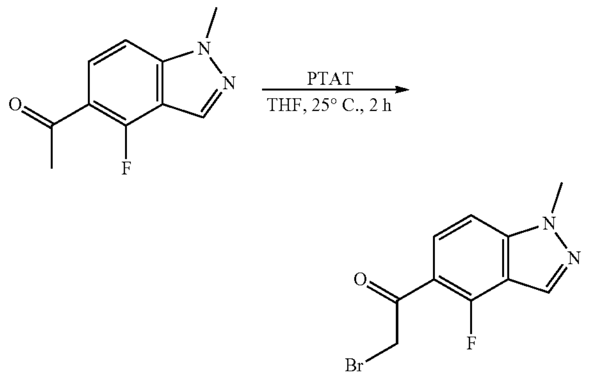

To a solution of 1-(4-fluoro-1-methyl-1H-indazol-5-yl) ethan-1-one (1.2 g, 6.24 mmol, 1 eq) in THF (12 mL) was added PTAT (3.05 g, 8.12 mmol, 1.3 eq). The mixture was stirred at 25° C. for 2 hours. LCMS showed reaction was completed. The mixture was added to $H_2O$ (30 mL), and then extracted with ethyl acetate (50 mL*3). The organic layers were combined, washed with water (100 mL), saturated brine (100 mL), dried over $Na_2SO_4$, filtered, and concentrated to give crude product. The residue was purified by prep-HPLC (column: Phenomenex luna C18 (250*70 mm, 15 um); mobile phase: [$H_2O$ (0.1% TFA)-ACN]; gradient: 35%-65% B over 25.0 min) to give 2-bromo-1-(4-fluoro-1-methyl-1H-indazol-5-yl) ethan-1-one (1 g, 3.66 mmol, 58.55% yield). LC-MS (ES+, m/z): 271.1 [$(M+H)^+$]; Rt=0.455 min.

Intermediate 23-1

Methyl 2-((4-fluoro-1-methyl-1H-indazol-5-yl) amino)acetate

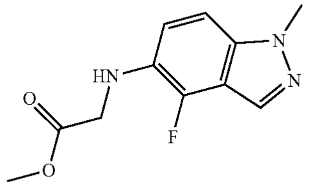

Step 1: methyl 2-((4-fluoro-1-methyl-1H-indazol-5-yl)amino)acetate

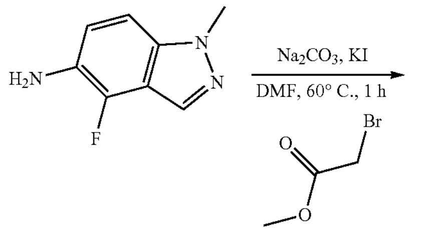

-continued

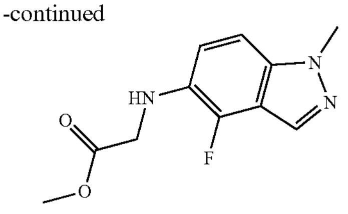

A mixture of 4-fluoro-1-methyl-1H-indazol-5-amine (200 mg, 1.21 mmol, 1 eq), methyl 2-bromoacetate (166.71 mg, 1.09 mmol, 103.16 μL, 0.9 eq), KI (201.01 mg, 1.21 mmol, 1 eq), $Na_2CO_3$ (385.02 mg, 3.63 mmol, 3 eq) in DMF (2 mL) was stirred at 60° C. for 1 hour under $N_2$ atmosphere. LCMS showed the reaction was completed. The residue was poured into $H_2O$ (100 mL), the aqueous phase was extracted with ethyl acetate (50 mL*3). The combined organic phase was washed with saturated brine (50 mL), dried with anhydrous $Na_2SO_4$, filtered, and concentrated in vacuum. The residue was purified by prep-TLC ($SiO_2$, Petroleum ether: Ethyl acetate=1:1) to give methyl 2-((4-fluoro-1-methyl-1H-indazol-5-yl)amino)acetate (150 mg, 632.30 μmol, 52.22% yield). LC-MS (ES+, m/z): 238.2 [$(M+H)^+$]; Rt=1.100 min.

Intermediate 24-1

2-bromo-1-(4-fluoro-1-methyl-1H-indazol-5-yl) propan-1-one

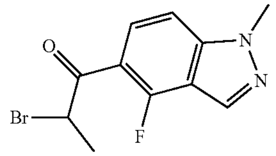 [SMILES: CC(Br)C(=O)c1ccc2c(cnn2C)c1F]

Step 1: 1-(4-fluoro-1-methyl-1H-indazol-5-yl) propan-1-one

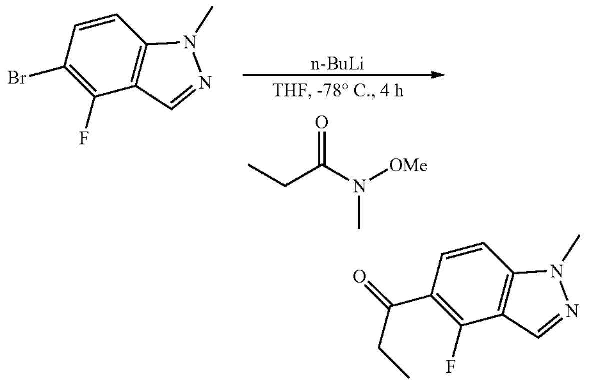

To a solution of 5-bromo-4-fluoro-1-methyl-1H-indazole (5 g, 21.83 mmol, 1 eq) and N-methoxy-N-methylpropionamide (3.32 g, 28.38 mmol, 1.3 eq) in THF (50 mL) was added n-BuLi (2.5 M, 10.48 mL, 1.2 eq) dropwise at −78° C. under $N_2$. The mixture was stirred at −78° C. for 4 hours under $N_2$. LCMS showed reaction was completed. The mixture was added to saturated $NH_4Cl$ (100 mL) and then extracted with ethyl acetate (100 mL*2). The organic layers were combined, washed with water (150 mL), saturated brine (150 mL), dried over $Na_2SO_4$, filtered, and concentrated to give crude product. The residue was purified by column chromatography ($SiO_2$, Petroleum ether/ethyl acetate=3/1 to 1/1) to give 1-(4-fluoro-1-methyl-1H-indazol-5-yl) propan-1-one (2.75 g, 11.60 mmol, 53.15% yield). LC-MS (ES+, m/z): 207:2 [$(M+H)^+$]; Rt=0.460 min.

Step 2: 2-bromo-1-(4-fluoro-1-methyl-1H-indazol-5-yl) propan-1-one

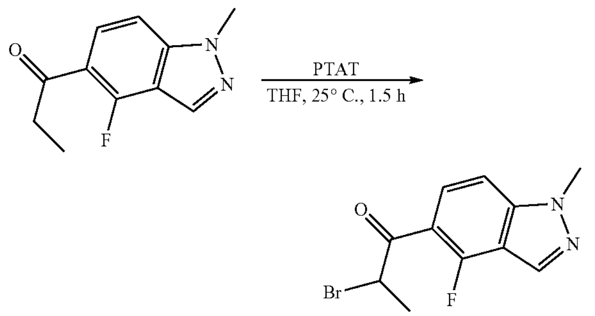

To a solution of 1-(4-fluoro-1-methyl-1H-indazol-5-yl) propan-1-one (1.8 g, 8.73 mmol, 1 eq) in THF (36 mL) was added PTAT (4.27 g, 11.35 mmol, 1.3 eq). The mixture was stirred at 25° C. for 1.5 hours. LCMS showed reaction was completed. The mixture was added to $H_2O$ (50 mL), and then extracted with ethyl acetate (50 mL*3). The organic layers were combined, washed with saturated brine (100 mL), dried over $Na_2SO_4$, filtered, and concentrated to give crude product. The residue was purified by column chromatography ($SiO_2$, Petroleum ether/ethyl acetate=10/1 to 3/1) to give 2-bromo-1-(4-fluoro-1-methyl-1H-indazol-5-yl) propan-1-one (2.2 g, 7.38 mmol, 84.60% yield). LC-MS (ES+, m/z): 285.0 [$(M+H)^+$]; Rt=0.511 min.

Scheme Intermediate 26-1

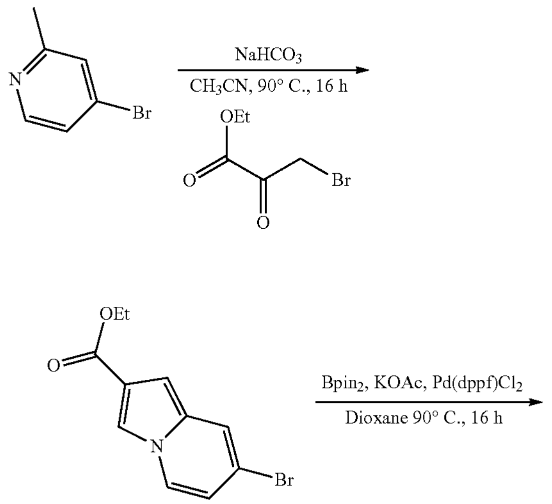

-continued

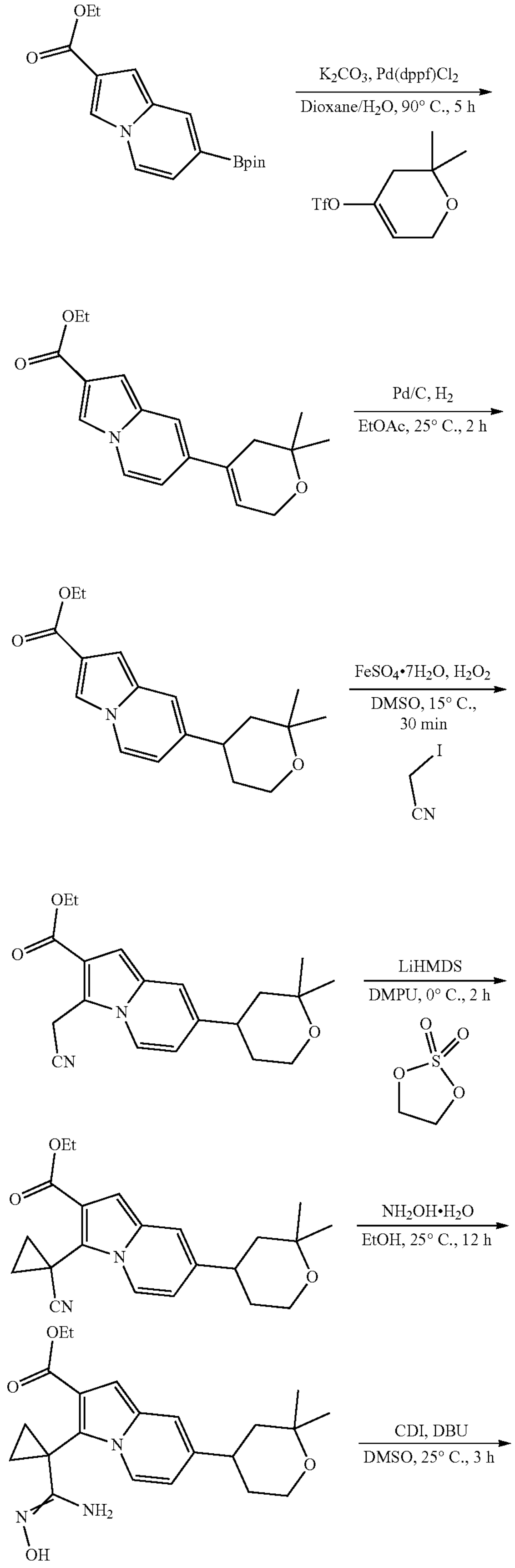

-continued

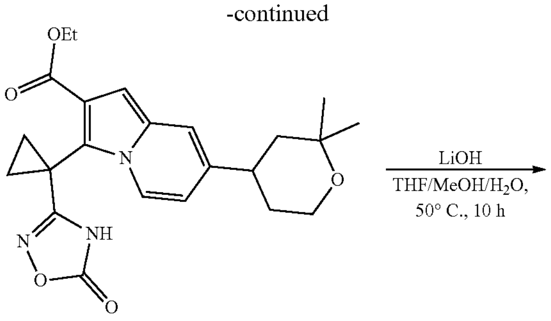

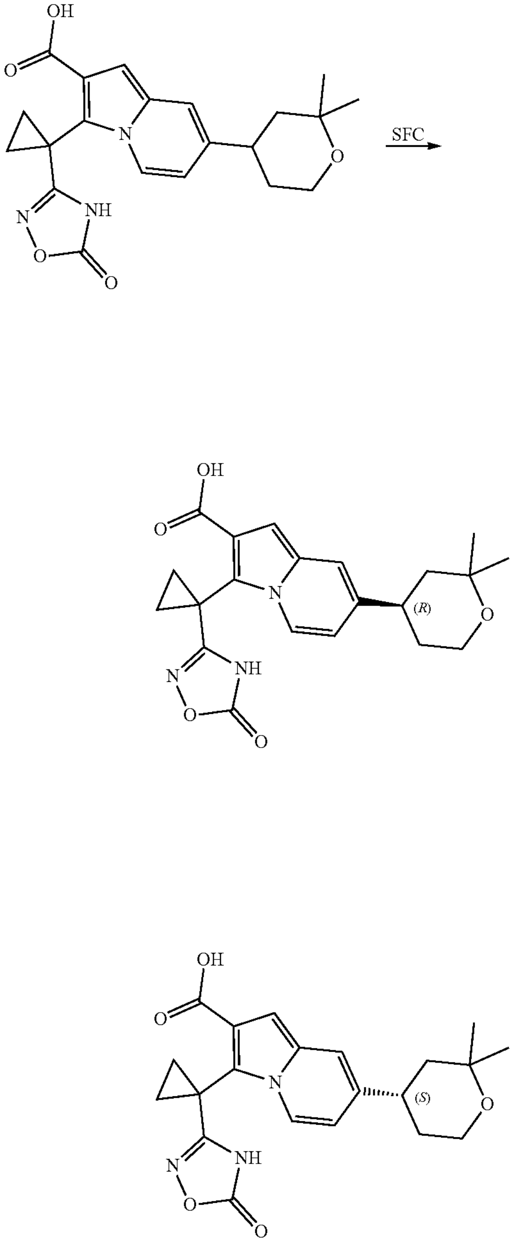

Intermediate 26-1

(R)-7-(2,2-dimethyltetrahydro-2H-pyran-4-yl)-3-(1-(5-oxo-4,5-dihydro-1,2,4-oxadiazol-3-yl) cyclopropyl) indolizine-2-carboxylic acid

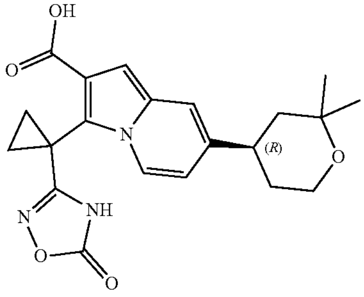

(S)-7-(2,2-dimethyltetrahydro-2H-pyran-4-yl)-3-(1-(5-oxo-4,5-dihydro-1,2,4-oxadiazol-3-yl)cyclopropyl) indolizine-2-carboxylic acid

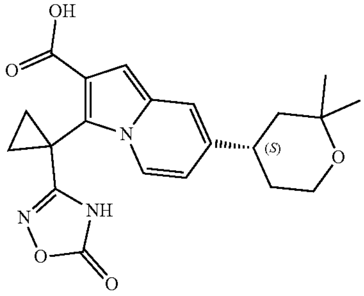

Step 1: ethyl 7-bromoindolizine-2-carboxylate

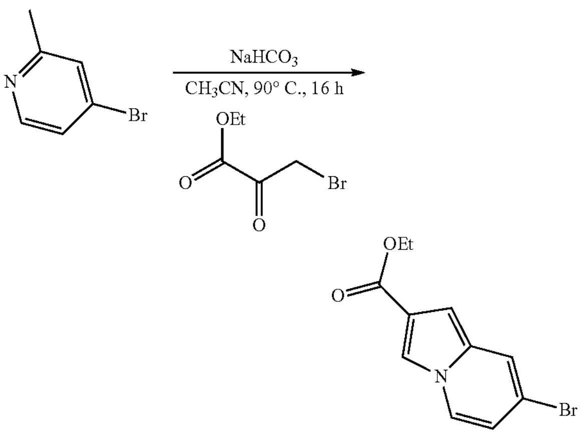

A mixture of 4-bromo-2-methyl-pyridine (60 g, 348.79 mmol, 1 eq), ethyl 3-bromo-2-oxo-propanoate (102.03 g, 523.19 mmol, 65.40 mL, 1.5 eq), $NaHCO_3$ (58.60 g, 697.58 mmol, 27.14 mL, 2 eq) and MeCN (400 mL) was stirred at 90° C. for 16 hours. LCMS indicated the reaction was completed. The mixture was poured into water (1000 mL) and extracted with ethyl acetate (1000 mL*2). The organic layers were washed with water (600 mL*2), saturated brine (600 mL*2), dried over $Na_2SO_4$, filtered, concentrated under reduced pressure. The crude product was purified by chromatography on silica gel (Petroleum ether:ethyl acetate=10:1) to give ethyl 7-bromoindolizine-2-carboxylate (5.7 g, 21.26 mmol, 6.10% yield). LC-MS (ES+, m/z): 267.9 [(M+H)$^+$]; Rt=0.566 min.

Step 2: ethyl 7-(4,4,5,5-tetramethyl-1,3,2-dioxaborolan-2-yl) indolizine-2-carboxylate

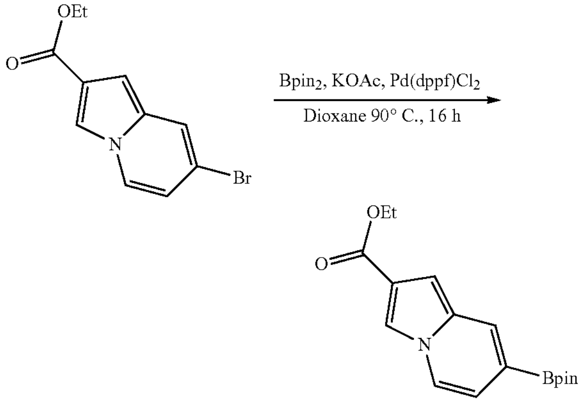

A mixture of ethyl 7-bromoindolizine-2-carboxylate (8.5 g, 31.70 mmol, 1 eq), 4 4,4,4',4',5,5,5',5'-octamethyl-2,2'-bi (1,3,2-dioxaborolane) (12.08 g, 47.56 mmol, 1.5 eq), Pd(dppf)$Cl_2$ (2.32 g, 3.17 mmol, 0.1 eq), KOAc (12.45 g, 126.82 mmol, 4 eq) and dioxane (100 mL) was stirred at 90° C. for 16 hours under $N_2$. LCMS indicated the reaction was completed. The residue was poured into saturated EDTA solution (600 mL) and ethyl acetate (400 mL), stirred for 0.5 hour, and then extracted with ethyl acetate (400 mL*2). The organic layers were combined and washed with water (300 mL*2), saturated brine (300 mL*2), dried over $Na_2SO_4$, filtered, concentrated under reduced pressure. The crude product was purified by chromatography on silica gel (Petroleum ether:ethyl acetate=6:1) to give ethyl 7-(4,4,5,5-tetramethyl-1,3,2-dioxaborolan-2-yl) indolizine-2-carboxylate (8.5 g, 26.97 mmol, 85.07% yield). LC-MS (ES+, m/z): 316.1 [(M+H)$^+$]; Rt=0.632 min.

Step 3: ethyl 7-(2,2-dimethyl-3,6-dihydro-2H-pyran-4-yl) indolizine-2-carboxylate

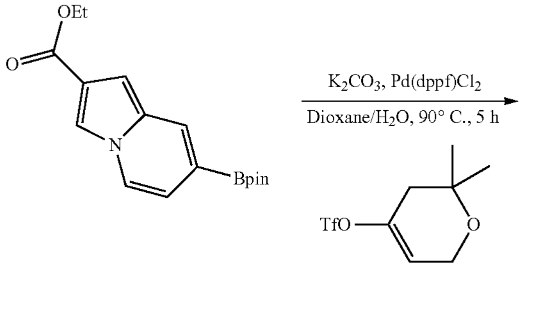

-continued

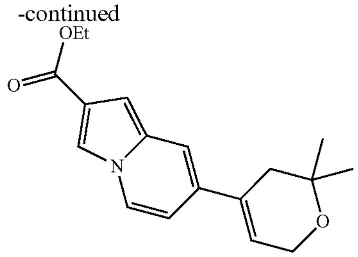

A mixture of ethyl 7-(4,4,5,5-tetramethyl-1,3,2-dioxaborolan-2-yl) indolizine-2-carboxylate (12 g, 38.07 mmol, 1 eq), 2,2-dimethyl-3,6-dihydro-2H-pyran-4-yl trifluoromethanesulfonate (24.77 g, 95.19 mmol, 2.5 eq), Pd(dppf)$Cl_2$ (2.79 g, 3.81 mmol, 0.1 eq), $K_2CO_3$ (26.31 g, 190.37 mmol, 5 eq) in dioxane (120 mL) and $H_2O$ (30 mL) was stirred at 90° C. for 5 hours under $N_2$. LCMS indicated the reaction was completed. The residue was poured into saturated EDTA solution (600 mL) and ethyl acetate (300 mL), stirred for 0.5 hour, and then extracted with ethyl acetate (400 mL*2). The organic layers were washed with water (300 mL*2), saturated brine (300 mL*2), dried over $Na_2SO_4$, filtered, concentrated under reduced pressure. The crude product was purified by chromatography on silica gel (Petroleum ether: ethyl acetate=3:1) to give ethyl 7-(2,2-dimethyl-3,6-dihydro-2H-pyran-4-yl) indolizine-2-carboxylate (7 g, 23.38 mmol, 61.41% yield). LC-MS (ES+, m/z): 300.1 [(M+H)$^+$]; Rt=0.584 min.

Step 4: ethyl 7-(2,2-dimethyltetrahydro-2H-pyran-4-yl) indolizine-2-carboxylate

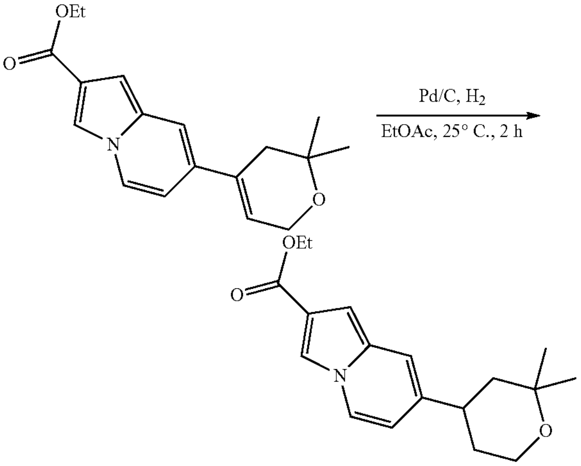

To a solution of Pd/C (3.20 g, 10% purity) in ethyl acetate (420 mL) was added ethyl 7-(2,2-dimethyl-3,6-dihydro-2H-pyran-4-yl) indolizine-2-carboxylate (8 g, 26.72 mmol, 1 eq). The mixture was stirred at 25° C. for 2 hours under $H_2$ (15 psi). LCMS indicated the reaction was completed. The mixture was filtered and concentrated. The crude product was purified by prep-HPLC (column: Phenomenex luna C18 250*150 mm*15 um; mobile phase: [$H_2O$ 0.05% TFA-ACN]; gradient: 45%-75% B over 20.0 min) to give ethyl 7-(2,2-dimethyltetrahydro-2H-pyran-4-yl) indolizine-2-carboxylate (5 g, 16.57 mmol, 62.01% yield). $^1H$ NMR (400 MHz, DMSO-$d_6$) δ=8.26 (d, J=7.3 Hz, 1H), 8.05 (d, J=1.0

Hz, 1H), 7.27 (s, 1H), 6.73-6.61 (m, 2H), 4.30 (q, J=7.1 Hz, 2H), 3.83-3.66 (m, 2H), 2.97-2.84 (m, 1H), 1.73 (br d, J=13.0 Hz, 2H), 1.60-1.43 (m, 2H), 1.35 (t, J=7.2 Hz, 3H), 1.29 (s, 3H), 1.23 (s, 3H). LC-MS (ES+, m/z): 302.1 [(M+H)+]; Rt=0.563 min.

Step 5: ethyl 3-(cyanomethyl)-7-(2,2-dimethyltetrahydro-2H-pyran-4-yl) indolizine-2-carboxylate

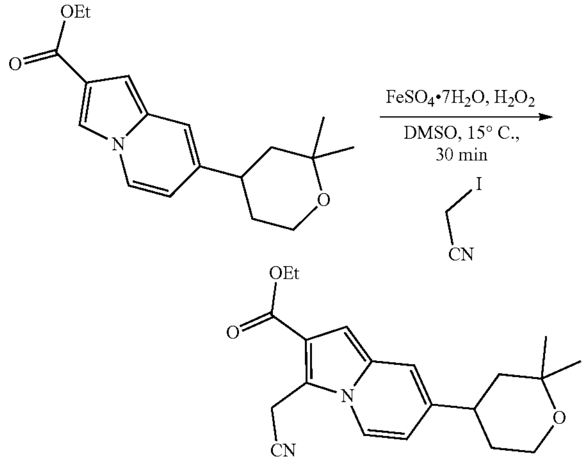

To a solution of 2-iodoacetonitrile (500 mg, 1.66 mmol, 1 eq), 2-iodoacetonitrile (553.95 mg, 3.32 mmol, 2 eq), $FeSO_4$·$7H_2O$ (230.61 mg, 829.52 μmol, 0.5 eq) in DMSO (50 mL) was added $H_2O_2$ (0.37 g, 3.26 mmol, 313.56 μL, 30% purity, 1.97 eq) at 15° C. The mixture was stirred at 15° C. for 30 min (4 parallel reaction). LCMS indicated the reaction was completed. The mixture was poured into saturated $Na_2S_2O_3$ (100 mL) and extracted with ethyl acetate (100 mL*2). The organic layers were washed with saturated $NaHCO_3$ (100 mL), water (80 mL*2), saturated brine (80 mL*2), dried over $Na_2SO_4$, filtered, concentrated under reduced pressure. The crude product was purified by chromatography on silica gel (Petroleum ether:ethyl acetate=1:1) to give ethyl 3-(cyanomethyl)-7-(2,2-dimethyltetrahydro-2H-pyran-4-yl) indolizine-2-carboxylate (250 mg, 729.26 μmol, 43.96% yield, 99.3% purity). $^1H$ NMR (400 MHz, DMSO-$d_6$) δ=8.27 (d, J=7.4 Hz, 1H), 7.35 (s, 1H), 6.86 (d, J=7.5 Hz, 1H), 6.76 (s, 1H), 4.67 (s, 2H), 4.31 (q, J=7.0 Hz, 2H), 3.81-3.66 (m, 2H), 2.93 (br t, J=12.4 Hz, 1H), 1.71 (br d, J=12.4 Hz, 2H), 1.54-1.40 (m, 2H), 1.34 (t, J=7.1 Hz, 3H), 1.26 (s, 3H), 1.19 (s, 3H); LC-MS (ES+, m/z): 341.1 [(M+H)+]; Rt=0.577 min.

Step 6: ethyl 3-(1-cyanocyclopropyl)-7-(2,2-dimethyltetrahydro-2H-pyran-4-yl) indolizine-2-carboxylate

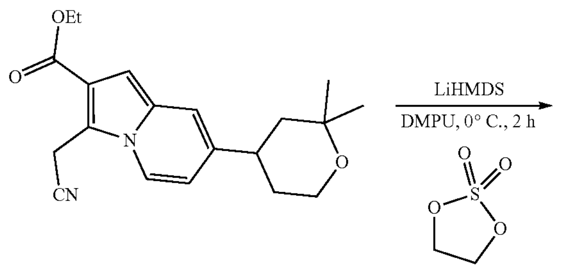

-continued

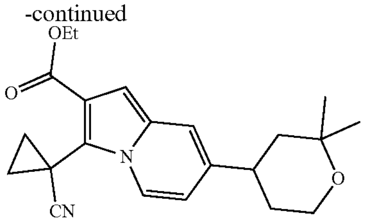

To a solution of ethyl 3-(cyanomethyl)-7-(2,2-dimethyltetrahydro-2H-pyran-4-yl) indolizine-2-carboxylate (350 mg, 1.03 mmol, 1 eq), 1,3,2-dioxathiolane 2,2-dioxide (382.83 mg, 3.08 mmol, 3 eq) in DMPU (3.5 mL) was added LiHMDS (1 M, 9.33 mL, 9.08 eq) dropwise at 0° C. under $N_2$. The mixture was stirred at 0° C. for 2 hours under $N_2$ (2 parallel reaction). LCMS indicated the reaction was completed. The mixture was poured into $NH_4Cl$ (100 mL) and extracted with ethyl acetate (100 mL*2). The organic layers were combined and washed with water (80 mL*2), saturated brine (80 mL*2), dried over $Na_2SO_4$, filtered, concentrated under reduced pressure. The crude product was purified by chromatography on silica gel (Petroleum ether:ethyl acetate=1:2) to give ethyl 3-(1-cyanocyclopropyl)-7-(2,2-dimethyltetrahydro-2H-pyran-4-yl) indolizine-2-carboxylate (150 mg, 372.08 μmol, 36.19% yield). $^1H$ NMR (400 MHz, DMSO-$d_6$) δ=8.35 (d, J=7.4 Hz, 1H), 7.39 (s, 1H), 6.90 (dd, J=1.6, 7.4 Hz, 1H), 6.77 (s, 1H), 4.33 (q, J=7.0 Hz, 2H), 3.20 (t, J=5.9 Hz, 2H), 3.02-2.90 (m, 1H), 2.02-1.96 (m, 2H), 1.75-1.67 (m, 2H), 1.60-1.41 (m, 4H), 1.37 (t, J=7.1 Hz, 3H), 1.28 (s, 3H), 1.20 (s, 3H). LC-MS (ES+, m/z): 367.2 [(M+H)+]; Rt=0.577 min.

Step 7: ethyl 7-(2,2-dimethyltetrahydro-2H-pyran-4-yl)-3-(1-(N'-hydroxycarbamimidoyl)cyclopropyl) indolizine-2-carboxylate

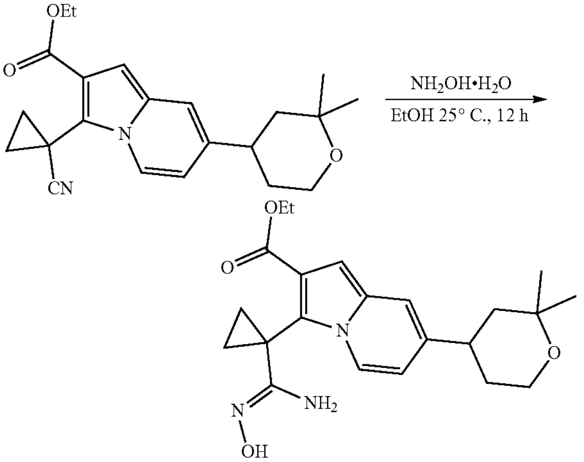

A mixture of ethyl 3-(1-cyanocyclopropyl)-7-(2,2-dimethyltetrahydro-2H-pyran-4-yl) indolizine-2-carboxylate (200 mg, 545.77 μmol, 1 eq), hydroxylamine (432.64 mg, 6.55 mmol, 12 eq, 50%) in EtOH (10 mL) was stirred at 25° C. for 12 hours. LCMS indicated the reaction was completed. The mixture was poured into water (70 mL) and extracted with ethyl acetate (70 mL*2). The organic layers was washed with water (40 mL*2), saturated brine (40 mL*2), dried over $Na_2SO_4$, filtered, concentrated under reduced pressure to give ethyl 7-(2,2-dimethyltetrahydro-2H-pyran-4-yl)-3-(1-(N'-hydroxycarbamimidoyl) cyclopropyl) indolizine-2-carboxylate (200 mg, crude). LC-MS (ES+, m/z): 400.1 [(M+H)$^+$]; Rt=0.405 min.

Step 8: ethyl 7-(2,2-dimethyltetrahydro-2H-pyran-4-yl)-3-(1-(5-oxo-4,5-dihydro-1,2,4-oxadiazol-3-yl) cyclopropyl) indolizine-2-carboxylate

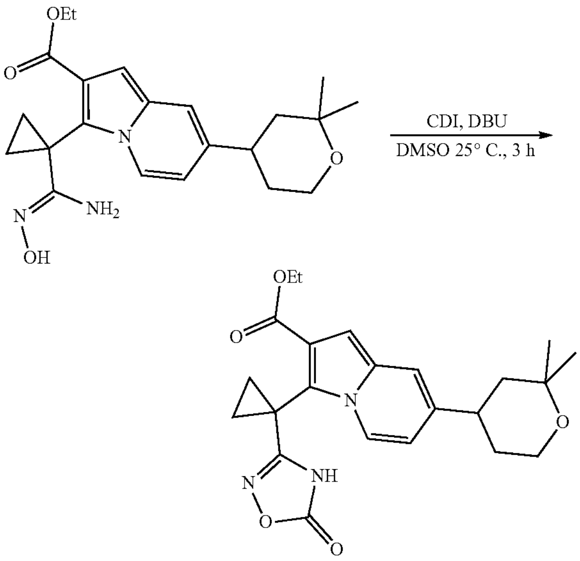

A mixture of ethyl 7-(2,2-dimethyltetrahydro-2H-pyran-4-yl)-3-(1-(N'-hydroxycarbamimidoyl) cyclopropyl) indolizine-2-carboxylate (200 mg, 500.65 μmol, 1 eq), CDI (162.36 mg, 1.00 mmol, 2 eq), DBU (228.65 mg, 1.50 mmol, 226.39 μL, 3 eq) and DMSO (10 mL) was stirred at 25° C. for 3 hours. LCMS indicated the reaction was completed. The mixture was poured into water (35 mL) and extracted with ethyl acetate (35 mL*2). The organic layers were washed with water (20 mL*2), saturated brine (20 mL*2), dried over $Na_2SO_4$, filtered, concentrated under reduced pressure. The crude product was purified by chromatography on silica gel (DCM: MeOH-30:1) to give ethyl 7-(2,2-dimethyltetrahydro-2H-pyran-4-yl)-3-(1-(5-oxo-4,5-dihydro-1,2,4-oxadiazol-3 yl) cyclopropyl) indolizine-2-carboxylate (200 mg, crude). LC-MS (ES+, m/z): 426.1 [(M+H)$^+$]; Rt=0.522 min.

Step 9: 7-(2,2-dimethyltetrahydro-2H-pyran-4-yl)-3-(1-(5-oxo-4,5-dihydro-1,2,4-oxadiazol-3-yl) cyclopropyl) indolizine-2-carboxylic acid

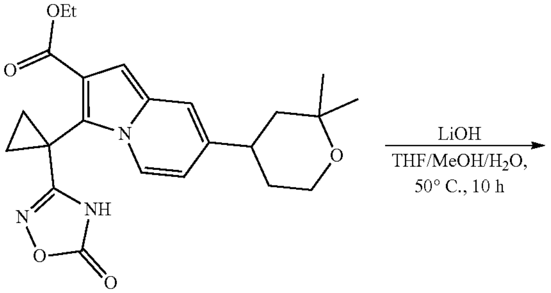

-continued

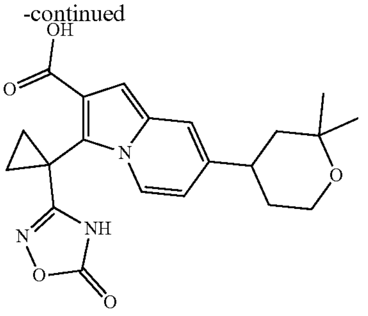

A mixture of ethyl 7-(2,2-dimethyltetrahydro-2H-pyran-4-yl)-3-(1-(5-oxo-4,5-dihydro-1,2,4-oxadiazol-3 yl) cyclopropyl) indolizine-2-carboxylate (200 mg, 470.06 μmol, 1 eq) $LiOH \cdot H_2O$ (98.63 mg, 2.35 mmol, 5 eq), THF (3 mL), MeOH (3 mL) and $H_2O$ (3 mL) was stirred at 50° C. for 10 hours. LCMS indicated the reaction was completed. The mixture was concentrated to remove the organic solvent. The aqueous layer was adjusted to pH=3 with HCl (1 M, 2 mL), and then extracted with ethyl acetate (40 mL*2). The organic layers were combined and washed with water (40 mL*2), saturated brine (40 mL*2), dried over $Na_2SO_4$, filtered, concentrated under reduced pressure to give 7-(2,2-dimethyltetrahydro-2H-pyran-4-yl)-3-(1-(5-oxo-4,5-dihydro-1,2,4-oxadiazol-3-yl)cyclopropyl) indolizine-2-carboxylic acid (140 mg, crude) as yellow oil. LC-MS (ES+, m/z): 398.2 [(M+H)$^+$]; Rt=0.437 min.

Step 10: (R)-7-(2,2-dimethyltetrahydro-2H-pyran-4-yl)-3-(1-(5-oxo-4,5-dihydro-1,2,4-oxadiazol-3-yl) cyclopropyl) indolizine-2-carboxylic acid and(S)-7-(2,2-dimethyltetrahydro-2H-pyran-4-yl)-3-(1-(5-oxo-4,5-dihydro-1,2,4-oxadiazol-3-yl)cyclopropyl) indolizine-2-carboxylic acid

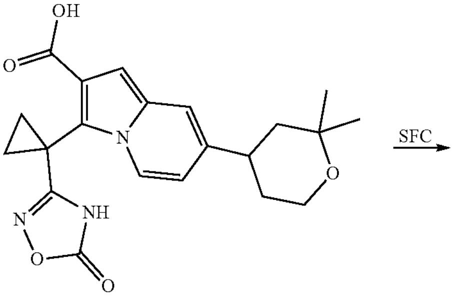

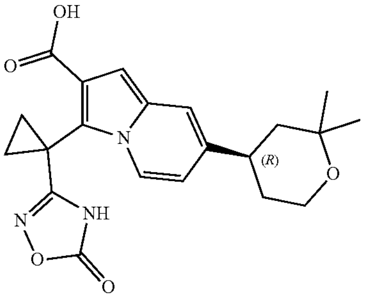

-continued

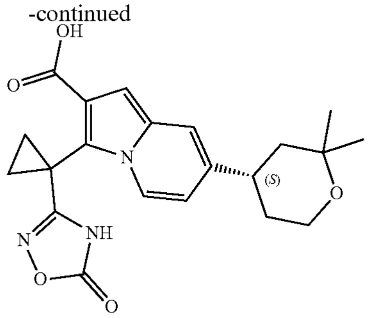

The compound of ethyl 7-(2,2-dimethyltetrahydro-2H-pyran-4-yl)-3-(1-(5-oxo-4,5-dihydro-1,2,4-oxadiazol-3 yl) cyclopropyl) indolizine-2-carboxylate (140 mg, 352.27 µmol, 1 eq) was purified by SFC (column: DAICEL CHIRALCEL OJ (250 mm*30 mm, 10 um); mobile phase: [$CO_2$-MeOH (0.1% $NH_3H_2O$)]; B %: 20%, isocratic elution mode) to give (R)-7-(2,2-dimethyltetrahydro-2H-pyran-4-yl)-3-(1-(5-oxo-4,5-dihydro-1,2,4-oxadiazol-3 yl) cyclopropyl) indolizine-2-carboxylic acid (first eluent 42 mg, 103.67 µmol, 29.43% yield) and(S)-7-(2,2-dimethyltetrahydro-2H-pyran-4-yl)-3-(1-(5-oxo-4,5-dihydro-1,2,4-oxadiazol-3-yl) cyclopropyl) indolizine-2-carboxylic acid (second eluent 43 mg, 108.20 µmol, 30.71% yield).

Intermediate 31-1

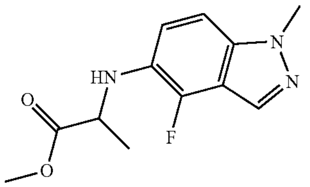

Step 1: methyl 2-((4-fluoro-1-methyl-1H-indazol-5-yl)amino) propanoate

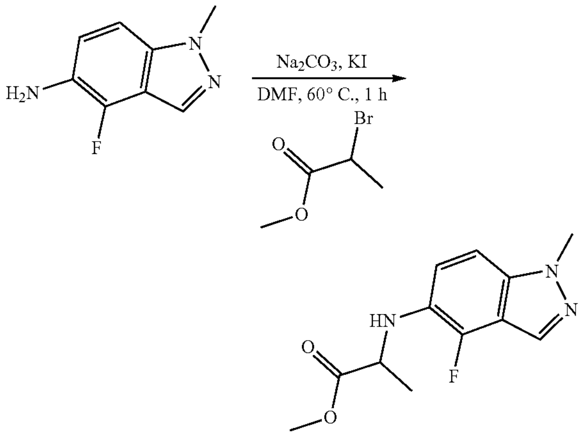

A mixture of 4-fluoro-1-methyl-1H-indazol-5-amine (390 mg, 2.36 mmol, 1 eq), methyl 2-bromopropanoate (354.90 mg, 2.13 mmol, 236.76 µL, 0.9 eq), KI (391.97 mg, 2.36 mmol, 1 eq) and $Na_2CO_3$ (750.80 mg, 7.08 mmol, 3 eq) in DMF (3 mL) was stirred at 60° C. for 1 hour under $N_2$ atmosphere. LCMS showed the reaction was completed. The residue was poured into water (50 mL). The aqueous phase was extracted with ethyl acetate (30 mL*3). The combined organic phase was washed with saturated brine (30 mL), dried with anhydrous $Na_2SO_4$, filtered, and concentrated in vacuum. The residue was purified by prep-TLC ($SiO_2$, Petroleum ether/ethyl acetate=1:1) to give methyl 2-((4-fluoro-1-methyl-1H-indazol-5-yl)amino) propanoate (120 mg, 477.60 µmol, 20.23% yield). LC-MS (ES+, m/z): 252.2 [$(M+H)^+$]; Rt=0.409 min.

Intermediate 32-1

N-(2,2-dimethoxyethyl)-1H-imidazole-1-carboxamide

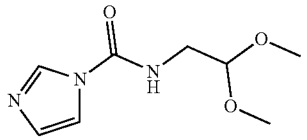

Step 1: N-(2,2-dimethoxyethyl)-1H-imidazole-1-carboxamide

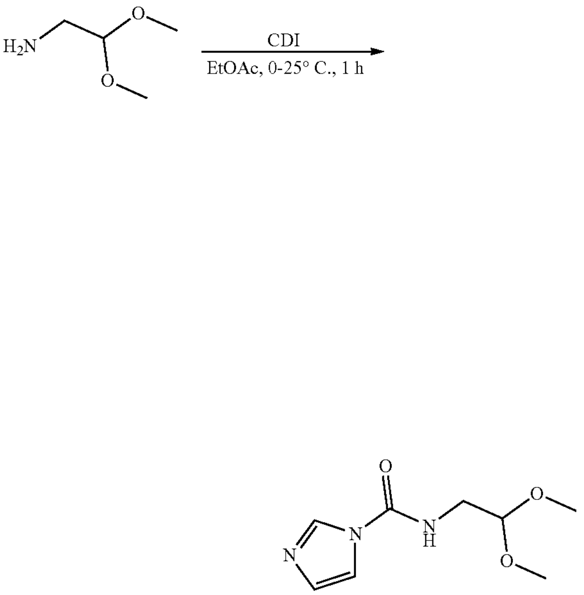

To a solution of CDI (15.42 g, 95.12 mmol, 1 eq) in EtOAc (40 mL) at 0° C. was added 2,2-dimethoxyethanamine (10 g, 95.12 mmol, 10.36 mL, 1 eq). The mixture was allowed to warm to 25° C. for 1 hour. LCMS indicated the reaction was completed. The mixture was filtered. The cake was dried in vacuum to give N-(2,2-dimethoxyethyl)-1H-imidazole-1-carboxamide (16 g, crude).

Intermediate 33-1
(4S)-3-(1-(4-fluoro-1-methyl-1H-indazol-5-yl)-5-methyl-1H-imidazol-4-yl)-2-(4-fluoro-3,5-dimethylphenyl)-4-methyl-4,5,6,7-tetrahydro-2H-pyrazolo[4,3-c]pyridine
Scheme Intermediate 33-1
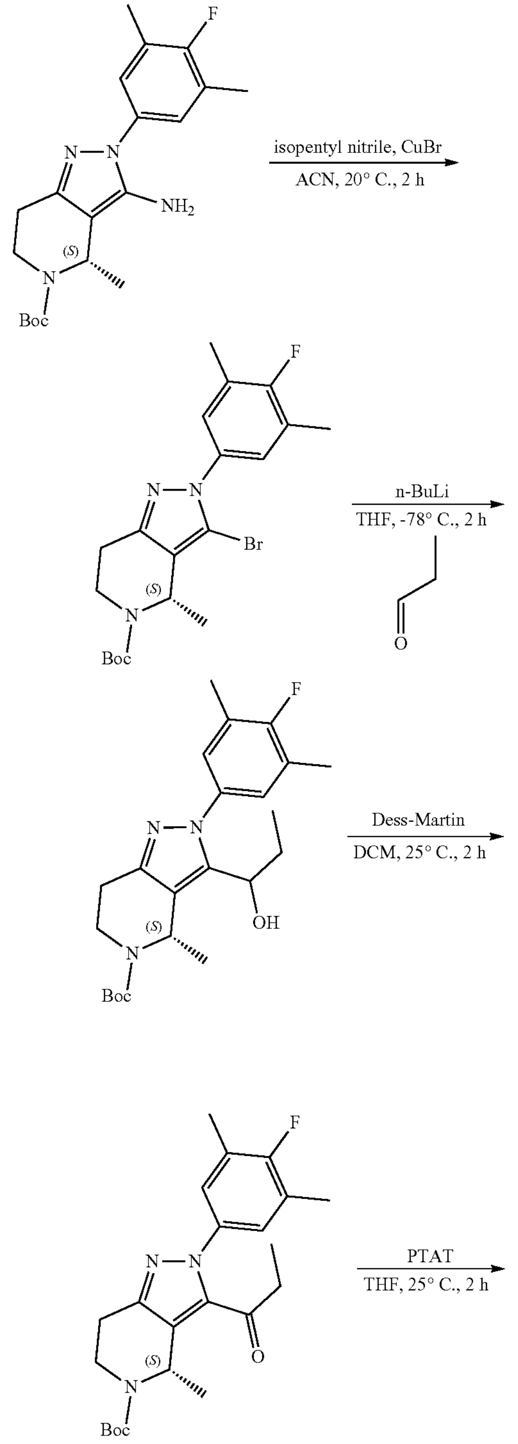
-continued
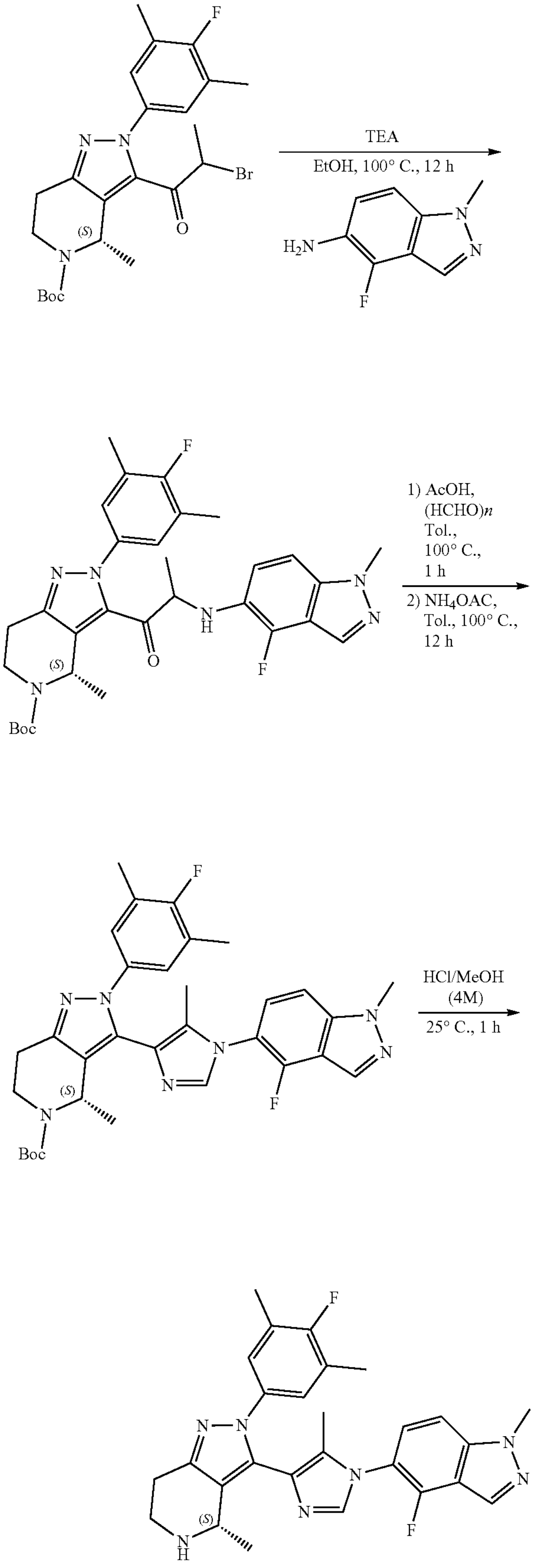

Step 1: (S)-tert-butyl 3-bromo-2-(4-fluoro-3,5-dimethylphenyl)-4-methyl-6,7-dihydro-2H-pyrazolo[4,3-c]pyridine-5 (4H)-carboxylate

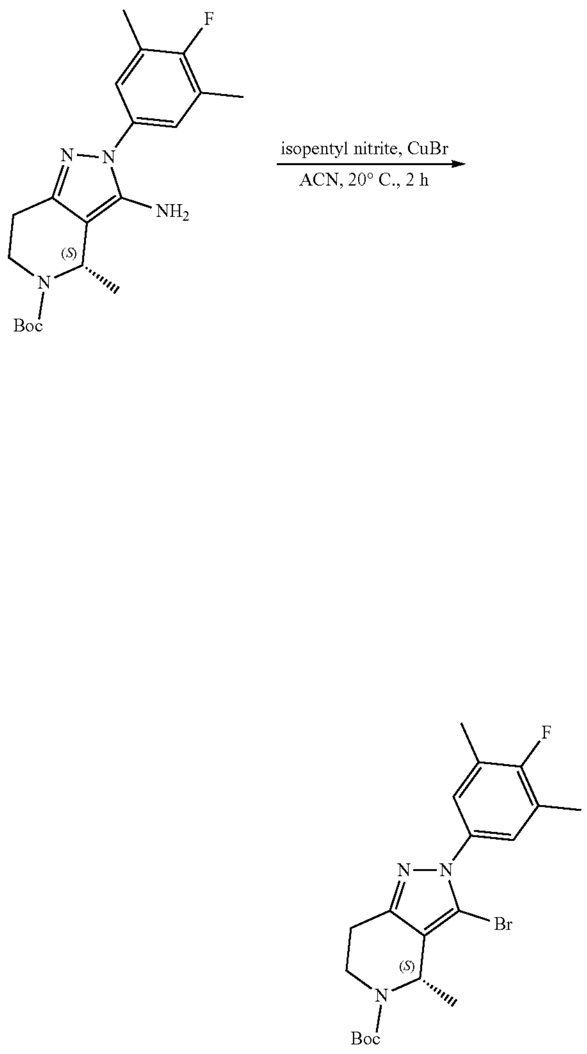

To a solution of(S)-tert-butyl 3-amino-2-(4-fluoro-3,5-dimethylphenyl)-4-methyl-6,7-dihydro-2H-pyrazolo[4,3-c] pyridine-5 (4H)-carboxylate (6 g, 16.02 mmol, 1 eq) in MeCN (120 mL) was added isopentyl nitrite (6.57 g, 56.08 mmol, 3.5 eq) and CuBr (45.97 g, 320.47 mmol, 20 eq). The mixture was stirred at 20° C. for 2 hours. LCMS indicated the reaction was completed. The mixture was poured into water (200 mL) and extracted with ethyl acetate (200 mL*2). The organic layers were combined and washed with water (100 mL*2), saturated brine (100 mL*2), dried over $Na_2SO_4$, filtered, concentrated under reduced pressure. The residue was purified by prep-HPLC (column: Phenomenex luna C18250*150 mm*15 um; mobile phase: [$H_2O$ (0.1% TFA)-ACN]; gradient: 70%-100% B over 15.0 min) to afford(S)-tert-butyl 3-bromo-2-(4-fluoro-3,5-dimethylphenyl)-4-methyl-6,7-dihydro-2H-pyrazolo[4,3-c]pyridine-5 (4H)-carboxylate (4.2 g, 9.58 mmol, 59.80% yield). LC-MS (ES+, m/z): 438.0 [$(M+H)^+$]. Rt=0.702 min.

Step 2: (4S)-tert-butyl 2-(4-fluoro-3,5-dimethylphenyl)-3-(1-hydroxypropyl)-4-methyl-6,7-dihydro-2H-pyrazolo[4,3-c]pyridine-5 (4H)-carboxylate

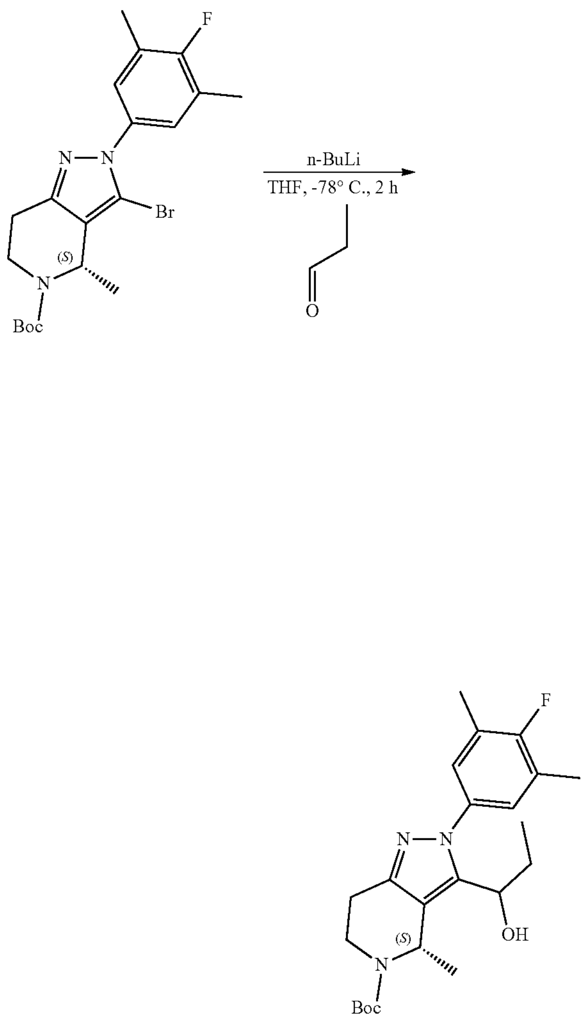

To a solution of(S)-tert-butyl 3-bromo-2-(4-fluoro-3,5-dimethylphenyl)-4-methyl-6,7-dihydro-2H-pyrazolo[4,3-c] pyridine-5 (4H)-carboxylate (1 g, 2.28 mmol, 1 eq) in THF (10 mL) was added n-BuLi (2.5 M, 1.10 mL, 1.2 eq) dropwise at −78° C. The mixture was stirred at −78° C. for 0.5 hour. A solution of propionaldehyde (132.50 mg, 2.28 mmol, 166.04 μL, 1 eq) in THF (2 mL) was added. The mixture was stirred at −78° C. for 1.5 hours under $N_2$ atmosphere. LCMS showed the reaction was completed. The residue was poured into saturated $NH_4Cl$ solution (200 mL) and extracted with ethyl acetate (100 mL*3). The combined organic phase was washed with saturated brine (200 mL), dried with anhydrous $Na_2SO_4$, filtered, and concentrated in vacuum. The residue was purified by column chromatography ($SiO_2$, Petroleum ether/ethyl acetate=1/0 to 5/1) to give (4S)-tert-butyl 2-(4-fluoro-3,5-dimethylphenyl)-3-(1-hydroxypropyl)-4-methyl-6,7-dihydro-2H-pyrazolo[4,3-c] pyridine-5 (4H)-carboxylate (600 mg, 1.34 mmol, 58.65% yield). LC-MS (ES+, m/z): 418.3 [$(M+H)^+$]; Rt=0.567 min.

Step 3: (S)-tert-butyl 2-(4-fluoro-3,5-dimethylphenyl)-4-methyl-3-propionyl-6,7-dihydro-2H-pyrazolo [4,3-c]pyridine-5 (4H)-carboxylate

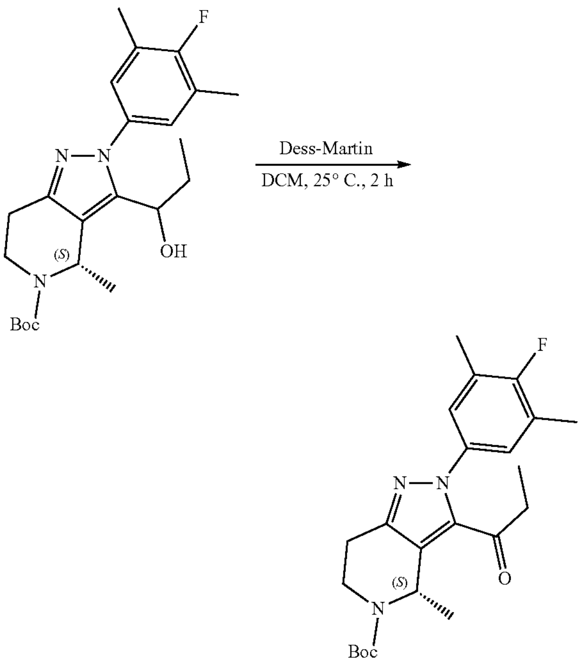

To a solution of (4S)-tert-butyl 2-(4-fluoro-3,5-dimethylphenyl)-3-(1-hydroxypropyl)-4-methyl-6,7-dihydro-2H-pyrazolo[4,3-c]pyridine-5 (4H)-carboxylate (400 mg, 958.05 μmol, 1 eq) in DCM (4 mL) was added Dess-Martin (812.70 mg, 1.92 mmol, 593.64 μL, 2 eq). The mixture was stirred at 25° C. for 2 hours. LCMS showed the reaction was completed. The residue was poured into water (50 mL) and extracted with DCM (30 mL*3). The combined organic phase was washed with saturated brine (40 mL), dried with anhydrous $Na_2SO_4$, filtered, and concentrated in vacuum. The residue was purified prep-TLC ($SiO_2$, Petroleum ether: Ethyl acetate=3:1) to give(S)-tert-butyl 2-(4-fluoro-3,5-dimethylphenyl)-4-methyl-3-propionyl-6,7-dihydro-2H-pyrazolo[4,3-c]pyridine-5 (4H)-carboxylate (300 mg, 698.20 μmol, 72.88% yield). LC-MS (ES+, m/z): 416.2 [$(M+H)^+$]; Rt=0.678 min.

Step 4: (4S)-tert-butyl 3-(2-bromopropanoyl)-2-(4-fluoro-3,5-dimethylphenyl)-4-methyl-6,7-dihydro-2H-pyrazolo[4,3-c]pyridine-5 (4H)-carboxylate

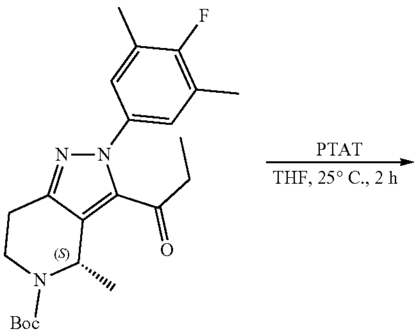

-continued

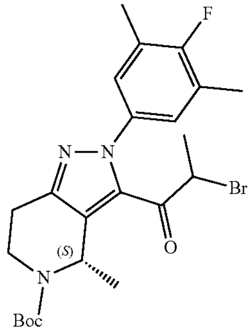

To a solution of(S)-tert-butyl 2-(4-fluoro-3,5-dimethylphenyl)-4-methyl-3-propionyl-6,7-dihydro-2H-pyrazolo [4,3-c]pyridine-5 (4H)-carboxylate (300 mg, 722.02 μmol, 1 eq) in THF (3 mL) was added PTAT (352.85 mg, 938.63 μmol, 1.3 eq). The mixture was stirred at 25° C. for 1 hour. DIEA (186.63 mg, 1.44 mmol, 251.53 μL, 2 eq) was added followed by $(Boc)_2O$ (157.58 mg, 722.02 μmol, 165.87 μL, 1 eq). The mixture was stirred at 25° C. for 1 hour. LCMS showed the reaction was completed. The residue was poured into water (50 mL) and extracted with ethyl acetate (30 mL*3). The combined organic phase was washed with saturated brine (50 mL), dried with anhydrous $Na_2SO_4$, filtered, and concentrated in vacuum. The residue was purified by prep-TLC ($SiO_2$, Petroleum ether:ethyl acetate=3:1) to give (4S)-tert-butyl 3-(2-bromopropanoyl)-2-(4-fluoro-3,5-dimethylphenyl)-4-methyl-6,7-dihydro-2H-pyrazolo[4,3-c]pyridine-5 (4H)-carboxylate (280 mg, 540.30 μmol, 74.83% yield). LC-MS (ES+, m/z): 494.0 [$(M+H)^+$]; Rt=0.692 min.

Step 5: (4S)-tert-butyl 3-(2-((4-fluoro-1-methyl-1H-indazol-5-yl)amino) propanoyl)-2-(4-fluoro-3,5-dimethylphenyl)-4-methyl-6,7-dihydro-2H-pyrazolo [4,3-c]pyridine-5 (4H)-carboxylate

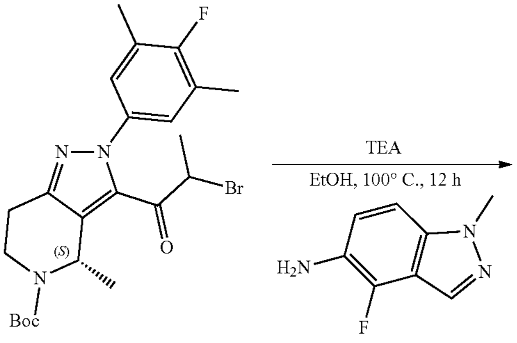

-continued

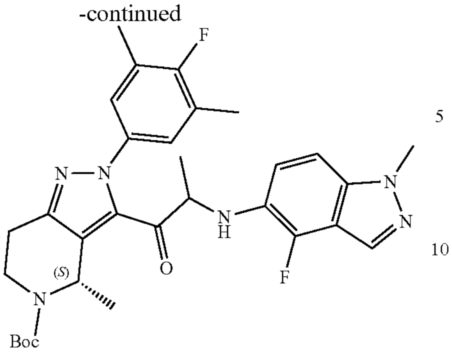

To a solution of (4S)-tert-butyl 3-(2-bromopropanoyl)-2-(4-fluoro-3,5-dimethylphenyl)-4-methyl-6,7-dihydro-2H-pyrazolo[4,3-c]pyridine-5 (4H)-carboxylate (280 mg, 627.03 μmol, 1 eq) and 4-fluoro-1-methyl-1H-indazol-5-amine (124.28 mg, 752.43 μmol, 1.2 eq) in EtOH (4 mL) was added TEA (126.90 mg, 1.25 mmol, 174.55 μL, 2 eq). The mixture was stirred at 100° C. for 12 hours. LCMS showed the reaction was completed. The residue was concentrated in vacuum. The residue was purified by prep-TLC ($SiO_2$, Petroleum ether/ethyl acetate=3:1) to give (4S)-tert-butyl 3-(2-((4-fluoro-1-methyl-1H-indazol-5-yl)amino) propanoyl)-2-(4-fluoro-3,5-dimethylphenyl)-4-methyl-6,7-dihydro-2H-pyrazolo[4,3-c]pyridine-5 (4H)-carboxylate (180 mg, 288.98 μmol, 46.09% yield). LC-MS (ES+, m/z): 579.4 [$(M+H)^+$]; Rt=0.660 min.

Step 6: (4S)-tert-butyl 3-(1-(4-fluoro-1-methyl-1H-indazol-5-yl)-5-methyl-1H-imidazol-4-yl)-2-(4-fluoro-3,5-dimethylphenyl)-4-methyl-6,7-dihydro-2H-pyrazolo[4,3-c]pyridine-5 (4H)-carboxylate

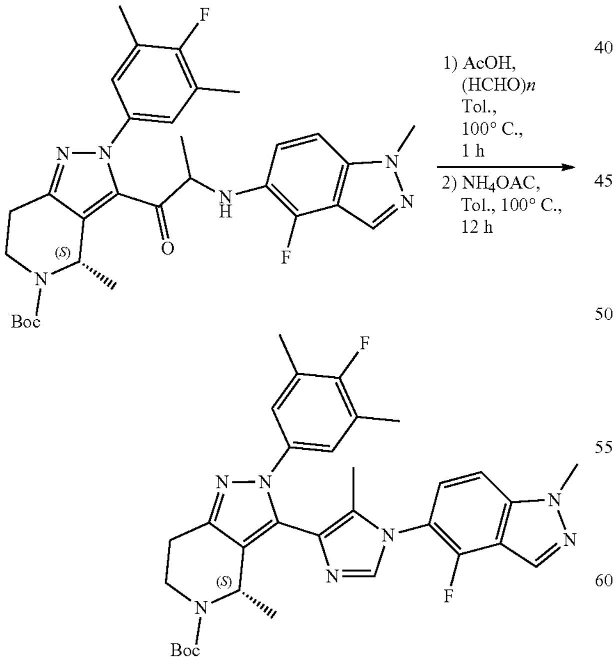

To a solution of (4S)-tert-butyl 3-(2-((4-fluoro-1-methyl-1H-indazol-5-yl)amino) propanoyl)-2-(4-fluoro-3,5-dimethylphenyl)-4-methyl-6,7-dihydro-2H-pyrazolo[4,3-c]pyridine-5 (4H)-carboxylate (200 mg, 345.63 μmol, 1 eq) in toluene (2 mL) was added HCHO (103.79 mg, 3.46 mmol, 95.22 μL, 10 eq) and AcOH (20.76 mg, 345.63 μmol, 19.79 μL, 1 eq). The mixture was stirred at 100° C. for 1 hour. $CH_3COONH_4$ (266.41 mg, 3.46 mmol, 10 eq) was then added. The mixture was stirred at 100° C. for 12 hours. LCMS showed the reaction was completed. The residue was poured into water (50 mL) and extracted with ethyl acetate (25 mL*3). The combined organic phase was washed with saturated brine (30 mL), dried with anhydrous $Na_2SO_4$, filtered, and concentrated in vacuum. The residue was purified by prep-TLC ($SiO_2$, Petroleum ether: Ethyl acetate=3:1) to give (4S)-tert-butyl 3-(1-(4-fluoro-1-methyl-1H-indazol-5-yl)-5-methyl-1H-imidazol-4-yl)-2-(4-fluoro-3,5-dimethylphenyl)-4-methyl-6,7-dihydro-2H-pyrazolo[4,3-c]pyridine-5 (4H)-carboxylate (35 mg, 59.56 μmol, 17.23% yield). LC-MS (ES+, m/z): 588.5 [$(M+H)^+$]; Rt=1.962 min.

Step 7: (4S)-3-(1-(4-fluoro-1-methyl-1H-indazol-5-yl)-5-methyl-1H-imidazol-4-yl)-2-(4-fluoro-3,5-dimethylphenyl)-4-methyl-4,5,6,7-tetrahydro-2H-pyrazolo[4,3-c]pyridine

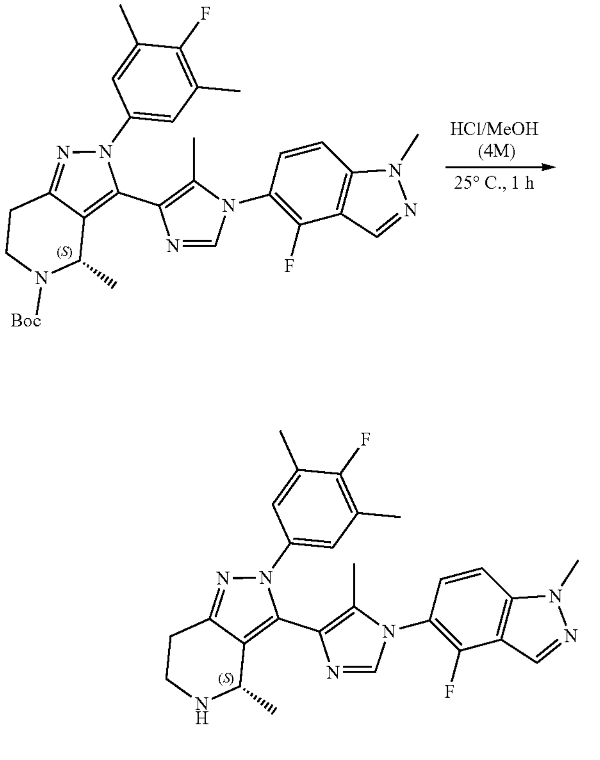

A solution of (4S)-tert-butyl 3-(1-(4-fluoro-1-methyl-1H-indazol-5-yl)-5-methyl-1H-imidazol-4-yl)-2-(4-fluoro-3,5-dimethylphenyl)-4-methyl-6,7-dihydro-2H-pyrazolo[4,3-c]pyridine-5 (4H)-carboxylate (40 mg, 68.07 μmol, 1 eq) in HCl/MeOH (4 M, 1 mL) was stirred at 25° C. for 1 hour. LCMS showed the reaction was completed. The residue was concentrated in vacuum to give (4S)-3-(1-(4-fluoro-1-methyl-1H-indazol-5-yl)-5-methyl-1H-imidazol-4-yl)-2-(4-fluoro-3,5-dimethylphenyl)-4-methyl-4,5,6,7-tetrahydro-2H-pyrazolo[4,3-c]pyridine (30 mg, crude). LC-MS (ES+, m/z): 488.3 [$(M+H)^+$]; Rt=0.404 min.

Intermediate 33-2

5-bromo-N-methyl-1-(1-(5-oxo-4,5-dihydro-1,2,4-oxadiazol-3-yl)cyclopropyl)-N-phenyl-1H-indole-2-carboxamide Scheme Intermediate 33-2

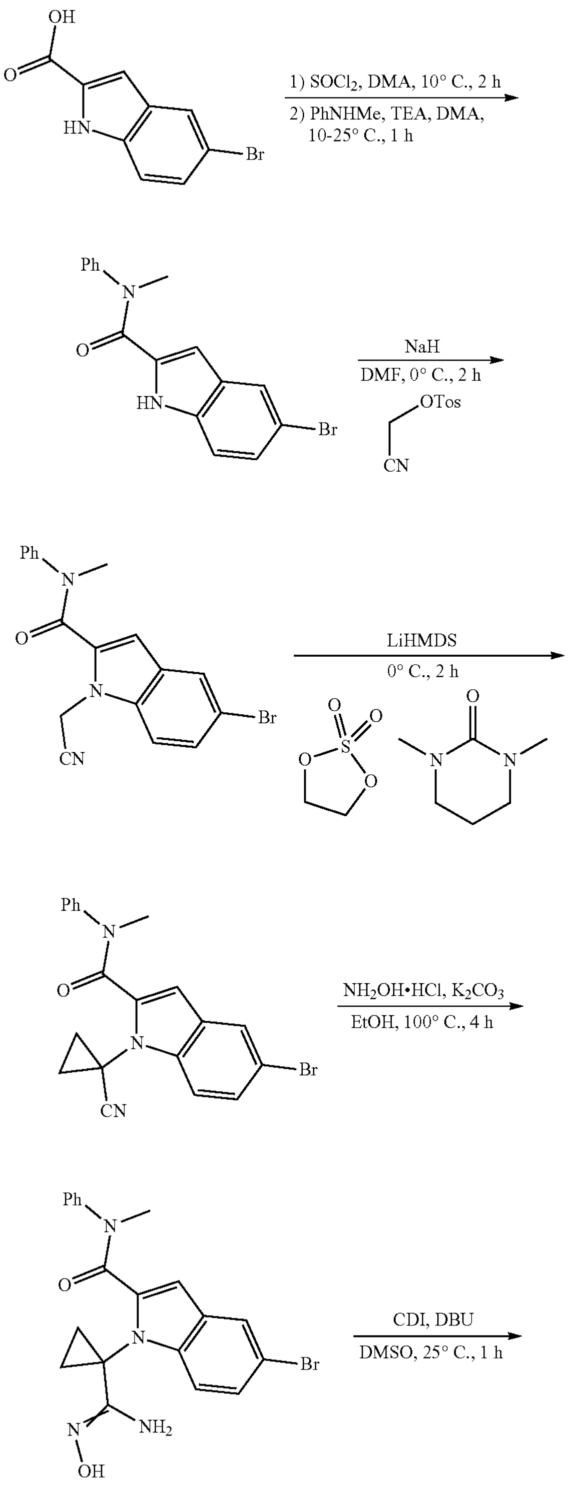

-continued

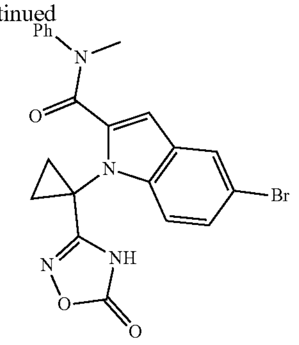

Step 1: 5-bromo-N-methyl-N-phenyl-1H-indole-2-carboxamide

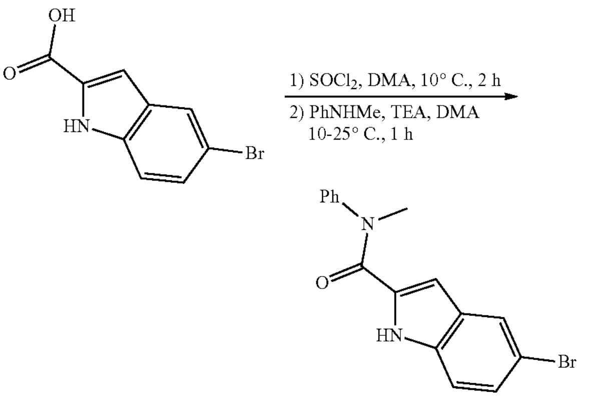

To a solution of 5-bromo-1H-indole-2-carboxylic acid (60 g, 249.94 mmol, 1 eq) in DMA (600 mL) was added $SOCl_2$ (35.68 g, 299.93 mmol, 21.78 mL, 1.2 eq) dropwise at 10° C. After stirring for 2 hours, N-methylaniline (32.14 g, 299.93 mmol, 32.56 mL, 1.2 eq) and TEA (60.70 g, 599.87 mmol, 83.49 mL, 2.4 eq) were added dropwise at 10° C. The mixture was stirred at 25° C. for 1 hour. LCMS showed the reaction was completed. The reaction mixture was added dropwise saturated $NaHCO_3$ (100 mL), and the precipitated solid was collected by filtration. The obtained solid was washed with water (150 mL) and dried under reduced pressure to give 5-bromo-N-methyl-N-phenyl-1H-indole-2-carboxamide (80 g, 237.43 mmol, 94.99% yield). LC-MS (ES+, m/z): 329.1 [$(M+H)^+$]; Rt=0.561 min.

Step 2: 5-bromo-1-(cyanomethyl)-N-methyl-N-phenyl-1H-indole-2-carboxamide

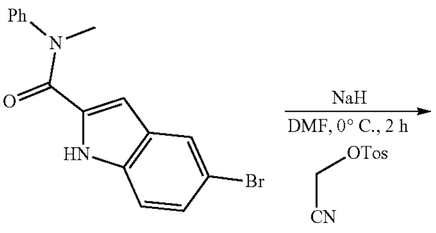

-continued

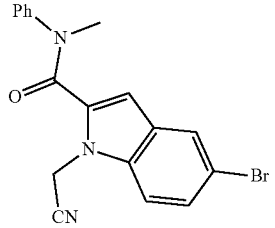

To a solution of 5-bromo-N-methyl-N-phenyl-1H-indole-2-carboxamide (30 g, 91.13 mmol, 1 eq) in DMF (300 mL) was added NaH (10.93 g, 273.40 mmol, 60% purity, 3 eq) under $N_2$. The mixture was stirred at 0° C. for 1 hour under $N_2$. Cyanomethyl 4-methylbenzenesulfonate (38.50 g, 182.27 mmol, 2 eq) was added. The mixture was stirred at 0° C. for 1 hour under $N_2$. LCMS indicated the reaction was completed. The mixture was added dropwise to saturated $NH_4Cl$ (150 mL) and then extracted with DCM (100 mL*3). The organic layers were combined, washed with water (150 mL), saturated brine (150 mL), dried over $Na_2SO_4$, filtered, and concentrated to give crude product. The crude product was purified by chromatography on silica gel (Petroleum ether/Ethyl acetate-5/1-1/1) to give 5-bromo-1-(cyanomethyl)-N-methyl-N-phenyl-1H-indole-2-carboxamide (30 g, 81.47 mmol, 89.40% yield). LC-MS (ES+, m/z): 368.1 [$(M+H)^+$]; Rt=0.572 min.

Step 3: 5-bromo-1-(1-cyanocyclopropyl)-N-methyl-N-phenyl-1H-indole-2-carboxamide

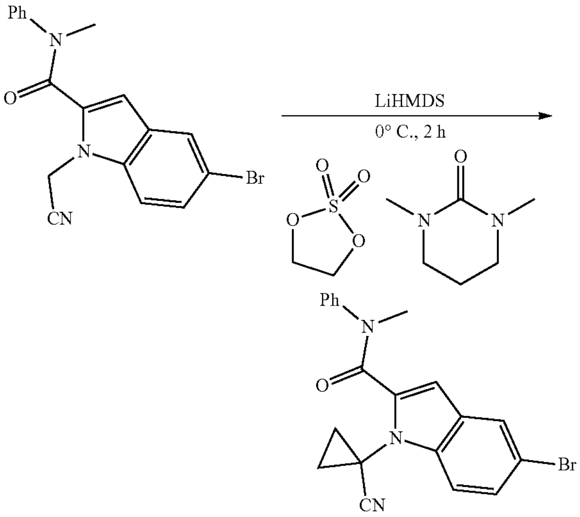

To a solution of 5-bromo-1-(cyanomethyl)-N-methyl-N-phenyl-1H-indole-2-carboxamide (12 g, 32.59 mmol, 1 eq) and 1, 3, 2-dioxathiolane 2, 2-dioxide (12.13 g, 97.77 mmol, 3 eq) in 1, 3-dimethyltetrahydropyrimidin-2 (1H)-one (120 mL) was added LiHMDS (1 M in THF, 130.35 mL, 4 eq) dropwise at 0° C. under $N_2$. The mixture was stirred at 0° C. for 2 hours under $N_2$. LCMS showed reaction was completed. The mixture was added dropwise to saturated $NH_4Cl$ (400 mL), and then extracted with ethyl acetate (300 mL*3). The organic layers were combined, washed with water (500 mL*2), saturated brine (500 mL), dried over $Na_2SO_4$, filtered, and concentrated to give crude product. The crude product was purified by chromatography on silica gel (Petroleum ether:ethyl acetate=6/1 to 1/3) to give 5-bromo-1-(1-cyanocyclopropyl)-N-methyl-N-phenyl-1H-indole-2-carboxamide (8.4 g, 20.86 mmol, 64.00% yield). LC-MS (ES+, m/z): 393.9 [$(M+H)^+$]; Rt=0.560 min.

Step 4: 5-bromo-1-(1-(N'-hydroxycarbamimidoyl) cyclopropyl)-N-methyl-N-phenyl-1H-indole-2-carboxamide

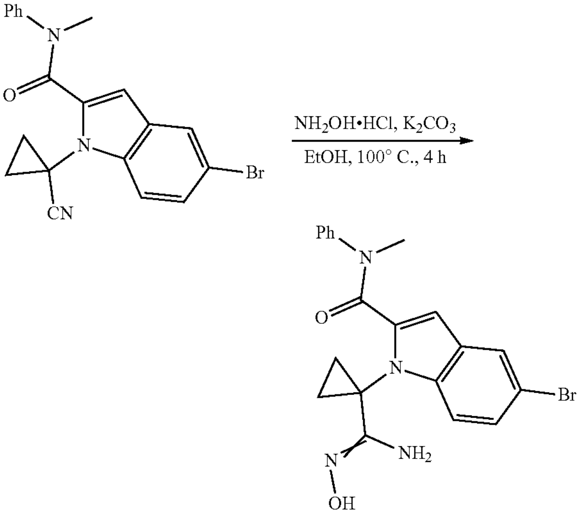

To a mixture of 5-bromo-1-(1-cyanocyclopropyl)-N-methyl-N-phenyl-1H-indole-2-carboxamide (17 g, 43.12 mmol, 1 eq) and $K_2CO_3$ (32.78 g, 237.15 mmol, 5.5 eq) in EtOH (170 mL) was added $NH_2OH·HCl$ (14.98 g, 215.59 mmol, 5 eq). The mixture was stirred at 100° C. for 4 hours. LCMS indicated the reaction was completed. The mixture was added dropwise to $H_2O$ (150 mL), and then extracted with ethyl acetate (100 mL*3). The organic layers were combined, washed with water (200 mL*2), saturated brine (200 mL), dried over $Na_2SO_4$, filtered, and concentrated to give 5-bromo-1-(1-(N'-hydroxycarbamimidoyl) cyclopropyl)-N-methyl-N-phenyl-1H-indole-2-carboxamide (17.8 g, crude). LC-MS (ES+, m/z): 427.1 [$(M+H)^+$]; Rt=0.451 min.

Step 5:5-bromo-N-methyl-1-(1-(5-oxo-4,5-dihydro-1, 2, 4-oxadiazol-3-yl)cyclopropyl)-N-phenyl-1H-indole-2-carboxamide

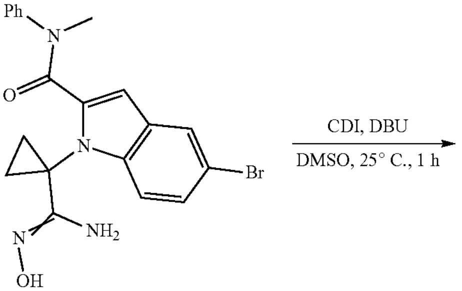

-continued

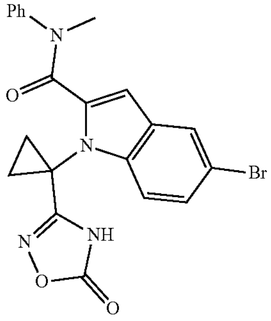

To a solution of 5-bromo-1-(1-(N'-hydroxycarbamimidoyl) cyclopropyl)-N-methyl-N-phenyl-1H-indole-2-carboxamide (17.8 g, 34.78 mmol, 1 eq) in DMSO (180 mL) was added DBU (13.24 g, 86.96 mmol, 13.11 mL, 2.5 eq) and CDI (11.28 g, 69.57 mmol, 2 eq). The mixture was stirred at 25° C. for 1 hour. LCMS indicated the reaction was completed. The mixture was added to $H_2O$ (150 mL), and then extracted with DCM (100 mL*3). The organic layers were combined, washed with water (200 mL*2), saturated brine (200 mL), dried over $Na_2SO_4$, filtered, and concentrated to give crude product. The residue was purified by column chromatography ($SiO_2$, ethyl acetate/Methanol=50/1 to 1/2) to give 5-bromo-N-methyl-1-(1-(5-oxo-4, 5-dihydro-1, 2, 4-oxadiazol-3-yl)cyclopropyl)-N-phenyl-1H-indole-2-carboxamide (15 g, 28.72 mmol, 82.58% yield). LC-MS (ES+, m/z): 452.9 [(M+H)$^+$]; Rt=0.552 min.

Intermediate 37-1 methyl 2-((4-fluoro-1-methyl-1H-indazol-5-yl) amino)-2-methylpropanoate

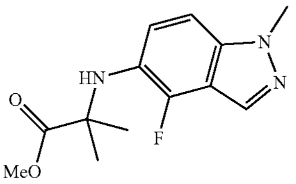 [SMILES: COC(=O)C(C)(C)Nc1ccc2c(cnn2C)c1F]

Step 1: methyl 2-((4-fluoro-1-methyl-1H-indazol-5-yl)amino)-2-methylpropanoate

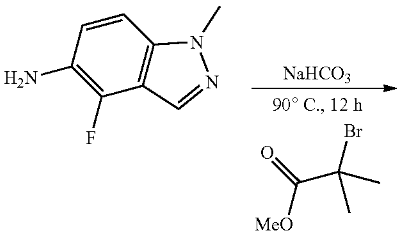

-continued

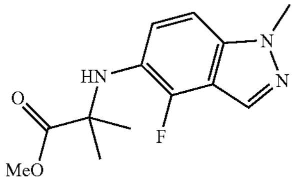

To a solution of 4-fluoro-1-methyl-1H-indazol-5-amine (500 mg, 3.03 mmol, 1 eq) in methyl 2-bromo-2-methylpropanoate (17.49 g, 96.60 mmol, 12.50 mL, 31.91 eq) was added $NaHCO_3$ (762.92 mg, 9.08 mmol, 353.37 μL, 3 eq). The mixture was stirred at 90° C. for 12 hours. LCMS indicated the reaction was completed. The reaction mixture was poured into $H_2O$ (30 mL) and extracted with ethyl acetate (50 mL*3). The organic layers were combined, washed with water (60 mL*2), saturated brine (50 mL*2), dried over $Na_2SO_4$, filtered, and concentrated under reduced pressure. The residue was purified by column chromatography ($SiO_2$, Petroleum ether/ethyl acetate=50/1 to 1/1) to afford methyl 2-((4-fluoro-1-methyl-1H-indazol-5-yl) amino)-2-methylpropanoate (300 mg, 758.81 μmol, 25.07% yield). LC-MS (ES+, m/z): 266.2 [(M+H)$^+$]; Rt=0.413 min.

Intermediate 38-1

1-(4-Fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one Scheme 38-1

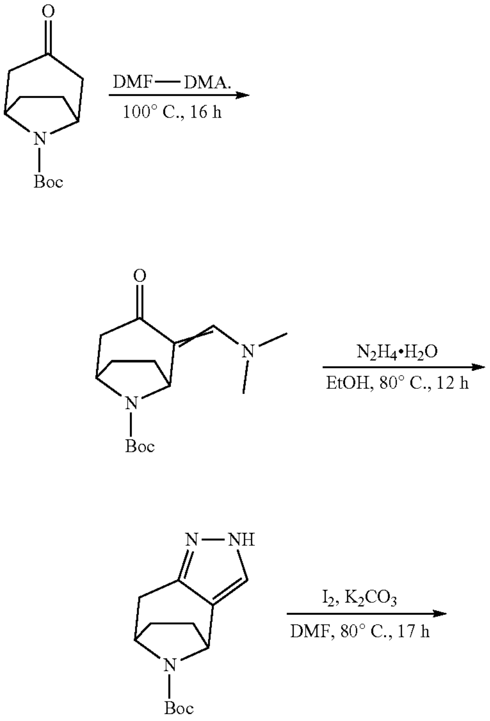

-continued
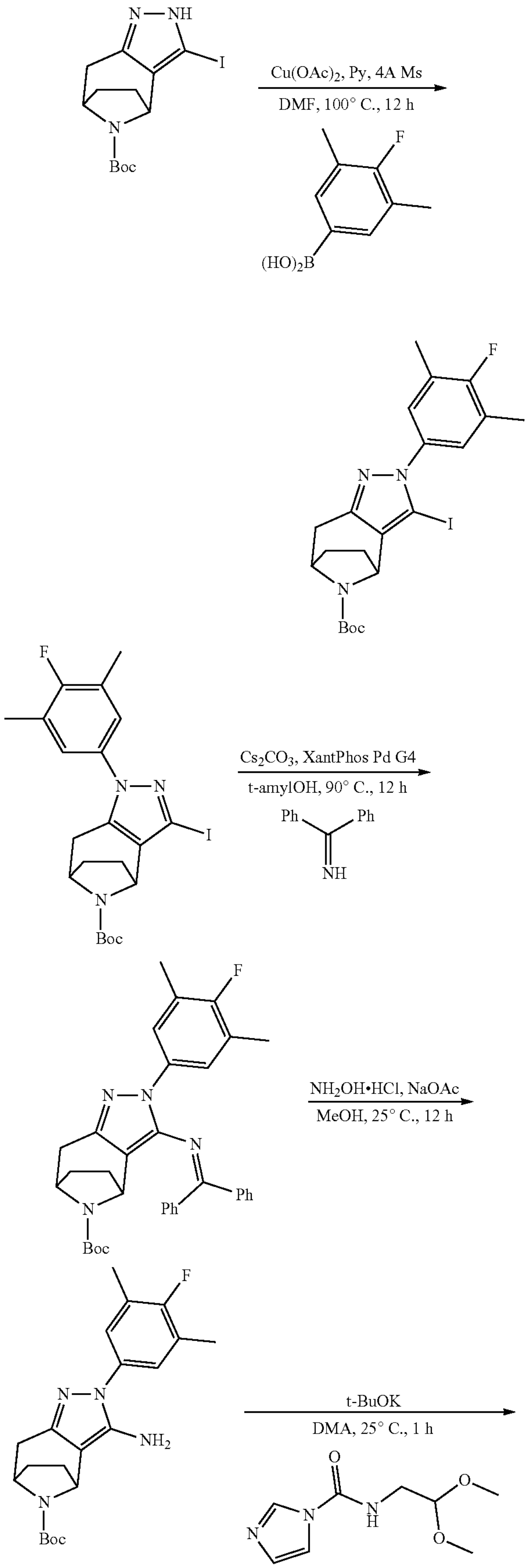
-continued
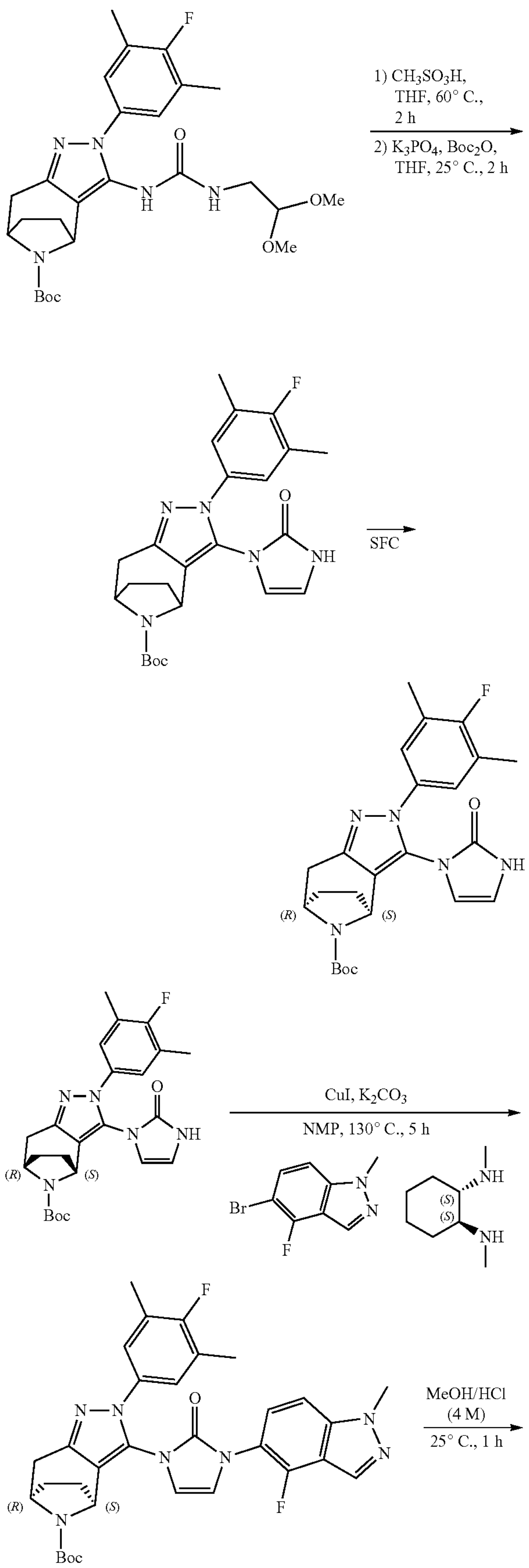

-continued

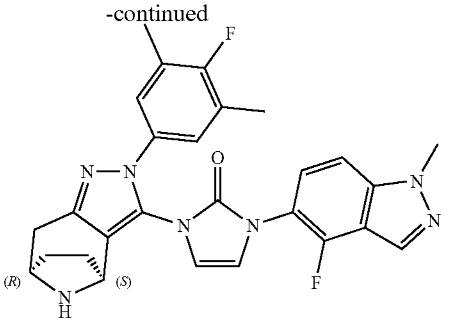

Step 1: tert-butyl 2-((dimethylamino)methylene)-3-oxo-8-azabicyclo[3.2.1]octane-8-carboxylate

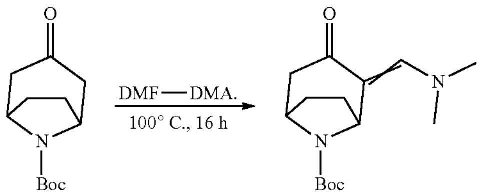

A mixture of tert-butyl 3-oxo-8-azabicyclo[3.2.1]octane-8-carboxylate (50 g, 88.78 mmol, 1 eq) in 1,1-dimethoxy-N,N-dimethyl-methanamine (500 mL) was stirred at 100° C. for 16 hours under $N_2$ atmosphere. LCMS showed reaction was completed. The reaction mixture was concentrated to give crude product. The residue was purified by column chromatography ($SiO_2$, Petroleum ether/ethyl acetate=100/1 to 1/1) to give tert-butyl 2-((dimethylamino)methylene)-3-oxo-8-azabicyclo[3.2.1]octane-8-carboxylate (20 g, 64.35 mmol, 28.99% yield). LC-MS (ES+, m/z): 281.2 [$(M+H)^+$]; Rt=0.379 min.

Step 2: tert-butyl 2,4,5,6,7,8-hexahydro-4,7-epiminocyclohepta [c]pyrazole-9-carboxylate

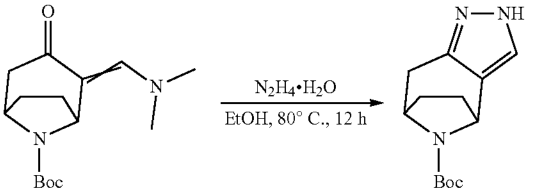 [SMILES: CN(C)C=C1C(=O)CC2CCC1N2C(=O)OC(C)(C)C ; "N2H4·H2O" ; CC(C)(C)OC(=O)N1C2CCC1c1c[nH]nc1C2]

To a solution of tert-butyl 2-((dimethylamino)methylene)-3-oxo-8-azabicyclo[3.2.1]octane-8-carboxylate (15 g, 53.50 mmol, 1 eq) in EtOH (160 mL) was added $N_2H_4 \cdot H_2O$ (5.34 g, 85.34 mmol, 5.17 mL, 80% purity, 1.60 eq). The mixture was stirred for 12 hours at 80° C. under $N_2$ atmosphere. LCMS showed reaction was completed. The reaction mixture was quenched by addition $H_2O$ (300 mL), extracted with ethyl acetate (200 mL*3). The combined organic layers were washed with saturated brine (100 mL), dried over anhydrous $Na_2SO_4$, filtered, and concentrated under reduced pressure to give a residue. The residue was purified by column chromatography ($SiO_2$, Petroleum ether/Ethyl acetate=1/0 to 1/3) to give tert-butyl 2,4,5,6,7,8-hexahydro-4,7-epiminocyclohepta [c]pyrazole-9-carboxylate (12 g, 43.61 mmol, 81.51% yield) as white solid. LC-MS (ES+, m/z): 249.9 [$(M+H)^+$]; Rt=0.377 min.

Step 3: tert-butyl 3-iodo-2,4,5,6,7,8-hexahydro-4,7-epiminocyclohepta [c]pyrazole-9-carboxylate

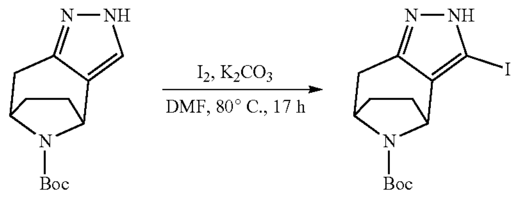 [SMILES: CC(C)(C)OC(=O)N1C2CCC1c1c[nH]nc1C2 ; CC(C)(C)OC(=O)N1C2CCC1c1c(n[nH]c1I)C2]

A mixture of (4S,7R)-tert-butyl 2,4,5,6,7,8-hexahydro-4,7-epiminocyclohepta [c]pyrazole-9-carboxylate (11 g, 44.12 mmol, 1 eq), $K_2CO_3$ (22.40 g, 88.24 mmol, 17.78 mL, 2 eq), $I_2$ (22.40 g, 88.24 mmol, 17.78 mL, 2 eq) in DMF (110 mL) was stirred at 80° C. for 17 hours under $N_2$ atmosphere. LCMS indicated the reaction was completed. The reaction mixture was quenched by addition $H_2O$ (500 mL), extracted with ethyl acetate (200 mL*3). The combined organic layers were washed with saturated brine (100 mL), dried over anhydrous $Na_2SO_4$, filtered, and concentrated under reduced pressure to give a residue. The residue was purified by column chromatography ($SiO_2$, Petroleum ether/Ethyl acetate=1/0 to 1/1) to give tert-butyl 3-iodo-2,4,5,6,7,8-hexahydro-4,7-epiminocyclohepta [c]pyrazole-9-carboxylate (7 g, 16.55 mmol, 37.51% yield) as yellow solid. LC-MS (ES+, m/z): 376.1 [$(M+H)^+$]; Rt=0.481 min.

Step 4: tert-butyl 2-(4-fluoro-3,5-dimethylphenyl)-3-iodo-2,4,5,6,7,8-hexahydro-4,7-epiminocyclohepta [c]pyrazole-9-carboxylate

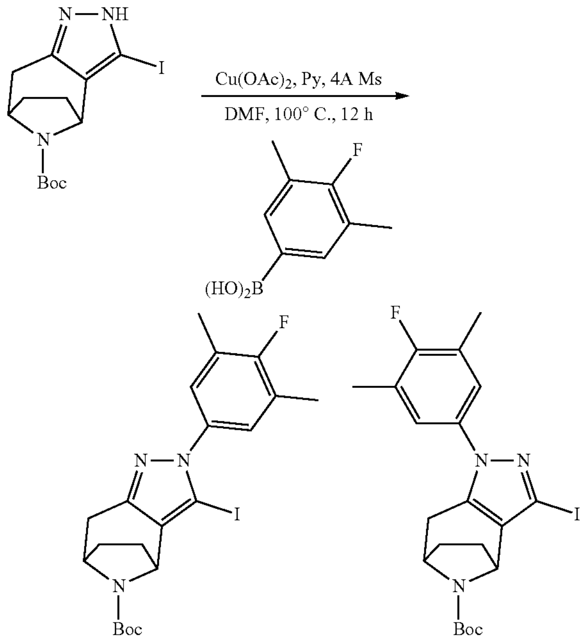

To a solution of tert-butyl 3-iodo-2,4,5,6,7,8-hexahydro-4,7-epiminocyclohepta [c]pyrazole-9-carboxylate (5 g, 13.33 mmol, 1 eq), (4-fluoro-3,5-dimethylphenyl) boronic acid (4.48 g, 26.65 mmol, 2 eq) in DMF (50 mL) was added Py (2.11 g, 26.65 mmol, 2.15 mL, 2 eq), $Cu(OAc)_2$ (242.04 mg, 1.33 mmol, 0.1 eq), 4A MS (200 mg, 26.65 mmol, 2 eq). The mixture was stirred for 12 hours at 100° C. under $O_2$ (15 Psi). LCMS indicated the reaction was completed. The reaction mixture was quenched by saturated addition saturated EDTA solution (200 mL) and ethyl acetate (50 mL), stirred for 0.5 hour, and then extracted with ethyl acetate (100 mL*3). The combined organic layers were washed with saturated brine (50 mL), dried over anhydrous $Na_2SO_4$, filtered, and concentrated under reduced pressure to give a residue. The residue was purified by column chromatography ($SiO_2$, Petroleum ether/Ethyl acetate=100/1 to 4/1) to give tert-butyl 4-(4-fluoro-3,5-dimethyl-phenyl)-3-iodo-4,5,11-triazatricyclo[6.2.1.02,6]undeca-2,5-diene-11-carboxylate (2.5 g, 4.00 mmol, 23.07% yield) and tert-butyl 2-(4-fluoro-3,5-dimethylphenyl)-3-iodo-2,4,5,6,7,8-hexahydro-4,7-epiminocyclohepta [c]pyrazole-9-carboxylate (3.2 g, 5.93 mmol, 44.47% yield). LC-MS (ES+, m/z): 497.9 [$(M+H)^+$]; Rt=2.415 min.

Step 5: tert-butyl 3-((diphenylmethylene)amino)-2-(4-fluoro-3,5-dimethylphenyl)-2,4,5,6,7,8-hexahydro-4,7-epiminocyclohepta [c]pyrazole-9-carboxylate

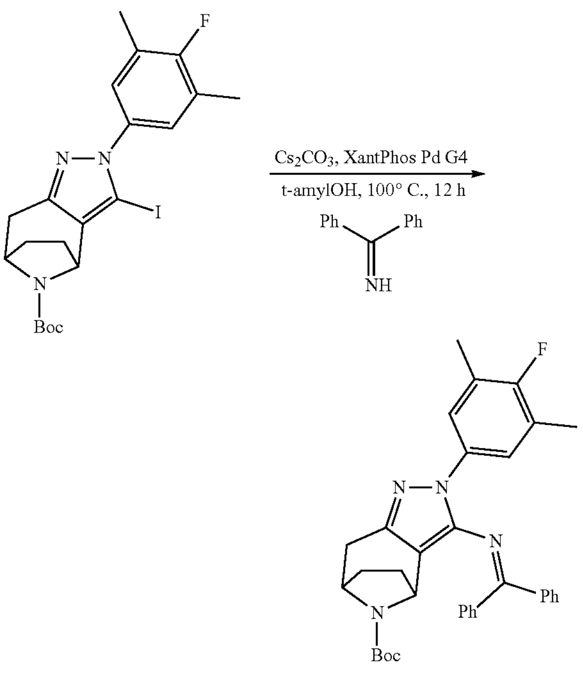

A mixture of tert-butyl 2-(4-fluoro-3,5-dimethylphenyl)-3-iodo-2,4,5,6,7,8-hexahydro-4,7-epiminocyclohepta [c]pyrazole-9-carboxylate (2.5 g, 4.54 mmol, 1 eq), diphenylmethanimine (2.47 g, 13.62 mmol, 2.29 mL, 3 eq), Xantphos Pd G4 (436.83 mg, 453.91 μmol, 0.1 eq), $Cs_2CO_3$ (2.96 g, 9.08 mmol, 2 eq) in t-AmylOH (20 mL) was stirred at 100° C. for 12 hours under $N_2$ atmosphere. LCMS indicated the reaction was completed. The reaction mixture was quenched by addition saturated EDTA solution (100 mL) and ethyl acetate (50 mL), stirred for 0.5 hour, and then extracted with ethyl acetate (50 mL*3). The combined organic layers were washed with saturated brine (30 mL), dried over anhydrous $Na_2SO_4$, filtered, and concentrated under reduced pressure to give a residue. The residue was purified by column chromatography ($SiO_2$, Petroleum ether/ethyl acetate=100/1 to 4/1) to give tert-butyl 3-((diphenylmethylene)amino)-2-(4-fluoro-3,5-dimethylphenyl)-2,4,5,6,7,8-hexahydro-4,7-epiminocyclohepta [c]pyrazole-9-carboxylate (2 g, 3.25 mmol, 71.61% yield). LC-MS (ES+, m/z): 551.3 [$(M+H)^+$]; Rt=0.716 min.

Step 6: tert-butyl 3-amino-2-(4-fluoro-3,5-dimethylphenyl)-2,4,5,6,7,8-hexahydro-4,7-epiminocyclohepta [c]pyrazole-9-carboxylate

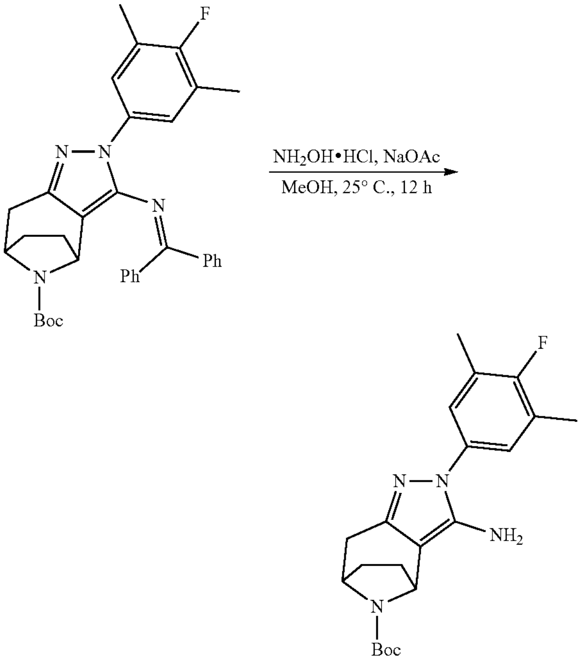

A mixture of tert-butyl 3-((diphenylmethylene)amino)-2-(4-fluoro-3,5-dimethylphenyl)-2,4,5,6,7,8-hexahydro-4,7-epiminocyclohepta [c]pyrazole-9-carboxylate (1.8 g, 2.93 mmol, 1 eq), NaOAc (719.98 mg, 8.78 mmol, 3 eq), $NH_2OH \cdot HCl$ (406.60 mg, 5.85 mmol, 2 eq) in MeOH (18 mL) was stirred at 25° C. for 12 hours under $N_2$ atmosphere. LCMS showed reaction was completed. The reaction mixture was quenched by addition $H_2O$ (100 mL), extracted with ethyl acetate (50 mL*3). The combined organic layers were washed with saturated brine (20 mL), dried over anhydrous $Na_2SO_4$, filtered, and concentrated under reduced pressure to give a residue. The residue was purified by column chromatography ($SiO_2$, Petroleum ether/Ethyl acetate=100/1 to 4/1) to give tert-butyl 3-amino-2-(4-fluoro-3,5-dimethylphenyl)-2,4,5,6,7,8-hexahydro-4,7-epiminocyclohepta [c]pyrazole-9-carboxylate (1 g, 2.38 mmol, 81.46% yield). LC-MS (ES+, m/z): 387.2 [$(M+H)^+$]; Rt=0.438 min. $^1H$ NMR (400 MHz, DMSO-$d_6$) δ=7.29-7.17 (m, 2H), 5.27 (s, 2H), 5.03-4.85 (m, 1H), 4.36 (br s, 1H), 2.91 (br d, J=15.5 Hz, 1H), 2.35 (br d, J=16.2 Hz, 1H), 2.24 (d, J=2.0 Hz, 6H), 2.22-2.11 (m, 1H), 1.95-1.85 (m, 1H), 1.68 (br t, J=9.6 Hz, 1H), 1.57-1.47 (m, 1H), 1.37 (br s, 9H)

Step 7: tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate

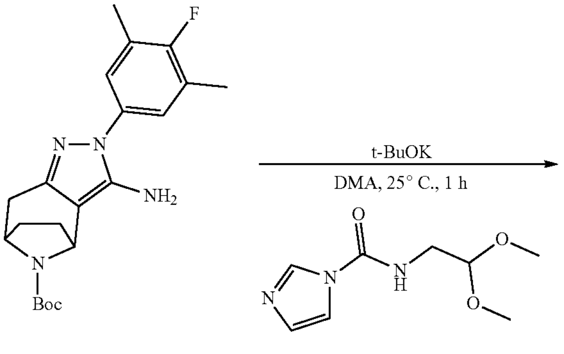

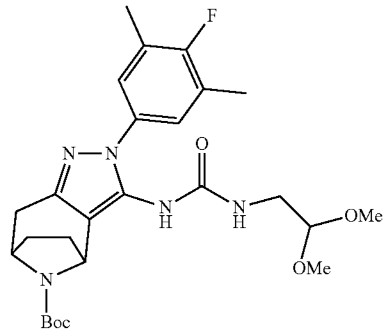

A mixture of tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (1 g, 2.38 mmol, 1 eq), N-(2,2-dimethoxyethyl)-1H-imidazole-1-carboxamide (949.48 mg, 4.77 mmol, 2 eq), t-BuOK (1 M, 11.92 mL, 5 eq) in DMA (10 mL) was stirred at 25° C. for 1 hour under $N_2$ atmosphere. LCMS showed reaction was completed. The reaction mixture was quenched by addition $H_2O$ (50 mL), extracted with Ethyl acetate (20 mL*3). The combined organic layers were washed with saturated brine (20 mL), dried over anhydrous $Na_2SO_4$, filtered, and concentrated under reduced pressure to give a residue. The residue was purified by column chromatography ($SiO_2$, Petroleum ether/Ethyl acetate=100/1 to 1/1) to give tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (1 g, 1.80 mmol, 75.48% yield). LC-MS (ES+, m/z): 518.4 [$(M+H)^+$]; Rt=0.526 min.

Step 8: tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate

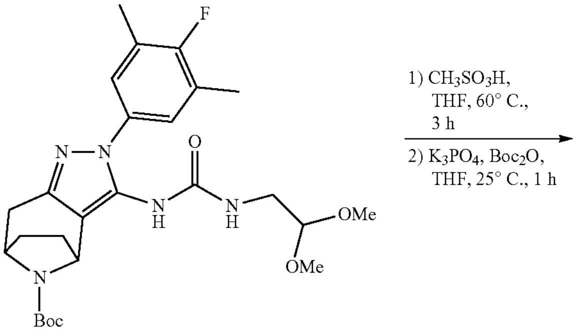

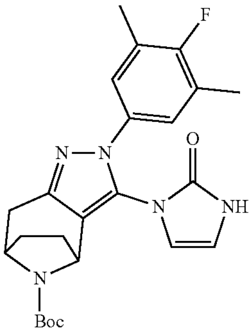

To a solution of tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (1 g, 1.80 mmol, 1 eq) in THF (10 mL) was added $CH_3SO_3H$ (259.30 mg, 2.70 mmol, 192.79 µL, 1.5 eq). The mixture was stirred for 3 hours at 60° C. To it was added $K_3PO_4$ (1.15 g, 5.40 mmol, 3 eq) in $H_2O$ (10 mL) followed by $Boc_2O$ (392.56 mg, 1.80 mmol, 413.22 µL, 1 eq) at 25° C. The mixture was stirred for 1 hour at 25° C. LCMS showed reaction was completed. The reaction mixture was quenched by addition $H_2O$ (100 mL), extracted with ethyl acetate (100 mL*3). The combined organic layers were washed with saturated brine (50 mL), dried over anhydrous $Na_2SO_4$, filtered, and concentrated under reduced pressure to give a residue. The residue was purified by column chromatography ($SiO_2$, Petroleum ether/ethyl acetate=100/1 to 1/1) to give (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (450 mg, 913.88 µmol, 50.81% yield). LC-MS (ES+, m/z): 454.3 [$(M+H)^+$]; Rt=0.507 min.

Step 9: (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate and (4R,7S)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate

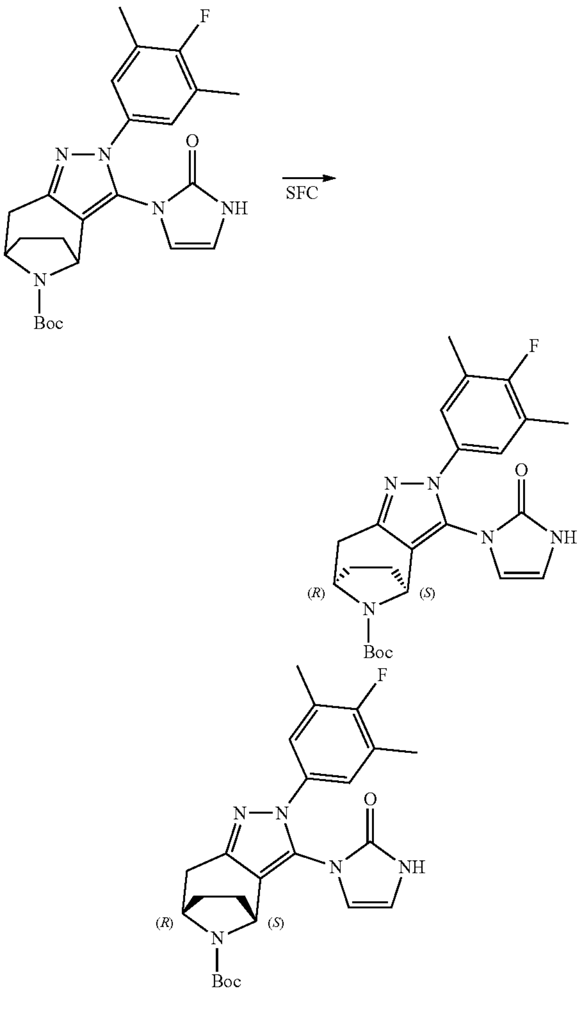

The tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate was purified by SFC (column: DAICEL CHIRALCEL OD (250 mm*30 mm, 10 um); mobile phase: [$CO_2$-IPA (0.1% $NH_3H_2O$)]; B %: 40%, isocratic elution mode) to give (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (Peak 1, 200 mg, 441.01 μmol, 44.44% yield, LC-MS (ES+, m/z): 454.2 [$(M+H)^+$]; Rt=0.492 min) and (4R,7S)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (Peak 2, 180 mg, 396.91 μmol, 40.00% yield, LC-MS (ES+, m/z): 454.2 [$(M+H)^+$]; Rt=0.486 min).

Step 10: (4S,7R)-tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

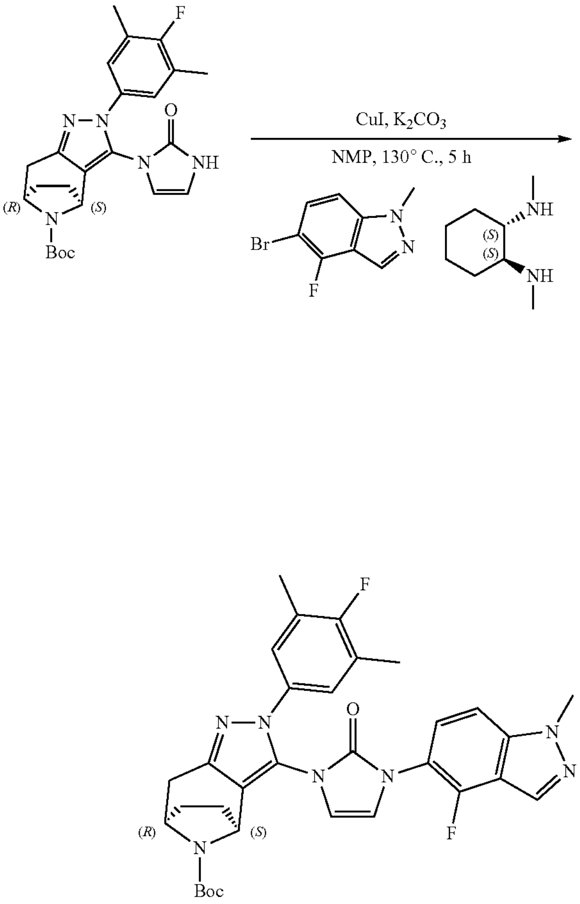

To a solution of (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (200 mg, 441.01 μmol, 1 eq), 5-bromo-4-fluoro-1-methyl-1H-indazole (202.02 mg, 882.01 μmol, 2 eq) in NMP (5 mL) was added $K_2CO_3$ (121.90 mg, 882.01 μmol, 2 eq), CuI (167.98 mg, 882.01 μmol, 2 eq), (1S,2S)—N1, N2-dimethylcyclohexane-1,2-diamine (188.19 mg, 1.32 mmol, 3 eq). The mixture was stirred at 130° C. for 5 hours under $N_2$ atmosphere. LCMS indicated the reaction was completed. The reaction mixture was poured into saturated EDTA solution (100 mL) and stirred for 0.5 hour, extracted with ethyl acetate (100 mL*3). The combined organic layers were washed with saturated brine (50 mL), dried over anhydrous $Na_2SO_4$, filtered, and concentrated under reduced pressure to give a residue. The residue was purified by prep-TLC ($SiO_2$, DCM/MeOH=10/1) to give (4S,7R)-tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200 mg, 320.79 μmol, 72.74% yield). LC-MS (ES+, m/z): 602.2 [$(M+H)^+$]; Rt=0.601 min.

Step 11:1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one

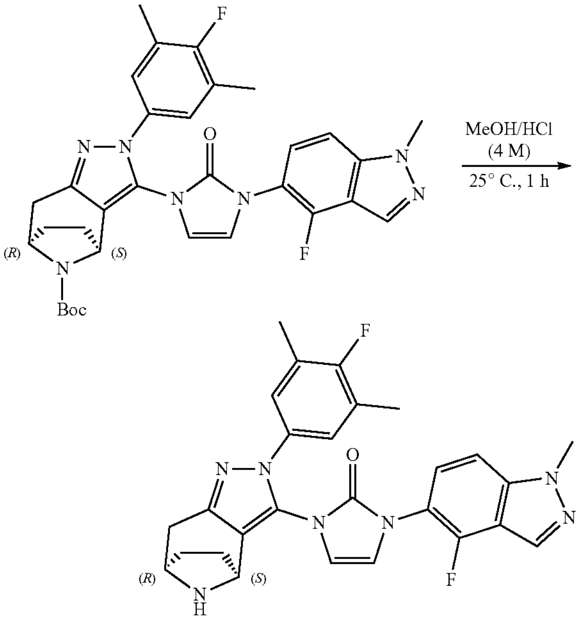

A mixture was (4S,7R)-tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200 mg, 320.79 μmol, 1 eq) in HCl/MeOH (4 M, 3 mL) was stirred at 25° C. for 1 hour. LCMS showed reaction was completed. The reaction mixture was concentrated under reduced pressure to give 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (0.15 g, 295.80 μmol, 92.21% yield). LC-MS (ES+, m/z): 502.1 [(M+H)$^+$]; Rt=0.398 min.

Intermediate 208-1

1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid Scheme 208-1

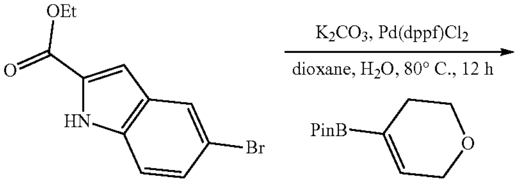

-continued

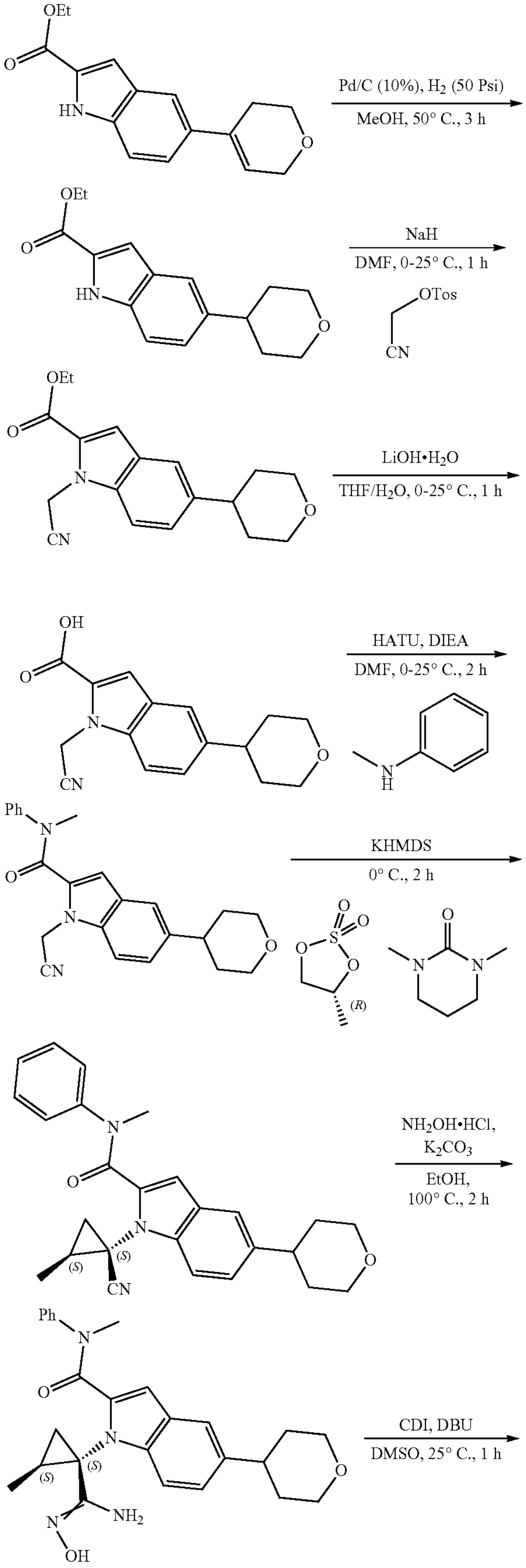

-continued

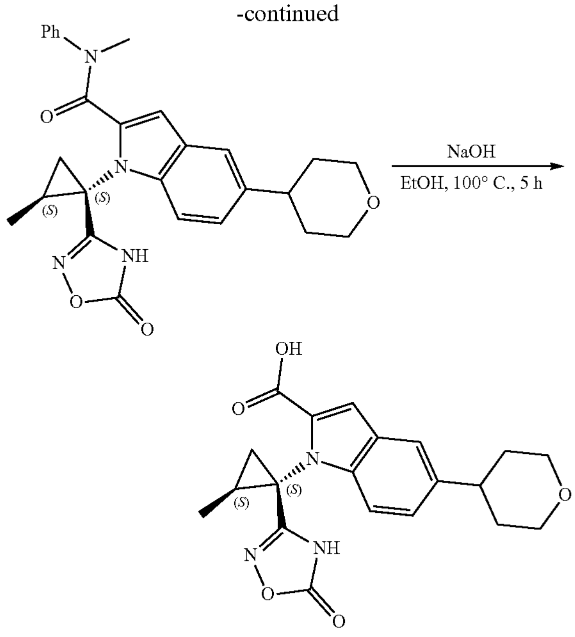

Step 1: ethyl 5-(3,6-dihydro-2H-pyran-4-yl)-1H-indole-2-carboxylate

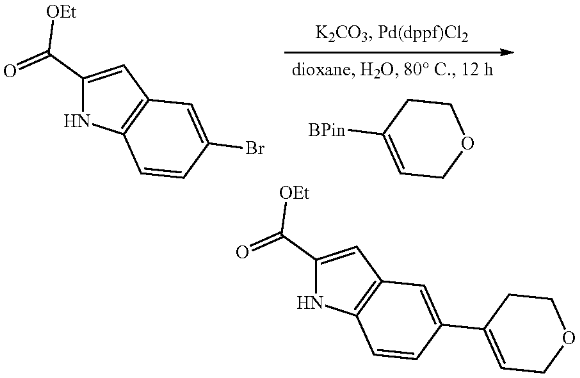

To a solution of ethyl 5-bromo-1H-indole-2-carboxylate (30 g, 111.90 mmol, 1 eq) and 2-(3,6-dihydro-2H-pyran-4-yl)-4,4,5,5-tetramethyl-1,3,2-dioxaborolane (25.86 g, 123.09 mmol, 1.1 eq) in dioxane (300 mL) and $H_2O$ (75 mL) was added Pd(dppf)$Cl_2$·$CH_2Cl_2$ (9.14 g, 11.19 mmol, 0.1 eq) and $K_2CO_3$ (46.40 g, 335.69 mmol, 3 eq). The mixture was stirred at 80° C. for 12 hours under $N_2$ atmosphere. LCMS showed the reaction was completed. The reaction mixture was diluted with saturated EDTA (1000 mL) and stirred 1 hour, extracted with Ethyl acetate (500 mL*3). The combined organic layers were washed with saturated NaCl (1000 mL*2). The combined organic layers were dried over $Na_2SO_4$, filtered and concentrated in vacuum. The residue was purified by flash silica gel chromatography (ISCO®; 660 g SepaFlash® Silica Flash Column, Eluent of 0~100% Ethyl acetate/Petroleum ether gradient @ 200 mL/min) to give ethyl 5-(3,6-dihydro-2H-pyran-4-yl)-1H-indole-2-carboxylate (32 g, 106.15 mmol, 94.87% yield, 90% purity). LC-MS (ES+, m/z): 272.2 [$(M+H)^+$]; Rt=1.686 min.

Step 2: ethyl 5-(tetrahydro-2H-pyran-4-yl)-1H-indole-2-carboxylate

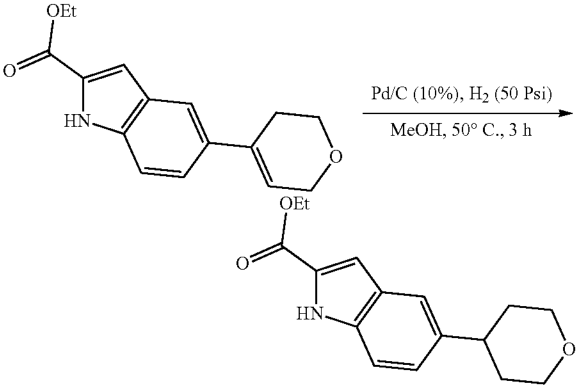

To a solution of ethyl 5-(3,6-dihydro-2H-pyran-4-yl)-1H-indole-2-carboxylate (15 g, 55.29 mmol, 1 eq) in MeOH (450 mL) was added Pd/C (9.00 g, 8.46 mmol, 10% purity). The mixture was stirred at 50° C. for 3 hours under $H_2$ (50 Psi). LCMS showed the reaction was completed. The reaction mixture was filtered and concentrated in vacuum. The residue was purified by flash silica gel chromatography (ISCO®; 330 g SepaFlash® Silica Flash Column, Eluent of 0~100% Ethyl acetate/Petroleum ether gradient@ 200 mL/min) to give ethyl 5-tetrahydropyran-4-yl-1H-indole-2-carboxylate (10 g, 36.40 mmol, 65.84% yield, 99.5% purity). LC-MS (ES+, m/z): 274.2 [$(M+H)^+$]; Rt=0.491 min.

Step 3: ethyl 1-(cyanomethyl)-5-(tetrahydro-2H-pyran-4-yl)-1H-indole-2-carboxylate

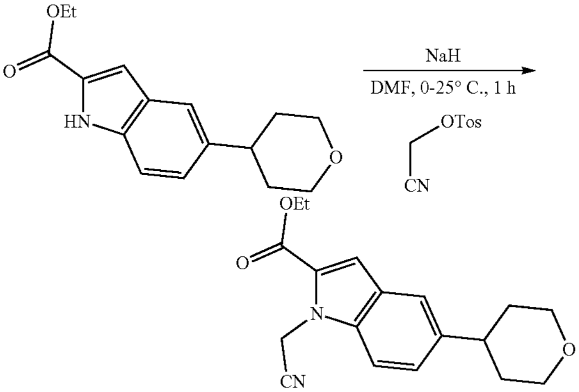

To a solution of ethyl 5-(tetrahydro-2H-pyran-4-yl)-1H-indole-2-carboxylate (2 g, 7.32 mmol, 1 eq) in DMF (40 mL) was added NaH (439.04 mg, 10.98 mmol, 60% purity, 1.5 eq) at 0° C., the mixture was stirred 0.5 hour at 0° C. under $N_2$. Cyanomethyl 4-methylbenzenesulfonate (3.09 g, 14.63 mmol, 2 eq) was added. The reaction mixture was stirred at 25° C. for 0.5 hour under $N_2$ atmosphere. LCMS showed the reaction was completed. The reaction mixture was diluted with saturated $NH_4Cl$ (100 mL), extracted with Ethyl acetate (100 mL*3). The combined organic layers were washed with saturated NaCl (100 mL*2). The combined organic layers were dried over $Na_2SO_4$, filtered and concentrated in vacuum to give ethyl 1-(cyanomethyl)-5-(tetrahydro-2H-pyran-4-yl)-1H-indole-2-carboxylate (2 g, 5.47 mmol, 74.82% yield, 85.5% purity). LC-MS (ES+, m/z): 313.2 [(M+H)$^+$]; Rt=0.517 min.

Step 4: 1-(cyanomethyl)-5-(tetrahydro-2H-pyran-4-yl)-1H-indole-2-carboxylic acid

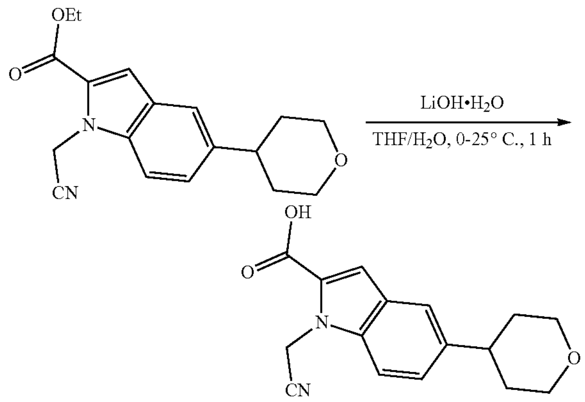

To a solution of ethyl ethyl 1-(cyanomethyl)-5-(tetrahydro-2H-pyran-4-yl)-1H-indole-2-carboxylate (1.8 g, 4.93 mmol, 1 eq) in $H_2O$ (16 mL) and THF (30 mL) was added $LiOH \cdot H_2O$ (310.10 mg, 7.39 mmol, 1.5 eq) at 0° C. The mixture was stirred at 25° C. for 1 hour. LCMS showed the reaction was completed. The reaction mixture was diluted with water (100 mL) and adjust to pH=4 with HCl (2M), extracted with Ethyl acetate (100 mL*3). The combined organic layers were washed with saturated NaCl (100 mL*2). The combined organic layers were dried over $Na_2SO_4$, filtered and concentrated in vacuum to give 1-(cyanomethyl)-5-(tetrahydro-2H-pyran-4-yl)-1H-indole-2-carboxylic acid (1.5 g, 4.71 mmol, 95.52% yield, 89.2% purity). LC-MS (ES+, m/z): 285.1 [(M+H)$^+$]; Rt=0.762 min.

Step 5: 1-(cyanomethyl)-N-methyl-N-phenyl-5-(tetrahydro-2H-pyran-4-yl)-1H-indole-2-carboxamide

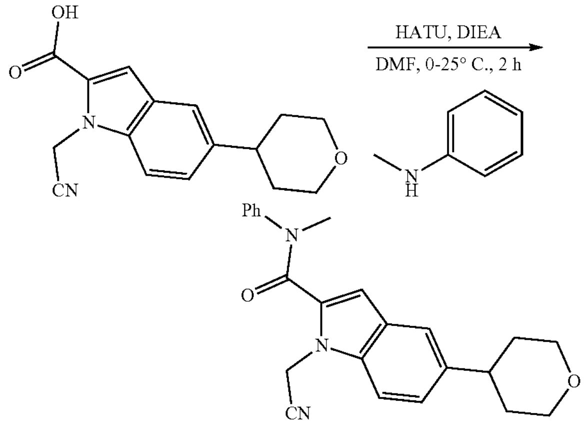

To a solution of 1-(cyanomethyl)-5-(tetrahydro-2H-pyran-4-yl)-1H-indole-2-carboxylic acid (1.5 g, 4.71 mmol, 1 eq) in DMF (30 mL) was added HATU (2.68 g, 7.06 mmol, 1.5 eq), DIEA (1.82 g, 14.12 mmol, 2.46 mL, 3 eq) followed by N-methylaniline (756.41 mg, 7.06 mmol, 766.38 μL, 1.5 eq) at 0° C. The mixture was stirred at 25° C. for 2 hours. LCMS showed the reaction was completed. The reaction mixture was diluted with water (100 mL), extracted with Ethyl acetate (100 mL*3). The combined organic layers were washed with saturated NaCl (100 mL*2), dried over $Na_2SO_4$, filtered and concentrated in vacuum. The residue was purified by column chromatography ($SiO_2$, Petroleum ether gradient/Ethyl acetate=10/1 to 3/1) to give 1-(cyanomethyl)-N-methyl-N-phenyl-5-(tetrahydro-2H-pyran-4-yl)-1H-indole-2-carboxamide (0.75 g, 1.83 mmol, 38.79% yield, 90.9% purity). LC-MS (ES+, m/z): 374.2 [(M+H)$^+$]; Rt=0.500 min.

Step 6: 1-((1S,2S)-1-cyano-2-methylcyclopropyl)-N-methyl-N-phenyl-5-(tetrahydro-2H-pyran-4-yl)-1H-indole-2-carboxamide

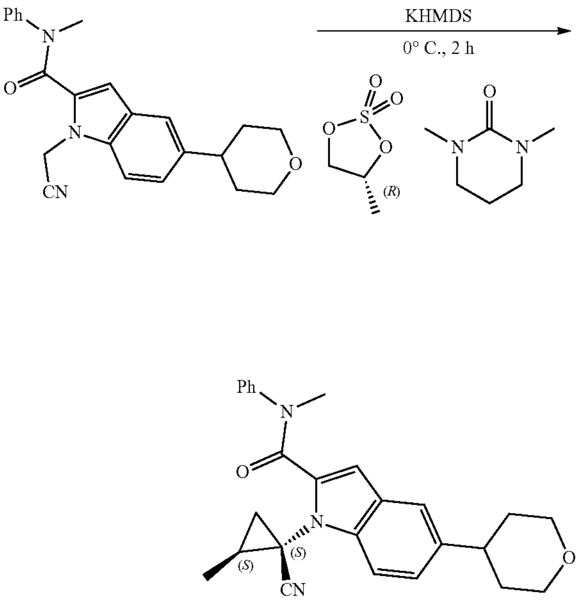

To a solution of 1-(cyanomethyl)-N-methyl-N-phenyl-5-(tetrahydro-2H-pyran-4-yl)-1H-indole-2-carboxamide (0.7 g, 1.87 mmol, 1 eq) and (4R)-4-methyl-1,3,2-dioxathiolane 2,2-dioxide (647.34 mg, 4.69 mmol, 2.5 eq) in 1,3-dimethylhexahydropyrimidin-2-one (10 mL) was added KHMDS (1 M, 7.50 mL, 4 eq) at 0° C. The mixture was stirred at 0° C. for 2 hours under $N_2$ atmosphere. LCMS showed the reaction was completed. The reaction mixture was diluted with saturated $NH_4Cl$ (200 mL), extracted with Ethyl acetate (100 mL*3). The combined organic layers were washed with saturated NaCl (100 mL*2). The combined organic layers were dried over $Na_2SO_4$, filtered and concentrated in vacuum. The residue was purified by flash silica gel chromatography (ISCO®; 20 g SepaFlash® Silica Flash Column, Eluent of 0~100% Ethyl acetate/Petroleum ether gradient @ 120 mL/min) to give 1-((1S,2S)-1-cyano-2-methylcyclopropyl)-N-methyl-N-phenyl-5-(tetrahydro-2H-pyran-4-yl)-1H-indole-2-carboxamide (0.2 g, 385.96 μmol, 20.59% yield). LC-MS (ES+, m/z): 414.0 [(M+H)$^+$]; Rt=0.538 min.

Step 7: 1-((1S,2S)-1-(N'-hydroxycarbamimidoyl)-2-methylcyclopropyl)-N-methyl-N-phenyl-5-(tetrahydro-2H-pyran-4-yl)-1H-indole-2-carboxamide

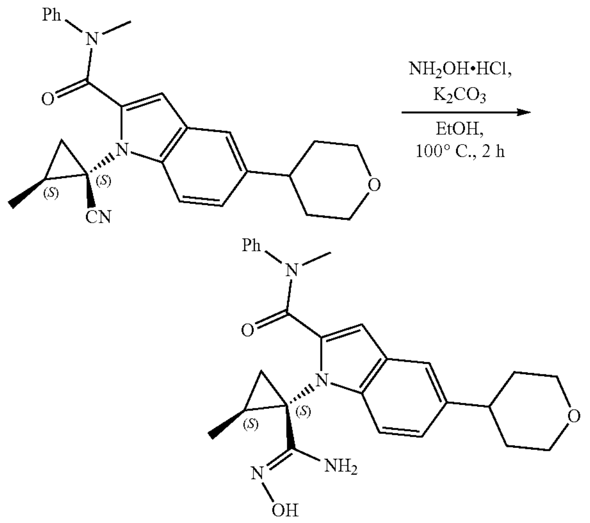

To a solution of 1-((1S,2S)-1-cyano-2-methylcyclopropyl)-N-methyl-N-phenyl-5-(tetrahydro-2H-pyran-4-yl)-1H-indole-2-carboxamide (0.2 g, 412.57 μmol, 1 eq) in EtOH (2 mL) was added $NH_2OH{\cdot}HCl$ (143.35 mg, 2.06 mmol, 5 eq) and $K_2CO_3$ (313.61 mg, 2.27 mmol, 5.5 eq). The mixture was stirred at 100° C. for 2 hours. TLC showed the reaction was completed. The reaction mixture was diluted with water (100 mL), extracted with Ethyl acetate (50 mL*3). The combined organic layers were washed with saturated NaCl (50 mL*2), dried over $Na_2SO_4$, filtered and concentrated in vacuum to give 1-((1S,2S)-1-(N'-hydroxycarbamimidoyl)-2-methylcyclopropyl)-N-methyl-N-phenyl-5-(tetrahydro-2H-pyran-4-yl)-1H-indole-2-carboxamide (0.11 g, 196.58 μmol, 55% yield).

Step 8: N-methyl-1-((1S,2S)-2-methyl-1-(5-oxo-4,5-dihydro-1,2,4-oxadiazol-3-yl)cyclopropyl)-N-phenyl-5-(tetrahydro-2H-pyran-4-yl)-1H-indole-2-carboxamide

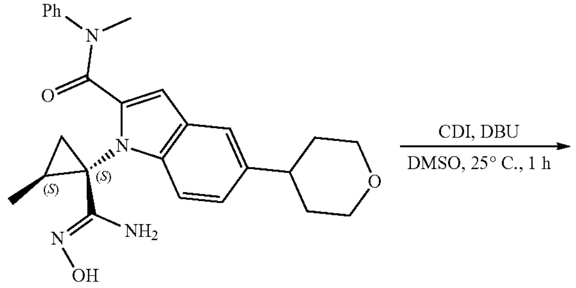

-continued

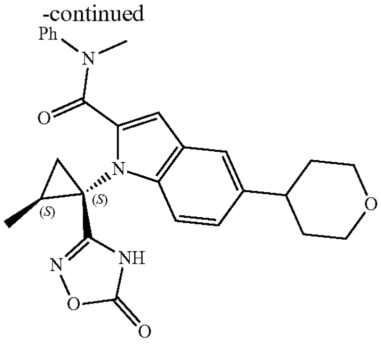

To a solution of 1-((1S,2S)-1-(N'-hydroxycarbamimidoyl)-2-methylcyclopropyl)-N-methyl-N-phenyl-5-(tetrahydro-2H-pyran-4-yl)-1H-indole-2-carboxamide (0.11 g, 196.58 μmol, 1 eq) in DMSO (2 mL) was added CDI (63.75 mg, 393.16 μmol, 2 eq) and DBU (74.82 mg, 491.45 μmol, 74.08 μL, 2.5 eq). The mixture was stirred at 25° C. for 1 hour. LCMS showed the reaction was completed. The reaction mixture was diluted with water (100 mL), extracted with Ethyl acetate (50 mL*3). The combined organic layers were washed with saturated NaCl (50 mL*2), dried over $Na_2SO_4$, filtered and concentrated in vacuum. The residue was purified by prep-TLC ($SiO_2$, Petroleum ether gradient: Ethyl acetate=3:1) to give N-methyl-1-((1S,2S)-2-methyl-1-(5-oxo-4,5-dihydro-1,2,4-oxadiazol-3-yl) cyclopropyl)-N-phenyl-5-(tetrahydro-2H-pyran-4-yl)-1H-indole-2-carboxamide (0.05 g, 88.35 μmol, 44.95% yield, 83.5% purity). LC-MS (ES+, m/z): 473.2 $[(M+H)^+]$; Rt=0.562 min.

Step 9: 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid

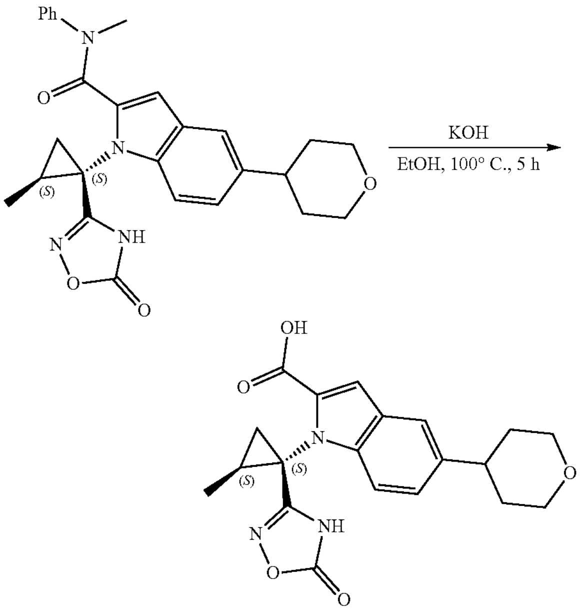

To a solution of N-methyl-1-((1S,2S)-2-methyl-1-(5-oxo-4,5-dihydro-1,2,4-oxadiazol-3-yl) cyclopropyl)-N-phenyl-5-(tetrahydro-2H-pyran-4-yl)-1H-indole-2-carboxamide (50 mg, 88.35 μmol, 1 eq) in EtOH (1 mL) was added KOH (141.37 mg, 3.53 mmol, 40 eq). The mixture was stirred at 100° C. for 5 hours. LCMS showed the reaction was completed. The residue was purified by prep-HPLC (column: 3_Phenomenex Luna C18 75*30 mm*3 um; mobile phase: [$H_2O$ (0.1% TFA)-ACN]; gradient: 25%-60% B over 8.0 min) to give 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (25 mg, 63.90 μmol, 72.33% yield, 98% purity). LC-MS (ES+, m/z): 384.2 [$(M+H)^+$]; Rt=1.547 min.

Intermediate 211-1 and 211-2

5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid And 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid Scheme 211-1

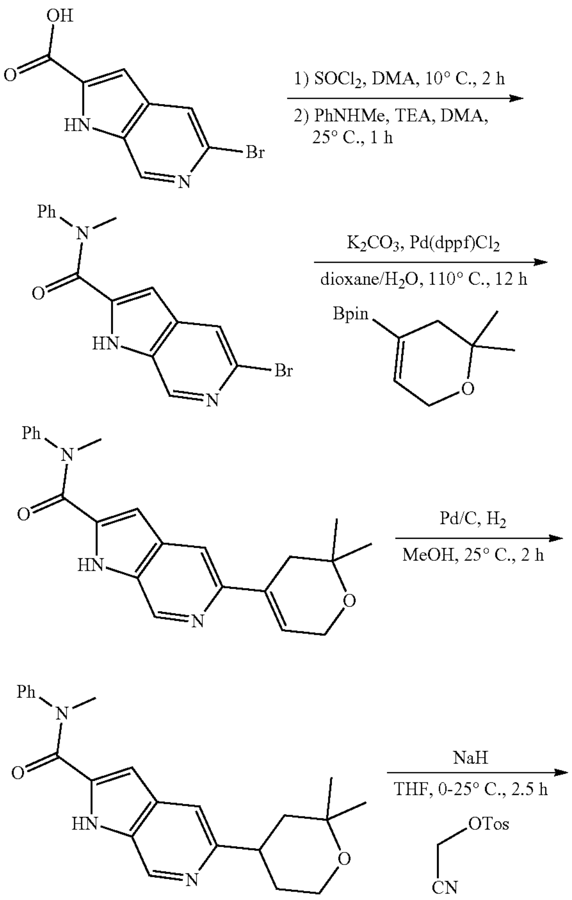

-continued

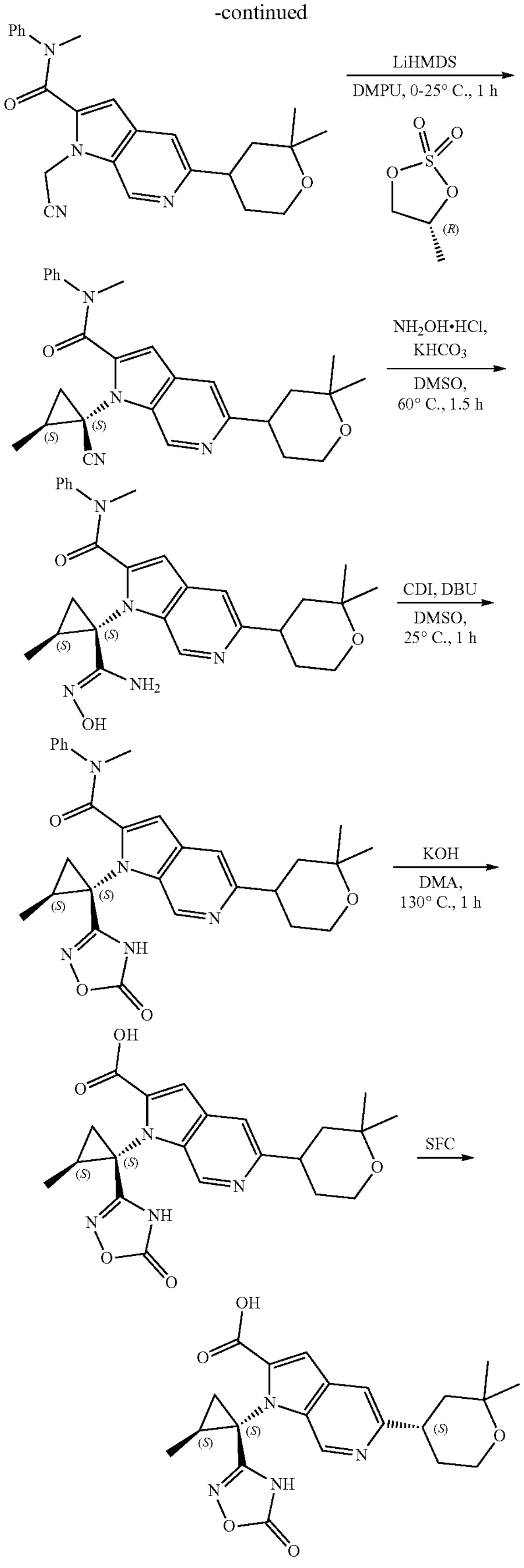

211-1, first eluent

-continued

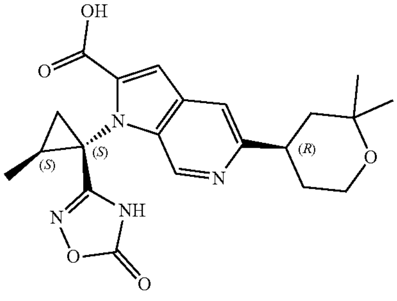

211-2, second eluent

Step 1: 5-bromo-N-methyl-N-phenyl-1H-pyrrolo[2,3-c]pyridine-2-carboxamide

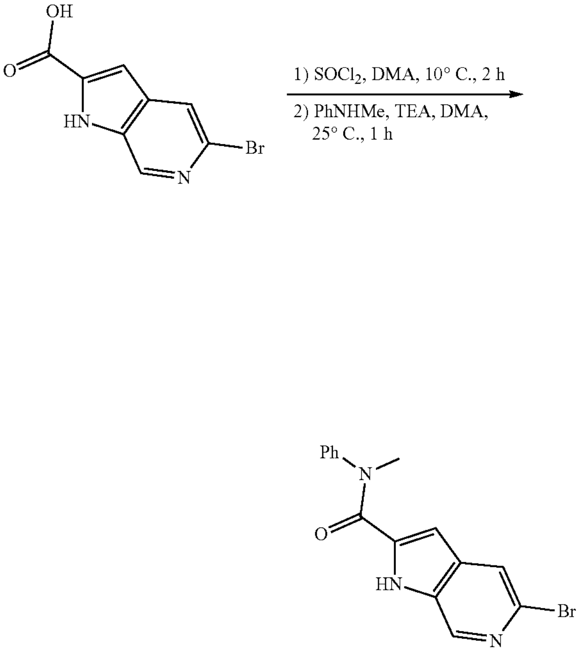

To a solution of 5-bromo-1H-pyrrolo[2,3-c]pyridine-2-carboxylic acid (20 g, 82.97 mmol, 1 eq) in DMA (200 mL), $SOCl_2$ (11.85 g, 99.57 mmol, 7.23 mL, 1.2 eq) was added dropwise at 10° C. After stirring for 2 hours, N-methylaniline (10.67 g, 99.57 mmol, 10.81 mL, 1.2 eq) and TEA (20.15 g, 199.14 mmol, 27.72 mL, 2.4 eq) were dropwise added at 10° C. The mixture was stirred at 25° C. for 1 hour. LC-MS showed the desired was detected. The reaction mixture was quenched by saturated $NaHCO_3$ (500 mL), and the precipitated solid was collected by filtration. The obtained solid was washed with water (200 mL) and dried under reduced pressure to provide 5-bromo-N-methyl-N-phenyl-1H-pyrrolo[2,3-c]pyridine-2-carboxamide (25 g, 72.69 mmol, 87.60% yield). $^1H$ NMR (400 MHz, $CDCl_3$) δ=10.58-10.38 (m, 1H), 8.73-8.61 (m, 1H), 7.57-7.48 (m, 3H), 7.48-7.43 (m, 1H), 7.37-7.29 (m, 2H), 5.24-5.04 (m, 1H), 3.65-3.47 (m, 3H). LC-MS (ES+, m/z): 332.2 [$(M+H)^+$]; Rt=0.462 min.

Step 2: 5-(2,2-dimethyl-3,6-dihydro-2H-pyran-4-yl)-N-methyl-N-phenyl-1H-pyrrolo[2,3-c]pyridine-2-carboxamide

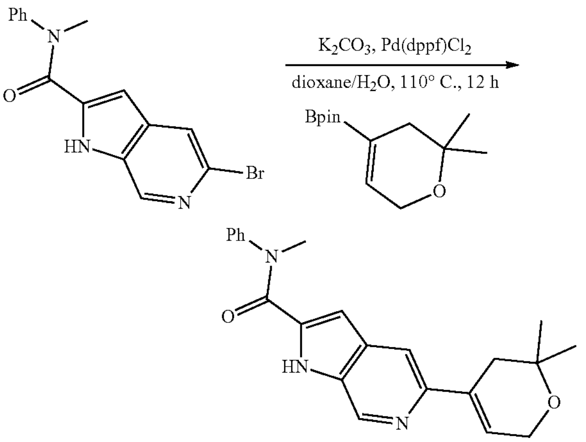

To a mixture of 5-bromo-N-methyl-N-phenyl-1H-pyrrolo[2,3-c]pyridine-2-carboxamide (23 g, 69.66 mmol, 1 eq), 2-(2,2-dimethyl-3,6-dihydro-2H-pyran-4-yl)-4,4,5,5-tetramethyl-1,3,2-dioxaborolane (24.88 g, 104.49 mmol, 1.5 eq), Pd(dppf)$Cl_2$ (5.10 g, 6.97 mmol, 0.1 eq), $K_2CO_3$ (19.26 g, 139.32 mmol, 2 eq) in dioxane (230 mL) and $H_2O$ (57.5 mL) was degassed and purged with $N_2$ for 3 times, and then the mixture was stirred at 110° C. for 12 hours under $N_2$ atmosphere. LC-MS showed the desired was detected. The reaction mixture was quenched by saturated EDTA 500 mL, and then extracted with DCM (200 mL*3). The combined organic layers were washed with saturated brine (200 mL*1), dried over anhydrous $Na_2SO_4$, filtered and concentrated under reduced pressure to give a residue. The residue was purified by column chromatography ($SiO_2$, Petroleum ether/Ethyl acetate=10/1 to 0/1) to provide 5-(2,2-dimethyl-3,6-dihydro-2H-pyran-4-yl)-N-methyl-N-phenyl-1H-pyrrolo[2,3-c]pyridine-2-carboxamide (13 g, 35.25 mmol, 50.60% yield). $^1H$ NMR (400 MHz, $CDCl_3$) δ=10.17-10.00 (m, 1H), 8.88-8.82 (m, 1H), 7.54-7.48 (m, 3H), 7.37-7.29 (m, 3H), 6.64-6.54 (m, 1H), 5.24-5.17 (m, 1H), 4.39-4.37 (m, 1H), 3.97-3.91 (m, 1H), 3.57-3.54 (m, 3H), 2.55-2.44 (m, 2H), 1.36-1.29 (m, 6H). LC-MS (ES+, m/z): 362.2 [$(M+H)^+$]; Rt=0.389 min.

Step 3: 5-(2,2-dimethyltetrahydro-2H-pyran-4-yl)-N-methyl-N-phenyl-1H-pyrrolo[2,3-c]pyridine-2-carboxamide

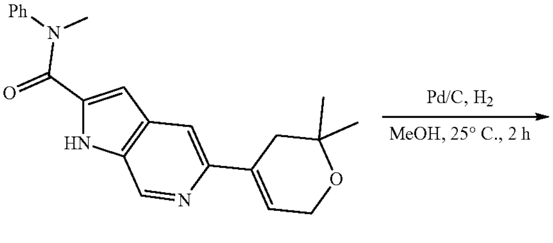

-continued

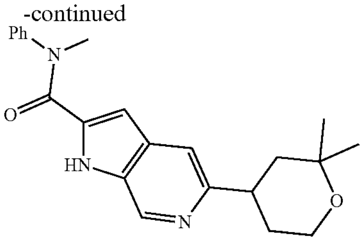

To a mixture of 5-(2,2-dimethyl-3,6-dihydro-2H-pyran-4-yl)-N-methyl-N-phenyl-1H-pyrrolo[2,3-c]pyridine-2-carboxamide (13 g, 35.97 mmol, 1 eq), 10% Pd/C (2.60 g) in MeOH (260 mL) was degassed and purged with $H_2$ for 3 times, and then the mixture was stirred at 25° C. for 2 hours under $H_2$ atmosphere. LC-MS showed desired was detected. The reaction mixture was filtered and concentrated under reduced pressure to give 5-(2,2-dimethyltetrahydro-2H-pyran-4-yl)-N-methyl-N-phenyl-1H-pyrrolo[2,3-c]pyridine-2-carboxamide (12 g, 31.37 mmol, 87.21% yield). $^1$H NMR (400 MHz, $CDCl_3$) δ=10.12-9.99 (m, 1H), 8.88-8.79 (m, 1H), 7.54-7.48 (m, 3H), 7.37-7.30 (m, 2H), 7.14-7.07 (m, 1H), 5.24-5.12 (m, 1H), 3.90-3.75 (m, 2H), 3.57-3.52 (m, 3H), 3.20-3.07 (m, 1H), 1.89-1.67 (m, 4H), 1.34-1.29 (m, 3H), 1.27-1.25 (m, 3H). LC-MS (ES+, m/z): 364.2 [$(M+H)^+$]; Rt=1.119 min.

Step 4: 1-(cyanomethyl)-5-(2,2-dimethyltetrahydro-2H-pyran-4-yl)-N-methyl-N-phenyl-1H-pyrrolo[2,3-c]pyridine-2-carboxamide

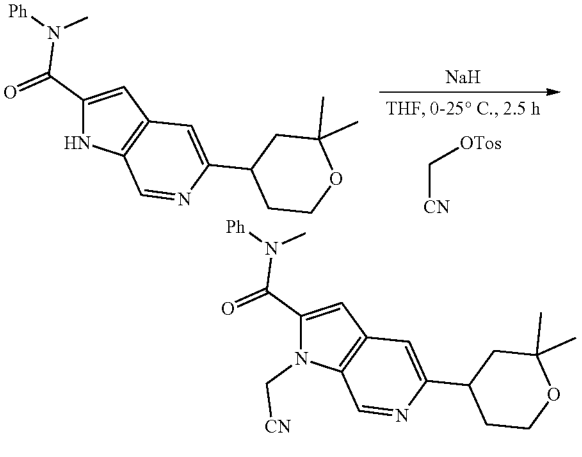

To a mixture of 5-(2,2-dimethyltetrahydro-2H-pyran-4-yl)-N-methyl-N-phenyl-1H-pyrrolo[2,3-c]pyridine-2-carboxamide (6 g, 16.51 mmol, 1 eq) in THF (120 mL) was added NaH (1.98 g, 49.53 mmol, 60% purity, 3 eq) at 0° C. and stirred for 0.5 hour. Cyanomethyl 4-methylbenzenesulfonate (6.97 g, 33.02 mmol, 2 eq) was added at 0° C., and then the mixture was stirred at 25° C. for 2 hours under $N_2$ atmosphere. LC-MS showed the desired was detected. The residue was poured into saturated $NH_4Cl$ (200 mL). The aqueous phase was extracted with DCM (50 mL*3). The combined organic phase was washed with saturated brine (50 mL*2), dried with anhydrous $Na_2SO_4$, filtered and concentrated in vacuum. The residue was purified by column chromatography ($SiO_2$, Petroleum ether/Ethyl acetate=10/1 to 1/1) to give 1-(cyanomethyl)-5-(2,2-dimethyltetrahydro-2H-pyran-4-yl)-N-methyl-N-phenyl-1H-pyrrolo[2,3-c]pyridine-2-carboxamide (4.5 g, 10.51 mmol, 63.66% yield). $^1$H NMR (400 MHz, DMSO-$d_6$) δ=8.97-8.92 (m, 1H), 7.41-7.21 (m, 7H), 5.75-5.69 (m, 2H), 3.69-3.64 (m, 2H), 3.45-3.42 (m, 3H), 3.13-2.99 (m, 1H), 1.69-1.50 (m, 4H), 1.23-1.21 (m, 3H), 1.15-1.12 (m, 3H). LC-MS (ES+, m/z): 403.3 [$(M+H)^+$]; Rt=1.132 min.

Step 5: 1-((1S,2S)-1-cyano-2-methylcyclopropyl)-5-(2,2-dimethyltetrahydro-2H-pyran-4-yl)-N-methyl-N-phenyl-1H-pyrrolo[2,3-c]pyridine-2-carboxamide

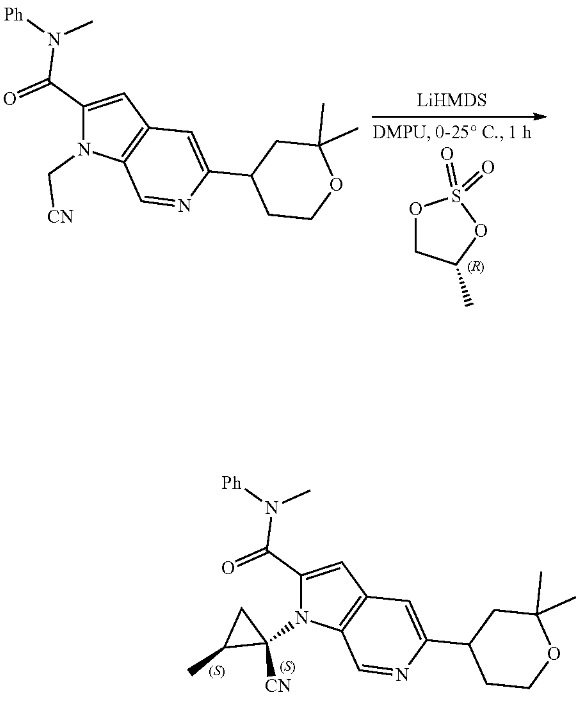

To a mixture of 1-(cyanomethyl)-5-(2,2-dimethyltetrahydro-2H-pyran-4-yl)-N-methyl-N-phenyl-1H-pyrrolo[2,3-c]pyridine-2-carboxamide (4.5 g, 11.18 mmol, 1 eq), (R)-4-methyl-1,3,2-dioxathiolane 2,2-dioxide (3.09 g, 22.36 mmol, 2 eq) in 1,3-dimethylhexahydropyrimidin-2-one (45 mL), was added LiHMDS (1 M, 55.90 mL, 5 eq) into the mixture at 0° C. The mixture was stirred at 25° C. for 1 hour under $N_2$ atmosphere. LC-MS showed the desired was detected. The reaction mixture was quenched by $H_2O$ (200 mL) and extracted with EA (50 mL*3). The combined organic layers were washed with saturated brine (50 mL*2), dried over anhydrous $Na_2SO_4$, filtered and concentrated under reduced pressure to give a residue. The residue was purified by column chromatography ($SiO_2$, Petroleum ether/Ethyl acetate=10/1 to 1/1) to give 1-[(1S,2S)-1-cyano-2-methyl-cyclopropyl]-5-(2,2-dimethyltetrahydropyran-4-yl)-N-methyl-N-phenyl-pyrrolo[2,3-c]pyridine-2-carboxamide (2 g, 4.16 mmol, 37.19% yield). $^1$H NMR (400 MHz, DMSO-$d_6$) δ=8.88-8.78 (m, 1H), 7.47-7.18 (m, 7H), 3.71-3.65 (m, 2H), 3.45-3.43 (m, 3H), 3.13-3.02 (m, 1H), 1.90-1.80 (m, 2H), 1.72-1.52 (m, 5H), 1.50-1.41 (m, 3H), 1.24-1.21 (m, 3H), 1.15-1.13 (m, 3H). LC-MS (ES+, m/z): 443.3 [$(M+H)^+$]; Rt=0.413 min.

Step 6: 5-(2,2-dimethyltetrahydro-2H-pyran-4-yl)-1-((1S,2S)-1-(M-hydroxycarbamimidoyl)-2-methylcyclopropyl)-N-methyl-N-phenyl-1H-pyrrolo[2,3-c]pyridine-2-carboxamide

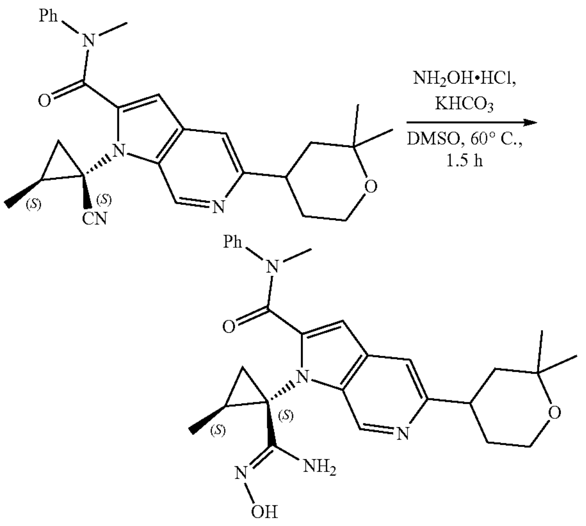

To a mixture of 1-((1S,2S)-1-cyano-2-methylcyclopropyl)-5-(2,2-dimethyltetrahydro-2H-pyran-4-yl)-N-methyl-N-phenyl-1H-pyrrolo[2,3-c]pyridine-2-carboxamide (2 g, 4.52 mmol, 1 eq), hydroxylamine; hydrochloride (3.14 g, 45.19 mmol, 10 eq) in DMSO (40 mL) was added $KHCO_3$ (4.52 g, 45.19 mmol, 10 eq). The reaction mixture was stirred at 60° C. for 1.5 hours under $N_2$ atmosphere. LC-MS showed the desired was detected. The reaction mixture was quenched by $H_2O$ (50 mL) and extracted with DCM (50 mL*3). The combined organic layers were washed with saturated brine (50 mL*2), dried over anhydrous $Na_2SO_4$, filtered and concentrated under reduced pressure to give 5-(2,2-dimethyltetrahydro-2H-pyran-4-yl)-1-((1S,2S)-1-(M-hydroxycarbamimidoyl)-2-methylcyclopropyl)-N-methyl-N-phenyl-1H-pyrrolo[2,3-c]pyridine-2-carboxamide (2 g, crude). LC-MS (ES+, m/z): 476.3 [$(M+H)^+$]; Rt=0.378 min.

Step 7: 5-(2,2-dimethyltetrahydro-2H-pyran-4-yl)-N-methyl-1-((1S,2S)-2-methyl-1-(5-oxo-4,5-dihydro-1,2,4-oxadiazol-3-yl)cyclopropyl)-N-phenyl-1H-pyrrolo[2,3-c]pyridine-2-carboxamide

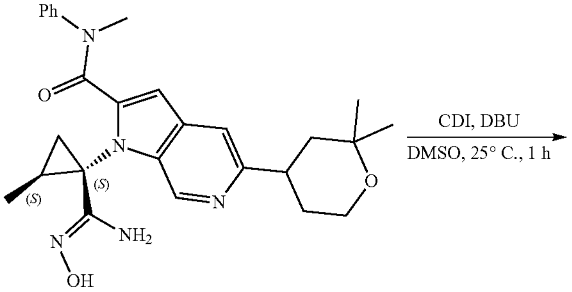

-continued

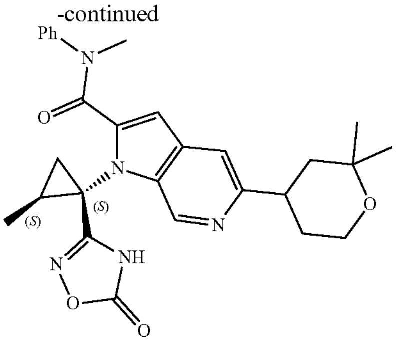

A mixture of 5-(2,2-dimethyltetrahydro-2H-pyran-4-yl)-1-((1S,2S)-1-(N'-hydroxycarbamimidoyl)-2-methylcyclopropyl)-N-methyl-N-phenyl-1H-pyrrolo[2,3-c]pyridine-2-carboxamide (2 g, 4.21 mmol, 1 eq), CDI (1.36 g, 8.41 mmol, 2 eq), DBU (1.60 g, 10.51 mmol, 1.58 mL, 2.5 eq) in DMSO (40 mL) was degassed and purged with $N_2$ for 3 times. The mixture was stirred at 25° C. for 1 hour under $N_2$ atmosphere. LC-MS showed the desired was detected. The reaction mixture was quenched by addition $H_2O$ 100 mL, and then extracted with DCM (30 mL*3). The combined organic layers were washed with saturated brine (50 mL*2), dried over anhydrous $Na_2SO_4$, filtered and concentrated under reduced pressure to give a residue. The residue was purified by column chromatography ($SiO_2$, Petroleum ether/Ethyl acetate=10/1 to 0/1) to give 5-(2,2-dimethyltetrahydro-2H-pyran-4-yl)-N-methyl-1-((1S,2S)-2-methyl-1-(5-oxo-4,5-dihydro-1,2,4-oxadiazol-3-yl)cyclopropyl)-N-phenyl-1H-pyrrolo[2,3-c]pyridine-2-carboxamide (1.7 g, 2.98 mmol, 70.92% yield). LC-MS (ES+, m/z): 502.2 [$(M+H)^+$]; Rt=0.393 min.

Step 8: 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid

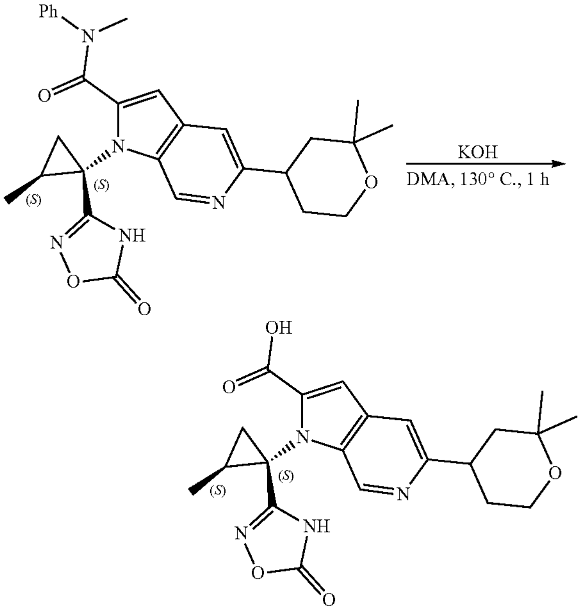

A mixture of 5-(2,2-dimethyltetrahydro-2H-pyran-4-yl)-N-methyl-1-((1S,2S)-2-methyl-1-(5-oxo-4,5-dihydro-1,2,4-oxadiazol-3-yl)cyclopropyl)-N-phenyl-1H-pyrrolo[2,3-c]pyridine-2-carboxamide (1.7 g, 3.39 mmol, 1 eq), KOH (1.90 g, 33.89 mmol, 10 eq) in DMA (17 mL) was degassed and purged with $N_2$ for 3 times. The mixture was stirred at 130° C. for 1 hour under $N_2$ atmosphere. LC-MS showed the desired was detected. The reaction mixture was quenched by $H_2O$ 10 mL, and then filtered and concentrated under reduced pressure to give a residue. The residue was purified by prep-HPLC (column: Phenomenex luna C18 250*200 mm*15 um; mobile phase: [$H_2O$ (0.02% FA)-ACN]; gradient: 15%-45% B over 20.0 min) to give 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid (700 mg, 1.68 mmol, 49.57% yield). LC-MS (ES+, m/z): 413.1 [$(M+H)^+$]; Rt=0.700 min.

Step 9: 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid and 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid

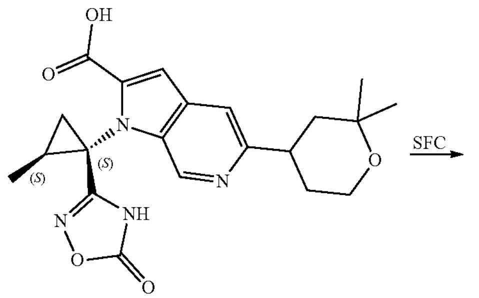

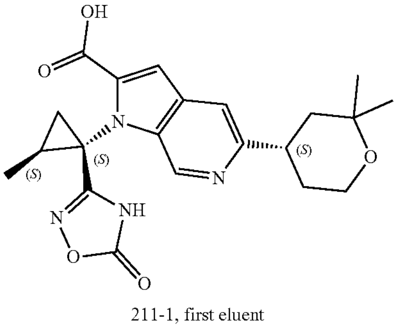

211-1, first eluent

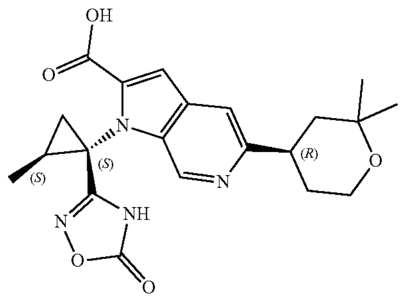

211-2, second eluent

The residue was purified by SFC (column: DAICEL CHIRALCEL OX (250 mm*30 mm, 10 um); mobile phase: [$CO_2$-MeOH (0.1% $NH_3H_2O$)]; B %: 40%, isocratic elution moden) to give 5-((S)-2,2-dimethyltetrahydro-2H-pyran-4-yl)-1-((1S,2S)-2-methyl-1-(5-oxo-4,5-dihydro-1,2,4-oxadiazol-3-yl) cyclopropyl)-1H-pyrrolo[2,3-c]pyridine-2-carboxylic acid (first eluent, 45 mg, 109.11 μmol, 45.45% yield). And 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid (second eluent, 45 mg, 109.11 μmol, 45.45% yield).

Intermediate 211-3

2-(2,2-dimethyl-3,6-dihydro-2H-pyran-4-yl)-4,4,5,5-tetramethyl-1,3,2-dioxaborolane Scheme 160-3

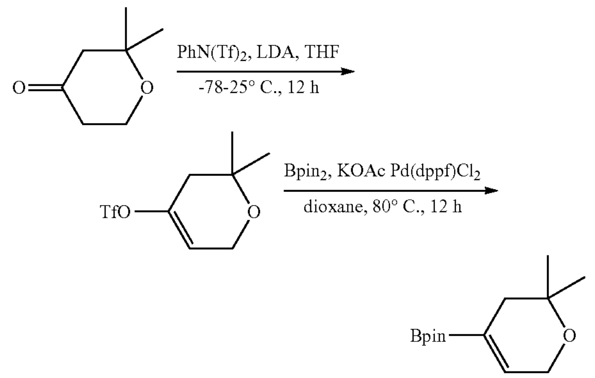

Step 1: 2,2-dimethyl-3,6-dihydro-2H-pyran-4-yl trifluoromethanesulfonate

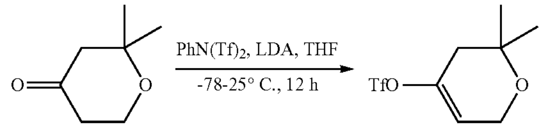

To a solution of 2,2-dimethyltetrahydropyran-4-one (70 g, 546.16 mmol, 1 eq) in THF (950 mL) was added LDA (2 M, 338.62 mL, 1.24 eq) dropwise at −78° C. over a period of 30 minutes. N-phenyl-O-((trifluoromethyl) sulfonyl)-N-(((trifluoromethyl) sulfonyl)oxy) hydroxylamine (234.14 g, 655.39 mmol, 1.2 eq) was then added at −78° C. (3 reactions were performed on the same scale in parallel). The mixture was allowed to warm to 25° C. stirred for 11.5 hours. TLC showed the reaction was completed. The crude was adjusted to pH=7 with saturated $NH_4Cl$ (1.5 L) and extracted with ethyl acetate (1 L*2). The combined organic layer was washed with $H_2O$ (1 L), saturated brine (1 L), filtered, and concentrated. The crude product was purified by chromatography on silica gel (Petroleum ether: Ethyl acetate=40:1) to afford 2,2-dimethyl-3,6-dihydro-2H-pyran-4-yl trifluoromethanesulfonate (135 g, 363.14 mmol, 66.49% yield).

Step 2: 2-(2,2-dimethyl-3,6-dihydro-2H-pyran-4-yl)-4,4,5,5-tetramethyl-1,3,2-dioxaborolane

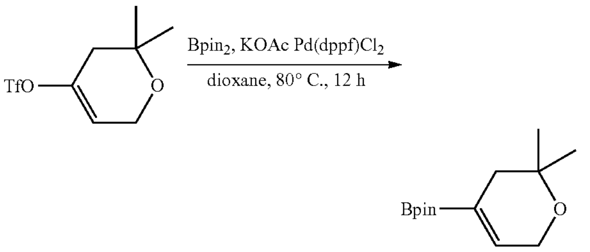

To a solution of 2,2-dimethyl-3,6-dihydro-2H-pyran-4-yl trifluoromethanesulfonate (20 g, 53.80 mmol, 1 eq) in dioxane (200 mL) was added BPD (27.32 g, 107.60 mmol, 2 eq) and KOAc (31.68 g, 322.79 mmol, 6 eq). The suspension was degassed under vacuum and purged with $N_2$ for several times. $Pd(dppf)Cl_2$ (3.94 g, 5.38 mmol, 0.1 eq) was added to the mixture. The suspension was degassed under vacuum and purged with $N_2$ several times. The mixture was stirred at 80° C. for 12 hours (6 batches). TLC showed the reaction was completed. The mixture was poured into saturated EDTA solution (1500 mL) stirred and ethyl acetate (1500 mL) stirred for 0.5 hour. The aqueous phase was extracted with ethyl acetate (1000 mL*3). The combined organic phase was washed with saturated brine (1500 mL), dried with anhydrous $Na_2SO_4$, filtered and concentrated in vacuum. The residue was purified by silica gel chromatography (Petroleum ether/Ethyl acetate=1/0, 99/1) to afford 2-(6,6-dimethyl-2,5-dihydropyran-4-yl)-4,4,5,5-tetramethyl-1,3,2-dioxaborolane (155 g, 260.36 mmol, 80.66% yield).

Intermediate 214-1

4-oxaspiro[2.5]oct-6-en-7-yl trifluoromethanesulfonate

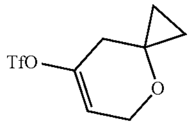 [SMILES: O=S(=O)(OC1=CCOC2(CC2)C1)C(F)(F)F]

Step 1: 4-oxaspiro[2.5]oct-6-en-7-yl trifluoromethanesulfonate

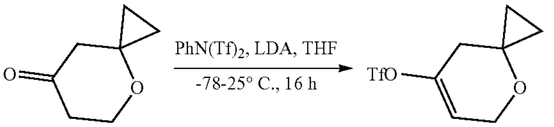 [SMILES: O=C1CCOC2(CC2)C1 ; O=S(=O)(OC1=CCOC2(CC2)C1)C(F)(F)F]

To a solution of 4-oxaspiro[2.5]octan-7-one (4 g, 31.71 mmol, 1 eq) in THF (40 mL) was added LDA (2 M, 19.02 mL, 1.2 eq) stirred at −78° C. for 1 hour, then was added 1,1,1-trifluoro-N-phenyl-N-(trifluoromethylsulfonyl) methanesulfonamide (13.59 g, 38.05 mmol, 1.2 eq). The mixture was stirred at 25° C. for 15 hours. TLC showed the reaction was completed. The reaction mixture was poured into saturated $NH_4Cl$ (300 mL), then extracted with ethyl acetate (100 mL*3). The combined organic layers were washed with saturated brine (200 mL), dried over anhydrous $Na_2SO_4$, filtered and concentrated under reduced pressure. The residue was purified by column chromatography ($SiO_2$, Petroleum ether/ethyl acetate=1/0 to 10/1) to give 4-oxaspiro[2.5]oct-6-en-7-yl trifluoromethanesulfonate (7 g, 24.40 mmol, 76.95% yield). $^1H$ NMR (400 MHz, DMSO-$d_6$) δ=6.29-5.85 (m, 1H), 4.24 (q, J=2.8 Hz, 1H), 3.91 (t, J=5.4 Hz, 1H), 2.55 (br s, 2H), 1.09-0.60 (m, 4H).

Intermediate 214-2

1-((1S,2S)-2-methyl-1-(5-oxo-4,5-dihydro-1,2,4-oxadiazol-3-yl)cyclopropyl)-5-(4-oxaspiro[2.5]octan-7-yl)-1H-indole-2-carboxylic acid Scheme 214-2

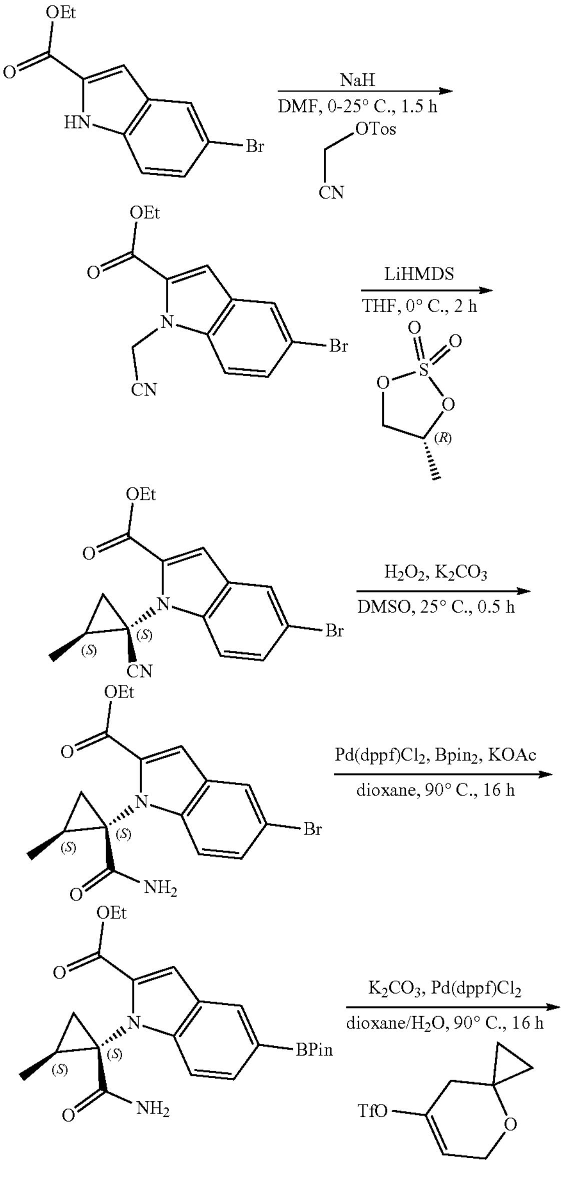

-continued

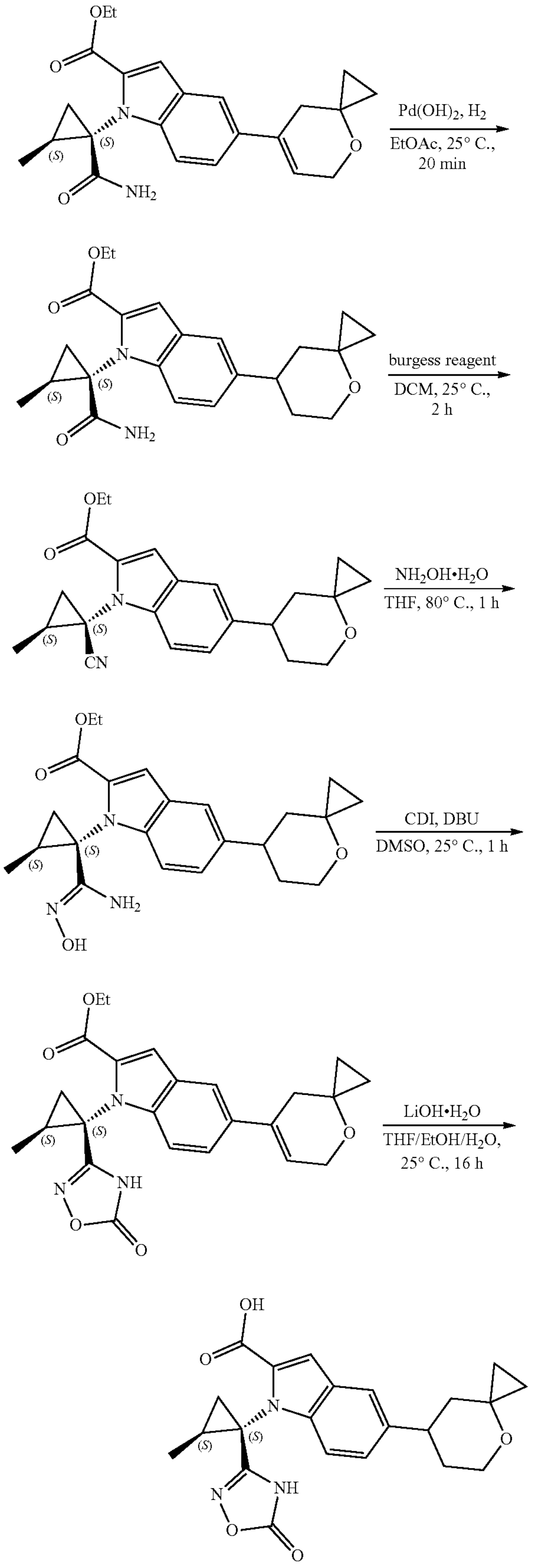

Step 1: ethyl 5-bromo-1-(cyanomethyl)-1H-indole-2-carboxylate

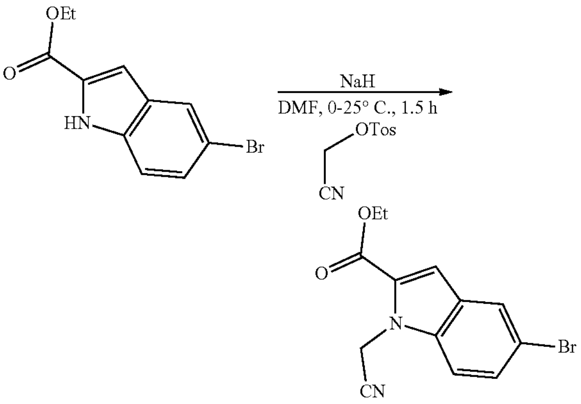

To a solution of ethyl 5-bromo-1H-indole-2-carboxylate (50 g, 186.49 mmol, 1 eq) in DMF (500 mL) was added NaH (22.38 g, 559.48 mmol, 60% purity, 3 eq). The mixture was stirred at 0° C. for 0.5 hour. Cyanomethyl trifluoromethanesulfonate (70.54 g, 372.99 mmol, 2 eq) was then added. The mixture was stirred at 25° C. for 1 hour. LCMS showed the reaction was completed. The reaction mixture was poured into saturated $NH_4Cl$ (500 mL), then extracted with ethyl acetate (300 mL*3). The combined organic layers were washed with saturated brine (500 mL), dried over anhydrous $Na_2SO_4$, filtered and concentrated under reduced pressure. The residue was purified by column chromatography ($SiO_2$, Petroleum ether/ethyl acetate=50/1 to 10/1) to give ethyl 5-bromo-1-(cyanomethyl) indole-2-carboxylate (35 g, 109.74 mmol, 58.84% yield). LC-MS (ES+, m/z): 307.0 $[(M+H)^+]$; Rt=1.870 min.

Step 2: ethyl 5-bromo-1-((1S,2S)-1-cyano-2-methylcyclopropyl)-1H-indole-2-carboxylate

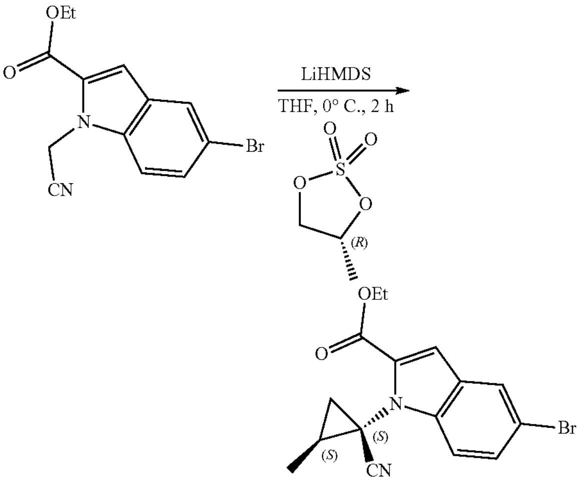

To a mixture of ethyl 5-bromo-1-(cyanomethyl) indole-2-carboxylate (10 g, 32.56 mmol, 1 eq) in THF (100 mL) was added (4R)-4-methyl-1,3,2-dioxathiolane 2,2-dioxide (11.24 g, 81.40 mmol, 2.5 eq). The mixture was cooled to 0°

C. LiHMDSi (1 M, 130.23 mL, 4 eq) was then added dropwise. The mixture was stirred at 0° C. for 2 hours. LCMS showed the reaction was completed. The reaction mixture was quenched by addition saturated $NH_4Cl$ (100 mL) at 0° C., and then extracted with ethyl acetate (300 mL*3). The combined organic layers were washed with saturated brine (100 mL), dried over $Na_2SO_4$, filtered and concentrated under reduced pressure to give ethyl 5-bromo-1-((1S,2S)-1-cyano-2-methylcyclopropyl)-1H-indole-2-carboxylate (2.6 g, 7.49 mmol, 23.00% yield). LC-MS (ES+, m/z): 346.9 [(M+H)$^+$]; Rt=0.619 min.

Step 3: ethyl 5-bromo-1-((1S,2S)-1-carbamoyl-2-methylcyclopropyl)-1H-indole-2-carboxylate

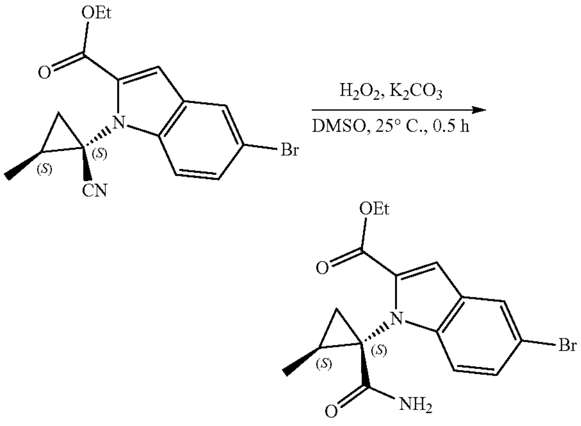

To a solution of 5-bromo-1-((1S,2S)-1-cyano-2-methylcyclopropyl)-1H-indole-2-carboxylate (2.60 g, 7.49 mmol, 1 eq) and $K_2CO_3$ (1.03 g, 7.49 mmol, 1 eq) in DMSO (40 mL) was added $H_2O_2$ (6.34 g, 55.92 mmol, 5.37 mL, 30% purity, 7.47 eq). The mixture was stirred at 25° C. for 0.5 hour. LCMS showed the reaction was completed. The residue was poured into saturated $Na_2SO_3$ (100 mL) and stirred for 10 min. The aqueous phase was extracted with ethyl acetate (100 mL*3). The combined organic phase was washed with saturated brine (100 mL), dried with anhydrous $Na_2SO_4$, filtered and concentrated in vacuum to give ethyl 5-bromo-1-((1S,2S)-1-carbamoyl-2-methylcyclopropyl)-1H-indole-2-carboxylate (1.5 g, 4.11 mmol, 54.85% yield). LC-MS (ES+, m/z): 365.1 [(M+H)$^+$]; Rt=0.620 min.

Step 4: ethyl 1-((1S,2S)-1-carbamoyl-2-methylcyclopropyl)-5-(4,4,5,5-tetramethyl-1,3,2-dioxaborolan-2-yl)-1H-indole-2-carboxylate

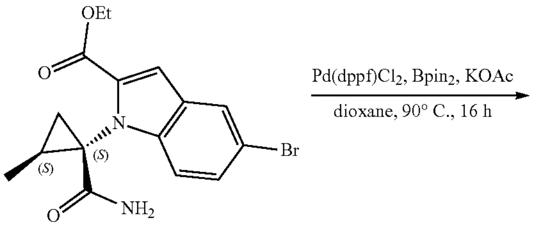

-continued

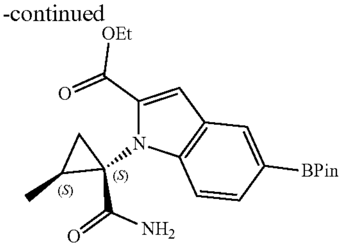

To a solution of ethyl 5-bromo-1-((1S,2S)-1-carbamoyl-2-methylcyclopropyl)-1H-indole-2-carboxylate (1.5 g, 4.11 mmol, 1 eq) and 4,4,5,5-tetramethyl-2-(4,4,5,5-tetramethyl-1,3,2-dioxaborolan-2-yl)-1,3,2-dioxaborolane (2.09 g, 8.21 mmol, 2 eq) in dioxane (20 mL) was added $Pd(dppf)Cl_2$ (300.52 mg, 410.71 μmol, 0.1 eq), KOAc (1.21 g, 12.32 mmol, 3 eq). The mixture was stirred at 90° C. for 16 hours under $N_2$. LCMS showed the reaction was completed. The reaction mixture was poured into saturated EDTA (200 mL) and ethyl acetate (50 mL) stirred for 1 hour, then extracted with ethyl acetate (100 mL*3). The combined organic layers were washed with saturated brine (200 mL), dried over anhydrous $Na_2SO_4$, filtered and concentrated under reduced pressure. The residue was purified by column chromatography ($SiO_2$, Petroleum ether/Ethyl acetate-50/1 to 2/1) to give ethyl 1-((1S,2S)-1-carbamoyl-2-methylcyclopropyl)-5-(4,4,5,5-tetramethyl-1,3,2-dioxaborolan-2-yl)-1H-indole-2-carboxylate (1.4 g, 3.40 mmol, 82.68% yield). LC-MS (ES+, m/z): 413.2 [(M+H)$^+$]; Rt=0.582 min.

Step 5: ethyl 1-((1S,2S)-1-carbamoyl-2-methylcyclopropyl)-5-(4-oxaspiro[2.5]oct-6-en-7-yl)-1H-indole-2-carboxylate

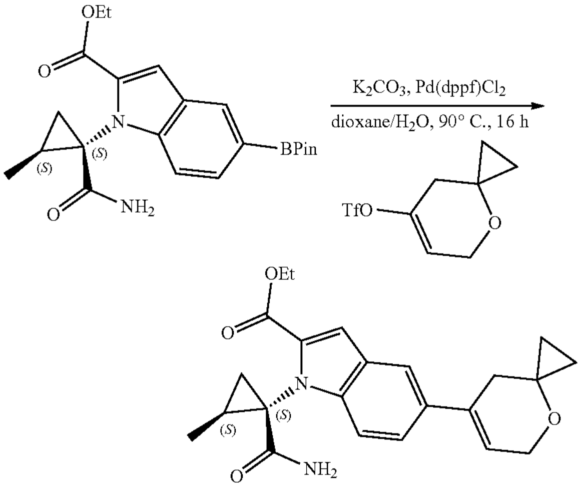

To a solution of ethyl 1-((1S,2S)-1-carbamoyl-2-methylcyclopropyl)-5-(4,4,5,5-tetramethyl-1,3,2-dioxaborolan-2-yl)-1H-indole-2-carboxylate (900 mg, 1.96 mmol, 1 eq) and 4-oxaspiro[2.5]oct-6-en-7-yl trifluoromethanesulfonate (1.01 g, 3.93 mmol, 2 eq) in dioxane (16 mL) and $H_2O$ (4 mL) was added $Pd(dppf)Cl_2$ (143.75 mg, 196.47 μmol, 0.1 eq) and $K_2CO_3$ (814.58 mg, 5.89 mmol, 3 eq). The mixture was stirred at 90° C. for 16 hours under $N_2$. LCMS showed the reaction was completed. The reaction mixture was poured into saturated EDTA (200 mL) and ethyl acetate (50 mL) stirred for 1 hour, then extracted with ethyl acetate (100 mL*3). The combined organic layers were washed with saturated brine (200 mL), dried over anhydrous $Na_2SO_4$, filtered and concentrated under reduced pressure. The residue was purified by column chromatography ($SiO_2$, Petroleum ether/ethyl acetate=80/1 to 3/1) to give ethyl 1-((1S,2S)-1-carbamoyl-2-methylcyclopropyl)-5-(4-oxaspiro[2.5] oct-6-en-7-yl)-1H-indole-2-carboxylate (1.5 g, 3.04 mmol, 77.42% yield). LC-MS (ES+, m/z): 395.2 [(M+H)$^+$]; Rt=1.861 min.

Step 6: ethyl 1-((1S,2S)-1-carbamoyl-2-methylcyclopropyl)-5-(4-oxaspiro[2.5]octan-7-yl)-1H-indole-2-carboxylate

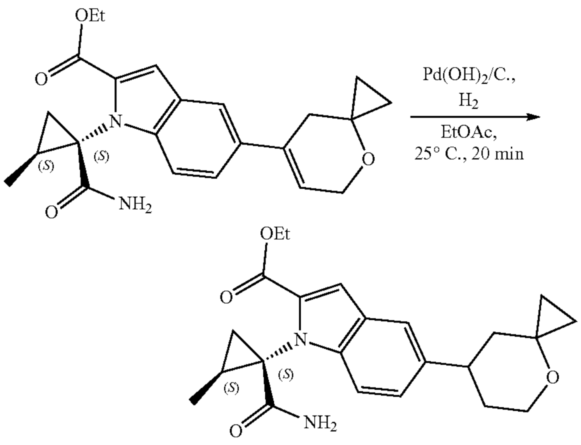

To a suspension of $Pd(OH)_2/C$ (3 g, 1.99 mmol, 20% purity, 5.62e-1 eq) in ethyl acetate (60 mL) was added ethyl 1-((1S,2S)-1-carbamoyl-2-methylcyclopropyl)-5-(4-oxaspiro[2.5] oct-6-en-7-yl)-1H-indole-2-carboxylate (1.4 g, 3.55 mmol, 1 eq). The mixture was stirred at 25° C. for 20 min under $H_2$ (15 Psi). LCMS showed the reaction was completed. The reaction mixture was filtered and concentrated under reduced pressure. The residue was purified by prep-HPLC (column: Welch Xtimate C18 180*70 mm #10 um; mobile phase: [$H_2O$ (10 mM $NH_4HCO_3$)-ACN]; gradient: 35%-65% B over 17.0 min) to give ethyl 1-((1S,2S)-1-carbamoyl-2-methylcyclopropyl)-5-(4-oxaspiro[2.5]octan-7-yl)-1H-indole-2-carboxylate (600 mg, 1.51 mmol, 42.64% yield). LC-MS (ES+, m/z): 397.3 [(M+H)$^+$]; Rt=1.781 min.

Step 7: ethyl 1-((1S,2S)-1-cyano-2-methylcyclopropyl)-5-(4-oxaspiro[2.5]octan-7-yl)-1H-indole-2-carboxylate

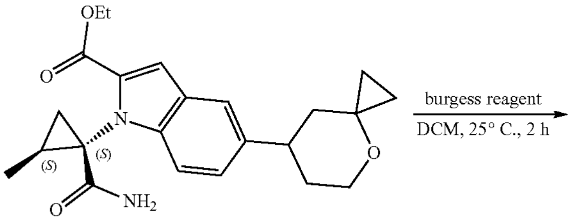

-continued

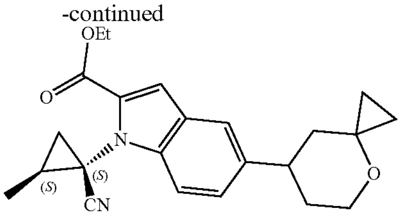

To a solution of ethyl 1-((1S,2S)-1-carbamoyl-2-methylcyclopropyl)-5-(4-oxaspiro[2.5]octan-7-yl)-1H-indole-2-carboxylate (500 mg, 1.26 mmol, 1 eq) in DCM (20 mL) was added methoxycarbonyl-(triethylammonio) sulfonyl-azanide (1.50 g, 6.31 mmol, 5 eq). The mixture was stirred at 25° C. for 2 hours. LCMS showed the reaction was completed. The reaction mixture was poured into water (100 mL), then extracted with ethyl acetate (50 mL*3). The combined organic layers were washed with saturated brine (50 mL), dried over anhydrous $Na_2SO_4$, filtered and concentrated under reduced pressure. The residue was purified by prep-TLC ($SiO_2$, Petroleum ether/Ethyl acetate-5:1) to give ethyl 1-((1S,2S)-1-cyano-2-methylcyclopropyl)-5-(4-oxaspiro[2.5]octan-7-yl)-1H-indole-2-carboxylate (400 mg, 1.05 mmol, 82.97% yield). LC-MS (ES+, m/z): 379.3 [(M+H)$^+$]; Rt=2.055 min.

Step 8: ethyl 1-((1S,2S)-1-(N'-hydroxycarbamimidoyl)-2-methylcyclopropyl)-5-(4-oxaspiro[2.5]octan-7-yl)-1H-indole-2-carboxylate

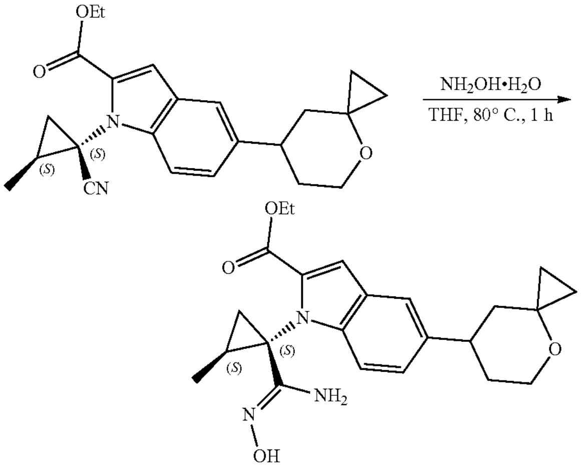

To a solution of ethyl 1-((1S,2S)-1-cyano-2-methylcyclopropyl)-5-(4-oxaspiro[2.5]octan-7-yl)-1H-indole-2-carboxylate (360 mg, 941.70 μmol, 1 eq) in THF (4 mL) was added hydroxylamine (622.09 mg, 9.42 mmol, 26.42 μL, 50% purity, 10 eq). The mixture was stirred at 80° C. for 1 hour. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by column chromatography ($SiO_2$, Petroleum ether/ethyl acetate=5:1) to give ethyl 1-((1S,2S)-1-(N'-hydroxycarbamimidoyl)-2-methylcyclopropyl)-5-(4-oxaspiro[2.5]octan-7-yl)-1H-indole-2- carboxylate (280 mg, 585.87 μmol, 62.21% yield). LC-MS (ES+, m/z): 412.3 [(M+H)+]; Rt=1.485 min.

Step 9: ethyl 1-((1S,2S)-2-methyl-1-(5-oxo-4,5-dihydro-1,2,4-oxadiazol-3-yl)cyclopropyl)-5-(4-oxaspiro[2.5]octan-7-yl)-1H-indole-2-carboxylate

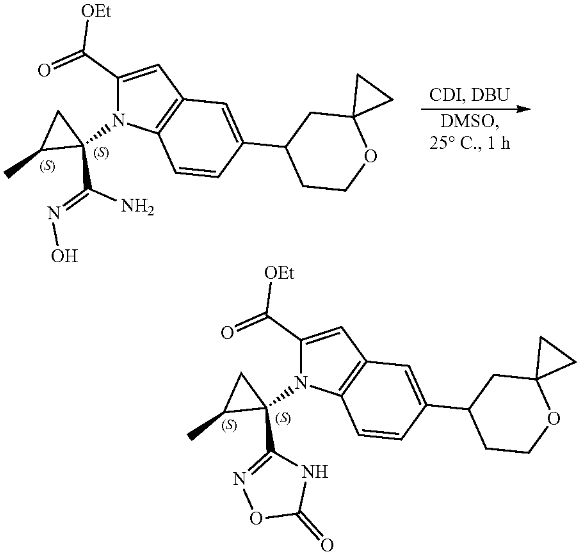

To a solution of ethyl 1-((1S,2S)-1-(N'-hydroxycarbamimidoyl)-2-methylcyclopropyl)-5-(4-oxaspiro[2.5]octan-7-yl)-1H-indole-2-carboxylate (260 mg, 544.02 μmol, 1 eq) in DMSO (5 mL) was added DBU (207.05 mg, 1.36 mmol, 205.00 μL, 2.5 eq) and CDI (176.42 mg, 1.09 mmol, 2 eq). The mixture was stirred at 25° C. for 1 hour. LCMS showed the reaction was completed. The reaction mixture was poured into water (150 mL), then extracted with ethyl acetate (80 mL*3). The combined organic layers were washed with saturated brine (80 mL), dried over anhydrous $Na_2SO_4$, filtered and concentrated under reduced pressure. The residue was purified by column chromatography ($SiO_2$, Petroleum ether/ethyl acetate=3:1) to give ethyl 1-((1S,2S)-2-methyl-1-(5-oxo-4,5-dihydro-1,2,4-oxadiazol-3-yl) cyclopropyl)-5-(4-oxaspiro[2.5]octan-7-yl)-1H-indole-2-carboxylate (200 mg, 435.67 μmol, 80.08% yield). LC-MS (ES+, m/z): 438.3 [(M+H)+]; Rt=1.930 min.

Step 10: 1-((1S,2S)-2-methyl-1-(5-oxo-4,5-dihydro-1,2,4-oxadiazol-3-yl)cyclopropyl)-5-(4-oxaspiro[2.5]octan-7-yl)-1H-indole-2-carboxylic acid

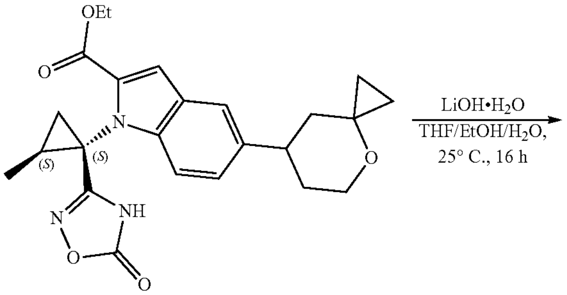

-continued

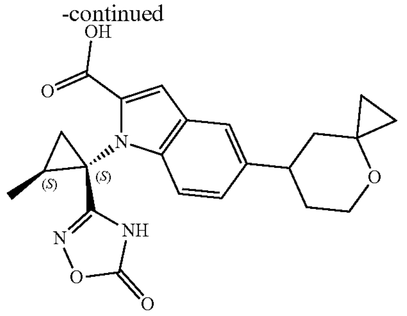

To a solution of ethyl 1-((1S,2S)-2-methyl-1-(5-oxo-4,5-dihydro-1,2,4-oxadiazol-3-yl) cyclopropyl)-5-(4-oxaspiro[2.5]octan-7-yl)-1H-indole-2-carboxylate (200 mg, 435.67 μmol, 1 eq) in THF (1 mL) and $H_2O$ (1 mL), EtOH (1 mL) was added LiOH $H_2O$ (182.82 mg, 4.36 mmol, 10 eq). The mixture was stirred at 25° C. for 16 hours. LCMS showed the reaction was completed. The reaction mixture was poured into water (50 mL) and adjust to pH=3 for HCl (2 M), then extracted with ethyl acetate (30 mL*3). The combined organic layers were washed with saturated brine (30 mL), dried over anhydrous $Na_2SO_4$, filtered and concentrated under reduced pressure to give 1-((1S,2S)-2-methyl-1-(5-oxo-4,5-dihydro-1,2,4-oxadiazol-3-yl)cyclopropyl)-5-(4-oxaspiro[2.5]octan-7-yl)-1H-indole-2-carboxylic acid (150 mg, crude). LC-MS (ES+, m/z): 410.1 [(M+H)+]; Rt=0.491 min.

Intermediate 221-1

1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one Scheme 221-1

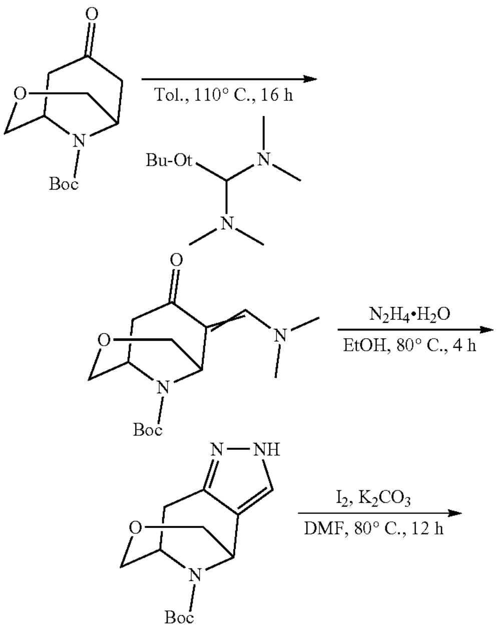

-continued
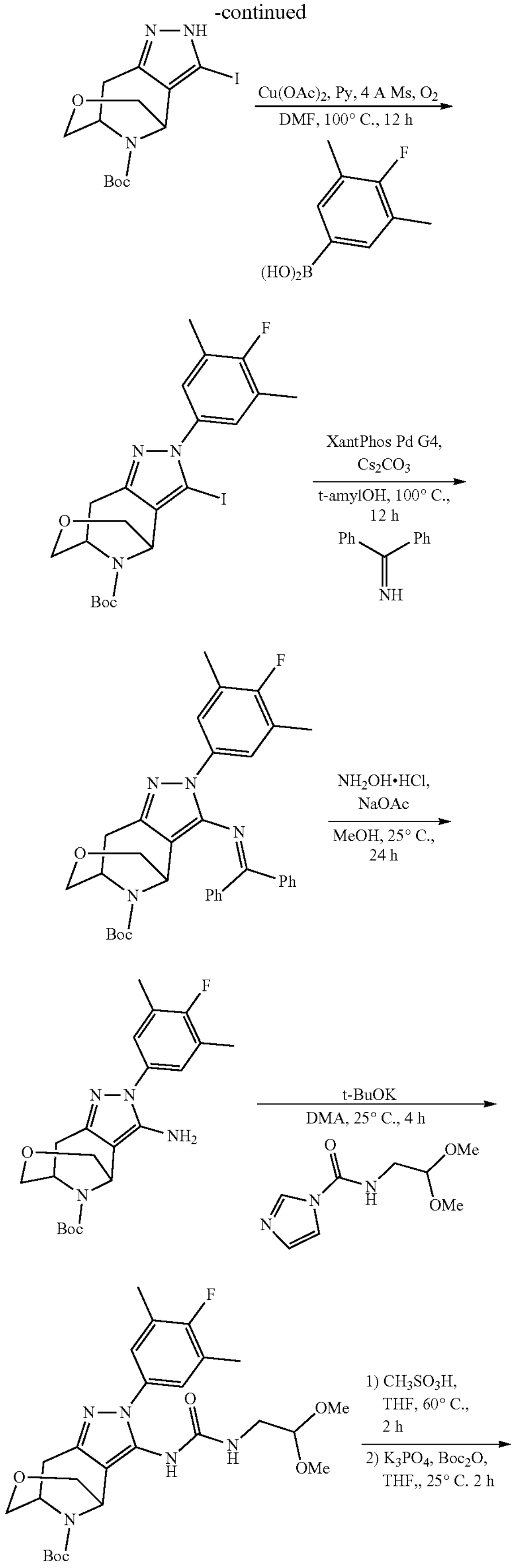
-continued
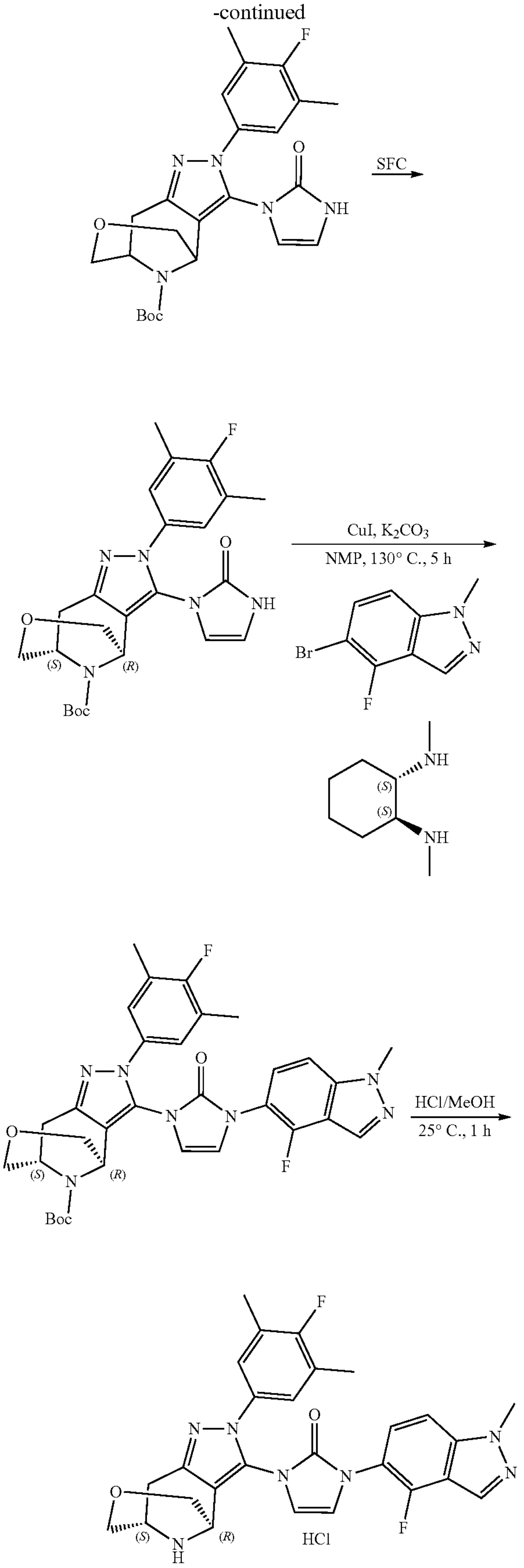

Step 1: tert-butyl 6-((dimethylamino)methylene)-7-oxo-3-oxa-9-azabicyclo[3.3.1]nonane-9-carboxylate

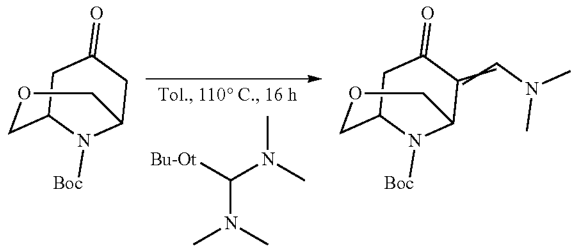

A mixture of tert-butyl 7-oxo-3-oxa-9-azabicyclo[3.3.1] nonane-9-carboxylate (200 g, 828.90 mmol, 1 eq), 1-tert-butoxy-N,N,N',N'-tetramethylmethanediamine (828.90 mmol, 171.17 mL, 1 eq) in toluene (2 L) was degassed and purged with $N_2$ for 3 times, and then the mixture was stirred at 110° C. for 16 hours under $N_2$ atmosphere. LCMS showed reaction was completed. The reaction mixture was concentrated in vacuo. The residue was purified by silica gel chromatography (Petroleum ether/ethyl acetate=1/0 to 0/1) to give tert-butyl 6-((dimethylamino)methylene)-7-oxo-3-oxa-9-azabicyclo[3.3.1] nonane-9-carboxylate (132 g, 445.40 mmol, 53.73% yield). LC-MS (ES+, m/z): 297.1 $[(M+H)^+]$; Rt=0.922 min.

Step 2: tert-butyl 2,4,5,7,8,9-hexahydro-4,8-epiminooxocino [5,4-c]pyrazole-10-carboxylate

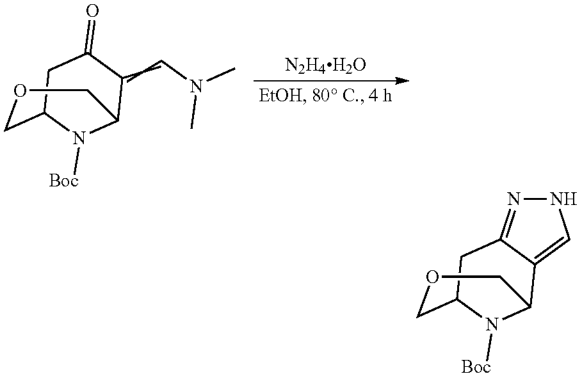

To a mixture of tert-butyl 6-((dimethylamino)methylene)-7-oxo-3-oxa-9-azabicyclo[3.3.1] nonane-9-carboxylate (132 g, 445.40 mmol, 1 eq) in EtOH (1.5 L) was added $N_2H_4 \cdot H_2O$ (551.66 mmol, 33.45 mL, 1.24 eq) under $N_2$. The mixture was stirred at 80° C. for 4 hours. LCMS showed the reaction was completed. The reaction mixture was quenched by addition $H_2O$ (2000 mL), extracted with ethyl acetate (3000 mL). The combined organic layers were washed with saturated brine (1000 mL), dried over anhydrous $Na_2SO_4$, filtered and concentrated under reduced pressure to give tert-butyl 2,4,5,7,8,9-hexahydro-4,8-epiminooxocino [5,4-c]pyrazole-10-carboxylate (95 g, crude). LC-MS (ES+, m/z): 265.9 $[(M+H)^+]$; Rt=0.343 min.

Step 3: tert-butyl 3-iodo-2,4,5,7,8,9-hexahydro-4,8-epiminooxocino [5,4-c]pyrazole-10-carboxylate

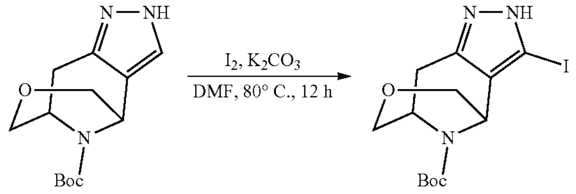

A mixture of tert-butyl 2,4,5,7,8,9-hexahydro-4,8-epiminooxocino [5,4-c]pyrazole-10-carboxylate (95 g, 358.08 mmol, 1 eq), $I_2$ (181.76 g, 716.15 mmol, 2 eq), $K_2CO_3$ (148.46 g, 1.07 mol, 3 eq) in DMF (1 L) was degassed and purged with $N_2$ for 3 times, and then the mixture was stirred at 80° C. for 12 hours under $N_2$ atmosphere. LCMS showed the reaction was completed. The reaction mixture was quenched by addition $H_2O$ (2000 mL), extracted with ethyl acetate (3000 mL). The combined organic layers were washed with saturated $NaHSO_3$ (1000 mL), dried over anhydrous $Na_2SO_4$, filtered and concentrated under reduced pressure. The crude product was triturated with ethyl acetate (200 mL) at 25° C. for 60 minutes and filtered to give tert-butyl 3-iodo-2,4,5,7,8,9-hexahydro-4,8-epiminooxocino [5,4-c]pyrazole-10-carboxylate (113 g, 282.18 mmol, 78.80% yield). LC-MS (ES+, m/z): 392.0 $[(M+H)^+]$; Rt=1.118 min.

Step 4: tert-butyl 2-(4-fluoro-3,5-dimethylphenyl)-3-iodo-2,4,5,7,8,9-hexahydro-4,8-epiminooxocino [5,4-c]pyrazole-10-carboxylate

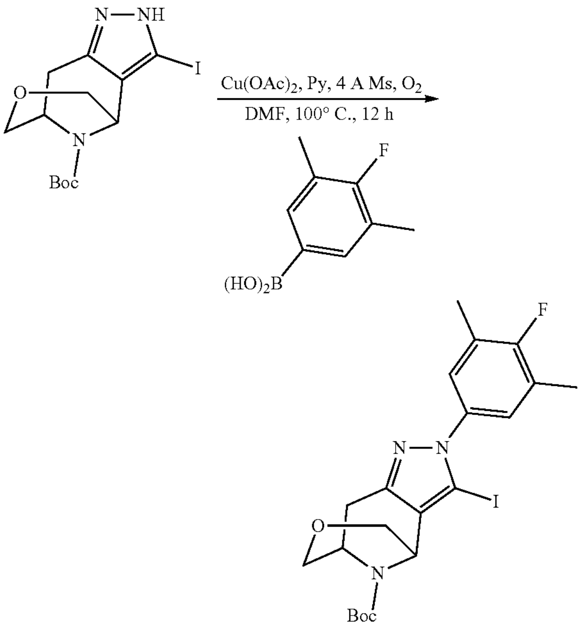

A mixture of tert-butyl 3-iodo-2,4,5,7,8,9-hexahydro-4,8-epiminooxocino [5,4-c]pyrazole-10-carboxylate (113 g, 288.85 mmol, 1 eq), (4-fluoro-3,5-dimethylphenyl) boronic acid (97.04 g, 577.70 mmol, 2 eq), $Cu(OAc)_2$ (10.49 g, 57.77 mmol, 0.2 eq), Py (1.16 mol, 93.26 mL, 4 eq) and 4A MS (113 g, 288.85 mmol) in DMF (1130 mL) was degassed and purged with Oz for 3 times, and then the mixture was stirred at 100° C. for 12 hours under $O_2$ (15 psi). LCMS showed the reaction was completed. The reaction mixture was quenched by addition $H_2O$ (2000 mL), extracted with ethyl acetate (3000 mL). The combined organic layers were washed with saturated brine (1000 mL), dried over anhydrous $Na_2SO_4$, filtered and concentrated under reduced pressure. The residue was purified by silica gel chromatography (Petroleum ether/ethyl acetate=1/0 to 0/1) to give tert-butyl 2-(4-fluoro-3,5-dimethylphenyl)-3-iodo-2,4,5,7,8,9-hexahydro-4,8-epiminooxocino [5,4-c]pyrazole-10-carboxylate (9 g, 15.81 mmol, 7.37% yield). LC-MS (ES+, m/z): 514.1 [(M+H)$^+$]; Rt=0.599 min.

Step 5: tert-butyl 3-((diphenylmethylene)amino)-2-(4-fluoro-3,5-dimethylphenyl)-2,4,5,7,8,9-hexahydro-4,8-epiminooxocino [5,4-c]pyrazole-10-carboxylate

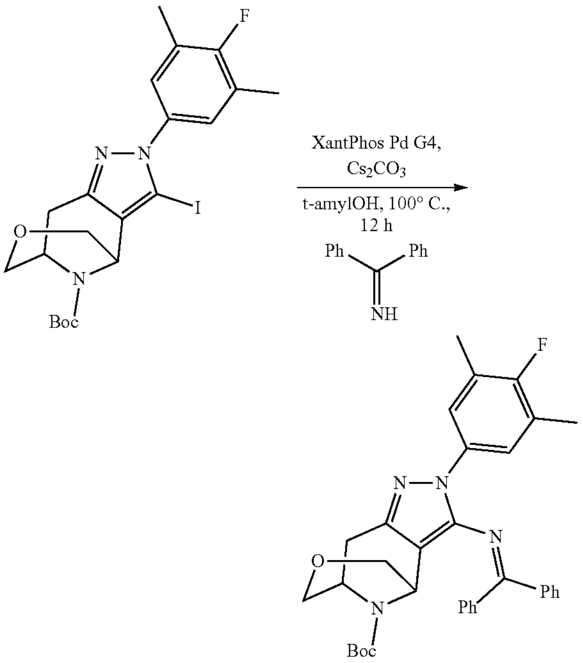

A mixture of tert-butyl 2-(4-fluoro-3,5-dimethylphenyl)-3-iodo-2,4,5,7,8,9-hexahydro-4,8-epiminooxocino [5,4-c] pyrazole-10-carboxylate (6 g, 11.69 mmol, 1 eq), diphenylmethanimine (6.35 g, 35.06 mmol, 5.88 mL, 3 eq), Xantphos Pd G4 (1.12 g, 1.17 mmol, 0.1 eq), $Cs_2CO_3$ (7.62 g, 23.38 mmol, 2 eq) in 2-methylbutan-2-ol (34 mL) was degassed and purged with $N_2$ for 3 times, and then the mixture was stirred at 100° C. for 12 hours under $N_2$ atmosphere. LCMS showed the reaction was completed. The reaction mixture was quenched by addition saturated EDTA (100 mL), extracted with ethyl acetate (240 mL). The combined organic layers were washed with saturated brine (100 mL), dried over anhydrous $Na_2SO_4$, filtered and concentrated under reduced pressure. The residue was purified by silica gel chromatography (Petroleum ether/ethyl acetate=1/0 to 0/1) to give tert-butyl 3-((diphenylmethylene)amino)-2-(4-fluoro-3,5-dimethylphenyl)-2,4,5,7,8,9-hexahydro-4,8-epiminooxocino [5,4-c]pyrazole-10-carboxylate (6 g, 10.00 mmol, 85.57% yield). LC-MS (ES+, m/z): 567.4 [(M+H)$^+$]. Rt=0.687 min.

Step 6: tert-butyl 3-amino-2-(4-fluoro-3,5-dimethylphenyl)-2,4,5,7,8,9-hexahydro-4,8-epiminooxocino [5,4-c]pyrazole-10-carboxylate

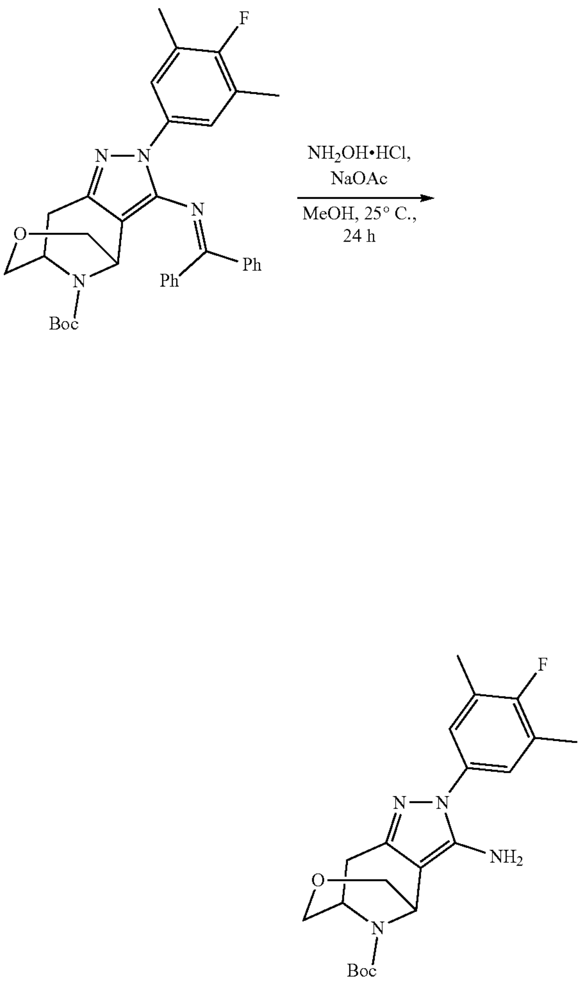

A mixture of tert-butyl 3-((diphenylmethylene)amino)-2-(4-fluoro-3,5-dimethylphenyl)-2,4,5,7,8,9-hexahydro-4,8-epiminooxocino [5,4-c]pyrazole-10-carboxylate (6 g, 10.59 mmol, 1 eq), $NH_2OH{\cdot}HCl$ (1.47 g, 21.18 mmol, 2 eq), NaOAc (2.61 g, 31.76 mmol, 3 eq) in MeOH (25 mL) was degassed and purged with $N_2$ for 3 times, and then the mixture was stirred at 25° C. for 24 hours under $N_2$ atmosphere. LCMS showed the reaction was completed. The reaction mixture was quenched by addition $H_2O$ (100 mL), and then diluted with ethyl acetate (300 mL) and extracted with ethyl acetate (300 mL). The combined organic layers were washed with saturated brine (200 mL), dried over anhydrous $Na_2SO_4$, filtered and concentrated under reduced pressure to give tert-butyl 3-amino-2-(4-fluoro-3,5-dimethylphenyl)-2,4,5,7,8,9-hexahydro-4,8-epiminooxocino [5,4-c]pyrazole-10-carboxylate (4 g, crude). LC-MS (ES+, m/z): 403.2 [(M+H)$^+$]. Rt=1.217 min.

Step 7: tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate

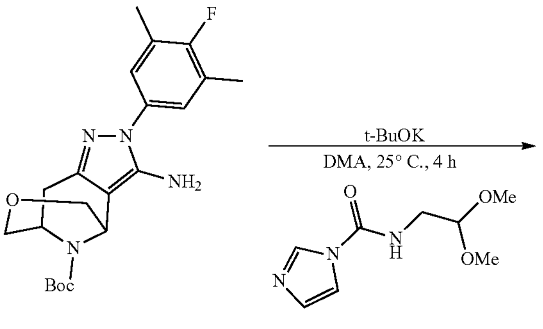

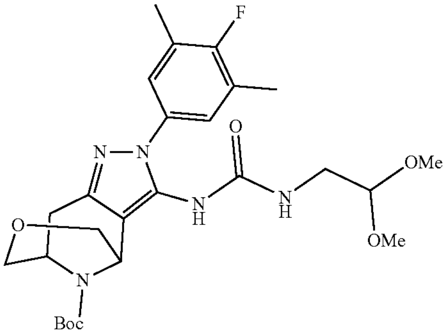

A mixture of tert-butyl 3-amino-2-(4-fluoro-3,5-dimethylphenyl)-2,4,5,7,8,9-hexahydro-4,8-epiminooxocino [5,4-c]pyrazole-10-carboxylate (4 g, 9.94 mmol, 1 eq), N-(2,2-dimethoxyethyl) imidazole-1-carboxamide (3.96 g, 19.88 mmol, 2 eq), t-BuOK (5.58 g, 49.69 mmol, 5 eq) in DMA (32 mL) was degassed and purged with $N_2$ for 3 times, and then the mixture was stirred at 25° C. for 4 hours under $N_2$ atmosphere. LCMS showed the reaction was completed. The reaction mixture was quenched by addition $H_2O$ (100 mL), and then diluted with ethyl acetate (300 mL) and extracted with ethyl acetate (300 mL). The combined organic layers were washed with saturated brine (200 mL), dried over anhydrous $Na_2SO_4$, filtered and concentrated under reduced pressure. The residue was purified by silica gel chromatography (Petroleum ether/ethyl acetate=1/0, 0/1) to give tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate (4 g, 7.36 mmol, 74.06% yield). LC-MS (ES+, m/z): 534.2 [$(M+H)^+$]. Rt=1.147 min.

Step 8: tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate

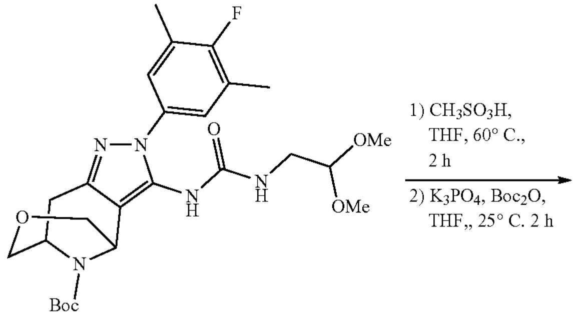

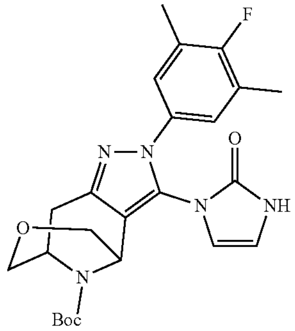

To a mixture of tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate (4 g, 7.50 mmol, 1 eq) in THF (53 mL) was added $CH_3SO_3H$ (1.08 g, 11.24 mmol, 803.47 μL, 1.5 eq), the mixture was stirred at 60° C. for 2 hours, then $K_3PO_4$ (4.77 g, 22.49 mmol, 3 eq) in $H_2O$ (5.3 mL) was added at 25° C. to keep pH>8. $Boc_2O$ (7.50 mmol, 1.72 mL, 1 eq) was then added, and the mixture was stirred at 25° C. for 2 hours. LCMS showed the reaction was completed. The reaction mixture was quenched by addition $H_2O$ (100 mL), and then diluted with ethyl acetate (100 mL) and extracted with ethyl acetate (200 mL). The combined organic layers were washed with saturated brine (200 mL), dried over anhydrous $Na_2SO_4$, filtered and concentrated under reduced pressure. The residue was purified by silica gel chromatography (Petroleum ether/ethyl acetate=1/0, 0/1) to give tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (3 g, 5.95 mmol, 79.36% yield). LC-MS (ES+, m/z): 470.3 [$(M+H)^+$]. Rt=0.483 min.

Step 9: tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c] pyrazole-10-carboxylate

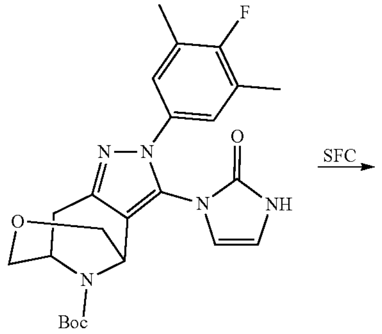

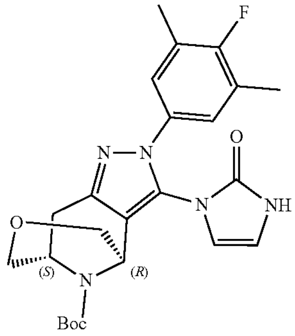

first eluent

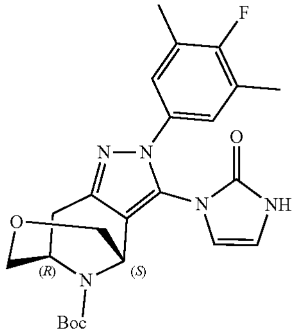

second eluent

The residue was purified by SFC separation (column: Daicel ChiralPak IM (250*25 mm i.d. 10 um); mobile phase: [$CO_2$-MeOH]; B %: 35%, isocratic elution mode) to give tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (first eluent, 1.2 g, 2.51 mmol, 39.28% yield) and compound tert-butyl (4S,8R)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (second eluent, 1.2 g, 2.51 mmol, 39.28% yield).

Step 10: tert-butyl (4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate

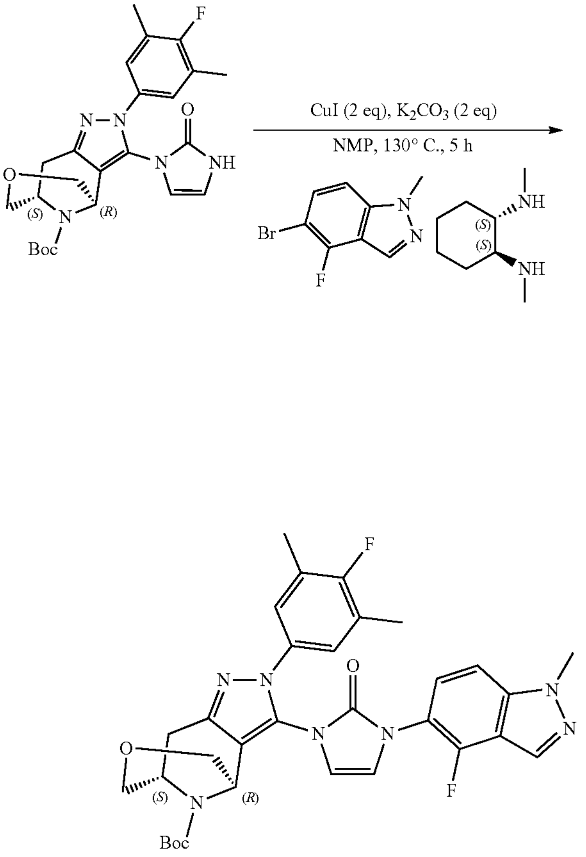

A mixture of tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (1 g, 2.13 mmol, 1 eq), 5-bromo-4-fluoro-1-methyl-1H-indazole (975.70 mg, 4.26 mmol, 2 eq), (1S, 2S)—N1,N2-dimethylcyclohexane-1,2-diamine (908.87 mg, 6.39 mmol, 3 eq), CuI (811.28 mg, 4.26 mmol, 2 eq) and $K_2CO_3$ (588.73 mg, 4.26 mmol, 2 eq) in NMP (10 mL) was degassed and purged with $N_2$ for 3 times, and then the mixture was stirred at 130° C. for 5 hours under $N_2$ atmosphere. LCMS showed the reaction was completed. The reaction mixture was quenched by addition $H_2O$ (100 mL), and then diluted with ethyl acetate (30 mL) and extracted with ethyl acetate (100 mL). The combined organic layers were washed with saturated brine (200 mL), dried over anhydrous $Na_2SO_4$, filtered and concentrated under reduced pressure. The residue was purified by silica gel chromatography (Petroleum ether/ethyl acetate=1/1 to 0/1) to give compound tert-butyl (4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (1 g, 1.55 mmol, 72.83% yield). LC-MS (ES+, m/z): 618.2 [$(M+H)^+$]. Rt=1.418 min.

Step 11:1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one

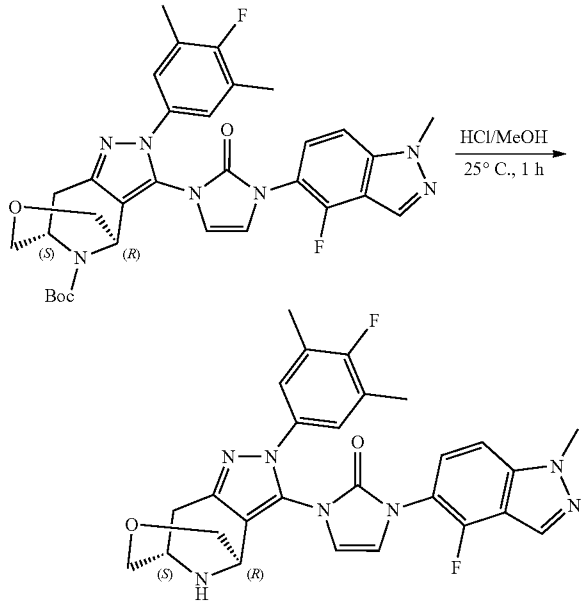

A mixture of tert-butyl (4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (1 g, 1.62 mmol, 1 eq), HCl/MeOH (4 M, 10.00 mL, 24.71 eq) was degassed and purged with $N_2$ for 3 times, and then the mixture was stirred at 25° C. for 1 hour under $N_2$ atmosphere. LCMS showed the reaction was completed. The reaction mixture was concentrated in vacuum to get compound 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (620 mg, crude). LC-MS (ES+, m/z): 518.3 $[(M+H)^+]$; Rt=0.401 min.

Intermediate 208-1

1-(4,7-difluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one Scheme 208-1

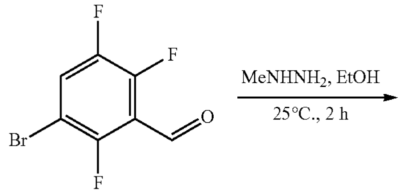

-continued

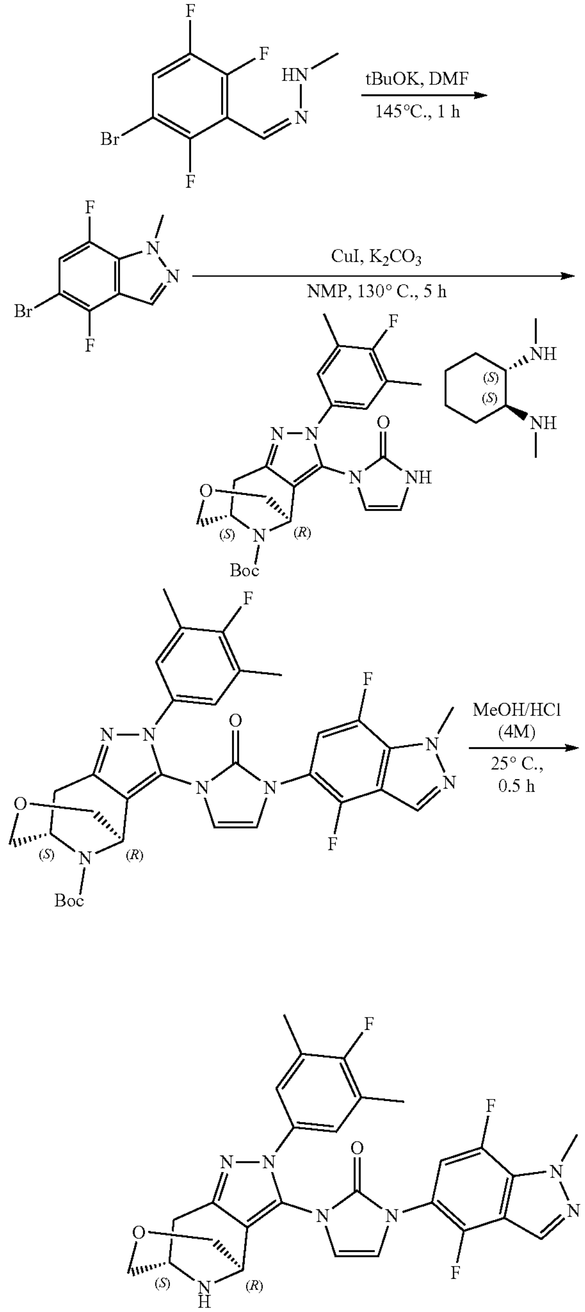

Step 1: (Z)-1-(3-bromo-2,5,6-trifluorobenzylidene)-2-methylhydrazine

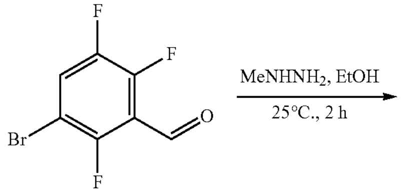

-continued

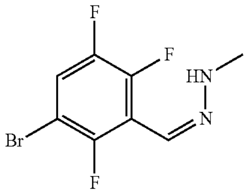

To a solution of 3-bromo-2,5,6-trifluorobenzaldehyde (1 g, 4.18 mmol, 1 eq) in EtOH (10 mL) was added methylhydrazine (2.55 g, 22.14 mmol, 2.91 mL, 5.29 eq). The mixture was stirred at 25° C. for 2 hours. LCMS indicated the reaction was completed. The mixture was concentrated to afford (Z)-1-(3-bromo-2,5,6-trifluorobenzylidene)-2-methylhydrazine (1.12 g, crude). LC-MS (ES+, m/z): 267.0 [(M+H)$^+$]; Rt=0.525 min.

Step 2: 5-bromo-4,7-difluoro-1-methyl-1H-indazole

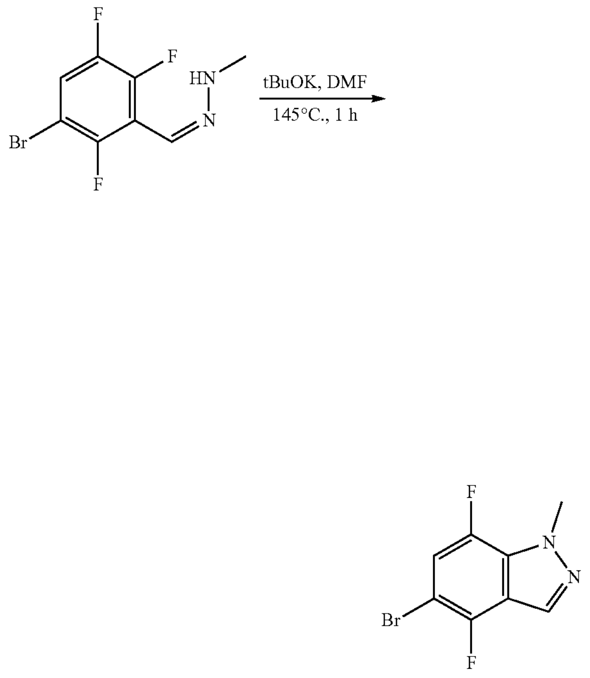

To a solution of (Z)-1-(3-bromo-2,5,6-trifluorobenzylidene)-2-methylhydrazine (300 mg, 1.12 mmol, 1 eq) in DMF (6 mL) was added t-BuOK (252.11 mg, 2.25 mmol, 2 eq). The mixture was stirred at 145° C. for 1 hour. (3 batches in parallel). LCMS indicated the reaction was completed. The mixture was added dropwise to $H_2O$ (10 mL), and then extracted with ethyl acetate (20 mL*3). The organic layers were combined, washed with water (20 mL), saturated brine (20 mL), dried over $Na_2SO_4$, filtered and concentrated to give crude product. The residue was purified by prep-TLC ($SiO_2$, Petroleum ether: ethyl acetate=10:1) to afford 5-bromo-4,7-difluoro-1-methyl-1H-indazole (88 mg, 336.63 μmol, 29.96% yield). $^1$H NMR (400 MHz, DMSO-$d_6$) δ=8.29-8.24 (m, 1H), 7.65-7.56 (m, 1H), 4.18-4.17 (m, 3H). LC-MS (ES+, m/z): 247.1 [(M+H)$^+$]; Rt=0.539 min.

Step 3: tert-butyl (4R,8S)-3-(3-(4,7-difluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carboxylate

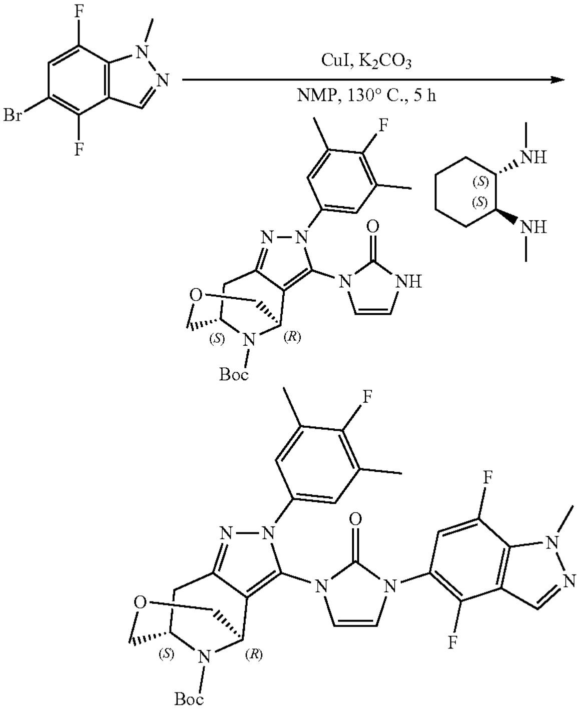

To a solution of tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (80 mg, 170.39 μmol, 1 eq) and 5-bromo-4,7-difluoro-1-methyl-1H-indazole (84.19 mg, 340.78 μmol, 2 eq) in NMP (1.6 mL) was added $K_2CO_3$ (94.20 mg, 681.57 μmol, 4 eq) and (1S,2S)—N$^1$,N$^2$-dimethylcyclohexane-1,2-diamine (48.47 mg, 340.78 μmol, 2 eq). CuI (64.90 mg, 340.78 μmol, 2 eq) was then added. The mixture was stirred at 130° C. for 5 hours under $N_2$ atmosphere. LCMS indicated the reaction was completed. The residue was poured into saturated EDTA solution (10 mL) and ethyl acetate (20 mL) stirred for 0.5 hr, and then extracted with ethyl acetate (20 mL*2). The organic layers were washed with water (20 mL*2), saturated brine (20 mL*2), dried over $Na_2SO_4$, filtered, concentrated under reduced pressure. The residue was purified by prep-TLC ($SiO_2$, Petroleum ether:ethyl acetate=2:1) to afford tert-butyl (4R,8S)-3-(3-(4,7-difluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (80 mg, 119.19 μmol, 69.95% yield). $^1$H NMR (400 MHz, DMSO-$d_6$) δ=8.41-8.35 (m, 1H), 7.55-7.39 (m, 1H), 7.17-7.07 (m, 2H), 7.06-6.99 (m, 1H), 6.89-6.80 (m, 1H), 5.04-4.81 (m, 1H), 4.40-4.29 (m, 1H), 4.24-4.20 (m, 3H), 3.98-3.87 (m, 1H), 3.69-3.65 (m, 1H), 3.18-3.16 (m, 2H), 3.09-3.02 (m, 1H), 2.88-2.79 (m, 1H), 2.24-2.21 (m, 6H), 1.43-1.35 (m, 9H). LC-MS (ES+, m/z): 636.3 [(M+H)$^+$]; Rt=0.576 min.

Step 4: 1-(4,7-difluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one

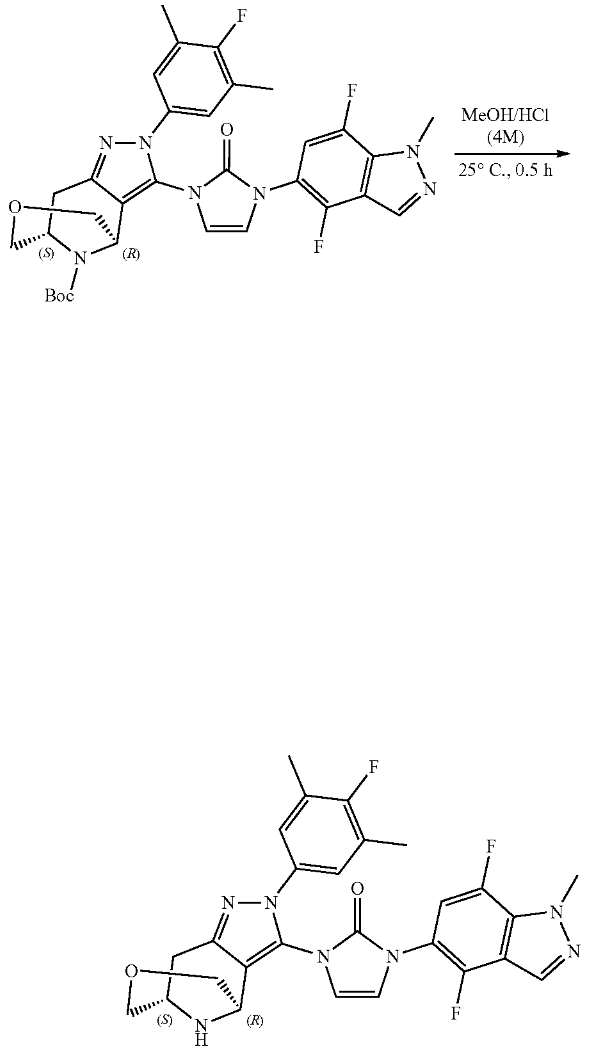

A solution of tert-butyl (4R,8S)-3-(3-(4,7-difluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (100 mg, 157.32 μmol, 1 eq) in HCl/MeOH (4 M, 10 mL, 254.25 eq). The mixture was stirred at 25° C. for 0.5 hour. LCMS indicated the reaction was completed. The reaction mixture was concentrated under reduced pressure to afford 1-(4,7-difluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (80 mg, crude, 2HCl). $^1$H NMR (400 MHz, DMSO-$d_6$) δ=10.32-10.08 (m, 1H), 9.59-9.33 (m, 1H), 8.44-8.33 (m, 1H), 7.46-7.38 (m, 1H), 7.26-7.18 (m, 1H), 7.15-7.10 (m, 2H), 7.08-7.03 (m, 1H), 6.86-6.76 (m, 1H), 4.81-4.70 (m, 1H), 4.23-4.19 (m, 3H), 4.06-4.02 (m, 2H), 3.98-3.87 (m, 2H), 3.15-3.09 (m, 1H), 2.30-2.21 (m, 8H). LC-MS (ES+, m/z): 536.3 [(M+H)$^+$]; Rt=0.415 min.

Intermediate 312

5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid and Intermediate 313

5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid Step 1: 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid and 5-((S)-2,2-dimethyltetrahydro-2H-pyran-4-yl)-1-((1S,2S)-2-methyl-1-(5-oxo-4,5-dihydro-1,2,4-oxadiazol-3-yl) cyclopropyl)-1H-pyrrolo[2,3-b]pyridine-2-carboxylic acid

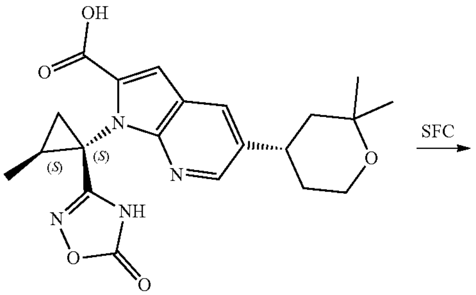

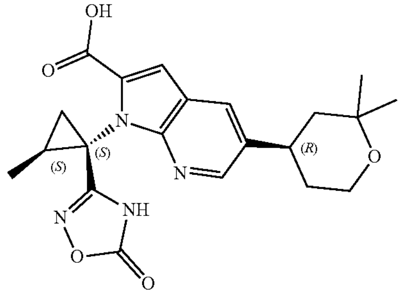

1st eluent

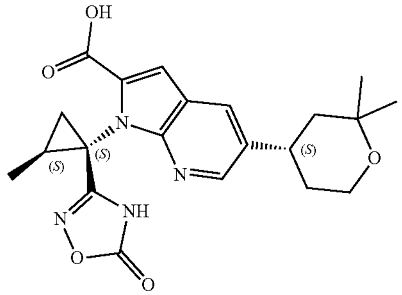

2nd eluent

The 5-(2,2-dimethyltetrahydro-2H-pyran-4-yl)-1-((1S,2S)-2-methyl-1-(5-oxo-4,5-dihydro-1,2,4-oxadiazol-3-yl)

cyclopropyl)-1H-pyrrolo[2,3-b]pyridine-2-carboxylic acid (220 mg) was separated by SFC (column: DAICEL CHIRALCEL OD (250 mm*30 mm, 10 um); mobile phase: [$CO_2$-MeOH (0.1% $NH_3H_2O$)]; gradient: 20%-50% B over 12.0 min) to afford 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid (first eluent, Rt=3.242; 80 mg, 192.03 μmol, 72.72% yield) as white solid. LC-MS (ES+, m/z): 413.1 [$(M+H)^+$]. Rt=0.424 min. and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid (second eluent, Rt=3.844 by SFC; 80 mg, 192.03 μmol, 72.72% yield) as yellow solid. LC-MS (ES+, m/z): 413.1 [$(M+H)^+$]. Rt=0.441 min.

Intermediate 410-1 di-tert-Butyl 6-bromo-5-fluorophthalazine-2,3 (1H,4H)-dicarboxylate

Scheme 410-1

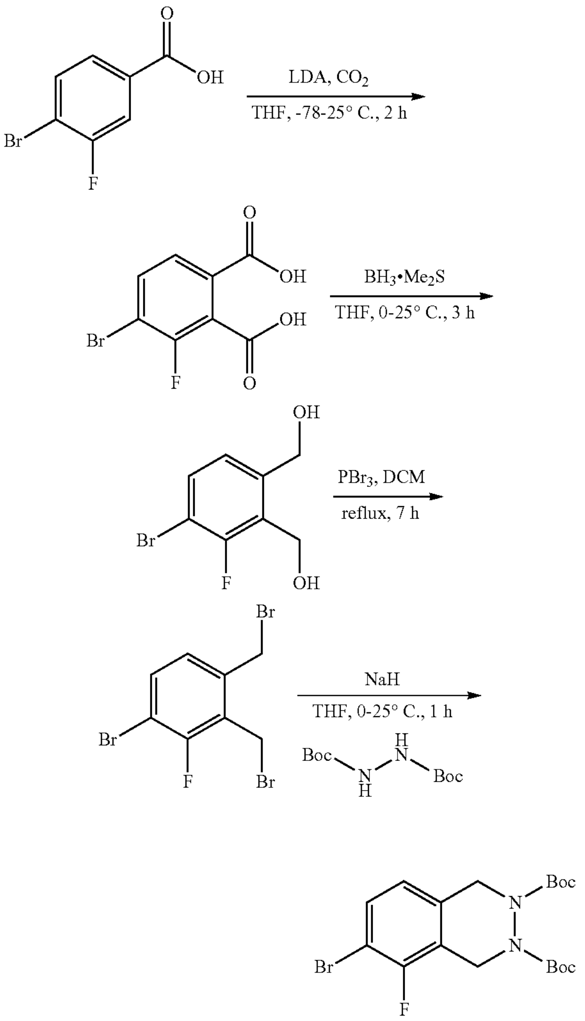

Step 1: 4-bromo-3-fluorophthalic acid

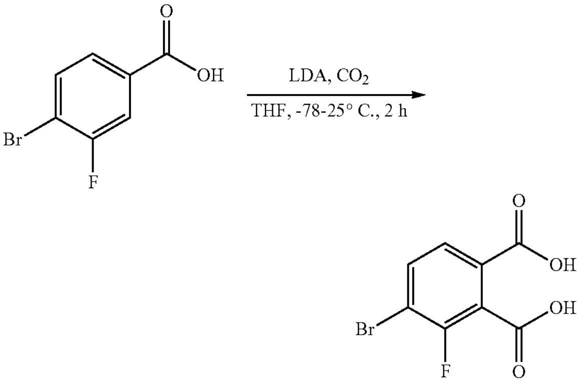

To a solution of 4-bromo-3-fluoro-benzoic acid (15 g, 68.49 mmol, 1 eq) in THF (150 mL) was added LDA (2 M, 102.74 mL, 3 eq) dropwise at −78° C. under $N_2$. The mixture was stirred at −78° C. for 1.5 hours. Then the mixture was stirred at −78° C. for 0.5 hour under $CO_2$ (15 Psi). LC-MS showed the reaction was completed. The reaction mixture was quenched with 1M HCl (500 mL), extracted with ethyl acetate (500 mL*3). The combined organic layers were washed with saturated brine (500 mL*2). The combined organic layers were dried over $Na_2SO_4$, filtered and concentrated in vacuum to give 4-bromo-3-fluorophthalic acid (16 g, 54.99 mmol, 80.29% yield). $^1H$ NMR (400 MHz, DMSO-$d_6$) δ=13.74 (br s, 2H), 7.94-7.87 (m, 1H), 7.71-7.63 (m, 1H)

Step 2: (4-bromo-3-fluoro-1,2-phenylene) dimethanol

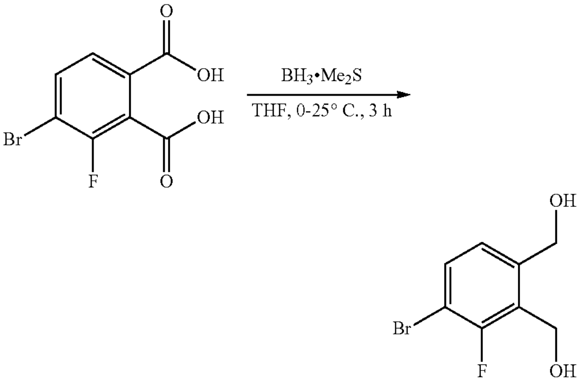

To a solution of 4-bromo-3-fluoro-phthalic acid (10 g, 38.02 mmol, 1 eq) in THF (100 mL) was added $BH_3$-$Me_2S$ (10 M, 19.01 mL, 5 eq) at 0° C. under $N_2$. The mixture was stirred at 25° C. for 3 hours under $N_2$. LC-MS showed the reaction was completed. The reaction mixture was quenched with MeOH (200 mL) and stirred for 1 hour, diluted with $H_2O$ (500 mL) and stirred for 0.2 hour, extracted with ethyl acetate (500 mL*3). The combined organic layers were washed with saturated brine (500 mL*2). The combined organic layers were dried over $Na_2SO_4$, filtered and concentrated in vacuum. The residue was purified by prep- HPLC ($NH_4HCO_3$ condition) column: Agela DuraShell C18 250*70 mm*10 um; mobile phase: [$H_2O$ (10 mM $NH_4HCO_3$)-ACN]; gradient: 5%-40% B over 17.0 min to give (4-bromo-3-fluoro-1,2-phenylene) dimethanol (6.5 g, 27.52 mmol, 72.37% yield). LC-MS (ES+, m/z): 233.0 $[(M-H)^-]$; Rt=0.800 min.

Step 3: 1-bromo-3,4-bis(bromomethyl)-2-fluorobenzene

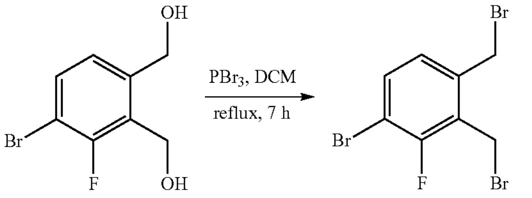 [SMILES: OCc1ccc(Br)c(F)c1CO ; Fc1c(Br)ccc(CBr)c1CBr]

To a solution of (4-bromo-3-fluoro-1,2-phenylene) dimethanol (6.5 g, 27.52 mmol, 1 eq) in DCM (70 mL) was added $PBr_3$ (22.34 g, 82.55 mmol, 3 eq). The mixture was stirred at 50° C. for 7 hours under $N_2$. LC-MS showed the reaction was completed. The reaction mixture was diluted with water (50 mL) and stirred for 0.2 hour, extracted with ethyl acetate (50 mL*3). The combined organic layers were washed with saturated brine (50 mL*2). The combined organic layers were dried over $Na_2SO_4$, filtered and concentrated in vacuum. The residue was purified by column chromatography ($SiO_2$, Petroleum ether/ethyl acetate=100/1 to 10/1) to give 1-bromo-3, 4-bis(bromomethyl)-2-fluorobenzene (7 g, 19.26 mmol, 70.01% yield). $^1H$ NMR (400 MHz, DMSO-$d_6$) δ=7.76-7.68 (m, 1H), 7.35-7.28 (m, 1H), 4.84-4.78 (m, 4H).

Step 4: di-tert-butyl 6-bromo-5-fluorophthalazine-2,3 (1H,4H)-dicarboxylate

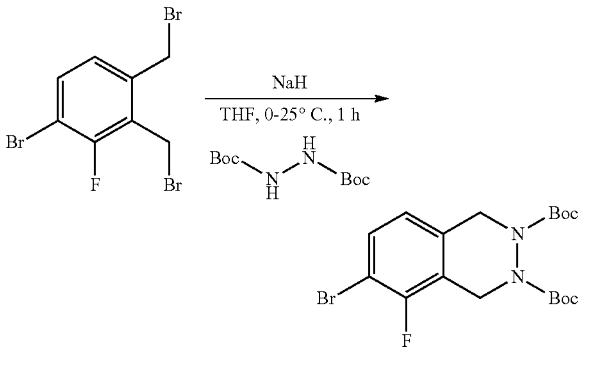

To a solution of tert-butyl N-(tert-butoxycarbonylamino) carbamate (4.47 g, 19.26 mmol, 4.30 mL, 1 eq) in THF (70 mL) was added NaH (1.54 g, 38.53 mmol, 2 eq) and stirred at 0° C. for 0.5 hour under $N_2$. Then 1-bromo-3,4-bis (bromomethyl)-2-fluorobenzene (7 g, 19.26 mmol, 1 eq) was added in the mixture. The mixture was stirred at 25° C. for 0.5 hour under $N_2$. LC-MS showed the reaction was completed. The reaction mixture was diluted with saturated $NH_4Cl$ (200 mL), extracted with ethyl acetate (200 mL*3). The combined organic layers were washed with saturated brine (200 mL*2). The combined organic layers were dried over $Na_2SO_4$, filtered and concentrated to give di-tert-butyl 6-bromo-5-fluorophthalazine-2, 3 (1H, 4H)-dicarboxylate (8 g, 17.62 mmol, 91.48% yield). LC-MS (ES+, m/z): 231.1 $[(M+H-200)^+]$; Rt=0.665 min.

Intermediate 415-1

4-oxaspiro[2.5] oct-6-en-7-yl trifluoromethanesulfonate

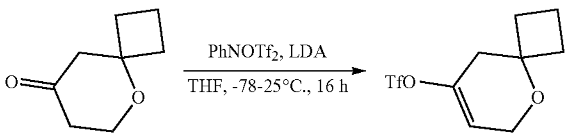 [SMILES: O=C1CCOC2(CCC2)C1 ; O=S(=O)(OC1=CCOC2(CCC2)C1)C(F)(F)F]

To a solution of 5-oxaspiro[3.5]nonan-8-one (3 g, 21.40 mmol, 1 eq) in THF (60 mL) was added LDA (2 M, 25.68 mL, 2.4 eq) stirred at −78° C. for 1 hour, then was added 1,1,1-trifluoro-N-phenyl-N-(trifluoromethylsulfonyl) methanesulfonamide (18.35 g, 51.36 mmol, 2.4 eq). The mixture was stirred at 25° C. for 15 hours (2 parallel reaction). TLC showed the reaction was completed. The reaction mixture was poured into saturated $NH_4Cl$ (150 mL), then extracted with ethyl acetate (80 mL*3). The combined organic layers were washed with saturated brine (100 mL), dried over anhydrous $Na_2SO_4$, filtered and concentrated under reduced pressure. The residue was purified by column chromatography ($SiO_2$, Petroleum ether/Ethyl acetate) to give 5-oxaspiro[3.5]non-7-en-8-yl trifluoromethanesulfonate (2.5 g, 7.35 mmol, 34.33% yield). $^1H$ NMR (400 MHz, DMSO-$d_6$) δ=6.41-5.99 (m, 1H), 4.23-4.13 (m, 1H), 3.77-3.67 (m, 1H), 2.57-2.53 (m, 2H), 2.14-1.88 (m, 4H), 1.81-1.67 (m, 2H).

Intermediate 415-2

1-((1S,2S)-2-methyl-1-(5-oxo-4,5-dihydro-1,2,4-oxadiazol-3-yl)cyclopropyl)-5-(5-oxaspiro[3.5] nonan-8-yl)-1H-indole-2-carboxylic acid Scheme 415-2

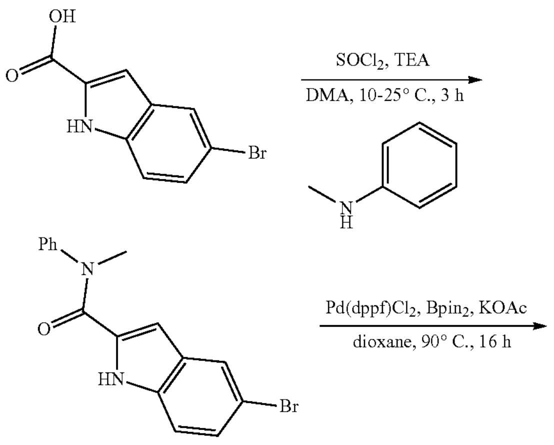

-continued

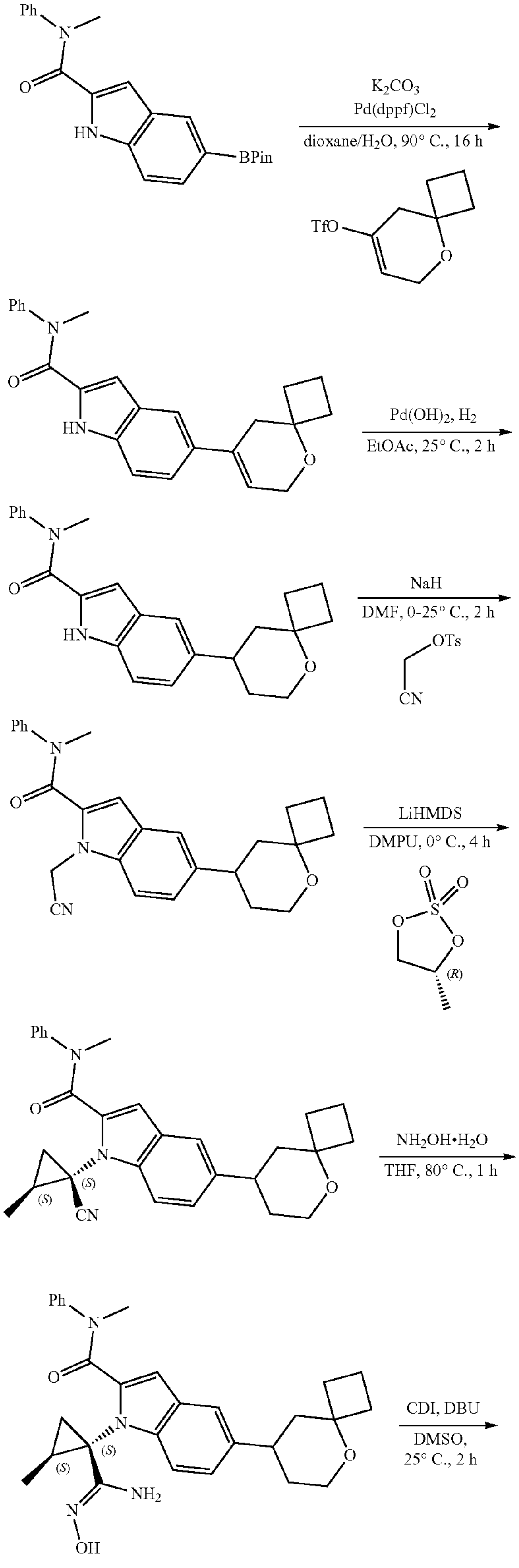

-continued

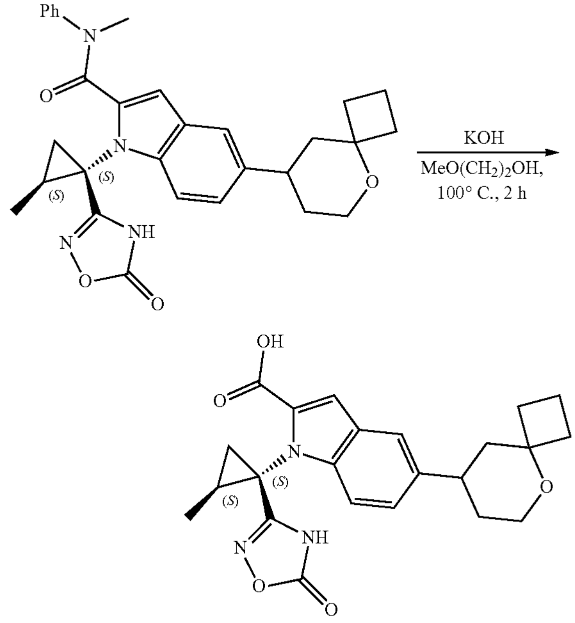

Step 1: 5-bromo-N-methyl-N-phenyl-1H-indole-2-carboxamide

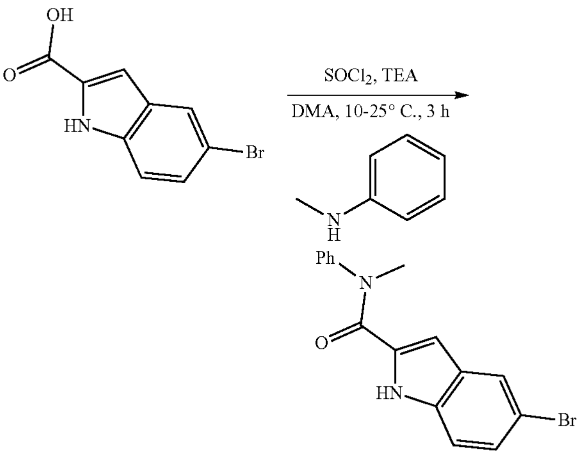

To a solution of 5-bromo-1H-indole-2-carboxylic acid (60 g, 249.94 mmol, 1 eq) in DMA (600 mL) was added dropwise $SOCl_2$ (35.68 g, 299.93 mmol, 21.78 mL, 1.2 eq) at 10° C. After stirring for 2 hours, N-methylaniline (32.14 g, 299.93 mmol, 1.2 eq) and TEA (60.70 g, 599.87 mmol, 83.49 mL, 2.4 eq) were added dropwise at 10° C. The mixture was stirred at 25° C. for 1 hour. LC-MS showed the reaction was completed. The reaction mixture was diluted with saturated $NaHCO_3$ (600 mL), extracted with ethyl acetate (600 mL*3). The combined organic layers were washed with saturated brine (600 mL*2). The combined organic layers were dried over $Na_2SO_4$, filtered and concentrated to give 5-bromo-N-methyl-N-phenyl-1H-indole-2-carboxamide (80 g, 237.43 mmol, 94.99% yield). LC-MS (ES+, m/z): 329.1 $[(M+H)^+]$; Rt=0.561 min.

Step 2: N-methyl-N-phenyl-5-(4,4,5,5-tetramethyl-1,3,2-dioxaborolan-2-yl)-1H-indole-2-carboxamide

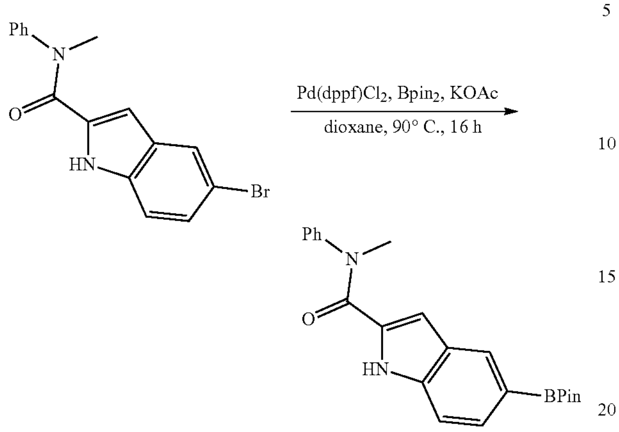

To a solution of 5-bromo-N-methyl-N-phenyl-1H-indole-2-carboxamide (10 g, 30.38 mmol, 1 eq) and 4,4,5,5-tetramethyl-2-(4,4,5,5-tetramethyl-1,3,2-dioxaborolan-2-yl)-1,3,2-dioxaborolane (15.43 g, 60.76 mmol, 2 eq) in dioxane (100 mL) was added Pd(dppf)$Cl_2$ (2.22 g, 3.04 mmol, 0.1 eq), KOAc (8.94 g, 91.13 mmol, 3 eq). The mixture was stirred at 90° C. for 16 hours under $N_2$. LCMS showed the reaction was completed. The reaction mixture was poured into saturated EDTA (500 mL) and ethyl acetate (50 mL) stirred for 1 hour, then extracted with ethyl acetate (100 mL*3). The combined organic layers were washed with saturated brine (200 mL), dried over anhydrous $Na_2SO_4$, filtered and concentrated under reduced pressure. The residue was purified by column chromatography ($SiO_2$, Petroleum ether/ethyl acetate=50/1 to 2/1) to give N-methyl-N-phenyl-5-(4,4,5,5-tetramethyl-1,3,2-dioxaborolan-2-yl)-1H-indole-2-carboxamide (13 g, 34.55 mmol, 37.91% yield). LC-MS (ES+, m/z): 377.2 [(M+H)$^+$]; Rt=0.593 min.

Step 3: N-methyl-N-phenyl-5-(5-oxaspiro[3.5]non-7-en-8-yl)-1H-indole-2-carboxamide

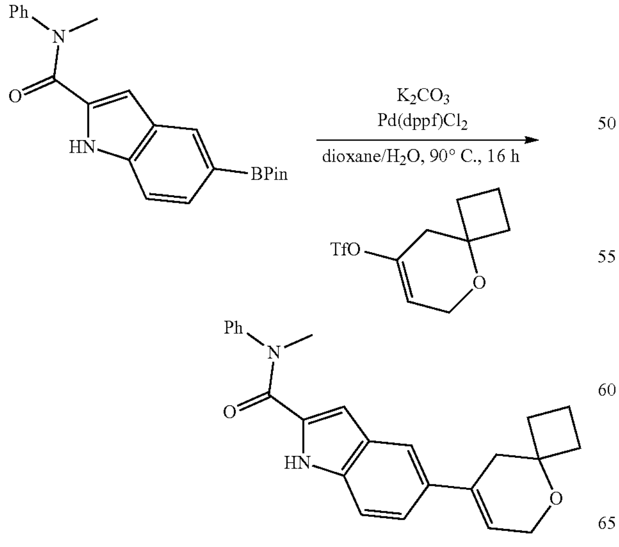

To a solution of N-methyl-N-phenyl-5-(4,4,5,5-tetramethyl-1,3,2-dioxaborolan-2-yl)-1H-indole-2-carboxamide (1.11 g, 2.94 mmol, 1 eq) and 5-oxaspiro[3.5]non-7-en-8-yl trifluoromethanesulfonate (800 mg, 2.94 mmol, 1 eq) in dioxane (8 mL) and $H_2O$ (2 mL) was added Pd(dppf)$Cl_2$ (215.02 mg, 293.86 μmol, 0.1 eq) and $K_2CO_3$ (1.22 g, 8.82 mmol, 3 eq). The mixture was stirred at 90° C. for 16 hours under $N_2$ atmosphere. LCMS showed the reaction was completed. The reaction mixture was poured into saturated EDTA (150 mL) stirred for 1 hour. Then the mixture was extracted with ethyl acetate (80 mL*3). The combined organic layers were washed with saturated brine (150 mL), dried over anhydrous $Na_2SO_4$, filtered and concentrated under reduced pressure. The residue was purified by column chromatography ($SiO_2$, Petroleum ether/ethyl acetate=80/1 to 3/1) to give N-methyl-N-phenyl-5-(5-oxaspiro[3.5]non-7-en-8-yl)-1H-indole-2-carboxamide (600 mg, 1.47 mmol, 50.00% yield). The reaction was repeated on a larger scale to produce more N-methyl-N-phenyl-5-(5-oxaspiro[3.5]non-7-en-8-yl)-1H-indole-2-carboxamide (1.5 g, 3.64 mmol, 49.50% yield). LC-MS (ES+, m/z): 373.2 [(M+H)$^+$]; Rt=0.595 min.

Step 4: N-methyl-N-phenyl-5-(5-oxaspiro[3.5]nonan-8-yl)-1H-indole-2-carboxamide

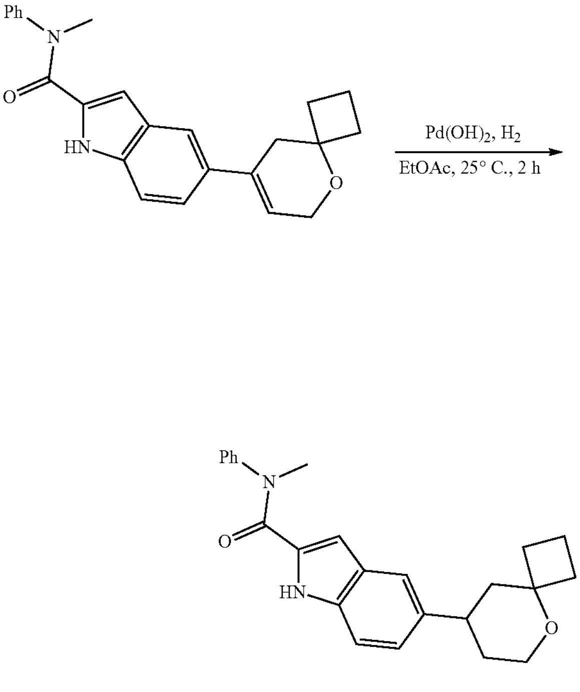

To a solution of Pd$(OH)_2$ (1.21 g, 1.73 mmol, 20% purity) in ethyl acetate (4 mL) was added N-methyl-N-phenyl-5-(5-oxaspiro[3.5]non-7-en-8-yl)-1H-indole-2-carboxamide (1 g, 2.68 mmol, 1 eq). The mixture was stirred at 25° C. for 2 hours under $H_2$ (15 Psi) (2 parallel reaction). LCMS showed the reaction was completed. The mixture was filtered and concentrated under reduced pressure to give N-methyl-N-phenyl-5-(5-oxaspiro[3.5]nonan-8-yl)-1H-indole-2-carboxamide (1.6 g, 3.99 mmol, 74.24% yield). LC-MS (ES+, m/z): 375.2 [(M+H)$^+$]; Rt=1.858 min.

Step 5:1-(cyanomethyl)-N-methyl-N-phenyl-5-(5-oxaspiro[3.5]nonan-8-yl)-1H-indole-2-carboxamide

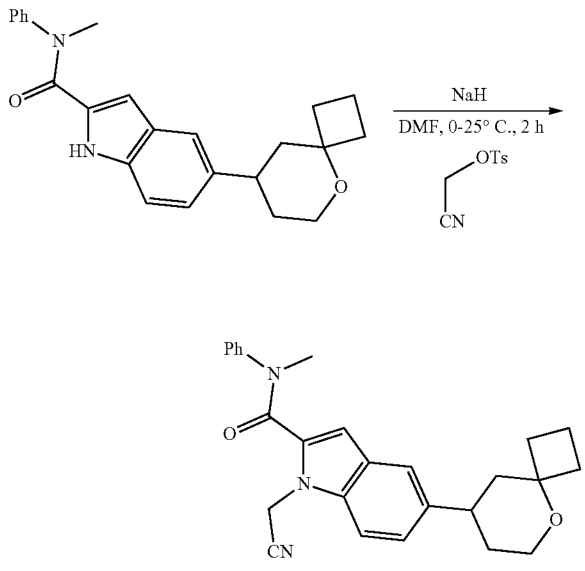

To a solution of N-methyl-N-phenyl-5-(5-oxaspiro[3.5]nonan-8-yl)-1H-indole-2-carboxamide (1.5 g, 4.01 mmol, 1 eq) in DMF (15 mL) was added NaH (320.45 mg, 8.01 mmol, 60% purity, 2 eq) at 0° C. and then stirred 0.5 hour under $N_2$, then was added cyanomethyl 4-methylbenzenesulfonate (1.69 g, 8.01 mmol, 2 eq). The mixture was stirred at 25° C. for 1.5 hours. LCMS showed the reaction was completed. The reaction mixture was poured into saturated $NH_4Cl$ (150 mL), then extracted with ethyl acetate (50 mL*3). The combined organic layers were washed with saturated brine (100 mL*3), dried over anhydrous $Na_2SO_4$, filtered and concentrated under reduced pressure. The residue was purified by column chromatography ($SiO_2$, Petroleum ether/ethyl acetate) to give 1-(cyanomethyl)-N-methyl-N-phenyl-5-(5-oxaspiro[3.5]nonan-8-yl)-1H-indole-2-carboxamide (1 g, 2.18 mmol, 54.34% yield). LC-MS (ES+, m/z): 414.3 [$(M+H)^+$]; Rt=1.943 min.

Step 6: 1-((1S,2S)-1-cyano-2-methylcyclopropyl)-N-methyl-N-phenyl-5-(5-oxaspiro[3.5]nonan-8-yl)-1H-indole-2-carboxamide

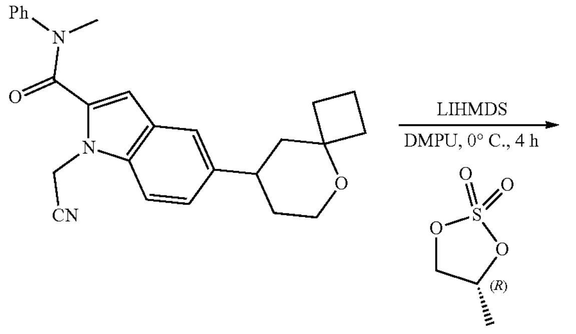

-continued

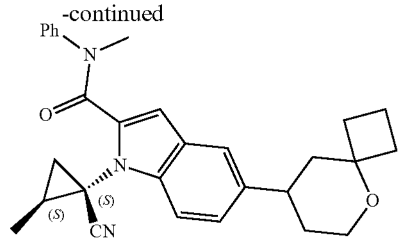

To a solution of 1-(cyanomethyl)-N-methyl-N-phenyl-5-(5-oxaspiro[3.5]nonan-8-yl)-1H-indole-2-carboxamide (0.9 g, 1.96 mmol, 1 eq) and (4R)-4-methyl-1,3,2-dioxathiolane 2,2-dioxide (541.20 mg, 3.92 mmol, 2 eq) in DMPU (18 mL) was added LiHMDS (1 M, 7.84 mL, 4 eq) at 0° C., The mixture was stirred at 0° C. for 4 hours under $N_2$. LCMS showed the reaction was completed. The reaction mixture was poured into saturated $NH_4Cl$ (150 mL), then extracted with ethyl acetate (50 mL*3). The combined organic layers were washed with saturated brine (100 mL*3), dried over anhydrous $Na_2SO_4$, filtered and concentrated under reduced pressure. The residue was purified by column chromatography ($SiO_2$, Petroleum ether/Ethyl acetate=30:1 to 1:1) to give 1-((1S,2S)-1-cyano-2-methylcyclopropyl)-N-methyl-N-phenyl-5-(5-oxaspiro[3.5]nonan-8-yl)-1H-indole-2-carboxamide (0.6 g, 1.19 mmol, 60.78% yield). LC-MS (ES+, m/z): 454.2 [$(M+H)^+$]; Rt=0.615 min.

Step 7: 1-((1S,2S)-1-(N'-hydroxycarbamimidoyl)-2-methylcyclopropyl)-N-methyl-N-phenyl-5-(5-oxaspiro[3.5]nonan-8-yl)-1H-indole-2-carboxamide

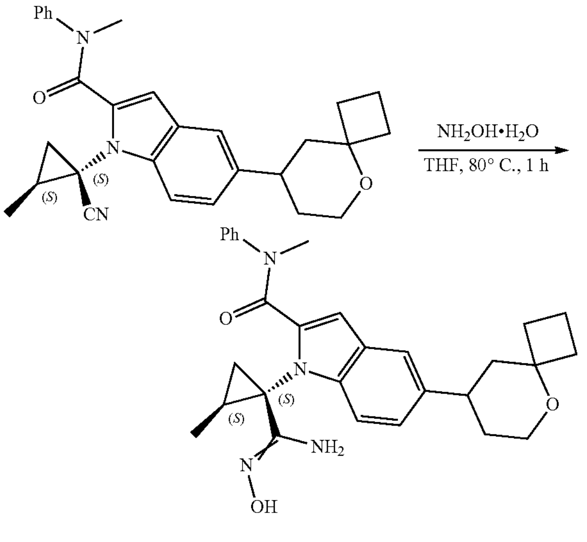

To a solution of 1-((1S,2S)-1-cyano-2-methylcyclopropyl)-N-methyl-N-phenyl-5-(5-oxaspiro[3.5]nonan-8-yl)-1H-indole-2-carboxamide (550 mg, 1.21 mmol, 1 eq) in THF (5.5 mL) was added hydroxylamine (801.04 mg, 12.13 mmol, 50% purity, 10 eq). The mixture was stirred at 80° C. for 1 hour under $N_2$ atmosphere. LCMS showed the reaction was completed. The reaction mixture was poured into water (150 mL), then extracted with ethyl acetate (50 mL*3). The combined organic layers were washed with saturated brine (100 mL*3), dried over anhydrous $Na_2SO_4$, filtered and concentrated under reduced pressure. The residue was purified by column chromatography ($SiO_2$, Petroleum ether/ethyl acetate=50:1 to 3:1) to give 1-((1S,2S)-1-(N'-hydroxycarbamimidoyl)-2-methylcyclopropyl)-N-methyl-N-phenyl-5-(5-oxaspiro[3.5]nonan-8-yl)-1H-indole-2-carboxamide (400 mg, 748.86 μmol, 61.76% yield). LC-MS (ES+, m/z): 487.4 [$(M+H)^+$]; Rt=1.544 min.

Step 8: N-methyl-1-((1S,2S)-2-methyl-1-(5-oxo-4,5-dihydro-1,2,4-oxadiazol-3-yl)cyclopropyl)-N-phenyl-5-(5-oxaspiro[3.5]nonan-8-yl)-1H-indole-2-carboxamide

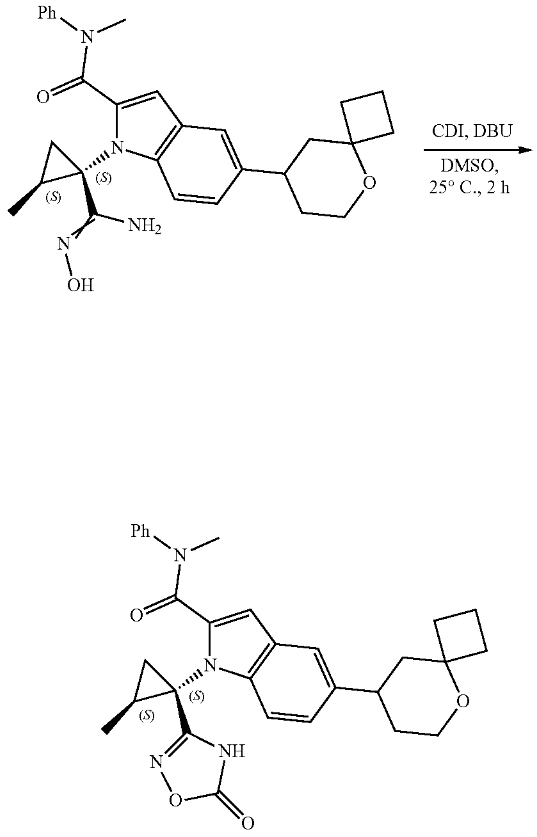

To a solution of 1-((1S,2S)-1-(N'-hydroxycarbamimidoyl)-2-methylcyclopropyl)-N-methyl-N-phenyl-5-(5-oxaspiro[3.5]nonan-8-yl)-1H-indole-2-carboxamide (400 mg, 822.02 μmol, 1 eq) in DMSO (4 mL) was added DBU (312.85 mg, 2.06 mmol, 309.76 μL, 2.5 eq) and CDI (266.58 mg, 1.64 mmol, 2 eq). The mixture was stirred at 25° C. for 2 hours under $N_2$ atmosphere. LCMS showed the reaction was completed. The reaction mixture was poured into water (150 mL), then extracted with ethyl acetate (50 mL*3). The combined organic layers were washed with saturated brine (100 mL*3), dried over anhydrous $Na_2SO_4$, filtered and concentrated under reduced pressure. The residue was purified by column chromatography ($SiO_2$, Petroleum ether/Ethyl acetate-20:1 to 1:1) to give N-methyl-1-[(1S,2S)-2-methyl-1-(5-oxo-4H-1,2,4-oxadiazol-3-yl)cyclopropyl]-5-(5-oxaspiro[3.5]nonan-8-yl)-N-phenyl-indole-2-carboxamide (350 mg, 614.52 μmol, 74.76% yield). LC-MS (ES+, m/z): 513.3 [$(M+H)^+$]; Rt=0.625 min.

Step 9: 1-((1S,2S)-2-methyl-1-(5-oxo-4,5-dihydro-1,2,4-oxadiazol-3-yl)cyclopropyl)-5-(5-oxaspiro[3.5]nonan-8-yl)-1H-indole-2-carboxylic acid

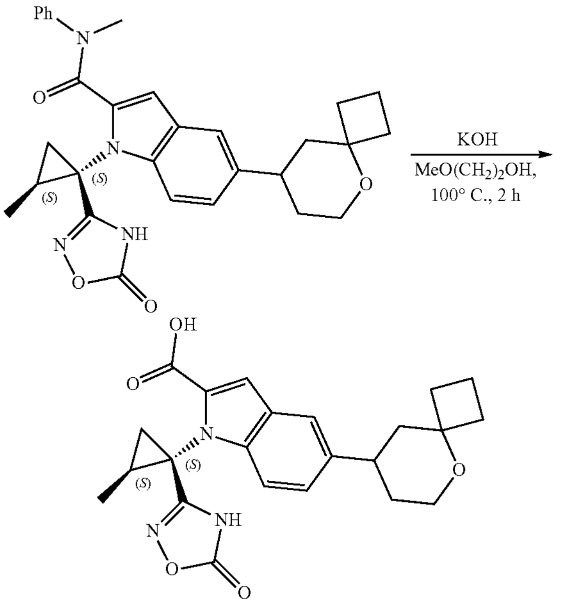

To a solution of N-methyl-1-[(1S,2S)-2-methyl-1-(5-oxo-4H-1,2,4-oxadiazol-3-yl)cyclopropyl]-5-(5-oxaspiro[3.5]nonan-8-yl)-N-phenyl-indole-2-carboxamide (300 mg, 585.25 μmol, 1 eq) in 2-methoxyethanol (3 mL) was added KOH (985.08 mg, 17.56 mmol, 30 eq). The mixture was stirred at 100° C. for 2 hours under $N_2$ atmosphere. LCMS showed the reaction was completed. The reaction mixture was poured into water (150 mL) and adjust to pH=3 with HCl (2 M), then extracted with ethyl acetate (50 mL*3). The combined organic layers were washed with saturated brine (100 mL*3), dried over anhydrous $Na_2SO_4$, filtered and concentrated under reduced pressure to give 1-((1S,2S)-2-methyl-1-(5-oxo-4,5-dihydro-1,2,4-oxadiazol-3-yl)cyclopropyl)-5-(5-oxaspiro[3.5]nonan-8-yl)-1H-indole-2-carboxylic acid (200 mg, crude). LC-MS (ES−, m/z): 421.9 [$(M-H)^-$]; Rt=0.845 min.

Intermediate 415-3

N-(2,2-dimethoxyethyl)-1H-imidazole-1-carboxamide

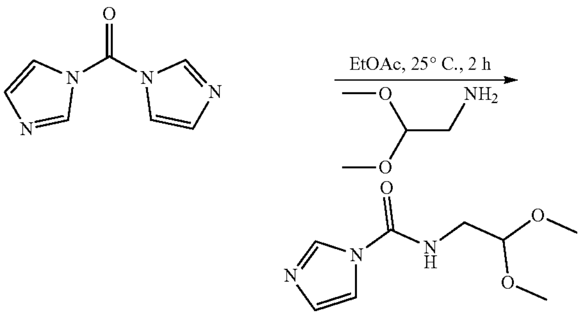

To a mixture of di(1H-imidazol-1-yl) methanone (38 g, 234.35 mmol, 1 eq) in ethyl acetate (380 mL) was added 2,2-dimethoxyethanamine (24.64 g, 234.35 mmol, 25.53 mL, 1 eq). The mixture was stirred at 25° C. for 2 hours (10 parallel reaction). TLC (ethyl acetate:Petroleum ether=2:1, Rf=0.25) showed the reaction was completed. The reaction mixture was concentrated under reduced pressure. The crude product was triturated with Petroleum ether and ethyl acetate (10:1, 500 mL) at 25° C. for 1 hour and filtered. The solid was triturated again with Ethyl acetate: Petroleum ether (2:1, 300 mL) at 25° C. for 1 hour, filtered and dried in vacuum to afford N-(2, 2-dimethoxyethyl) imidazole-1-carboxamide (412 g, 2.07 mol, 88.25% yield).

Intermediate 415-4

1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

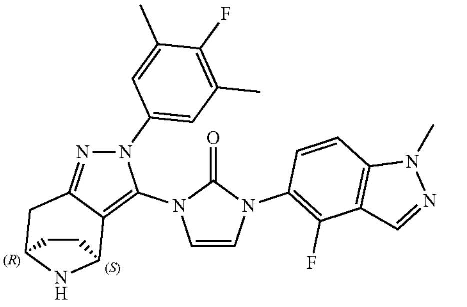

Scheme 415-4

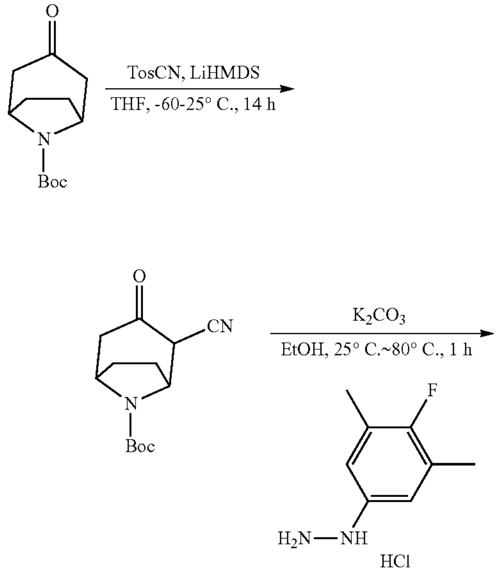

-continued

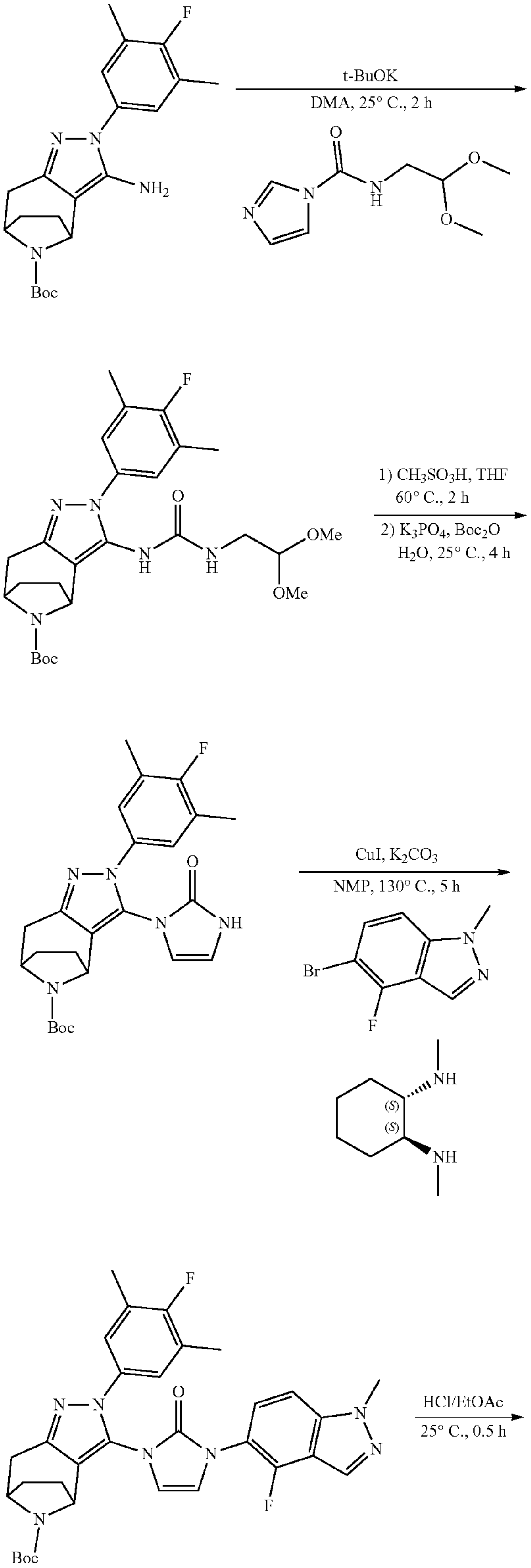

-continued

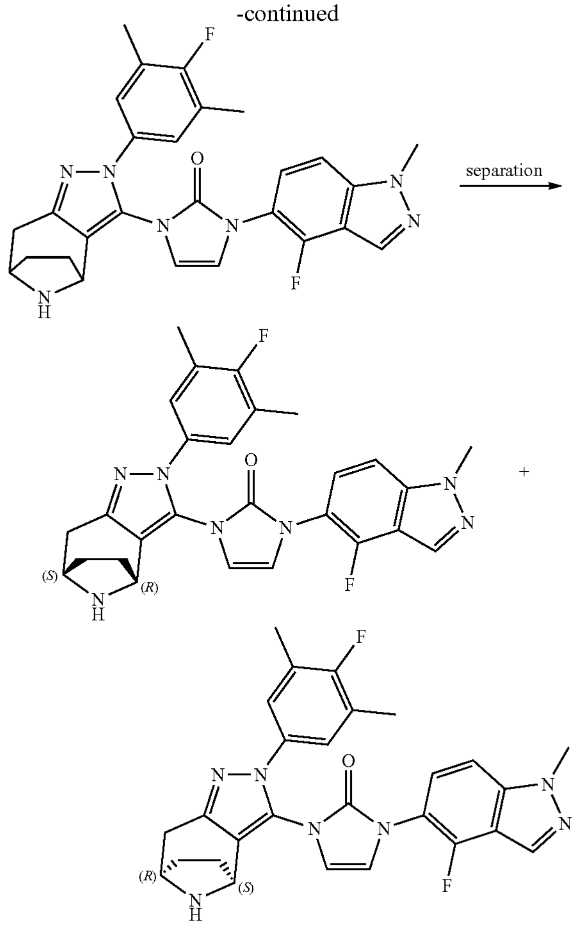

Step 1: tert-butyl-2-cyano-3-oxo-8-azabicyclo[3.2.1] octane-8-carboxylate

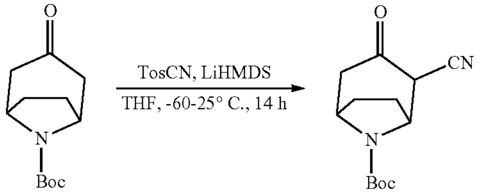 [SMILES: CC(C)(C)OC(=O)N1C2CCC1CC(=O)C2 ; CC(C)(C)OC(=O)N1C2CCC1C(C#N)C(=O)C2]

To a 3-necked flask was successively added THF (1.50 L) and tert-butyl-3-oxo-8-azabicyclo [3.2.1]octane-8-carboxylate (75.0 g, 332 mmol, 1.00 eq) at 25° C. The suspension was degassed under vacuum and purged with $N_2$ several times. The mixture was then cooled to −60° C., and LiHMDS (1 M, 732 mL, 2.20 eq) was added to the mixture at −60° C. for 0.5 hour. The mixture was then warmed to −40° C. and stirred for 2 hours. After cooling to −60° C., p-tolylsulfonylformonitrile (121 g, 665. mmol, 2.00 eq) in THF (667 g, 9.26 mol, 750 mL, 27.8 eq) was added dropwise at −60° C. for 0.5 hour. The mixture was stirred at −60° C. for 1 hour before warming up to 25° C. After stirring for additional 10 hours at 25° C., the reaction turned into brown (8 parallel reactions). The reaction mixture was poured into saturated $NH_4Cl$ (1500 mL) and extracted with ethyl acetate (1000 mL*3). The organic extracts were combined and washed with brine (500 mL), dried over $Na_2SO_4$ and concentrated under reduce pressure. The crude product tert-butyl-2-cyano-3-oxo-8-azabicyclo[3.2.1]octane-8-carboxylate (83.3 g, 332 mmol, 99.9% yield).

Step 2: tert-butyl-3-amino-2-(4-fluoro-3,5-dimethylphenyl)-2,4,5,6,7,8-hexahydro-4,7-epiminocyclohepta [c]pyrazole-9-carboxylate

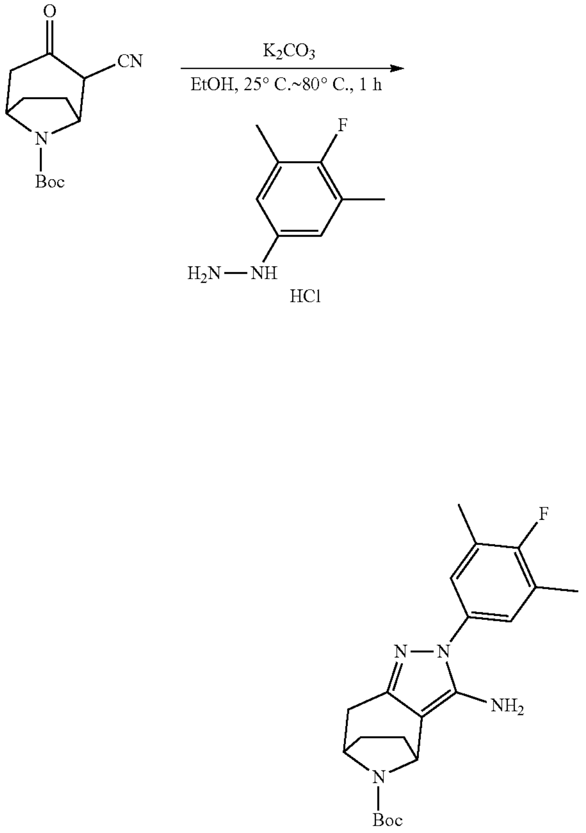

To a solution of tert-butyl-2-cyano-3-oxo-8-azabicyclo [3.2.1]octane-8-carboxylate (83.3 g, 332 mmol, 1.00 eq) and (4-fluoro-3,5-dimethyl-phenyl) hydrazine (63.4 g, 332 mmol, 1.00 eq, HCl) in EtOH (1100 mL) was added $K_2CO_3$ (50.6 g, 366 mmol, 1.10 eq) at 25° C. The mixture was then heated to 80° C. and stirred for 1 hour (8 parallel reactions). LCMS indicated the reaction was completed. The reaction mixture was poured into $H_2O$ (2000 mL) and extracted with ethyl acetate (1000 mL*2). The organic extracts were combined, washed with brine (500 mL), dried over $Na_2SO_4$ and concentrated under reduced pressure. The residue was purified by silica gel chromatography (Petroleum ether:ethyl acetate=10/1 to 1/1) to give tert-butyl-3-amino-2-(4-fluoro-3,5-dimethylphenyl)-2,4,5,6,7,8-hexahydro-4,7-epiminocyclohepta [c]pyrazole-9-carboxylate (62.7 g, 149 mmol, 44.9% yield). $^1H$ NMR (400 MHz, $CDCl_3$) δ=7.09 (br d, J=6.3 Hz, 2H), 4.95-4.66 (m, 1H), 4.42 (br s, 1H), 3.57 (br s, 2H), 3.26-2.94 (m, 1H), 2.44 (d, J=16.0 Hz, 1H), 2.21 (d, J=1.5 Hz, 7H), 2.05 (br s, 1H), 1.82-1.72 (m, 1H), 1.63 (br d, J=9.6 Hz, 1H), 1.38 (s, 9H). LC-MS (ES+, m/z): 387.3 $[(M+H)^+]$; Rt=1.493 min.

Step 3: tert-butyl-3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate

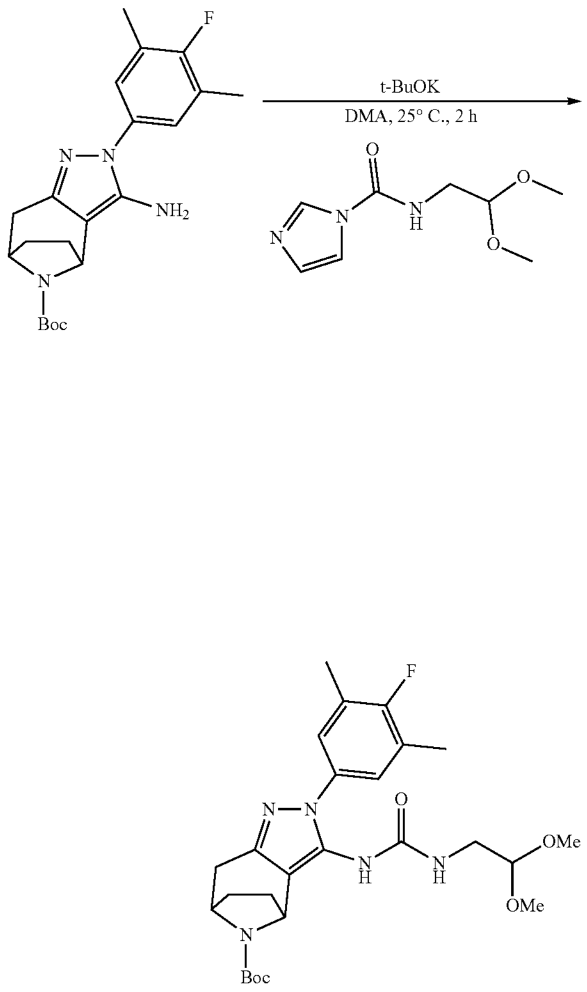

To a mixture of tert-butyl-3-amino-2-(4-fluoro-3,5-dimethylphenyl)-2,4,5,6,7,8-hexahydro-4,7-epiminocyclohepta [c]pyrazole-9-carboxylate (97.5 g, 252.29 mmol, 1 eq) in DMA (1000 mL) was added t-BuOK (141.55 g, 1.26 mol, 5 eq), N-(2,2-dimethoxyethyl) imidazole-1-carboxamide (100.52 g, 504.58 mmol, 2 eq). The mixture was stirred at 25° C. for 2 hours (4 parallel reactions). LCMS showed the reaction was completed. The reaction mixture was poured into water (1500 mL), then extracted with ethyl acetate (500 mL*3). The combined organic layers were washed with saturated brine (1000 mL), dried over anhydrous $Na_2SO_4$, filtered and concentrated under reduced pressure. Additional 3 parallel reactions were set following the same procedure. The residue was purified by silica gel chromatography (Petroleum ether: Ethyl acetate=20:1 to 3:2) to afford tert-butyl-3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (416 g, 795.69 mmol, 78.85% yield). LC-MS (ES+, m/z): 518.2 [$(M+H)^+$]; Rt=0.532 min.

Step 4: tert-butyl-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate

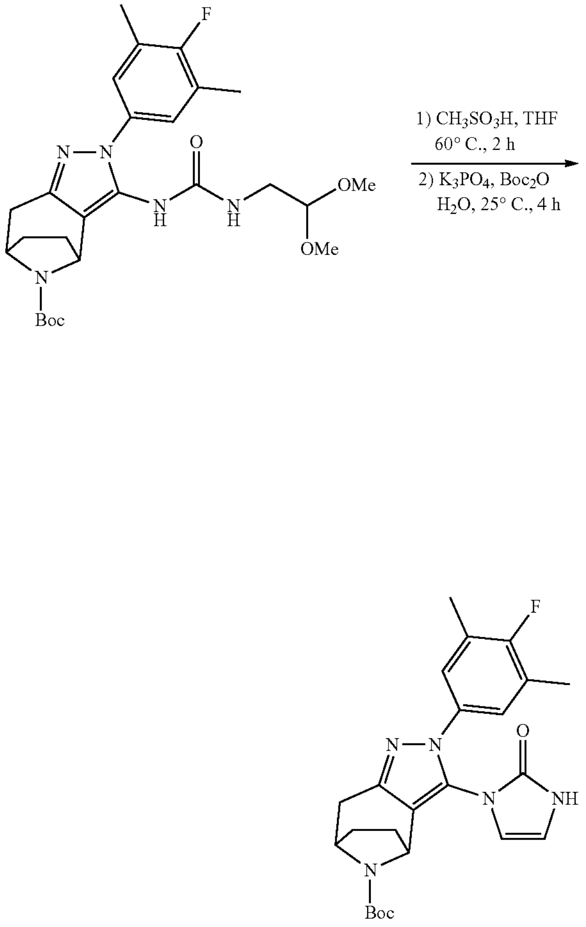

To a mixture of tert-butyl-3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (65 g, 125.58 mmol, 1 eq) in THF (650 mL) was added methanesulfonic acid (18.10 g, 188.37 mmol, 13.46 mL, 1.5 eq). The mixture was stirred at 60° C. for 2 hours. Then $K_3PO_4$ (79.97 g, 376.74 mmol, 3 eq) in $H_2O$ (200 mL) was added followed by $(Boc)_2O$ (13.70 g, 62.79 mmol, 14.43 mL, 0.5 eq). The mixture was stirred at 25° C. for 4 hours (2 parallel reactions). LCMS showed the reaction was completed. The reaction mixture was poured into water (800 mL), then extracted with ethyl acetate (300 mL*3). The combined organic layers were washed with saturated brine (500 mL), dried over anhydrous $Na_2SO_4$, filtered and concentrated under reduced pressure. The crude product was triturated with Petroleum ether and MTBE (3:2, 500 mL) at 25° C. for 1 hour and filtered. The filter cake was dried in vacuum to afford tert-butyl-2-(4- fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (46 g, 86.22 mmol, 68.65% yield). LC-MS (ES+, m/z): 454.1 [$(M+H)^+$]; Rt=0.490 min.

Step 5: tert-butyl-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

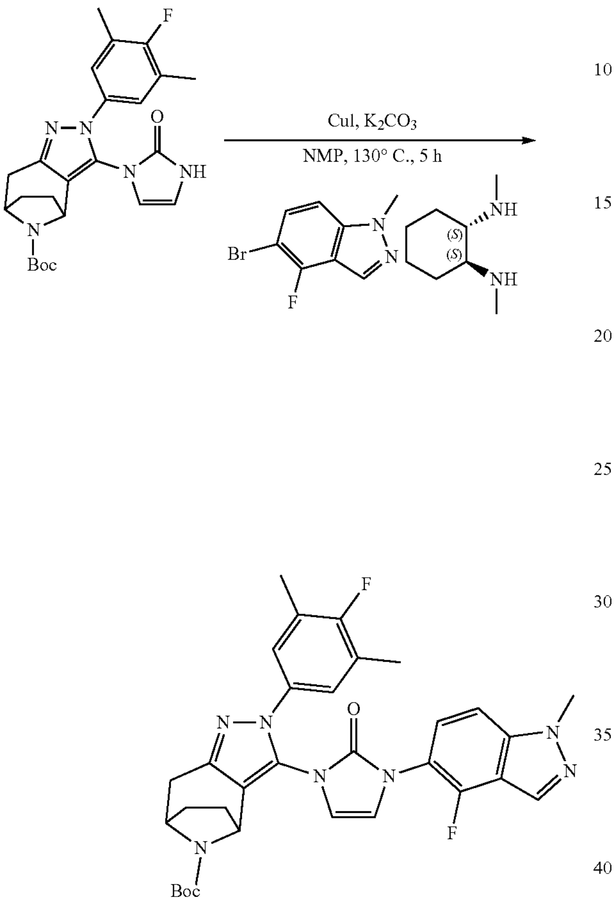

To a mixture of tert-butyl-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (51 g, 112.46 mmol, 1 eq) and 5-bromo-4-fluoro-1-methyl-1H-indazole (51.52 g, 224.91 mmol, 2 eq) in NMP (1020 mL) was added $K_2CO_3$ (31.08 g, 224.91 mmol, 2 eq), (1S,2S)—N1,N2-dimethylcyclohexane-1,2-diamine (31.99 g, 224.91 mmol, 2 eq). The suspension was degassed under vacuum and purged with $N_2$ several times. CuI (42.83 g, 224.91 mmol, 2 eq) was added to the mixture. The reaction was stirred at 130° C. for 5 hours under $N_2$. LCMS showed the reaction was completed. The reaction mixture was poured into saturated EDTA (500 mL) and ethyl acetate (500 mL) stirred for 1 hour, then extracted with ethyl acetate (500 mL*3). The combined organic layers were washed with saturated brine (200 mL), dried over anhydrous $Na_2SO_4$, filtered and concentrated under reduced pressure. The residue was purified by column chromatography ($SiO_2$, Petroleum ether/ethyl acetate=100/1 to 50/1) to afford tert-butyl-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (55 g, 91.42 mmol, 81.29% yield). LC-MS (ES+, m/z): 602.3 [(M+H)$^+$]; Rt=0.597 min.

Step 6: 1-(4-fluoro-1-methyl-1H-indazol-5-yl)-3-(2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

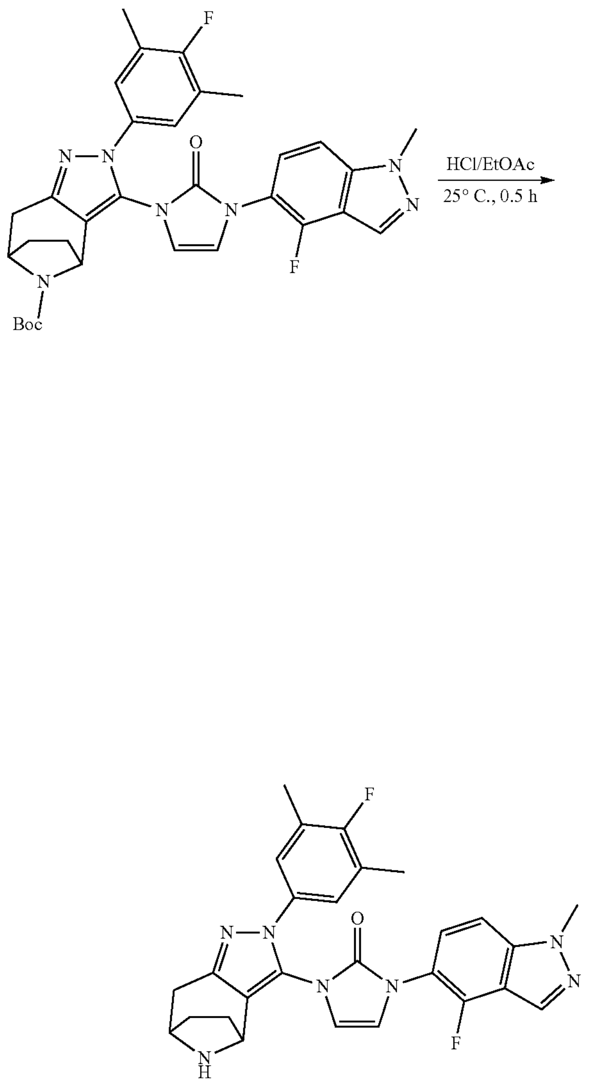

A solution of tert-butyl-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (28 g, 46.54 mmol, 1 eq) in ethyl acetate (4 M, 280 mL, 24.07 eq). The mixture was stirred at 25° C. for 0.5 hour. LCMS showed the reaction was completed. The mixture was concentrated, and the residue was dissolved in water (300 mL), adjusted to pH=7 with saturated $NaHCO_3$ (500 mL), and then extracted with ethyl acetate (300 mL*3). The organic layers were combined, washed with water (300 mL), saturated brine (300 mL), dried over $Na_2SO_4$, filtered and concentrated to give 1-(4-fluoro-1-methyl-1H-indazol-5-yl)-3-(2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (22.8 g, 45.46 mmol, 97.68% yield). LC-MS (ES+, m/z): 502.3 [(M+H)$^+$]; Rt=1.284 min.

Step 8: 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

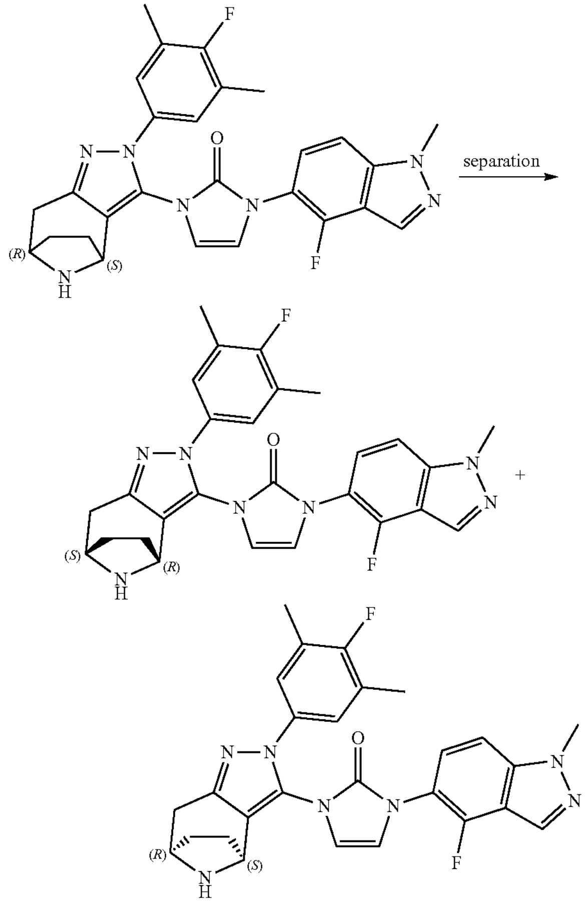

To a solution of 1-(4-fluoro-1-methyl-1H-indazol-5-yl)-3-(2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (22.8 g, 45.46 mmol, 1 eq) in propan-2-ol (570 mL) was added (2S)-2-hydroxy-2-phenyl-acetic acid (3.80 g, 25.00 mmol, 0.55 eq). The mixture was stirred at 50° C. for 2 hours. The mixture was cooled to 25° C. and stirred for 18 hours. SFC indicated the reaction was complete (dr ~3:97). The reaction mixture was filtered to obtain filtrate and filter cake. The filtrate was concentrated in vacuum to afford 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (14 g, 25.77 mmol, 56.68% yield). de=93.72%, RT=0.700 by SFC, SFC column: (S,S)-WHELK-O1,50×4.6 mm I.D., 3.5 um. Mobile phase: A: $CO_2$ B: MeOH [0.2% $NH_3$ (7M in MeOH)]. Gradient: A:B=50:50. Flow rate: 4 mL/min. Column temp.: 35° C.

ABPR: 1800 psi.

The filter cake was washed with propan-2-ol (100 mL*5). The crude product was triturated with propan-2-ol (100 mL) at 25° C. for 15 minutes. The mixture was filtered, and the cake was washed with propan-2-ol (50 mL*5). The filter cake was then dissolved in water (100 mL), adjusted to pH=8 with saturated $NaHCO_3$, extracted with DCM (100 mL*3). The organic layers were combined, washed with water (100 mL), saturated brine (100 mL), dried over $Na_2SO_4$, filtered and concentrated to give 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (9.4 g, 18.74 mmol, 82.5% recovery yield). $^1H$ NMR (400 MHz, DMSO-$d_6$) δ=8.30 (s, 1H), 7.63 (d, J=8.9 Hz, 1H), 7.45 (dd, J=7.1, 8.7 Hz, 1H), 7.07 (d, J=6.3 Hz, 2H), 7.02 (d, J=3.0 Hz, 1H), 6.84 (d, J=3.0 Hz, 1H), 4.17-4.09 (m, 4H), 3.90 (br d, J=4.3 Hz, 1H), 2.96 (dd, J=4.5, 16.0 Hz, 1H), 2.53 (br s, 1H), 2.23 (d, J=1.3 Hz, 6H), 2.11-2.00 (m, 1H), 1.98-1.82 (m, 2H), 1.60-1.46 (m, 1H). de=94.30%, RT=0.911 by SFC, SFC column: (S,S)-WHELK-01,50×4.6 mm I.D., 3.5 um. Mobile phase: A: $CO_2$ B: MeOH [0.2% $NH_3$ (7M in MeOH)]. Gradient: A:B=50:50. Flow rate: 4 mL/min. Column temp.: 35° C.

ABPR: 1800 psi.

Intermediate 416-1

1-(4-fluoro-1-methyl-1H-indazol-5-yl)-3-(2-(4-fluoro-3,5-dimethylphenyl)-2,4,5,6,7,8-hexahydropyrazolo[4,3-c]azepin-3-yl)-1,3-dihydro-2H-imidazol-2-one Scheme 416-1

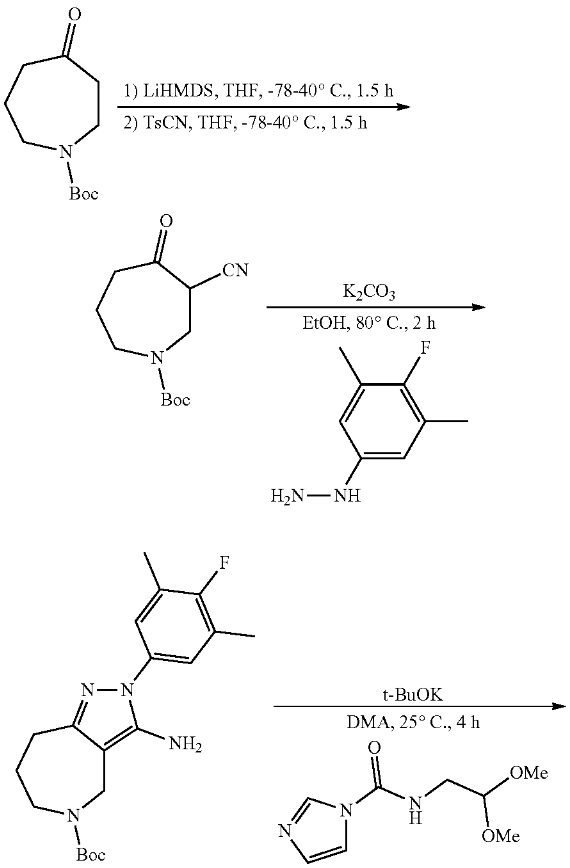

-continued

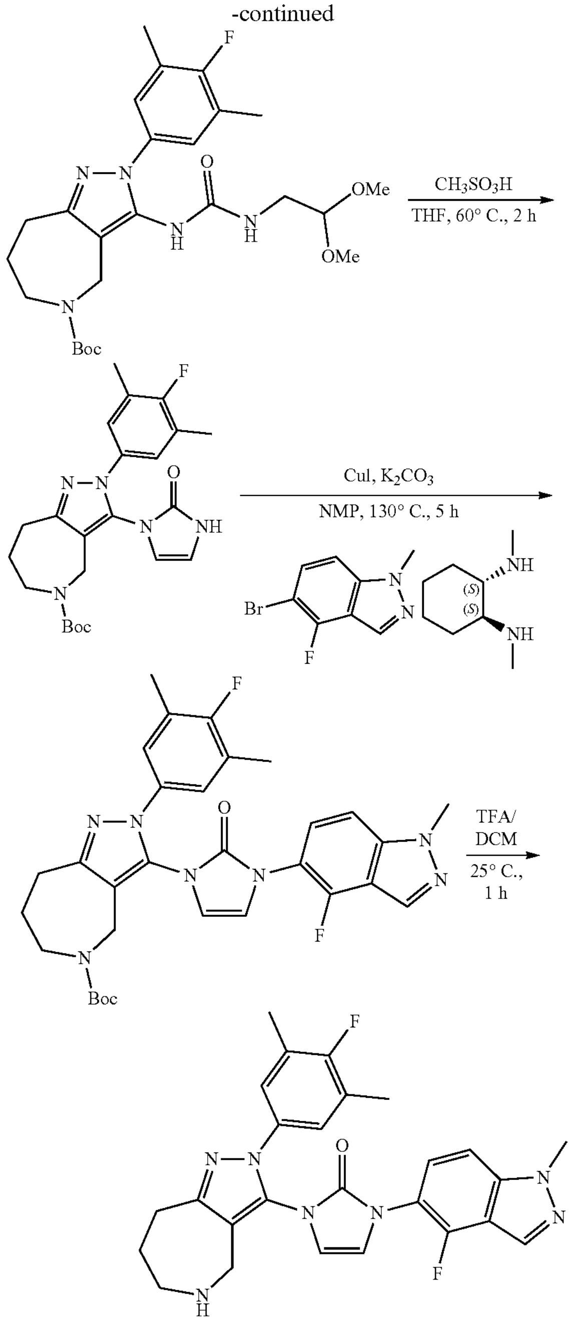

Step 1: tert-butyl 3-cyano-4-oxoazepane-1-carboxylate

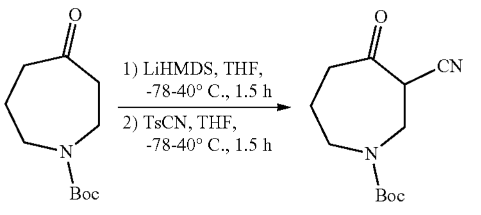 [SMILES: CC(C)(C)OC(=O)N1CCCC(=O)CC1 ; CC(C)(C)OC(=O)N1CCCC(=O)C(C#N)C1]

To a solution of tert-butyl 4-oxoazepane-1-carboxylate (2 g, 9.38 mmol, 1 eq) in THF (20 mL) was added LiHMDS (1 M, 20.63 mL, 2.2 eq) in one portion at −78° C. under $N_2$. The mixture was stirred at −40° C. for 1.5 hours. 4-Methylbenzenesulfonyl cyanide (3.74 g, 20.63 mmol, 2.2 eq) in THF (4 mL) was the added in one portion at −78° C. under $N_2$. The mixture was stirred at −40° C. for 1.5 hours. LCMS showed the reaction was completed. The reaction solution is quenched with saturated $NH_4Cl$ (200 mL). The aqueous phase was extracted with ethyl acetate (100 mL*3). The combined organic phase was washed with saturated brine (200 mL), dried with anhydrous $Na_2SO_4$, filtered and concentrated in vacuum to give a residue. The residue was purified by column chromatography ($SiO_2$, petroleum ether/ethyl acetate=10/1 to 0/1) to afford the title compound tert-butyl 3-cyano-4-oxoazepane-1-carboxylate (1.2 g, 4.03 mmol, 42.96% yield). LC-MS (ES−, m/z): 237.1 [$(M-H)^-$]. Rt=0.866 min.

Step 2: tert-butyl 3-amino-2-(4-fluoro-3, 5-dimethylphenyl)-2, 6, 7, 8-tetrahydropyrazolo[4, 3-c] azepine-5 (4H)-carboxylate

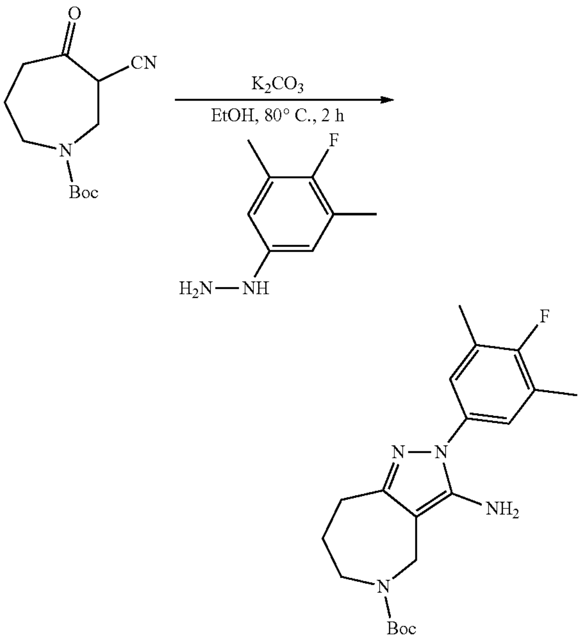

To a solution of tert-butyl 3-cyano-4-oxoazepane-1-carboxylate (1.20 g, 4.03 mmol, 1 eq) and (4-fluoro-3, 5-dimethylphenyl) hydrazine (683.30 mg, 4.43 mmol, 1.1 eq) in EtOH (12 mL) was added $K_2CO_3$ (612.49 mg, 4.43 mmol, 1.1 eq) in one portion under $N_2$. The mixture was stirred at 80° C. for 2 hours. LCMS showed the reaction was completed. The reaction mixture was quenched by addition $H_2O$ (100 mL), extracted with ethyl acetate (50 mL*3). The combined organic layers were washed with saturated brine (100 mL), dried over anhydrous $Na_2SO_4$, filtered and concentrated under reduced pressure to give a residue. The residue was purified by column chromatography ($SiO_2$, petroleum ether/ethyl acetate=10/1 to 0/1) to afford the title compound tert-butyl 3-amino-2-(4-fluoro-3, 5-dimethylphenyl)-2, 6, 7, 8-tetrahydropyrazolo[4, 3-c]azepine-5 (4H)-carboxylate (700 mg, 1.68 mmol, 41.76% yield). 1H NMR (400 MHz, DMSO-$d_6$) δ=7.29-7.21 (m, 2H), 5.03 (br s, 2H), 4.17 (s, 2H), 3.53 (br s, 2H), 2.62 (br d, J=5.7 Hz, 2H), 2.24 (d, J=1.7 Hz, 6H), 1.65 (br s, 2H), 1.38-1.34 (m, 9H). LC-MS. (ES+, m/z): 375.1 [$(M+H)^+$]; Rt=0.470 min.

Step 3: tert-butyl 3-(3-(2,2-dimethoxyethyl) ureido)-2-(4-fluoro-3,5-dimethylphenyl)-2,6,7,8-tetrahydropyrazolo[4,3-c]azepine-5 (4H)-carboxylate

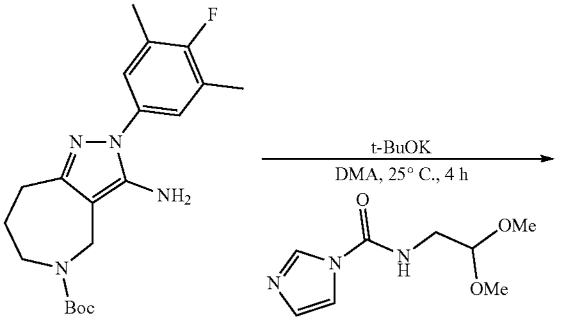

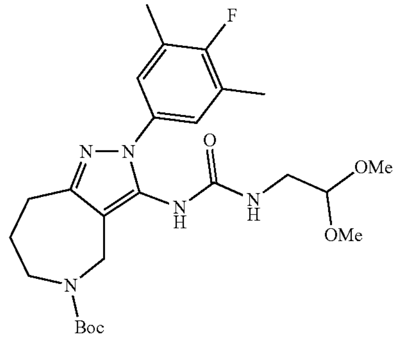

To a solution of tert-butyl 3-amino-2-(4-fluoro-3,5-dimethylphenyl)-2,6,7,8-tetrahydropyrazolo[4,3-c]azepine-5 (4H)-carboxylate (700 mg, 1.68 mmol, 1 eq) and N-(2,2-dimethoxyethyl)-1H-imidazole-1-carboxamide (1.01 g, 5.05 mmol, 3 eq) in DMA (7 mL) was added t-BuOK (943.96 mg, 8.41 mmol, 5 eq) in one portion under $N_2$. The mixture was stirred at 25° C. for 4 hours. LCMS showed the reaction was completed. The reaction mixture was quenched by addition $H_2O$ (100 mL), extracted with ethyl acetate (50 mL*3). The combined organic layers were washed with saturated brine (100 mL), dried over anhydrous $Na_2SO_4$, filtered and concentrated under reduced pressure to give a residue. The residue was purified by column chromatography ($SiO_2$, petroleum ether/ethyl acetate=10/1 to 0/1) to afford the title compound tert-butyl 3-(3-(2,2-dimethoxyethyl) ureido)-2-(4-fluoro-3,5-dimethylphenyl)-2,6,7,8-tetrahydropyrazolo [4,3-c]azepine-5 (4H)-carboxylate (500 mg, 919.73 μmol, 54.67% yield). LC-MS (ES+, m/z): 506.2 [$(M+H)^+$]; Rt=1.296 min.

Step 4: tert-butyl 2-(4-fluoro-3,5-dimethylphenyl)-3-(2-oxo-2,3-dihydro-1H-imidazol-1-yl)-2,6,7,8-tetrahydropyrazolo[4,3-c]azepine-5 (4H)-carboxylate

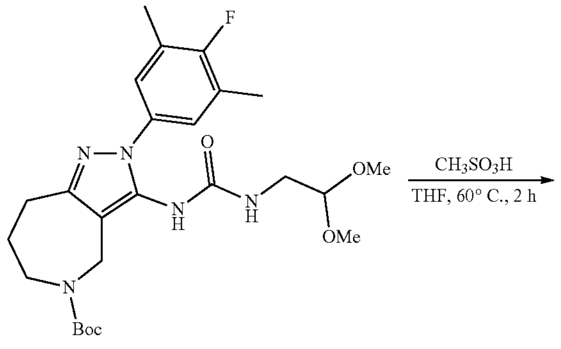

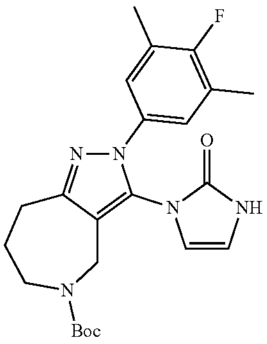

To a mixture of tert-butyl 3-(3-(2,2-dimethoxyethyl) ureido)-2-(4-fluoro-3,5-dimethylphenyl)-2,6,7,8-tetrahydropyrazolo[4,3-c]azepine-5 (4H)-carboxylate (500 mg, 919.73 μmol, 1 eq) in THF (5 mL) was added $CH_3SO_3H$ (97.23 mg, 1.01 mmol, 1.1 eq) in one portion under $N_2$. The mixture was stirred at 60° C. for 2 hours. LCMS showed the reaction was completed. The reaction mixture was quenched by addition $H_2O$ (50 mL), extracted with ethyl acetate (30 mL*3). The combined organic layers were washed with saturated brine (80 mL), dried over anhydrous $Na_2SO_4$, filtered and concentrated under reduced pressure to give a residue. The residue was purified by column chromatography ($SiO_2$, petroleum ether/ethyl acetate=3/1 to 0/1) to afford tert-butyl 2-(4-fluoro-3,5-dimethylphenyl)-3-(2-oxo-2,3-dihydro-1H-imidazol-1-yl)-2,6,7,8-tetrahydropyrazolo [4,3-c]azepine-5 (4H)-carboxylate (280 mg, 608.84 μmol, 66.20% yield). LC-MS. (ES+, m/z): 442.3 [$(M+H)^+$]; Rt=1.669 min.

Step 5: tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,6,7,8-tetrahydropyrazolo[4,3-c]azepine-5 (4H)-carboxylate

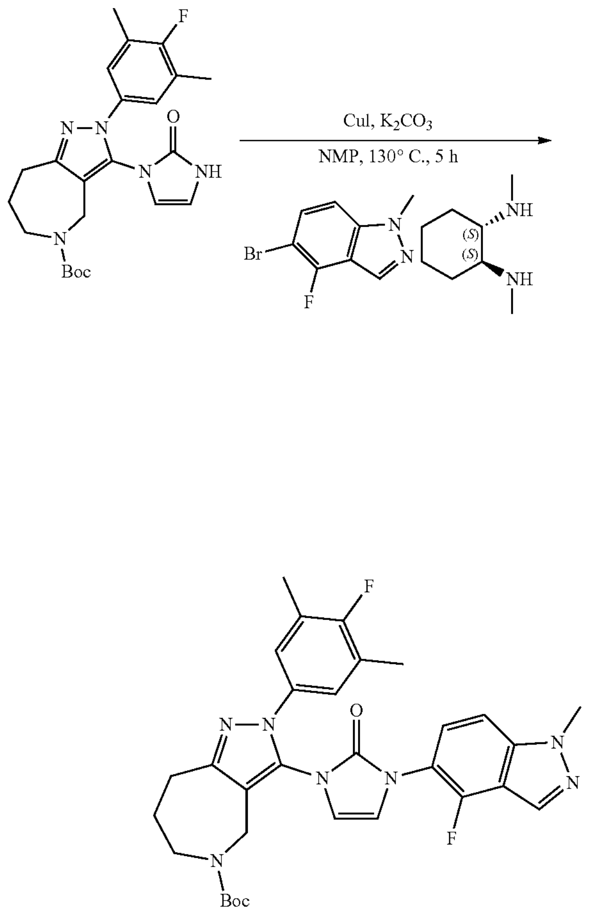

To a solution of tert-butyl 2-(4-fluoro-3,5-dimethylphenyl)-3-(2-oxo-2,3-dihydro-1H-imidazol-1-yl)-2,6,7,8-tetrahydropyrazolo[4,3-c]azepine-5 (4H)-carboxylate (100 mg, 217.44 μmol, 1 eq), (1S,2S)—$N^1$,$N^2$-dimethylcyclohexane-1,2-diamine (92.79 mg, 652.33 μmol, 3 eq) and 5-bromo-4-fluoro-1-methyl-1H-indazole (99.61 mg, 434.88 μmol, 2 eq) in NMP (1 mL) was added CuI (82.82 mg, 434.88 μmol, 2 eq) and $K_2CO_3$ (60.10 mg, 434.88 μmol, 2 eq) in one portion under $N_2$. The mixture was stirred at 130° C. for 5 hours under $N_2$. LCMS showed the reaction was completed. The reaction mixture was quenched by addition EDTA solution (30 mL) and ethyl acetate (10 mL), stirred for 0.5 hour, extracted with ethyl acetate (20 mL*3). The combined organic layers were washed with saturated brine (15 mL), dried over anhydrous $Na_2SO_4$, filtered and concentrated under reduced pressure to give a residue. The residue was purified by prep-TLC ($SiO_2$, Petroleum ether/ethyl acetate=0/1) to afford tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,6,7,8-tetrahydropyrazolo [4,3-c]azepine-5 (4H)-carboxylate (100 mg, 152.64 μmol, 70.20% yield). LC-MS (ES+, m/z): 590.4 [(M+H)$^+$]; Rt=1.928 min.

Step 6: 1-(4-fluoro-1-methyl-1H-indazol-5-yl)-3-(2-(4-fluoro-3,5-dimethylphenyl)-2,4,5,6,7,8-hexahydropyrazolo[4,3-c]azepin-3-yl)-1,3-dihydro-2H-imidazol-2-one

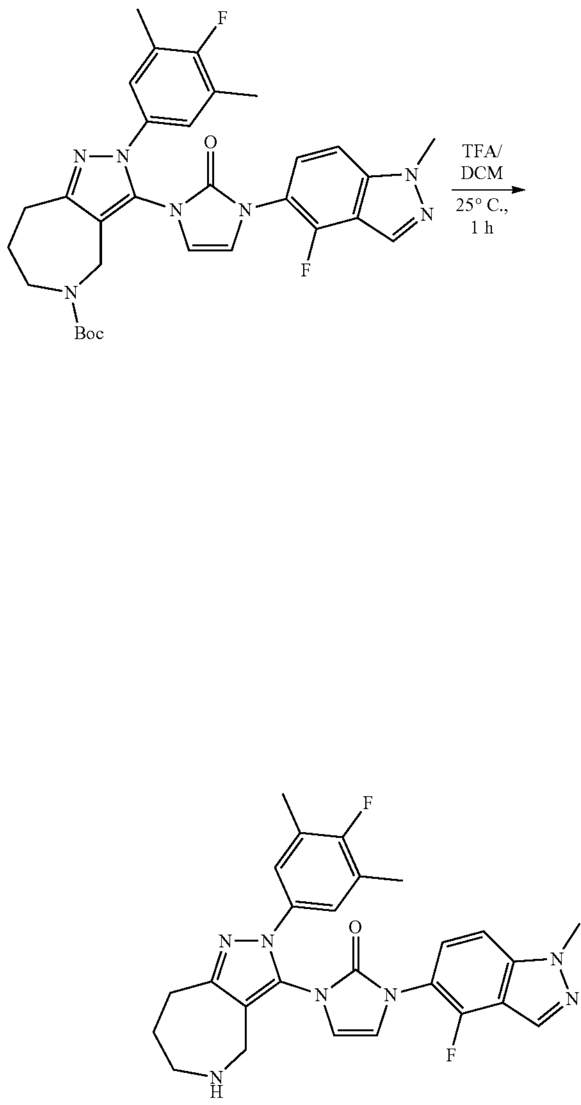

To a solution of tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,6,7,8-tetrahydropyrazolo[4,3-c]azepine-5 (4H)-carboxylate (100 mg, 152.64 μmol, 1 eq) in DCM (0.8 mL) was added TFA (0.2 mL) in one portion at 25° C. The mixture was stirred at 25° C. for 1 hour. The reaction mixture was adjusted to pH=7 with addition $NaHCO_3$ solution (20 mL) at 0° C., extracted with dichloromethane (10 mL*3). The combined organic layers were washed with saturated brine (30 mL), dried over anhydrous $Na_2SO_4$, filtered and concentrated under reduced pressure to afford 1-(4-fluoro-1-methyl-1H-indazol-5-yl)-3-(2-(4-fluoro-3,5-dimethylphenyl)-2,4,5,6,7,8-hexahydropyrazolo [4,3-c]azepin-3-yl)-1,3-dihydro-2H-imidazol-2-one (80 mg, 91% yield, crude). LC-MS (ES+, m/z): 490.2 [(M+H)$^+$]; Rt=0.400 min.

Intermediate 417-1

3-((1S,2S)-1-(2-(chloromethyl)-5-((S)-2,2-dimethyltetrahydro-2H-pyran-4-yl)-1H-indol-1-yl)-2-methylcyclopropyl)-1,2,4-oxadiazol-5(4H)-one Scheme 417-1

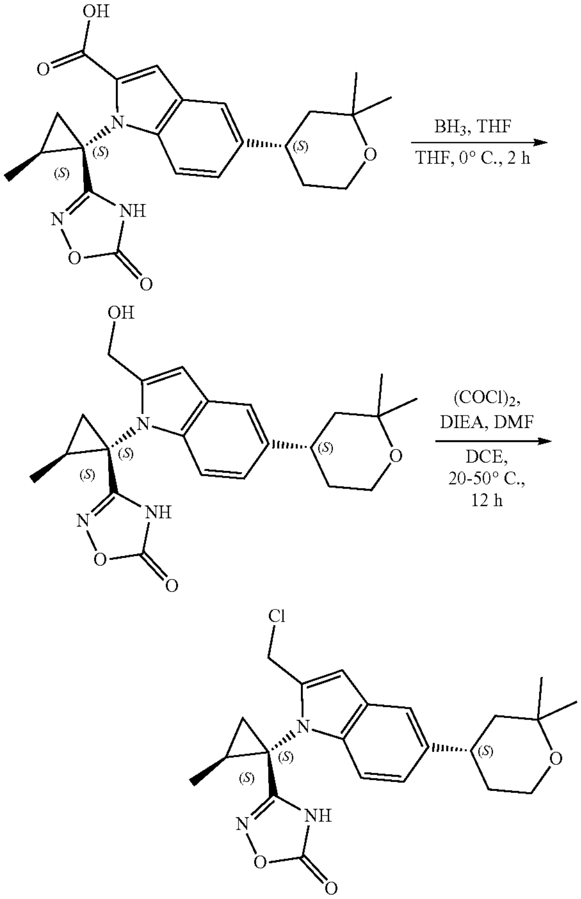

Step 1: 3-((1S,2S)-1-(5-((S)-2, 2-dimethyltetrahydro-2H-pyran-4-yl)-2-(hydroxymethyl)-1H-indol-1-yl)-2-methylcyclopropyl)-1, 2, 4-oxadiazol-5 (4H)-one

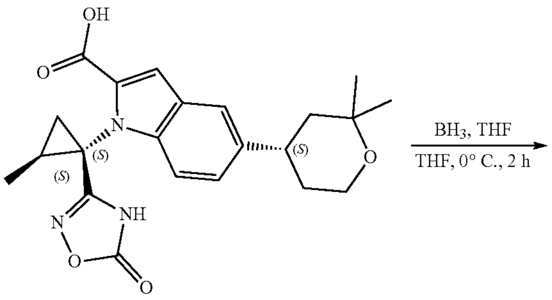

-continued

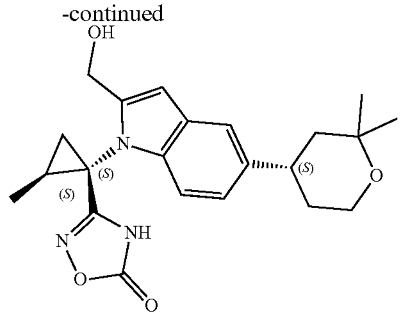

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (2 g, 4.86 mmol, 1 eq) in THF (20 mL) was added $BH_3$·THF (15 mL, 14.58 mmol, 1 M, 3 eq) at 0° C. under $N_2$. The mixture was stirred at 0° C. for 2 hours. LCMS showed the reaction was completed. The residue was quenched by addition of methanol (10 mL) and concentrated in vacuum to remove THF. The residue was diluted with water (50 mL). The aqueous phase was extracted with ethyl acetate (30 mL*3). The combined organic phase was washed with saturated brine (100 mL), dried with anhydrous $Na_2SO_4$, filtered and concentrated in vacuum. The residue was purified by column chromatography ($SiO_2$, Petroleum ether/ethyl acetate=1/1) to give compound 3-((1S,2S)-1-(5-((S)-2, 2-dimethyltetrahydro-2H-pyran-4-yl)-2-(hydroxymethyl)-1H-indol-1-yl)-2-methylcyclopropyl)-1, 2, 4-oxadiazol-5 (4H)-one (1 g, 2.39 mmol, 49.17% yield). LC-MS (ES+, m/z): 398.1 [(M+H)$^+$]; Rt=1.014 min.

Step 2: 3-((1S,2S)-1-(2-(chloromethyl)-5-((S)-2,2-dimethyltetrahydro-2H-pyran-4-yl)-1H-indol-1-yl)-2-methylcyclopropyl)-1,2,4-oxadiazol-5 (4H)-one

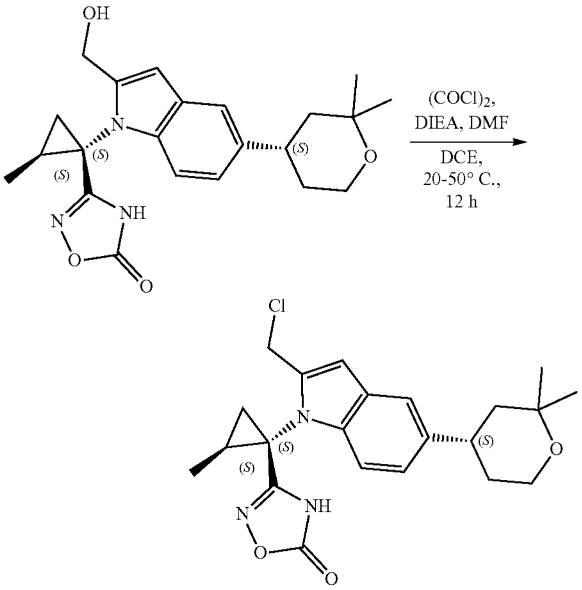

To a solution of 3-((1S,2S)-1-(5-((S)-2, 2-dimethyltetrahydro-2H-pyran-4-yl)-2-(hydroxymethyl)-1H-indol-1-yl)-2-methylcyclopropyl)-1, 2, 4-oxadiazol-5 (4H)-one (80 mg, 201.27 μmol, 1 eq) in DCE (2 mL) was added DIEA (26.01 mg, 201.27 μmol, 1 eq) and DMF (7.36 mg, 100.64 μmol, 0.5 eq) in one portion at 20° C. under $N_2$. Then added $(COCl)_2$ (38.32 mg, 301.91 μmol, 1.5 eq) in one portion at 20° C. under $N_2$. The mixture was stirred at 20° C. for 1 hour. Then additional added $(COCl)_2$ (25.55 mg, 201.27 μmol, 1 eq) in one portion at 20° C. under $N_2$. The mixture was stirred at 50° C. for 11 hours. LCMS showed the reaction was completed. The reaction mixture was concentrated under reduced pressure to afford the title compound 3-((1S,2S)-1-(2-(chloromethyl)-5-((S)-2,2-dimethyltetrahydro-2H-pyran-4-yl)-1H-indol-1-yl)-2-methylcyclopropyl)-1,2,4-oxadiazol-5 (4H)-one (80 mg, crude). LC-MS (ES-, m/z): 414.1 $[(M-H)^-]$. Rt=1.142 min.

Intermediate 436-1

1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one Scheme 436-1

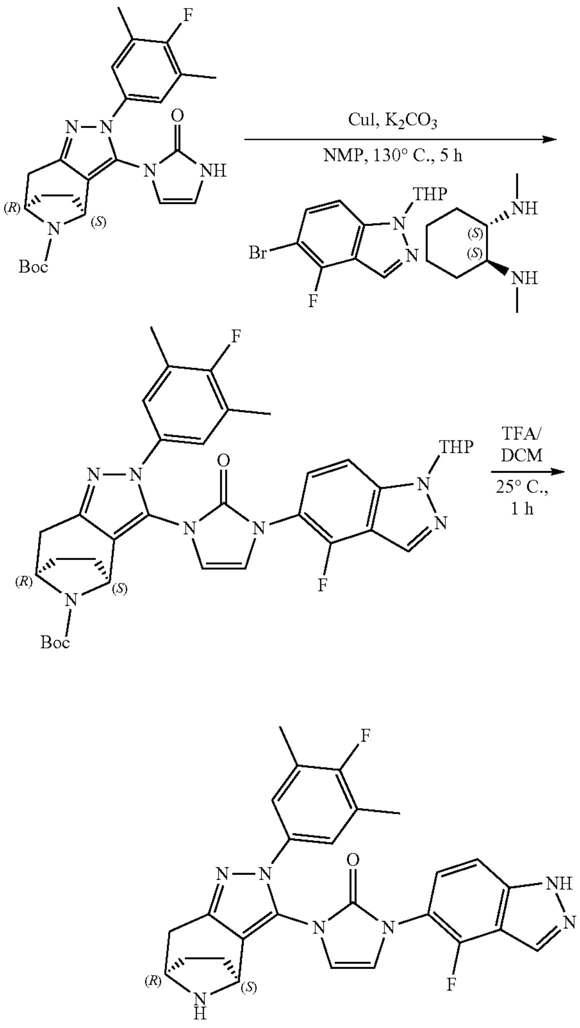

Step 1: tert-butyl (4S,7R)-3-(3-(4-fluoro-1-(tetrahydro-2H-pyran-2-yl)-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

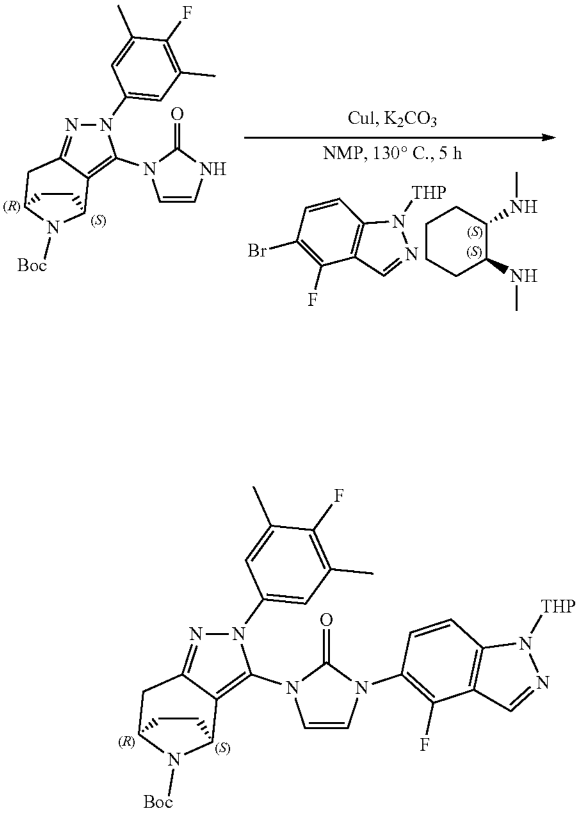

To a solution of tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (200 mg, 441.01 μmol, 1 eq), 5-bromo-4-fluoro-1-(tetrahydro-2H-pyran-2-yl)-1H-indazole (263.84 mg, 882.01 μmol, 2 eq) and (1S,2S)—$N^1$,$N^2$-dimethylcyclohexane-1,2-diamine (188.19 mg, 1.32 mmol, 3 eq) in NMP (2 mL) was added CuI (167.98 mg, 882.01 μmol, 2 eq) and $K_2CO_3$ (121.90 mg, 882.01 μmol, 2 eq) in one portion under $N_2$. The mixture was stirred at 130° C. for 5 hours under $N_2$. LCMS showed the reaction was completed. The reaction mixture was quenched by addition saturated EDTA solution (30 mL) and ethyl acetate (10 mL), stirred for 0.5 hour, extracted with ethyl acetate (20 mL*3). The combined organic layers were washed with saturated brine (50 mL), dried over anhydrous $Na_2SO_4$, filtered and concentrated under reduced pressure to give a residue. The residue was purified by prep-TLC ($SiO_2$, petroleum ether/ethyl acetate=0/1) to afford the title compound tert-butyl (4S,7R)-3-(3-(4-fluoro-1-(tetrahydro-2H-pyran-2-yl)-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200 mg, 285.83 μmol, 64.81% yield). LC-MS (ES+, m/z): 672.4 $[(M+H)^+]$. Rt=2.130 min.

Step 2: 1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

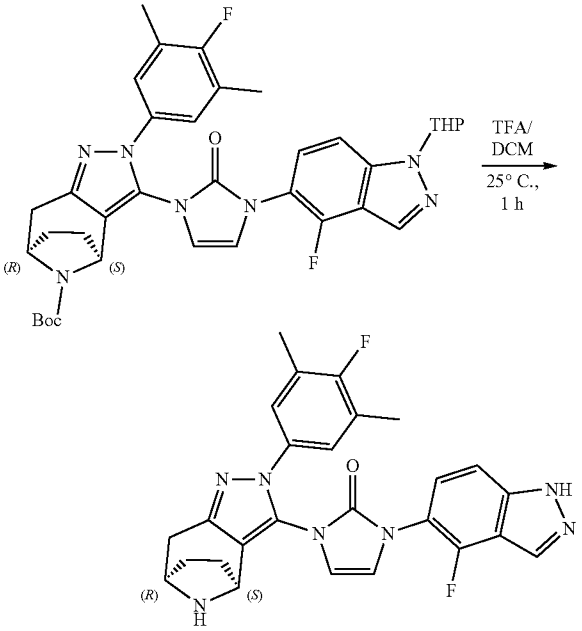

To a solution of tert-butyl (4S,7R)-3-(3-(4-fluoro-1-(tetrahydro-2H-pyran-2-yl)-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200 mg, 285.83 μmol, 1 eq) in DCM (1.6 mL) was added TFA (0.4 mL) in one portion. The mixture was stirred at 25° C. for 1 hour. LCMS showed the reaction was completed. The reaction mixture was quenched by addition saturated $NaHCO_3$ solution (20 mL) at 0° C., extracted with DCM (10 mL*3). The combined organic layers were washed with saturated brine (30 mL), dried over anhydrous $Na_2SO_4$, filtered and concentrated under reduced pressure to give a residue. To afford the title compound 1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (130 mg, 285.83 μmol, 72% yield). LC-MS (ES+, m/z): 488.3 $[(M+H)^+]$. Rt=0.382 min.

Intermediate 436-2

1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid Scheme 436-2

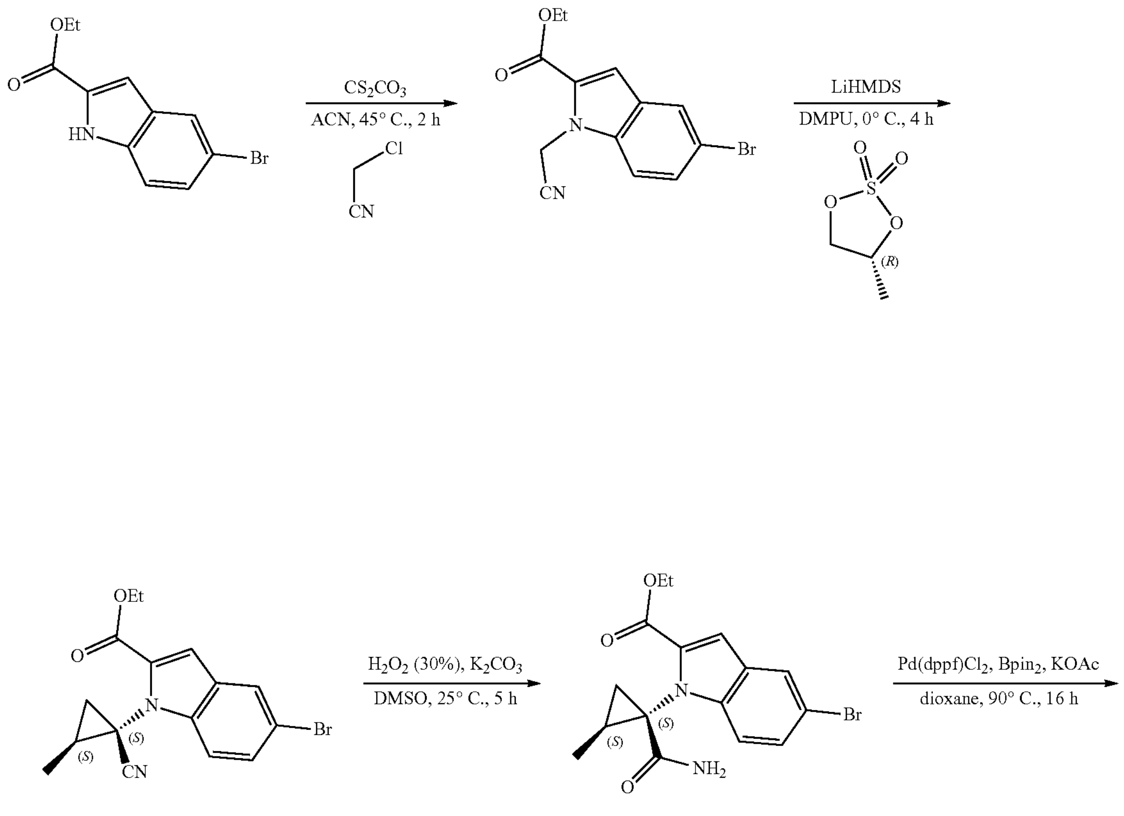

-continued
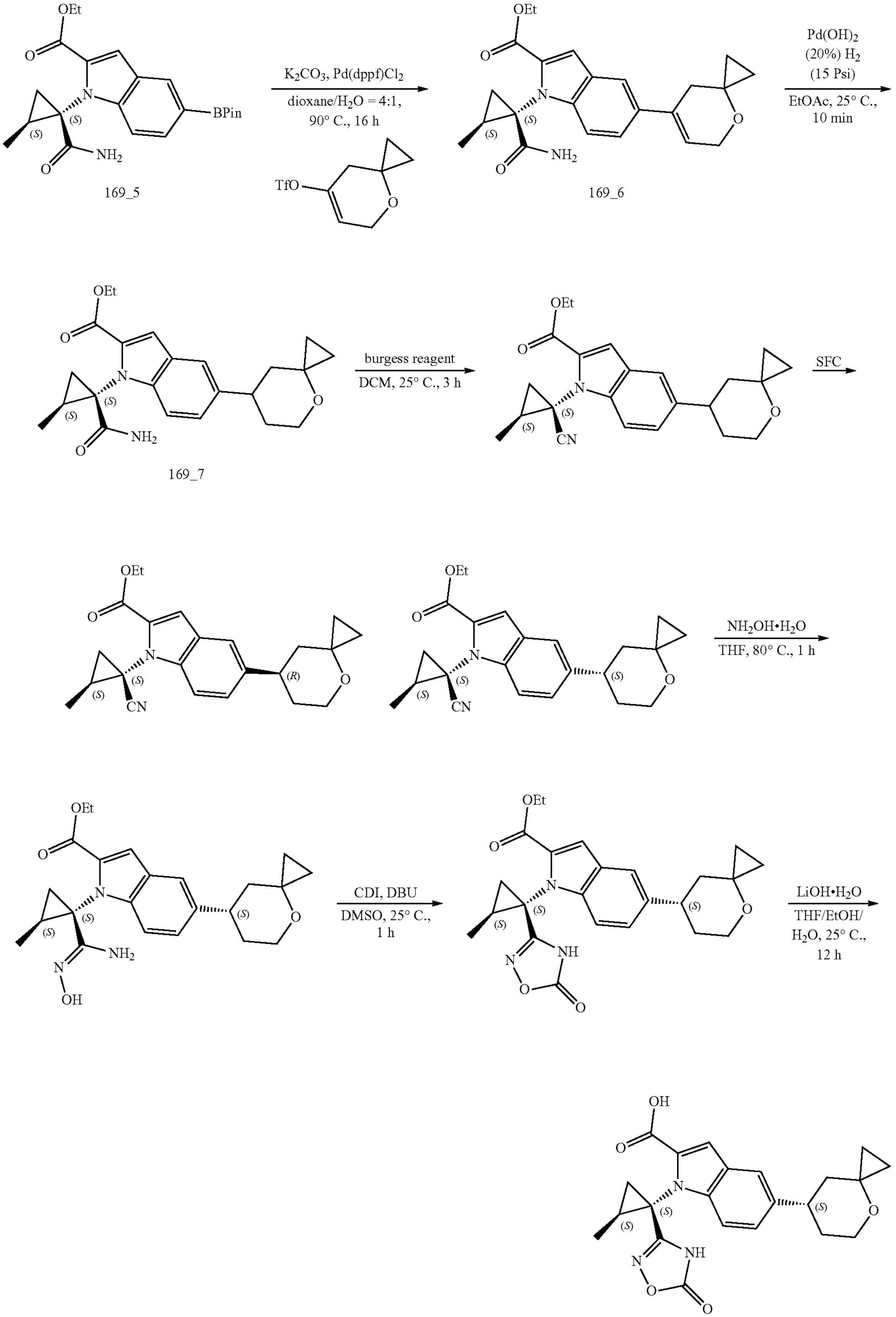
169_5
169_6
169_7

Step 1: ethyl 5-bromo-1-(cyanomethyl)-1H-indole-2-carboxylate

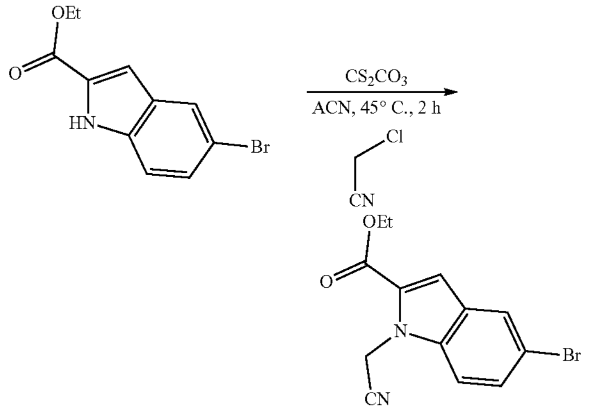

To a solution of ethyl 5-bromo-1H-indole-2-carboxylate (200 g, 745.97 mmol, 1 eq) in ACN (2000 mL) was added $Cs_2CO_3$ (729.16 g, 2.24 mol, 3 eq), then was added 2-chloroacetonitrile (112.64 g, 1.49 mol, 94.42 mL, 2 eq). The mixture was stirred at 45° C. for 2 hours. LCMS showed the reaction was completed. The reaction mixture was poured into water (8000 mL), filtered and concentrated under reduced pressure to give ethyl 5-bromo-1-(cyanomethyl)-1H-indole-2-carboxylate (200 g, 629.68 mmol, 84.41% yield). LC-MS (ES+, m/z): 307.1 [$(M+H)^+$]. Rt=0.565 min.

Step 2: ethyl 5-bromo-1-((1S,2S)-1-cyano-2-methylcyclopropyl)-1H-indole-2-carboxylate

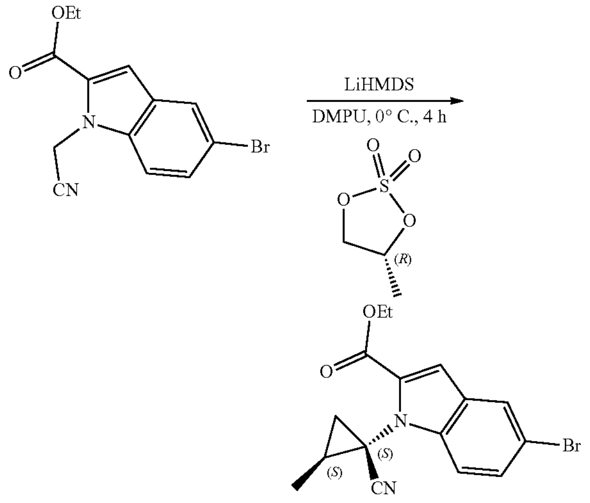

To a solution of ethyl 5-bromo-1-(cyanomethyl) indole-2-carboxylate (40 g, 130.23 mmol, 1 eq) and (4R)-4-methyl-1,3,2-dioxathiolane 2,2-dioxide (35.98 g, 260.47 mmol, 2 eq) in DMPU (400 mL) was added LiHMDS (1 M, 494.88 mL, 3.8 eq) stirred at 0° C. The mixture was stirred at 0° C. for 4 hours (4 parallel reaction). LCMS showed the reaction was completed. The mixture was poured into saturated $NH_4Cl$ (500 mL), then extracted with ethyl acetate (200 mL*3). The combined organic layers were washed with saturated brine (300 mL*3), dried over anhydrous $Na_2SO_4$, filtered and concentrated under reduced pressure. The residue was purified by column chromatography ($SiO_2$, Petroleum ether/ethyl acetate=1:0 to 5:1) to give ethyl 5-bromo-1-((1S,2S)-1-cyano-2-methylcyclopropyl)-1H-indole-2-carboxylate (40 g, 27.04 mmol, 20.77% yield). LC-MS (ES+, m/z): 347.1 [$(M+H)^+$]. Rt=0.630 min.

Step 3: ethyl 5-bromo-1-((1S,2S)-1-carbamoyl-2-methylcyclopropyl)-1H-indole-2-carboxylate

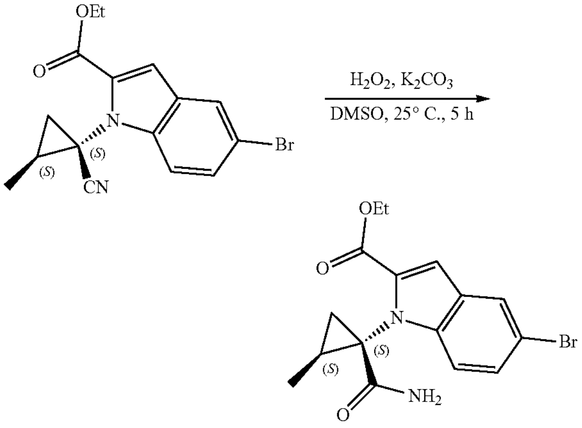

To a solution of ethyl 5-bromo-1-((1S,2S)-1-cyano-2-methylcyclopropyl)-1H-indole-2-carboxylate (11 g, 28.51 mmol, 1 eq) in DMSO (800 mL) was added $K_2CO_3$ (3.94 g, 28.51 mmol, 1 eq) and $H_2O_2$ (29.39 g, 259.21 mmol, 24.91 mL, 30% purity, 9.09 eq) under $N_2$ at 25° C. The mixture was stirred at 25° C. for 5 hours under $N_2$ (3 parallel reactions). LCMS indicated that the reaction was completed. The reaction mixture was quenched by addition $Na_2SO_3$ solution (200 mL) and $H_2O$ (500 mL) at 0° C., extracted with ethyl acetate (300 mL*3). The combined organic layers were washed with saturated brine (100 mL), dried over anhydrous $Na_2SO_4$, filtered and concentrated under reduced pressure. The residue was purified by column chromatography ($SiO_2$, Petroleum ether/ethyl acetate=100/1 to 4/1) to give ethyl 5-bromo-1-((1S,2S)-1-carbamoyl-2-methylcyclopropyl)-1H-indole-2-carboxylate (18 g, 48.78 mmol, 57.04% yield). LC-MS (ES+, m/z): 365.1 [$(M+H)^+$]; Rt=0.525 min.

Step 4: ethyl 1-((1S,2S)-1-carbamoyl-2-methylcyclopropyl)-5-(4,4,5,5-tetramethyl-1,3,2-dioxaborolan-2-yl)-1H-indole-2-carboxylate

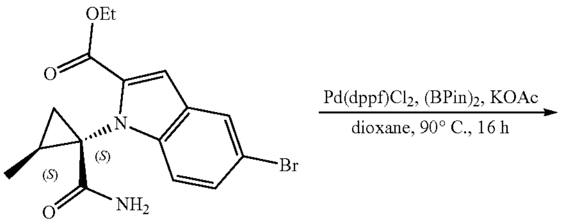

-continued

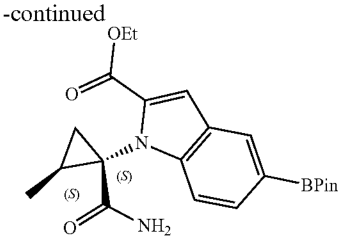

A mixture of ethyl 5-bromo-1-((1S,2S)-1-carbamoyl-2-methylcyclopropyl)-1H-indole-2-carboxylate (18 g, 48.79 mmol, 1 eq), 4,4,5,5-tetramethyl-2-(4,4,5,5-tetramethyl-1,3,2-dioxaborolan-2-yl)-1,3,2-dioxaborolane (24.78 g, 97.58 mmol, 2 eq), $Pd(dppf)Cl_2$ (3.57 g, 4.88 mmol, 0.1 eq), KOAc (14.37 g, 146.38 mmol, 3 eq) in dioxane (180 mL) was stirred at 90° C. for 16 hours under $N_2$ atmosphere. LCMS indicated that the reaction was completed. The reaction mixture was quenched by saturated addition saturated EDTA solution (200 mL) and ethyl acetate (100 mL), stirred for 0.5 hour, extracted with ethyl acetate (100 mL*3). The combined organic layers were washed with saturated brine (100 mL), dried over anhydrous $Na_2SO_4$, filtered and concentrated under reduced pressure. The residue was purified by prep-TLC ($SiO_2$, Petroleum ether/Ethyl acetate=100/1 to 4/1) to afford ethyl 1-((1S,2S)-1-carbamoyl-2-methylcyclopropyl)-5-(4,4,5,5-tetramethyl-1,3,2-dioxaborolan-2-yl)-1H-indole-2-carboxylate (20 g, 41.23 mmol, 84.51% yield). LC-MS (ES+, m/z): 413.3 [(M+H)$^+$]. Rt=0.584 min.

Step 5: ethyl 1-((1S,2S)-1-carbamoyl-2-methylcyclopropyl)-5-(4-oxaspiro[2.5] oct-6-en-7-yl)-1H-indole-2-carboxylate

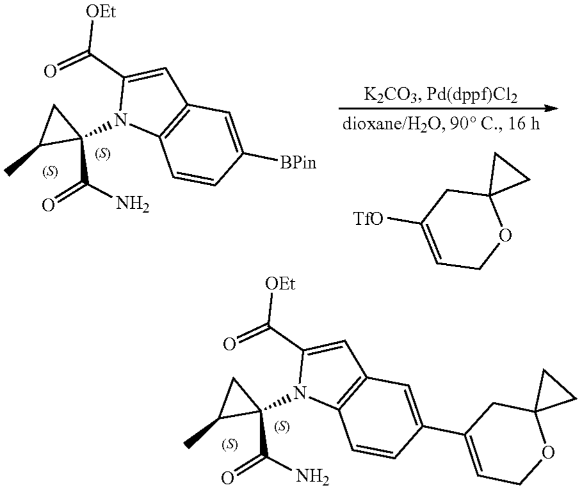

A mixture of ethyl 1-((1S,2S)-1-carbamoyl-2-methylcyclopropyl)-5-(4,4,5,5-tetramethyl-1,3,2-dioxaborolan-2-yl)-1H-indole-2-carboxylate (19.99 g, 41.21 mmol, 0.95 eq), 4-oxaspiro[2.5] oct-6-en-7-yl trifluoromethanesulfonate (14 g, 43.37 mmol, 1 eq), $K_2CO_3$ (17.98 g, 130.12 mmol, 3 eq), $Pd(dppf)Cl_2$ (3.17 g, 4.34 mmol, 0.1 eq) in dioxane (160 mL), $H_2O$ (40 mL) was stirred at 90° C. for 16 hours under $N_2$ atmosphere. LCMS showed the reaction was completed. The reaction mixture was poured into saturated EDTA (200 mL) and ethyl acetate (100 mL) stirred for 1 hour, then extracted with ethyl acetate (100 mL*3). The combined organic layers were washed with saturated brine (100 mL), dried over anhydrous $Na_2SO_4$, filtered and concentrated under reduced pressure. The residue was purified by column chromatography ($SiO_2$, Petroleum ether/ethyl acetate=100/1 to 3/1) to give ethyl 1-((1S,2S)-1-carbamoyl-2-methylcyclopropyl)-5-(4-oxaspiro[2.5] oct-6-en-7-yl)-1H-indole-2-carboxylate (14 g, 24.84 mmol, 57.28% yield). LC-MS (ES+, m/z): 395.3 [(M+H)$^+$]; Rt=1.738 min.

Step 6: ethyl 1-((1S,2S)-1-carbamoyl-2-methylcyclopropyl)-5-(4-oxaspiro[2.5]octan-7-yl)-1H-indole-2-carboxylate

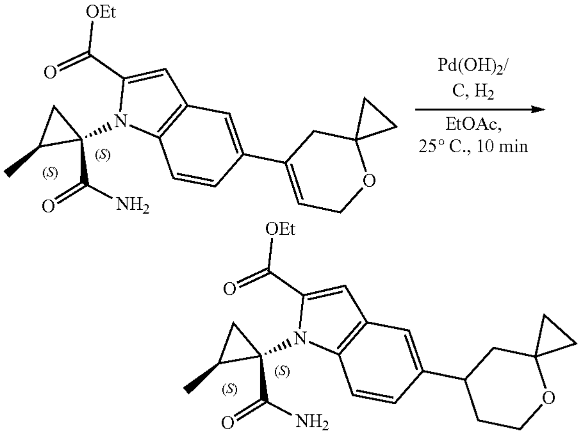

To a solution of $Pd(OH)_2$/C (8.72 g, 12.42 mmol, 20% purity, 0.5 eq) in ethyl acetate (500 mL) was added ethyl 1-((1S,2S)-1-carbamoyl-2-methylcyclopropyl)-5-(4-oxaspiro[2.5] oct-6-en-7-yl)-1H-indole-2-carboxylate (14 g, 24.84 mmol, 1 eq). The mixture was stirred at 25° C. for 10 min under $H_2$ (15 Psi). LCMS showed the reaction was completed. The reaction mixture was filtered and concentrated under reduced pressure. The residue was purified by prep-HPLC (column: Welch Xtimate C18 250*100 mm #10 um; mobile phase: [$H_2O$ (10 mM $NH_4HCO_3$)-ACN]; gradient: 40%-70% B over 18.0 min to give ethyl 1-((1S,2S)-1-carbamoyl-2-methylcyclopropyl)-5-(4-oxaspiro[2.5]octan-7-yl)-1H-indole-2-carboxylate (5 g, 12.23 mmol, 49.24% yield). LC-MS (ES+, m/z): 397.3 [(M+H)$^+$]; Rt=0.545 min.

Step 7: ethyl 1-((1S,2S)-1-cyano-2-methylcyclopropyl)-5-(4-oxaspiro[2.5]octan-7-yl)-1H-indole-2-carboxylate

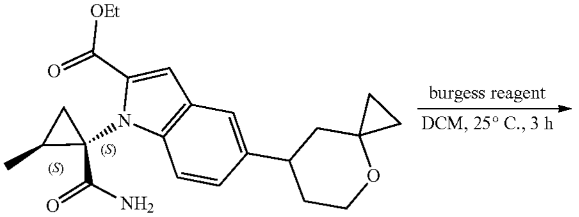

-continued

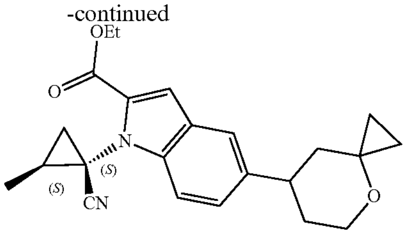

To a solution of ethyl 1-((1S,2S)-1-carbamoyl-2-methylcyclopropyl)-5-(4-oxaspiro[2.5]octan-7-yl)-1H-indole-2-carboxylate (5 g, 12.23 mmol, 1 eq) in DCM (32 mL) was added methoxycarbonyl-(triethylammonio) sulfonyl-azanide (8.75 g, 36.70 mmol, 3 eq). The mixture was stirred at 25° C. for 3 hrs. LCMS showed the reaction was completed. The reaction mixture was poured into water (200 mL), then extracted with ethyl acetate (100 mL*3). The combined organic layers were washed with saturated brine (50 mL), dried over anhydrous $Na_2SO_4$, filtered and concentrated under reduced pressure. The residue was purified by column chromatography ($SiO_2$, Petroleum ether/ethyl acetate=100/1 to 2/1) to give ethyl 1-((1S,2S)-1-cyano-2-methylcyclopropyl)-5-(4-oxaspiro[2.5]octan-7-yl)-1H-indole-2-carboxylate (4.1 g, 10.83 mmol, 88.56% yield). LC-MS (ES+, m/z): 379.2 [$(M+H)^+$]; Rt=0.620 min.

Step 8: ethyl 1-((1S,2S)-1-cyano-2-methylcyclopropyl)-5-((R)-4-oxaspiro[2.5]octan-7-yl)-1H-indole-2-carboxylate & ethyl 1-((1S,2S)-1-cyano-2-methylcyclopropyl)-5-((S)-4-oxaspiro[2.5]octan-7-yl)-1H-indole-2-carboxylate

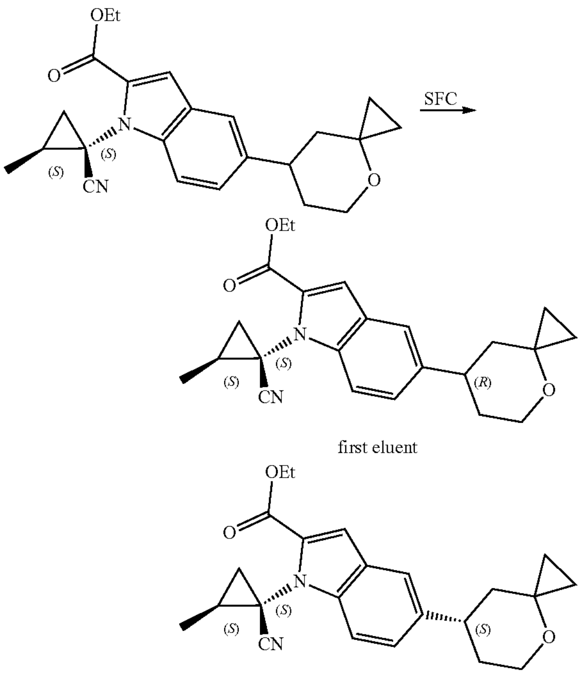

The compound (4 g) was separated by SFC (column: DAICEL CHIRALPAK AD (250 mm*50 mm, 10 um); mobile phase: [$CO_2$-MeOH (0.1% $NH_3H_2O$)]; B %: 45%, isocratic elution mode). To give ethyl 1-((1S,2S)-1-cyano-2-methylcyclopropyl)-5-((R)-4-oxaspiro[2.5]octan-7-yl)-1H-indole-2-carboxylate (1st eluent, de=93.8% de, 1.9 g, 5.02 mmol, 50.00% yield). LC-MS (ES+, m/z): 379.3 [$(M+H)^+$]; Rt=0.617 min.

And ethyl 1-((1S,2S)-1-cyano-2-methylcyclopropyl)-5-((S)-4-oxaspiro[2.5]octan-7-yl)-1H-indole-2-carboxylate ($2^{nd}$ eluent, de=98.3%, 1.8 g, 4.76 mmol, 47.37% yield). LC-MS (ES+, m/z): 379.3 [$(M+H)^+$]; Rt=0.608 min.

Step 9: ethyl 1-((1S,2S)-1-(N'-hydroxycarbamimidoyl)-2-methylcyclopropyl)-5-((S)-4-oxaspiro[2.5]octan-7-yl)-1H-indole-2-carboxylate

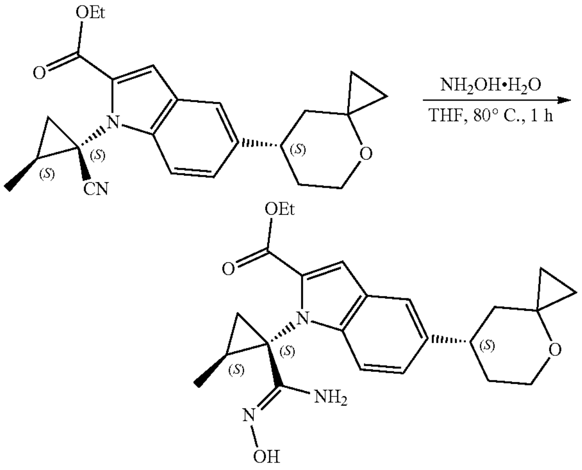

A mixture of ethyl 1-((1S,2S)-1-cyano-2-methylcyclopropyl)-5-((S)-4-oxaspiro[2.5]octan-7-yl)-1H-indole-2-carboxylate (1.8 g, 4.76 mmol, 1 eq), hydroxylamine (3.14 g, 47.56 mmol, 50% purity, 10 eq) in THF (18 mL) was stirred at 80° C. for 1 hour under $N_2$ atmosphere. LCMS indicated the reaction was completed. The reaction mixture was quenched by addition $H_2O$ (100 mL), extracted with ethyl acetate (100 mL*3). The combined organic layers were washed with saturated brine (100 mL), dried over anhydrous $Na_2SO_4$, filtered and concentrated under reduced pressure to give ethyl 1-((1S,2S)-1-(N'-hydroxycarbamimidoyl)-2-methylcyclopropyl)-5-((S)-4-oxaspiro[2.5]octan-7-yl)-1H-indole-2-carboxylate (1.8 g, 3.54 mmol, 74.50% yield). LC-MS (ES+, m/z): 412.2 [$(M+H)^+$]; Rt=0.445 min.

Step 10: ethyl 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate

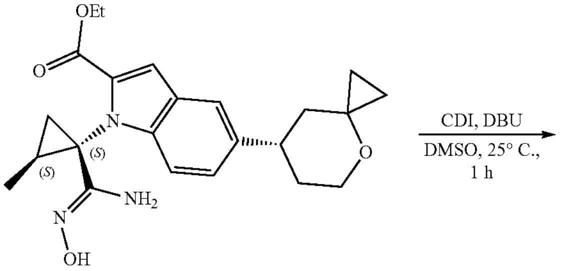

-continued

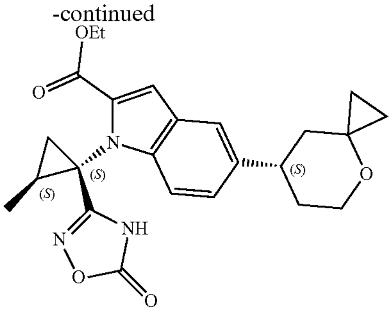

-continued

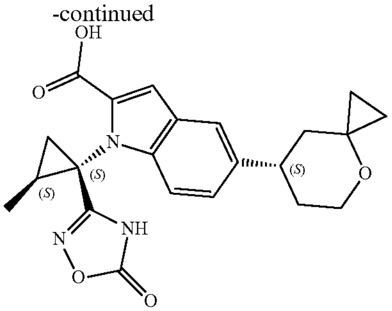

A mixture of ethyl 1-((1S,2S)-1-(N'-hydroxycarbamimidoyl)-2-methylcyclopropyl)-5-((S)-4-oxaspiro[2.5]octan-7-yl)-1H-indole-2-carboxylate (1.8 g, 3.54 mmol, 1 eq), CDI (1.15 g, 7.09 mmol, 2 eq), DBU (1.35 g, 8.86 mmol, 1.34 mL, 2.5 eq) in DMSO (18 mL) was stirred at 25° C. for 1 hour under $N_2$ atmosphere. LCMS indicated the reaction was completed. The reaction mixture was quenched by addition $H_2O$ (50 mL), extracted with ethyl acetate (50 mL*3). The combined organic layers were washed with saturated brine (50 mL), dried over anhydrous $Na_2SO_4$, filtered and concentrated under reduced pressure. The residue was purified by column chromatography ($SiO_2$, Petroleum ether/ethyl acetate=100/1 to 2/1) to give ethyl 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate (1.5 g, 3.39 mmol, 95.61% yield). LC-MS (ES+, m/z): 438.2 [(M+H)$^+$]; Rt=0.571 min.

Step 11: 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid

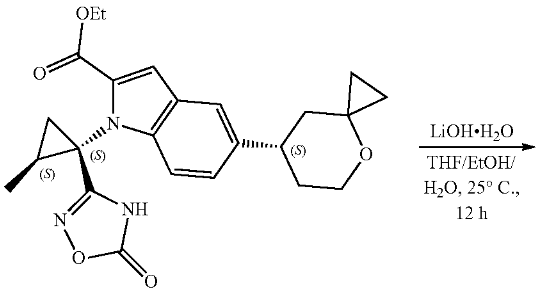

A mixture of ethyl 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate (1.5 g, 3.39 mmol, 1 eq), LiOH·$H_2O$ (1.42 g, 33.88 mmol, 15 eq) in THF (8 mL), $H_2O$ (8 mL), EtOH (8 mL) was stirred at 25° C. for 12 hours. LCMS indicated the reaction was completed. The reaction mixture was quenched by addition $H_2O$ (100 mL) and adjust to pH=4 by addition HCl (2 M, 10 mL), extracted with ethyl acetate (150 mL*3). The combined organic layers were washed with saturated brine (50 mL), dried over anhydrous $Na_2SO_4$, filtered and concentrated under reduced pressure to give 1-((1S,2S)-2-methyl-1-(5-oxo-4,5-dihydro-1,2,4-oxadiazol-3-yl) cyclopropyl)-5-((S)-4-oxaspiro[2.5]octan-7-yl)-1H-indole-2-carboxylic acid (1.2 g, 2.87 mmol, 84.79% yield). LC-MS (ES+, m/z): 410.2 [(M+H)$^+$]; Rt=0.511 min.

Intermediate 411-1

Ethyl 1-((1S,2S)-1-cyano-2-methylcyclopropyl)-5-((S)-4-oxaspiro[2.5]octan-7-yl)-1H-indole-2-carboxylate and Intermediate 414-1

Ethyl 1-((1S,2S)-1-cyano-2-methylcyclopropyl)-5-((R)-4-oxaspiro[2.5]octan-7-yl)-1H-indole-2-carboxylate Scheme 411-1/414-1

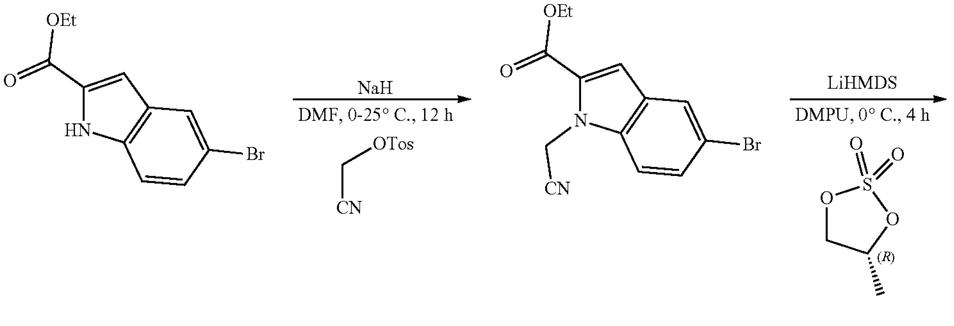

-continued
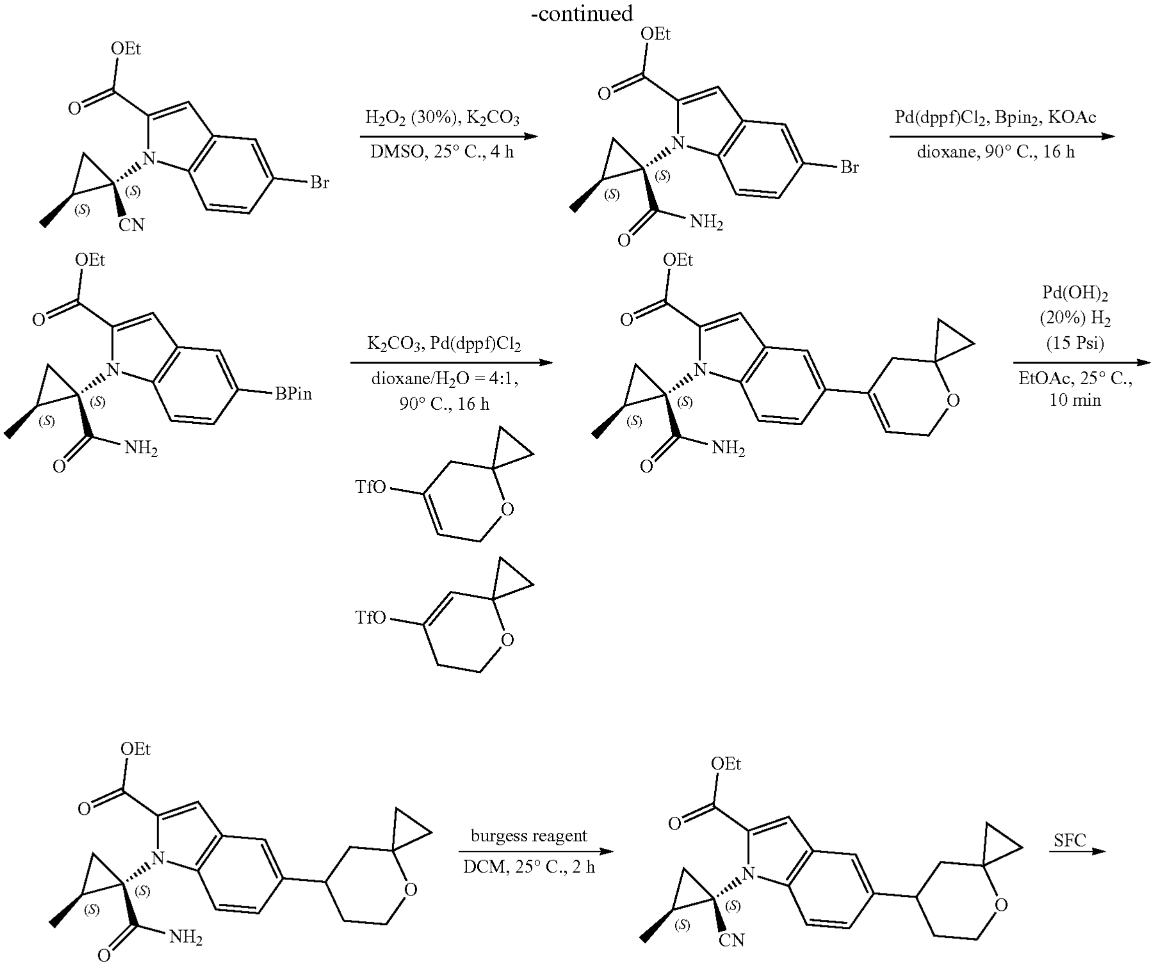
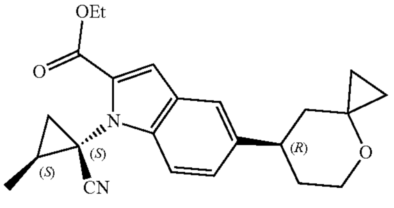
1st eluent
Intermediate 414-1
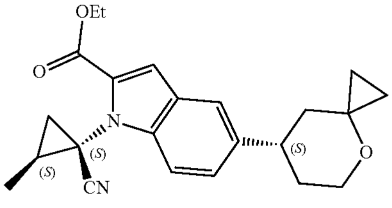
2nd eluent
Intermediate 411-1
Step 1: ethyl 5-bromo-1-(cyanomethyl)-1H-indole-2-carboxylate
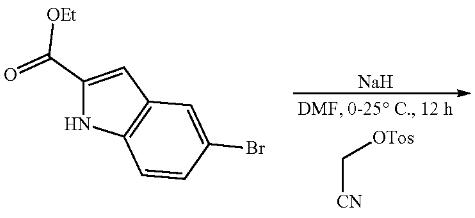
-continued
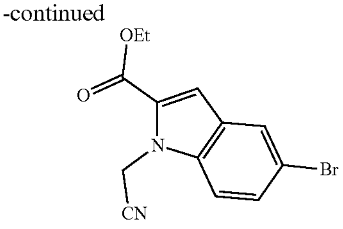
To a solution of ethyl 5-bromo-1H-indole-2-carboxylate (50 g, 186.49 mmol, 1 eq) in DMF (500 mL) was added NaH (14.92 g, 372.99 mmol, 60% purity, 2 eq) at 0° C. under $N_2$. The mixture was stirred at 0° C. for 0.5 hour. Cyanomethyl 4-methylbenzenesulfonate (78.79 g, 372.99 mmol, 2 eq) was added under $N_2$ at 0° C. The mixture was stirred at 25° C. for 11.5 hours under $N_2$ (4 parallel reactions). LCMS indicated that the reaction was completed. The reaction mixture was poured into saturated $NH_4Cl$ (500 mL), then extracted with ethyl acetate (300 mL*3). The combined organic layers were washed with saturated brine (500 mL*3), dried over anhydrous $Na_2SO_4$, filtered and concentrated under reduced pressure. The residue was purified by column chromatography ($SiO_2$, Petroleum ether/ethyl acetate=10/1 to 2/1) to give ethyl 5-bromo-1-(cyanomethyl)-1H-indole-2-carboxylate (45 g, 139.19 mmol, 74% yield). $^1$H NMR (400 MHz, DMSO-$d_6$) δ=8.05-7.93 (m, 1H), 7.84-7.75 (m, 1H), 7.66-7.54 (m, 1H), 7.37 (s, 1H), 5.85-5.73 (m, 2H), 4.45-4.31 (m, 2H), 1.43-1.29 (m, 3H); LC-MS (ES+, m/z): 307.1 [(M+H)$^+$]. Rt=0.583 min.

Step 2: ethyl 5-bromo-1-((1S,2S)-1-cyano-2-methylcyclopropyl)-1H-indole-2-carboxylate

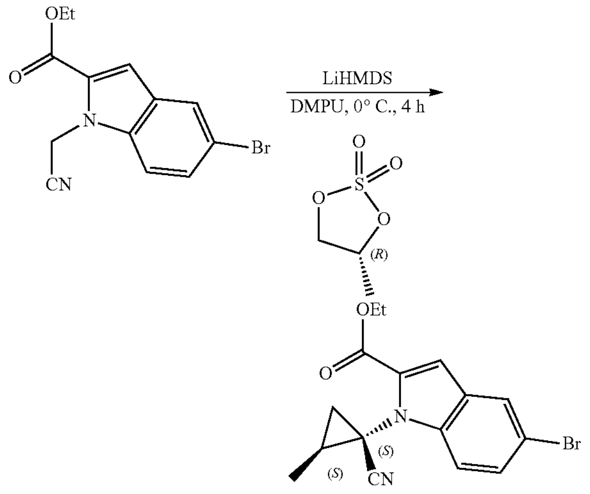

To a solution of ethyl 5-bromo-1-(cyanomethyl)-1H-indole-2-carboxylate (40 g, 130.23 mmol, 1 eq), (4R)-4-methyl-1,3,2-dioxathiolane 2,2-dioxide (35.98 g, 260.47 mmol, 2 eq) in 1,3-dimethylhexahydropyrimidin-2-one (400 mL) was added LiHMDS (1 M, 520.93 mL, 4 eq) under $N_2$ at 0° C. The mixture was stirred at 0° C. for 4 hours (4 parallel reactions). LCMS indicated that the reaction was completed. The reaction mixture was quenched by addition $NH_4Cl$ (1000 mL) at 0° C. and then extracted with ethyl acetate (800 mL*3). The combined organic layers were washed with saturated brine (500 mL*5), dried over $Na_2SO_4$, filtered and concentrated under reduced pressure. The residue was purified by prep-HPLC (column: Phenomenex luna C18 250*150 mm*15 um; mobile phase: [$H_2O$ (0.1% TFA)-ACN]; gradient: 55%-75% B over 30.0 min) to give ethyl 5-bromo-1-((1S,2S)-1-cyano-2-methylcyclopropyl)-1H-indole-2-carboxylate (10.17 g, 29.29 mmol, 22.49% yield). LC-MS (ES+, m/z): 347.0 [(M+H)$^+$]. Rt=2.050 min.

Step 3: ethyl 5-bromo-1-((1S,2S)-1-carbamoyl-2-methylcyclopropyl)-1H-indole-2-carboxylate

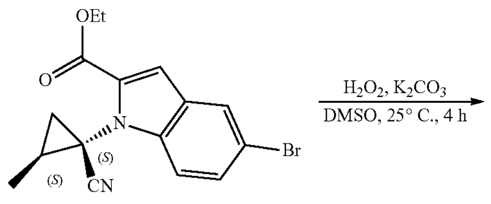

-continued

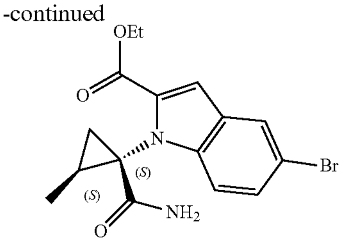

To a solution of ethyl 5-bromo-1-((1S,2S)-1-cyano-2-methylcyclopropyl)-1H-indole-2-carboxylate (40 g, 115.20 mmol, 1 eq) in DMSO (800 mL) was added $K_2CO_3$ (15.92 g, 115.20 mmol, 1 eq) and $H_2O_2$ (130.80 g, 1.15 mol, 110.88 mL, 30% purity, 10.01 eq) under $N_2$ at 25° C. The mixture was stirred at 25° C. for 4 hours under $N_2$. LCMS indicated that the reaction was completed. The reaction mixture was quenched by addition $H_2O$ (2400 mL) and extracted with ethyl acetate (1600 mL*3). The combined organic layers were washed with saturated Na$_2$S203 (1600 mL*3), dried over anhydrous $Na_2SO_4$, filtered and concentrated under reduced. The residue was purified by column chromatography ($SiO_2$, Petroleum ether/ethyl acetate=20/1 to 5/1) to give ethyl 5-bromo-1-((1S,2S)-1-carbamoyl-2-methylcyclopropyl)-1H-indole-2-carboxylate (19.6 g, 48.32 mmol, 46.58% yield). LC-MS (ES+, m/z): 365.1 [(M+H)$^+$]. Rt=0.554 min.

Step 4: ethyl 1-((1S,2S)-1-carbamoyl-2-methylcyclopropyl)-5-(4,4,5,5-tetramethyl-1,3,2-dioxaborolan-2-yl)-1H-indole-2-carboxylate

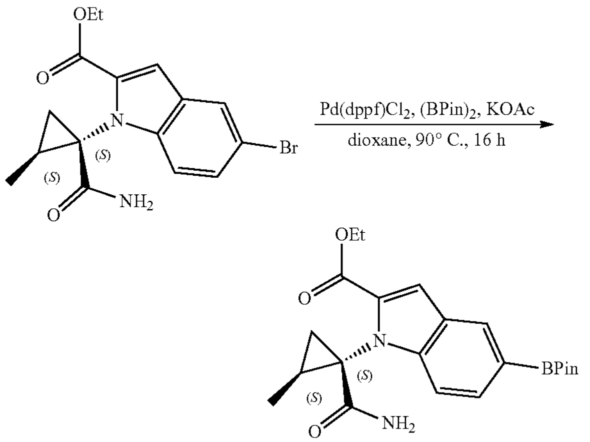

A mixture of ethyl ethyl 5-bromo-1-((1S,2S)-1-carbamoyl-2-methylcyclopropyl)-1H-indole-2-carboxylate (19.6 g, 48.32 mmol, 1 eq), 4,4,5,5-tetramethyl-2-(4,4,5,5-tetramethyl-1,3,2-dioxaborolan-2-yl)-1,3,2-dioxaborolane (24.52 g, 96.58 mmol, 2 eq), Pd(dppf)Cl$_2$ (3.53 g, 4.83 mmol, 0.1 eq), KOAc (14.21 g, 144.87 mmol, 3 eq) in dioxane (340 mL) was degassed and purged with $N_2$ for 3 times, and then the mixture was stirred at 90° C. for 16 hours under $N_2$ atmosphere. LCMS indicated that the reaction was completed. The reaction mixture was quenched by saturated addition saturated EDTA solution (600 mL) and ethyl acetate (800 mL), stirred for 0.5 hour, extracted with ethyl acetate (600 mL*3). The combined organic layers were washed with saturated brine (600 mL), dried over anhydrous $Na_2SO_4$, filtered and concentrated under reduced pressure. The residue was purified by prep-TLC ($SiO_2$, PE:EA=1/0 to 3/1) to ethyl 1-((1S,2S)-1-carbamoyl-2-methylcyclopropyl)-5-(4,4,5,5-tetramethyl-1,3,2-dioxaborolan-2-yl)-1H-indole-2-carboxylate (22 g, 47.33 mmol, 88.70% yield). LC-MS (ES+, m/z): 413.3 [$(M+H)^+$]. Rt=1.880 min.

Step 5: ethyl 1-((1S,2S)-1-carbamoyl-2-methylcyclopropyl)-5-(4-oxaspiro[2.5] oct-6-en-7-yl)-1H-indole-2-carboxylate

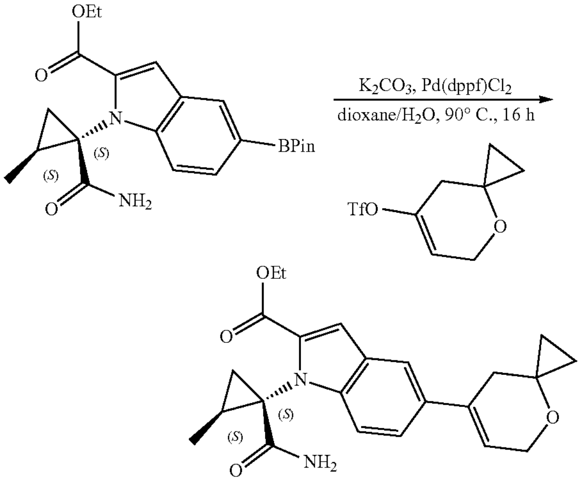

A mixture of ethyl 1-((1S,2S)-1-carbamoyl-2-methylcyclopropyl)-5-(4,4,5,5-tetramethyl-1,3,2-dioxaborolan-2-yl)-1H-indole-2-carboxylate (19.16 g, 46.47 mmol, 1.2 eq), 4-oxaspiro[2.5] oct-6-en-7-yl trifluoromethanesulfonate (10 g, 38.73 mmol, 1 eq), $K_2CO_3$ (16.06 g, 116.18 mmol, 3 eq), $Pd(dppf)Cl_2$ (2.83 g, 3.87 mmol, 0.1 eq) in dioxane (100 mL), $H_2O$ (25 mL) was stirred at 90° C. for 16 hours under $N_2$ atmosphere. LCMS showed the reaction was completed. The reaction mixture was poured into saturated EDTA (200 mL) and Ethyl acetate (100 mL) stirred for 1 hour, then extracted with ethyl acetate (100 mL*3). The combined organic layers were washed with saturated brine (100 mL), dried over anhydrous $Na_2SO_4$, filtered and concentrated under reduced pressure. The residue was purified by column chromatography ($SiO_2$, Petroleum ether/Ethyl acetate=100/1 to 3/1) to give ethyl 1-((1S,2S)-1-carbamoyl-2-methylcyclopropyl)-5-(4-oxaspiro[2.5] oct-6-en-7-yl)-1H-indole-2-carboxylate (14 g, 24.84 mmol, 64.15% yield). LC-MS (ES+, m/z): 395.2 [$(M+H)^+$]; Rt=1.764 min.

Step 6: ethyl 1-((1S,2S)-1-carbamoyl-2-methylcyclopropyl)-5-(4-oxaspiro[2.5]octan-7-yl)-1H-indole-2-carboxylate

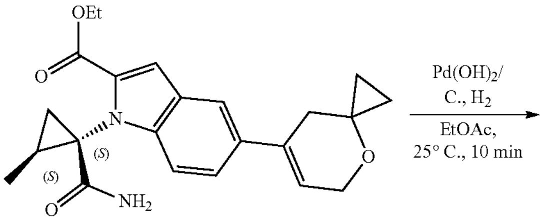

-continued

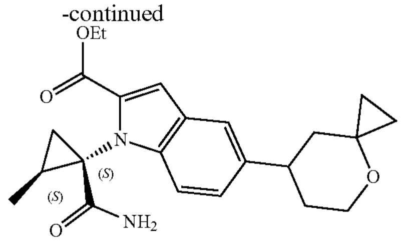

To a solution of $Pd(OH)_2/C$ (13.96 g, 19.88 mmol, 20% purity, 0.8 eq) in ethyl acetate (400 mL) was added ethyl 1-((1S,2S)-1-carbamoyl-2-methylcyclopropyl)-5-(4-oxaspiro[2.5] oct-6-en-7-yl)-1H-indole-2-carboxylate (14 g, 24.84 mmol, 1 eq). The mixture was stirred at 25° C. for 10 minutes under $H_2$ (15 Psi). LCMS showed the reaction was completed. The reaction mixture was filtered and concentrated under reduced pressure. The residue was purified by prep-HPLC (column: Welch Xtimate C18 250*100 mm #10 um; mobile phase: [$H_2O$ (10 mM $NH_4HCO_3$)-ACN]; gradient: 35%-70% B over 20.0 min) to give ethyl 1-((1S,2S)-1-carbamoyl-2-methylcyclopropyl)-5-(4-oxaspiro[2.5]octan-7-yl)-1H-indole-2-carboxylate (5.5 g, 13.32 mmol, 53.60% yield) as a white solid. LC-MS (ES+, m/z): 397.25 [$(M+H)^+$]; Rt=1.765 min.

Step 7: ethyl 1-((1S,2S)-1-cyano-2-methylcyclopropyl)-5-(4-oxaspiro[2.5]octan-7-yl)-1H-indole-2-carboxylate

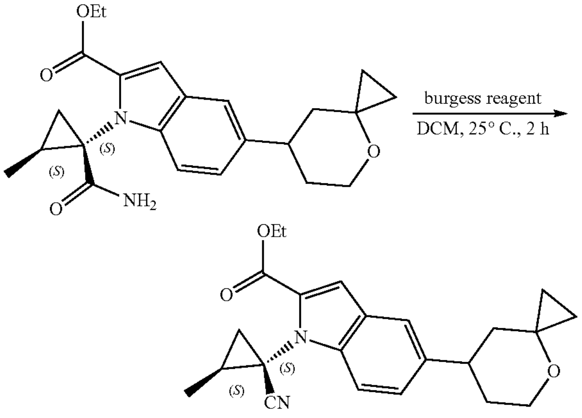

To a solution of ethyl 1-((1S,2S)-1-carbamoyl-2-methylcyclopropyl)-5-(4-oxaspiro[2.5]octan-7-yl)-1H-indole-2-carboxylate (5.5 g, 13.32 mmol, 1 eq) in DCM (32 mL) was added methoxycarbonyl-(triethylammonio) sulfonyl-azanide (9.52 g, 39.95 mmol, 5 eq). The mixture was stirred at 25° C. for 2 hours. LCMS showed the reaction was completed. The reaction mixture was poured into water (200 mL), then extracted with ethyl acetate (100 mL*3). The combined organic layers were washed with saturated brine (50 mL), dried over anhydrous $Na_2SO_4$, filtered and concentrated under reduced pressure. The residue was purified by column chromatography ($SiO_2$, Petroleum ether/ethyl acetate=100/1 to 2/1) to give ethyl 1-((1S,2S)-1-cyano-2-methylcyclopropyl)-5-(4-oxaspiro[2.5]octan-7-yl)-1H-indole-2-carboxylate (4 g, 10.04 mmol, 75.40% yield). LC-MS (ES+, m/z): 379.3 [$(M+H)^+$]; Rt=0.610 min.

Step 8: ethyl 1-((1S,2S)-1-cyano-2-methylcyclopropyl)-5-((R)-4-oxaspiro[2.5]octan-7-yl)-1H-indole-2-carboxylate & ethyl 1-((1S,2S)-1-cyano-2-methylcyclopropyl)-5-((S)-4-oxaspiro[2.5]octan-7-yl)-1H-indole-2-carboxylate

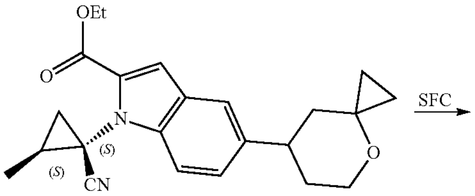

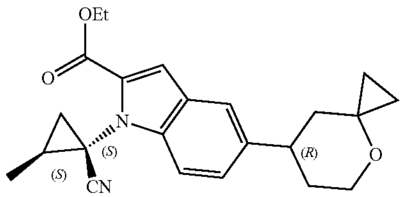

1st eluent
Intermediate 414-1

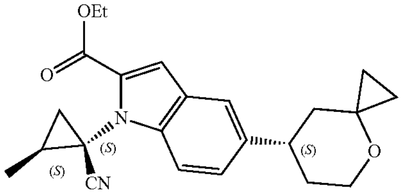

2nd eluent
Intermediate 411-1

Ethyl 1-((1S,2S)-1-cyano-2-methylcyclopropyl)-5-(4-oxaspiro[2.5]octan-7-yl)-1H-indole-2-carboxylate (4 g, 10.04 mmol) was separated by SFC (column: DAICEL CHIRALPAK AD (250 mm*50 mm, 10 um); mobile phase: [$CO_2$-MeOH (0.1% $NH_3H_2O$)]; B %: 45%, isocratic elution mode) to give ethyl 1-((1S,2S)-1-cyano-2-methylcyclopropyl)-5-((R)-4-oxaspiro[2.5]octan-7-yl)-1H-indole-2-carboxylate (1st eluent, RT=1.497 min by SFC, 1.9 g, 5.02 mmol, 50.00% yield). LC-MS (ES+, m/z): 379.3 [$(M+H)^+$]; Rt=0.617 min.

And ethyl 1-((1S,2S)-1-cyano-2-methylcyclopropyl)-5-((S)-4-oxaspiro[2.5]octan-7-yl)-1H-indole-2-carboxylate ($2^{nd}$ eluent, RT=1.865 min by SFC, 1.8 g, 4.76 mmol, 47.37% yield, desired isomer). LC-MS (ES+, m/z): 379.3 [$(M+H)^+$]; Rt=0.608 min.

Intermediate 503-1

5-(2, 2-dimethyltetrahydro-2H-pyran-4-yl)-1-(phenylsulfonyl)-1H-indole-2-sulfonyl chloride Scheme 503-1

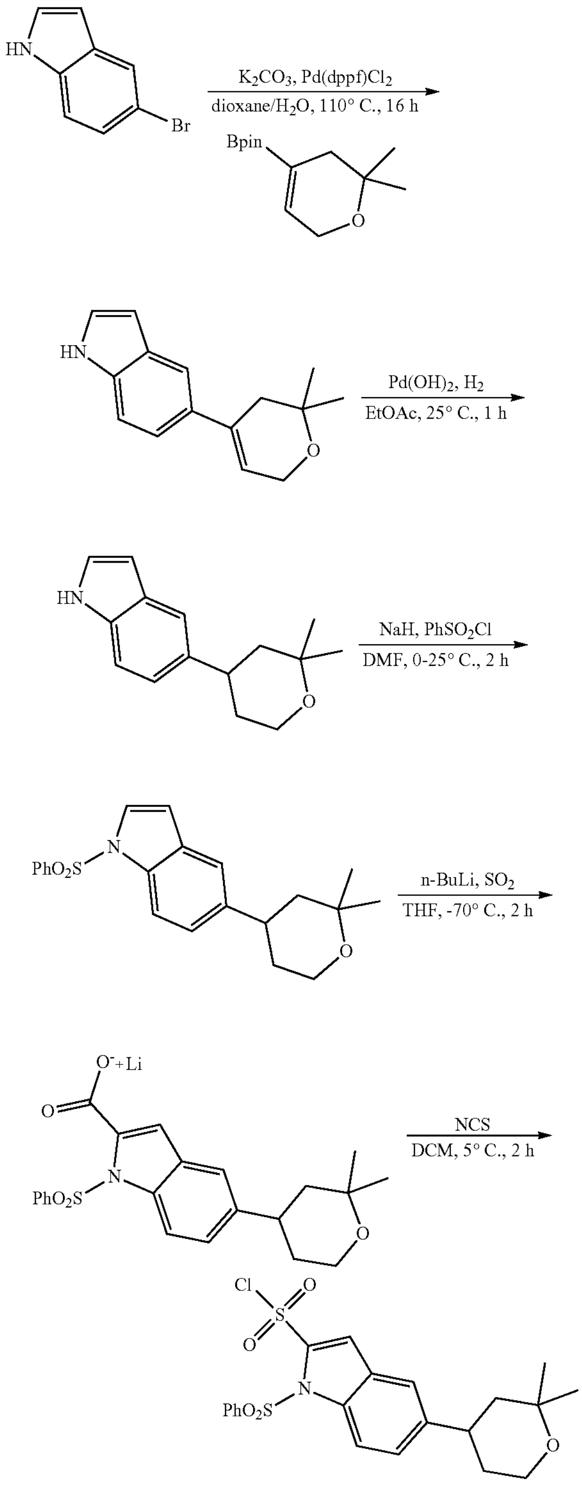

Step 1: 5-(2, 2-dimethyl-3, 6-dihydro-2H-pyran-4-yl)-1H-indole

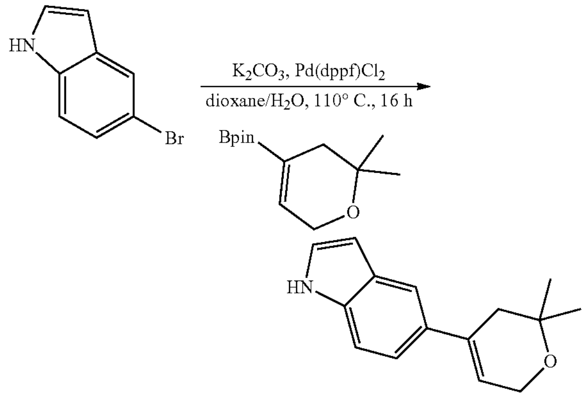

To a solution of 5-bromo-1H-indole (10 g, 51.01 mmol, 1 eq), 2-(2, 2-dimethyl-3, 6-dihydro-2H-pyran-4-yl)-4, 4, 5, 5-tetramethyl-1, 3, 2-dioxaborolane (14.58 g, 61.21 mmol, 1.2 eq) and $K_2CO_3$ (21.15 g, 153.03 mmol, 3 eq) in dioxane (80 mL) and $H_2O$ (20 mL) was added Pd(dppf)$Cl_2$ (3.73 g, 5.10 mmol, 0.1 eq). The mixture was stirred at 110° C. for 16 hours under $N_2$. LCMS showed the reaction was completed. The residue was poured into saturated EDTA solution (200 mL) and ethyl acetate (200 mL), stirred for 0.5 hour, and then extracted with ethyl acetate (200 mL*2). The organic layers were combined, washed with water (500 mL), saturated brine (500 mL), dried over $Na_2SO_4$, filtered and concentrated in vacuo. The residue was purified by column chromatography ($SiO_2$, hexanes/Ethyl acetate=50/1 to 10/1) to give 5-(2, 2-dimethyl-3, 6-dihydro-2H-pyran-4-yl)-1H-indole (6.5 g, 24.62 mmol, 48.27% yield). LC-MS (ES+, m/z): 228.1 [(M+H)$^+$]; Rt=0.510 min.

The reaction was repeated using 5-bromo-1H-indole (20 g, 102.02 mmol) to give 5-(2, 2-dimethyl-3, 6-dihydro-2H-pyran-4-yl)-1H-indole (12.5 g, 47.35 mmol, 46.41% yield).

Step 2: 5-(2,2-dimethyltetrahydro-2H-pyran-4-yl)-1H-indole

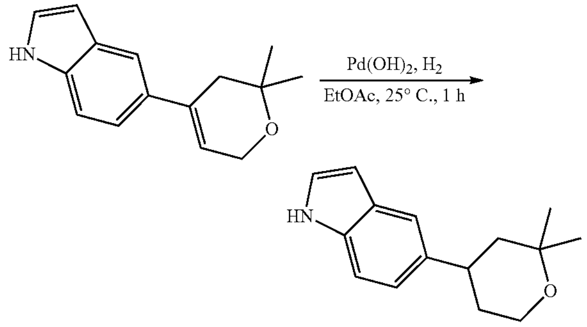

To a solution of Pd$(OH)_2$ (17.00 g, 24.21 mmol, 20% purity, 3.24e-1 eq) in EtOAc (1700 mL) was added 5-(2,2-dimethyl-3, 6-dihydro-2H-pyran-4-yl)-1H-indole (17 g, 74.79 mmol, 1 eq). The mixture was stirred at 25° C. for 1 hour under 15 Psi of $H_2$. LCMS showed the reaction was completed. The reaction mixture was filtered and concentrated in vacuo to give 5-(2, 2-dimethyltetrahydro-2H-pyran-4-yl)-1H-indole (14.5 g, crude). LC-MS (ES+, m/z): 230.2 [(M+H)$^+$]; Rt=0.524 min.

Step 3: 5-(2, 2-dimethyltetrahydro-2H-pyran-4-yl)-1-(phenylsulfonyl)-1H-indole

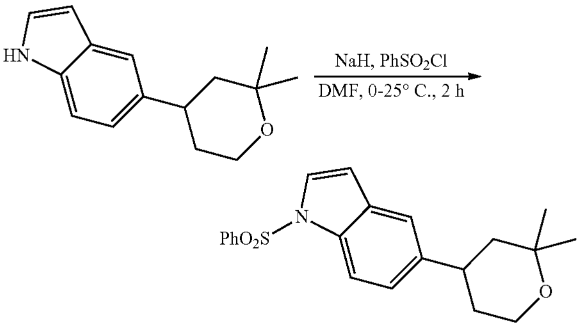

To a solution of 5-(2, 2-dimethyltetrahydro-2H-pyran-4-yl)-1H-indole (14.5 g, 63.23 mmol, 1 eq) in DMF (145 mL) was added NaH (5.06 g, 126.46 mmol, 60% purity, 2 eq) at 0° C. under $N_2$. The mixture was stirred at 0° C. for 1 hour. $PhSO_2Cl$ (22.34 g, 126.46 mmol, 16.14 mL, 2 eq) was then added. The mixture was stirred at 25° C. for 1 hour under $N_2$. LCMS showed the reaction was completed. The mixture was added dropwise to $NH_4Cl$ (150 mL), and then extracted with DCM (150 mL*3). The organic layers were combined, washed with water (300 mL), saturated brine (300 mL), dried over $Na_2SO_4$, filtered and concentrated in vacuo. The crude product was purified by chromatography on silica gel (hexanes: Ethyl acetate-20/1-7/1) to give 5-(2, 2-dimethyl-tetrahydro-2H-pyran-4-yl)-1-(phenylsulfonyl)-1H-indole (13 g, 31.53 mmol, 49.86% yield). LC-MS (ES+, m/z): 370.2 [(M+H)$^+$]; Rt=0.630 min.

Step 4: 5-(2, 2-dimethyltetrahydro-2H-pyran-4-yl)-1-(phenylsulfonyl)-1H-indole-2-sulfinate lithium (I)

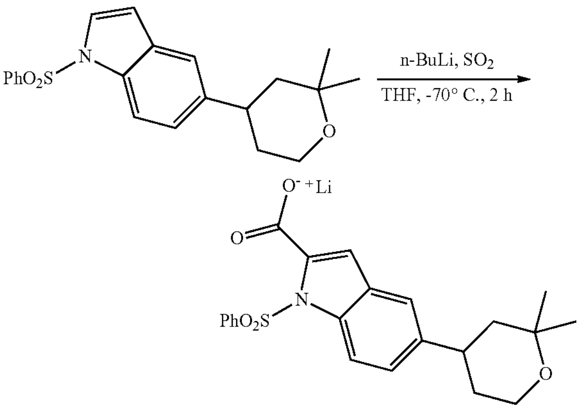

To a solution of 5-(2, 2-dimethyltetrahydro-2H-pyran-4-yl)-1-(phenylsulfonyl)-1H-indole (2 g, 5.41 mmol, 1 eq) in THF (20 mL) was added n-BuLi (2.5 M, 2.60 mL, 1.2 eq) at −70° C. under $N_2$. The mixture was stirred at −70° C. for 1.5 hours. The mixture was stirred at −70° C. for 0.5 hour under 15 Psi of $SO_2$. Five Batches were performed in parallel. LCMS showed the reaction was completed. The reaction mixture was diluted with hexanes (100 mL), filtered, the filter residue was concentrated in vacuo to give 5-(2, 2-dimethyltetrahydro-2H-pyran-4-yl)-1-(phenylsulfonyl)-1H-indole-2-sulfinate lithium (I) (4 g, crude). LC-MS (ES+, m/z): 432.1 [$(M-H)^+$]; Rt=0.958 min.

Step 5:5-(2, 2-dimethyltetrahydro-2H-pyran-4-yl)-1-(phenylsulfonyl)-1H-indole-2-sulfonyl chloride

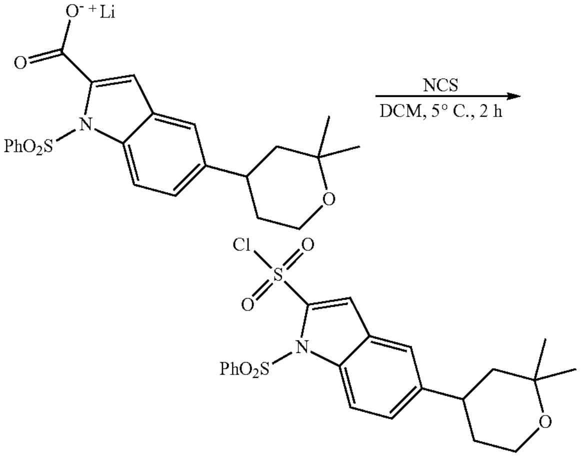

To a solution of 5-(2, 2-dimethyltetrahydro-2H-pyran-4-yl)-1-(phenylsulfonyl)-1H-indole-2-sulfinate lithium (I) (3.4 g, 7.86 mmol, 1 eq) in DCM (34 mL) was added NCS (1.26 g, 9.43 mmol, 1.2 eq) at 5° C. under $N_2$. The mixture was stirred at 5° C. for 2 hours under $N_2$. The reaction mixture was quenched by 1-(4-fluoro-1-methyl-1H-indazol-5-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (10 mg) at 25° C. TLC (Petroleum ether/Ethyl acetate=1/2) indicated that the reaction was completed. The reaction mixture was concentrated in vacuo to give 5-(2, 2-dimethyltetrahydro-2H-pyran-4-yl)-1-(phenylsulfonyl)-1H-indole-2-sulfonyl chloride (3.4 g, crude).

Intermediate 507-1 trans-tert-butyl-8-fluoro-2,4,5,6,7,8-hexahydro-4,7-epiminocyclohepta [c]pyrazole-9-carboxylate and Intermediate 507-2 cis-tert-butyl-8-fluoro-2,4,5,6,7,8-hexahydro-4,7-epiminocyclohepta [c]pyrazole-9-carboxylate Scheme 507-1/507-2

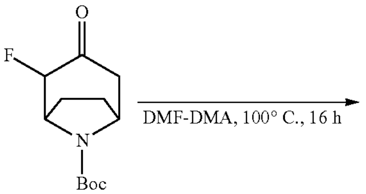

-continued

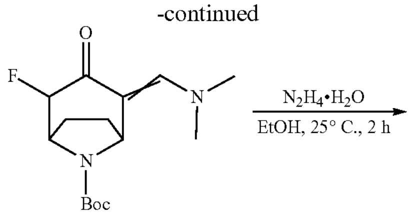

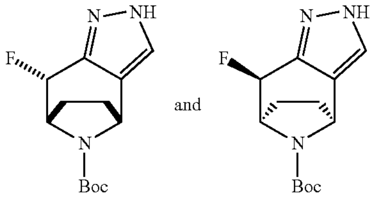

1st eluent
mixture of two trans isomers

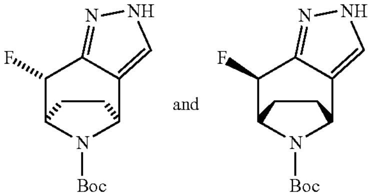

2nd eluent
mixture of two cis isomers)

Step 1: tert-butyl (1S,5R)-2-((dimethylamino)methylene)-4-fluoro-3-oxo-8-azabicyclo[3.2.1]octane-8-carboxylate

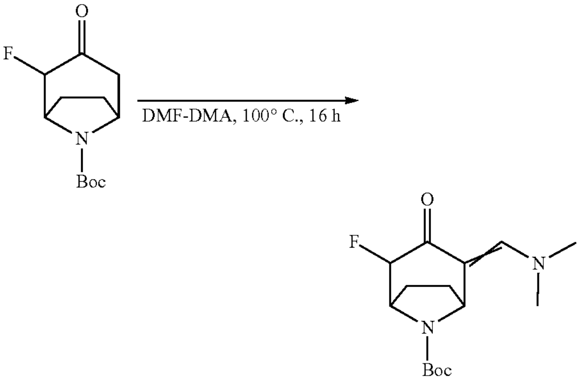

To a mixture of tert-butyl (1R,5S)-2-fluoro-3-oxo-8-azabicyclo[3.2.1]octane-8-carboxylate (10 g, 41.11 mmol, 1 eq) in DMF-DMA (100 mL) in one portion at 100° C. under $N_2$. The mixture was stirred at 100° C. for 16 hours. LCMS showed the reaction was completed. Four Batches in parallel. The crude was purified by column chromatography ($SiO_2$, hexanes/ethyl acetate=20/1 to 1/1) to give tert-butyl (1S,5R)-2-((dimethylamino)methylene)-4-fluoro-3-oxo-8-azabicyclo[3.2.1]octane-8-carboxylate (18 g, 48.27 mmol, 29.35% yield). LC-MS (ES+, m/z): 299.3 [$(M+H)^+$]; Rt=1.205 min.

Step 2: trans-tert-butyl-8-fluoro-2,4,5,6,7,8-hexahydro-4,7-epiminocyclohepta [c]pyrazole-9-carboxylate and cis-tert-butyl-8-fluoro-2,4,5,6,7,8-hexahydro-4,7-epiminocyclohepta [c]pyrazole-9-carboxylate and cis-tert-butyl-8-fluoro-2,4,5,6,7,8-hexahydro-4,7-epiminocyclohepta [c]pyrazole-9-carboxylate

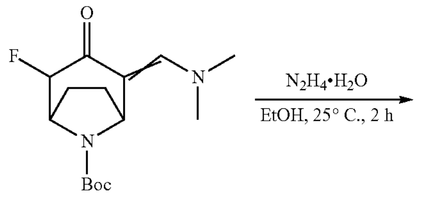

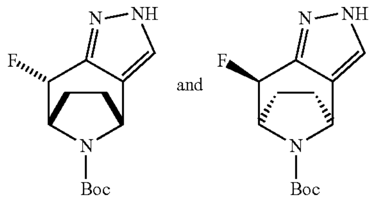

and $1^{st}$ eluent
mixture of two trans isomers

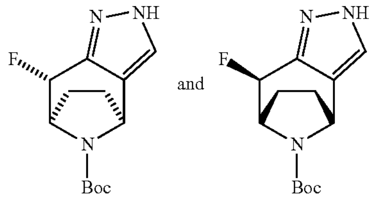

and $2^{nd}$ eluent
mixture of two cis isomers)

To a mixture of tert-butyl (1S,5R)-2-((dimethylamino) methylene)-4-fluoro-3-oxo-8-azabicyclo [3.2.1]octane-8-carboxylate (18 g, 48.27 mmol, 1 eq) in EtOH (180 mL) was added $N_2H_4 \cdot H_2O$ (3.480 g, 55.61 mmol, 1.15 eq) under $N_2$. The mixture was stirred at 25° C. for 2 hours. LCMS showed the reaction was completed. The residue was poured into water (2000 mL). The aqueous phase was extracted with ethyl acetate (1000 mL*3). The combined organic phase was washed with saturated brine (3000 mL), dried with anhydrous $Na_2SO_4$, filtered and concentrated in vacuo. The residue was purified by prep-HPLC (column: Phenomenex Luna C18 75*30 mm*3 um; mobile phase: [$H_2O$ (0.1% TFA)-ACN]; gradient: 15%-45% B over 8.0 min) to afford trans-tert-butyl-8-fluoro-2,4,5,6,7,8-hexahydro-4,7-epiminocyclohepta [c]pyrazole-9-carboxylate (1st eluent, 4 g, 14.22 mmol, 29.45% yield). LC-MS (ES+, m/z): 268.3 [$(M+H)^+$]; Rt=1.253 min.

And cis-tert-butyl-8-fluoro-2,4,5,6,7,8-hexahydro-4,7-epiminocyclohepta [c]pyrazole-9-carboxylate ($2^{nd}$ eluent, 4 g, 14.22 mmol, 29.45% yield). LC-MS (ES+, m/z): 268.3 [$(M+H)^+$]; Rt=1.344 min.

Intermediate 516-1

Ethyl 1-((1R,2R)-1-cyano-2-methylcyclopropyl)-5-((R)-4-oxaspiro[2.5]octan-7-yl)-1H-indole-2-carboxylate And Intermediate 519-1

Ethyl 1-((1R,2R)-1-cyano-2-methylcyclopropyl)-5-((S)-4-oxaspiro[2.5]octan-7-yl)-1H-indole-2-carboxylate Scheme 516-1/519-1

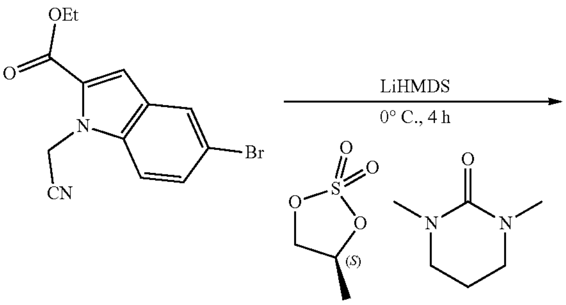

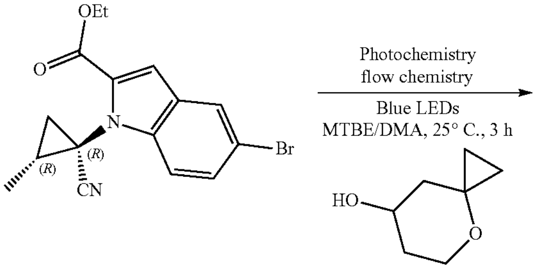

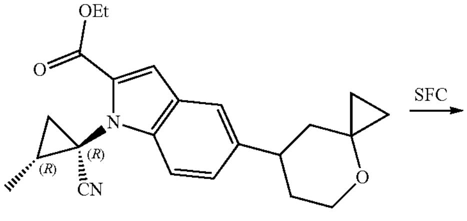

-continued

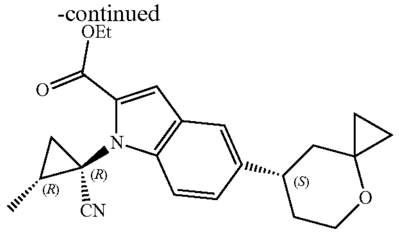

1st eluent
Intermediate 519-1

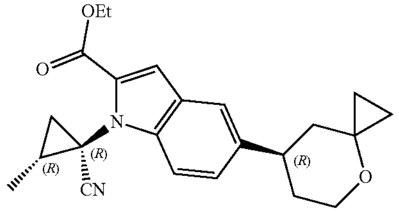

2nd eluent
Intermediate 516-1

Step 1: ethyl 5-bromo-1-((1R,2R)-1-cyano-2-methylcyclopropyl)-1H-indole-2-carboxylate

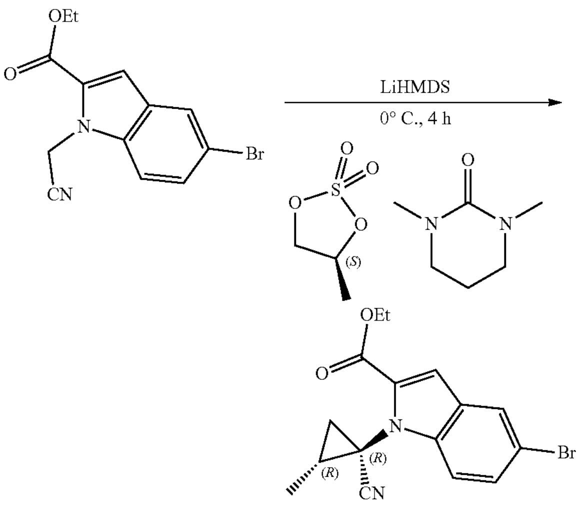

To a solution of ethyl 5-bromo-1-(cyanomethyl)-1H-indole-2-carboxylate (38 g, 123.72 mmol, 1 eq) and (4S)-4-methyl-1,3,2-dioxathiolane 2,2-dioxide (34.18 g, 247.44 mmol, 2 eq) in DMPU (400 mL) was added LiHMDS (1 M in THF, 494.88 mL, 4 eq) stirred at 0° C. under $N_2$. The mixture was stirred at 0° C. for 4 hours under $N_2$. LCMS showed the reaction was completed. The reaction mixture was poured into saturated $NH_4Cl$ (500 mL), then extracted with ethyl acetate (300 mL*3). The combined organic layers were washed with saturated brine (300 mL*5), dried over anhydrous $Na_2SO_4$, filtered and concentrated under reduced pressure. The residue was purified by column chromatography ($SiO_2$, Petroleum ether/ethyl acetate=1:0 to 3:1) to give ethyl 5-bromo-1-((1R,2R)-1-cyano-2-methylcyclopropyl)-1H-indole-2-carboxylate (12 g, 34.56 mmol, 27.94% yield) was obtained as a white solid. LC-MS (ES+, m/z): 347.1 [$(M+H)^+$]; Rt=1.961 min.

Step 2: ethyl 1-((1R,2R)-1-cyano-2-methylcyclopropyl)-5-(4-oxaspiro[2.5]octan-7-yl)-1H-indole-2-carboxylate

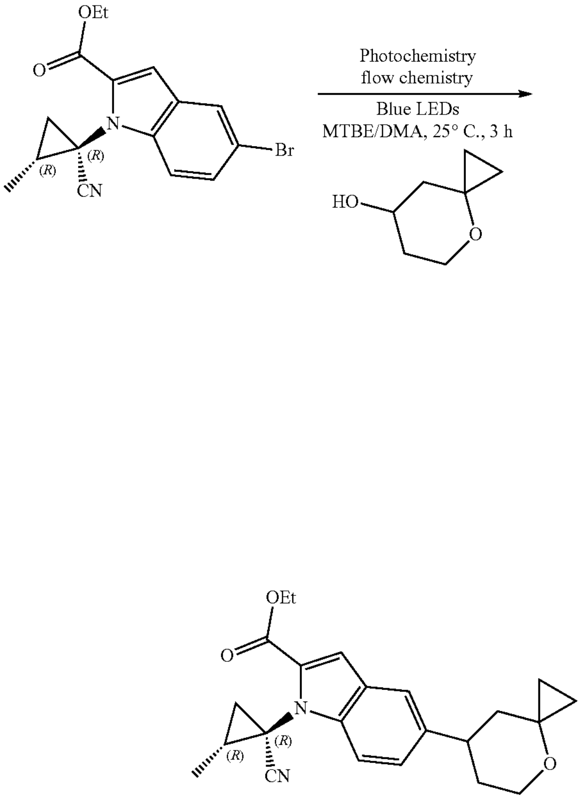

A solution of 5,7-ditert-butyl-3-phenyl-1,3-benzoxazol-3-ium; tetrafluoroborate (5.46 g, 13.82 mmol, 1.6 eq) and 4-oxaspiro[2.5]octan-7-ol (1.94 g, 15.12 mmol, 1.75 eq) in MTBE (15 mL) was stirred the reaction mixture at 25° C. for 30 min under $N_2$. A solution of pyridine (1.09 g, 13.82 mmol, 1.12 mL, 1.6 eq) in MTBE (15 mL) was added dropwise to the above reaction mixture at 25° C. Filter and collect the filtrated as R1. At the same time, ethyl 5-bromo-1-((1R,2R)-1-cyano-2-methylcyclopropyl)-1H-indole-2-carboxylate (3 g, 8.64 mmol, 1 eq), ditert-butyl (tetrafluoro) spiro[BLAH]; hexafluorophosphate (127.78 mg, 129.61 μmol, 0.015 eq), quinuclidine (1.68 g, 15.12 mmol, 1.75 eq) and 4-tert-butyl-2-(4-tert-butyl-2-pyridyl) pyridine dibromonickel (210.35 mg, 432.02 μmol, 0.05 eq) were mixed in DMA (30 mL) at 25° C. in another flask as R2. The R1 was then transferred into the R2. The reaction mixture at 25° C. under blue LEDs (450 nm, 520 W) fan for 2 hours. LCMS showed the reaction was completed. The reaction mixture was poured into water (150 mL), then extracted with ethyl acetate (150 mL*3). The combined organic layers were washed with saturated brine (200 mL*5), dried over anhydrous $Na_2SO_4$, filtered and concentrated under reduced pressure. The residue was purified by column chromatography ($SiO_2$, Petroleum ether/Ethyl acetate=1:0 to 3:1) to give ethyl 1-((1R,2R)-1-cyano-2-methylcyclopropyl)-5-(4-oxaspiro[2.5]octan-7-yl)-1H-indole-2-carboxylate (1 g, 2.51 mmol, 29.05% yield). LC-MS (ES+, m/z): 379.3 [$(M+H)^+$]; Rt=1.998 min.

Step 3: ethyl 1-((1R,2R)-1-cyano-2-methylcyclopropyl)-5-((S)-4-oxaspiro[2.5]octan-7-yl)-1H-indole-2-carboxylate & ethyl 1-((1R,2R)-1-cyano-2-methylcyclopropyl)-5-((R)-4-oxaspiro[2.5]octan-7-yl)-1H-indole-2-carboxylate

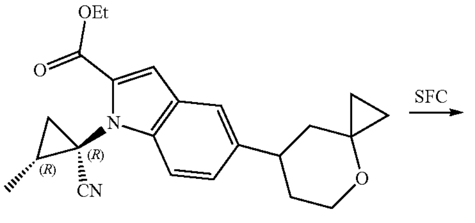

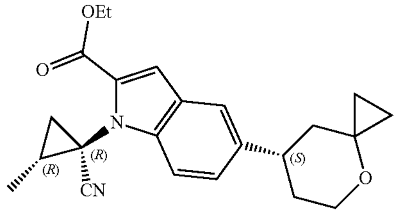

$1^{st}$ eluent
Intermediate 519-1

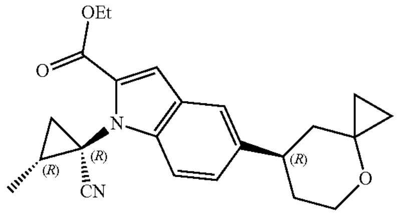

$2^{nd}$ eluent
Intermediate 516-1

Ethyl 1-((1R,2R)-1-cyano-2-methylcyclopropyl)-5-(4-oxaspiro[2.5]octan-7-yl)-1H-indole-2-carboxylate (800 mg) was further separated by SFC (column: DAICEL CHIRALPAK IF (250 mm*30 mm, 10 um); mobile phase: [$CO_2$-MeOH (0.1% $NH_3H_2O$)]; B %: 46%, isocratic elution mode) to give ethyl 1-((1R,2R)-1-cyano-2-methylcyclopropyl)-5-((S)-4-oxaspiro[2.5]octan-7-yl)-1H-indole-2-carboxylate (1st eluent, RT=1.607 min by SFC, 400 mg, 972.35 μmol, 46.00% yield). and ethyl 1-((1R,2R)-1-cyano-2-methylcyclopropyl)-5-((R)-4-oxaspiro[2.5]octan-7-yl)-1H-indole-2-carboxylate ($2^{nd}$ eluent, RT=1.833 min by SFC, 330 mg, 972.35 μmol, 46.00% yield) as a white solid.

Intermediate 518-1 tert-butyl (S)-2-(4-fluoro-3,5-dimethylphenyl)-4-methyl-3-(2-oxo-2,3-dihydro-1H-imidazol-1-yl)-2,6,7,8-tetrahydropyrazolo[4,3-c]azepine-5(4H)-carboxylate Scheme 518-1

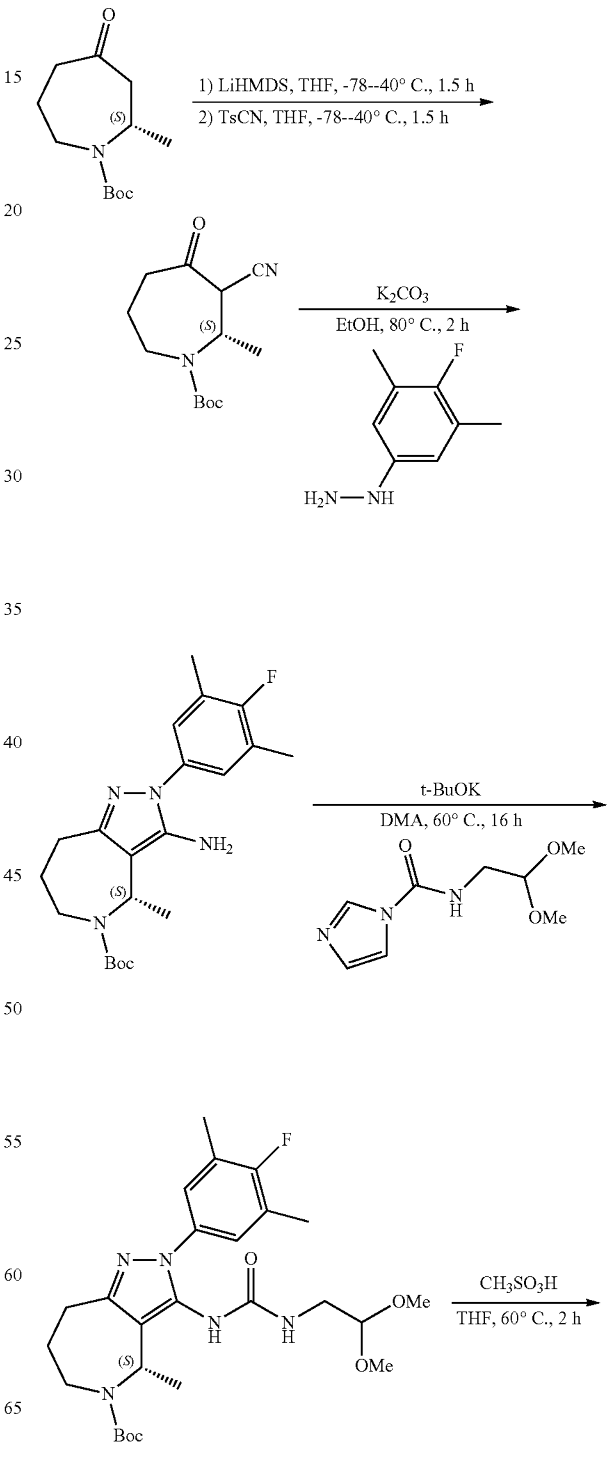

-continued

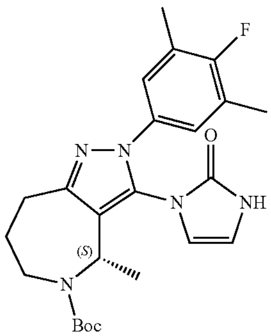

Step 1: tert-butyl (2S)-3-cyano-2-methyl-4-oxoazepane-1-carboxylate

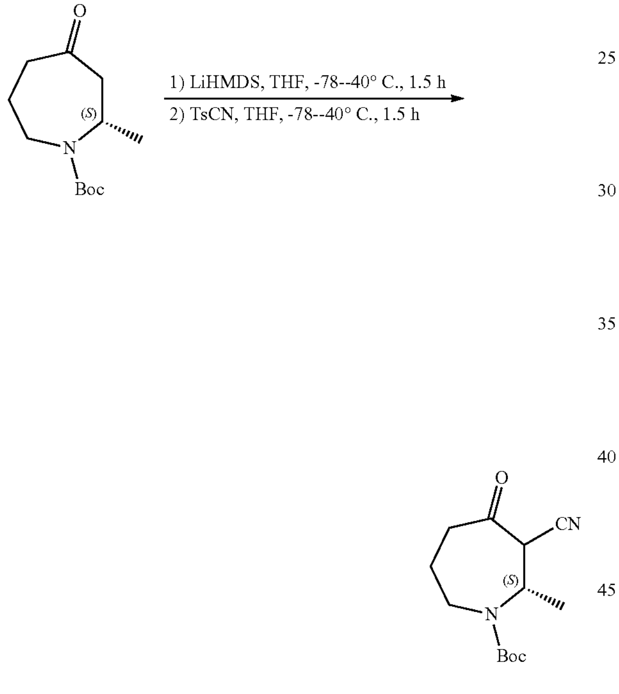

To a solution of tert-butyl (S)-2-methyl-4-oxoazepane-1-carboxylate (2 g, 8.80 mmol, 1 eq) in THF (20 mL) was added LiHMDS (1 M, 17.60 mL, 2 eq) at −78° C. under $N_2$. The mixture was stirred at −40° C. for 1.5 hours under $N_2$, and then p-tolylsulfonylformonitrile (3.19 g, 17.60 mmol, 2 eq) in THF (5 mL) was added at −78° C. under $N_2$. The mixture was stirred at −40° C. for 1.5 hours under $N_2$. LCMS showed the reaction was completed. The residue was poured into saturated $NH_4Cl$ (200 mL). The aqueous phase was extracted with ethyl acetate (100 mL*3). The combined organic phase was washed with saturated brine (300 mL), dried with anhydrous $Na_2SO_4$, filtered and concentrated in vacuo. The residue was purified by prep-TLC ($SiO_2$, hexanes:ethyl acetate=3:1) to give tert-butyl (2S)-3-cyano-2-methyl-4-oxoazepane-1-carboxylate (1.2 g, 3.80 mmol, 43.24% yield). LC-MS (ES+, m/z): 253.0 [$(M+H)^+$]; Rt=0.875 min.

Step 2: (S)-tert-butyl 3-amino-2-(4-fluoro-3,5-dimethylphenyl)-4-methyl-4,6,7,8-tetrahydropyrazolo[4,3-c] azepine-5 (2H)-carboxylate

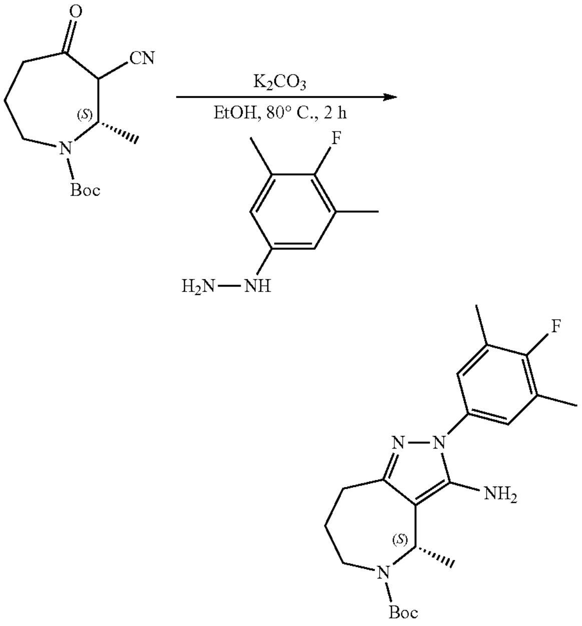

To a solution of tert-butyl (2S)-3-cyano-2-methyl-4-oxoazepane-1-carboxylate (1.20 g, 3.80 mmol, 1 eq) in EtOH (12 mL) was added $K_2CO_3$ (1.58 g, 11.41 mmol, 3 eq) and (4-fluoro-3,5-dimethylphenyl) hydrazine (797.92 mg, 4.19 mmol, 1.1 eq, HCl). The mixture was stirred at 80° C. for 2 hours under $N_2$. LCMS showed the reaction was completed. The residue was poured into water (100 mL), extracted with ethyl acetate (50 mL*3). The combined organic phase was washed with saturated brine (150 mL), dried with anhydrous $Na_2SO_4$, filtered and concentrated in vacuo. The residue was purified by column chromatography ($SiO_2$, hexanes:ethyl acetate=2/1) to give(S)-tert-butyl 3-amino-2-(4-fluoro-3,5-dimethylphenyl)-4-methyl-4,6,7,8-tetrahydropyrazolo[4,3-c]azepine-5 (2H)-carboxylate (0.8 g, 1.85 mmol, 48.71% yield). LC-MS (ES+, m/z): 389.2 [$(M+H)^+$]; Rt=0.482 min.

Step 3: (S)-tert-butyl 3-(3-(2,2-dimethoxyethyl) ureido)-2-(4-fluoro-3,5-dimethylphenyl)-4-methyl-4,6,7,8-tetrahydropyrazolo[4,3-c]azepine-5 (2H)-carboxylate

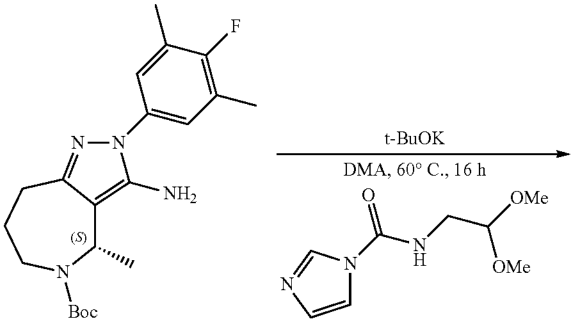

-continued

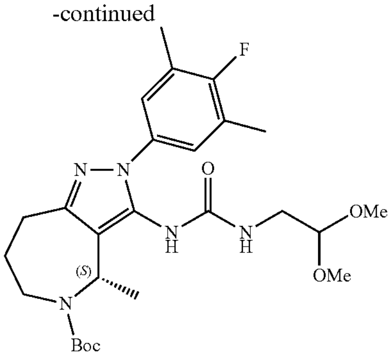

To a solution of (S)-tert-butyl 3-(3-(2,2-dimethoxyethyl) ureido)-2-(4-fluoro-3,5-dimethylphenyl)-4-methyl-4,6,7,8-tetrahydropyrazolo[4,3-c]azepine-5 (2H)-carboxylate (0.8 g, 1.85 mmol, 1 eq) in DMA (8 mL) was added t-BuOK (2.08 g, 18.53 mmol, 10 eq) and N-(2,2-dimethoxyethyl)-1H-imidazole-1-carboxamide (2.22 g, 11.12 mmol, 6 eq). The mixture was stirred at 60° C. for 16 hours under $N_2$. LCMS showed the reaction was completed. The residue was poured into water (100 mL). The aqueous phase was extracted with ethyl acetate (100 mL*3). The combined organic phase was washed with saturated brine (300 mL), dried with anhydrous $Na_2SO_4$, filtered and concentrated in vacuo. The residue was purified by column chromatography ($SiO_2$, Commercial hexanes: ethyl acetate=3/1) to give(S)-tert-butyl 3-(3-(2,2-dimethoxyethyl) ureido)-2-(4-fluoro-3,5-dimethylphenyl)-4-methyl-2,6,7,8-tetrahydropyrazolo[4,3-c]azepine-5(4H)-carboxylate (0.5 g, 866.04 μmol, 46.73% yield). LC-MS (ES+, m/z): 520.3 [(M+H)$^+$]; Rt=0.540 min.

Step 4: tert-butyl (S)-2-(4-fluoro-3,5-dimethylphenyl)-4-methyl-3-(2-oxo-2,3-dihydro-1H-imidazol-1-yl)-2,6,7,8-tetrahydropyrazolo[4,3-c]azepine-5 (4H)-carboxylate

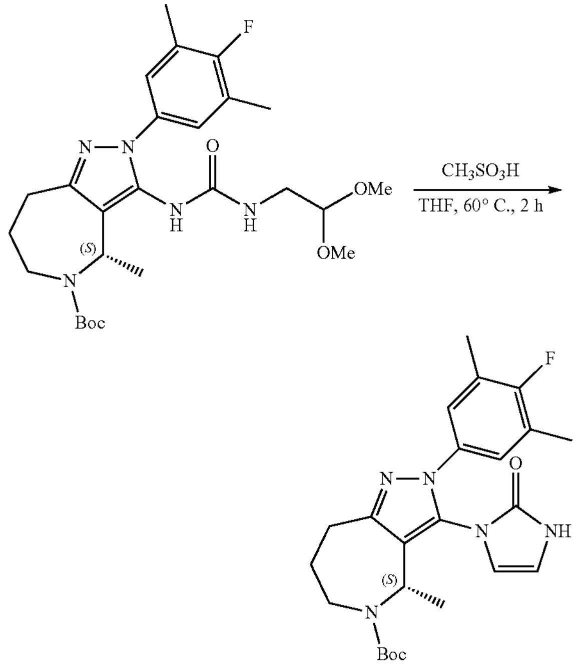

To a solution of tert-butyl (S)-3-(3-(2,2-dimethoxyethyl) ureido)-2-(4-fluoro-3,5-dimethylphenyl)-4-methyl-2,6,7,8-tetrahydropyrazolo[4,3-c]azepine-5 (4H)-carboxylate (0.5 g, 866.04 μmol, 1 eq) in THF (5 mL) was added $CH_3SO_3H$ (91.55 mg, 952.64 μmol, 1.1 eq). The mixture was stirred at 60° C. for 2 hours. LCMS showed the reaction was completed. The residue was poured into water (50 mL). The aqueous phase was extracted with ethyl acetate (50 mL*3). The combined organic phase was washed with saturated brine (150 mL), dried with anhydrous $Na_2SO_4$, filtered and concentrated in vacuo. The residue was purified by column chromatography ($SiO_2$, Commercial hexanes: ethyl acetate=2/1) to give tert-butyl (S)-2-(4-fluoro-3,5-dimethylphenyl)-4-methyl-3-(2-oxo-2,3-dihydro-1H-imidazol-1-yl)-2,6,7,8-tetrahydropyrazolo[4,3-c]azepine-5 (4H)-carboxylate (250 mg, 521.38 μmol, 60.20% yield). LC-MS (ES+, m/z): 456.3 [(M+H)$^+$]; Rt=0.545 min.

Intermediate 525-1

(S)-5-(2, 2-dimethyltetrahydro-2H-pyran-4-yl)-1-(phenylsulfonyl)-1H-indole-2-sulfonyl chloride Scheme 525-1

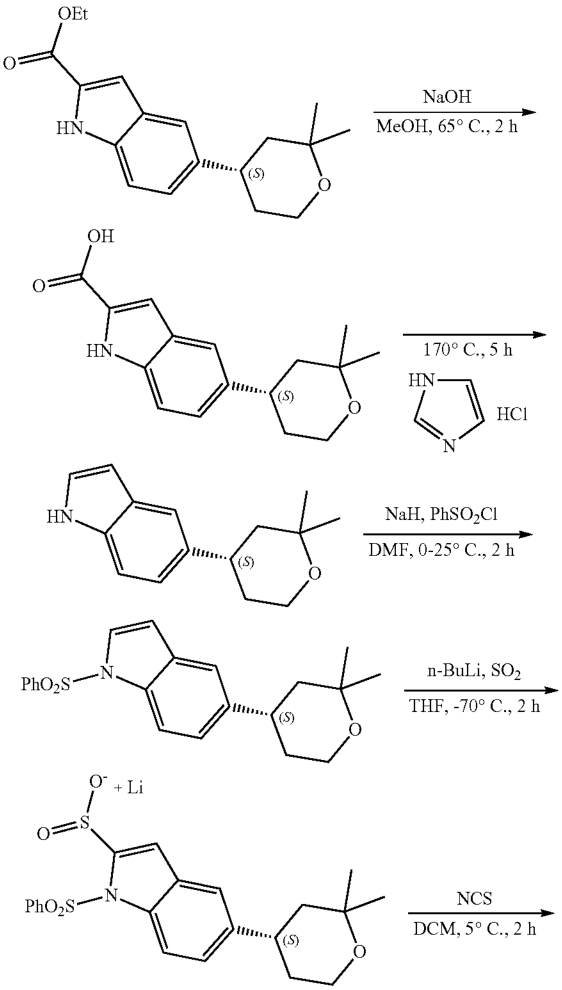

-continued

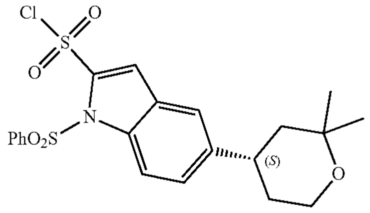

Step 1: (S)-5-(2, 2-dimethyltetrahydro-2H-pyran-4-yl)-1H-indole-2-carboxylic acid

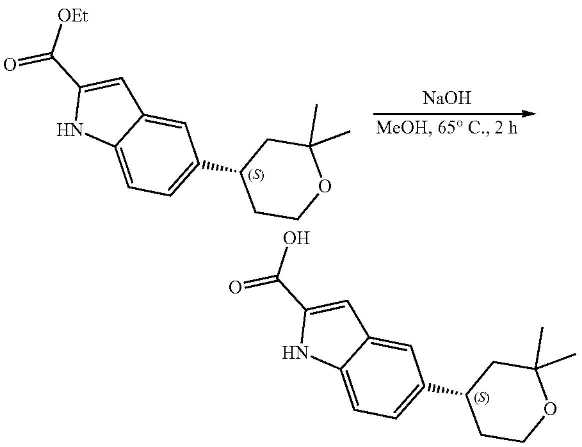

To a solution of ethyl(S)-5-(2, 2-dimethyltetrahydro-2H-pyran-4-yl)-1H-indole-2-carboxylate (59 g, 195.77 mmol, 1 eq) in MeOH (900 mL), NaOH (2 M, 216.33 mL, 2.21 eq) was added dropwise, the mixture was stirred at 65° C. for 2 hours under $N_2$ (2 parallel reaction). LCMS showed the reaction was completed. The reaction solution was cooled at an external temperature of 15° C., and 5N hydrochloric acid (90 mL) was added dropwise. Water (420 mL) was added dropwise, and the precipitated solid was collected by filtration. The obtained solid was washed with water (700 mL) and dried in vacuo to give (S)-5-(2, 2-dimethyltetrahydro-2H-pyran-4-yl)-1H-indole-2-carboxylic acid (44 g, crude). LC-MS (ES+, m/z): 274.1 [$(M+H)^+$]; Rt=0.457 min.

Step 2: (S)-5-(2, 2-dimethyltetrahydro-2H-pyran-4-yl)-1H-indole

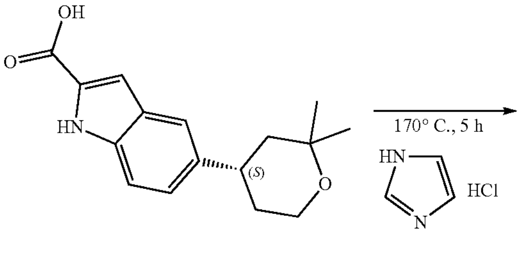

-continued

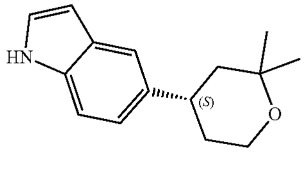

A solution of(S)-5-(2, 2-dimethyltetrahydro-2H-pyran-4-yl)-1H-indole-2-carboxylic acid (10 g, 36.59 mmol, 1 eq) in 1H-imidazole hydrochloride (38.25 g, 365.86 mmol, 10 eq) was stirred at 170° C. for 5 hours under $N_2$ (5 parallel reaction). LCMS showed the reaction was completed. The reaction mixture was diluted with water (100 mL) and then extracted with DCM (100 mL*3). The combined organic layers were washed with saturated brine (300 mL). The combined organic layers were dried over $Na_2SO_4$, filtered and concentrated in vacuo. The residue was purified by column chromatography ($SiO_2$, hexanes/ethyl acetate=25/1 to 3/1) to give (S)-5-(2, 2-dimethyltetrahydro-2H-pyran-4-yl)-1H-indole (4.8 g, 18.50 mmol, 50.58% yield). LC-MS (ES+, m/z): 230.2 [$(M+H)^+$]; Rt=0.510 min.

Step 3: (S)-5-(2, 2-dimethyltetrahydro-2H-pyran-4-yl)-1-(phenylsulfonyl)-1H-indole

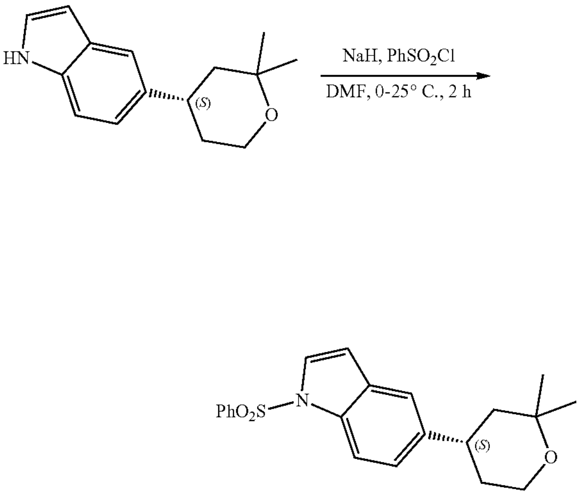

To a solution of(S)-5-(2, 2-dimethyltetrahydro-2H-pyran-4-yl)-1H-indole (4.8 g, 20.93 mmol, 1 eq) in DMF (48 mL) was added NaH (1.67 g, 41.86 mmol, 60% purity, 2 eq) at 0° C. under $N_2$. The mixture was stirred at 0° C. for 1 hour. $PhSO_2Cl$ (7.39 g, 41.86 mmol, 5.34 mL, 2 eq) was then added. The mixture was stirred at 25° C. for 1 hour under $N_2$. LCMS showed the reaction was completed. The mixture was added dropwise to $NH_4Cl$ (100 mL), and then extracted with DCM (100 mL*3). The organic layers were combined, washed with water (200 mL), saturated brine (200 mL), dried over $Na_2SO_4$, filtered and concentrated in vacuo. The crude product was purified by chromatography on silica gel (hexanes: ethyl acetate=20/1-7/1) to give (S)-5-(2, 2-dimethyltetrahydro-2H-pyran-4-yl)-1-(phenylsulfonyl)-1H-indole (6.3 g, 16.05 mmol, 76.65% yield). LC-MS (ES+, m/z): 370.1 [$(M+H)^+$]; Rt=0.604 min.

Step 4: (S)-5-(2, 2-dimethyltetrahydro-2H-pyran-4-yl)-1-(phenylsulfonyl)-1H-indole-2-sulfinate lithium (I)

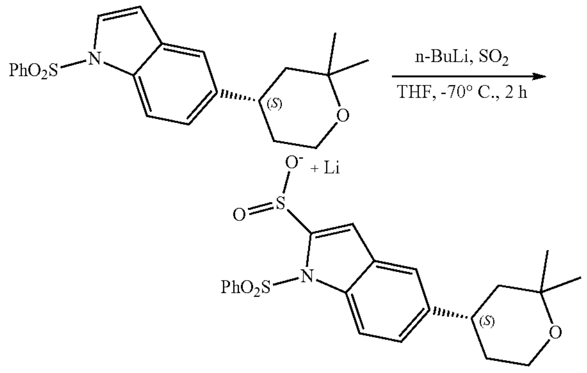

To a solution of(S)-5-(2, 2-dimethyltetrahydro-2H-pyran-4-yl)-1-(phenylsulfonyl)-1H-indole (6 g, 16.24 mmol, 1 eq) in THF (60 mL) was added n-BuLi (2.5 M, 7.80 mL, 1.20 eq) at −70° C. under $N_2$. The mixture was stirred at −70° C. for 1.5 hours. The mixture was stirred at −70° C. for 0.5 hour under $SO_2$ (15 Psi) (5 parallel reaction). LCMS showed the reaction was completed. The reaction mixture was diluted with commercial hexanes (200 mL), filtered, the filter residue was concentrated in vacuo to give (S)-5-(2, 2-dimethyltetrahydro-2H-pyran-4-yl)-1-(phenylsulfonyl)-1H-indole-2-sulfinate lithium (I) (6.5 g, crude). $^1H$ NMR (400 MHz, DMSO-$d_6$) δ=8.35-8.23 (m, 2H), 7.84-7.73 (m, 1H), 7.66-7.47 (m, 3H), 7.42-7.31 (m, 1H), 7.17-7.07 (m, 1H), 6.88-6.78 (m, 1H), 3.73-3.64 (m, 2H), 3.04-2.87 (m, 1H), 1.68-1.39 (m, 4H), 1.31-1.08 (m, 6H). LC-MS (ES-, m/z): 432.1 $[(M-H)^-]$; Rt=0.936 min.

Step 5: (S)-5-(2, 2-dimethyltetrahydro-2H-pyran-4-yl)-1-(phenylsulfonyl)-1H-indole-2-sulfonyl chloride

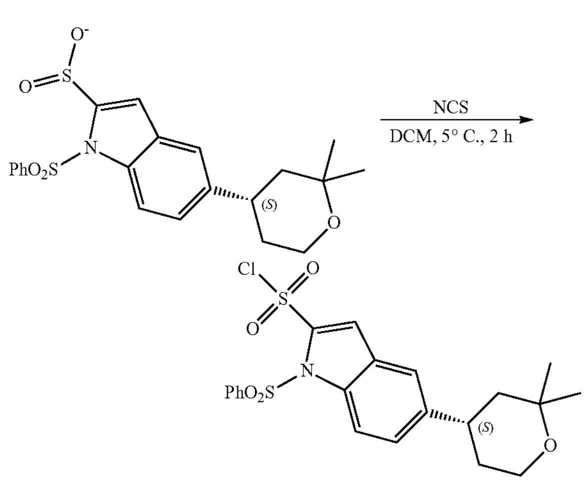

To a solution of(S)-5-(2,2-dimethyltetrahydro-2H-pyran-4-yl)-1-(phenylsulfonyl)-1H-indole-2-sulfinate (3.00 g, 6.94 mmol, 1 eq) in DCM (30 mL) was added NCS (1.11 g, 8.32 mmol, 1.2 eq). The mixture was stirred at 5° C. for 2 hours under $N_2$. TLC indicated the reaction was completed. The reaction mixture was concentrated in vacuo to give(S)-5-(2, 2-dimethyltetrahydro-2H-pyran-4-yl)-1-(phenylsulfonyl)-1H-indole-2-sulfonyl chloride (3 g, crude), which was used for the nect step directly without further purification.

Intermediate 528-1 ethyl (S)-1-(cyanomethyl)-5-(4-oxaspiro[2.5]octan-7-yl)-1H-indole-2-carboxylate and ethyl (R)-1-(cyanomethyl)-5-(4-oxaspiro[2.5]octan-7-yl)-1H-indole-2-carboxylate Scheme 528-1

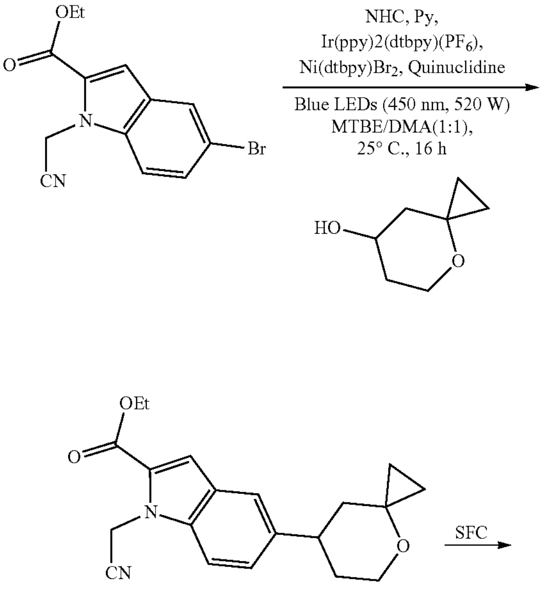

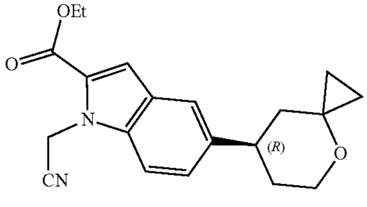

1st eluent

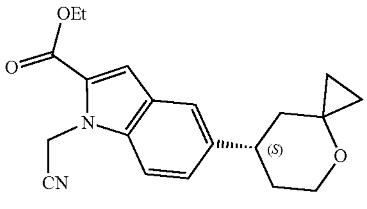

2nd eluent

Step 1: ethyl 1-(cyanomethyl)-5-(4-oxaspiro[2.5]octan-7-yl)-1H-indole-2-carboxylate

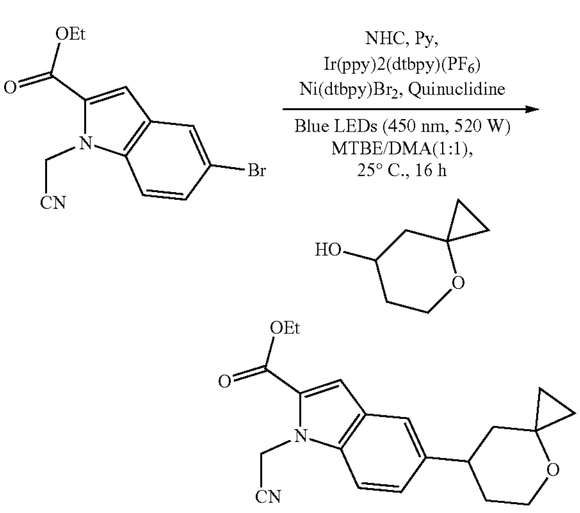

A mixture of 5,7-ditert-butyl-3-phenyl-1,3-benzoxazol-3-ium; tetrafluoroborate (41.18 g, 104.19 mmol, 1.6 eq) and 4-oxaspiro[2.5]octan-7-ol (14.61 g, 113.95 mmol, 1.75 eq) and MTBE (180 mL) was stirred at 25° C. for 30 minutes under $N_2$. A solution of pyridine (8.24 g, 104.19 mmol, 8.41 mL, 1.6 eq) in MTBE (180 mL) dropwise to the above reaction mixture at 25° C. The reaction mixture was stirred at 25° C. for 30 minutes, under $N_2$. Filter and collect the filtrate. The filtrate was transferred into a solution of ethyl 5-bromo-1-(cyanomethyl)-1H-indole-2-carboxylate (20 g, 65.12 mmol, 1 eq) and $[Ir(dFppy)_2(dtbbpy)]PF_6$ (962.99 mg, 976.75 μmol, 0.015 eq) and quinuclidine (12.67 g, 113.95 mmol, 1.75 eq) and 4-tert-butyl-2-(4-tert-butyl-2-pyridyl)pyridine; dibromonickel (1.59 g, 3.26 mmol, 0.05 eq) in DMA (360 mL) at 25° C. The reaction mixture at 25° C. under blue LEDs (450 nm, 520 W) for 15 hours. HPLC showed the reaction was completed. The mixture was added dropwise to $H_2O$ (500 mL) and then extracted with ethyl acetate (700 mL*3). The organic layers were combined, washed with water (500 mL), saturated brine (500 mL), dried over $Na_2SO_4$, filtered and concentrated in vacuo. The residue was purified by column chromatography ($SiO_2$, hexanes:ethyl acetate=100/0 to 10/1). Compound ethyl 1-(cyanomethyl)-5-(4-oxaspiro[2.5]octan-7-yl)-1H-indole-2-carboxylate (7.39 g, 21.23 mmol, 32.60% yield). LC-MS (ES+, m/z): 339.1 [$(M+H)^+$]. Rt=0.602 min.

Step 2: ethyl(S)-1-(cyanomethyl)-5-(4-oxaspiro[2.5]octan-7-yl)-1H-indole-2-carboxylate and ethyl (R)-1-(cyanomethyl)-5-(4-oxaspiro[2.5]octan-7-yl)-1H-indole-2-carboxylate

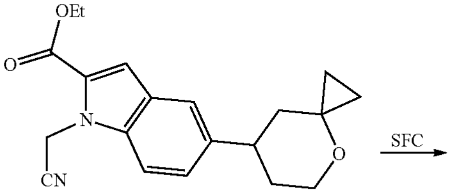

-continued

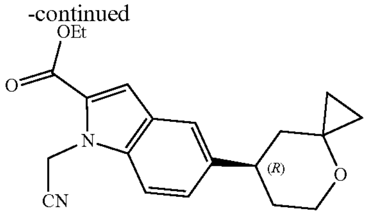

1st eluent

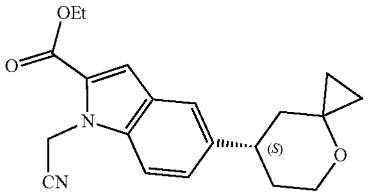

2nd eluent

The compound ethyl 1-(cyanomethyl)-5-(4-oxaspiro[2.5]octan-7-yl)-1H-indole-2-carboxylate (7.3 g, 21.57 mmol, 1 eq) was separated by SFC (column: DAICEL CHIRALPAK IG (250 mm*50 mm, 10 um); mobile phase: [$CO_2$-EtOH]; B %: 35%, isocratic elution mode) to give ethyl (R)-1-(cyanomethyl)-5-(4-oxaspiro[2.5]octan-7-yl)-1H-indole-2-carboxylate (1st eluent, RT=2.391 min by SFC, 3.5 g, 10.13 mmol, 46.94% yield). LC-MS (ES+, m/z): 339.2 [$(M+H)^+$]. Rt=0.601 min And ethyl(S)-1-(cyanomethyl)-5-(4-oxaspiro[2.5]octan-7-yl)-1H-indole-2-carboxylate ($2^{nd}$ eluent, RT=2.628 min by SFC, 2.7 g, 7.72 mmol, 35.80% yield). LC-MS (ES+, m/z): 339.2 [$(M+H)^+$]. Rt=0.613 min.

Intermediate 528-2

1-((1R,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid Scheme 528-2

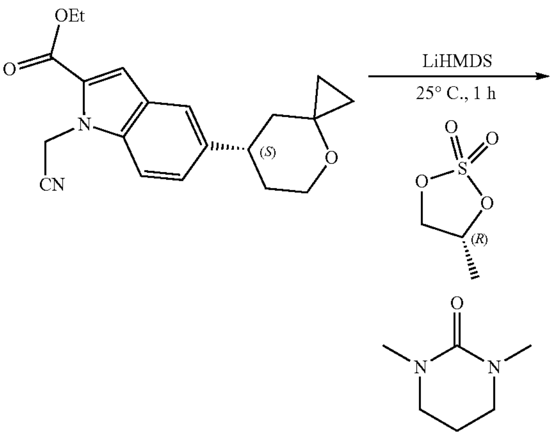

-continued

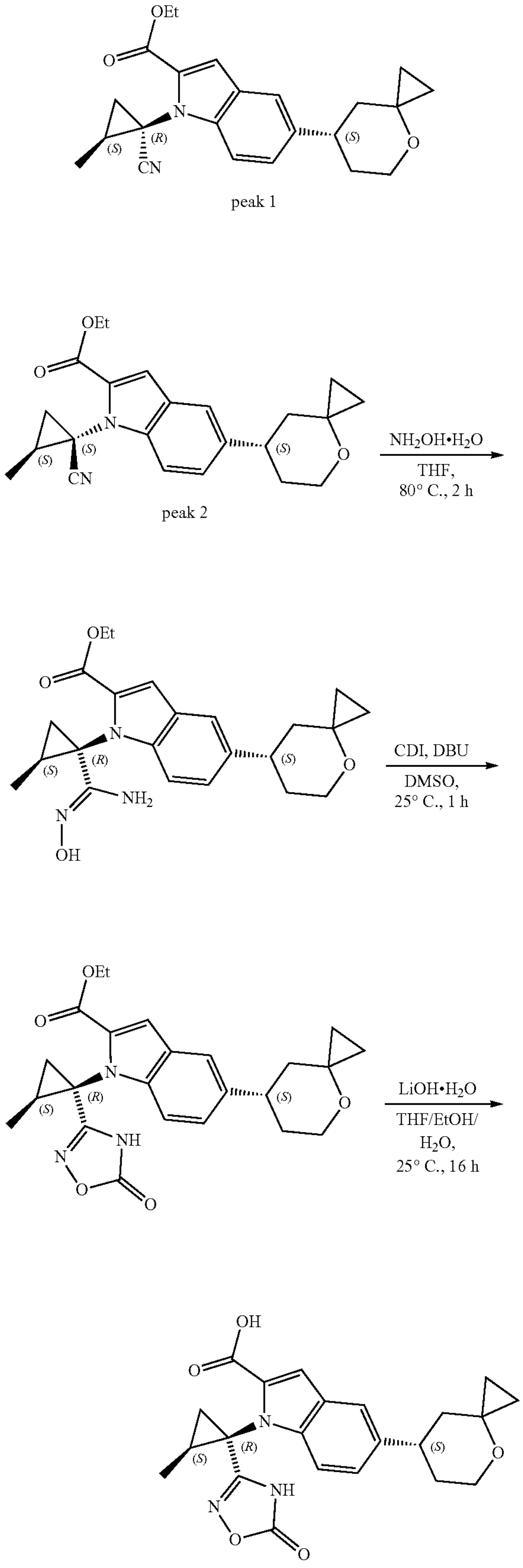

Step 1: ethyl 1-((1R,2S)-1-cyano-2-methylcyclopropyl)-5-((S)-4-oxaspiro[2.5]octan-7-yl)-1H-indole-2-carboxylate & ethyl 1-((1S,2S)-1-cyano-2-methylcyclopropyl)-5-((S)-4-oxaspiro[2.5]octan-7-yl)-1H-indole-2-carboxylate

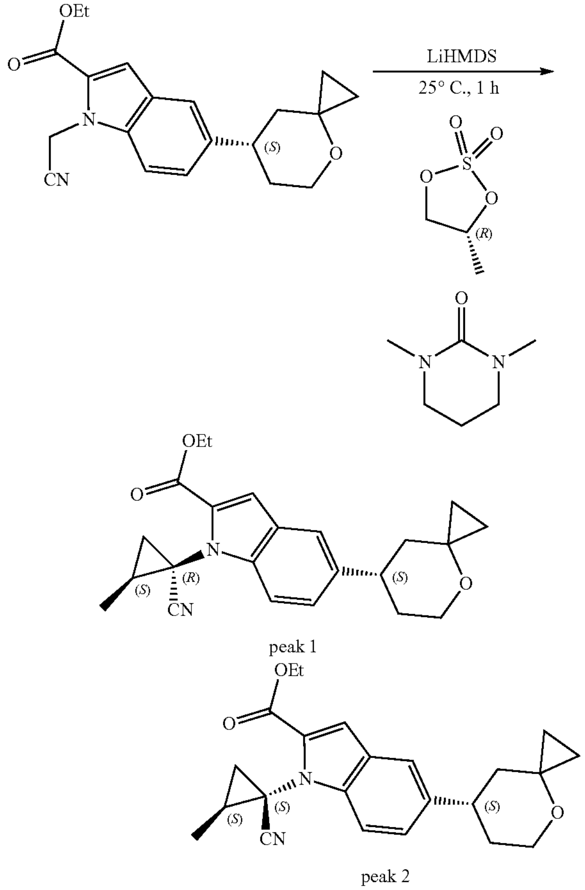

To a solution of ethyl(S)-1-(cyanomethyl)-5-(4-oxaspiro[2.5]octan-7-yl)-1H-indole-2-carboxylate (500.00 mg, 1.48 mmol, 1 eq) and (R)-4-methyl-1, 3, 2-dioxathiolane 2, 2-dioxide (408.22 mg, 2.96 mmol, 2 eq) in 1, 3-dimethyltetrahydropyrimidin-2 (1H)-one (5 mL) was added LiHMDS (1 M, 5.91 mL, 4 eq) under $N_2$. The mixture was stirred at 25° C. for 1 hour under $N_2$. LCMS showed the reaction was completed. The mixture was added dropwise to $NH_4Cl$ (20 mL) and then extracted with ethyl acetate (20 mL*3). The organic layers were combined, washed with water (50 mL), saturated brine (50 mL), dried over $Na_2SO_4$, filtered and concentrated in vacuo. The crude product was purified by prep-HPLC column: Welch Ultimate XB—CN 250*50*10 um; mobile phase: [Heptane-EtOH (0.1% $NH_3H_2O$)]; gradient: 10%-25% B over 10.0 min) to give ethyl 1-((1R,2S)-1-cyano-2-methylcyclopropyl)-5-((S)-4-oxaspiro[2.5]octan-7-yl)-1H-indole-2-carboxylate (peak 1, 70 mg, 177.19 μmol, 11.99% yield). LC-MS (ES+, m/z): 379.2 [$(M+H)^+$]; Rt=9.552 min.

And ethyl 1-((1S,2S)-1-cyano-2-methylcyclopropyl)-5-((S)-4-oxaspiro[2.5]octan-7-yl)-1H-indole-2-carboxylate (peak 2, 200 mg, 495.16 μmol, 33.51% yield). LC-MS (ES+, m/z): 379.2 [$(M+H)^+$]; Rt=9.711 min.

The reaction was repeated with ethyl(S)-1-(cyanomethyl)-5-(4-oxaspiro[2.5]octan-7-yl)-1H-indole-2-carboxylate (2.00 g, 5.91 mmol, 1 eq) to give ethyl 1-((1R,2S)-1-cyano-2-methylcyclopropyl)-5-((S)-4-oxaspiro[2.5]octan-7-yl)-1H-indole-2-carboxylate (250 mg, 632.82 μmol, 10.71% yield) and ethyl 1-((1S,2S)-1-cyano-2-methylcyclopropyl)-5-((S)-4-oxaspiro[2.5]octan-7-yl)-1H-indole-2-carboxylate (800 mg, 1.98 mmol, 33.51% yield).

Step 2: ethyl 1-((1R,2S)-1-(N'-hydroxycarbamimidoyl)-2-methylcyclopropyl)-5-((S)-4-oxaspiro[2.5] octan-7-yl)-1H-indole-2-carboxylate

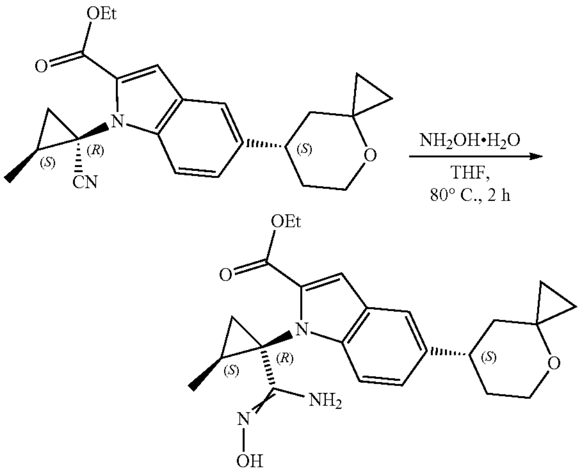

To a solution of ethyl 1-((1R,2S)-1-cyano-2-methylcyclopropyl)-5-((S)-4-oxaspiro[2.5]octan-7-yl)-1H-indole-2-carboxylate (300.00 mg, 792.68 μmol, 1 eq) in THF (3 mL) was added $NH_2OH·H_2O$ (523.64 mg, 7.93 mmol, 50% purity, 10 eq). The mixture was stirred at 80° C. for 2 hours under $N_2$. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated to give ethyl 1-((1R, 2S)-1-(N'-hydroxycarbamimidoyl)-2-methylcyclopropyl)-5-((S)-4-oxaspiro[2.5]octan-7-yl)-1H-indole-2-carboxylate (300 mg, crude). LC-MS (ES+, m/z): 412.2 [(M+H)$^+$]; Rt=0.453 min.

Step 3: ethyl 1-((1R,2S)-2-methyl-1-(5-oxo-4,5-dihydro-1, 2, 4-oxadiazol-3-yl)cyclopropyl)-5-((S)-4-oxaspiro[2.5]octan-7-yl)-1H-indole-2-carboxylate

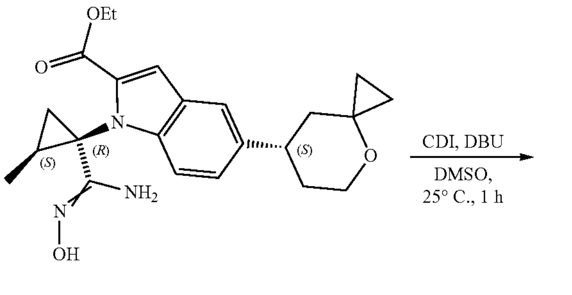

-continued

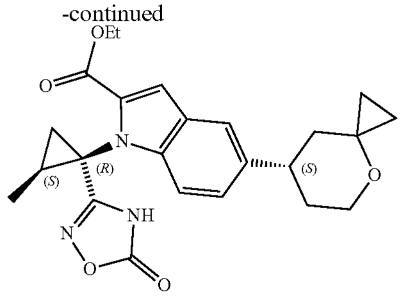

To a solution of ethyl 1-((1R,2S)-1-(N'-hydroxycarbamimidoyl)-2-methylcyclopropyl)-5-((S)-4-oxaspiro[2.5]octan-7-yl)-1H-indole-2-carboxylate (300.00 mg, 621.15 μmol, 1 eq) in DMSO (3 mL) was added CDI (201.44 mg, 1.24 mmol, 2 eq) and DBU (236.40 mg, 1.55 mmol, 2.5 eq). The mixture was stirred at 25° C. for 1 hour under $N_2$. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated. The residue was purified by prep-TLC ($SiO_2$, hexanes/ethyl acetate=1/5) to give ethyl 1-((1R,2S)-2-methyl-1-(5-oxo-4,5-dihydro-1, 2, 4-oxadiazol-3-yl)cyclopropyl)-5-((S)-4-oxaspiro[2.5]octan-7-yl)-1H-indole-2-carboxylate (260 mg, 577.66 μmol, 93.00% yield). LC-MS (ES+, m/z): 438.1 [(M+H)$^+$]; Rt=0.589 min.

Step 4: 1-((1R,2S)-2-methyl-1-(5-oxo-4,5-dihydro-1, 2, 4-oxadiazol-3-yl)cyclopropyl)-5-((S)-4-oxaspiro[2.5]octan-7-yl)-1H-indole-2-carboxylic acid

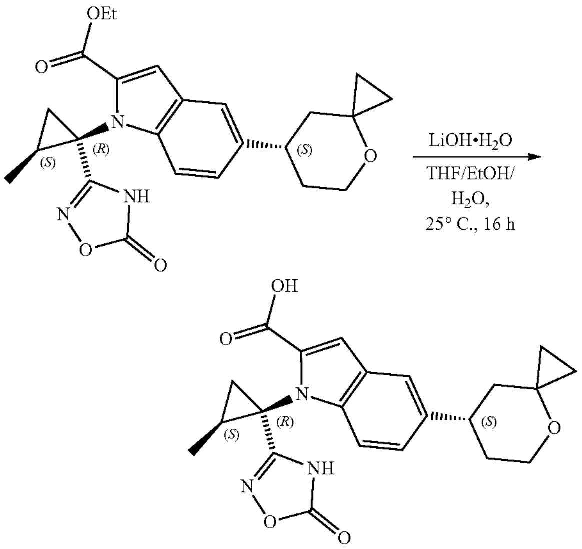

To a solution of ethyl 1-((1R,2S)-2-methyl-1-(5-oxo-4,5-dihydro-1, 2, 4-oxadiazol-3-yl) cyclopropyl)-5-((S)-4-oxaspiro[2.5]octan-7-yl)-1H-indole-2-carboxylate (260.00 mg, 577.66 μmol, 1 eq) in THF (0.9 mL), EtOH (0.9 mL) and $H_2O$ (0.9 mL) was added $LiOH·H_2O$ (242.41 mg, 5.78 mmol, 10 eq). The mixture was stirred at 25° C. for 16 hours under $N_2$. LCMS showed the reaction was completed. The mixture was concentrated in vacuo. The residue was dissolved in water (10 mL), adjusted to pH=4 with HCl (2 M), and then extracted with DCM (15 mL*3). The organic layers were combined, washed with water (50 mL), saturated brine (50 mL), dried over $Na_2SO_4$, filtered and concentrated to give 1-((1R, 2S)-2-methyl-1-(5-oxo-4,5-dihydro-1, 2, 4-oxadiazol-3-yl)cyclopropyl)-5-((S)-4-oxaspiro[2.5]octan-7-yl)-1H-indole-2-carboxylic acid (180 mg, crude). LC-MS (ES+, m/z): 410.2 [$(M+H)^+$]; Rt=0.511 min.

Intermediate 529-1

1-((1R,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid Scheme 529-1

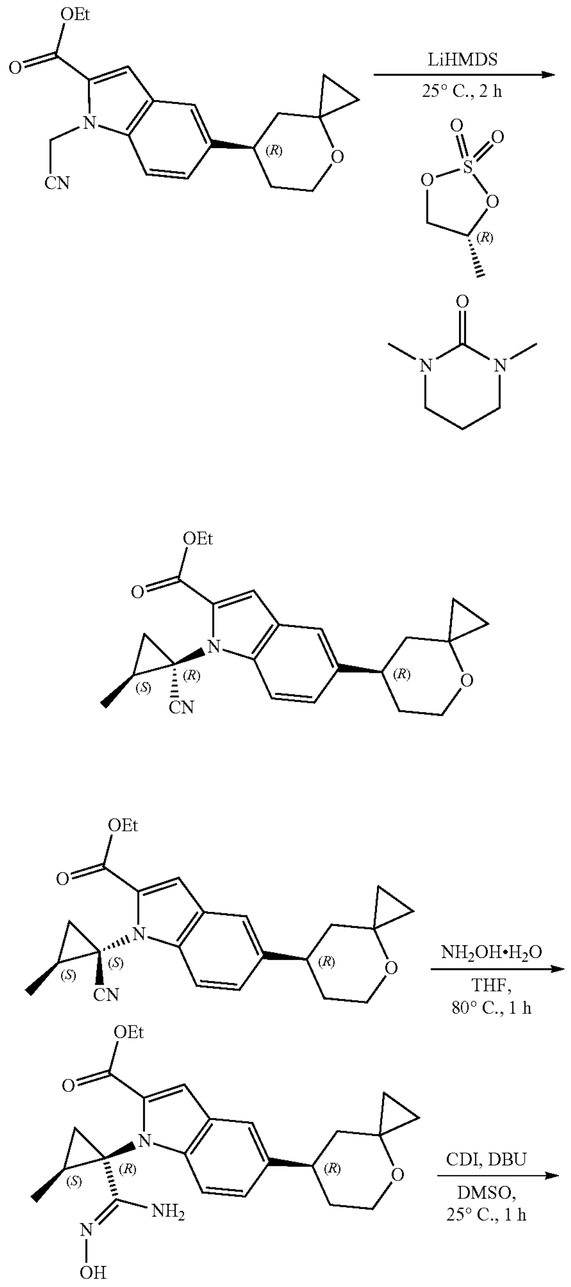

-continued

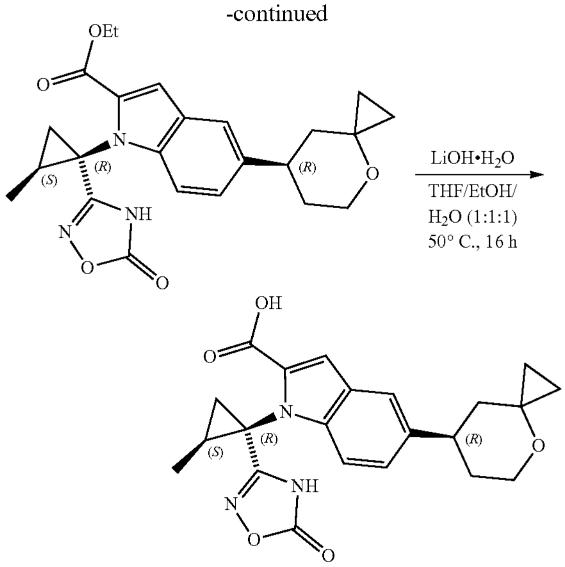

Step 1: ethyl 1-((1R,2S)-1-cyano-2-methylcyclopropyl)-5-((R)-4-oxaspiro[2.5]octan-7-yl)-1H-indole-2-carboxylate and ethyl 1-((1S,2S)-1-cyano-2-methylcyclopropyl)-5-((R)-4-oxaspiro[2.5]octan-7-yl)-1H-indole-2-carboxylate

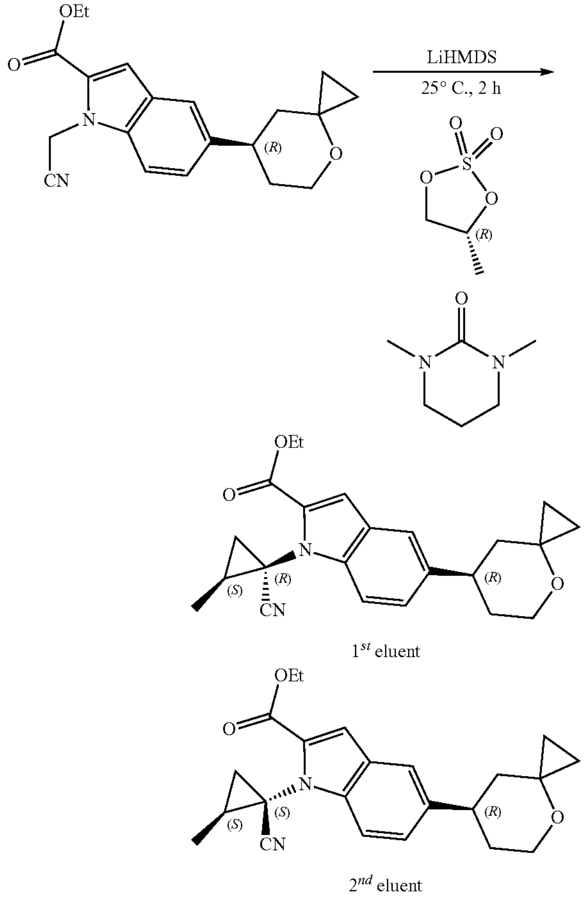

To a solution of ethyl (R)-1-(cyanomethyl)-5-(4-oxaspiro[2.5]octan-7-yl)-1H-indole-2-carboxylate (1.00 g, 2.96 mmol, 1 eq) and (R)-4-methyl-1,3,2-dioxathiolane 2,2-dioxide (816.44 mg, 5.91 mmol, 2 eq) in DMPU (10 mL) was added LiHMDS (1 M, 11.82 mL, 4 eq). The mixture was stirred at 25° C. for 2 hours under $N_2$ (2 parallel reaction). LCMS indicated the reaction was completed. The mixture was added dropwise to $NH_4Cl$ (20 mL) and then extracted with ethyl acetate (30 mL*3). The organic layers were combined, washed with water (30 mL), saturated brine (20 mL), dried over $Na_2SO_4$, filtered and concentrated in vacuo. The residue was purified by column chromatography ($SiO_2$, Commercial hexanes:ethyl acetate=100/1 to 20/1). The residue was further purified by prep-HPLC (column: Welch Ultimate XB—CN 250*50*10 um; mobile phase: [Heptane-EtOH (0.1% $NH_3H_2O$)]; gradient: 10%-25% B over 10.0 min) to give ethyl 1-((1R,2S)-1-cyano-2-methylcyclopropyl)-5-((R)-4-oxaspiro[2.5]octan-7-yl)-1H-indole-2-carboxylate (1st eluent, RT=1.184 min by SFC, 151 mg, 391.80 μmol, 13.26% yield, 2 batches in parallel). $^1H$ NMR (400 MHz, DMSO-$d_6$) δ=7.70-7.55 (m, 2H), 7.45-7.26 (m, 2H), 4.46-4.29 (m, 2H), 3.91-3.82 (m, 1H), 3.56 (dt, J=3.8, 10.9 Hz, 1H), 3.11-2.95 (m, 1H), 2.34 (dd, J=6.3, 9.6 Hz, 1H), 2.24-2.07 (m, 2H), 1.85-1.71 (m, 2H), 1.60-1.49 (m, 1H), 1.40-1.24 (m, 4H), 0.85-0.70 (m, 4H), 0.64-0.43 (m, 3H). LC-MS (ES+, m/z): 379.1 [$(M+H)^+$]; Rt=7.884 min.

And ethyl 1-((1S,2S)-1-cyano-2-methylcyclopropyl)-5-((R)-4-oxaspiro[2.5]octan-7-yl)-1H-indole-2-carboxylate ($2^{nd}$ eluent, RT=1.308 min by SFC, 314 mg, 829.67 μmol, 28.08% yield). $^1H$ NMR (400 MHz, DMSO-$d_6$) δ=7.66-7.34 (m, 3H), 7.29 (s, 1H), 4.46-4.24 (m, 2H), 3.86 (br d, J=10.1 Hz, 1H), 3.56 (dt, J=4.0, 10.7 Hz, 1H), 3.10-2.90 (m, 1H), 2.19 (br t, J=12.3 Hz, 1H), 2.02-1.70 (m, 5H), 1.59-1.22 (m, 7H), 0.85-0.41 (m, 4H). LC-MS (ES+, m/z): 379.2 [$(M+H)^+$]; Rt=0.630 min.

Step 2: ethyl 1-((1R,2S)-1-(N'-hydroxycarbamimidoyl)-2-methylcyclopropyl)-5-((R)-4-oxaspiro[2.5]octan-7-yl)-1H-indole-2-carboxylate

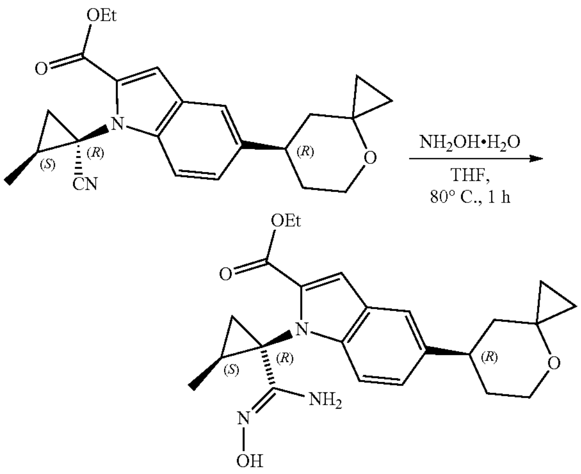

To a solution of ethyl 1-((1R,2S)-1-cyano-2-methylcyclopropyl)-5-((R)-4-oxaspiro[2.5]octan-7-yl)-1H-indole-2-carboxylate (420.00 mg, 1.11 mmol, 1 eq) in THF (4 mL) was added hydroxylamine (733.10 mg, 11.10 mmol, 50% purity, 10 eq). The mixture was stirred at 80° C. for 1 hour under $N_2$. LCMS indicated the reaction was completed. The mixture was added to $H_2O$ (10 mL) and then extracted with ethyl acetate (15 mL*3). The organic layers were combined, washed with water (10 mL*2), saturated brine (10 mL), dried over $Na_2SO_4$, filtered and concentrated to give ethyl 1-((1R,2S)-1-(N'-hydroxycarbamimidoyl)-2-methylcyclopropyl)-5-((R)-4-oxaspiro[2.5]octan-7-yl)-1H-indole-2-carboxylate (450 mg, crude). LC-MS (ES+, m/z): 412.2 [$(M+H)^+$]. Rt=0.453 min.

Step 3: ethyl 1-((1R,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylate

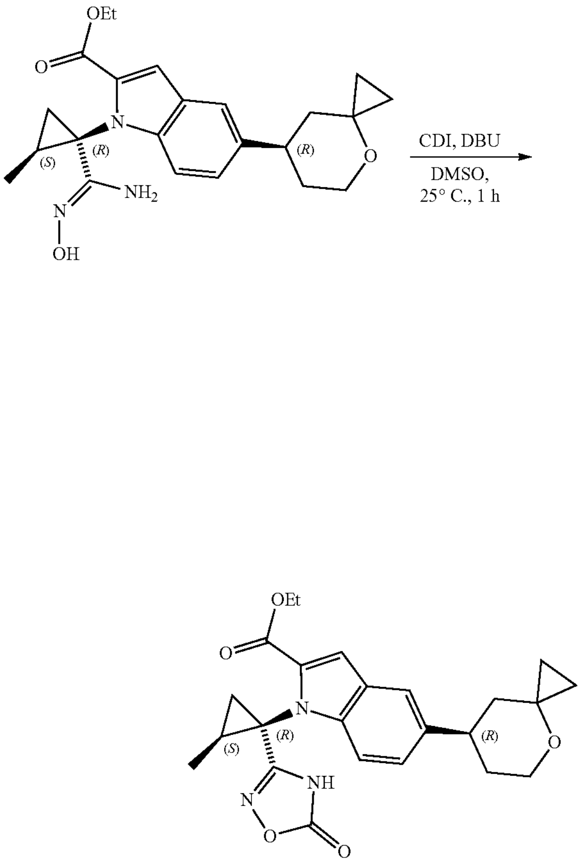

To a solution of ethyl 1-((1R,2S)-1-(N'-hydroxycarbamimidoyl)-2-methylcyclopropyl)-5-((R)-4-oxaspiro[2.5]octan-7-yl)-1H-indole-2-carboxylate (450.00 mg, 935.01 μmol, 1 eq) in DMSO (9 mL) was added CDI (303.22 mg, 1.87 mmol, 2 eq) and DBU (355.86 mg, 2.34 mmol, 352.34 μL, 2.5 eq). The mixture was stirred at 25° C. for 1 hour under $N_2$. LCMS indicated the reaction was completed. The mixture was added to $H_2O$ (20 mL) and then extracted with ethyl acetate (30 mL*3). The organic layers were combined, washed with water (20 mL*2), saturated brine (20 mL), dried over $Na_2SO_4$, filtered and concentrated in vacuo. The residue was purified by prep-TLC ($SiO_2$, hexanes:ethyl acetate=1:1) to give ethyl 1-((1R,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylate (360 mg, crude). LC-MS (ES+, m/z): 438.2 [$(M+H)^+$]. Rt=0.569 min.

Step 4: 1-((1R,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid

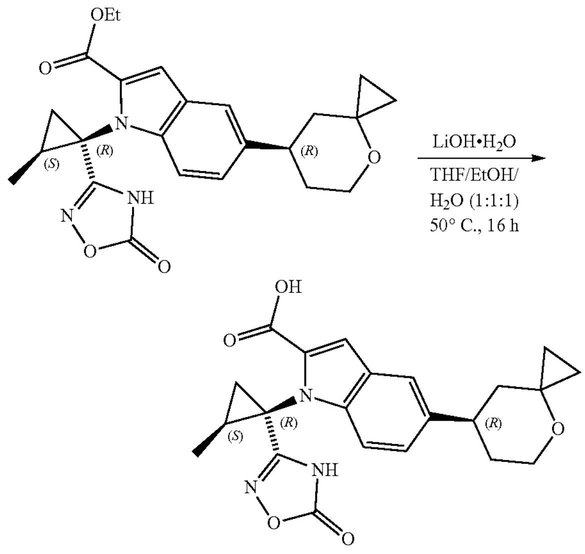

To a solution of ethyl 1-((1R,2S)-2-methyl-1-(5-oxo-4,5-dihydro-1,2,4-oxadiazol-3-yl) cyclopropyl)-5-((R)-4-oxaspiro[2.5]octan-7-yl)-1H-indole-2-carboxylate (360.00 mg, 822.88 µmol, 1 eq) in THF (1.2 mL), EtOH (1.2 mL) and $H_2O$ (1.2 mL) was added $LiOH{\cdot}H_2O$ (345.31 mg, 8.23 mmol, 10 eq). The mixture was stirred at 50° C. for 16 hours under $N_2$. LCMS indicated the reaction was completed. The mixture was dissolved in water (10 mL), adjusted to pH=4 with HCl (2M), and then extracted with DCM (20 mL*3). The organic layers were combined, washed with water (30 mL), saturated brine (30 mL), dried over $Na_2SO_4$, filtered and concentrated to give 1-((1R,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid (160 mg, crude). LC-MS (ES+, m/z): 410.1 [$(M+H)^+$]; Rt=7.884 min.

Intermediate 539-1

1-((1S,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid Scheme 539-1

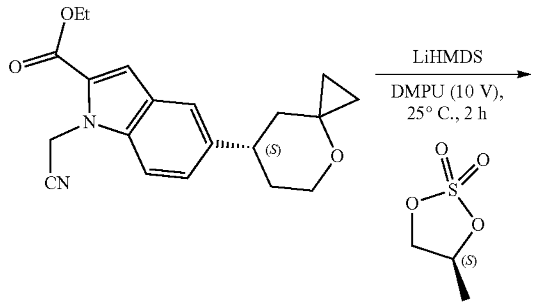

-continued

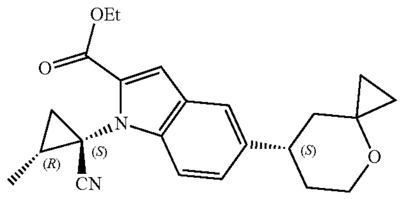

peak 1

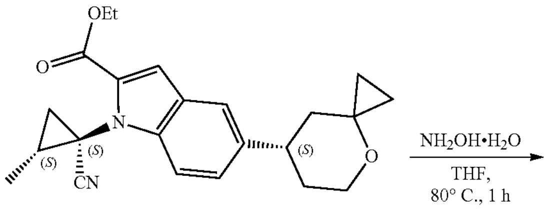

peak 2

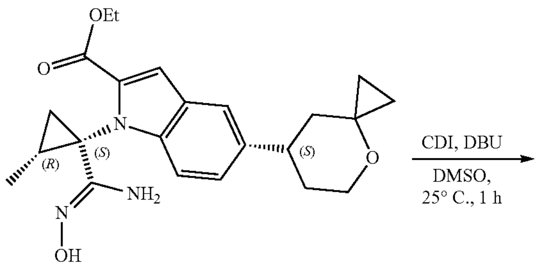

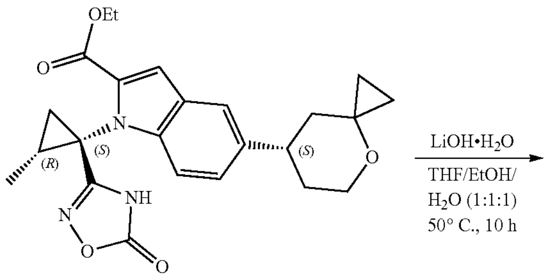

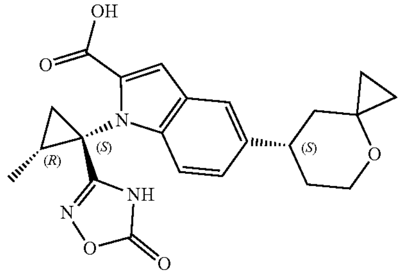

Step 1: ethyl 1-((1S,2R)-1-cyano-2-methylcyclopropyl)-5-((S)-4-oxaspiro[2.5]octan-7-yl)-1H-indole-2-carboxylate and ethyl 1-((1R,2R)-1-cyano-2-methylcyclopropyl)-5-((S)-4-oxaspiro[2.5]octan-7-yl)-1H-indole-2-carboxylate

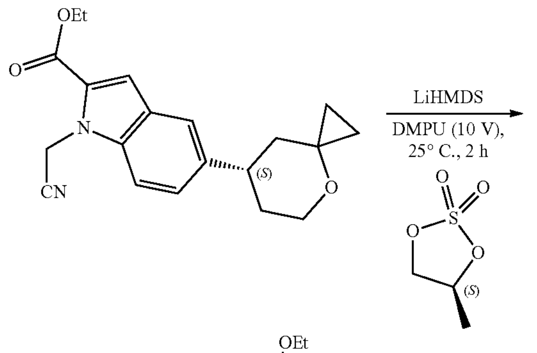

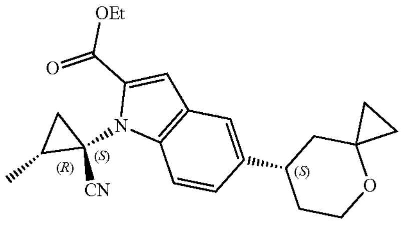

peak 1

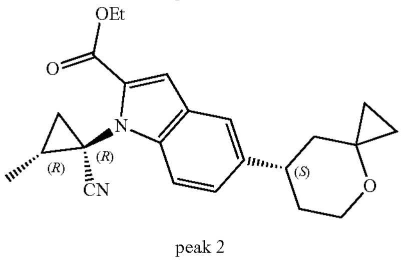

peak 2

To a solution of ethyl 1-(cyanomethyl)-5-[(7S)-4-oxaspiro[2.5]octan-7-yl]indole-2-carboxylate (2.00 g, 5.67 mmol, 1 eq), (4S)-4-methyl-1,3,2-dioxathiolane 2,2-dioxide (1.57 g, 11.35 mmol, 2 eq) in 1,3-dimethylhexahydropyrimidin-2-one (20 mL) was added LiHMDS (1 M, 22.70 mL, 4 eq) at 25° C. under $N_2$ (2 parallel reaction). The mixture was stirred at 25° C. for 2 hours under $N_2$ atmosphere. LCMS showed the reaction was completed. The reaction mixture was quenched by addition $NH_4Cl$ (100 mL) at 0° C., extracted with ethyl acetate (100 mL*3). The combined organic layers were washed with saturated brine (50 mL), dried over anhydrous $Na_2SO_4$, filtered and concentrated under reduced pressure. The residue was purified by prep-HPLC (column: Welch Ultimate XB—CN 250*50*10 um; mobile phase: [Heptane-EtOH (0.1% $NH_3H_2O$)]; B %: 12%, isocratic elution mode) to give ethyl 1-((1S,2R)-1-cyano-2-methylcyclopropyl)-5-((S)-4-oxaspiro[2.5]octan-7-yl)-1H-indole-2-carboxylate (peak 1, 350 mg, 879.48 μmol, 7.75% yield). LC-MS (ES+, m/z): 379.2 [(M+H)$^+$]; Rt=9.506 min And ethyl 1-((1R,2R)-1-cyano-2-methylcyclopropyl)-5-((S)-4-oxaspiro[2.5]octan-7-yl)-1H-indole-2-carboxylate (peak 2, 750 mg, 1.90 mmol, 16.70% yield) was obtained as a white solid. LC-MS (ES+, m/z): 379.2 [(M+H)$^+$]; Rt=9.664 min.: Step 2: ethyl 1-((1S,2R)-1-(N'-hydroxycarbamimidoyl)-2-methylcyclopropyl)-5-((S)-4-oxaspiro[2.5]octan-7-yl)-1H-indole-2-carboxylate

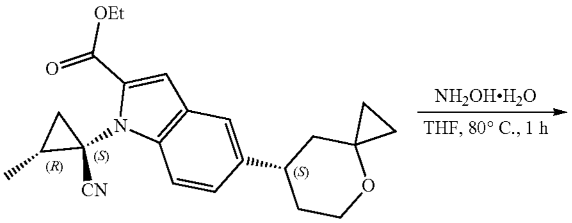

peak 1

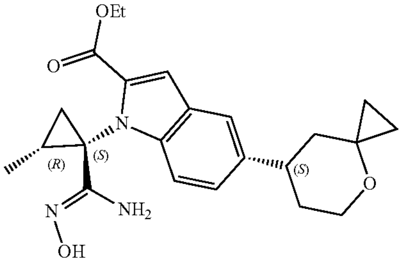

A mixture of ethyl 1-((1S,2R)-1-cyano-2-methylcyclopropyl)-5-((S)-4-oxaspiro[2.5]octan-7-yl)-1H-indole-2-carboxylate (350 mg, 879.48 μmol, 1 eq), hydroxylamine (580.98 mg, 8.79 mmol, 50% purity, 10 eq) in THF (3.5 mL) was stirred at 80° C. for 1 hour under $N_2$. LCMS showed the reaction was completed. The reaction mixture was quenched by addition $H_2O$ (100 mL), extracted with ethyl acetate (100 mL*3). The combined organic layers were washed with saturated brine (50 mL), dried over anhydrous $Na_2SO_4$, filtered and concentrated under reduced pressure to give ethyl 1-((1S,2R)-1-(N'-hydroxycarbamimidoyl)-2-methylcyclopropyl)-5-((S)-4-oxaspiro[2.5]octan-7-yl)-1H-indole-2-carboxylate (350 mg, 704.26 μmol, 80.08% yield). LC-MS (ES+, m/z): 412.2 [(M+H)$^+$]; Rt=0.444 min.

Step 3: ethyl 1-((1S,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate

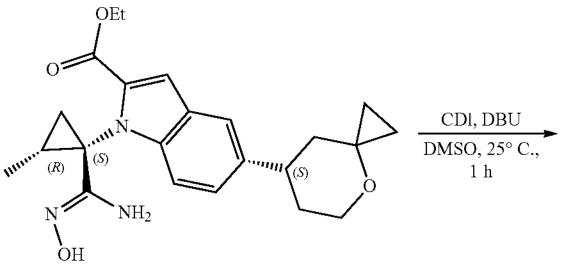

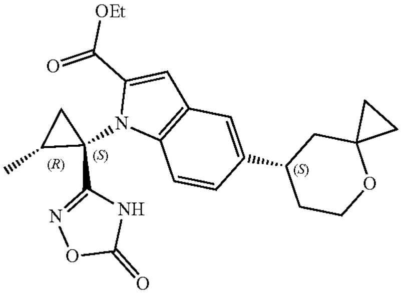

A mixture of ethyl 1-((1S,2R)-1-(N'-hydroxycarbamimidoyl)-2-methylcyclopropyl)-5-((S)-4-oxaspiro[2.5]octan- 7-yl)-1H-indole-2-carboxylate (350 mg, 704.26 μmol, 1 eq), CDI (228.39 mg, 1.41 mmol, 2 eq), DBU (268.04 mg, 1.76 mmol, 265.38 μL, 2.5 eq) in DMSO (7 mL) was stirred at 25° C. for 1 hour under $N_2$. LCMS showed the reaction was completed. The reaction mixture was quenched by addition $H_2O$ (100 mL), extracted with ethyl acetate (50 mL*3). The combined organic layers were washed with saturated brine (50 mL), dried over anhydrous $Na_2SO_4$, filtered and concentrated under reduced pressure. The residue was purified by prep-TLC ($SiO_2$, Commercial hexanes:ethyl acetate=1:1) to give ethyl 1-((1S,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate (250 mg, 537.73 μmol, 76.35% yield). LC-MS (ES+, m/z): 438.1 [(M+H)$^+$]; Rt=0.563 min.

Step 4: 1-((1S,2R)-2-methyl-1-(5-oxo-4,5-dihydro-1,2,4-oxadiazol-3-yl)cyclopropyl)-5-((S)-4-oxaspiro [2.5]octan-7-yl)-1H-indole-2-carboxylic acid

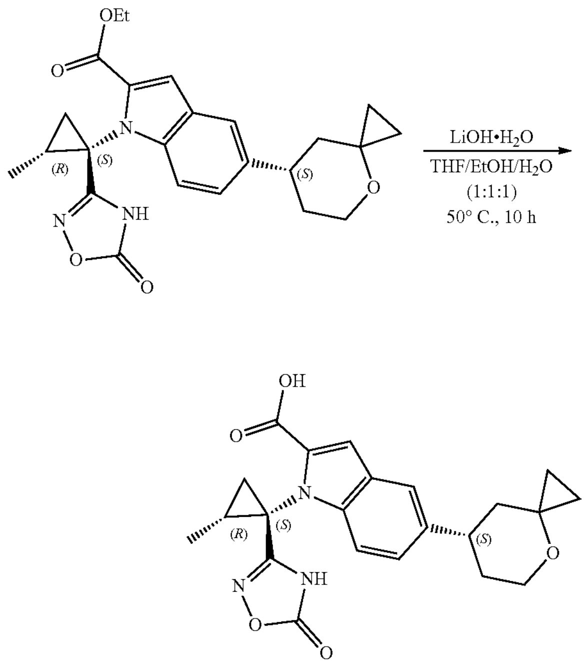

A mixture of ethyl 1-((1S,2R)-2-methyl-1-(5-oxo-4,5-dihydro-1,2,4-oxadiazol-3-yl) cyclopropyl)-5-((S)-4-oxaspiro [2.5]octan-7-yl)-1H-indole-2-carboxylate (250.00 mg, 537.73 μmol, 1 eq), LiOH·$H_2O$ (451.30 mg, 10.75 mmol, 20 eq) in EtOH (1 mL), THF (1 mL), $H_2O$ (1 mL) was stirred at 50° C. for 10 hours under $N_2$. LCMS showed the reaction was completed. The reaction mixture was quenched by addition $H_2O$ 50 (mL) and adjust to pH-4 by addition HCl (2 M), extracted with ethyl acetate (50 mL*3). The combined organic layers were washed with saturated brine (30 mL), dried over anhydrous $Na_2SO_4$, filtered and concentrated under reduced pressure to give 1-((1S,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (150 mg, 330.09 μmol, 61.39% yield). LC-MS (ES+, m/z): 410.1 [(M+H)$^+$]; Rt=0.493 min.

Intermediate 540-1

1-((1S,2R)-2-methyl-1-(5-oxo-4,5-dihydro-1,2,4-oxadiazol-3-yl)cyclopropyl)-5-((R)-4-oxaspiro[2.5] octan-7-yl)-1H-indole-2-carboxylic acid Scheme 540-1

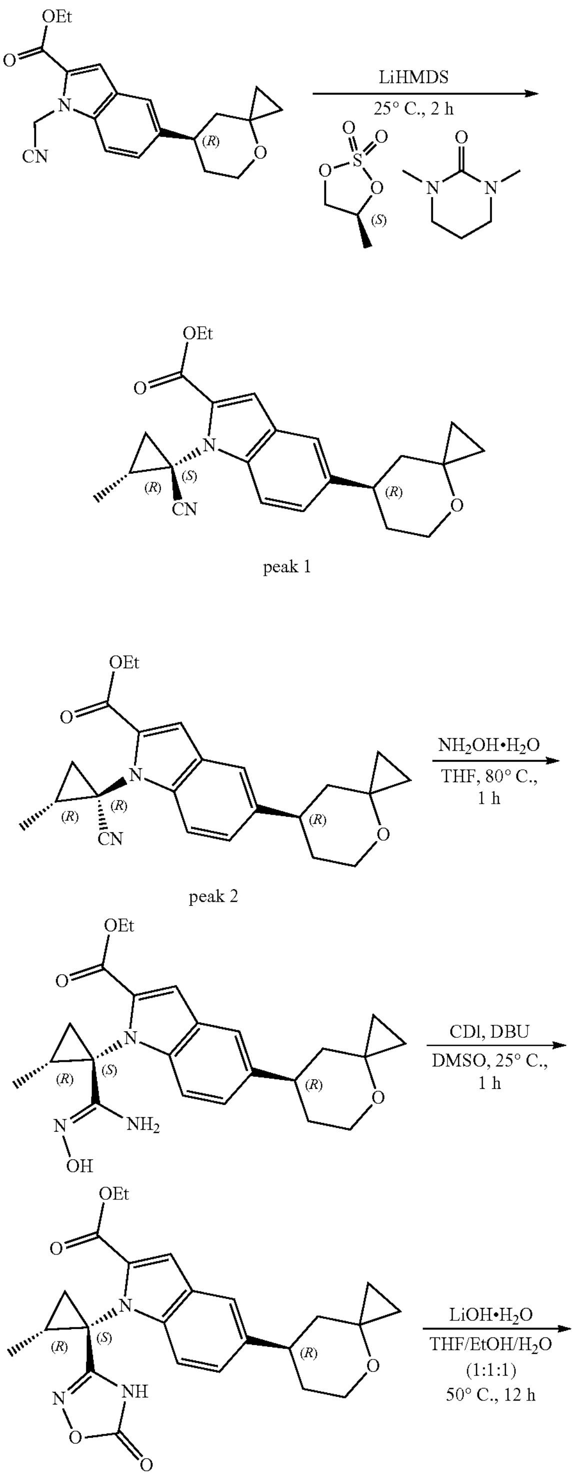

-continued

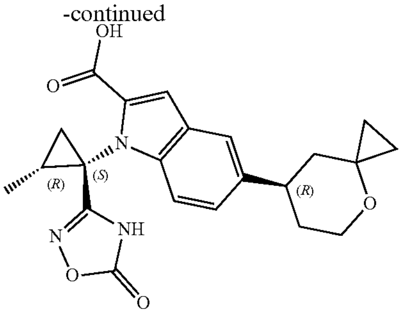

Step 1: ethyl 1-((1S,2R)-1-cyano-2-methylcyclopropyl)-5-((R)-4-oxaspiro[2.5]octan-7-yl)-1H-indole-2-carboxylate

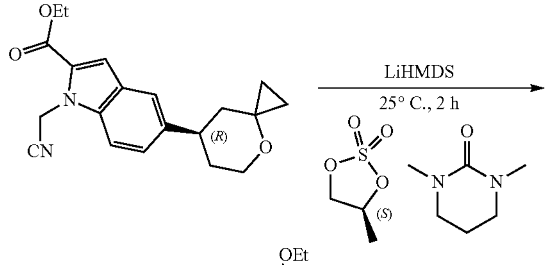

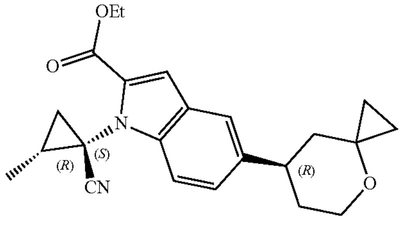

peak 1

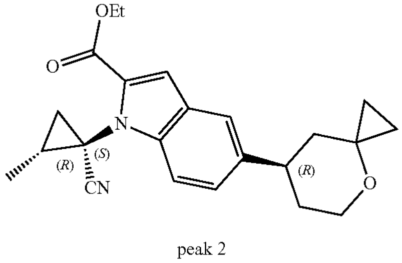

peak 2

To a solution of ethyl (R)-ethyl 1-(cyanomethyl)-5-(4-oxaspiro[2.5]octan-7-yl)-1H-indole-2-carboxylate (2 g, 5.91 mmol, 1 eq) and (4S)-4-methyl-1,3,2-dioxathiolane 2,2-dioxide (1.63 g, 11.82 mmol, 2 eq) in 1,3-dimethylhexahydropyrimidin-2-one (20 mL) was added LiHMDS (1 M, 23.64 mL, 4 eq). The mixture was stirred at 25° C. for 2 hours under $N_2$. LC-MS showed the reaction was completed. The reaction mixture was diluted with saturated $NH_4Cl$ (50 mL) and stirred for 1 hour, extracted with ethyl acetate (50 mL*3). The combined organic layers were washed with saturated brine (50 mL*2), dried over $Na_2SO_4$, filtered and concentrated in vacuo. The residue was purified by prep-HPLC (EtOH condition) column: Welch Ultimate XB—CN 250*50*10 um; mobile phase: [Heptane-EtOH]; B %: 5%, isocratic elution mode) to give ethyl 1-((1S,2R)-1-cyano-2-methylcyclopropyl)-5-((R)-4-oxaspiro[2.5]octan-7-yl)-1H- indole-2-carboxylate (peak 1, 720 mg, 1.86 mmol, 31.55% yield). LC-MS (ES+, m/z): 379.1 [$(M+H)^+$]; Rt=7.849 min.

And a mixture of peak 1: peak 2 (4:5) (1 g, 2.64 mmol, 44.71% yield). LC-MS Peak 1 (ES+, m/z): 379.1 [$(M+H)^+$]; Rt=7.849 min. Peak 2: LC-MS (ES+, m/z): 379.1. [$(M+H)^+$]; Rt=8.057 min.

Step 2: ethyl 1-((1S,2R)-1-(N'-hydroxycarbamimidoyl)-2-methylcyclopropyl)-5-((R)-4-oxaspiro[2.5]octan-7-yl)-1H-indole-2-carboxylate

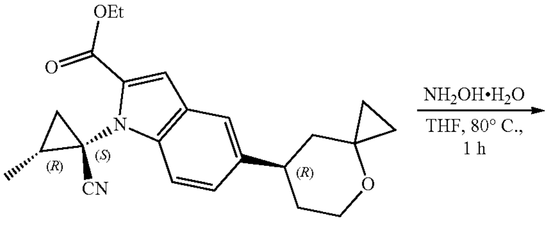

peak 1

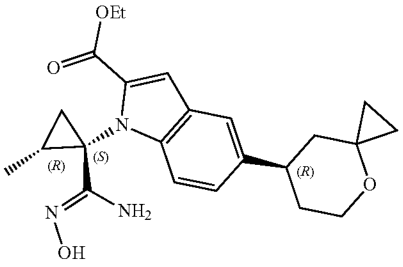

To a solution of ethyl 1-((1S,2R)-1-cyano-2-methylcyclopropyl)-5-((R)-4-oxaspiro[2.5]octan-7-yl)-1H-indole-2-carboxylate (0.7 g, 1.85 mmol, 1 eq) in THF (10 mL) was added hydroxylamine (1.22 g, 18.50 mmol, 10 eq). The mixture was stirred at 80° C. for 1 hour under $N_2$. LC-MS showed the reaction was completed. The reaction mixture was diluted with water (50 mL) and stirred for 1 hour, extracted with ethyl acetate (50 mL*3). The combined organic layers were washed with saturated brine (50 mL*2), dried over $Na_2SO_4$, filtered and concentrated in vacuo to give ethyl 1-((1S,2R)-1-(N'-hydroxycarbamimidoyl)-2-methylcyclopropyl)-5-((R)-4-oxaspiro[2.5]octan-7-yl)-1H-indole-2-carboxylate (0.6 g, 1.27 mmol, 68.59% yield). LC-MS (ES+, m/z): 412.2 [$(M+H)^+$]; Rt=0.456 min.

Step 3: ethyl 1-((1S,2R)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylate

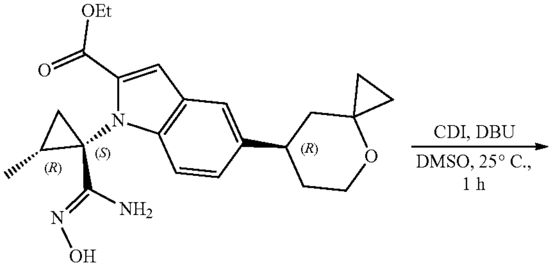

-continued

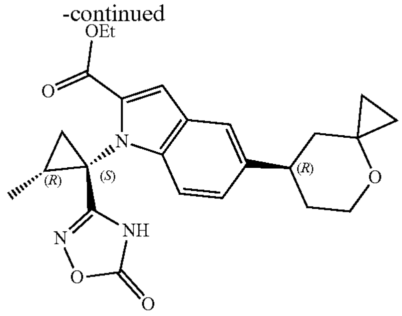

To a solution of ethyl 1-((1S,2R)-1-(N'-hydroxycarbamimidoyl)-2-methylcyclopropyl)-5-((R)-4-oxaspiro[2.5]octan-7-yl)-1H-indole-2-carboxylate (0.6 g, 1.46 mmol, 1 eq) in DMSO (6 mL) was added CDI (472.86 mg, 2.92 mmol, 2 eq) and DBU (554.95 mg, 3.65 mmol, 549.46 μL, 2.5 eq). The mixture was stirred at 25° C. for 1 hour under $N_2$. LC-MS showed the reaction was completed. The reaction mixture was diluted with water (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuo. The residue was purified by prep-TLC ($SiO_2$, DCM:MeOH=10:1) to give ethyl 1-((1S,2R)-2-methyl-1-(5-oxo-4,5-dihydro-1,2,4-oxadiazol-3-yl) cyclopropyl)-5-((R)-4-oxaspiro[2.5]octan-7-yl)-1H-indole-2-carboxylate (0.4 g, 908.83 μmol, 62.33% yield). LC-MS (ES+, m/z): 438.2 [(M+H)$^+$]; Rt=0.570 min.

Step 4: 1-((1S,2R)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid

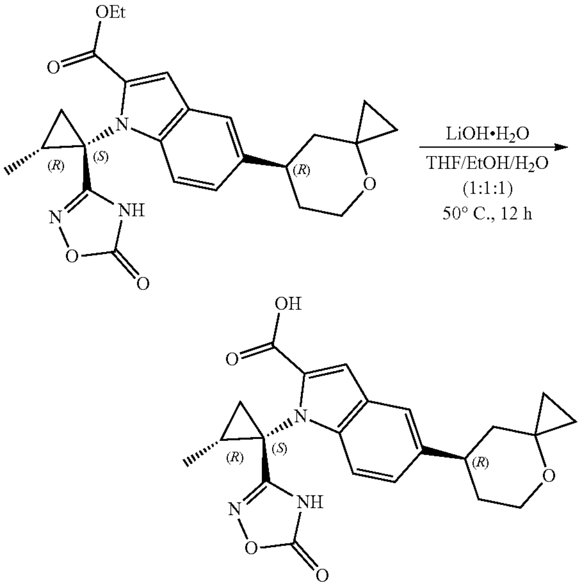

To a solution of ethyl 1-((1S,2R)-2-methyl-1-(5-oxo-4,5-dihydro-1,2,4-oxadiazol-3-yl) cyclopropyl)-5-((R)-4-oxaspiro[2.5]octan-7-yl)-1H-indole-2-carboxylate (400.00 mg, 914.31 μmol, 1 eq) in THF (2 mL) and EtOH (2 mL) and $H_2O$ (2 mL) was added LiOH·$H_2O$ (767.29 mg, 18.29 mmol, 20 eq). The mixture was stirred at 50° C. for 12 hours under $N_2$. LC-MS showed the reaction was completed. The reaction mixture was diluted with water (30 mL), and this was adjusted pH=4 with 1N HCl, extracted with ethyl acetate (50 mL*3). The combined organic layers were washed with saturated NaCl (50 mL*2). The combined organic layers were dried over $Na_2SO_4$, filtered and concentrated in vacuo to give 1-((1S,2R)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid (280 mg, 649.68 μmol, 71.06% yield). LC-MS (ES+, m/z): 410.1 [(M+H)$^+$]; Rt=0.500 min.

Intermediate 610-1 tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta[c]pyrazole-10-carboxylate

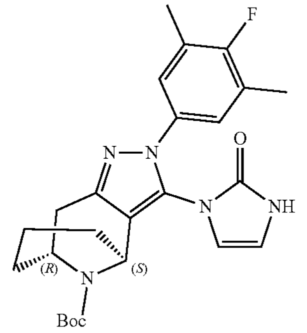

Scheme 610-1

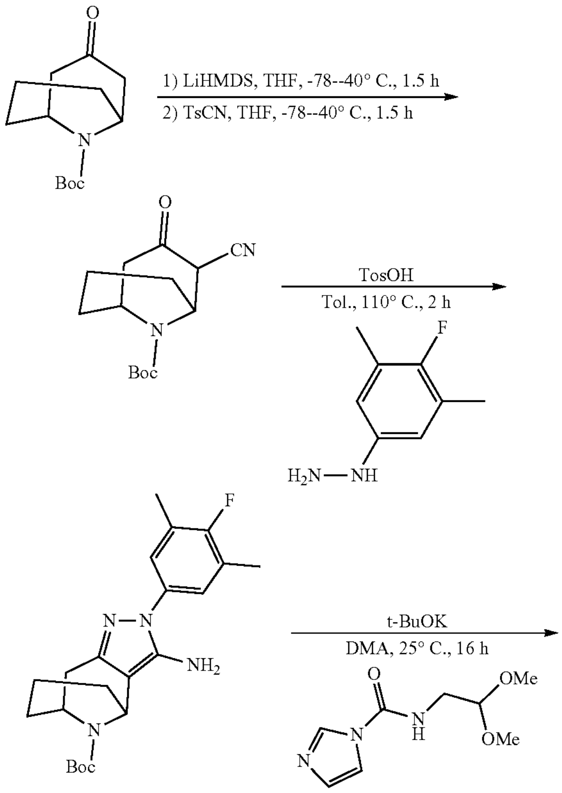

-continued

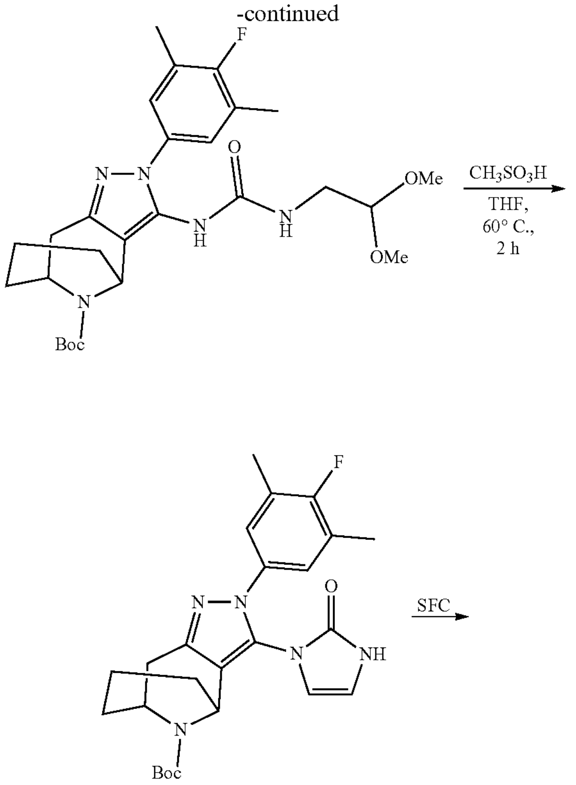

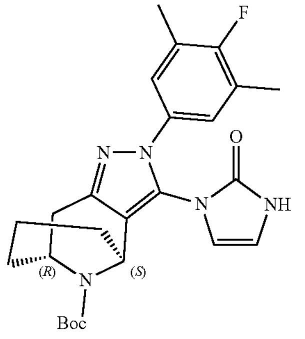

1st eluent

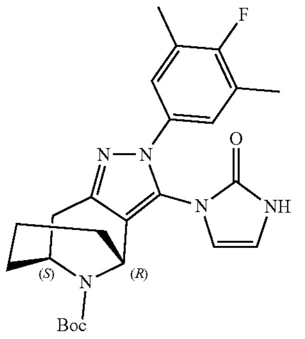

2nd eluent

Step 1: tert-butyl 2-cyano-3-oxo-9-azabicyclo[3.3.1] nonane-9-carboxylate

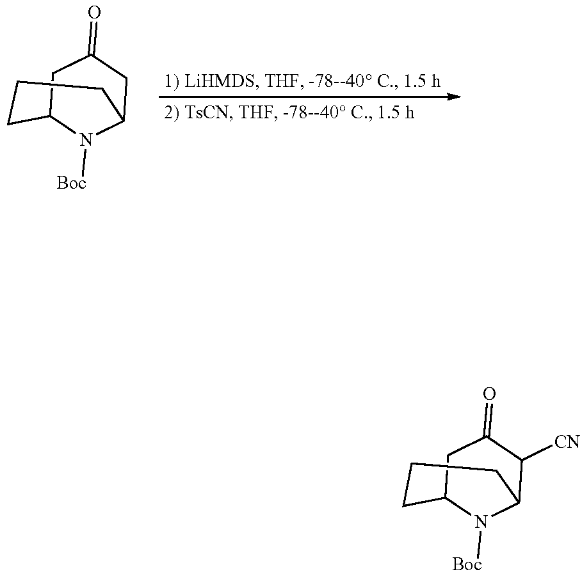

To a solution of tert-butyl 3-oxo-9-azabicyclo[3.3.1] nonane-9-carboxylate (110 g, 229.83 mmol, 1 eq) in THF (1100 mL) was added LiHMDS (1 M, 1011 mL, 2.2 eq) in dropwise at −78° C. under $N_2$. The mixture was stirred at −40° C. for 1.5 hours under $N_2$. Then added 4-methylbenzenesulfonyl cyanide (208.24 g, 574.57 mmol, 2.5 eq) in THF (220 mL) at −78° C. under $N_2$. The mixture was stirred at −40° C. for 1.5 hours. LCMS showed the reaction was completed. The reaction solution is quenched with saturated $NH_4Cl$ (3000 mL). The aqueous phase was extracted with ethyl acetate (3000 mL*3). The combined organic phase was washed with saturated brine (6000 mL), dried with anhydrous $Na_2SO_4$, filtered and concentrated in vacuo. The residue was purified by column chromatography ($SiO_2$, hexanes/ethyl acetate=10/1 to 0/1) to afford tert-butyl 2-cyano-3-oxo-9-azabicyclo[3.3.1]nonane-9-carboxylate (72 g, 266.95 mmol, 58.08% yield). LC-MS (ES-, m/z): 263.1 $[(M-H)^-]$. Rt=0.906 min.

Step 2: tert-butyl 3-amino-2-(4-fluoro-3,5-dimethylphenyl)-4,5,6,7,8,9-hexahydro-2H-4,8-epiminocycloocta [c]pyrazole-10-carboxylate

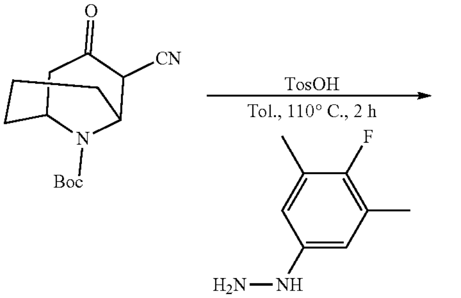

-continued

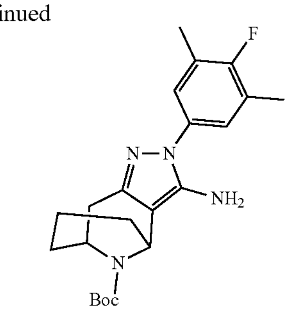

To a solution of tert-butyl 2-cyano-3-oxo-9-azabicyclo[3.3.1]nonane-9-carboxylate (72 g, 266.95 mmol, 1 eq) and (4-fluoro-3,5-dimethylphenyl) hydrazine (46.20 g, 293.64 mmol, 1.1 eq) in Tol. (720 mL) was added TosOH (4.60 g, 26.69 mmol, 0.1 eq) in one portion under $N_2$. The mixture was stirred at 110° C. for 2 hours. LCMS showed the reaction was completed. The reaction mixture was quenched by addition $H_2O$ (1000 mL), extracted with ethyl acetate (1000 mL*3). The combined organic layers were washed with saturated brine (2000 mL), dried over anhydrous $Na_2SO_4$, filtered and concentrated under reduced pressure. The residue was purified by column chromatography ($SiO_2$, hexanes/ethyl acetate=10/1 to 0/1) to afford tert-butyl 3-amino-2-(4-fluoro-3,5-dimethylphenyl)-4,5,6,7,8,9-hexahydro-2H-4,8-epiminocycloocta [c]pyrazole-10-carboxylate (73 g, 173.16 mmol, 64.87% yield). LC-MS (ES+, m/z): 401.2 [(M+H)$^+$]. Rt=1.442 min.

Step 3: tert-butyl 3-(3-(2,2-dimethoxyethyl) ureido)-2-(4-fluoro-3,5-dimethylphenyl)-4,5,7,8-tetrahydropyrazolo[3,4-d]azepine-6 (2H)-carboxylate

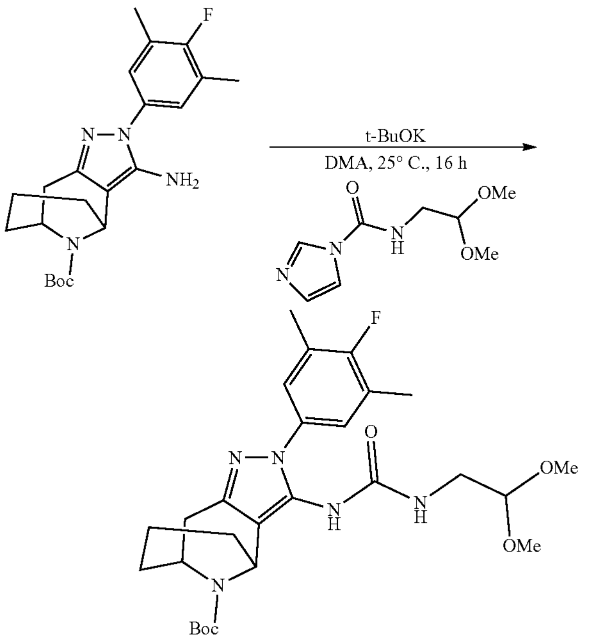

To a solution of tert-butyl 3-amino-2-(4-fluoro-3,5-dimethylphenyl)-4,5,6,7,8,9-hexahydro-2H-4,8-epiminocycloocta [c]pyrazole-10-carboxylate (53 g, 125.72 mmol, 1 eq) and N-(2,2-dimethoxyethyl)-1H-imidazole-1-carboxamide (50.09 g, 251.44 mmol, 2 eq) in DMA (530 mL) was added t-BuOK (70.54 g, 628.61 mmol, 5 eq) in one portion under $N_2$. The mixture was stirred at 25° C. for 16 hours. LCMS showed the reaction was completed. The reaction mixture was quenched by addition $H_2O$ (2000 mL), extracted with ethyl acetate (1000 mL*3). The combined organic layers were washed with saturated brine (2000 mL), dried over anhydrous $Na_2SO_4$, filtered and concentrated under reduced pressure. The residue was purified by column chromatography ($SiO_2$, hexanes/ethyl acetate=10/1 to 0/1) to afford tert-butyl 3-(3-(2,2-dimethoxyethyl) ureido)-2-(4-fluoro-3,5-dimethylphenyl)-4,5,7,8-tetrahydropyrazolo[3,4-d] azepine-6 (2H)-carboxylate (41 g, 75.58 mmol, 60.12% yield). LC-MS (ES+, m/z): 532.4 [(M+H)$^+$]. Rt=1.993 min.

Step 4: tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate

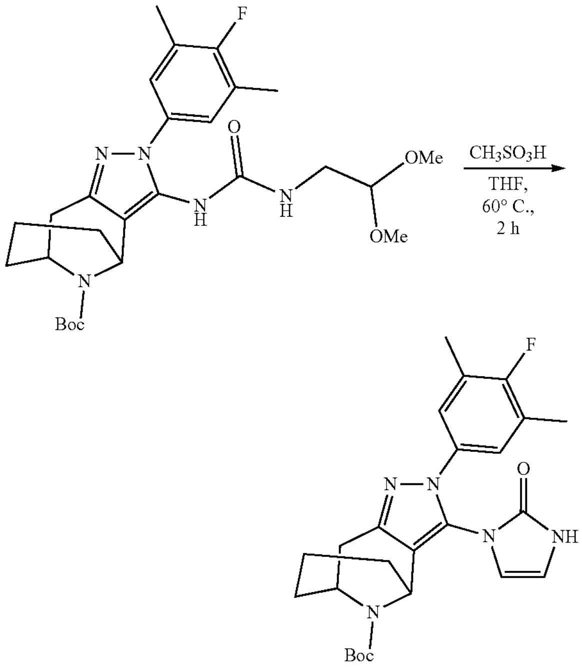

To a mixture of tert-butyl 3-(3-(2,2-dimethoxyethyl) ureido)-2-(4-fluoro-3,5-dimethylphenyl)-4,5,7,8-tetrahydropyrazolo[3,4-d]azepine-6 (2H)-carboxylate (41 g, 75.58 mmol, 1 eq) in THF (410 mL) was added $CH_3SO_3H$ (7.99 g, 83.14 mmol, 1.1 eq) in one portion under $N_2$. The mixture was stirred at 60° C. for 2 hours. LCMS showed the reaction was completed. The reaction mixture was quenched by addition $H_2O$ (400 mL), extracted with ethyl acetate (400 mL*3). The combined organic layers were washed with saturated brine (1000 mL), dried over anhydrous $Na_2SO_4$, filtered and concentrated under reduced pressure. The residue was purified by column chromatography ($SiO_2$, hexanes/ethyl acetate=3/1 to 0/1) to afford tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (23 g, 47.72 mmol, 63.14% yield). LC-MS. (ES+, m/z): 468.3 [(M+H)$^+$]. Rt=1.710 min.

Step 5: tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate & tert-butyl (4R,8S)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate

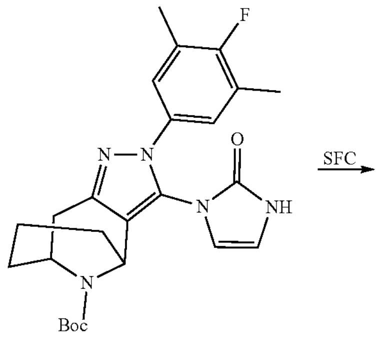

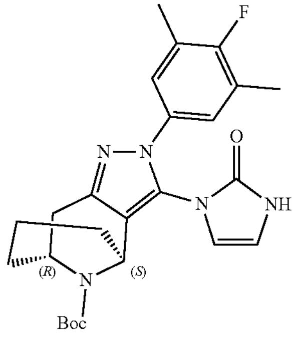

1st eluent

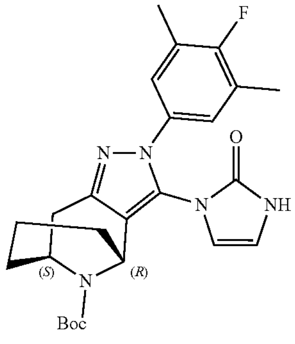

2nd eluent

The tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (23 g) was separated by SFC column: Daicel Chiralpak IM 250*50 mm i.d. 10 um; mobile phase: [$CO_2$-MeOH (0.1% $NH_3H_2O$)]; B %: 30%, isocratic elution mode to afford tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (1st eluent, RT=1.034 by SFC, 9.5 g, 19.91 mmol, 41.73% yield). LC-MS (ES+, m/z): 468.2 [$(M+H)^+$]. Rt=0.540 min.

And tert-butyl (4R,8S)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (2nd eluent, RT=1.161 by SFC, 9.5 g, 19.91 mmol, 41.73% yield) as yellow solid. LC-MS (ES+, m/z): 468.1 [$(M+H)^+$]. Rt=0.549 min.

Intermediate 615-1

5-(2, 2-dimethyltetrahydro-2H-pyran-4-yl)-7-fluoro-1-((1S,2S)-2-methyl-1-(5-oxo-4,5-dihydro-1, 2, 4-oxadiazol-3-yl)cyclopropyl)-1H-indole-2-carboxylic acid Scheme 615-1

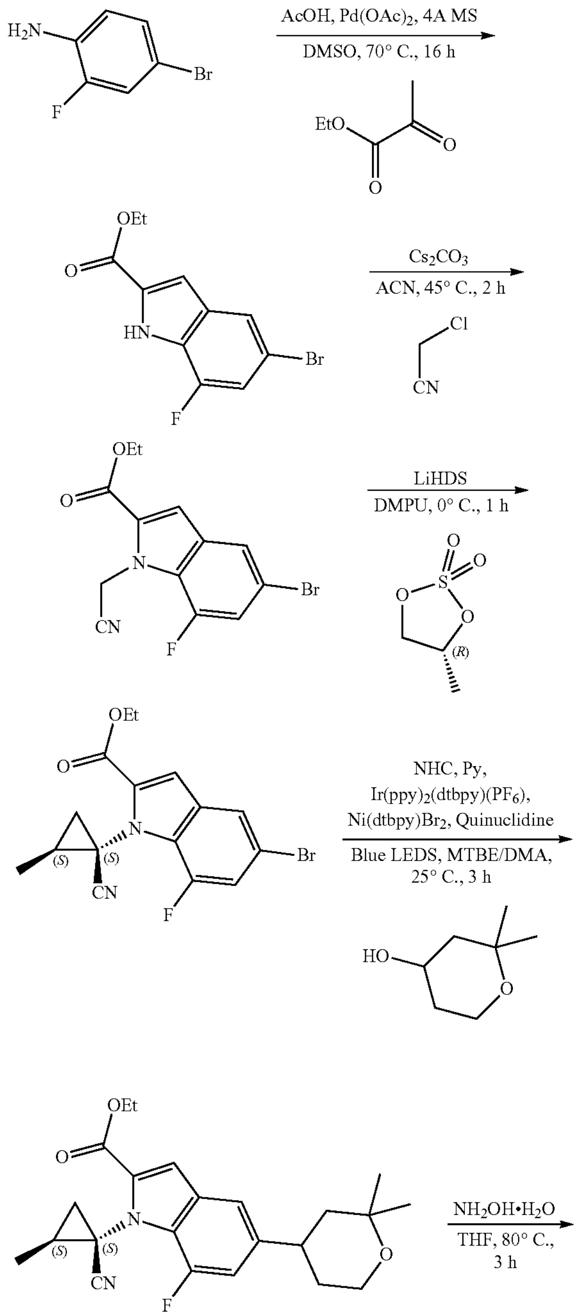

-continued

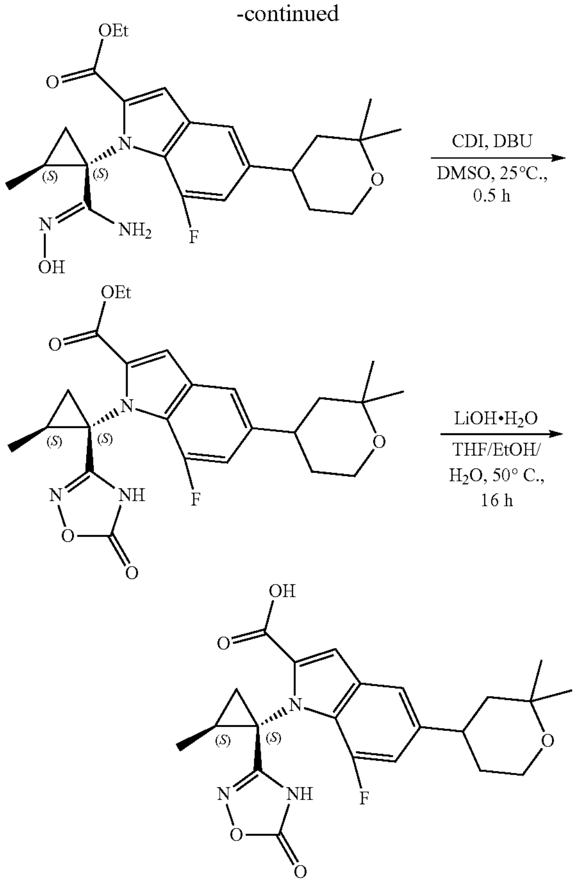

Step 1: ethyl 5-bromo-7-fluoro-1H-indole-2-carboxylate

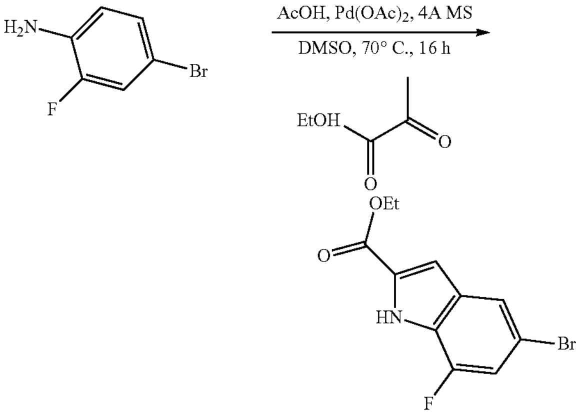

To a solution of 4-bromo-2-fluoroaniline (50 g, 263.14 mmol, 1 eq), ethyl 2-oxopropanoate (61.11 g, 526.28 mmol, 58.48 mL, 2 eq), 4A MS (50 g, 263.14 mmol, 1.00 eq) and AcOH (63.21 g, 1.05 mol, 60.26 mL, 4 eq) in DMSO (500 mL) was added $Pd(OAc)_2$ (5.91 g, 26.31 mmol, 0.1 eq). The mixture was stirred at 70° C. for 16 hours under $O_2$ of 15 Psi. LCMS showed the reaction was completed. The reaction mixture was filtered. The filtrate was poured into saturated EDTA solution (500 mL) and ethyl acetate (500 mL) stirred for 0.5 hour and then extracted with ethyl acetate (500 mL*2). The organic layers were combined, washed with water (1000 mL), saturated brine (1000 mL), dried over $Na_2SO_4$, filtered and concentrated in vacuo. The residue was purified by prep-HPLC column: Welch Xtimate C18 250*100 mm #10 um; mobile phase: [$H_2O$ (10 mM $NH_4HCO_3$)-ACN]; gradient: 45%-75% B over 20.0 min) to give ethyl 5-bromo-7-fluoro-1H-indole-2-carboxylate (5 g, 17.20 mmol, 6.54% yield). LC-MS (ES-, m/z): 284.0 [(M−H)$^-$]; Rt=1.357 min.

Step 2: ethyl 5-bromo-1-(cyanomethyl)-7-fluoro-1H-indole-2-carboxylate

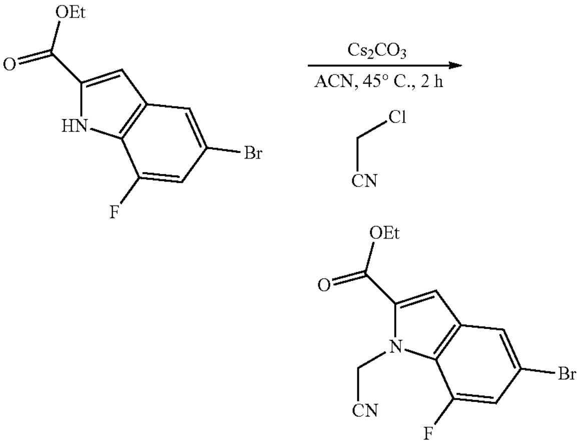

To a solution of ethyl 5-bromo-7-fluoro-1H-indole-2-carboxylate (4 g, 13.98 mmol, 1 eq) in ACN (40 mL) was added $Cs_2CO_3$ (13.67 g, 41.94 mmol, 3 eq), then was added 2-chloroacetonitrile (2.11 g, 27.96 mmol, 1.77 mL, 2 eq). The mixture was stirred at 45° C. for 2 hours under $N_2$. TLC showed the reaction was completed. The mixture was added dropwise to $H_2O$ (50 mL) and then extracted with DCM (50 mL*3). The organic layers were combined, washed with water (150 mL), saturated brine (150 mL), dried over $Na_2SO_4$, filtered and concentrated in vacuo. The crude product was purified by chromatography on silica gel (hexanes: Ethyl acetate=50/1-20/1) to give ethyl 5-bromo-1-(cyanomethyl)-7-fluoro-1H-indole-2-carboxylate (4 g, 12.27 mmol, 87.73% yield). $^1H$ NMR (400 MHz, DMSO-$d_6$) δ=7.95-7.77 (m, 1H), 7.68-7.55 (m, 1H), 7.52-7.38 (m, 1H), 5.90-5.66 (m, 2H), 4.55-4.32 (m, 2H), 1.50-1.33 (m, 3H).

Step 3: ethyl 5-bromo-1-((1S,2S)-1-cyano-2-methylcyclopropyl)-7-fluoro-1H-indole-2-carboxylate

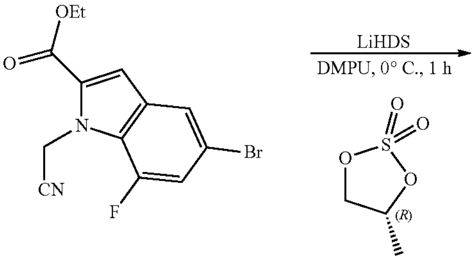

-continued

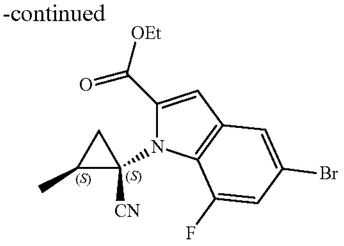

To a solution of ethyl 5-bromo-1-(cyanomethyl)-7-fluoro-1H-indole-2-carboxylate (2 g, 6.15 mmol, 1 eq) and (R)-4-methyl-1, 3, 2-dioxathiolane 2, 2-dioxide (2.55 g, 18.45 mmol, 3 eq) in DMPU (20 mL) was added LiHMDS (1 M, 24.61 mL, 4 eq) at 0° C. under $N_2$. The mixture was stirred at 0° C. for 1 hour under $N_2$. LCMS showed the reaction was completed. The mixture was added dropwise to $NH_4Cl$ (50 mL) and then extracted with ethyl acetate (50 mL*3). The organic layers were combined, washed with water (150 mL), saturated brine (150 mL), dried over $Na_2SO_4$, filtered and concentrated in vacuo. The residue was purified by column chromatography ($SiO_2$, hexanes/ethyl acetate=50/1 to 20/1). The enriched product was further purified by prep-HPLC column: Welch Ultimate XB—CN 250*50*10 um; mobile phase: [Heptane-EtOH]; gradient: 5%-25% B over 10.0 min) to give ethyl 5-bromo-1-((1S,2S)-1-cyano-2-methylcyclopropyl)-7-fluoro-1H-indole-2-carboxylate (600 mg, 1.62 mmol, 26.42% yield). LC-MS (ES+, m/z): 365.0 [$(M+H)^+$]; Rt=9.775 min.

Step 4: ethyl 1-((1S,2S)-1-cyano-2-methylcyclopropyl)-5-(2, 2-dimethyltetrahydro-2H-pyran-4-yl)-7-fluoro-1H-indole-2-carboxylate

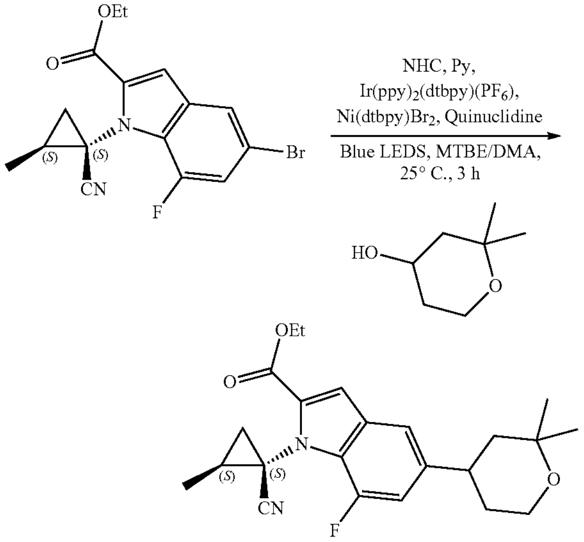

A mixture of NHC (1.04 g, 2.63 mmol, 1.6 eq) and 2, 2-dimethyltetrahydro-2H-pyran-4-ol (374.30 mg, 2.88 mmol, 1.75 eq) in MTBE (6 mL) was stirred at 25° C. for 30 min under $N_2$. A solution of Py (207.93 mg, 2.63 mmol, 212.17 µL, 1.6 eq) in MTBE (6 mL) was added dropwise to the above reaction mixture at 25° C. The reaction mixture was stirred at 25° C. for 30 min under $N_2$. Filter and collect the filtrate. The filtrate was transferred into a solution of ethyl 5-bromo-1-((1S,2S)-1-cyano-2-methylcyclopropyl)-7-fluoro-1H-indole-2-carboxylate (600 mg, 1.64 mmol, 1 eq), $Ir(ppy)_2$ (dtbpy) $(PF_6)$ (24.30 mg, 24.64 µmol, 0.015 eq), quinuclidine (319.67 mg, 2.88 mmol, 1.75 eq) and Ni (dtbpy) $Br_2$ (40.00 mg, 82.15 µmol, 0.05 eq) in DMA (6 mL) at 25° C. The reaction mixture at 25° C. under blue LEDs (450 nm, 520 W) for 2 hours. LCMS showed the reaction was completed. The mixture was added dropwise to $H_2O$ (30 mL) and then extracted with ethyl acetate (30 mL*3). The organic layers were combined, washed with water (100 mL), saturated brine (100 mL), dried over $Na_2SO_4$, filtered and concentrated in vacuo. The crude product was purified by chromatography on silica gel (Commercial hexanes:ethyl acetate=50/1-20/1) to give ethyl 1-((1S,2S)-1-cyano-2-methylcyclopropyl)-5-(2, 2-dimethyltetrahydro-2H-pyran-4-yl)-7-fluoro-1H-indole-2-carboxylate (300 mg, 700.93 µmol, 42.66% yield). LC-MS (ES+, m/z): 399.2 [$(M+H)^+$]; Rt=0.640 min.

Step 5: ethyl 5-(2, 2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate

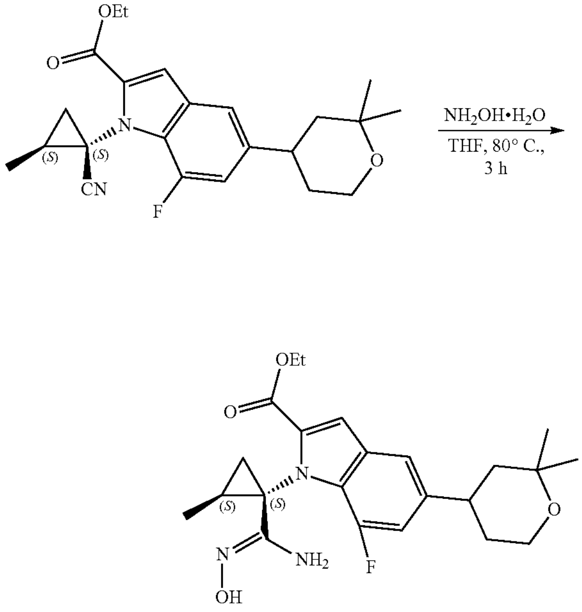

To a solution of ethyl 1-((1S,2S)-1-cyano-2-methylcyclopropyl)-5-(2, 2-dimethyltetrahydro-2H-pyran-4-yl)-7-fluoro-1H-indole-2-carboxylate (300 mg, 752.88 µmol, 1 eq) in THF (3 mL) was added $NH_2OH{\cdot}H_2O$ (497.35 mg, 7.53 mmol, 50% purity, 10 eq). The mixture was stirred at 80° C. for 3 hours under $N_2$. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated to give ethyl 5-(2, 2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate (300 mg, crude). LC-MS (ES+, m/z): 432.3 [$(M+H)^+$]; Rt=0.456 min.

Step 6: ethyl 5-(2, 2-dimethyltetrahydro-2H-pyran-4-yl)-7-fluoro-1-((1S,2S)-2-methyl-1-(5-oxo-4, 5-dihydro-1, 2, 4-oxadiazol-3-yl)cyclopropyl)-1H-indole-2-carboxylate

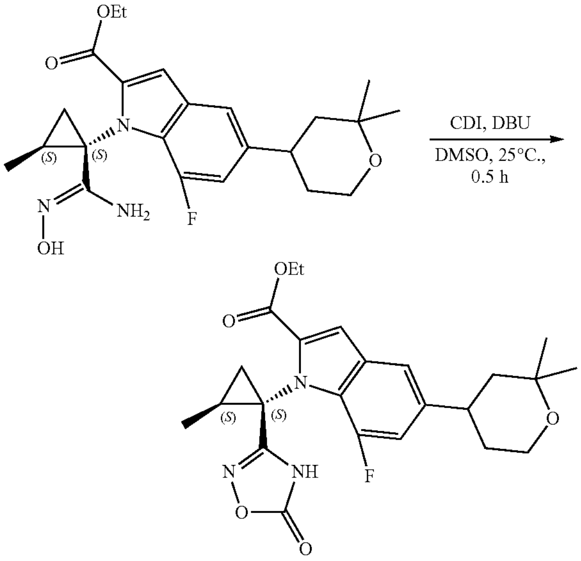

To a solution of ethyl 5-(2, 2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate (300 mg, 695.25 μmol, 1 eq) in DMSO (3 mL) was added CDI (225.47 mg, 1.39 mmol, 2 eq) and DBU (264.61 mg, 1.74 mmol, 261.99 μL, 2.5 eq). The mixture was stirred at 25° C. for 0.5 hour under $N_2$. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated in vacuo. The residue was purified by prep-TLC ($SiO_2$, Commercial hexanes/ethyl acetate=1/1) to give ethyl 5-(2, 2-dimethyltetrahydro-2H-pyran-4-yl)-7-fluoro-1-((1S, 2S)-2-methyl-1-(5-oxo-4,5-dihydro-1, 2, 4-oxadiazol-3-yl) cyclopropyl)-1H-indole-2-carboxylate (200 mg, 378.15 μmol, 54.39% yield). LC-MS (ES+, m/z): 458.2 [$(M+H)^+$]; Rt=0.614 min.

Step 7: 5-(2, 2-dimethyltetrahydro-2H-pyran-4-yl)-7-fluoro-1-((1S,2S)-2-methyl-1-(5-oxo-4,5-dihydro-1, 2, 4-oxadiazol-3-yl)cyclopropyl)-1H-indole-2-carboxylic acid

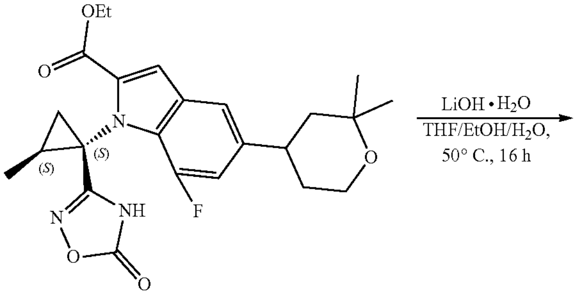

-continued

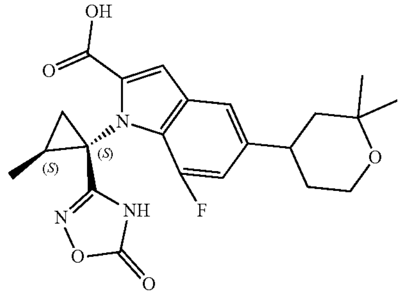

To a solution of ethyl 5-(2, 2-dimethyltetrahydro-2H-pyran-4-yl)-7-fluoro-1-((1S,2S)-2-methyl-1-(5-oxo-4,5-dihydro-1, 2, 4-oxadiazol-3-yl)cyclopropyl)-1H-indole-2-carboxylate (200 mg, 437.16 μmol, 1 eq) in THF (0.7 mL), EtOH (0.7 mL) and $H_2O$ (0.7 mL) was added $LiOH{\cdot}H_2O$ (183.45 mg, 4.37 mmol, 10 eq). The mixture was stirred at 50° C. for 16 hours under $N_2$. LCMS showed the reaction was completed. The mixture was concentrated in vacuo. The residue was dissolved in water (10 mL), adjusted to pH=4 with HCl (2 M), and then extracted with DCM (15 mL*3). The organic layers were combined, washed with water (50 mL), saturated brine (50 mL), dried over $Na_2SO_4$, filtered and concentrated to give 5-(2, 2-dimethyltetrahydro-2H-pyran-4-yl)-7-fluoro-1-((1S,2S)-2-methyl-1-(5-oxo-4, 5-dihydro-1, 2, 4-oxadiazol-3-yl)cyclopropyl)-1H-indole-2-carboxylic acid (150 mg, crude). LC-MS (ES+, m/z): 430.1 [$(M+H)^+$]; Rt=0.526 min.

Intermediate 617-1 tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate Scheme 617-1

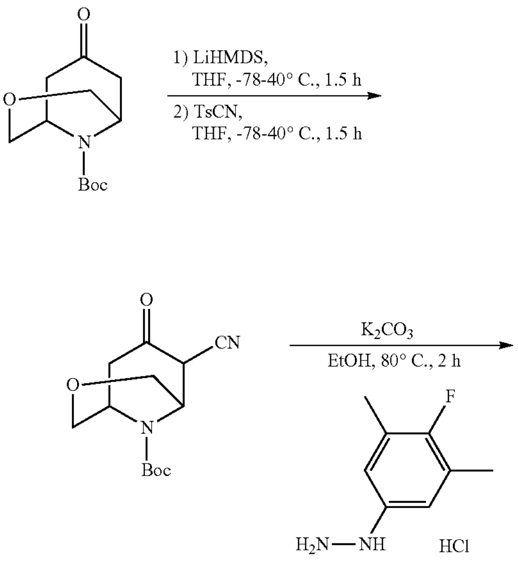

-continued

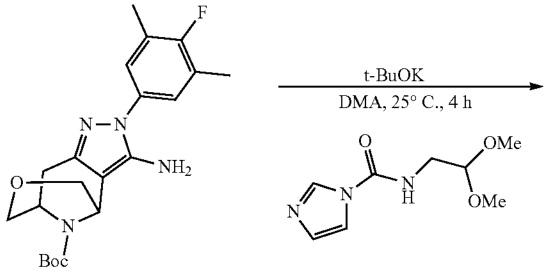

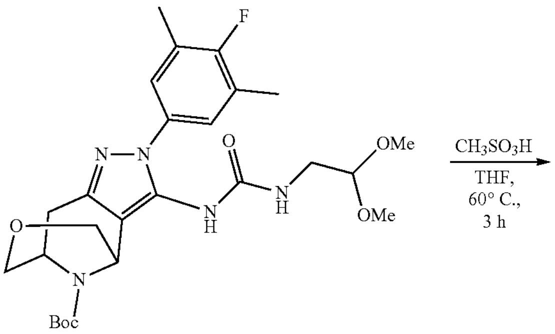

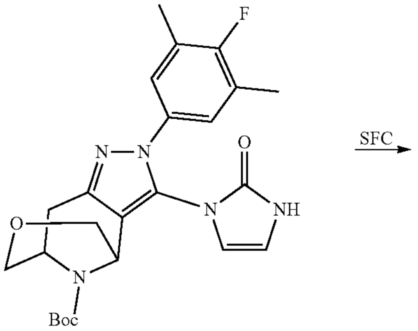

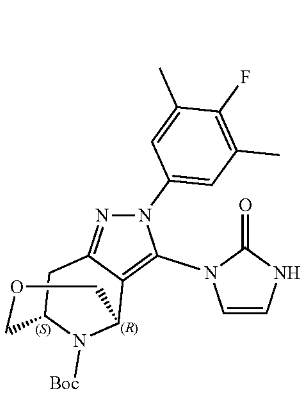

1st eluent

-continued

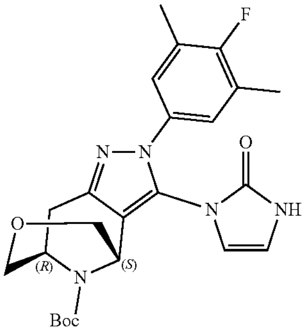

2nd eluent

Intermediate 617-1

Step 1: tert-butyl 6-cyano-7-oxo-3-oxa-9-azabicyclo [3.3.1]nonane-9-carboxylate

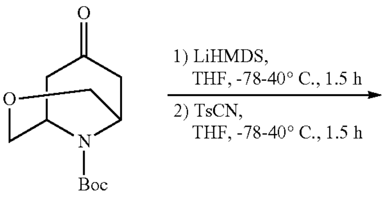

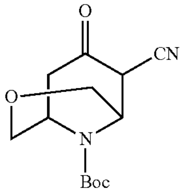

To a mixture of tert-butyl 7-oxo-3-oxa-9-azabicyclo [3.3.1]nonane-9-carboxylate (40 g, 165.78 mmol, 1 eq) in THF (400 mL) was added LiHMDS (1 M, 364.72 mL, 2.2 eq) dropwise at −78° C. under $N_2$. The mixture was stirred at −40° C. for 1.5 hours, and then TsCN (66.09 g, 364.72 mmol, 2.2 eq) in THF (80 mL) at −78° C. under $N_2$. The mixture was stirred at −40° C. for 1.5 hours. LCMS showed the reaction was completed. The residue was poured into water (2000 mL). The aqueous phase was extracted with ethyl acetate (1000 mL*3). Then the mixture was adjusted to pH=7 with 10% AcOH solution (45 mL), the aqueous phase was extracted with ethyl acetate (1000 mL*3). The combined organic phase was washed with saturated brine (2000 mL), dried with anhydrous $Na_2SO_4$, filtered and concentrated in vacuo to give tert-butyl 6-cyano-7-oxo-3-oxa-9-azabicyclo[3.3.1]nonane-9-carboxylate (41 g, crude). LC-MS (ES−, m/z): 265.1 [$(M-H)^-$]; Rt=0.749 min.

Step 2: tert-butyl 3-amino-2-(4-fluoro-3,5-dimethylphenyl)-2,4,5,7,8,9-hexahydro-4,8-epiminooxocino [5,4-c]pyrazole-10-carboxylate

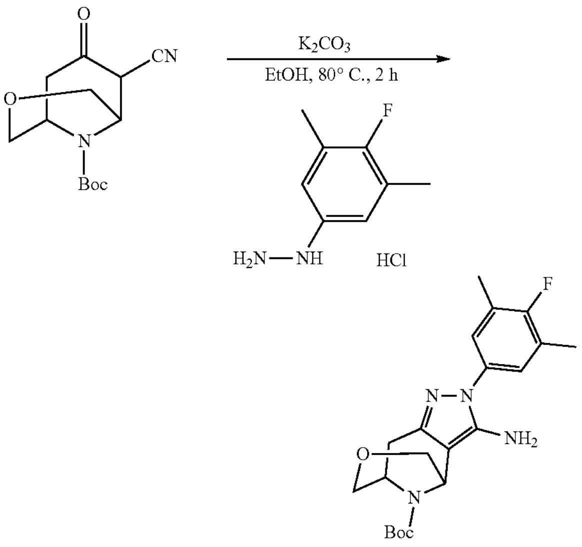

To a mixture of tert-butyl 6-cyano-7-oxo-3-oxa-9-azabicyclo[3.3.1]nonane-9-carboxylate (41 g, 135.49 mmol, 1 eq) and (4-fluoro-3, 5-dimethylphenyl) hydrazine (28.41 g, 149.04 mmol, 1.1 eq, HCl) in EtOH (410 mL) was added $K_2CO_3$ (20.60 g, 149.04 mmol, 1.1 eq) under $N_2$. The mixture was stirred at 80° C. for 2 hours under $N_2$. LCMS showed the reaction was completed. The residue was poured into water (1000 mL). The aqueous phase was extracted with ethyl acetate (500 mL*3). The combined organic phase was washed with saturated brine (500 mL), dried with anhydrous $Na_2SO_4$, filtered and concentrated in vacuo. The residue was purified by column chromatography ($SiO_2$, Petroleum ether/ethyl acetate=20/1 to 5/1) to give tert-butyl 3-amino-2-(4-fluoro-3,5-dimethylphenyl)-2,4,5,7,8,9-hexahydro-4,8-epiminooxocino [5,4-c]pyrazole-10-carboxylate (31 g, 76.26 mmol, 56.28% yield). LC-MS (ES+, m/z): 403.3 [$(M+H)^+$]; Rt=0.431 min.

Step 3: tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate

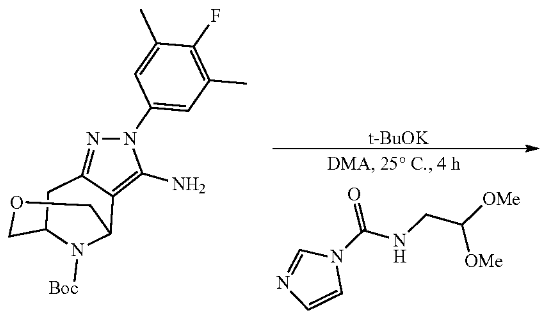

-continued

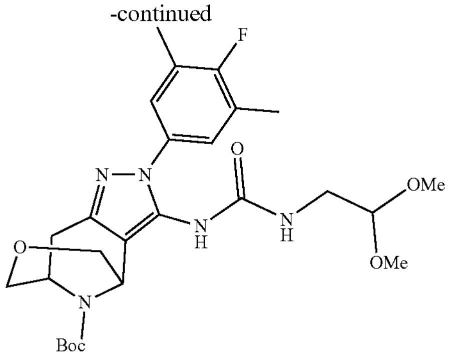

To a mixture of tert-butyl 3-amino-2-(4-fluoro-3,5-dimethylphenyl)-2,4,5,7,8,9-hexahydro-4,8-epiminooxocino [5,4-c]pyrazole-10-carboxylate (31 g, 76.26 mmol, 1 eq) and N-(2,2-dimethoxyethyl)-1H-imidazole-1-carboxamide (30.38 g, 152.51 mmol, 2 eq) in DMA (310 mL) was added t-BuOK (42.78 g, 381.28 mmol, 5 eq) in one portion at 25° C. under $N_2$. The mixture was stirred at 25° C. for 4 hours under $N_2$. LCMS showed the reaction was completed. The residue was poured into water (1000 mL). The aqueous phase was extracted with ethyl acetate (500 mL*3). The combined organic phase was washed with saturated brine (1000 mL), dried with anhydrous $Na_2SO_4$, filtered and concentrated in vacuo. The residue was purified by column chromatography ($SiO_2$, Petroleum ether/ethyl acetate=20/1 to 1/1) to give tert-butyl 3-(3-(2,2-dimethoxyethyl) ureido)-2-(4-fluoro-3,5-dimethylphenyl)-2,4,5,7,8,9-hexahydro-4, 8-epiminooxocino [5,4-c]pyrazole-10-carboxylate (31 g, 56.94 mmol, 74.66% yield): LC-MS (ES+, m/z): 534.3 [$(M+H)^+$]. Rt=0.508 min.

Step 4: tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate

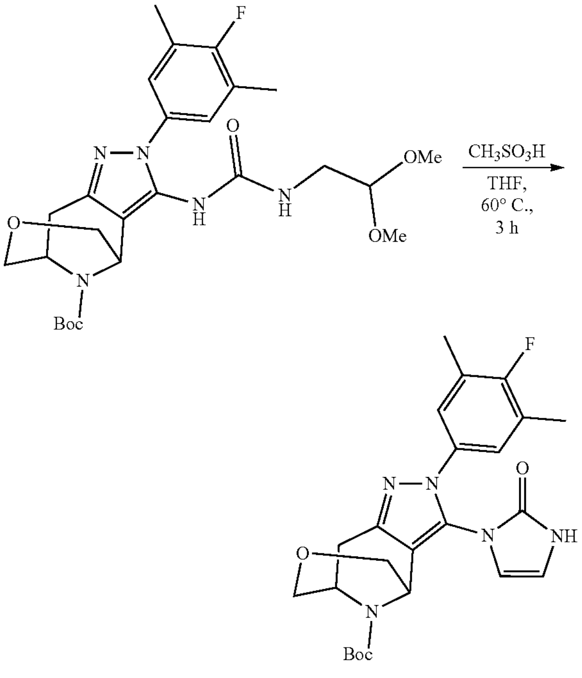

To a mixture of tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate (8 g, 13.64 mmol, 1 eq) in THF (80 mL) was added $CH_3SO_3H$ (1.97 g, 20.47 mmol, 1.5 eq) in one portion under $N_2$. The mixture was stirred at 60° C. for 3 hours under $N_2$. LCMS showed the reaction was completed. The residue was poured into water (200 mL). The aqueous phase was extracted with ethyl acetate (100 mL*3). The combined organic phase was washed with saturated brine (300 mL), dried with anhydrous $Na_2SO_4$, filtered and concentrated in vacuo to give tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (4.5 g, crude). LC-MS (ES+, m/z): 470.3 [(M+H)$^+$]. Rt=1.521 min.

Step 5: tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c] pyrazole-10-carboxylate & tert-butyl (4S,8R)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate

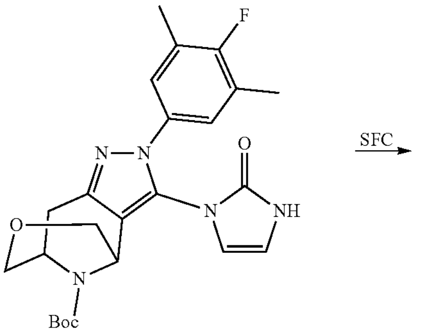

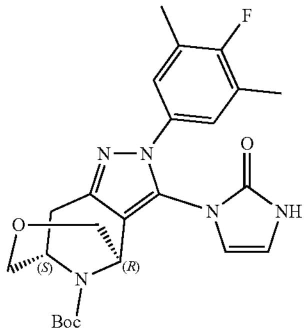

1$^{st}$ eluent

-continued

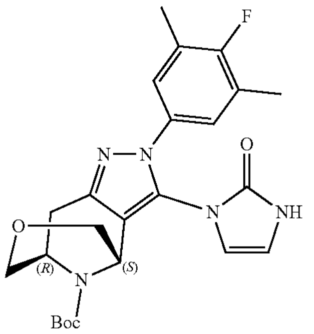

2$^{nd}$ eluent

The residue tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (500 mg, crude) was purified by SFC (column: Daicel ChiralPak IM (250*25 mm i.d. 10 um); mobile phase: [$CO_2$-MeOH (0.1% $NH_3H_2O$)]; B %: 25%, isocratic elution mode) to give tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (1st eluent, RT=1.116 by SFC, 200 mg, 404.68 μmol, 82.61% yield).

And tert-butyl (4S,8R)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (2$^{nd}$ eluent, RT=1.245 by SFC, 100 mg, 202.34 μmol, 41.30% yield).

Intermediate 707-1

5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid Scheme 707-1

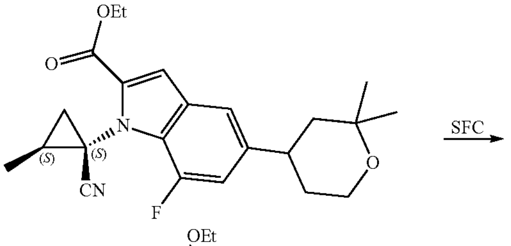

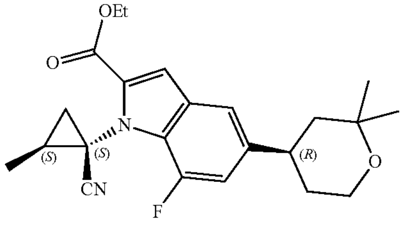

1$^{st}$ eluent

-continued

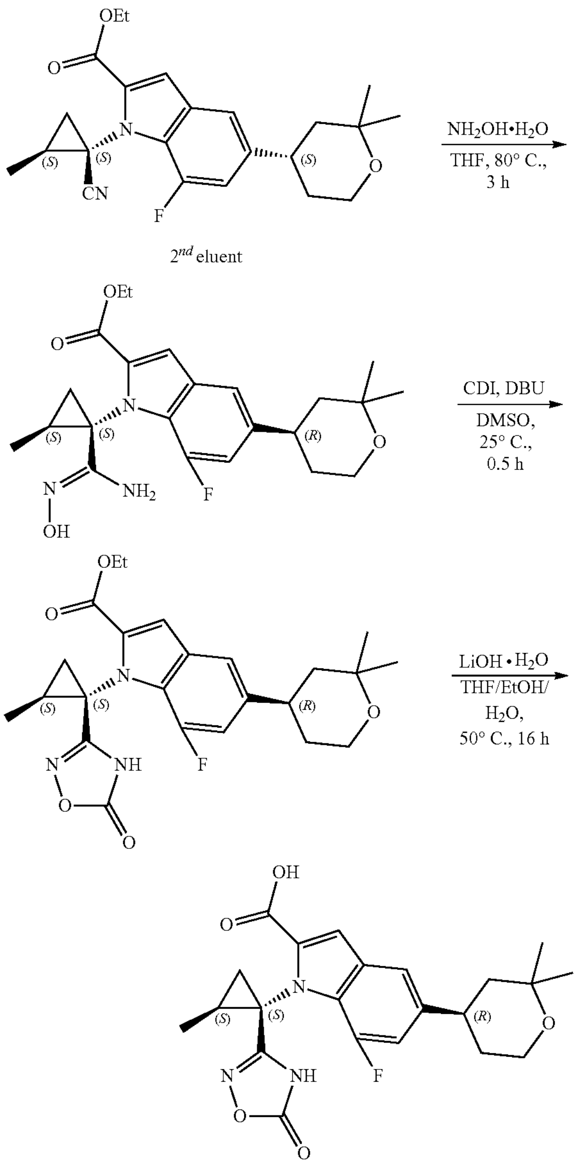

Step 1: ethyl 1-((1S,2S)-1-cyano-2-methylcyclopropyl)-5-((R)-2,2-dimethyltetrahydro-2H-pyran-4-yl)-7-fluoro-1H-indole-2-carboxylate & ethyl 1-((1S,2S)-1-cyano-2-methylcyclopropyl)-5-((S)-2,2-dimethyltetrahydro-2H-pyran-4-yl)-7-fluoro-1H-indole-2-carboxylate

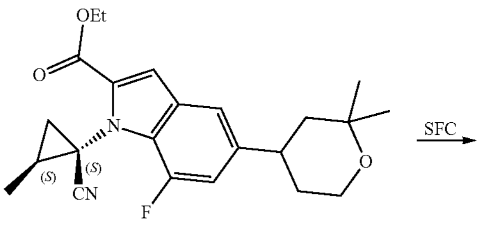

-continued

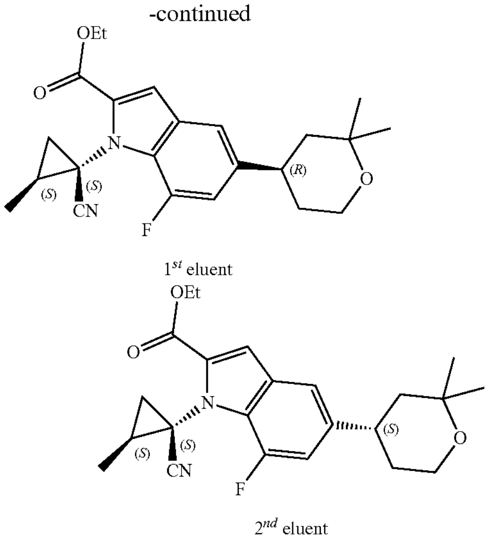

The compound ethyl 1-((1S,2S)-1-cyano-2-methylcyclopropyl)-5-(2, 2-dimethyltetrahydro-2H-pyran-4-yl)-7-fluoro-1H-indole-2-carboxylate (1.8 g, 4.52 mmol, 1 eq) was purified by SFC separation column: DAICEL CHIRALPAK IG (250 mm*50 mm, 10 um); mobile phase: [$CO_2$-MeOH]; B %: 45%, isocratic elution mode) to give ethyl 1-((1S,2S)-1-cyano-2-methylcyclopropyl)-5-((R)-2,2-dimethyltetrahydro-2H-pyran-4-yl)-7-fluoro-1H-indole-2-carboxylate (1st eluent, RT=1.854 by SFC, 700 mg, 1.74 mmol, 38.46% yield). LC-MS (ES+, m/z): 399.1 [$(M+H)^+$]; Rt=0.671 min. And ethyl 1-((1S,2S)-1-cyano-2-methylcyclopropyl)-5-((S)-2,2-dimethyltetrahydro-2H-pyran-4-yl)-7-fluoro-1H-indole-2-carboxylate ($2^{nd}$ eluent, RT=2.311 by SFC, 650 mg, 1.55 mmol, 34.34% yield). LC-MS (ES+, m/z): 399.3 [$(M+H)^+$]; Rt=0.656 min.

Step 2: ethyl 5-((R)-2,2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate

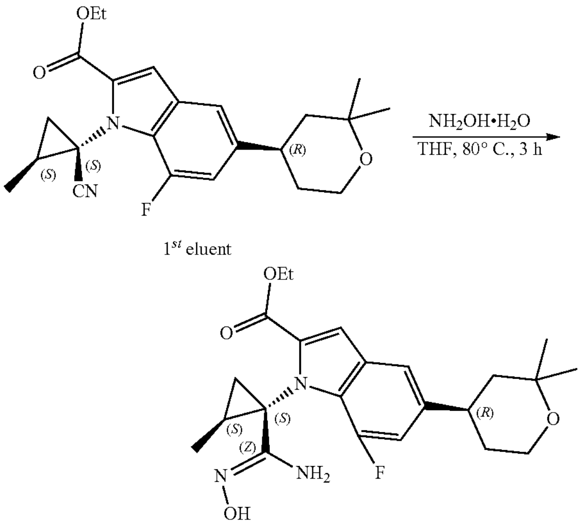

To a solution of ethyl 1-((1S,2S)-1-cyano-2-methylcyclopropyl)-5-((R)-2,2-dimethyltetrahydro-2H-pyran-4-yl)-7-fluoro-1H-indole-2-carboxylate (700.00 mg, 1.76 mmol, 1 eq) in THF (7 mL) was added $NH_2OH \cdot H_2O$ (1.16 g, 17.57 mmol, 50% purity, 10 eq). The mixture was stirred at 80° C. for 3 hrs under $N_2$. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated to give ethyl 5-((R)-2,2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate (700 mg, crude). LC-MS (ES+, m/z): 432.1 [(M+H)$^+$]; Rt=0.467 min.

Step 3: ethyl 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylate

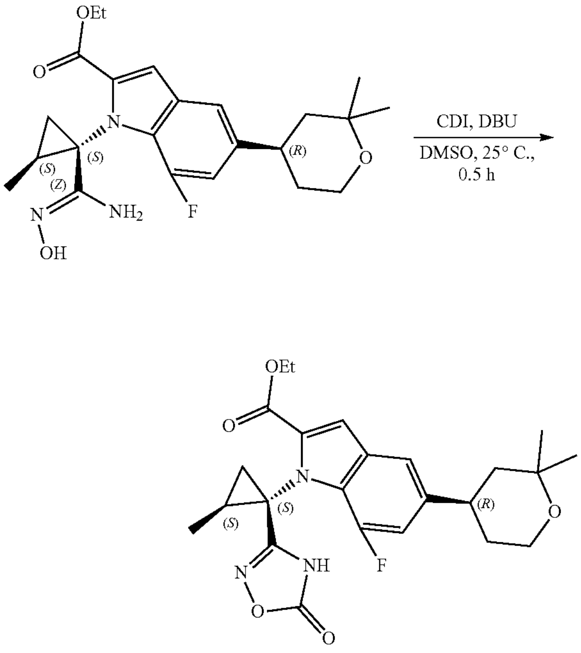

To a solution of ethyl 5-((R)-2,2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate (700.00 mg, 1.62 mmol, 1 eq) in DMSO (7 mL) was added CDI (526.09 mg, 3.24 mmol, 2 eq) and DBU (617.41 mg, 4.06 mmol, 2.5 eq). The mixture was stirred at 25° C. for 0.5 hour under $N_2$. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated in vacuo. The residue was purified by prep-TLC ($SiO_2$, Dichloromethane/Methanol=20/1) to give ethyl 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylate (500 mg, 1.07 mmol, 65.96% yield). LC-MS (ES+, m/z): 458.1 [(M+H)$^+$]; Rt=0.613 min.

Step 4: 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid

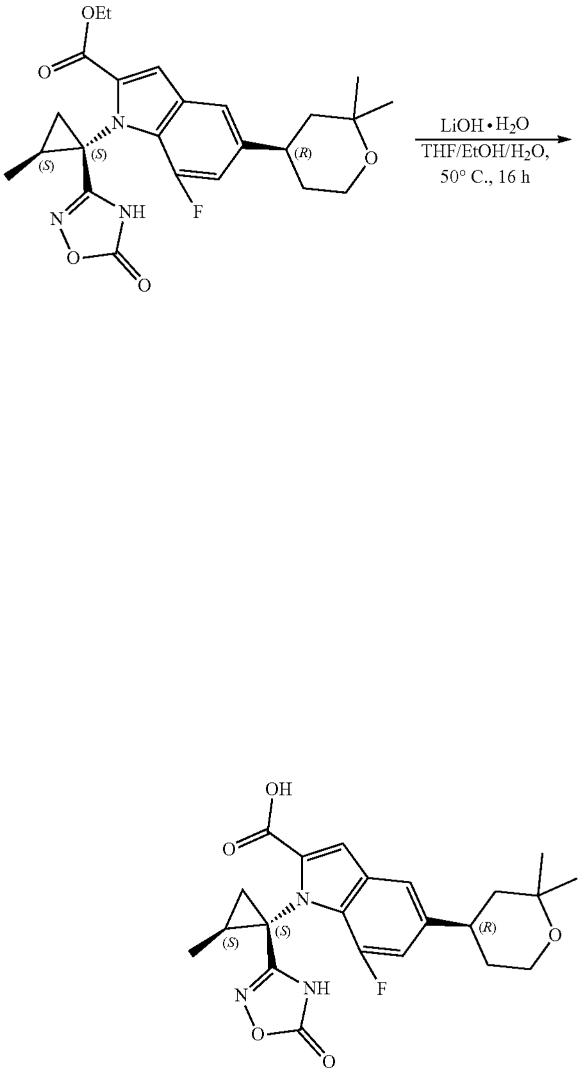

To a solution of ethyl 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylate (500 mg, 1.09 mmol, 1 eq) in THF (2 mL), EtOH (2 mL) and $H_2O$ (2 mL) was added $LiOH \cdot H_2O$ (458.59 mg, 10.93 mmol, 10 eq). The mixture was stirred at 50° C. for 16 hours under $N_2$. LCMS showed the reaction was completed. The mixture was concentrated in vacuo. The residue was dissolved in water (20 mL), adjusted to pH=4 with HCl (2 M), and then extracted with DCM (20 mL*3). The organic layers were combined, washed with water (50 mL), saturated brine (50 mL), dried over $Na_2SO_4$, filtered and concentrated to give 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (400 mg, crude). LC-MS (ES+, m/z): 430.1 [(M+H)$^+$]; Rt=0.520 min.

EXAMPLES
Example 1 (Compound 1)
3-((1S,2S)-1-(5-((S)-2,2-dimethyltetrahydro-2H-pyran-4-yl)-2-((S)-3-(4-(4-fluoro-1-methyl-1H-indazol-5-yl)-1H-1,2,3-triazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one
Scheme 1
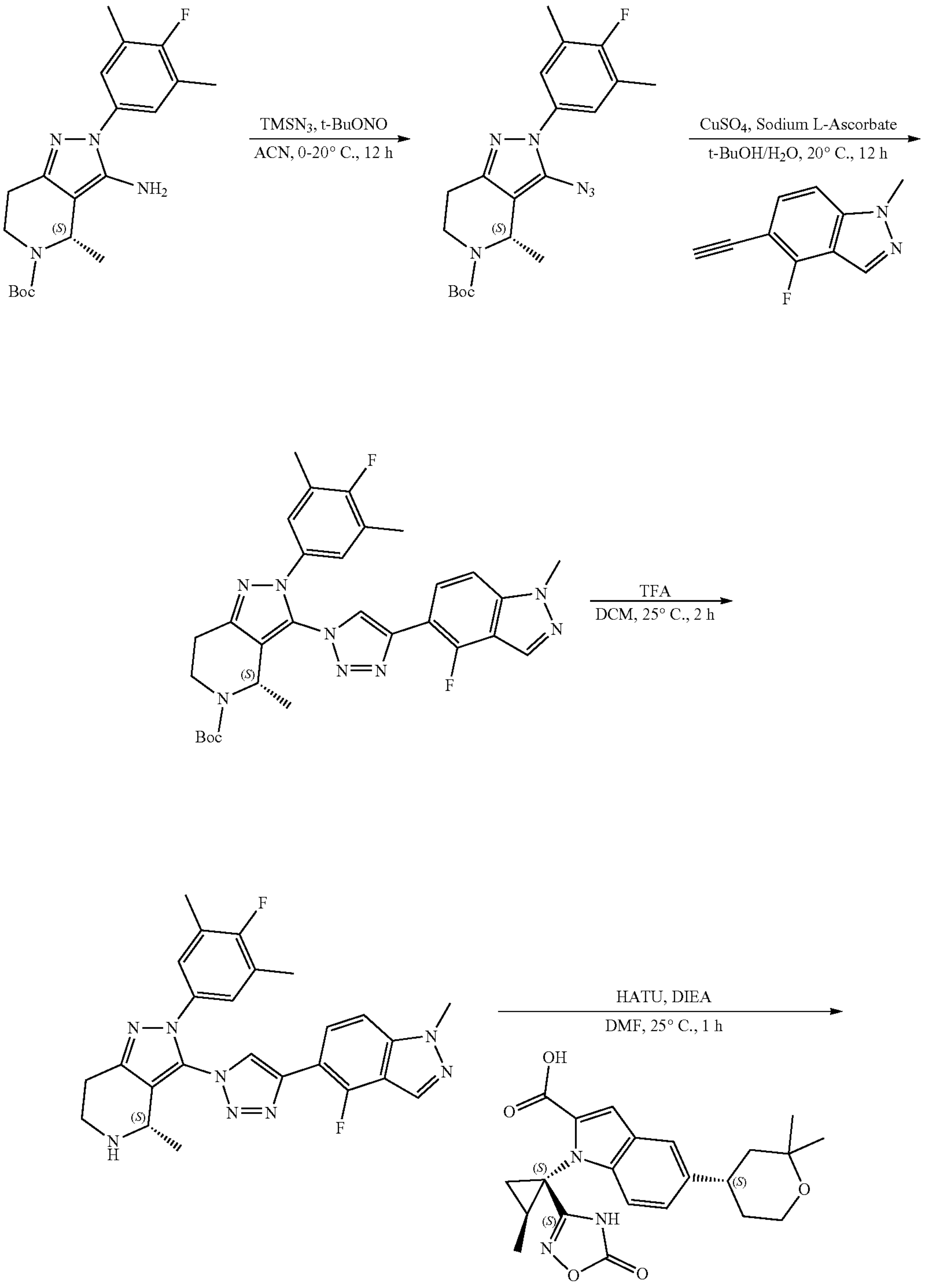

-continued

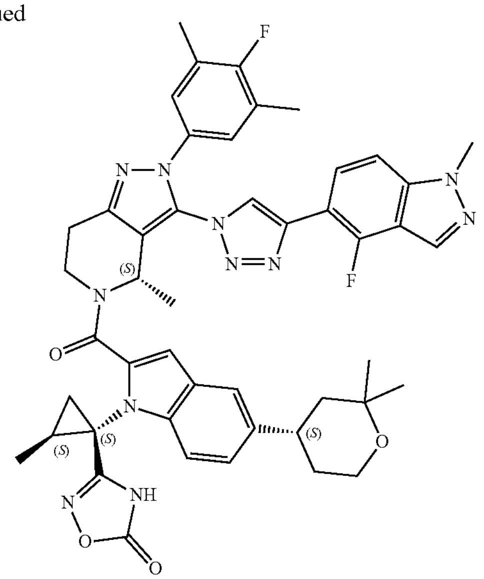

Step 1: tert-butyl (S)-3-azido-2-(4-fluoro-3,5-dimethylphenyl)-4-methyl-2,4,6,7-tetrahydro-5H-pyrazolo[4,3-c]pyridine-5-carboxylate

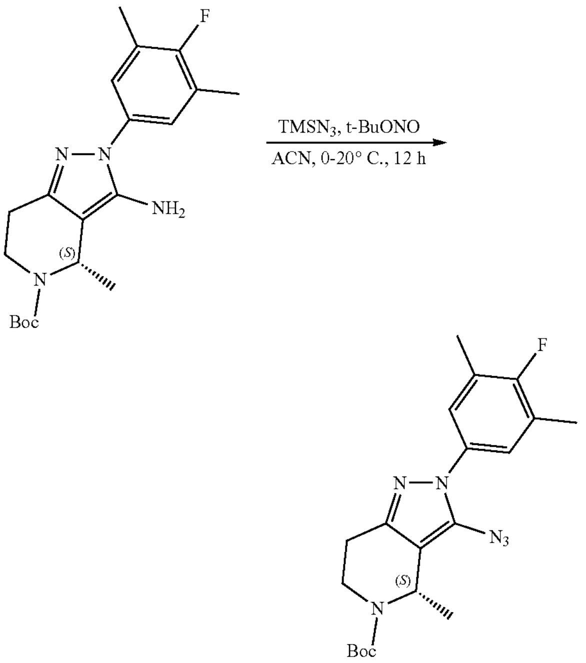

To a solution of tert-butyl (S)-3-amino-2-(4-fluoro-3,5-dimethylphenyl)-4-methyl-2,4,6,7-tetrahydro-5H-pyrazolo[4,3-c]pyridine-5-carboxylate (500 mg, 1.34 mmol, 1 eq) in ACN (10 mL) at 0° C. was added t-BuONO (206.54 mg, 2.00 mmol, 238.23 μL, 1.5 eq). Then $TMSN_3$ (307.67 mg, 2.67 mmol, 351.23 μL, 2 eq) was added. The mixture was stirred at 20° C. for 12 hours under $N_2$ atmosphere. LCMS indicated the reaction was completed. The reaction mixture was adjusted to pH=9 with saturated $Na_2CO_3$ (20 mL). The aqueous phase was extracted with DCM (30 mL*3). The combined organic layers were washed with saturated brine (20 mL*3), dried over anhydrous $Na_2SO_4$, filtered, and concentrated under reduced pressure to afford tert-butyl (S)-3-azido-2-(4-fluoro-3,5-dimethylphenyl)-4-methyl-2,4,6,7-tetrahydro-5H-pyrazolo[4,3-c]pyridine-5-carboxylate (534 mg, crude). LC-MS (ES+, m/z): 401.2 $[(M+H)^+]$; Rt=1.593 min.

Step 2: tert-butyl (S)-3-(4-(4-fluoro-1-methyl-1H-indazol-5-yl)-1H-1,2,3-triazol-1-yl)-2-(4-fluoro-3,5-dimethylphenyl)-4-methyl-2,4,6,7-tetrahydro-5H-pyrazolo[4,3-c]pyridine-5-carboxylate

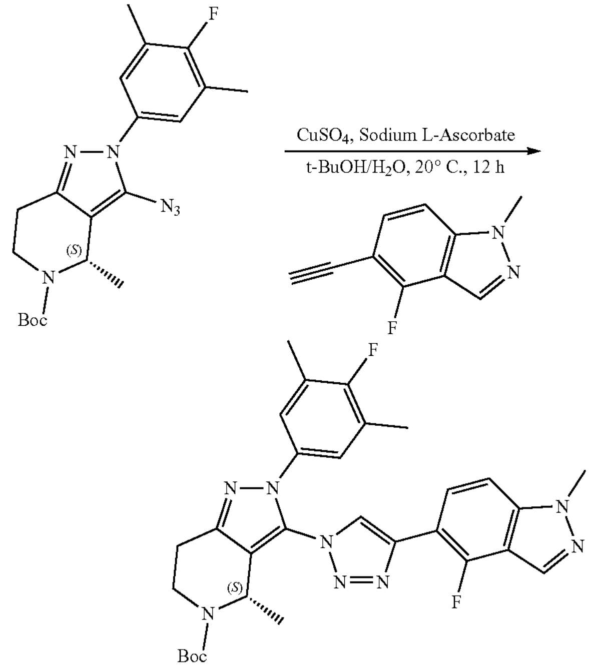

To a solution of tert-butyl (S)-3-azido-2-(4-fluoro-3,5-dimethylphenyl)-4-methyl-2,4,6,7-tetrahydro-5H-pyrazolo[4,3-c]pyridine-5-carboxylate (450.29 mg, 1.12 mmol, 1.22 eq) and 5-ethynyl-4-fluoro-1-methyl-1H-indazole (160 mg, 918.62 μmol, 1 eq) in t-BuOH (5 mL) and $H_2O$ (5 mL) was added $CuSO_4$ (29.32 mg, 183.72 μmol, 28.20 μL, 0.2 eq) and sodium L-Ascorbate (72.79 mg, 367.45 μmol, 0.4 eq). The mixture was stirred at 20° C. for 12 hours under $N_2$ atmosphere. LCMS indicated the reaction was completed. The reaction mixture was poured into saturated EDTA solution (25 mL) and EtOAc (230 mL) and stirred for 1 hour, and then extracted with EtOAc (30 mL*2). The organic layers were combined and washed with water (25 mL*2), saturated brine (25 mL*2), dried over $Na_2SO_4$, filtered, concentrated under reduced pressure. The residue was purified by column chromatography ($SiO_2$, Petroleum ether/Ethyl acetate=50/1 to 1/1) to afford tert-butyl (S)-3-(4-(4-fluoro-1-methyl-1H-indazol-5-yl)-1H-1,2,3-triazol-1-yl)-2-(4-fluoro-3,5-dimethylphenyl)-4-methyl-2,4,6,7-tetrahydro-5H-pyrazolo[4,3-c]pyridine-5-carboxylate (440 mg, 727.43 μmol, 79.19% yield). LC-MS (ES+, m/z): 575.4 [$(M+H)^+$]; Rt=0.652 min.

Step 3: (S)-3-(4-(4-fluoro-1-methyl-1H-indazol-5-yl)-1H-1,2,3-triazol-1-yl)-2-(4-fluoro-3,5-dimethylphenyl)-4-methyl-4,5,6,7-tetrahydro-2H-pyrazolo[4,3-c]pyridine

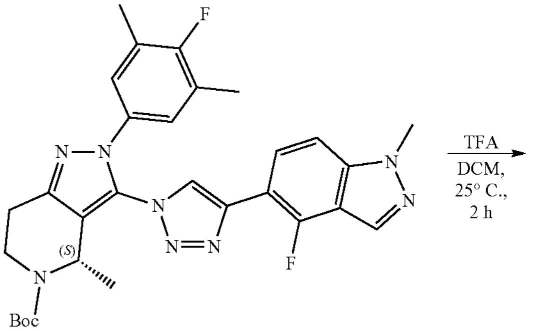

-continued

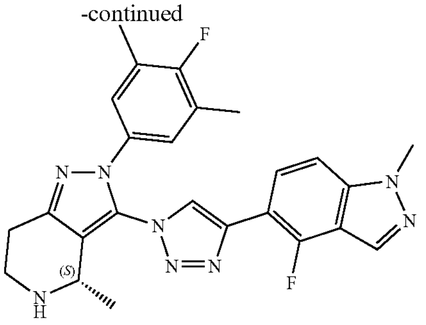

To a solution of tert-butyl (S)-3-(4-(4-fluoro-1-methyl-1H-indazol-5-yl)-1H-1,2,3-triazol-1-yl)-2-(4-fluoro-3,5-dimethylphenyl)-4-methyl-2,4,6,7-tetrahydro-5H-pyrazolo[4,3-c]pyridine-5-carboxylate (250 mg, 435.07 μmol, 1 eq) in HCl/MeOH (4 M, 10 mL). The mixture was stirred at 25° C. for 2 hours. LCMS indicated the reaction was completed. The reaction mixture was concentrated under reduced pressure to afford(S)-3-(4-(4-fluoro-1-methyl-1H-indazol-5-yl)-1H-1,2,3-triazol-1-yl)-2-(4-fluoro-3,5-dimethylphenyl)-4-methyl-4,5,6,7-tetrahydro-2H-pyrazolo[4,3-c]pyridine (200 mg, crude). LC-MS (ES+, m/z): 475.2 [$(M+H)^+$]; Rt=0.405 min Step 4: 3-((1S,2S)-1-(5-((S)-2,2-dimethyltetrahydro-2H-pyran-4-yl)-2-((S)-3-(4-(4-fluoro-1-methyl-1H-indazol-5-yl)-1H-1,2,3-triazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one

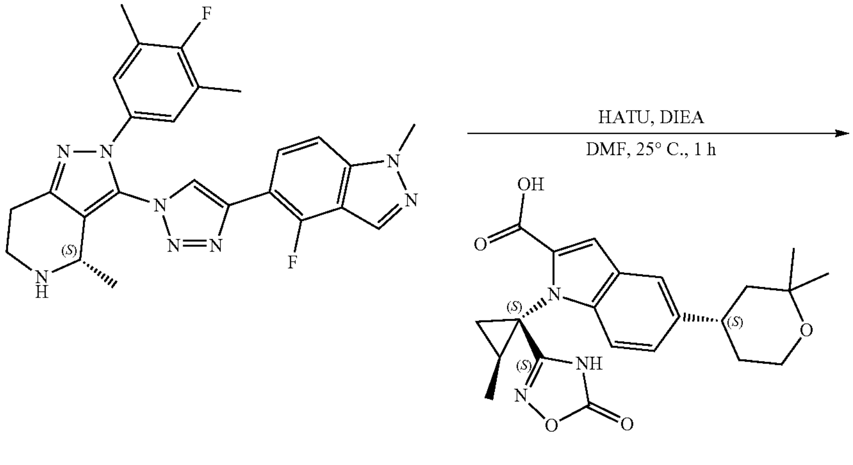

-continued

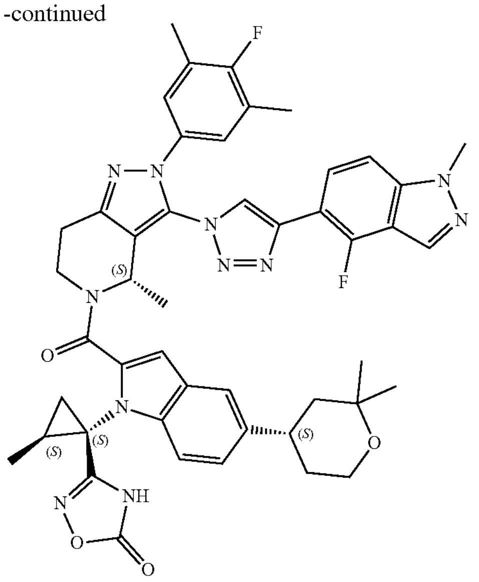

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (30 mg, 72.91 μmol, 1.2 eq) in DMF (0.6 mL) was added DIEA (39.26 mg, 303.80 μmol, 52.92 μL, 5 eq) and(S)-3-(4-(4-fluoro-1-methyl-1H-indazol-5-yl)-1H-1,2,3-triazol-1-yl)-2-(4-fluoro-3,5-dimethylphenyl)-4-methyl-4,5,6,7-tetrahydro-2H-pyrazolo[4,3-c]pyridine (30 mg, 63.22 μmol, 1.04 eq). HATU (34.65 mg, 91.14 μmol, 1.5 eq) was then added. The mixture was stirred at 25° C. for 1 hour. LCMS indicated the reaction was completed. The reaction mixture was filtered to give a residue. The residue was purified by prep-HPLC (column: Phenomenex Luna C18 75*30 mm*3 um; mobile phase: [$H_2O$ (0.1% TFA)-ACN]; gradient: 55%-85% B over 8.0 min) to afford 3-((1S,2S)-1-(5-((S)-2,2-dimethyltetrahydro-2H-pyran-4-yl)-2-((S)-3-(4-(4-fluoro-1-methyl-1H-indazol-5-yl)-1H-1,2,3-triazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one (10.67 mg, 12.26 μmol, 20.17% yield). $^1H$ NMR (400 MHz, DMSO-$d_6$) δ=11.91-11.22 (m, 1H), 8.94-8.58 (m, 1H), 8.23-8.15 (m, 1H), 8.11-8.02 (m, 1H), 7.61 (d, J=8.8 Hz, 1H), 7.52 (s, 1H), 7.44-7.39 (m, 1H), 7.28-7.23 (m, 1H), 7.03 (d, J=6.2 Hz, 2H), 6.94-6.78 (m, 1H), 5.79-5.35 (m, 1H), 4.70-4.31 (m, 1H), 4.10 (s, 3H), 3.78-3.63 (m, 3H), 3.13-2.92 (m, 3H), 2.16 (d, J=1.9 Hz, 6H), 1.75-1.50 (m, 7H), 1.36 (br s, 2H), 1.29-1.26 (m, 4H), 1.20 (s, 6H). LC-MS (ES+, m/z): 868.6 [$(M+H)^+$]; Rt=0.689 min. HRMS (EI): m/z $[M+H]^+$ found: 868.3847.

Example 5 (Compound 5)

3-((1S,2S)-1-(5-((S)-2,2-dimethyltetrahydro-2H-pyran-4-yl)-2-((S)-3-(5-(4-fluoro-1-methyl-1H-indazol-5-yl)-1,3,4-oxadiazol-2-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 5

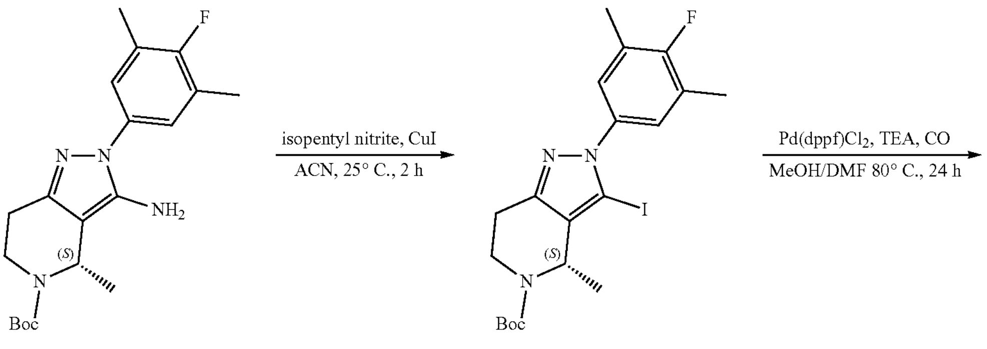

-continued
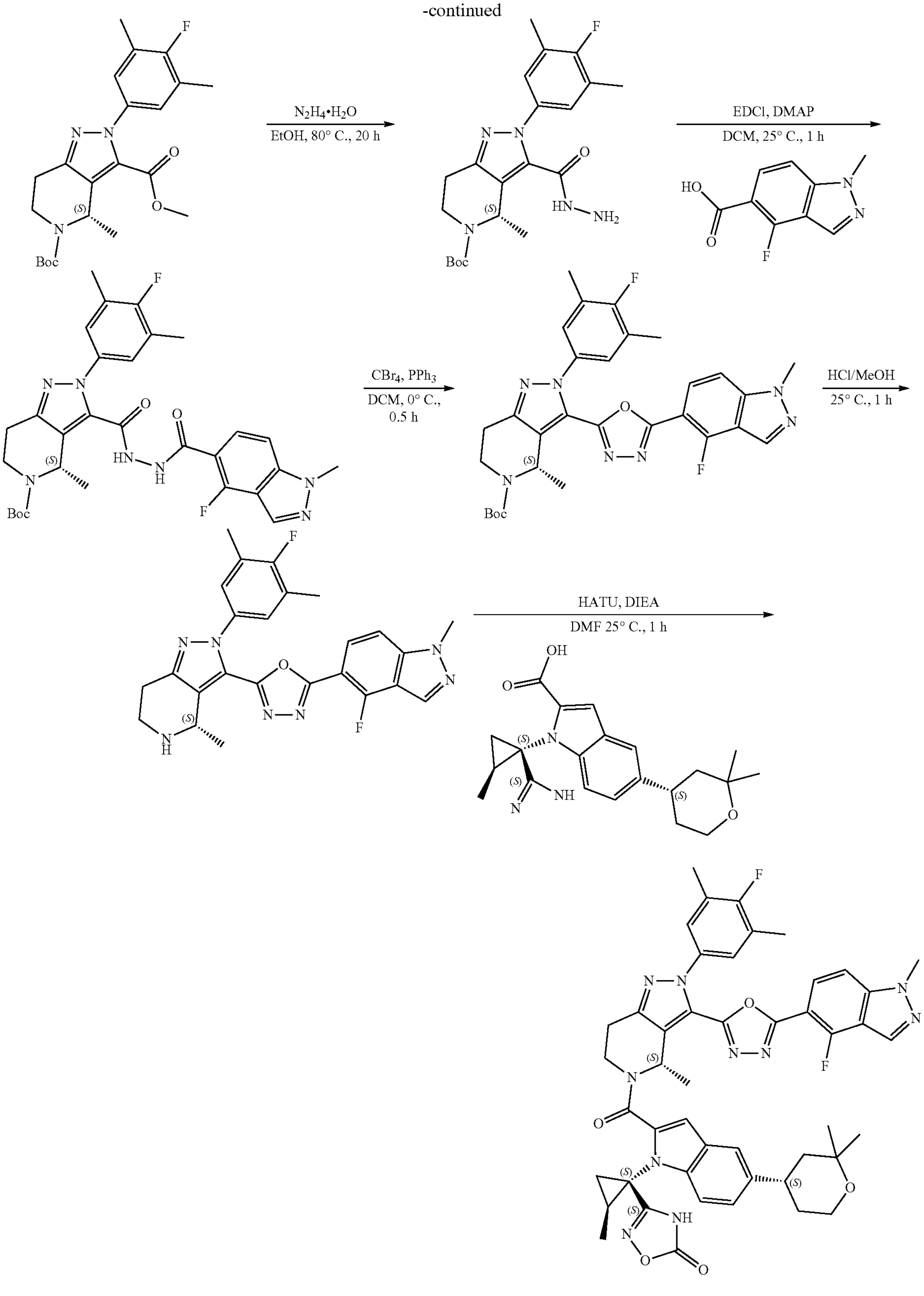
The compound was prepared following the method described in the above synthetic scheme.
$^1$H NMR (400 MHz, DMSO-$d_6$) δ=11.78 (br d, J=5.8 Hz, 1H), 8.40 (s, 1H), 7.68 (br d, J=5.6 Hz, 1H), 7.66-7.44 (m, 2H), 7.43-7.26 (m, 3H), 7.25-6.68 (m, 2H), 6.08-5.27 (m, 1H), 4.86-4.36 (m, 1H), 4.10 (s, 3H), 3.99-3.91 (m, 2H), 3.71 (br d, J=7.3 Hz, 1H), 3.20-2.93 (m, 2H), 2.91-2.62 (m, 1H), 2.34-2.24 (m, 6H), 1.69 (br s, 4H), 1.67-1.32 (m, 6H), 1.28-1.24 (m, 3H), 1.23 (br s, 6H). 1H NMR (400 MHz, MeOD-$d_4$) δ=8.28-8.01 (m, 1H), 7.78-7.59 (m, 1H), 7.58-7.42 (m, 2H), 7.42-7.21 (m, 3H), 7.21-6.76 (m, 2H), 5.43-4.91 (m, 1H), 4.49 (br s, 1H), 4.09 (d, J=11.1 Hz, 3H), 3.91-3.77 (m, 2H), 3.48 (s, 1H), 3.27 (br s, 2H), 3.05-2.95 (m, 1H), 2.41-2.24 (m, 6H), 2.08-1.78 (m, 4H), 1.76-1.38 (m, 6H), 1.35 (br d, J=6.4 Hz, 3H), 1.29-1.08 (m, 6H). LC-MS (ES+, m/z): 869.4 $[(M+H)^+]$. Rt=3.368 min. HRMS (EI): m/z $[M+H]^+$ found: 869.3694.

Example 8 (Compound 8)

3-((1S,2S)-1-(5-((S)-2,2-dimethyltetrahydro-2H-pyran-4-yl)-2-((S)-2-(4-fluoro-3,5-imethylphenyl)-4-methyl-3-(1-(1-methyl-1H-indazol-5-yl)-1H-1,2,3-triazol-4-yl)-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 8

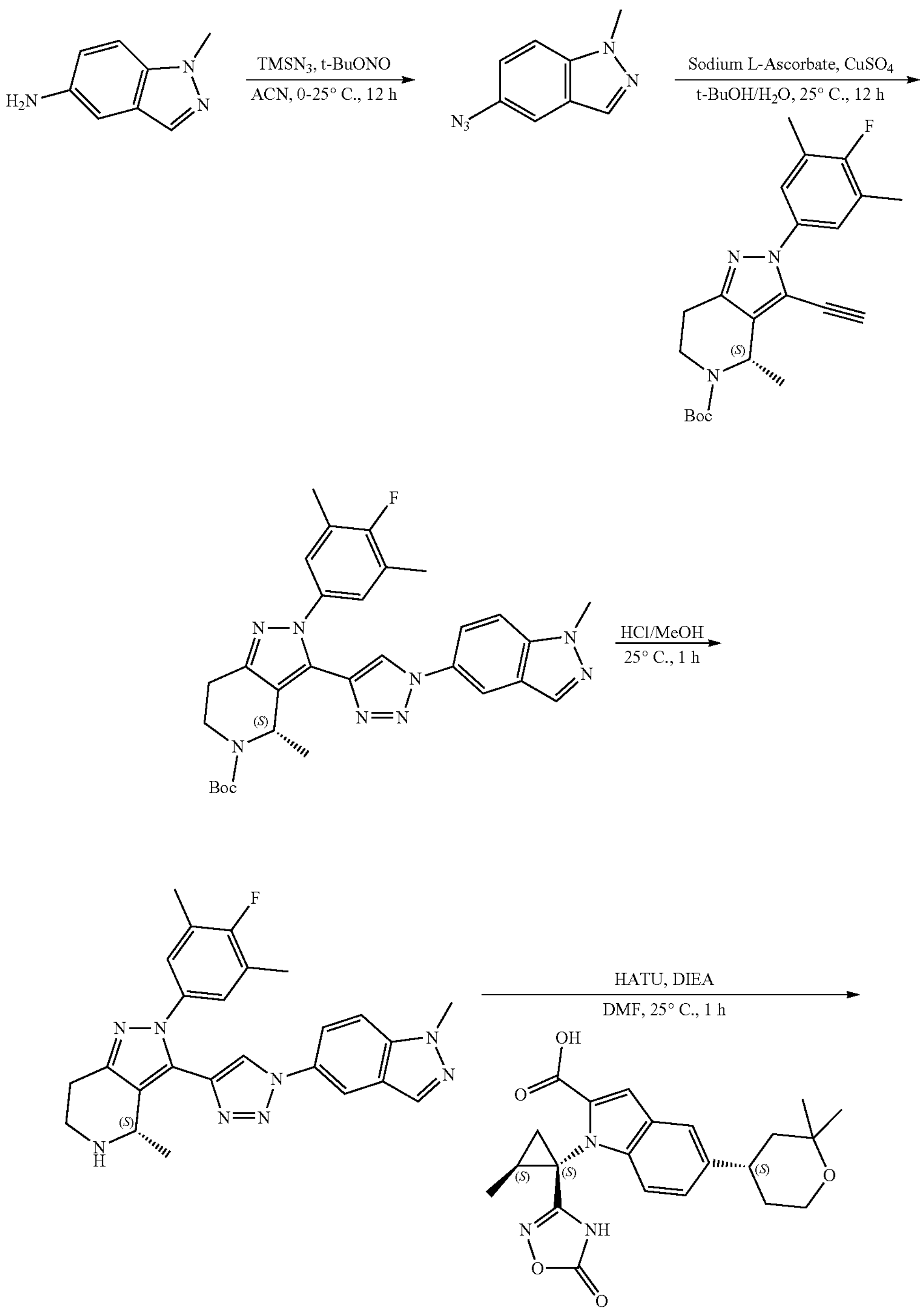

-continued

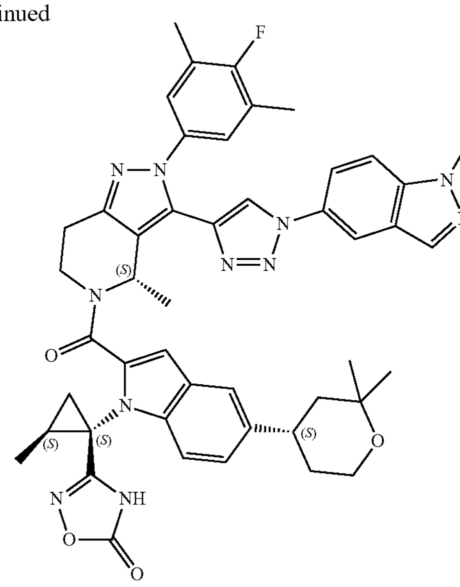

The compound was prepared following the method described in the above synthetic scheme.

$^1$H NMR (400 MHz, DMSO-$d_6$) δ=11.86-11.42 (m, 1H), 8.69-8.32 (m, 1H), 8.31-7.96 (m, 2H), 7.93-7.68 (m, 2H), 7.56-7.49 (m, 1H), 7.45-7.36 (m, 1H), 7.30-7.22 (m, 1H), 7.21-7.07 (m, 2H), 7.02-6.74 (m, 1H), 6.12-5.52 (m, 1H), 4.83-4.20 (m, 1H), 4.15-4.02 (m, 3H), 3.76-3.62 (m, 3H), 3.13-2.86 (m, 3H), 2.25-2.21 (m, 6H), 1.78-1.46 (m, 10H), 1.29 (s, 3H), 1.20 (s, 6H). $^1$H NMR (400 MHz, MeOD-$d_6$) δ=8.23-8.06 (m, 2H), 7.98-7.74 (m, 2H), 7.72-7.61 (m, 1H), 7.57-7.43 (m, 2H), 7.30-7.23 (m, 1H), 7.21-7.05 (m, 2H), 6.95-6.70 (m, 1H), 6.18-5.70 (m, 1H), 4.56-4.42 (m, 1H), 4.15-4.08 (m, 3H), 3.92-3.71 (m, 3H), 3.18-2.94 (m, 3H), 2.27 (br d, J=11.6 Hz, 6H), 1.82-1.50 (m, 10H), 1.37-1.25 (m, 9H). LC-MS (ES+, m/z): 850.6 [$(M+H)^+$]; Rt=0.664 min; HRMS (EI): m/z $[M+H]^+$ found: 850.3935.

Example 9 (Compound 9)

3-((1S,2S)-1-(5-((S)-2,2-dimethyltetrahydro-2H-pyran-4-yl)-2-((S)-3-(5-(4-fluoro-1-methyl-1H-indazol-5-yl)-1,3,4-thiadiazol-2-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 9

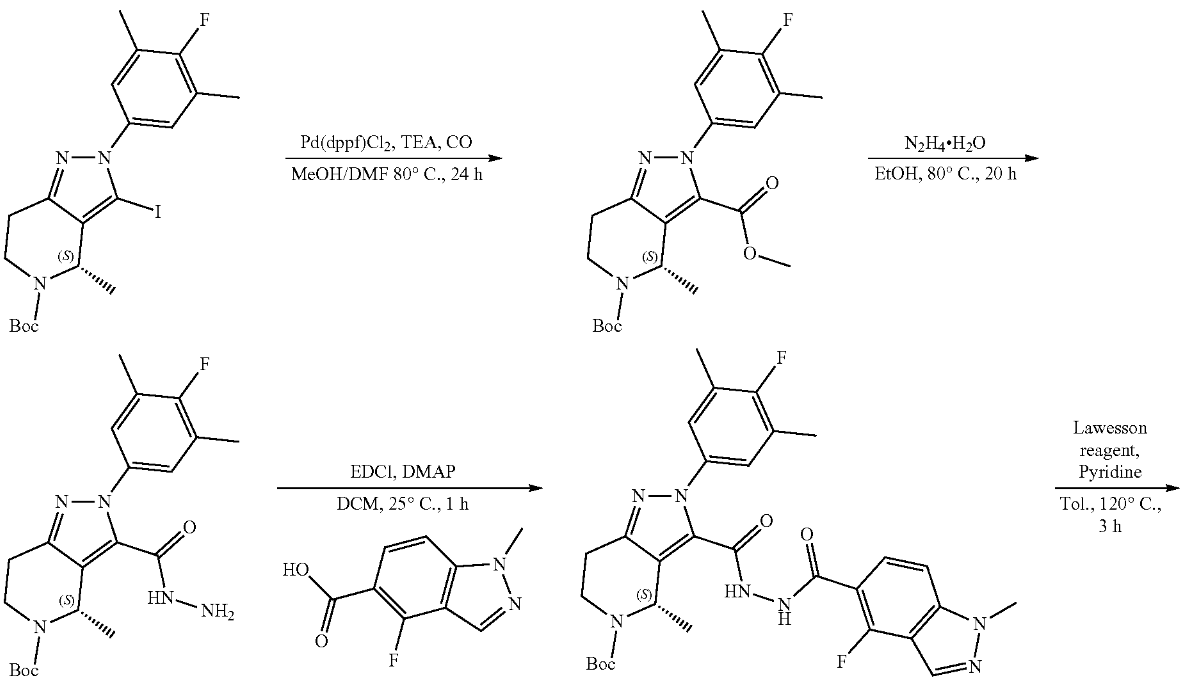

-continued
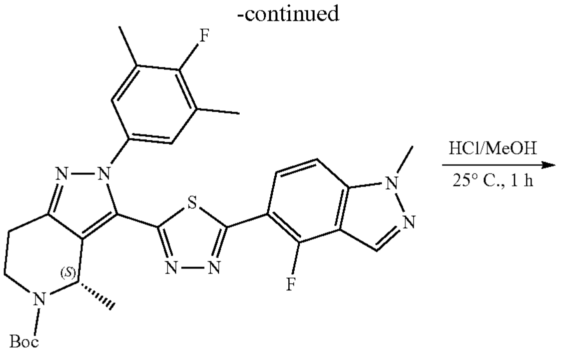
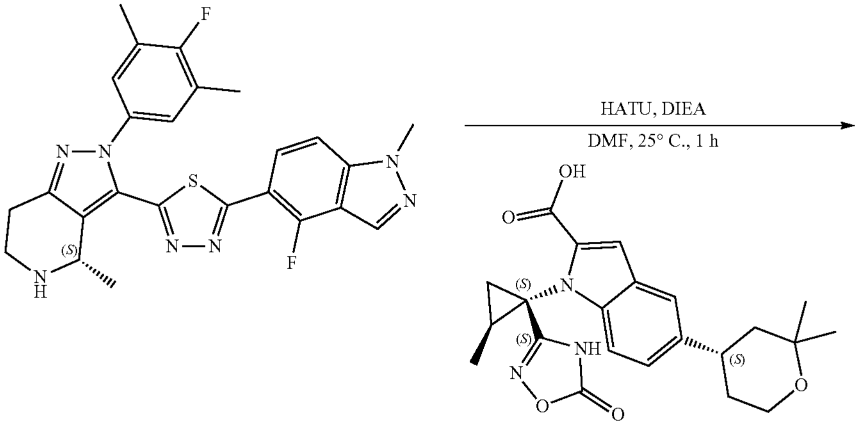
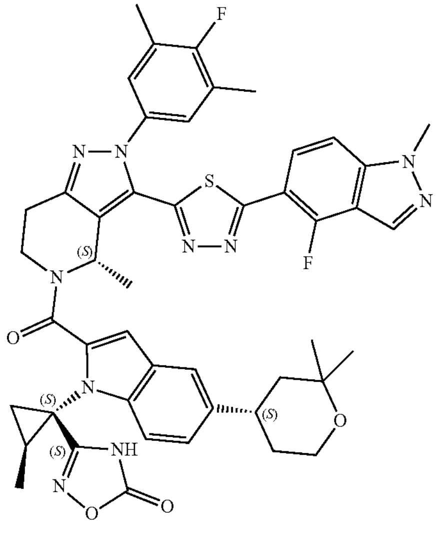
The compound was prepared following the method described in the above synthetic scheme.
$^1$H NMR (400 MHz, DMSO-$d_6$) δ=11.76-11.52 (m, 1H), 8.36-8.26 (m, 1H), 8.18 (br s, 1H), 7.73-7.50 (m, 2H), 7.46-7.29 (m, 3H), 7.28-6.82 (m, 2H), 6.25-5.85 (m, 1H), 4.73-4.33 (m, 1H), 4.16-4.07 (m, 3H), 3.74 (br d, J=7.6 Hz, 2H), 3.32-3.24 (m, 1H), 3.09-2.90 (m, 3H), 2.35-2.26 (m, 6H), 2.06-1.51 (m, 10H), 1.26 (s, 3H), 1.22-0.83 (m, 6H). $^1$H NMR (400 MHz, MeOD-$d_4$) δ=8.36-8.19 (m, 1H), 8.17-8.05 (m, 1H), 7.62-7.50 (m, 2H), 7.49-7.27 (m, 3H), 7.26-6.73 (m, 2H), 6.37-5.27 (m, 1H), 4.50 (br d, J=8.6 Hz, 1H), 4.10 (d, J=17.3 Hz, 3H), 3.91-3.80 (m, 2H), 3.79-3.55 (m, 1H), 3.26-2.91 (m, 3H), 2.41-2.23 (m, 6H) 2.24-1.79 (m, 4H), 1.76 (br s, 6H), 1.37 (s, 3H), 1.29-1.10 (m, 6H). LC-MS (ES+, m/z): 885.2 [(M+H)$^+$]. Rt=3.362 min. HRMS (EI): m/z [M+H]$^+$ found: 885.3502.

Example 11 (Compound 11)
3-((1S,2S)-1-(5-((S)-2,2-dimethyltetrahydro-2H-pyran-4-yl)-2-((4S)-3-(2-(4-fluoro-1-methyl-1H-indazol-5-yl)-1-methyl-1H-imidazol-5-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one
Scheme 11
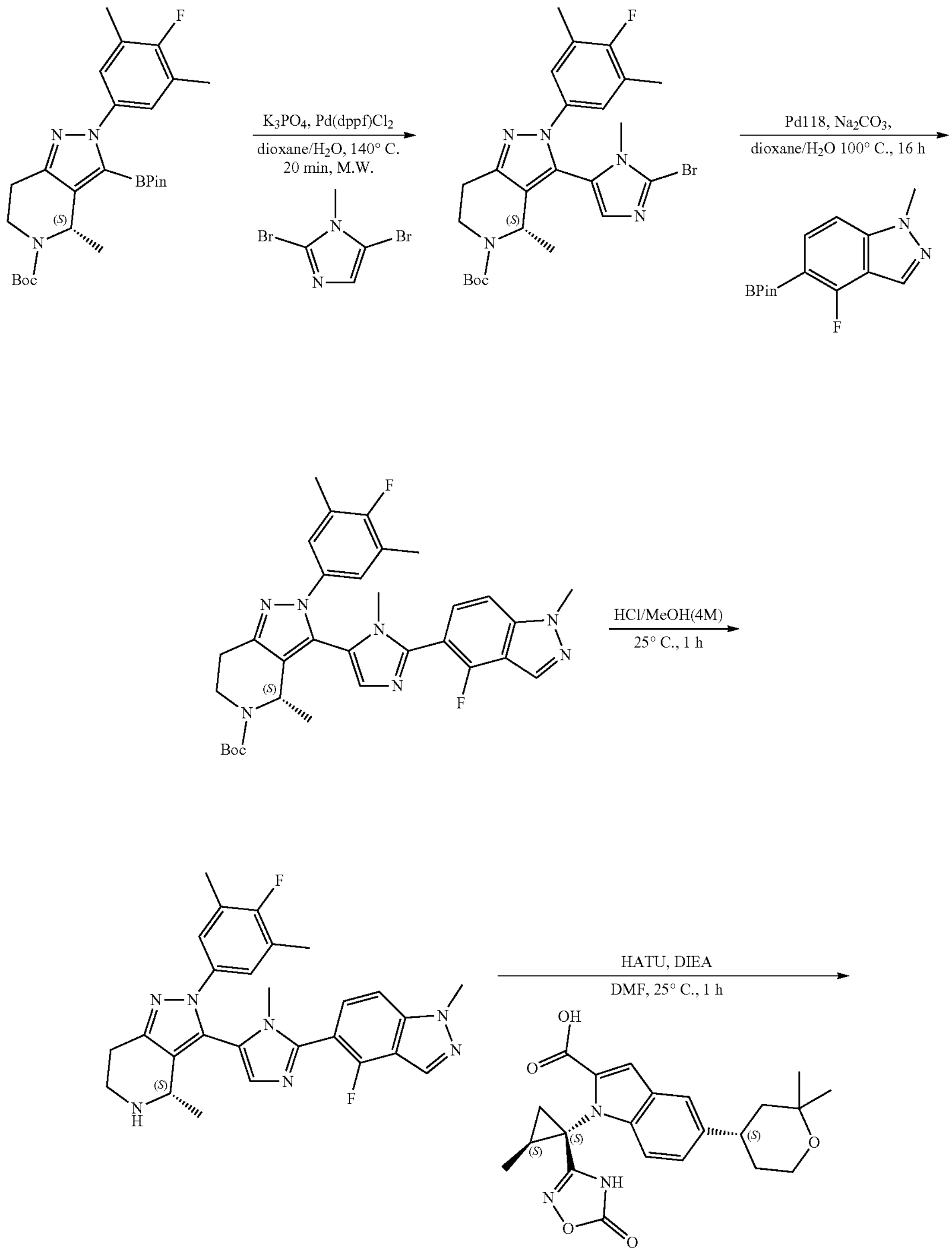

-continued

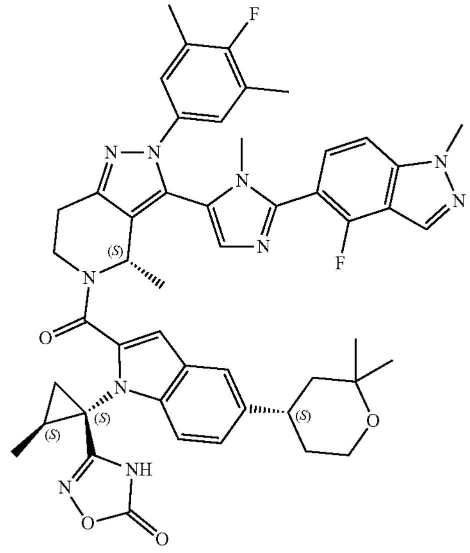

The compound was prepared following the method described in the above synthetic scheme.

$^1$H NMR (400 MHz, DMSO-$d_6$) δ=11.75 (br d, J=10.1 Hz, 1H), 8.29 (s, 1H), 7.68-7.62 (m, 1H), 7.59-7.46 (m, 3H), 7.39 (br d, J=8.0 Hz, 1H), 7.25 (br d, J=8.8 Hz, 1H), 7.07-7.01 (m, 2H), 6.98-6.91 (m, 1H), 5.93-5.09 (m, 1H), 4.45-4.33 (m, 1H), 4.11 (s, 3H), 3.71 (br d, J=7.0 Hz, 3H), 3.05-2.91 (m, 5H), 2.80-2.72 (m, 1H), 2.20 (br s, 6H), 1.67 (br d, J=8.8 Hz, 4H), 1.56-1.48 (m, 3H), 1.27 (s, 6H), 1.18 (s, 6H). $^1$H NMR (400 MHz, DMSO-$d_6$, T=273+80 K) δ=8.21 (s, 1H), 7.58 (br d, J=8.2 Hz, 1H), 7.48-7.39 (m, 3H), 7.32 (br s, 1H), 7.20 (br d, J=8.8 Hz, 1H), 7.04 (d, J=6.2 Hz, 2H), 6.78-6.57 (m, 1H), 6.16-5.30 (m, 1H), 4.10 (s, 4H), 3.73 (br d, J=7.5 Hz, 3H), 3.31-3.21 (m, 3H), 2.94 (br s, 2H), 2.85-2.80 (m, 1H), 2.19 (d, J=1.3 Hz, 6H), 1.77-1.66 (m, 4H), 1.63-1.55 (m, 3H), 1.38 (br s, 3H), 1.29 (s, 3H), 1.20 (s, 6H) (The active N—H was not detected). LC-MS (ES+, m/z): 881.4 [$(M+H)^+$]; Rt=2.812 min. HRMS (EI): m/z $[M+H]^+$ found: 881.4100.

Example 12 (Compound 12)

3-((1S,2S)-1-(5-((S)-2,2-dimethyltetrahydro-2H-pyran-4-yl)-2-((S)-3-(1-(4-fluoro-1-methyl-1H-indazol-5-yl)-2-methyl-1H-imidazol-4-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 12

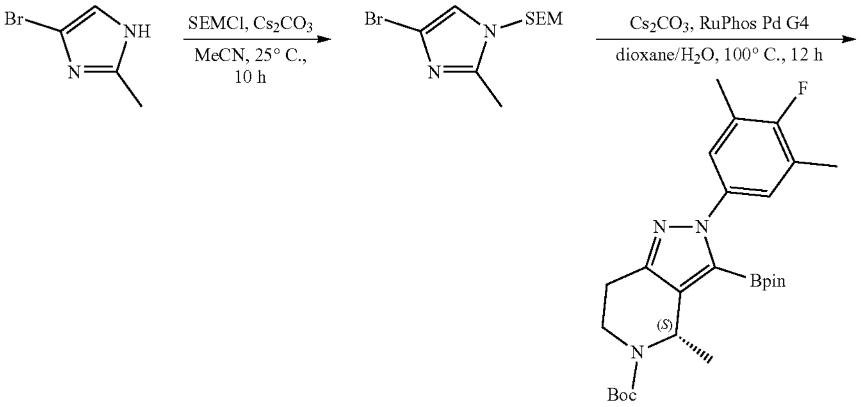

-continued
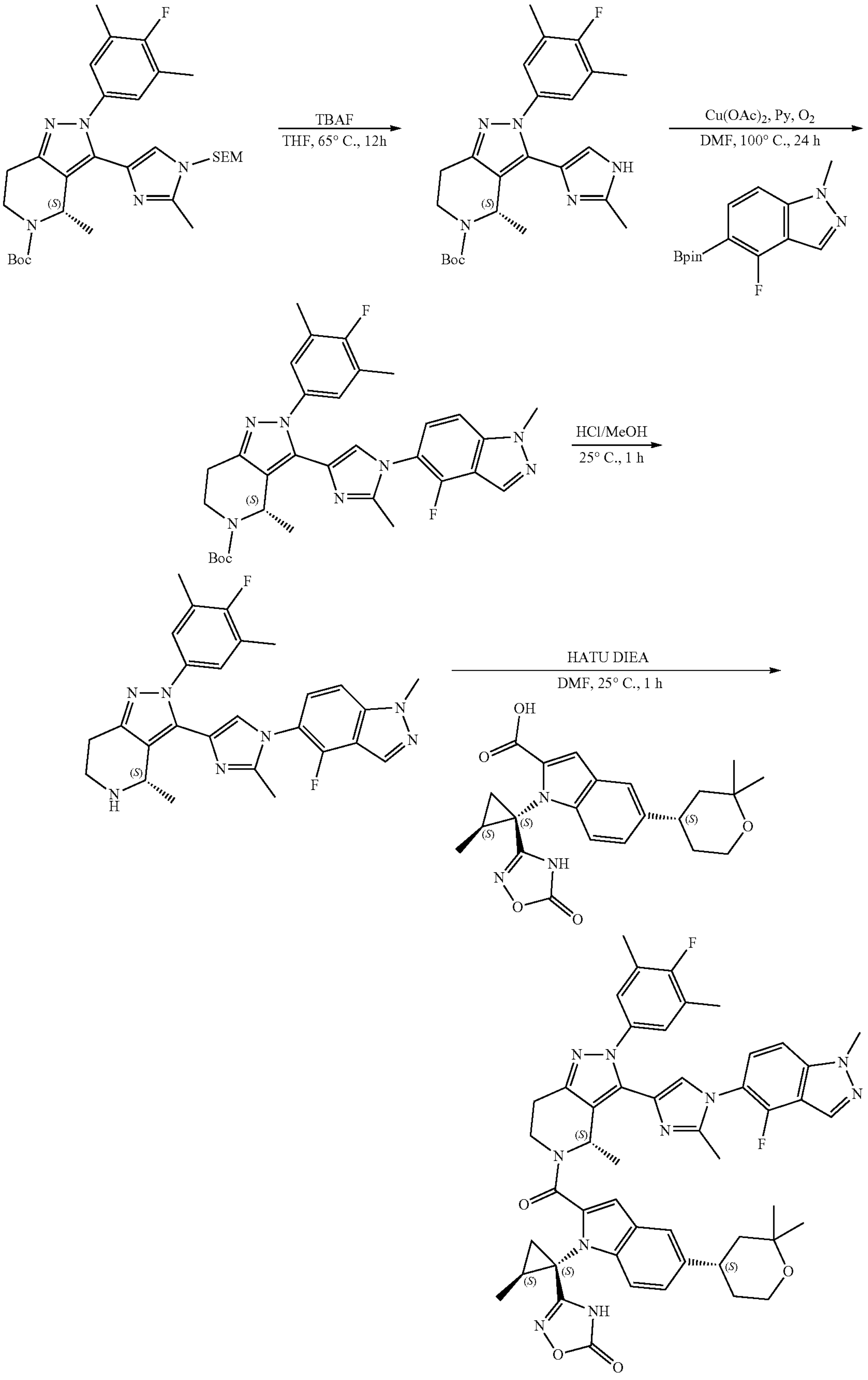

The compound was prepared following the method described in the above synthetic scheme.-1-yl)-2-methylcyclopropyl)-1,2,4-oxadiazol-5 (4H)-one (6.95 mg, 7.69 μmol, 9.62% yield, 97.5% purity). $^{1}$H NMR (400 MHz, DMSO-$d_6$) δ=11.80-11.58 (m, 1H), 8.28-8.23 (m, 1H), 7.65-7.56 (m, 1H), 7.54-7.35 (m, 3H), 7.28-7.23 (m, 1H), 7.20-7.09 (m, 2H), 6.96-6.77 (m, 2H), 6.03-5.81 (m, 1H), 4.46-4.25 (m, 1H), 4.11 (s, 3H), 3.81-3.66 (m, 3H), 2.98-2.81 (m, 3H), 2.23 (d, J=1.5 Hz, 9H), 1.76-1.53 (m, 10H), 1.29 (s, 3H), 1.20 (s, 6H). $^{1}$H NMR (400 MHz, MeOD-$d_4$) δ=8.29-8.18 (m, 1H), 7.66-7.61 (m, 1H), 7.56-7.49 (m, 3H), 7.41-7.21 (m, 2H), 7.16-7.04 (m, 2H), 6.90 (s, 1H), 6.07-5.55 (m, 1H), 4.51 (br dd, J=4.9, 13.7 Hz, 1H), 4.17-4.11 (m, 3H), 3.92-3.70 (m, 3H), 3.14-2.93 (m, 3H), 2.47-2.23 (m, 9H), 1.82-1.52 (m, 10H), 1.36 (s, 3H), 1.27-1.13 (m, 6H). LC-MS (ES+, m/z): 881.3 [(M+H)$^+$]. Rt=2.915 min. HRMS (EI): m/z [M+H]$^+$ found: 881.4040.

Example 13 (Compound 13)

3-((1S,2S)-1-(5-((S)-2,2-dimethyltetrahydro-2H-pyran-4-yl)-2-((S)-3-(1-(4-fluoro-1-methyl-1H-indazol-5-yl)-1H-1,2,3-triazol-4-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 13

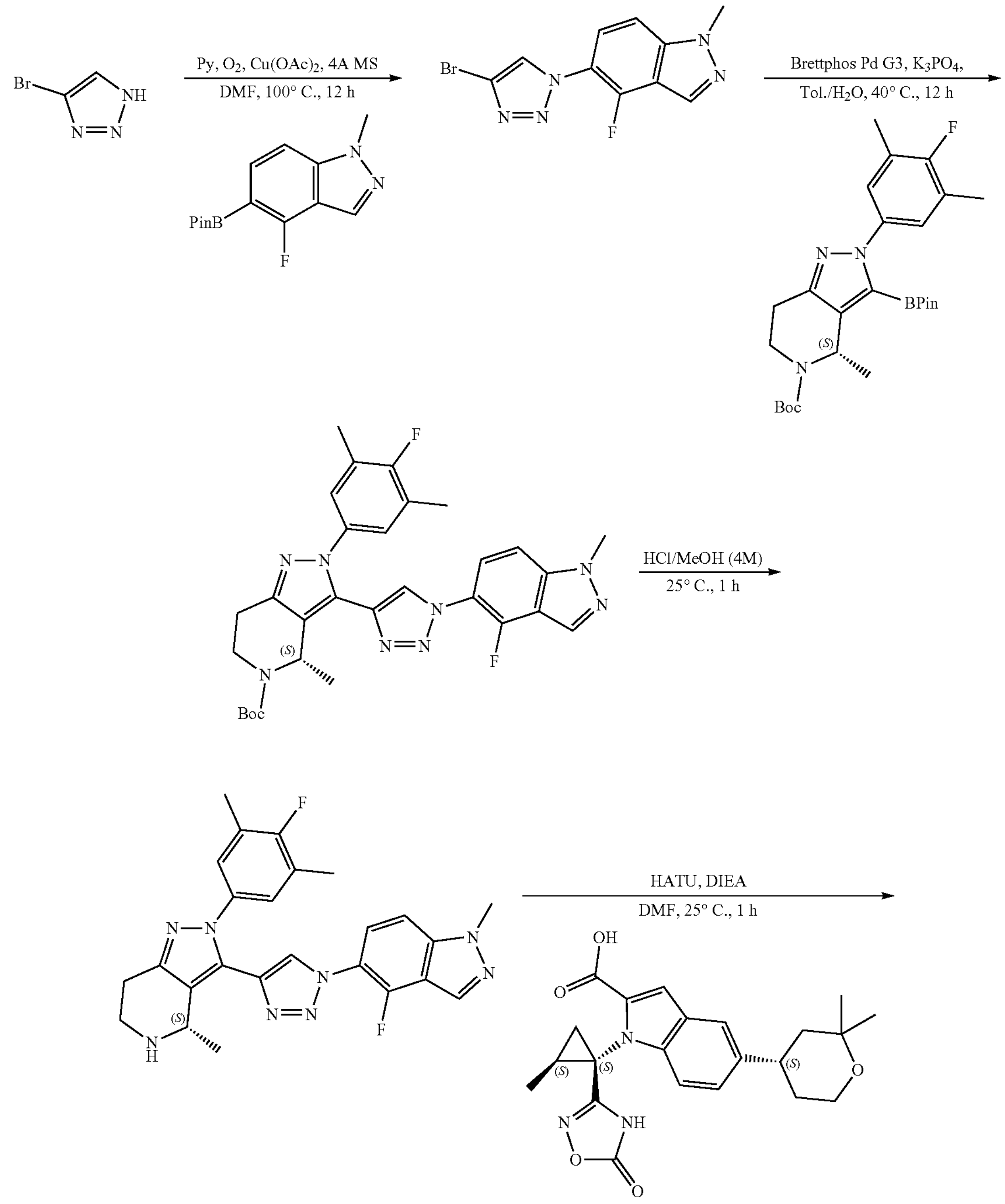

-continued

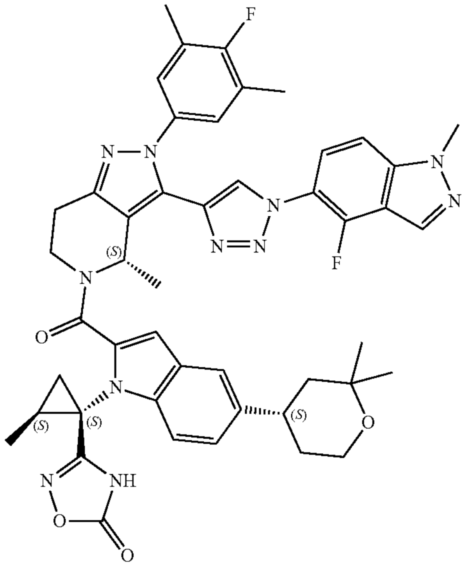

The compound was prepared following the method described in the above synthetic scheme.

1H NMR (400 MHz, DMSO-$d_6$) δ=11.84-11.73 (m, 1H), 8.46-8.26 (m, 2H), 7.83-7.70 (m, 2H), 7.69-7.56 (m, 1H), 7.55-7.49 (m, 1H), 7.42-7.33 (m, 1H), 7.25-7.18 (m, 2H), 6.99-6.91 (m, 1H), 6.00-5.57 (m, 1H), 4.44-4.35 (m, 1H), 4.16-4.12 (m, 3H), 3.73-3.68 (m, 3H), 3.27-2.83 (m, 3H), 2.26-2.23 (m, 6H), 1.74-1.50 (m, 10H), 1.29-1.26 (m, 3H), 1.20-1.15 (m, 6H). LC-MS (ES+, m/z): 868.6 [$(M+H)^+$]; Rt=0.677 min. HRMS (EI): m/z $[M+H]^+$ found: 868.3856.

Example 14 (Compound 14)

3-((1S,2S)-1-(5-((S)-2,2-dimethyltetrahydro-2H-pyran-4-yl)-2-((S)-2-(4-fluoro-3,5-dimethylphenyl)-4-methyl-3-(5-methyl-4-(1-methyl-1H-indazol-5-yl)-1H-imidazol-1-yl)-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 14

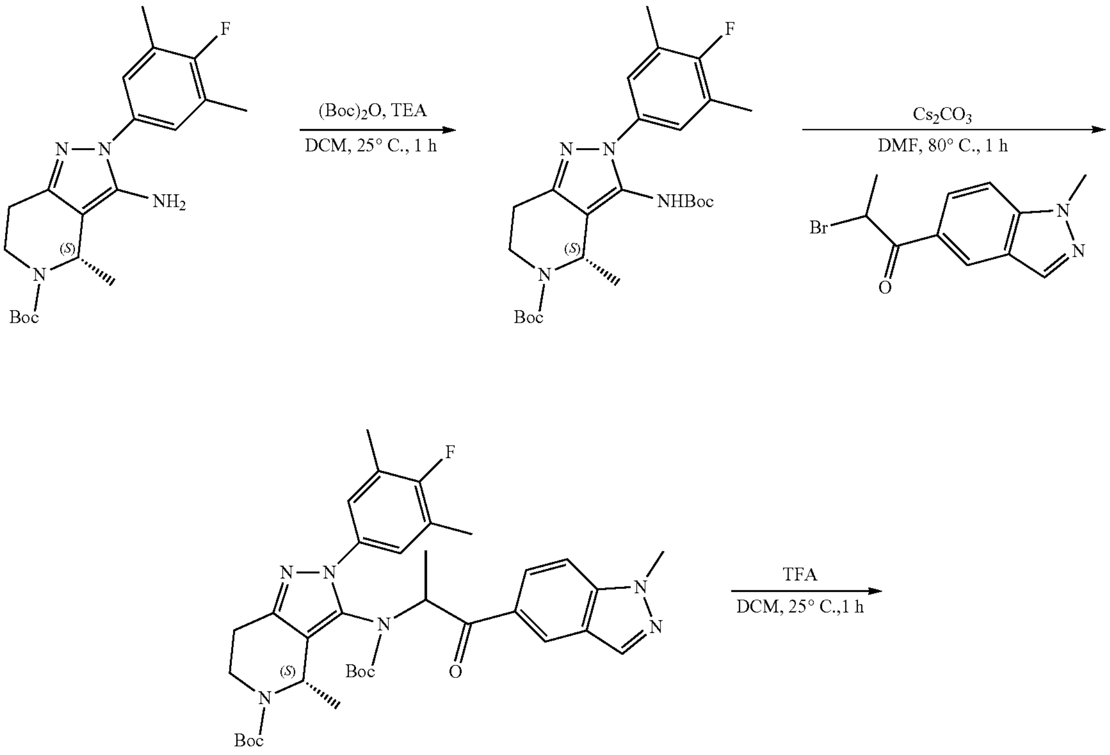

-continued
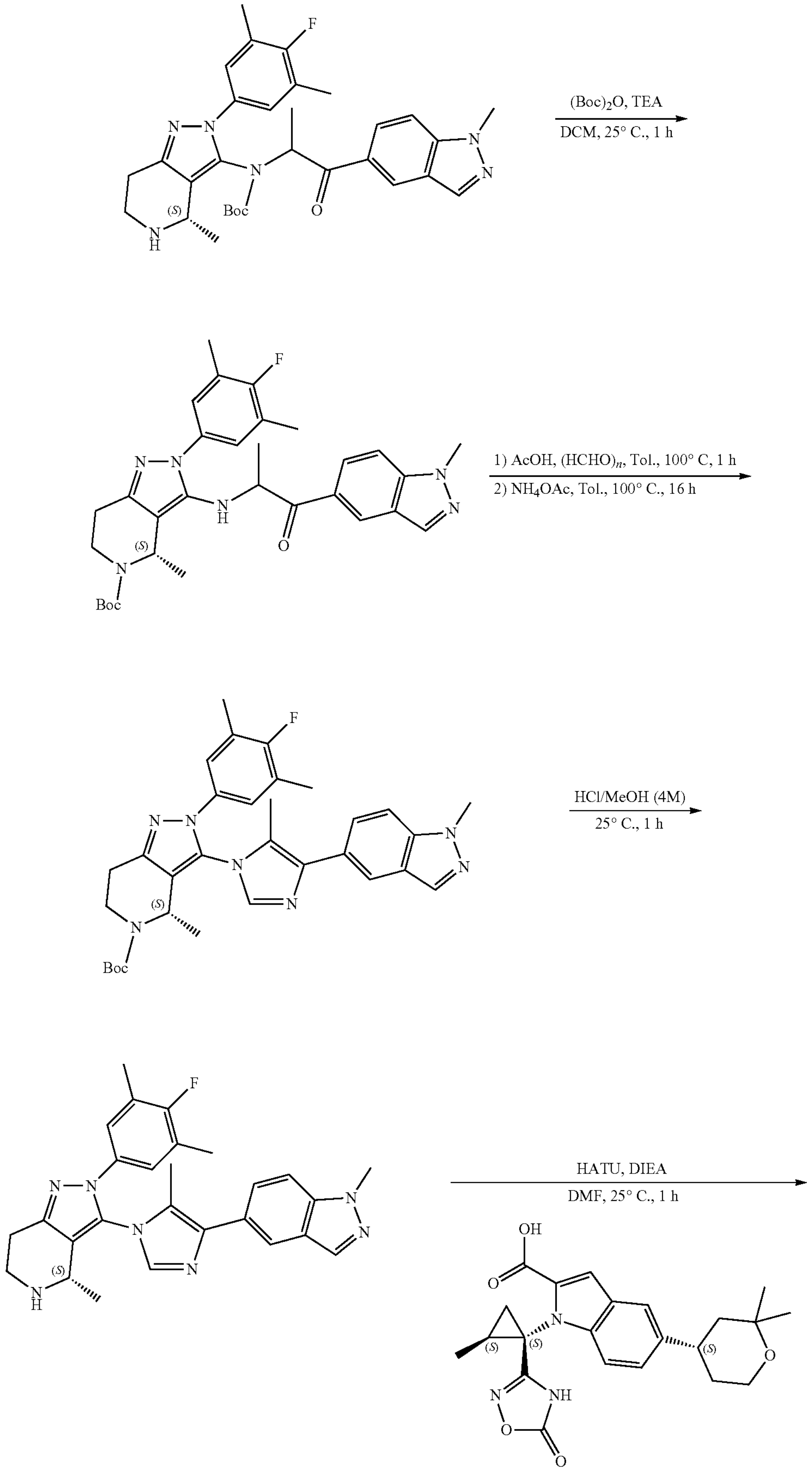

-continued

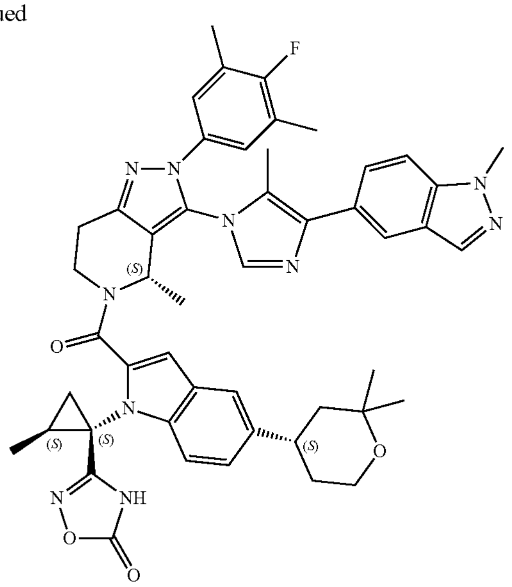

The compound was prepared following the method described in the above synthetic scheme.

$^1$H NMR (400 MHz, DMSO-$d_6$) δ=11.73 (br d, J=6.4 Hz, 1H), 8.46-7.92 (m, 2H), 7.88-7.13 (m, 6H), 6.99 (br s, 3H), 5.68-5.44 (m, 1H), 4.62-4.29 (m, 1H), 4.10-4.00 (m, 3H), 3.81-3.56 (m, 3H), 3.29-2.78 (m, 2H), 2.22 (br s, 1H), 2.16 (br s, 6H), 2.01-1.93 (m, 2H), 1.73-1.60 (m, 5H), 1.55-1.36 (m, 3H), 1.29-1.08 (m, 12H). $^1$H NMR (400 MHz, MeOD-$d_4$) δ=9.10-7.93 (m, 2H), 7.80-7.38 (m, 5H), 7.33-7.26 (m, 1H), 7.18-6.84 (m, 3H), 6.07-5.58 (m, 1H), 4.65-4.48 (m, 1H), 4.15-4.05 (m, 3H), 3.91-3.73 (m, 3H), 3.12-3.01 (m, 2H), 2.33 (s, 1H), 2.26-2.20 (m, 6H), 2.09-1.96 (m, 2H), 1.86-1.73 (m, 5H), 1.63 (br s, 3H), 1.41-1.31 (m, 6H), 1.27-1.17 (m, 6H). LC-MS (ES+, m/z): 863.4 [$(M+H)^+$]; Rt=3.013 min. HRMS (EI): m/z $[M+H]^+$ found: 863.4150.

Example 15 (Compound 15)

3-((1S,2S)-1-(5-((S)-2, 2-dimethyltetrahydro-2H-pyran-4-yl)-2-((S)-3-(1-(4-fluoro-1-methyl-1H-indazol-5-yl)-5-methyl-1H-imidazol-4-yl)-2-(4-fluoro-3, 5-dimethylphenyl)-4-methyl-4, 5, 6, 7-tetrahydro-2H-pyrazolo[4, 3-c]pyridine-5-carbonyl)-1H-indol-1-yl)-2-methylcyclopropyl)-1, 2, 4-oxadiazol-5 (4H)-one Scheme 15

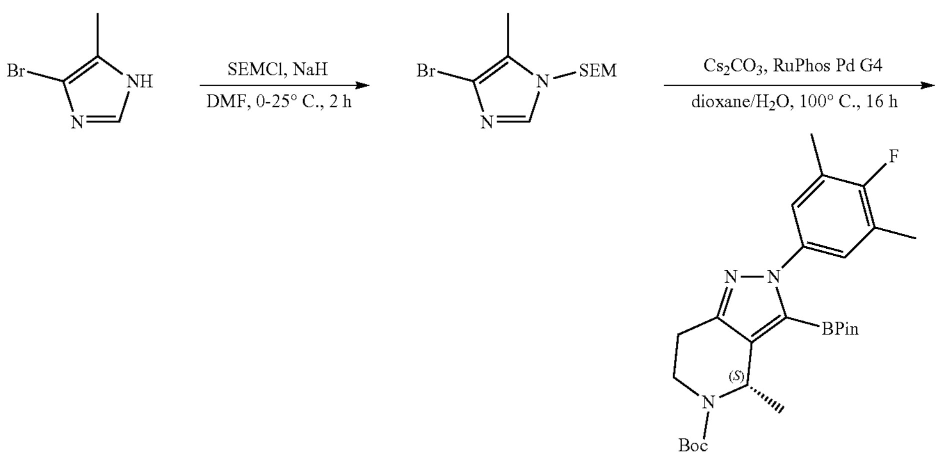

-continued
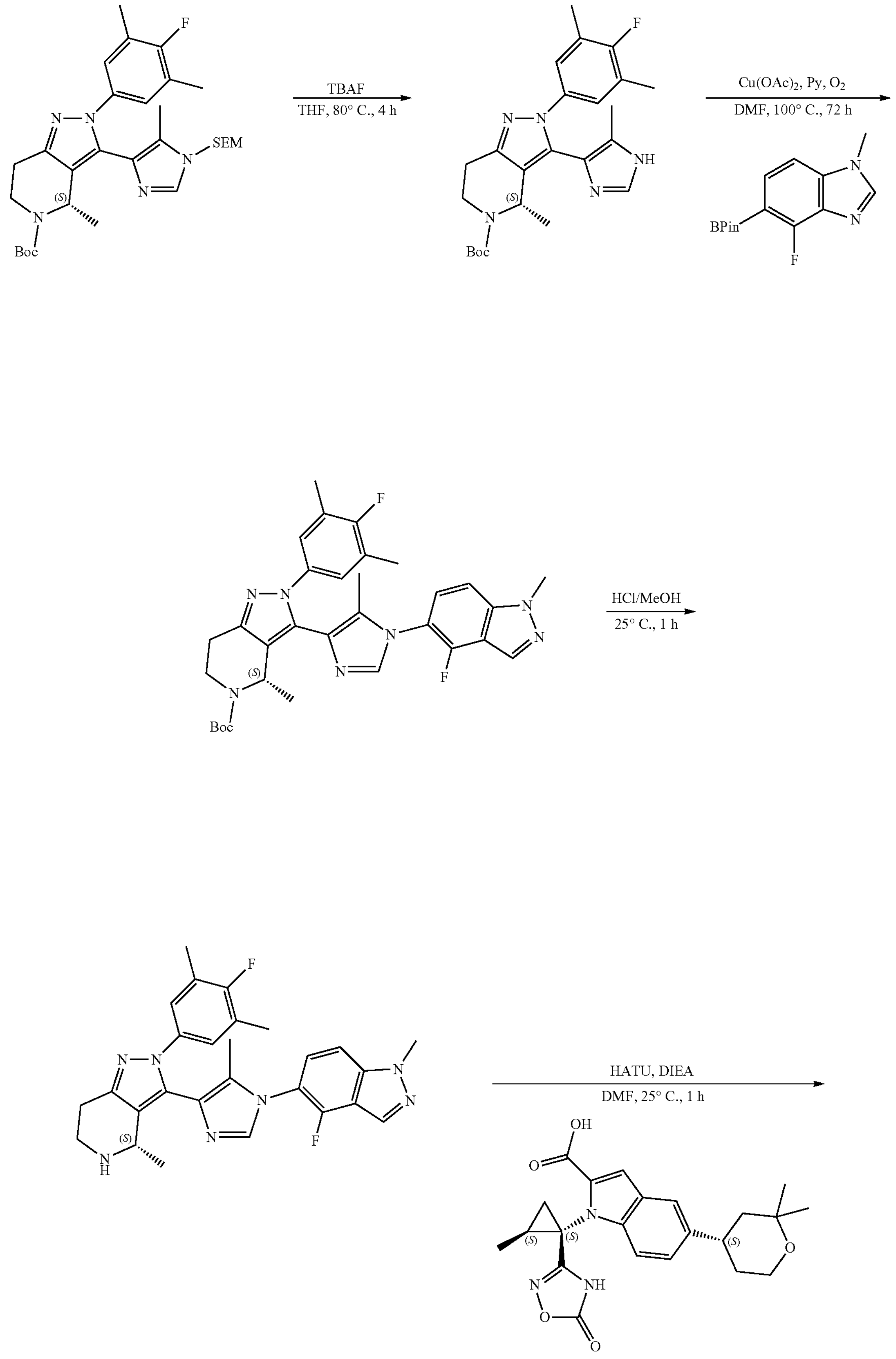

-continued

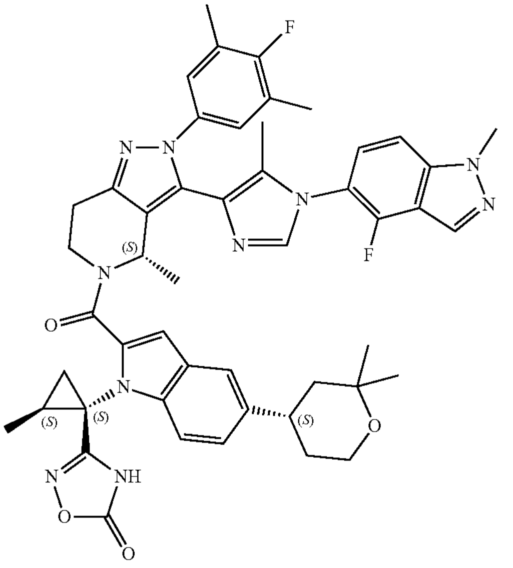

The compound was prepared following the method described in the above synthetic scheme.

$^{1}$H NMR (400 MHz, DMSO-$d_6$) δ=11.86-11.69 (m, 1H), 8.41-8.26 (m, 1H), 8.19-7.88 (m, 1H), 7.71 (d, J=8.9 Hz, 1H), 7.66-7.49 (m, 2H), 7.45-7.36 (m, 1H), 7.31-7.21 (m, 1H), 7.11-6.85 (m, 3H), 5.72-5.22 (m, 1H), 4.39-4.35 (m, 1H), 4.14 (s, 3H), 3.76-3.65 (m, 3H), 3.28-3.13 (m, 1H), 3.08-2.87 (m, 2H), 2.26-2.14 (m, 6H), 1.76-1.42 (m, 12H), 1.30-1.15 (m, 10H). $^{1}$H NMR (400 MHz, MeOD-$d_4$) δ=8.21 (s, 1H), 8.17-7.98 (m, 1H), 7.62-7.54 (m, 1H), 7.53-7.42 (m, 3H), 7.24 (br d, J=7.6 Hz, 1H), 7.05-6.91 (m, 2H), 6.89-6.79 (m, 1H), 5.85-5.40 (m, 1H), 4.52-4.40 (m, 1H), 4.16-4.02 (m, 3H), 3.88-3.63 (m, 3H), 3.10 (br s, 3H), 2.26-2.14 (m, 6H), 1.81-1.66 (m, 6H), 1.62-1.56 (m, 1H), 1.54-1.42 (m, 4H), 1.38 (s, 1H), 1.32 (s, 3H), 1.26-1.14 (m, 6H), 1.11-1.06 (m, 1H). LC-MS (ES+, m/z): 881.3 [$(M+H)^+$]; Rt=2.997 min. HRMS (EI): m/z $[M+H]^+$ found: 881.4097.

Example 16 (Compound 16)

3-((1S,2S)-1-(5-((S)-2, 2-dimethyltetrahydro-2H-pyran-4-yl)-2-((S)-3-(4-(4-fluoro-1-methyl-1H-indazol-5-yl)-5-methyloxazol-2-yl)-2-(4-fluoro-3, 5-dimethylphenyl)-4-methyl-4, 5, 6, 7-tetrahydro-2H-pyrazolo[4, 3-c]pyridine-5-carbonyl)-1H-indol-1-yl)-2-methylcyclopropyl)-1, 2, 4-oxadiazol-5 (4H)-one Scheme 16

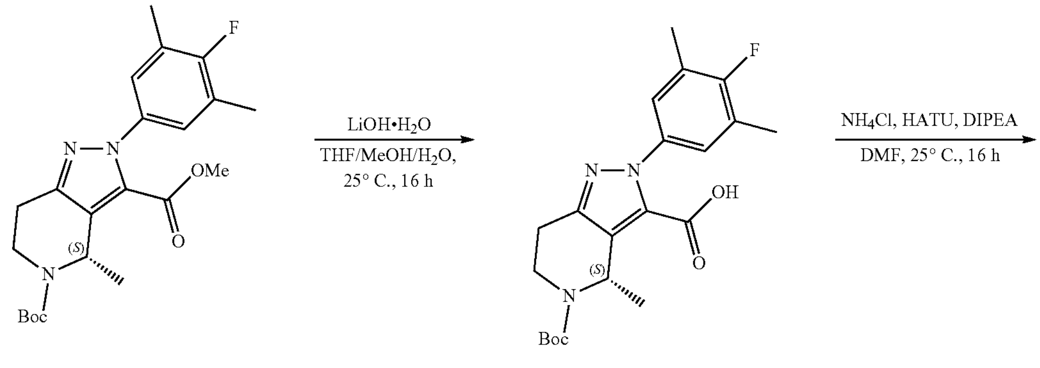

-continued
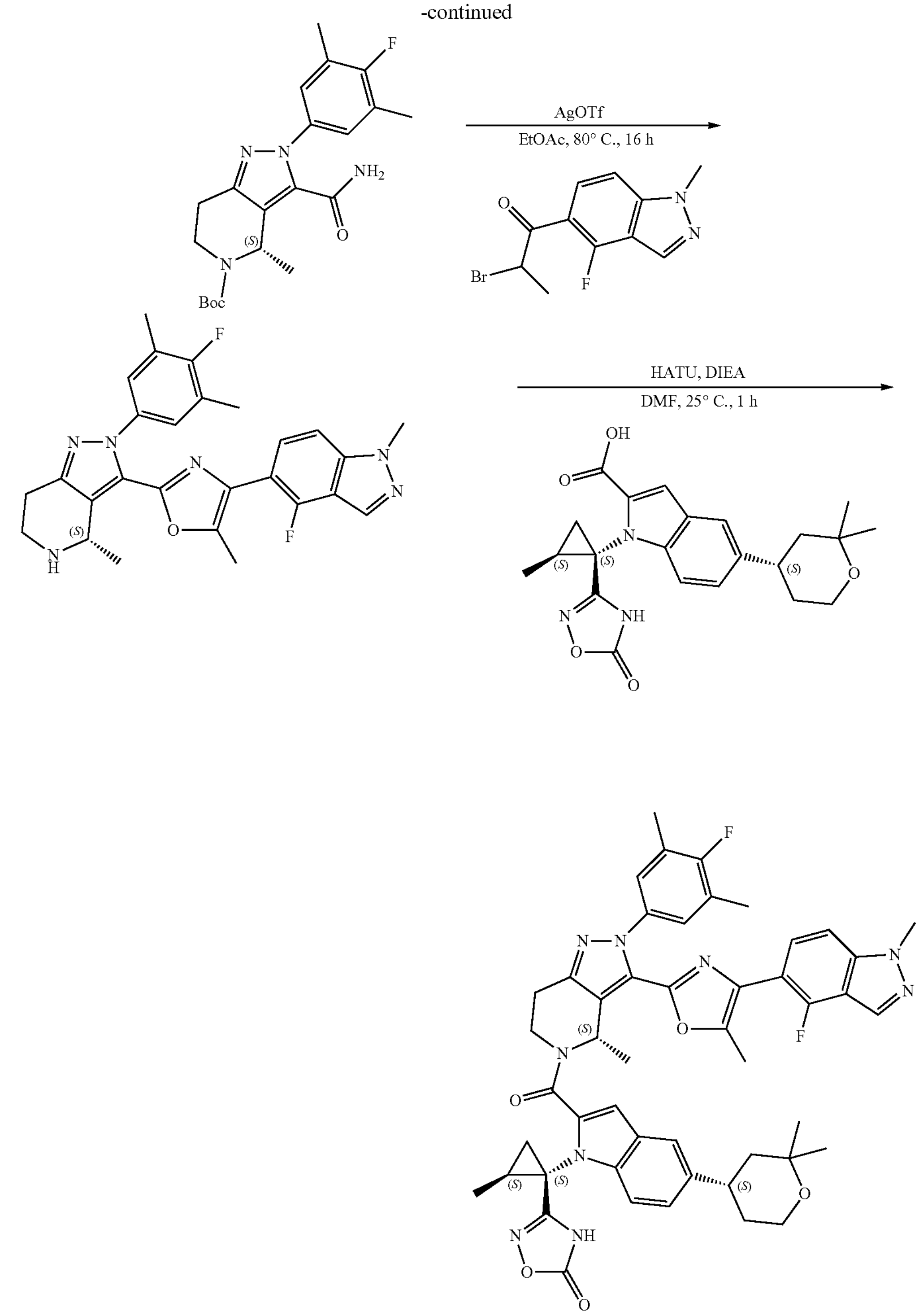
The compound was prepared following the method described in the above synthetic scheme.
$^1$H NMR (400 MHz, DMSO-$d_6$) δ=11.36 (s, 1H), 8.17 (s, 1H), 7.65-7.36 (m, 4H), 7.32-7.19 (m, 3H), 6.98-6.80 (m, 1H), 6.12-5.76 (m, 1H), 4.70-4.21 (m, 1H), 4.14-4.05 (s, 3H), 3.81-3.56 (m, 3H), 3.10-2.90 (m, 3H), 2.40-2.24 (m, 9H), 1.87-1.48 (m, 10H), 1.32-1.17 (m, 9H). LC-MS (ES+, m/z): 882.4 [$(M+H)^+$]; Rt=3.556 min; HRMS (EI): m/z $[M+H]^+$ found: 882.3936.

Example 17 (Compound 17)

3-(1-(5-((S)-2,2-dimethyltetrahydro-2H-pyran-4-yl)-2-((S)-2-(4-fluoro-3,5-dimethylphenyl)-4-methyl-3-(5-methyl-4-(1-methyl-1H-indazol-5-yl)-1H-imidazol-1-yl)-4,5,6,7-tetrahydro-2H-pyrazolo[4,3-c]pyridine-5-carbonyl)-1H-indol-1-yl)cyclopropyl)-1,2,4-oxadiazol-5 (4H)-one Scheme 17

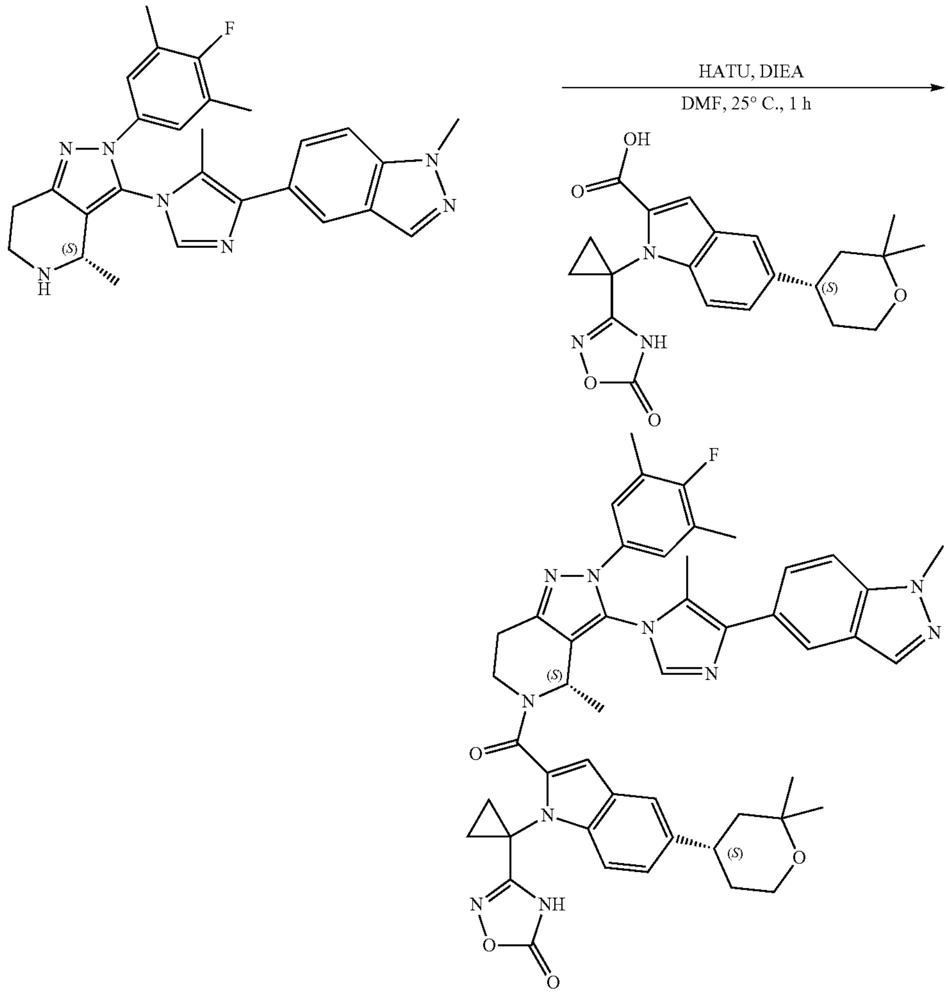

The compound was prepared following the method described in the above synthetic scheme.

$^1H$ NMR (400 MHz, DMSO-$d_6$) δ=12.07 (br s, 1H), 8.71-8.21 (m, 1H), 8.11-7.85 (m, 2H), 7.81-7.62 (m, 2H), 7.55-7.42 (m, 2H), 7.23 (br d, J=8.4 Hz, 1H), 7.06-6.71 (m, 3H), 5.84-5.20 (m, 1H), 4.55-4.31 (m, 1H), 4.06 (br s, 3H), 3.75-3.49 (m, 3H), 3.07-2.85 (m, 3H), 2.26-2.10 (m, 7H), 2.02-1.90 (m, 2H), 1.82-1.48 (m, 8H), 1.37-1.14 (m, 9H). $^1H$ NMR (400 MHz, MeOD-$d_4$) δ=9.21-8.19 (m, 1H), 8.15-7.74 (m, 2H), 7.71-7.47 (m, 4H), 7.35-7.21 (m, 1H), 7.11-6.69 (m, 3H), 6.12-5.17 (m, 1H), 4.79-4.36 (m, 1H), 4.10 (br s, 3H), 3.94-3.64 (m, 3H), 3.16-2.87 (m, 3H), 2.36-2.28 (m, 1H), 2.23 (br s, 6H), 2.03 (br s, 2H), 1.81-1.50 (m, 8H), 1.44-1.18 (m, 9H). LC-MS (ES+, m/z): 849.4 [$(M+H)^+$]; Rt=2.870 min. HRMS (EI): m/z $[M+H]^+$ found: 849.4039.

Example 18 (Compound 18)
3-((1S,2S)-1-(5-((S)-2,2-dimethyltetrahydro-2H-pyran-4-yl)-2-((S)-3-(5-(4-fluoro-1-methyl-1H-indazol-5-yl)-4-methyloxazol-2-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one
Scheme 18
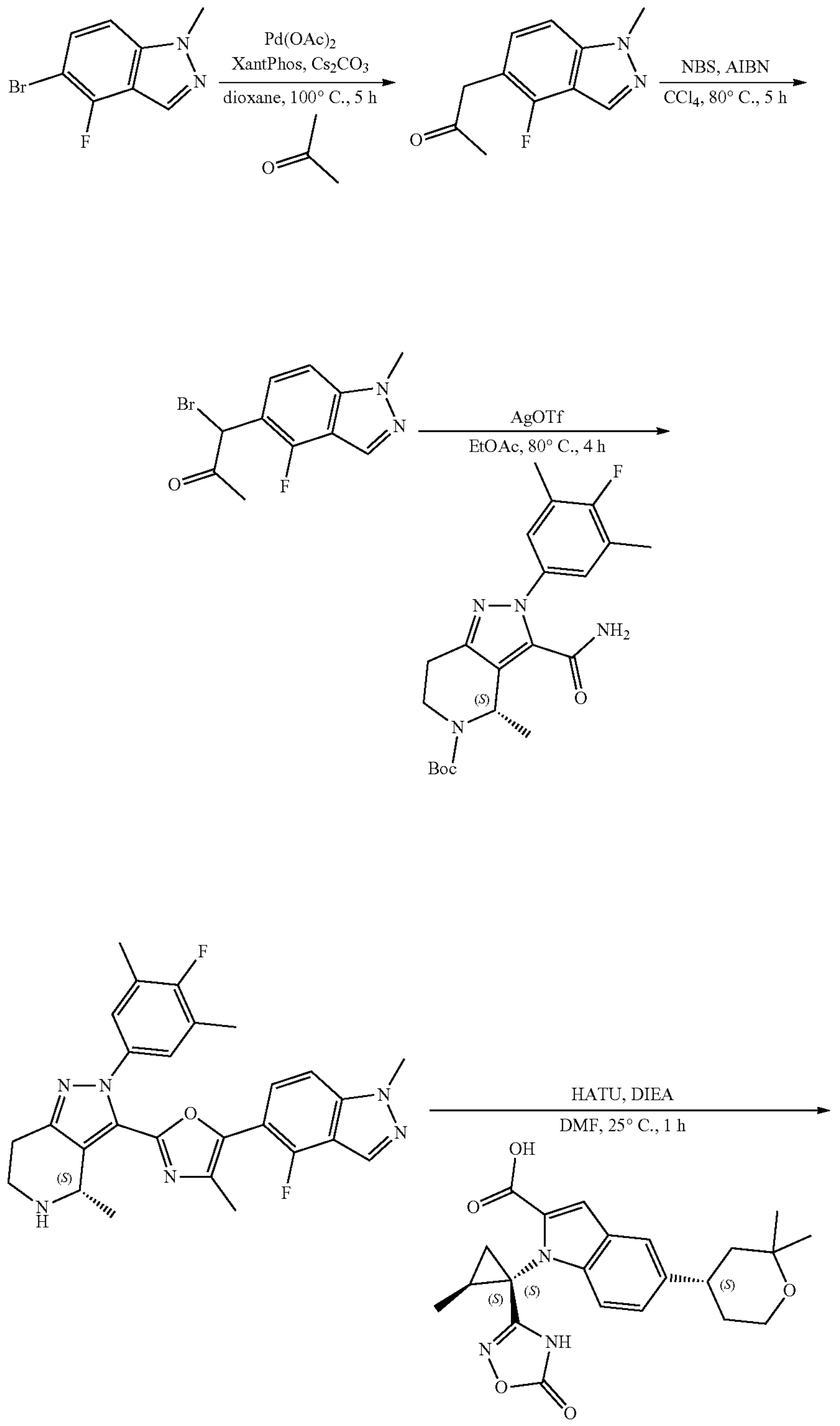

-continued

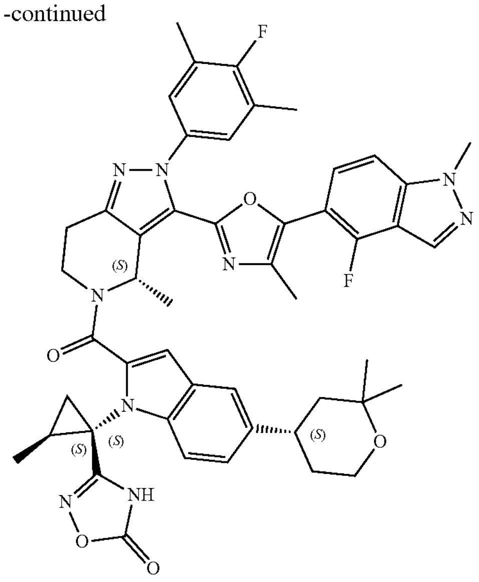

The compound was prepared following the method described in the above synthetic scheme.

$^1$H NMR (400 MHz, DMSO-$d_6$) δ=11.80-11.73 (m, 1H), 8.27-8.22 (m, 1H), 7.62 (d, J=8.5 Hz, 1H), 7.57-7.49 (m, 1H), 7.43-7.37 (m, 1H), 7.31 (br s, 2H), 7.26 (br d, J=9.1 Hz, 1H), 7.18-7.08 (m, 1H), 7.00-6.92 (m, 1H), 6.00-5.93 (m, 1H), 4.41-4.33 (m, 1H), 4.12-4.08 (m, 3H), 3.75 (br d, J=3.0 Hz, 3H), 3.24-3.15 (m, 1H), 3.07-3.00 (m, 1H), 2.97-2.79 (m, 1H), 2.31-2.24 (m, 9H), 1.76-1.52 (m, 9H), 1.28-1.15 (m, 10H). $^1$H NMR (400 MHz, DMSO-$d_6$) δ=11.70-11.56 (m, 1H), 8.20-8.15 (m, 1H), 7.54-7.50 (m, 2H), 7.44-7.39 (m, 1H), 7.26 (s, 2H), 7.24 (br s, 1H), 7.19-7.13 (m, 1H), 6.95-6.84 (m, 1H), 6.11-5.87 (m, 1H), 4.58-4.26 (m, 1H), 4.10-4.09 (m, 3H), 3.73 (br d, J=7.4 Hz, 3H), 3.06-3.03 (m, 1H), 3.02-2.96 (m, 1H), 2.95-2.89 (m, 1H), 2.33-2.27 (m, 9H), 1.72-1.56 (m, 9H), 1.29-1.19 (m, 10H). LC-MS (ES+, m/z): 882.3 [$(M+H)^+$]; Rt=3.543 min. HRMS (EI): m/z $[M+H]^+$ found: 882.3920.

Example 20 (Compound 20)

3-((1S,2S)-1-(5-((S)-2,2-dimethyltetrahydro-2H-pyran-4-yl)-2-((S)-3-(4-(4-fluoro-1-methyl-1H-indazol-5-yl)-5-methyl-1H-imidazol-1-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 20

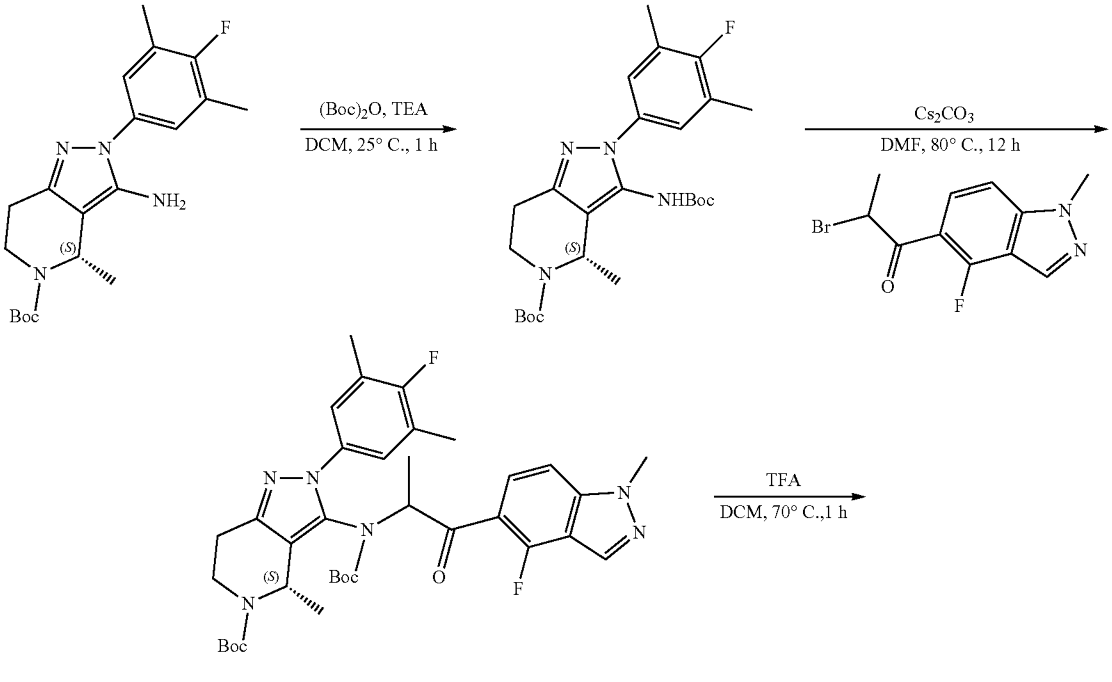

-continued
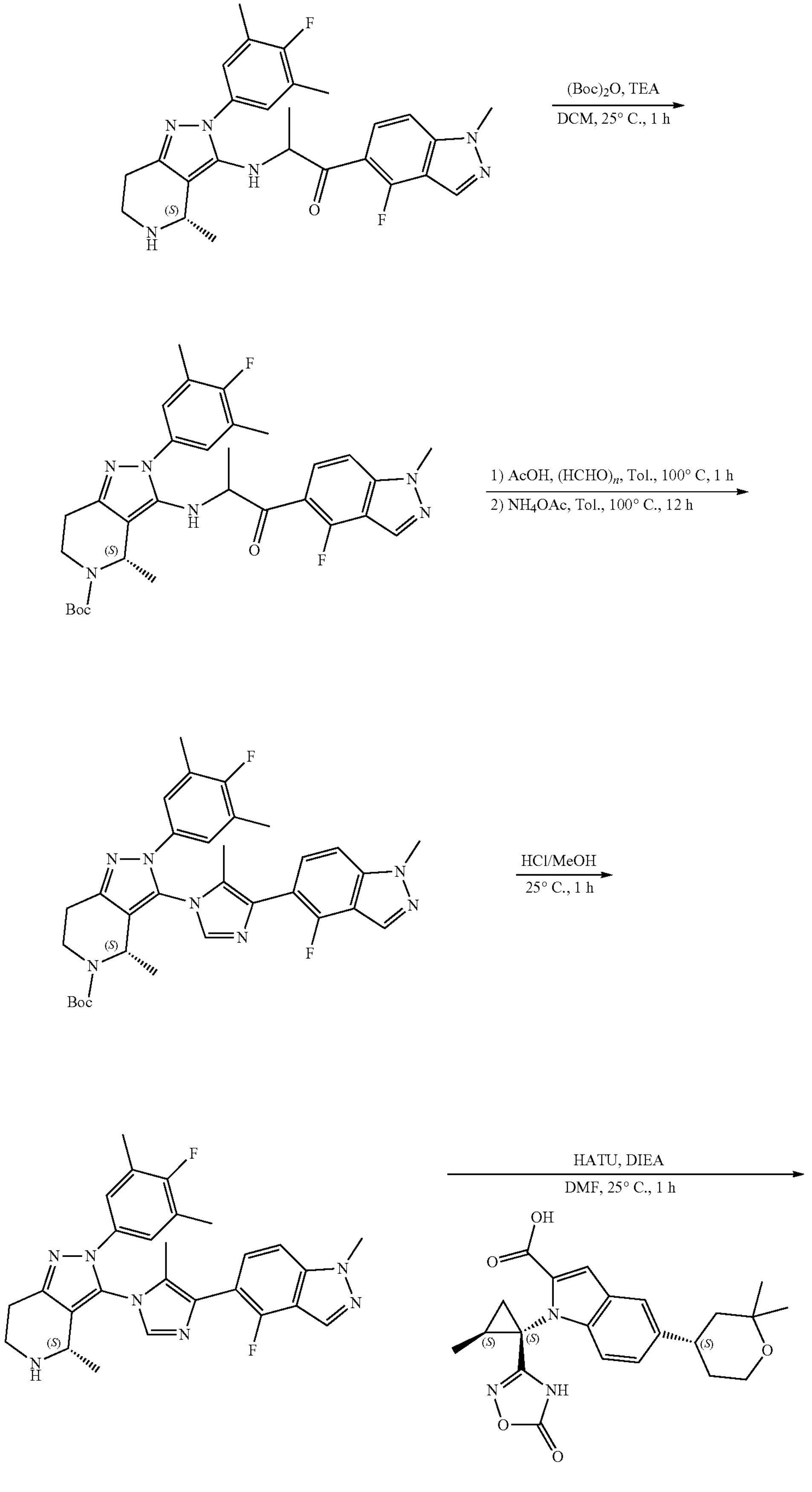

-continued

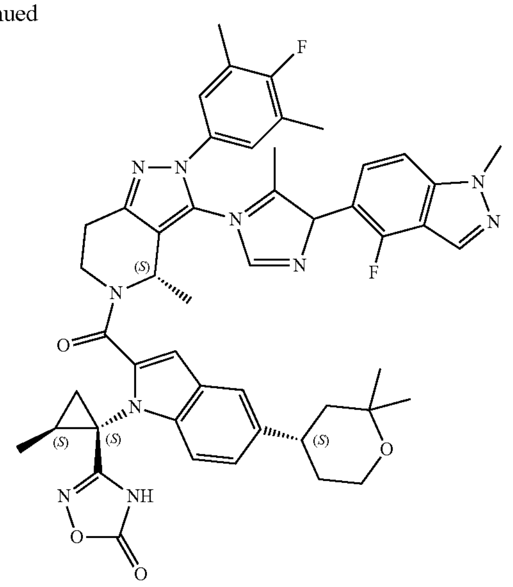

The compound was prepared following the method described in the above synthetic scheme.

$^1$H NMR (400 MHz, MeOD-$d_4$) δ=8.50 (br s, 1H), 8.19-7.98 (m, 1H), 7.63-7.37 (m, 4H), 7.28 (br d, J=8.5 Hz, 1H), 7.13-6.81 (m, 3H), 5.95-5.31 (m, 1H), 4.71-4.45 (m, 1H), 4.20-4.02 (m, 3H), 3.95-3.66 (m, 3H), 3.14-3.03 (m, 2H), 2.30-2.14 (m, 7H), 2.03-1.51 (m, 10H), 1.50-1.06 (m, 12H). $^1$H NMR (400 MHz, DMSO-$d_6$. T=273+80K) δ=12.00-11.30 (m, 1H), 8.32-7.95 (m, 2H), 7.57-7.47 (m, 3H), 7.42 (br t, J=8.5 Hz, 1H), 7.30-7.23 (m, 1H), 6.95-6.83 (m, 3H), 5.70-5.30 (m, 1H), 4.63-4.39 (m, 1H), 4.08 (s, 3H), 3.78-3.49 (m, 3H), 3.07-2.93 (m, 2H), 2.18 (s, 6H), 2.00-1.88 (m, 1H), 1.81-1.45 (m, 10H), 1.41-1.09 (m, 12H). LC-MS (ES+, m/z): 881.4 [$(M+H)^+$]; Rt=3.147 min. HRMS (EI): m/z $[M+H]^+$ found: 881.4064.

Example 21 (Compound 21)

3-((1S,2S)-1-(5-((S)-2, 2-dimethyltetrahydro-2H-pyran-4-yl)-2-((S)-3-(4-(4-fluoro-1-methyl-1H-indazol-5-yl)-1-methyl-1H-imidazol-2-yl)-2-(4-fluoro-3, 5-dimethylphenyl)-4-methyl-4, 5, 6, 7-tetrahydro-2H-pyrazolo[4, 3-c]pyridine-5-carbonyl)-1H-indol-1-yl)-2-methylcyclopropyl)-1, 2, 4-oxadiazol-5 (4H)-one Scheme 21

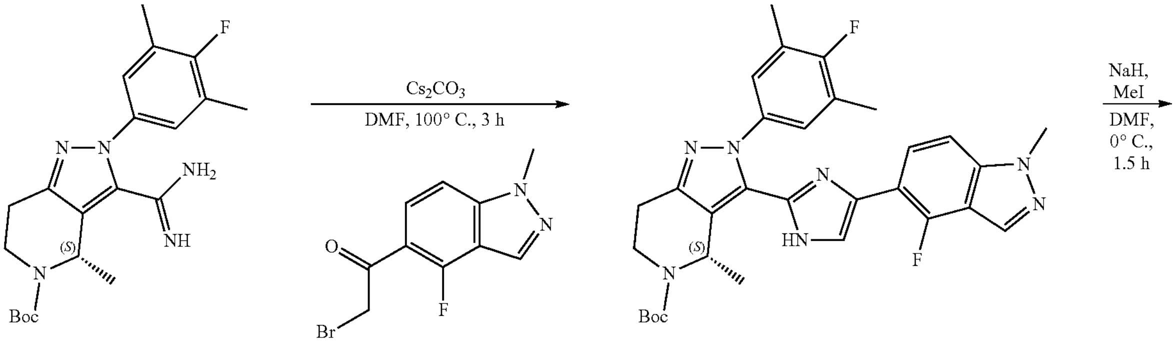

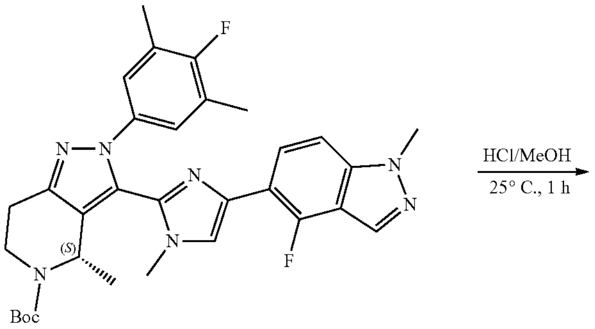

-continued
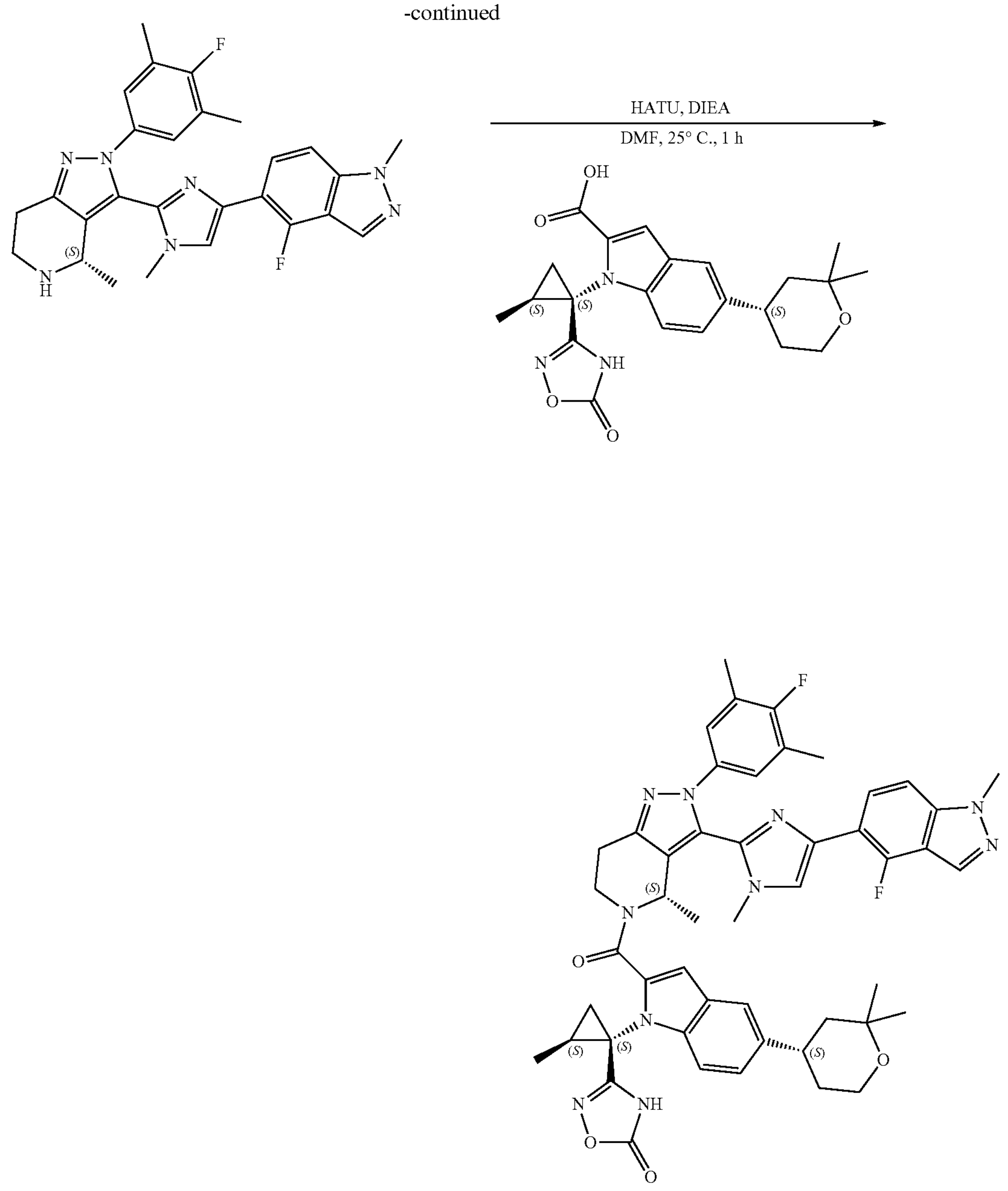
The compound was prepared following the method described in the above synthetic scheme.
$^1$H NMR (400 MHz, $CDCl_3$-d) δ=11.27-11.14 (m, 1H), 8.15-7.78 (m, 2H), 7.57-7.33 (m, 3H), 7.31-7.23 (m, 1H), 7.15 (br s, 1H), 7.01-6.81 (m, 2H), 6.71-6.56 (m, 1H), 5.81-5.25 (m, 1H), 4.88-4.39 (m, 1H), 4.09-3.97 (s, 3H), 3.85-3.73 (m, 2H), 3.59-3.54 (m, 1H), 3.29-2.95 (m, 6H), 2.23-2.01 (m, 6H), 1.86 (br s, 10H), 1.32-1.17 (m, 6H), 1:15-0.98 (m, 3H). $^1$H NMR (400 MHz, DMSO-$d_6$) δ=11.83-11.38 (m, 1H), 8.23-7.78 (m, 2H), 7.74-7.35 (m, 4H), 7.27 (d, J=8.6 Hz, 1H), 7.11-6.76 (m, 3H), 5.85-5.31 (m, 1H), 4.65-4.28 (m, 1H), 4.08 (s, 3H), 3.73 (br d, J=7.7 Hz, 2H), 3.67-3.57 (m, 1H), 3.38-2.83 (m, 6H), 2.22-2.09 (m, 6H), 1.86-1.40 (m, 10H), 1.32-1.10 (m, 9H). LC-MS (ES+, m/z): 881.3 [$(M+H)^+$]; Rt=3.161 min. HRMS (EI): m/z $[M+H]^+$ found: 881.4059.

Example 22 (Compound 22)
3-(1-(5-(2,2-dimethylmorpholino)-2-((4S)-3-(1-(4-fluoro-1-methyl-1H-indazol-5-yl)-5-methyl-1H-imidazol-4-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)cyclopropyl)-1,2,4-oxadiazol-5 (4H)-one
Scheme 22
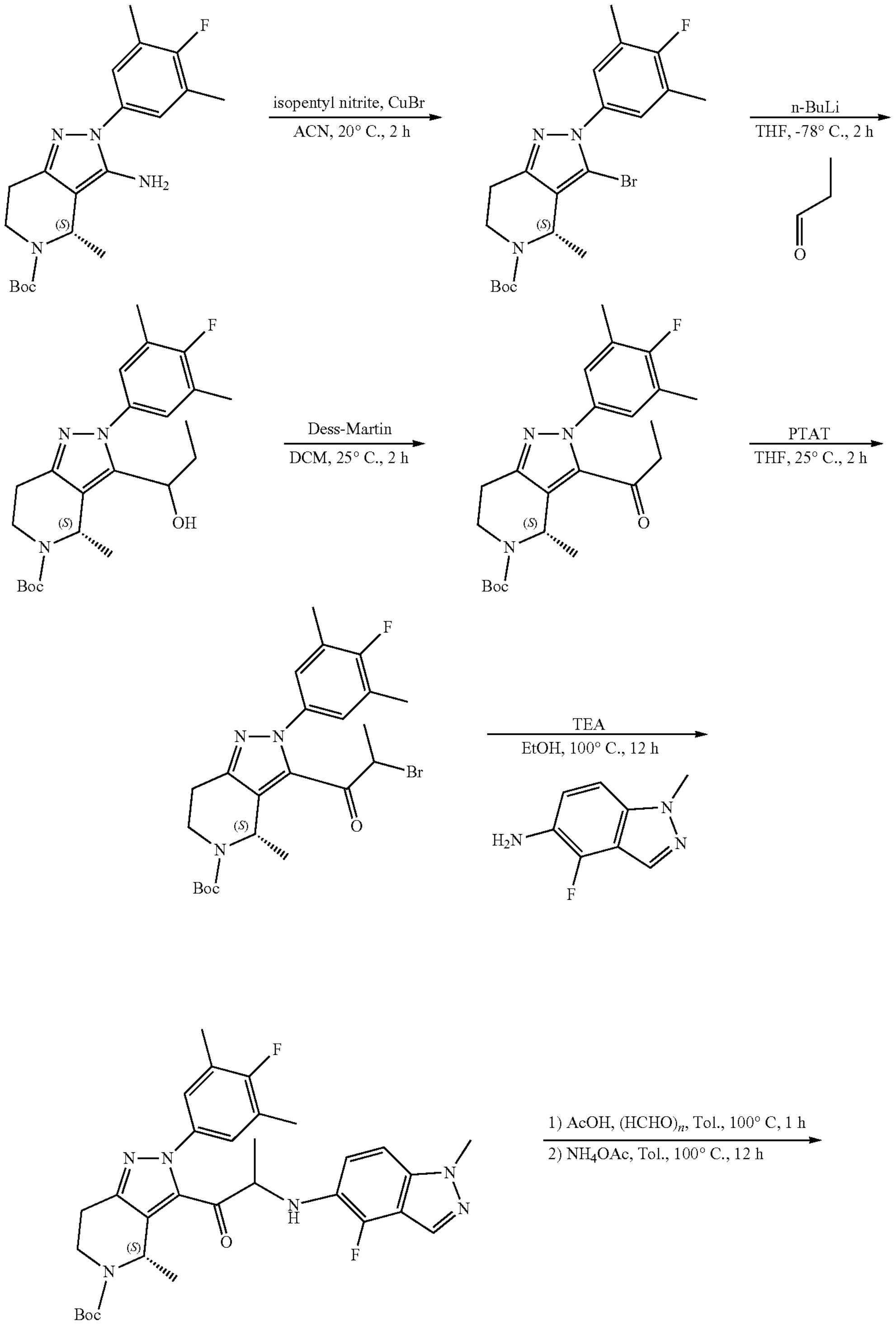

-continued

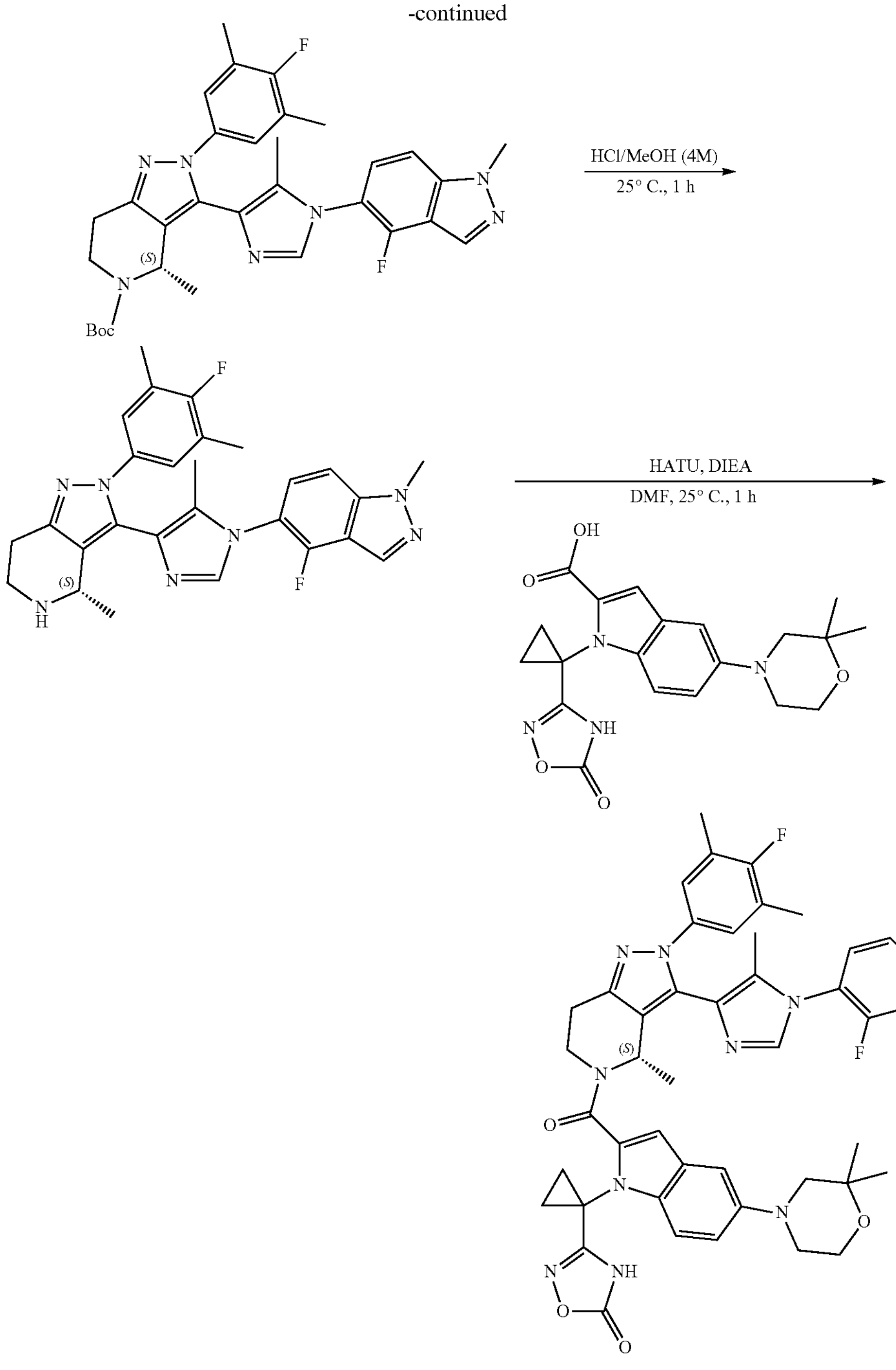

The compound was prepared following the method described in the above synthetic scheme.

$^1$H NMR (400 MHz, DMSO-$d_6$) δ=12.22-11.95 (m, 1H), 8.37-8.26 (m, 1H), 8.04-7.84 (m, 1H), 7.69 (br d, J=8.6 Hz, 1H), 7.56-7.45 (m, 1H), 7.44-7.37 (m, 1H), 7.14-6.96 (m, 4H), 6.77-6.59 (m, 1H), 5.95-5.03 (m, 1H), 4.37-4.05 (m, 4H), 3.78 (br s, 2H), 2.99 (br s, 2H), 2.88-2.80 (m, 3H), 2.20 (br s, 6H), 1.87-1.55 (m, 6H), 1.50-1.10 (m, 12H). $^1$H NMR (400 MHz, MeOD-$d_4$) δ=8.25-8.14 (m, 1H), 8.01-7.80 (m, 1H), 7.61-7.24 (m, 3H), 7.20-7.11 (m, 2H), 7.08-6.92 (m, 2H), 6.85-6.68 (m, 1H), 5.51 (br s, 1H), 4.67-4.41 (m, 1H), 4.19-4.07 (m, 3H), 3.89 (br s, 2H), 3.04 (br d, J=11.3 Hz, 2H), 2.97-2.85 (m, 3H), 2.30-2.17 (m, 6H), 2.06-1.64 (m, 4H), 1.61-1.29 (m, 14H). $^1$H NMR (400 MHz, DMSO-$d_6$) δ=12.52-11.01 (m, 1H), 8.30-8.22 (m, 1H), 7.93-7.84 (m, 1H), 7.68-7.57 (m, 1H), 7.46-7.36 (m, 2H), 7.13-7.08 (m, 1H), 7.07-7.00 (m, 3H), 6.71-6.62 (m, 1H), 5.79-5.45 (m, 1H), 4.43 (br d, J=3.7 Hz, 1H), 4.12 (s, 3H), 3.82-3.77 (m, 2H), 3.02 (br d, J=4.5 Hz, 2H), 2.89-2.80 (m, 3H), 2.20 (s, 6H), 1.87-1.47 (m, 7H), 1.47-1.34 (m, 4H), 1.28 (s, 7H). LC-MS (ES+, m/z): 868.4 [$(M+H)^+$]; Rt=2.876 min. HRMS (EI): m/z $[M+H]^+$ found: 868.3866.

Example 23 (Compound 23)
3-((S)-5-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-1-(4-fluoro-1-methyl-1H-indazol-5-yl) imidazolidine-2,4-dione
Scheme 23
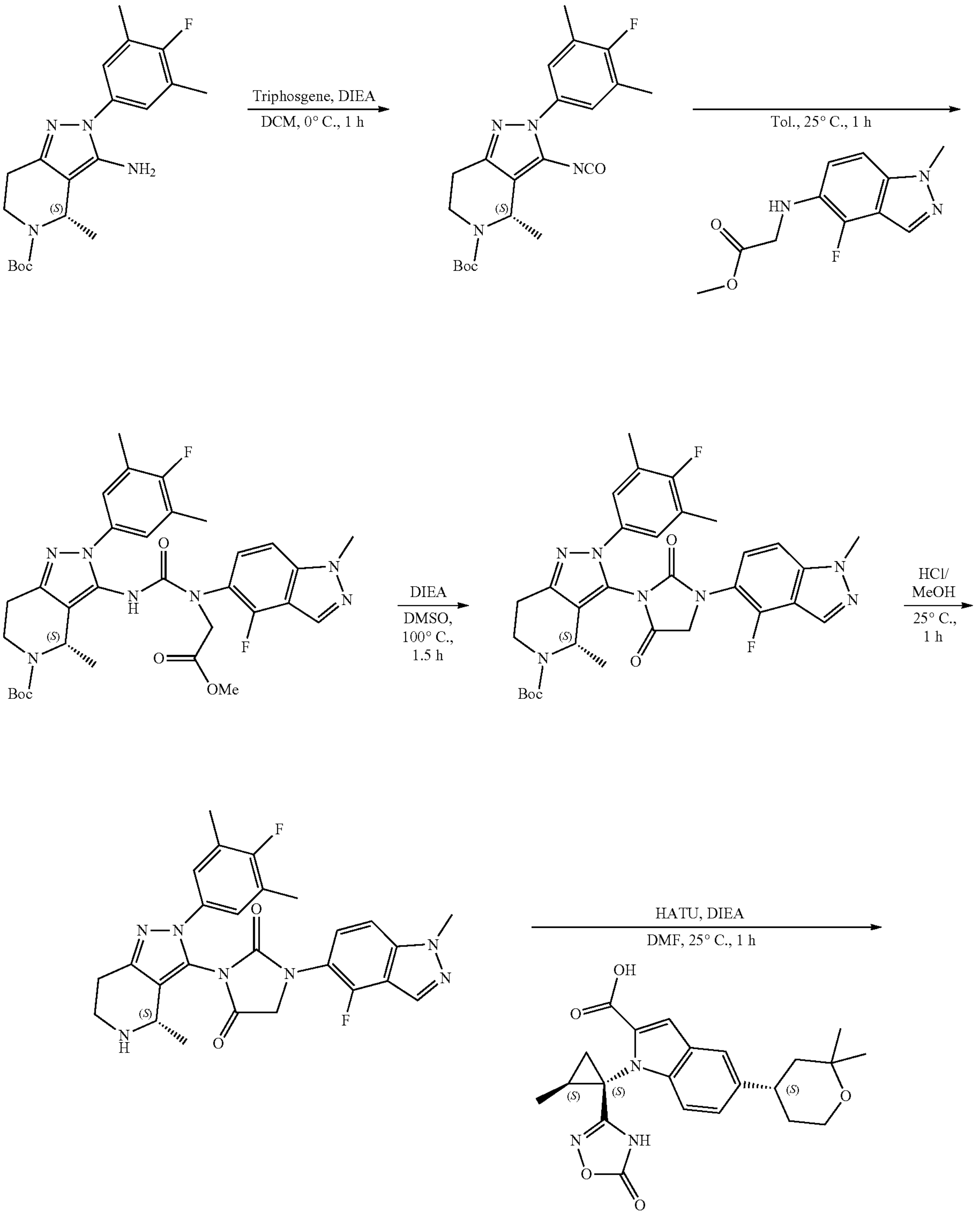

-continued

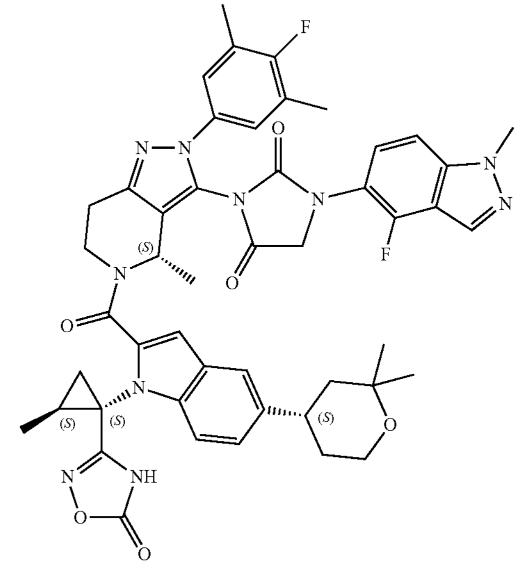

The compound was prepared following the method described in the above synthetic scheme.

$^1$H NMR (400 MHz, DMSO-$d_6$) δ=11.82-11.71 (m, 1H), 8.31-8.22 (m, 1H), 7.65-7.63 (m, 1H), 7.58-7.49 (m, 2H), 7.41-7.37 (m, 1H), 7.29-7.25 (m, 1H), 7.21-7.13 (m, 2H), 6.88 (br s, 1H), 5.90-5.57 (m, 1H), 4.90-4.81 (m, 1H), 4.77-4.48 (m, 2H), 4.42-4.34 (m, 1H), 4.11-4.03 (m, 4H), 3.27-3.16 (m, 1H), 3.08-2.87 (m, 3H), 2.32-2.29 (m, 6H), 1.61 (br s, 10H), 1.27 (br d, J=2.8 Hz, 3H), 1.18 (br s, 6H). $^1$H NMR (400 MHz, DMSO-$d_6$, T=273+80K) δ=11.72-11.52 (m, 1H), 8.22-8.12 (m, 1H), 7.59-7.55 (m, 1H), 7.54-7.47 (m, 2H), 7.43-7.39 (m, 1H), 7.28-7.24 (m, 1H), 7.17-7.11 (m, 2H), 6.94-6.83 (m, 1H), 5.83-5.52 (m, 1H), 4.84-4.72 (m, 1H), 4.70-4.51 (m, 2H), 4.50-4.37 (m, 1H), 4.11-4.06 (m, 4H), 3.17-3.08 (m, 1H), 3.07-2.89 (m, 3H), 2.30 (s, 6H), 1.74-1.53 (m, 10H), 1.29 (s, 3H), 1.20 (br d, J=4.4 Hz, 6H). LC-MS (ES+, m/z): 899.3 [$(M+H)^+$]; Rt=3.195 min. HRMS (EI): m/z $[M+H]^+$ found: 899.3844.

Example 24 (Compound 24)

3-((1S,2S)-1-(5-((S)-2,2-dimethyltetrahydro-2H-pyran-4-yl)-2-((S)-3-(4-(4-fluoro-1-methyl-1H-indazol-5-yl)-5-methyl-1H-imidazol-2-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)-2-methylcyclopropyl)-1,2,4-oxadiazol-5 (4H)-one Scheme 24

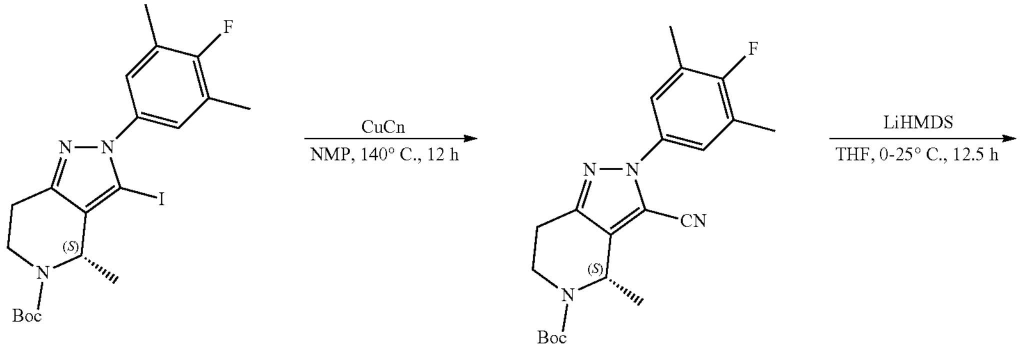

-continued
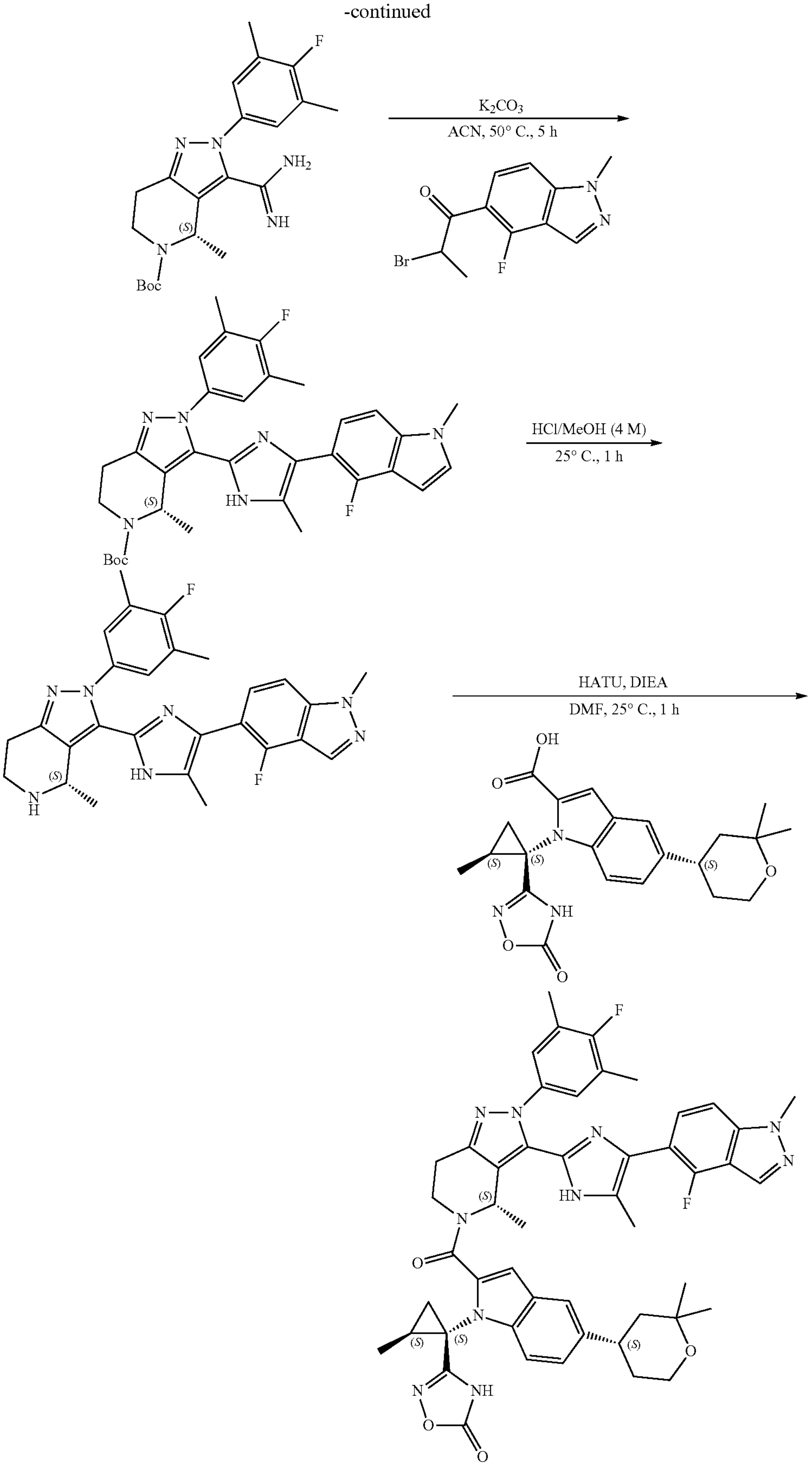

The compound was prepared following the method described in the above synthetic scheme.

$^1$H NMR (400 MHz, DMSO-$d_6$) δ=12.25-11.67 (m, 1H), 8.31-8.15 (m, 1H), 7.68-7.60 (m, 1H), 7.58-7.44 (m, 2H), 7.43-7.34 (m, 1H), 7.29-7.21 (m, 1H), 7.17-7.03 (m, 2H), 6.09 (br s, 2H), 5.93-5.48 (m, 1H), 4.74-4.34 (m, 1H), 4.13-4.08 (m, 3H), 3.76-3.66 (m, 2H), 3.27-2.79 (m, 3H), 2.18 (m, 9H), 1.39 (md, J=6.1 Hz, 8H), 1.29-1.25 (m, 3H), 1.23-1.04 (m, 6H). $^1$H NMR (400 MHz, DMSO-$d_6$, T=273+80K) δ=11.91-11.15 (m, 1H), 8.21-8.03 (m, 1H), 7.61-7.34 (m, 5H), 7.29-7.24 (m, 1H), 7.13-7.05 (m, 2H), 6.94-6.84 (m, 1H), 5.85-4.42 (m, 1H), 4.10-4.07 (m, 3H), 3.76-3.70 (m, 2H), 3.66-3.51 (m, 1H), 3.19-2.82 (m, 3H), 2.28-2.19 (m, 9H), 1.87-1.37 (m, 11H), 1.31-1.28 (m, 3H), 1.24-1.13 (m, 6H). LC-MS (ES+, m/z): 881.4 [(M+H)$^+$]; Rt=2.830 min. HRMS (EI): m/z [M+H]$^+$ found: 881.4061.

Example 26 (Compound 26)

3-(1-(7-((S)-2,2-dimethyltetrahydro-2H-pyran-4-yl)-2-((4S)-3-(1-(4-fluoro-1-methyl-1H-indazol-5-yl)-5-methyl-1H-imidazol-4-yl)-2-(4-fluoro-3,5-dimethylphenyl)-4-methyl-4,5,6,7-tetrahydro-2H-pyrazolo [4,3-c]pyridine-5-carbonyl) indolizin-3-yl) cyclopropyl)-1,2,4-oxadiazol-5 (4H)-one The compound was prepared following the method described in the above synthetic scheme.

$^1$H NMR (400 MHz, DMSO-$d_6$) δ=12.11-11.94 (m, 1H), 8.39-8.31 (m, 1H), 8.24-7.86 (m, 2H), 7.84-7.45 (m, 2H), 7.36-7.24 (m, 1H), 7.08-6.97 (m, 2H), 6.78-6.61 (m, 1H), 6.50-6.32 (m, 1H), 5.82-5.71 (m, 0.5H), 5.10-5.03 (m, 0.5H), 4.15-4.11 (m, 3H), 4.04 (br d, J=11.5 Hz, 1H), 3.75-3.65 (m, 2H), 3.49-3.33 (m, 1H), 2.97-2.70 (m, 3H), 2.25-2.15 (m, 6H), 1.77-1.47 (m, 8H), 1.38-1.13 (m, 12H). $^1$H NMR (400 MHz, MeOD-$d_4$) δ=8.41-8.07 (m, 3H), 7.66 (d, J=8.8 Hz, 1H), 7.57-7.50 (m, 1H), 7.42-7.23 (m, 1H), 7.05-6.97 (m, 1H), 6.90-6.67 (m, 1H), 6.47 (s, 1H), 6.78-6.37 (m, 1H), 6.08-5.97 (m, 0.5H), 5.28 (br d, J=5.9 Hz, 0.5H), 4.18 (s, 3H), 3.95-3.72 (m, 3H), 3.57-3.44 (m, 1H), 3.08-2.91 (m, 3H), 2.26-2.18 (m, 6H), 1.88-1.54 (m, 8H), 1.39-1.22 (m, 12H). LC-MS (ES+, m/z): 867.3 [(M+H)$^+$]; Rt=2.832 min. HRMS (EI): m/z [M+H]$^+$ found: 867.3964.

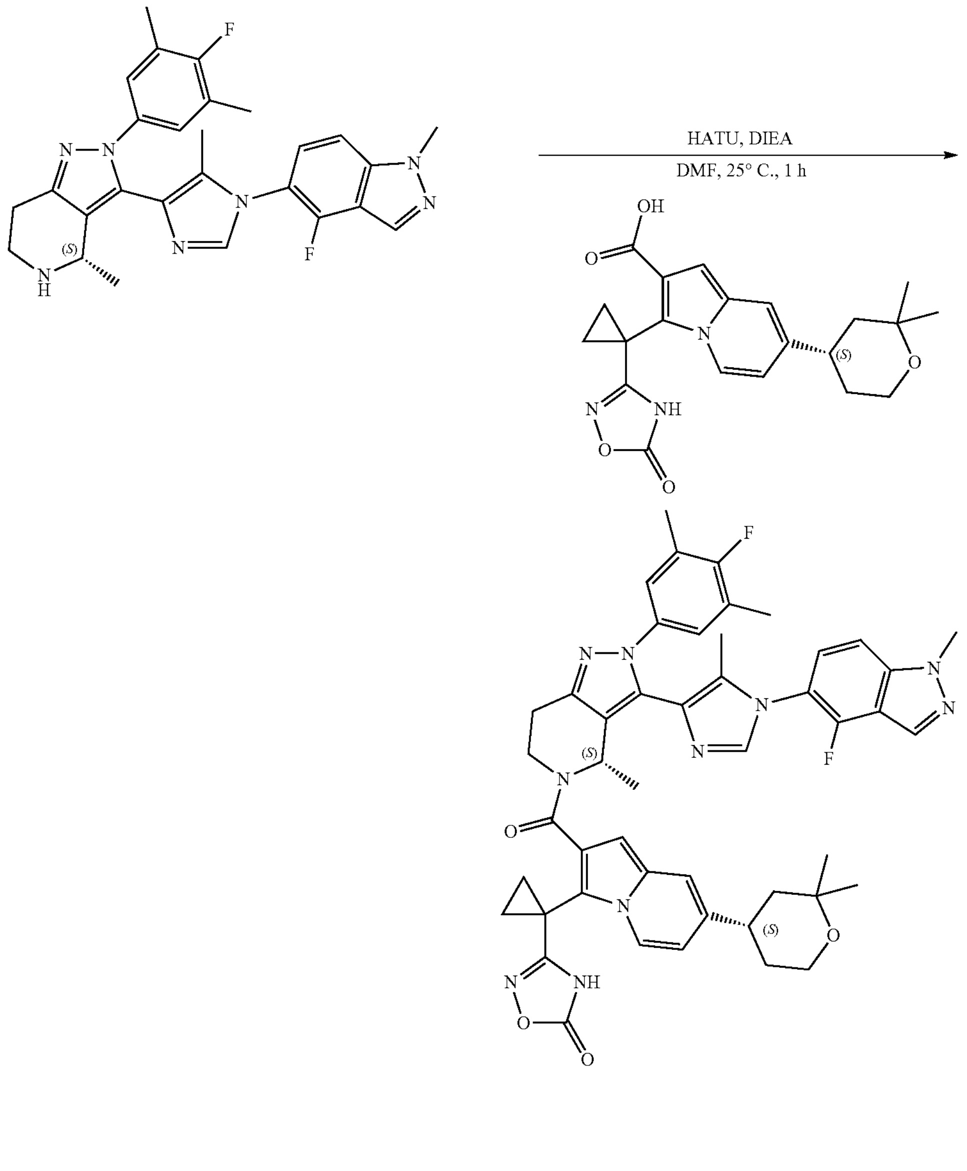

Example 27 (Compound 27)
(S)-3-(1-(2-(3-(1-(4-fluoro-1-methyl-1H-indazol-5-yl)-5-methyl-1H-imidazol-4-yl)-2-(4-fluoro-3, 5-dimethylphenyl)-4-methyl-4, 5, 6, 7-tetrahydro-2H-pyrazolo[4, 3-c]pyridine-5-carbonyl)-5-morpholino-1H-indol-1-yl)cyclopropyl)-1, 2, 4-oxadiazol-5 (4H)-one
Scheme 27
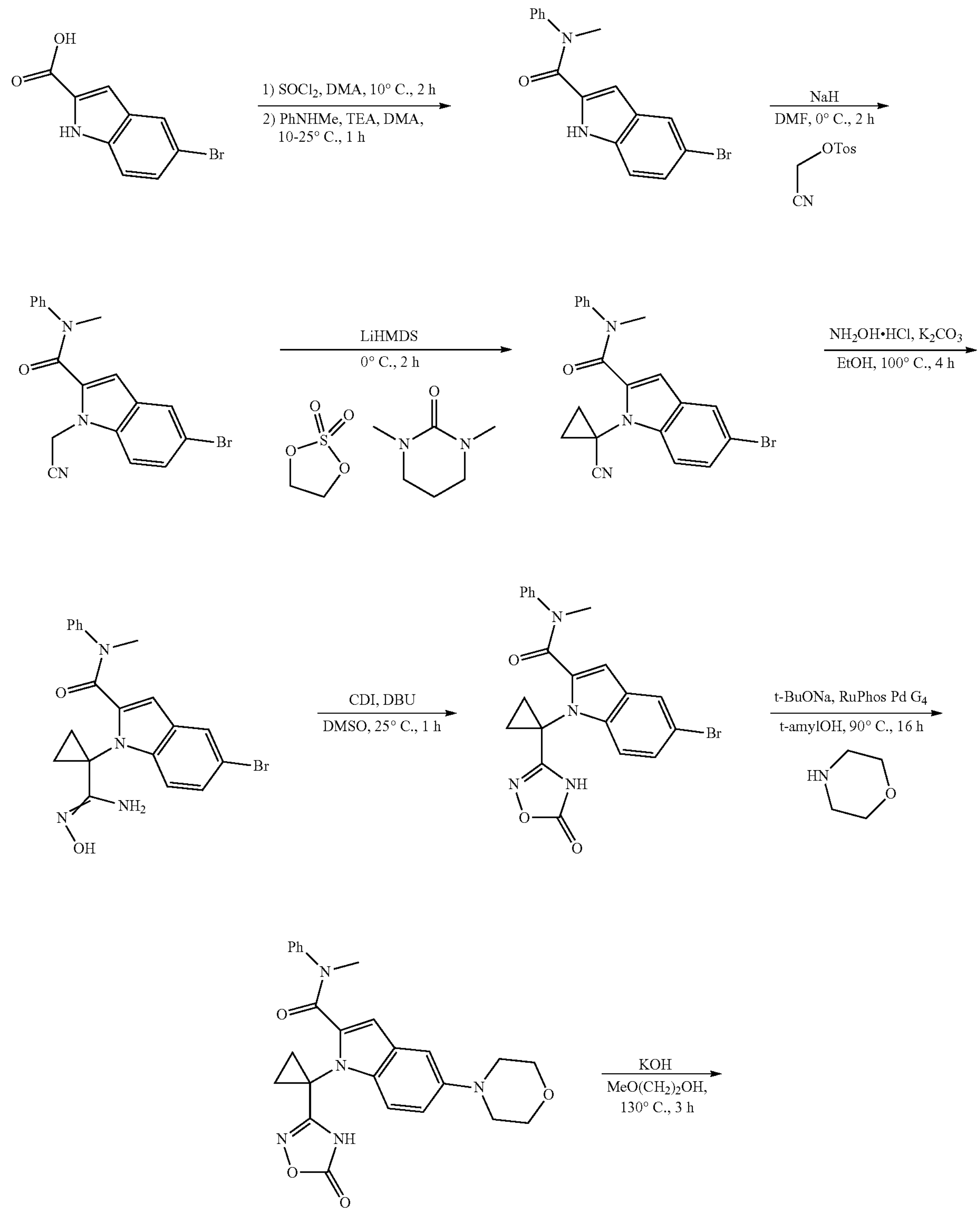

-continued
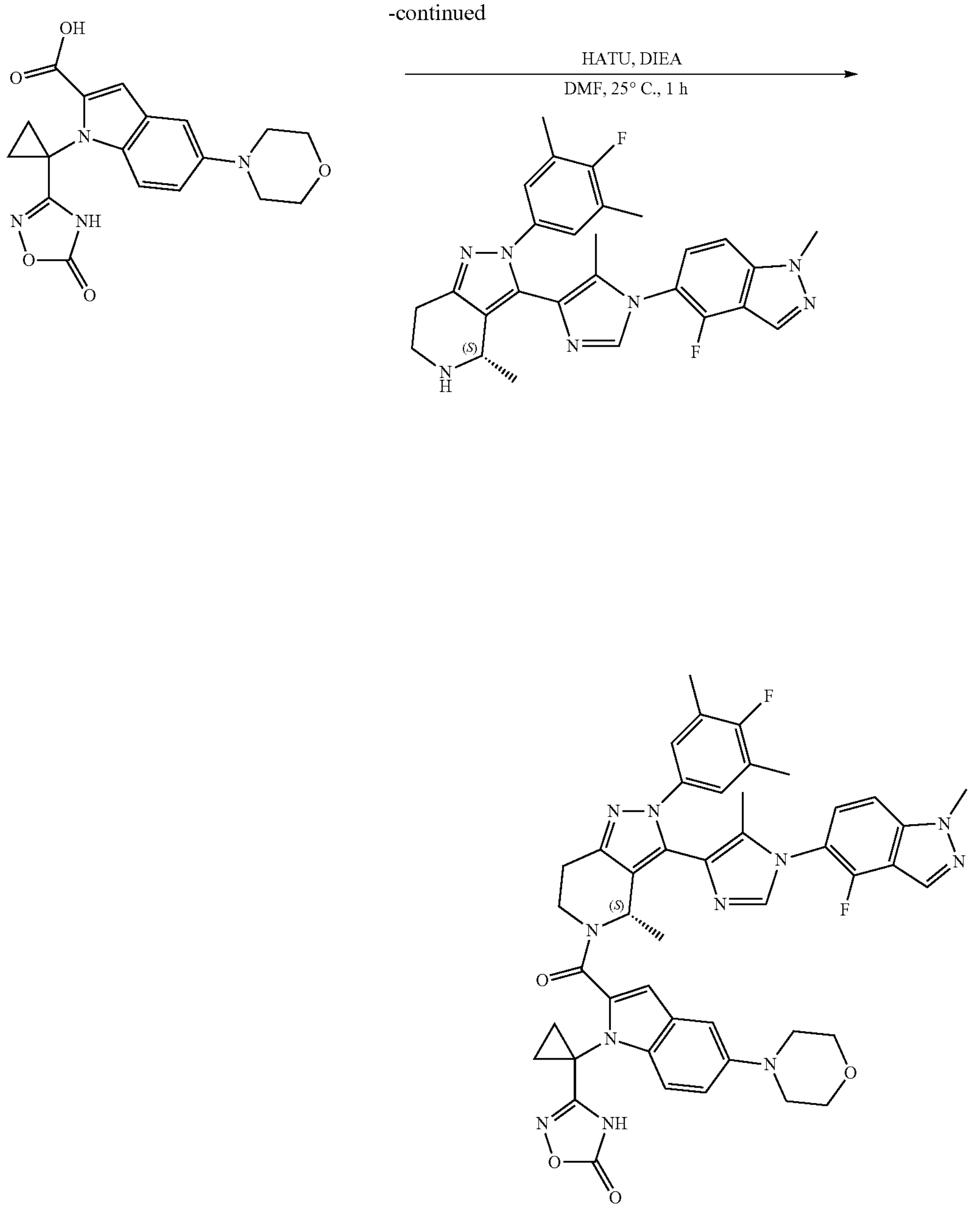
The compound was prepared following the method described in the above synthetic scheme.
$^1$H NMR (400 MHz, DMSO-$d_6$) δ=12.30-11.08 (m, 1H), 8.33-8.23 (m, 1H), 7.96-7.82 (m, 1H), 7.63 (d, J=8.3 Hz, 1H), 7.50-7.35 (m, 2H), 7.15-7.00 (m, 4H), 6.69-6.61 (m, 1H), 5.78-5.45 (m, 1H), 4.56-4.29 (m, 1H), 4.13 (s, 3H), 3.81-3.77 (m, 4H), 3.53-3.45 (m, 1H), 3.06-2.75 (m, 6H), 2.24-2.17 (m, 6H), 1.77-1.67 (m, 2H), 1.58 (br s, 2H), 1.41 (br d, J=6.6 Hz, 3H), 1.31-1.17 (m, 3H). $^1$H NMR (400 MHz, $CDCl_3$-d) δ=8.14-7.99 (m, 1H), 7.66-7.39 (m, 2H), 7.27-7.22 (m, 1H), 7.11-6.85 (m, 5H), 6.64-6.48 (m, 1H), 6.19-5.60 (m, 1H), 5.27-4.32 (m, 1H), 4.15-3.95 (m, 3H), 3.87-3.78 (m, 4H), 3.61-3.34 (m, 1H), 3.11-2.85 (m, 6H), 2.18-2.11 (m, 6H), 1.71-1.61 (m, 4H), 1.39-1.25 (m, 6H). LC-MS (ES+, m/z): 840.3 [$(M+H)^+$]; Rt=2.403 min. HRMS (EI): m/z $[M+H]^+$ found: 840.3563.

Example 28 (Compound 28)
1-((S)-5-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-4-(4-fluoro-1-methyl-1H-indazol-5-yl) piperazine-2,3-dione
Scheme 28
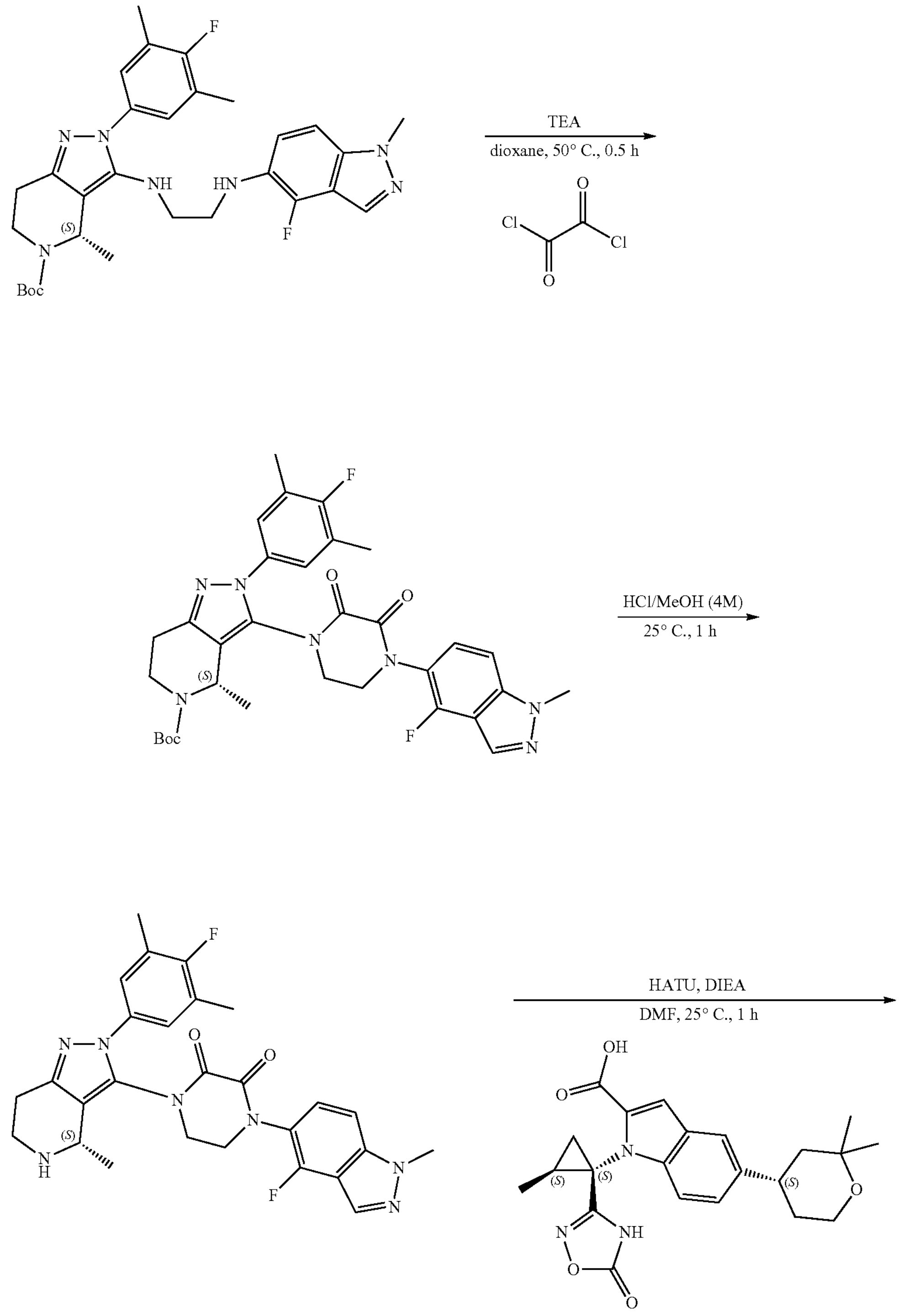

-continued

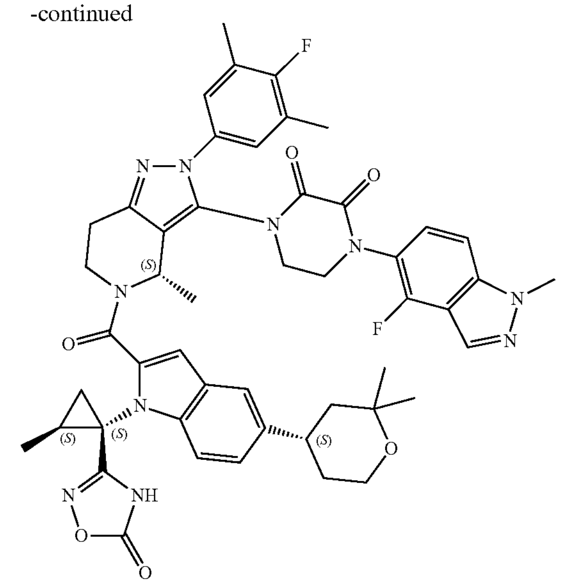

The compound was prepared following the method described in the above synthetic scheme.

$^1$H NMR (400 MHz, DMSO-$d_6$) δ=7.48 (m, 2H), 7.40 (br d, J=8.4 Hz, 1H), 7.31-7.22 (m, 3H), 7.00-6.88 (m, 1H), 5.80-5.50 (m, 1H), 4.39-4.34 (m, 1H), 4.09 (s, 3H), 4.01-3.77 (m, 3H), 3.74-3.66 (m, 3H), 3.56 (br d, J=0.9 Hz, 2H), 3.06-3.01 (m, 1H), 2.87 (br d, J=11.8 Hz, 1H), 2.31 (br d, J=7.4 Hz, 6H), 1.80-1.63 (m, 6H), 1.51 (br d, J=6.8 Hz, 4H), 1.27 (s, 3H), 1.18 (s, 6H). $^1$H NMR (400 MHz, DMSO-$d_6$, T=273+80K) δ=11.75-11.37 (m, 1H), 8.19-8.17 (m, 1H), 7.54-7.51 (m, 2H), 7.42 (br d, J=8.6 Hz, 2H), 7.27-7.22 (m, 3H), 6.93-6.85 (m, 1H), 5.81-5.52 (m, 1H), 4.50-4.35 (m, 1H), 4.08 (s, 3H), 3.96-3.82 (m, 3H), 3.75-3.71 (m, 3H), 3.66-3.48 (m, 2H), 3.04-3.01 (m, 1H), 2.87 (br d, J=15.3 Hz, 1H), 2.31 (d, J=1.4 Hz, 6H), 1.75-1.61 (m, 6H), 1.55 (br dd, J=5.8, 6.7 Hz, 4H), 1.29 (s, 3H), 1.20 (s, 6H). LC-MS (ES+, m/z): 913.4 [$(M+H)^+$]; Rt=3.055 min. HRMS (EI): m/z $[M+H]^+$ found: 913.3973.

Example 30 (Compound 30)

3-(1-(5-((S)-2,2-dimethyltetrahydro-2H-pyran-4-yl)-2-((4S)-3-(1-(4-fluoro-1-methyl-1H-indazol-5-yl)-5-methyl-1H-imidazol-4-yl)-2-(4-fluoro-3,5-dimethylphenyl)-4-methyl-4,5,6,7-tetrahydro-2H-pyrazolo[4,3-c]pyridine-5-carbonyl)-1H-indol-1-yl)cyclopropyl)-1,2,4-oxadiazol-5 (4H)-one Scheme 30

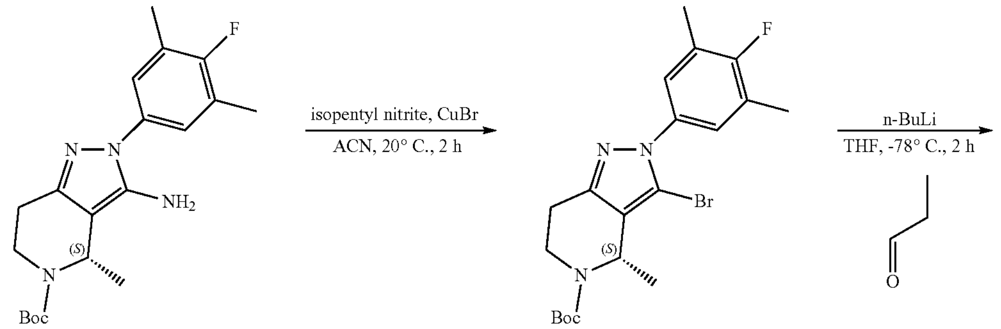

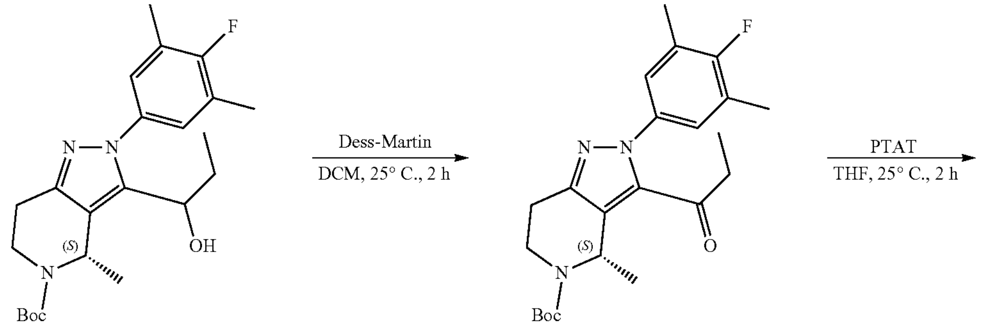

-continued
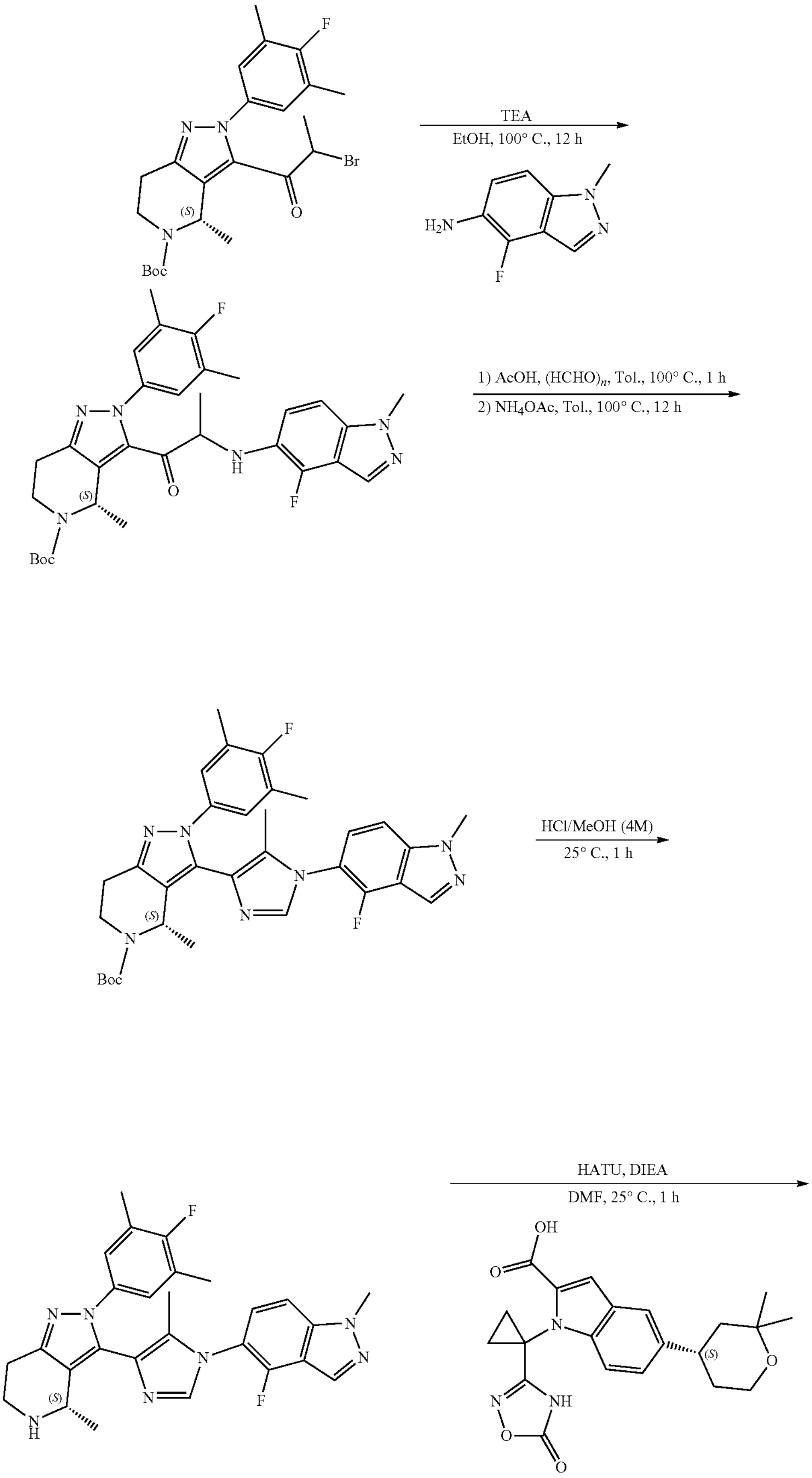

-continued

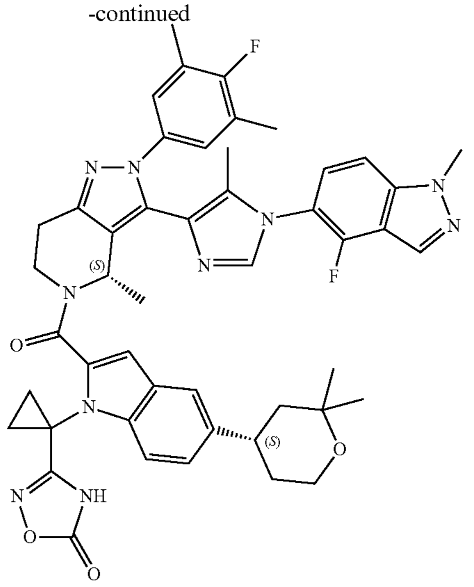

The compound was prepared following the method described in the above synthetic scheme.

$^1$H NMR (400 MHz, DMSO-$d_6$) δ=12.15-12.02 (m, 1H), 8.38-8.26 (m, 1H), 7.92 (br s, 1H), 7.77-7.62 (m, 1H), 7.59 (br s, 3H), 7.26-7.18 (m, 1H), 7.08 (br s, 2H), 6.89-6.73 (m, 1H), 5.83-5.17 (m, 1H), 4.37-4.24 (m, 1H), 4.15-4.08 (m, 3H), 3.72 (br d, J=8.0 Hz, 3H), 3.17-2.96 (m, 2H), 2.90-2.80 (m, 1H), 2.20 (br s, 6H), 1.89-1.49 (m, 10H), 1.47-1.32 (m, 3H), 1.32-1.22 (m, 4H), 1.19 (s, 3H). $^1$H NMR (400 MHz, DMSO-$d_6$. T=273+80K) δ=12.10-11.44 (m, 1H), 8.27 (s, 1H), 7.96-7.87 (m, 1H), 7.66-7.59 (m, 1H), 7.51-7.46 (m, 2H), 7.44-7.34 (m, 1H), 7.23-7.20 (m, 1H), 7.07-7.01 (m, 2H), 6.79-6.74 (m, 1H), 5.75-5.48 (m, 1H), 4.57-4.31 (m, 1H), 4.14-4.10 (m, 3H), 3.74 (br d, J=7.5 Hz, 3H), 3.09-2.96 (m, 2H), 2.82 (br s, 1H), 2.21 (d, J=1.4 Hz, 6H), 1.86-1.54 (m, 10H), 1.43 (br s, 3H), 1.30 (s, 4H), 1.20 (s, 3H). LC-MS (ES+, m/z): 867.3 [$(M+H)^+$]; Rt=2.976 min. HRMS (EI): m/z $[M+H]^+$ found: 867.3911.

Example 31 (Compound 31)

3-((S)-5-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-1-(4-fluoro-1-methyl-1H-indazol-5-yl)-5-methylimidazolidine-2,4-dione Scheme 31

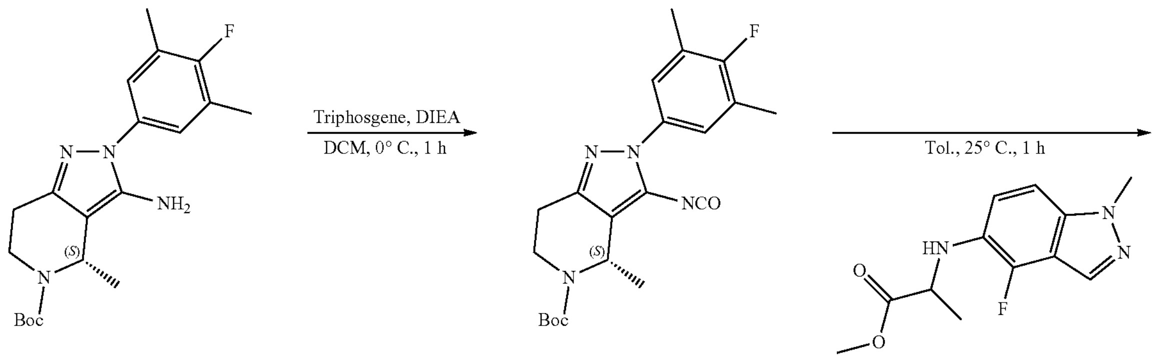

-continued
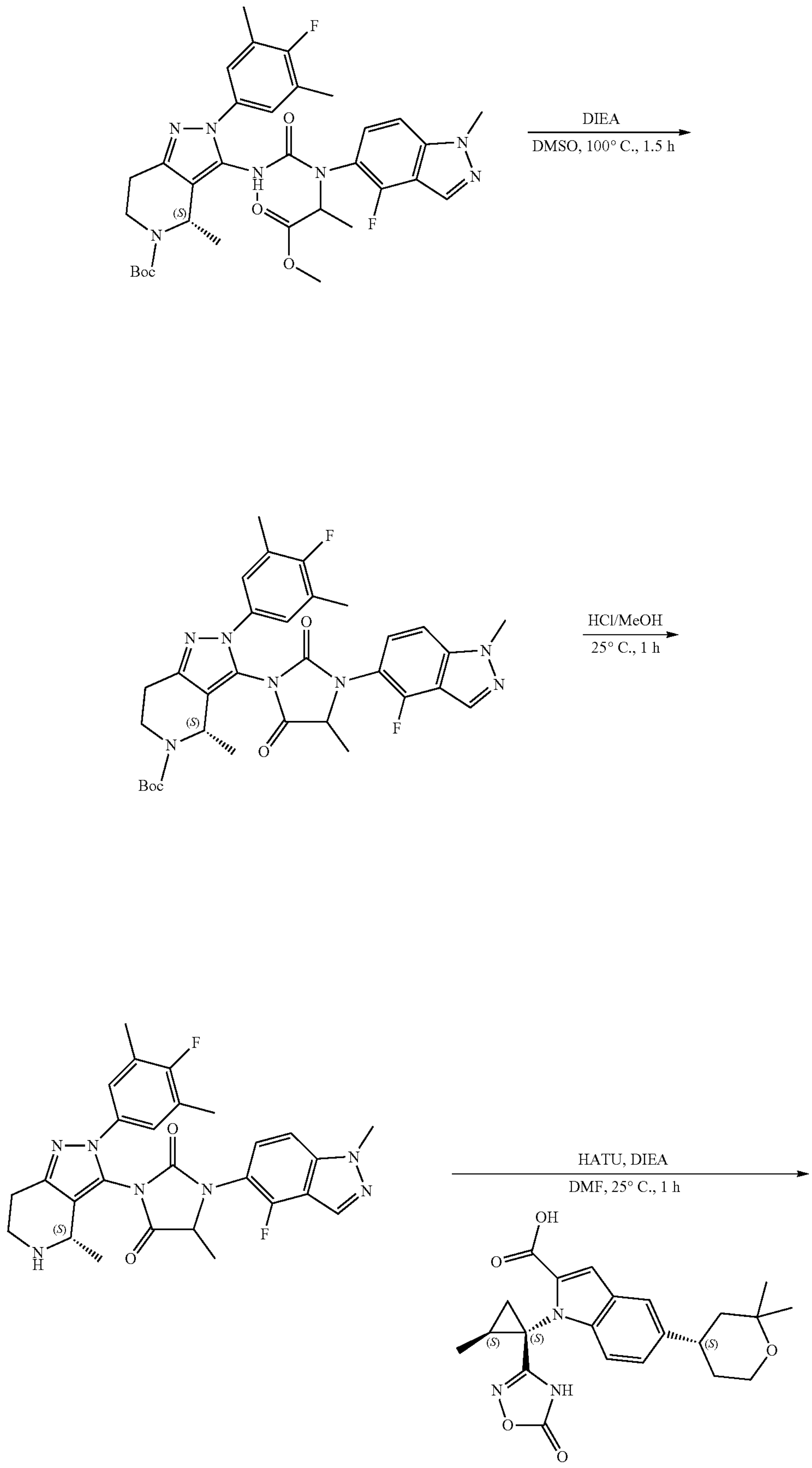

-continued

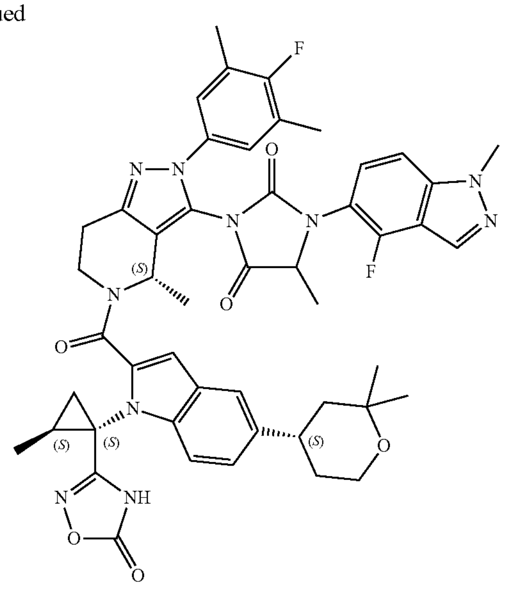

The compound was prepared following the method described in the above synthetic scheme.

$^1$H NMR (400 MHz, DMSO-$d_6$) δ=11.82-11.69 (m, 1H), 8.35-8.23 (m, 1H), 7.68-7.61 (m, 1H), 7.59-7.45 (m, 2H), 7.42-7.36 (m, 1H), 7.29-7.22 (m, 1H), 7.18-7.10 (m, 2H), 7.08-6.95 (m, 1H), 5.82-5.50 (m, 1H), 5.12-4.96 (m, 1H), 4.91-4.48 (m, 1H), 4.43-4.33 (m, 1H), 4.23-4.00 (m, 4H), 3.28-3.18 (m, 1H), 3.08-2.86 (m, 3H), 2.31 (br s, 6H), 1.55 (br d, J=11.9 Hz, 10H), 1.28 (br s, 3H), 1.21-1.08 (m, 9H). $^1$H NMR (400 MHz, DMSO-$d_6$, T=273+80K) δ=11.72-11.49 (m, 1H), 8.25-8.16 (m, 1H), 7.62-7.55 (m, 1H), 7.54-7.45 (m, 2H), 7.43-7.40 (m, 1H), 7.28-7.23 (m, 1H), 7.16-7.11 (m, 2H), 6.96-6.85 (m, 1H), 5.84-5.49 (m, 1H), 4.93 (br s, 1H), 4.91-4.54 (m, 1H), 4.53-4.32 (m, 1H), 4.13-4.06 (m, 4H), 3.05 (br s, 1H), 3.02 (br s, 3H), 2.32-2.29 (m, 6H), 1.72-1.51 (m, 10H), 1.29 (s, 3H), 1.21-1.09 (m, 9H). LC-MS (ES+, m/z): 913.3 [$(M+H)^+$]; Rt=3.243 min. HRMS (EI): m/z $[M+H]^+$ found: 913.3978.

Example 32 (Compound 32)

3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one Scheme 32

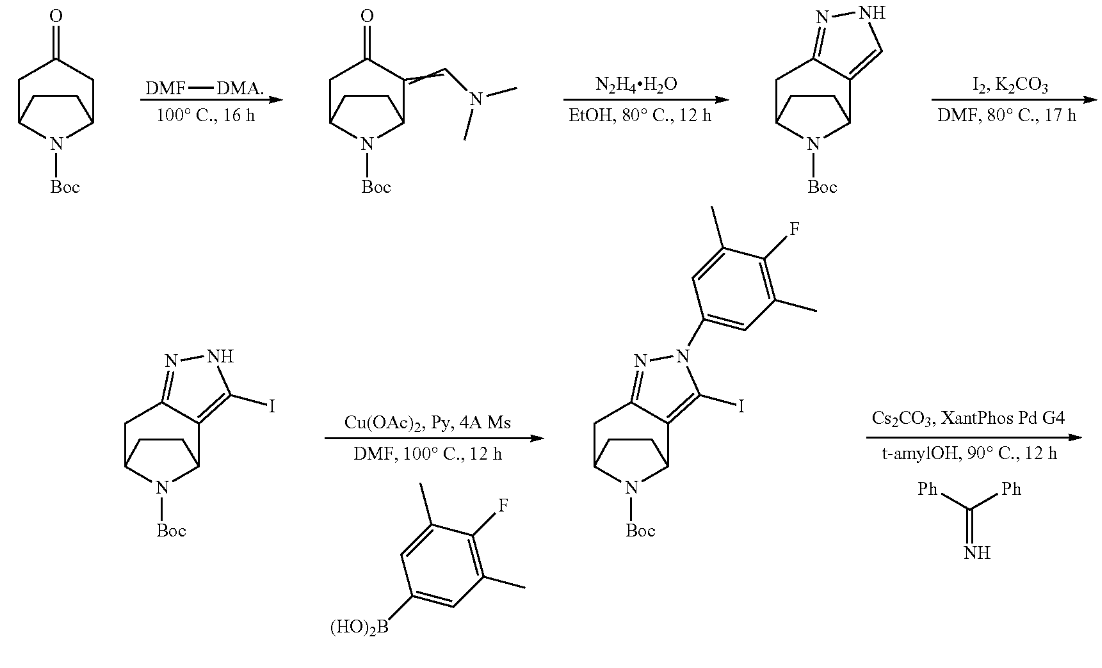

-continued
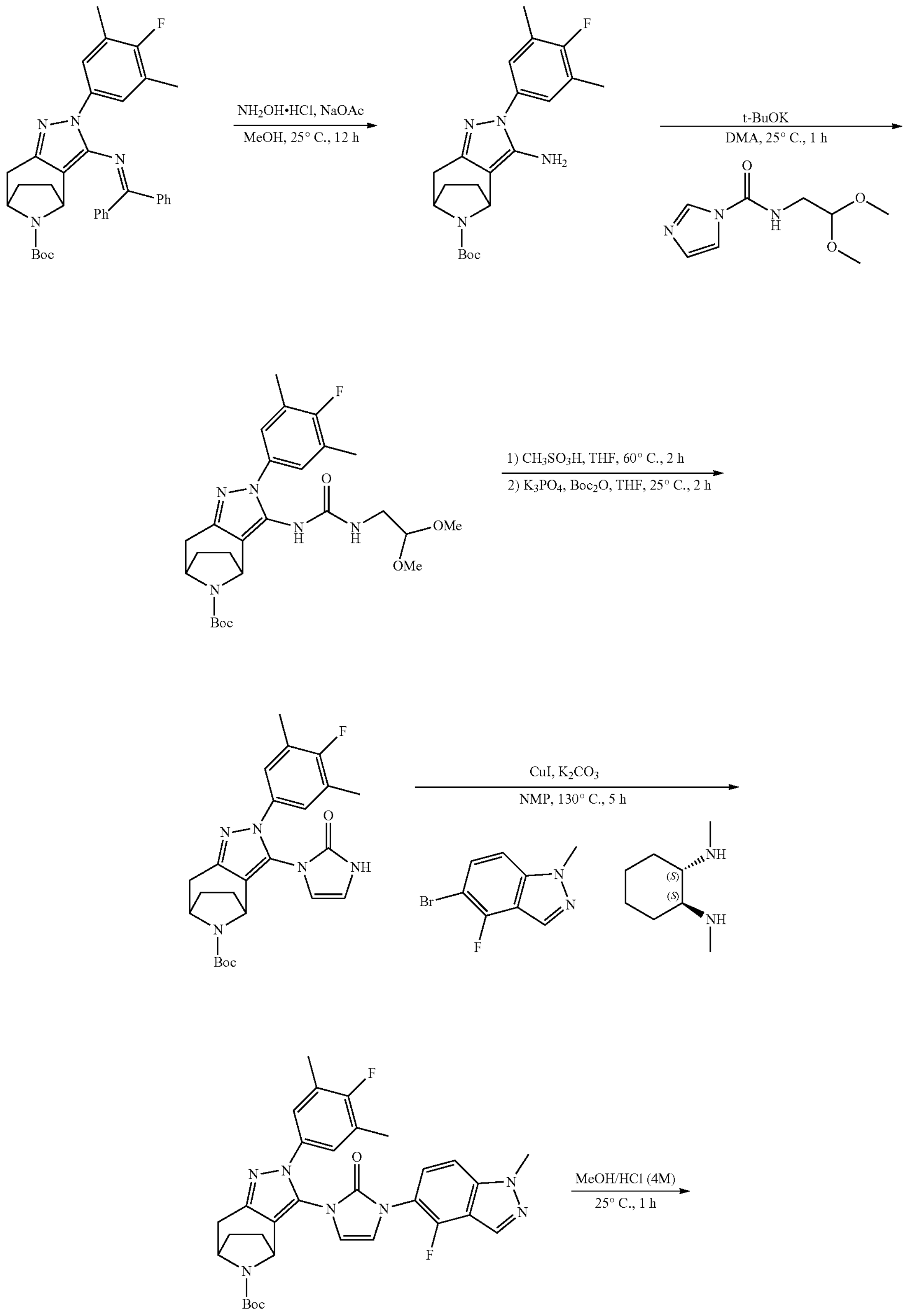

-continued

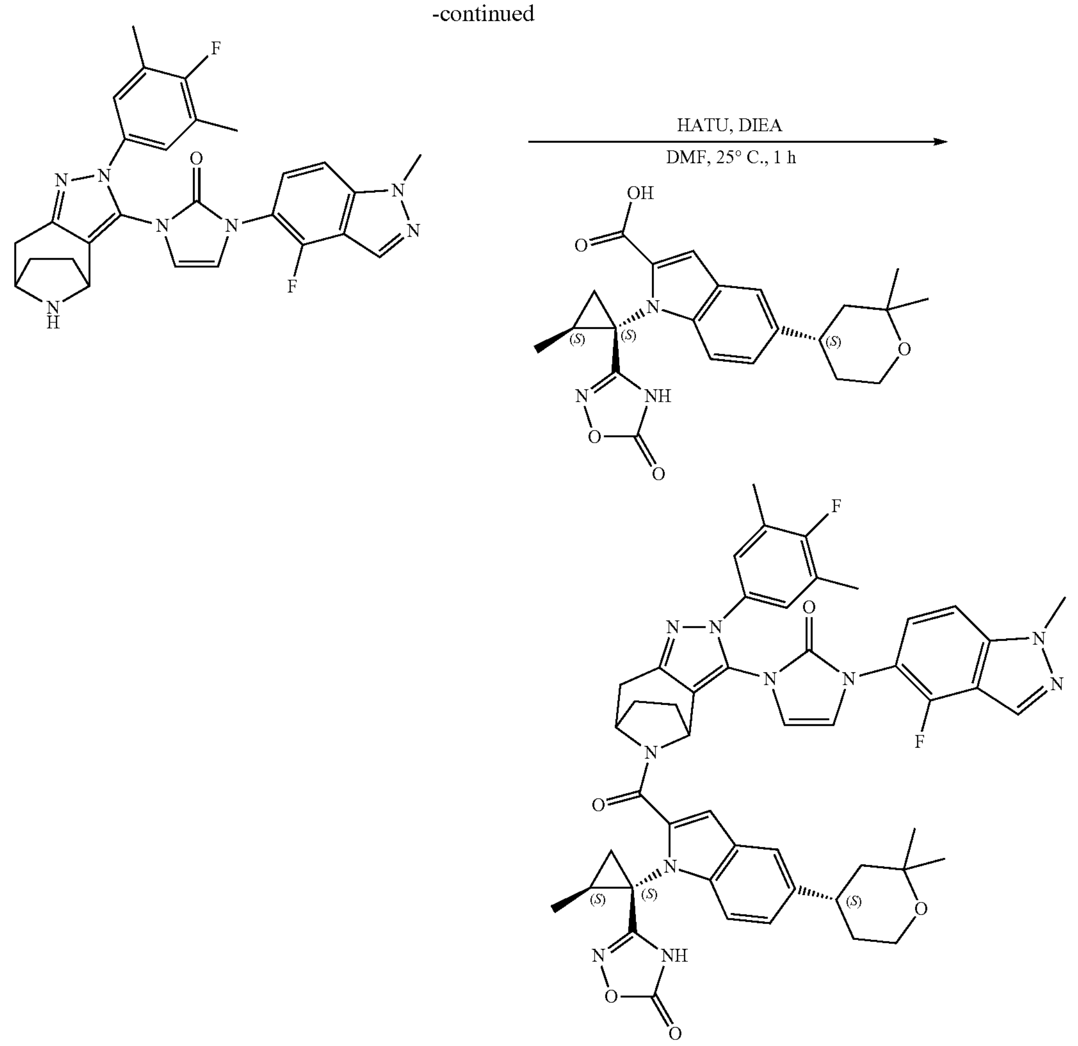

Step 1: tert-butyl 2-((dimethylamino)methylene)-3-oxo-8-azabicyclo[3.2.1]octane-8-carboxylate

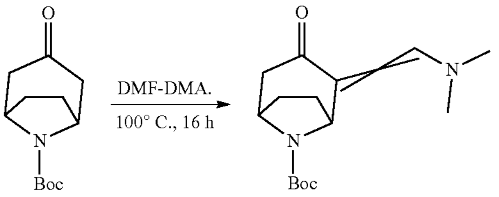 [SMILES: CC(C)(C)OC(=O)N1C2CCC1CC(=O)C2 ; CN(C)CC(C)(C)C1C(=O)CC2CCC1N2C(=O)OC(C)(C)C]

A mixture of tert-butyl 3-oxo-8-azabicyclo[3.2.1]octane-8-carboxylate (20 g, 88.78 mmol, 1 eq) in 1,1-dimethoxy-N,N-dimethyl-methanamine (200 mL) was stirred at 100° C. for 16 hours under $N_2$ atmosphere. LCMS showed reaction was completed. The residue was concentrated to give crude product. The residue was purified by column chromatography ($SiO_2$, Petroleum ether/ethyl acetate=100/1 to 1/1) to give tert-butyl 2-((dimethylamino)methylene)-3-oxo-8-azabicyclo[3.2.1]octane-8-carboxylate (12 g, 39.12 mmol, 44.07% yield). LC-MS (ES+, m/z): 281.3 [$(M+H)^+$]; Rt=0.375 min.

Step 2: tert-butyl 2,4,5,6,7,8-hexahydro-4,7-epiminocyclohepta[c]pyrazole-9-carboxylate

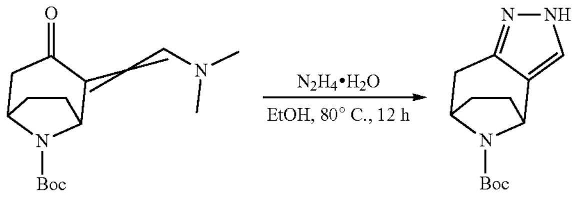

To a solution of tert-butyl 2-((dimethylamino)methylene)-3-oxo-8-azabicyclo[3.2.1]octane-8-carboxylate (12 g, 42.80 mmol, 1 eq) in EtOH (120 mL) was added $N_2H_4 \cdot H_2O$ (3.68 g, 58.81 mmol, 3.57 mL, 80% purity, 1.37 eq). The mixture was stirred for 12 hours at 80° C. under $N_2$ atmosphere. LCMS showed reaction was completed. The reaction mixture was quenched by addition $H_2O$ (300 mL), extracted with ethyl acetate (200 mL*3). The combined organic layers were washed with saturated brine (100 mL), dried over anhydrous $Na_2SO_4$, filtered, and concentrated under reduced pressure to give a residue. The residue was purified by column chromatography ($SiO_2$, Petroleum ether/Ethyl acetate=100/1 to 2/1) to give tert-butyl 2,4,5,6,7,8-hexahydro-4,7-epiminocyclohepta [c]pyrazole-9-carboxylate (8.1 g, 29.96 mmol, 69.99% yield). LC-MS (ES+, m/z): 250.2 [(M+H)$^+$]; Rt=0.390 min.

Step 3: tert-butyl 3-iodo-2,4,5,6,7,8-hexahydro-4,7-epiminocyclohepta [c]pyrazole-9-carboxylate

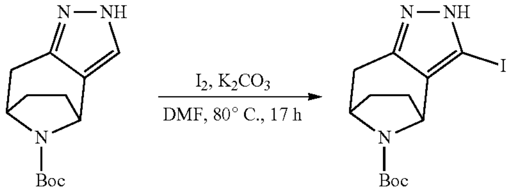

A mixture of tert-butyl 2,4,5,6,7,8-hexahydro-4,7-epiminocyclohepta [c]pyrazole-9-carboxylate (9 g, 36.10 mmol, 1 eq), $K_2CO_3$ (14.97 g, 108.30 mmol, 3 eq) and $I_2$ (18.32 g, 72.20 mmol, 14.54 mL, 2 eq) in DMF (90 mL) was stirred at 80° C. for 17 hours under $N_2$ atmosphere. LCMS indicated the reaction was completed. The reaction mixture was quenched by addition $H_2O$ (500 mL), extracted with ethyl acetate (200 mL*3). The combined organic layers were washed with saturated brine (100 mL), dried over anhydrous $Na_2SO_4$, filtered, and concentrated under reduced pressure to give a residue. The residue was purified by prep-HPLC (neutral condition column: Welch Xtimate C18 250*100 mm #10 um; mobile phase: [$H_2O$ (10 mM $NH_4HCO_3$)-ACN]; gradient: 30%-60% B over 20.0 min) to give tert-butyl 3-iodo-2,4,5,6,7,8-hexahydro-4,7-epiminocyclohepta [c]pyrazole-9-carboxylate (8 g, 19.72 mmol, 54.63% yield). LC-MS (ES+, m/z): 376.2 [(M+H)$^+$]; Rt=0.468 min.

Step 4: tert-butyl 2-(4-fluoro-3,5-dimethylphenyl)-3-iodo-2,4,5,6,7,8-hexahydro-4,7-epiminocyclohepta [c]pyrazole-9-carboxylate

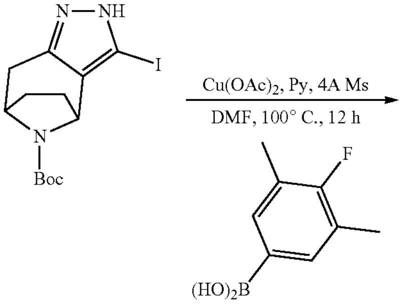

-continued

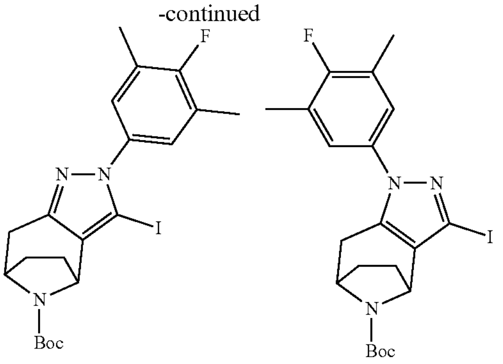

To a solution of tert-butyl 3-iodo-2,4,5,6,7,8-hexahydro-4,7-epiminocyclohepta [c]pyrazole-9-carboxylate (5 g, 13.33 mmol, 1 eq), (4-fluoro-3,5-dimethylphenyl) boronic acid (4.48 g, 26.65 mmol, 2 eq) in DMF (50 mL) was added Py (2.11 g, 26.65 mmol, 2.15 mL, 2 eq), $Cu(OAc)_2$ (242.04 mg, 1.33 mmol, 0.1 eq) and 4A MS (200 mg, 26.65 mmol, 2 eq). The mixture was stirred for 12 hours at 100° C. under $O_2$ (15 Psi). LCMS indicated the reaction was completed. The reaction mixture was quenched by saturated addition saturated EDTA solution (200 mL) and ethyl acetate (50 mL), stirred for 0.5 hour, and then extracted with ethyl acetate (100 mL*3). The combined organic layers were washed with saturated brine (50 mL), dried over anhydrous $Na_2SO_4$, filtered, and concentrated under reduced pressure to give a residue. The residue was purified by column chromatography ($SiO_2$, Petroleum ether/Ethyl acetate=100/1 to 4/1) to provide tert-butyl 2-(4-fluoro-3,5-dimethylphenyl)-3-iodo-2,4,5,6,7,8-hexahydro-4,7-epiminocyclohepta [c]pyrazole-9-carboxylate (1.5 g, 2.75 mmol, 20.64% yield). LC-MS (ES+, m/z): 498.3 [(M+H)$^+$]; Rt=2.324 min and (tert-butyl 1-(4-fluoro-3,5-dimethylphenyl)-3-iodo-1,4,5,6,7,8-hexahydro-4,7-epiminocyclohepta [c]pyrazole-9-carboxylate (3.2 g, 5.93 mmol, 44.47% yield). $^1$H NMR (400 MHz, DMSO-$d_6$) δ=7.35-7.23 (m, 2H), 4.65-4.54 (m, 1H), 4.51-4.38 (m, 1H), 3.27-3.10 (m, 1H), 2.71-2.57 (m, 1H), 2.30-2.16 (m, 7H), 2.10-1.92 (m, 1H), 1.78-1.65 (m, 1H), 1.64-1.53 (m, 1H), 1.42-1.28 (m, 9H). LC-MS (ES+, m/z): 498.3 [(M+H)$^+$]; Rt=2.429 min.

Step 5: tert-butyl 3-((diphenylmethylene)amino)-2-(4-fluoro-3,5-dimethylphenyl)-2,4,5,6,7,8-hexahydro-4,7-epiminocyclohepta [c]pyrazole-9-carboxylate

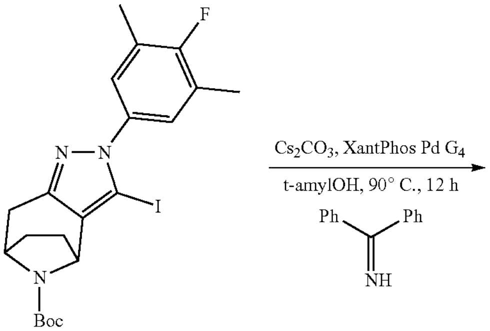

-continued

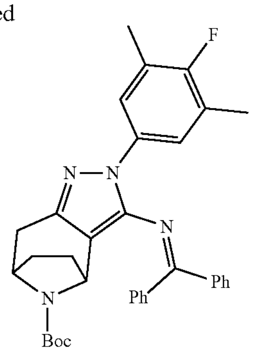

A mixture of tert-butyl 2-(4-fluoro-3,5-dimethylphenyl)-3-iodo-2,4,5,6,7,8-hexahydro-4,7-epiminocyclohepta [c]pyrazole-9-carboxylate (1.2 g, 2.41 mmol, 1 eq), diphenylmethanimine (874.56 mg, 4.83 mmol, 809.78 μL, 2 eq), Xantphos Pd G4 (232.20 mg, 241.28 μmol, 0.1 eq) and $Cs_2CO_3$ (1.57 g, 4.83 mmol, 2 eq) in t-AmylOH (12 mL) was stirred at 90° C. for 12 hours under $N_2$ atmosphere. LCMS indicated the reaction was completed. The reaction mixture was quenched by addition saturated EDTA solution (100 mL) and ethyl acetate (50 mL), stirred for 0.5 hour, and then extracted with ethyl acetate (50 mL*3). The combined organic layers were washed with saturated brine (30 mL), dried over anhydrous $Na_2SO_4$, filtered, and concentrated under reduced pressure to give a residue. The residue was purified by column chromatography ($SiO_2$, Petroleum ether/ethyl acetate=100/1 to 1/1). to give tert-butyl 3-((diphenylmethylene)amino)-2-(4-fluoro-3,5-dimethylphenyl)-2,4,5,6,7,8-hexahydro-4,7-epiminocyclohepta [c]pyrazole-9-carboxylate (1 g, 1.77 mmol, 73.23% yield). LC-MS (ES+, m/z): 551.4 [$(M+H)^+$]; Rt=0.729 min.

Step 6: tert-butyl 3-amino-2-(4-fluoro-3,5-dimethylphenyl)-2,4,5,6,7,8-hexahydro-4,7-epiminocyclohepta [c]pyrazole-9-carboxylate

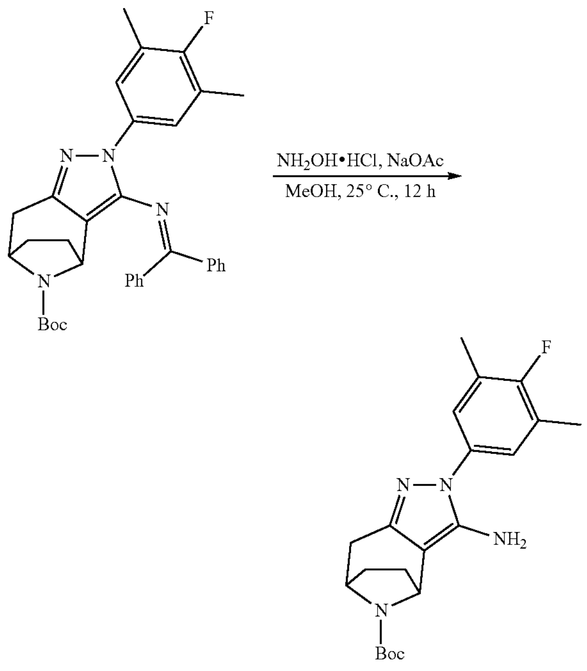

A mixture of tert-butyl 3-((diphenylmethylene)amino)-2-(4-fluoro-3,5-dimethylphenyl)-2,4,5,6,7,8-hexahydro-4,7-epiminocyclohepta [c]pyrazole-9-carboxylate (1 g, 1.82 mmol, 1 eq), NaOAc (446.92 mg, 5.45 mmol, 3 eq) and $NH_2OH{\cdot}HCl$ (252.39 mg, 3.63 mmol, 2 eq) in MeOH (10 mL) was stirred at 25° C. for 12 hours under $N_2$ atmosphere. LCMS showed reaction was completed. The reaction mixture was quenched by addition $H_2O$ (200 mL), extracted with ethyl acetate (100 mL*3). The combined organic layers were washed with saturated brine (50 mL), dried over anhydrous $Na_2SO_4$, filtered, and concentrated under reduced pressure to give a residue. The residue was purified by column chromatography ($SiO_2$, Petroleum ether/Ethyl acetate=100/1 to 1/1) to give tert-butyl 3-amino-2-(4-fluoro-3,5-dimethylphenyl)-2,4,5,6,7,8-hexahydro-4,7-epiminocyclohepta [c]pyrazole-9-carboxylate (500 mg, 1.23 mmol, 67.82% yield). LC-MS (ES+, m/z): 387.2 [$(M+H)^+$]; Rt=0.477 min.

Step 7: tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate

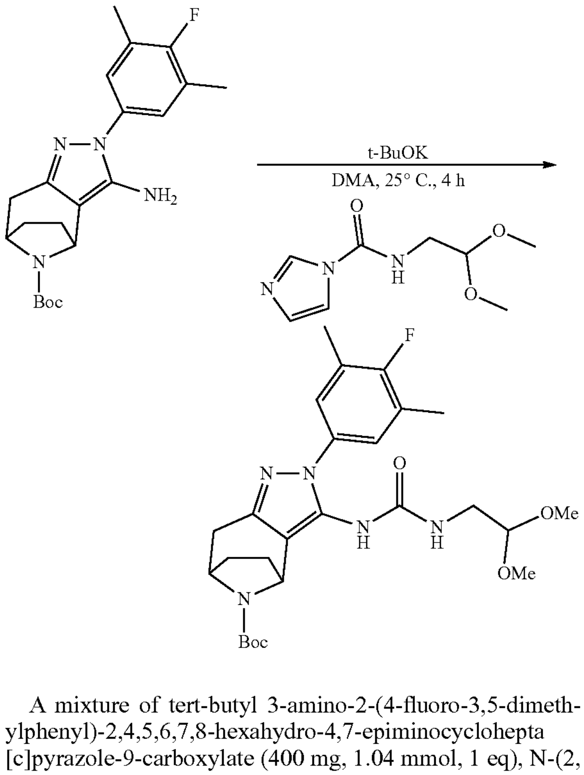

A mixture of tert-butyl 3-amino-2-(4-fluoro-3,5-dimethylphenyl)-2,4,5,6,7,8-hexahydro-4,7-epiminocyclohepta [c]pyrazole-9-carboxylate (400 mg, 1.04 mmol, 1 eq), N-(2,2-dimethoxyethyl)-1H-imidazole-1-carboxamide (412.37 mg, 2.07 mmol, 2 eq) and t-BuOK (1 M, 5.18 mL, 5 eq) in DMA (4 mL) was stirred at 25° C. for 1 hour under $N_2$ atmosphere. LCMS indicated the reaction was completed. The reaction mixture was quenched by addition $H_2O$ (100 mL), extracted with DCM (100 mL*3). The combined organic layers were washed with saturated brine (50 mL), dried over anhydrous $Na_2SO_4$, filtered, and concentrated under reduced pressure to give a residue. The residue was purified by prep-TLC ($SiO_2$, Petroleum ether/ethyl acetate=1:1) to give tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (300 mg, 528.02 μmol, 51.02% yield). LC-MS (ES+, m/z): 518.4 [$(M+H)^+$]; Rt=0.508 min.

Step 8: tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate

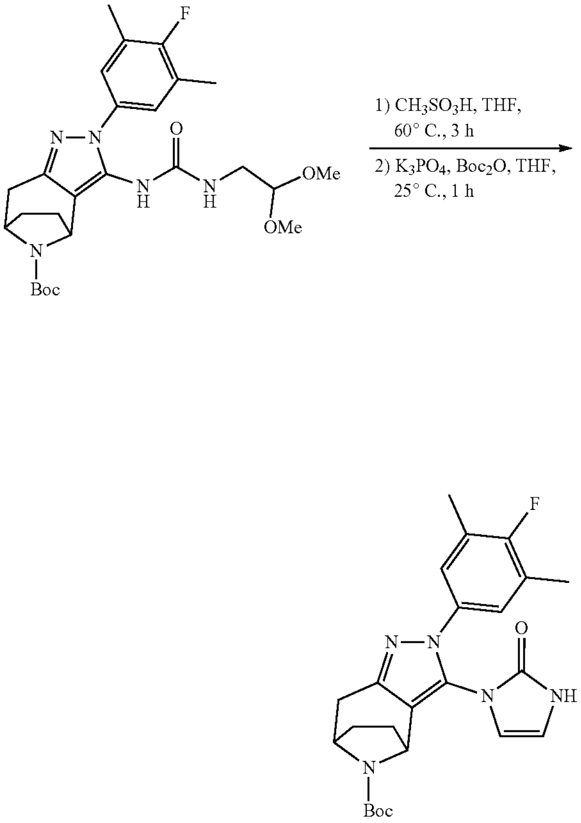 [SMILES: COC(CNC(=O)Nc1c2c(nn1-c1cc(C)c(F)c(C)c1)CC1CCC2N1C(=O)OC(C)(C)C)OC ; Cc1cc(-n2nc3c(c2-n2cc[nH]c2=O)C2CCC(C3)N2C(=O)OC(C)(C)C)cc(C)c1F]

To a solution of tert-butyl 3-(3-(2,2-dimethoxyethyl) ureido)-2-(4-fluoro-3,5-dimethylphenyl)-2,4,5,6,7,8-hexahydro-4,7-epiminocyclohepta [c]pyrazole-9-carboxylate (300 mg, 579.61 μmol, 1 eq) in THF (5 mL) was added $CH_3SO_3H$ (83.56 mg, 869.41 μmol, 62.12 μL, 1.5 eq). The mixture was stirred for 3 hours at 60° C. $K_3PO_4$ (369.09 mg, 1.74 mmol, 3 eq) was then added followed by $Boc_2O$ (126.50 mg, 579.61 μmol, 133.15 μL, 1 eq) at 25° C. The mixture was stirred for 1 hour at 25° C. LCMS showed reaction was completed. The reaction mixture was quenched by addition $H_2O$ (100 mL), extracted with ethyl acetate (100 mL*3). The combined organic layers were washed with saturated brine (50 mL), dried over anhydrous $Na_2SO_4$, filtered, and concentrated under reduced pressure to give a residue. The residue was purified by column chromatography ($SiO_2$, Petroleum ether/ethyl acetate=100/1 to 1/1) to give tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (200 mg, 416.75 μmol, 71.90% yield). LC-MS (ES+, m/z): 454.3 [$(M+H)^+$]; Rt=0.497 min.

Step 9: tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

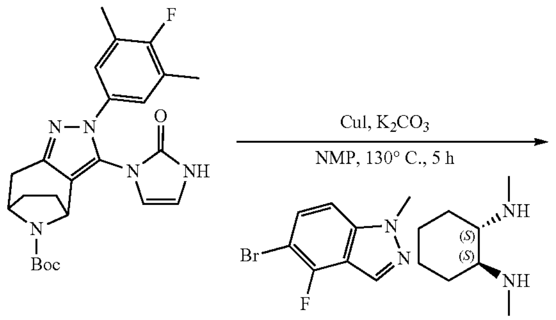

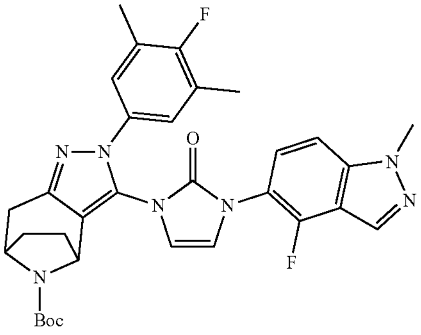

To a solution of tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (200 mg, 441.01 μmol, 1 eq), 5-bromo-4-fluoro-1- methyl-1H-indazole (202.02 mg, 882.01 μmol, 2 eq) in NMP (4 mL) was added CuI (167.98 mg, 882.01 μmol, 2 eq), $K_2CO_3$ (121.90 mg, 882.01 μmol, 2 eq) followed by (1S,2S)—N1,N2-dimethylcyclohexane-1,2-diamine (125.46 mg, 882.01 μmol, 2 eq). The mixture was stirred at 130° C. for 5 hours under $N_2$ atmosphere. LCMS indicated the reaction was completed. The reaction mixture was quenched by addition $H_2O$ (100 mL), extracted with ethyl acetate (100 mL*3). The combined organic layers were washed with saturated brine (50 mL), dried over anhydrous $Na_2SO_4$, filtered, and concentrated under reduced pressure. The residue was purified by prep-TLC ($SiO_2$, Petroleum ether/Ethyl acetate=4/1) to give tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (150 mg, 237.35 μmol, 53.82% yield). LC-MS (ES+, m/z): 602.5 [(M+H)$^+$]; Rt=2.002 min.

Step 10:1-(4-fluoro-1-methyl-1H-indazol-5-yl)-3-(2-(4-fluoro-3,5-dimethylphenyl)-2,4,5,6,7,8-hexahydro-4,7-epiminocyclohepta [c]pyrazol-3-yl)-1H-imidazol-2 (3H)-one

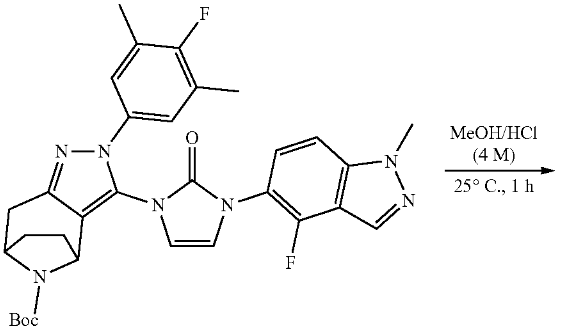

-continued

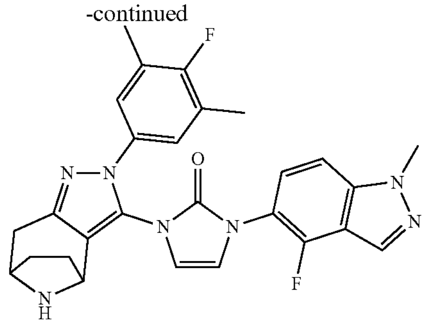

A mixture of tert-butyl 4-(4-fluoro-3,5-dimethyl-phenyl)-3-[3-(4-fluoro-1-methyl-indazol-5-yl)-2-oxo-imidazol-1-yl]-4,5,11-triazatricyclo[6.2.1.0$^{2,6}$]undeca-2,5-diene-11-carboxylate (80 mg, 132.97 μmol, 1 eq) in HCl/MeOH (4 M, 2 mL) was stirred at 25° C. for 1 hour. LCMS indicated the reaction was completed. The reaction mixture was concentrated under reduced pressure to give 1-(4-fluoro-1-methyl-1H-indazol-5-yl)-3-(2-(4-fluoro-3,5-dimethylphenyl)-2,4,5,6,7,8-hexahydro-4,7-epiminocyclohepta [c]pyrazol-3-yl)-1H-imidazol-2 (3H)-one (60 mg, 111.50 μmol, 83.85% yield). LC-MS (ES+, m/z): 502.4 [(M+H)$^+$]; Rt=0.389 min.

Step 11: 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

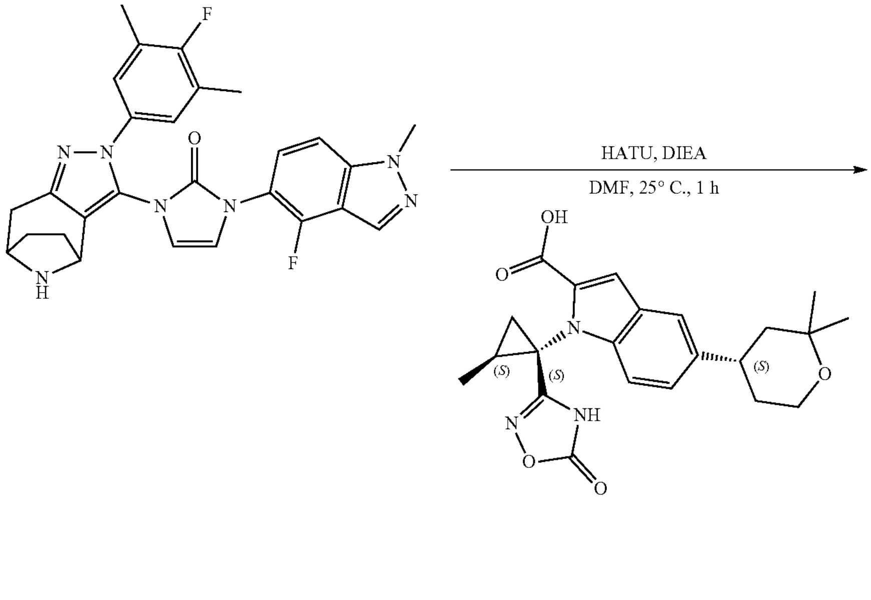

-continued

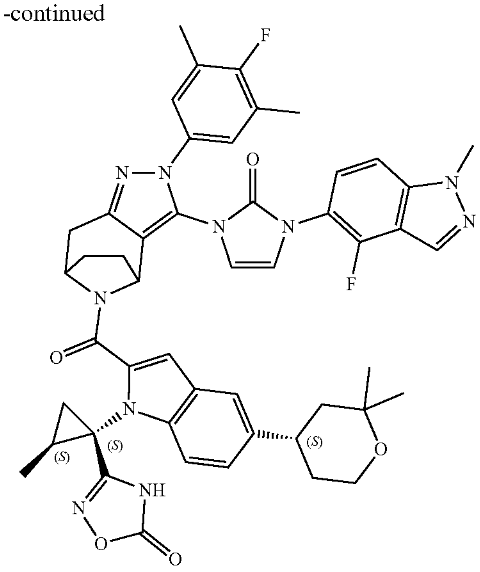

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (10 mg, 24.30 μmol, 1 eq) in DMF (1 mL) was added HATU (13.86 mg, 36.46 μmol, 1.5 eq), DIEA (9.42 mg, 72.91 μmol, 12.70μ, 3 eq), 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (13.08 mg, 24.30 μmol, 1 eq). The mixture was stirred at 25° C. for 1 hour. LCMS showed reaction was completed. The reaction mixture was filtered. The filtrate was purified by prep-HPLC (TFA condition column: 3_Phenomenex Luna C18 75*30 mm*3 um; mobile phase: [$H_2O$ (0.1% TFA)-ACN]; gradient: 55%-85% B over 8.0 min) to give 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (2.01 mg, 2.25 μmol, 9.24% yield, 100% purity). $^1$H NMR (400 MHz, DMSO-$d_6$) δ=12.15-11.73 (m, 1H), 8.35-8.08 (m, 1H), 7.66-6.75 (m, 10H), 5.60-4.90 (m, 2H), 4.12-4.05 (m, 3H), 3.78-3.59 (m, 3H), 3.24-2.81 (m, 3H), 2.28-2.07 (m, 8H), 1.90-1.72 (m, 2H), 1.64-1.33 (m, 6H), 1.26-0.98 (m, 9H). $^1$H NMR (400 MHz, DMSO-$d_6$, T=273+80K) δ=11.77-11.61 (m, 1H), 8.26-8.17 (m, 1H), 7.59-7.15 (m, 8H), 6.94-6.84 (m, 2H), 5.46-5.10 (m, 2H), 4.11-4.07 (m, 3H), 3.75-3.52 (m, 3H), 3.10 (m, 3H), 2.30 (m, 8H), 1.96-1.74 (m, 2H), 1.68-1.41 (m, 6H), 1.27-1.08 (m, 9H). LC-MS (ES+, m/z): 895.4 [$(M+H)^+$]; Rt=3.168 min. HRMS (EI): m/z $[M+H]^+$ found: 895.3844.

Example 35 (Compound 35)

3-((1S,2S)-1-(5-((S)-2,2-dimethyltetrahydro-2H-pyran-4-yl)-2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

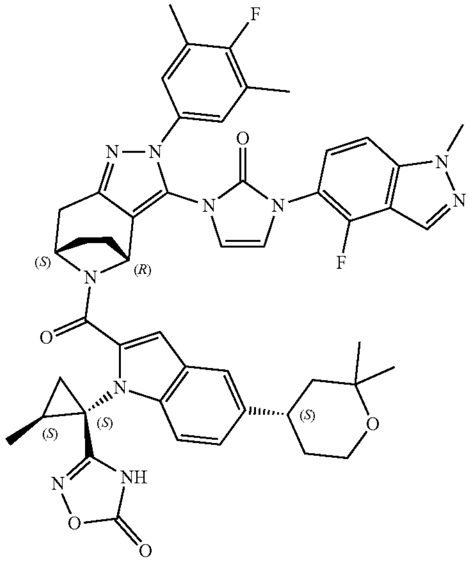

And
Example 36 (Compound 36)
3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one
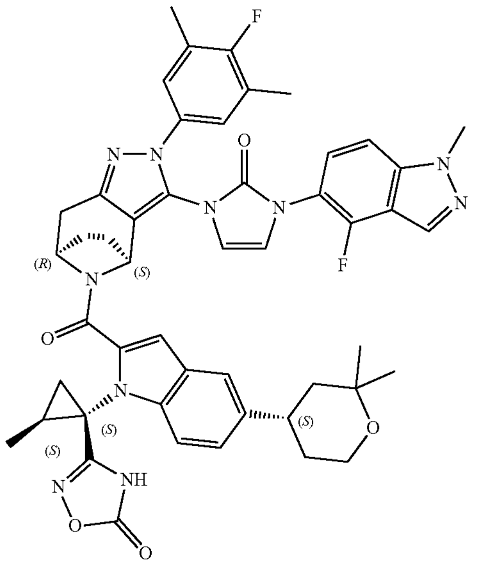
Scheme 35
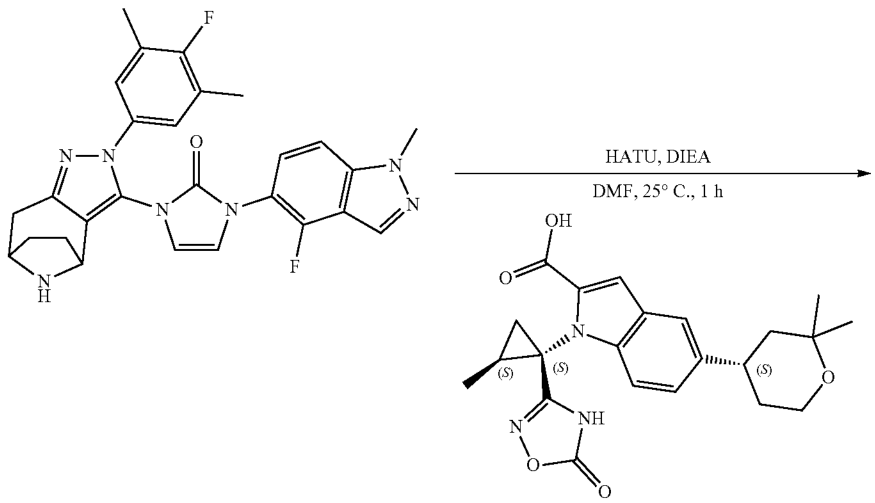

-continued
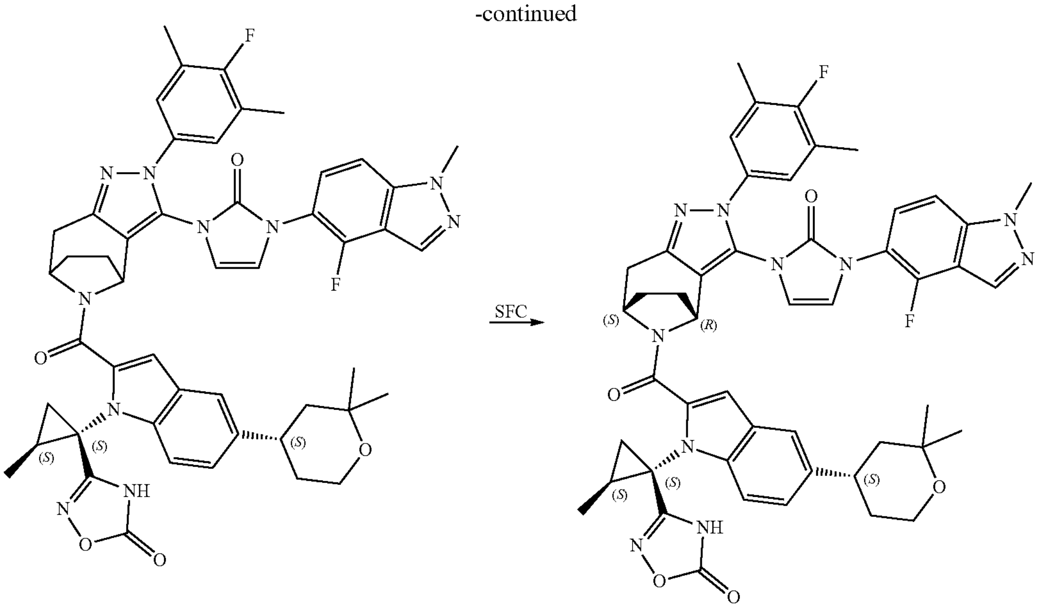
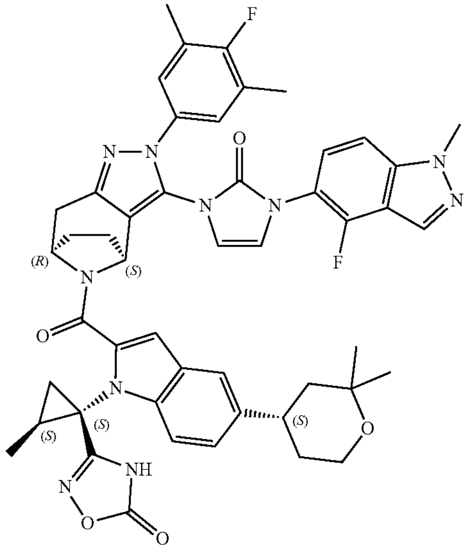

Step 1: 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

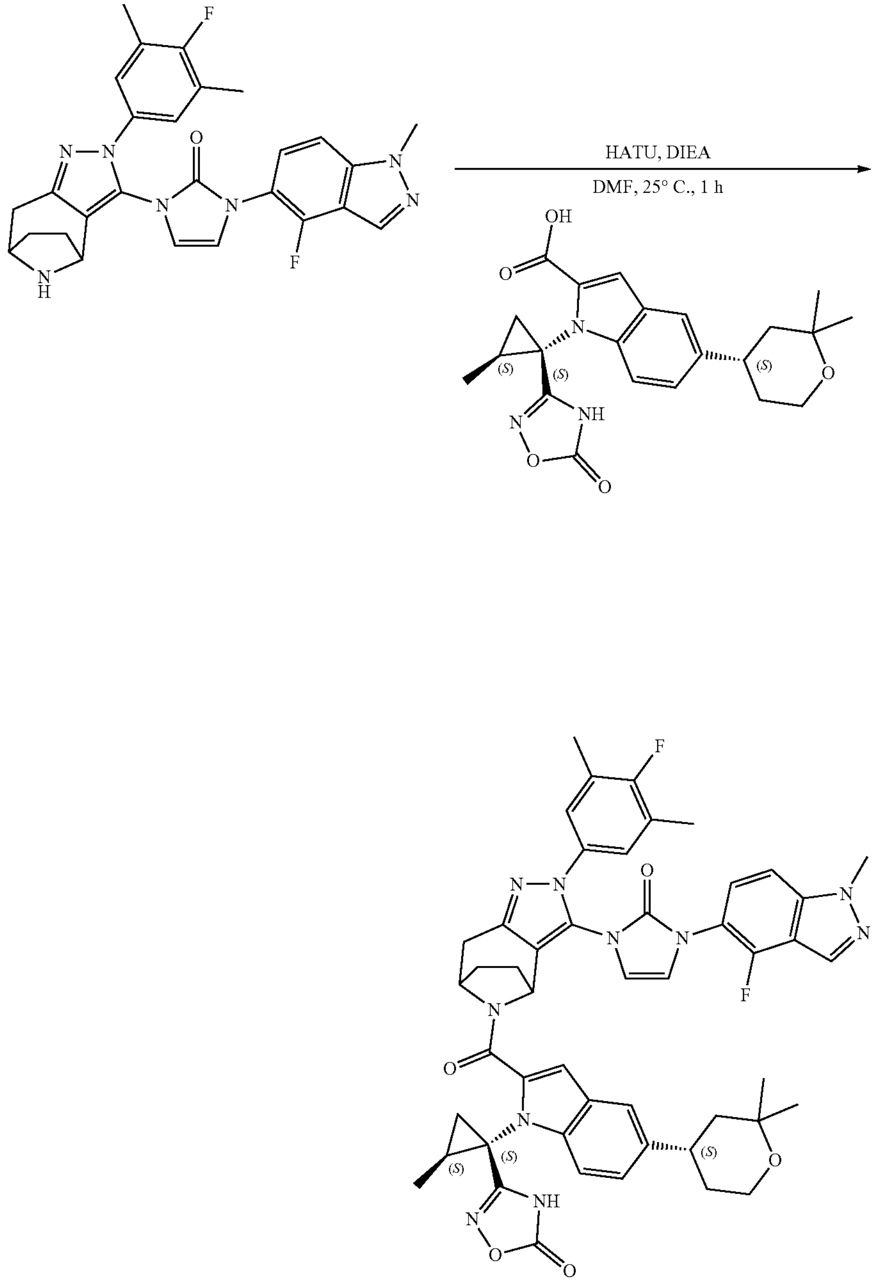

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (50 mg, 115.45 μmol, 1 eq) in DMF (1 mL) was added 65.84 mg, 173.17 μmol, 1.5 eq), DIEA (44.76 mg, 346.34 μmol, 60.32 μL, 3 eq), and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (57.90 mg, 115.45 μmol, 1 eq). The mixture was stirred at 25° C. for 1 hour. LCMS showed reaction was completed. The reaction mixture was filtered. The filtrate was purified by prep-HPLC (TFA condition column: 3_Phenomenex Luna C18 75*30 mm*3 um; mobile phase: [$H_2O$ (0.1% TFA)-ACN]; gradient: 55%-85% B over 8.0 min) to give 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (20.0 mg, 22.35 μmol, 22.42% yield). LC-MS (ES+, m/z): 895.3 [$(M+H)^+$]; Rt=2.360 min.

Step 2: 3-((1S,2S)-1-(5-((S)-2,2-dimethyltetrahydro-2H-pyran-4-yl)-2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one and 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

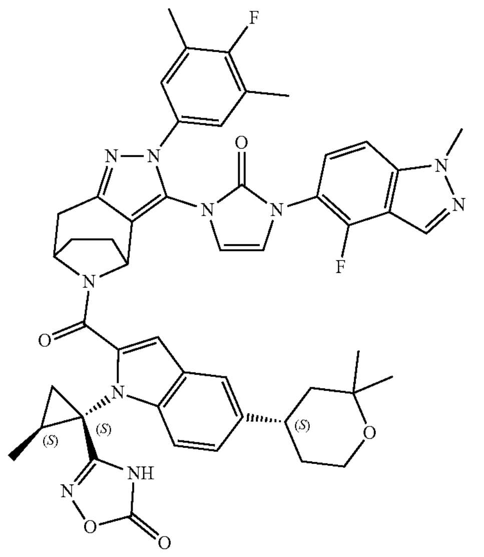

SFC

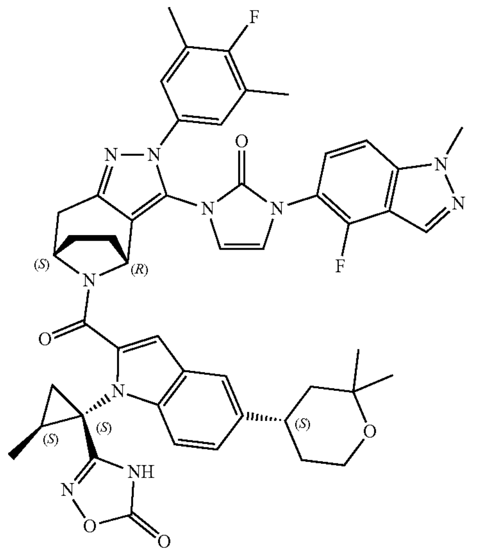

first eluent

-continued

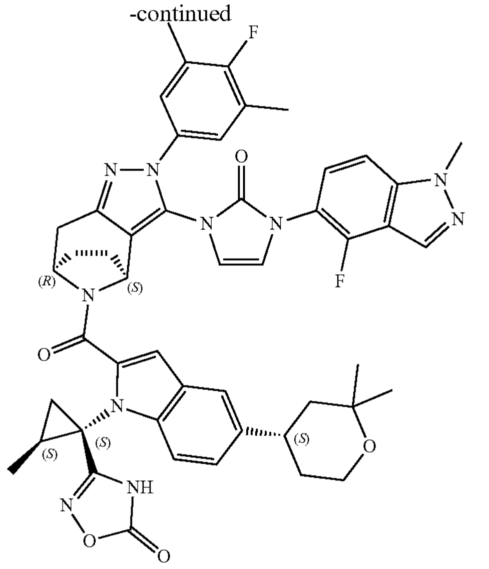

second eluent

The 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (20 mg) was further purified by SFC (column: REGIS (S,S) WHELK-O1, 250 mm*25 mm, 10 um); mobile phase: [$CO_2$-EtOH:ACN=1:1 (0.1% $NH_3H_2O$)]; B %: 50%, isocratic elution mode) to give 3-((1S,2S)-1-(5-((S)-2,2-dimethyltetrahydro-2H-pyran-4-yl)-2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (7.48 mg, 8.36 μmol, 43.8% yield, first eluent). $^1H$ NMR (400 MHz, DMSO-$d_6$) δ=12.20-11.72 (m, 1H), 8.38-8.16 (m, 1H), 6.74 (br s, 10H), 5.50-4.79 (m, 2H), 4.15-4.02 (m, 3H), 3.80-3.33 (m, 3H), 3.25-2.61 (m, 3H), 2.29-2.08 (m, 8H), 1.97-1.78 (m, 2H), 1.72-1.58 (m, 2H), 1.53 (m, 4H), 1.06 (m, 9H). $^1H$ NMR (400 MHz, DMSO-$d_6$, T=273+80K) δ=12.00-11.43 (m, 1H), 8.25-8.17 (m, 1H), 7.61-7.50 (m, 1H), 7.42-7.25 (m, 3H), 7.24-7.11 (m, 3H), 7.06-6.66 (m, 3H), 5.54-4.95 (m, 2H), 4.06 (s, 3H), 3.71-3.52 (m, 2H), 3.40-3.19 (m, 1H), 2.98-2.74 (m, 2H), 2.44-2.33 (m, 1H), 2.31-2.07 (m, 8H), 1.93-1.77 (m, 2H), 1.71-1.34 (m, 6H), 1.28-1.02 (m, 9H). LC-MS (ES+, m/z): 895.4 [$(M+H)^+$]; Rt=3.166 min. HRMS (EI): m/z $[M+H]^+$ found: 895.3857.

And 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (7.11 mg, 7.94 μmol, 41.6% yield, second eluent). $^1H$ NMR (400 MHz, DMSO-$d_6$) δ=12.34-11.39 (m, 1H), 8.34-8.16 (m, 1H), 7.68-6.69 (m, 10H), 5.62-4.84 (m, 2H), 4.15-4.03 (m, 3H), 3.43 (m, 3H), 3.23 (m, 3H), 2.28-2.09 (m, 8H), 1.90-1.69 (m, 2H), 1.61-1.33 (m, 6H), 1.28-0.98 (m, 9H). $^1H$ NMR (400 MHz, DMSO-$d_6$, T=273+80K) δ=11.87-11.08 (m, 1H), 8.28-8.09 (m, 1H), 7.10 (m, 7H), 6.97-6.67 (m, 3H), 5.74-4.65 (m, 2H), 4.10-4.07 (m, 3H), 3.83-3.10 (m, 3H), 3.04-2.75 (m, 3H), 2.27-2.13 (m, 8H), 1.99-1.71 (m, 2H), 1.65-1.42 (m, 6H), 1.31-1.09 (m, 9H). LC-MS (ES+, m/z): 895.4 [(M+H)$^+$]; Rt=3.154 min. HRMS (EI): m/z [M+H]$^+$ found: 895.3857.
Example 37 (Compound 37)
3-((S)-5-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-1-(4-fluoro-1-methyl-1H-indazol-5-yl)-5,5-dimethylimidazolidine-2,4-dione
Scheme 37
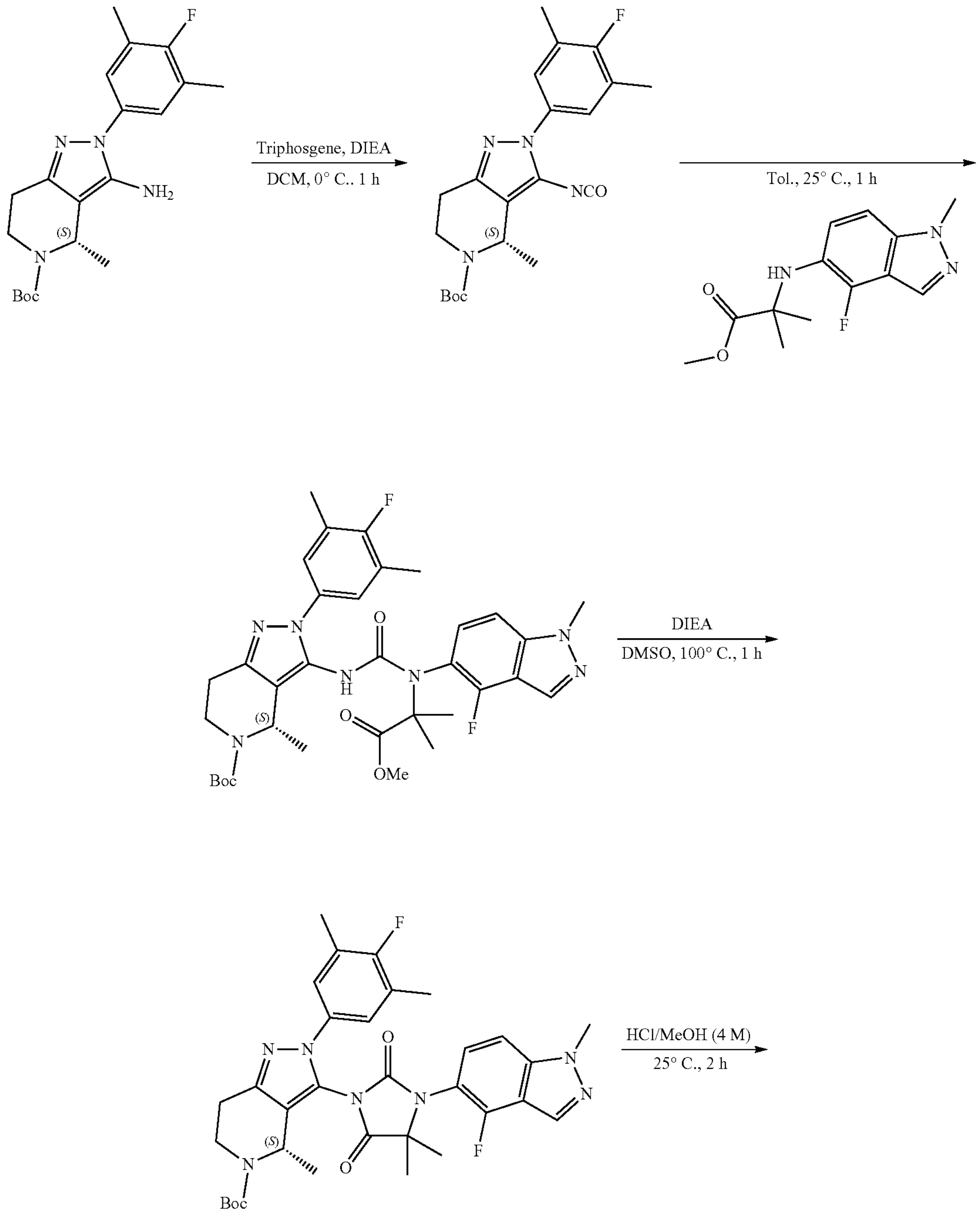

-continued

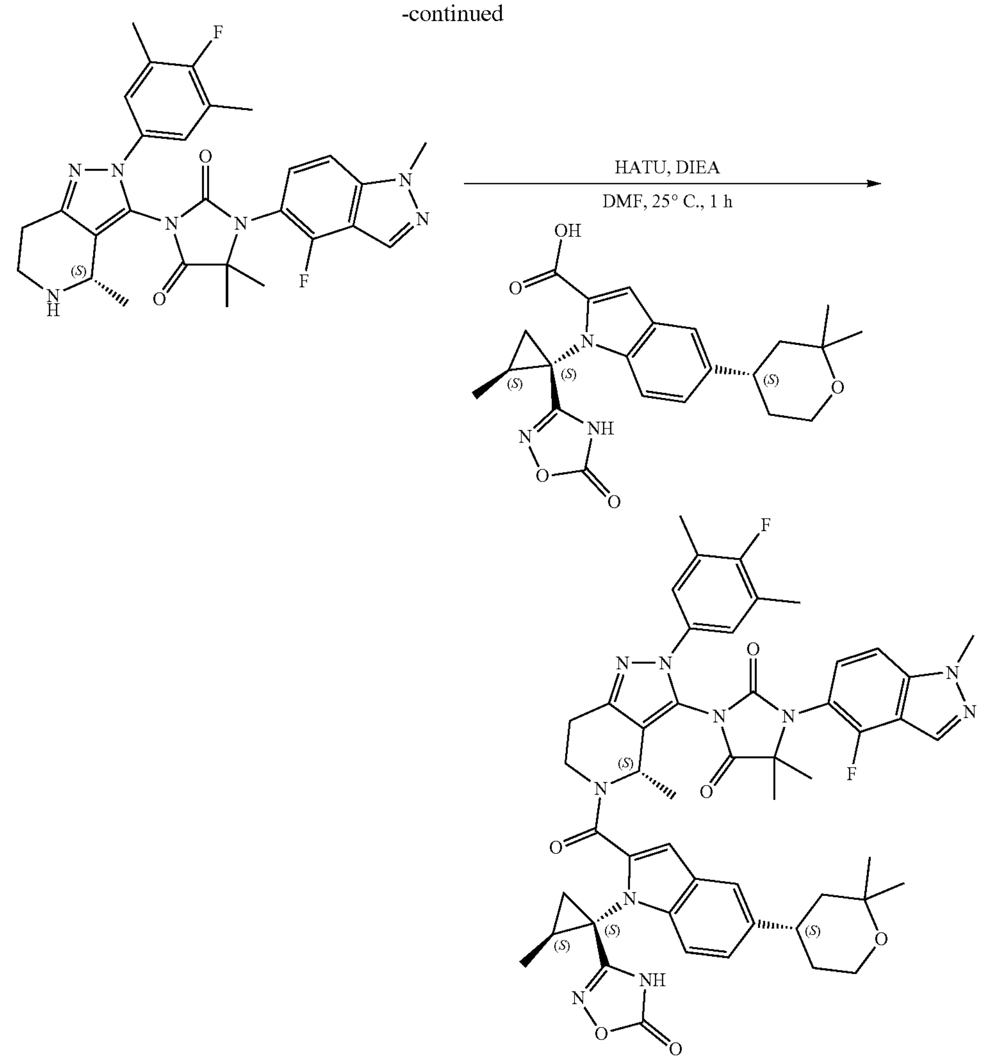

Step 1: tert-butyl (S)-2-(4-fluoro-3,5-dimethylphenyl)-3-isocyanato-4-methyl-2,4,6,7-tetrahydro-5H-pyrazolo[4,3-c]pyridine-5-carboxylate

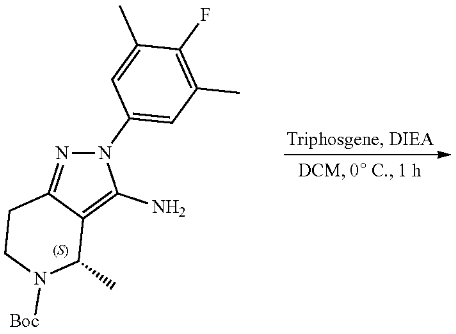

-continued

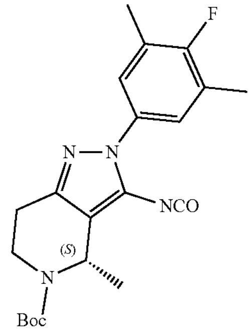

To a solution of tert-butyl (S)-3-amino-2-(4-fluoro-3,5-dimethylphenyl)-4-methyl-2,4,6,7-tetrahydro-5H-pyrazolo[4,3-c]pyridine-5-carboxylate (2 g, 5.34 mmol, 1 eq) in DCM (20 mL) was added triphosgene (1.61 g, 5.43 mmol, 1.02 eq) and DIPEA (2.76 g, 21.36 mmol, 3.72 mL, 4 eq). The mixture was stirred at 0° C. for 1 hour. LCMS indicated the reaction was completed. The residue was concentrated under $N_2$ to afford tert-butyl (S)-2-(4-fluoro-3,5-dimethylphenyl)-3-isocyanato-4-methyl-2,4,6,7-tetrahydro-5H- pyrazolo[4,3-c]pyridine-5-carboxylate (2.14 g, crude). LC-MS (ES+, m/z) (quenched with MeOH): 433.3 [(M+H+32)$^+$]; Rt=1.815 min.

Step 2: tert-butyl (S)-3-(3-(4-fluoro-1-methyl-1H-indazol-5-yl)-3-(1-methoxy-2-methyl-1-oxopropan-2-yl) ureido)-2-(4-fluoro-3,5-dimethylphenyl)-4-methyl-2,4,6,7-tetrahydro-5H-pyrazolo[4,3-c] pyridine-5-carboxylate

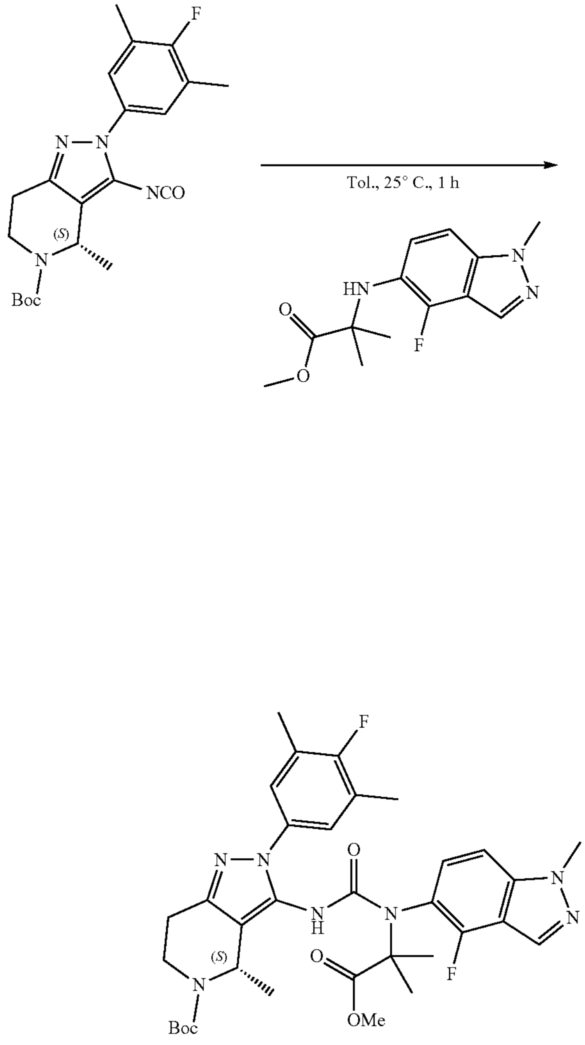

To a solution of methyl 2-((4-fluoro-1-methyl-1H-indazol-5-yl)amino)-2-methylpropanoate (210 mg, 530.38 μmol, 1 eq) in toluene (20 mL) was added tert-butyl (S)-2-(4-fluoro-3,5-dimethylphenyl)-3-isocyanato-4-methyl-2,4,6,7-tetrahydro-5H-pyrazolo[4,3-c]pyridine-5-carboxylate (1.70 g, 4.24 mmol, 8 eq). The mixture was stirred at 25° C. for 1 hour. LCMS indicated the reaction was completed. The reaction mixture was concentrated under reduced pressure to give a residue. The residue was purified by column chromatography ($SiO_2$, Petroleum ether/Ethyl acetate=50/1 to 1/1) to afford tert-butyl (S)-3-(3-(4-fluoro-1-methyl-1H-indazol-5-yl)-3-(1-methoxy-2-methyl-1-oxopropan-2-yl) ureido)-2-(4-fluoro-3,5-dimethylphenyl)-4-methyl-2,4,6,7-tetrahydro-5H-pyrazolo[4,3-c]pyridine-5-carboxylate (228 mg, 273.99 μmol, 51.66% yield). LC-MS (ES+, m/z): 666.4 [(M+H)$^+$]; Rt=0.586 min.

Step 3: tert-butyl (S)-3-(3-(4-fluoro-1-methyl-1H-indazol-5-yl)-4,4-dimethyl-2,5-dioxoimidazolidin-1-yl)-2-(4-fluoro-3,5-dimethylphenyl)-4-methyl-2,4,6,7-tetrahydro-5H-pyrazolo[4,3-c]pyridine-5-carboxylate

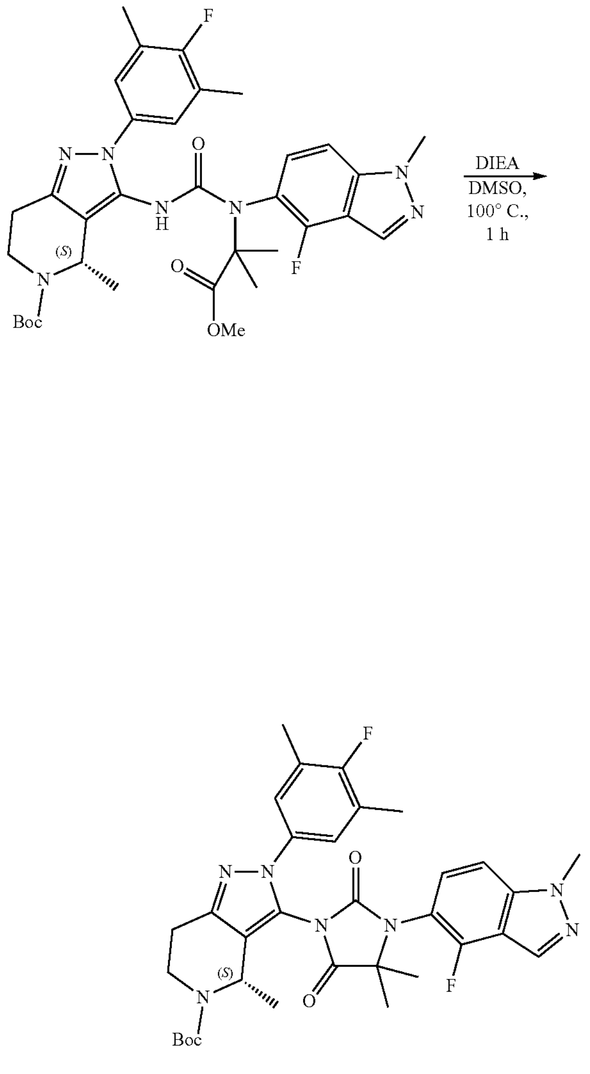

To a solution of tert-butyl (S)-3-(3-(4-fluoro-1-methyl-1H-indazol-5-yl)-3-(1-methoxy-2-methyl-1-oxopropan-2-yl) ureido)-2-(4-fluoro-3,5-dimethylphenyl)-4-methyl-2,4,6,7-tetrahydro-5H-pyrazolo[4,3-c]pyridine-5-carboxylate (228 mg, 342.48 μmol, 1 eq) in DMSO (30 mL) was added DIEA (132.79 mg, 1.03 mmol, 178.96 μL, 3 eq). The mixture was stirred at 100° C. for 1 hour. LCMS indicated the reaction was completed. The reaction mixture was poured into $H_2O$ (50 mL), then extracted with ethyl acetate (80 mL*3). The combined organic layers were washed with saturated brine (60 mL), dried over anhydrous $Na_2SO_4$, filtered, and concentrated under reduced pressure to give a residue. The residue was purified by column chromatography ($SiO_2$, Petroleum ether/ethyl acetate=50/1 to 1/1) to afford tert-butyl (S)-3-(3-(4-fluoro-1-methyl-1H-indazol-5-yl)-4,4-dimethyl-2,5-dioxoimidazolidin-1-yl)-2-(4-fluoro-3,5-dimethylphenyl)-4-methyl-2,4,6,7-tetrahydro-5H-pyrazolo[4,3-c]pyridine-5-carboxylate (210 mg, 272.41 μmol, 79.54% yield). LC-MS (ES+, m/z): 634.4 [(M+H)$^+$]; Rt=0.624 min.

Step 4: (S)-1-(4-fluoro-1-methyl-1H-indazol-5-yl)-3-(2-(4-fluoro-3,5-dimethylphenyl)-4-methyl-4,5,6,7-tetrahydro-2H-pyrazolo[4,3-c]pyridin-3-yl)-5,5-dimethylimidazolidine-2,4-dione

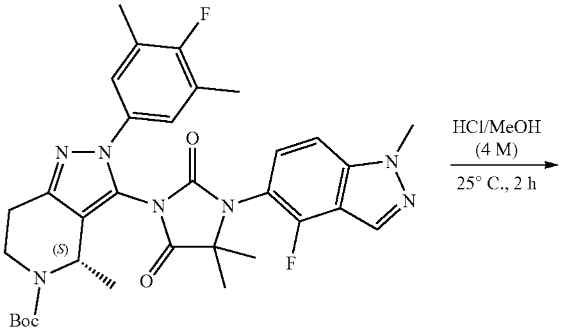

-continued

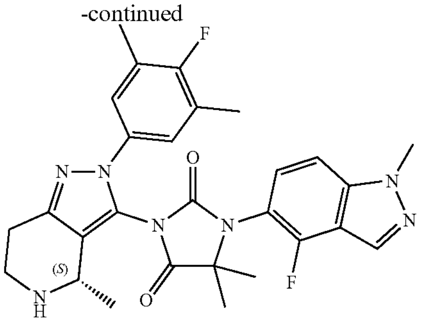

A solution of tert-butyl (S)-3-(3-(4-fluoro-1-methyl-1H-indazol-5-yl)-4,4-dimethyl-2,5-dioxoimidazolidin-1-yl)-2-(4-fluoro-3,5-dimethylphenyl)-4-methyl-2,4,6,7-tetrahydro-5H-pyrazolo[4,3-c]pyridine-5-carboxylate (190 mg, 299.83 μmol, 1 eq) in HCl/MeOH (20 mL) was stirred at 25° C. for 2 hours. LCMS indicated the reaction was completed. The reaction mixture was poured into $H_2O$ (50 mL), then extracted with ethyl acetate (80 mL*3). The combined organic layers were washed with saturated brine (60 mL), dried over anhydrous $Na_2SO_4$, filtered and concentrated under reduced pressure to afford(S)-1-(4-fluoro-1-methyl-1H-indazol-5-yl)-3-(2-(4-fluoro-3,5-dimethylphenyl)-4-methyl-4,5,6,7-tetrahydro-2H-pyrazolo[4,3-c]pyridin-3-yl)-5,5-dimethylimidazolidine-2,4-dione (80 mg, crude). LC-MS (ES+, m/z): 534.4 [(M+H)$^+$]; Rt=0.413 min.

Step 5: 3-((S)-5-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-1-(4-fluoro-1-methyl-1H-indazol-5-yl)-5,5-dimethylimidazolidine-2,4-dione

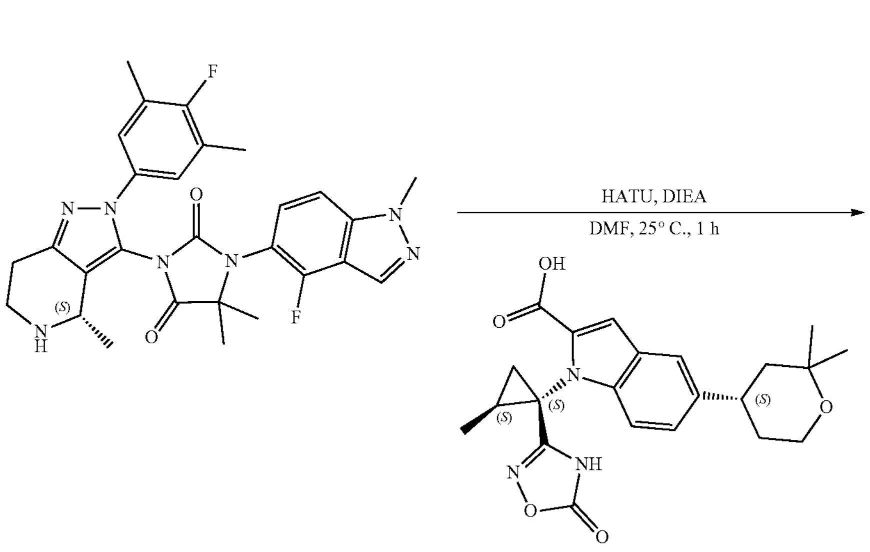

-continued

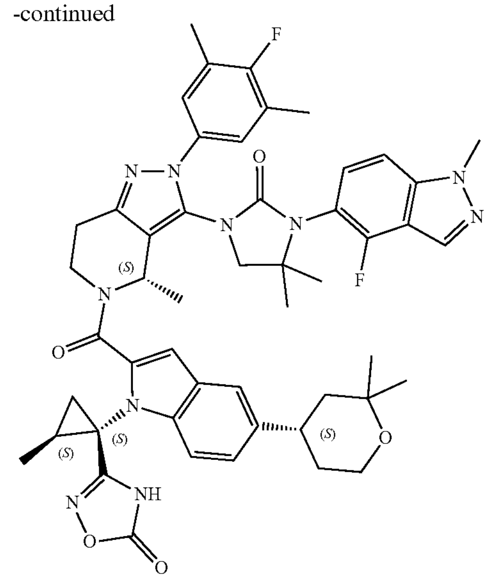

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (40 mg, 97.22 μmol, 1.2 eq) in DMF (0.5 mL) was added DIPEA (52.35 mg, 405.07 μmol, 70.56 μL, 5 eq), (S)-1-(4-fluoro-1-methyl-1H-indazol-5-yl)-3-(2-(4-fluoro-3,5-dimethylphenyl)-4-methyl-4,5,6,7-tetrahydro-2H-pyrazolo[4,3-c]pyridin-3-yl)-5,5-dimethylimidazolidine-2,4-dione (43.23 mg, 81.01 μmol, 1 eq) and HATU (46.21 mg, 121.52 μmol, 1.5 eq). The mixture was stirred at 25° C. for 1 hour. LCMS indicated the reaction was completed. The reaction mixture was filtered. The filtrate was purified by prep-HPLC (column: Phenomenex Luna C18 75*30 mm*3 um; mobile phase: [$H_2O$ (0.1% TFA)-ACN]; gradient: 60%-90% B over 8.0 min) to afford 3-((S)-5-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4-methyl-4,5,6,7-tetrahydro-2H-pyrazolo[4,3-c]pyridin-3-yl)-1-(4-fluoro-1-methyl-1H-indazol-5-yl)-5,5-dimethylimidazolidine-2,4-dione (9.53 mg, 10.17 μmol, 12.55% yield). $^1H$ NMR (400 MHz, DMSO-$d_6$) δ=11.83-11.36 (m, 1H), 8.30-8.13 (m, 1H), 7.62-7.34 (m, 4H), 7.28-7.22 (m, 1H), 7.18-7.07 (m, 2H), 6.98-6.79 (m, 1H), 5.79-5.38 (m, 1H), 4.57-4.31 (m, 1H), 4.17-4.03 (m, 3H), 3.73 (br d, J=8.0 Hz, 3H), 3.04-2.86 (m, 3H), 2.33-2.30 (m, 6H), 1.75-1.41 (m, 13H), 1.30-1.26 (m, 5H), 1.23-1.17 (m, 7H). $^1H$ NMR (400 MHz, MeOD-$d_6$) δ=8.26-7.73 (m, 1H), 7.59-7.05 (m, 7H), 6.99-6.74 (m, 1H), 5.75-5.17 (m, 1H), 4.84-4.43 (m, 1H), 4.20-3.99 (m, 3H), 3.91-3.61 (m, 3H), 3.29-2.93 (m, 3H), 2.45-2.24 (m, 6H), 1.84-1.56 (m, 10H), 1.41-1.08 (m, 15H). LC-MS (ES+, m/z): 927.4 [$(M+H)^+$]; Rt=3.297 min; HRMS (EI): m/z $[M+H]^+$ found: 927.4153.

Example 38 (Compound 114)

3-(1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)cyclopropyl)-1,2,4-oxadiazol-5 (4H)-one Scheme 38

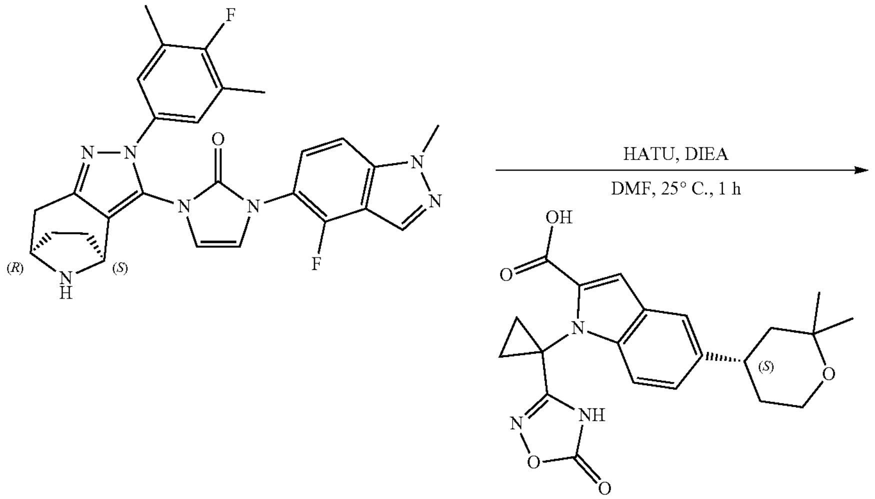

-continued

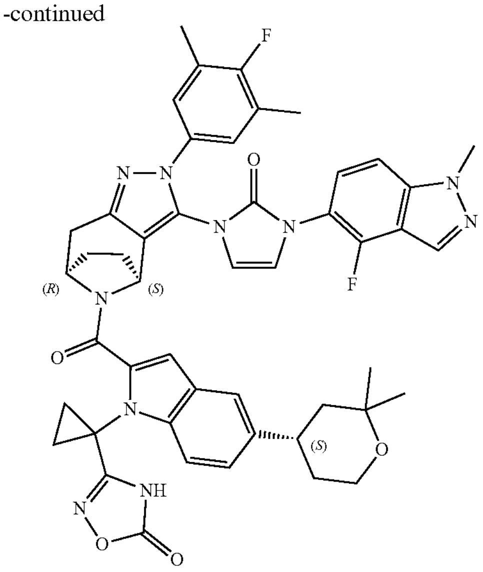

Step 1: 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one To a solution of(S)-5-(2,2-dimethyltetrahydro-2H-pyran-4-yl)-1-(1-(5-oxo-4,5-dihydro-1,2,4-oxadiazol-3-yl)cyclopropyl)-1H-indole-2-carboxylic acid (50 mg, 115.45 μmol, 1 eq) in DMF (1 mL) was added HATU (56.24 mg, 147.90 μmol, 1.5 eq), DIEA (44.76 mg, 346.34 μmol, 60.32 μL, 3 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (57.90 mg, 115.45 μmol, 1 eq). The mixture was stirred at 25° C. for 1 hour. LCMS showed reaction was completed. The reaction mixture was filtered. The filtrate was purified by prep-HPLC (TFA condition column: 3_Phenomenex Luna C18 75*30 mm*3 um; mobile phase: [$H_2O$ (0.1% TFA)-ACN]; gradient: 45%-75% B over 8.0 min) to give 3-(1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)cyclopropyl)-1,2,4-oxadiazol-5 (4H)-one (10.26 mg, 11.55 μmol, 11.72% yield, 99.2% purity). $^1H$ NMR (400 MHz, DMSO-$d_6$) δ=12.16-11.92 (m, 1H), 8.30 (s, 1H), 7.73-6.64 (m, 10H), 5.55-4.79 (m, 2H), 4.10 (s, 3H), 3.34-2.64 (m, 5H), 2.32-2.10 (m, 8H), 1.86-1.34 (m, 8H), 1.31-0.96 (m, 8H); $^1H$ NMR (400 MHz, DMSO-$d_6$, T=273+80 K) δ=12.13-11.35 (m, 1H), 8.21 (s, 1H), 7.76-6.46 (m, 10H), 5.59-4.74 (m, 2H), 4.09 (s, 3H), 3.73-3.56 (m, 2H), 3.33-3.25 (m, 1H), 2.82 (br d, J=16.1 Hz, 2H), 2.32-2.10 (m, 8H), 1.87-1.53 (m, 6H), 1.53-1.01 (m, 10H); LC-MS (ES+, m/z): 895.4 [$(M+H)^+$]; Rt=3.166 min; HRMS (EI): m/z $[M+H]^+$ found: 895.3857.

Example 39 Compound 116

3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one Scheme 39

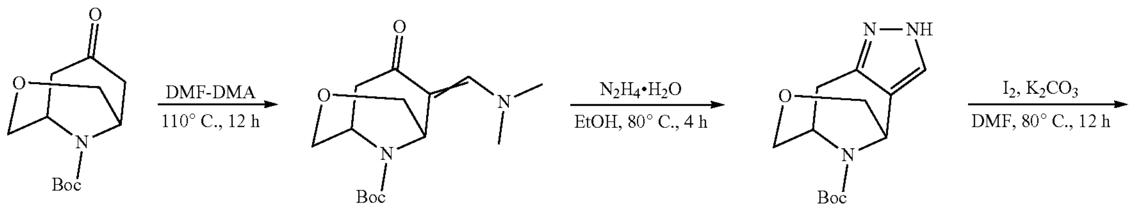

-continued
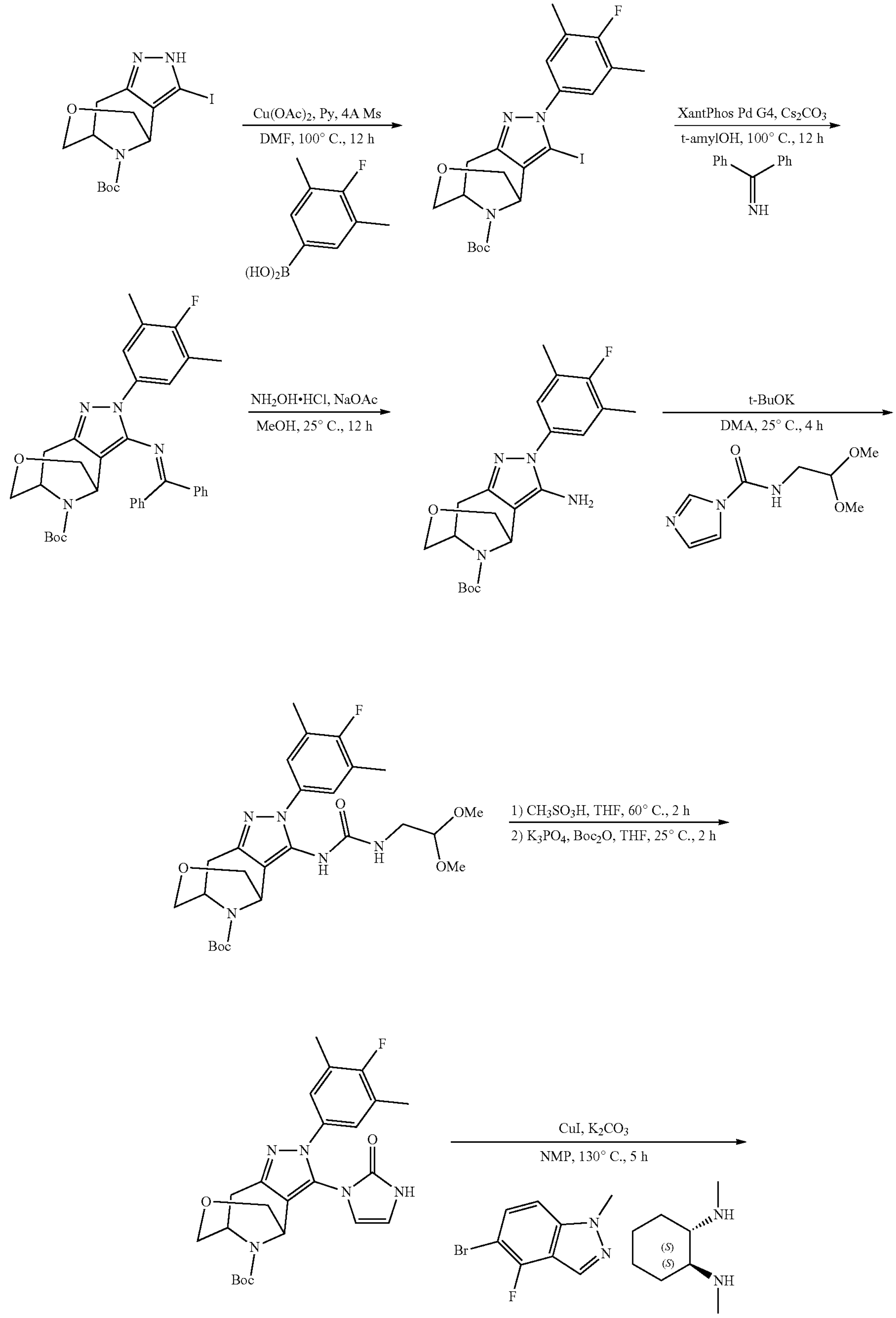

-continued
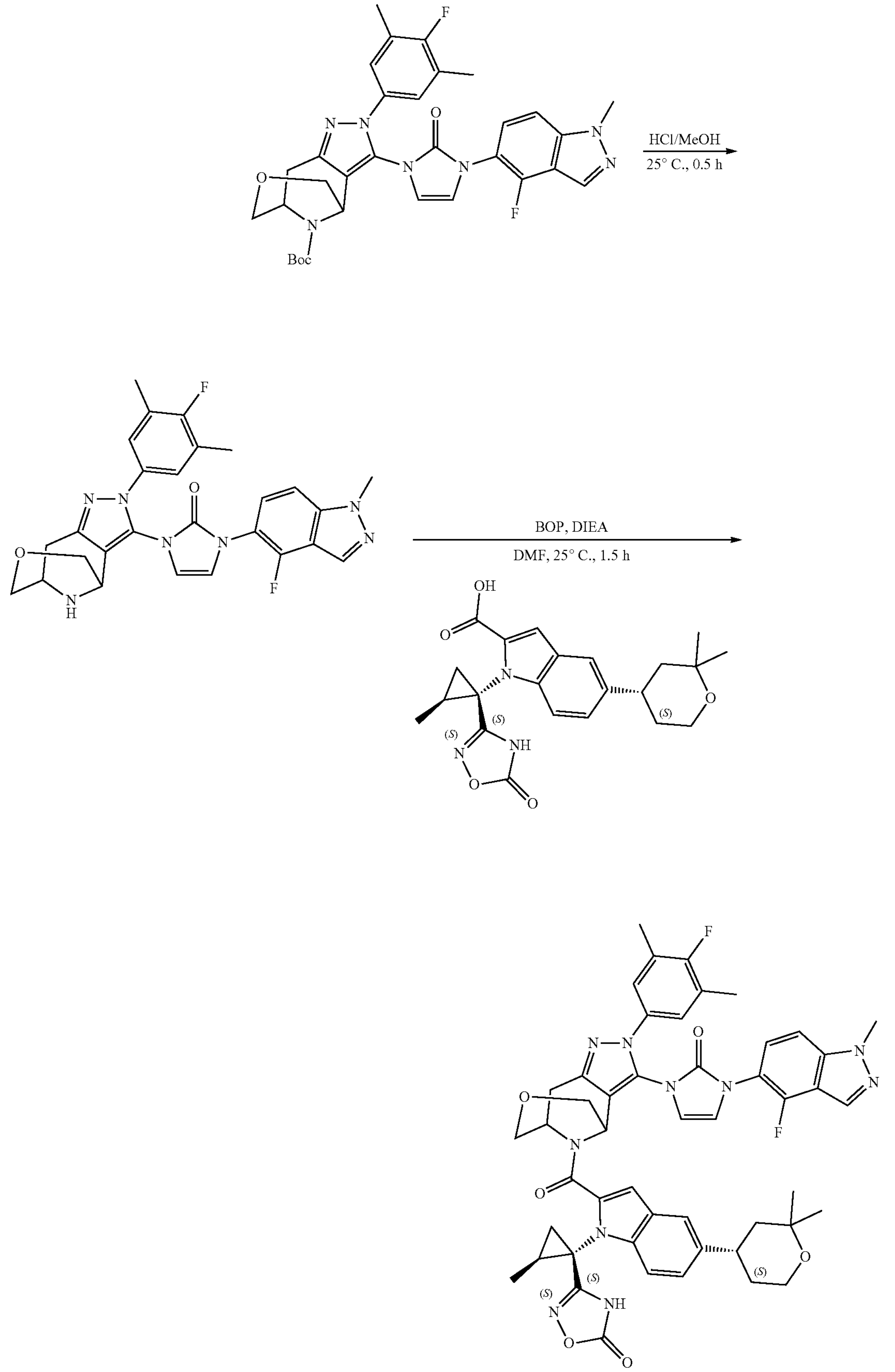

Step 1: ter-butyl 6-(dimethylamino)methylene)-7-oxo-3-oxa-9-azabicyclo[3.3.1]nonane-9-carboxylate

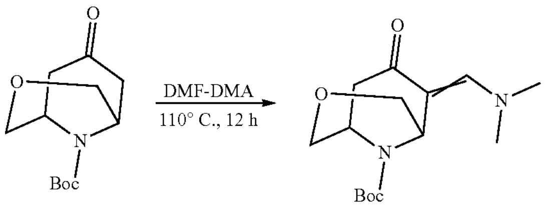

To a mixture of tert-butyl 7-oxo-3-oxa-9-azabicyclo [3.3.1]nonane-9-carboxylate (23 g, 95.32 mmol, 1 eq) in DMF-DMA (230 mL) was degassed and purged with $N_2$ for 3 times, and then the mixture was stirred at 110° C. for 12 hours under $N_2$ atmosphere. The reaction mixture was concentrated under reduced pressure to give a residue, which was purified by column chromatography ($SiO_2$, Petroleum ether/Ethyl acetate=10/1 to 0/1) to provide tert-butyl 6-((dimethylamino)methylene)-7-oxo-3-oxa-9-azabicyclo[3.3.1] nonane-9-carboxylate (15 g, 50.61 mmol, 53.10% yield). $^1H$ NMR (400 MHz, CHLOROFORM-d) δ=7.49-7.39 (m, 1H), 5.40-5.22 (m, 1H), 4.36-4.19 (m, 1H), 3.88-3.66 (m, 4H), 3.14-3.03 (m, 6H), 2.83-2.60 (m, 1H), 2.45-2.34 (m, 1H), 1.50-1.44 (m, 9H). LC-MS (ES+, m/z): 297.1 [$(M+H)^+$]; Rt=0.995 min.

Step 2: tert-butyl 2,4,5,7,8,9-hexahydro-4,8-epiminooxocino [5,4-c]pyrazole-10-carboxylate

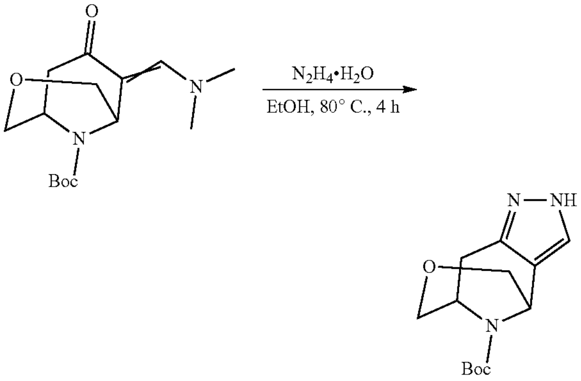

To a mixture of tert-butyl 6-((dimethylamino)methylene)-7-oxo-3-oxa-9-azabicyclo[3.3.1] nonane-9-carboxylate (14 g, 47.24 mmol, 1 eq) in EtOH (140 mL) was added $N_2H_4 \cdot H_2O$ (4 g, 63.92 mmol, 3.88 mL, 1.35 eq). The reaction mixture was stirred at 80° C. for 4 hours under $N_2$ atmosphere. The reaction mixture was quenched by addition $H_2O$ (500 mL), extracted with ethyl acetate (200 mL*3). The combined organic layers were washed with saturated brine (200 mL), dried over anhydrous $Na_2SO_4$, filtered and concentrated under reduced pressure to give a residue, which was purified by column chromatography ($SiO_2$, Petroleum ether/Ethyl acetate=10/1 to 0/1) to provide tert-butyl 2,4,5,7,8,9-hexahydro-4,8-epiminooxocino [5,4-c]pyrazole-10-carboxylate (10 g, 36.94 mmol, 78.19% yield). $^1H$ NMR (400 MHz, DMSO-$d_6$) δ=12.61-12.24 (m, 1H), 7.63-7.08 (m, 1H), 5.09-4.82 (m, 1H), 4.31-4.13 (m, 1H), 3.88-3.77 (m, 1H), 3.69-3.54 (m, 2H), 3.50-3.39 (m, 1H), 3.04-2.89 (m, 1H), 2.78-2.63 (m, 1H), 1.46-1.24 (m, 9H). LC-MS (ES+, m/z): 265.9 [$(M+H)^+$]; Rt=0.342 min.

Step 3: tert-butyl 3-iodo-2,4,5,7,8,9-hexahydro-4,8-epiminooxocino [5,4-c]pyrazole-10-carboxylate

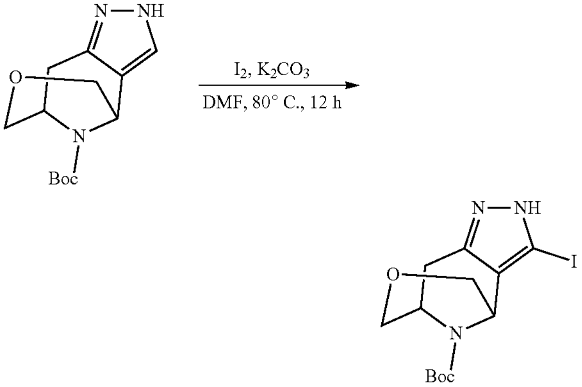

To a solution of tert-butyl 10-oxa-4,5,12-triazatricyclo [6.3.1.02,6] dodeca-2,5-diene-12-carboxylate (10 g, 37.69 mmol, 1 eq) in DMF (100 mL) was added $I_2$ (19.13 g, 75.38 mmol, 15.19 mL, 2 eq) and $K_2CO_3$ (15.63 g, 113.08 mmol, 3 eq). The mixture was stirred at 80° C. for 12 hours. The reaction mixture was quenched by addition water (100 mL) at 25° C., and then extracted with ethyl acetate (100 mL*3). The combined organic layers were washed with saturated $NaHSO_3$ (200 mL*2), dried over anhydrous $Na_2SO_4$, filtered, and concentrated under reduced pressure to give tert-butyl 3-iodo-2,4,5,7,8,9-hexahydro-4,8-epiminooxocino [5,4-c]pyrazole-10-carboxylate (13 g, 31.40 mmol, 83.31% yield, 94.5% purity). $^1H$ NMR (400 MHz, DMSO-$d_6$) δ=13.05-12.89 (m, 1H), 4.73-4.52 (m, 1H), 4.28-4.16 (m, 1H), 3.89-3.75 (m, 1H), 3.71-3.51 (m, 2H), 3.40-3.36 (m, 1H), 3.03-2.90 (m, 1H), 2.78-2.61 (m, 1H), 1.46-1.27 (m, 9H). LC-MS (ES+, m/z): 391.9 [$(M+H)^+$]. Rt=1.108 min.

Step 4: tert-butyl 2-(4-fluoro-3,5-dimethylphenyl)-3-iodo-2,4,5,7,8,9-hexahydro-4,8-epiminooxocino [5,4-c]pyrazole-10-carboxylate

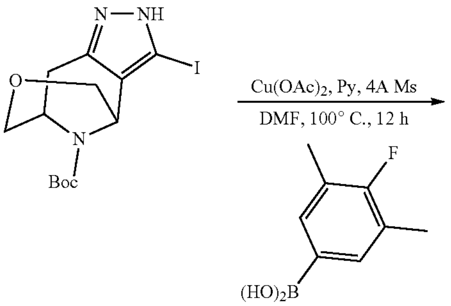

-continued

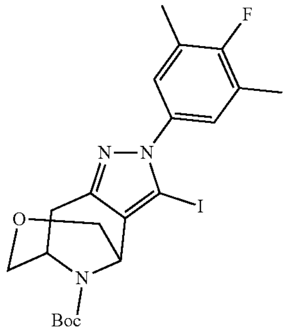

A mixture of tert-butyl 3-iodo-2,4,5,7,8,9-hexahydro-4,8-epiminooxocino [5,4-c]pyrazole-10-carboxylate (3 g, 7.67 mmol, 1 eq), (4-fluoro-3,5-dimethyl-phenyl) boronic acid (2.58 g, 15.34 mmol, 2 eq), $Cu(OAc)_2$ (278.57 mg, 1.53 mmol, 0.2 eq), Py (2.43 g, 30.67 mmol, 2.48 mL, 4 eq) and 4A MS (1.00 eq) in DMF (30 mL) was degassed and purged with $O_2$ for 3 times, and then stirred at 100° C. for 12 hours under $O_2$ atmosphere (15 Psi). The reaction mixture was quenched by addition saturated EDTA (30 mL) and stirred for 0.5 hour, diluted with DCM (30 mL) and extracted with DCM (40 mL*3). The combined organic layers were washed with saturated brine (100 mL*2), dried over anhydrous $Na_2SO_4$, filtered, and concentrated under reduced pressure to give a residue, which was purified by column chromatography ($SiO_2$, Petroleum ether/Ethyl acetate=30/1 to 1/1) to provide tert-butyl 2-(4-fluoro-3,5-dimethylphenyl)-3-iodo-2,4,5,7,8,9-hexahydro-4,8-epiminooxocino [5,4-c] pyrazole-10-carboxylate (0.4 g, 711.42 μmol, 9.28% yield, 91.3% purity). LC-MS (ES+, m/z): 514.2 [$(M+H)^+$]. Rt=0.636 min.

Step 5: tert-butyl 3-((diphenylmethylene)amino)-2-(4-fluoro-3,5-dimethylphenyl)-2,4,5,7,8,9-hexahydro-4,8-epiminooxocino [5,4-c]pyrazole-10-carboxylate

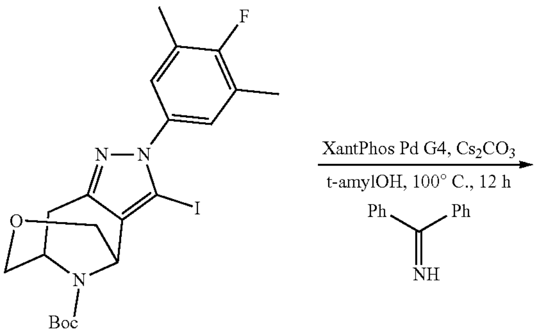

-continued

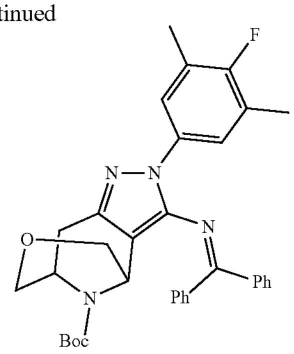

A mixture of tert-butyl 2-(4-fluoro-3,5-dimethylphenyl)-3-iodo-2,4,5,7,8,9-hexahydro-4,8-epiminooxocino [5,4-c] pyrazole-10-carboxylate (400 mg, 779.21 μmol, 1 eq), diphenylmethanimine (423.65 mg, 2.34 mmol, 392.27 μL, 3 eq), Xantphos Pd G4 (74.99 mg, 77.92 μmol, 0.1 eq), $Cs_2CO_3$ (507.76 mg, 1.56 mmol, 2 eq) in t-AmylOH (5 mL) was degassed and purged with $N_2$ for 3 times, and then stirred at 100° C. for 12 hours under $N_2$ atmosphere. The reaction mixture was quenched by addition saturated EDTA (10 mL) at 25° C., and then stirred for 0.5 hour, diluted with DCM (10 mL) and extracted with DCM (10 mL*3). The combined organic layers were washed with saturated brine (30 mL*2), dried over anhydrous $Na_2SO_4$, filtered, and concentrated under reduced pressure to give a residue, which was purified by prep-TLC ($SiO_2$, petroleum ether:ethyl acetate=2:1) to provide tert-butyl 3-((diphenylmethylene) amino)-2-(4-fluoro-3,5-dimethylphenyl)-2,4,5,7,8,9-hexahydro-4,8-epiminooxocino [5,4-c]pyrazole-10-carboxylate (200 mg, 265.41 μmol, 34.06% yield, 75.2% purity). LC-MS (ES+, m/z): 567.2 [$(M+H)^+$]. Rt=1.765 min.

Step 6: tert-butyl 3-amino-2-(4-fluoro-3,5-dimethylphenyl)-2,4,5,7,8,9-hexahydro-4,8-epiminooxocino [5,4-c]pyrazole-10-carboxylate

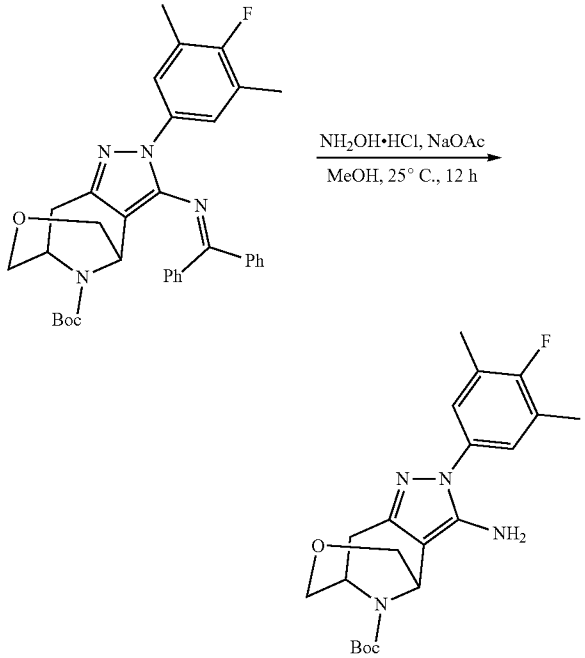

A mixture of tert-butyl 3-((diphenylmethylene)amino)-2-(4-fluoro-3,5-dimethylphenyl)-2,4,5,7,8,9-hexahydro-4,8-epiminooxocino [5,4-c]pyrazole-10-carboxylate (200 mg, 352.94 μmol, 1 eq), $NH_2OH{\cdot}HCl$ (49.05 mg, 705.89 μmol, 2 eq), NaOAc (86.86 mg, 1.06 mmol, 3 eq) in MeOH (2 mL) was degassed and purged with $N_2$ for 3 times, and then stirred at 25° C. for 12 hours under $N_2$ atmosphere. The reaction mixture was quenched by addition water (5 mL) at 25° C., diluted with ethyl acetate (5 mL) and extracted with ethyl acetate (10 mL*3). The combined organic layers were washed with saturated brine (20 mL*2), dried over anhydrous $Na_2SO_4$, filtered, and concentrated under reduced pressure to give tert-butyl 3-amino-2-(4-fluoro-3,5-dimethylphenyl)-2,4,5,7,8,9-hexahydro-4,8-epiminooxocino [5,4-c]pyrazole-10-carboxylate (120 mg, 241.51 μmol, 68.43% yield, 81.0% purity). LC-MS (ES+, m/z): 403.0 [$(M+H)^+$]. Rt=1.252 min.

Step 7: tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate

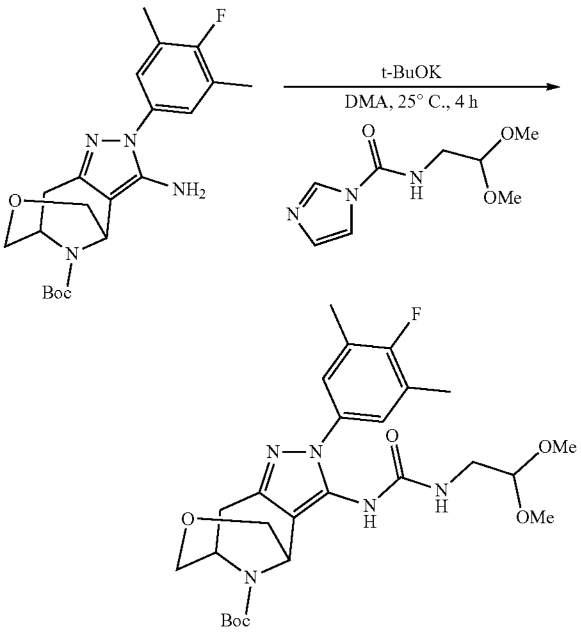

A mixture of tert-butyl 3-amino-2-(4-fluoro-3,5-dimethylphenyl)-2,4,5,7,8,9-hexahydro-4,8-epiminooxocino [5,4-c]pyrazole-10-carboxylate (120 mg, 298.17 μmol, 1 eq), N-(2,2-dimethoxyethyl) imidazole-1-carboxamide (118.79 mg, 596.33 μmol, 2 eq), t-BuOK (167.29 mg, 1.49 mmol, 5 eq) in DMA (1 mL) was degassed and purged with $N_2$ for 3 times, and then stirred at 25° C. for 4 hours under $N_2$ atmosphere. The reaction mixture was quenched by addition water (5 mL) at 25° C., and then diluted with ethyl acetate (5 mL) and extracted with ethyl acetate (10 mL*3). The combined organic layers were washed with saturated brine (20 mL*2), dried over anhydrous $Na_2SO_4$, filtered, and concentrated under reduced pressure to give a residue. The residue was purified by prep-TLC ($SiO_2$, petroleum ether: ethyl acetate=1:1) to provide tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate (60 mg, 111.43 μmol, 37.37% yield, 99.1% purity). LC-MS (ES+, m/z): 534.2 [$(M+H)^+$]. Rt=1.236 min.

Step 8: tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate

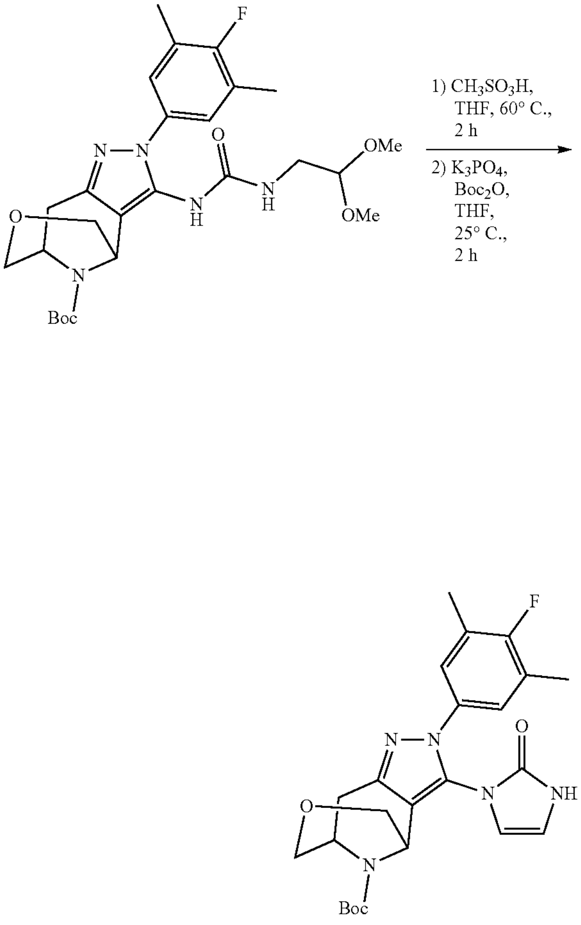

To a mixture of tert-butyl 3-(3-(2,2-dimethoxyethyl) ureido)-2-(4-fluoro-3,5-dimethylphenyl)-2,4,5,7,8,9-hexahydro-4,8-epiminooxocino [5,4-c]pyrazole-10-carboxylate (60 mg, 112.45 μmol, 1 eq) in THF (1 mL) was added $CH_3SO_3H$ (16.21 mg, 168.67 μmol, 12.05 μL, 1.5 eq), the mixture was stirred at 60° C. for 2 hours. $K_3PO_4$ (71.61 mg, 337.34 μmol, 3 eq) in $H_2O$ (0.1 mL) was added at 25° C. followed by $Boc_2O$ (24.54 mg, 112.45 μmol, 25.83 μL, 1 eq). The mixture was stirred at 25° C. for 2 hours. The reaction mixture was quenched by addition water (5 mL) at 25° C., and then diluted with ethyl acetate (5 mL) and extracted with ethyl acetate (10 mL*3). The combined organic layers were washed with saturated brine (20 mL*2), dried over anhydrous $Na_2SO_4$, filtered, and concentrated under reduced pressure to give tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (40 mg, 72.59 μmol, 64.55% yield, 85.2% purity). LC-MS (ES+, m/z): 470.0 [$(M+H)^+$]. Rt=1.217 min.

Step 9: tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate

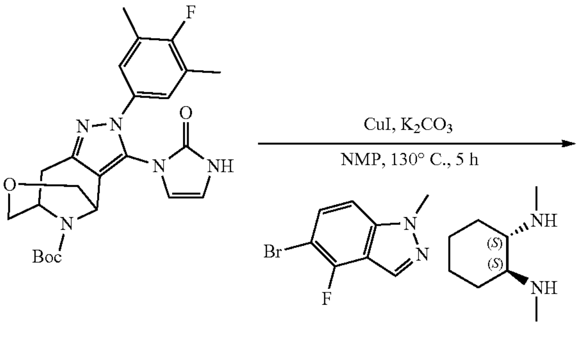

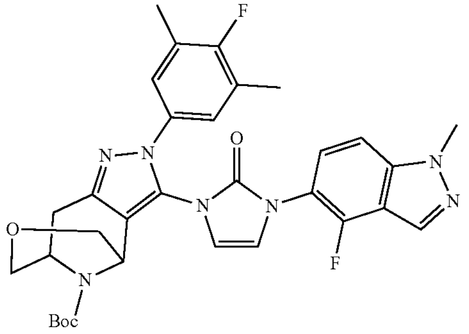

A mixture of tert-butyl 2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (40 mg, 85.20 μmol, 1 eq), 5-bromo-4-fluoro-1-methyl-indazole (39.03 mg, 170.39 μmol, 2 eq), CuI (32.45 mg, 170.39 μmol, 2 eq), $K_2CO_3$ (23.55 mg, 170.39 μmol, 2 eq) and (1S,2S)—N1,N2-dimethylcyclohexane-1,2-diamine (36.35 mg, 255.59 μmol, 3 eq) in NMP (1 mL) was degassed and purged with $N_2$ for 3 times, and then stirred at 130° C. for 5 hours under $N_2$ atmosphere. The reaction mixture was quenched by addition water (5 mL) at 25° C., diluted with DCM (5 mL), and then extracted with DCM (10 mL*3). The combined organic layers were washed with saturated brine (20 mL*2), dried over anhydrous $Na_2SO_4$, filtered and concentrated under reduced pressure to give a residue, which was purified by prep-TLC ($SiO_2$, petroleum ether:ethyl acetate=1:1) to provide tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (20 mg, 24.29 μmol, 28.51% yield, 75.0% purity). LC-MS (ES+, m/z): 618.3 [(M+H)$^+$]. Rt=1.447 min.

Step 10:1-(4-fluoro-1-methyl-1H-indazol-5-yl)-3-(2-(4-fluoro-3,5-dimethylphenyl)-2,4,5,7,8,9-hexahydro-4,8-epiminooxocino [5,4-c]pyrazol-3-yl)-1H-imidazol-2 (3H)-one

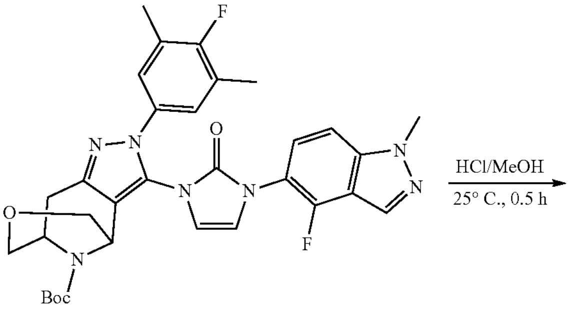

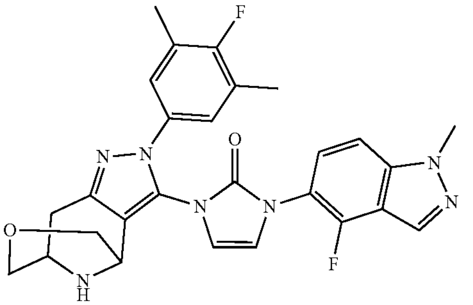

To a solution of tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (20 mg, 32.38 μmol, 1 eq) in HCl/MeOH (4 M, 1.00 mL, 123.53 eq) was stirred at 25° C. for 0.5 hour. The reaction mixture was concentrated under reduced pressure to give 1-(4-fluoro-1-methyl-1H-indazol-5-yl)-3-(2-(4-fluoro-3,5-dimethylphenyl)-2,4,5,7,8,9-hexahydro-4,8-epiminooxocino [5,4-c] pyrazol-3-yl)-1H-imidazol-2 (3H)-one (20 mg, 28.37 μmol, 87.60% yield, 73.4% purity). LC-MS (ES+, m/z): 518.2 [(M+H)$^+$]. Rt=0.401 min.

Step 11: 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one

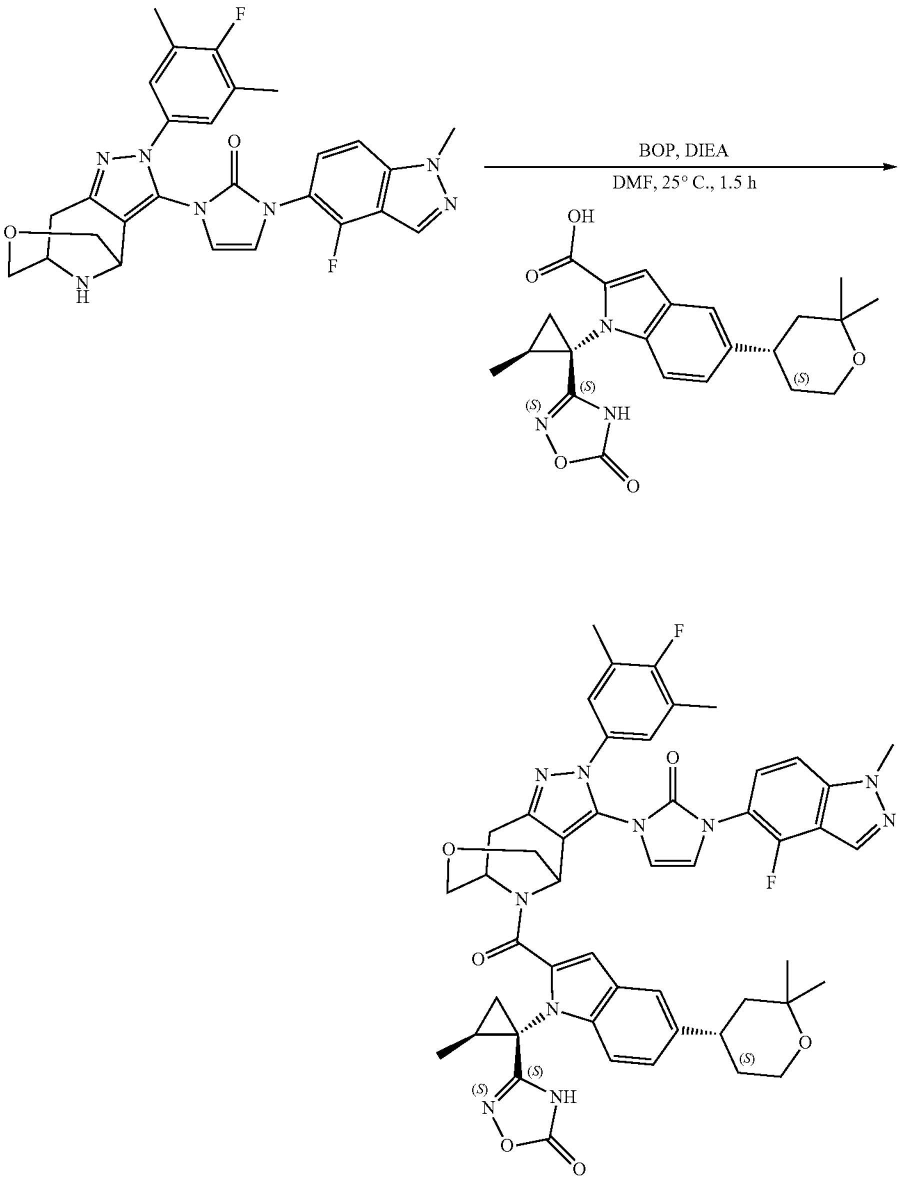

To a mixture of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (7.95 mg, 19.32 μmol, 1 eq) in DMF (1 mL) was added BOP (10.26 mg, 23.19 μmol, 1.2 eq) and DIEA (5.99 mg, 46.37 μmol, 8.08 μL, 2.4 eq). The reaction mixture was stirred at 25° C. for 0.5 hour. 1-(4-Fluoro-1-methyl-1H-indazol-5-yl)-3-(2-(4-fluoro-3,5-dimethylphenyl)-2,4,5,7,8,9-hexahydro-4,8-epiminooxocino [5,4-c]pyrazol-3-yl)-1H-imidazol-2 (3H)-one (10 mg, 19.32 μmol, 1 eq) was added, and the mixture was continued to stir at 25° C. for 1 hour. The reaction mixture was concentrated under reduced pressure to give a residue, which was purified by prep-HPLC (column: 3_Phenomenex Luna C18 75*30 mm*3 um; mobile phase: [$H_2O$ (0.1% TFA)-ACN]; gradient: 50%-80% B over 8.0 min) to provide 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (1.02 mg, 1.12 μmol, 5.79% yield, 100% purity). $^1$H NMR (400 MHz, DMSO-$d_6$) δ=11.72 (s, 1H), 8.33-8.15 (m, 1H), 7.67-7.59 (m, 1H), 7.56-7.46 (m, 1H), 7.41-6.98 (m, 6H), 6.94-6.81 (m, 1H), 6.78-6.64 (m, 1H), 5.68-5.51 (m, 1H), 5.27-4.71 (m, 1H), 4.20-4.05 (m, 5H), 3.68 (br d, J=15.5 Hz, 4H), 3.10-2.99 (m, 3H), 2.31-2.17 (m, 6H), 1.83-1.32 (m, 6H), 1.30-0.82 (m, 10H). LC-MS (ES+, m/z): 911.3 [(M+H)$^+$]. Rt=0.613 min. HRMS (EI): m/z [M+H]$^+$ found: 911.3760.

Example 40
Compound 118
1-((4S,7R)-9-(1-(1-(1H-tetrazol-5-yl)cyclopropyl)-5-((S)-2,2-dimethyltetrahydro-2H-pyran-4-yl)-1H-indole-2-carbonyl)-2-(4-fluoro-3,5-dimethylphenyl)-2,4,5,6,7,8-hexahydro-4,7-epiminocyclohepta[c]pyrazol-3-yl)-3-(4-fluoro-1-methyl-1H-indazol-5-yl)-1H-imidazol-2 (3H)-one
Scheme 40
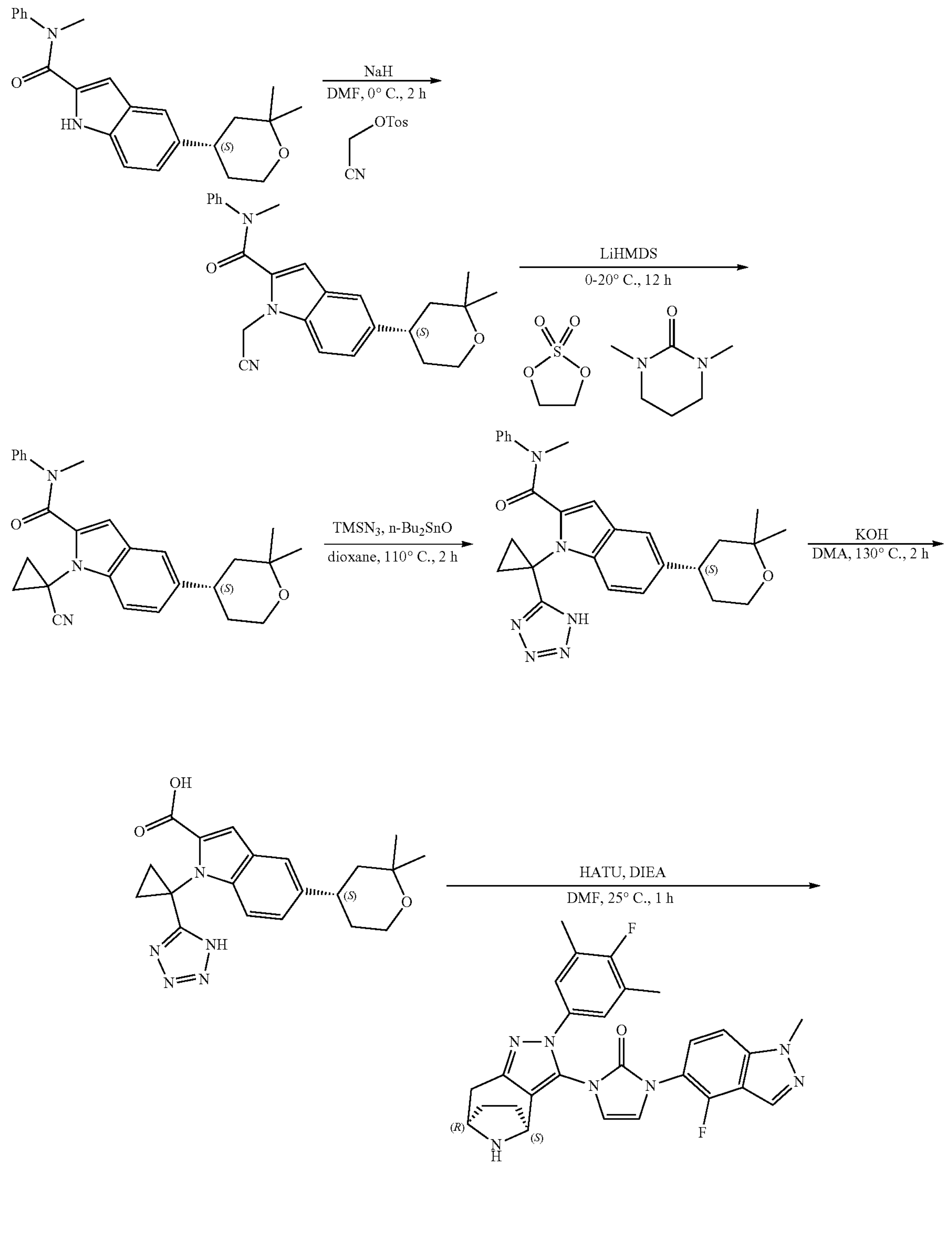

-continued

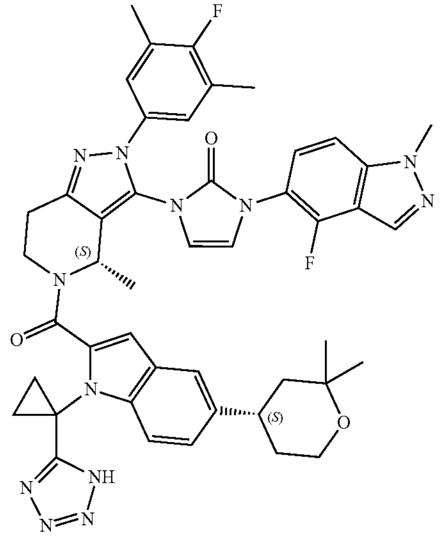

Step 1: (S)-1-(cyanomethyl)-5-(2,2-dimethyltetrahydro-2H-pyran-4-yl)-N-methyl-N-phenyl-1H-indole-2-carboxamide

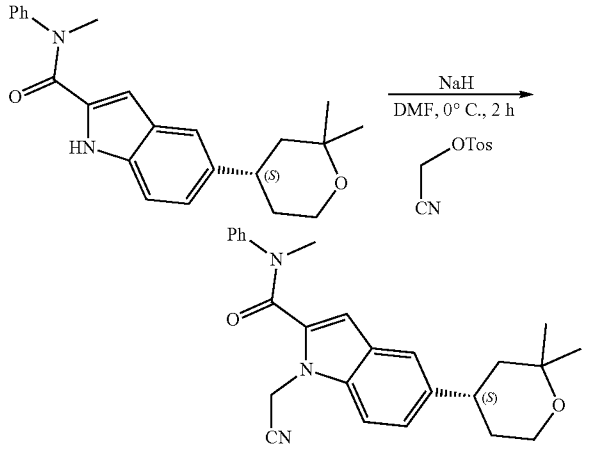

To a solution of 5-[(4S)-2,2-dimethyltetrahydropyran-4-yl]-N-methyl-N-phenyl-1H-indole-2-carboxamide (350 mg, 965.61 μmol, 1 eq) in DMF (3.5 mL) was added NaH (115.86 mg, 2.90 mmol, 60% purity, 3 eq) at 0° C. The mixture was stirred at 0° C. for 1 hour. Cyanomethyl 4-methylbenzenesulfonate (407.95 mg, 1.93 mmol, 2 eq) was added and the resulting mixture was stirred at 0° C. for 1 hour. LCMS indicated the reaction was completed. The residue was poured into ice-water (50 mL), the aqueous phase was extracted with ethyl acetate (30 mL*3). The combined organic phase was washed with saturated brine (60 mL*2), dried with anhydrous $Na_2SO_4$, filtered, and concentrated in vacuum. The crude product was purified by chromatography on silica gel (Petroleum ether: ethyl acetate=3:1) to give 1-(cyanomethyl)-5-[(4S)-2,2-dimethyltetrahydropyran-4-yl]-N-methyl-N-phenyl-indole-2-carboxamide (270 mg, 672.48 μmol, 69.64% yield). LC-MS (ES+, m/z): 402.1 [(M+H)+]; Rt=0.549 min.

Step 2: (S)-1-(1-cyanocyclopropyl)-5-(2,2-dimethyltetrahydro-2H-pyran-4-yl)-N-methyl-N-phenyl-1H-indole-2-carboxamide

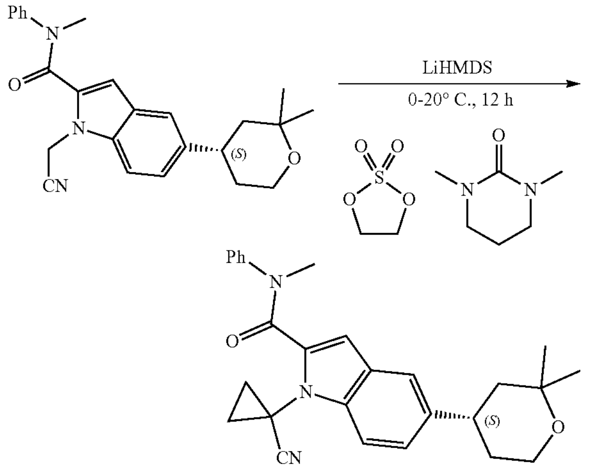

To a solution of 1-(cyanomethyl)-5-[(4S)-2,2-dimethyltetrahydropyran-4-yl]-N-methyl-N-phenyl-indole-2-carboxamide (340 mg, 846.83 μmol, 1 eq) and 1,3,2-dioxathiolane 2,2-dioxide (630.63 mg, 5.08 mmol, 6 eq) in 1,3-dimethylhexahydropyrimidin-2-one (7 mL) was added LiHMDS (1 M, 6.77 mL, 8 eq) dropwise at 0° C. under $N_2$. The mixture was stirred at 0° C. for 1 hour and then 20° C. for 12 hours. LCMS indicated the reaction was completed. The residue was poured into water (50 mL), the aqueous phase was extracted with ethyl acetate (40 mL*3). The combined organic phase was washed with saturated brine (40 mL*2), dried with anhydrous $Na_2SO_4$, filtered, and concentrated in vacuum. The crude product was purified by chromatography on silica gel (Petroleum ether:ethyl acetate=5:1) to give 1-(1-cyanocyclopropyl)-5-[(4S)-2,2-dimethyltetrahydropyran-4-yl]-N-methyl-N-phenyl-indole-2-carboxamide (480 mg, 561.36 μmol, 66.29% yield, 50% purity). LC-MS (ES+, m/z): 428.3 [(M+H)+]; Rt=1.860 min.

Step 3: (S)-1-(1-(1H-tetrazol-5-yl)cyclopropyl)-5-(2,2-dimethyltetrahydro-2H-pyran-4-yl)-N-methyl-N-phenyl-1H-indole-2-carboxamide

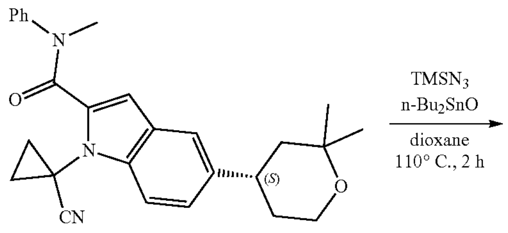

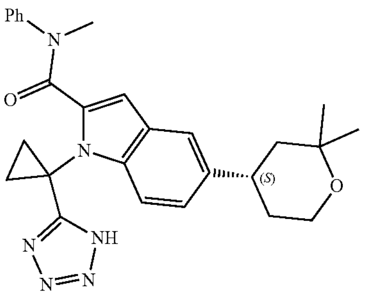

To a solution of 1-(1-cyanocyclopropyl)-5-[(4S)-2,2-dimethyltetrahydropyran-4-yl]-N-methyl-N-phenyl-indole-2-carboxamide (600 mg, 701.69 μmol, 1 eq) in dioxane (12 mL) was added azido (trimethyl) silane (323.37 mg, 2.81 mmol, 369.14 μL, 4 eq) and dibutyl(oxo) tin (55 mg, 220.94 μmol, 0.3 eq). The mixture was stirred at 110° C. for 2 hours. LCMS indicated the reaction was completed. The mixture was filtered and concentrated in vacuum. The crude product was purified by chromatography on silica gel (Petroleum ether:ethyl acetate-2:3) to give 5-[(4S)-2,2-dimethyltetrahydropyran-4-yl]-N-methyl-N-phenyl-1-[1-(1H-tetrazol-5-yl)cyclopropyl] indole-2-carboxamide (300 mg, 478.15 μmol, 68.14% yield, 75% purity). $^1H$ NMR (400 MHz, CHLOROFORM-d) δ ppm 7.62 (d, J-8.63 Hz, 1H) 7.36-7.43 (m, 2H) 7.30-7.35 (m, 1H) 7.13-7.24 (m, 4H) 5.83-6.10 (m, 1H) 3.72-3.87 (m, 2H) 3.61 (s, 3H) 2.47-2.60 (m, 1H) 1.59-1.73 (m, 6H) 1.52-1.59 (m, 2H) 1.28 (s, 3H) 1.23 (s, 3H). LC-MS (ES+, m/z): 471.3 [(M+H)$^+$]; Rt=0.513 min.

Step 4: (S)-1-(1-(1H-tetrazol-5-yl)cyclopropyl)-5-(2,2-dimethyltetrahydro-2H-pyran-4-yl)-1H-indole-2-carboxylic acid

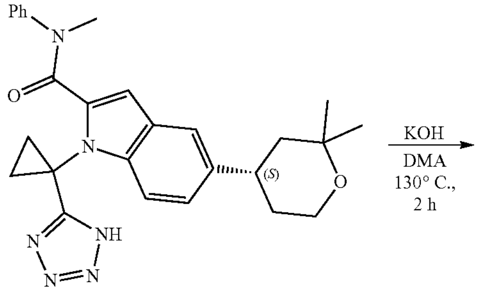

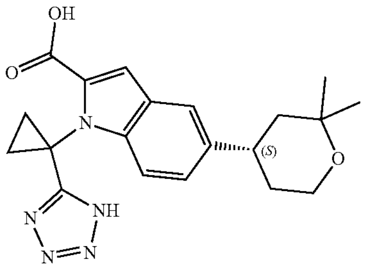

To a solution of 5-[(4S)-2,2-dimethyltetrahydropyran-4-yl]-N-methyl-N-phenyl-1-[1-(1H-tetrazol-5-yl)cyclopropyl] indole-2-carboxamide (300 mg, 478.15 μmol, 1 eq) in DMA (3 mL) was added KOH (268.27 mg, 4.78 mmol, 10 eq). The mixture was stirred at 130° C. for 1 hour. LCMS indicated the reaction was completed. The mixture was adjusted PH to 5 with saturated citric acid aqueous. The aqueous phase was extracted with ethyl acetate (20 mL*3). The combined organic phase was washed with saturated brine (50 mL*2), dried with anhydrous $Na_2SO_4$, filtered and concentrated in vacuum to give 5-[(4S)-2,2-dimethyltetrahydropyran-4-yl]-1-[1-(1H-tetrazol-5-yl)cyclopropyl] indole-2-carboxylic acid (300 mg, 314.61 μmol, 65.80% yield, 40% purity). $^1H$ NMR (400 MHz, CHLOROFORM-d) δ ppm 7.59-7.74 (m, 1H) 7.48 (br s, 1H) 7.28-7.39 (m, 2H) 3.70-3.98 (m, 2H) 2.89-3.13 (m, 1H) 2.18-2.35 (m, 1H) 1.55-1.79 (m, 7H) 1.33 (s, 3H) 1.26 (s, 3H). LC-MS (ES+, m/z): 382.2 [(M+H)$^+$]; Rt=0.432 min.

Step 5: 1-((4S,7R)-9-(1-(1-(1H-tetrazol-5-yl)cyclopropyl)-5-((S)-2,2-dimethyltetrahydro-2H-pyran-4-yl)-1H-indole-2-carbonyl)-2-(4-fluoro-3,5-dimethylphenyl)-2,4,5,6,7,8-hexahydro-4,7-epiminocyclohepta [c]pyrazol-3-yl)-3-(4-fluoro-1-methyl-1H-indazol-5-yl)-1H-imidazol-2 (3H)-one nyl]-4-(4-fluoro-3,5-dimethyl-phenyl)-4,5,11-triazatricyclo [6.2.1.02,6]undeca-2,5-dien-3-yl]-3-(4-fluoro-1-methyl-indazol-5-yl) imidazol-2-one (8.39 mg, 17.34 μmol, 6.06% yield). $^1$H NMR (400 MHz, METHANOL-$d_4$) δ ppm 8.17 (br s, 1H) 7.47-7.65 (m, 1H) 7.34-7.47 (m, 2H) 7.07-7.34 (m, 4H) 6.91-7.06 (m, 1H) 6.85 (br s, 2H) 5.37-5.66 (m, 1H)

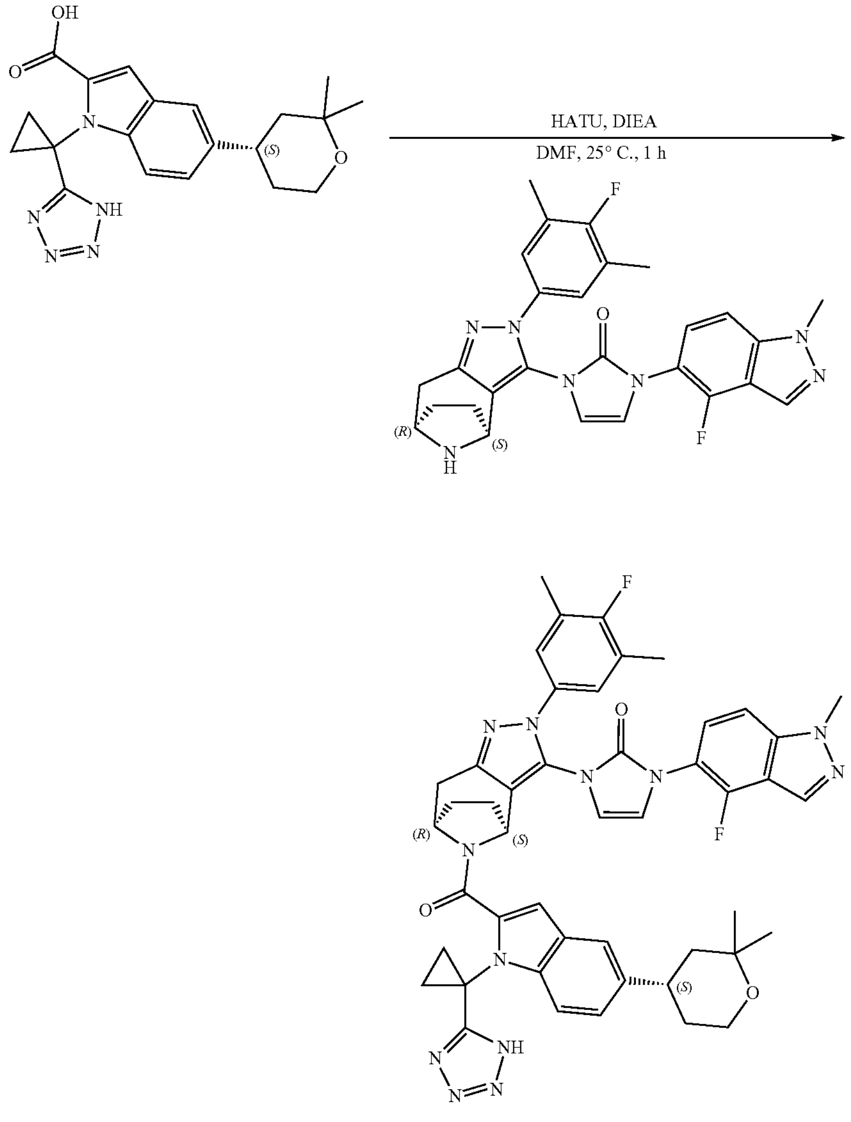

To a solution of 5-[(4S)-2,2-dimethyltetrahydropyran-4-yl]-1-[1-(1H-tetrazol-5-yl) cyclopropyl] indole-2-carboxylic acid (60 mg, 157.30 μmol, 1 eq) and 1-[(1S,8R)-4-(4-fluoro-3,5-dimethyl-phenyl)-4,5,11-triazatricyclo[6.2.1.02,6]undeca-2,5-dien-3-yl]-3-(4-fluoro-1-methyl-indazol-5-yl) imidazol-2-one (169.26 mg, 314.61 μmol, 2 eq, HCl) in DMF (1.0 mL) was added DIEA (81.32 mg, 629.22 μmol, 109.60 μL, 4 eq) and HATU (125.60 mg, 330.34 μmol, 2.1 eq). The mixture was stirred at 20° C. for 3 hours. LCMS indicated the reaction was completed. The mixture was filtered. The filtrate was purified by prep-HPLC (column: WePure Biotech XPt C18150*40*7 um; mobile phase: [$H_2O$ (10 mM $NH_4HCO_3$)-ACN]; gradient: 30%-50% B over 8.0 min) to give 1-[(1S,8R)-11-[5-[(4S)-2,2-dimethyltetrahydropyran-4-yl]-1-[1-(1H-tetrazol-5-yl)cyclopropyl] indole-2-carbo- 5.04-5.31 (m, 1H) 4.02-4.20 (m, 3H) 3.60-3.97 (m, 2H) 3.49-3.60 (m, 1H) 2.74-3.12 (m, 2H) 2.40-2.51 (m, 1H) 2.17-2.39 (m, 8H) 2.03-2.16 (m, 1H) 1.85-2.00 (m, 2H) 1.44-1.83 (m, 5H) 1.35 (br d, J-9.76 Hz, 1H) 1.21-1.32 (m, 3H) 0.86-1.21 (m, 3H). $^1$H NMR (400 MHz, DMSO-$d_6$) δ ppm 8.21 (s, 1H) 7.54 (br d, J-8.70 Hz, 1H) 7.38-7.45 (m, 1H) 7.29-7.37 (m, 2H) 7.11-7.21 (m, 3H) 6.91 (br s, 1H) 6.84 (s, 2H) 5.37 (br s, 1H) 4.94-5.11 (m, 1H) 4.09 (s, 3H) 3.56-3.72 (m, 2H) 3.23-3.31 (m, 1H) 2.94 (br d, J=1.79 Hz, 1H) 2.78 (br d, J=16.33 Hz, 1H) 2.29-2.34 (m, 1H) 2.26 (d, J=1.43 Hz, 7H) 2.10 (br s, 2H) 1.76-1.88 (m, 3H) 1.69 (br d, J=8.82 Hz, 1H) 1.57 (br dd, J=15.14, 8.23 Hz, 2H) 1.37-1.49 (m, 2H) 1.23 (s, 3H) 1.11 (br s, 3H). LC-MS (ES+, m/z): 865.3 [$(M+H)^+$]; Rt=2.789 min. HRMS (EI): m/z $[M+H]^+$ found: 865.3875.

Example 41

Compound 120

3-((1S,2S)-1-(5-((S)-2,2-dimethyltetrahydro-2H-pyran-4-yl)-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5(4H)-one

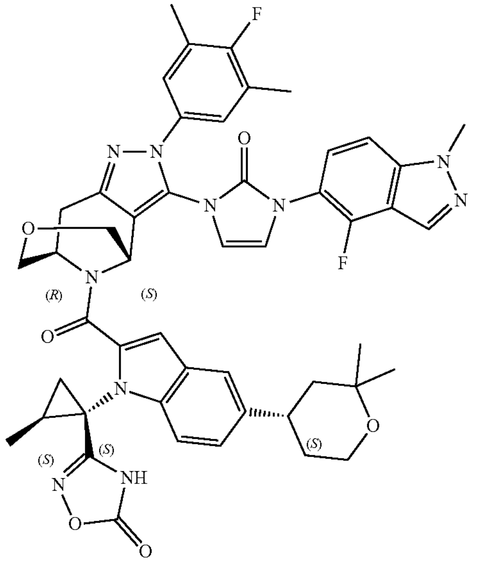

And

Compound 121

3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one

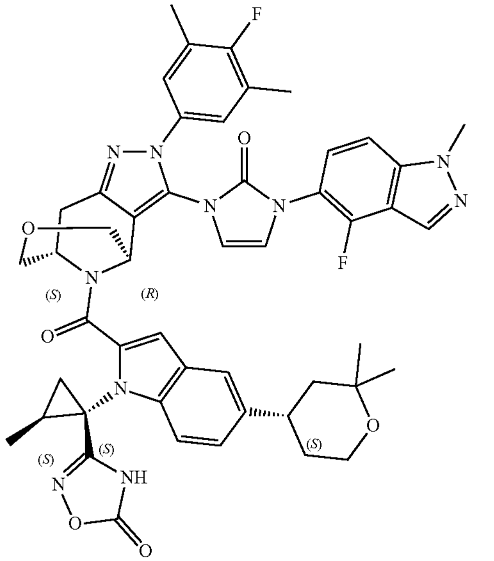

Step 1: 3-((1S,2S)-1-(5-((S)-2,2-dimethyltetrahydro-2H-pyran-4-yl)-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one and 3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one

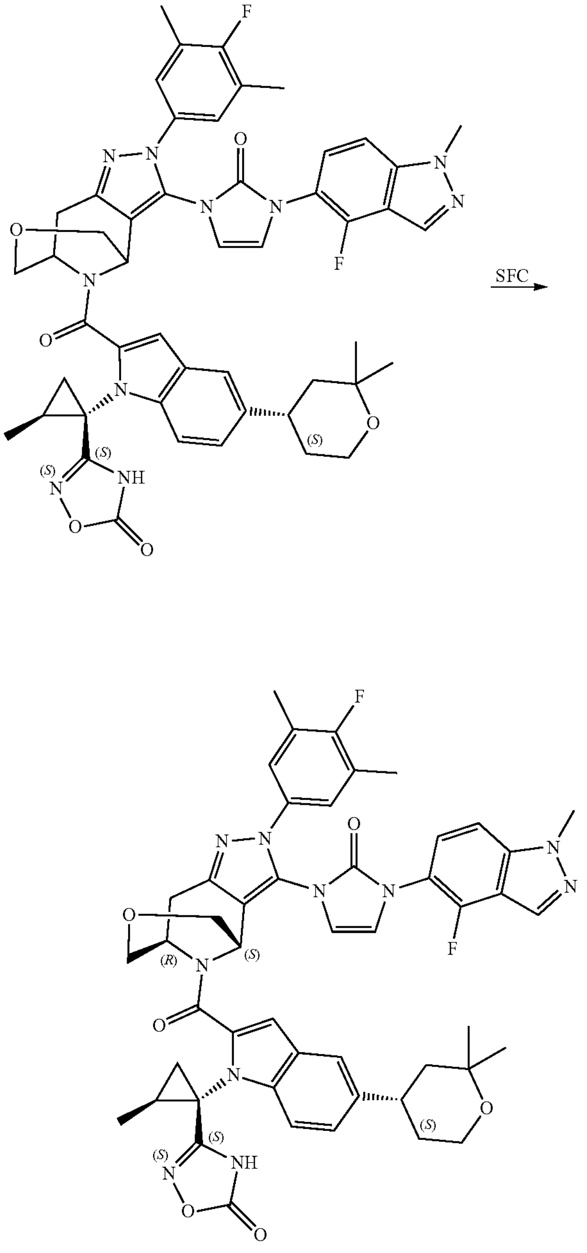

first eluent

-continued

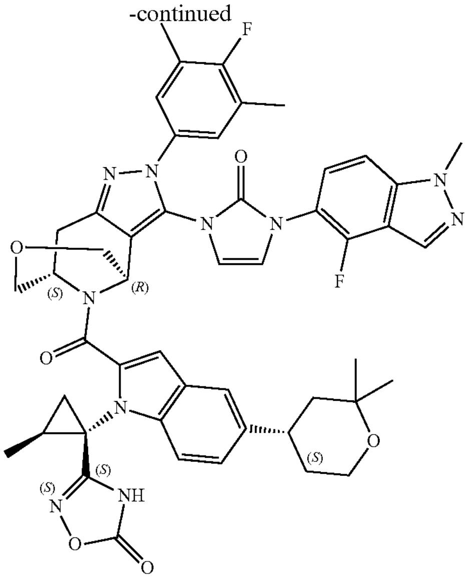

second eluent

The 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (45 mg, 49.40 µmol, 1 eq) was separated by SFC (column: REGIS (S,S) WHELK-O1 (250 mm*25 mm, 10 um); mobile phase: [$CO_2$-IPA: ACN=1:1 (0.1% $NH_3H_2O$)]; B %: 44%, isocratic elution mode) to provide 3-((1S,2S)-1-(5-((S)-2,2-dimethyltetrahydro-2H-pyran-4-yl)-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (15.38 mg, 16.74 µmol, 33.88% yield, 99.14% purity, first eluent). $^1$H NMR (400 MHz, DMSO-$d_6$) δ=12.23-11.69 (m, 1H), 8.37-8.18 (m, 1H), 7.69-7.47 (m, 2H), 7.42-7.29 (m, 2H), 7.28-7.09 (m, 4H), 7.07-6.95 (m, 1H), 6.85 (br d, J=16.6 Hz, 1H), 5.64-5.53 (m, 1H), 5.17-4.74 (m, 1H), 4.22-3.83 (m, 5H), 3.55 (br s, 4H), 3.29-2.64 (m, 3H), 2.36-2.17 (m, 6H), 1.73-1.35 (m, 6H), 1.31-0.84 (m, 10H). LC-MS (ES+, m/z): 911.4 [$(M+H)^+$]. Rt=2.911 min. HRMS (EI): m/z $[M+H]^+$ found: 911.3780; and 3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (12.33 mg, 13.48 µmol, 27.30% yield, 99.62% purity, second eluent). $^1$H NMR (400 MHz, DMSO-$d_6$) δ=12.22-11.67 (m, 1H), 8.34-8.13 (m, 1H), 7.68-7.60 (m, 1H), 7.56-7.44 (m, 1H), 7.42-7.17 (m, 4H), 7.16-6.98 (m, 2H), 6.94-6.82 (m, 1H), 6.78-6.66 (m, 1H), 5.70-5.24 (m, 1H), 5.08-4.75 (m, 1H), 4.18-4.02 (m, 4H), 4.00-3.85 (m, 1H), 3.81-3.52 (m, 4H), 3.23-2.83 (m, 3H), 2.30-2.18 (m, 6H), 1.78-1.36 (m, 6H), 1.34 (s, 8H), 1.05-0.94 (m, 2H). LC-MS (ES+, m/z): 911.3 [$(M+H)^+$]. Rt=2.906 min. HRMS (EI): m/z $[M+H]^+$ found: 911.3780.

Example 42

Compound 124

3-(1-(5-((S)-2,2-dimethyltetrahydro-2H-pyran-4-yl)-2-((4S,7R)-2-(4-fluoro-3,5-dimethylphenyl)-3-(2-oxo-3-(phthalazin-6-yl)-2,3-dihydro-1H-imidazol-1-yl)-2,4,5,6,7,8-hexahydro-4,7-epiminocyclohepta [c]pyrazole-9-carbonyl)-1H-indol-1-yl)cyclopropyl)-1,2,4-oxadiazol-5 (4H)-one Scheme 42

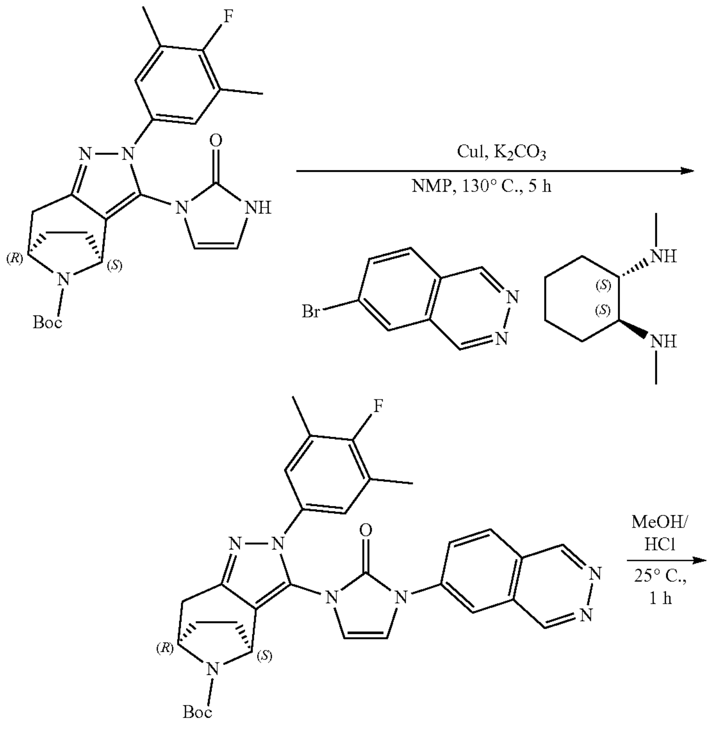

-continued

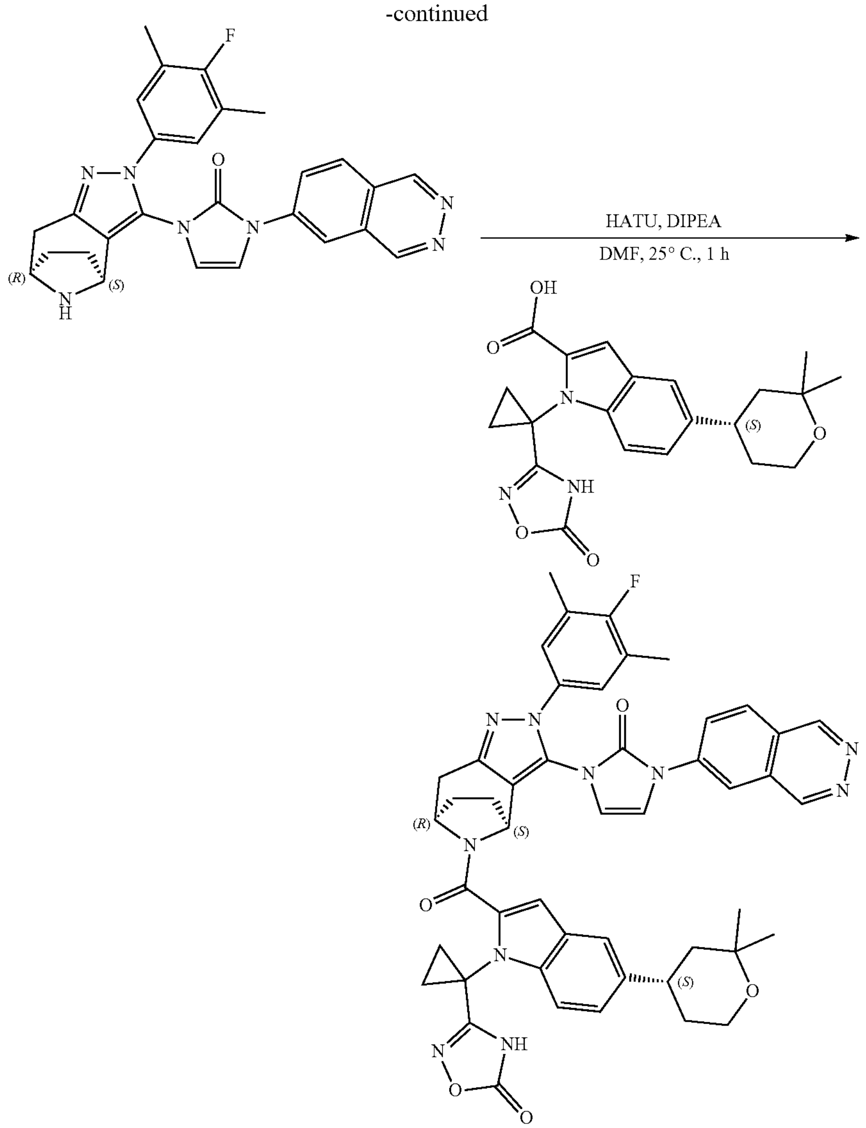

Step 1: (4S,7R)-tert-butyl 2-(4-fluoro-3,5-dimethylphenyl)-3-(2-oxo-3-(phthalazin-6-yl)-2,3-dihydro-1H-imidazol-1-yl)-2,4,5,6,7,8-hexahydro-4,7-epiminocyclohepta [c]pyrazole-9-carboxylate

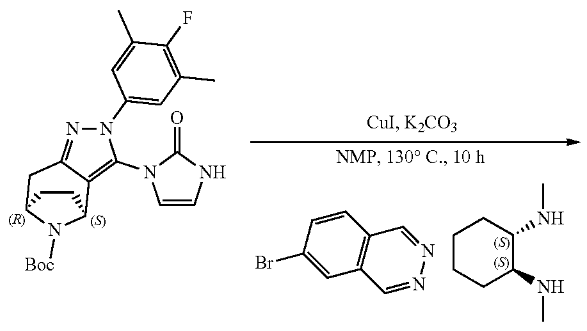

-continued

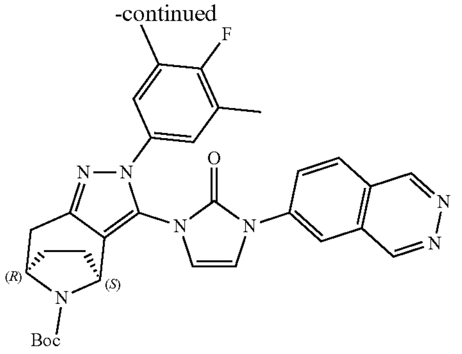

To a solution of (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (100 mg, 220.50 μmol, 1 eq), 6-bromophthalazine (138.28 mg, 661.51 μmol, 3 eq), $K_2CO_3$ (152.37 mg, 1.10 mmol, 5 eq) in NMP (2.5 mL) was added CuI (83.99 mg, 441.01 μmol, 2 eq) and (1S,2S)—

N1,N2-dimethylcyclohexane-1,2-diamine (62.73 mg, 441.01 μmol, 2 eq). The mixture was stirred at 130° C. for 10 hours under $N_2$. The residue was poured into saturated EDTA solution (50 mL) and ethyl acetate (50 mL) stirred for 0.5 hour, and then extracted with ethyl acetate (30 mL*2). The organic layers were combined and washed with water (40 mL*2), saturated brine (40 mL*2), dried over $Na_2SO_4$, filtered, concentrated under reduced pressure. The crude product was purified by chromatography on silica gel (Petroleum ether: ethyl acetate=1:1) to give (4S,7R)-tert-butyl 2-(4-fluoro-3,5-dimethylphenyl)-3-(2-oxo-3-(phthalazin-6-yl)-2,3-dihydro-1H-imidazol-1-yl)-2,4,5,6,7,8-hexahydro-4,7-epiminocyclohepta [c]pyrazole-9-carboxylate (100 mg, 166.43 μmol, 75.48% yield). LC-MS (ES+, m/z): 582.2 $[(M+H)^+]$; Rt=0.497 min.

Step 2: 1-((4S,7R)-2-(4-fluoro-3,5-dimethylphenyl)-2,4,5,6,7,8-hexahydro-4,7-epiminocyclohepta [c]pyrazol-3-yl)-3-(phthalazin-6-yl)-1H-imidazol-2 (3H)-one

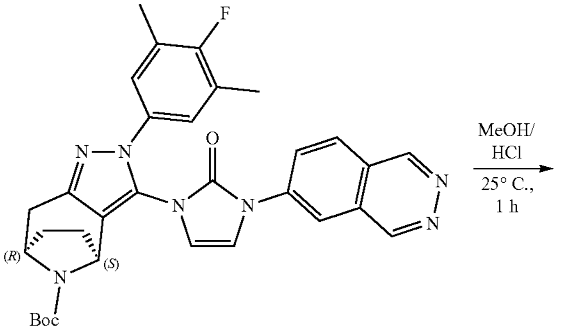

-continued

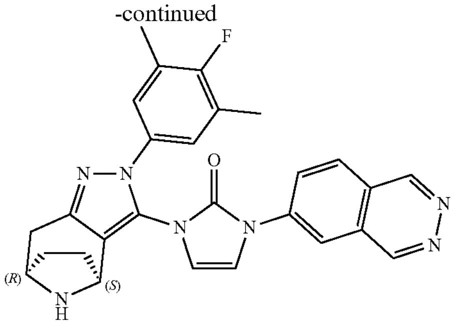

A mixture of (4S,7R)-tert-butyl 2-(4-fluoro-3,5-dimethylphenyl)-3-(2-oxo-3-(phthalazin-6-yl)-2,3-dihydro-1H-imidazol-1-yl)-2,4,5,6,7,8-hexahydro-4,7-epiminocyclohepta [c]pyrazole-9-carboxylate (100 mg, 171.93 μmol, 1 eq), HCl/MeOH (4 M, 20 mL) was stirred at 25° C. for 1 hour. LCMS indicated the reaction was completed. The mixture was concentrated to give 1-((4S,7R)-2-(4-fluoro-3,5-dimethylphenyl)-2,4,5,6,7,8-hexahydro-4,7-epiminocyclohepta [c]pyrazol-3-yl)-3-(phthalazin-6-yl)-1H-imidazol-2 (3H)-one (80 mg, crude, HCl). LC-MS (ES+, m/z): 482.3 $[(M+H)^+]$; Rt=0.348 min.

Step 3: 3-(1-(5-((S)-2,2-dimethyltetrahydro-2H-pyran-4-yl)-2-((4S,7R)-2-(4-fluoro-3,5-dimethylphenyl)-3-(2-oxo-3-(phthalazin-6-yl)-2,3-dihydro-1H-imidazol-1-yl)-2,4,5,6,7,8-hexahydro-4,7-epiminocyclohepta [c]pyrazole-9-carbonyl)-1H-indol-1-yl)cyclopropyl)-1,2,4-oxadiazol-5 (4H)-one

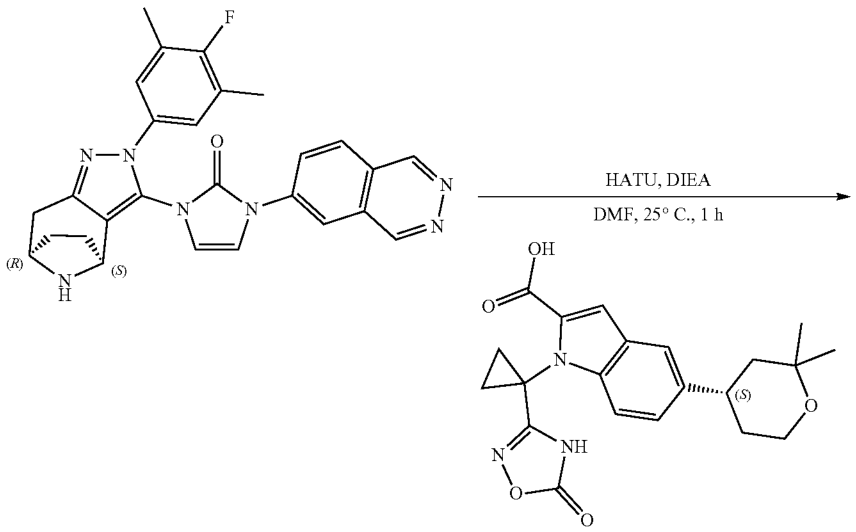

-continued

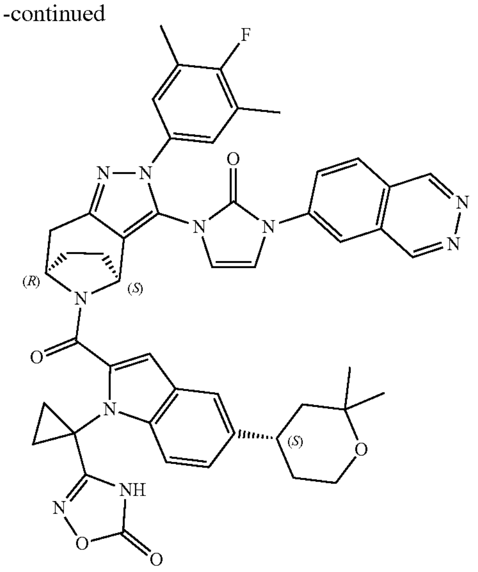

To a solution of 1-((4S,7R)-2-(4-fluoro-3,5-dimethylphenyl)-2,4,5,6,7,8-hexahydro-4,7-epiminocyclohepta [c]pyrazol-3-yl)-3-(phthalazin-6-yl)-1H-imidazol-2 (3H)-one (40 mg, 77.22 μmol, 1 eq, HCl), (S)-5-(2,2-dimethyltetrahydro-2H-pyran-4-yl)-1-(1-(5-oxo-4,5-dihydro-1,2,4-oxadiazol-3-yl) cyclopropyl)-1H-indole-2-carboxylic acid (36.83 mg, 92.67 μmol, 1.2 eq), DIPEA (49.90 mg, 386.11 μmol, 67.25 μL, 5 eq) in DMF (1 mL) was added HATU (44.04 mg, 115.83 μmol, 1.5 eq). The mixture was stirred at 25° C. for 1 hour. LCMS indicated the reaction was completed. The mixture was filtered. The filtrate was purified by prep-HPLC (column: Phenomenex Luna C18 75*30 mm*3 um; mobile phase: [$H_2O$ (0.1% TFA)-ACN]; gradient: 35%-65% B over 8.0 min) to give 3-(1-(5-((S)-2,2-dimethyltetrahydro-2H-pyran-4-yl)-2-((4S,7R)-2-(4-fluoro-3,5-dimethylphenyl)-3-(2-oxo-3-(phthalazin-6-yl)-2,3-dihydro-1H-imidazol-1-yl)-2,4,5,6,7,8-hexahydro-4,7-epiminocyclohepta [c]pyrazole-9-carbonyl)-1H-indol-1-yl) cyclopropyl)-1,2,4-oxadiazol-5 (4H)-one (8.85 mg, 10.03 μmol, 12.99% yield). $^1H$ NMR (400 MHz, DMSO-$d_6$) δ=12.04-11.57 (m, 1H), 9.64 (s, 2H), 8.59-8.08 (m, 3H), 7.54-7.33 (m, 3H), 7.25-7.14 (m, 3H), 7.10-6.98 (m, 1H), 6.82 (s, 1H), 5.48-4.92 (m, 2H), 3.71-3.54 (m, 2H), 3.07-2.73 (m, 3H), 2.39-2.33 (m, 1H), 2.25-2.13 (m, 8H), 1.85-1.37 (m, 9H), 1.23-1.12 (m, 6H). $^1H$ NMR (400 MHz, MeOD-$d_4$) δ=9.96-9.43 (m, 2H), 8.92-7.85 (m, 3H), 7.72-6.85 (m, 8H), 5.54-5.36 (m, 1H), 5.17-4.99 (m, 1H), 3.86-3.61 (m, 2H), 3.01-2.81 (m, 2H), 2.61-2.47 (m, 1H), 2.24 (br d, J=18.5 Hz, 6H), 2.03-1.05 (m, 18H). LC-MS (ES+, m/z): 861.3 [$(M+H)^+$]; Rt=2.589 min. HRMS (EI): m/z $[M+H]^+$ found: 861.3618.

Example 43

Compound 127

3-((1S,2S)-1-(5-((S)-2, 2-dimethyltetrahydro-2H-pyran-4-yl)-2-((4S,7R)-2-(4-fluoro-3, 5-dimethylphenyl)-3-(2-oxo-3-(phthalazin-6-yl)-2,3-dihydro-1H-imidazol-1-yl)-2, 4, 5, 6, 7, 8-hexahydro-4, 7-epiminocyclohepta [c]pyrazole-9-carbonyl)-1H-indol-1-yl)-2-methylcyclopropyl)-1, 2, 4-oxadiazol-5 (4H)-one

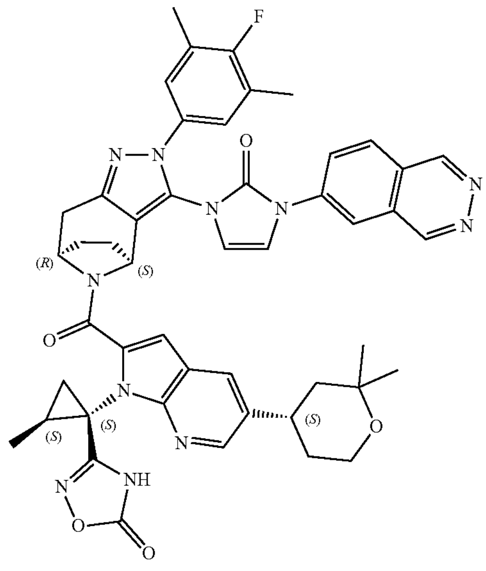

Step 1: 3-((1S,2S)-1-(5-((S)-2, 2-dimethyltetrahydro-2H-pyran-4-yl)-2-((4S,7R)-2-(4-fluoro-3, 5-dimethylphenyl)-3-(2-oxo-3-(phthalazin-6-yl)-2,3-dihydro-1H-imidazol-1-yl)-2, 4, 5, 6, 7, 8-hexahydro-4, 7-epiminocyclohepta [c]pyrazole-9-carbonyl)-1H-indol-1-yl)-2-methylcyclopropyl)-1, 2, 4-oxadiazol-5 (4H)-one

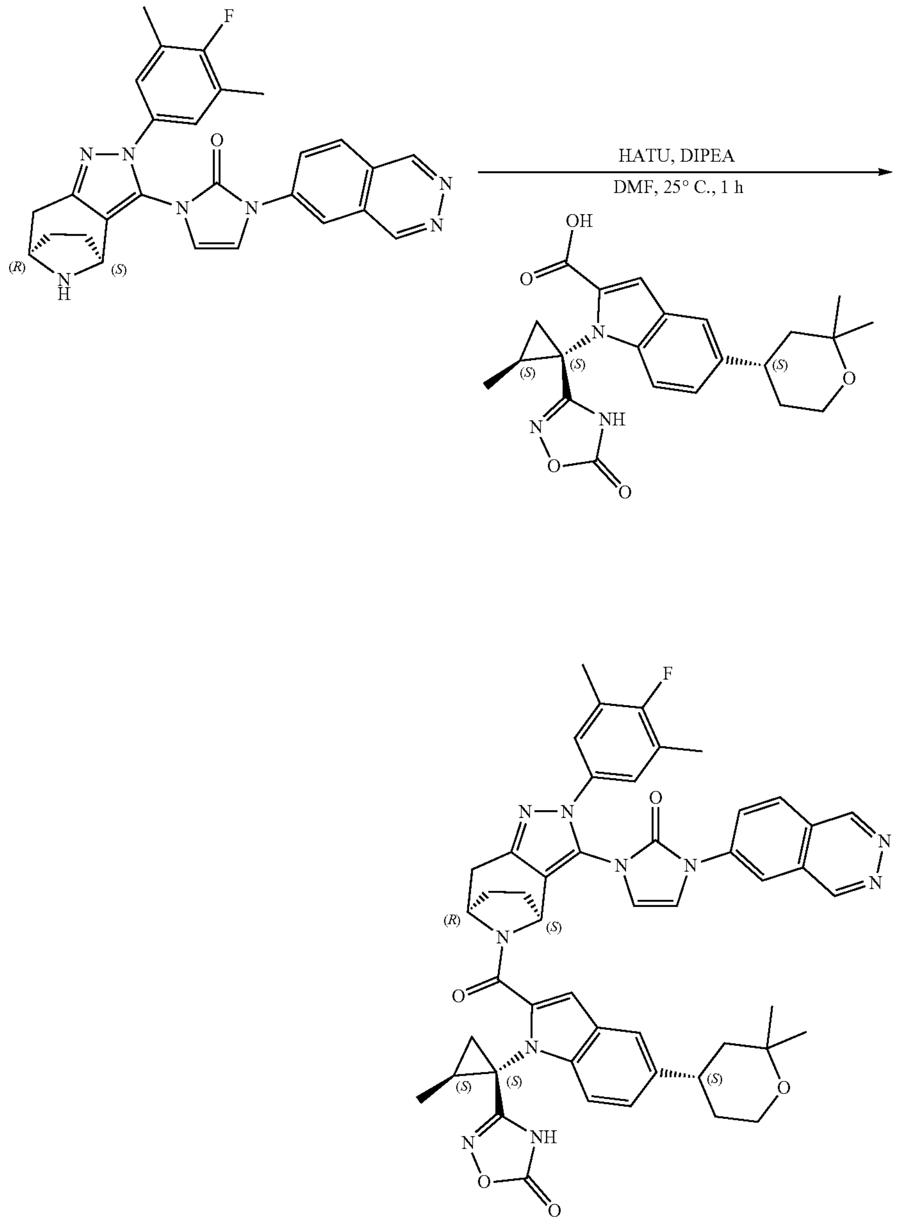

To a solution of 1-((4S,7R)-2-(4-fluoro-3, 5-dimethylphenyl)-2, 4, 5, 6, 7, 8-hexahydro-4, 7-epiminocyclohepta [c]pyrazol-3-yl)-3-(phthalazin-6-yl)-1, 3-dihydro-2H-imidazol-2-one (40 mg, 77.22 μmol, 1 eq, HCl), 5-((S)-2, 2-dimethyltetrahydro-2H-pyran-4-yl)-1-((1S,2S)-2-methyl-1-(5-oxo-4, 5-dihydro-1, 2, 4-oxadiazol-3-yl)cyclopropyl)-1H-indole-2-carboxylic acid (38.13 mg, 92.67 μmol, 1.2 eq) and DIPEA (49.90 mg, 386.11 μmol, 67.25 μL, 5 eq) in DMF (0.8 mL) was added HATU (44.04 mg, 115.83 μmol, 1.5 eq). The mixture was stirred at 25° C. for 1 hour. LCMS showed the reaction was completed. The mixture was filtered. The filtrate was purified by prep-HPLC column: Waters Xbridge BEH C18 100*30 mm*10 um; mobile phase: [$H_2O$ (10 mM $NH_4HCO_3$)-ACN]; gradient: 30%-60% B over 8.0 min) to give 3-((1S,2S)-1-(5-((S)-2, 2-dimethyltetrahydro-2H-pyran-4-yl)-2-((4S,7R)-2-(4-fluoro-3, 5-dimethylphenyl)-3-(2-oxo-3-(phthalazin-6-yl)-2,3-dihydro-1H-imidazol-1-yl)-2, 4, 5, 6, 7, 8-hexahydro-4, 7-epiminocyclohepta [c]pyrazole-9-carbonyl)-1H-indol-1-yl)-2-methylcyclopropyl)-1, 2, 4-oxadiazol-5 (4H)-one (8.96 mg, 9.56 μmol, 12.38% yield). $^1H$ NMR (400 MHz, DMSO-$d_6$) δ=12.36-11.62 (m, 1H), 9.82-9.32 (m, 2H), 8.68-8.18 (m, 2H), 8.13-6.61 (m, 9H), 5.41-5.12 (m, 1H), 5.06-4.61 (m, 1H), 3.76-3.50 (m, 2H), 3.09-2.77 (m, 3H), 2.26-2.04 (m, 8H), 1.87-0.91 (m, 18H); LC-MS (ES+, m/z): 875.3 [$(M+H)^+$]; Rt=2.702 min. HRMS (EI): m/z $[M+H]^+$ found: 875.3793.

Example 44
Compound 128
1-((4S,7R)-9-(5-((S)-2,2-dimethyltetrahydro-2H-pyran-4-yl)-1-((1S,2S)-2-methyl-1-(1H-tetrazol-5-yl) cyclopropyl)-1H-indole-2-carbonyl)-2-(4-fluoro-3,5-dimethylphenyl)-2,4,5,6,7,8-hexahydro-4,7-epiminocyclohepta [c]pyrazol-3-yl)-3-(4-fluoro-1-methyl-1H-indazol-5-yl)-1H-imidazol-2 (3H)-one
Scheme 44
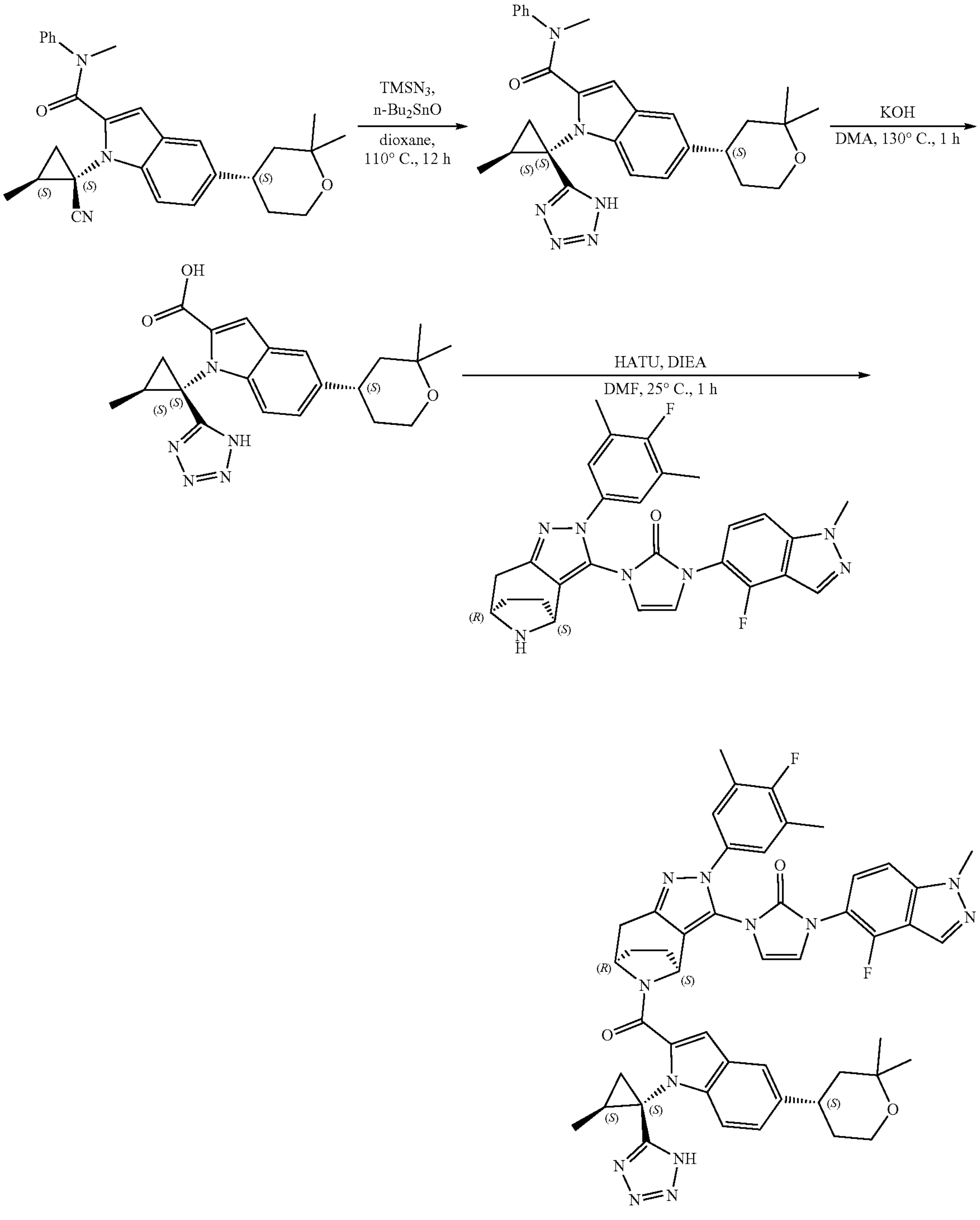

Step 1: 5-((S)-2,2-dimethyltetrahydro-2H-pyran-4-yl)-N-methyl-1-((1S,2S)-2-methyl-1-(1H-tetrazol-5-yl) cyclopropyl)-N-phenyl-1H-indole-2-carboxamide

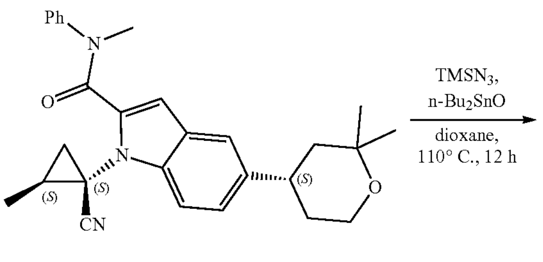

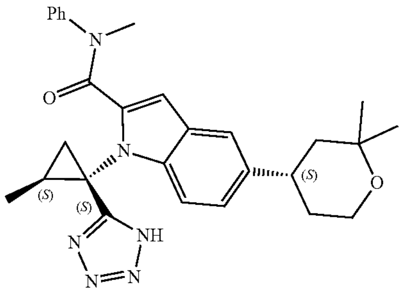

To a solution of 1-((1S,2S)-1-cyano-2-methylcyclopropyl)-5-((S)-2,2-dimethyltetrahydro-2H-pyran-4-yl)-N-methyl-N-phenyl-1H-indole-2-carboxamide (300 mg, 679.40 μmol, 1 eq) in dioxane (6 mL) was added azido (trimethyl) silane (626.19 mg, 5.44 mmol, 714.83 μL, 8 eq) and dibutyl(oxo) tin (180 mg, 723.07 μmol, 1.06 eq). The mixture was stirred at 110° C. for 12 hours. LCMS indicated the reaction was completed. The mixture was concentrated in vacuum. The crude product was purified by chromatography on silica gel (Petroleum ether:ethyl acetate-4:1) to give 5-((S)-2,2-dimethyltetrahydro-2H-pyran-4-yl)-N-methyl-1-((1S,2S)-2-methyl-1-(1H-tetrazol-5-yl)cyclopropyl)-N-phenyl-1H-indole-2-carboxamide (240 mg, 495.26 μmol, 72.90% yield). LC-MS (ES+, m/z): 485.3 [(M+H)$^+$]; Rt=0.556 min.

Step 2: 5-((S)-2,2-dimethyltetrahydro-2H-pyran-4-yl)-1-((1S,2S)-2-methyl-1-(1H-tetrazol-5-yl) cyclopropyl)-1H-indole-2-carboxylic acid

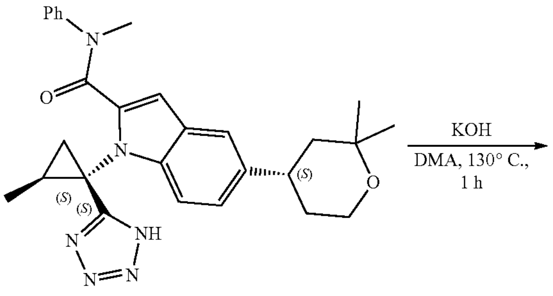

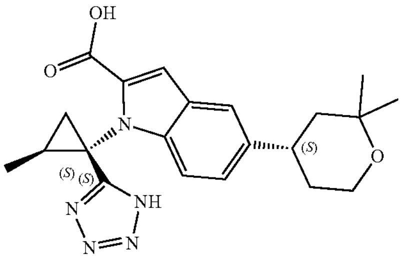

A solution of 5-((S)-2,2-dimethyltetrahydro-2H-pyran-4-yl)-N-methyl-1-((1S,2S)-2-methyl-1-(1H-tetrazol-5-yl)cyclopropyl)-N-phenyl-1H-indole-2-carboxamide (190 mg, 392.08 μmol, 1 eq) and KOH (219.98 mg, 3.92 mmol, 10 eq) in DMA (3 mL) was stirred at 130° C. for 1 hour. LCMS indicated the reaction was completed. The mixture was poured into $H_2O$ (50 mL). The aqueous layer was extracted with ethyl acetate (20 mL). The aqueous layer was adjusted pH to 1 with 1M HCl (15 mL). The aqueous was extracted with ethyl acetate (30 mL*3). The combined organic phase was washed with brine (50 mL*2), dried with anhydrous $Na_2SO_4$, filtered and concentrated in vacuum to give 5-((S)-2,2-dimethyltetrahydro-2H-pyran-4-yl)-1-((1S,2S)-2-methyl-1-(1H-tetrazol-5-yl)cyclopropyl)-1H-indole-2-carboxylic acid (130 mg, 328.74 μmol, 83.84% yield). $^1$H NMR (400 MHz, $CDCl_3$) δ=7.80 (d, J=8.46 Hz, 1H), 7.47 (s, 1H), 7.30-7.37 (m, 2H), 3.78-3.92 (m, 2H), 2.06 (br t, J=6.85 Hz, 1H), 1.84-1.93 (m, 1H), 1.69-1.79 (m, 4H), 1.58-1.67 (m, 1H), 1.41-1.51 (m, 1H), 1.34 (s, 3H), 1.29 (s, 3H), 1.06 (d, J-6.08 Hz, 3H) (The active N—H and O—H was not detected). LC-MS (ES+, m/z): 396.2 [(M+H)$^+$]; Rt=0.445 min.

Step 3: 1-((4S,7R)-9-(5-((S)-2,2-dimethyltetrahydro-2H-pyran-4-yl)-1-((1S,2S)-2-methyl-1-(1H-tetrazol-5-yl)cyclopropyl)-1H-indole-2-carbonyl)-2-(4-fluoro-3,5-dimethylphenyl)-2,4,5,6,7,8-hexahydro-4,7-epiminocyclohepta [c]pyrazol-3-yl)-3-(4-fluoro-1-methyl-1H-indazol-5-yl)-1H-imidazol-2 (3H)-one

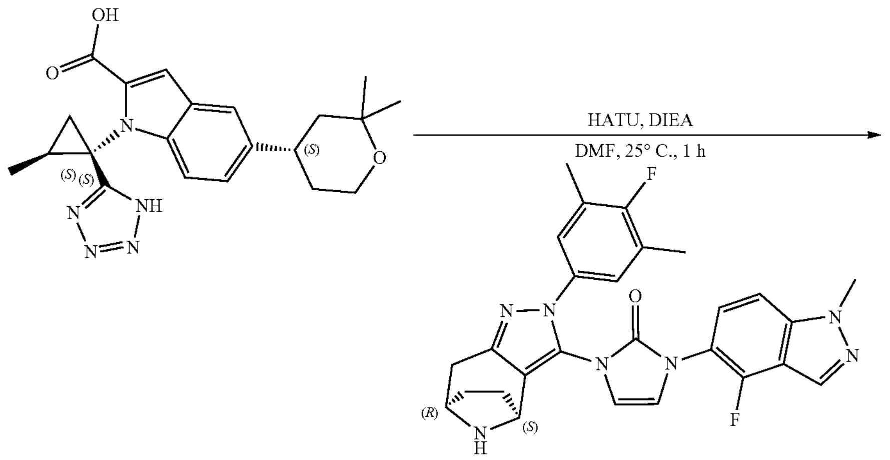

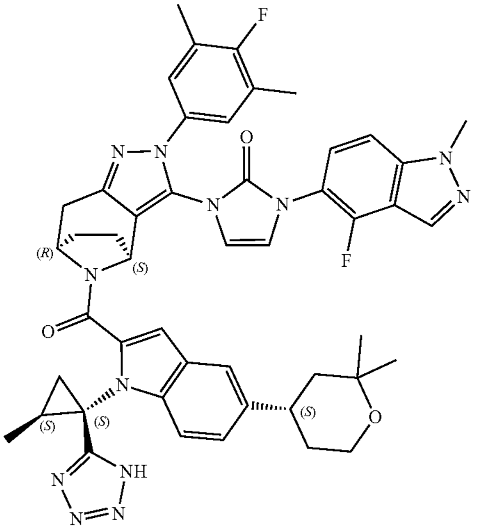

To a solution of 5-((S)-2,2-dimethyltetrahydro-2H-pyran-4-yl)-1-((1S,2S)-2-methyl-1-(1H-tetrazol-5-yl)cyclopropyl)-1H-indole-2-carboxylic acid (70 mg, 177.01 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (104.75 mg, 194.71 μmol, 1.1 eq, HCl) in DMF (5 mL) was added HATU (100.96 mg, 265.52 μmol, 1.5 eq) and DIEA (91.51 mg, 708.05 μmol, 123.33 μL, 4 eq). The mixture was stirred at 25° C. for 1 hour. LCMS indicated the reaction was completed. The mixture was filtered. The filtrate was purified by prep-HPLC (column: Phenomenex luna C18 100*40 mm*5 um; mobile phase: [$H_2O$ (0.2% FA)-ACN]; gradient: 35%-65% B over 8.0 min) to give 1-((4S,7R)-9-(5-((S)-2,2-dimethyltetrahydro-2H-pyran-4-yl)-1-((1S,2S)-2-methyl-1-(1H-tetrazol-5-yl) cyclopropyl)-1H-indole-2-carbonyl)-2-(4-fluoro-3,5-dimethylphenyl)-2,4,5,6,7,8-hexahydro-4,7-epiminocyclohepta [c]pyrazol-3-yl)-3-(4-fluoro-1-methyl-1H-indazol-5-yl)-1H-imidazol-2 (3H)-one (11.71 mg, 22.72 μmol, 12.84% yield). $^1$H NMR (400 MHz, MeOD-$d_4$) δ=7.98-8.26 (m, 1H), 7.38-7.61 (m, 2H), 6.97-7.38 (m, 5H), 6.80-6.97 (m, 2H), 6.33-6.77 (m, 1H), 5.46-5.76 (m, 1H), 4.97-5.20 (m, 1H), 4.00-4.20 (m, 3H), 3.69-3.92 (m, 2H), 3.52-3.67 (m, 1H), 3.15-3.28 (m, 1H), 2.98-3.27 (m, 1H), 2.77-2.97 (m, 1H), 2.49-2.68 (m, 1H), 2.17-2.47 (m, 7H), 1.82-2.13 (m, 3H), 1.46-1.82 (m, 5H), 1.43 (br d, J=4.75 Hz, 1H), 1.14-1.37 (m, 6H), 1.08 (br s, 1H), 0.97 (br d, J=5.13 Hz, 1H). $^1$H NMR (400 MHz, DMSO-$d_6$) δ=8.20 (s, 1H), 7.37-7.58 (m, 2H), 7.21-7.34 (m, 2H), 7.12-7.20 (m, 3H), 6.72-6.97 (m, 3H), 5.27-5.49 (m, 1H), 4.80-5.09 (m, 1H), 4.09 (s, 3H), 3.58-3.74 (m, 2H), 2.96 (br s, 2H), 2.80 (br d, J=15.85 Hz, 1H), 2.25 (d, J=1.07 Hz, 7H), 2.07-2.18 (m, 2H), 1.81 (br s, 2H), 1.68-1.76 (m, 2H), 1.58-1.67 (m, 2H), 1.37-1.53 (m, 2H), 1.24 (s, 3H), 1.13 (br s, 6H) (The active N—H was not detected). LC-MS (ES+, m/z): 879.3 [(M+H)$^+$]; Rt=2.906 min; HRMS (EI): m/z [M+H]$^+$ found: 879.4055.

Example 45

Compound 208

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(tetrahydro-2H-pyran-4-yl)-1H-indol-1-yl)-2-methylcyclopropyl)-1,2,4-oxadiazol-5 (4H)-one

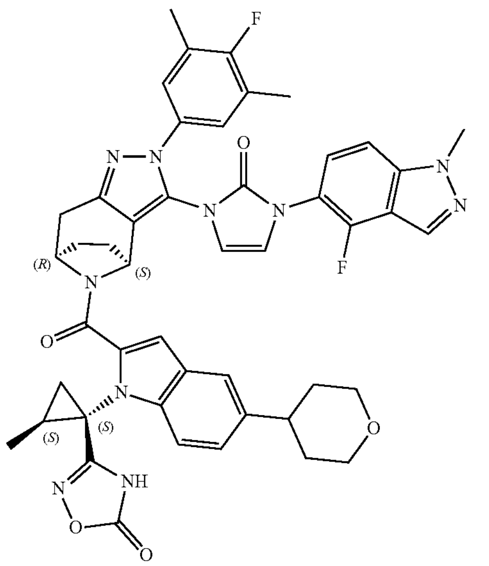

Step 1: 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(tetrahydro-2H-pyran-4-yl)-1H-indol-1-yl)-2-methylcyclopropyl)-1,2,4-oxadiazol-5 (4H)-one

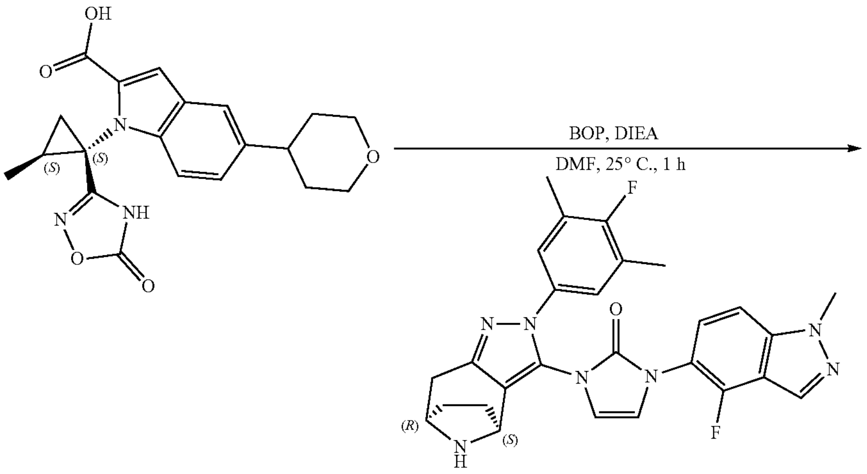

-continued

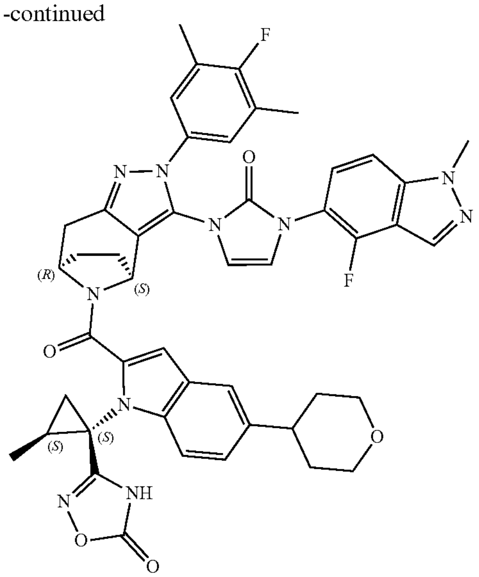

To a solution of 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (25 mg, 63.64 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (32.54 mg, 63.64 μmol, 1 eq) in DMF (0.5 mL) was added DIEA (82.25 mg, 636.42 μmol, 110.85 μL, 10 eq), BOP (28.15 mg, 63.64 μmol, 1 eq). The mixture was stirred at 25° C. for 1 hour. LCMS showed the reaction was completed. The reaction mixture was diluted with water (100 mL), extracted with Ethyl acetate (50 mL*3). The combined organic layers were washed with saturated NaCl (50 mL*2), dried over $Na_2SO_4$, filtered and concentrated in vacuum. The filtrate was purified by prep-HPLC (column: Phenomenex Luna C18 75*30 mm*3 um; mobile phase: [$H_2O$ (0.1% TFA)-ACN]; gradient: 50%-80% B over 8.0 min) to give 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(tetrahydro-2H-pyran-4-yl)-1H-indol-1-yl)-2-methylcyclopropyl)-1,2,4-oxadiazol-5 (4H)-one (8.41 mg, 9.70 μmol, 15.24% yield, 100% purity). $^1$H NMR (DMSO) (400 MHz, DMSO-$d_6$) δ=12.27-11.69 (m, 1H), 8.34-8.12 (m, 1H), 7.67-6.65 (m, 10H), 5.69-4.77 (m, 2H), 4.11 (s, 3H), 3.99-3.67 (m, 2H), 3.33-3.12 (m, 3H), 3.05-2.69 (m, 2H), 2.28-2.19 (m, 6H), 2.14-2.08 (m, 1H), 1.99-1.76 (m, 2H), 1.76-1.41 (m, 6H), 1.41-0.75 (m, 5H); $^1$H NMR (DMSO, T=273+80K) (400 MHz, DMSO-$d_6$) δ=12.34-10.98 (m, 1H), 8.19 (br s, 1H), 7.60-6.69 (m, 10H), 5.64-4.83 (m, 2H), 4.09 (s, 3H), 4.04-3.73 (m, 2H), 3.62-3.26 (m, 3H), 2.91-2.73 (m, 2H), 2.25 (s, 6H), 2.17-2.12 (m, 1H), 1.93-1.74 (m, 2H), 1.72-1.54 (m, 6H), 1.52-0.90 (m, 5H). LC-MS (ES+, m/z): 867.2 [(M+H)$^+$]; Rt=2.925 min. HRMS (EI): m/z [M+H]$^+$ found: 867.3557.

Example 46

Compound 209

3-((1S,2S)-1-(5-(2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one

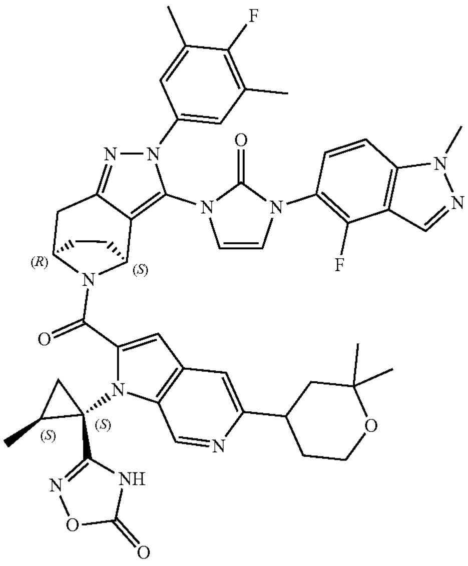

Step 1: 3-((1S,2S)-1-(5-(2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one

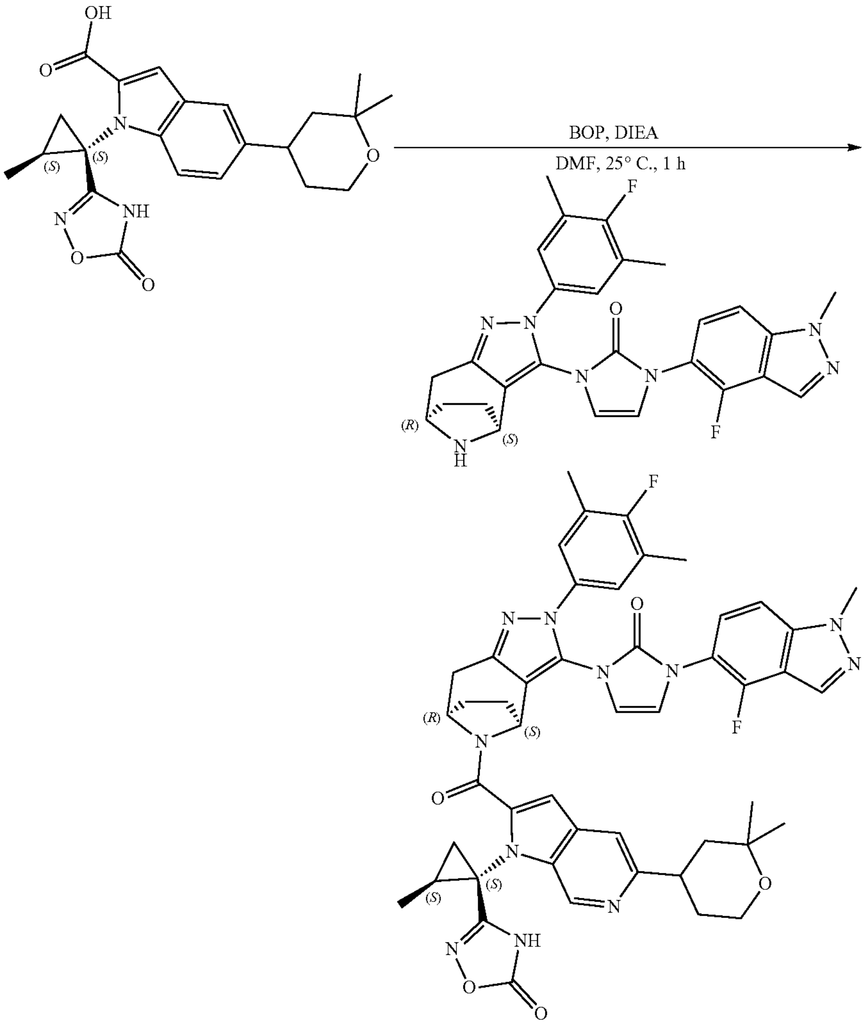

A mixture of 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid (90 mg, 218.21 μmol, 1 eq), 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (109.44 mg, 218.21 μmol, 1 eq), DIEA (141.01 mg, 1.09 mmol, 190.04 μL, 5 eq), BOP (106.16 mg, 240.04 μmol, 1.1 eq) in DMF (1.8 mL) was stirred at 25° C. for 1 hour under $N_2$ atmosphere. LC-MS showed the desired was detected. The reaction mixture was quenched by addition $H_2O$ 20 mL, and then extracted with DCM (10 mL*3). The combined organic layers were washed with saturated brine (20 mL*2), dried over anhydrous $Na_2SO_4$, filtered and concentrated under reduced pressure to give a residue. The residue was purified by prep-HPLC (column: 3_Phenomenex Luna C18 75*30 mm*3 um; mobile phase: [$H_2O$ (0.1% TFA)-ACN]; gradient: 30%-60% B over 8.0 min) to give 3-((1S,2S)-1-(5-(2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one (18.2 mg, 20.23 μmol, 9.27% yield, 99.60% purity). $^1H$ NMR (400 MHz, DMSO-$d_6$) δ=12.52-11.77 (m, 1H), 9.24-8.89 (m, 1H), 8.35-7.86 (m, 1H), 7.68-7.40 (m, 2H), 7.26 (s, 2H), 7.14-6.96 (m, 3H), 6.94-6.65 (m, 1H), 5.65-4.74 (m, 2H), 4.14-4.07 (m, 3H), 3.82 (br s, 2H), 3.29-3.11 (m, 2H), 2.93-2.80 (m, 1H), 2.14 (br s, 8H), 2.10-1.42 (m, 7H), 1.39 (d, J=6.3 Hz, 11H). $^1H$ NMR (400 MHz, MeOD) δ=8.97-8.84 (m, 1H), 8.24-8.13 (m, 1H), 8.02-7.78 (m, 1H), 7.60-7.26 (m, 2H), 7.25-7.07 (m, 2H), 7.02-6.71 (m, 2H), 6.61-6.38 (m, 1H), 5.40-5.29 (m, 1H), 5.21-5.05 (m, 1H), 4.18-4.06 (m, 3H), 3.83-3.64 (m, 2H), 3.61-3.35 (m, 1H), 3.27-3.01 (m, 1H), 3.00-2.88 (m, 1H), 2.72-2.41 (m, 2H), 2.39-1.87 (m, 10H), 1.80-1.47 (m, 4H), 1.39-1.00 (m, 10H). LC-MS (ES+, m/z): 896.4 [$(M+H)^+$]; Rt=2.516 min. HRMS (EI): m/z $[M+H]^+$ found: 896.3804.

Example 47

Compound 211

3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one

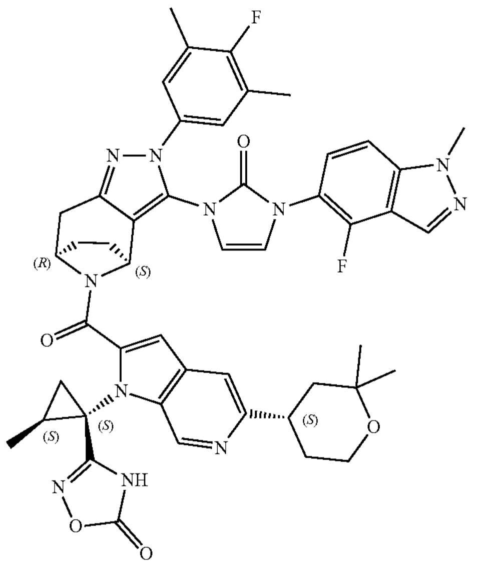

Step 1: 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one

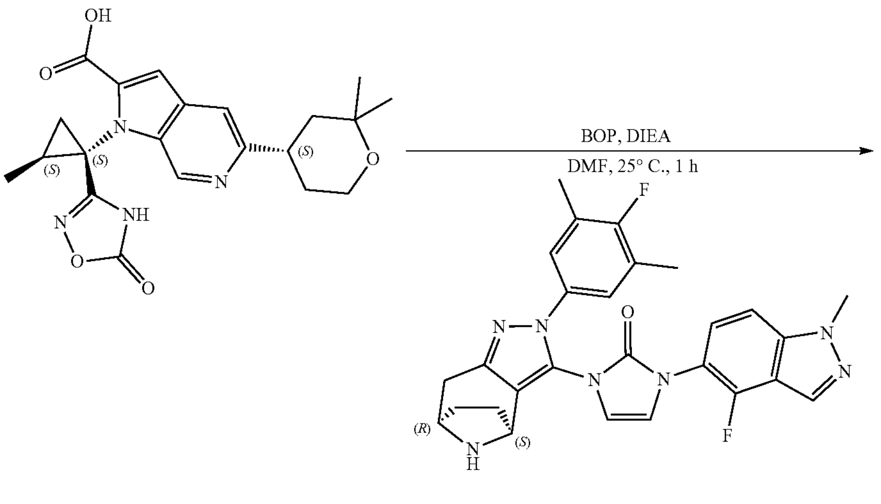

-continued

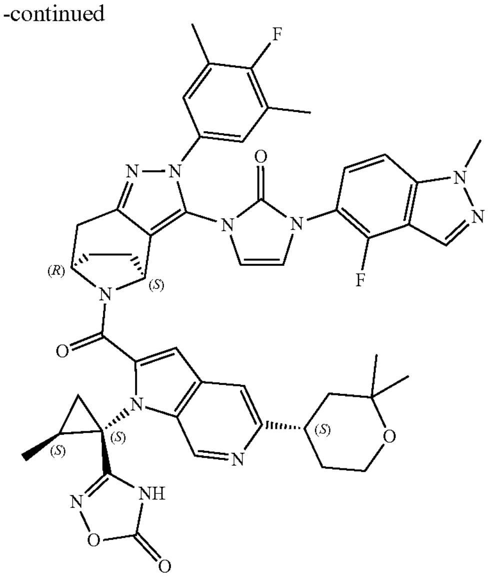

A mixture of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid (45 mg, 109.11 μmol, 1 eq), 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (54.72 mg, 109.11 μmol, 1 eq), BOP (53.08 mg, 120.02 μmol, 1.1 eq), DIEA (70.51 mg, 545.54 μmol, 95.02μ, 5 eq) in DMF (0.9 mL) was degassed and purged with $N_2$ for 3 times. The mixture was stirred at 25° C. for 1 hour under $N_2$ atmosphere. LC-MS showed the desired was detected. The reaction mixture was quenched by addition $H_2O$ 20 mL, and then extracted with DCM (10 mL*3). The combined organic layers were washed with saturated brine (10 mL*2), dried over anhydrous $Na_2SO_4$, filtered and concentrated under reduced pressure to give a residue. The residue was purified by prep-HPLC (column: 3_Phenomenex Luna C18 75*30 mm*3 um; mobile phase: [$H_2O$ (0.1% TFA)-ACN]; gradient: 30%-60% B over 8.0 min) to give 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one (12.29 mg, 13.66 μmol, 12.52% yield, 99.56% purity). $^1H$ NMR (400 MHz, DMSO-$d_6$) δ=12.38-11.83 (m, 1H), 9.21-8.92 (m, 1H), 8.33-7.90 (m, 1H), 7.69-7.57 (m, 1H), 7.54-7.38 (m, 1H), 7.35-7.18 (m, 2H), 7.17-6.99 (m, 3H), 6.97-6.69 (m, 1H), 5.64-4.76 (m, 2H), 4.15-4.04 (m, 3H), 3.80-3.57 (m, 2H), 3.25-3.12 (m, 2H), 2.92-2.82 (m, 1H), 2.28-2.12 (m, 8H), 2.03-1.37 (m, 9H), 1.32-0.95 (m, 9H). $^1H$ NMR (400 MHz, MeOD) δ=8.93-8.85 (m, 1H), 8.21-8.14 (m, 1H), 8.05-7.77 (m, 1H), 7.58-7.26 (m, 2H), 7.25-7.06 (m, 2H), 7.06-6.69 (m, 2H), 6.61-6.39 (m, 1H), 5.38-5.10 (m, 2H), 4.19-4.07 (m, 3H), 3.86-3.65 (m, 2H), 3.59-3.39 (m, 1H), 3.29-3.05 (m, 1H), 3.00-2.87 (m, 1H), 2.74-2.40 (m, 2H), 2.38-1.85 (m, 10H), 1.82-1.48 (m, 4H), 1.46-0.99 (m, 10H). LC-MS (ES+, m/z): 896.3 [$(M+H)^+$]; Rt=2.525 min. HRMS (EI): m/z $[M+H]^+$ found: 896.3818

Example 48

Compound 212

3-((1S,2S)-1-(5-((R)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one

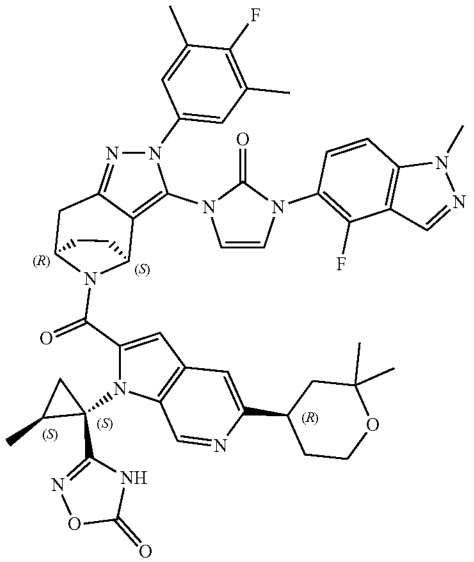

Step 1; 3-((1S,2S)-1-(5-((R)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5(4H)-one

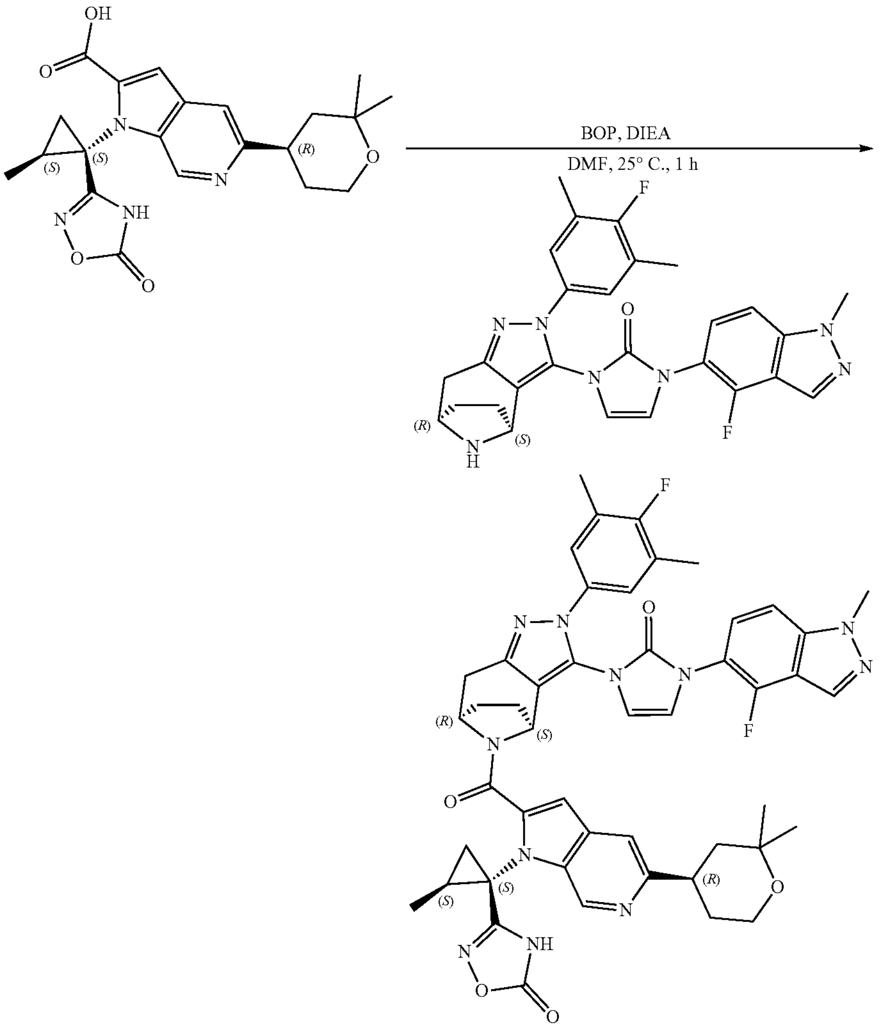

A mixture of 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid (45 mg, 109.11 μmol, 1 eq), 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (54.72 mg, 109.11 μmol, 1 eq), DIEA (70.51 mg, 545.54 μmol, 95.02 μL, 5 eq), BOP (53.08 mg, 120.02 μmol, 1.1 eq) in DMF (0.9 mL) was degassed and purged with $N_2$ for 3 times. The mixture was stirred at 25° C. for 1 hour under $N_2$ atmosphere. LC-MS showed the desired was detected. The reaction mixture was quenched by addition $H_2O$ 20 mL, and then extracted with DCM (10 mL*3). The combined organic layers were washed with saturated brine (10 mL*2), dried over anhydrous $Na_2SO_4$, filtered and concentrated under reduced pressure to give a residue. The residue was purified by prep-HPLC (column: 3_Phenomenex Luna C18 75*30 mm*3 um; mobile phase: [$H_2O$ (0.1% TFA)-ACN]; gradient: 30%-60% B over 8.0 min) to give 3-((1S,2S)-1-(5-((R)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-c]pyridin-1-yl)-2-methylcyclopropyl)-1,2,4-oxadiazol-5 (4H)-one (12.16 mg, 13.52 μmol, 12.39% yield, 99.63% purity). $^1H$ NMR (400 MHz, DMSO-$d_6$) δ=12.38-11.77 (m, 1H), 9.11-8.88 (m, 1H), 8.36-7.81 (m, 1H), 7.71-7.38 (m, 2H), 7.37-7.17 (m, 2H), 7.16-6.97 (m, 3H), 6.96-6.64 (m, 1H), 5.64-4.68 (m, 2H), 4.14-4.08 (m, 3H), 3.81-3.58 (m, 2H), 3.26-3.19 (m, 2H), 2.91-2.82 (m, 1H), 2.28-2.13 (m, 8H), 2.03-1.42 (m, 7H), 1.40-1.04 (m, 11H). $^1H$ NMR (400 MHz, MeOD) δ=8.95-8.84 (m, 1H), 8.23-8.13 (m, 1H), 7.95-7.80 (m, 1H), 7.67-7.24 (m, 2H), 7.23-7.04 (m, 2H), 7.04-6.66 (m, 2H), 6.61-6.37 (m, 1H), 5.40-5.06 (m, 2H), 4.17-4.10 (m, 3H), 3.79-3.66 (m, 2H), 3.62-3.38 (m, 1H), 3.20-3.03 (m, 1H), 3.00-2.86 (m, 1H), 2.73-2.41 (m, 2H), 2.34-1.85 (m, 10H), 1.40 (s, 4H), 1.36-1.01 (m, 10H). LC-MS (ES+, m/z): 896.3 [$(M+H)^+$]; Rt=2.526 min. HRMS (EI): m/z $[M+H]^+$ found: 896.3818.

Example 49

Compound 213

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(4-oxaspiro[2.5]octan-7-yl)-1H-indol-1-yl)-2-methylcyclopropyl)-1,2,4-oxadiazol-5 (4H)-one

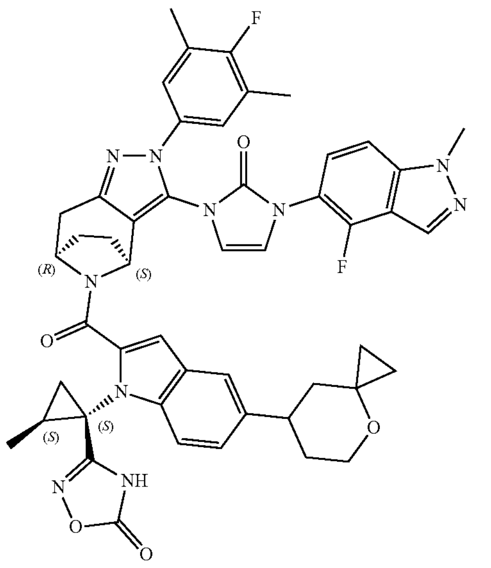

Step 1: 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(4-oxaspiro[2.5]octan-7-yl)-1H-indol-1-yl)-2-methylcyclopropyl)-1,2,4-oxadiazol-5 (4H)-one

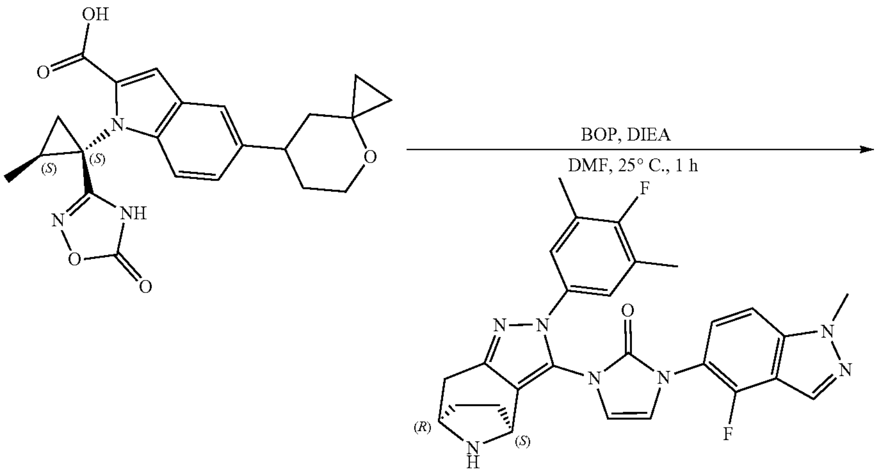

-continued

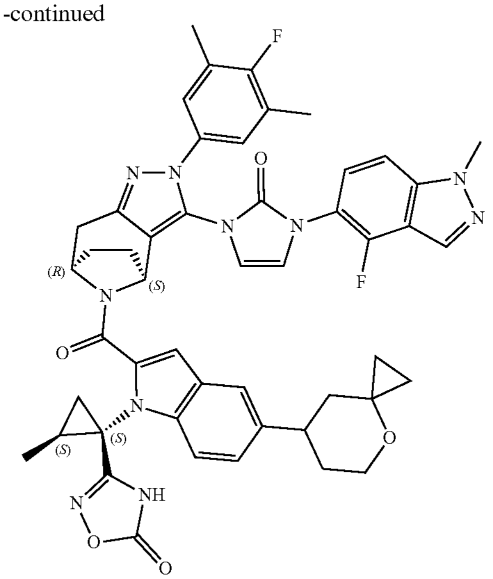

To a solution of 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (70 mg, 131.20 μmol, 1 eq) and 1-((1S,2S)-2-methyl-1-(5-oxo-4,5-dihydro-1,2,4-oxadiazol-3-yl) cyclopropyl)-5-(4-oxaspiro[2.5]octan-7-yl)-1H-indole-2-carboxylic acid (71.62 mg, 157.44 μmol, 1.2 eq) in DMF (2 mL) was added DIEA (84.78 mg, 655.99 μmol, 114.26 μL, 5 eq) and BOP (87.04 mg, 196.80 μmol, 1.5 eq). The mixture was stirred at 25° C. for 1 hour. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (column: Phenomenex luna C18 100*40 mm*3 um; mobile phase: [$H_2O$ (0.1% TFA)-ACN]; gradient: 55%-85% B over 18.0 min). Compound 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(4-oxaspiro[2.5]octan-7-yl)-1H-indol-1-yl)-2-methylcyclopropyl)-1,2,4-oxadiazol-5 (4H)-one (35 mg, 39.12 μmol, 29.82% yield). $^1H$ NMR (400 MHz, DMSO-$d_6$, T=273+80K) δ=12.36-11.56 (m, 1H), 8.41-8.10 (m, 1H), 7.76-6.62 (m, 10H), 5.68-4.84 (m, 2H), 4.14-4.05 (m, 3H), 3.65-3.37 (m, 3H), 3.23-2.66 (m, 2H), 2.40-2.02 (m, 9H), 2.00-0.93 (m, 11H), 0.86-0.25 (m, 4H), $^1H$ NMR (400 MHz, DMSO-$d_6$) δ=12.06-11.16 (m, 1H), 8.20 (br s, 1H), 7.70-6.52 (m, 10H), 5.58-5.22 (m, 1H), 5.15-4.82 (m, 1H), 4.10 (d, J=1.2 Hz, 3H), 3.91-3.52 (m, 3H), 3.07-2.78 (m, 2H), 2.31-2.09 (m, 9H), 1.93-0.94 (m, 11H), 0.81-0.38 (m, 4H), LC-MS (ES+, m/z): 893.3 [$(M+H)^+$]; Rt=3.054 min. HRMS (EI): m/z $[M+H]^+$ found: 893.3736.

Example 50

Compound 214

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

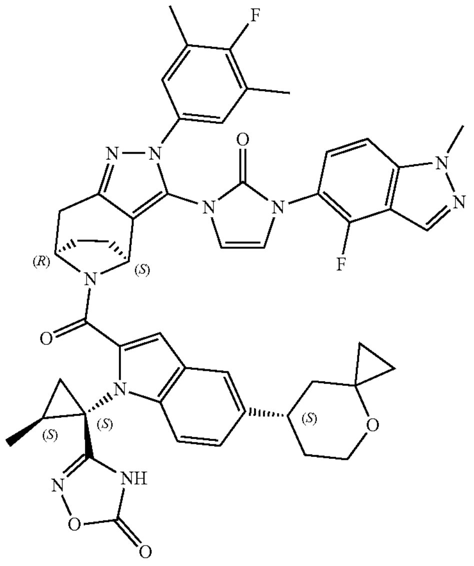

and

Compound 215

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

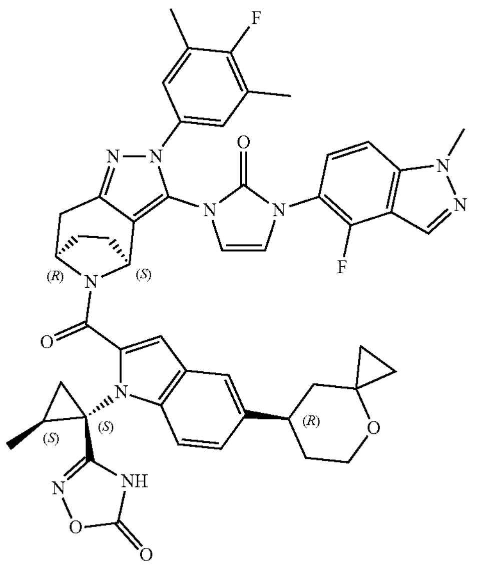

Step 1: 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one and 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

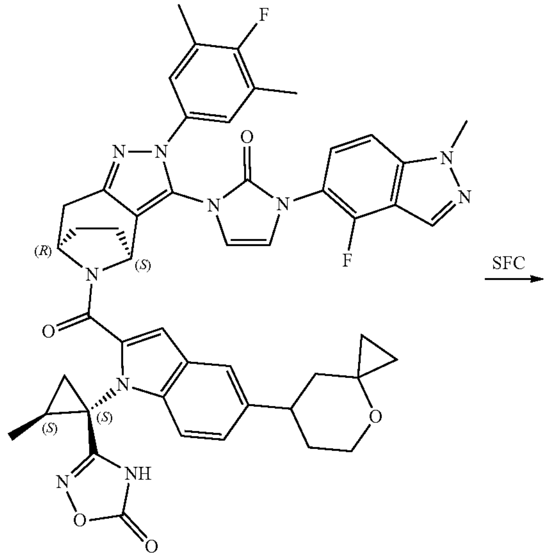

-continued

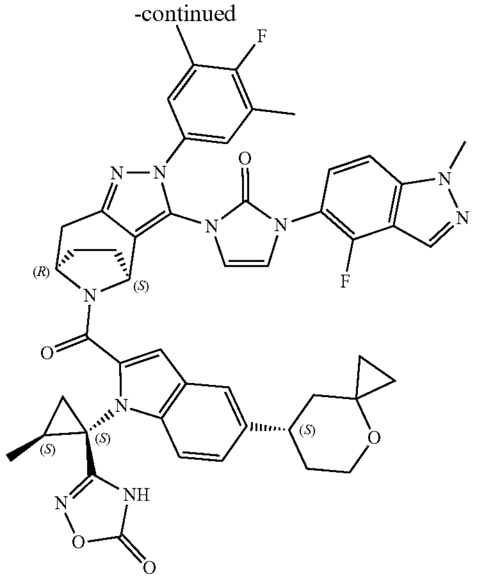

first eluent

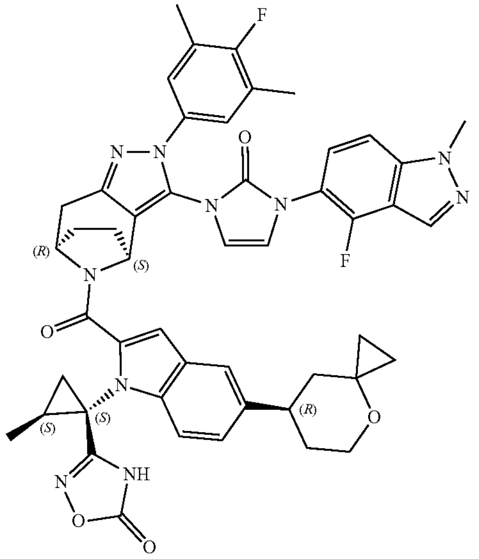

second eluent

The compound 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(4-oxaspiro[2.5]octan-7-yl)-1H-indol-1-yl)-2-methylcyclopropyl)-1,2,4-oxadiazol-5 (4H)-one (30 mg, purity 100%) was further separated by SFC (column: DAICEL CHIRALPAK IC (250 mm*30 mm, 10 um); mobile phase: [$CO_2$-MeOH (0.1% $NH_3H_2O$)—$H_2O$=95:5]; B %: 65%, isocratic elution mode) to give 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (first eluent, Rt=2.747 min; 10.33 mg, 11.57 μmol, 34.50% yield). $^1$H NMR (400 MHz, DMSO-$d_6$) δ=12.06-11.16 (m, 1H), 8.20 (br s, 1H), 7.70-6.52 (m, 10H), 5.58-5.22 (m, 1H), 5.15-4.82 (m, 1H), 4.10 (d, J=1.2 Hz, 3H), 3.91-3.52 (m, 3H), 3.07-2.78 (m, 2H), 2.31-2.09 (m, 9H), 1.93-0.94 (m, 11H), 0.81-0.38 (m, 4H). LC-MS (ES+, m/z): 893.3 [(M+H)$^+$]; Rt=3.168 min. HRMS (EI): m/z [M+H]$^+$ found: 893.3681.

And 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one (second eluent, Rt=4.457 min; 10.70 mg, 11.98 μmol, 35.74% yield). $^1$H NMR (400 MHz, DMSO-$d_6$) δ=12.33-11.61 (m, 1H), 8.41-8.09 (m, 1H), 7.74-6.59 (m, 10H), 5.63-4.87 (m, 2H), 4.18-4.02 (m, 3H), 3.94-3.55 (m, 2H), 3.25-2.61 (m, 3H), 2.39-1.98 (m, 9H), 1.94-0.97 (m, 11H), 0.83-0.25 (m, 4H). LC-MS (ES+, m/z): 893.3 [(M+H)$^+$]; Rt=3.054 min. HRMS (EI): m/z [M+H]$^+$ found: 893.3736.

Example 51

Compound 221

3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(tetrahydro-2H-pyran-4-yl)-1H-indol-1-yl)-2-methylcyclopropyl)-1,2,4-oxadiazol-5 (4H)-one

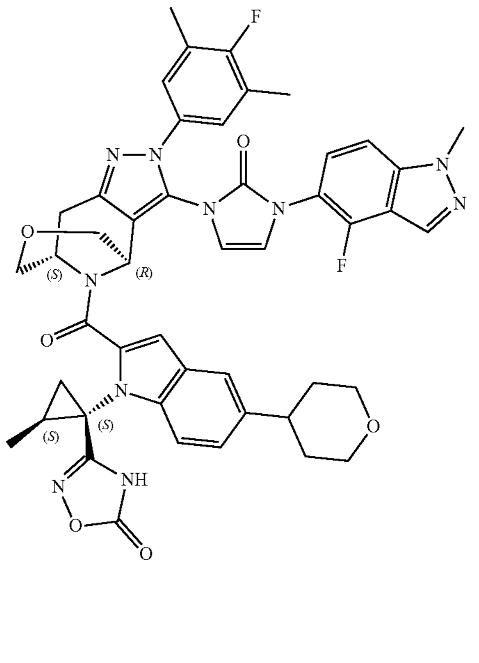

Step 1: 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-(tetrahydro-2H-pyran-4-yl)-1H-indol-1-yl)-2-methylcyclopropyl)-1,2,4-oxadiazol-5(4H)-one

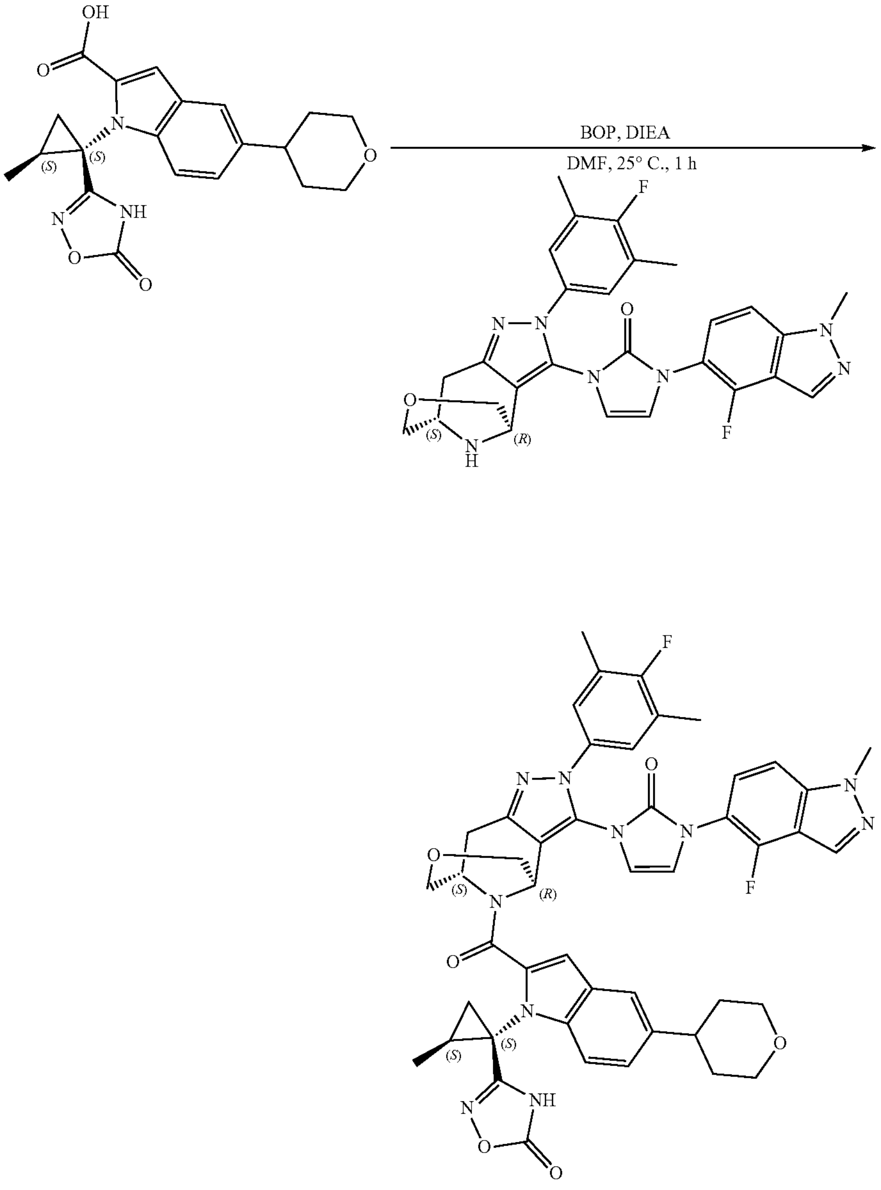

To a solution of 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1H-imidazol-2 (3H)-one (35 mg, 67.63 μmol, 1 eq), 1-((1S,2S)-2-methyl-1-(5-oxo-4,5-dihydro-1,2,4-oxadiazol-3-yl) cyclopropyl)-5-(tetrahydro-2H-pyran-4-yl)-1H-indole-2-carboxylic acid (57.62 mg, 135.26 μmol, 2 eq), DIEA (26.22 mg, 202.89 μmol, 35.34 μL, 3 eq) in DMF (1 mL) was added BOP (44.87 mg, 101.44 μmol, 1.5 eq). The reaction mixture was stirred at 25° C. for 1 hour. LCMS showed the reaction was completed. The reaction mixture was quenched by addition $H_2O$ (50 mL), extracted with ethyl acetate (50 mL*3). The combined organic layers were washed with saturated brine (30 mL) dried over anhydrous $Na_2SO_4$, filtered and concentrated under reduced pressure. The filtrate was purified by prep-HPLC (TFA condition column: Phenomenex Luna C18 75*30 mm*3 um; mobile phase: [$H_2O$ (0.1% TFA)-ACN]; gradient: 45%-75% B over 8.0 min) to give 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(tetrahydro-2H-pyran-4-yl)-1H-indol-1-yl)-2-methylcyclopropyl)-1,2,4-oxadiazol-5 (4H)-one (8.42 mg, 9.51 μmol, 14.07% yield). $^1H$ NMR (400 MHz, DMSO-$d_6$) δ=12.23-11.61 (m, 1H), 8.36-7.83 (m, 1H), 6.70 (s, 10H), 5.77-4.65 (m, 2H), 4.13-4.05 (m, 3H), 4.00-3.89 (m, 2H), 3.84-3.56 (m, 4H), 3.31-2.75 (m, 5H), 2.31-2.12 (m, 6H), 1.85-0.96 (m, 10H). LC-MS (ES+, m/z): 883.3 [$(M+H)^+$]; Rt=2.924 min. HRMS (EI): m/z $[M+H]^+$ found: 883.3474.

Example 52
Compound 222
3-((1S,2S)-1-(2-((4R,8S)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((S)-2,2-dimethyltetrahydro-2H-pyran-4-yl)-1H-indol-1-yl)-2-methylcyclopropyl)-1,2,4-oxadiazol-5(4H)-one
Scheme 180
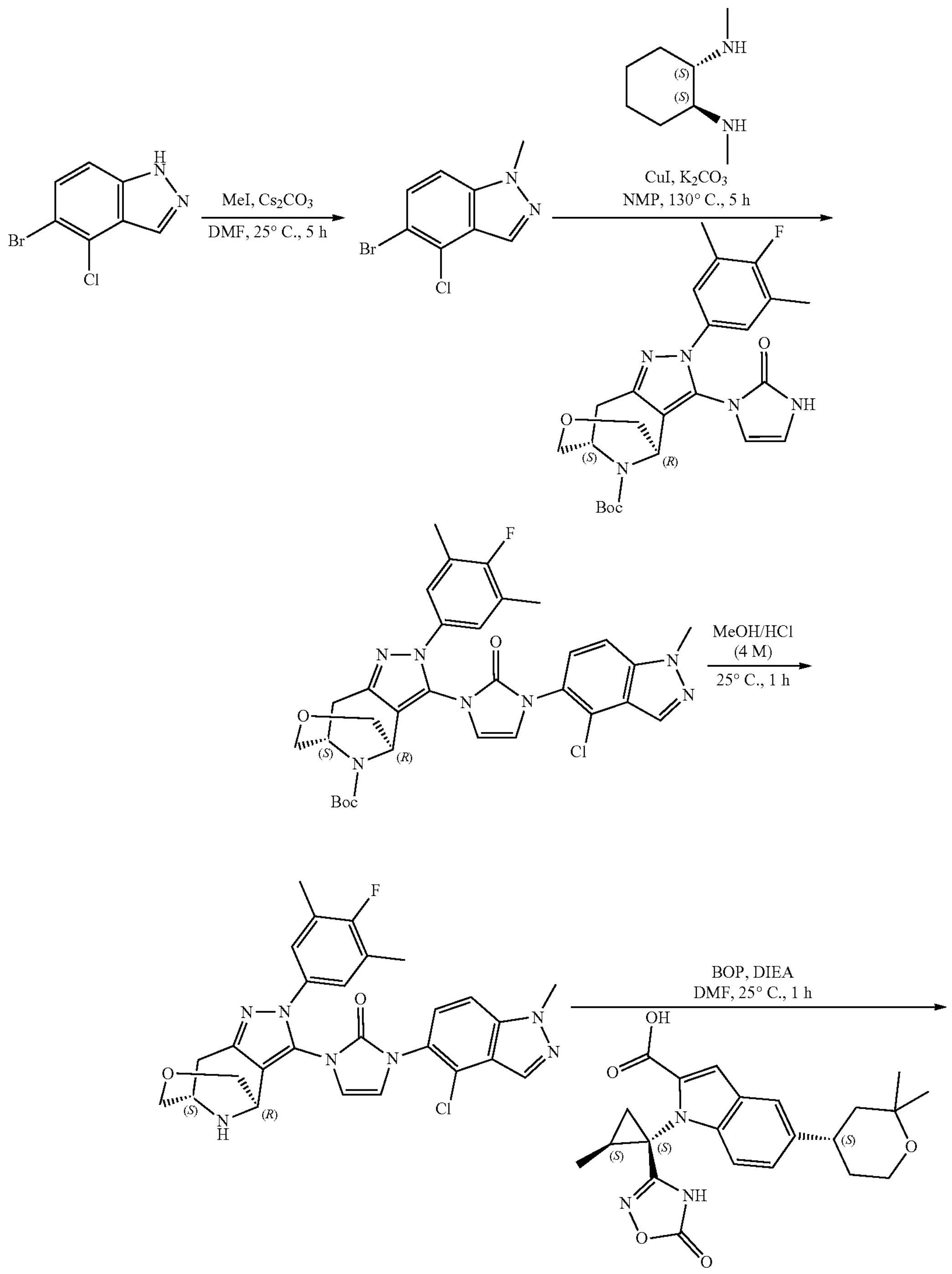

-continued

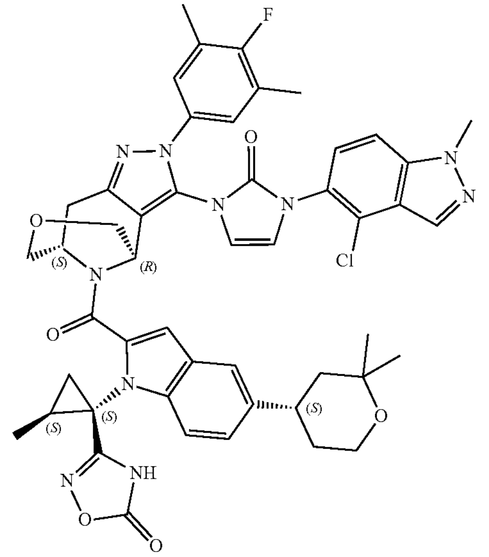

Step 1: 5-bromo-4-chloro-1-methyl-1H-indazole

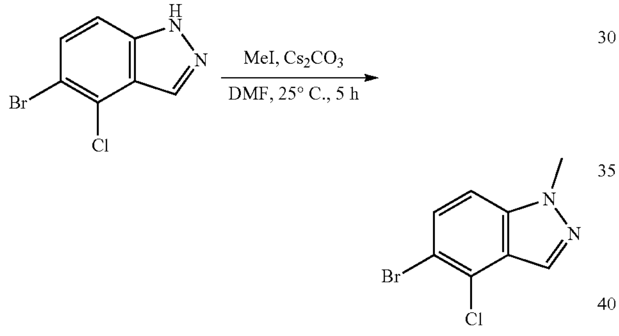

To a solution of 5-bromo-4-chloro-1H-indazole (5 g, 21.60 mmol, 1 eq) in DMF (50 mL) was added MeI (3.37 g, 23.76 mmol, 1.48 mL, 1.1 eq) and $Cs_2CO_3$ (14.08 g, 43.20 mmol, 2 eq). The mixture was stirred at 25° C. for 5 hours. LCMS showed the reaction was completed. The reaction mixture was diluted with water (200 mL), extracted with ethyl acetate (200 mL*3). The combined organic layers were washed with saturated brine (200 mL*2). The combined organic layers were dried over $Na_2SO_4$, filtered and concentrated in vacuum. The residue was purified by flash silica gel chromatography (ISCO®; 80 g SepaFlash® Silica Flash Column, Eluent of 0~100% Ethyl acetate/Petroleum ether gradient @ 120 mL/min) to give 5-bromo-4-chloro-1-methyl-indazole (3.5 g, 14.26 mmol, 66.00% yield). LC-MS (ES+, m/z): 245.1 [(M+H)$^+$]; Rt=1.612 min.

Step 2: tert-butyl (4R,8S)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate

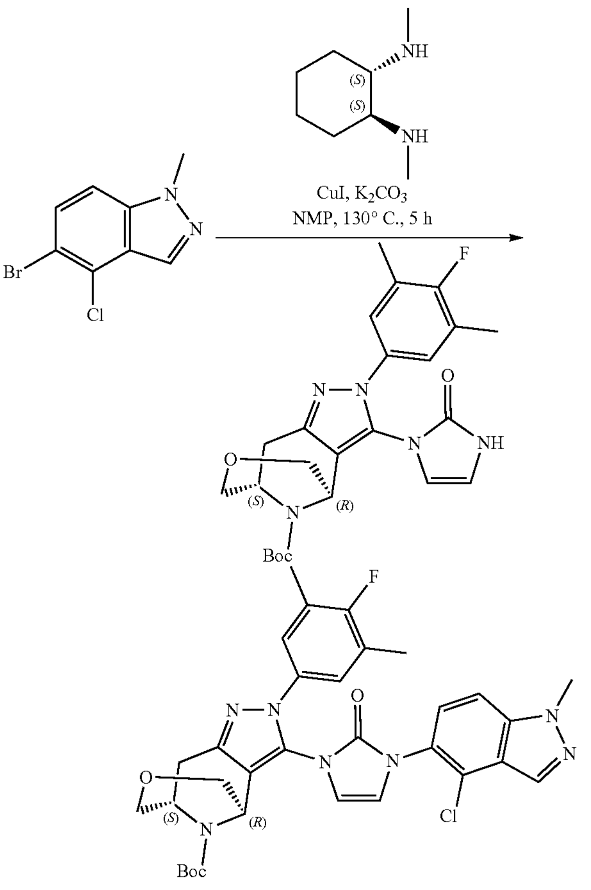

To a solution of 5-bromo-4-chloro-1-methyl-indazole (62.75 mg, 255.59 μmol, 1 eq) and tert-butyl (1R,8S)-4-(4-fluoro-3,5-dimethyl-phenyl)-3-(2-oxo-1H-imidazol-3-yl)-10-oxa-4,5,12-triazatricyclo[6.3.1.02,6]dodeca-2,5-diene-12-carboxylate (120 mg, 255.59 μmol, 1 eq) and (1S,2S)—N1,N2-dimethylcyclohexane-1,2-diamine (72.71 mg, 511.17 μmol, 2 eq) in NMP (2.5 mL) was added CuI (97.35 mg, 511.17 μmol, 2 eq) and $K_2CO_3$ (105.97 mg, 766.76 μmol, 3 eq). The mixture was stirred at 130° C. for 5 hours under $N_2$. LCMS showed the reaction was completed. The reaction mixture was diluted with saturated EDTA (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuum. The residue was purified by prep-HPLC ($NH_4HCO_3$ condition: column: Waters Xbridge BEH C18 100*30 mm*10 um; mobile phase: [$H_2O$ (10 mM $NH_4HCO_3$)-ACN]; gradient: 55%-75% B over 8.0 min) to give tert-butyl (4R,8S)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (50 mg, 78.85 μmol, 30.85% yield). LC-MS (ES+, m/z): 634.3 [(M+H)$^+$]; Rt=0.574 min.

Step 3: 1-(4-chloro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one

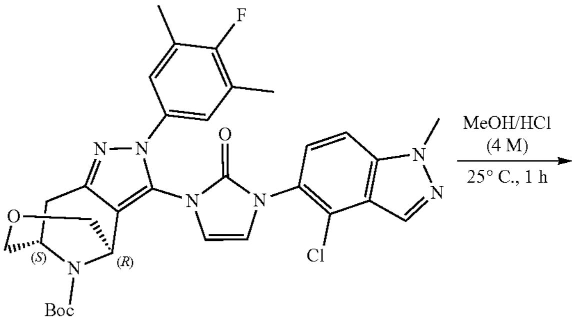

-continued

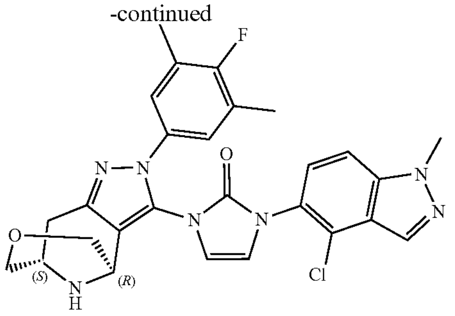

To a solution of tert-butyl (4R,8S)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (0.1 g, 149.82 μmol, 1 eq) in HCl/MeOH (5 mL) was stirred at 25° C. for 1 hour. LCMS showed the reaction was completed. The reaction mixture was concentrated in vacuo to give 1-(4-chloro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (0.08 g, 142.33 μmol, 95.00% yield, 95% purity). LC-MS (ES+, m/z): 534.3 [(M+H)$^+$]; Rt=0.396 min.

Step 4: 3-((1S,2S)-1-(2-((4R,8S)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-((S)-2,2-dimethyltetrahydro-2H-pyran-4-yl)-1H-indol-1-yl)-2-methylcyclopropyl)-1,2,4-oxadiazol-5 (4H)-one

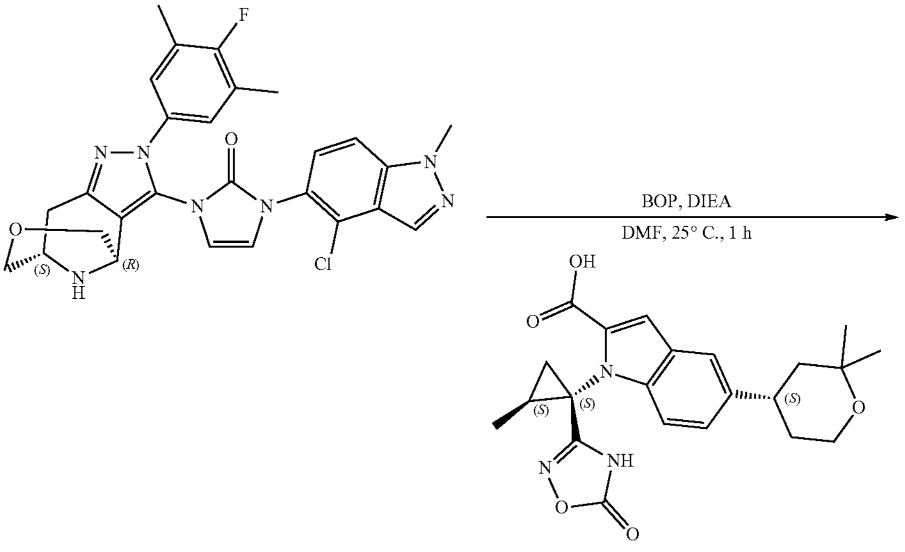

-continued

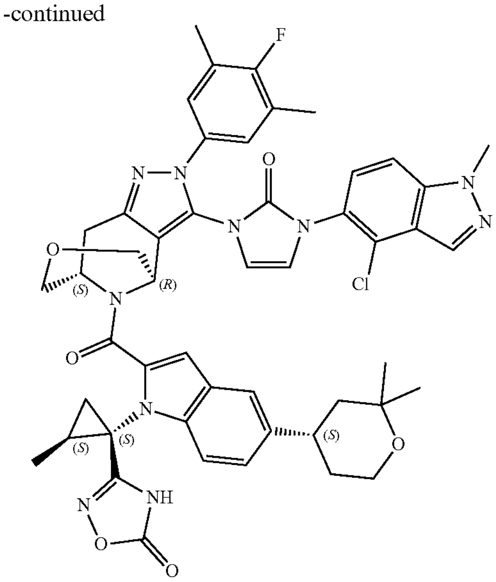

To a solution of 1-(4-chloro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (50 mg, 88.95 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (36.60 mg, 88.95 μmol, 1 eq) in DMF (1.5 mL) was added DIEA (57.48 mg, 444.77 μmol, 77.47 μL, 5 eq), BOP (78.69 mg, 177.91 μmol, 2 eq). The mixture was stirred at 25° C. for 1 hour. LC-MS showed the reaction was completed. The reaction mixture was diluted with water (50 mL), extracted with ethyl acetate (50 mL*3). The combined organic layers were washed with saturated brine (50 mL*2). The combined organic layers were dried over $Na_2SO_4$, filtered and concentrated in vacuo. The residue was purified by prep-HPLC (TFA condition column: 3_Phenomenex Luna C18 75*30 mm*3 um; mobile phase: [$H_2O$ (0.1% TFA)-ACN]; gradient: 50%-80% B over 8.0 min) to give 3-((1S,2S)-1-(2-((4R,8S)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((S)-2,2-dimethyltetrahydro-2H-pyran-4-yl)-1H-indol-1-yl)-2-methylcyclopropyl)-1,2,4-oxadiazol-5 (4H)-one (26.74 mg, 28.83 μmol, 32.41% yield). $^1$H NMR (400 MHz, DMSO-$d_6$) δ=12.27-11.65 (m, 1H), 8.31-7.89 (m, 1H), 7.87-7.44 (m, 2H), 7.44-7.05 (m, 5H), 7.05-6.54 (m, 3H), 5.68-4.76 (m, 2H), 4.13-4.05 (m, 3H), 4.03-3.51 (m, 6H), 3.27-2.80 (m, 3H), 2.39-2.16 (m, 6H), 2.03-1.43 (m, 6H), 1.41-0.76 (m, 10H). $^1$H NMR (400 MHz, DMSO-$d_6$, T=273+80K) δ=12.22-11.04 (m, 1H), 8.28-7.90 (m, 1H), 7.81-7.42 (m, 2H), 7.41-7.01 (m, 5H), 6.98-6.68 (m, 3H), 5.92-4.57 (m, 2H), 4.18-3.59 (m, 9H), 3.08 (br s, 3H), 2.35-2.23 (m, 6H), 1.76-1.44 (m, 6H), 1.42-0.79 (m, 10H). LC-MS (ES+, m/z): 927.3 [(M+H)$^+$]; Rt=2.965 min. HRMS (EI): m/z [M+H]$^+$ found: 927.3506.

Example 53

Compound 225

3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-pyrrolo[2,3-c]pyridin-1-yl)-2-methylcyclopropyl)-1,2,4-oxadiazol-5 (4H)-one

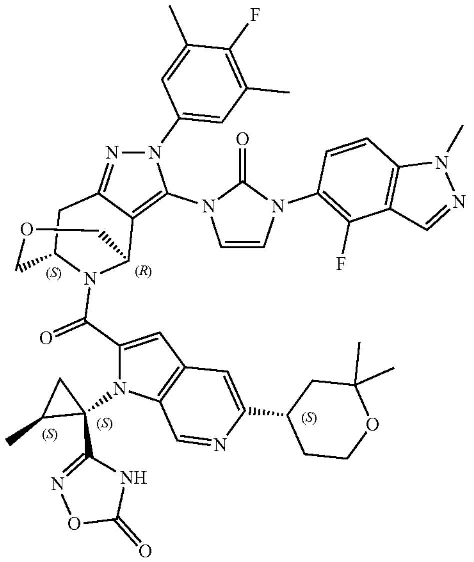

Step 1: 3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-pyrrolo[2,3-c]pyridin-1-yl)-2-methylcyclopropyl)-1,2,4-oxadiazol-5 (4H)-one

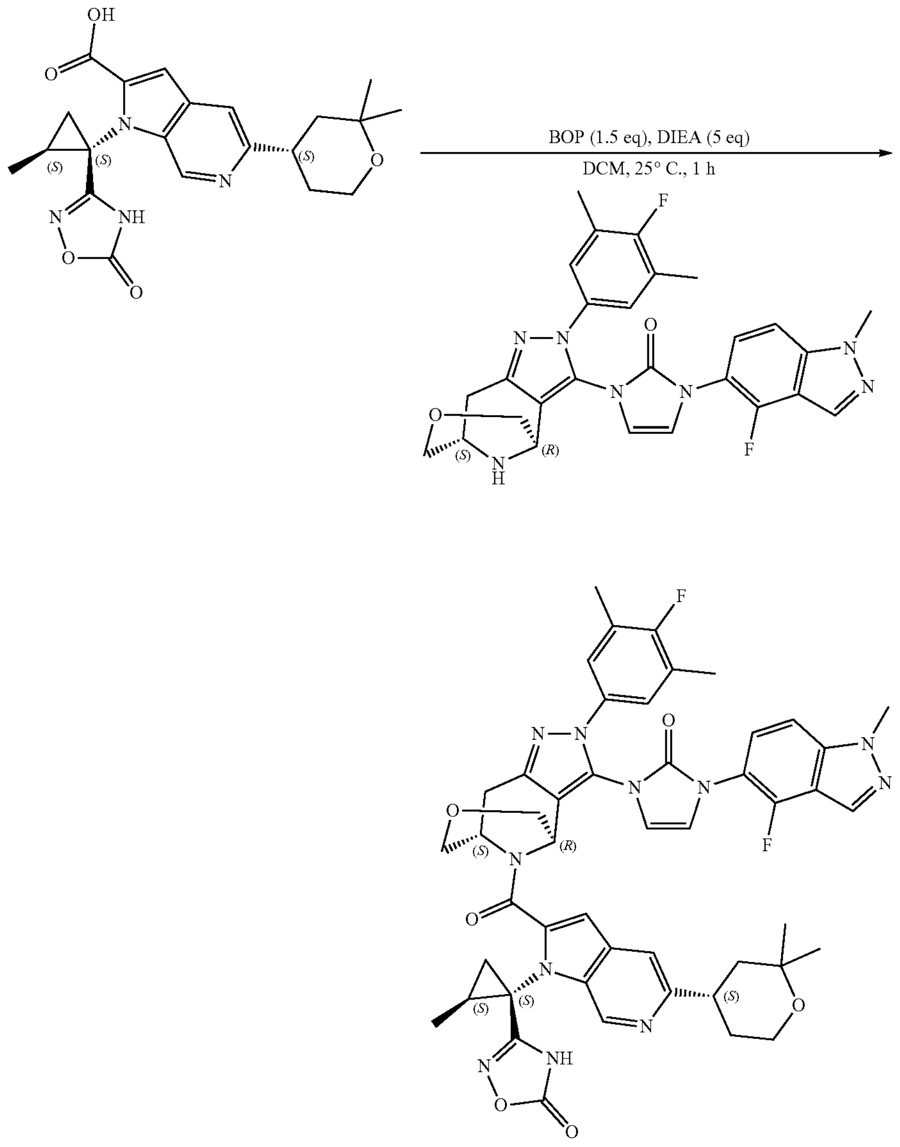

To a solution of 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (40 mg, 72.20 μmol, 1 eq, HCl), 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-c]pyridine-2-carboxylic acid (29.78 mg, 72.20 μmol, 1 eq), DIPEA (46.66 mg, 361.02 μmol, 62.88 μL, 5 eq) in DMF (0.35 mL) was added BOP (47.90 mg, 108.31 μmol, 1.5 eq). The mixture was stirred at 25° C. for 1 hour. LCMS indicated the reaction was completed. The mixture was filtered. The filtrate was purified by prep-HPLC (column: Phenomenex Luna C18 75*30 mm*3 um; mobile phase: [$H_2O$ (0.1% TFA)-ACN]; gradient: 30%-50% B over 8.0 min) to give 3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-pyrrolo [2,3-c]pyridin-1-yl)-2-methylcyclopropyl)-1,2,4-oxadiazol-5 (4H)-one (8.28 mg, 8.95 μmol, 12.40% yield). $^1$H NMR (400 MHz, DMSO-$d_6$) δ=12.80-11.02 (m, 1H), 9:04-8.70 (m, 1H), 8.38-8.03 (m, 1H), 7.70-6.68 (m, 8H), 5.80-4.51 (m, 2H), 4.17-4.05 (m, 4H), 3.98-3.67 (m, 5H), 2.96-2.74 (m, 3H), 2.27 (s, 6H), 1.89-1.54 (m, 6H), 1.38-1.09 (m, 10H). $^1$H NMR (400 MHz, MeOD-$d_4$) δ=8.96 (s, 1H), 8.28-8.14 (m, 1H), 8.03 (s, 1H), 7.53-7.01 (m, 5H), 6.92-6.30 (m, 1H), 5.46-5.02 (m, 2H), 4.27-4.06 (m, 6H), 3.99-3.66 (m, 4H), 3.58-3.48 (m, 1H), 3.22-3.15 (m, 1H), 2.35-2.26 (m, 6H), 2.01-1.91 (m, 1H), 1.98-1.75 (m, 3H), 1.66-1.44 (m, 4H), 1.38-1.27 (m, 6H), 1.17-1.01 (m, 3H). LC-MS (ES+, m/z): 912.3 [$(M+H)^+$]; Rt=2.330 min. HRMS (EI): m/z $[M+H]^+$ found: 912.3765.

Example 54

Compound 220

3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(4-oxaspiro[2.5]octan-7-yl)-1H-indol-1-yl)-2-methylcyclopropyl)-1,2,4-oxadiazol-5 (4H)-one

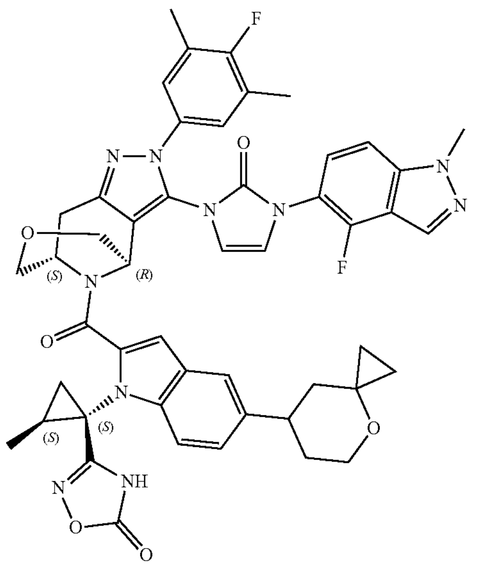

Step 1: 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-(4-oxaspiro[2.5]octan-7-yl)-1H-indol-1-yl)-2-methylcyclopropyl)-1,2,4-oxadiazol-5(4H)-one

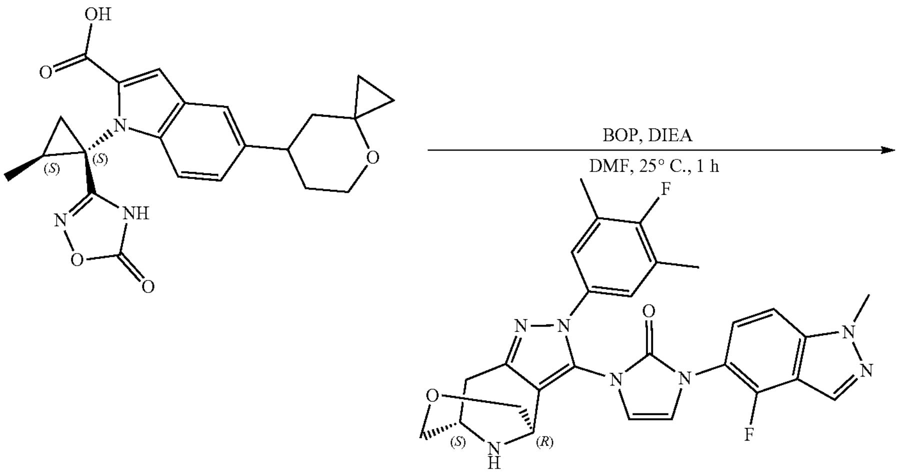

-continued

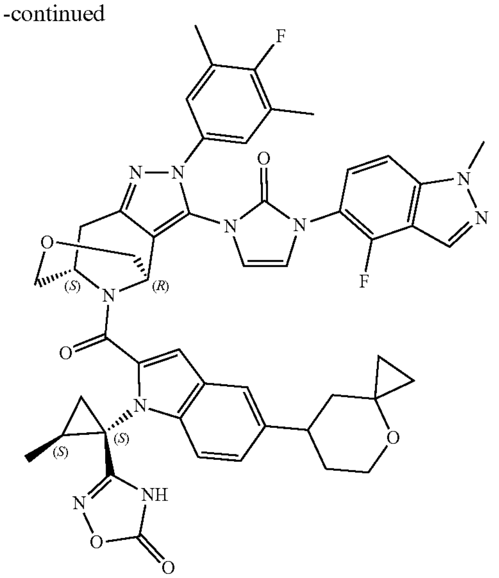

To a solution of 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (15 mg, 27.08 μmol, 1 eq, HCl), 1-((1S,2S)-2-methyl-1-(5-oxo-4,5-dihydro-1,2,4-oxadiazol-3-yl)cyclopropyl)-5-(4-oxaspiro[2.5]octan-7-yl)-1H-indole-2-carboxylic acid (12.05 mg, 27.08 μmol, 1 eq) in DMF (1 mL) was added DIEA (17.50 mg, 135.38 μmol, 23.58 μL, 5 eq) and BOP (14.37 mg, 32.49 μmol, 1.2 eq). The mixture was stirred at 25° C. for 2 hours. LCMS indicated that the reaction was completed. The reaction mixture was partitioned between ethyl acetate (30 mL) and $H_2O$ (10 mL). The organic phase was separated, washed with saturated brine (30 mL*3), dried over $Na_2SO_4$, filtered and concentrated under reduced pressure. The residue was purified by prep-HPLC (column: Phenomenex Luna C18 75*30 mm*3 um; mobile phase: [$H_2O$ (0.1% TFA)-ACN]; gradient: 50%-80% B over 8.0 min) to give 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(4-oxaspiro[2.5]octan-7-yl)-1H-indol-1-yl)-2-methylcyclopropyl)-1,2,4-oxadiazol-5 (4H)-one (5.09 mg, 5.56 μmol, 20.55% yield). $^1H$ NMR (400 MHz, DMSO-$d_6$) δ=12.23-11.68 (m, 1H), 8.34-8.11 (m, 1H), 6.68 (s, 10H), 5.77-4.70 (m, 2H), 4.15-4.05 (m, 3H), 4.01-3.63 (m, 5H), 3.22-2.81 (m, 4H), 2.31-2.16 (m, 6H), 2.00-1.86 (m, 1H), 1.81-1.70 (m, 2H), 1.68-1.51 (m, 2H), 1.38-1.21 (m, 4H), 1.15-0.95 (m, 1H), 0.81-0.26 (m, 4H). LC-MS (ES+, m/z): 909.3 [$(M+H)^+$]. Rt=3.039 min. HRMS (EI): m/z $[M+H]^+$ found: 909.3632.

Example 55

Compound 226

3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one

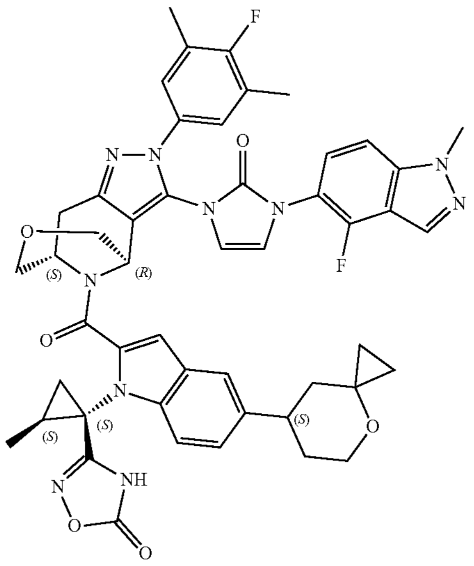

and

Compound 227

3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((R)-4-oxaspiro[2.5]octan-7-yl)-1H-indol-1-yl)-2-methylcyclopropyl)-1,2,4-oxadiazol-5 (4H)-one

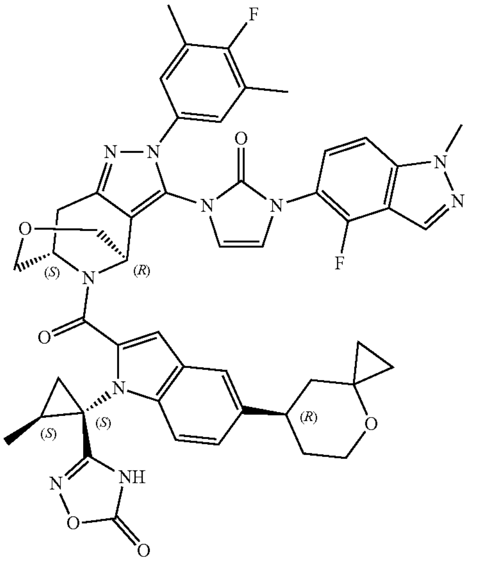

Step 1: 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-((S)-4-oxaspiro[2.5]octan-7-yl)-1H-indol-1-yl)-2-methylcyclopropyl)-1,2,4-oxadiazol-5 (4H)-one and 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((R)-4-oxaspiro[2.5]octan-7-yl)-1H-indol-1-yl)-2-methylcyclopropyl)-1,2,4-oxadiazol-5(4H)-one

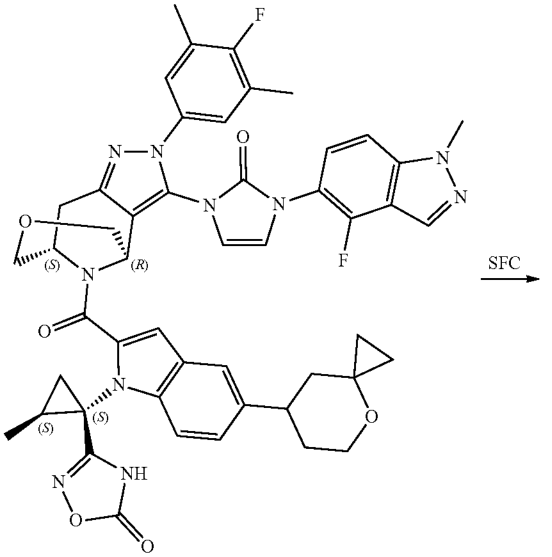

-continued

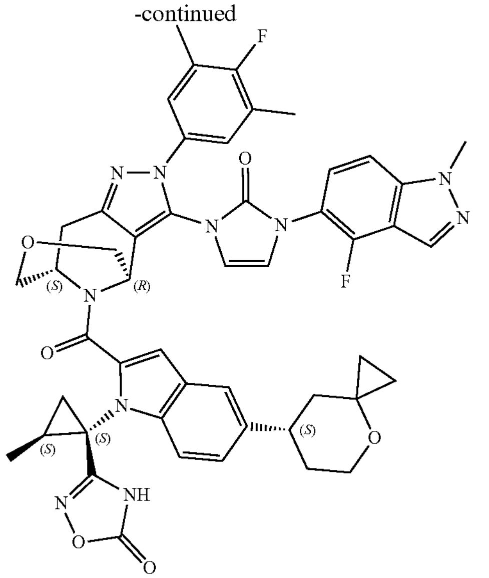

first eluent

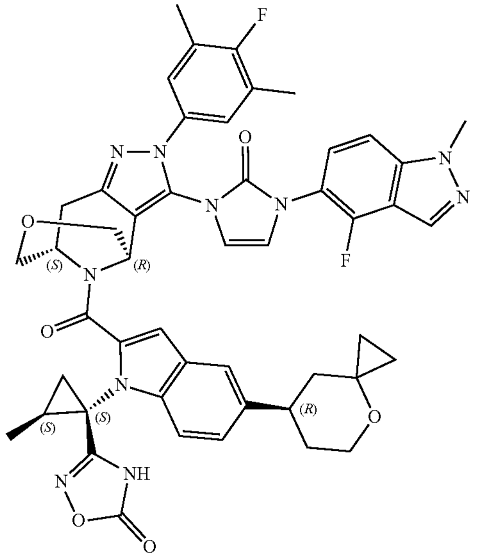

second eluent 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(4-oxaspiro[2.5]octan-7-yl)-1H-indol-1-yl)-2-methylcyclopropyl)-1,2,4-oxadiazol-5 (4H)-one (35 mg, 38.47 μmol, 1 eq) was separated by SFC (column: DAICEL CHIRALPAK IC (250 mm*30 mm, 10 um); mobile phase: [$CO_2$-MeOH (0.1% $NH_3H_2O$)—$H_2O$=95:5]; B %: 65%, isocratic elution mode) to give 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one (first eluent, Rt=3.490 min; 9.15 mg, 10.07 μmol, 26.17% yield); $^1H$ NMR (400 MHz, DMSO-$d_6$) δ=12.25-11.65 (m, 1H), 8.38-8.13 (m, 1H), 7.72-6.49 (m, 10H), 5.76-4.73 (m, 2H), 4.16-4.06 (m, 3H), 4.03-3.57 (m, 5H), 3.26-2.99 (m, 4H), 2.30-2.19 (m, 6H), 1.96-1.51 (m, 5H), 1.41-1.31 (m, 2H), 1.30-1.20 (m, 2H), 1.10 (br s, 1H), 0.77-0.33 (m, 4H); LC-MS (ES+, m/z): 909.3 [(M+H)$^+$]. Rt=3.037 min; HRMS (EI): m/z [M+H]$^+$ found: 909.3652; and 3-((1S,2S)-1-(2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((R)-4-oxaspiro[2.5]octan-7-yl)-1H-indol-1-yl)-2-methylcyclopropyl)-1,2,4-oxadiazol-5 (4H)-one (second eluent, Rt=4.961 min; 9.20 mg, 10.12 μmol, 26.31% yield); 1H NMR (400 MHz, DMSO-$d_6$) δ=12.23 (s, 1H), 8.36-8.15 (m, 1H), 7.77-6.47 (m, 10H), 5.72-4.74 (m, 2H), 4.14-4.06 (m, 3H), 3.99-3.44 (m, 5H), 3.27-2.98 (m, 4H), 2.29-2.17 (m, 6H), 2.00-1.88 (m, 1H), 1.86-1.70 (m, 2H), 1.67-1.52 (m, 2H), 1.38-0.98 (m, 5H), 0.74 (br s, 4H); LC-MS (ES+, m/z): 909.3 [(M+H)$^+$]. Rt=3.037 min; HRMS (EI): m/z [M+H]$^+$ found: 909.3652.

Example 56

Compound 229

3-((1S,2S)-1-(5-(2,2-dimethylmorpholino)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one Scheme 229

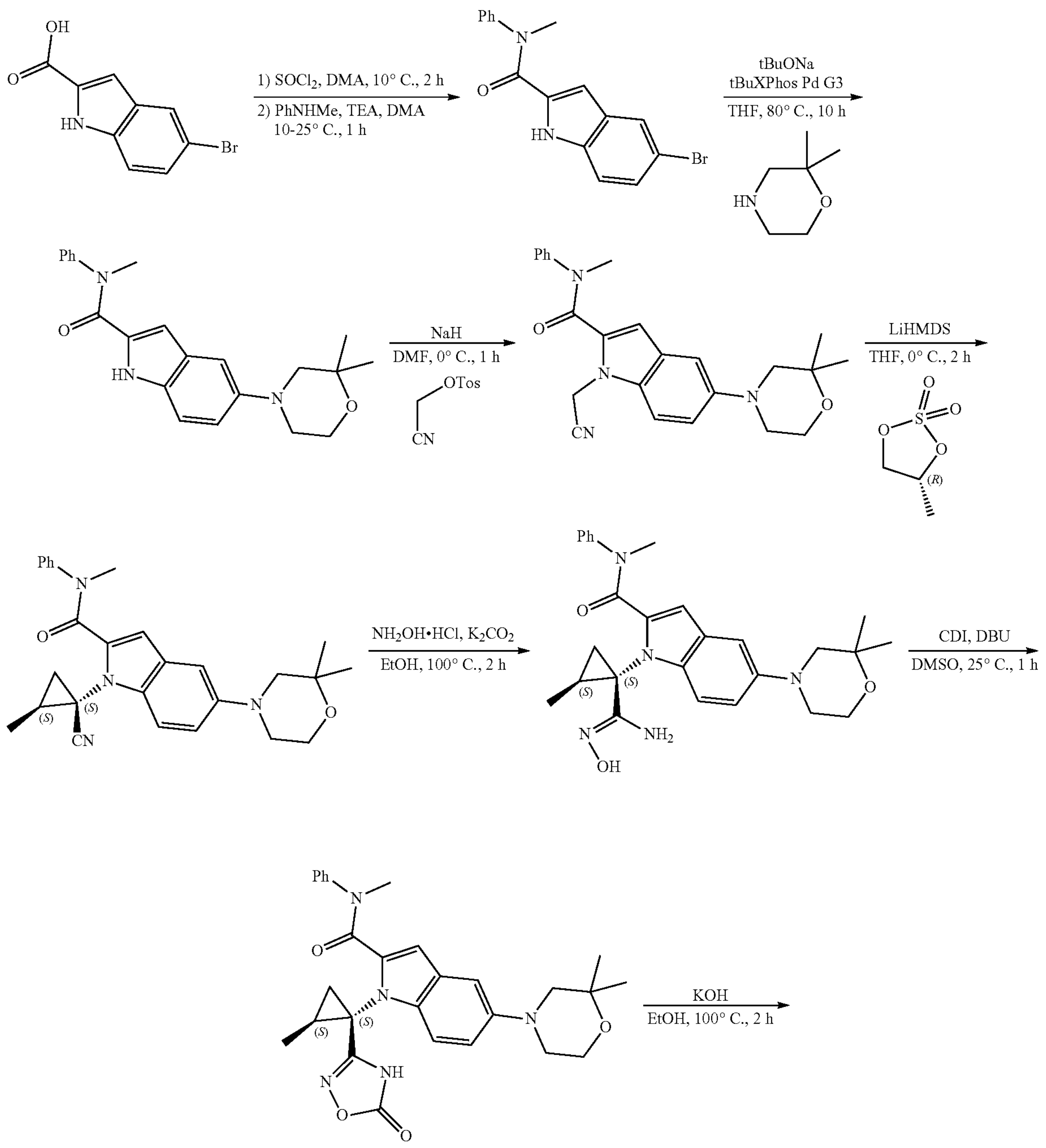

-continued

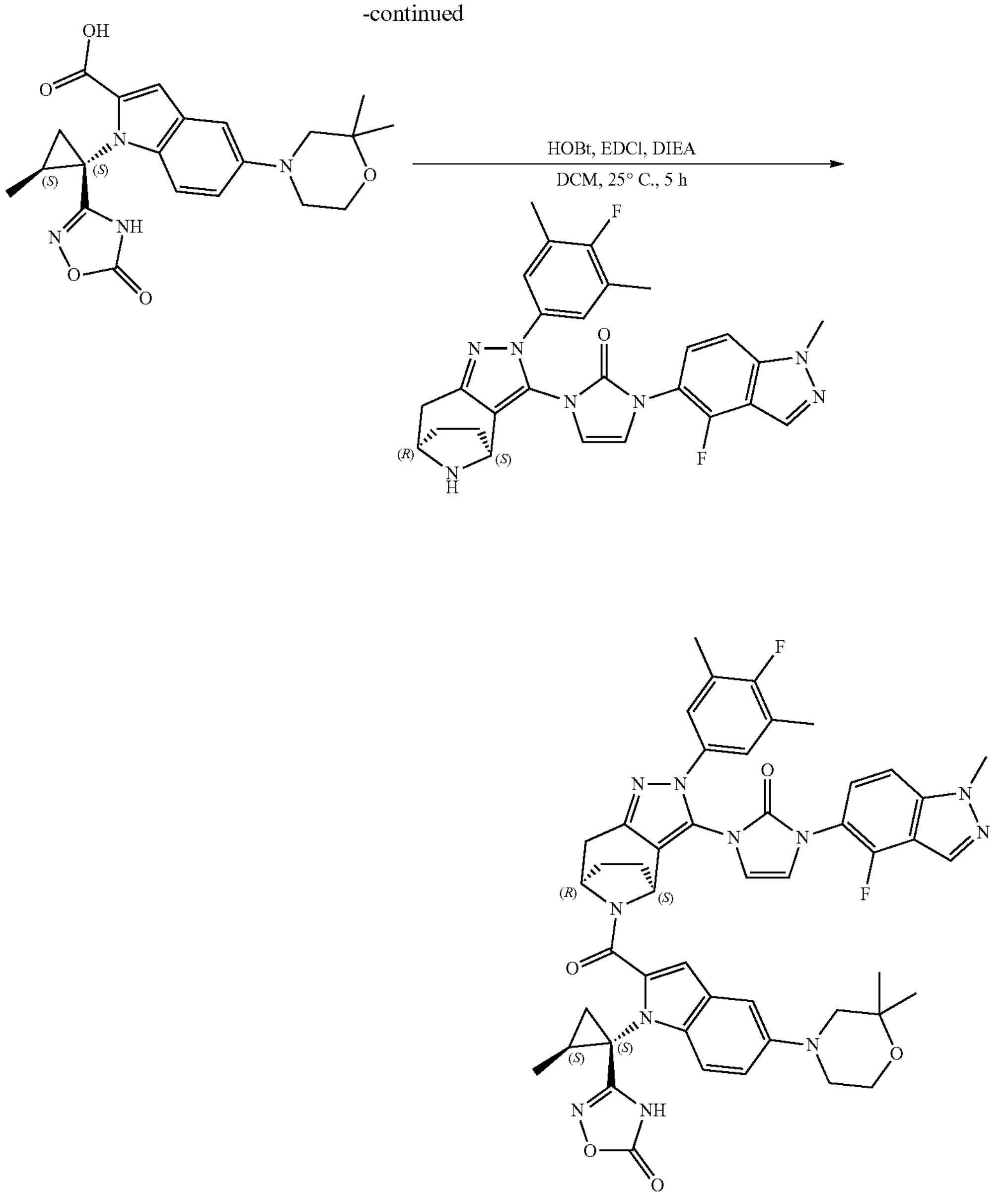

Step 1: 5-bromo-N-methyl-N-phenyl-1H-indole-2-carboxamide

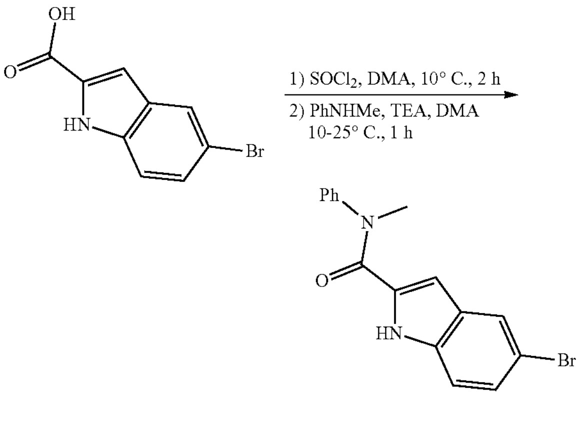

To a solution of 5-bromo-1H-indole-2-carboxylic acid (60 g, 249.94 mmol, 1 eq) in DMA (600 mL) was added dropwise $SOCl_2$ (35.68 g, 299.93 mmol, 21.78 mL, 1.2 eq) at 10° C. After stirring for 2 hours, N-methylaniline (32.14 g, 299.93 mmol, 32.56 mL, 1.2 eq) and TEA (60.70 g, 599.87 mmol, 83.49 mL, 2.4 eq) were added dropwise at 10° C. The mixture was stirred at 25° C. for 1 hour. LCMS showed the reaction was completed. The reaction mixture was added dropwise saturated $NaHCO_3$ (100 mL), and the precipitated solid was collected by filtration. The obtained solid was washed with water (150 mL) and dried under reduced pressure to give 5-bromo-N-methyl-N-phenyl-1H-indole-2-carboxamide (80 g, 237.43 mmol, 94.99% yield). LC-MS (ES+, m/z): 329.1 [$(M+H)^+$]; Rt=0.561 min.

Step 2: 5-(2,2-dimethylmorpholino)-N-methyl-N-phenyl-1H-indole-2-carboxamide

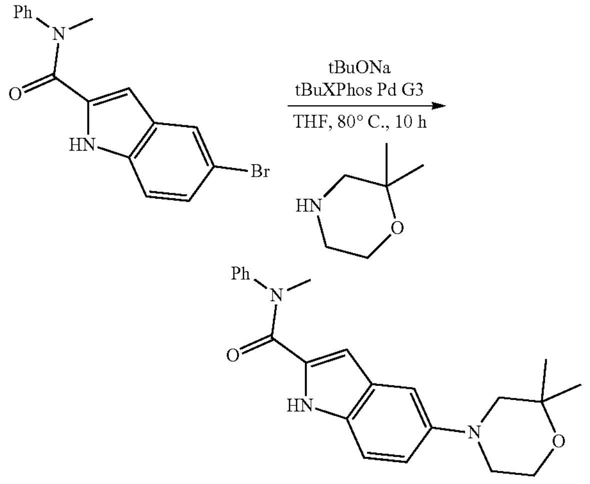

To a mixture of 5-bromo-N-methyl-N-phenyl-1H-indole-2-carboxamide (4 g, 12.15 mmol, 1 eq) and 2,2-dimethylmorpholine (2.80 g, 24.30 mmol, 2 eq) in THF (40 mL) was added t-BuONa (3.50 g, 36.45 mmol, 3 eq), t-BuXPhos Pd G3 (965.24 mg, 1.22 mmol, 0.1 eq) in one portion under $N_2$. The mixture was stirred at 80° C. for 10 hours. LCMS showed reaction was completed. The reaction was poured into water (400 mL) and extracted with ethyl acetate (400 mL*2). The organic layers were combined, washed with saturated brine (400 mL), dried over $Na_2SO_4$, filtered and concentrated. The residue was dissolved in ethyl acetate (100 mL). Scavenger (Pd) was added and stirred at 25° C. for 1 hour, and then filtered. The residue was purified by column chromatography ($SiO_2$, Petroleum ether/ethyl acetate=20/1 to 0/1) to afford 5-(2,2-dimethylmorpholino)-N-methyl-N-phenyl-1H-indole-2-carboxamide (1.2 g, 2.64 mmol, 21.74% yield). LC-MS (ES+, m/z): 364.3 [$(M+H)^+$]; Rt=0.440 min.

Step 3: 1-(cyanomethyl)-5-(2,2-dimethylmorpholino)-N-methyl-N-phenyl-1H-indole-2-carboxamide

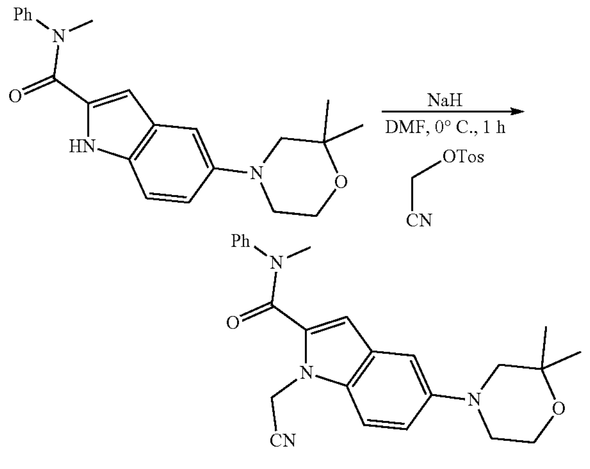

To a mixture of 5-(2,2-dimethylmorpholino)-N-methyl-N-phenyl-1H-indole-2-carboxamide (1 g, 2.20 mmol, 1 eq) in DMF (10 mL) was added NaH (264.11 mg, 6.60 mmol, 60% purity, 3 eq) in one portion at 0° C. under $N_2$. The mixture was stirred at 0° C. for 0.5 hour. To the mixture was added cyanomethyl 4-methylbenzenesulfonate (929.92 mg, 4.40 mmol, 2 eq), and stirred at 0° C. for 0.5 hour. LCMS showed reaction was completed. The reaction solution is quenched with saturated $NH_4Cl$ (100 mL). The aqueous phase was extracted with ethyl acetate (100 mL*3). The combined organic layers were washed with saturated brine (100 mL*3), dried over anhydrous $Na_2SO_4$, filtered and concentrated under reduced pressure. The residue was purified by column chromatography ($SiO_2$, Petroleum ether/ethyl acetate=20/1 to 1/1) to afford 1-(cyanomethyl)-5-(2,2-dimethylmorpholino)-N-methyl-N-phenyl-1H-indole-2-carboxamide (0.75 g, 1.68 mmol, 76.19% yield). LC-MS (ES+, m/z): 403.2 [$(M+H)^+$]; Rt=0.487 min.

Step 4: 1-((1S,2S)-1-cyano-2-methylcyclopropyl)-5-(2,2-dimethylmorpholino)-N-methyl-N-phenyl-1H-indole-2-carboxamide

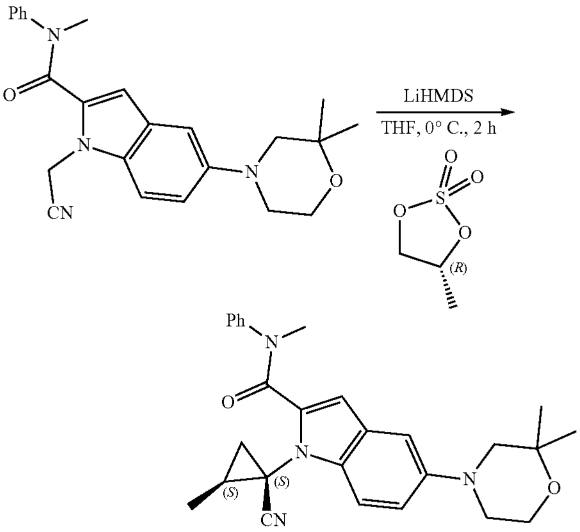

To a mixture of 1-(cyanomethyl)-5-(2,2-dimethylmorpholino)-N-methyl-N-phenyl-1H-indole-2-carboxamide (750 mg, 1.68 mmol, 1 eq) and (R)-4-methyl-1,3,2-dioxathiolane 2,2-dioxide (1.39 g, 10.06 mmol, 6 eq) in THF (7.5 mL), was added LiHMDS (1 M, 4 eq) in one portion at 0° C. under $N_2$. The mixture was stirred at 0° C. for 2 hours. LCMS showed reaction was completed. The reaction solution is quenched with saturated $NH_4Cl$ (100 mL) at 0° C. The aqueous phase was extracted with ethyl acetate (100 mL*3). The combined organic layers were washed with saturated brine (100 mL*3), dried over anhydrous $Na_2SO_4$, filtered and concentrated under reduced pressure. The residue was purified by column chromatography ($SiO_2$, Petroleum ether/ethyl acetate=20/1 to 1/1) to afford 1-((1S,2S)-1-cyano-2-methylcyclopropyl)-5-(2,2-dimethylmorpholino)-N-methyl-N-phenyl-1H-indole-2-carboxamide (0.55 g, 1.12 mmol, 66.69% yield). LC-MS (ES+, m/z): 443.2 [$(M+H)^+$]; Rt=1.373 min.

Step 5:5-(2,2-dimethylmorpholino)-1-((1,2S)-1-(N'-hydroxycarbamimidoyl)-2-methylcyclopropyl)-N-methyl-N-phenyl-1H-indole-2-carboxamide

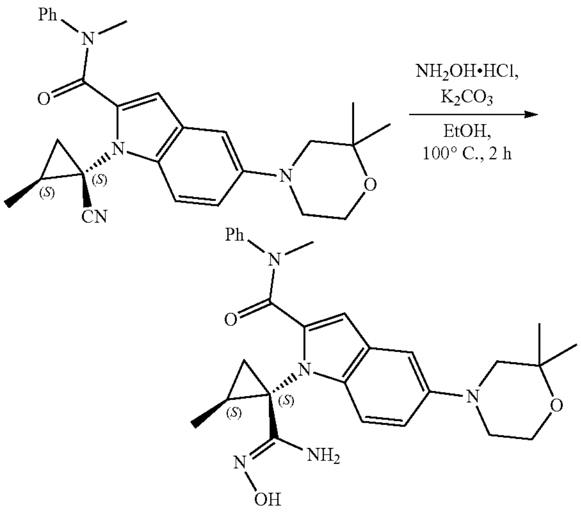

To a mixture of 1-((1S,2S)-1-cyano-2-methylcyclopropyl)-5-(2,2-dimethylmorpholino)-N-methyl-N-phenyl-1H-indole-2-carboxamide (550 mg, 1.12 mmol, 1 eq) in EtOH (5.5 mL) was added $NH_2OH \cdot HCl$ (388.63 mg, 5.59 mmol, 5 eq), $K_2CO_3$ (772.95 mg, 5.59 mmol, 5 eq) in one portion under $N_2$. The mixture was stirred at 100° C. for 2 hours. LCMS showed reaction was completed. The reaction solution is quenched with $H_2O$ (50 mL). The aqueous phase was extracted with ethyl acetate (50 mL*3). The combined organic layers were washed with saturated brine (50 mL*3), dried over anhydrous $Na_2SO_4$, filtered and concentrated under reduced pressure to afford 5-(2,2-dimethylmorpholino)-1-((1S,2S)-1-(N'-hydroxycarbamimidoyl)-2-methylcyclopropyl)-N-methyl-N-phenyl-1H-indole-2-carboxamide (0.5 g, crude). LC-MS (ES+, m/z): 476.3 [$(M+H)^+$]; Rt=0.412 min.

Step 6: 5-(2,2-dimethylmorpholino)-N-methyl-1-((1S,2S)-2-methyl-1-(5-oxo-4,5-dihydro-1,2,4-oxadiazol-3-yl)cyclopropyl)-N-phenyl-1H-indole-2-carboxamide To a mixture of 5-(2,2-dimethylmorpholino)-1-((1S,2S)-1-(N'-hydroxycarbamimidoyl)-2-methylcyclopropyl)-N-methyl-N-phenyl-1H-indole-2-carboxamide (0.5 g, 946.21 μmol, 1 eq) in DMSO (5 mL) was added CDI (306.85 mg, 1.89 mmol, 2 eq), DBU (360.12 mg, 2.37 mmol, 2.5 eq) in one portion under $N_2$. The mixture was stirred at 25° C. for 1 hour. LCMS showed reaction was completed. The reaction solution is quenched with water (50 mL). The aqueous phase was extracted with chloroform:isopropanol=3:1 (50 mL*3). The combined organic layers were washed with saturated brine (100 mL), dried over anhydrous $Na_2SO_4$, filtered and concentrated under reduced pressure. The residue was purified by column chromatography ($SiO_2$, Petroleum ether/ethyl acetate=20/1 to 1/1) to afford 5-(2,2-dimethylmorpholino)-N-methyl-1-((1S,2S)-2-methyl-1-(5-oxo-4,5-dihydro-1,2,4-oxadiazol-3-yl) cyclopropyl)-N-phenyl-1H-indole-2-carboxamide (0.40 g, 717.74 μmol, 75.85% yield). LC-MS (ES+, m/z): 502.3 [$(M+H)^+$]; Rt=0.548 min.

Step 7: 5-(2,2-dimethylmorpholino)-1-((1S,2S)-2-methyl-1-(5-oxo-4,5-dihydro-1,2,4-oxadiazol-3-yl) cyclopropyl)-1H-indole-2-carboxylic acid

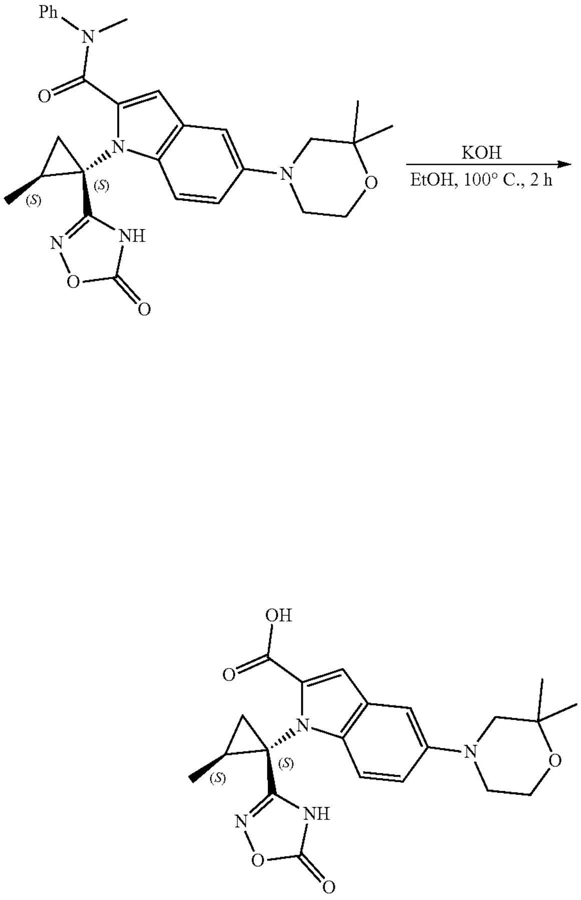

To a mixture of 5-(2,2-dimethylmorpholino)-N-methyl-1-((1S,2S)-2-methyl-1-(5-oxo-4,5-dihydro-1,2,4-oxadiazol-3-yl)cyclopropyl)-N-phenyl-1H-indole-2-carboxamide (0.1 g, 179.43 μmol, 1 eq) in EtOH (2 mL), was added KOH (402.69 mg, 7.18 mmol, 40 eq) in one portion under $N_2$. The mixture was stirred at 100° C. for 2 hours. LCMS showed reaction was complete. The reaction solution is adjusted to pH=5 with saturated citric acid (30 mL). The aqueous phase was extracted with chloroform:isopropanol=3:1 (30 mL*3). The combined organic layers were dried over anhydrous $Na_2SO_4$, filtered and concentrated under reduced pressure. The residue was purified by prep-HPLC (TFA condition) (column: Phenomenex Luna C18 75*30 mm*3 um; mobile phase: [$H_2O$ (0.1% TFA)-ACN]; gradient: 20%-50% B over 8.0 min) to afford 5-(2,2-dimethylmorpholino)-1-((1,2S)-2-methyl-1-(5-oxo-4,5-dihydro-1,2,4-oxadiazol-3-yl)cyclopropyl)-1H-indole-2-carboxylic acid (35 mg, 84.01 μmol, 46.82% yield). $^1H$ NMR (400 MHz, DMSO-$d_6$) δ=12.41-11.83 (m, 1H), 7.41-7.01 (m, 4H), 3.78 (q, J=5.0 Hz, 2H), 3.02-2.95 (m, 2H), 2.87 (d, J=7.6 Hz, 2H), 2.02-1.86 (m, 1H), 1.83-1.71 (m, 1H), 1.66-1.46 (m, 1H), 1.42-1.23 (m, 9H) (The active O—H was not detected). LC-MS (ES+, m/z): 413.2 [$(M+H)^+$]; Rt=0.420 min.

Step 7: 3-((1S,2S)-1-(5-(2,2-dimethylmorpholino)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

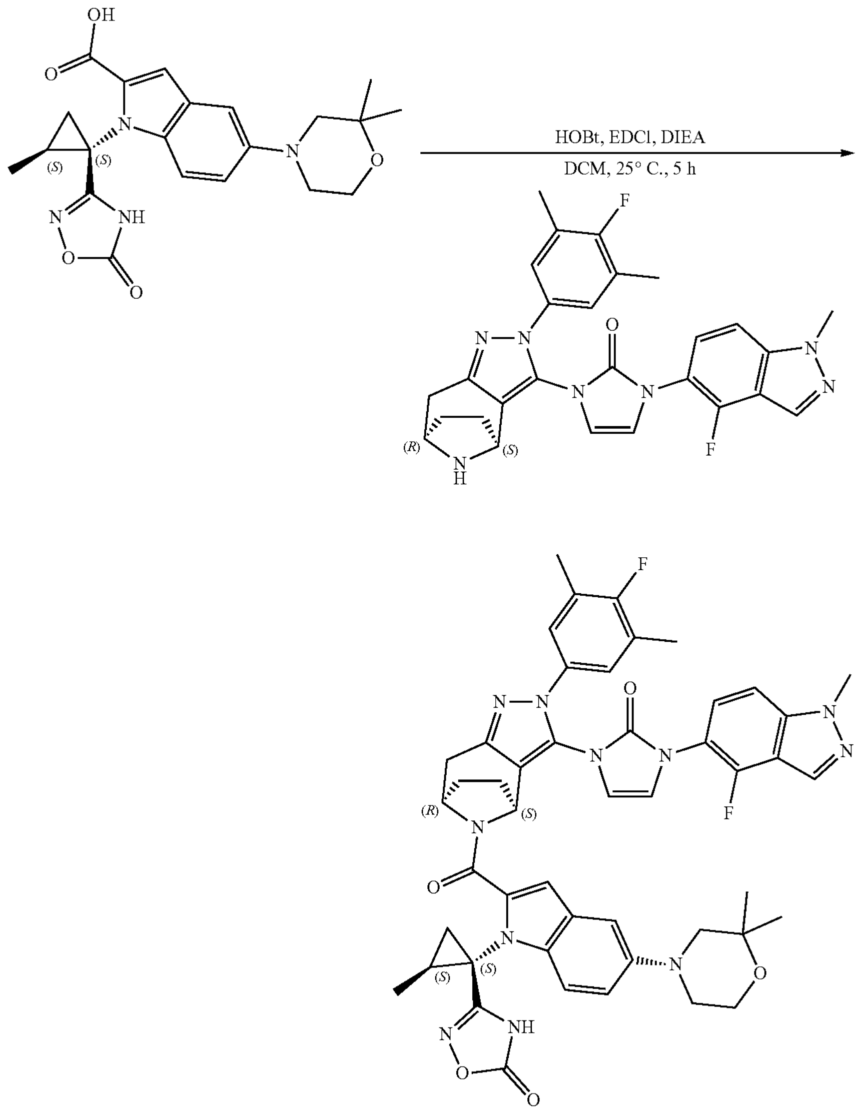

To a mixture of 5-(2,2-dimethylmorpholino)-1-((1S,2S)-2-methyl-1-(5-oxo-4,5-dihydro-1,2,4-oxadiazol-3-yl)cyclopropyl)-1H-indole-2-carboxylic acid (35 mg, 84.01 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (42.13 mg, 84.01 μmol, 1 eq) in DCM (0.7 mL), was added DIEA (54.29 mg, 420.06 μmol, 5 eq), EDCI (20.94 mg, 109.22 μmol, 1.3 eq), HOBt (17.03 mg, 126.02 μmol, 1.5 eq) in one portion at 25° C. under $N_2$. The mixture was stirred at 25° C. for 5 hours. LCMS showed reaction was completed. The reaction solution is quenched with $H_2O$ (20 mL). The aqueous phase was extracted with ethyl acetate (20 mL*3). The combined organic layers were washed with saturated brine (20 mL*3), dried over anhydrous $Na_2SO_4$, filtered and concentrated under reduced pressure. The residue was purified by prep-HPLC (TFA condition) (column: Phenomenex Luna C18 75*30 mm*3 um; mobile phase: [$H_2O$ (0.1% TFA)-ACN]; gradient: 45%-75% B over 8.0 min) to afford 3-((1S,2S)-1-(5-(2,2-dimethylmorpholino)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (33.36 mg, 35.74 μmol, 42.54% yield). $^1H$ NMR (400 MHz, DMSO-$d_6$) δ=12.28-11.46 (m, 1H), 8.44-8.05 (m, 1H), 7.70-6.56 (m, 10H), 5.61-4.91 (m, 2H), 4.16-4.04 (m, 3H), 3.84-3.73 (m, 2H), 3.46-3.33 (m, 2H), 3.18-2.80 (m, 4H), 2.33-2.04 (m, 8H), 2.00-1.34 (m, 5H), 1.33-0.94 (m, 9H). $^1H$ NMR (400 MHz, DMSO-$d_6$+$D_2O$) δ=8.35-8.05 (m, 1H), 7.68-6.52 (m, 10H), 5.70-4.73 (m, 2H), 4.20-3.88 (m, 3H), 3.85-3.76 (m, 2H), 3.62-3.22 (m, 2H), 3.14-2.77 (m, 4H), 2.30-2.04 (m, 8H), 1.89-1.31 (m, 5H), 1.28-0.89 (m, 9H). LC-MS (ES+, m/z): 896.3 [$(M+H)^+$]; Rt=2.947 min. HRMS (EI): m/z $[M+H]^+$ found: 896.3821.

Example 57
Compound 237
3-((1R,28)-1-(3-((48, 7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-28-pyran-4-yl) quinolin-2-yl)-2-methylcyclopropyl)-1,2,4-oxadiazol-5(4H)-one
Scheme 237
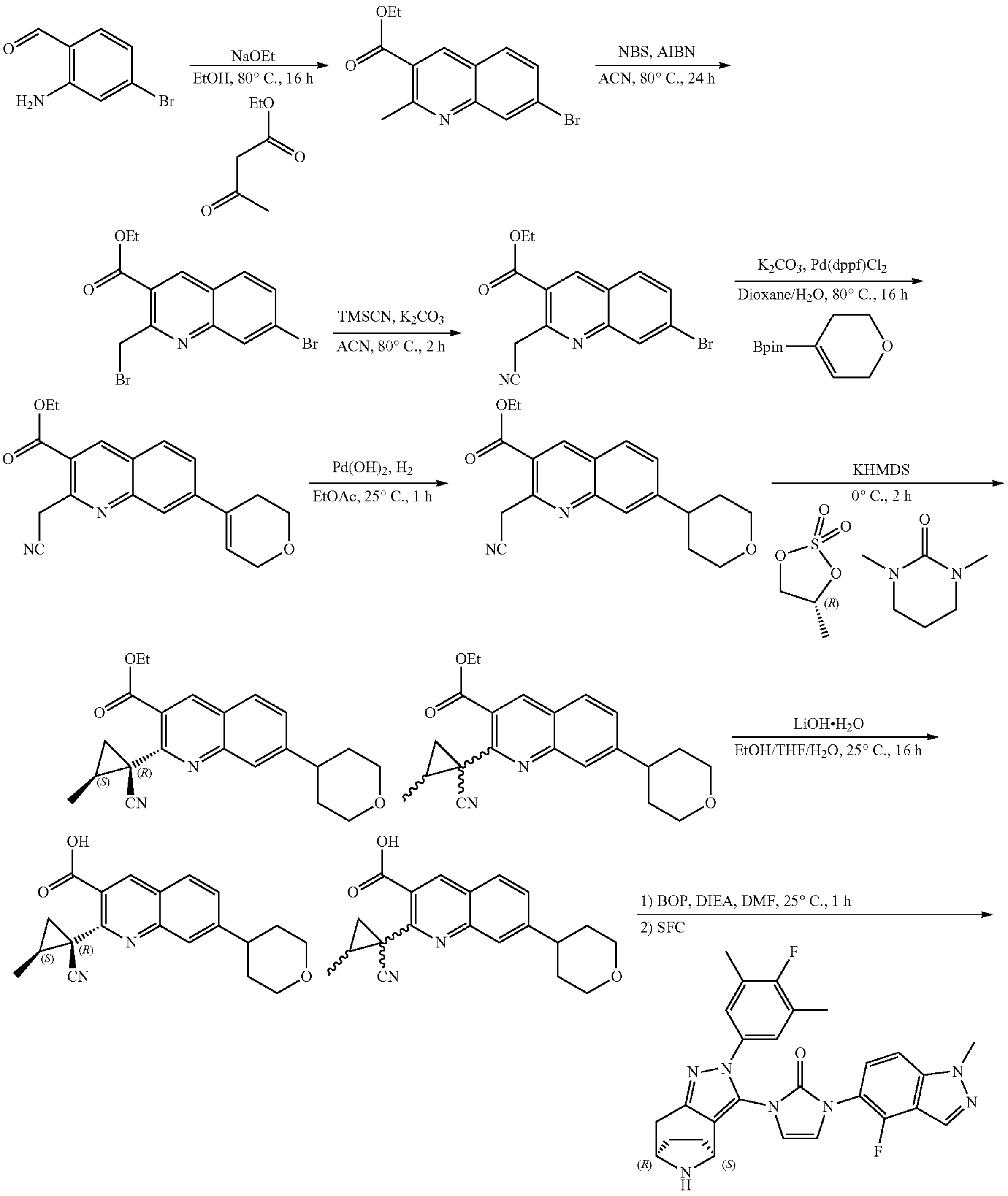

-continued

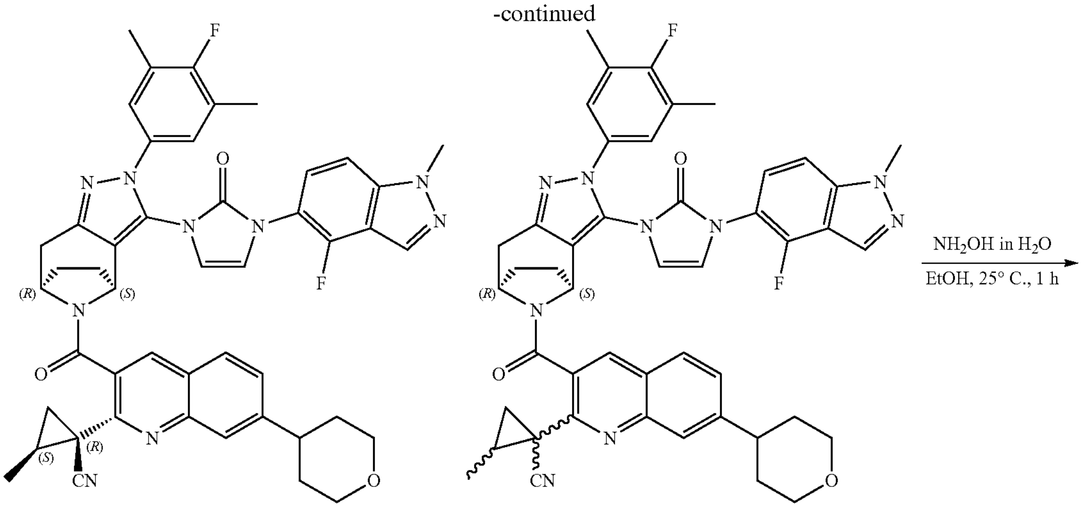

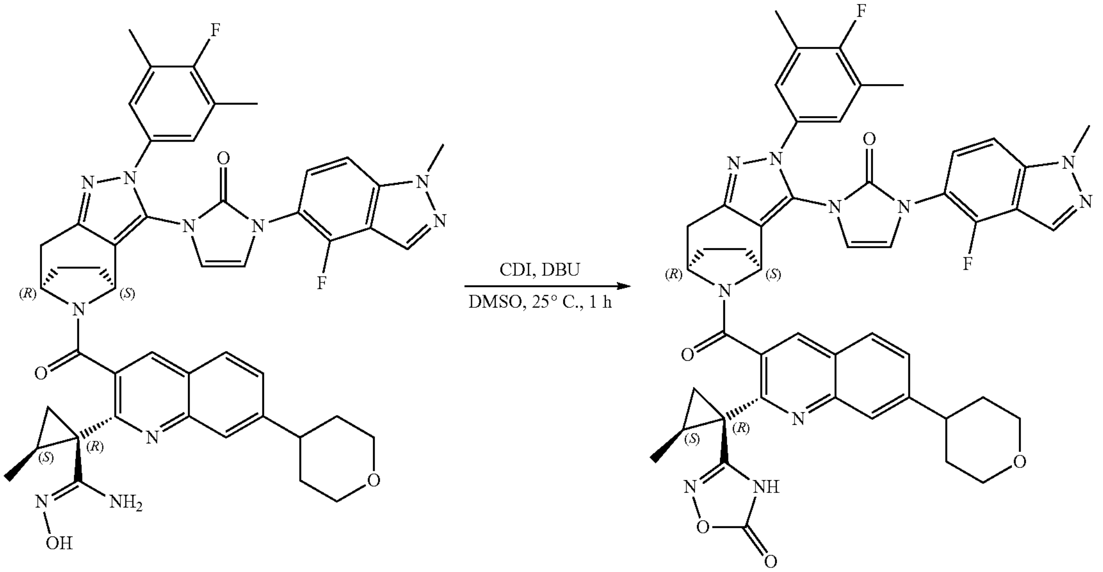

Step 1: ethyl 7-bromo-2-methylquinoline-3-carboxylate

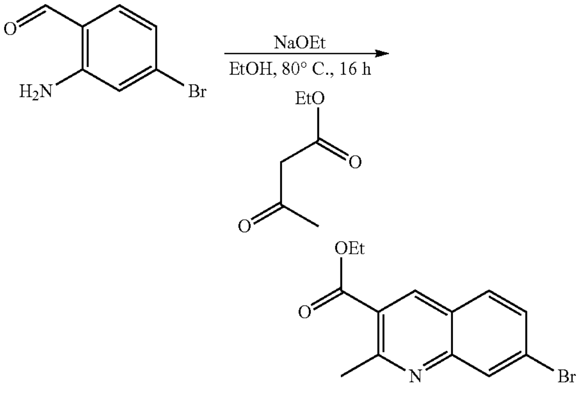

To a solution of 2-amino-4-bromobenzaldehyde (40 g, 199.97 mmol, 1 eq) and ethyl 3-oxobutanoate (39.04 g, 299.95 mmol, 37.97 mL, 1.5 eq) in EtOH (400 mL), was added NaOEt (20.41 g, 299.95 mmol, 1.5 eq). The mixture was stirred at 80° C. for 16 hours (2 parallel reactions). LCMS showed the reaction was completed. The mixture was added to $H_2O$ (200 mL), and then extracted with DCM (200 mL*3). The organic layers were combined, washed with water (400 mL*2), saturated brine (400 mL), dried over $Na_2SO_4$, filtered and concentrated. The residue was purified by prep-HPLC column: Phenomenex luna C18 250*150 mm*15 um; mobile phase: [$H_2O$ (0.1% TFA)-ACN]; gradient: 45%-75% B over 20.0 min) to give ethyl 7-bromo-2-methylquinoline-3-carboxylate (25 g, 84.57 mmol, 42.29% yield). $^1H$ NMR (400 MHz, DMSO-$d_6$) δ=8.88 (s, 1H), 8.22-8.15 (m, 1H), 8.08 (d, J=8.7 Hz, 1H), 7.81-7.74 (m, 1H), 4.38 (q, J=7.1 Hz, 2H), 2.85 (s, 3H), 1.44-1.30 (m, 3H). LC-MS (ES+, m/z): 293.8 [(M+H)$^+$]; Rt=0.526 min.

Step 2: ethyl 7-bromo-2-(bromomethyl) quinoline-3-carboxylate

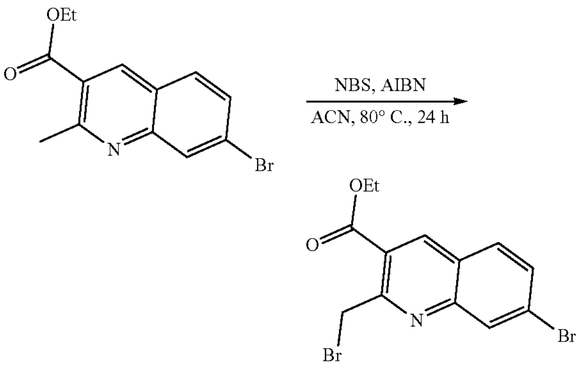

To a solution of ethyl 7-bromo-2-methylquinoline-3-carboxylate (31 g, 105.39 mmol, 1 eq) in ACN (310 mL) was added NBS (90.04 g, 505.88 mmol, 4.8 eq) and AIBN (34.61 g, 210.78 mmol, 2 eq). The mixture was stirred at 80° C. for 24 hours under $N_2$. LCMS showed the reaction was completed. The mixture was added to $H_2O$ (300 mL), and then extracted with DCM (300 mL*3). The organic layers were combined, washed with water (500 mL), saturated brine (500 mL), dried over $Na_2SO_4$, filtered and concentrated. The residue was purified by prep-HPLC column: Phenomenex luna C18 250*150 mm*15 um; mobile phase: [$H_2O$ (0.1% TFA)-ACN]; gradient: 60%-90% B over 20.0 min) to give ethyl 7-bromo-2-(bromomethyl) quinoline-3-carboxylate (14.4 g, 36.71 mmol, 34.83% yield). LC-MS (ES+, m/z): 372.0 [$(M+H)^+$]; Rt=0.619 min.

Step 3: ethyl 7-bromo-2-(cyanomethyl) quinoline-3-carboxylate

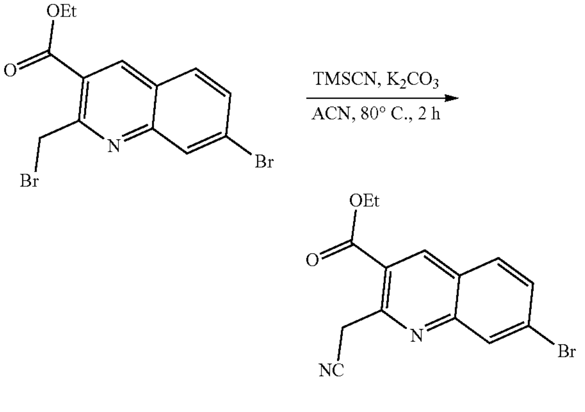

To a solution of ethyl 7-bromo-2-(bromomethyl) quinoline-3-carboxylate (10.4 g, 27.88 mmol, 1 eq) and $K_2CO_3$ (11.56 g, 83.64 mmol, 3 eq) in ACN (312 mL), was added TMSCN (7.26 g, 73.18 mmol, 9.16 mL, 2.62 eq). The mixture was stirred at 80° C. for 2 hours. LCMS showed the reaction was completed. The reaction mixture was diluted with $H_2O$ (100 mL) and extracted with ethyl acetate (100 mL*3). The organic layers were combined, washed with water (200 mL), saturated brine (200 mL), dried over $Na_2SO_4$, filtered, and concentrated under reduced pressure. The crude product was purified by chromatography on silica gel (Petroleum ether/Ethyl acetate=3/1-1/1) to give ethyl 7-bromo-2-(cyanomethyl) quinoline-3-carboxylate (4.4 g, 12.41 mmol, 44.51% yield). LC-MS (ES+, m/z): 318.8 [$(M+H)^+$]; Rt=0.528 min.

Step 4: ethyl 2-(cyanomethyl)-7-(3, 6-dihydro-2H-pyran-4-yl) quinoline-3-carboxylate

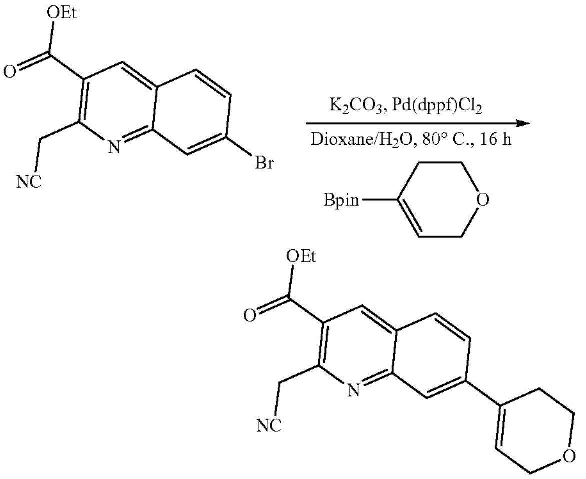

To a solution of ethyl 7-bromo-2-(cyanomethyl) quinoline-3-carboxylate (2.5 g, 7.83 mmol, 1 eq), 2-(3, 6-dihydro-2H-pyran-4-yl)-4, 4, 5, 5-tetramethyl-1, 3, 2-dioxaborolane (1.81 g, 8.62 mmol, 1.1 eq) and $K_2CO_3$ (3.25 g, 23.50 mmol, 3 eq) in dioxane (20 mL) and $H_2O$ (5 mL), was added Pd(dppf)$Cl_2$ (573.16 mg, 783.32 μmol, 0.1 eq). The mixture was stirred at 80° C. for 16 hours under $N_2$. LCMS indicated the reaction was completed. The residue was poured into saturated EDTA solution (30 mL) and ethyl acetate (30 mL) stirred for 0.5 hour, extracted with ethyl acetate (30 mL*2). The organic layers were combined, washed with water (100 mL), saturated brine (100 mL), dried over $Na_2SO_4$, filtered and concentrated to give crude product. The residue was purified by column chromatography ($SiO_2$, Petroleum ether/ethyl acetate=5/1 to 1/3) to give ethyl 2-(cyanomethyl)-7-(3, 6-dihydro-2H-pyran-4-yl) quinoline-3-carboxylate (1.92 g, 5.80 mmol, 74.06% yield). LC-MS (ES+, m/z): 323.1 [$(M+H)^+$]; Rt=0.512 min.

Step 5: ethyl 2-(cyanomethyl)-7-(tetrahydro-2H-pyran-4-yl) quinoline-3-carboxylate

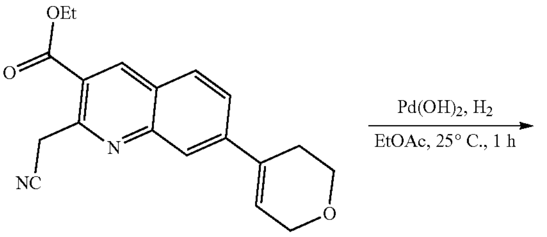

-continued

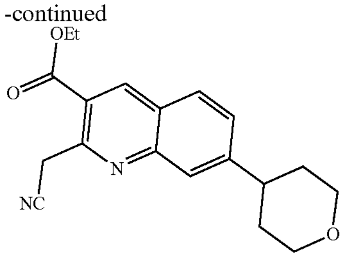

To a suspension of $Pd(OH)_2$ (2.00 g, 1.42 mmol, 20% purity, 0.23 eq) in ethyl acetate (200 mL) was added ethyl 2-(cyanomethyl)-7-(3, 6-dihydro-2H-pyran-4-yl) quinoline-3-carboxylate (2 g, 6.20 mmol, 1 eq). The mixture was stirred at 25° C. for 1 hour under $H_2$ (15 Psi). LCMS indicated the reaction was completed. The reaction mixture was filtered and concentrated under reduced pressure. The residue was purified by prep-HPLC (column: Phenomenex luna c18 250 mm*100 mm*15 um; mobile phase: [$H_2O$ (0.1% TFA)-ACN]; gradient: 30%-60% B over 26.0 min) to give ethyl 2-(cyanomethyl)-7-(tetrahydro-2H-pyran-4-yl) quinoline-3-carboxylate (1.04 g, 3.17 mmol, 51.11% yield). LC-MS (ES+, m/z): 325.2 [$(M+H)^+$]. Rt=1.674 min.

Step 6: ethyl 2-((1R,2S)-1-cyano-2-methylcyclopropyl)-7-(tetrahydro-2H-pyran-4-yl) quinoline-3-carboxylate

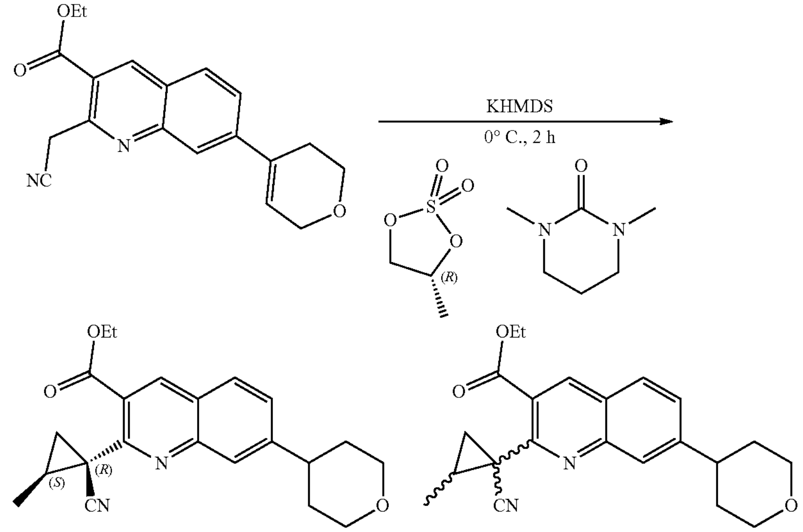

To a solution of ethyl 2-(cyanomethyl)-7-(tetrahydro-2H-pyran-4-yl) quinoline-3-carboxylate (800 mg, 2.47 mmol, 1 eq) and (R)-4-methyl-1, 3, 2-dioxathiolane 2, 2-dioxide (1.02 g, 7.40 mmol, 3 eq) in 1, 3-dimethyltetrahydropyrimidin-2 (1H)-one (8 mL), was added KHMDS (1 M, 9.87 mL, 4 eq) dropwise at 0° C. under $N_2$. The mixture was stirred at 0° C. for 2 hours under $N_2$. LCMS indicated that the reaction was completed. The mixture was added dropwise to $NH_4Cl$ (20 mL), and then extracted with ethyl acetate (20 mL*3). The organic layers were combined, washed with water (50 mL), saturated brine (50 mL), dried over $Na_2SO_4$, filtered and concentrated. The crude product was purified by prep-TLC ($SiO_2$, Petroleum ether: Ethyl acetate=1:1) to give ethyl 2-((1R,2S)-1-cyano-2-methylcyclopropyl)-7-(tetrahydro-2H-pyran-4-yl) quinoline-3-carboxylate and ethyl 2-(1-cyano-2-methylcyclopropyl)-7-(tetrahydro-2H-pyran-4-yl) quinoline-3-carboxylate (400 mg, 1.01 mmol, 40.77% yield). LC-MS (ES+, m/z): 365.2 [$(M+H)^+$]. Rt=0.560 min.

Step 7: 2-((1R,2S)-1-cyano-2-methylcyclopropyl)-7-(tetrahydro-2H-pyran-4-yl) quinoline-3-carboxylic acid

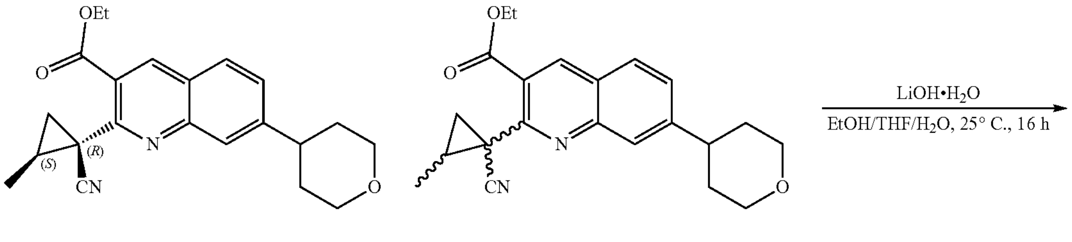

-continued

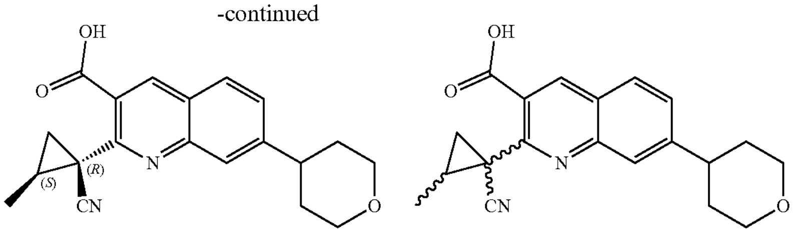

To a solution of ethyl 2-((1R,2S)-1-cyano-2-methylcyclopropyl)-7-(tetrahydro-2H-pyran-4-yl) quinoline-3-carboxylate and ethyl 2-(1-cyano-2-methylcyclopropyl)-7-(tetrahydro-2H-pyran-4-yl) quinoline-3-carboxylate (400 mg, 1.10 mmol, 1 eq) in THF (1.7 mL), EtOH (1.7 mL) and $H_2O$ (1.7 mL), was added $LiOH{\cdot}H_2O$ (460.59 mg, 10.98 mmol, 10 eq). The mixture was stirred at 25° C. for 16 hours. LCMS showed the reaction was completed. The mixture was concentrated to give crude product. The residue was dissolved in water (10 mL), adjusted to pH=4 with HCl (2M), and then extracted with DCM (20 mL*3). The organic layers were combined, washed with water (50 mL), saturated brine (50 mL), dried over $Na_2SO_4$, filtered and concentrated to give 2-((1R,2S)-1-cyano-2-methylcyclopropyl)-7-(tetrahydro-2H-pyran-4-yl) quinoline-3-carboxylic acid and 2-(1-cyano-2-methylcyclopropyl)-7-(tetrahydro-2H-pyran-4-yl) quinoline-3-carboxylic acid (300 mg, 816.03 μmol, 74.35% yield). LC-MS (ES+, m/z): 337.2 [(M+H)$^+$]; Rt=0.452 min.

Step 8: (1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-2H-pyran-4-yl) quinolin-2-yl)-2-methylcyclopropane-1-carbonitrile

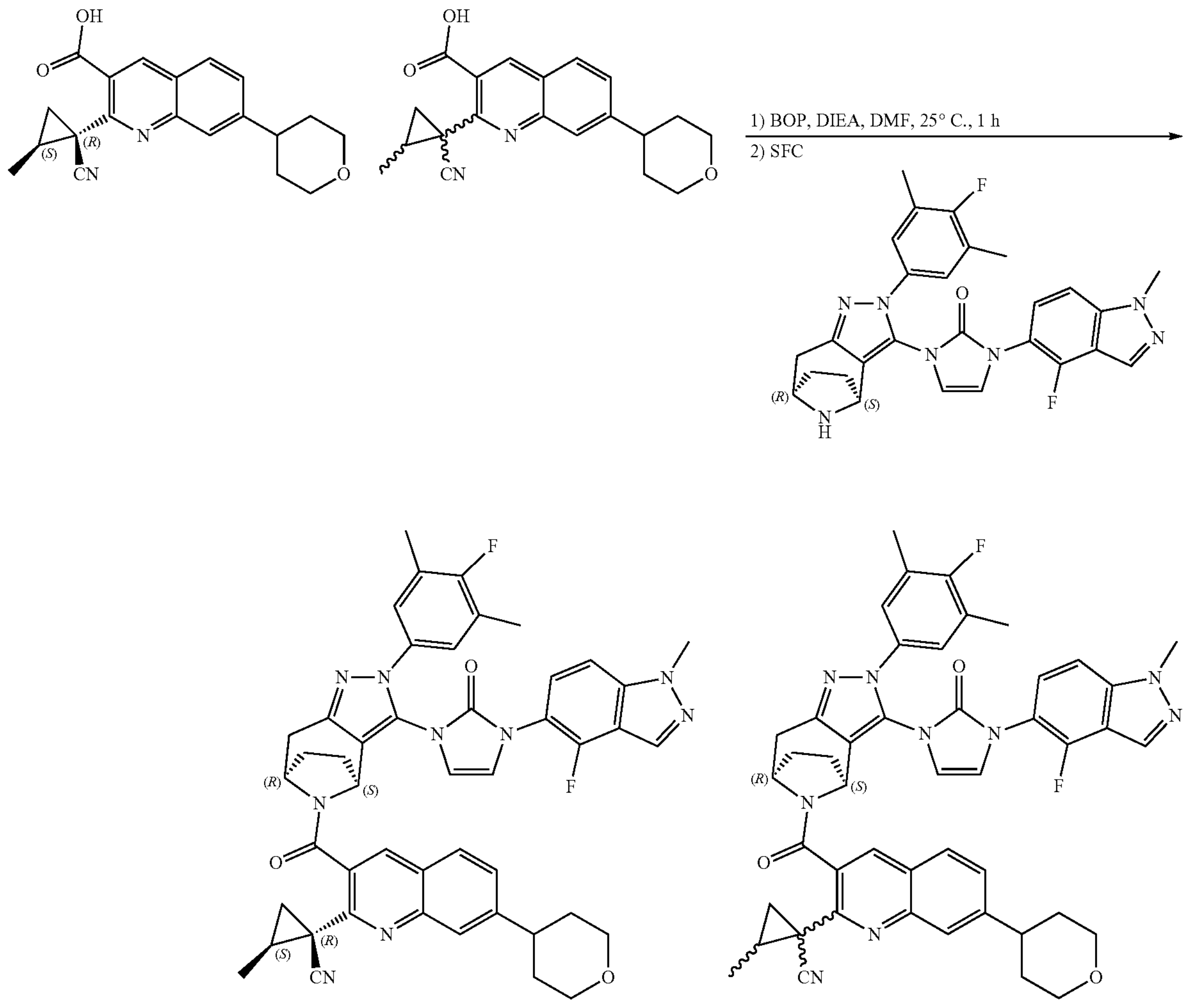

first eluent second eluent

To a solution of 2-((1R,2S)-1-cyano-2-methylcyclopropyl)-7-(tetrahydro-2H-pyran-4-yl) quinoline-3-carboxylic acid and 2-(1-cyano-2-methylcyclopropyl)-7-(tetrahydro-2H-pyran-4-yl) quinoline-3-carboxylic acid (100 mg, 297.28 μmol, 1 eq), 1-(4-fluoro-1-methyl-1H-indazol-5-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (159.93 mg, 297.28 μmol, 1 eq, HCl) and DIPEA (384.20 mg, 2.97 mmol, 517.80 μL, 10 eq) in DMF (2 mL), was added BOP (144.63 mg, 327.01 μmol, 1.1 eq). The mixture was stirred at 25° C. for 1 hour. LCMS showed the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated to give crude product. The residue was purified by prep-TLC ($SiO_2$, Petroleum ether/Ethyl acetate=1/10. The two isomers were separated by SFC separation column: DAICEL CHIRALCEL OD (250 mm*30 mm, 10 um); mobile phase: [$CO_2$-IPA: ACN=1:1]; B %: 45%, isocratic elution mode) to give (1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epimino-cyclohepta [c]pyrazole-9-carbonyl)-7-(tetrahydro-2H-pyran-4-yl) quinolin-2-yl)-2-methylcyclopropane-1-carbonitrile (60 mg, 71.35 μmol, 24.00% yield, first eluent). LC-MS (ES+, m/z): 820.3 [$(M+H)^+$]; Rt=0.604 min.

And 1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epimino-cyclohepta [c]pyrazole-9-carbonyl)-7-(tetrahydro-2H-pyran-4-yl) quinolin-2-yl)-2-methylcyclopropane-1-carbonitrile (50 mg, 58.91 μmol, 19.82% yield, second eluent). LC-MS (ES+, m/z): 820.4 [$(M+H)^+$]; Rt=0.589 min.

-continued

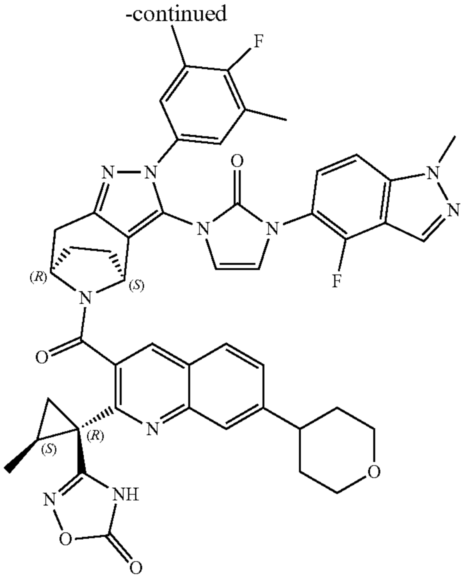

Step 9: (1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-2H-pyran-4-yl) quinolin-2-yl)-N'-hydroxy-2-methylcyclopropane-1-carboximidamide

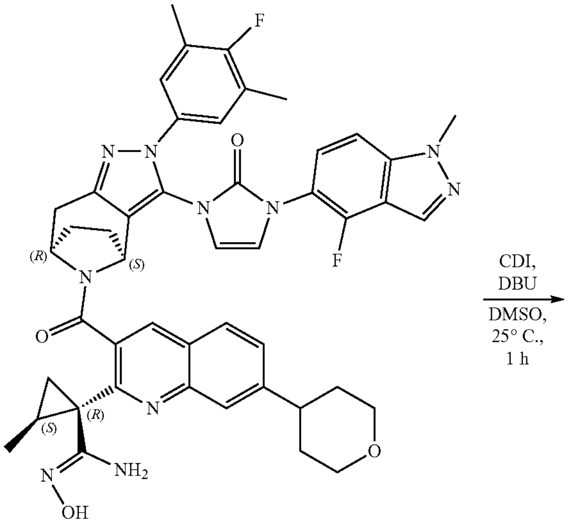

To a solution of (1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-2H-pyran-4-yl) quinolin-2-yl)-2-methylcyclopropane-1-carbonitrile (60 mg, 71.35 μmol, 1 eq) in EtOH (1 mL), was added $NH_2OH$ (47.13 mg, 713.50 μmol, 50% purity, 10 eq). The mixture was stirred at 25° C. for 1 hour. LCMS showed the reaction was completed. The mixture was added dropwise to $H_2O$ (15 mL), and then extracted with DCM (20 mL*3). The organic layers were combined, washed with water (50 mL), saturated brine (50 mL), dried over $Na_2SO_4$, filtered and concentrated to give (1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epimino-cyclohepta [c]pyrazole-9-carbonyl)-7-(tetrahydro-2H-pyran-4-yl) quinolin-2-yl)-N'-hydroxy-2-methylcyclopropane-1-carboximidamide (60 mg, crude). LC-MS (ES+, m/z): 853.3 [$(M+H)^+$]; Rt=0.487 min.

Step 10: 3-((1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-2H-pyran-4-yl) quinolin-2-yl)-2-methylcyclopropyl)-1, 2, 4-oxadiazol-5 (4H)-one

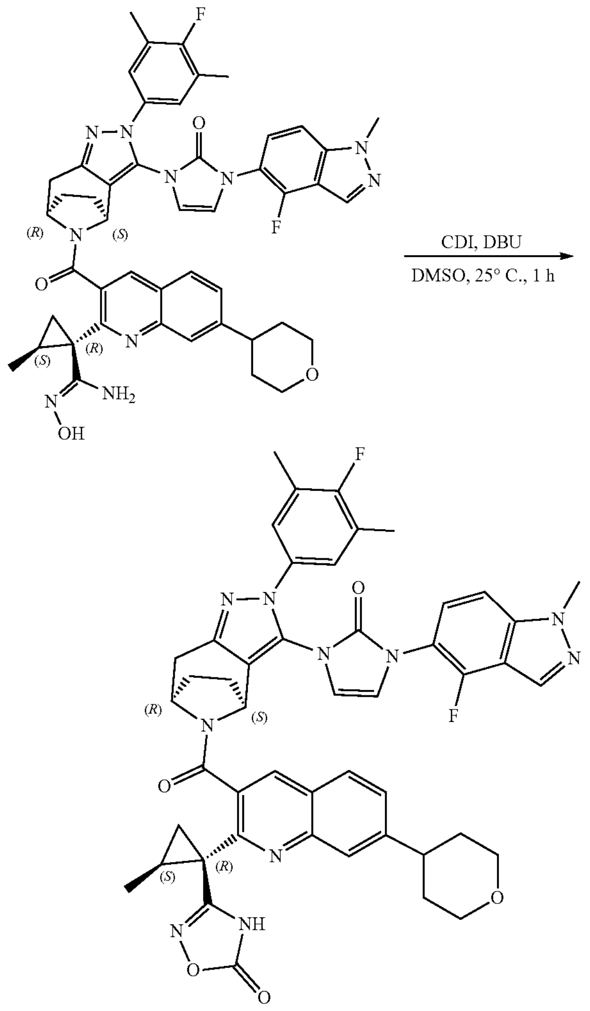

To a solution of (1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-2H-pyran-4-yl) quinolin-2-yl)-N'-hydroxy-2-methylcyclopropane-1-carboximidamide (60 mg, 44.60 μmol, 1 eq) and DBU (16.97 mg, 111.50 μmol, 16.81 μL, 2.5 eq) in DMSO (1.2 mL), was added CDI (14.46 mg, 89.20 μmol, 2 eq). The mixture was stirred at 25° C. for 1 hour. LCMS showed the reaction was completed. The mixture was filtered. The filtrate was purified by prep-HPLC column: Phenomenex Luna C18 75*30 mm*3 um; mobile phase: [$H_2O$ (0.1% TFA)-ACN]; gradient: 45%-75% B over 8.0 min) to give 3-((1R,2S)-1-(3-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-7-(tetrahydro-2H-pyran-4-yl) quinolin-2-yl)-2-methylcyclopropyl)-1, 2, 4-oxadiazol-5 (4H)-one (12.56 mg, 14.25 μmol, 31.95% yield). $^1$H NMR (400 MHz, DMSO-$d_6$) δ=12.19-11.77 (m, 1H), 8.58-8.45 (m, 1H), 8.33-8.05 (m, 2H), 7.91-7.82 (m, 1H), 7.73-7.48 (m, 3H), 7.31-7.02 (m, 3H), 6.95-6.71 (m, 1H), 5.00 (br s, 1H), 4.82-4.30 (m, 1H), 4.15-4.07 (m, 3H), 4.01 (br d, J=9.1 Hz, 2H), 3.72-3.65 (m, 2H), 3.20 (br d, J=15.3 Hz, 2H), 2.83-2.71 (m, 1H), 2.31-2.02 (m, 10H), 1.85-1.57 (m, 6H), 1.50-1.38 (m, 1H), 0.87-0.74 (m, 3H). $^1$H NMR (400 MHz, MeOD-$d_4$) δ=8.51-7.82 (m, 4H), 7.78-7.05 (m, 5H), 6.97-6.26 (m, 2H), 5.69-4.94 (m, 1H), 4.50-4.35 (m, 1H), 4.27-4.00 (m, 5H), 3.70-3.60 (m, 2H), 3.39-3.35 (m, 1H), 3.13-2.99 (m, 1H), 2.92-2.79 (m, 1H), 2.56 (br s, 2H), 2.37-1.72 (m, 14H), 1.57-1.42 (m, 1H), 1.06-0.80 (m, 3H). LC-MS (ES+, m/z): 879.3 [$(M+H)^+$]; Rt=2.646 min. HRMS (EI): m/z $[M+H]^+$ found: 879.3516.

Example 58 Compound 242

3-((1S,2S)-1-(2-((4R,8S)-3-(3-(4,7-difluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-(4-oxaspiro[2.5]octan-7-yl)-1H-indol-1-yl)-2-methylcyclopropyl)-1,2,4-oxadiazol-5 (4H)-one

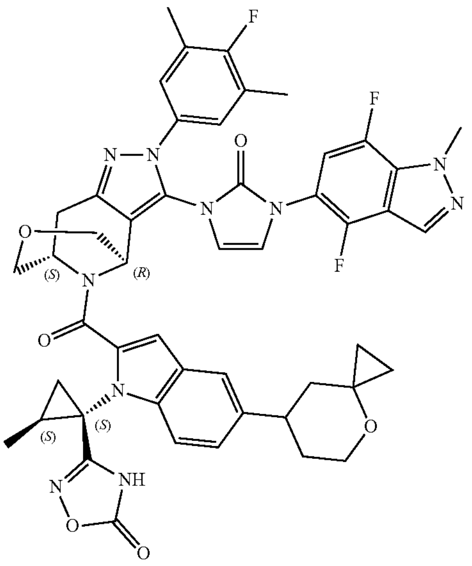

Step 1: 3-((1S,2S)-1-(2-((4R,8S)-3-(3-(4,7-difluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-(4-oxaspiro[2.5]octan-7-yl)-1H-indol-1-yl)-2-methylcyclopropyl)-1,2,4-oxadiazol-5(4H)-one extracted with ethyl acetate (20 mL*3). The organic layers were combined, washed with water (20 mL), saturated brine (20 mL), dried over $Na_2SO_4$, filtered and concentrated. The residue was purified by prep-HPLC (column: Phenomenex Luna C18 75*30 mm*3 um; mobile phase: [$H_2O$ (0.1% TFA)-ACN]; gradient: 55%-85% B over 8.0 min) to afford 3-((1S,2S)-1-(2-((4R,8S)-3-(3-(4,7-difluoro-1-methyl-1H-

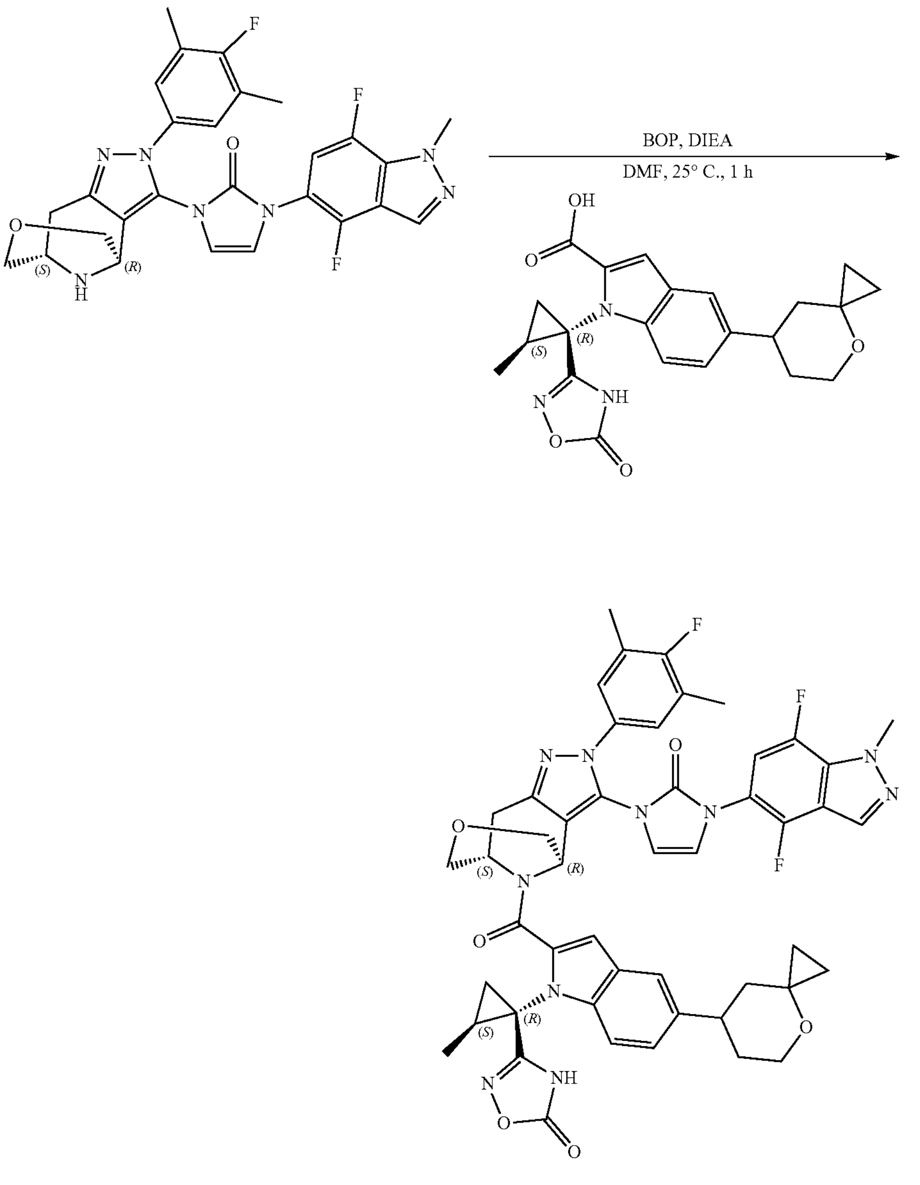

To a solution of 1-(4,7-difluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (15 mg, 26.22 μmol, 1 eq, HCl) and 1-((1S,2S)-2-methyl-1-(5-oxo-4,5-dihydro-1,2,4-oxadiazol-3-yl)cyclopropyl)-5-(4-oxaspiro[2.5]octan-7-yl)-1H-indole-2-carboxylic acid (16.11 mg, 39.34 μmol, 1.5 eq) in DMF (0.3 mL) was added DIPEA (16.95 mg, 131.12 μmol, 22.84 μL, 5 eq) and BOP (12.76 mg, 28.85 μmol, 1.1 eq). The mixture was stirred at 25° C. for 2 hours (2 batches in parallel). LCMS indicated the reaction was completed. The mixture was added dropwise to $H_2O$ (10 mL), and then indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(4-oxaspiro[2.5]octan-7-yl)-1H-indol-1-yl)-2-methylcyclopropyl)-1,2,4-oxadiazol-5 (4H)-one (9.66 mg, 10.42 μmol, 39.74% yield). $^1H$ NMR (400 MHz, DMSO-$d_6$) δ=12.13-11.11 (m, 1H), 8.48-8.06 (m, 1H), 7.71-6.47 (m, 9H), 5.76-4.62 (m, 2H), 4.28-3.48 (m, 9H), 3.12-2.86 (m, 3H), 2.29-2.22 (m, 6H), 1.93-0.41 (m, 14H). $^1H$ NMR (400 MHz, MeOD-$d_6$) δ=8.25-8.02 (m, 1H), 7.59-6.31 (m, 9H), 5.91-4.89 (m, 2H), 4.26 (s, 10H), 3.20-3.01 (m, 2H), 2.32-2.23 (m, 6H), 1.94-0.49 (m, 14H). LC-MS (ES+, m/z): 927.3 [$(M+H)^+$]; Rt=3.102 min. HRMS (EI): m/z $[M+H]^+$ found: 927.3522.

Example 59 Compound 302
3-((1S,2S)-1-(5-((S)-2,2-dimethyltetrahydro-2H-pyran-4-yl)-2-((4S,7R)-2-(4-fluoro-3,5-dimethylphenyl)-3-(3-(1-methyl-1H-indazol-5-yl)-2-oxo-2,3-dihydro-1H-imidazol-1-yl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one
Scheme 302
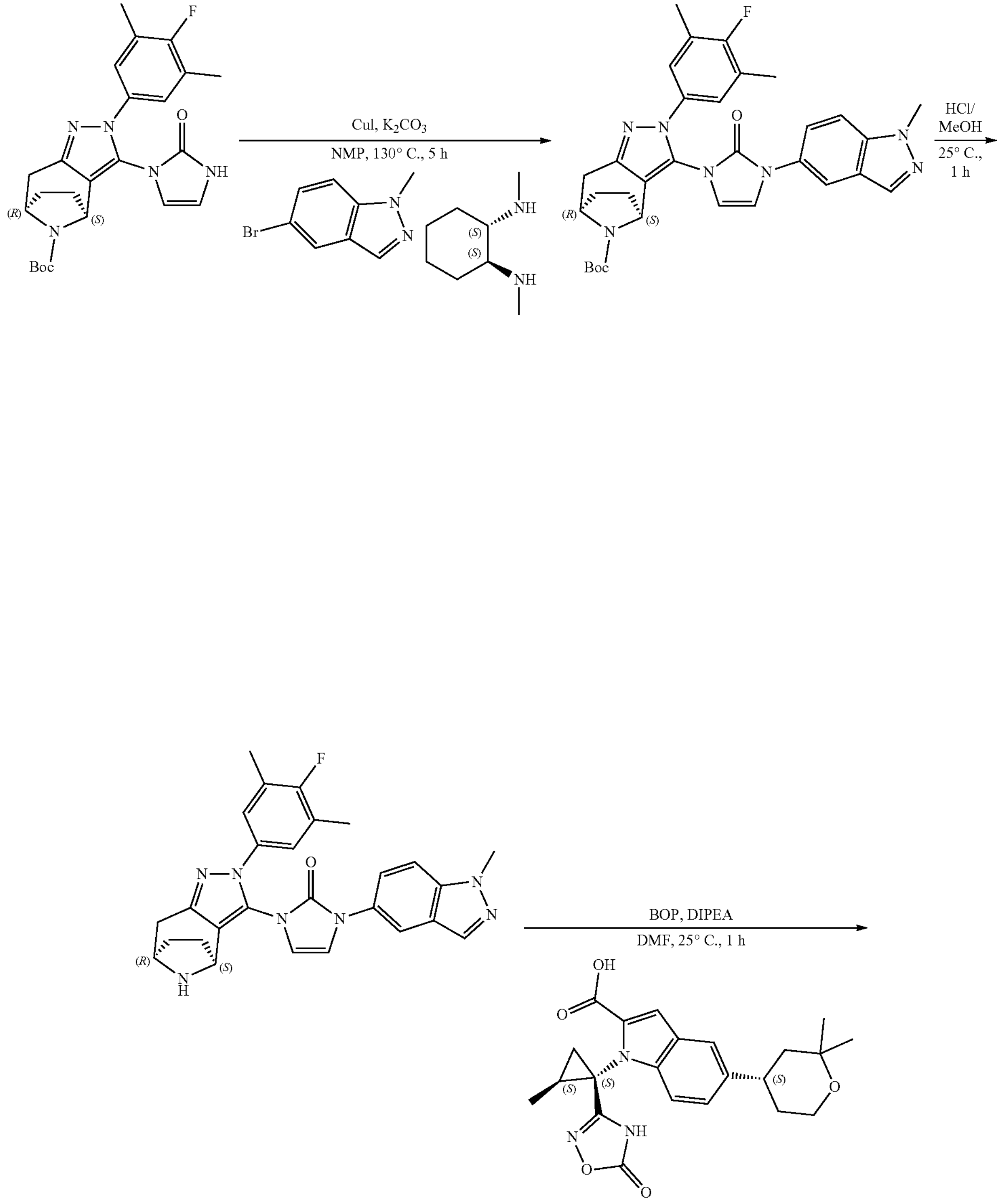

-continued

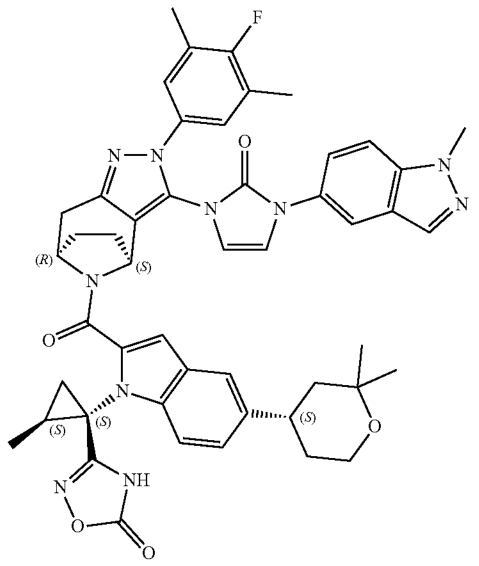

Step 1: tert-butyl (4S,7R)-2-(4-fluoro-3,5-dimethylphenyl)-3-(3-(1-methyl-1H-indazol-5-yl)-2-oxo-2,3-dihydro-1H-imidazol-1-yl)-2,4,5,6,7,8-hexahydro-4,7-epiminocyclohepta [c]pyrazole-9-carboxylate

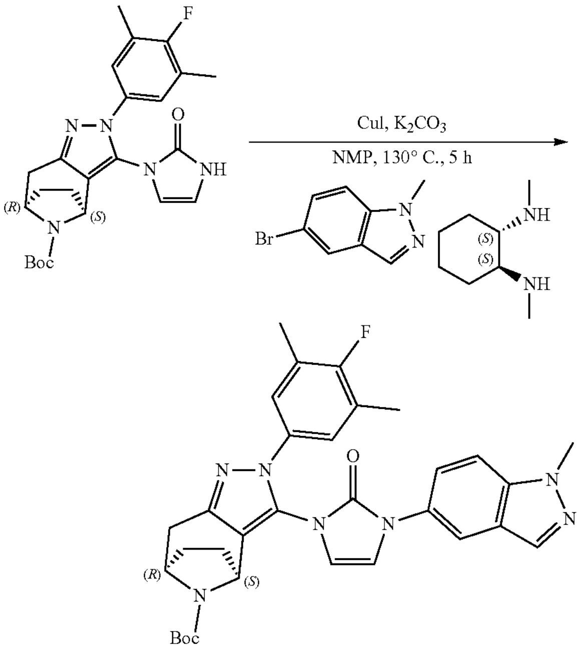

To a solution of tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (200 mg, 441.01 μmol, 1 eq), 5-bromo-1-methyl-1H-indazole (186.16 mg, 882.01 μmol, 2 eq), $K_2CO_3$ (243.80 mg, 1.76 mmol, 4 eq) in NMP (6 mL) was added (1S,2S)—$N_1$,$N_2$-dimethylcyclohexane-1,2-diamine (94.09 mg, 661.51 μmol, 1.5 eq), CuI (167.98 mg, 882.01 μmol, 2 eq). The mixture was stirred at 130° C. for 5 hours under $N_2$. LCMS indicated the reaction was completed. The residue was poured into saturated EDTA solution (100 mL) and ethyl acetate (100 mL) stirred for 0.5 hour, and then extracted with ethyl acetate (100 mL*2). The organic layers were washed with water (80 mL*2), saturated brine (80 mL*2), dried over $Na_2SO_4$, filtered, concentrated under reduced pressure. The crude product was purified by chromatography on silica gel (Petroleum ether:ethyl acetate=2:1) to give tert-butyl (4S,7R)-2-(4-fluoro-3,5-dimethylphenyl)-3-(3-(1-methyl-1H-indazol-5-yl)-2-oxo-2,3-dihydro-1H-imidazol-1-yl)-2,4,5,6,7,8-hexahydro-4,7-epiminocyclohepta [c]pyrazole-9-carboxylate (200 mg, 329.99 μmol, 74.83% yield). LC-MS (ES+, m/z): 584.3 [$(M+H)^+$]; Rt=0.566 min.

Step 2: 1-((4S,7R)-2-(4-fluoro-3,5-dimethylphenyl)-2,4,5,6,7,8-hexahydro-4,7-epiminocyclohepta [c]pyrazol-3-yl)-3-(1-methyl-1H-indazol-5-yl)-1,3-dihydro-2H-imidazol-2-one

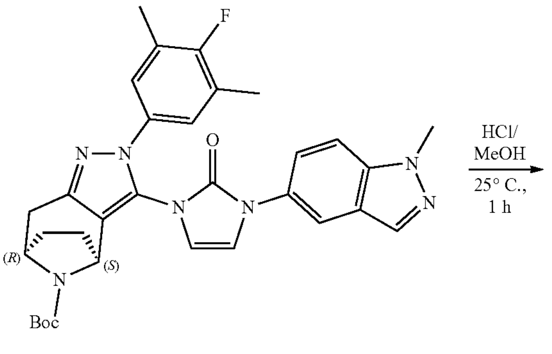

-continued

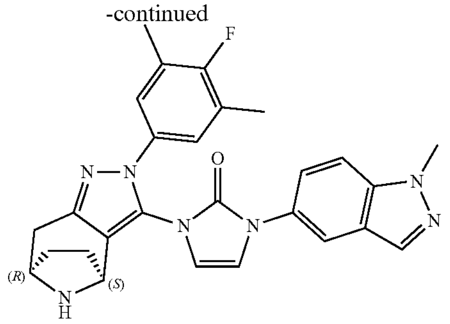

A mixture of tert-butyl (4S,7R)-2-(4-fluoro-3,5-dimethylphenyl)-3-(3-(1-methyl-1H-indazol-5-yl)-2-oxo-2,3-dihydro-1H-imidazol-1-yl)-2,4,5,6,7,8-hexahydro-4,7-epiminocyclohepta [c]pyrazole-9-carboxylate (200 mg, 342.67 μmol, 1 eq), HCl/MeOH (4 M, 20 mL) was stirred at 25° C. for 1 hour. LCMS indicated the reaction was completed. The mixture was concentrated to dryness to give 1-((4S,7R)-2-(4-fluoro-3,5-dimethylphenyl)-2,4,5,6,7,8-hexahydro-4,7-epiminocyclohepta [c]pyrazol-3-yl)-3-(1-methyl-1H-indazol-5-yl)-1,3-dihydro-2H-imidazol-2-one (160 mg, crude, HCl). LC-MS (ES+, m/z): 484.2 [$(M+H)^+$]; Rt=0.398 min.

Step 3: 3-((1S,2S)-1-(5-((S)-2,2-dimethyltetrahydro-2H-pyran-4-yl)-2-((4S,7R)-2-(4-fluoro-3,5-dimethylphenyl)-3-(1-methyl-1H-indazol-5-yl)-2-oxo-2,3-dihydro-1H-imidazol-1-yl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one

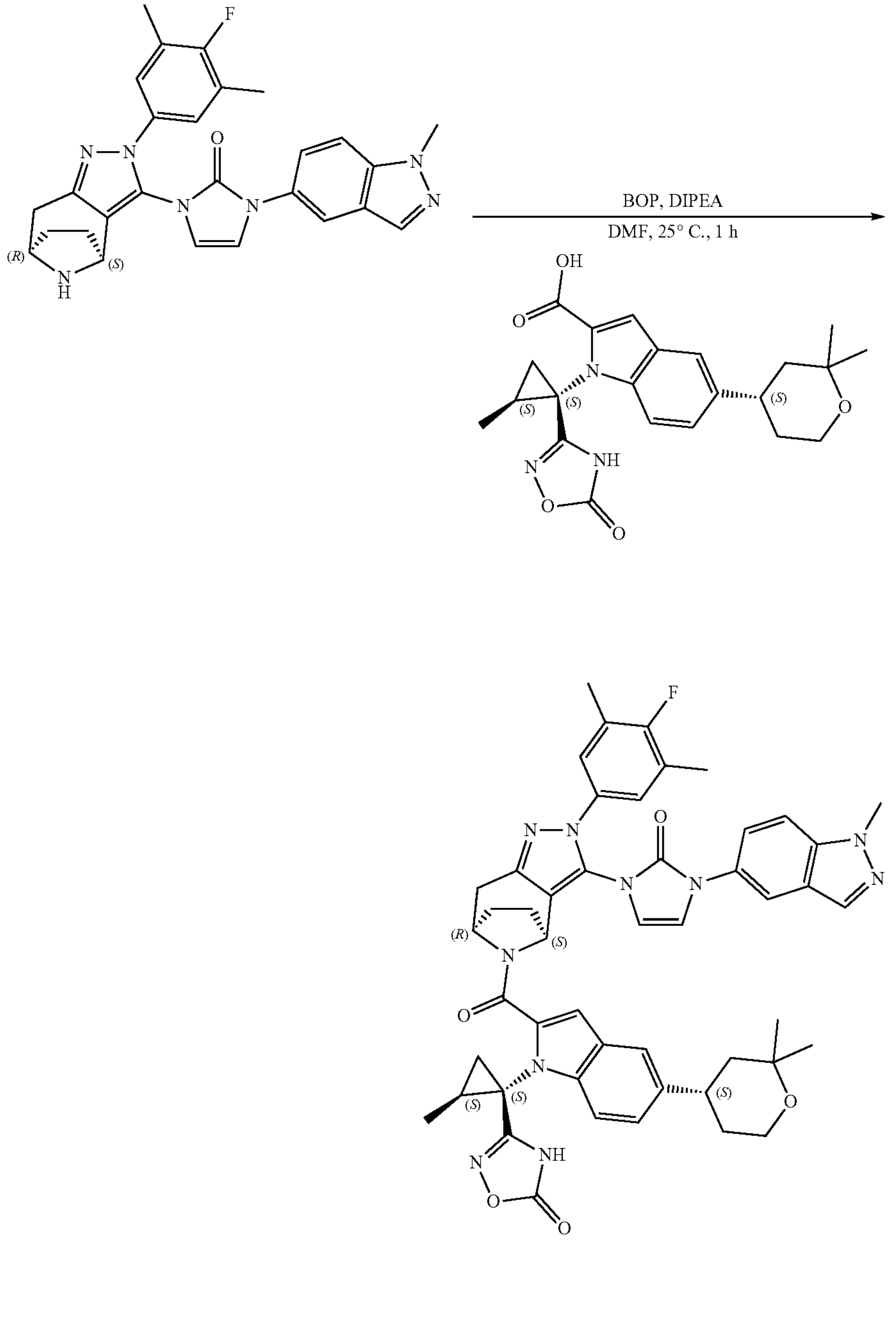

To a solution of 1-((4S,7R)-2-(4-fluoro-3,5-dimethylphenyl)-2,4,5,6,7,8-hexahydro-4,7-epiminocyclohepta [c]pyrazol-3-yl)-3-(1-methyl-1H-indazol-5-yl)-1,3-dihydro-2H-imidazol-2-one (50 mg, 96.15 μmol, 1 eq, HCl), 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (79.13 mg, 192.31 μmol, 2 eq) in DMF (0.5 mL) was added DIPEA (62.14 mg, 480.77 μmol, 83.74 μL, 5 eq) and BOP (63.79 mg, 144.23 μmol, 1.5 eq). The mixture was stirred at 25° C. for 1 hour. LCMS indicated the reaction was completed. The mixture was filtered. The filtrate was purified by prep-HPLC (column: Phenomenex Luna C18 75*30 mm*3 um; mobile phase: [$H_2O$ (0.1% TFA)-ACN]; gradient: 55%-85% B over 8.0 min) to give 3-((1S,2S)-1-(5-((S)-2,2-dimethyltetrahydro-2H-pyran-4-yl)-2-((4S,7R)-2-(4-fluoro-3,5-dimethylphenyl)-3-(3-(1-methyl-1H-indazol-5-yl)-2-oxo-2,3-dihydro-1H-imidazol-1-yl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (8.58 mg, 9.55 μmol, 9.93% yield). $^1$H NMR (400 MHz, DMSO-$d_6$) δ=11.98-11.37 (m, 1H), 8.15-6.47 (m, 12H), 5.61-4.78 (m, 2H), 4.06 (s, 3H), 3.79-3.57 (m, 2H), 3.09-2.73 (m, 3H), 2.32-2.06 (m, 8H), 2.03-1.73 (m, 2H), 1.68-1.42 (m, 6H), 1.39-0.92 (m, 10H). LC-MS (ES+, m/z): 877.3 [$(M+H)^+$]; Rt=3.161 min. HRMS (EI): m/z $[M+H]^+$ found: 877.4032.

Example 60 Compound 305

3-((1S,2S)-1-(2-((45,7R)-3-(3-(1,4-dimethyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one Scheme 305

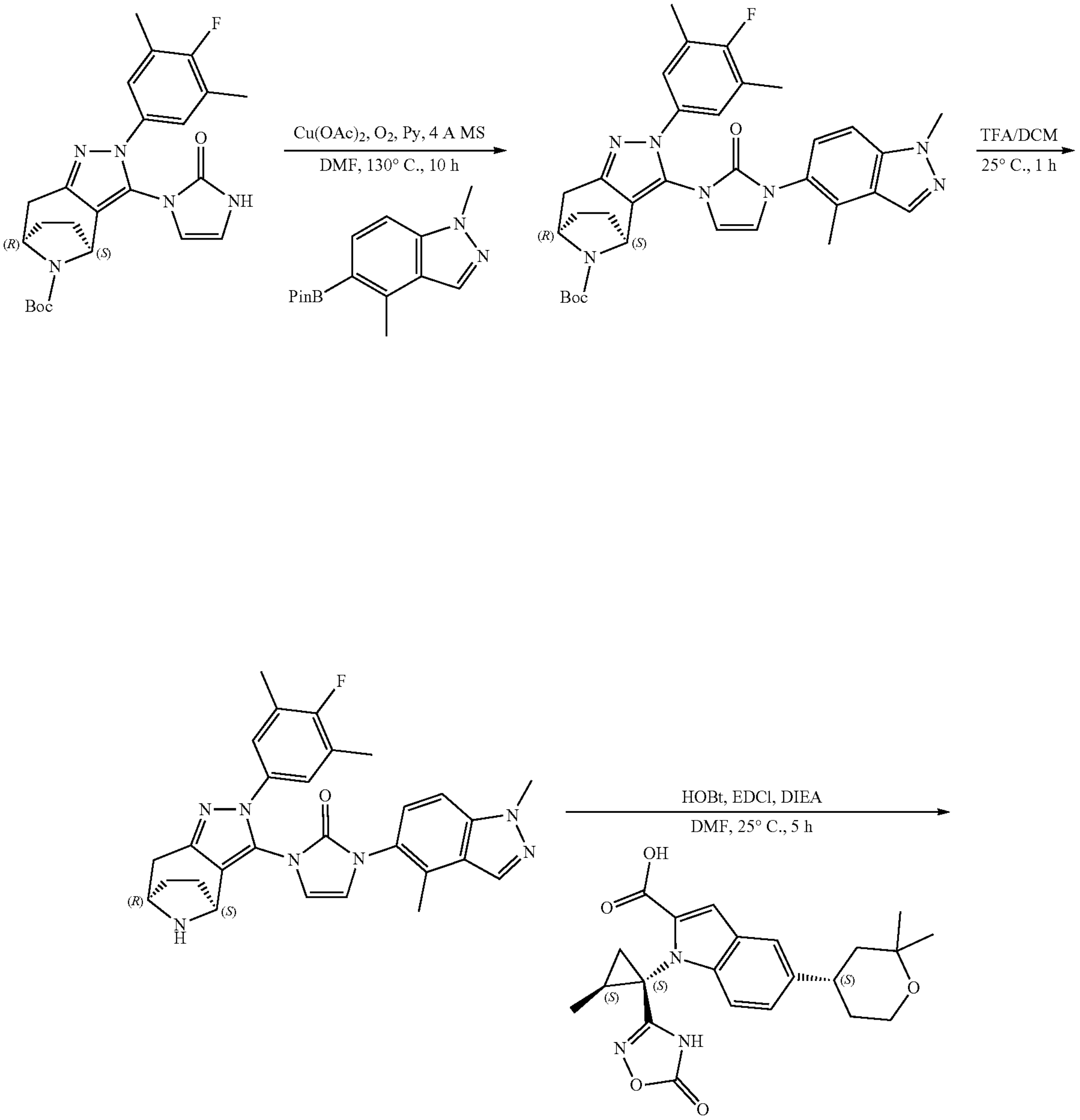

-continued

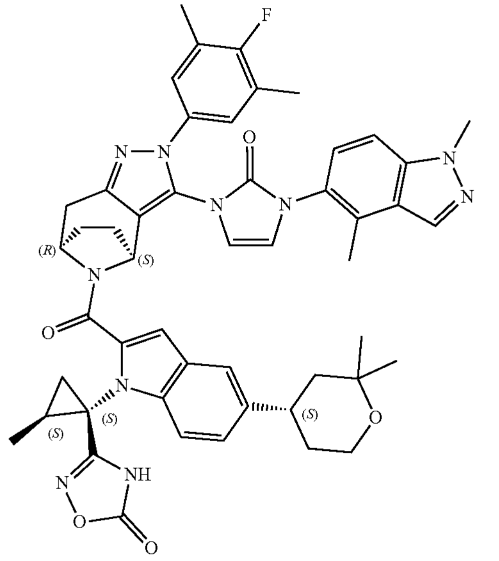

Step 1: tert-butyl (4S,7R)-3-(3-(1,4-dimethyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

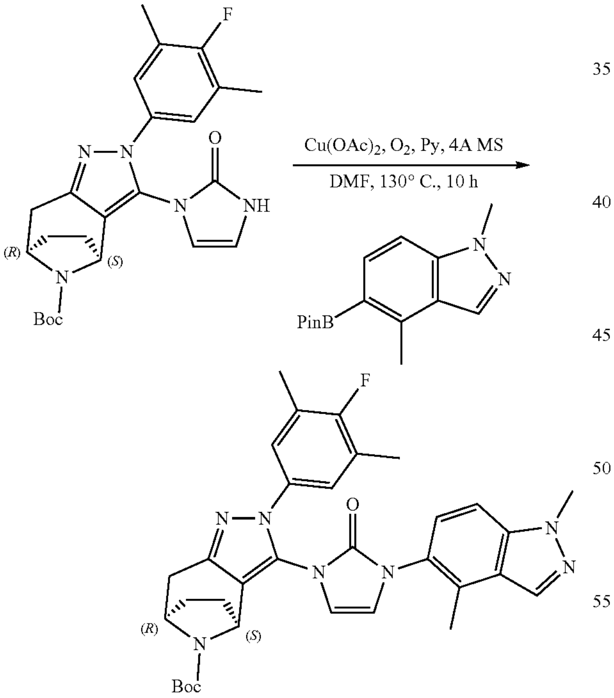

To a mixture of tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (150 mg, 330.75 μmol, 1 eq), 1,4-dimethyl-5-(4,4,5,5-tetramethyl-1,3,2-dioxaborolan-2-yl)-1H-indazole (180.03 mg, 661.51 μmol, 2 eq) in DMF (1.5 mL) was added $Cu(OAc)_2$ (6.01 mg, 33.08 μmol, 0.1 eq), Py (52.33 mg, 661.51 μmol, 2 eq), 4A MS (300 mg) in one portion. The mixture was stirred at 130° C. under 02 (15 Psi) for 10 hours. LCMS showed reaction was completed. The reaction solution is quenched with water (50 mL). The aqueous phase was extracted with ethyl acetate (50 mL*3). The combined organic layers were washed with saturated brine (20 mL*3), dried over anhydrous $Na_2SO_4$, filtered and concentrated under reduced pressure. The residue was purified by prep-TLC ($SiO_2$, Petroleum ether/ethyl acetate=1:1) to afford tert-butyl (4S,7R)-3-(3-(1,4-dimethyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (0.2 g, 301.16 μmol, 45.53% yield). LC-MS (ES+, m/z): 598.3 [$(M+H)^+$]; Rt=0.578 min.

Step 2: 1-(1,4-dimethyl-1H-indazol-5-yl)-3-((4S, 7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

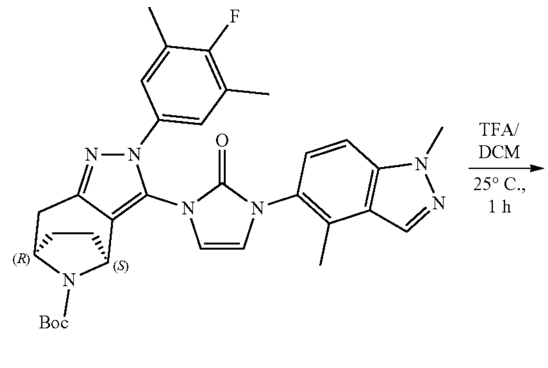

-continued

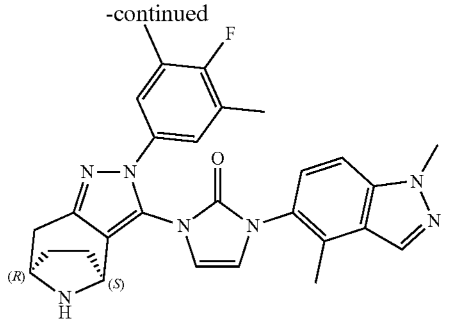

To a mixture of tert-butyl (4S,7R)-3-(3-(1,4-dimethyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200.00 mg, 301.16 μmol, 1 eq) in DCM (1 mL) was added TFA (1 mL) in one portion at 25° C. The mixture was stirred at 25° C. for 1 hour. LCMS showed reaction was completed. Then the residue was adjusted to about pH=10 with saturated $Na_2CO_3$ solution, the aqueous phase was extracted with dichloromethane (50 mL*3). The combined organic layers were washed with saturated brine (20 mL*3), dried over anhydrous $Na_2SO_4$, filtered and concentrated under reduced pressure to give 1-(1,4-dimethyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (150 mg, crude). LC-MS (ES+, m/z): 498.3 [$(M+H)^+$]; Rt=0.404 min.

Step 3: 3-((1S,2S)-1-(2-((4S,7R)-3-(3-(1,4-dimethyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5(4H)-one

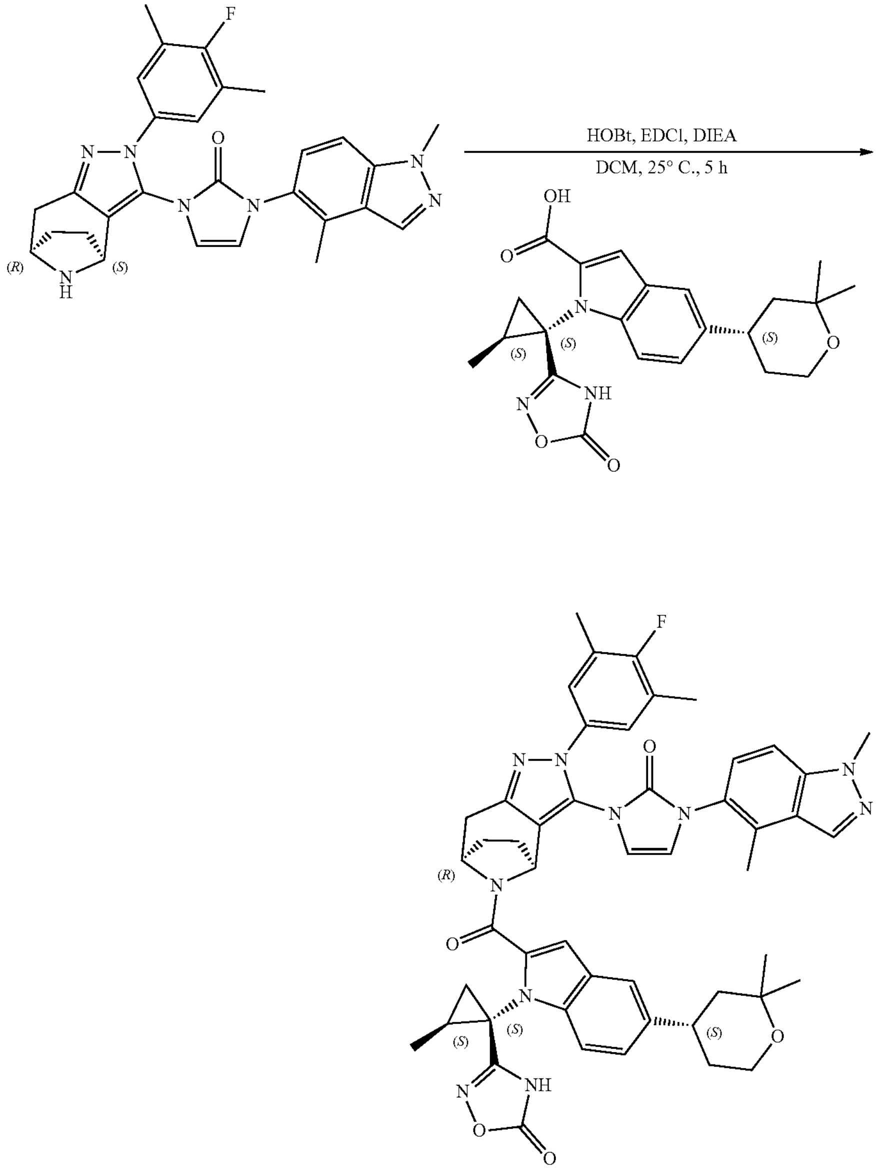

To a mixture of 1-(1,4-dimethyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (50 mg, 90.44 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl) cyclopropyl)-1H-indole-2-carboxylic acid (37.21 mg, 90.44 μmol, 1 eq) in DCM (1 mL) was added DIEA (58.44 mg, 452.20 μmol, 5 eq), HOBt (18.33 mg, 135.66 μmol, 1.5 eq), EDCI (22.54 mg, 117.57 μmol, 1.3 eq) in one portion at 25° C. under $N_2$. The mixture was stirred at 25° C. for 5 hours. LCMS showed reaction was complete. The reaction solution is quenched with saturated water (20 mL). The aqueous phase was extracted with ethyl acetate (20 mL*3). The combined organic layers were washed with saturated brine (20 mL*3), dried over anhydrous $Na_2SO_4$, filtered and concentrated under reduced pressure. The residue was purified by prep-HPLC (neutral condition, column: WePure Biotech XP tC18 150*40*70 um; mobile phase: [$H_2O$ (10 mM $NH_4HCO_3$)-ACN]; gradient: 35%-65% B over 8.0 min) to afford 3-((1S,2S)-1-(2-((4S,7R)-3-(3-(1,4-dimethyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one (17.43 mg, 19.02 μmol, 21.03% yield). $^1$H NMR (400 MHz, DMSO-$d_6$) δ=12.14 (br s, 1H), 8.34-7.90 (m, 1H), 7.65-6.59 (m, 10H), 5.72-4.72 (m, 2H), 4.13-3.92 (m, 3H), 3.74-3.49 (m, 2H), 3.28-2.72 (m, 3H), 2.43-2.02 (m, 11H), 1.90-1.35 (m, 9H), 1.30-0.94 (m, 9H). $^1$H NMR (400 MHz, DMSO-$d_6$, T=273+80K) δ=12.01-11.48 (m, 1H), 8.19-7.95 (m, 1H), 6.73 (br s, 10H), 5.55-4.80 (m, 2H), 4.04 (s, 3H), 3.69 (br d, J=1.4 Hz, 2H), 2.83 (br d, J=17.0 Hz, 3H), 2.41-2.03 (m, 11H), 1.96-1.45 (m, 9H), 1.33-1.06 (m, 9H). LC-MS (ES+, m/z): 891.3 [$(M+H)^+$]; Rt=2.968 min. HRMS (EI): m/z $[M+H]^+$ found: 891.4104.

Example 61 Compound 308

3-((1S,2S)-1-(2-((4S,7R)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5(4H)-one Scheme 308

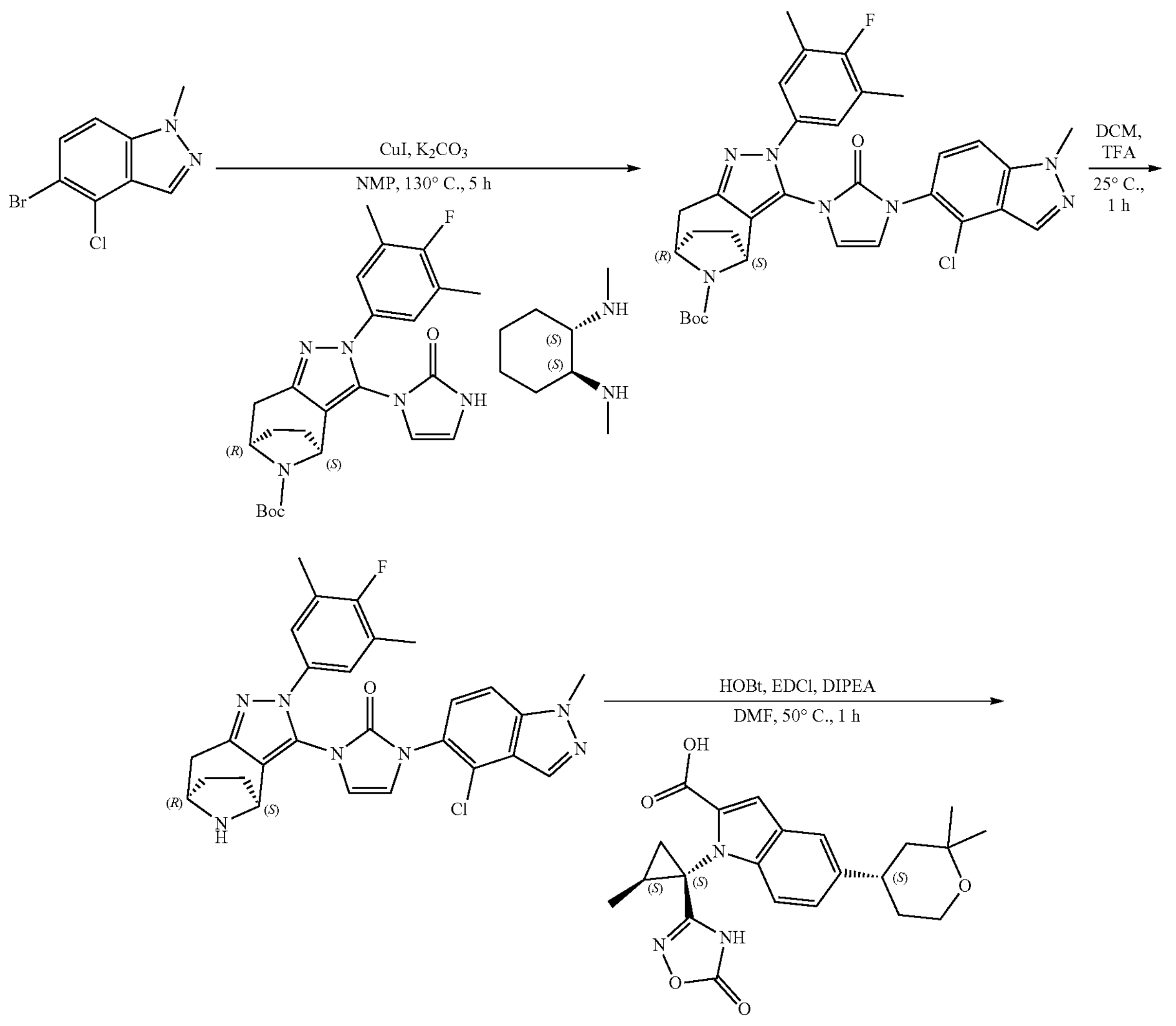

-continued

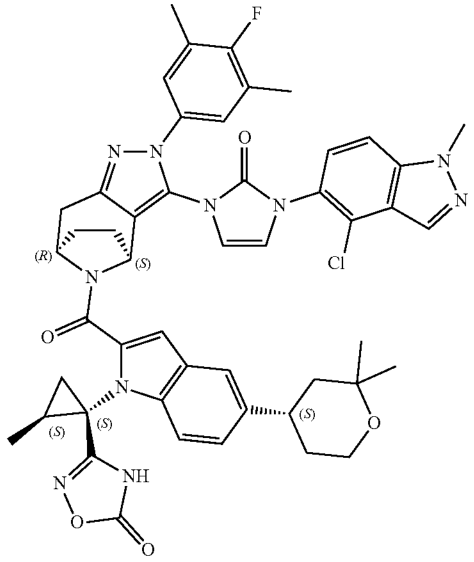

Step 1: (4S,7R)-tert-butyl 3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

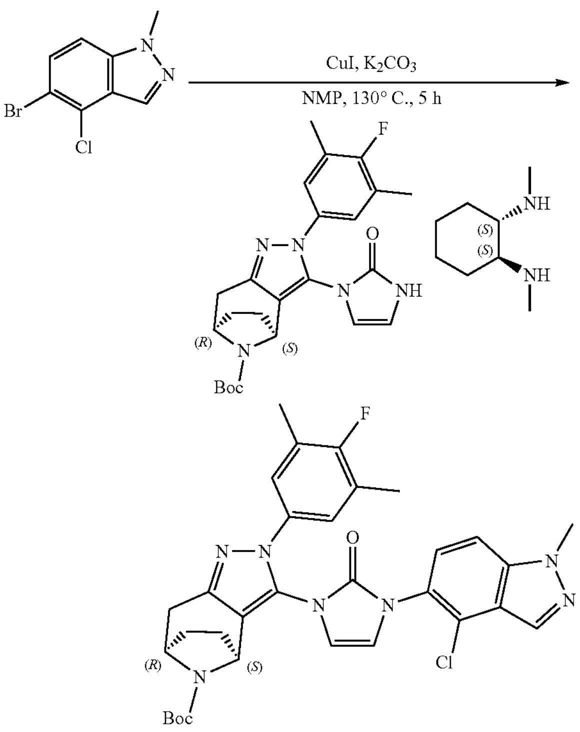

To a solution of (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (300 mg, 661.51 μmol, 1 eq) and 5-bromo-4-chloro-1-methyl-indazole (162.40 mg, 661.51 μmol, 1 eq) and (1S,2S)—N1,N2-dimethylcyclohexane-1,2-diamine (188.19 mg, 1.32 mmol, 2 eq) in NMP (10 mL) was added CuI (251.97 mg, 1.32 mmol, 2 eq) and $K_2CO_3$ (274.28 mg, 1.98 mmol, 3 eq). The mixture was stirred at 130° C. for 5 hours under $N_2$. LC-MS showed the reaction was completed. The reaction mixture was diluted with saturated EDTA (100 mL) and stirred for 1 hour, extracted with Ethyl acetate (100 mL*3). The combined organic layers were washed with saturated brine (100 mL*2). The combined organic layers were dried over $Na_2SO_4$, filtered and concentrated in vacuum. The residue was purified by prep-HPLC (($NH_4HCO_3$ condition) column: WePure Biotech XP tC18 150*40*7 um; mobile phase: [$H_2O$ (10 mM $NH_4HCO_3$)-ACN]; gradient: 35%-75% B over 8.0 min) to provide (4S,7R)-tert-butyl 3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (95 mg, 147.55 μmol, 22.30% yield). LC-MS (ES+, m/z): 618.2 [$(M+H)^+$]; Rt=0.592 min.

Step 2: 1-(4-chloro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one

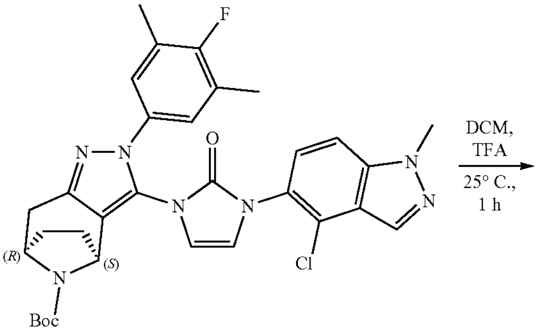

-continued

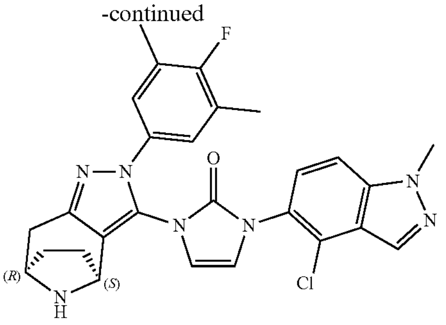

To a solution of tert-butyl (4S,7R)-tert-butyl 3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (95 mg, 147.55 μmol, 1 eq) in DCM (0.9 mL) was added TFA (0.3 mL). The mixture was stirred at 25° C. for 1 hour. LC-MS showed the reaction was completed. The reaction mixture was concentrated in vacuum to provide 1-(4-chloro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (80 mg, 125.31 μmol, 84.93% yield, TFA). LC-MS (ES+, m/z): 518.2 [(M+H)$^+$]; Rt=0.405 min.

Step 3: 3-((1S,2S)-1-(2-((4S,7R)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one

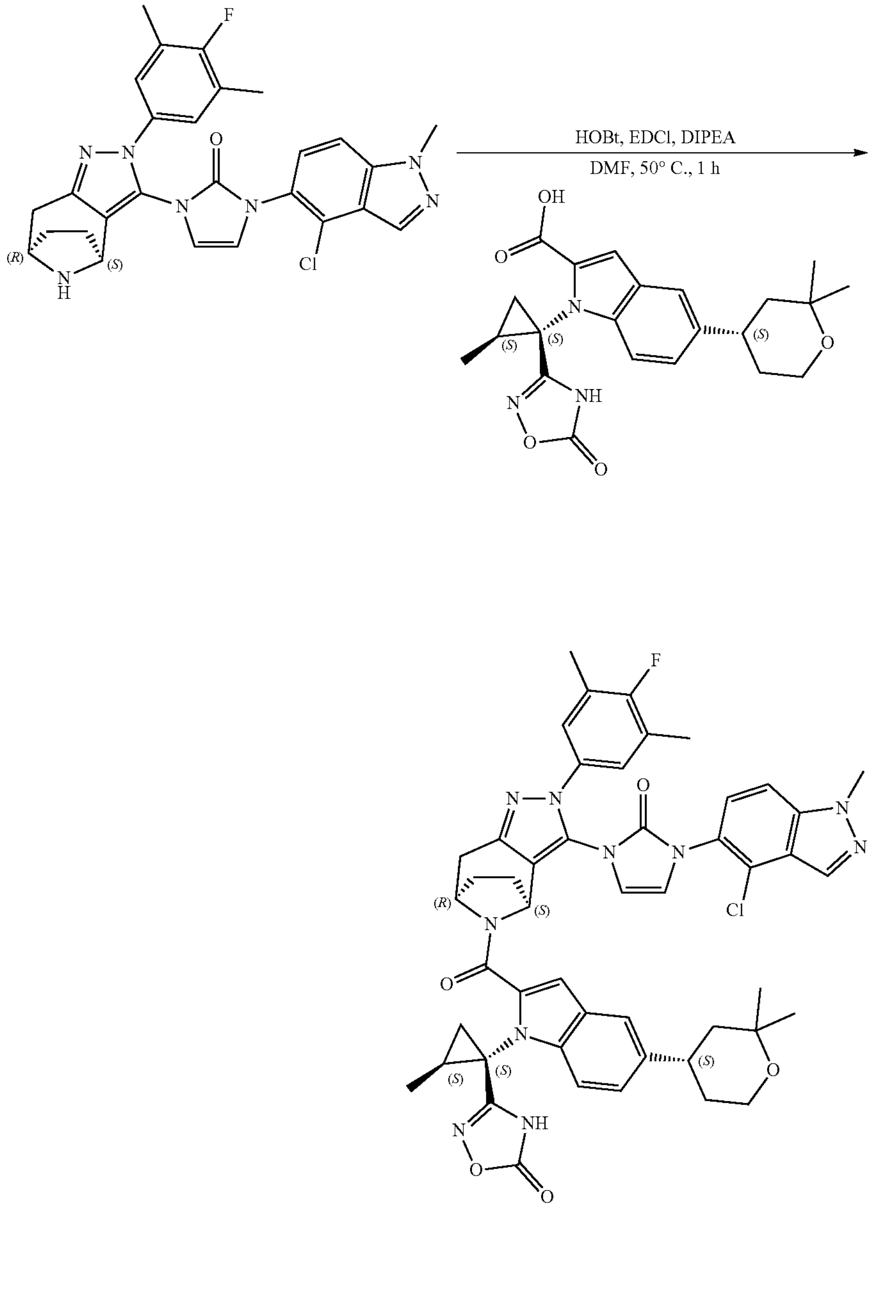

To a solution of 1-(4-chloro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (50 mg, 95.56 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (39.32 mg, 95.56 μmol, 1 eq) in DMF (1 mL) was added DIEA (37.05 mg, 286.69 μmol, 49.93 μL, 3 eq). HOBt (25.82 mg, 191.13 μmol, 2 eq) and EDCI (36.64 mg, 191.13 μmol, 2 eq) was then added. The mixture was stirred at 50° C. for 1 hour. LCMS showed the reaction was completed. The reaction mixture was diluted with water (50 mL), extracted with ethyl acetate (50 mL*3). The combined organic layers were washed with saturated brine (50 mL*2). The combined organic layers were dried over $Na_2SO_4$, filtered and concentrated in vacuum. The residue was purified by prep-HPLC ((TFA condition) column: 3_Phenomenex Luna C18 75*30 mm*3 um; mobile phase: [$H_2O$ (0.1% TFA)-ACN]; gradient: 50%-80% B over 8.0 min) to provide 3-((1S,2S)-1-(2-((4S,7R)-3-(3-(4-chloro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one (23.11 mg, 25.36 μmol, 26.53% yield). $^1H$ NMR (400 MHz, DMSO-$d_6$) δ=12.30-11.65 (m, 1H), 8.30-7.88 (m, 1H), 7.85-6.69 (m, 10H), 5.75-4.75 (m, 2H), 4.17-4.02 (m, 3H), 3.78-3.56 (m, 2H), 3.21-2.77 (m, 3H), 2.30-2.08 (m, 8H), 1.88-1.45 (m, 7H), 1.38-0.92 (m, 11H), 1H NMR (400 MHz, DMSO-$d_6$, T=273+80K) δ=12.04-11.33 (m, 1H), 8.23-7.95 (m, 1H), 7.84-6.54 (m, 10H), 5.66-4.67 (m, 2H), 4.09 (s, 3H), 3.82-3.52 (m, 2H), 3.04-2.70 (m, 3H), 2.31-2.11 (m, 8H), 1.92-1.51 (m, 7H), 1.47-0.98 (m, 11H), LC-MS (ES+, m/z): 911.3 [$(M+H)^+$]; Rt=3.050 min. HRMS (EI): m/z $[M+H]^+$ found: 911.3583.

Example 62 Compound 309

3-((1S,2S)-1-(2-((4S,7R)-3-(3-(2-(difluoromethyl)-4-fluoro-2H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one Scheme 309

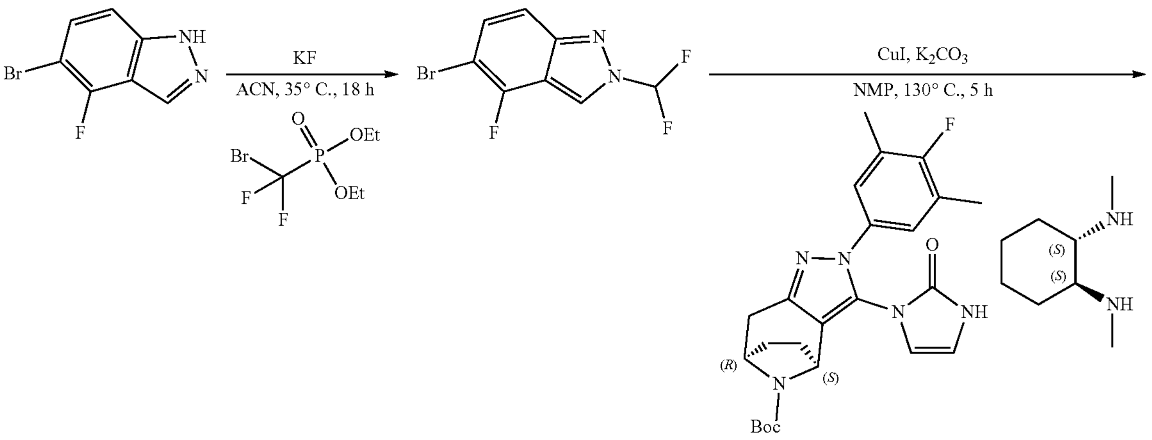

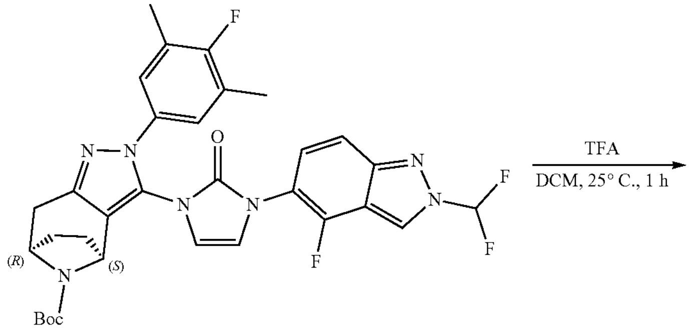

-continued

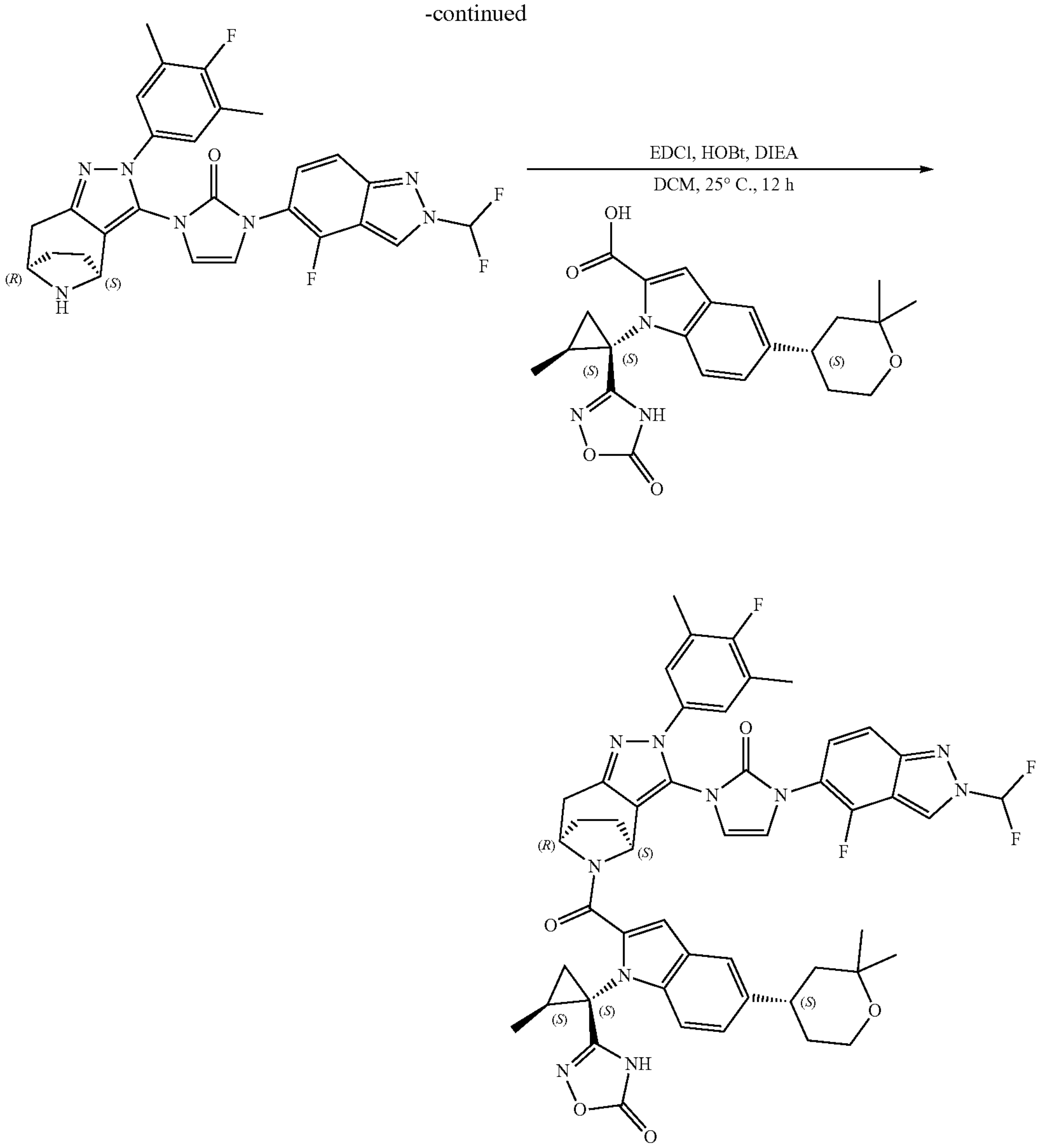

Step 1: 5-bromo-2-(difluoromethyl)-4-fluoro-2H-indazole

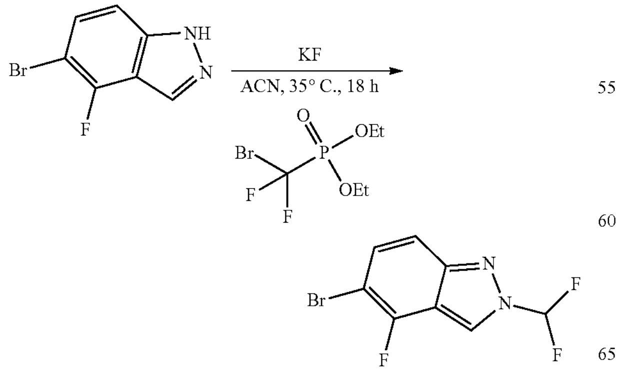

To a solution of 5-bromo-4-fluoro-1H-indazole (500 mg, 2.33 mmol, 1 eq) in ACN (7.5 mL) was added KF (270.19 mg, 4.65 mmol, 2 eq) and diethyl (bromodifluoromethyl) phosphonate (1.24 g, 4.65 mmol, 2 eq). The mixture was stirred at 35° C. for 18 hours. LCMS indicated the reaction was completed. The mixture was added dropwise to $H_2O$ (40 mL), and then extracted with ethyl acetate (60 mL*3). The organic layers were combined, washed with water (30 mL), saturated brine (30 mL), dried over $Na_2SO_4$, filtered and concentrated. The residue was purified by prep-TLC ($SiO_2$, Petroleum ether/Ethyl acetate=10:1) to afford 5-bromo-2-(difluoromethyl)-4-fluoro-2H-indazole (420 mg, 1.49 mmol, 63.99% yield). $^1H$ NMR (400 MHz, DMSO-$d_6$) δ=9.25-9.14 (m, 1H), 8.34-7.99 (m, 1H), 7.64-7.50 (m, 2H). LC-MS (ES+, m/z): 265.0 $[(M+H)^+]$; Rt=1.679 min.

Step 2: tert-butyl (4S,7R)-3-(3-(2-(difluoromethyl)-4-fluoro-2H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

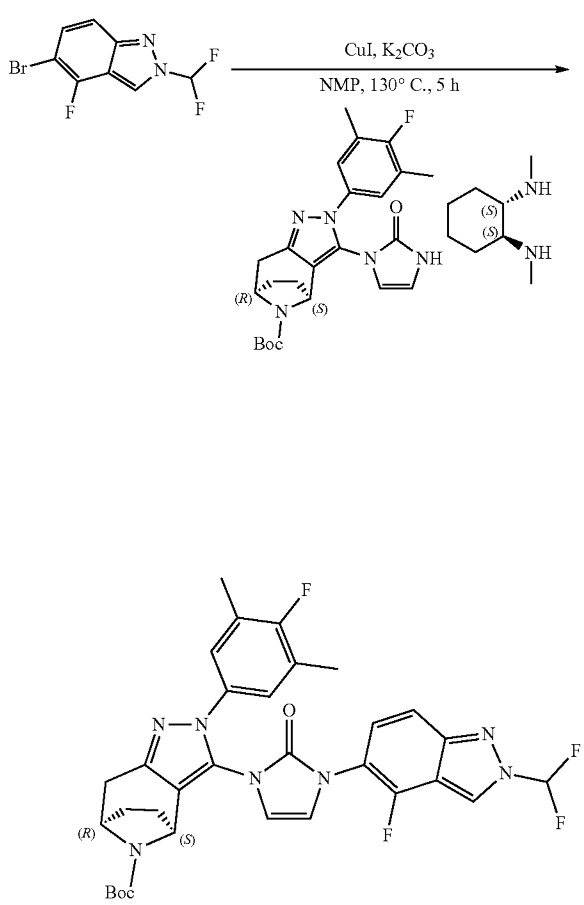

To a solution of 5-bromo-2-(difluoromethyl)-4-fluoro-2H-indazole (116.88 mg, 441.01 μmol, 2 eq) and tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (100 mg, 220.50 μmol, 1 eq) in NMP (2 mL) was added $K_2CO_3$ (121.90 mg, 882.01 μmol, 4 eq), (1S,2S)—$N^1$,$N^2$-dimethylcyclohexane-1,2-diamine (47.05 mg, 330.75 μmol, 1.5 eq) and CuI (83.99 mg, 441.01 μmol, 2 eq). The mixture was stirred at 130° C. for 5 hours under $N_2$. LCMS indicated the reaction was completed. The residue was poured into saturated EDTA solution (10 mL) and ethyl acetate (20 mL) stirred for 0.5 hour, and then extracted with ethyl acetate (20 mL*2). The organic layers were washed with water (20 mL*2), saturated brine (20 mL*2), dried over $Na_2SO_4$, filtered, concentrated under reduced pressure. The residue was purified by prep-TLC ($SiO_2$, Petroleum ether/ethyl acetate=2:1) to afford tert-butyl (4S,7R)-3-(3-(2-(difluoromethyl)-4-fluoro-2H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (90 mg, 137.34 μmol, 62.28% yield). LC-MS (ES+, m/z): 638.3 [(M+H)$^+$]; Rt=0.581 min.

Step 3: 1-(2-(difluoromethyl)-4-fluoro-2H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

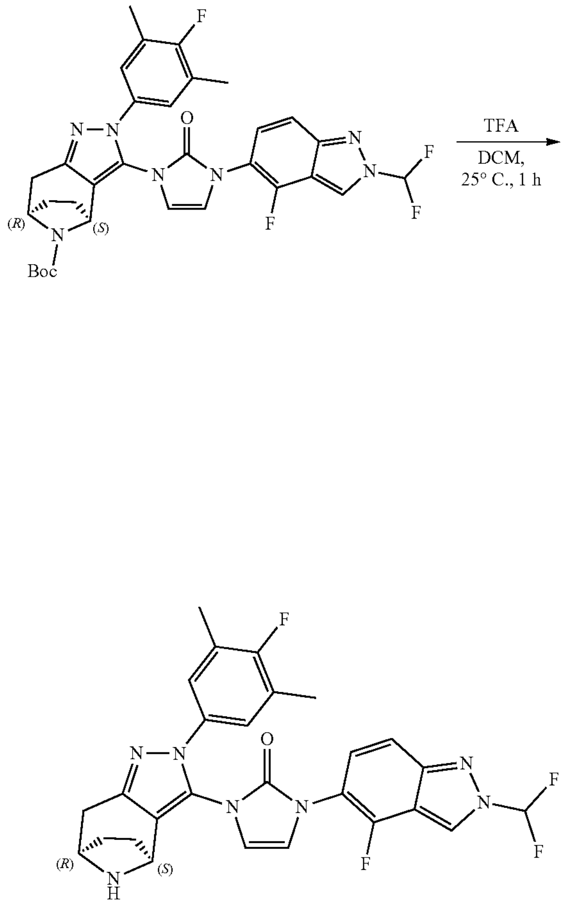

To a solution of tert-butyl (4S,7R)-3-(3-(2-(difluoromethyl)-4-fluoro-2H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (90 mg, 141.15 μmol, 1 eq) in DCM (1 mL) was added TFA (80.47 mg, 705.74 μmol, 52.42 μL, 5 eq). The mixture was stirred at 25° C. for 1 hour. LCMS indicated the reaction was completed. The reaction mixture was concentrated on a rota-vapor and adjusted to pH=7 with saturated $NaHCO_3$ (10 mL), and then extracted with DCM (20 mL*3). The organic layers were combined and washed with water (15 mL*2), saturated brine (18 mL*2), dried over $Na_2SO_4$, filtered, concentrated under reduced pressure to afford 1-(2-(difluoromethyl)-4-fluoro-2H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (70 mg, crude). $^1$H NMR (400 MHz, DMSO-$d_6$) δ=9.34-9.16 (m, 1H), 8.32-7.86 (m, 1H), 7.68-7.58 (m, 1H), 7.40-7.31 (m, 1H), 7.02-6.94 (m, 3H), 6.83-6.74 (m, 1H), 5.72-5.62 (m, 1H), 4.04-3.97 (m, 1H), 3.82-3.72 (m, 1H), 2.89-2.81 (m, 1H), 2.40-2.36 (m, 1H), 2.15-2.11 (m, 6H), 1.95-1.74 (m, 3H), 1.47-1.36 (m, 1H). LC-MS (ES+, m/z): 538.3 [(M+H)$^+$]; Rt=0.425 min.

Step 4: 3-((1S,2S)-1-(2-((4S,7R)-3-(3-(2-(difluoromethyl)-4-fluoro-2H-indazol-5-yl)-2-oxo-2,3-dihydro-1H-imidazol-1-yl)-2-(4-fluoro-3,5-dimethylphenyl)-2,4,5, 6,7,8-hexahydro-4,7-epiminocyclohepta [c]pyrazole-9-carbonyl)-5-((S)-2, 2-dimethyltetrahydro-2H-pyran-4-yl)-1H-indol-1-yl)-2-methylcyclopropyl)-1,2,4-oxadiazol-5 (4H)-one

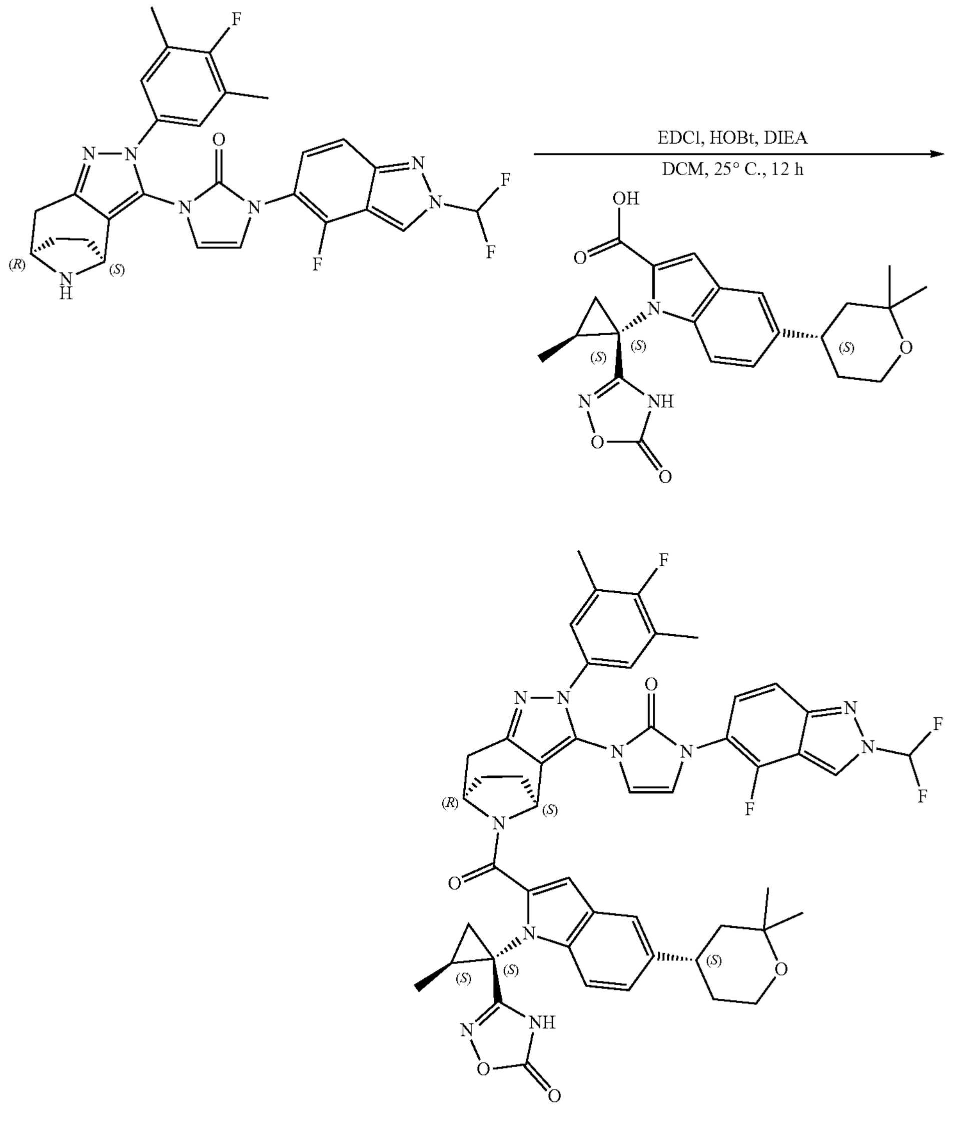

To a solution of 1-(2-(difluoromethyl)-4-fluoro-2H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (40 mg, 74.42 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl) cyclopropyl)-1H-indole-2-carboxylic acid (45.93 mg, 111.63 μmol, 1.5 eq) in DCM (0.8 mL) was added DIEA (48.09 mg, 372.09 μmol, 64.81 μL, 5 eq) HOBt (15.08 mg, 111.63 μmol, 1.5 eq) and EDCI (18.55 mg, 96.74 μmol, 1.3 eq). The mixture was stirred at 25° C. for 12 hours. LCMS indicated the reaction was completed. The mixture was added dropwise to $H_2O$ (10 mL), and then extracted with ethyl acetate (20 mL*3). The organic layers were combined, washed with water (20 mL), saturated brine (20 mL), dried over $Na_2SO_4$, filtered and concentrated. The residue was purified by prep-HPLC (column: Phenomenex Luna C18 75*30 mm*3 um; mobile phase: [$H_2O$ (0.1% TFA)-ACN]; gradient: 55%-85% B over 8.0 min) to afford 3-((1S,2S)-1-(2-((4S,7R)-3-(3-(2-(difluoromethyl)-4-fluoro-2H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one (14.27 mg, 15.33 μmol, 20.60% yield). $^1H$ NMR (400 MHz, DMSO-$d_6$) δ=12.08-11.32 (m, 1H), 9.31-8.95 (m, 1H), 8.32-7.89 (m, 1H), 7.68-6.68 (m, 10H), 5.64-4.71 (m, 2H), 3.75-3.56 (m, 2H), 3.15-2.74 (m, 3H), 2.29-2.13 (m, 8H), 1.08 (br s, 18H). $^1H$ NMR (400 MHz, MeOD-$d_6$) δ=9.13-8.74 (m, 1H), 8.07-6.42 (m, 11H), 5.96-4.91 (m, 2H), 3.95-3.55 (m, 3H), 3.10-2.81 (m, 2H), 2.64-2.54 (m, 1H), 2.34-2.21 (m, 7H), 2.03-1.01 (m, 18H). LC-MS (ES+, m/z): 931.3 [$(M+H)^+$]; Rt=3.104 min. HRMS (EI): m/z $[M+H]^+$ found: 931.3644.

Example 63 Compound 310
3-((1S,2S)-1-(2-((4S,7R)-3-(3-(1-(difluoromethyl)-4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5(4H)-one
Scheme 310
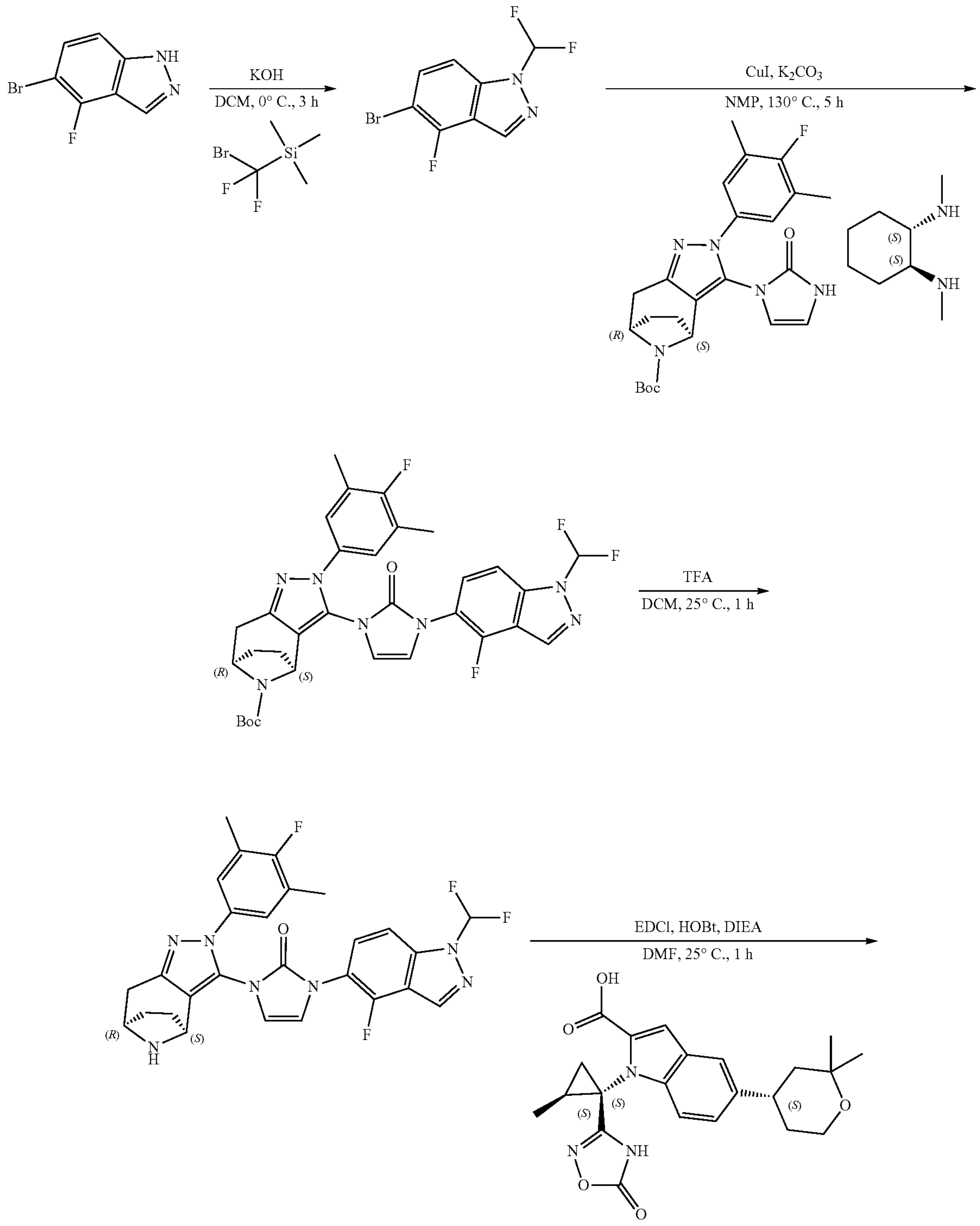

-continued

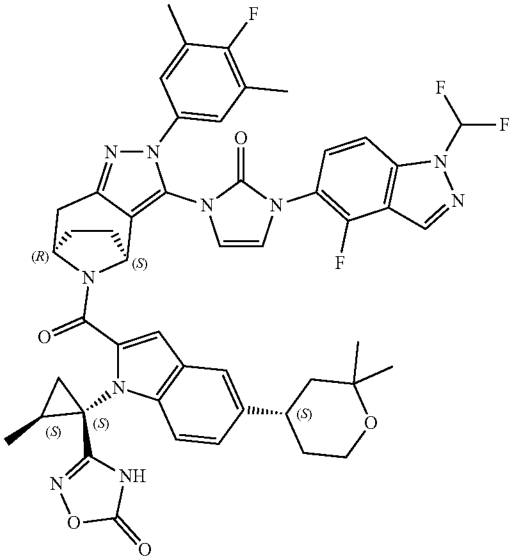

Step 1: 5-bromo-1-(difluoromethyl)-4-fluoro-1H-indazole

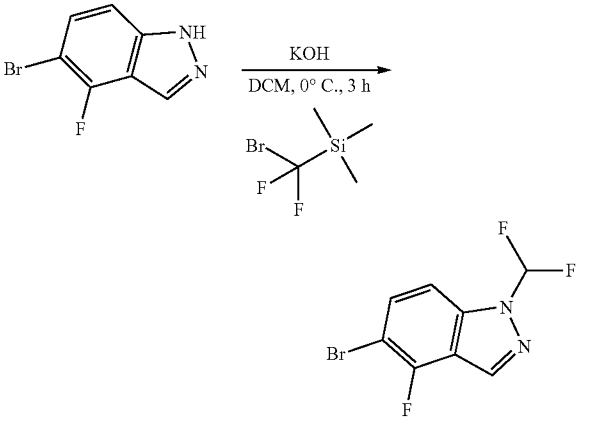

To a solution of 5-bromo-4-fluoro-1H-indazole (2.2 g, 10.23 mmol, 1 eq) in DCM (23 mL) was added KOH (3.8 M, 13.72 mL, 5.10 eq) at 0° C. followed by (bromodifluoromethyl)trimethylsilane (4.16 g, 20.46 mmol, 2 eq). The mixture was stirred at 0° C. for 3 hours under $N_2$ atmosphere. LCMS indicated the reaction was completed. The reaction mixture was cooled to 0° C., and then poured into $H_2O$ (30 mL) at 0° C. The aqueous phase was extracted with ethyl acetate (50 mL*3). The combined organic layers were washed with saturated brine (30 mL*3), dried over anhydrous $Na_2SO_4$, filtered and concentrated under reduced pressure. The residue was purified by prep-TLC ($SiO_2$, Petroleum ether/ethyl acetate=10:1) to afford 5-bromo-1-(difluoromethyl)-4-fluoro-1H-indazole (150 mg, 532.58 μmol, 5.21% yield). $^1H$ NMR (400 MHz, DMSO-$d_6$) δ=8.67-8.56 (m, 1H), 8.41-8.11 (m, 1H), 7.91-7.78 (m, 1H), 7.71-7.66 (m, 1H). LC-MS (ES+, m/z): 265.0 [$(M+H)^+$]; Rt=0.545 min.

Step 2: tert-butyl (4S,7R)-3-(3-(1-(difluoromethyl)-4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carboxylate

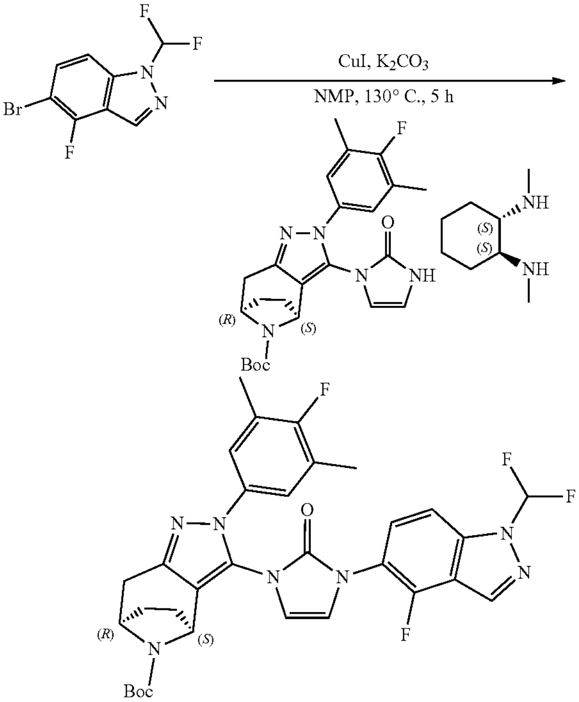

To a solution of 5-bromo-1-(difluoromethyl)-4-fluoro-1H-indazole (116.88 mg, 441.01 μmol, 2 eq) and tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (100 mg, 220.50 μmol, 1 eq) in NMP (2 mL) was added (1S,2S)—$N^1$,$N^2$-dimethylcyclohexane-1,2-diamine (47.05 mg, 330.75 μmol, 1.5 eq) $K_2CO_3$ (121.90 mg, 882.01 μmol, 4 eq) and CuI (83.99 mg, 441.01 μmol, 2 eq). The mixture was stirred at 130° C. for 5 hours under $N_2$ atmosphere. LCMS indicated the reaction was completed. The residue was poured into saturated EDTA solution (10 mL) and ethyl acetate (20 mL) stirred for 0.5 hr, and then extracted with ethyl acetate (20 mL+2). The organic layers were washed with water (20 mL*2), saturated brine (20 mL*2), dried over $Na_2SO_4$, filtered, concentrated under reduced pressure. The residue was purified by prep-TLC ($SiO_2$, Petroleum ether/ethyl acetate=2:1) to afford tert-butyl (4S,7R)-3-(3-(1-(difluoromethyl)-4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (90 mg, 132.82 μmol, 60.24% yield). $^1H$ NMR (400 MHz, DMSO-$d_6$) δ=8.75-8.68 (m, 1H), 8.48-8.11 (m, 1H), 7.87-7.77 (m, 1H), 7.76-7.64 (m, 1H), 7.15-7.03 (m, 3H), 6.90-6.82 (m, 1H), 4.94-4.67 (m, 1H), 4.58-4.41 (m, 1H), 3.16-3.03 (m, 1H), 2.64-2.57 (m, 1H), 2.24-2.21 (m, 6H), 2.17-1.90 (m, 3H), 1.69-1.59 (m, 1H), 1.42-1.28 (m, 9H). LC-MS (ES+, m/z): 638.4 [(M+H)$^+$]; Rt=0.622 min.

Step 3: 1-(1-(difluoromethyl)-4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

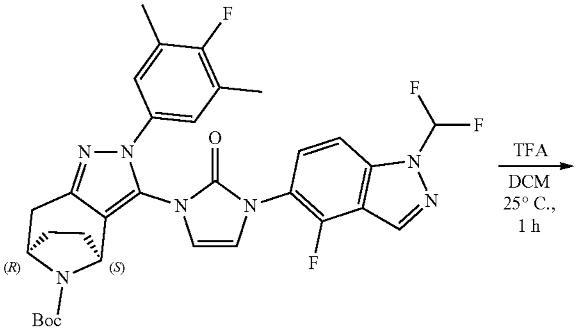

-continued

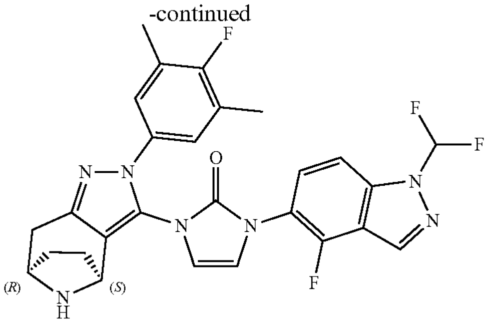

To a solution of tert-butyl (4S,7R)-3-(3-(1-(difluoromethyl)-4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (90 mg, 141.15 μmol, 1 eq) in DCM (1 mL) was added TFA (690.75 mg, 6.06 mmol, 450.00 μL, 42.92 eq). The mixture was stirred at 25° C. for 1 hour. LCMS indicated the reaction was completed. The reaction mixture was concentrated on a rota-vapor and adjusted to pH=7 with saturated $NaHCO_3$ (10 mL), and then extracted with DCM (20 mL*3). The organic layers were combined and washed with water (15 mL*2), saturated brine (15 mL*2), dried over $Na_2SO_4$, filtered, concentrated under reduced pressure to afford 1-(1-(difluoromethyl)-4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (75 mg, crude). LC-MS (ES+, m/z): 538.3 [(M+H)$^+$]; Rt=0.424 min.

Step 4: 3-((1S,2S)-1-(2-((4S,7R)-3-(3-(1-(difluoromethyl)-4-fluoro-1H-indazol-5-yl)-2-oxo-2,3-dihydro-1H-imidazol-1-yl)-2-(4-fluoro-3,5-dimethylphenyl)-2,4, 5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one

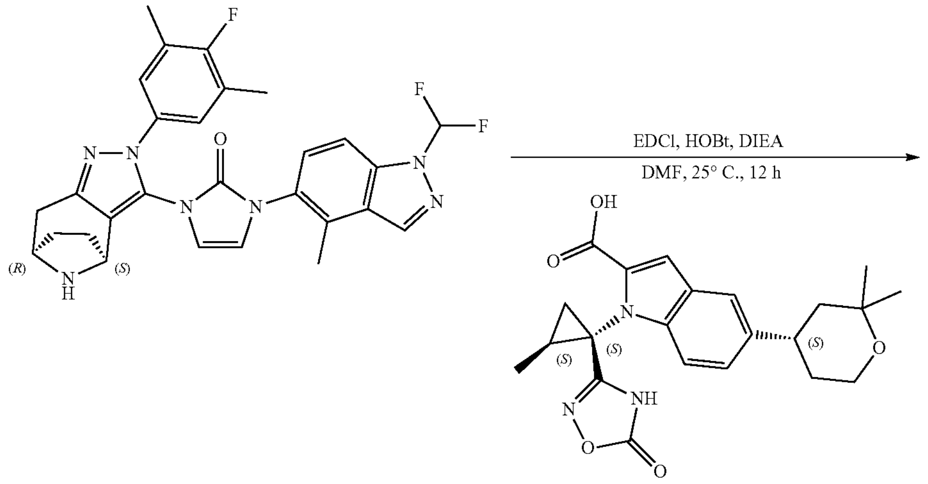

-continued

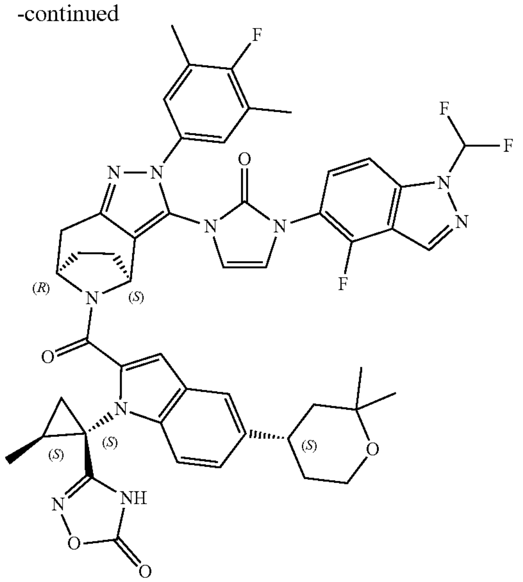

To a solution of 1-(1-(difluoromethyl)-4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (40 mg, 74.42 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (45.93 mg, 111.63 μmol, 1.5 eq) in DCM (0.8 mL) was added DIPEA (48.09 mg, 372.09 μmol, 64.81 μL, 5 eq), HOBt (15.08 mg, 111.63 μmol, 1.5 eq) and EDCI (18.55 mg, 96.74 μmol, 1.3 eq). The mixture was stirred at 25° C. for 12 hours. LCMS indicated the reaction was completed. The mixture was added dropwise to $H_2O$ (10 mL), and then extracted with ethyl acetate (20 mL*3). The organic layers were combined, washed with water (20 mL), saturated brine (20 mL), dried over $Na_2SO_4$, filtered and concentrated to give crude product. The residue was purified by prep-HPLC (column: Phenomenex Luna C18 75*30 mm*3 um; mobile phase: [$H_2O$ (0.1% TFA)-ACN]; gradient: 55%-85% B over 8.0 min) to afford 3-((1S,2S)-1-(2-((4S,7R)-3-(3-(1-(difluoromethyl)-4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-2,2-dimethyltetrahydro-2H-pyran-4-yl)-1H-indol-1-yl)-2-methylcyclopropyl)-1,2,4-oxadiazol-5 (4H)-one (8.53 mg, 9.16 μmol, 12.31% yield). $^1$H NMR (400 MHz, DMSO-$d_6$) δ=12.06-11.32 (m, 1H), 8.67-8.48 (m, 1H), 8.34-7.97 (m, 1H), 7.81-6.66 (m, 10H), 5.59-4.72 (m, 2H), 3.82-3.39 (m, 3H), 3.03-2.79 (m, 2H), 2.30-2.11 (m, 8H), 1.86-1.09 (m, 18H). $^1$H NMR (400 MHz, MeOD-$d_6$) δ=8.48-8.28 (m, 1H), 8.07-6.43 (m, 11H), 5.85-4.91 (m, 2H), 3.96-3.52 (m, 3H), 3.11-2.82 (m, 2H), 2.65-2.56 (m, 1H), 2.37-2.16 (m, 7H), 1.96-1.00 (m, 18H). LC-MS (ES+, m/z): 931.3 [(M+H)$^+$]; Rt=3.154 min. HRMS (EI): m/z [M+H]$^+$ found: 931.3699.

Example 64 Compound 311

3-((1S,2S)-1-(5-(2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5(4H)-one Scheme 311

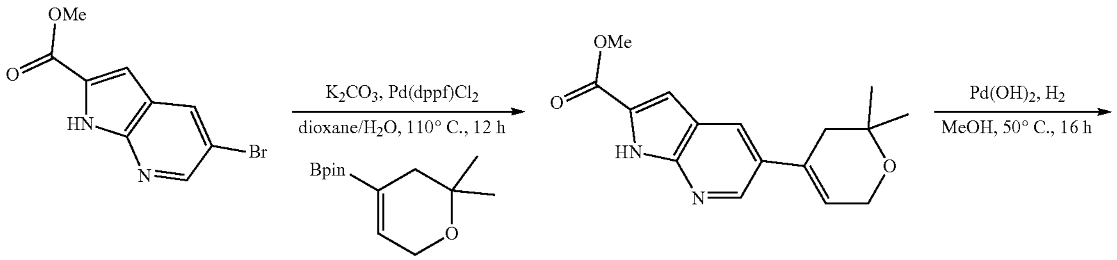

-continued
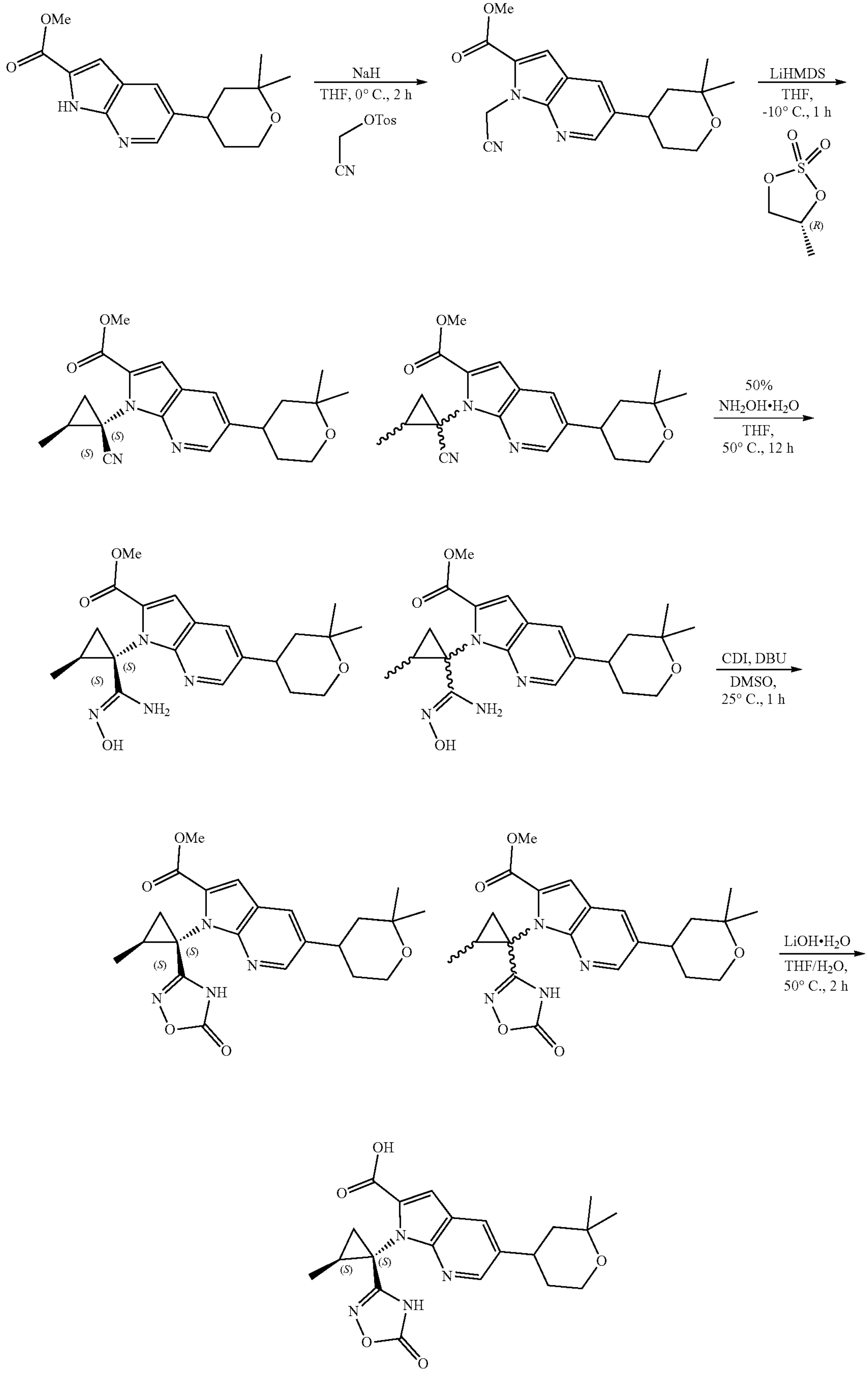

-continued

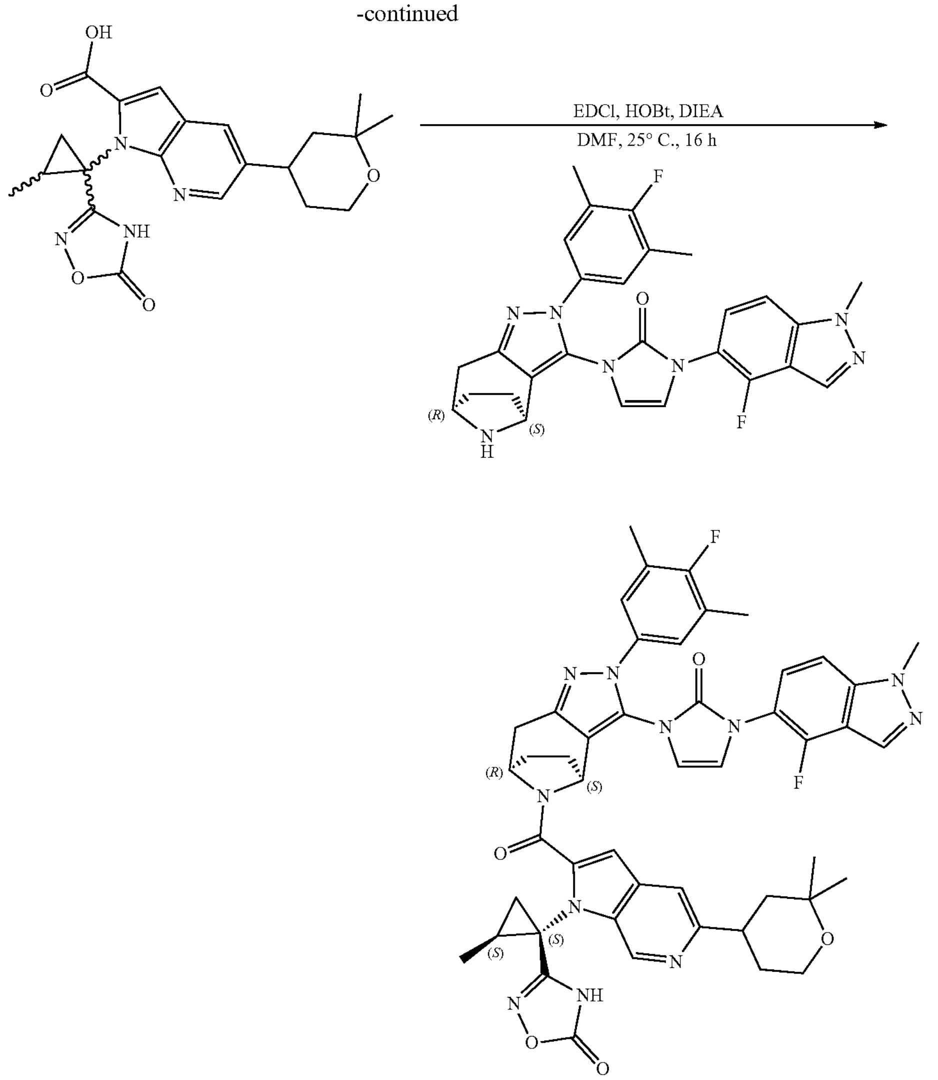

Step 1: methyl 5-(2,2-dimethyl-3,6-dihydro-2H-pyran-4-yl)-LH-pyrrolo[2,3-b]pyridino-2-carboxylate

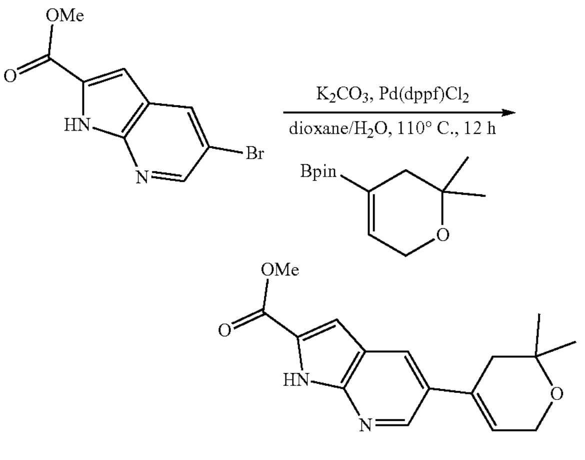

To a solution of methyl 5-bromo-LH-pyrrolo[2,3-b]pyridino-2-carboxylate (10 g, 39.21 mmol, 1 q) and 2-(2,2-dimethyl-3,6-dihydro-2H-pyran-4-yl)-4,4,5,5-tetramethyl-1,3,2-dioxaborolane (11.20 g. 47.05 mmol, 1.2 cg) in dioxane (200 mL) and $H_2O$ (50 mL) was added $K_2CO_3$ (27.09 g, 196.03 mmol, 5 eq) and Pd(dppf)$Cl_2$ (5.74 g, 7.84 mmol, 0.2 eq) in one portion under $N_2$. The mixture was stirred at 110° C. for 12 hours under $N_2$ atmosphere. LCMS showed the reaction was completed. The reaction mixture was quenched by addition saturated EDTA solution (900 mL) and ethyl acetate (300 mL), stirred for 0.5 hour, extracted with ethyl acetate (600 mL*3). The combined organic layers were washed with saturated brine (2000 mL), dried over anhydrous $Na_2SO_4$, filtered and concentrated under reduced pressure. The residue was purified by column chromatography ($SiO_2$, Petroleum ether/ethyl acetate=10/1 to 0/1) to afford methyl 5-(2, 2-dimethyl-3, 6-dihydro-2H-pyran-4-yl)-1H-pyrrolo[2, 3-b]pyridine-2-carboxylate (7 g, 22.00 mmol, 56.12% yield). LC-MS (ES+, m/z): 287.2 $[(M+H)^+]$. Rt=1.439 min.

Step 2: methyl 5-(2, 2-dimethyltetrahydro-2H-pyran-4-yl)-1H-pyrrolo[2,3-b] pyridine-2-carboxylate

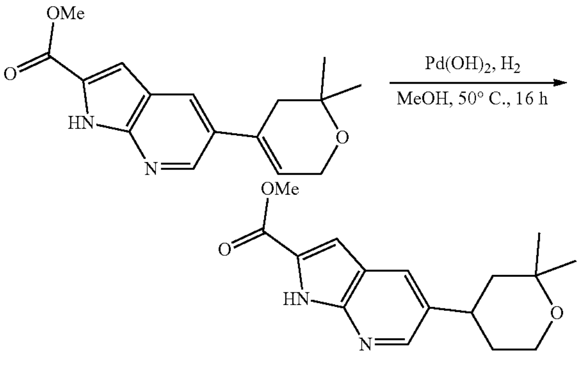

To a suspension of Pd(OH) 2 (1.54 g, 2.20 mmol, 20% purity, 0.1 eq) in MeOH (700 mL) was added methyl 5-(2,2-dimethyl-3,6-dihydro-2H-pyran-4-yl)-1H-pyrrolo[2,3-b]pyridine-2-carboxylate (7 g, 22.00 mmol, 1 eq). The mixture was stirred at 50° C. for 16 hours under $H_2$ (50 Psi). LCMS showed the reaction was completed. The residue was filtered and concentrated in vacuum. The residue was dissolved in methyl alcohol (1000 mL), scavenger (Pd) was added and then stirred at 25° C. for 1 hour, and then filtered. The residue was purified by column chromatography ($SiO_2$, Petroleum ether/ethyl acetate=10/1 to 0/1) to afford methyl 5-(2,2-dimethyltetrahydro-2H-pyran-4-yl)-1H-pyrrolo[2,3-b]pyridine-2-carboxylate (4.5 g, 14.36 mmol, 65.25% yield). LC-MS (ES+, m/z): 289.0 [$(M+H)^+$]. Rt=1.611 min.

Step 3: methyl 1-(cyanomethyl)-5-(2,2-dimethyltetrahydro-2H-pyran-4-yl)-1H-pyrrolo[2,3-b]pyridine-2-carboxylate

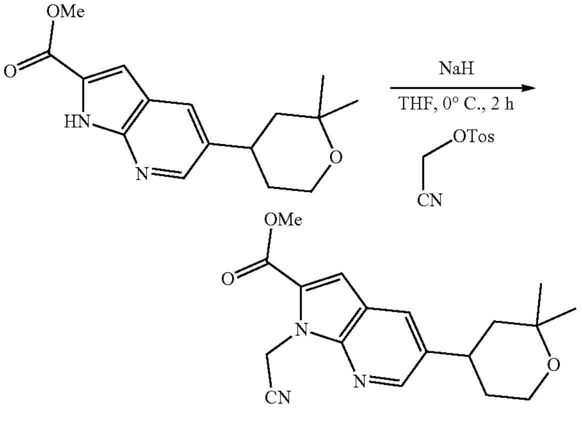

To a solution of methyl 5-(2,2-dimethyltetrahydro-2H-pyran-4-yl)-1H-pyrrolo[2,3-b]pyridine-2-carboxylate (4.5 g, 14.36 mmol, 1 eq) in DMF (45 mL) was added NaH (1.44 g, 35.90 mmol, 60% purity, 2.5 eq) in one portion at 0° C. under $N_2$. The mixture was stirred at 0° C. for 30 mins. Then cyanomethyl 4-methylbenzenesulfonate (6.07 g, 28.72 mmol, 2 eq) was added in one portion under $N_2$. The mixture was stirred at 0° C. for 1.5 hours. LCMS showed the reaction was completed. The reaction mixture was quenched by addition saturated $NH_4Cl$ (500 mL), extracted with ethyl acetate (300 mL*3). The combined organic layers were washed with saturated brine (800 mL), dried over anhydrous $Na_2SO_4$, filtered and concentrated under reduced pressure. The residue was purified by column chromatography ($SiO_2$, Petroleum ether/ethyl acetate=10/1 to 0/1) to afford 1-(cyanomethyl)-5-(2, 2-dimethyltetrahydro-2H-pyran-4-yl)-1H-pyrrolo[2,3-b]pyridine-2-carboxylate (2.6 g, 7.15 mmol, 49.78% yield). LC-MS. (ES+, m/z): 328.0 [$(M+H)^+$]. Rt=1.191 min.

Step 4: methyl 1-((1S,2S)-1-cyano-2-methylcyclopropyl)-5-(2,2-dimethyltetrahydro-2H-pyran-4-yl)-1H-pyrrolo[2,3-b]pyridine-2-carboxylate & methyl 1-(1-cyano-2-methylcyclopropyl)-5-(2,2-dimethyltetrahydro-2H-pyran-4-yl)-1H-pyrrolo[2,3-b]pyridine-2-carboxylate

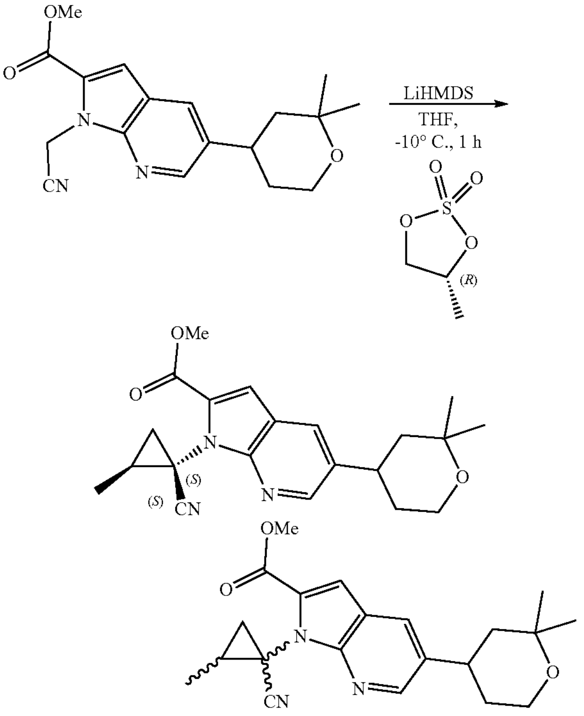

To a solution of methyl 1-(cyanomethyl)-5-(2,2-dimethyltetrahydro-2H-pyran-4-yl)-1H-pyrrolo[2,3-b] pyridine-2-carboxylate (2.1 g, 5.77 mmol, 1 eq) and (R)-4-methyl-1,3,2-dioxathiolane 2,2-dioxide (2.39 g, 17.32 mmol, 3 eq) in THF (21 mL) was added LiHMDS (1 M, 23.09 mL, 4 eq) in one portion at −10° C. under $N_2$. The mixture was stirred at −10° C. and stirred for 1 hour. LCMS showed the reaction was completed. The reaction solution is quenched with saturated $NH_4Cl$ (80 mL). The aqueous phase was extracted with ethyl acetate (40 mL*3). The combined organic phase was washed with saturated brine (100 mL), dried with anhydrous $Na_2SO_4$, filtered and concentrated under reduced pressure. The residue was purified by column chromatography ($SiO_2$, Petroleum ether/ethyl acetate=10/1 to 0/1) to afford a mixture of 1-((1S,2S)-1-cyano-2-methylcyclopropyl)-5-(2,2-dimethyltetrahydro-2H-pyran-4-yl)-1H-pyrrolo [2,3-b]pyridine-2-carboxylate and methyl 1-(1-cyano-2- methylcyclopropyl)-5-(2,2-dimethyltetrahydro-2H-pyran-4-yl)-1H-pyrrolo[2,3-b]pyridine-2-carboxylate (900 mg, ratio=3:1, 2.28 mmol, 39.46% yield). LC-MS (ES+, m/z): 368.2 [$(M+H)^+$]. Rt=1.973/2.025 min.

Step 5: methyl 5-(2,2-dimethyltetrahydro-2H-pyran-4-yl)-1-((1S,2S)-1-(N'-hydroxycarbamimidoyl)-2-methylcyclopropyl)-1H-pyrrolo[2,3-b]pyridine-2-carboxylate & methyl 5-(2,2-dimethyltetrahydro-2H-pyran-4-yl)-1-(1-(N'-hydroxycarbamimidoyl)-2-methylcyclopropyl)-1H-pyrrolo[2,3-b]pyridine-2-carboxylate

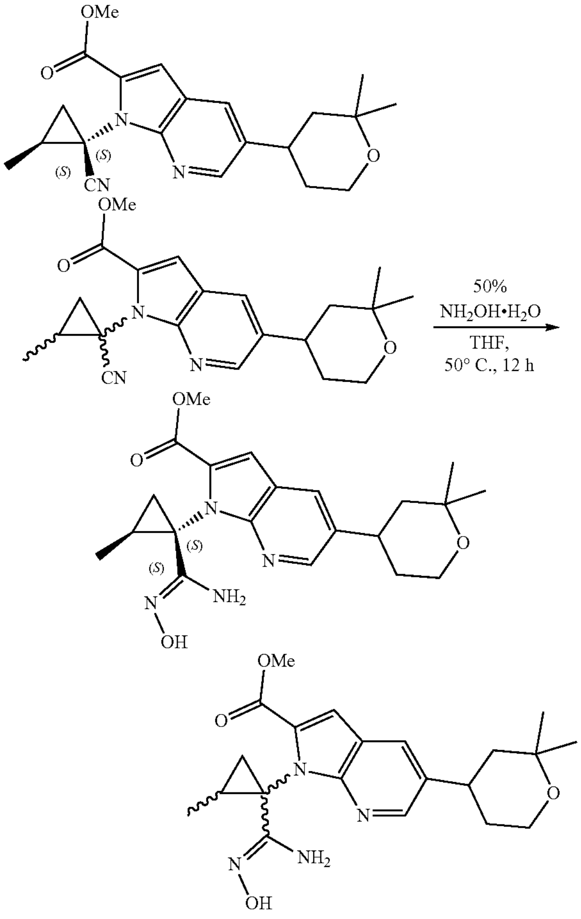

To a mixture of methyl 1-((1S,2S)-1-cyano-2-methylcyclopropyl)-5-(2,2-dimethyltetrahydro-2H-pyran-4-yl)-1H-pyrrolo[2,3-b]pyridine-2-carboxylate and methyl 1-(1-cyano-2-methylcyclopropyl)-5-(2,2-dimethyltetrahydro-2H-pyran-4-yl)-1H-pyrrolo[2,3-b]pyridine-2-carboxylate (900 mg, ratio=3:1, 2.28 mmol, 1 eq) in THF (9 mL) was added $NH_2OH·H_2O$ (1.50 g, 22.78 mmol, 50% purity, 10 eq) in one portion under $N_2$. The mixture was stirred at 50° C. and stirred for 12 hours. The reaction mixture was quenched by addition $H_2O$ (50 mL), extracted with ethyl acetate (30 mL*3). The combined organic layers were washed with saturated brine (60 mL), dried over anhydrous $Na_2SO_4$, filtered and concentrated under reduced pressure to afford a mixture of methyl 5-(2,2-dimethyltetrahydro-2H-pyran-4-yl)-1-((1S,2S)-1-(N-hydroxycarbamimidoyl)-2-methylcyclopropyl)-1H-pyrrolo[2,3-b]pyridine-2-carboxylate and methyl 5-(2,2-dimethyltetrahydro-2H-pyran-4-yl)-1-(1-(N'-hydroxycarbamimidoyl)-2-methylcyclopropyl)-1H-pyrrolo[2,3-b]pyridine-2-carboxylate (700 mg, ratio=3:1, crude) as yellow oil. LC-MS (ES+, m/z): 401.2 [$(M+H)^+$]. Rt=0.372/0.390 min.

Step 6: methyl 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylate & methyl 5-(2,2-dimethyltetrahydro-2H-pyran-4-yl)-1-(2-methyl-1-(5-oxo-4,5-dihydro-1,2,4-oxadiazol-3-yl)cyclopropyl)-1H-pyrrolo[2,3-b]pyridine-2-carboxylate

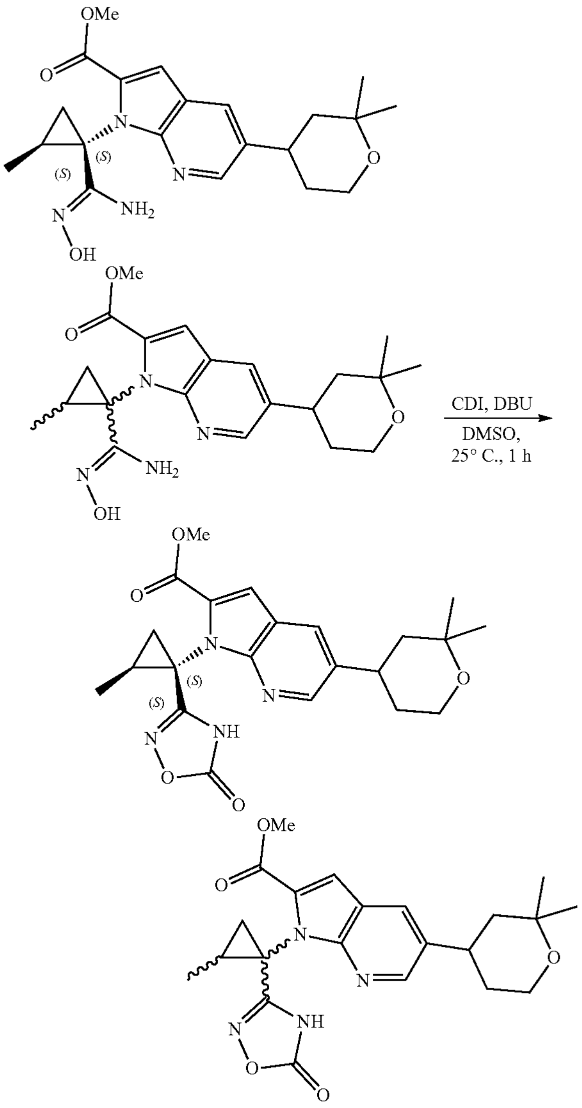

To a mixture of methyl 5-(2,2-dimethyltetrahydro-2H-pyran-4-yl)-1-((1S,2S)-1-(N'-hydroxycarbamimidoyl)-2-methylcyclopropyl)-1H-pyrrolo[2,3-b]pyridine-2-carboxylate and methyl 5-(2,2-dimethyltetrahydro-2H-pyran-4-yl)-1-(1-(N'-hydroxycarbamimidoyl)-2-methylcyclopropyl)-1H-pyrrolo[2,3-b]pyridine-2-carboxylate (700 mg, ratio=3:1, 1.49 mmol, 1 eq) in DMSO (14 mL) was added CDI (481.83 mg, 2.97 mmol, 2 eq) and DBU (565.46 mg, 3.71 mmol, 2.5 eq) in one portion under $N_2$. The mixture was stirred at 25° C. and stirred for 1 hour. LCMS showed the reaction was completed. The reaction mixture was quenched by addition $H_2O$ (50 mL), extracted with ethyl acetate (30 mL*3). The combined organic layers were washed with saturated brine (60 mL), dried over anhydrous $Na_2SO_4$, filtered and concentrated under reduced pressure to afford a mixture of methyl 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylate and methyl 5-(2,2-dimethyltetrahydro-2H-pyran-4-yl)-1-(2-methyl-1-(5-oxo-4,5-dihydro-1,2,4-oxadiazol-3-yl)cyclopropyl)-1H-pyrrolo[2,3-b]pyridine-2-carboxylate (500 mg, ratio=3:1, crude) as yellow oil. LC-MS (ES+, m/z): 427.3 [(M+H)$^+$]. Rt=0.465/0.487 min.

Step 7: 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid & 5-(2,2-dimethyltetrahydro-2H-pyran-4-yl)-1-(2-methyl-1-(5-oxo-4,5-dihydro-1,2,4-oxadiazol-3-yl)cyclopropyl)-1H-pyrrolo[2,3-b]pyridine-2-carboxylic acid

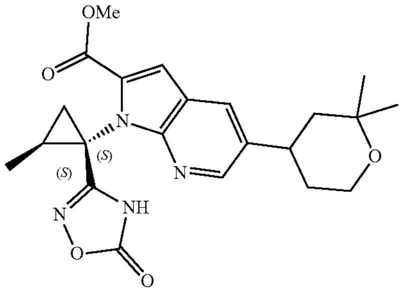

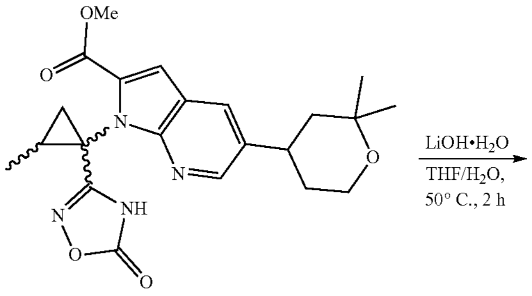

-continued

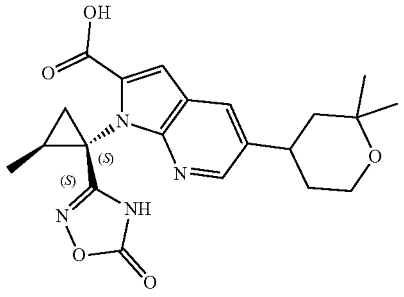

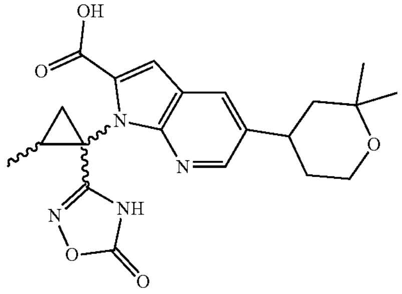

To a mixture of methyl 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylate and methyl 5-(2,2-dimethyltetrahydro-2H-pyran-4-yl)-1-(2-methyl-1-(5-oxo-4,5-dihydro-1,2,4-oxadiazol-3-yl) cyclopropyl)-1H-pyrrolo[2,3-b]pyridine-2-carboxylate (500 mg, ratio=3:1, crude) in THF (2.5 mL) and $H_2O$ (2.5 mL) was added LiOH·$H_2O$ (393.56 mg, 9.38 mmol, 10 eq) in one portion under $N_2$. The mixture was stirred at 50° C. and stirred for 2 hours. LCMS showed the reaction was completed. The residue was poured into water (30 mL) and adjusted to pH=2 with 1N HCl (10 mL). The aqueous phase was extracted with dichloromethane: methyl alcohol=10:1, (20 mL*3). The combined organic phase was washed with saturated brine (30 mL), dried with anhydrous $Na_2SO_4$, filtered and concentrated under reduced pressure. The residue was purified by prep-HPLC ((TFA condition) column: Phenomenex Luna C18 75*30 mm*3 um; mobile phase: [$H_2O$ (0.1% TFA)-ACN]; gradient: 20%-50% B over 8.0 min) to afford 5-(2,2-dimethyltetrahydro-2H-pyran-4-yl)-1-((1S,2S)-2-methyl-1-(5-oxo-4,5-dihydro-1,2,4-oxadiazol-3-yl) cyclopropyl)-1H-pyrrolo[2,3-b]pyridine-2-carboxylic acid (220 mg, 528.08 μmol, 56.30% yield). LC-MS (ES+, m/z): 413.2 [(M+H)$^+$]. Rt=1.422 min.

And 5-(2,2-dimethyltetrahydro-2H-pyran-4-yl)-1-(2-methyl-1-(5-oxo-4,5-dihydro-1,2,4-oxadiazol-3-yl) cyclopropyl)-1H-pyrrolo[2,3-b]pyridine-2-carboxylic acid (70 mg, 166.33 μmol, 17.73% yield). LC-MS (ES+, m/z): 413.2 [(M+H)$^+$]. Rt=1.357 min.

Step 8: 3-((1S,2S)-1-(5-(2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5(4H)-one

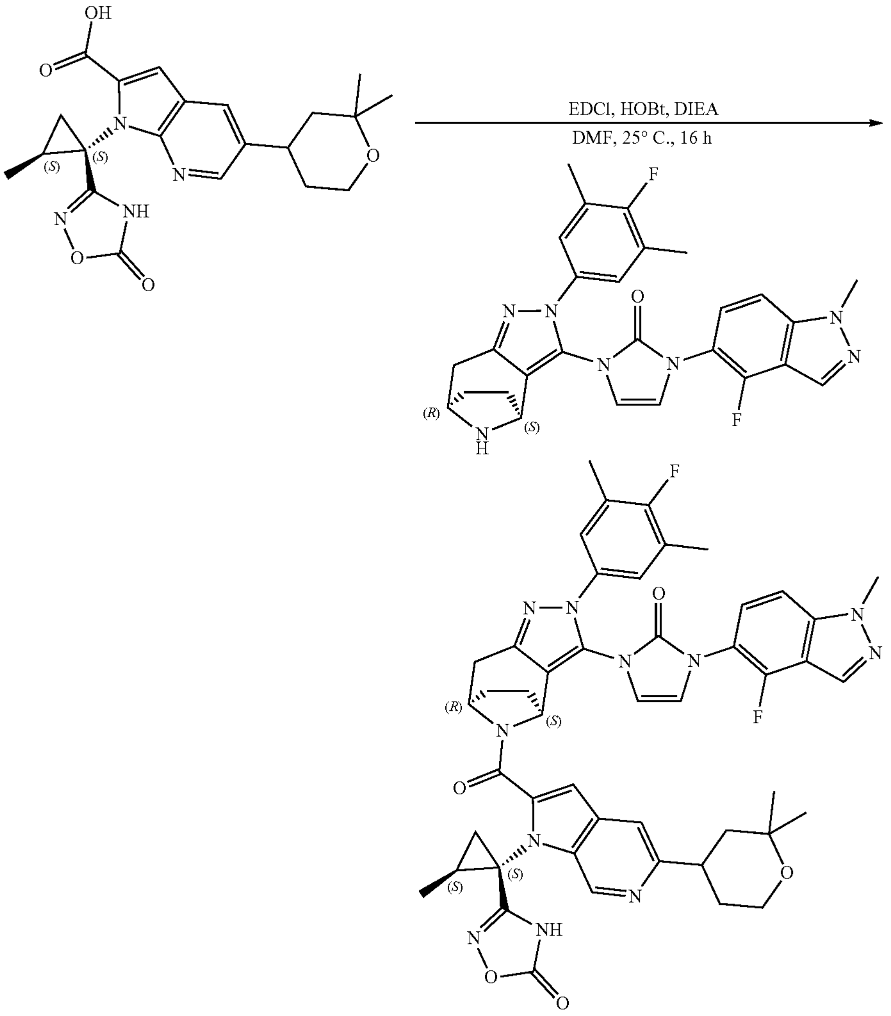

To a solution of 5-(2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid (50 mg, 94.02 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (47.16 mg, 94.02 μmol, 1 eq) in DMF (0.5 mL) was added EDCI (23.43 mg, 122.23 μmol, 1.3 eq), HOBt (19.06 mg, 141.04 μmol, 1.5 eq) and DIEA (121.52 mg, 940.24 μmol, 10 eq) in one portion under $N_2$. The mixture was stirred at 25° C. for 16 hours. LCMS showed the reaction was completed. The reaction mixture was quenched by addition $H_2O$ (5 mL), extracted with dichloromethane (3 mL*3). The combined organic layers were washed with saturated brine (8 mL), dried over anhydrous $Na_2SO_4$, filtered and concentrated under reduced pressure. The residue was purified by prep-HPLC (TFA condition) column: Phenomenex luna C18 100*40 mm*3 um; mobile phase: [$H_2O$ (0.1% TFA)-ACN]; gradient: 30%-70% B over 8.0 min to afford 3-((1S,2S)-1-(5-(2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5(4H)-one (14.05 mg, 15.68 μmol, 16.68% yield). $^1H$ NMR (400 MHz, DMSO-$d_6$) δ=11.81-12.05 (m, 1H), 6.63-8.43 (m, 10H), 4.86-5.55 (m, 2H), 4.10 (s, 3H), 2.93-3.56 (m, 4H), 2.78-2.88 (m, 1H), 2.32 (br dd, J=3.6, 1.7 Hz, 7H), 1.32-2.17 (m, 10H), 0.95-1.31 (m, 9H). $^1H$ NMR (400 MHz, DMSO-$d_6$+$D_2O$) δ=6.52-8.33 (m, 10H), 4.76-5.51 (m, 2H), 3.96 (br s, 3H), 2.91-3.71 (m, 4H), 2.79 (br d, J=16.1 Hz, 1H), 2.20 (br s, 7H), 1.25-2.07 (m, 10H), 0.85-1.24 (m, 9H). $^1H$ NMR (400 MHz, DMSO-$d_6$, T=273+80K) δ=11.50-11.79 (m, 1H), 6.64-8.42 (m, 10H), 4.83-5.54 (m, 2H), 4.09 (s, 3H), 3.60-3.73 (m, 2H), 2.92-3.29 (m, 2H), 2.83 (d, J=16.2 Hz, 1H), 2.25 (d, J=1.9 Hz, 7H), 1.39-2.19 (m, 10H), 1.12-1.28 (m, 9H). LC-MS (ES+, m/z): 896.3 [(M+H)$^+$]. Rt=2.910 min. HRMS (EI): m/z [M+H]$^+$ found: 896.3886.

Example 65 Compound 312

3-((1S,2S)-1-(5-((R)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5(4H)-one

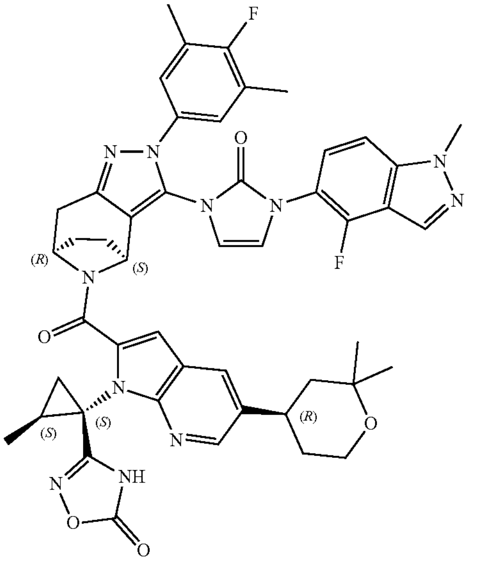

Step 1: 3-((1S,2S)-1-(5-((R)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5 (4H)-one

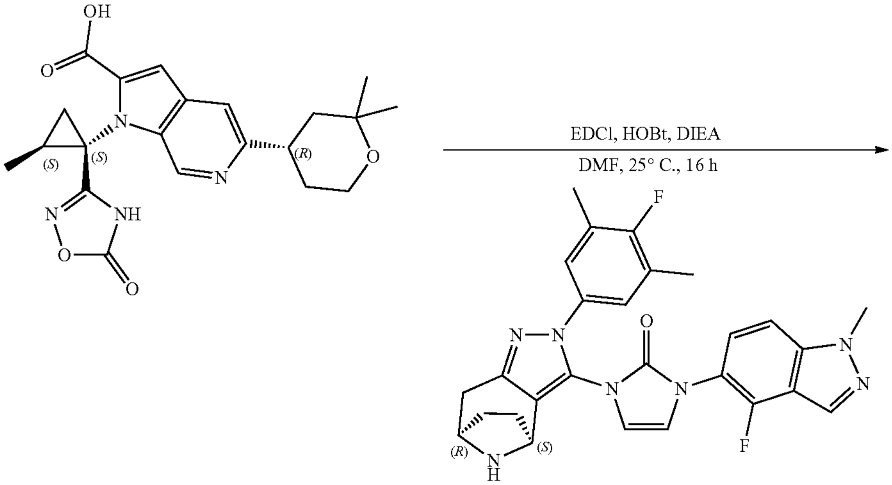

-continued

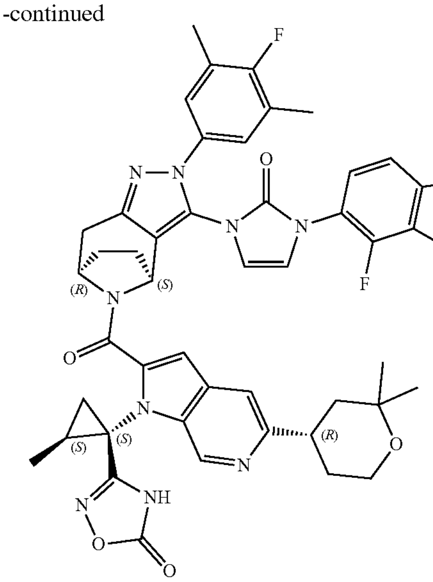

To a solution of 5-((R)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid (40 mg, 96.01 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (48.15 mg, 96.01 μmol, 1 eq) in DMF (0.4 mL) was added EDCI (23.93 mg, 124.82 μmol, 1.3 eq), HOBt (19.46 mg, 144.02 μmol, 1.5 eq) and DIEA (124.09 mg, 960.14 μmol, 10 eq) in one portion under $N_2$. The mixture was stirred at 25° C. for 16 hours. LCMS showed the reaction was completed. The reaction mixture was quenched by addition $H_2O$ (5 mL), extracted with dichloromethane (3 mL*3). The combined organic layers were washed with saturated brine (8 mL), dried over anhydrous $Na_2SO_4$, filtered and concentrated under reduced pressure. The residue was purified by prep-HPLC (TFA condition) column: Phenomenex Luna C18 75*30 mm*3 um; mobile phase: [$H_2O$ (0.1% TFA)-ACN]; gradient: 40%-70% B over 8.0 min to afford 3-((1S,2S)-1-(5-((R)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5 (4H)-one (15.43 mg, 17.22 μmol, 17.94% yield). $^1$H NMR (400 MHz, DMSO-$d_6$) δ=11.71-12.02 (m, 1H), 6.66-8.41 (m, 10H), 4.87-5.54 (m, 2H), 4.10 (s, 3H), 2.94-3.52 (m, 4H), 2.80-2.87 (m, 1H), 2.10-2.26 (m, 7H), 1.58-2.07 (m, 5H), 1.28-1.56 (m, 5H), 0.84-1.24 (m, 9H). $^1$H NMR (400 MHz, DMSO-$d_6$+$D_2O$) δ=6.68-8.35 (m, 10H), 4.71-5.55 (m, 2H), 4.00-4.11 (m, 3H), 2.89-3.67 (m, 4H), 2.77-2.87 (m, 1H), 2.10-2.23 (m, 7H), 1.56-2.06 (m, 5H), 1.25-1.52 (m, 5H), 0.82-1.20 (m, 9H). $^1$H NMR (400 MHz, DMSO-$d_6$+D2O, T=273+80K) δ=6.71-8.26 (s, 10H), 5.19-5.42 (m, 1H), 4.84-5.14 (m, 1H), 4.05 (d, J=2.7 Hz, 3H), 3.55-3.75 (m, 2H), 2.92-3.31 (m, 2H), 2.81 (br d, J=16.6 Hz, 1H), 2.14-2.23 (m, 7H), 1.60-2.08 (m, 5H), 1.23-1.56 (m, 5H), 0.85-1.21 (m, 9H). LC-MS (ES+, m/z): 896.2 [$(M+H)^+$]. Rt=3.086 min. HRMS (EI): m/z $[M+H]^+$ found: 896.3795.

Example 66 Compound 313

3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5 (4H)-one

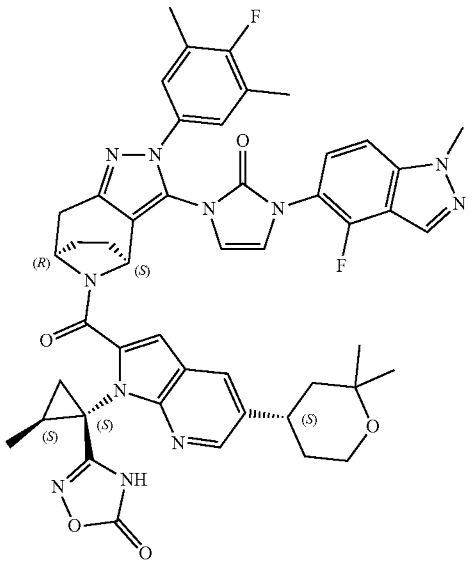

Step 1: 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5(4H)-one

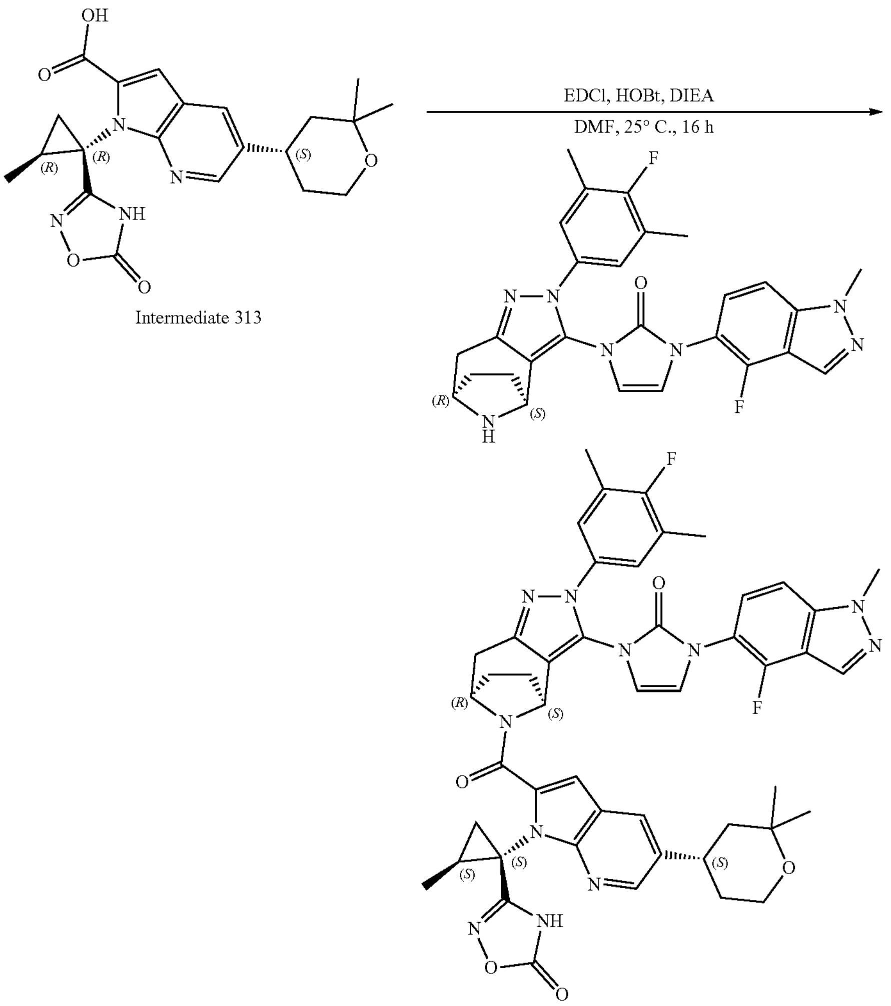

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-pyrrolo[2,3-b]pyridine-2-carboxylic acid (40 mg, 96.01 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (48.15 mg, 96.01 μmol, 1 eq) in DMF (0.4 mL) was added EDCI (23.93 mg, 124.82 μmol, 1.3 eq), HOBt (19.46 mg, 144.02 μmol, 1.5 eq) and DIEA (124.09 mg, 960.14 μmol, 10 eq) in one portion under $N_2$. The mixture was stirred at 25° C. for 16 hours. LCMS showed the reaction was completed. The reaction mixture was quenched by addition $H_2O$ (5 mL), extracted with dichloromethane (3 mL*3). The combined organic layers were washed with saturated brine (8 mL), dried over anhydrous $Na_2SO_4$, filtered and concentrated under reduced pressure. The residue was purified by prep-HPLC (TFA condition) (column: Phenomenex Luna C18 75*30 mm*3 um; mobile phase: [$H_2O$ (0.1% TFA)-ACN]; gradient: 45%-75% B over 8.0 min) to afford 3-((1S,2S)-1-(5-((S)-2,2-dimethyltetrahydro-2H-pyran-4-yl)-2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-pyrrolo[2,3-b]pyridin-1-yl)-2-methylcyclopropyl)-1,2,4-oxadiazol-5(4H)-one (15.32 mg, 17.10 μmol, 17.81% yield). $^1$H NMR (400 MHz, DMSO-$d_6$) δ=11.78-12.10 (m, 1H), 6.78-8.36 (m, 10H), 4.79-5.61 (m, 2H), 4.10 (br s, 3H), 2.92-3.35 (m, 4H), 2.77-2.87 (m, 1H), 2.25 (br s, 7H), 1.58-1.96 (m, 5H), 1.29-1.53 (m, 5H), 0.88-1.24 (m, 9H). $^1$H NMR (400 MHz, DMSO-$d_6$+$D_2O$) δ=6.65-8.31 (m, 10H), 5.43 (s, 2H), 4.06 (br s, 3H), 2.96-3.60 (m, 4H), 2.76-2.85 (m, 1H), 2.10-2.23 (m, 7H), 1.57-2.03 (m, 5H), 1.29 (br d, J=4.0 Hz, 5H), 0.86-1.20 (m, 9H). $^1$H NMR (400 MHz, DMSO-$d_6$+D2O, T=273+80K) δ=6.60-8.37 (m, 10H), 5.30 (br d, J=2.0 Hz, 1H), 4.89-5.10 (m, 1H), 4.03-4.06 (m, 3H), 3.57-3.72 (m, 2H), 2.98-3.31 (m, 2H), 2.81 (br d, J=16.3 Hz, 1H), 2.22 (d, J=1.5 Hz, 7H), 1.61-2.13 (m, 5H), 1.38-1.59 (m, 5H), 0.88-1.22 (m, 9H). LC-MS (ES+, m/z): 896.2 [(M+H)$^+$]. Rt=3.084 min. HRMS (EI): m/z [M+H]$^+$ found: 896.3795

Example 67 Compound 406
3-((1S,2S)-1-(5-((S)-2,2-dimethyltetrahydro-2H-pyran-4-yl)-2-((4S,7R)-3-(3-(4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one
Scheme 406
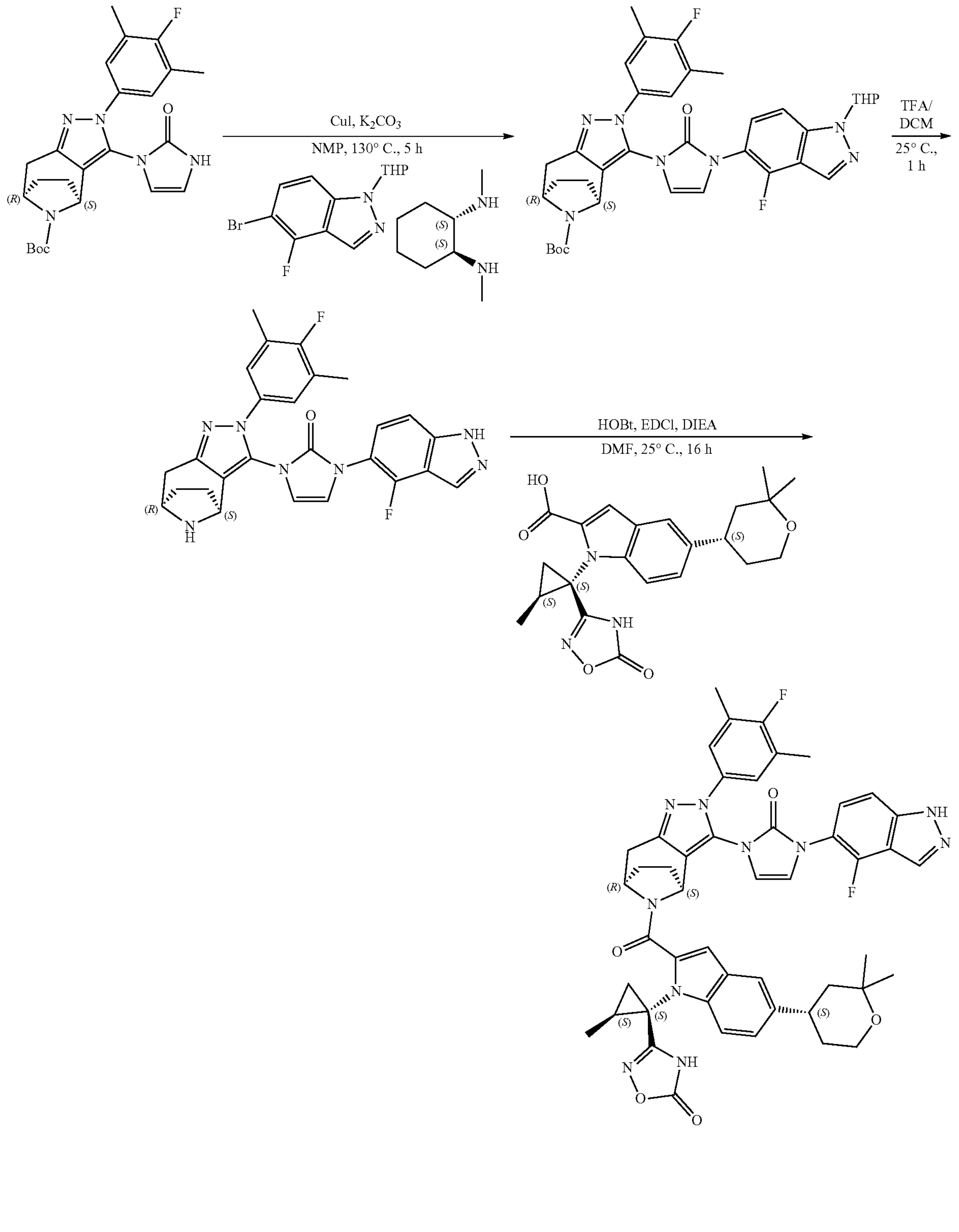

Step 1: tert-butyl (4S,7R)-3-(3-(4-fluoro-1-(tetrahydro-2H-pyran-2-yl)-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

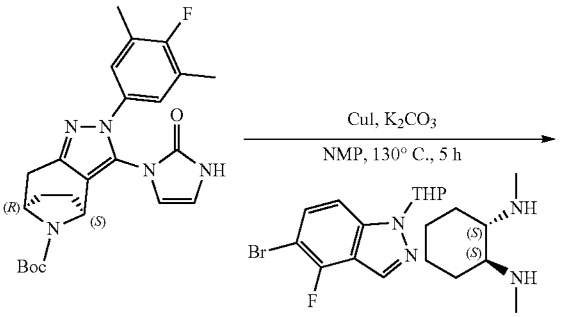

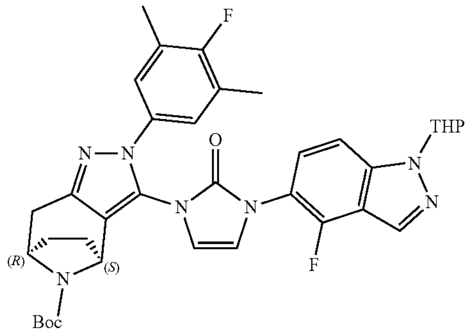

To a solution of tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (200 mg, 441.01 μmol, 1 eq), 5-bromo-4-fluoro-1-(tetrahydro-2H-pyran-2-yl)-1H-indazole (263.84 mg, 882.01 μmol, 2 eq) and (1S,2S)—$N^1$,$N^2$-dimethylcyclohexane-1,2-diamine (188.19 mg, 1.32 mmol, 3 eq) in NMP (2 mL) was added CuI (167.98 mg, 882.01 μmol, 2 eq) and $K_2CO_3$ (121.90 mg, 882.01 μmol, 2 eq) in one portion under $N_2$. The mixture was stirred at 130° C. for 5 hours under $N_2$. LCMS showed the reaction was completed. The reaction mixture was quenched by addition EDTA solution (30 mL) and ethyl acetate (10 mL), stirred for 0.5 hour, extracted with ethyl acetate (20 mL*3). The combined organic layers were washed with saturated brine (50 mL), dried over anhydrous $Na_2SO_4$, filtered and concentrated under reduced pressure. The residue was purified by prep-TLC ($SiO_2$, petroleum ether/ethyl acetate=0/1) to afford the title compound tert-butyl (4S,7R)-3-(3-(4-fluoro-1-(tetrahydro-2H-pyran-2-yl)-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200 mg, 285.83 μmol, 64.81% yield). LC-MS (ES+, m/z): 672.4 [$(M+H)^+$]; Rt=2.130 min.

Step 2: 1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

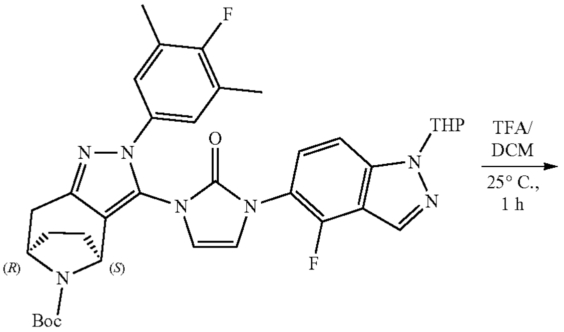

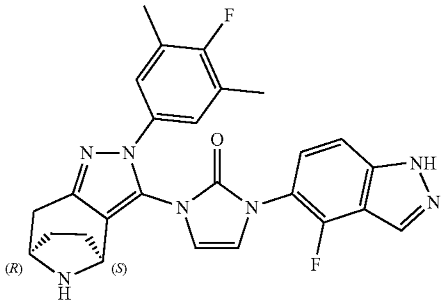

To a solution of tert-butyl (4S,7R)-3-(3-(4-fluoro-1-(tetrahydro-2H-pyran-2-yl)-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (200 mg, 285.83 μmol, 1 eq) in DCM (1.6 mL) was added TFA (0.4 mL) in one portion. The mixture was stirred at 25° C. for 1 hour. LCMS showed the reaction was completed. The reaction mixture was quenched by addition saturated $NaHCO_3$ solution (20 mL) at 0° C., extracted with DCM (10 mL*3). The combined organic layers were washed with saturated brine (30 mL), dried over anhydrous $Na_2SO_4$, filtered and concentrated under reduced pressure to afford the title compound 1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (130 mg, 285.83 μmol, 72% yield). LC-MS (ES+, m/z): 488.3 [$(M+H)^+$]; Rt=0.382 min.

Step 3: 3-((1S,2S)-1-(5-((S)-2,2-dimethyltetrahydro-2H-pyran-4-yl)-2-((4S,7R)-3-(3-(4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

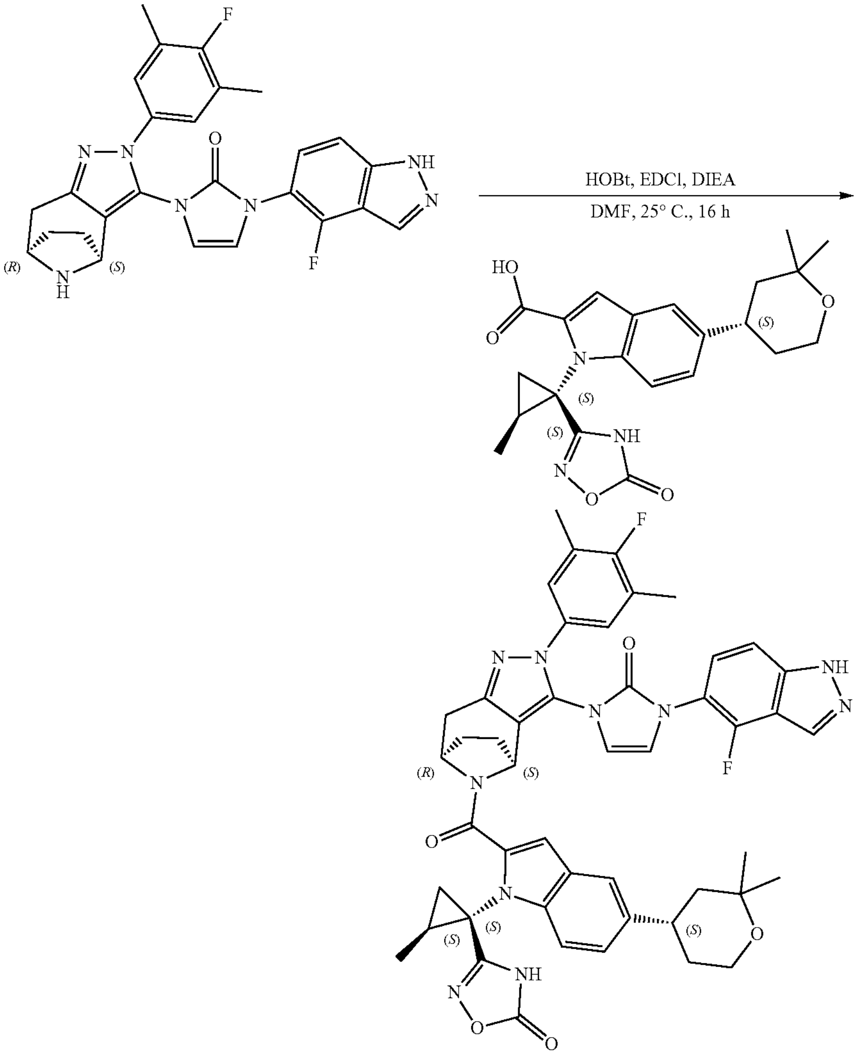

To a solution of 1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (50 mg, 95.38 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (39.25 mg, 95.38 μmol, 1 eq) in DMF (0.5 mL) was added HOBt (19.33 mg, 143.08 μmol, 1.5 eq), EDCI (23.77 mg, 124.00 μmol, 1.3 eq), DIEA (123.28 mg, 953.84 μmol, 10 eq) in one portion at 25° C. under $N_2$. The mixture was stirred at 25° C. for 16 hours under $N_2$. LCMS showed the reaction was completed. The reaction mixture was quenched by addition $H_2O$ (5 mL), extracted with dichloromethane (3 mL*3). The combined organic layers were washed with saturated brine (8 mL), dried over anhydrous $Na_2SO_4$, filtered and concentrated under reduced pressure. The residue was purified by prep-HPLC (TFA condition) column: Phenomenex Luna C18 75*30 mm*3 um; mobile phase: [$H_2O$ (0.1% TFA)-ACN]; gradient: 45%-75% B over 8.0 min to afford the title compound 3-((1S,2S)-1-(5-((S)-2,2-dimethyltetrahydro-2H-pyran-4-yl)-2-((4S,7R)-3-(3-(4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (14.03 mg, 15.93 μmol, 16.70% yield). $^1H$ NMR (400 MHz, DMSO-$d_6$) δ=13.73-13.39 (m, 1H), 12.20-11.69 (m, 1H), 8.47-6.49 (m, 11H), 5.66-4.86 (m, 2H), 3.77-3.58 (m, 2H), 3.27-2.77 (m, 3H), 2.30-2.15 (m, 7H), 1.80-0.98 (m, 19H). $^1H$ NMR (400 MHz, DMSO-$d_6$+D20) δ=8.34-6.46 (m, 11H), 5.59-4.80 (m, 2H), 3.68-2.78 (m, 5H), 2.24-2.07 (m, 7H), 1.79-0.93 (m, 19H). $^1H$ NMR (400 MHz, DMSO-$d_6$+D2O, T=273+80K) δ=8.29-6.42 (m, 11H), 5.53-4.68 (m, 2H), 3.78-3.41 (m, 3H), 3.04-2.74 (m, 2H), 2.24-2.10 (m, 7H), 1.88-1.04 (m, 19H). LC-MS (ES+, m/z): 881.3 [$(M+H)^+$]. Rt=2.959 min. HRMS (EI): m/z $[M+H]^+$ found: 881.3715.

Example 68 Compound 410
3-((1S,2S)-1-(5-((S)-2,2-dimethyltetrahydro-2H-pyran-4-yl)-2-((4S,7R)-2-(4-fluoro-3,5-dimethylphenyl)-3-(3-(5-fluorophthalazin-6-yl)-2-oxo-2,3-dihydro-1H-imidazol-1-yl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one
Scheme 410
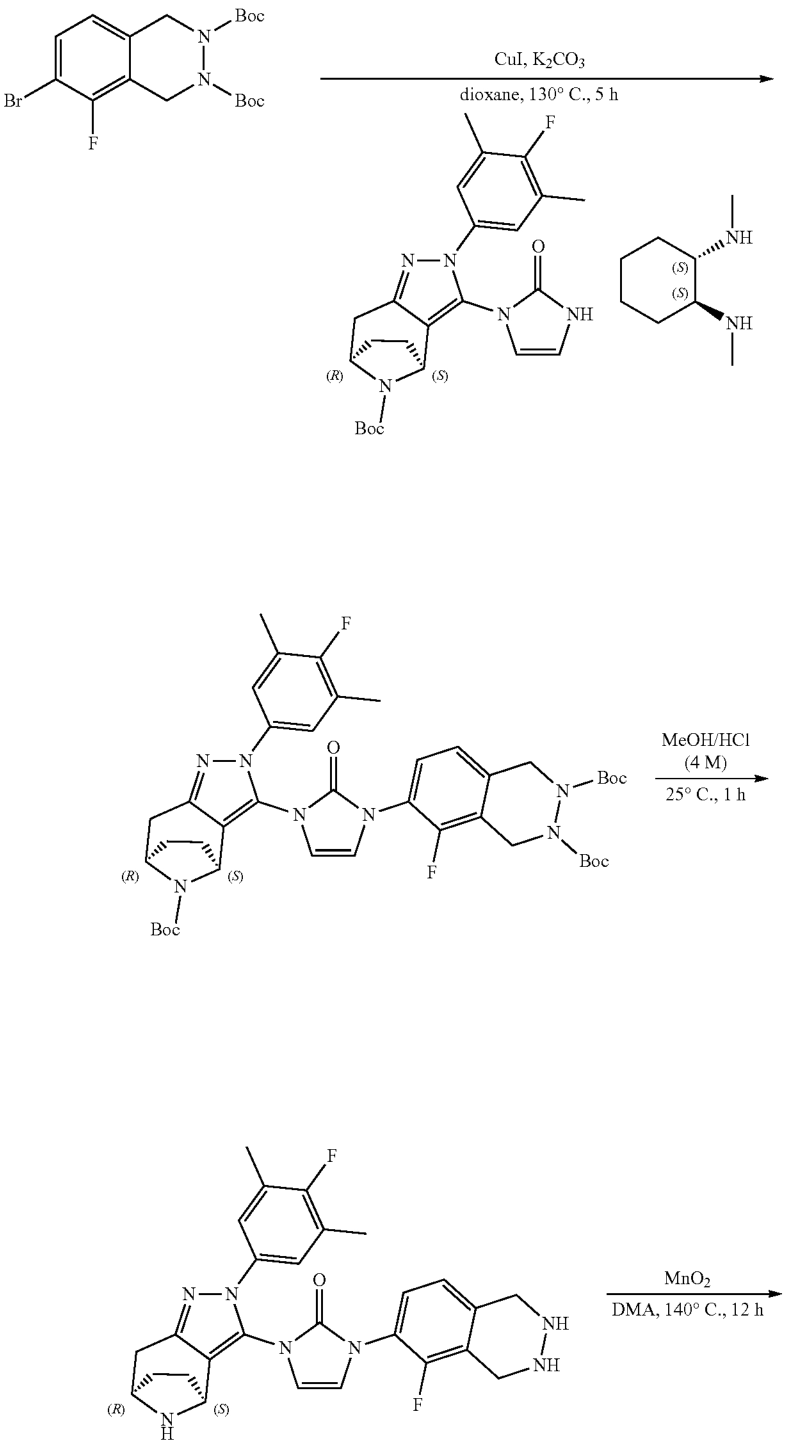

-continued
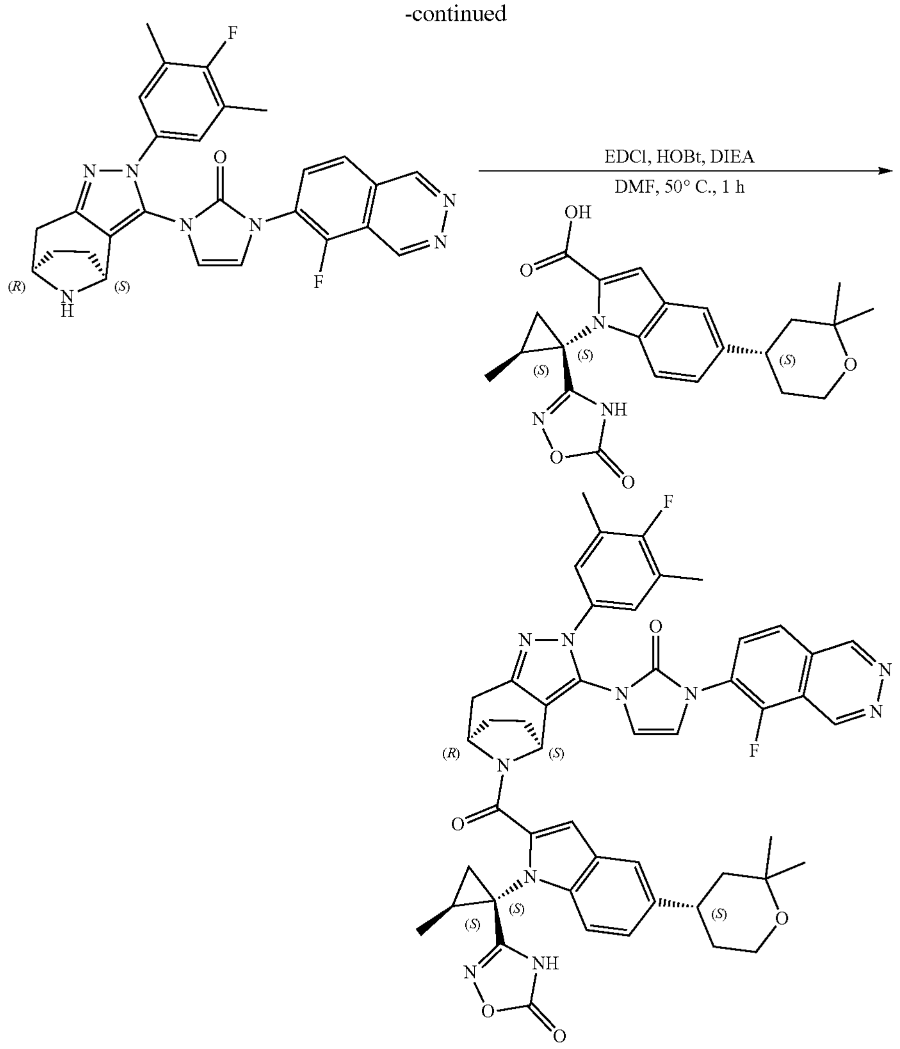
Step 1: di-tert-butyl 6-(3-((4S,7R)-9-(tert-butoxycarbonyl)-2-(4-fluoro-3,5-dimethylphenyl)-2,4,5,6,7,8-hexahydro-4,7-epiminocyclohepta [c]pyrazol-3-yl)-2-oxo-2,3-dihydro-1H-imidazol-1-yl)-5-fluorophthalazine-2,3 (1H,4H)-dicarboxylate
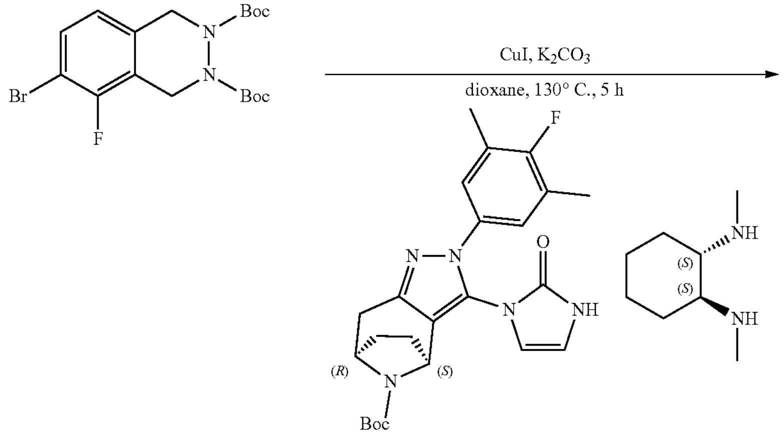

-continued

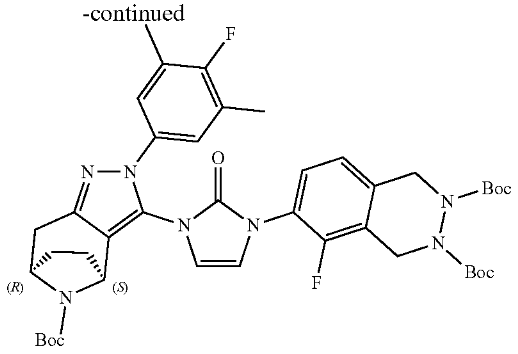

To a solution of di-tert-butyl 6-bromo-5-fluorophthalazine-2,3 (1H,4H)-dicarboxylate (1 g, 2.32 mmol, 1.5 eq) and (4S,7R)-tert-butyl 2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (701.00 mg, 1.55 mmol, 1 eq) and (1S,2S)—N1,N2-dimethylcyclohexane-1,2-diamine (439.73 mg, 3.09 mmol, 2 eq) in NMP (10 mL) was added CuI (588.77 mg, 3.09 mmol, 2 eq) and $K_2CO_3$ (640.91 mg, 4.64 mmol, 3 eq). The mixture was stirred at 130° C. for 5 hours under $N_2$. LC-MS showed the reaction was completed. The reaction mixture was diluted with saturated EDTA (200 mL) and stirred for 1 hour, extracted with ethyl acetate (200 mL*3). The combined organic layers were washed with saturated brine (200 mL*2). The combined organic layers were dried over $Na_2SO_4$, filtered and concentrated in vacuum. The residue was purified by column chromatography ($SiO_2$, Petroleum ether/ethyl acetate=10/1 to 2/1) to give di-tert-butyl 6-(3-((4S,7R)-9-(tert-butoxycarbonyl)-2-(4-fluoro-3,5-dimethylphenyl)-2,4,5,6,7,8-hexahydro-4,7-epiminocyclohepta [c]pyrazol-3-yl)-2-oxo-2,3-dihydro-1H-imidazol-1-yl)-5-fluorophthalazine-2,3 (1H,4H)-dicarboxylate (1 g, 976.50 μmol, 63.17% yield). LC-MS (ES+, m/z): 804.4 [(M+H)$^+$]; Rt=0.702 min.

Step 2: 1-(5-fluoro-1,2,3,4-tetrahydrophthalazin-6-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one -continued

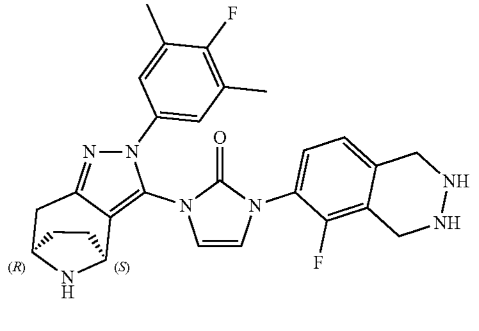

To a solution of di-tert-butyl 6-(3-((4S,7R)-9-(tert-butoxycarbonyl)-2-(4-fluoro-3,5-dimethylphenyl)-2,4,5,6,7,8-hexahydro-4,7-epiminocyclohepta [c]pyrazol-3-yl)-2-oxo-2,3-dihydro-1H-imidazol-1-yl)-5-fluorophthalazine-2,3 (1H,4H)-dicarboxylate (1 g, 1.24 mmol, 1 eq) in DCM (10 mL) was added TFA (3 mL). The mixture was stirred at 25° C. for 1 hour under $N_2$. LC-MS showed the reaction was completed. The reaction mixture was concentrated under reduced pressure. The reaction mixture was adjusted to pH-7 with saturated $NaHCO_3$ (50 mL) and stirred for 0.5 hour, extracted with DCM (50 mL*3). The combined organic layers were washed with saturated brine (50 mL*2). The combined organic layers were dried over $Na_2SO_4$, filtered and concentrated to give 1-(5-fluoro-1,2,3,4-tetrahydrophthalazin-6-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (0.6 g, 1.00 mmol, 80.46% yield). LC-MS (ES+, m/z): 504.3 [(M+H)$^+$]; Rt=0.314 min.

Step 3: 1-((4S,7R)-2-(4-fluoro-3,5-dimethylphenyl)-2,4,5,6,7,8-hexahydro-4,7-epiminocyclohepta [c]pyrazol-3-yl)-3-(5-fluorophthalazin-6-yl)-1H-imidazol-2 (3H)-one

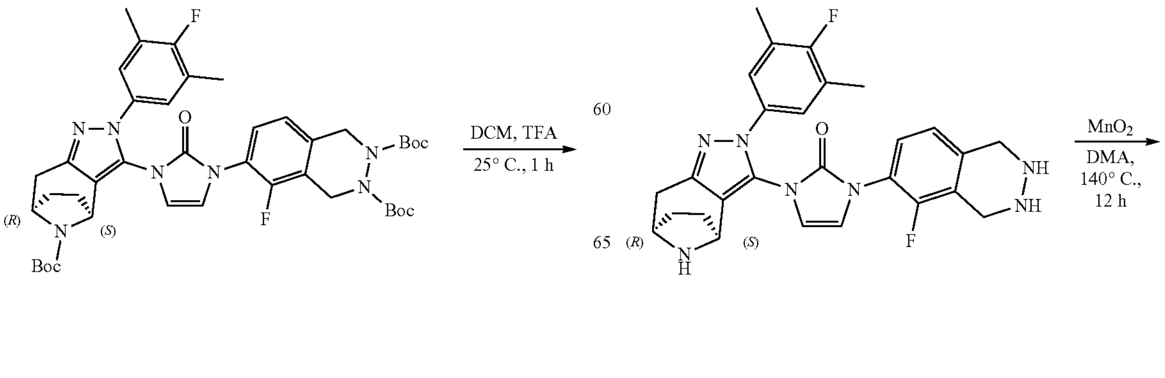

-continued

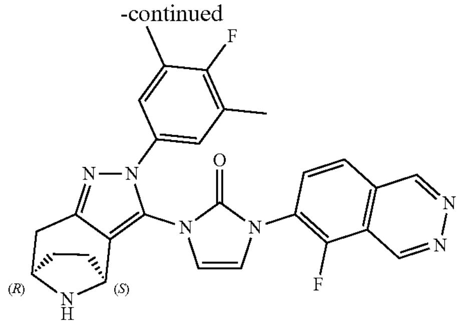

To a solution of 1-(5-fluoro-1,2,3,4-tetrahydrophthalazin-6-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (0.6 g, 1.19 mmol, 1 eq) in DMA (10 mL) was added $MnO_2$ (1.14 g, 13.11 mmol, 11 eq). The mixture was stirred at 140° C. for 12 hours under $N_2$. LC-MS showed the reaction was completed. The reaction mixture was filtered and diluted with water (50 mL), extracted with ethyl acetate (50 mL*3). The combined organic layers were washed with saturated brine (50 mL*2). The combined organic layers were dried over $Na_2SO_4$, filtered and concentrated. The residue was purified by prep-HPLC ($NH_4HCO_3$ condition) column: Welch Xtimate C18 180*70 mm #10 um; mobile phase: [$H_2O$ (10 mM $NH_4HCO_3$)-ACN]; gradient: 10%-50% B over 17.0 min to give 1-((4S,7R)-2-(4-fluoro-3,5-dimethylphenyl)-2,4,5,6,7,8-hexahydro-4,7-epiminocyclohepta [c]pyrazol-3-yl)-3-(5-fluorophthalazin-6-yl)-1H-imidazol-2 (3H)-one (30 mg, 53.69 μmol, 4.51% yield). LC-MS (ES+, m/z): 500.3 [(M+H)$^+$]; Rt=1.141 min.

Step 4: 3-((1S,2S)-1-(5-((S)-2,2-dimethyltetrahydro-2H-pyran-4-yl)-2-((4S,7R)-2-(4-fluoro-3,5-dimethylphenyl)-3-(3-(5-fluorophthalazin-6-yl)-2-oxo-2,3-dihydro-1H-imidazol-1-yl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

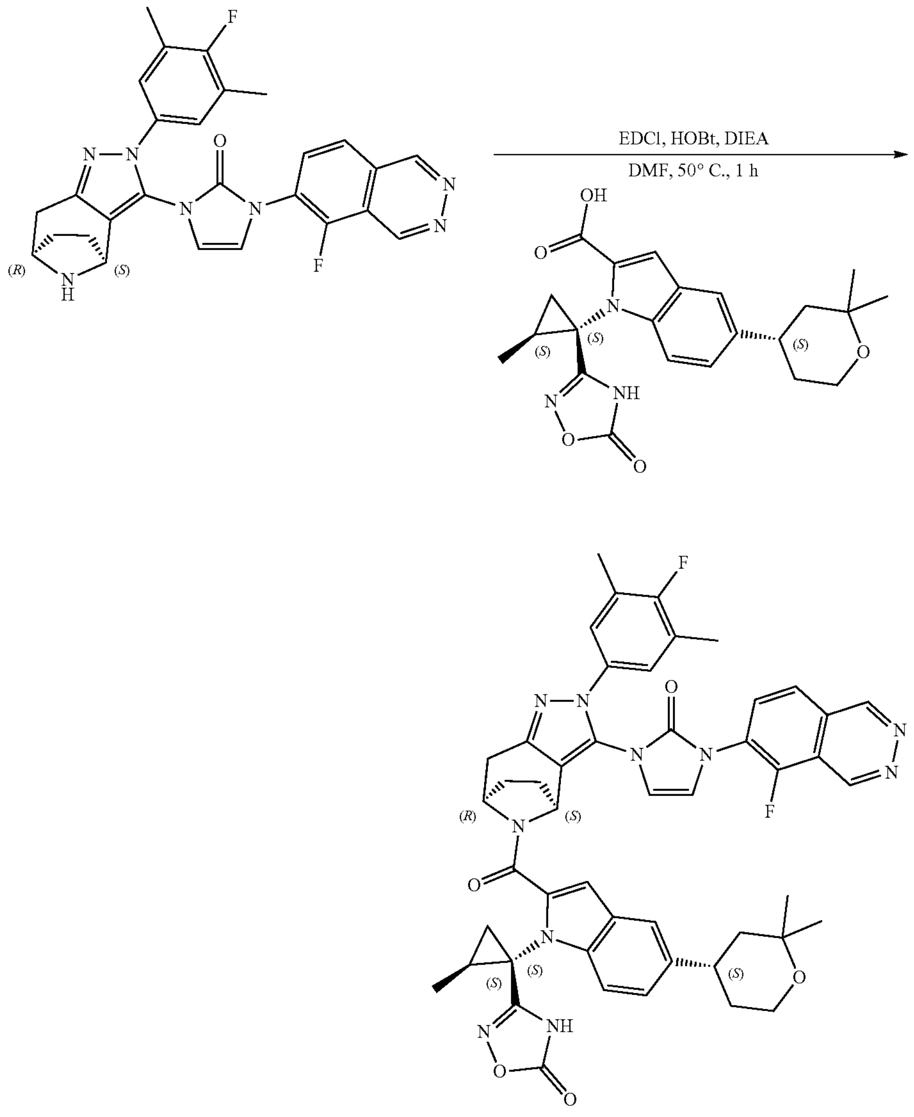

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (16.47 mg, 40.04 μmol, 1 eq) in DMF (1 mL) was added HOBt (10.82 mg, 80.08 μmol, 2 eq) and EDCI (15.35 mg, 80.08 μmol, 2 eq) and DIEA (15.52 mg, 120.12 μmol, 20.92 μL, 3 eq). Then 1-((4S,7R)-2-(4-fluoro-3,5-dimethylphenyl)-2,4,5,6,7,8-hexahydro-4,7-epiminocyclohepta [c]pyrazol-3-yl)-3-(5-fluorophthalazin-6-yl)-1H-imidazol-2 (3H)-one (20 mg, 40.04 μmol, 1 eq) was added. The mixture was stirred at 50° C. for 1 hour under $N_2$. LC-MS showed the reaction was completed. The reaction mixture was diluted with saturated water (50 mL) and stirred for 0.5 hour, extracted with ethyl acetate (50 mL*3). The combined organic layers were washed with saturated brine (50 mL*2). The combined organic layers were dried over $Na_2SO_4$, filtered and concentrated. The residue was purified by prep-HPLC (TFA condition) column: 3_Phenomenex Luna C18 75*30 mm*3 um; mobile phase: [$H_2O$ (0.1% TFA)-ACN]; gradient: 45%-75% B over 8.0 min to give 3-((1S,2S)-1-(5-((S)-2,2-dimethyltetrahydro-2H-pyran-4-yl)-2-((4S,7R)-2-(4-fluoro-3,5-dimethylphenyl)-3-(3-(5-fluorophthalazin-6-yl)-2-oxo-2,3-dihydro-1H-imidazol-1-yl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one (4.16 mg, 4.64 μmol, 11.60% yield). $^1$H NMR (400 MHz, DMSO-$d_6$) δ=12.24-11.69 (m, 1H), 10.00-9.67 (m, 2H), 8.34-8.15 (m, 1H), 7.82-6.70 (m, 9H), 5.73-4.78 (m, 2H), 3.76-3.61 (m, 2H), 3.18-2.72 (m, 3H), 2.30-2.05 (m, 8H), 1.85-0.96 (m, 18H). LC-MS (ES+, m/z): 893.3 [(M+H)$^+$]; Rt=2.794 min. HRMS (EI): m/z [M+H]$^+$ found: 893.3661.

Example 69 Compound 411

3-((1S,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5(4H)-one

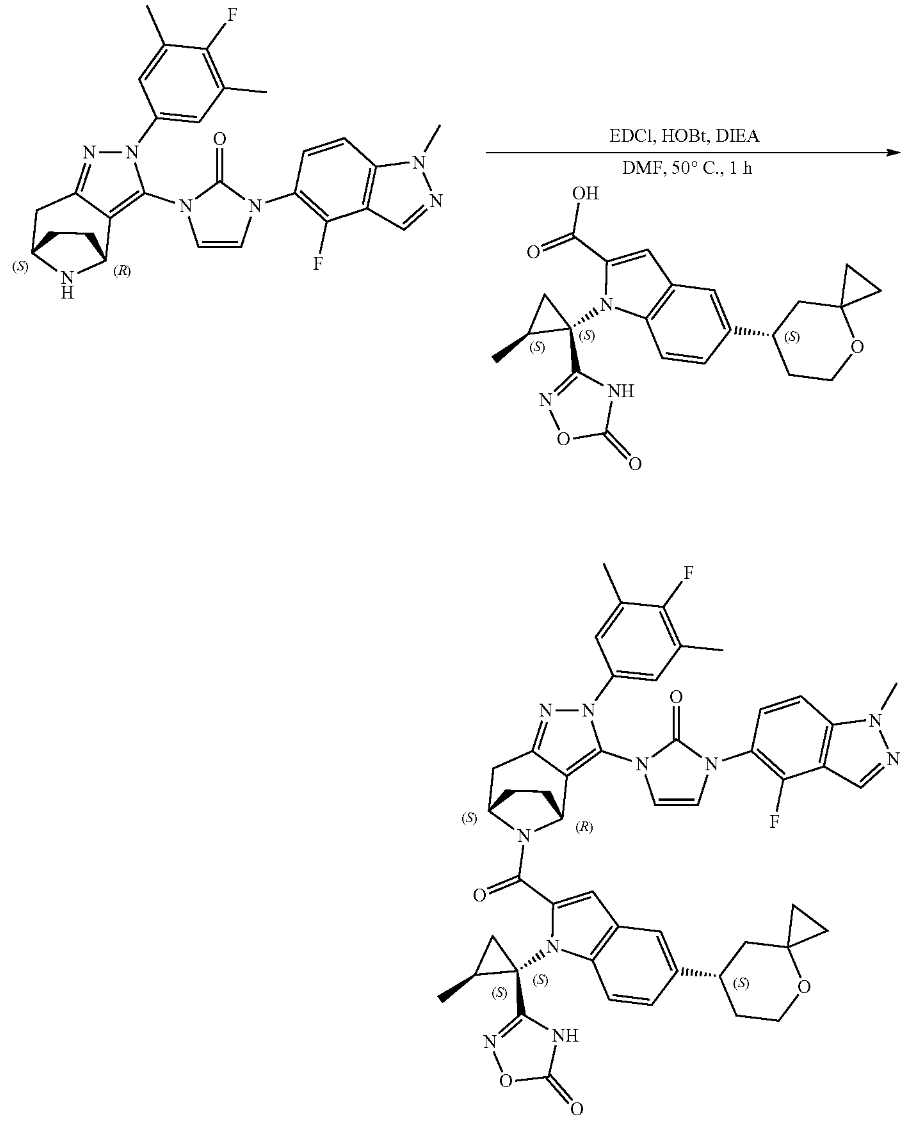

To a solution of 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (40 mg, 97.70 μmol, 1 eq) in DMF (1 mL) was added HOBt (26.40 mg, 195.39 μmol, 2 eq) and EDCI (37.46 mg, 195.39 μmol, 2 eq) and DIEA (63.13 mg, 488.48 μmol, 85.08μ, 5 eq). Then 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1H-imidazol-2 (3H)-one (49.00 mg, 97.70 μmol, 1 eq) was added. The mixture was stirred at 50° C. for 1 hour. LC-MS showed the reaction was completed. The reaction mixture was diluted with water (50 mL) and stirred for 0.5 hour, extracted with ethyl acetate (50 mL*3). The combined organic layers were washed with saturated brine (50 mL*2). The combined organic layers were dried over $Na_2SO_4$, filtered and concentrated. The residue was purified by prep-HPLC (TFA condition) column: Welch Ultimate C18 120*30 mm*5 um; mobile phase: [$H_2O$ (0.1% TFA)-ACN]; gradient: 55%-85% B over 8.0 min to give 3-((1S,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (17.26 mg, 19.16 μmol, 19.61% yield). $^1$H NMR (400 MHz, DMSO-$d_6$) δ=12.33-11.59 (m, 1H), 8.31 (s, 1H), 7.74-6.63 (m, 10H), 5.51-4.83 (m, 2H), 4.11 (s, 3H), 3.65-3.21 (m, 3H), 2.88 (br d, J=16.1 Hz, 2H), 2.37-2.05 (m, 9H), 2.01-1.04 (m, 11H), 0.86-0.25 (m, 4H). LC-MS (ES+, m/z): 893.3 [(M+H)$^+$]; Rt=3.053 min. HRMS (EI): m/z [M+H]$^+$ found: 893.3661.

Example 70 Compound 416

3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydropyrazolo[4,3-c]azepine-5-carbonyl)-1H-indol-1-yl)-2-methylcyclopropyl)-1,2,4-oxadiazol-5 (4H)-one

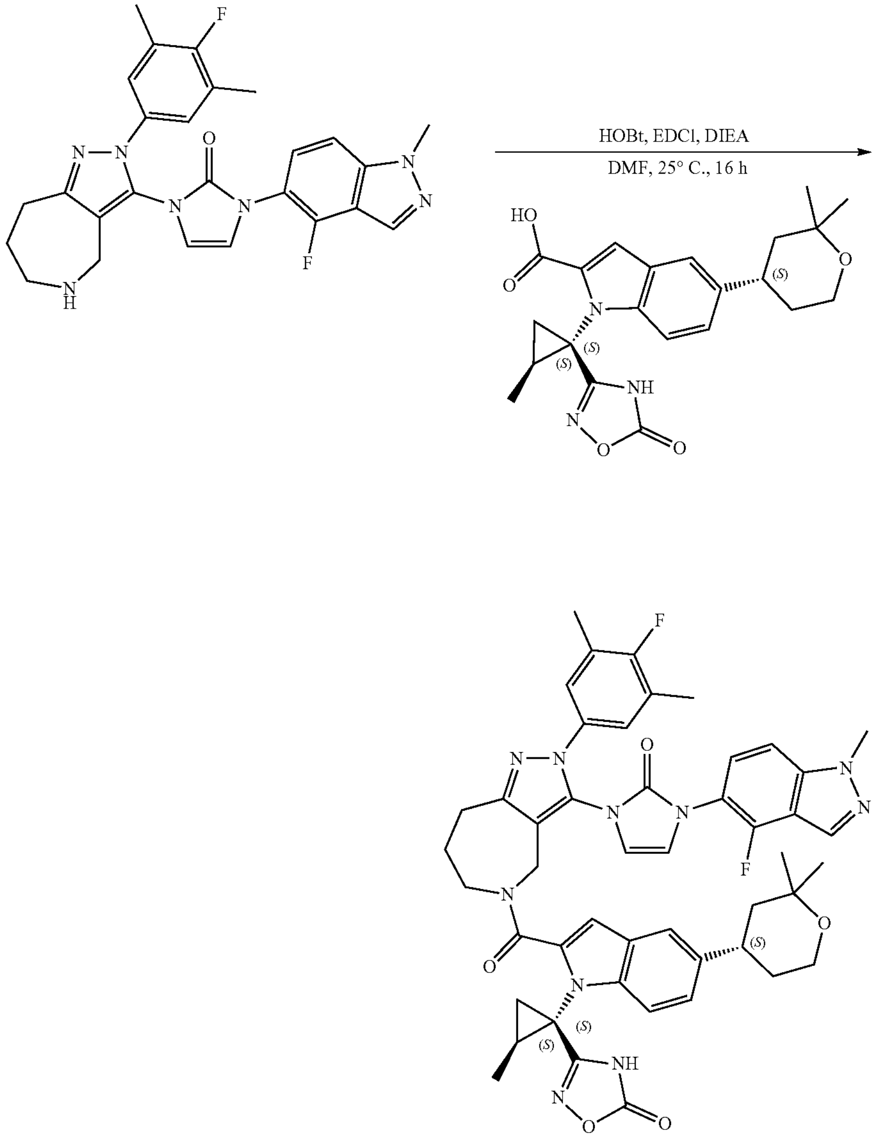

To a solution of 1-(4-fluoro-1-methyl-1H-indazol-5-yl)-3-(2-(4-fluoro-3,5-dimethylphenyl)-2,4,5,6,7,8-hexahydro-pyrazolo[4,3-c]azepin-3-yl)-1,3-dihydro-2H-imidazol-2-one (40 mg, 69.46 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (28.58 mg, 69.46 μmol, 1 eq) in DMF (0.4 mL) was added EDCI (17.31 mg, 90.29 μmol, 1.3 eq), DIEA (89.77 mg, 694.56 μmol, 10 eq), HOBt (14.08 mg, 104.18 μmol, 1.5 eq) in one portion at 25° C. under $N_2$. The mixture was stirred at 25° C. for 16 hours. LCMS showed the reaction was completed. The reaction mixture was quenched by addition $H_2O$ (5 mL), extracted with dichloromethane (3 mL*3). The combined organic layers were washed with saturated brine (8 mL), dried over anhydrous $Na_2SO_4$, filtered and concentrated under reduced pressure. The residue was purified by prep-HPLC (TFA condition) column: Phenomenex Luna C18 75*30 mm*3 um; mobile phase: [$H_2O$ (0.1% TFA)-ACN]; gradient: 45%-75% B over 8.0 min to afford the title compound 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydropyrazolo[4,3-c]azepine-5-carbonyl)-1H-indol-1-yl)-2-methylcyclopropyl)-1,2,4-oxadiazol-5 (4H)-one (12.79 mg, 14.40 μmol, 20.74% yield). $^1$H NMR (400 MHz, DMSO-$d_6$) δ=12.17-11.58 (m, 1H), 8.38-8.14 (m, 1H), 7.68-6.95 (m, 8H), 6.87-6.47 (m, 2H), 4.95-4.61 (m, 2H), 4.09 (s, 3H), 3.63-3.39 (m, 4H), 3.09-2.83 (m, 3H), 2.24-1.94 (m, 8H), 1.64-0.94 (m, 16H). $^1$H NMR (400 MHz, DMSO-$d_6$+$D_2O$) δ=8.33-8.04 (m, 1H), 7.60-6.54 (m, 9H), 6.34-5.89 (m, 1H), 5.01-4.45 (m, 2H), 4.15 (br s, 3H), 3.91-3.12 (m, 4H), 2.97 (br s, 3H), 2.22-1.91 (m, 8H), 1.62-0.81 (m, 16H). LC-MS (ES+, m/z): 883.3 [$(M+H)^+$]. Rt=3.001 min. HRMS (EI): m/z $[M+H]^+$ found: 883.3849.

Example 71 Compound 417

3-((1S,2S)-1-(5-((S)-2,2-dimethyltetrahydro-2H-pyran-4-yl)-2-(((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazol-9-yl) methyl)-1H-indol-1-yl)-2-methylcyclopropyl)-1,2,4-oxadiazol-5(4H)-one

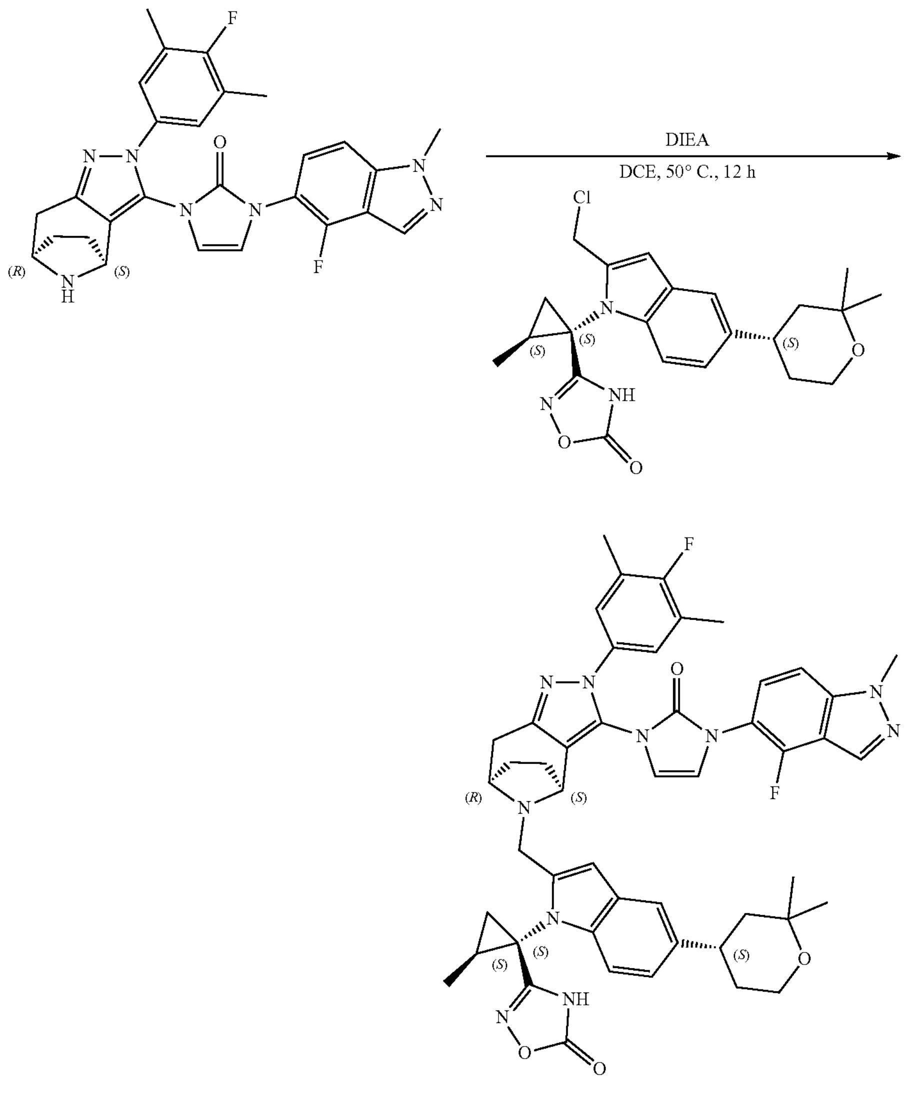

To a solution of 3-((1S,2S)-1-(2-(chloromethyl)-5-((S)-2,2-dimethyltetrahydro-2H-pyran-4-yl)-1H-indol-1-yl)-2-methylcyclopropyl)-1,2,4-oxadiazol-5 (4H)-one (50 mg, 48.09 μmol, 1 eq), 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (24.12 mg, 48.09 μmol, 1 eq) in DCE (0.5 mL) was added DIEA (18.64 mg, 144.26 μmol, 3 eq). The mixture was stirred at 50° C. for 12 hours under $N_2$. LC-MS showed the reaction was completed. The residue was filtered and concentrated in vacuum. The residue was purified by prep-HPLC (column: WePure Biotech XP tC18 150*40*7 um; mobile phase: [$H_2O$ (10 mM $NH_4HCO_3$)-ACN]; gradient: 45%-70% B over 8.0 min) to afford 3-((1S,2S)-1-(5-((S)-2,2-dimethyltetrahydro-2H-pyran-4-yl)-2-(((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazol-9-yl)methyl)-1H-indol-1-yl)-2-methylcyclopropyl)-1,2,4-oxadiazol-5 (4H)-one (8.63 mg, 9.50 μmol, 19.76% yield). $^1$H NMR (400 MHz, DMSO-$d_6$) δ=8.48-8.09 (m, 1H), 7.64 (d, J=8.6 Hz, 1H), 7.54-6.86 (m, 8H), 6.82-6.53 (m, 1H), 4.48 (br d, J=13.4 Hz, 1H), 4.20-4.08 (m, 4H), 3.87 (br d, J=14.0 Hz, 1H), 3.75-3.65 (m, 2H), 3.48-3.41 (m, 1H), 3.06-2.80 (m, 3H), 2.41 (br s, 1H), 2.27 (s, 6H), 2.14-2.06 (m, 1H), 1.99-1.86 (m, 2H), 1.77-1.18 (m, 14H), 1.11 (s, 2H) (N—H was not detected). LC-MS (ES+, m/z): 881.3 [$(M+H)^+$]; Rt=3.314 min. HRMS (EI): m/z $[M+H]^+$ found: 881.4028.

Example 72 Compound 415

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(5-oxaspiro[3.5]nonan-8-yl)-1H-indol-1-yl)-2-methylcyclopropyl)-1,2,4-oxadiazol-5 (4H)-one

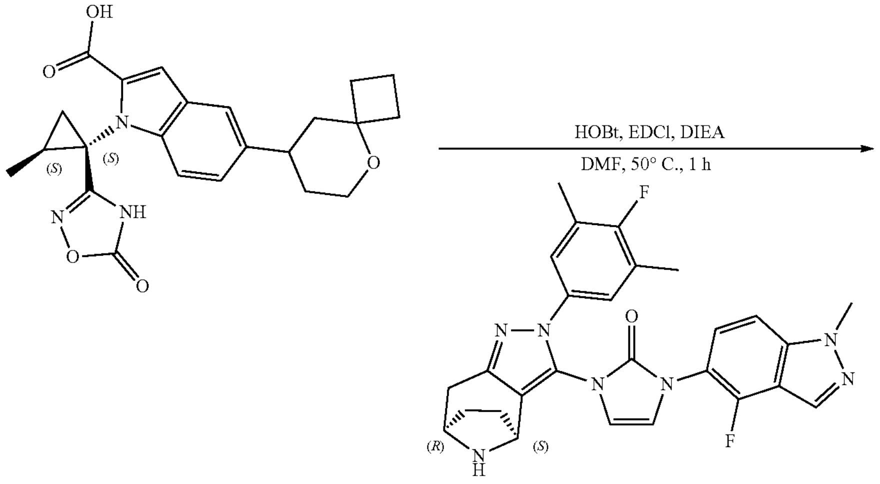

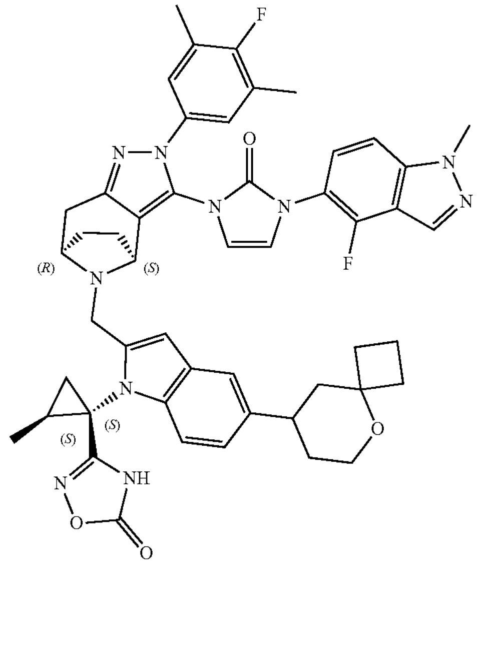

To a solution of 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (50 mg, 93.71 μmol, 1 eq) and 1-((1S,2S)-2-methyl-1-(5-oxo-4,5-dihydro-1,2,4-oxadiazol-3-yl) cyclopropyl)-5-(5-oxaspiro[3.5]nonan-8-yl)-1H-indole-2-carboxylic acid (48.22 mg, 93.71 μmol, 1 eq) in DMF (2 mL) was added EDCI (35.93 mg, 187.43 μmol, 2 eq) and DIEA (60.56 mg, 468.57 μmol, 81.61 μL, 5 eq), HOBt (25.33 mg, 187.43 μmol, 2 eq). The mixture was stirred at 50° C. for 1 hour under $N_2$ atmosphere. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (column: Phenomenex Luna C18 75*30 mm*3 um; mobile phase: [$H_2O$ (0.1% TFA)-ACN]; gradient: 50%-80% B over 8.0 min). Compound 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(5-oxaspiro[3.5]nonan-8-yl)-1H-indol-1-yl)-2-methylcyclopropyl)-1,2,4-oxadiazol-5 (4H)-one (13.72 mg, 15.08 μmol, 16.09% yield). $^1H$ NMR (400 MHz, DMSO-$d_6$) δ=12.28-11.66 (m, 1H), 8.40-8.10 (m, 1H), 7.74-6.58 (m, 10H), 5.58-4.89 (m, 2H), 4.11 (br d, J=2.9 Hz, 3H), 3.68-3.16 (m, 3H), 2.97-2.69 (m, 2H), 2.39-2.08 (m, 9H), 2.03-0.97 (m, 17H). LC-MS (ES+, m/z): 907.3 [$(M+H)^+$]; Rt=3.090 min. HRMS (EI): m/z $[M+H]^+$ found: 907.3815.

Example 73 Compound 426

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-(5-oxaspiro[3.5]nonan-8-yl)-1H-indol-1-yl)-2-methylcyclopropyl)-1,2,4-oxadiazol-5 (4H)-one Scheme 426

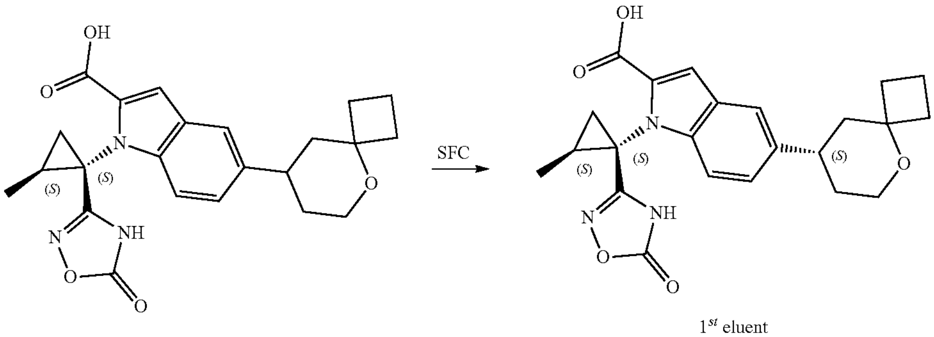

1st eluent

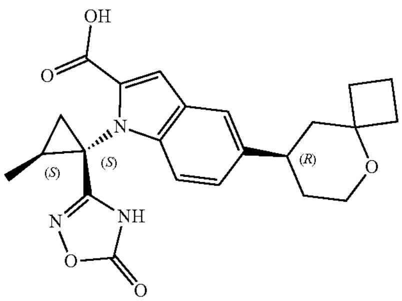

2nd eluent

-continued
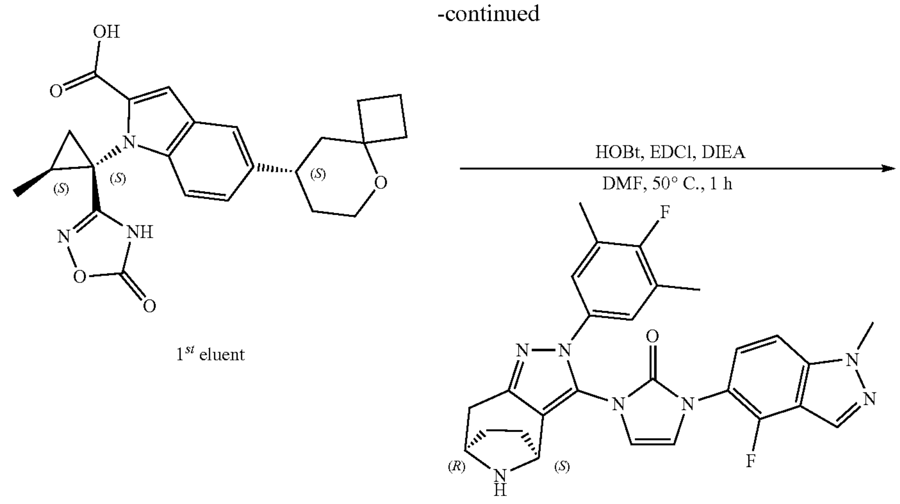
1st eluent
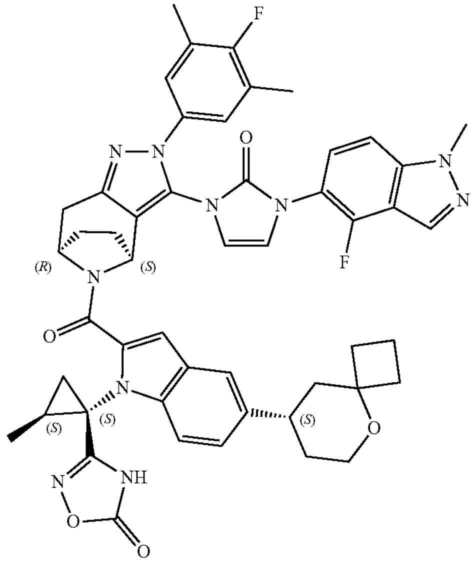
Step 1: 1-((1S,2S)-2-methyl-1-(5-oxo-4,5-dihydro-1,2,4-oxadiazol-3-yl)cyclopropyl)-5-((S)-5-oxaspiro[3.5]nonan-8-yl)-1H-indole-2-carboxylic acid
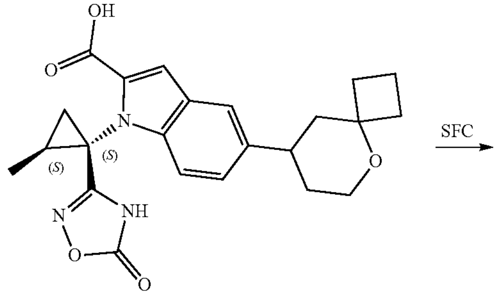
-continued
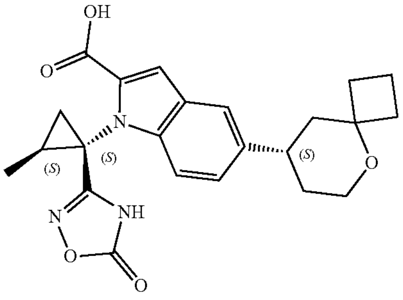
1st eluent -continued

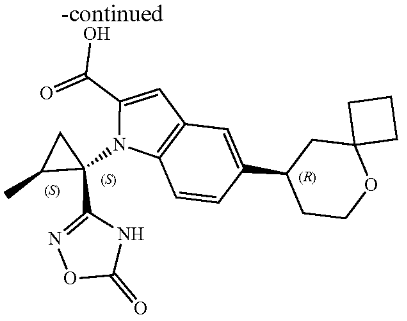

2nd eluent

The 1-((1S,2S)-2-methyl-1-(5-oxo-4,5-dihydro-1,2,4-oxadiazol-3-yl)cyclopropyl)-5-(5-oxaspiro[3.5]nonan-8-yl)-1H-indole-2-carboxylic acid (150 mg, crude) was separated by SFC (column: DAICEL CHIRALPAK AD (250 mm*30 mm, 10 um); mobile phase: [Heptane-EtOH (0.1% TFA)]; B %: 30%, isocratic elution mode) to give 1-((1S,2S)-2-methyl-1-(5-oxo-4,5-dihydro-1,2,4-oxadiazol-3-yl)cyclopropyl)-5-((S)-5-oxaspiro[3.5]nonan-8-yl)-1H-indole-2-carboxylic acid (1st eluent, RT=3.124 by SFC, 55 mg, 128.58 μmol, 36.30% yield) and 1-((1S,2S)-2-methyl-1-(5-oxo-4,5-dihydro-1,2,4-oxadiazol-3-yl)cyclopropyl)-5-((R)-5-oxaspiro[3.5]nonan-8-yl)-1H-indole-2-carboxylic acid (2nd eluent, RT=4.086 by SFC, 45 mg, 105.20 μmol, 29.70% yield).

Step 2: 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-5-((S)-5-oxaspiro[3.5]nonan-8-yl)-1H-indol-1-yl)-2-methylcyclopropyl)-1,2,4-oxadiazol-5(4H)-one

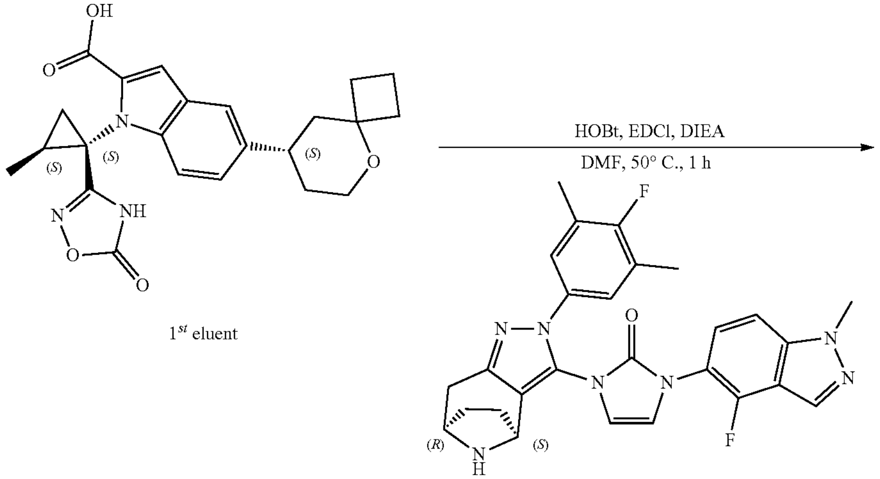

1st eluent

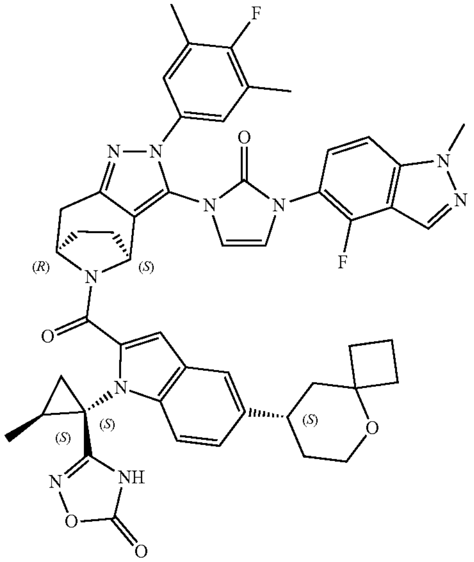

To a solution of 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (50 mg, 93.71 μmol, 1 eq) and 1-((1S,2S)-2-methyl-1-(5-oxo-4,5-dihydro-1,2,4-oxadiazol-3-yl) cyclopropyl)-5-((S)-5-oxaspiro[3.5]nonan-8-yl)-1H-indole-2-carboxylic acid (48.22 mg, 93.71 μmol, 1 eq) in DMF (2 mL) was added EDCI (35.93 mg, 187.43 μmol, 2 eq) and DIEA (60.56 mg, 468.57 μmol, 81.62 μL, 5 eq), HOBt (25.33 mg, 187.43 μmol, 2 eq). The mixture was stirred at 50° C. for 1 hour under $N_2$ atmosphere. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (column: Phenomenex Luna C18 75*30 mm*3 um; mobile phase: [$H_2O$ (0.1% TFA)-ACN]; gradient: 55%-85% B over 8.0 min) to give 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-5-oxaspiro[3.5]nonan-8-yl)-1H-indol-1-yl)-2-methylcyclopropyl)-1,2,4-oxadiazol-5 (4H)-one (14.33 mg, 15.72 μmol, 16.78% yield). $^1$H NMR (400 MHz, DMSO-$d_6$) δ=12.30-11.66 (m, 1H), 8.37-8.14 (m, 1H), 7.74-6.61 (m, 10H), 5.65-4.80 (m, 2H), 4.15-4.04 (m, 3H), 3.41-3.13 (m, 3H), 2.96-2.69 (m, 2H), 2.29-2.04 (m, 9H), 1.94-0.96 (m, 17H). LC-MS (ES+, m/z): 907.3 [$(M+H)^+$]; Rt=3.092 min. HRMS (EI): m/z $[M+H]^+$ found: 907.3883.

Example 74 Compound 424

3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-5-oxaspiro[3.5]nonan-8-yl)-1H-indol-1-yl)-2-methylcyclopropyl)-1,2,4-oxadiazol-5 (4H)-one

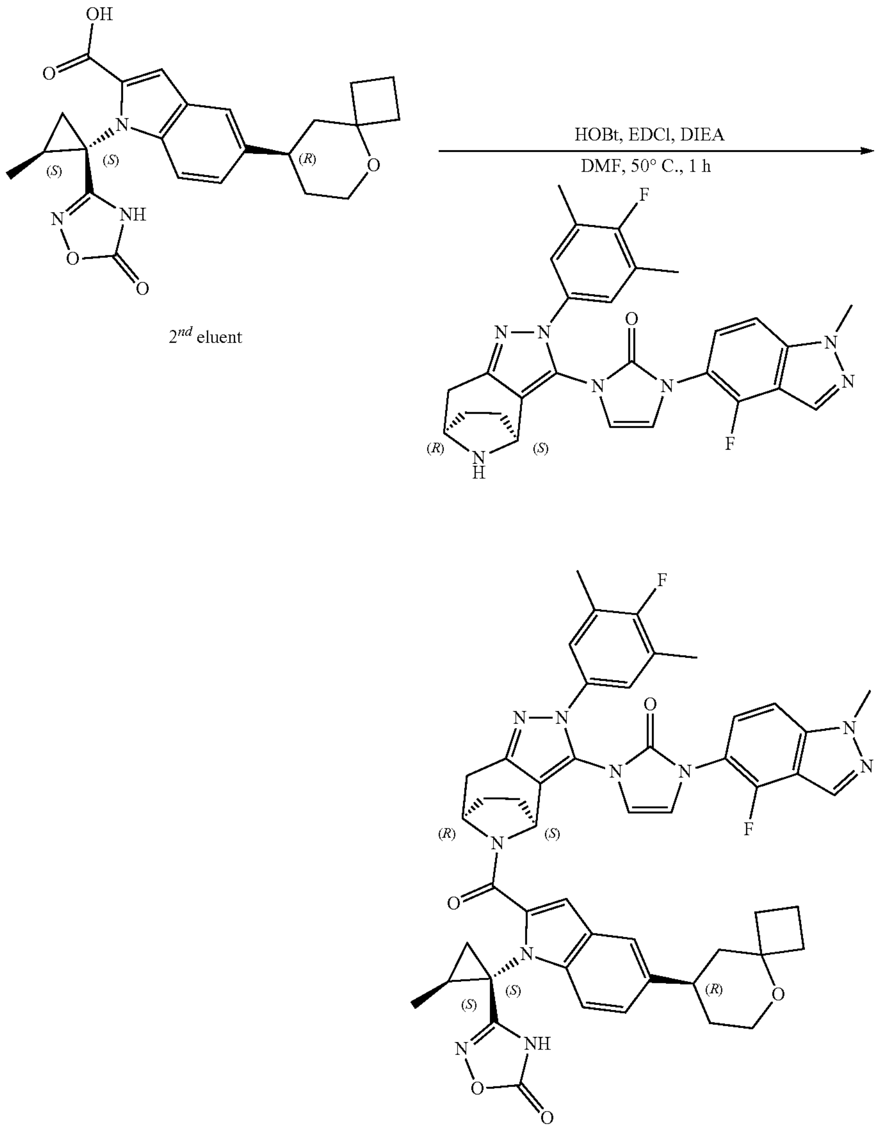

2nd eluent

To a solution of 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (53 mg, 105.68 µmol, 1 eq), 1-((1S,2S)-2-methyl-1-(5-oxo-4,5-dihydro-1,2,4-oxadiazol-3-yl) cyclopropyl)-5-((R)-5-oxaspiro[3.5]nonan-8-yl)-1H-indole-2-carboxylic acid (45 mg, 106.27 µmol, 1.01 eq), DIPEA (68.29 mg, 528.38 µmol 5 eq) in DMF (0.5 mL) was added EDCI (30.39 mg, 158.52 µmol, 1.5 eq), HOBt (21.42 mg, 158.52 µmol, 1.5 eq) under $N_2$. The mixture was stirred at 50° C. for 1 hour under $N_2$. LCMS indicated the reaction was completed. The mixture was filtered. The filtrate was purified by prep-HPLC (column: Phenomenex Luna C18 75*30 mm*3 um; mobile phase: [$H_2O$ (0.1% TFA)-ACN]; gradient: 55%-85% B over 8.0 min) to 3-((1S,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-5-oxaspiro[3.5]nonan-8-yl)-1H-indol-1-yl)-2-methylcyclopropyl)-1,2,4-oxadiazol-5 (4H)-one (10.2 mg, 11.11 µmol, 10.51% yield). $^1$H NMR (400 MHz, DMSO-$d_6$) δ=12.03-11.50 (m, 1H), 8.32-8.04 (m, 1H), 7.82-6.41 (m, 10H), 5.63-4.75 (m, 2H), 4.10 (s, 3H), 3.76-3.43 (m, 3H), 2.96-2.71 (m, 2H), 2.26 (s, 6H), 2.21-0.92 (m, 20H). LC-MS (ES+, m/z): 907.3 [$(M+H)^+$]; Rt=3.246 min. HRMS (EI): m/z $[M+H]^+$ found: 907.3833.

Example 75 Compound 427

3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one Scheme 427

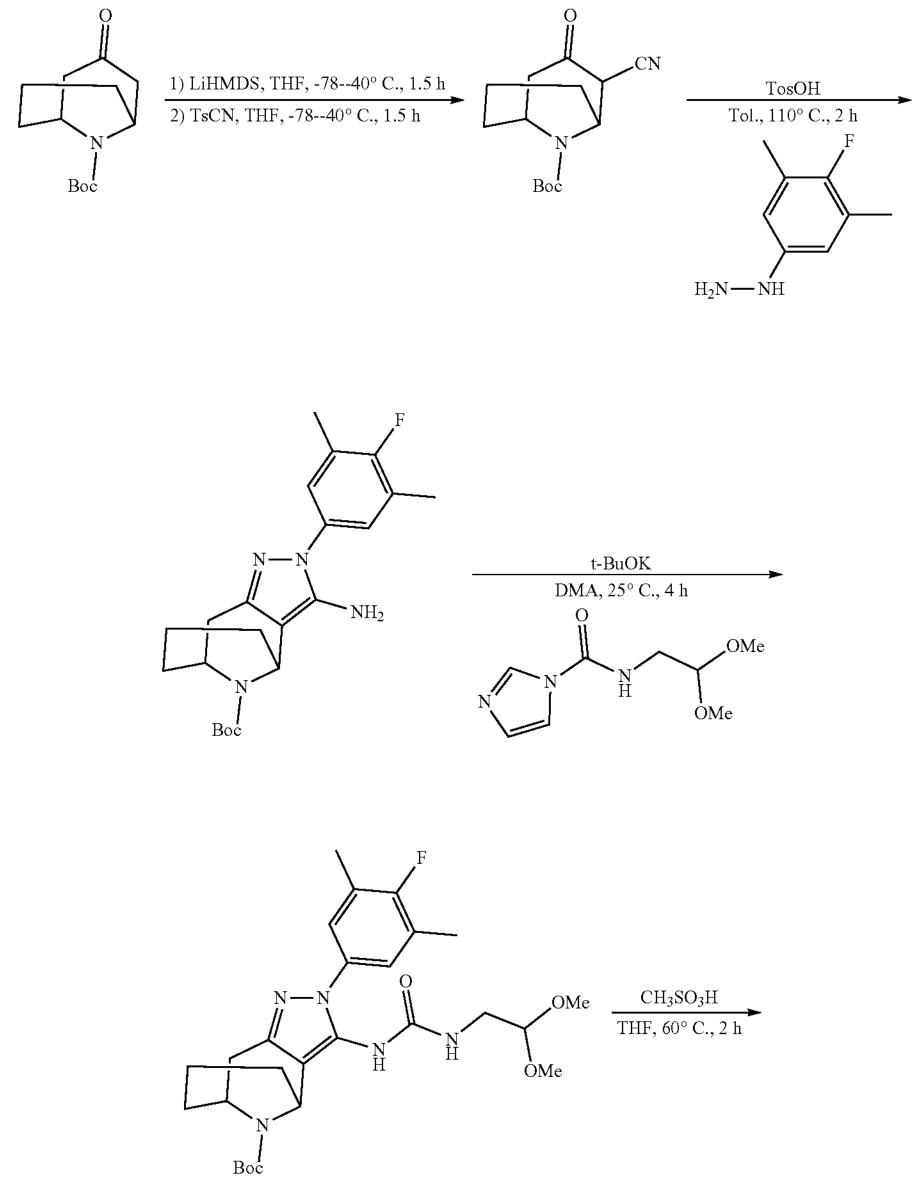

-continued
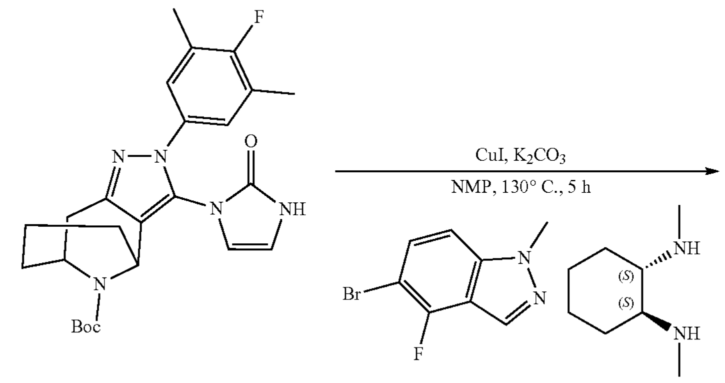
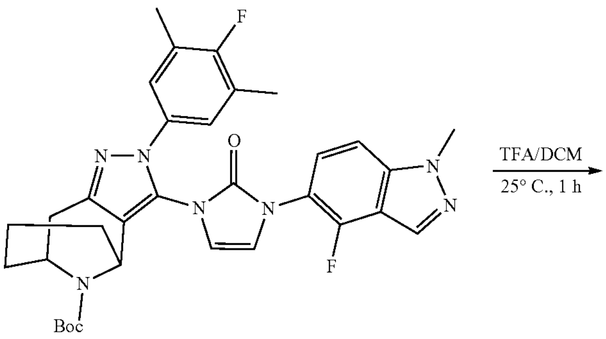
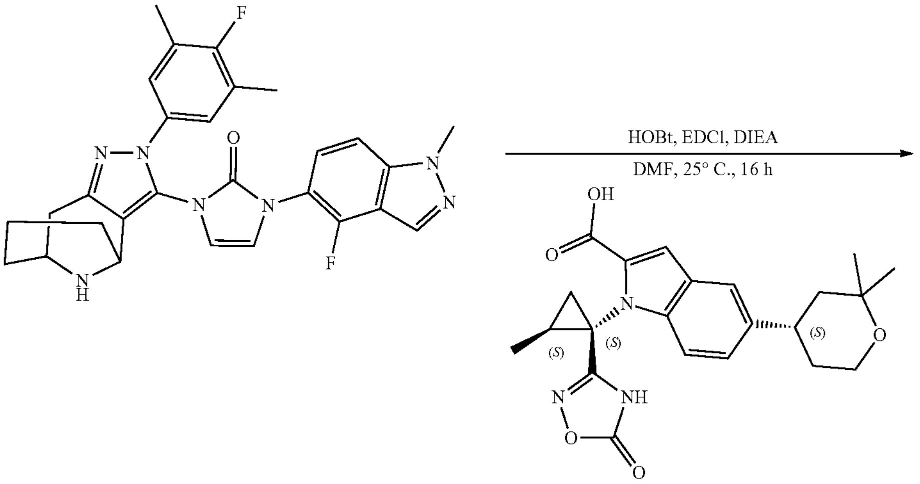

-continued

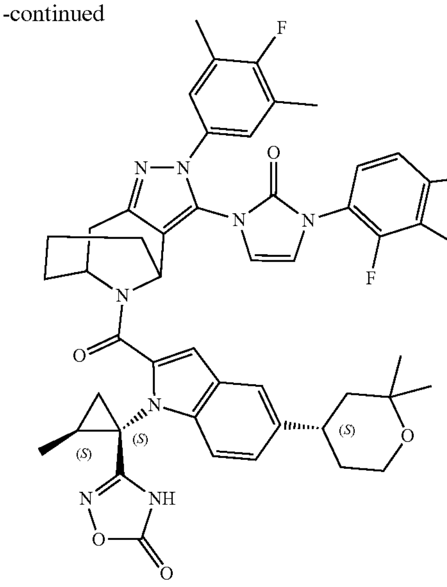

Step 1: tert-butyl 2-cyano-3-oxo-9-azabicyclo[3.3.1] nonane-9-carboxylate

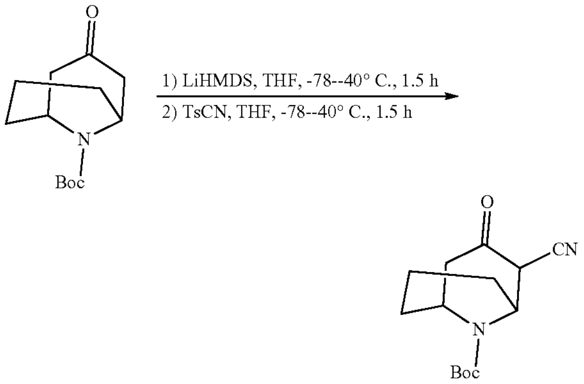

To a solution of tert-butyl 3-oxo-9-azabicyclo[3.3.1] nonane-9-carboxylate (5 g, 20.89 mmol, 1 eq) in THF (50 mL) was added LiHMDS (1 M, 45.97 mL, 2.2 eq) in one portion at −78° C. under $N_2$. The mixture was stirred at −40° C. for 1.5 hours. Then added 4-methylbenzenesulfonyl cyanide (9.47 g, 52.23 mmol, 2.5 eq) in THF (10 mL) in one portion at −78° C. under $N_2$. The mixture was stirred at −40° C. for 1.5 hours. LCMS showed the reaction was completed. The reaction solution is quenched with saturated $NH_4Cl$ (300 mL). The aqueous phase was extracted with ethyl acetate (150 mL*3). The combined organic phase was washed with saturated brine (200 mL), dried with anhydrous $Na_2SO_4$, filtered and concentrated in vacuum to give a residue. The residue was purified by column chromatography ($SiO_2$, petroleum ether/ethyl acetate=10/1 to 0/1) to afford the mixture compound tert-butyl 2-cyano-3-oxo-9-azabicyclo[3.3.1]nonane-9-carboxylate (3.5 g, 12.98 mmol, 62.11% yield) as yellow oil. LC-MS (ES-, m/z): 263.0 $[(M-H)^-]$. Rt=0.866 min.

Step 2: tert-butyl 3-amino-2-(4-fluoro-3,5-dimethylphenyl)-4,5,6,7,8,9-hexahydro-2H-4,8-epiminocycloocta [c]pyrazole-10-carboxylate

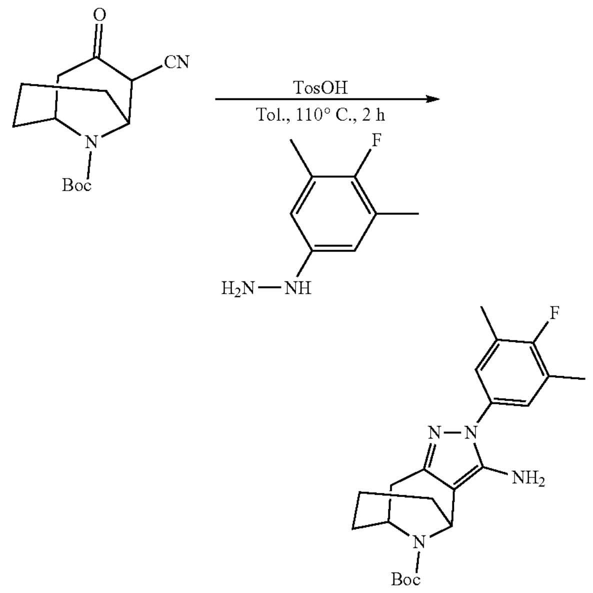

To a solution of tert-butyl 2-cyano-3-oxo-9-azabicyclo [3.3.1]nonane-9-carboxylate (3.4 g, 12.61 mmol, 1 eq) and (4-fluoro-3,5-dimethylphenyl) hydrazine (2.14 g, 13.87 mmol, 1.1 eq) in Tol. (30 mL) was added TosOH (217.08 mg, 1.26 mmol, 0.1 eq) in one portion under $N_2$. The mixture was stirred at 110° C. for 2 hours. LCMS showed the reaction was completed. The reaction mixture was quenched by addition $H_2O$ (200 mL), extracted with ethyl acetate (100 mL*3). The combined organic layers were washed with saturated brine (150 mL), dried over anhydrous $Na_2SO_4$, filtered and concentrated under reduced pressure to give a residue. The residue was purified by column chromatography ($SiO_2$, petroleum ether/ethyl acetate=10/1 to 0/1) to afford the mixture compound tert-butyl 3-amino-2-(4-fluoro-3,5-dimethylphenyl)-4,5,6,7,8,9-hexahydro-2H-4,8-epiminocycloocta [c]pyrazole-10-carboxylate (4 g, 9.09 mmol, 72.10% yield). LC-MS. (ES+, m/z): 401.1 [(M+H)$^+$]. Rt=1.406 min.

Step 3: tert-butyl 3-(3-(2,2-dimethoxyethyl) ureido)-2-(4-fluoro-3,5-dimethylphenyl)-4,5,7,8-tetrahydropyrazolo[3,4-d]azepine-6 (2H)-carboxylate

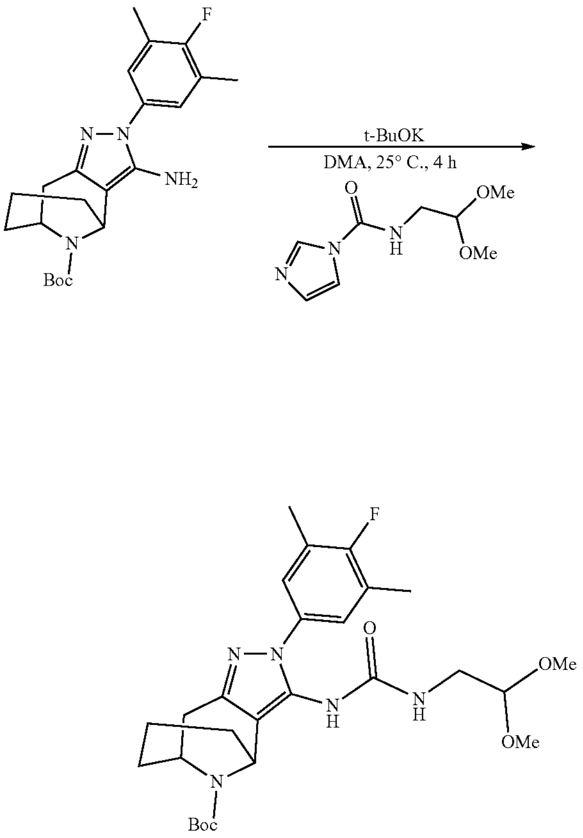

To a solution of tert-butyl 3-amino-2-(4-fluoro-3,5-dimethylphenyl)-4,5,6,7,8,9-hexahydro-2H-4,8-epiminocycloocta [c]pyrazole-10-carboxylate (4 g, 9.09 mmol, 1 eq) and N-(2,2-dimethoxyethyl)-1H-imidazole-1-carboxamide (3.62 g, 18.18 mmol, 2 eq) in DMA (40 mL) was added t-BuOK (5.10 g, 45.44 mmol, 5 eq) in one portion under $N_2$. The mixture was stirred at 25° C. for 4 hours. LCMS showed the reaction was completed. The reaction mixture was quenched by addition $H_2O$ (400 mL), extracted with ethyl acetate (200 mL*3). The combined organic layers were washed with saturated brine (500 mL), dried over anhydrous $Na_2SO_4$, filtered and concentrated under reduced pressure. The residue was purified by column chromatography ($SiO_2$, petroleum ether/ethyl acetate=10/1 to 0/1) to afford the title compound tert-butyl 3-(3-(2,2-dimethoxyethyl) ureido)-2-(4-fluoro-3,5-dimethylphenyl)-4,5,7,8-tetrahydropyrazolo [3,4-d]azepine-6 (2H)-carboxylate (3.5 g, 6.25 mmol, 68.81% yield). LC-MS (ES+, m/z): 532.3 [(M+H)$^+$]. Rt=2.021 min.

Step 4: tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate

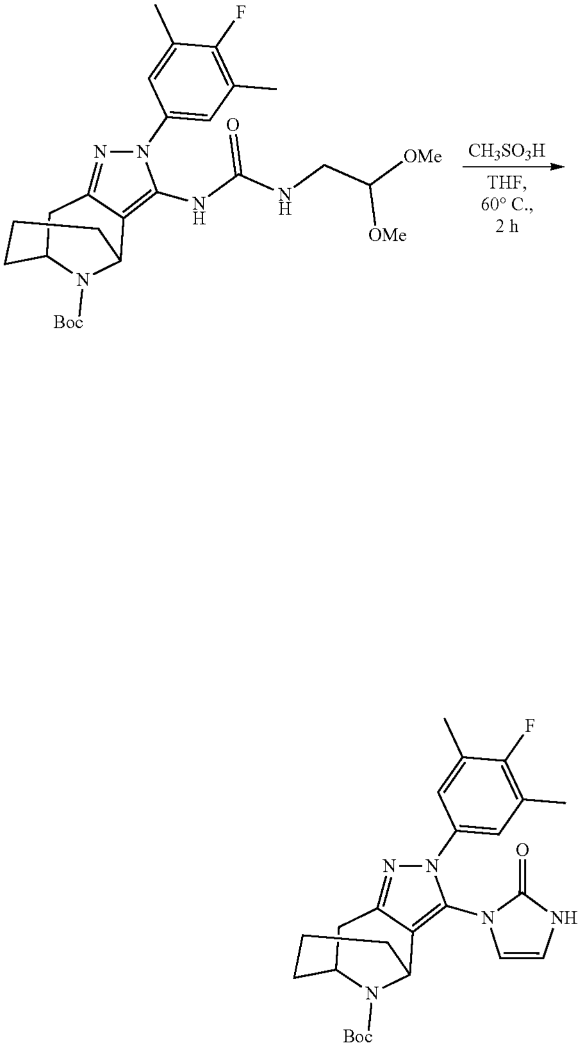

To a mixture of tert-butyl 3-(3-(2,2-dimethoxyethyl) ureido)-2-(4-fluoro-3,5-dimethylphenyl)-4,5,7,8-tetrahydropyrazolo[3,4-d]azepine-6 (2H)-carboxylate (3.5 g, 6.25 mmol, 1 eq) in THF (35 mL) was added $CH_3SO_3H$ (661.20 mg, 6.88 mmol, 1.1 eq) in one portion under $N_2$. The mixture was stirred at 60° C. for 2 hours. LCMS showed the reaction was completed. The reaction mixture was quenched by addition $H_2O$ (100 mL), extracted with ethyl acetate (50 mL*3). The combined organic layers were washed with saturated brine (100 mL), dried over anhydrous $Na_2SO_4$, filtered and concentrated under reduced pressure. The residue was purified by column chromatography ($SiO_2$, petroleum ether/ethyl acetate=3/1 to 0/1) to afford the title compound tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (2 g, 4.06 mmol, 64.98% yield). LC-MS. (ES+, m/z): 468.3 [(M+H)$^+$]. Rt=1.651 min.

Step 5: tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate

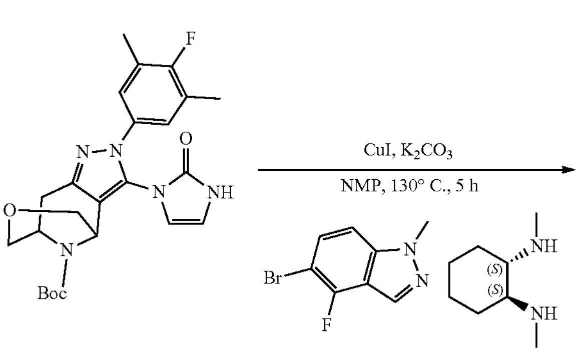

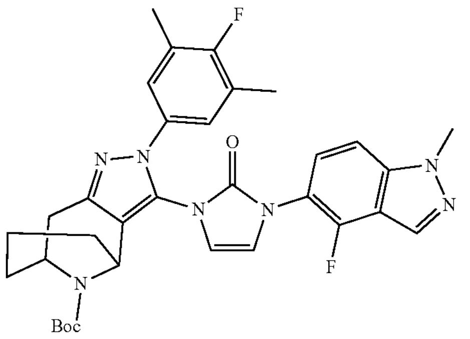

To a solution of tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (1.5 g, 3.05 mmol, 1 eq), (1S,2S)—$N^1$,$N^2$-dimethylcyclohexane-1,2-diamine (1.30 g, 9.14 mmol, 3 eq) and 5-bromo-4-fluoro-1-methyl-1H-indazole (1.40 g, 6.10 mmol, 2 eq) in NMP (15 mL) was added CuI (1.16 g, 6.10 mmol, 2 eq) and $K_2CO_3$ (842.47 mg, 6.10 mmol, 2 eq) in one portion under $N_2$. The mixture was stirred at 130° C. for 5 hours under $N_2$. LCMS showed the reaction was completed. The reaction mixture was quenched by addition saturated EDTA solution (150 mL) and ethyl acetate (50 mL), stirred for 0.5 hour, extracted with ethyl acetate (100 mL*3). The combined organic layers were washed with saturated brine (200 mL), dried over anhydrous $Na_2SO_4$, filtered and concentrated under reduced pressure. The residue was purified by column chromatography ($SiO_2$, petroleum ether/ethyl acetate=3/1 to 0/1) to afford the title compound tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (1.5 g, 2.19 mmol, 71.94% yield). LC-MS (ES+, m/z): 616.4 [$(M+H)^+$]. Rt=1.997 min.

Step 6: 1-(4-fluoro-1-methyl-1H-indazol-5-yl)-3-(2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one

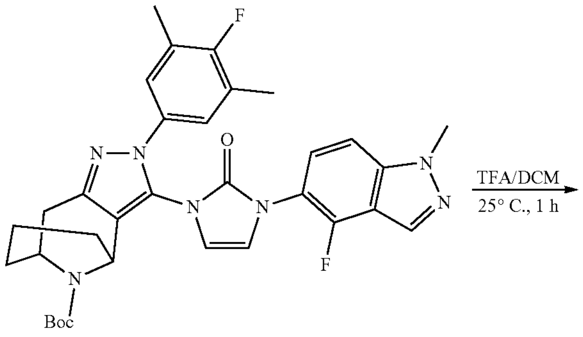

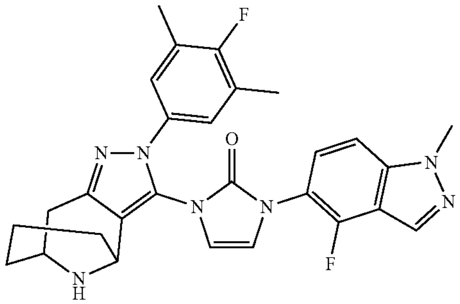

To a solution of tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (1.5 g, 2.19 mmol, 1 eq) in DCM (12 mL) was added TFA (3 mL) in one portion at 25° C. The mixture was stirred at 25° C. for 1 hour. LCMS showed the reaction was completed. The reaction mixture was quenched by addition saturated $NaHCO_3$ solution (200 mL) at 0° C., extracted with dichloromethane (100 mL*3). The combined organic layers were washed with saturated brine (300 mL), dried over anhydrous $Na_2SO_4$, filtered and concentrated under reduced pressure to afford the title compound 1-(4-fluoro-1-methyl-1H-indazol-5-yl)-3-(2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (1 g, 2.19 mmol, 83% yield). LC-MS (ES+, m/z): 516.3 [$(M+H)^+$]. Rt=1.305 min.

Step 7: 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one

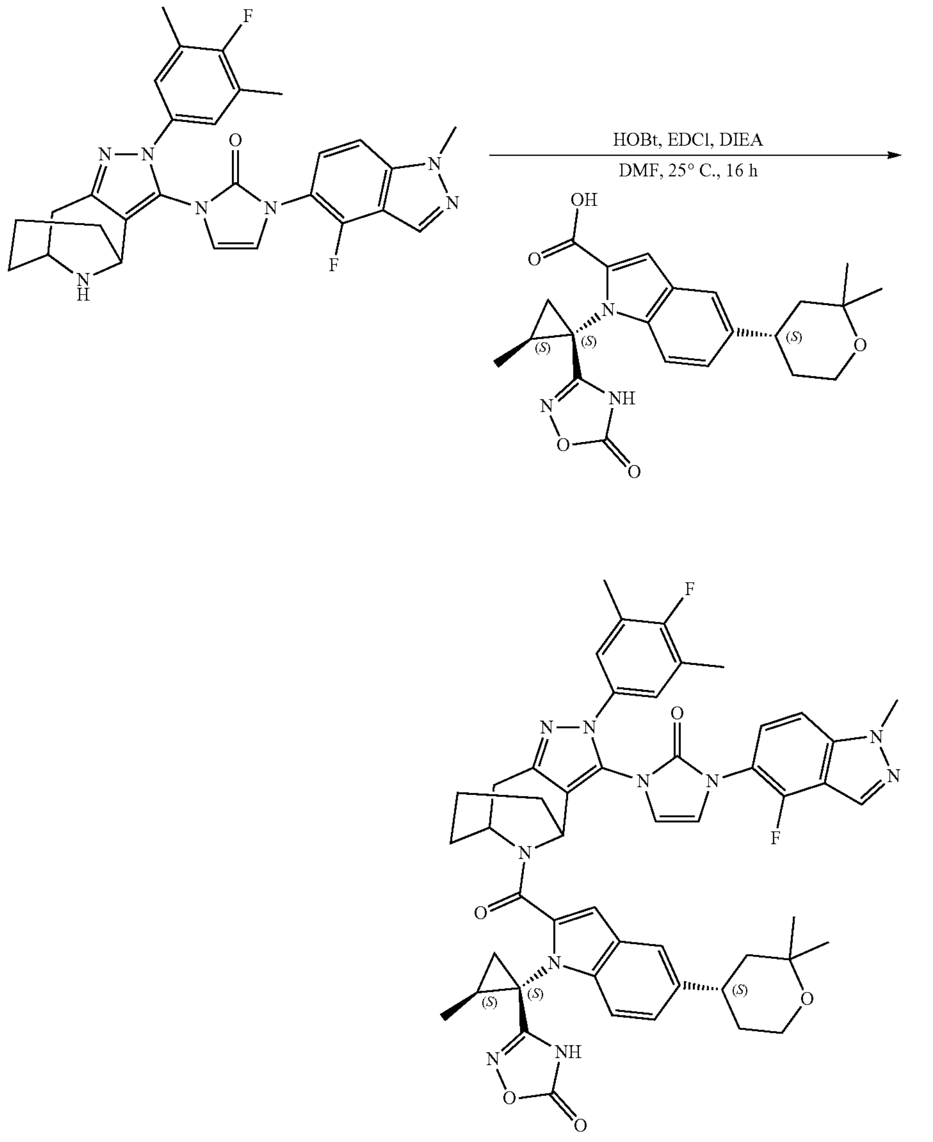

To a solution of 1-(4-fluoro-1-methyl-1H-indazol-5-yl)-3-(2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (50 mg, 91.16 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (37.51 mg, 91.16 μmol, 1 eq) in DMF (0.5 mL) was added HOBt (18.48 mg, 136.75 μmol, 1.5 eq), EDCI (22.72 mg, 118.51 μmol, 1.3 eq), DIEA (117.82 mg, 911.64 μmol, 10 eq) in one portion at 25° C. under $N_2$. The mixture was stirred at 25° C. for 16 hours under $N_2$. LCMS showed the reaction was completed. The reaction mixture was quenched by addition $H_2O$ (10 mL), extracted with dichloromethane (5 mL*3). The combined organic layers were washed with saturated brine (10 mL), dried over anhydrous $Na_2SO_4$, filtered and concentrated under reduced pressure. The residue was purified by prep-HPLC (TFA condition) column: Phenomenex Luna C18 75*30 mm*3 um; mobile phase: [$H_2O$ (0.1% TFA)-ACN]; gradient: 55%-85% B over 8.0 min to afford the title compound 3-((1S,2S)-1-(5-((S)-2,2-dimethyltetrahydro-2H-pyran-4-yl)-2-(3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one (11.60 mg, 12.76 μmol, 14.00% yield). $^1$H NMR (400 MHz, DMSO-$d_6$) δ=12.24-11.65 (m, 1H), 8.33-8.11 (m, 1H), 7.68-6.59 (m, 10H), 5.87-4.89 (m, 2H), 4.12-4.06 (m, 3H), 3.60-3.45 (m, 2H), 3.27-2.70 (m, 3H), 2.29-2.19 (m, 6H), 1.97-1.47 (m, 12H), 1.37-0.87 (m, 10H). LC-MS (ES+, m/z): 909.3 [(M+H)$^+$]. Rt=3.455 min. HRMS (EI): m/z [M+H]$^+$ found: 909.3994.

Example 76 Compound 428
3-((1S,2S)-1-(5-((S)-2,2-dimethyltetrahydro-2H-pyran-4-yl)-2-((4S,7R)-3-(3-(4-(ethylsulfonimidoyl)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one
Scheme 428
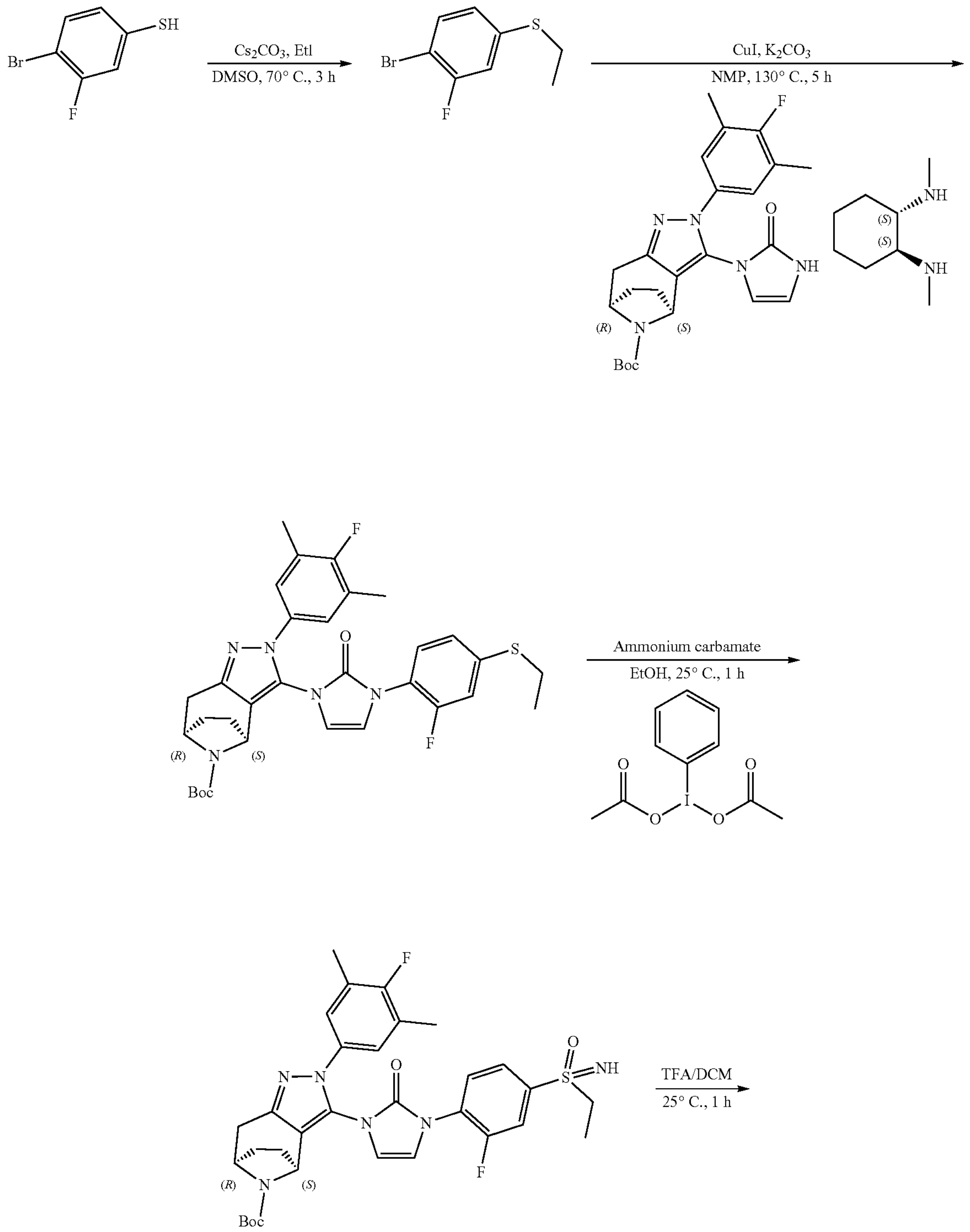

-continued

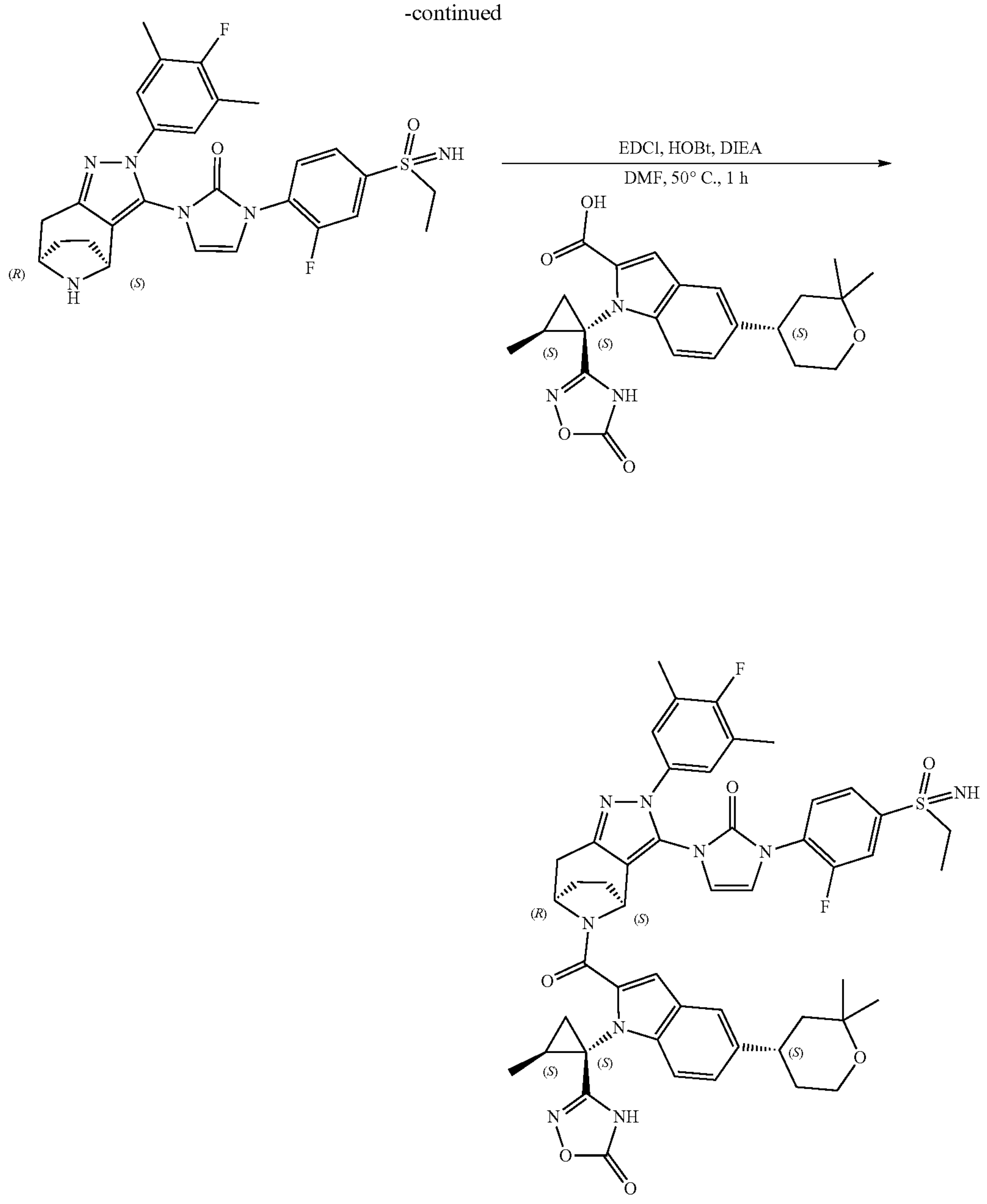

Step 1: (4-bromo-3-fluorophenyl) (ethyl) sulfane

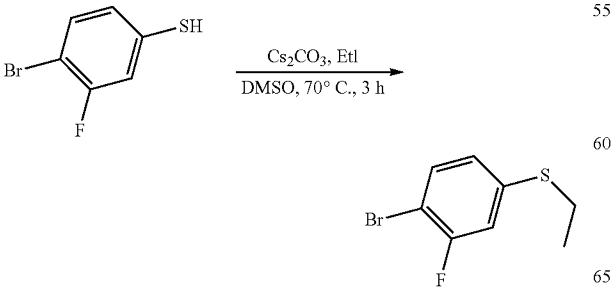

To a solution of 4-bromo-3-fluoro-benzenethiol (2 g, 9.66 mmol, 1 eq) in DMSO (20 mL) was added $Cs_2CO_3$ (9.44 g, 28.98 mmol, 3 eq) and EtI (4.52 g, 28.98 mmol, 2.32 mL, 3 eq). The mixture was stirred at 70° C. for 3 hours under $N_2$ atmosphere. TLC (Petroleum ether/Ethyl acetate=3:1) showed the reaction was completed. The reaction mixture was poured into water (200 mL), then extracted with ethyl acetate (100 mL*3). The combined organic layers were washed with saturated brine (150 mL*1), dried over anhydrous $Na_2SO_4$, filtered and concentrated under reduced pressure to give (4-bromo-3-fluorophenyl) (ethyl) sulfane (2 g, crude). $^1H$ NMR (400 MHz, DMSO-$d_6$) δ=7.60 (t, J=8.0 Hz, 1H), 7.33 (dd, J=2.1, 9.9 Hz, 1H), 7.08 (dd, J=1.9, 8.4 Hz, 1H), 3.03 (q, J=7.4 Hz, 2H), 1.24 (t, J=7.3 Hz, 3H).

Step 2: tert-butyl (4S,7R)-3-(3-(4-(ethylthio)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

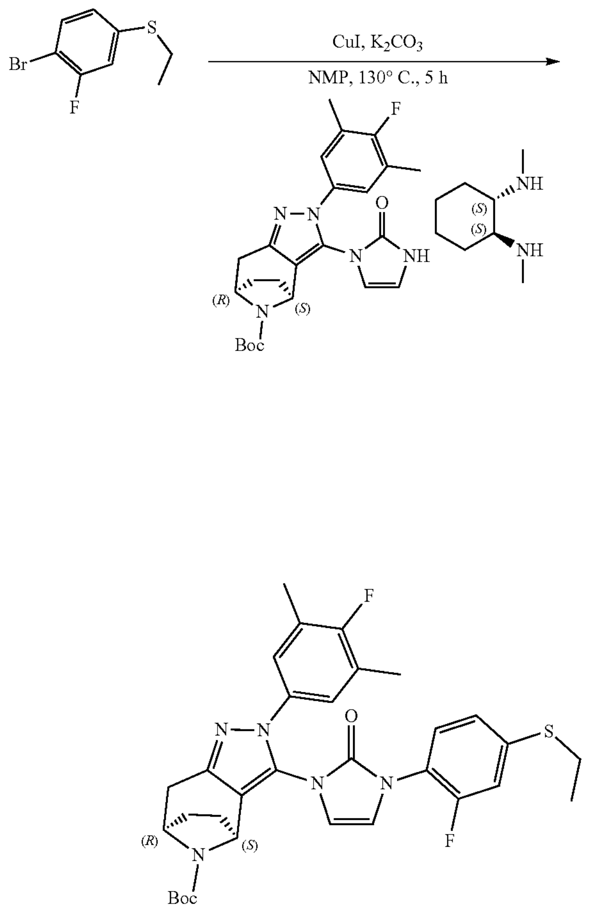

To a solution of tert-butyl (1S,8R)-4-(4-fluoro-3,5-dimethyl-phenyl)-3-(2-oxo-1H-imidazol-3-yl)-4,5,11-triazatricyclo[6.2.1.02,6]undeca-2,5-diene-11-carboxylate (500 mg, 1.10 mmol, 1 eq) and 1-bromo-4-ethylsulfanyl-2-fluorobenzene (518.44 mg, 2.21 mmol, 2 eq) in NMP (10 mL) was added $K_2CO_3$ (304.76 mg, 2.21 mmol, 2 eq), CuI (419.95 mg, 2.21 mmol, 2 eq), (1S,2S)—N1,N2-dimethylcyclohexane-1,2-diamine (470.47 mg, 3.31 mmol, 3 eq) stirred at 130° C. for 5 hours under $N_2$. LCMS showed the reaction was completed. The reaction mixture was poured into saturated EDTA (500 mL) and ethyl acetate (100 mL) stirred for 1 hour, then extracted with ethyl acetate (100 mL*3). The combined organic layers were washed with saturated brine (200 mL), dried over anhydrous $Na_2SO_4$, filtered and concentrated under reduced pressure. The residue was purified by column chromatography ($SiO_2$, Petroleum ether/ethyl acetate=30/1 to 0/1) to give tert-butyl (4S,7R)-3-(3-(4-(ethylthio)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (500 mg, 776.68 μmol, 70.45% yield, 94.4% purity). LC-MS (ES+, m/z): 608.3 [(M+H)$^+$]; Rt=2.228 min.

Step 3: tert-butyl (4S,7R)-3-(3-(4-(ethylsulfonimidoyl)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

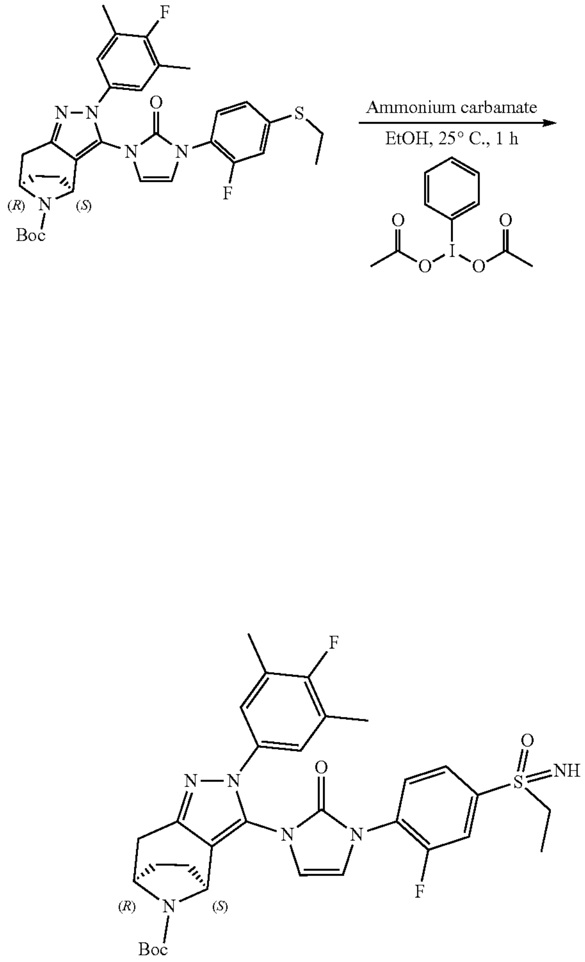

To a solution of tert-butyl (4S,7R)-3-(3-(4-(ethylthio)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (450 mg, 740.48 μmol, 1 eq) in EtOH (35 mL) was added Ammonium carbamate (228.31 mg, 2.96 mmol, 4 eq) and [acetoxy (phenyl)-iodanyl] acetate (715.52 mg, 2.22 mmol, 3 eq) stirred at 25° C. for 1 hour under $N_2$. LCMS showed the reaction was completed. The reaction mixture was poured into water (100 mL), then extracted with ethyl acetate (50 mL*3). The combined organic layers were washed with saturated brine (100 mL), dried over anhydrous $Na_2SO_4$, filtered and concentrated under reduced pressure. The residue was purified by column chromatography ($SiO_2$, Petroleum ether/Ethyl acetate=30/1 to 0/1) to give tert-butyl (4S,7R)-3-(3-(4-(ethylsulfonimidoyl)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (400 mg, 611.22 μmol, 82.54% yield). LC-MS (ES+, m/z): 639.3 [(M+H)$^+$]; Rt=1.706 min.

Step 4: 1-(4-(ethylsulfonimidoyl)-2-fluorophenyl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

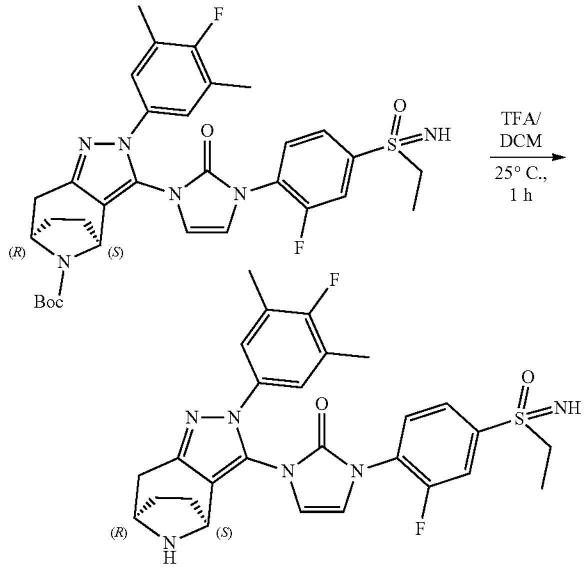

To a solution of tert-butyl (4S,7R)-3-(3-(4-(ethylsulfonimidoyl)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (400 mg, 626.25 μmol, 1 eq) in DCM (3 mL) and TFA (1 mL) stirred at 25° C. for 1 hour. LCMS showed the reaction was completed. The reaction mixture was poured water (100 mL) and adjust to pH=9 for $Na_2CO_3$ solid, then extracted with ethyl acetate (80 mL*3). The combined organic layers were washed with saturated brine (200 mL), dried over anhydrous $Na_2SO_4$, filtered and concentrated under reduced pressure to give 1-(4-(ethylsulfonimidoyl)-2-fluorophenyl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (300 mg, crude). LC-MS (ES+, m/z): 539.2 [$(M+H)^+$]; Rt=0.394 min.

Step 5: 3-((1S,2S)-1-(5-((S)-2,2-dimethyltetrahydro-2H-pyran-4-yl)-2-((4S,7R)-3-(3-(4-(ethylsulfonimidoyl)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one

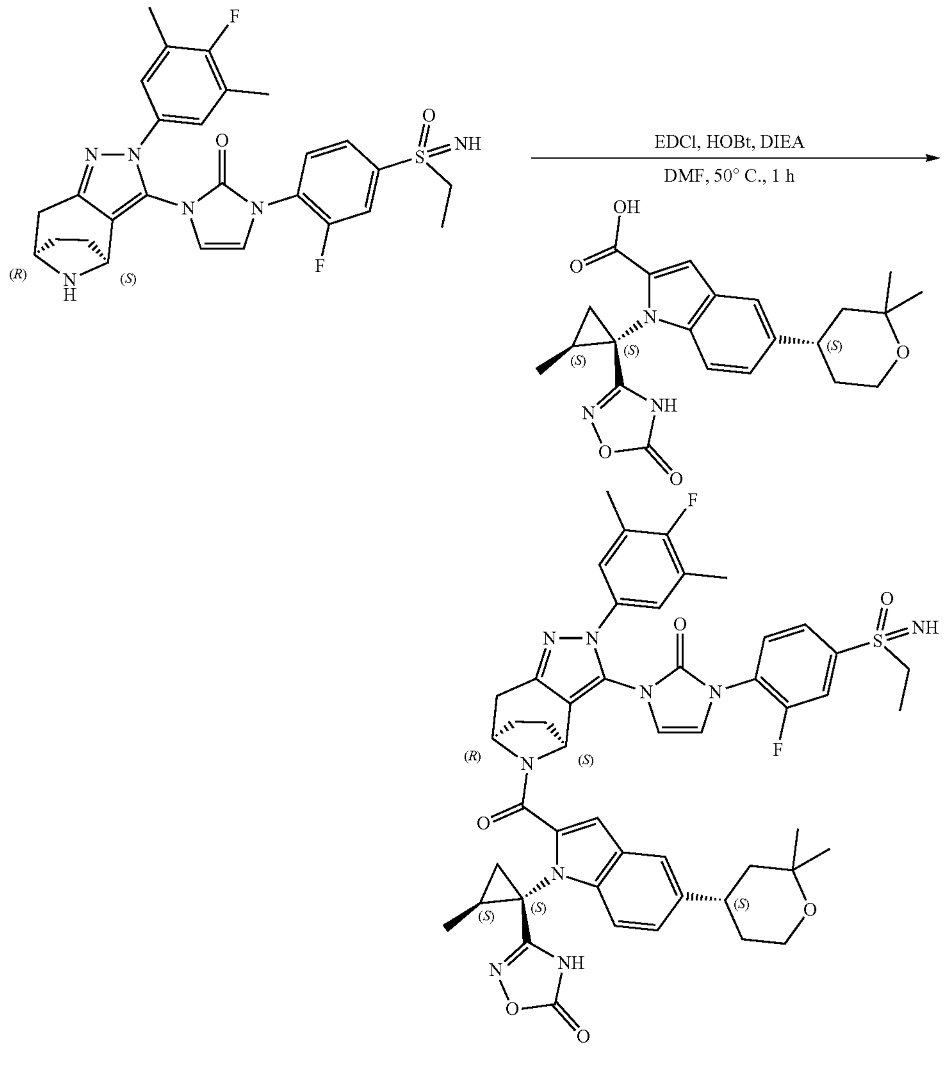

To a solution of 1-(4-(ethylsulfonimidoyl)-2-fluorophenyl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (50 mg, 92.83 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (38.20 mg, 92.83 μmol, 1 eq) in DMF (2 mL) was added EDCI (35.59 mg, 185.66 μmol, 2 eq) and DIEA (59.99 mg, 464.16 μmol, 80.85 μL, 5 eq), HOBt (25.09 mg, 185.66 μmol, 2 eq). The mixture was stirred at 50° C. for 1 hour under $N_2$. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (column: Phenomenex Luna C18 75*30 mm*3 um; mobile phase: [$H_2O$ (0.1% TFA)-ACN]; gradient: 40%-70% B over 8.0 min) to give 3-((1S,2S)-1-(5-((S)-2,2-dimethyltetrahydro-2H-pyran-4-yl)-2-((4S,7R)-3-(3-(4-(ethylsulfonimidoyl)-2-fluorophenyl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (18.57 mg, 16.09 μmol, 17.34% yield). $^1H$ NMR (400 MHz, DMSO-$d_6$) δ=12.33-11.64 (m, 1H), 7.98-6.66 (m, 12H), 5.60-4.90 (m, 2H), 3.72 (br d, J=8.8 Hz, 2H), 3.53 (br dd, J=3.7, 15.6 Hz, 1H), 3.36-3.23 (m, 2H), 3.18-2.80 (m, 2H), 2.29-2.06 (m, 8H), 1.82-1.48 (m, 7H), 1.44-0.93 (m, 14H). LC-MS (ES+, m/z): 932.3 [$(M+H)^+$]; Rt=2.778 min. HRMS (EI): m/z $[M+H]^+$ found: 932.3745.

Example 77 Compound 429

3-((1S,2S)-1-(5-((S)-2,2-dimethyltetrahydro-2H-pyran-4-yl)-2-((4S,7R)-3-(3-(4-fluoro-1-methyl-2-oxo-1,2-dihydropyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one Scheme 429

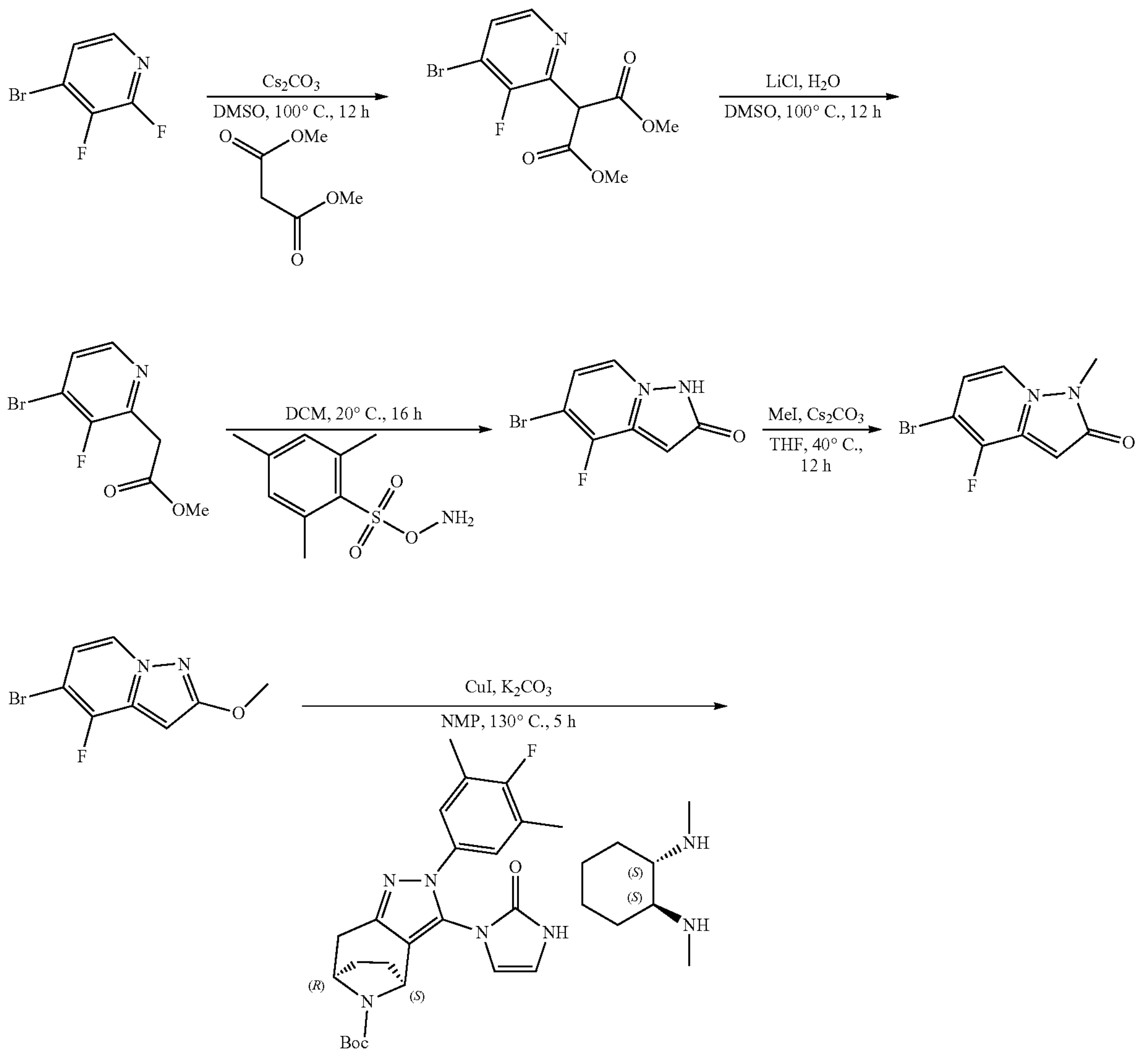

-continued
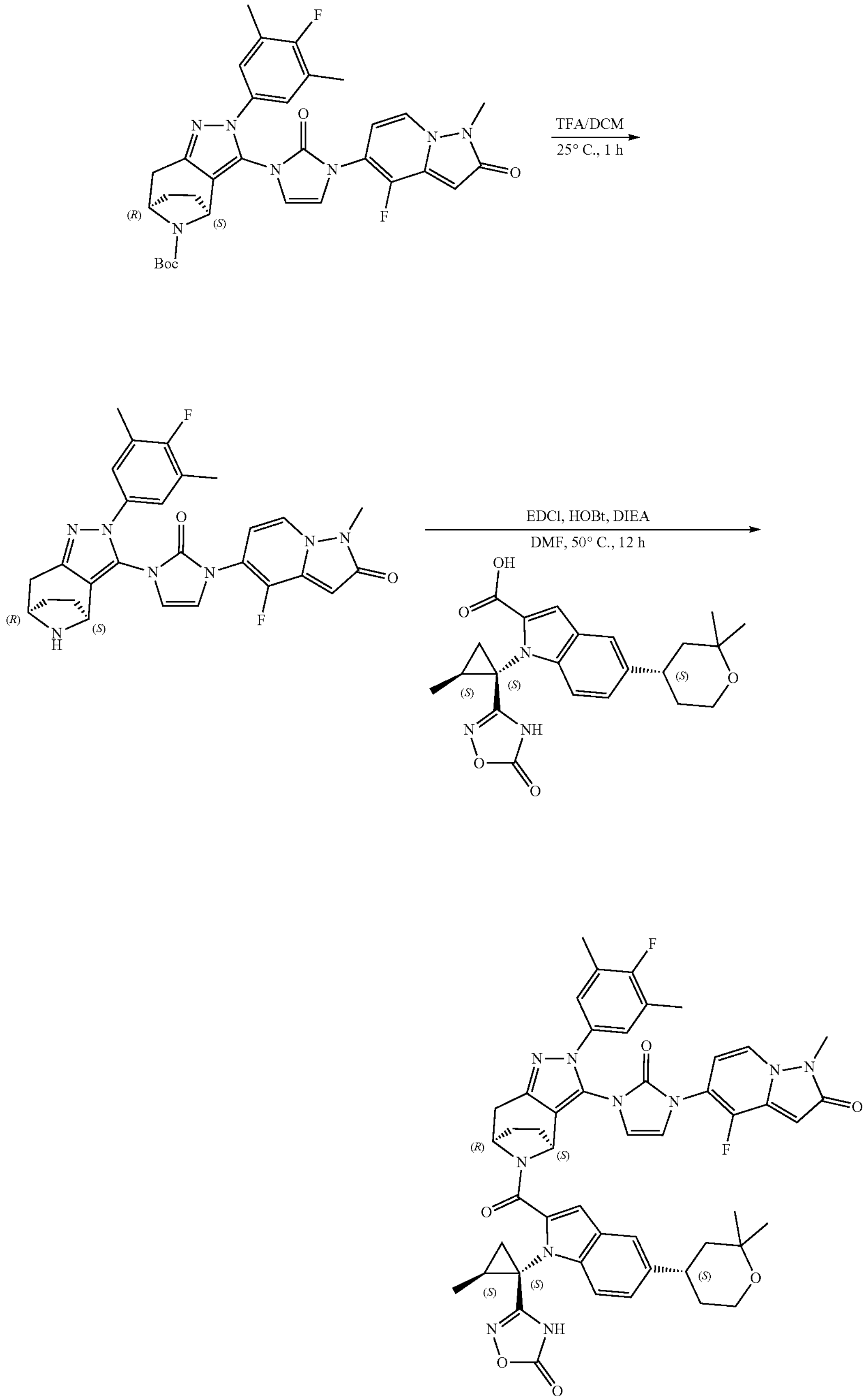

Step 1: dimethyl 2-(4-bromo-3-fluoropyridin-2-yl) malonate

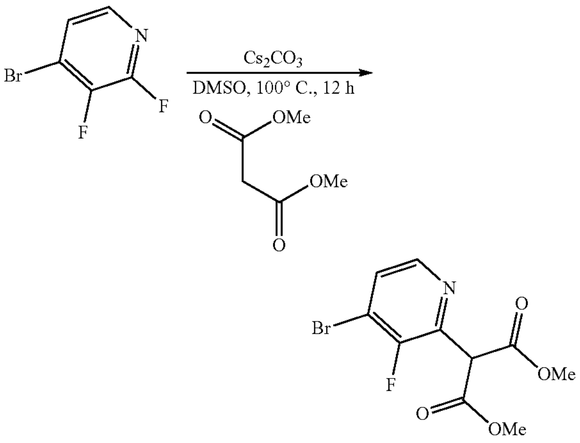

To a solution of dimethyl propanedioate (11.44 g, 86.61 mmol, 2.4 eq), 4-bromo-2,3-difluoro-pyridine (7 g, 36.09 mmol, 1 eq) in DMSO (70 mL) was added $Cs_2CO_3$ (28.22 g, 86.61 mmol, 2.4 eq). The mixture was stirred at 100° C. for 12 hours under $N_2$. LCMS showed the reaction was completed. The residue was poured into water (200 mL). The aqueous phase was extracted with ethyl acetate (100 mL*3). The combined organic phase was washed with saturated brine (300 mL), dried with anhydrous $Na_2SO_4$, filtered and concentrated in vacuum. The residue was purified by column chromatography ($SiO_2$, Petroleum ether/ethyl acetate=20/1) to give dimethyl 2-(4-bromo-3-fluoro-2-pyridyl) propanedioate (5.5 g, 16.17 mmol, 44.81% yield). LC-MS (ES+, m/z): 305.9 [$(M+H)^+$]; Rt=1.087 min.

Step 2: methyl 2-(4-bromo-3-fluoropyridin-2-yl) acetate

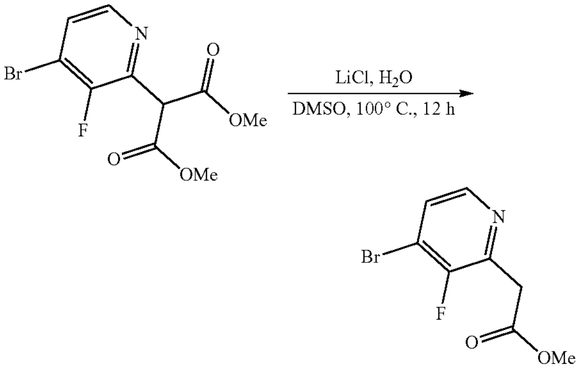

To a solution of dimethyl 2-(4-bromo-3-fluoro-2-pyridyl) propanedioate (5.5 g, 16.17 mmol, 1 eq) in DMSO (55 mL) was added LiCl (3.43 g, 80.86 mmol, 5 eq) and $H_2O$ (291.34 mg, 16.17 mmol, 1 eq). The mixture was stirred at 100° C. for 12 hours under $N_2$. LCMS showed the reaction was completed. The residue was poured into water (100 mL). The aqueous phase was extracted with ethyl acetate (50 mL*3). The combined organic phase was washed with saturated brine (150 mL), dried with anhydrous $Na_2SO_4$, filtered and concentrated in vacuum. The residue was purified by column chromatography ($SiO_2$, Petroleum ether/ethyl acetate=10/1) to give methyl 2-(4-bromo-3-fluoro-2-pyridyl) acetate (3 g, 11.49 mmol, 71.05% yield). LC-MS (ES+, m/z): 247.9 [$(M+H)^+$]; Rt=1.049 min.

Step 3: 5-bromo-4-fluoropyrazolo[1,5-a]pyridin-2 (1H)-one

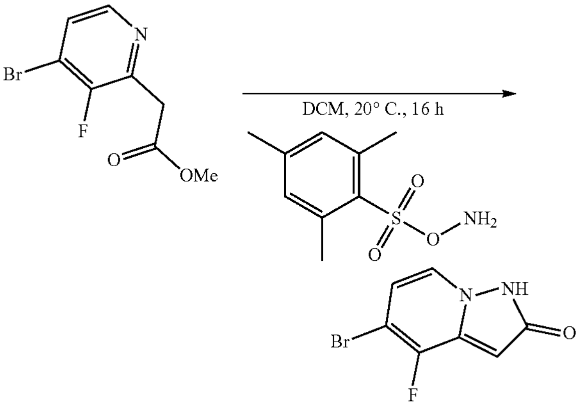

To a solution of amino 2, 4, 6-trimethylbenzenesulfonate (2.47 g, 11.49 mmol, 2 eq) in DCM (150 mL) was added methyl 2-(4-bromo-3-fluoro-2-pyridyl) acetate (1.5 g, 5.74 mmol, 1 eq). The mixture was stirred at 20° C. for 16 hours under $N_2$. LCMS showed the reaction was completed. The residue was poured into water (100 mL). The aqueous phase was extracted with DCM (50 mL*3). The combined organic phase was washed with saturated brine (150 mL), dried with anhydrous $Na_2SO_4$, filtered and concentrated in vacuum. The residue was purified by prep-TLC ($SiO_2$, Petroleum ether/ethyl acetate-3/1) to give 5-bromo-4-fluoro-1H-pyrazolo[1,5-a]pyridin-2-one (0.7 g, 2.88 mmol, 25.05% yield). LC-MS (ES-, m/z): 228.9 [$(M-H)^-$]; Rt=0.730 min.

Step 4: 5-bromo-4-fluoro-1-methylpyrazolo[1,5-a] pyridin-2 (1H)-one & 5-bromo-4-fluoro-2-methoxy-pyrazolo[1,5-a]pyridine

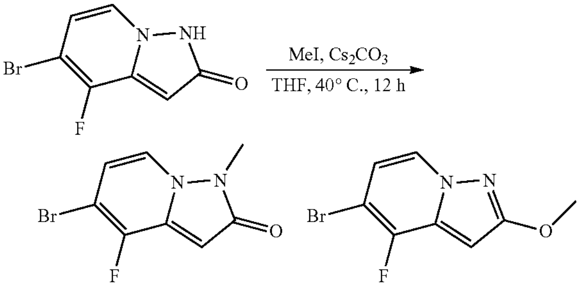

To a solution of 5-bromo-4-fluoro-1H-pyrazolo[1,5-a] pyridin-2-one (500 mg, 2.06 mmol, 1 eq) in THF (10 mL) was added $Cs_2CO_3$ (2.01 g, 6.17 mmol, 3 eq), MeI (1.46 g, 10.28 mmol, 5 eq). The mixture was stirred at 40° C. for 12 hours under $N_2$. LCMS showed the reaction was completed. The residue was poured into water (50 mL). The aqueous phase was extracted with ethyl acetate (30 mL*3). The combined organic phase was washed with saturated brine (100 mL), dried with anhydrous $Na_2SO_4$, filtered and concentrated in vacuum. The residue was purified by column chromatography ($SiO_2$, Petroleum ether/ethyl acetate=0/1) to give 5-bromo-4-fluoro-1-methylpyrazolo[1,5-a]pyridin-2 (1H)-one (60 mg, 220.36 μmol, 10.72% yield). LC-MS (ES+, m/z): 244.9 [(M+H)$^+$]; Rt=0.850 min. And 5-bromo-4-fluoro-2-methoxy-pyrazolo[1,5-a]pyridine (100 mg, 367.27 μmol, 17.86% yield). LC-MS (ES+, m/z): 244.9 [(M+H)$^+$]; Rt=1.284 min.

Step 5: tert-butyl (4S,7R)-3-(3-(4-fluoro-1-methyl-2-oxo-1,2-dihydropyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

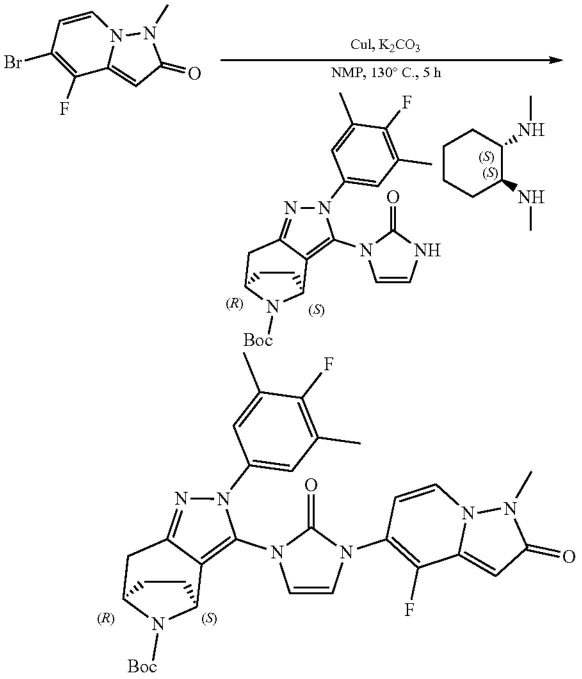

To a solution of 5-bromo-4-fluoro-1-methylpyrazolo[1,5-a]pyridin-2 (1H)-one (44.40 mg, 163.06 μmol, 1.5 eq), tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (50 mg, 108.71 μmol, 1 eq) in NMP (2.5 mL) was added (1S,2S)—$N^1$,$N^2$-dimethylcyclohexane-1,2-diamine (46.39 mg, 326.12 μmol, 3 eq), CuI (41.41 mg, 217.42 μmol, 2 eq) and $K_2CO_3$ (30.05 mg, 217.42 μmol, 2 eq). The mixture was stirred at 130° C. for 5 hours under $N_2$. LCMS showed the reaction was completed. The residue was poured into saturated EDTA (20 mL), ethyl acetate (10 mL) and stirred for 1 hour. The aqueous phase was extracted with ethyl acetate (20 mL*3). The combined organic phase was washed with saturated brine (60 mL), dried with anhydrous $Na_2SO_4$, filtered and concentrated in vacuum. The residue was purified by prep-TLC ($SiO_2$, dichloromethane:methanol=10:1) to give tert-butyl (4S,7R)-3-(3-(4-fluoro-1-methyl-2-oxo-1,2-dihydropyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (50 mg, 64.76 μmol, 59.57% yield). LC-MS (ES+, m/z): 618.2 [(M+H)$^+$]; Rt=1.302 min.

Step 6: 4-fluoro-5-(3-((4S,7R)-2-(4-fluoro-3,5-dimethylphenyl)-2,4,5,6,7,8-hexahydro-4,7-epiminocyclohepta [c]pyrazol-3-yl)-2-oxo-2,3-dihydro-1H-imidazol-1-yl)-1-methylpyrazolo[1,5-a] pyridin-2 (1H)-one

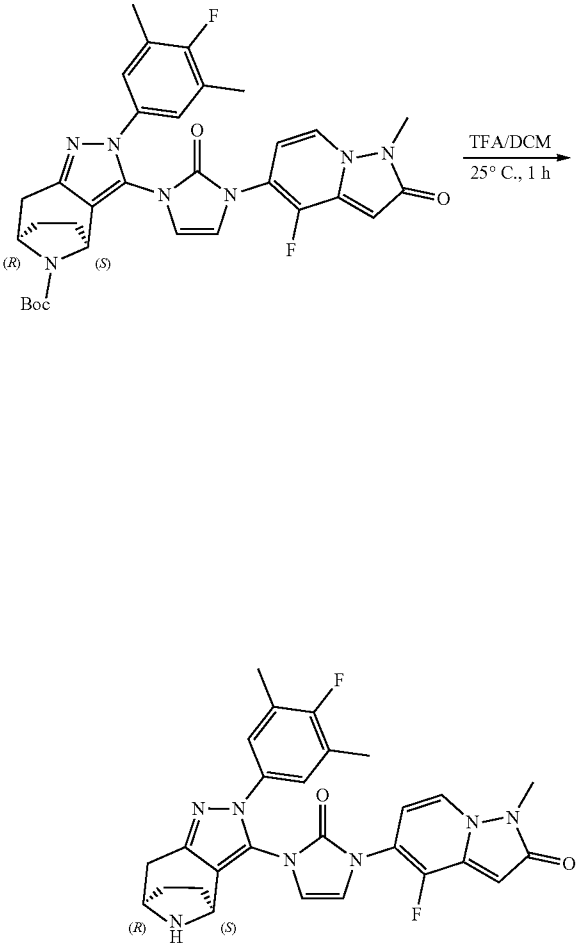

To a solution of tert-butyl (4S,7R)-3-(3-(4-fluoro-1-methyl-2-oxo-1,2-dihydropyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (50 mg, 64.76 μmol, 1 eq) in DCM (0.4 mL) was added TFA (0.1 mL). The mixture was stirred at 25° C. for 1 hour. LCMS showed the reaction was completed. The residue was poured into saturated $Na_2CO_3$ (20 mL). The aqueous phase was extracted with ethyl acetate (10 mL*3). The combined organic phase was washed with saturated brine (30 mL), dried with anhydrous $Na_2SO_4$, filtered and concentrated under reduced pressure to give 4-fluoro-5-(3-((4S,7R)-2-(4-fluoro-3,5-dimethylphenyl)-2,4,5,6,7,8-hexahydro-4,7-epiminocyclohepta [c]pyrazol-3-yl)-2-oxo-2,3-dihydro-1H-imidazol-1-yl)-1-methylpyrazolo [1,5-a]pyridin-2 (1H)-one (35 mg, crude). LC-MS (ES+, m/z): 518.2 [(M+H)$^+$]; Rt=1.035 min.

Step 7: 3-((1S,2S)-1-(5-((S)-2,2-dimethyltetrahydro-2H-pyran-4-yl)-2-((4S,7R)-3-(3-(4-fluoro-1-methyl-2-oxo-1,2-dihydropyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

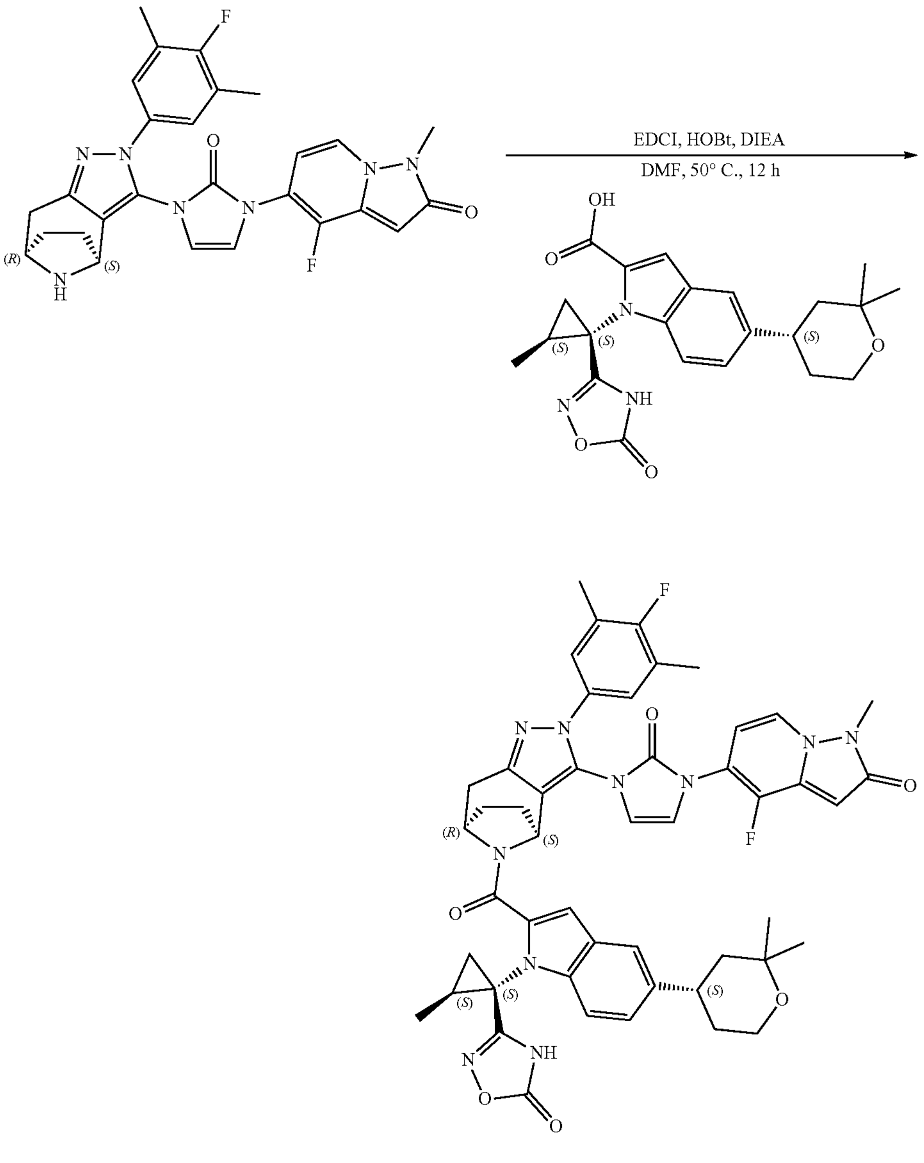

To a solution of 4-fluoro-5-(3-((4S,7R)-2-(4-fluoro-3,5-dimethylphenyl)-2,4,5,6,7,8-hexahydro-4,7-epiminocyclohepta [c]pyrazol-3-yl)-2-oxo-2,3-dihydro-1H-imidazol-1-yl)-1-methylpyrazolo[1,5-a]pyridin-2 (1H)-one (35 mg, 54.10 μmol, 1 eq), 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (22.26 mg, 54.10 μmol, 1 eq) in DMF (0.7 mL) was added HOBt (14.62 mg, 108.21 μmol, 2 eq) and EDCI (20.74 mg, 108.21 μmol, 2 eq), DIEA (34.96 mg, 270.52 μmol, 5 eq). The mixture was stirred at 50° C. for 12 hours under $N_2$. LCMS showed the reaction was completed. The residue was poured into water (10 mL). The aqueous phase was extracted with ethyl acetate (10 mL*3). The combined organic phase was washed with saturated brine (30 mL), dried with anhydrous $Na_2SO_4$, filtered and concentrated. The residue was purified by prep-HPLC (TFA condition; column: Phenomenex Luna C18 75*30 mm*3 um; mobile phase: [$H_2O$ (0.1% TFA)-ACN]; gradient: 40%-70% B over 8.0 min) to give 3-((1S,2S)-1-(5-((S)-2,2-dimethyltetrahydro-2H-pyran-4-yl)-2-((4S,7R)-3-(3-(4-fluoro-1-methyl-2-oxo-1,2-dihydropyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (9.32 mg, 10.23 μmol, 18.91% yield). $^1H$ NMR (400 MHz, DMSO-$d_6$) δ=12.26-11.63 (m, 1H), 8.61-7.92 (m, 1H), 7.63-6.00 (m, 9H), 5.76-4.82 (m, 3H), 3.75-3.40 (m, 6H), 3.24-2.99 (m, 1H), 2.91-2.81 (m, 1H), 2.33-2.02 (m, 8H), 1.93-1.46 (m, 7H), 1.39-0.96 (m, 11H). LC-MS (ES+, m/z): 911.4 [$(M+H)^+$]; Rt=2.847 min. HRMS (EI): m/z $[M+H]^+$ found: 911.3787.

Example 79 Compound 431
3-((1S,2S)-1-(5-((S)-2,2-dimethyltetrahydro-2H-pyran-4-yl)-2-((4S,7R)-3-(3-(4-fluoro-2-methoxy-pyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-1H-indol-1-yl)-2-methylcyclopropyl)-1,2,4-oxadiazol-5 (4H)-one
Scheme 431
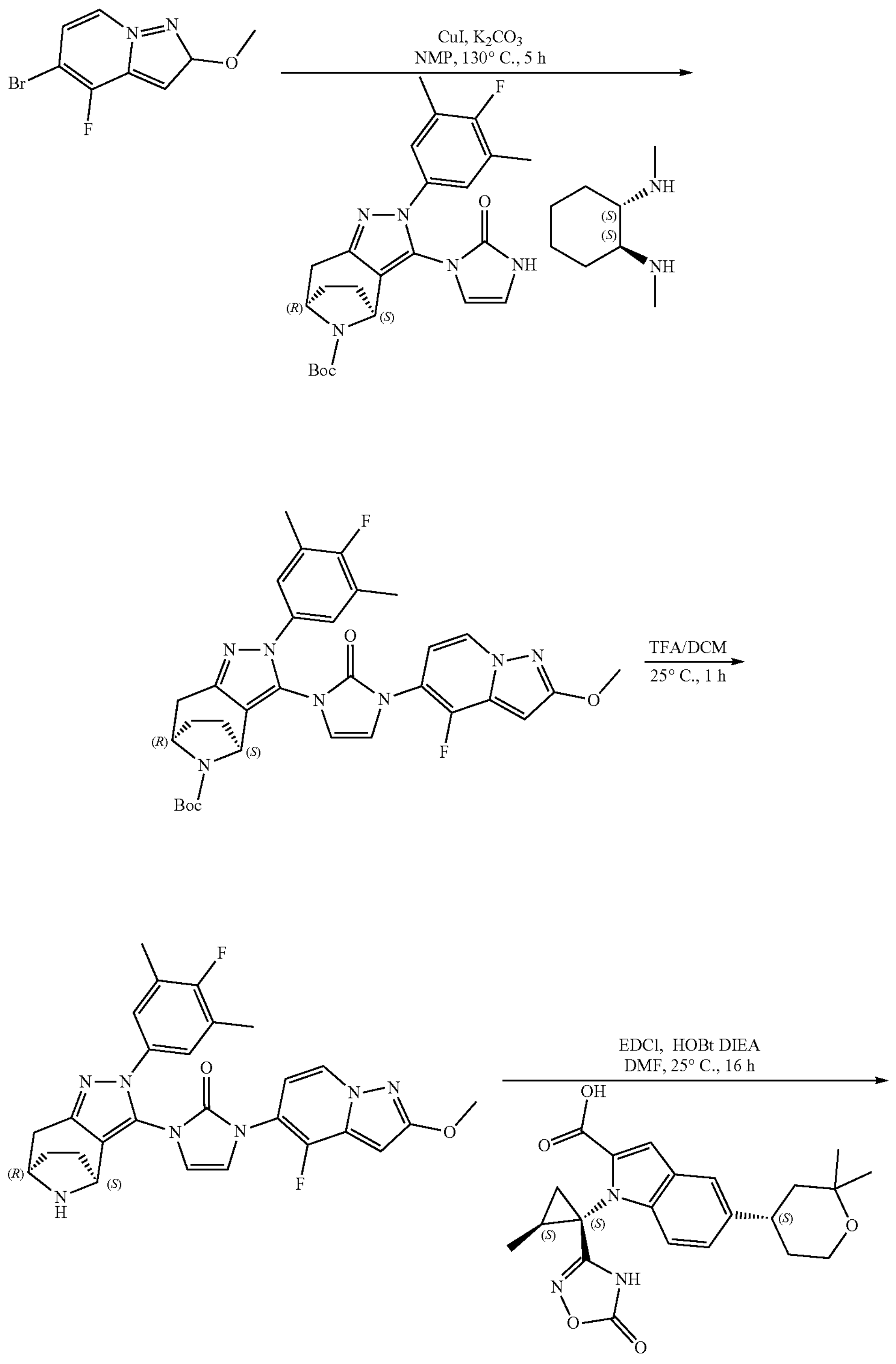

-continued

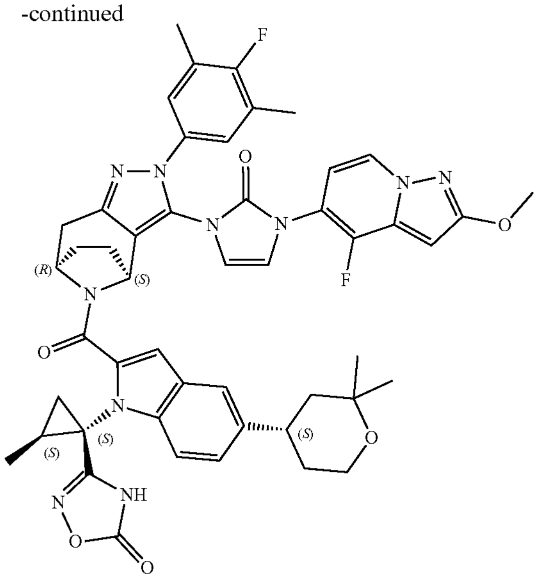

Step 1 tert-butyl (4S,7R)-3-(3-(4-fluoro-2-methoxy-pyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

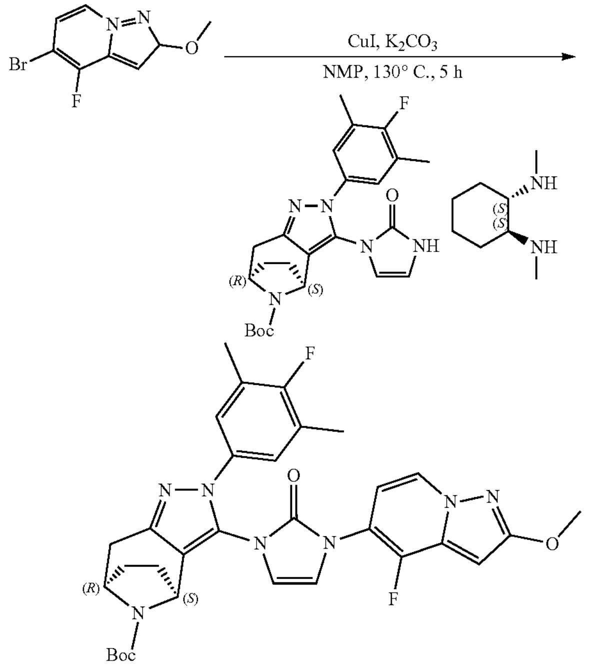

To a solution of tert-butyl (4S,7R)-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (100 mg, 220.50 μmol, 1 eq), (1S,2S)—$N^1$,$N^2$-dimethylcyclohexane-1,2-diamine (94.09 mg, 661.51 μmol, 3 eq) and 5-bromo-4-fluoro-2-methoxypyrazolo[1,5-a]pyridine (90.06 mg, 330.75 μmol, 1.5 eq) in NMP (1 mL) was added CuI (83.99 mg, 441.01 μmol, 2 eq) and $K_2CO_3$ (60.95 mg, 441.01 μmol, 2 eq) in one portion under $N_2$. The mixture was stirred at 130° C. for 5 hours under $N_2$. LCMS showed the reaction was completed. The reaction mixture was quenched by addition saturated EDTA solution (15 mL) and ethyl acetate (5 mL), stirred for 0.5 hour, extracted with ethyl acetate (10 mL*3). The combined organic layers were washed with saturated brine (20 mL), dried over anhydrous $Na_2SO_4$, filtered and concentrated under reduced pressure. The residue was purified by prep-TLC ($SiO_2$, petroleum ether/ethyl acetate=0/1) to afford the title compound tert-butyl (4S,7R)-3-(3-(4-fluoro-2-methoxypyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (80 mg, 116.57 μmol, 52.87% yield). LC-MS (ES+, m/z): 618.2 $[(M+H)^+]$. Rt=0.645 min.

Step 2: 1-(4-fluoro-2-methoxypyrazolo[1,5-a]pyridin-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

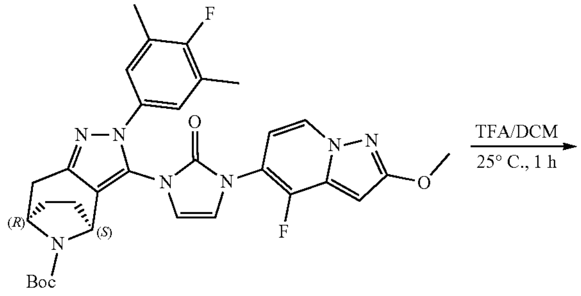

-continued

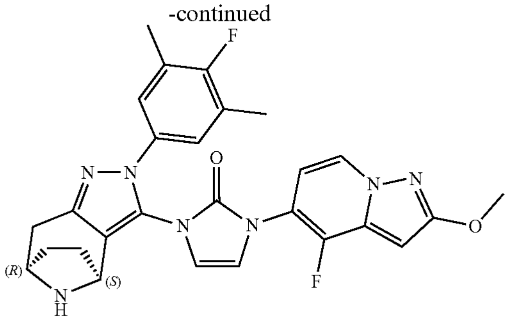

To a solution of tert-butyl (4S,7R)-3-(3-(4-fluoro-2-methoxypyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (80 mg, 116.57 μmol, 1 eq) in DCM (0.64 mL) was added TFA (0.16 mL) in one portion at 25° C. The mixture was stirred at 25° C. for 1 hour. LCMS showed the reaction was completed. The reaction mixture was quenched by addition saturated $NaHCO_3$ solution (10 mL) at 0° C., extracted with dichloromethane (5 mL*3). The combined organic layers were washed with saturated brine (15 mL), dried over anhydrous $Na_2SO_4$, filtered and concentrated under reduced pressure to afford the title compound 1-(4-fluoro-2-methoxypyrazolo[1,5-a]pyridin-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (60 mg, 116.57 μmol, 90% yield). LC-MS (ES+, m/z): 518.2 [(M+H)+]. Rt=0.435 min.

Step 3: 3-((1S,2S)-1-(5-((S)-2,2-dimethyltetrahydro-2H-pyran-4-yl)-2-((4S,7R)-3-(3-(4-fluoro-2-methoxypyrazolo[1,5-a]pyridin-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one

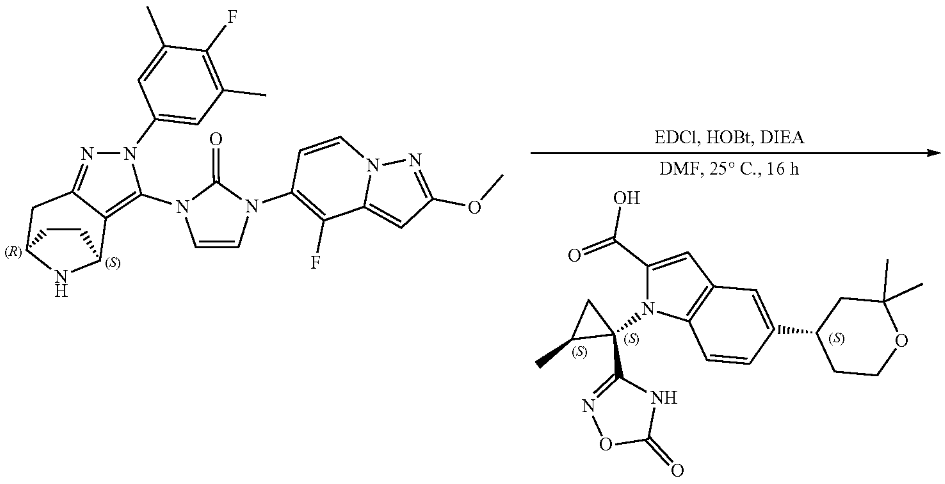

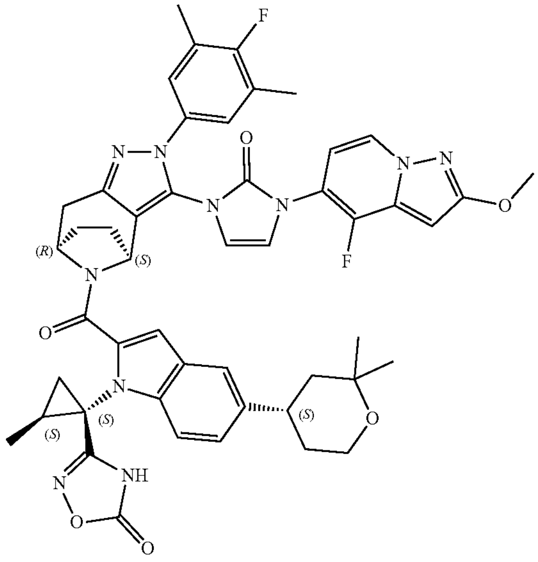

To a solution of 1-(4-fluoro-2-methoxypyrazolo[1,5-a]pyridin-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (30 mg, 52.17 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (21.47 mg, 52.17 μmol, 1 eq) in DMF (0.3 mL) was added HOBt (10.57 mg, 78.26 μmol, 1.5 eq), EDCI (13.00 mg, 67.82 μmol, 1.3 eq), DIEA (67.43 mg, 521.71 μmol, 10 eq) in one portion at 25° C. under $N_2$. The mixture was stirred at 25° C. for 16 hours. LCMS showed the reaction was completed. The reaction mixture was quenched by addition $H_2O$ (10 mL), extracted with dichloromethane (5 mL*3). The combined organic layers were washed with saturated brine (10 mL), dried over anhydrous $Na_2SO_4$, filtered and concentrated under reduced pressure. The residue was purified by prep-HPLC (TFA condition) column: Phenomenex Luna C18 75*30 mm*3 um; mobile phase: [$H_2O$ (0.1% TFA)-ACN]; gradient: 55%-85% B over 8.0 min to afford the title compound 3-((1S,2S)-1-(5-((S)-2,2-dimethyltetrahydro-2H-pyran-4-yl)-2-((4S,7R)-3-(3-(4-fluoro-2-methoxypyrazolo[1,5-a]pyridin-5-yl)-2-oxo-2,3-dihydro-1H-imidazol-1-yl)-

2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (13.82 mg, 15.17 μmol, 29.08% yield). $^1$H NMR (400 MHz, DMSO-$d_6$+$D_2O$) δ=8.40-7.90 (m, 1H), 7.65-6.51 (m, 9H), 6.31-5.99 (m, 1H), 5.63-4.67 (m, 2H), 3.93-3.85 (m, 3H), 3.52 (br s, 3H), 3.12-2.77 (m, 2H), 2.27-2.01 (m, 8H), 1.89-1.33 (m, 7H), 1.30-0.87 (m, 11H). JH NMR (400 MHz, DMSO-$d_6$+$D_2O$, T=273+80K) δ=8.42-7.77 (m, 1H), 7.47-6.01 (m, 10H), 5.40-4.74 (m, 2H), 3.91 (s, 3H), 3.64-3.32 (m, 3H), 2.96-2.75 (m, 2H), 2.21-2.04 (m, 8H), 1.86-1.43 (m, 7H), 1.36-0.93 (m, 11H). LC-MS (ES+, m/z): 911.3 [(M+H)$^+$]. Rt=3.479 min. HRMS (EI): m/z [M+H]$^+$ found: 911.3766.

Example 79a Compound 432

3-((1S,2S)-1-(5-((S)-2,2-dimethyltetrahydro-2H-pyran-4-yl)-2-((3-(3-(4-fluoro-1-methyl-1H-indazol-5-yl)-2-oxo-2,3-dihydro-1H-imidazol-1-yl)-2-(4-fluoro-3,5-dimethylphenyl)-2,6,7,8-tetrahydropyrazolo[4,3-c]azepin-5 (4H)-yl)methyl)-1H-indol-1-yl)-2-methylcyclopropyl)-1,2,4-oxadiazol-5(4H)-one

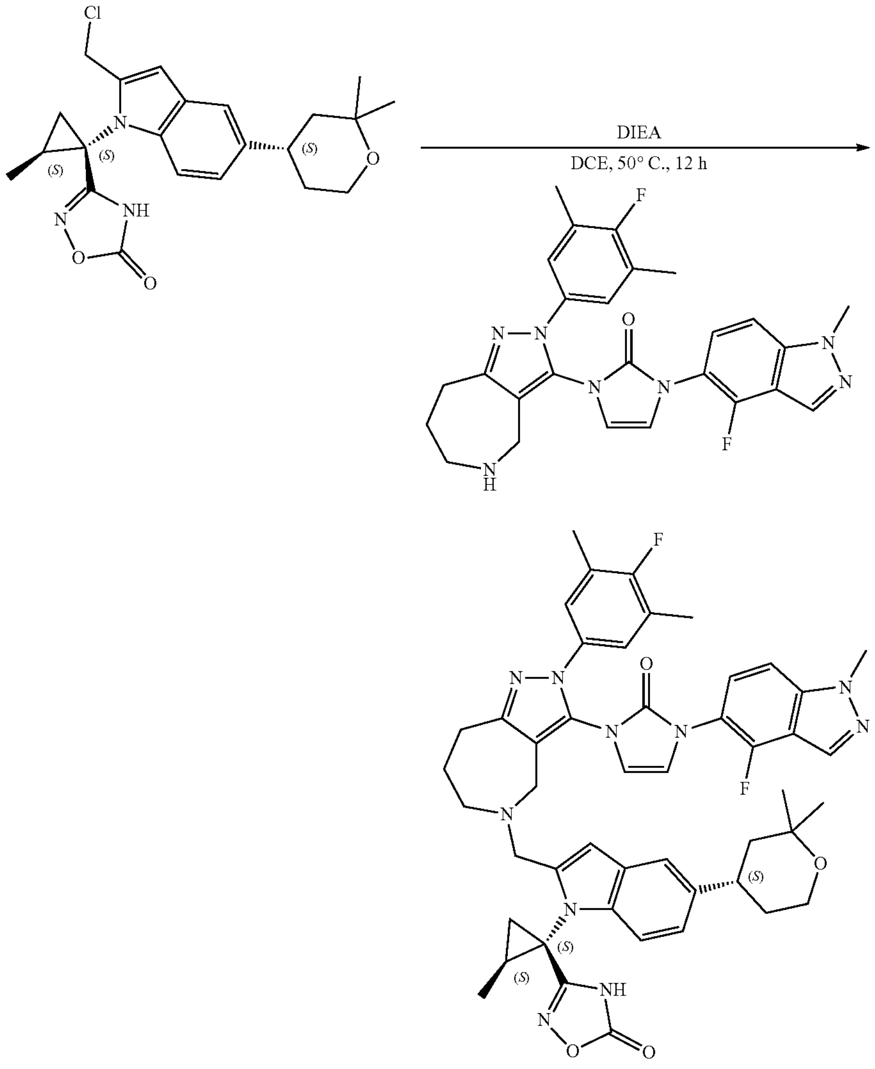

To a solution of 3-((1S,2S)-1-(2-(chloromethyl)-5-((S)-2,2-dimethyltetrahydro-2H-pyran-4-yl)-1H-indol-1-yl)-2-methylcyclopropyl)-1,2,4-oxadiazol-5 (4H)-one (80 mg, 153.88 μmol, 1 eq) and 1-(4-fluoro-1-methyl-1H-indazol-5-yl)-3-(2-(4-fluoro-3,5-dimethylphenyl)-2,4,5,6,7,8-hexahydropyrazolo[4,3-c]azepin-3-yl)-1,3-dihydro-2H-imidazol-2-one (75.33 mg, 153.88 μmol, 1 eq) in DCE (1.6 mL) was added DIEA (59.66 mg, 461.64 μmol, 3 eq) in one portion under $N_2$. The mixture was stirred at 50° C. for 12 hours. LCMS showed the reaction was completed. The reaction mixture was concentrated under reduced pressure to remove solvent. The residue was purified by prep-HPLC (neutral condition) column: WePure Biotech XP tC18 150*40*7 um; mobile phase: [$H_2O$ (10 mM $NH_4HCO_3$)-ACN]; gradient: 45%-65% B over 8.0 min to afford the title compound 3-((1S,2S)-1-(5-((S)-2,2-dimethyltetrahydro-2H-pyran-4-yl)-2-((3-(3-(4-fluoro-1-methyl-1H-indazol-5-yl)-2-oxo-2,3-dihydro-1H-imidazol-1-yl)-2-(4-fluoro-3,5-dimethylphenyl)-2,6,7,8-tetrahydropyrazolo[4,3-c]azepin-5 (4H)-yl)methyl)-1H-indol-1-yl)-2-methylcyclopropyl)-1,2,4-oxadiazol-5 (4H)-one (10.82 mg, 11.83 μmol, 7.69% yield). $^1$H NMR (400 MHz, DMSO-$d_6$) δ=8.38-8.09 (m, 1H), 7.63 (d, J=9.0 Hz, 1H), 7.42-5.84 (m, 9H), 4.41-4.15 (m, 2H), 4.14-3.99 (m, 5H), 3.71-3.49 (m, 4H), 3.01-2.82 (m, 3H), 2.26 (br s, 8H), 1.94-1.59 (m, 3H), 1.20 (s, 6H), 1.12-1.01 (m, 7H). LC-MS (ES+, m/z): 869.3 [(M+H)$^+$]. Rt=3.128 min. HRMS (EI): m/z [M+H]$^+$ found: 869.4089.

Example 80 Compound 430

3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one

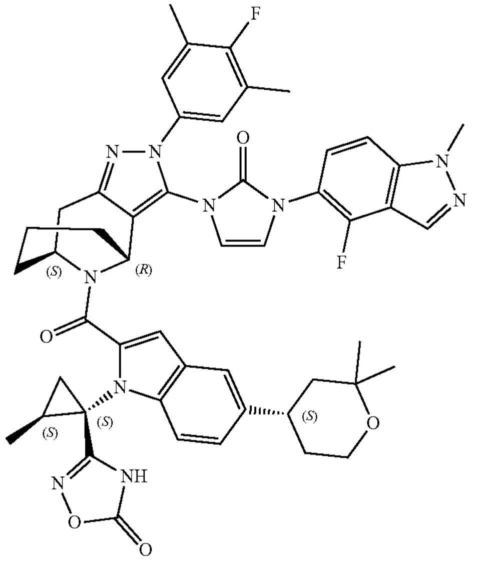

Scheme 430

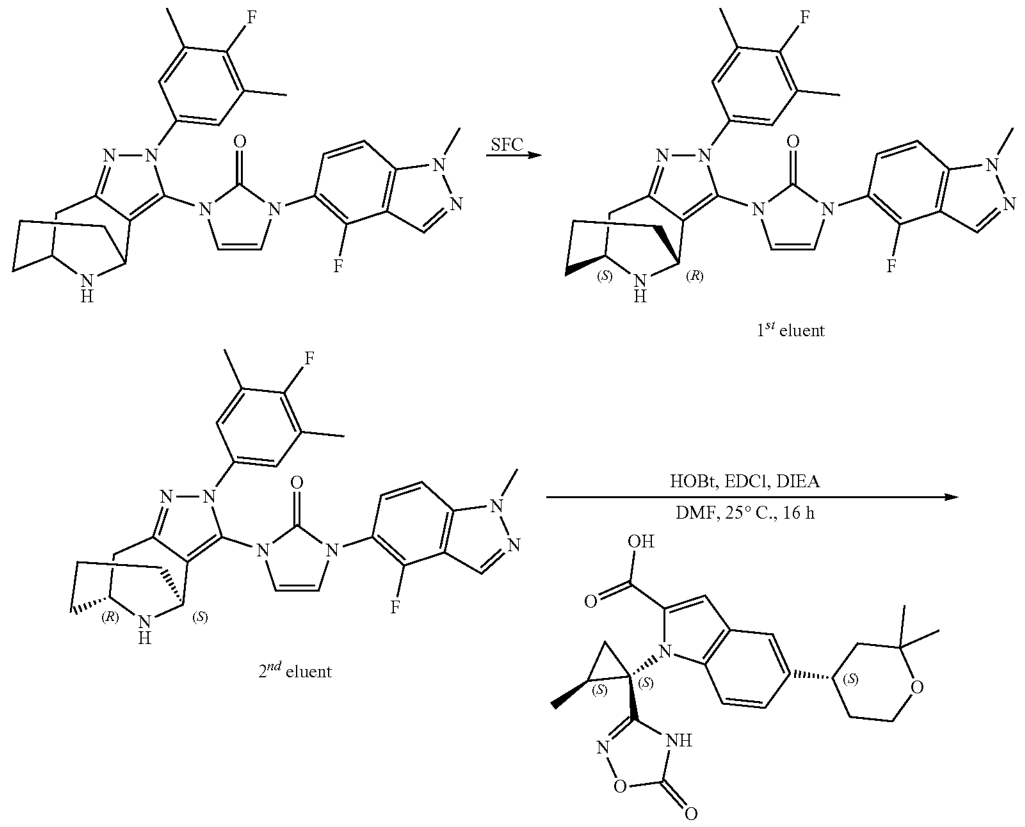

-continued

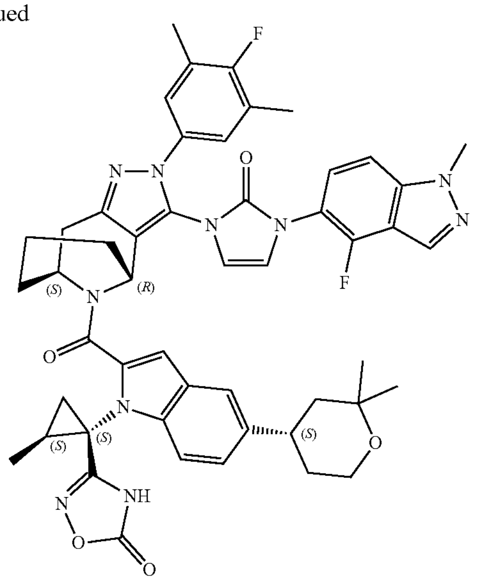

Step 1: 1-(4-fluoro-1-methyl-LH-indazol-5-yl)-3-((4R,8S)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one & 1-(4-fluoro-1-methyl-1H-indazol-5-yl)-3-((45,8R)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one

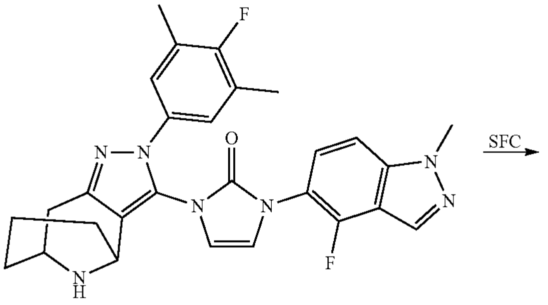

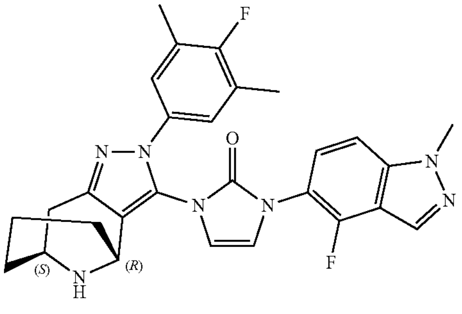

1st eluent

-continued

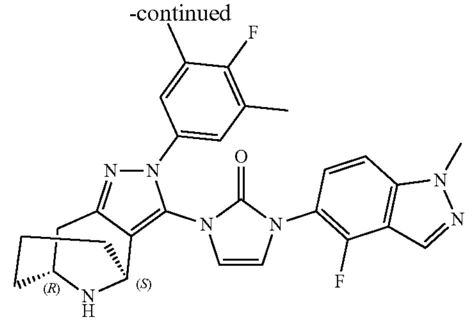

2nd eluent

The 1-(4-fluoro-1-methyl-1H-indazol-5-yl)-3-(2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (90 mg) was separated by SFC column: REGIS (s,s) WHELK-O1 (250 mm*30 mm, 5 um); mobile phase: [$CO_2$-MeOH (0.1% $NH_3H_2O$)]; B %: 50%, isocratic elution mode to afford 1-(4-fluoro-1-methyl-1H-indazol-5-yl)-3-((4R,8S)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (1st eluent, RT=0.709 by SFC, 35 mg, 65.85 μmol, 40.13% yield). LC-MS (ES+, m/z): 516.3 [$(M+H)^+$]. Rt=0.428 min.

And 1-(4-fluoro-1-methyl-1H-indazol-5-yl)-3-((4S,8R)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one ($2^{nd}$ eluent, RT=1.038 by SFC, 35 mg, 65.85 μmol, 40.13% yield). LC-MS (ES+, m/z): 516.3 [$(M+H)^+$]. Rt=0.433 min.

Step 2: 3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one

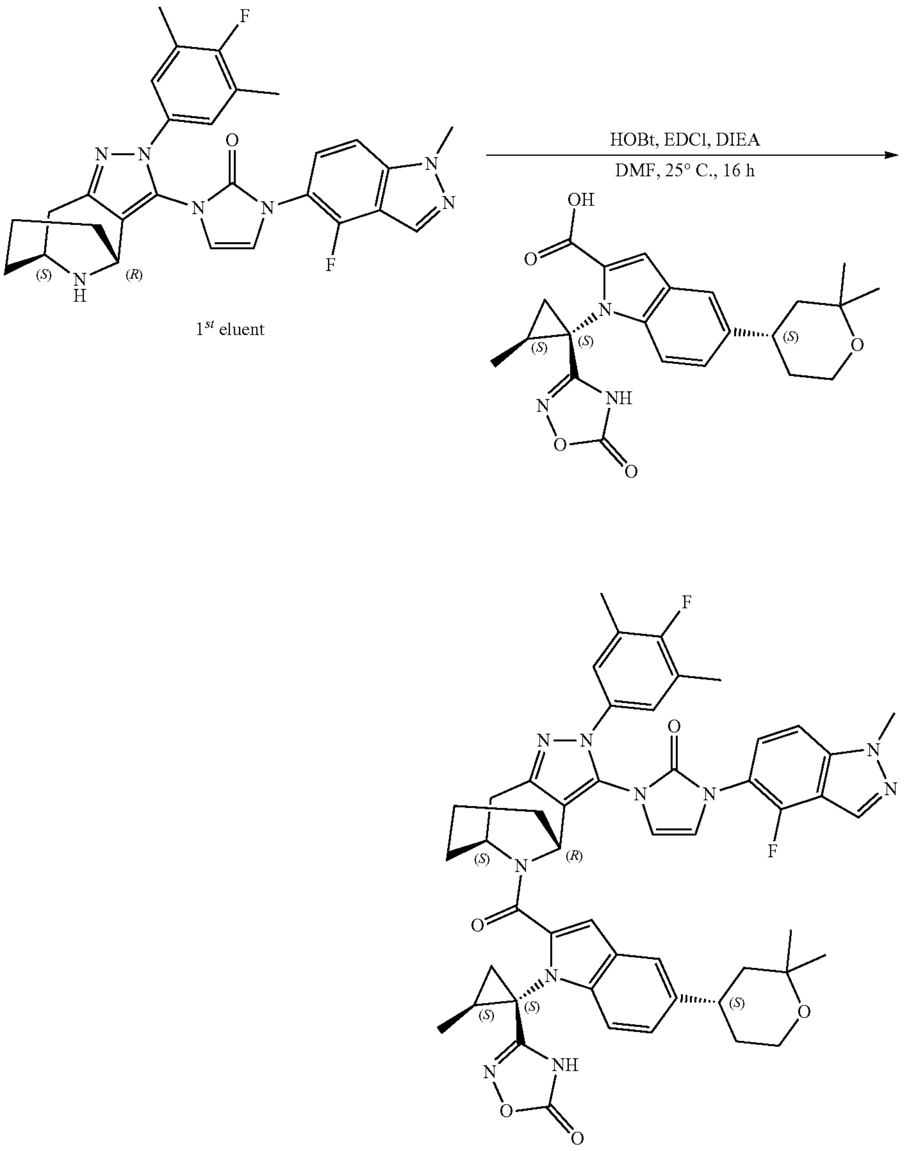

To a solution of 1-(4-fluoro-1-methyl-1H-indazol-5-yl)-3-((4R,8S)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (35 mg, 65.85 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (27.09 mg, 65.85 μmol, 1 eq) in DMF (0.35 mL) was added HOBt (13.35 mg, 98.78 μmol, 1.5 eq), EDCI (16.41 mg, 85.61 μmol, 1.3 eq), DIEA (85.11 mg, 658.51 μmol, 10 eq) in one portion at 25° C. under $N_2$. The mixture was stirred at 25° C. for 16 hours under $N_2$. LCMS showed the reaction was completed. The reaction mixture was quenched by addition $H_2O$ (10 mL), extracted with dichloromethane (5 mL*3). The combined organic layers were washed with saturated brine (10 mL), dried over anhydrous $Na_2SO_4$, filtered and concentrated under reduced pressure. The residue was purified by prep-HPLC (TFA condition) column: Phenomenex Luna C18 75*30 mm*3 um; mobile phase: [$H_2O$ (0.1% TFA)-ACN]; gradient: 55%-85% B over 8.0 min to give 3-((1S,2S)-1-(5-((S)-2,2-dimethyltetrahydro-2H-pyran-4-yl)-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one (RT=1.714 by SFC, 13.75 mg, 15.13 μmol, 22.97% yield). $^1H$ NMR (400 MHz, DMSO-$d_6$+$D_2O$, T=273+80K) δ=8.13 (br s, 1H), 7.53-7.05 (m, 7H), 6.91-6.56 (m, 3H), 5.84-4.83 (m, 2H), 4.02 (s, 3H), 3.55 (br d, J=3.0 Hz, 2H), 3.33-2.72 (m, 3H), 2.21 (d, J=1.4 Hz, 6H), 1.92-1.45 (m, 12H), 1.00 (br s, 10H). LC-MS (ES+, m/z): 909.3 [$(M+H)^+$]. Rt=3.449 min. HRMS (EI): m/z $[M+H]^+$ found: 909.4023.

Example 81 Compound 433

3-((1S,2S)-1-(5-((S)-2,2-dimethyltetrahydro-2H-pyran-4-yl)-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one

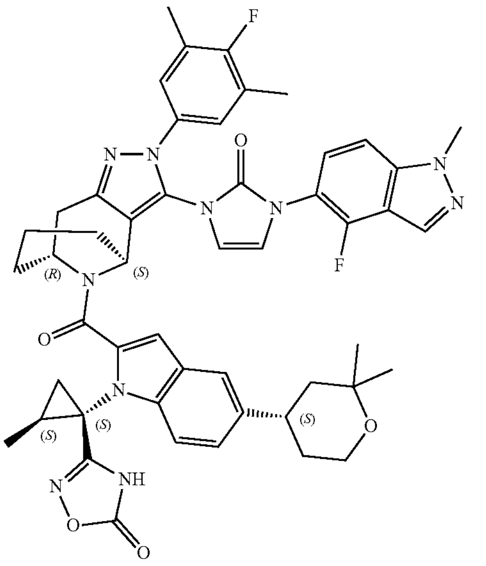

Step 1: 3-((1S,2S)-1-(5-((S)-2,2-dimethyltetrahydro-2H-pyran-4-yl)-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one

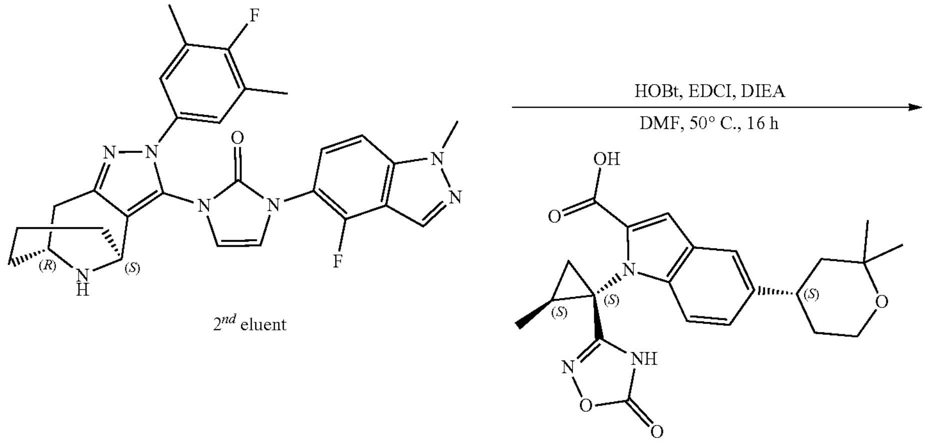

-continued

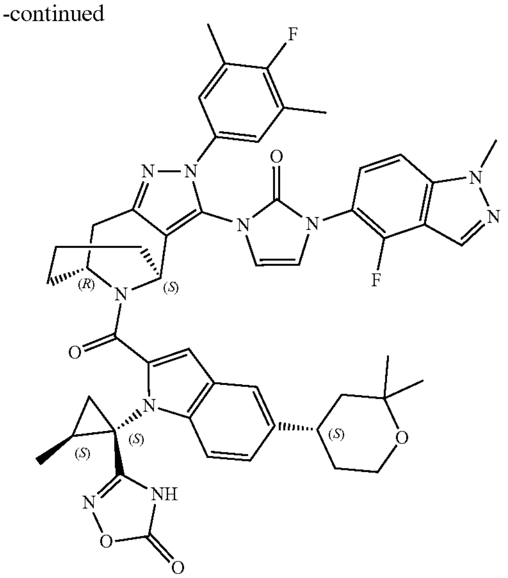

To a mixture of 1-(4-fluoro-1-methyl-1H-indazol-5-yl)-3-((4S,8R)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (35 mg, 65.85 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1: H-indole-2-carboxylic acid (27.09 mg, 65.85 μmol, 1 eq) in DMF (0.7 mL) was added DIEA (42.55 mg, 329.26 μmol, 5 eq) and finally added HOBt (13.35 mg, 98.78 μmol, 1.5 eq) and EDCI (16.41 mg, 85.61 μmol, 1.3 eq) in one portion at 25° C. under $N_2$. The mixture was stirred at 25° C. for 16 hrs under $N_2$. LCMS showed the reaction was completed. The residue was poured into water (10 mL). The aqueous phase was extracted with ethyl acetate (5 mL*3). The combined organic phase was washed with saturated brine (15 mL), dried with anhydrous $Na_2SO_4$, filtered and concentrated in vacuum. The residue was purified by prep-HPLC (column: Phenomenex Luna C18 75*30 mm*3 um; mobile phase: [$H_2O$ (0.1% TFA)-ACN]; gradient: 55%-85% B over 8.0 min) to give 3-((1S,2S)-1-(5-((S)-2,2-dimethyltetrahydro-2H-pyran-4-yl)-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one (RT=2.004 by SFC, 19.79 mg, 21.55 μmol, 32.73% yield). $^1H$ NMR (400 MHz, DMSO-$d_6$) δ=12.40-11.62 (m, 1H), 8.53-8.03 (m, 1H), 7.78-6.62 (m, 10H), 5.85-5.58 (m, 1H), 5.33-5.16 (m, 1H), 4.19-3.93 (m, 3H), 3.73-3.48 (m, 2H), 3.39-2.72 (m, 3H), 2.31-2.17 (m, 6H), 1.99-1.43 (m, 12H), 1.41-0.89 (m, 10H). LC-MS (ES+, m/z): 909.3 [$(M+H)^+$]; Rt=3.042 min. HRMS (EI): m/z $[M+H]^+$ found: 909.4034.

Example 82 Compound 436

3-((1S,2S)-1-(2-((4S,7R)-3-(3-(4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

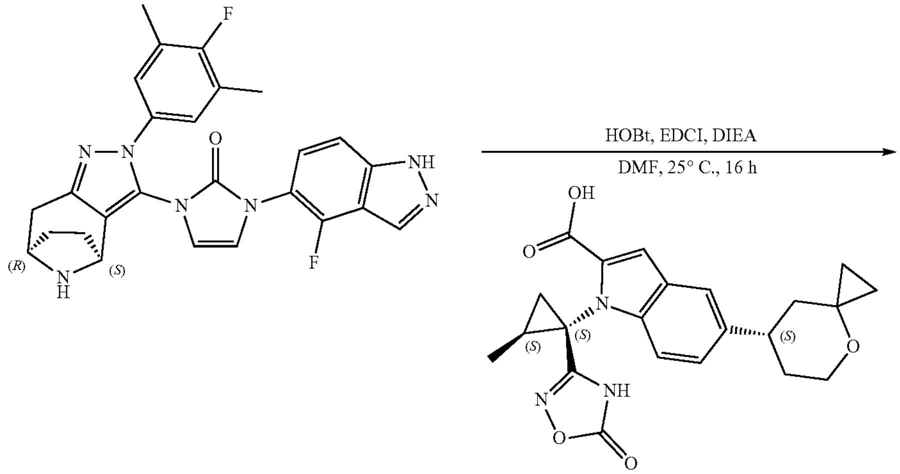

-continued

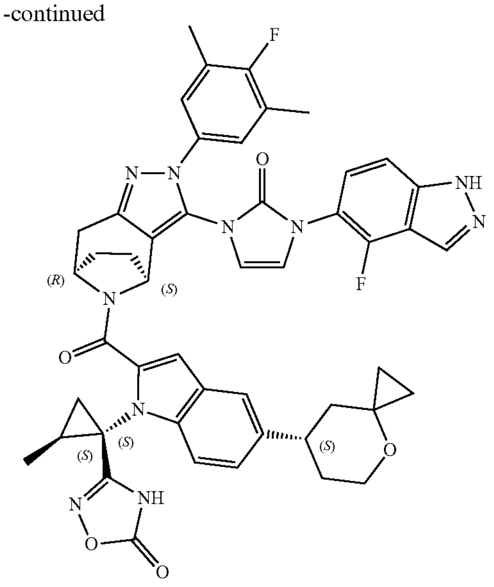

To a solution of 1-(4-fluoro-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (40 mg, 69.74 μmol, 1 eq) and 1-((1S,2S)-2-methyl-1-(5-oxo-4,5-dihydro-1,2,4-oxadiazol-3-yl) cyclopropyl)-5-((S)-4-oxaspiro[2.5]octan-7-yl)-1H-indole-2-carboxylic acid (28.56 mg, 69.74 μmol, 1 eq) in DMF (0.3 mL) was added HOBt (14.14 mg, 104.61 μmol, 1.5 eq), EDCI (17.38 mg, 90.67 μmol, 1.3 eq) and DIEA (90.14 mg, 697.43 μmol, 10 eq) in one portion at 25° C. under $N_2$. The mixture was stirred at 25° C. for 16 hours. LCMS showed the reaction was completed. The residue was poured into water (10 mL). The aqueous phase was extracted with dichloromethane (5 mL*3). The combined organic phase was washed with saturated brine (10 mL), dried with anhydrous $Na_2SO_4$, filtered and concentrated in vacuum. The residue was purified by prep-HPLC (TFA condition) (column: Phenomenex Luna C18 75*30 mm*3 um; mobile phase: [$H_2O$ (0.1% TFA)-ACN]; gradient: 45%-75% B over 8.0 min) to afford the title compound 3-((1S,2S)-1-(2-((4S,7R)-3-(3-(4-fluoro-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (13.23 mg, 14.96 μmol, 21.45% yield). $^1$H NMR (400 MHz, DMSO-$d_6$) δ=13.88-13.42 (m, 1H), 12.24-11.70 (m, 1H), 8.41-8.14 (m, 1H), 7.67-6.54 (m, 10H), 5.71-5.29 (m, 1H), 4.89 (br s, 1H), 3.84-3.52 (m, 2H), 3.39-2.78 (m, 3H), 2.30-2.10 (m, 8H), 2.02-0.97 (m, 12H), 0.83-0.29 (m, 4H). $^1$H NMR (400 MHz, DMSO-$d_6$+$D_2O$) δ=8.33-8.08 (m, 1H), 7.68-6.39 (m, 10H), 5.59-4.75 (m, 2H), 3.81-3.43 (m, 2H), 3.36-2.74 (m, 3H), 2.25-2.04 (m, 8H), 1.92-0.89 (m, 12H), 0.77-0.24 (m, 4H). LC-MS (ES+, m/z): 879.2 [$(M+H)^+$]; Rt=3.215 min. HRMS (EI): m/z $[M+H]^+$ found: 879.3539.

Example 83 Compound 437

3-((1S,2S)-1-(2-((4S,7R)-2-(4-fluoro-3, 5-dimethylphenyl)-3-(3-(5-fluorophthalazin-6-yl)-2-oxo-2, 3-dihydro-1H-imidazol-1-yl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one Scheme 437

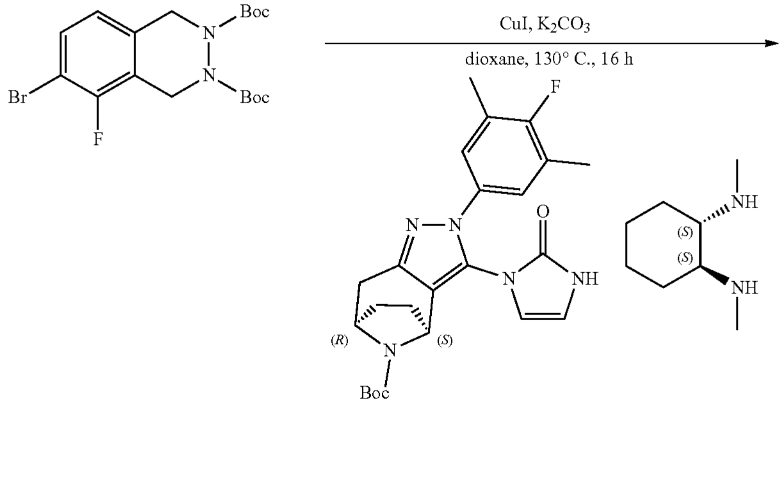

-continued
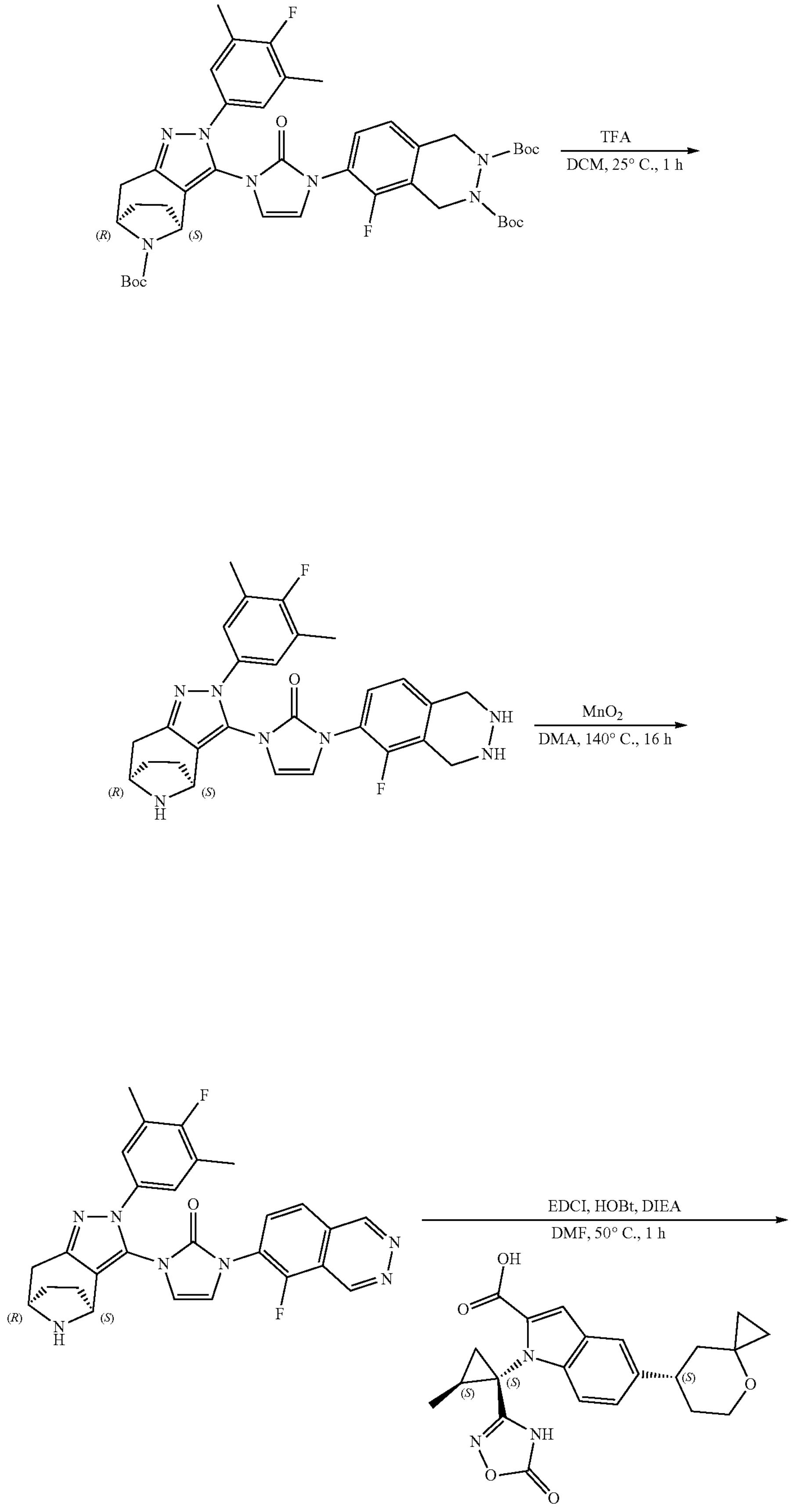

-continued

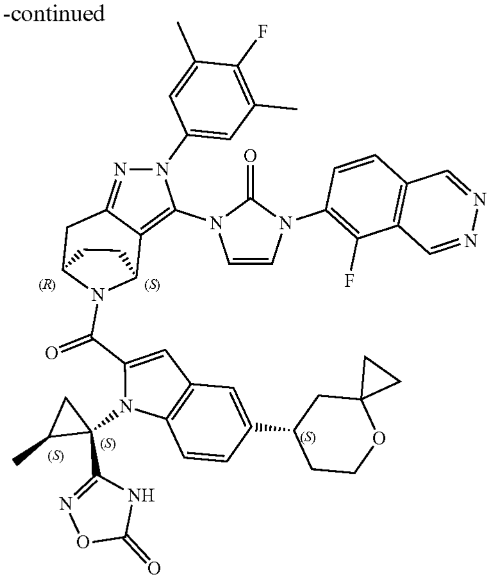

Step 1: di-tert-butyl 6-(3-((4S,7R)-9-(tert-butoxycarbonyl)-2-(4-fluoro-3, 5-dimethylphenyl)-2, 4, 5, 6, 7, 8-hexahydro-4, 7-epiminocyclohepta [c]pyrazol-3-yl)-2-oxo-2, 3-dihydro-1H-imidazol-1-yl)-5-fluoro-1, 4-dihydrophthalazine-2,3-dicarboxylate

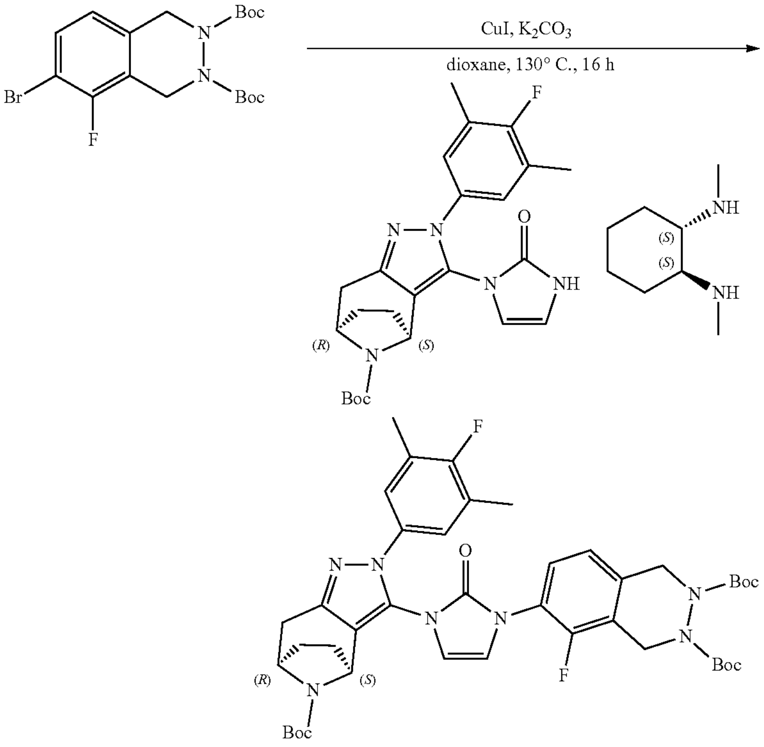

To a solution of tert-butyl (4S,7R)-2-(4-fluoro-3, 5-dimethylphenyl)-3-(2-oxo-2, 3-dihydro-1H-imidazol-1-yl)-2, 4, 5, 6, 7, 8-hexahydro-4, 7-epiminocyclohepta [c]pyrazole-9-carboxylate (1 g, 2.21 mmol, 1 eq), di-tert-butyl 6-bromo-5-fluoro-1,4-dihydrophthalazine-2,3-dicarboxylate (2.85 g, 6.62 mmol, 3 eq) and $K_2CO$; (914.24 mg, 6.62 mmol, 3 eq) in dioxane (10 mL) was added CuI (839.90 mg, 4.41 mmol, 2 eq) and (1S,2S)—$N^1$,$N^2$-dimethylcyclohexane-1,2-diamine (627.29 mg, 4.41 mmol, 2 eq). The mixture was stirred at 130° C. for 16 hours under $N_2$. LCMS indicated the reaction was completed. The residue was poured into saturated EDTA solution (50 mL) and DCM (50 mL) stirred for 0.5 hour, and then extracted with DCM (50 mL*2). The organic layers were combined, washed with water (150 mL), saturated brine (150 mL), dried over $Na_2SO_4$, filtered and concentrated to give crude product. The residue was purified by column chromatography ($SiO_2$, Petroleum ether/Ethyl acetate=5/1 to 1/1) to give di-tert-butyl 6-(3-((4S,7R)-9-(tert-butoxycarbonyl)-2-(4-fluoro-3, 5-dimethylphenyl)-2, 4, 5, 6, 7, 8-hexahydro-4, 7-epiminocyclohepta [c]pyrazol-3-yl)-2-oxo-2, 3-dihydro-1H-imidazol-1-yl)-5-fluoro-1, 4-dihydrophthalazine-2,3-dicarboxylate (1 g, 1.18 mmol, 53.48% yield). LC-MS (ES+, m/z): 804.3 $[(M+H)^+]$; Rt=0.730 min.

Step 2: 1-(5-fluoro-1, 2, 3, 4-tetrahydrophthalazin-6-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one

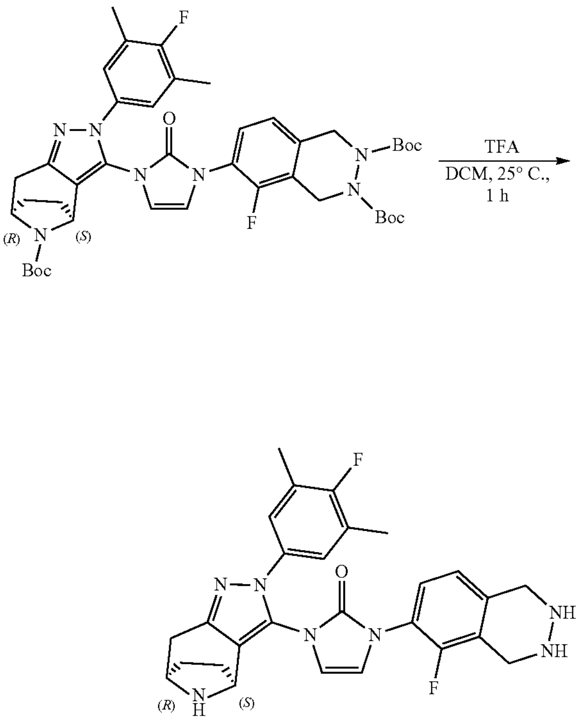

To a solution of di-tert-butyl 6-(3-((4S,7R)-9-(tert-butoxycarbonyl)-2-(4-fluoro-3, 5-dimethylphenyl)-2, 4, 5, 6, 7, 8-hexahydro-4, 7-epiminocyclohepta [c]pyrazol-3-yl)-2-oxo-2, 3-dihydro-1H-imidazol-1-yl)-5-fluoro-1,4-dihydrophthalazine-2,3-dicarboxylate (1 g, 1.24 mmol, 1 eq) in DCM (10 mL) was added TFA (4.61 g, 40.39 mmol, 3.00 mL, 32.47 eq). The mixture was stirred at 25° C. for 1 hour under $N_2$. LCMS indicated the reaction was completed. The mixture was concentrated to give crude product. The residue was dissolved in water (20 mL), adjusted to pH-7 with saturated $NaHCO_3$, and then extracted with ethyl acetate (30 mL*3). The organic layers were combined, washed with water (100 mL), saturated brine (100 mL), dried over $Na_2SO_4$, filtered and concentrated to give 1-(5-fluoro-1, 2, 3, 4-tetrahydrophthalazin-6-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (600 mg, crude). LC-MS (ES+, m/z): 504.3 $[(M+H)^+]$. Rt=0.355 min.

Step 3: 1-((4S,7R)-2-(4-fluoro-3, 5-dimethylphenyl)-2, 4, 5, 6, 7, 8-hexahydro-4, 7-epiminocyclohepta [c]pyrazol-3-yl)-3-(5-fluorophthalazin-6-yl)-1, 3-dihydro-2H-imidazol-2-one

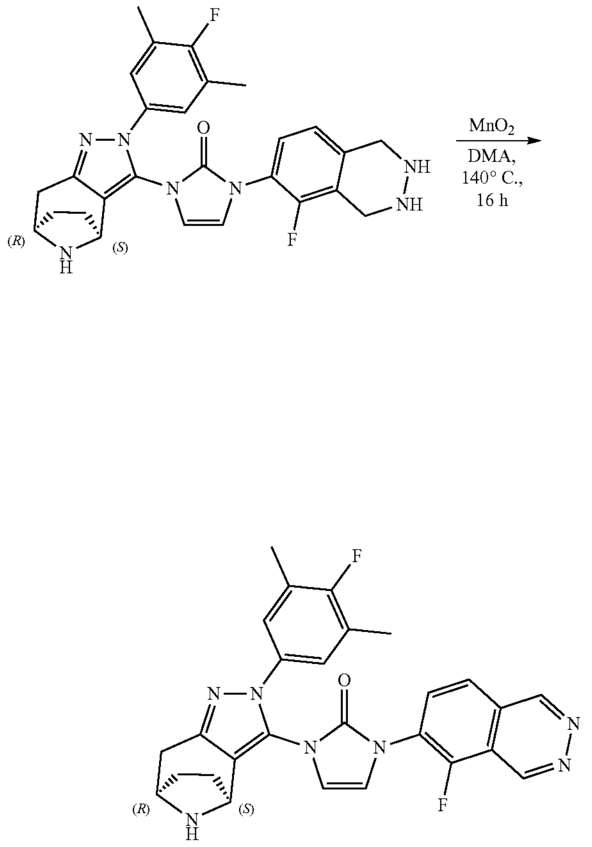

To a solution of 1-(5-fluoro-1, 2, 3, 4-tetrahydrophthalazin-6-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (600 mg, 1.19 mmol, 1 eq) in DMA (12 mL) was added $MnO_2$ (1.14 g, 13.11 mmol, 11 eq). The mixture was stirred at 140° C. for 16 hours under $N_2$. LCMS indicated that the reaction was completed. The reaction mixture was filtered. The filter liquor was added to $H_2O$ (30 mL), and then extracted with DCM (30 mL*3). The organic layers were combined, washed with water (100 mL), saturated brine (100 mL), dried over $Na_2SO_4$, filtered and concentrated to give crude product. The filtrate was purified by prep-HPLC column: Welch Xtimate C18 180*70 mm #10 um; mobile phase: [$H_2O$ (10 mM $NH_4HCO_3$)-ACN]; gradient: 10%-50% B over 17.0 min) to give 1-((4S,7R)-2-(4-fluoro-3, 5-dimethylphenyl)-2, 4, 5, 6, 7, 8-hexahydro-4, 7-epiminocyclohepta [c]pyrazol-3-yl)-3-(5-fluorophthalazin-6-yl)-1, 3-dihydro-2H-imidazol-2-one (30 mg, 44.26 μmol, 3.71% yield). $^1H$ NMR (400 MHz, DMSO-$d_6$) δ=8.92-8.78 (m, 1H), 8.14-7.92 (m, 1H), 7.88-7.55 (m, 2H), 4.50-4.26 (m, 2H), 3.99-3.87 (m, 2H), 3.47-3.37 (m, 2H), 3.07-2.91 (m, 1H), 2.17-1.56 (m, 7H), 1.42-1.11 (m, 6H) (the active N—H was not detected). LC-MS (ES+, m/z): 500.2 $[(M+H)^+]$. Rt=0.387 min.

Step 4: 3-((1S,2S)-1-(2-((4S,7R)-2-(4-fluoro-3, 5-dimethylphenyl)-3-(3-(5-fluorophthalazin-6-yl)-2-oxo-2, 3-dihydro-1H-imidazol-1-yl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one

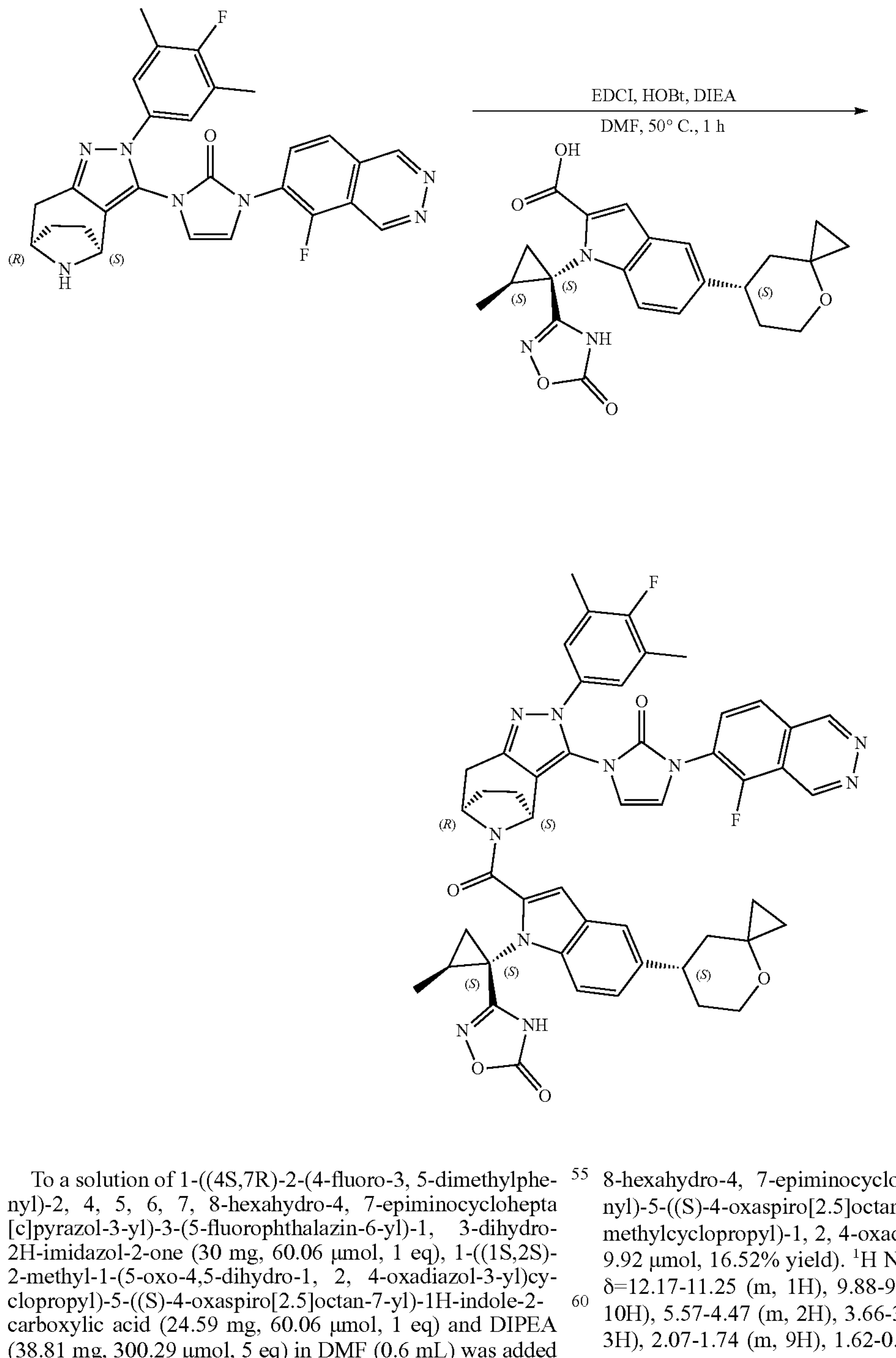

To a solution of 1-((4S,7R)-2-(4-fluoro-3, 5-dimethylphenyl)-2, 4, 5, 6, 7, 8-hexahydro-4, 7-epiminocyclohepta [c]pyrazol-3-yl)-3-(5-fluorophthalazin-6-yl)-1, 3-dihydro-2H-imidazol-2-one (30 mg, 60.06 μmol, 1 eq), 1-((1S,2S)-2-methyl-1-(5-oxo-4,5-dihydro-1, 2, 4-oxadiazol-3-yl)cyclopropyl)-5-((S)-4-oxaspiro[2.5]octan-7-yl)-1H-indole-2-carboxylic acid (24.59 mg, 60.06 μmol, 1 eq) and DIPEA (38.81 mg, 300.29 μmol, 5 eq) in DMF (0.6 mL) was added EDCI (14.97 mg, 78.08 μmol, 1.3 eq) and HOBt (12.17 mg, 90.09 μmol, 1.5 eq). The mixture was stirred at 50° C. for 1 hour under $N_2$. LCMS showed the reaction was completed. The mixture was filtered. The filtrate was purified by prep-HPLC column: Phenomenex Luna C18 75*30 mm*3 um; mobile phase: [$H_2O$ (0.1% TFA)-ACN]; gradient: 45%-75% B over 8.0 min. The filtrate was purified by prep-HPLC column: Waters Xbridge BEH C18 100*25 mm*10 um; mobile phase: [$H_2O$ (10 mM $NH_4HCO_3$)-ACN]; gradient: 15%-60% B over 8.0 min) to give 3-((1S,2S)-1-(2-((4S,7R)-2-(4-fluoro-3, 5-dimethylphenyl)-3-(3-(5-fluorophthalazin-6-yl)-2-oxo-2, 3-dihydro-1H-imidazol-1-yl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one (8.84 mg, 9.92 μmol, 16.52% yield). $^1$H NMR (400 MHz, DMSO-$d_6$) δ=12.17-11.25 (m, 1H), 9.88-9.29 (m, 2H), 8.14-6.39 (m, 10H), 5.57-4.47 (m, 2H), 3.66-3.20 (m, 2H), 3.05-2.45 (m, 3H), 2.07-1.74 (m, 9H), 1.62-0.70 (m, 11H), 0.56-0.01 (m, 4H). LC-MS (ES+, m/z): 891.4 [(M+H)$^+$]; Rt=2.804 min. HRMS (EI): m/z [M+H]$^+$ found: 891.3561.

The additional compounds are prepared or can be prepared by following synthetic methods given herein; and using the appropriate starting materials and reagents.

Example 83a Compound 414
3-((1S,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5(4H)-one
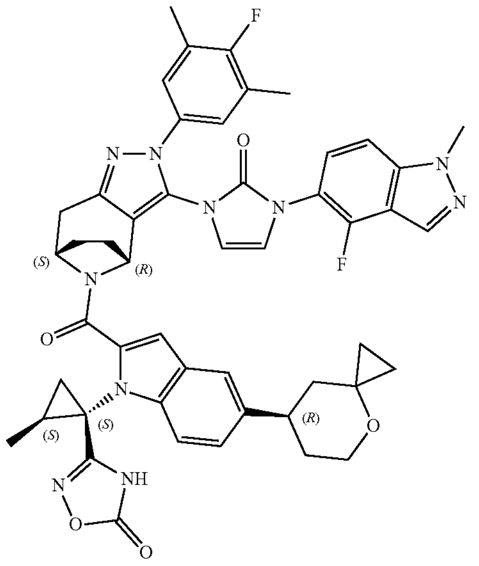
Scheme 414
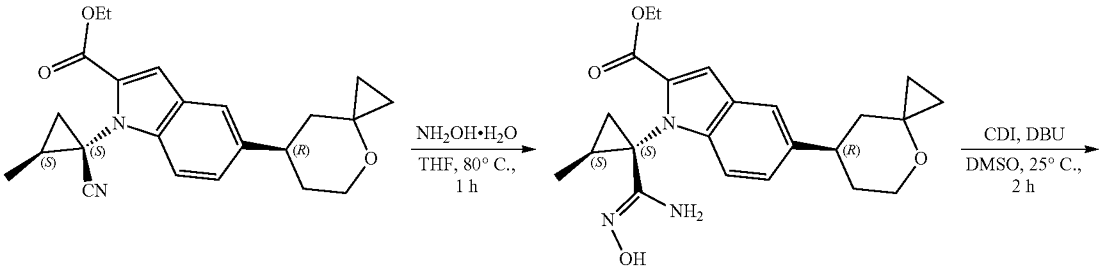
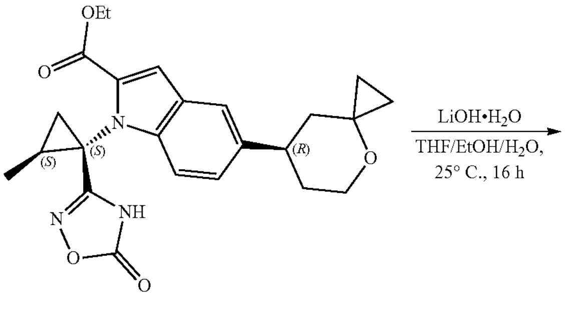

-continued
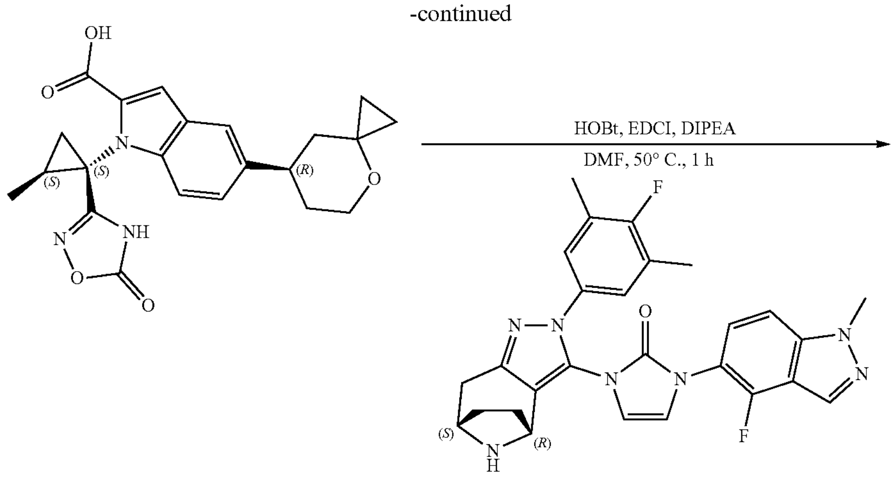
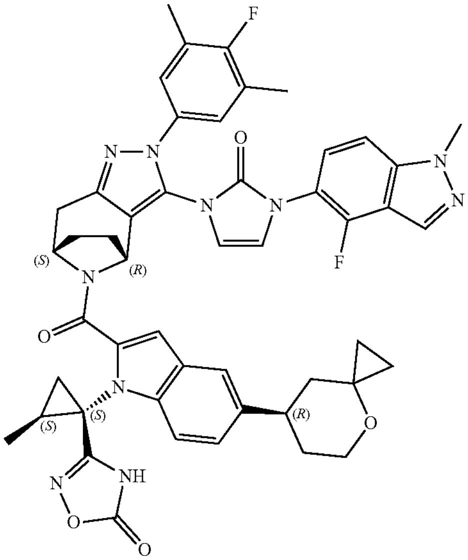
Step 1: ethyl 1-((1S,2S)-1-(N'-hydroxycarbamimidoyl)-2-methylcyclopropyl)-5-((R)-4-oxaspiro[2.5]octan-7-yl)-1H-indole-2-carboxylate
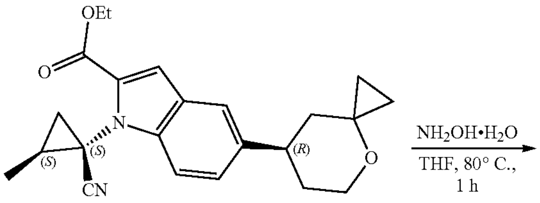
-continued
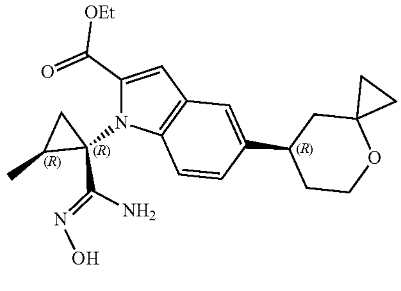

To a solution of ethyl 1-((1S,2S)-1-cyano-2-methylcyclopropyl)-5-((R)-4-oxaspiro[2.5]octan-7-yl)-1H-indole-2-carboxylate (1.9 g, 4.97 mmol, 1 eq) in THF (20 mL) was added hydroxylamine (3.28 g, 49.70 mmol, 50% purity, 10 eq). The mixture was stirred at 80° C. for 1 hour. LCMS showed the reaction was completed. The reaction mixture was poured into water (50 mL), then extracted with ethyl acetate (30 mL*3). The combined organic layers were washed with saturated brine (30 mL*1), dried over anhydrous $Na_2SO_4$, filtered and concentrated under reduced pressure to give ethyl 1-((1S,2S)-1-(N'-hydroxycarbamimidoyl)-2-methylcyclopropyl)-5-((R)-4-oxaspiro[2.5]octan-7-yl)-1H-indole-2-carboxylate (1.5 g, 3.28 mmol, 66.01% yield). LC-MS (ES+, m/z): 412.2 $[(M+H)^+]$; Rt=0.464 min.

Step 2: ethyl 1-((1S,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylate

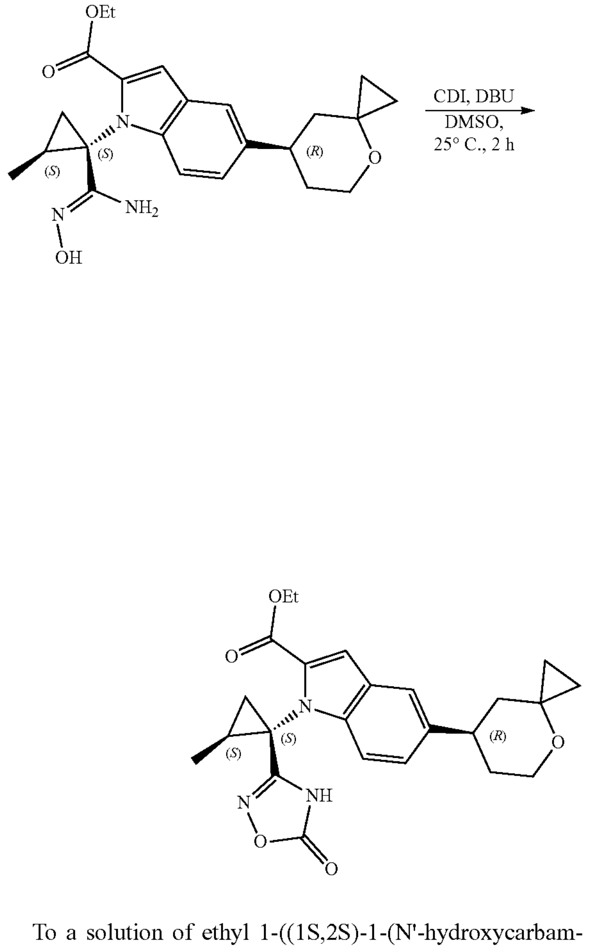

To a solution of ethyl 1-((1S,2S)-1-(N'-hydroxycarbamimidoyl)-2-methylcyclopropyl)-5-((R)-4-oxaspiro[2.5]octan-7-yl)-1H-indole-2-carboxylate (1.5 g, 3.14 mmol, 1 eq) in DMSO (15 mL) was added DBU (1.19 g, 7.85 mmol, 1.18 mL, 2.5 eq) and CDI (1.02 g, 6.28 mmol, 2 eq). The mixture was stirred at 25° C. for 2 hours. LCMS showed the reaction was completed. The reaction mixture was poured into water (150 mL), then extracted with ethyl acetate (80 mL*3). The combined organic layers were washed with saturated brine (80 mL), dried over anhydrous $Na_2SO_4$, filtered and concentrated under reduced pressure. The residue was purified by column chromatography ($SiO_2$, Petroleum ether/ethyl acetate=3:1) to give ethyl 1-((1S,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylate (1 g, 1.92 mmol, 61.03% yield). LC-MS (ES+, m/z): 438.1 $[(M+H)^+]$; Rt=0.569 min.

Step 3: 1-((1S,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid

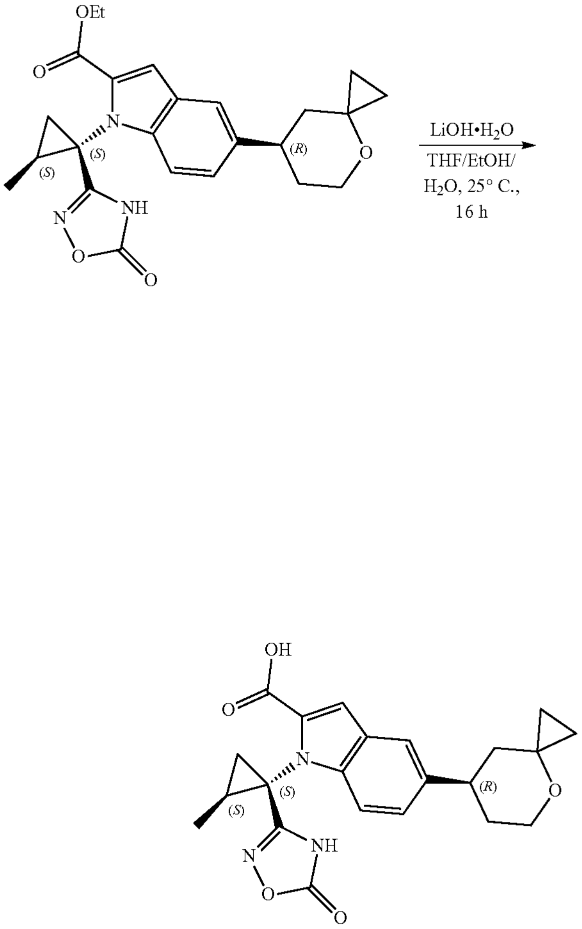

To a solution of ethyl 1-((1S,2S)-2-methyl-1-(5-oxo-4,5-dihydro-1,2,4-oxadiazol-3-yl) cyclopropyl)-5-((R)-4-oxaspiro[2.5]octan-7-yl)-1H-indole-2-carboxylate (1 g, 1.87 mmol, 1 eq) in THF (4 mL) and $H_2O$ (4 mL), EtOH (4 mL) was added LiOH·$H_2O$ (784.56 mg, 18.70 mmol, 10 eq). The mixture was stirred at 25° C. for 16 hours. LCMS showed the reaction was completed. The reaction mixture was poured into water (50 mL) and adjust to pH=3 for HCl (2 M), then extracted with ethyl acetate (30 mL*3). The combined organic layers were washed with saturated brine (30 mL), dried over anhydrous $Na_2SO_4$, filtered and concentrated under reduced pressure to give 1-((1S,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid (600 mg, crude). LC-MS (ES+, m/z): 410.3 $[(M+H)^+]$; Rt=1.584 min.

Step 4: 3-((1S,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-5-((R)-4-oxaspiro[2.5]octan-7-yl)-1H-indol-1-yl)-2-methylcyclopropyl)-1,2,4-oxadiazol-5(4H)-one

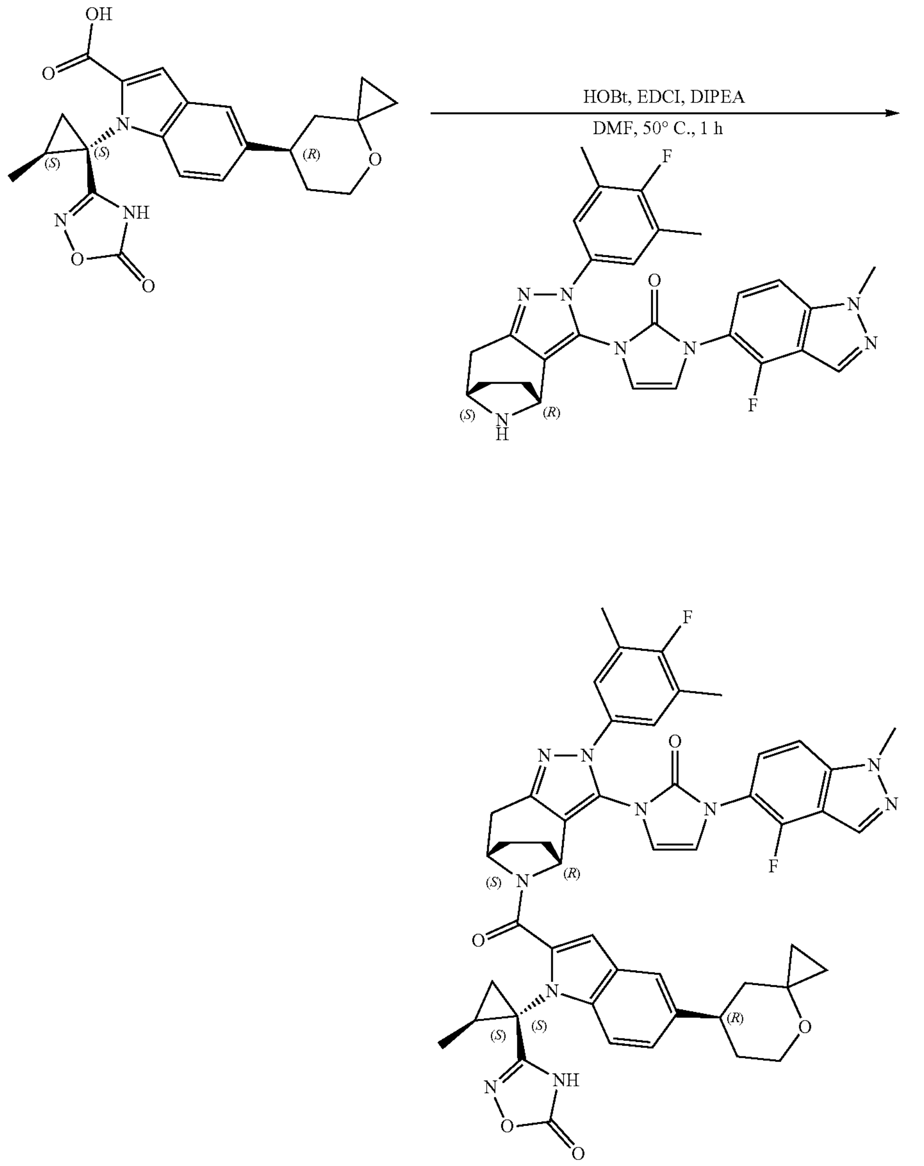

To a solution of 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (150 mg, 281.14 μmol, 1 eq) and 1-((1S,2S)-2-methyl-1-(5-oxo-4,5-dihydro-1,2,4-oxadiazol-3-yl) cyclopropyl)-5-((R)-4-oxaspiro[2.5]octan-7-yl)-1H-indole-2-carboxylic acid (139.86 mg, 281.14 μmol, 1 eq) in DMF (2 mL) was added EDCI (80.84 mg, 421.71 μmol, 1.5 eq), DIEA (181.67 mg, 1.41 mmol, 244.84 μL, 5 eq), and HOBt (56.98 mg, 421.71 μmol, 1.5 eq). The mixture was stirred at 50° C. for 1 hour under $N_2$ atmosphere. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (column: Phenomenex luna C18 250*50 mm*15 um; mobile phase: [$H_2O$ (0.1% TFA)-ACN]; gradient: 55%-85% B over 10.0 min) to give 3-((1S,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro [2.5]octan-7-yl)-1H-indol-1-yl)-2-methylcyclopropyl)-1,2,4-oxadiazol-5 (4H)-one (83.23 mg, 67.19 μmol, 23.90% yield). $^1$H NMR (400 MHz, DMSO-$d_6$) δ=12.23-11.68 (m, 1H), 8.31 (s, 1H), 7.73-6.69 (m, 10H), 5.54-5.24 (m, 2H), 4.15-4.01 (m, 3H), 3.86-3.24 (m, 3H), 3.06-2.77 (m, 2H), 2.36-2.06 (m, 9H), 2.00-1.00 (m, 11H), 0.81-0.24 (m, 4H). LC-MS (ES+, m/z): 893.3 [$(M+H)^+$]; Rt=3.054 min. HRMS (EI): m/z $[M+H]^+$ found: 893.3716.

Example 84 Compound 501
3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-2,4,5,6,7,8-hexahydropyrazolo[4,3-c]azepine-5-carbonyl)-5-((S)-2,2-dimethyltetrahydro-2H-pyran-4-yl)-1H-indol-1-yl)-2-methylcyclopropyl)-1,2,4-oxadiazol-5(4H)-one
Scheme 501
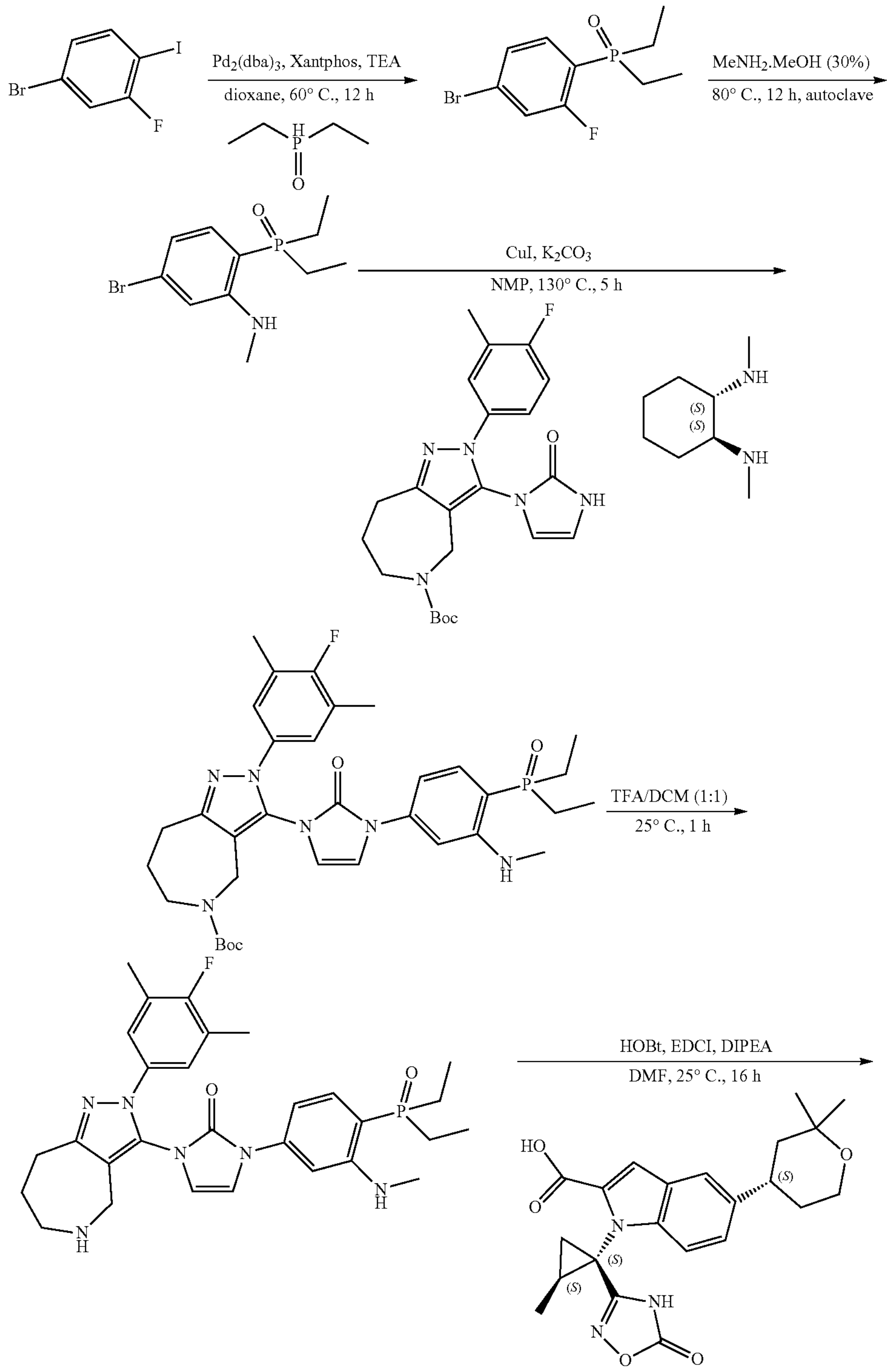

-continued

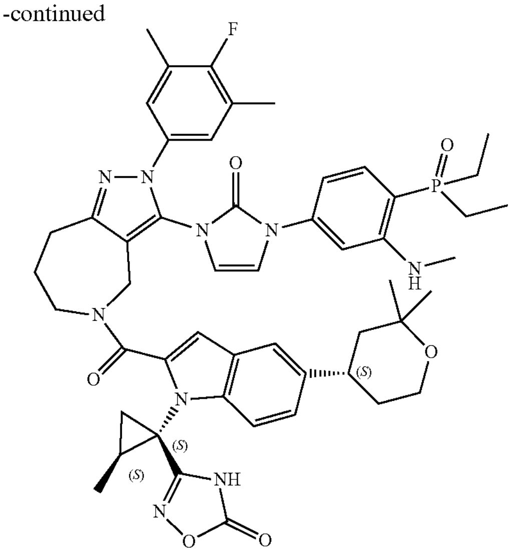

Step 1: (4-bromo-2-fluorophenyl) diethylphosphine oxide

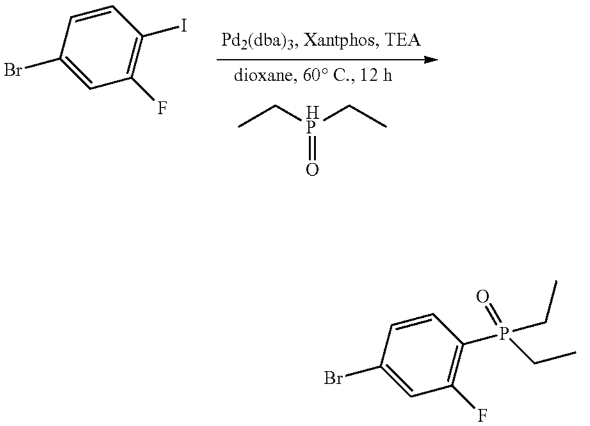

To a solution of 4-bromo-2-fluoro-1-iodobenzene (5 g, 16.62 mmol, 1 eq) and diethylphosphine oxide (1.94 g, 18.26 mmol, 1.10 eq) in dioxane (100 mL) was added Xantphos (961.50 mg, 1.66 mmol, 0.1 eq), TEA (3.25 g, 32.07 mmol, 4.46 mL, 1.93 eq) and $Pd_2(dba)_3$ (760.83 mg, 830.86 μmol, 0.05 eq). The mixture was stirred at 60° C. for 12 hours under $N_2$ atmosphere. LCMS indicated the reaction was completed. The residue was poured into saturated EDTA solution (120 mL) and ethyl acetate (150 mL) stirred for 0.5 hour, and then extracted with ethyl acetate (150 mL*2). The organic layers were combined and washed with water (100 mL*2), saturated brine (100 mL*2), dried over $Na_2SO_4$, filtered, concentrated in vacuo. The residue was purified by column chromatography ($SiO_2$, Petroleum ether/ethyl acetate=1/1 to DCM:MeOH=10:1) to afford (4-bromo-2-fluorophenyl) diethylphosphine oxide (4.3 g, 14.96 mmol, 90.03% yield). $^1H$ NMR (400 MHz, DMSO-$d_6$) δ=7.77-7.59 (m, 3H), 2.06-1.96 (m, 2H), 1.92-1.78 (m, 2H), 1.03-0.83 (m, 6H). LC-MS (ES+, m/z): 279.1 [$(M+H)^+$]. Rt=0.400 min.

Step 2: (4-bromo-2-(methylamino)phenyl) diethylphosphine oxide

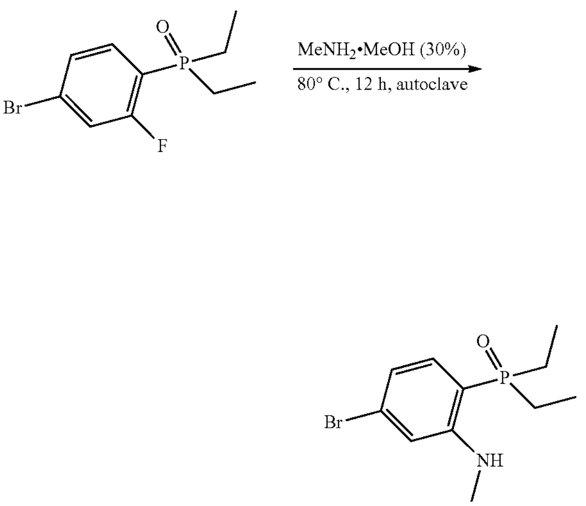

A solution of (4-bromo-2-fluorophenyl) diethylphosphine oxide (500 mg, 1.79 mmol, 1 eq) in $MeNH_2$ (4.12 g, 39.80 mmol, 5 mL, 22.21 eq) was stirred under 15 Psi at 80° C. for 12 hours in 30 mL of autoclave (2 batches reaction). LCMS indicated the reaction was completed. The mixture was added dropwise to $NH_4Cl$ (20 mL), and then extracted with ethyl acetate (30 mL*3). The organic layers were combined, washed with water (40 mL), saturated brine (30 mL), dried over $Na_2SO_4$, filtered and concentrated in vacuo to give crude product. The residue was purified by column chromatography ($SiO_2$, Petroleum ether/Ethyl acetate=50/1 to 1/1) to provide (4-bromo-2-(methylamino)phenyl) diethylphosphine oxide (419 mg, 1.42 mmol, 79.08% yield). $^1H$ NMR (400 MHz, DMSO-$d_6$) δ=7.84-7.68 (m, 1H), 7.18-7.05 (m, 1H), 6.79-6.65 (m, 2H), 2.76-2.66 (m, 3H), 1.98-1.83 (m, 4H), 1.06-0.89 (m, 6H). LC-MS (ES+, m/z): 290.1 [$(M+H)^+$]. Rt=0.482 min.

Step 3: tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-2,6,7,8-tetrahydropyrazolo[4,3-c]azepine-5 (4H)-carboxylate

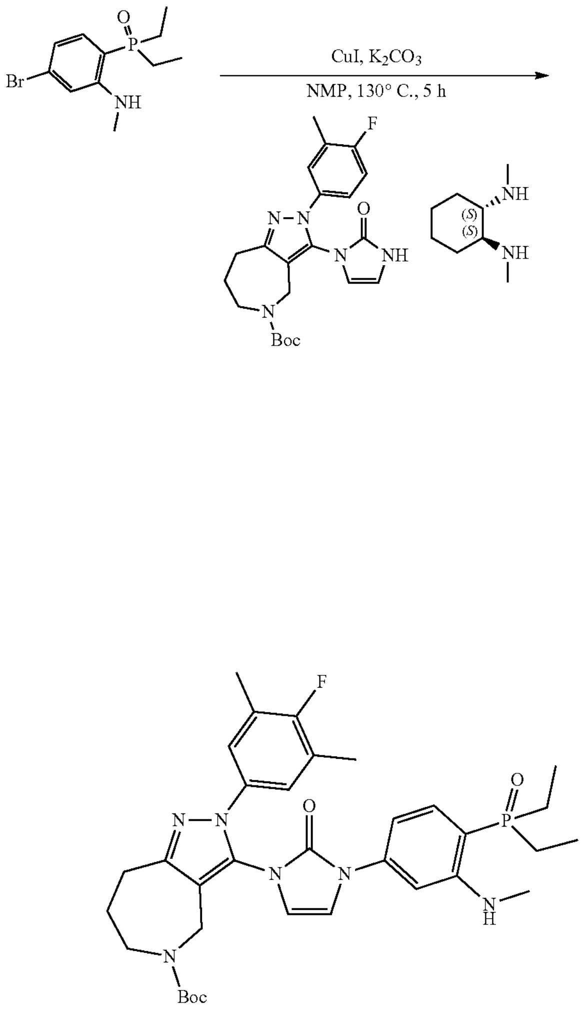

To a solution of tert-butyl 2-(4-fluoro-3-methylphenyl)-3-(2-oxo-2,3-dihydro-1H-imidazol-1-yl)-2,6,7,8-tetrahydropyrazolo[4,3-c]azepine-5 (4H)-carboxylate (200 mg, 453.00 μmol, 1 eq) and (4-bromo-2-(methylamino)phenyl) diethylphosphine oxide (262.87 mg, 906.01 μmol, 2 eq) in NMP (2 mL) was added $K_2CO_3$ (250.44 mg, 1.81 mmol, 4 eq), (1S,2S)—$N^1$,$N^2$-dimethylcyclohexane-1,2-diamine (96.65 mg, 679.51 μmol, 1.5 eq) and CuI (172.55 mg, 906.01 μmol, 2 eq). The mixture was stirred at 130° C. for 5 hours under $N_2$. LCMS indicated the reaction was completed. The residue was poured into saturated EDTA solution (10 mL) and ethyl acetate (15 mL) stirred for 0.5 hour, and then extracted with ethyl acetate (10 mL*2). The organic layers were combined and washed with water (10 mL*2), saturated brine (10 mL*2), dried over $Na_2SO_4$, filtered, concentrated in vacuo. The residue was purified by prep-TLC ($SiO_2$, Petroleum ether/Ethyl acetate-0:1) to provide tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-2,6,7,8-tetrahydropyrazolo[4,3-c]azepine-5 (4H)-carboxylate (200 mg, 287.07 μmol, 63.37% yield). LC-MS (ES+, m/z): 651.4 [(M+H)$^+$]. Rt=0.579 min.

Step 4: 1-(4-(diethylphosphoryl)-3-(methylamino)phenyl)-3-(2-(4-fluoro-3,5-dimethylphenyl)-2,4,5,6,7,8-hexahydropyrazolo[4,3-c]azepin-3-yl)-1,3-dihydro-2H-imidazol-2-one

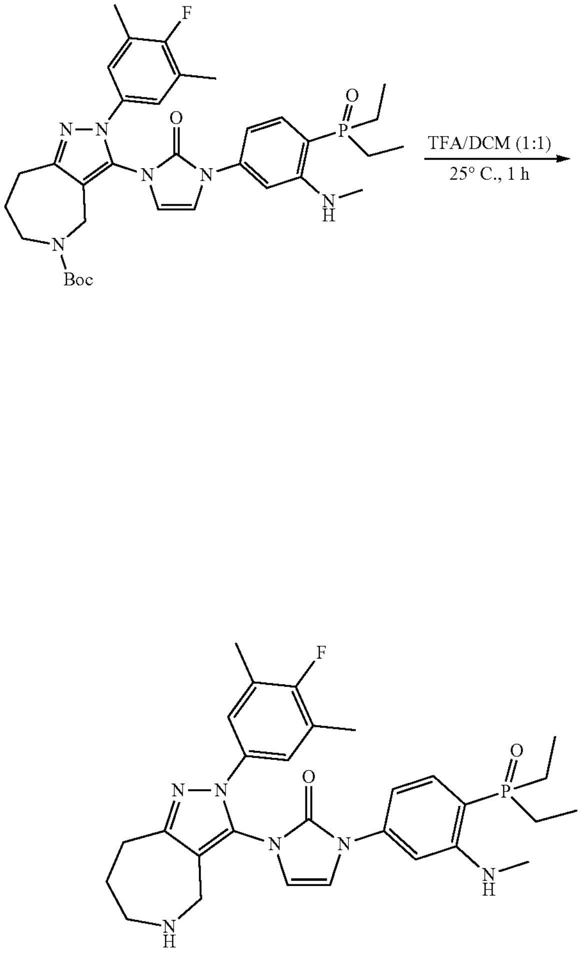

To a solution of tert-butyl 3-(3-(4-(diethylphosphoryl)-3-(methylamino)phenyl)-2-oxo-2,3-dihydro-1H-imidazol-1-yl)-2-(4-fluoro-3,5-dimethylphenyl)-2,6,7,8-tetrahydropyrazolo[4,3-c]azepine-5(4H)-carboxylate (200 mg, 307.35 μmol, 1 eq) in DCM (1 mL) was added TFA (1.54 g, 13.46 mmol, 1.00 mL, 43.80 eq). The mixture was stirred at 25° C. for 1 hour under $N_2$. LCMS indicated the reaction was completed. The reaction mixture was removed TFA and DCM and adjusted to pH=7 with saturated $NaHCO_3$ (10 mL), and then extracted with DCM (10 mL*3). The organic layers were combined and washed with water (10 mL*2), saturated brine (10 mL*2), dried over $Na_2SO_4$, filtered, concentrated in vacuo to provide 1-(4-(diethylphosphoryl)-3-(methylamino)phenyl)-3-(2-(4-fluoro-3,5-dimethylphenyl)-2,4,5,6,7,8-hexahydropyrazolo[4,3-c]azepin-3-yl)-1,3-dihydro-2H-imidazol-2-one (168 mg, crude). LC-MS (ES+, m/z): 551.3 [(M+H)$^+$]. Rt=0.420 min.

Step 5: 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-2,4,5,6,7,8-hexahydropyrazolo[4,3-c]azepine-5-carbonyl)-5-((S)-2,2-dimethyltetrahydro-2H-pyran-4-yl)-1H-indol-1-yl)-2-methylcyclopropyl)-1,2,4-oxadiazol-5 (4H)-one

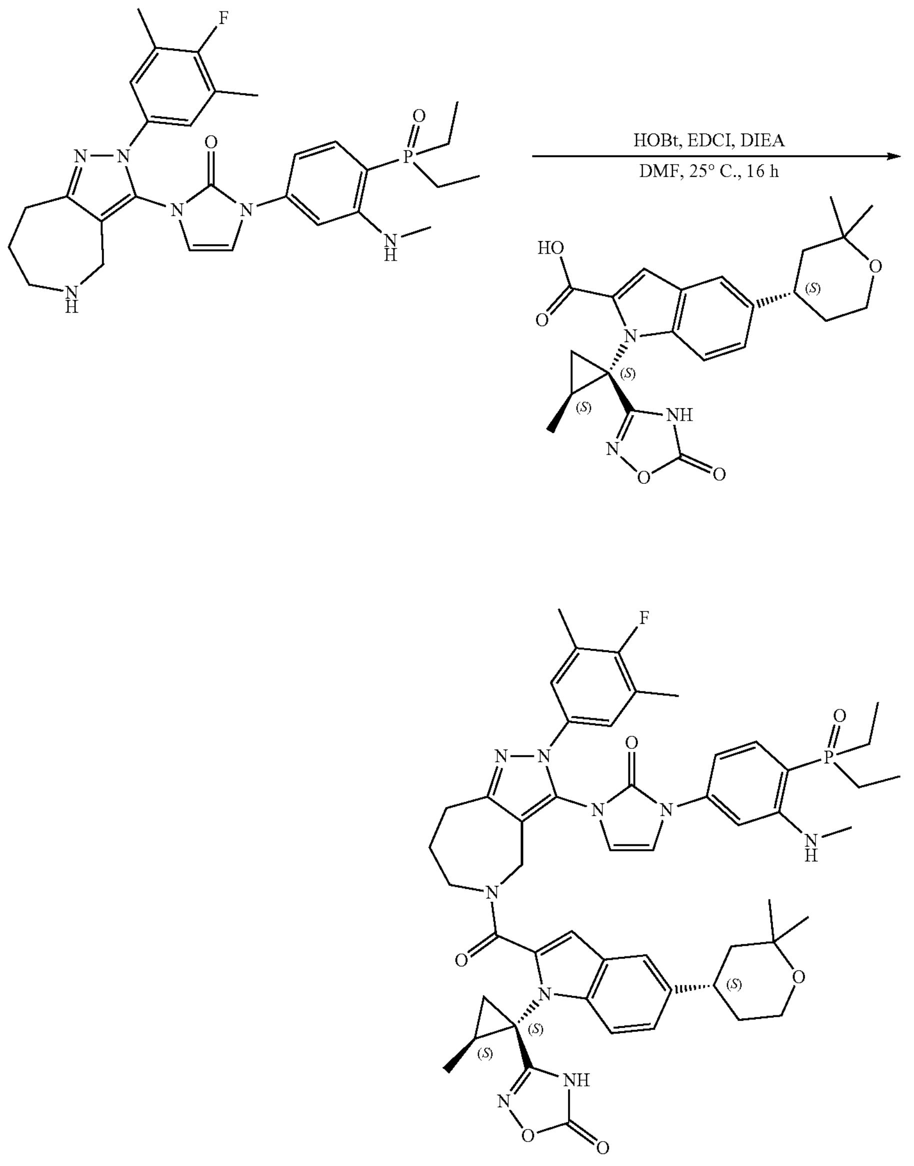

To a solution of 1-(4-(diethylphosphoryl)-3-(methylamino)phenyl)-3-(2-(4-fluoro-3,5-dimethylphenyl)-2,4,5,6,7,8-hexahydropyrazolo[4,3-c]azepin-3-yl)-1,3-dihydro-2H-imidazol-2-one (48.18 mg, 87.50 μmol, 1.2 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (30 mg, 72.91 μmol, 1 eq) in DMF (0.6 mL) was added DIEA (47.12 mg, 364.56 μmol, 63.50 μL, 5 eq), EDCI (18.17 mg, 94.79 μmol, 1.3 eq) and HOBt (14.78 mg, 109.37 μmol, 1.5 eq). The mixture was stirred at 25° C. for 16 hours under $N_2$. LCMS indicated the reaction was completed. The mixture was added dropwise to $H_2O$ (10 mL), and then extracted with ethyl acetate (20 mL*3). The organic layers were combined, washed with water (20 mL), saturated brine (20 mL), dried over $Na_2SO_4$, filtered and concentrated in vacuo to give crude product. The residue was purified by prep-HPLC (column: Phenomenex Luna C18 75*30 mm*3 um; mobile phase: [$H_2O$ (0.1% TFA)-ACN]; gradient: 50%-80% B over 8.0 min) to provide 3-((1S,2S)-1-(2-(3-(3-(4-(diethylphosphoryl)-3-(methylamino)phenyl)-2-oxo-2,3-dihydro-1H-imidazol-1-yl)-2-(4-fluoro-3,5-dimethylphenyl)-2,4,5,6,7,8-hexahydropyrazolo[4,3-c]azepine-5-carbonyl)-5-((S)-2,2-dimethyltetrahydro-2H-pyran-4-yl)-1H-indol-1-yl)-2-methylcyclopropyl)-1,2,4-oxadiazol-5 (4H)-one (19.06 mg, 20.13 μmol, 27.61% yield). $^1$H NMR (400 MHz, DMSO-$d_6$) δ=12.27-11.52 (m, 1H), 7.83-6.02 (m, 12H), 4.95-4.55 (m, 2H), 4.26-4.06 (m, 2H), 3.71-3.60 (m, 2H), 3.07-2.94 (m, 2H), 2.91-2.76 (m, 1H), 2.73-2.65 (m, 3H), 2.25-2.10 (m, 6H), 2.07-1.83 (m, 6H), 1.76-0.79 (m, 22H). $^1$H NMR (400 MHz, MeOD-$d_4$) δ=7.63-5.85 (m, 11H), 5.35-5.05 (m, 1H), 4.70-4.54 (m, 1H), 4.46-4.16 (m, 1H), 4.01-3.64 (m, 3H), 3.13 (td, J=1.7, 3.3 Hz, 2H), 3.02-2.71 (m, 4H), 2.27-2.17 (m, 6H), 2.16-1.94 (m, 6H), 1.78-0.93 (m, 22H). LC-MS (ES+, m/z): 944.4 [$(M+H)^+$]; Rt=3.005 min. HRMS (EI): m/z $[M+H]^+$ found: 944.4358.
Example 85 Compound 503
3-((1S,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one
Scheme 503
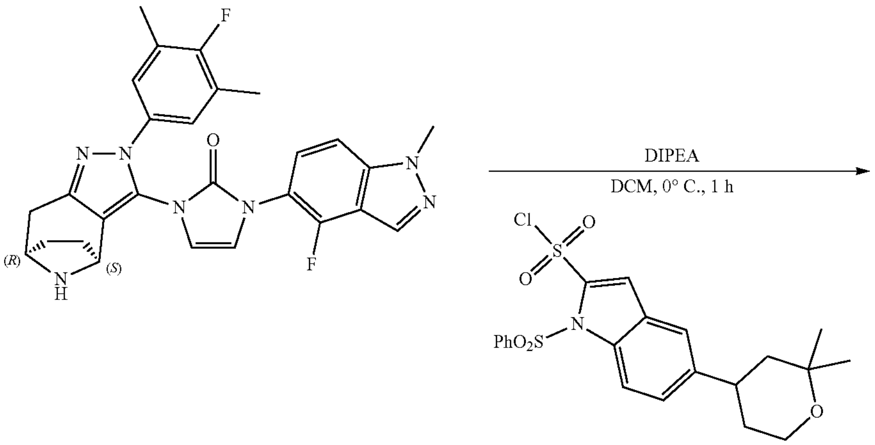
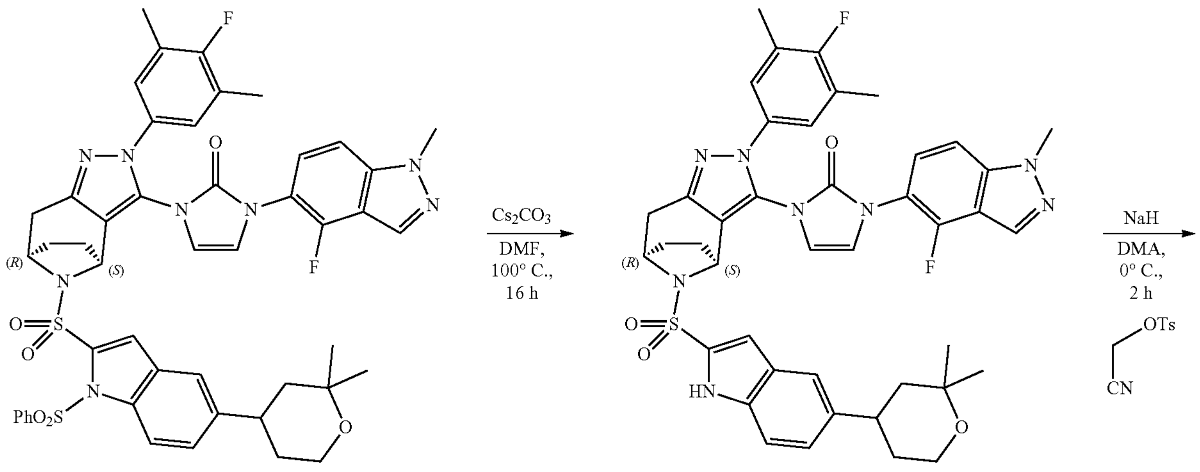

-continued
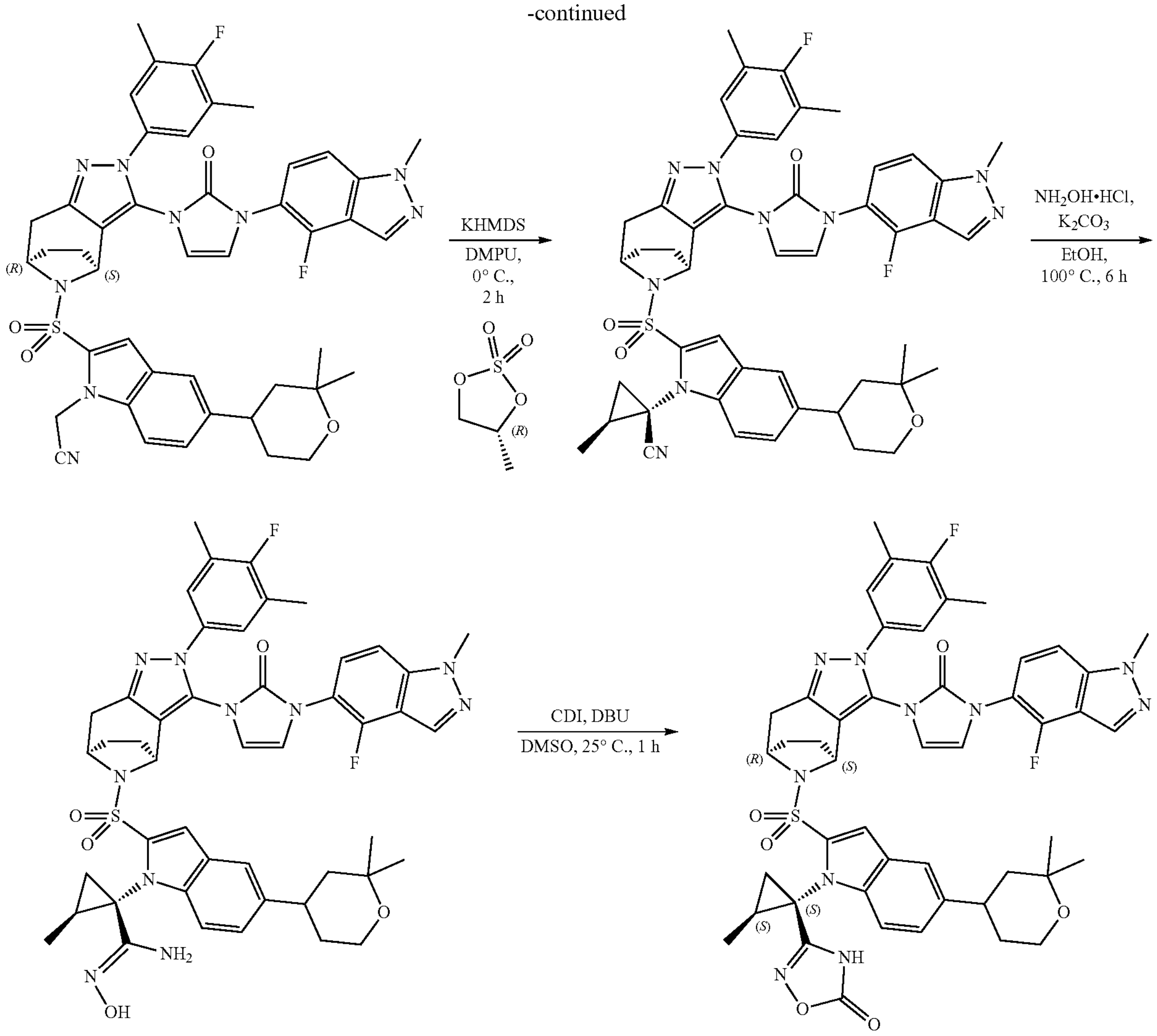
Step 1: 1-((4S,7R)-9-((5-(2, 2-dimethyltetrahydro-2H-pyran-4-yl)-1-(phenylsulfonyl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one
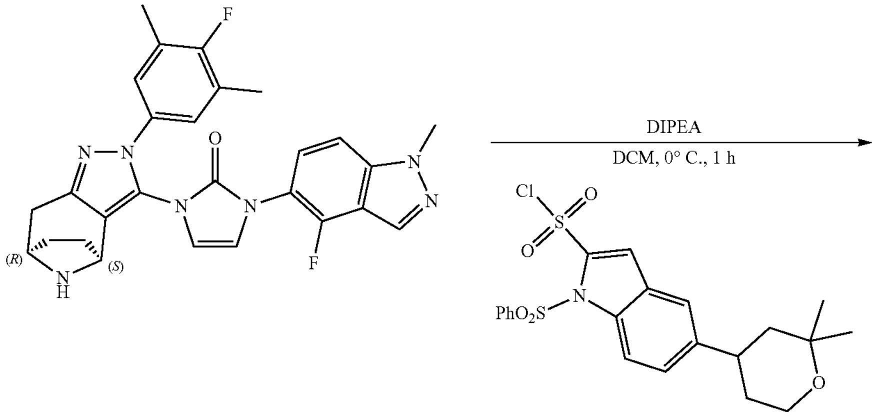

-continued

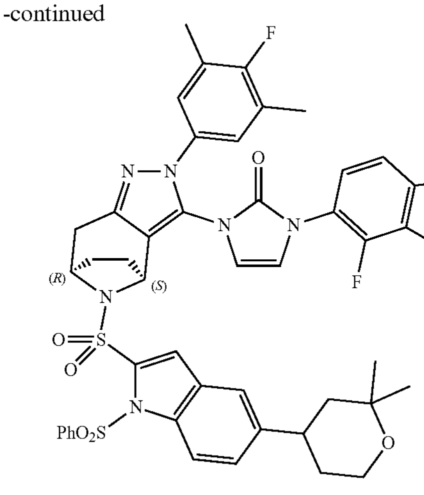

To a solution of 5-(2, 2-dimethyltetrahydro-2H-pyran-4-yl)-1-(phenylsulfonyl)-1H-indole-2-sulfonyl chloride (3.4 g, 7.27 mmol, 1 eq) and 1-(4-fluoro-1-methyl-1H-indazol-5-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (3.64 g, 7.27 mmol, 1 eq) in DCM (34 mL) was added DIPEA (2.82 g, 21.80 mmol, 3 eq) at 0° C. under $N_2$. The mixture was stirred at 0° C. for 1 hour under $N_2$. LCMS showed the reaction was completed. The mixture was added dropwise to $H_2O$ (50 mL) and then extracted with DCM (50 mL*3). The organic layers were combined, washed with water (150 mL), saturated brine (150 mL), dried over $Na_2SO_4$, filtered and concentrated in vacuo. The crude product was purified by chromatography on silica gel (hexanes: Ethyl acetate=3/1-1/2) to give 1-((4S, 7R)-9-((5-(2, 2-dimethyltetrahydro-2H-pyran-4-yl)-1-(phenylsulfonyl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (2.6 g, 2.62 mmol, 36.13% yield). LC-MS (ES+, m/z): 933.3 [(M+H)$^+$]; Rt=0.679 min.

Step 2: 1-((4S,7R)-9-((5-(2, 2-dimethyltetrahydro-2H-pyran-4-yl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one

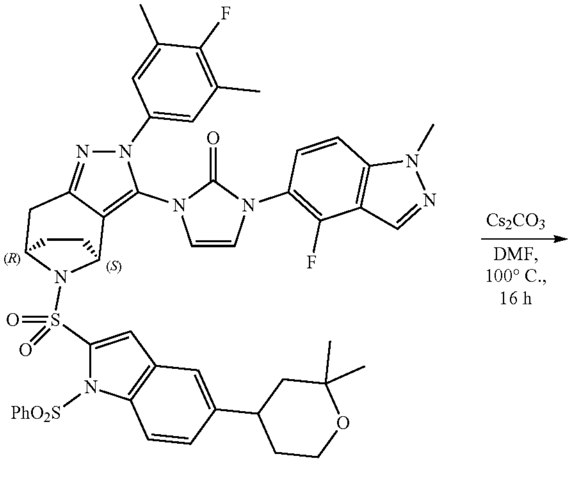

-continued

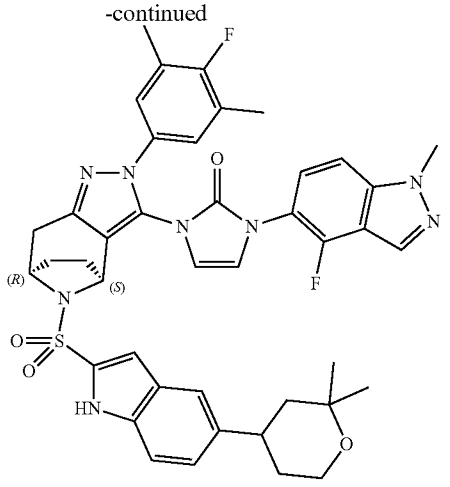

To a solution of 1-((4S,7R)-9-((5-(2, 2-dimethyltetrahydro-2H-pyran-4-yl)-1-(phenylsulfonyl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (2.3 g, 2.47 mmol, 1 eq) in DMF (23 mL) was added $Cs_2CO_3$ (4.02 g, 12.33 mmol, 5 eq). The mixture was stirred at 100° C. for 16 hours under $N_2$. LCMS showed the reaction was completed. The mixture was added dropwise to $H_2O$ (50 mL), and then extracted with DCM (50 mL*3). The organic layers were combined, washed with water (150 mL), saturated brine (150 mL), dried over $Na_2SO_4$, filtered and concentrated in vacuo. The crude product was purified by chromatography on silica gel (hexanes: Ethyl acetate=2/1-1/2) to give 1-((4S,7R)-9-((5-(2, 2-dimethyltetrahydro-2H-pyran-4-yl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (850 mg, 923.01 μmol, 37.44% yield). LC-MS (ES+, m/z): 793.3 [(M+H)$^+$]; Rt=0.634 min.

Step 3: 2-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl) acetonitrile

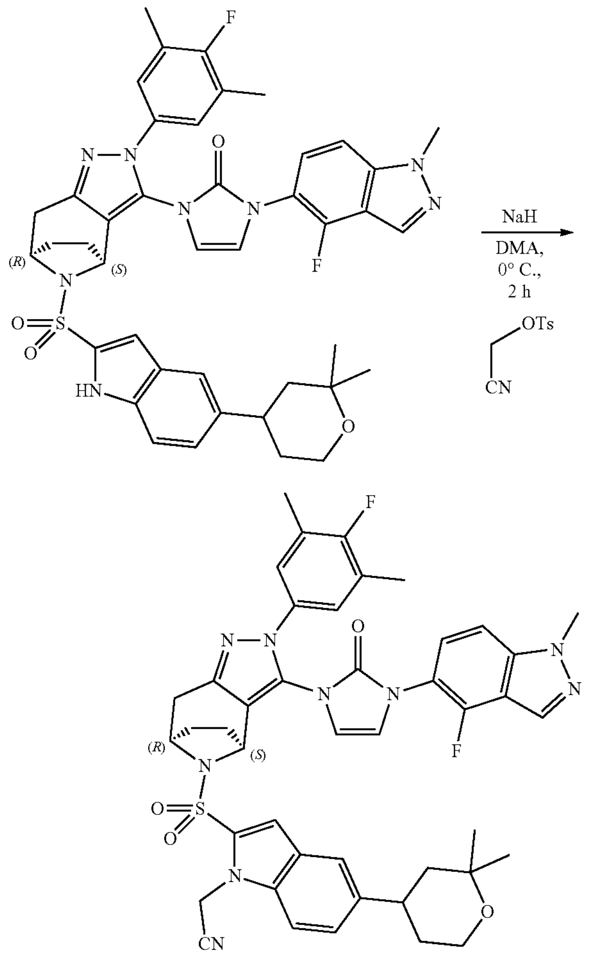

To a solution of 1-((4S,7R)-9-((5-(2, 2-dimethyltetrahydro-2H-pyran-4-yl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (600 mg, 756.72 μmol, 1 eq) in DMF (6 mL) was added NaH (151.33 mg, 3.78 mmol, 60% purity, 5 eq) at 0° C. under $N_2$. The mixture was stirred at 0° C. for 1 hour. Cyanomethyl 4-methylbenzenesulfonate (479.54 mg, 2.27 mmol, 3 eq) was then added. The mixture was stirred at 0° C. for 1 hour under $N_2$. LCMS showed the reaction was completed. The mixture was added dropwise to $H_2O$ (20 mL), and then extracted with DCM (20 mL*3). The organic layers were combined, washed with water (50 mL), saturated brine (50 mL), dried over $Na_2SO_4$, filtered and concentrated in vacuo. The residue was purified by prep-TLC ($SiO_2$, hexanes/Ethyl acetate=1/5) to give 2-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl) acetonitrile (350 mg, 381.58 μmol, 50.43% yield). LC-MS (ES+, m/z): 832.3 [$(M+H)^+$]; Rt=0.636 min.

Step 4: (1R,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile and (1S,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile

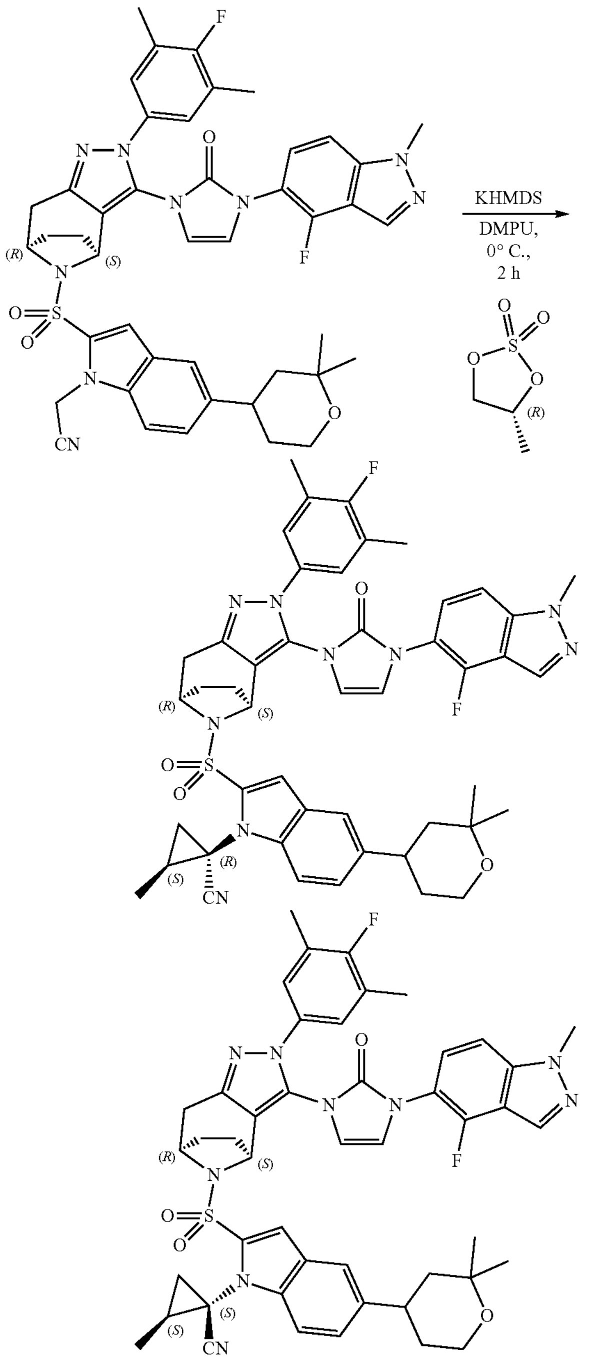

To a solution of 2-(5-(2, 2-dimethyltetrahydro-2H-pyran-4-yl)-2-(((4S,7R)-3-(3-(4-fluoro-1-methyl-1H-indazol-5- yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl) acetonitrile (150 mg, 163.54 μmol, 1 eq) and (R)-4-methyl-1, 3, 2-dioxathiolane 2, 2-dioxide (67.77 mg, 490.61 μmol, 3 eq) in DMPU (3 mL) was added KHMDS (1 M, 654.14 μL, 4 eq) at 0° C. under $N_2$. The mixture was stirred at 0° C. for 2 hours under $N_2$. LCMS showed the reaction was completed. The mixture was added dropwise to $NH_4Cl$ (10 mL), and then extracted with ethyl acetate (10 mL*3). The organic layers were combined, washed with water (30 mL), saturated brine (30 mL), dried over $Na_2SO_4$, filtered and concentrated in vacuo to give crude product. The crude product was purified by prep-TLC ($SiO_2$, hexanes:Ethyl acetate=1:5) to give a mixture of (1R,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile and (IS, 2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile (70 mg, 61.01 μmol, 37.31% yield). LC-MS (ES+, m/z): 872.3 $[(M+H)^+]$; Rt=0.680 min.

Step 5: (1R,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide and (1S,2S)-1-(5-(2, 2-dimethyltetrahydro-2H-pyran-4-yl)-2-(((4S, 7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide

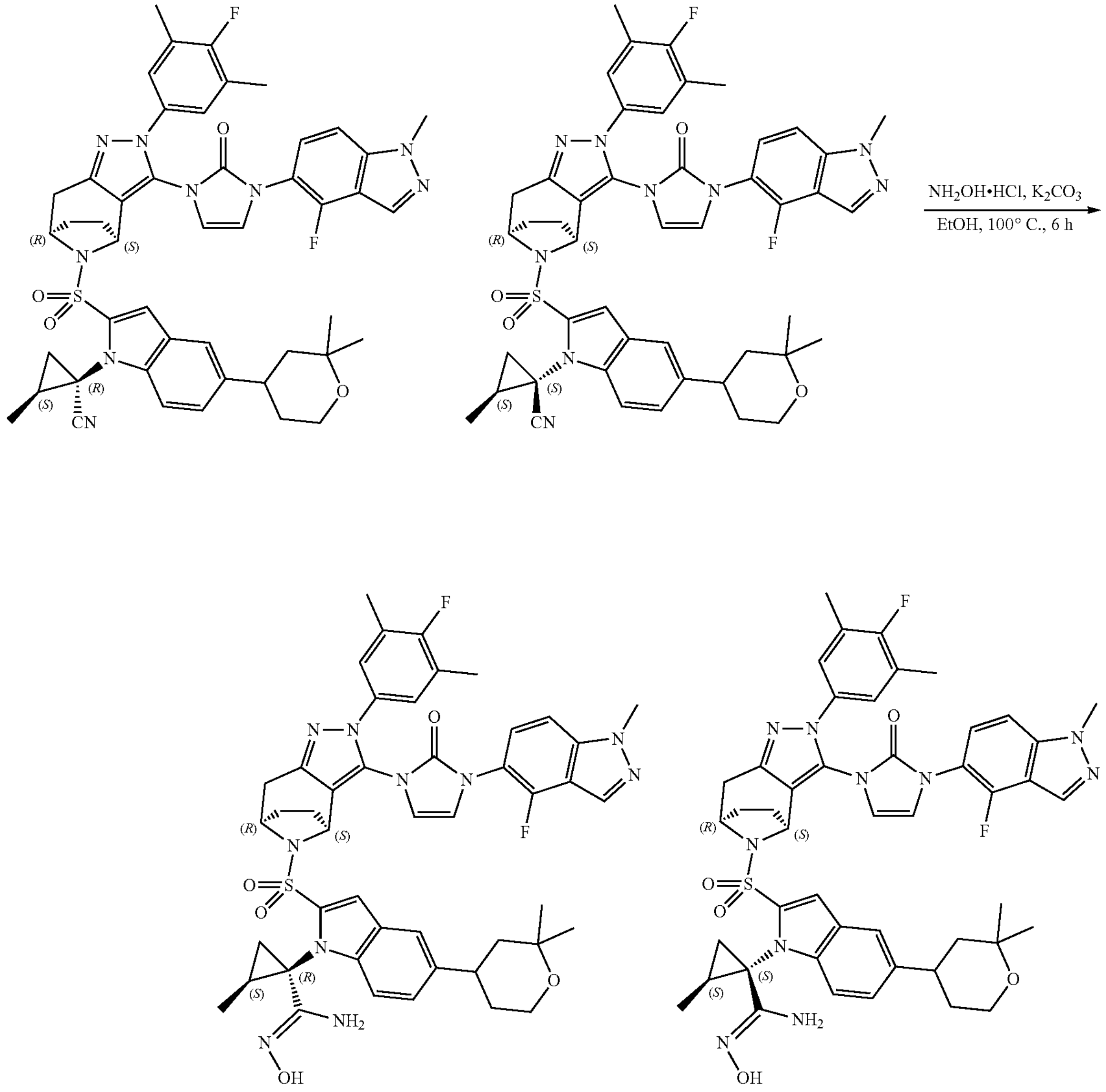

To a solution of (1R,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile and (1S,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile (70 mg, 61.01 μmol, 1 eq) in EtOH (1.4 mL) was added $NH_2OH{\cdot}HCl$ (21.20 mg, 305.05 μmol, 5 eq) and $K_2CO_3$ (46.38 mg, 335.55 μmol, 5.5 eq). The mixture was stirred at 100° C. for 6 hours under $N_2$. LCMS showed the reaction was completed. The mixture was added dropwise to $H_2O$ (10 mL), and then extracted with DCM (10 mL*3). The organic layers were combined, washed with water (30 mL), saturated brine (30 mL), dried over $Na_2SO_4$, filtered and concentrated in vacuo to give a mixture of (1R,2S)-1-(5-(2, 2-dimethyltetrahydro-2H-pyran-4-yl)-2-(((4S, 7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide and (1S,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide (70 mg, crude). LC-MS (ES+, m/z): 905.4 $[(M+H)^+]$; Rt=0.551 min.

Step 6: 3-((1R,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one and 3-((1S,2S)-1-(5-(2, 2-dimethyltetrahydro-2H-pyran-4-yl)-2-(((4S, 7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one

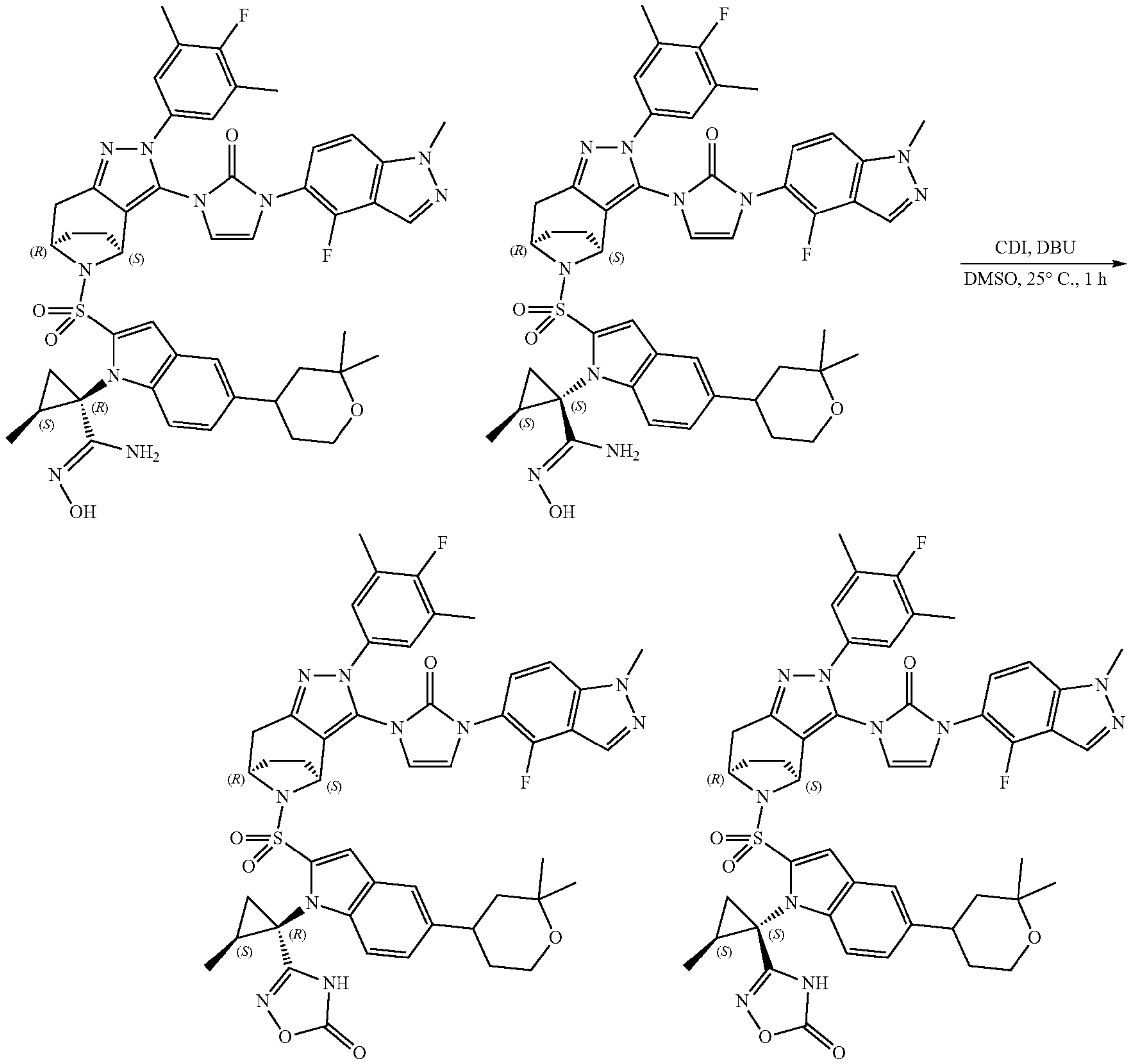

1st eluent

2nd eluent

To a solution of (1R,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide and (1S,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide (70 mg, 43.31 μmol, 1 eq) in DMSO (1.4 mL) was added CDI (14.05 mg, 86.63 μmol, 2 eq) and DBU (16.48 mg, 108.28 μmol, 2.5 eq). The mixture was stirred at 25° C. for 1 hour. LCMS showed the reaction was completed. The mixture was filtered. The filtrate was purified by prep-HPLC column: Phenomenex Luna C18 75*30 mm*3 um; mobile phase: [$H_2O$ (0.1% TFA)-ACN]; gradient: 50%-80% B over 8.0 min.; then by prep-HPLC column: WePure Biotech XP tC18 150*40*7 um; mobile phase: [$H_2O$ (10 mM $NH_4HCO_3$)-ACN]; gradient: 35%-65% B over 8.0 min; and then by prep-HPLC column: WePure Biotech XP tC18 150*30*7 um; mobile phase: [$H_2O$ (10 mM $NH_4HCO_3$)-ACN]; gradient: 40%-70% B over 8.0 min to give 3-((1R, 2S)-1-(5-(2, 2-dimethyltetrahydro-2H-pyran-4-yl)-2-(((4S, 7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one (1st eluent, 1.80 mg, 1.92 μmol, 4.42% yield) as white solid. $^1H$ NMR (400 MHz, DMSO-$d_6$) δ=12.26-11.34 (m, 1H), 8.40-8.23 (m, 1H), 7.70-7.42 (m, 4H), 7.39-7.25 (m, 2H), 7.17 (d, J=6.3 Hz, 2H), 7.08-6.97 (m, 1H), 6.85-6.70 (m, 1H), 5.09-4.86 (m, 1H), 4.55-4.40 (m, 1H), 4.21-4.04 (m, 3H), 3.76-3.67 (m, 2H), 3.12-2.87 (m, 3H), 2.27-1.48 (m, 17H), 1.30-1.17 (m, 6H), 0.97 (br dd, J=1.4, 5.9 Hz, 3H); LC-MS (ES+, m/z): 931.4 [$(M+H)^+$]; Rt=2.941 min; HRMS (EI): m/z $[M+H]^+$ found: 931.3508.

And 3-((1S,2S)-1-(5-(2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one ($2^{nd}$ eluent, 6.49 mg, 6.97 μmol, 16.09% yield) as white solid. $^1H$ NMR (400 MHz, DMSO-$d_6$) δ=12.63-11.88 (m, 1H), 8.36-8.24 (m, 1H), 7.69-7.48 (m, 3H), 7.47-7.26 (m, 3H), 7.17-7.09 (m, 2H), 7.06-6.99 (m, 1H), 6.77-6.69 (m, 1H), 5.14-4.41 (m, 2H), 4.19-4.04 (m, 3H), 3.79-3.62 (m, 2H), 3.19-2.94 (m, 2H), 2.69 (br s, 1H), 2.24 (s, 10H), 1.90-1.43 (m, 7H), 1.42-1.32 (m, 3H), 1.29-1.24 (m, 3H), 1.20-1.15 (m, 3H); LC-MS (ES+, m/z): 931.4 [$(M+H)^+$]; Rt=2.947 min; HRMS (EI): m/z $[M+H]^+$ found: 931.3508.

Example 86 Compound 509

3-((1S,2S)-1-(2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one Scheme 509

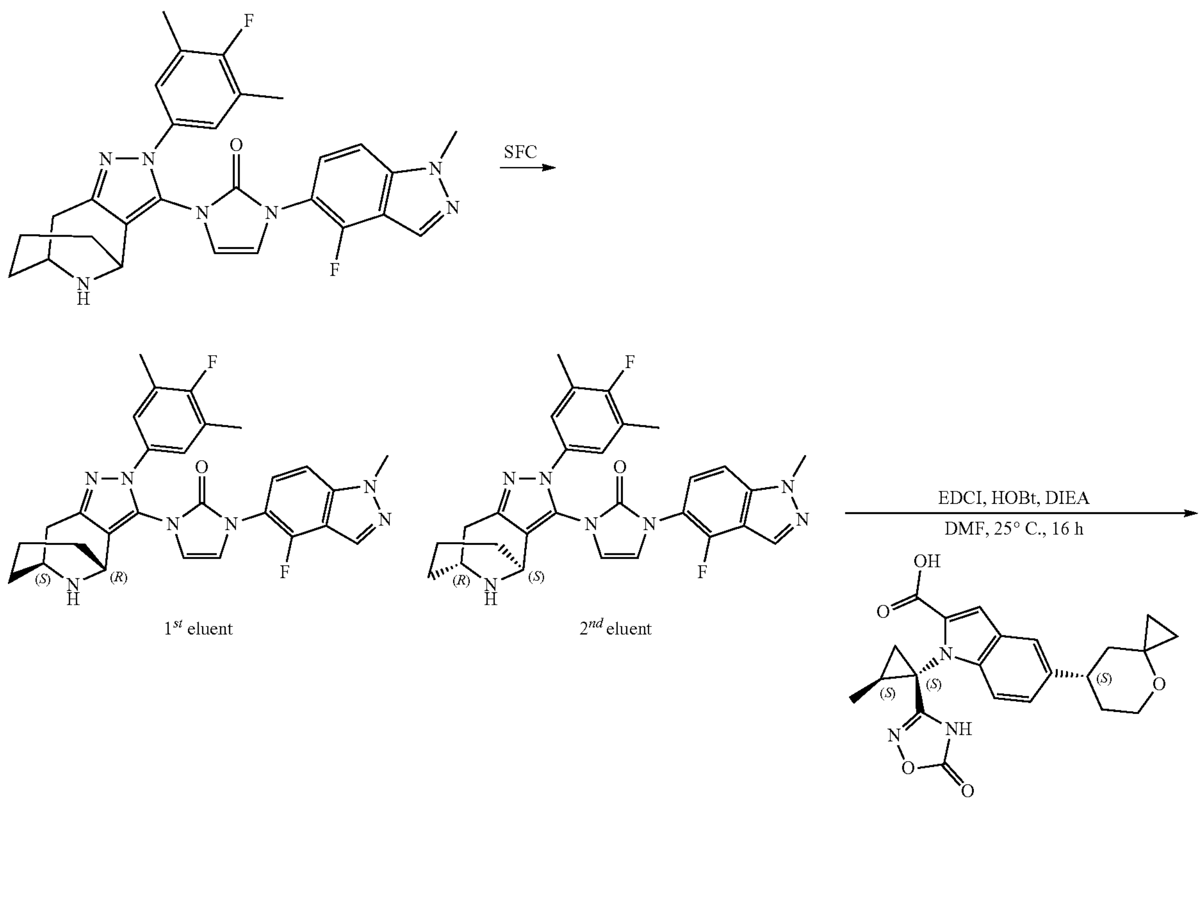

-continued

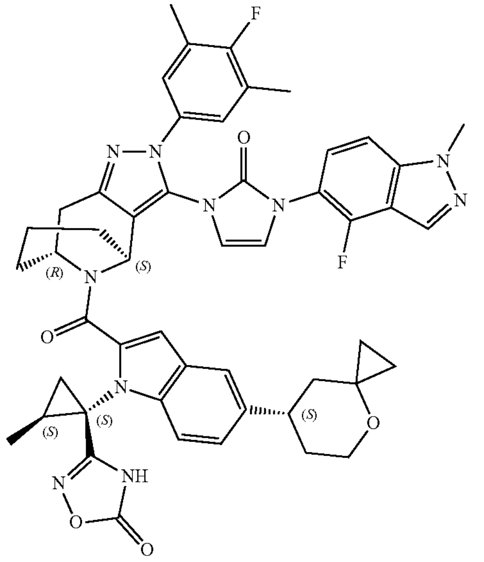

Step 1: 1-(4-fluoro-1-methyl-1H-indazol-5-yl)-3-((4R,8S)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one & 1-(4-fluoro-1-methyl-1H-indazol-5-yl)-3-((45,8R)-2-(4-fluoro-3,5-dimethylphenyl)-4,5,6,7,8,9-hexahydro-2H-4,8-epiminocycloocta[c]pyrazol-3-yl)-1,3-dihydro-2H-imidazol-2-one

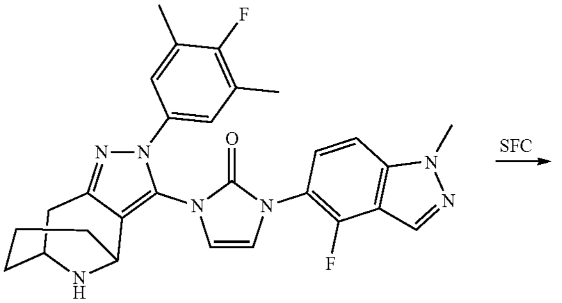

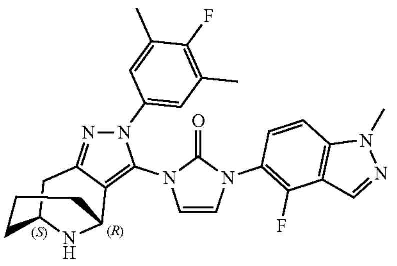

$1^{st}$ eluent

-continued

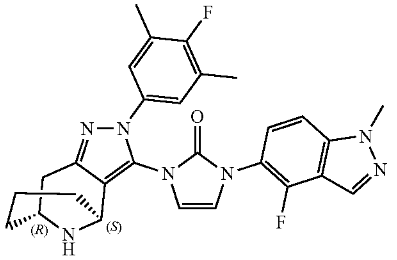

$2^{nd}$ eluent

The 1-(4-fluoro-1-methyl-1H-indazol-5-yl)-3-(2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (860 mg) was separated by SFC column: REGIS (S,S) WHELK-O1 (250 mm*25 mm, 10 um); mobile phase: [$CO_2$-MeOH (0.1% $NH_3H_2O$)]; B %: 55%, isocratic elution mode to afford 1-(4-fluoro-1-methyl-1H-indazol-5-yl)-3-((4R,8S)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (first eluent, RT=0.680 by SFC, 350 mg, 644.93 μmol, 41.13% yield). LC-MS (ES+, m/z): 516.3 [$(M+H)^+$]. Rt=1.323 min.

and 1-(4-fluoro-1-methyl-1H-indazol-5-yl)-3-((4S,8R)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (second eluent, RT=0.969 by SFC, 350 mg, 644.93 μmol, 41.13% yield). LC-MS (ES+, m/z): 516.3 [$(M+H)^+$]. Rt=1.325 min.

Step 2: 3-((1S,2S)-1-(2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta[c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one

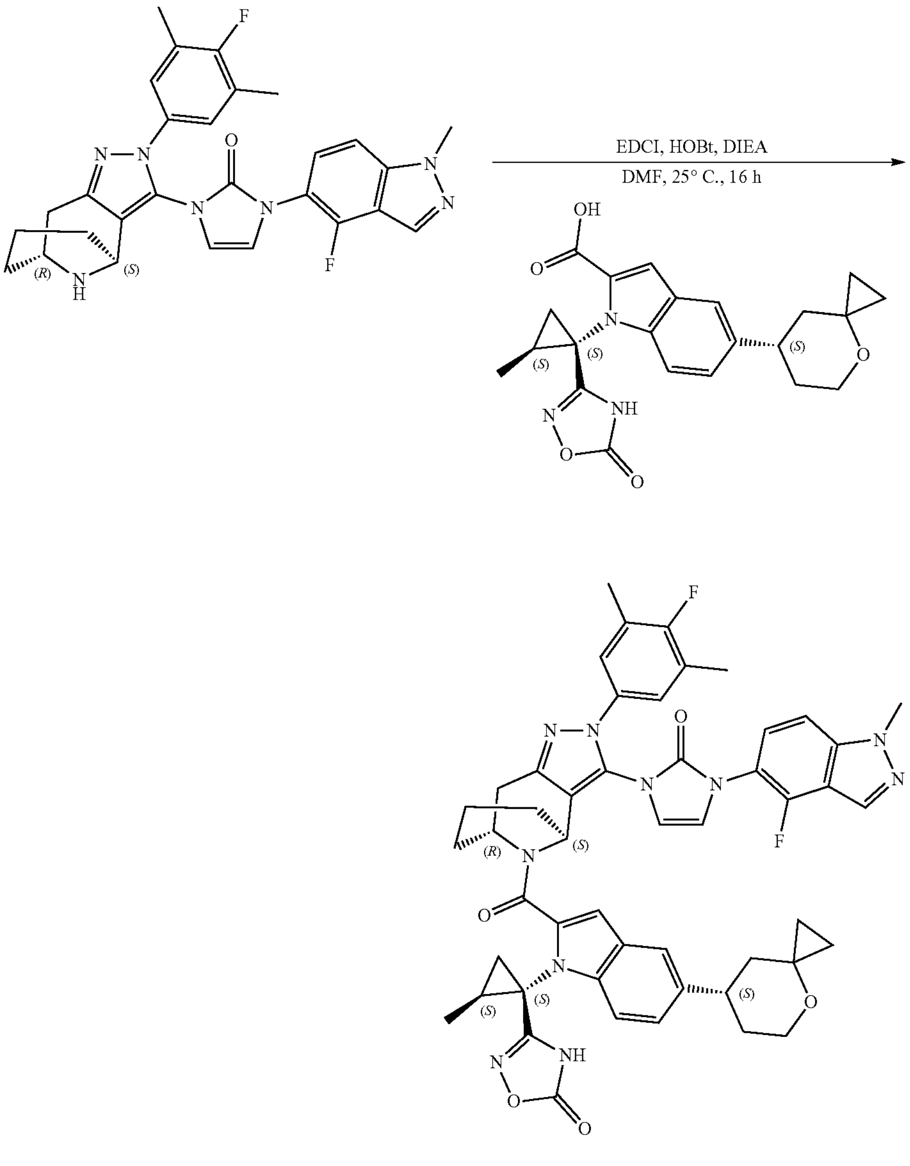

To a solution of 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (30 mg, 73.27 μmol, 1 eq) and 1-(4-fluoro-1-methyl-1H-indazol-5-yl)-3-((4S,8R)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (37.78 mg, 73.27 μmol, 1 eq) in DMF (0.6 mL) was added HOBt (14.85 mg, 109.91 μmol, 1.5 eq), EDCI (16.86 mg, 87.93 μmol, 1.2 eq), DIEA (94.70 mg, 732.72 μmol, 10 eq) in one portion at 25° C. under $N_2$. The mixture was stirred at 25° C. for 16 hours. LCMS showed the reaction was completed. The reaction mixture was quenched by addition $H_2O$ (10 mL), extracted with dichloromethane (5 mL*3). The combined organic layers were washed with saturated brine (10 mL), dried over anhydrous $Na_2SO_4$, filtered and concentrated in vacuo. The residue was purified by prep-HPLC (TFA condition) (column: Phenomenex Luna C18 75*30 mm*3 um; mobile phase: [$H_2O$ (0.1% TFA)-ACN]; gradient: 50%-80% B over 8.0 min) to afford the title compound 3-((1S,2S)-1-(2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one (RT=2.578 by SFC, 15.52 mg, 17.11 μmol, 23.35% yield). $^1H$ NMR (400 MHz, DMSO-$d_6$) δ=12.35-11.66 (m, 1H), 8.36-8.07 (m, 1H), 7.66-6.62 (m, 10H), 5.77-4.96 (m, 2H), 4.11-4.05 (m, 3H), 3.91-3.80 (m, 1H), 3.65-3.29 (m, 2H), 3.14-2.86 (m, 2H), 2.28-2.00 (m, 7H), 1.95-1.51 (m, 10H), 1.38-1.10 (m, 4H), 0.95-0.30 (m, 5H). LC-MS (ES+, m/z): 907.3 [$(M+H)^+$]. Rt=3.498 min. HRMS (EI): m/z $[M+H]^+$ found: 907.3813.

Example 87 Compound 507
cis-3-((1S,2S)-1-(5-((S)-2,2-dimethyltetrahydro-2H-pyran-4-yl)-2-(8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one
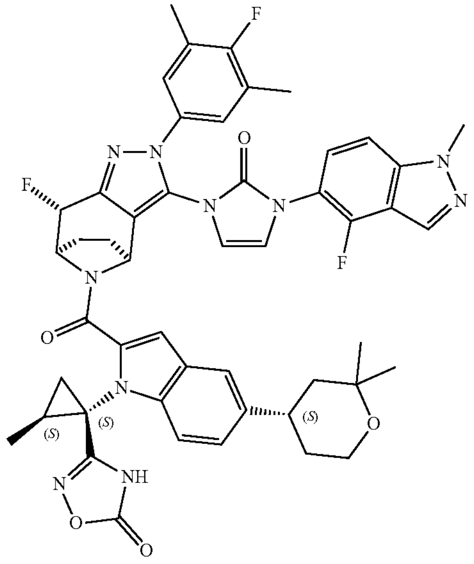
and
-continued
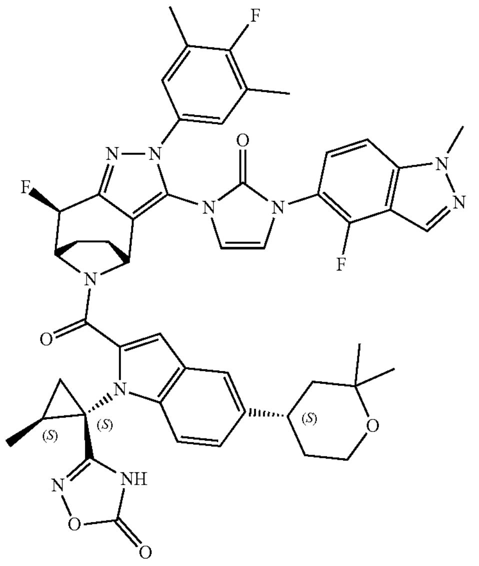
Scheme 507
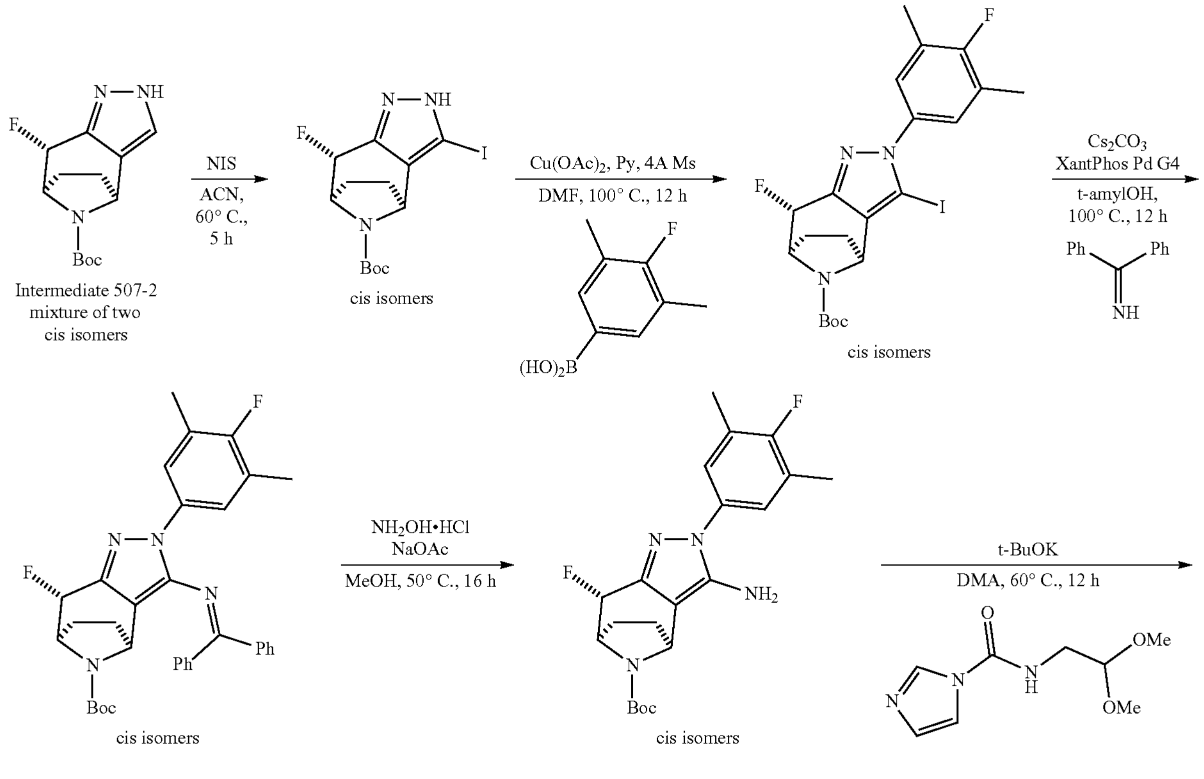

-continued
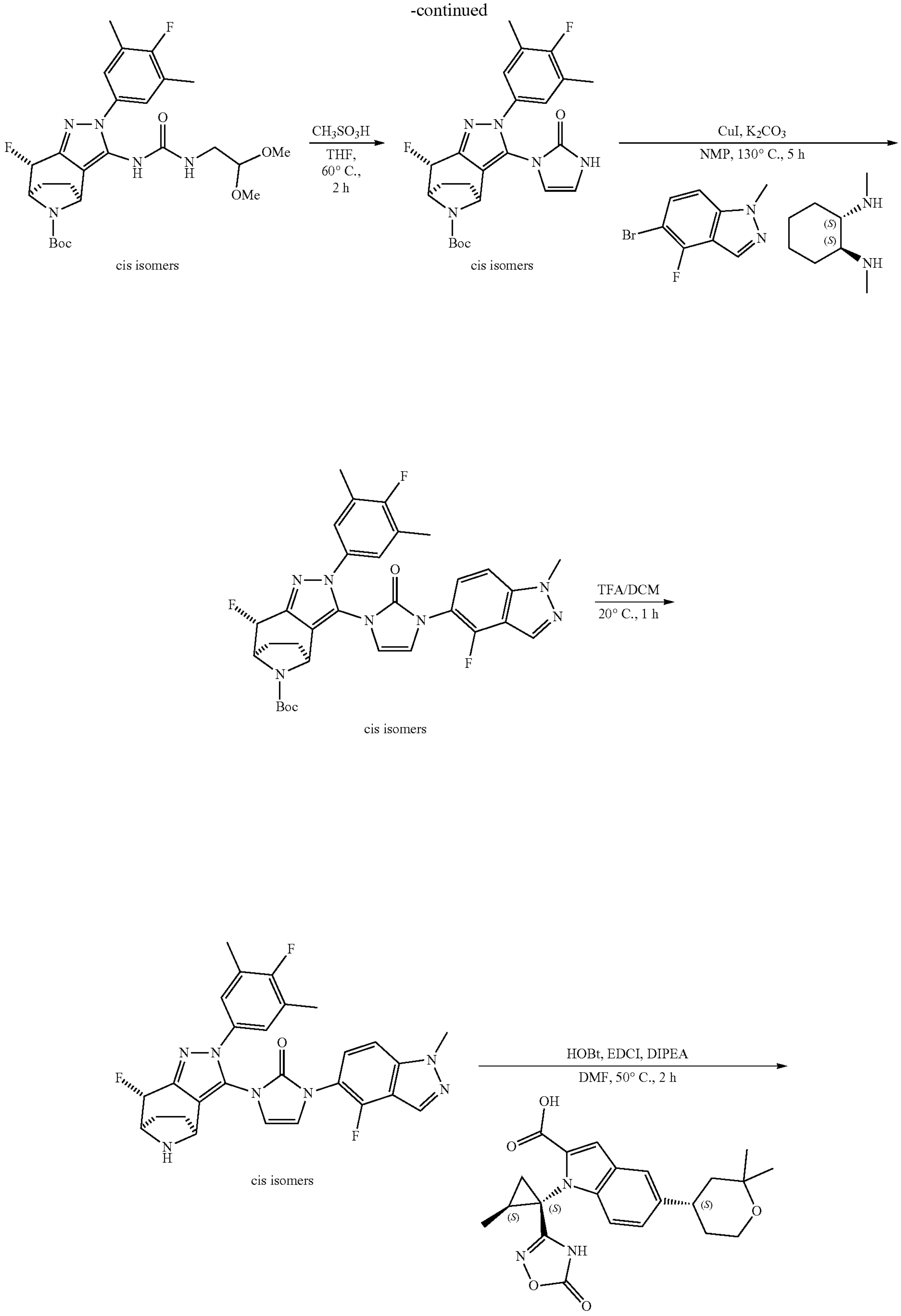

-continued

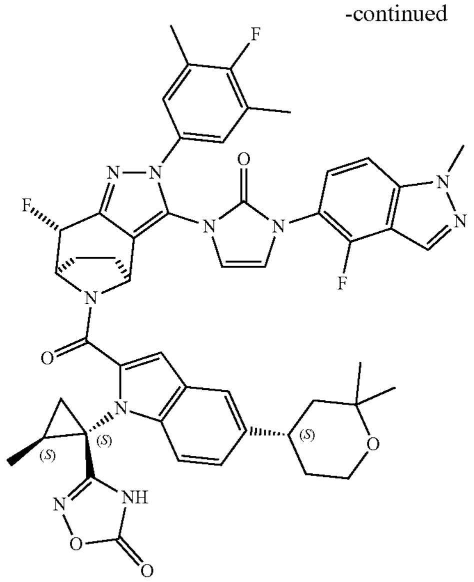

and

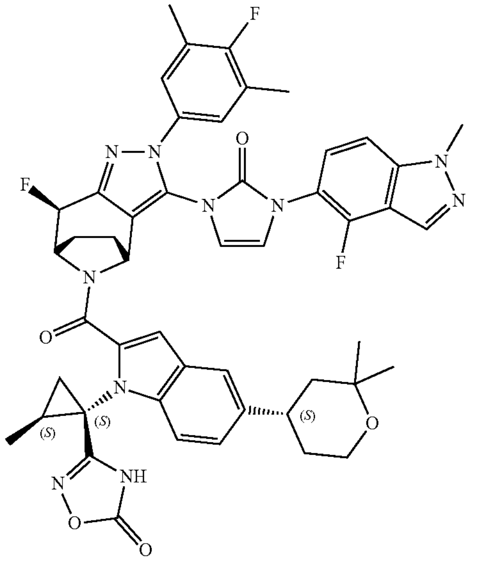

Step 1: cis-tert-butyl-8-fluoro-3-iodo-2, 4, 5, 6, 7, 8-hexahydro-4, 7-epiminocyclohepta [c]pyrazole-9-carboxylate

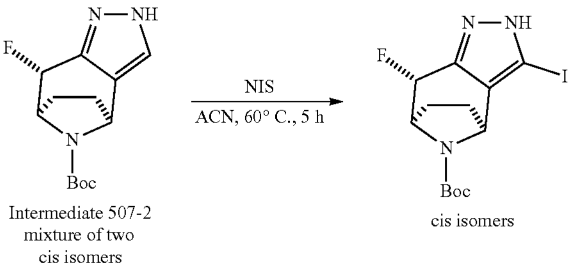 [SMILES: CC(C)(C)OC(=O)N1[C@@H]2CC[C@H]1c1c[nH]nc1[C@H]2F ; "NIS" ; CC(C)(C)OC(=O)N1[C@@H]2CC[C@H]1c1c(n[nH]c1I)[C@H]2F]

To a solution of cis-ter-butyl-8-fluoro-2,4,5,6,7,8-hexahydro-4,7-epiminocyclohepta [c]pyrazole-9-carboxylate (2.00 g, 7.11 mmol, 1 cg) in ACN (20 mL) was added NIS (3.20 g, 14.22 mmol, 2 eq). The mixture was stirred at 60° C. for 5 hours under $N_2$. LCMS showed the reaction was completed (Two Batches in parallel). The residue was poured into water (200 mL). The aqueous phase was extracted with ethyl acetate (100 mL*3). The combined organic phase was washed with sodium hydrogen sulfite (300 mL). The combined organic phase was washed with saturated brine (300 mL), dried with anhydrous $Na_2SO_4$, filtered and concentrated in vacuo. The residue was purified by column chromatography ($SiO_2$, hexanes:ethyl acetate=1/1) to give cis-tert-butyl-8-fluoro-3-iodo-2, 4, 5, 6, 7, 8-hexahydro-4, 7-epiminocyclohepta [c]pyrazole-9-carboxylate (3 g, 6.87 mmol, 48.30% yield): LC-MS (ES+, m/z): 394.1 [$(M+H)^+$]. Rt=1.512 min.

Step 2: cis-tert-butyl-8-fluoro-2-(4-fluoro-3, 5-dimethylphenyl)-3-iodo-2, 4, 5, 6, 7, 8-hexahydro-4, 7-epiminocyclohepta [c]pyrazole-9-carboxylate

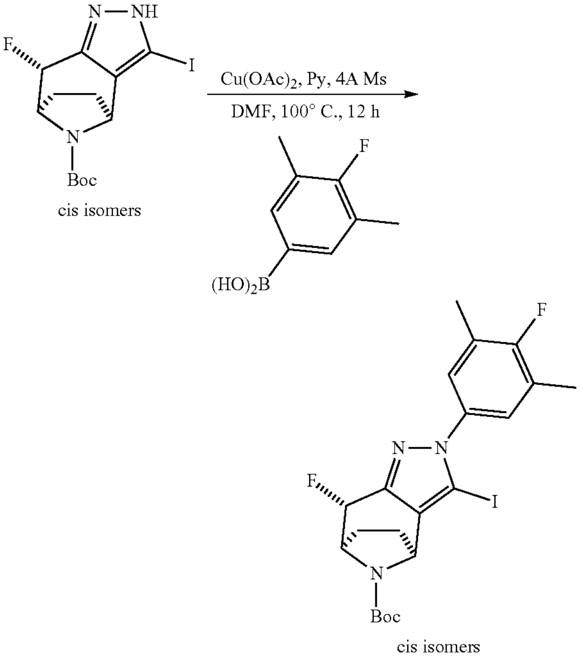

To a solution of cis-tert-butyl-8-fluoro-3-iodo-2,4,5,6,7,8-hexahydro-4,7-epiminocyclohepta [c]pyrazole-9-carboxylate (3.00 g, 6.87 mmol, 1 eq), (4-fluoro-3,5-dimethylphenyl) boronic acid (2.31 g, 13.73 mmol, 2 eq) in DMF (30 mL) was added Py (2.17 g, 27.47 mmol, 4 eq), $Cu(OAc)_2$ (249.44 mg, 1.37 mmol, 0.2 eq) and 4A MS (3 g). The mixture was stirred at 100° C. for 12 hours under $O_2$ (15 Psi). LCMS showed the reaction was completed. The residue was poured into saturated EDTA solution (50 mL) and ethyl acetate (50 mL) stirred for 0.5 hour. The aqueous phase was extracted with ethyl acetate (50 mL*3). The combined organic phase was washed with saturated brine (150 mL), dried with anhydrous $Na_2SO_4$, filtered and concentrated in vacuo. The residue was purified by column chromatography ($SiO_2$, hexanes:ethyl acetate=5/1) to give cis-tert-butyl-8-fluoro-2-(4-fluoro-3,5-dimethylphenyl)-3-iodo-2,4,5,6,7,8-hexahydro-4,7-epiminocyclohepta [c]pyrazole-9-carboxylate (0.9 g, 1.57 mmol, 22.89% yield). $^1H$ NMR (400 MHz, DMSO-$d_6$) δ=7.28 (br d, J=6.2 Hz, 2H), 6.09-5.77 (m, 1H), 4.83-4.56 (m, 2H), 2.28 (d, J=1.5 Hz, 6H), 2.19-1.99 (m, 3H), 1.73-1.61 (m, 1H), 1.37 (br s, 9H). LC-MS. (ES+, m/z): 516.0 [$(M+H)^+$]. Rt=1.697 min.

Step 3: cis-tert-butyl-3-((diphenylmethylene) amino)-8-fluoro-2-(4-fluoro-3,5-dimethylphenyl)-2, 4,5,6,7,8-hexahydro-4,7-epiminocyclohepta [c]pyrazole-9-carboxylate

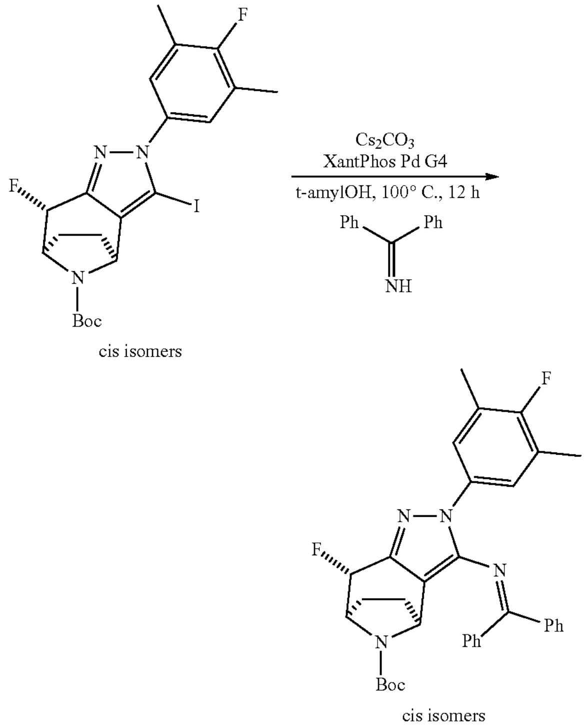

To a solution of cis-tert-butyl-8-fluoro-2-(4-fluoro-3,5-dimethylphenyl)-3-iodo-2,4,5,6,7,8-hexahydro-4,7-epiminocyclohepta [c]pyrazole-9-carboxylate (0.9 g, 1.57 mmol, 1 eq), diphenylmethanimine (854.58 mg, 4.72 mmol, 3 eq) in 2-methylbutan-2-ol (9 mL) was added $Cs_2CO_3$ (1.02 g, 3.14 mmol, 2 eq) and Xantphos Pd G4 (151.27 mg, 157.18 μmol, 0.1 eq). The mixture was stirred at 100° C. for 12 hours under $N_2$. LCMS showed the reaction was completed. The residue was poured into saturated EDTA (50 mL) and ethyl acetate (50 mL) and stirred for 1 hour. The aqueous phase was extracted with ethyl acetate (50 mL*3). The combined organic phase was washed with saturated brine (150 mL), dried with anhydrous $Na_2SO_4$, filtered and concentrated in vacuo. The residue was purified by column chromatography ($SiO_2$, hexanes:ethyl acetate=5/1) to give cis-tert-butyl-3-((diphenylmethylene)amino)-8-fluoro-2-(4-fluoro-3,5-dimethylphenyl)-2,4,5,6,7,8-hexahydro-4,7-epiminocyclohepta [c]pyrazole-9-carboxylate (0.6 g, 949.61 μmol, 60.42% yield). LC-MS (ES+, m/z): 569.3 [$(M+H)^+$]. Rt=1.858 min.

Step 4: cis-tert-butyl-3-amino-8-fluoro-2-(4-fluoro-3, 5-dimethylphenyl)-2, 4, 5, 6, 7, 8-hexahydro-4, 7-epiminocyclohepta [c]pyrazole-9-carboxylate

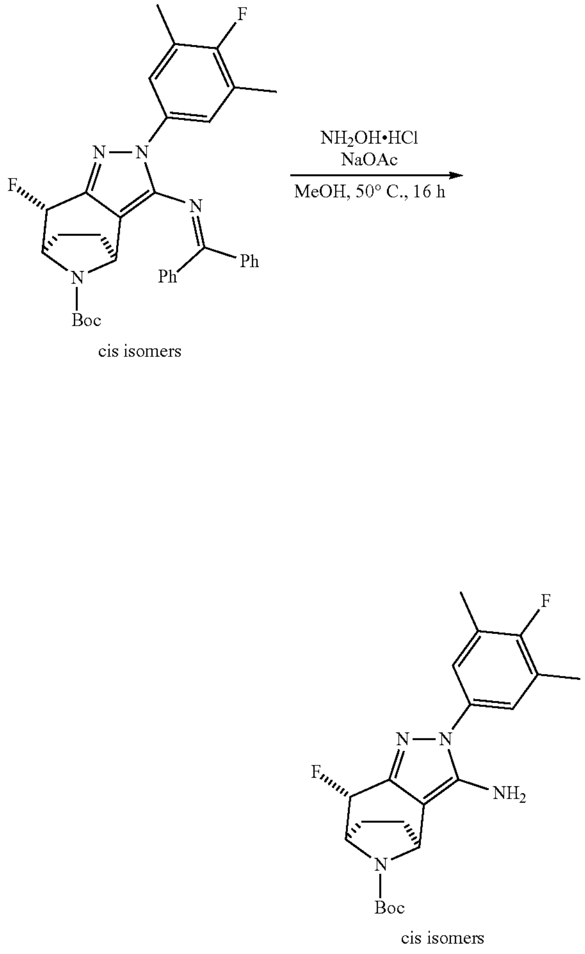

To a solution of cis-tert-butyl-3-((diphenylmethylene) amino)-8-fluoro-2-(4-fluoro-3,5-dimethylphenyl)-2,4,5,6,7,8-hexahydro-4,7-epiminocyclohepta [c]pyrazole-9-carboxylate (0.6 g, 949.61 μmol, 1 eq) in MeOH (6 mL) was added $NH_2OH·HCl$ (32.99 mg, 474.80 μmol, 0.5 eq) and NaOAc (77.90 mg, 949.61 μmol, 1 eq). The mixture was stirred at 50° C. for 16 hours under $N_2$. LCMS showed the reaction was completed. The residue was poured into water (50 mL). The aqueous phase was extracted with ethyl acetate (30 mL*3). The combined organic phase was washed with saturated brine (100 mL), dried with anhydrous $Na_2SO_4$, filtered and concentrated in vacuo. The residue was purified by column chromatography ($SiO_2$, hexanes:ethyl acetate=3/1) to give cis-tert-butyl-3-amino-8-fluoro-2-(4-fluoro-3,5-dimethylphenyl)-2,4,5,6,7,8-hexahydro-4,7-epiminocyclohepta [c]pyrazole-9-carboxylate (0.35 g, 778.83 μmol, 82.02% yield). LC-MS. (ES+, m/z): 405.2 [$(M+H)^+$]. Rt=2.056 min.

Step 5: cis-tert-butyl-3-(3-(2,2-dimethoxyethyl) ureido)-8-fluoro-2-(4-fluoro-3,5-dimethylphenyl)-2, 4,5,6,7,8-hexahydro-4,7-epiminocyclohepta [c]pyrazole-9-carboxylate

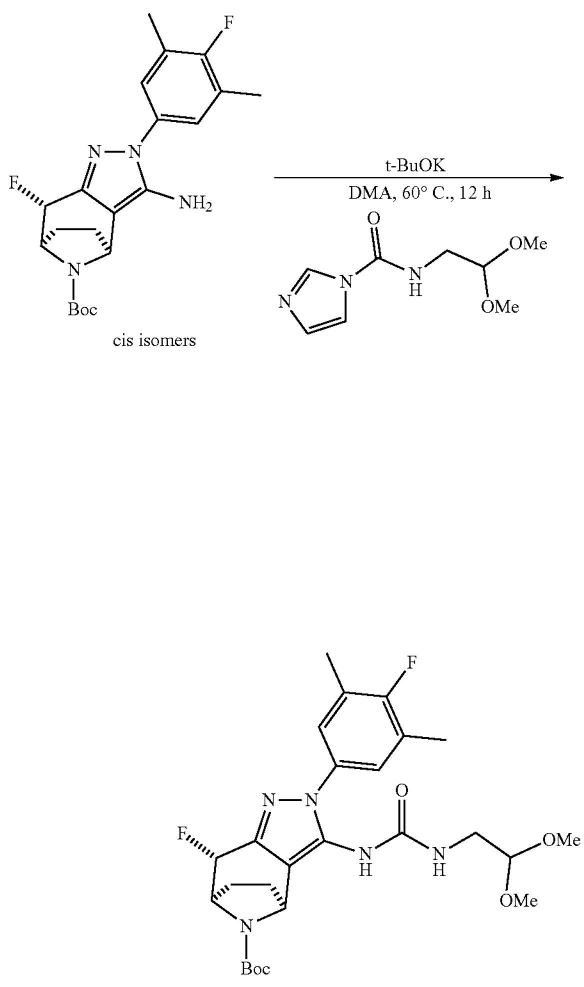

cis isomers cis isomers

To a solution of cis-tert-butyl-3-amino-8-fluoro-2-(4-fluoro-3,5-dimethylphenyl)-2,4,5,6,7,8-hexahydro-4,7-epiminocyclohepta [c]pyrazole-9-carboxylate (170 mg, 378.29 μmol, 1 eq) in DMA (1.7 mL) was added t-BuOK (212.24 mg, 1.89 mmol, 5 eq) and N-(2,2-dimethoxyethyl)-1H-imidazole-1-carboxamide (226.07 mg, 1.13 mmol, 3 eq). The mixture was stirred at 60° C. for 12 hours under $N_2$. LCMS showed the reaction was completed (two Batches in parallel). The residue was poured into water (30 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by prep-TLC ($SiO_2$, hexanes:ethyl acetate=3:1) to give cis-tert-butyl-3-(3-(2,2-dimethoxyethyl) ureido)-8-fluoro-2-(4-fluoro-3,5-dimethylphenyl)-2,4,5,6,7,8-hexahydro-4,7-epiminocyclohepta [c]pyrazole-9-carboxylate (250 mg, 443.44 μmol, 58.61% yield). LC-MS (ES+, m/z): 536.3 [$(M+H)^+$]. Rt=2.021 min.

Step 6: cis-tert-butyl-8-fluoro-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate

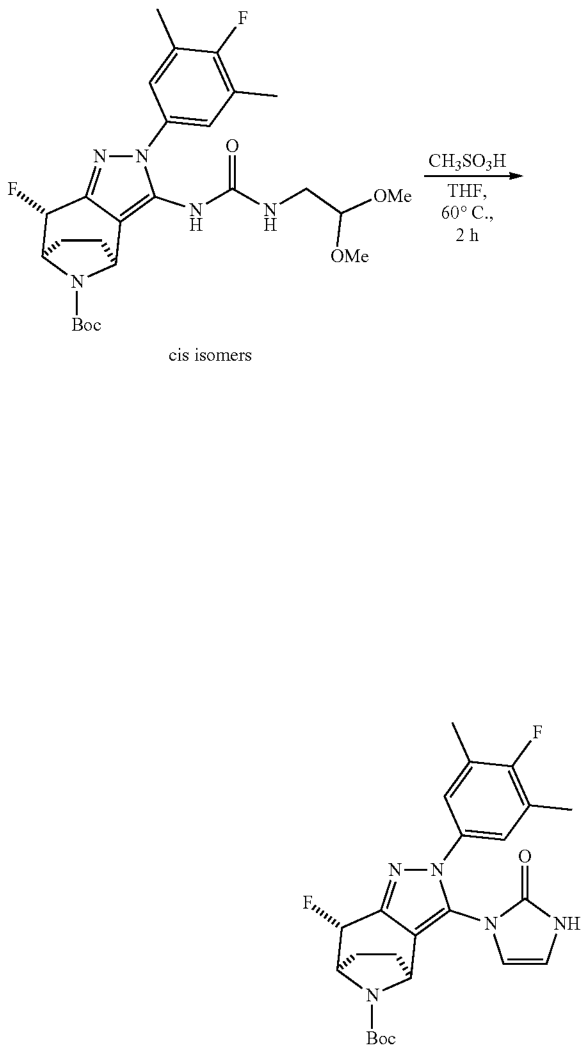

cis isomers cis isomers

To a solution of cis-tert-butyl-3-(3-(2,2-dimethoxyethyl) ureido)-8-fluoro-2-(4-fluoro-3,5-dimethylphenyl)-2,4,5,6,7,8-hexahydro-4,7-epiminocyclohepta [c]pyrazole-9-carboxylate (250 mg, 443.44 μmol, 1 eq) in THF (2.5 mL) was added $CH_3SO_3H$ (46.88 mg, 487.79 μmol, 1.1 eq). The mixture was stirred at 60° C. for 2 hours under $N_2$. LCMS showed the reaction was completed. The residue was poured into water (30 mL). The aqueous phase was extracted with ethyl acetate (20 mL*3). The combined organic phase was washed with saturated brine (60 mL), dried with anhydrous $Na_2SO_4$, filtered and concentrated in vacuo. The residue was purified by prep-TLC ($SiO_2$, hexanes:ethyl acetate=3:1) to give cis-tert-butyl-8-fluoro-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (120 mg, 254.51 μmol, 57.39% yield). LC-MS (ES+, m/z): 416.1 [$(M+H-56)^+$]. Rt=1.339 min.

Step 7: cis-tert-butyl-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

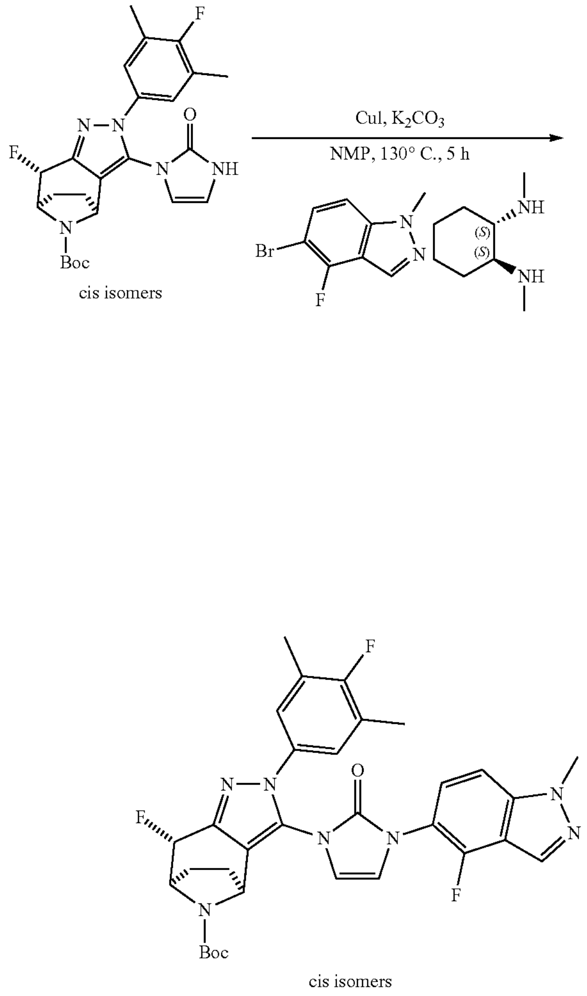

To a solution of cis-tert-butyl-8-fluoro-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (120.00 mg, 241.78 μmol, 1 eq), 5-bromo-4-fluoro-1-methyl-1H-indazole (110.76 mg, 483.56 μmol, 2 eq), (1,2S)—$N^1$,$N^2$-dimethylcyclohexane-1,2-diamine (103.17 mg, 725.35 μmol, 3 eq) in NMP (1.2 mL) was added $K_2CO_3$ (66.83 mg, 483.56 μmol, 2 eq) and CuI (92.09 mg, 483.56 μmol, 2 eq). The mixture was stirred at 130° C. for 5 hours under $N_2$. LCMS showed the reaction was completed. The residue was poured into saturated EDTA (20 mL), ethyl acetate (20 mL) and stirred for 1 hour. The aqueous phase was extracted with ethyl acetate (20 mL*3). The combined organic phase was washed with saturated brine (60 mL), dried with anhydrous $Na_2SO_4$, filtered and concentrated in vacuo. The residue was purified by prep-TLC ($SiO_2$, hexanes:ethyl acetate=1:1) to give cis-tert-butyl-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (120 mg, 174.30 μmol, 72.09% yield). LC-MS (ES+, m/z): 620.2 [$(M+H)^+$]. Rt=1.544 min.

Step 8: cis-1-(4-fluoro-1-methyl-1H-indazol-5-yl)-3-(8-fluoro-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

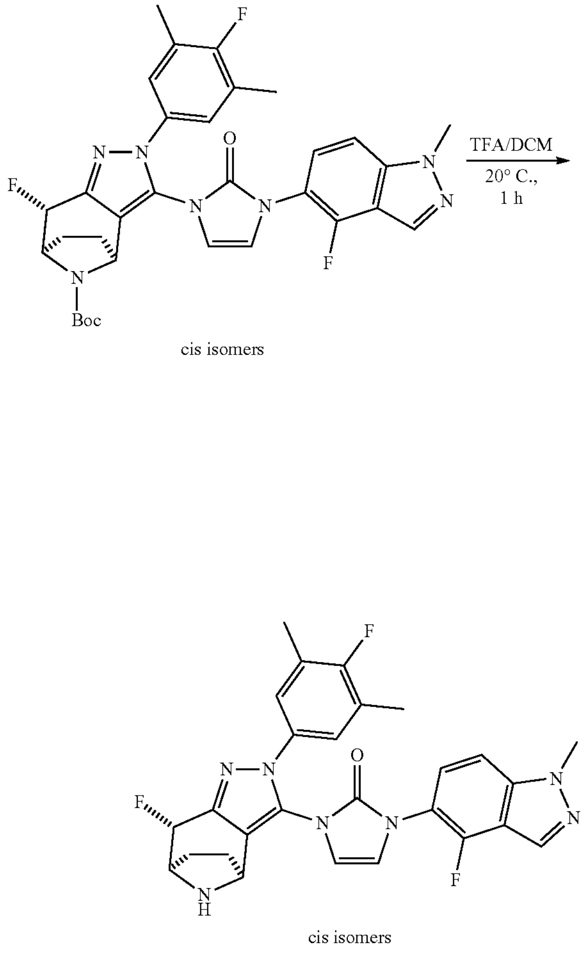

To a solution of cis-tert-butyl (4S,7R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (120.00 mg, 174.30 μmol, 1 eq) in DCM (0.6 mL) was added TFA (0.6 mL). The mixture was stirred at 20° C. for 1 hour. LCMS showed the reaction was completed. The residue was poured into saturated $Na_2CO_3$ (20 mL). The aqueous phase was extracted with ethyl acetate (20 mL*3). The combined organic phase was washed with saturated brine (60 mL), dried with anhydrous $Na_2SO_4$, filtered and concentrated in vacuo to give cis-1-(4-fluoro-1-methyl-1H-indazol-5-yl)-3-(8-fluoro-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (90 mg, crude). LC-MS (ES+, m/z): 520.3 [$(M+H)^+$]. Rt=1.315 min.

Step 9: cis-3-((1S,2S)-1-(5-((S)-2,2-dimethyltetrahydro-2H-pyran-4-yl)-2-(8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

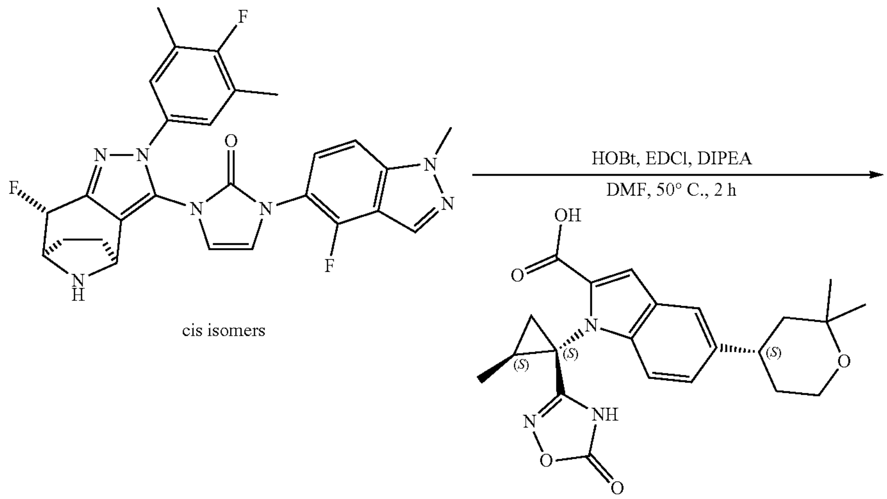

cis isomers

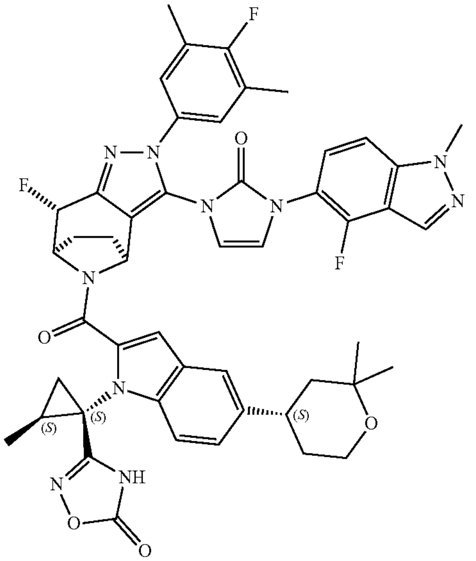

and

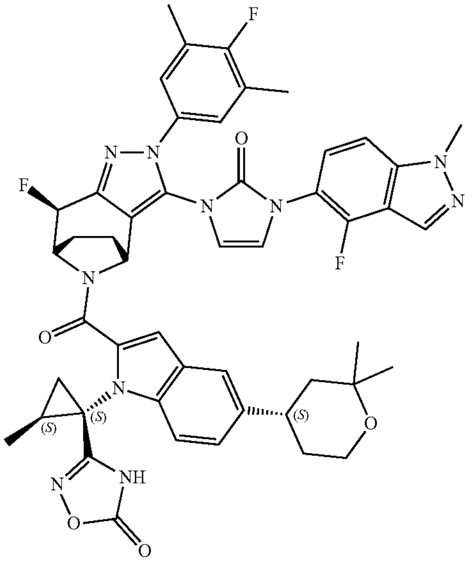

To a solution of cis-1-(4-fluoro-1-methyl-1H-indazol-5-yl)-3-(8-fluoro-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (90.00 mg, 155.91 µmol, 1 eq), 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (64.15 mg, 155.91 µmol, 1 eq) in DMF (0.9 mL) was added HOBt (42.13 mg, 311.83 µmol, 2 eq) and EDCI (59.78 mg, 311.83 µmol, 2 eq), DIEA (100.75 mg, 779.57 µmol, 5 eq). The mixture was stirred at 50° C. for 2 hours under $N_2$. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by prep-HPLC (TFA condition; column: Phenomenex Luna C18 75*30 mm*3 um; mobile phase: [$H_2O$ (0.1% TFA)-ACN]; gradient: 55%-85% B over 8.0 min) to give cis-3-((1S,2S)-1-(5-((S)-2,2-dimethyltetrahydro-2H-pyran-4-yl)-2-(8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (38.22 mg, 41.85 µmol, 26.83% yield). $^1H$ NMR (400 MHz, DMSO-$d_6$) δ=12.42-11.48 (m, 1H), 8.31 (br d, J=7.0 Hz, 1H), 7.78-6.37 (m, 10H), 6.19-5.01 (m, 3H), 4.10 (br d, J=2.4 Hz, 3H), 3.73-3.44 (m, 2H), 3.07-2.90 (m, 1H), 2.38-1.73 (m, 11H), 1.71-0.94 (m, 15H). LC-MS (ES+, m/z): 913.4 [$(M+H)^+$]. Rt=3.201 min. HRMS (EI): m/z $[M+H]^+$ found: 913.3763.

Example 88 Compound 514

3-((1S,2S)-1-(5-((S)-2,2-dimethyltetrahydro-2H-pyran-4-yl)-2-((4R,7S,8R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-1H-indol-1-yl)-2-methylcyclopropyl)-1,2,4-oxadiazol-5 (4H)-one

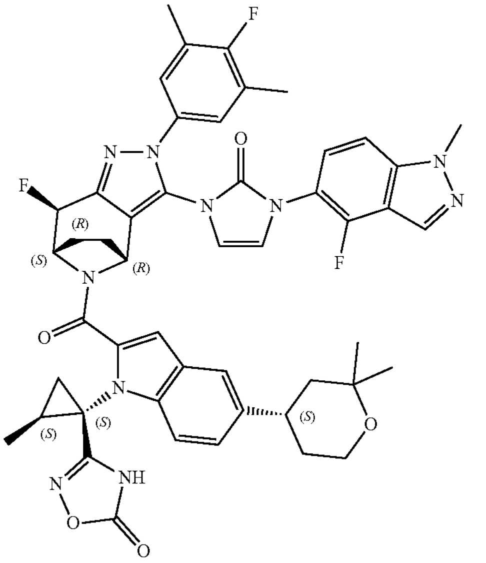

And

Example 89 Compound 515

3-((1S,2S)-1-(5-((S)-2,2-dimethyltetrahydro-2H-pyran-4-yl)-2-((4S,7R,8S)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-1H-indol-1-yl)-2-methylcyclopropyl)-1,2,4-oxadiazol-5 (4H)-one

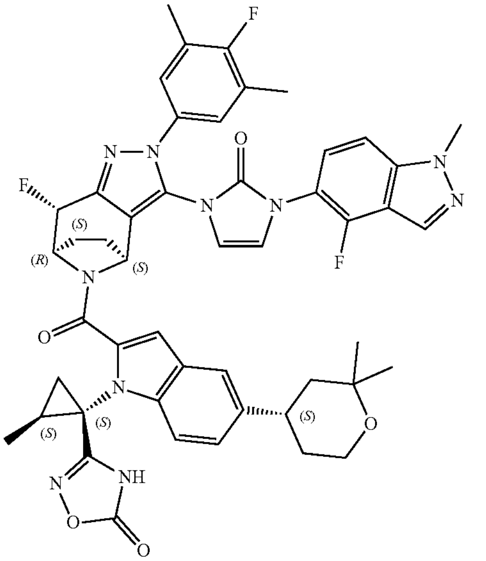

Step 1: 3-((1S,2S)-1-(5-((S)-2,2-dimethyltetrahydro-2H-pyran-4-yl)-2-((4R,7S,8R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one and 3-((1S,2S)-1-(5-((S)-2,2-dimethyltetrahydro-2H-pyran-4-yl)-2-((45,7R,8S)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

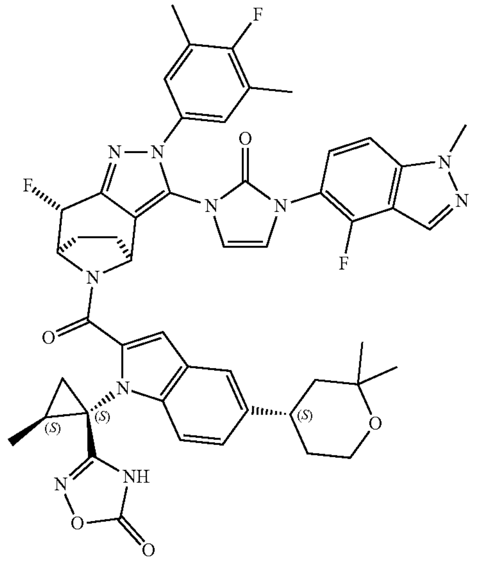

and

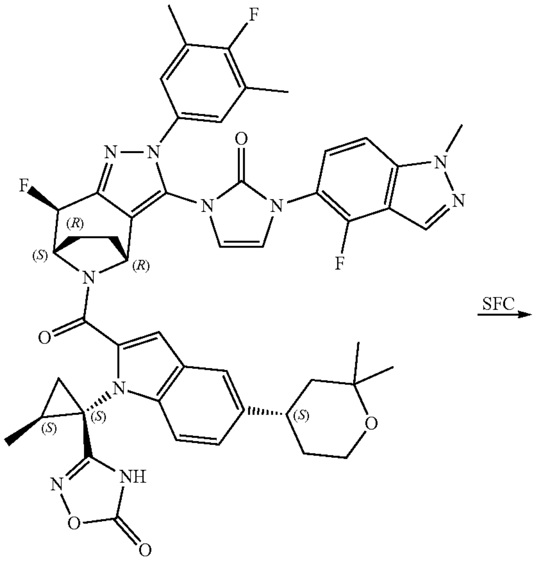

Example 507
mixture of two cis isomers

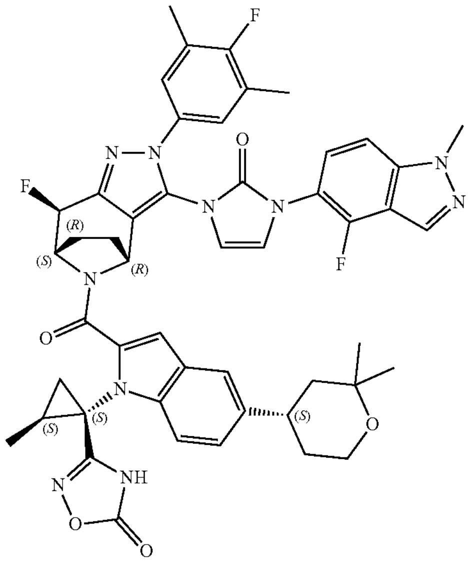

Example 514
$1^{st}$ eluent

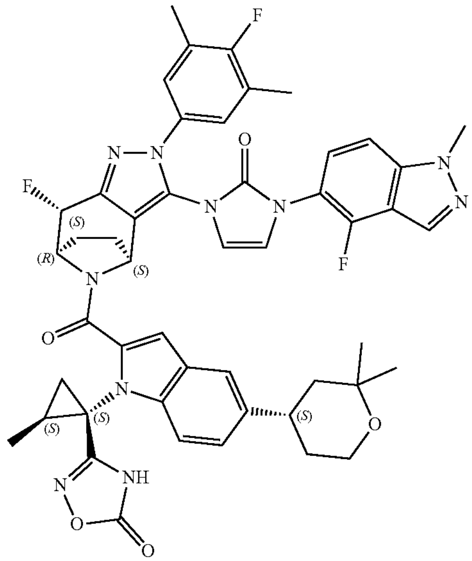

Example 515
$2^{nd}$ eluent

The cis-3-((1S,2S)-1-(5-((S)-2,2-dimethyltetrahydro-2H-pyran-4-yl)-2-((4S,7R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (30 mg) was separated by SFC (column: REGIS (S,S) WHELK-O1 (250 mm*25 mm, 10 um); mobile phase: [$CO_2$-EtOH: ACN=1:1 (0.1% $NH_3H_2O$)]; B %: 60%, isocratic elution mode) to afford 3-((1S,2S)-1-(5-((S)-2,2-dimethyltetrahydro-2H-pyran-4-yl)-2-((4R,7S,8R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (1st eluent, RT=1.612 by SFC, 8.26 mg, 8.98 μmol, 27.31% yield). $^1$H NMR (400 MHz, DMSO-$d_6$) δ=12.52-11.08 (m, 1H), 8.31 (s, 1H), 7.76-6.68 (m, 10H), 6.62-5.87 (m, 1H), 5.73-4.87 (m, 2H), 4.11 (s, 3H), 3.75-3.49 (m, 2H), 3.15-2.90 (m, 1H), 2.31-1.80 (m, 11H), 1.68-1.02 (m, 15H). LC-MS (ES+, m/z): 913.1 [$(M+H)^+$]. Rt=3.044 min. HRMS (EI): m/z $[M+H]^+$ found: 913.3718

And 3-((1S,2S)-1-(5-((S)-2,2-dimethyltetrahydro-2H-pyran-4-yl)-2-((4S,7R,8S)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (2nd eluent, RT=1.921 by SFC, 8.13 mg, 8.88 μmol, 27.02% yield). $^1$H NMR (400 MHz, DMSO-$d_6$) δ=12.56-11.49 (m, 1H), 8.54-8.09 (m, 1H), 7.77-6.69 (m, 10H), 6.61-5.96 (m, 1H), 5.66-4.92 (m, 2H), 4.21-4.03 (m, 3H), 3.72-3.47 (m, 2H), 2.91-2.79 (m, 1H), 2.36-1.70 (m, 11H), 1.69-0.98 (m, 15H). LC-MS (ES+, m/z): 913.1 [$(M+H)^+$]. Rt=2.988 min. HRMS (EI): m/z $[M+H]^+$ found: 913.3754

Example 90 Compound 511 trans-3-((1S,2S)-1-(5-((S)-2,2-dimethyltetrahydro-2H-pyran-4-yl)-2-(8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one

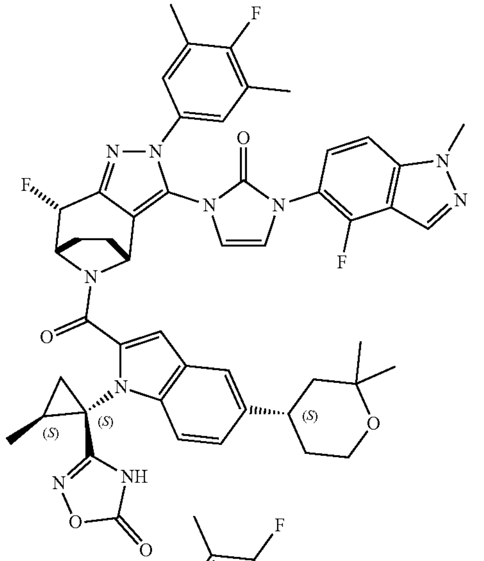

and

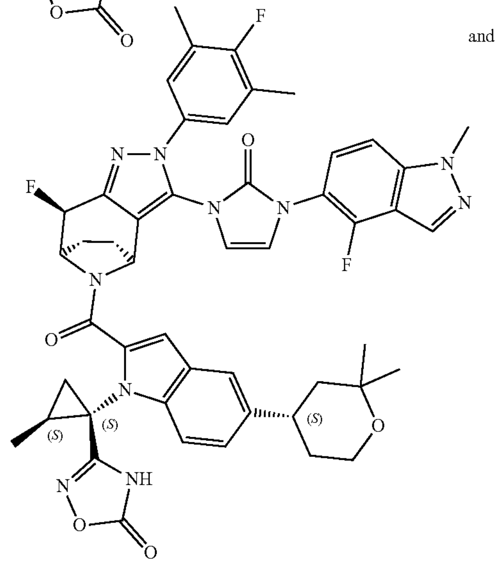

Scheme 511

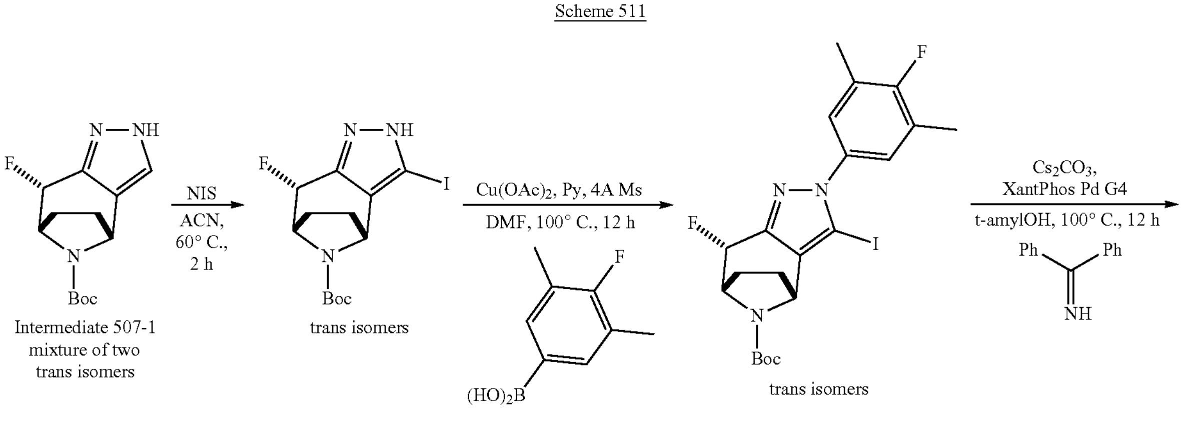

-continued
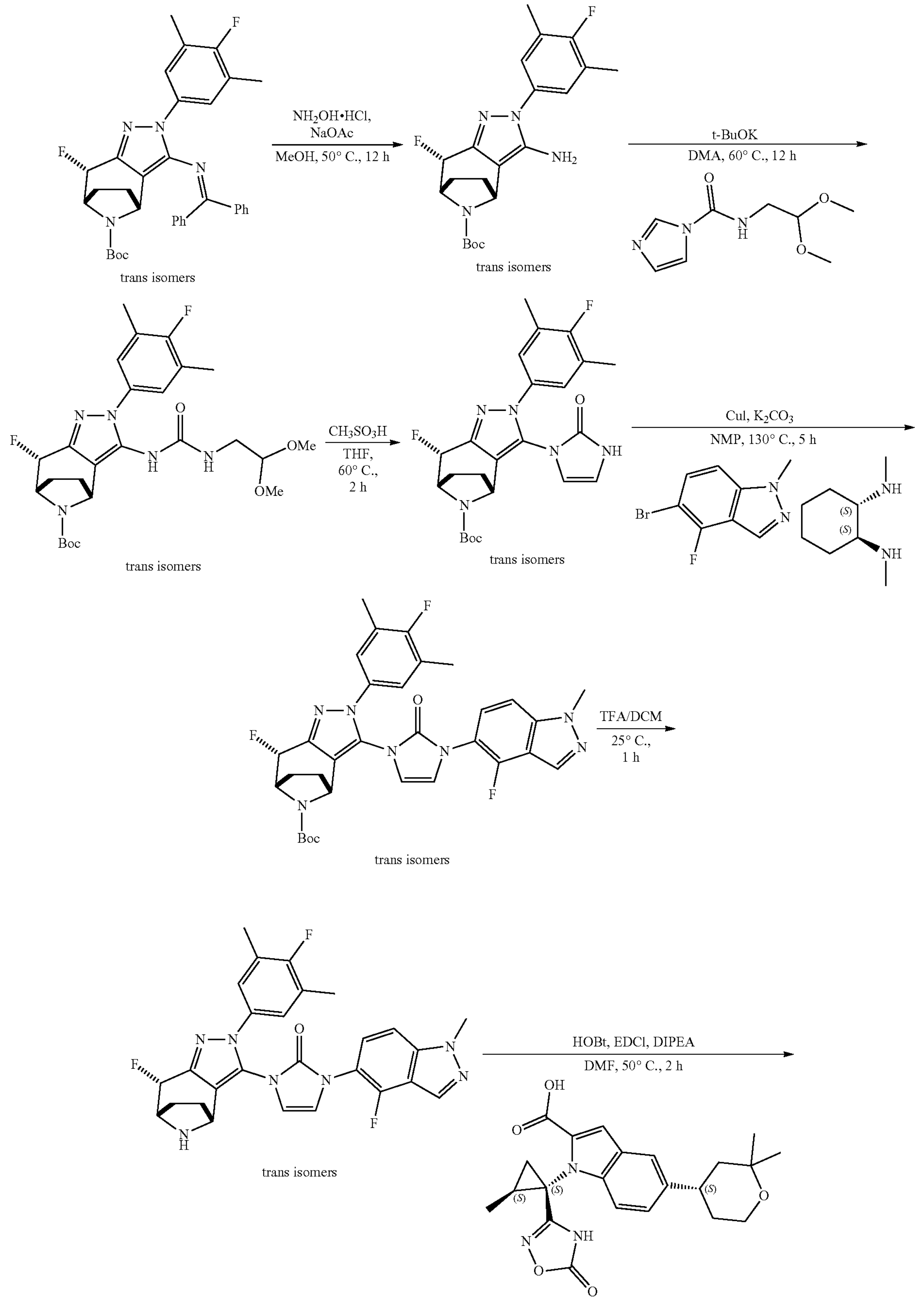

-continued

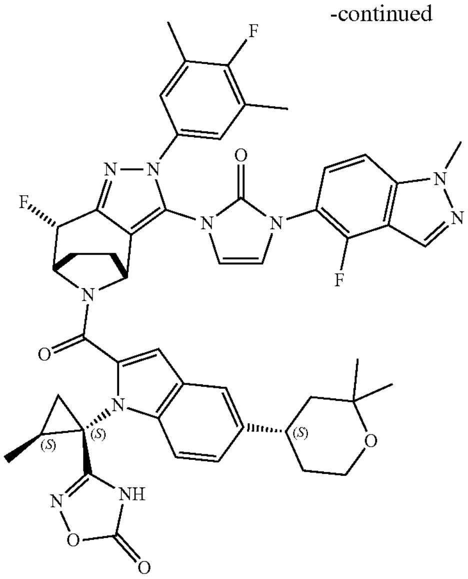

and

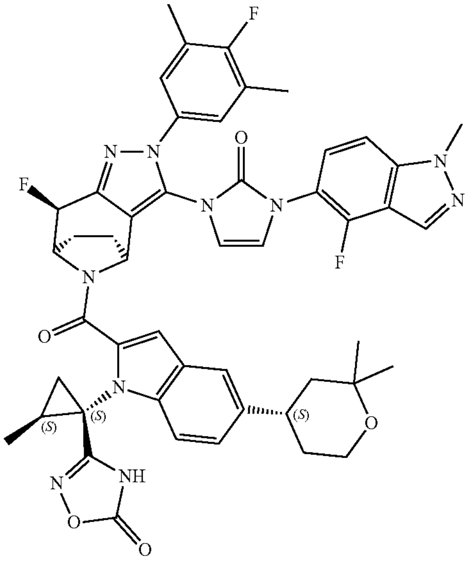

Step 1: trans-ter-butyl-8-fluoro-3-iodo-2,4,5,6,7,8-hexahydro-4,7-epiminocyclohepta [c]pyrazole-9-carboxylate

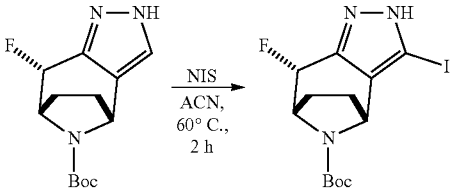

Intermediate 507-1 mixture of two trans isomers trans isomers

To a mixture of trans-ter-butyl-8-fluoro-2,4,5,6,7,8-hexahydro-4,7-epiminocyclohepta [c]pyrazole-9-carboxylate (1.5 g, 5.33 mmol, 1 cg) in ACN (15 mL) was added NIS (2.40 g, 10.66 mmol, 2 ca) in one portion at 60° C. under $N_2$. The mixture was stirred at 60° C. for 2 hours. LCMS showed the reaction was completed. The residue was poured into water (300 mL). The aqueous phase was extracted with ethyl acetate (150 mL*3). The combined organic phase was washed with saturated $NaHSO_3$ solution (450 mL), dried with anhydrous $Na_2SO_4$, filtered and concentrated in vacuo. The residue was purified by column chromatography ($SiO_2$, hexanes:ethyl acetate=20/1 to 5/1) to give trans-tert-butyl-8-fluoro-3-iodo-2,4,5,6,7,8-hexahydro-4,7-epiminocyclohepta [c]pyrazole-9-carboxylate (2.2 g, 4.98 mmol, 46.70% yield). LC-MS (ES+, m/z): 393.9 [$(M+H)^+$]; Rt=1.195 min.

Step 2: trans-tert-butyl-8-fluoro-2-(4-fluoro-3,5-dimethylphenyl)-3-iodo-2,4,5,6,7,8-hexahydro-4,7-epiminocyclohepta [c]pyrazole-9-carboxylate

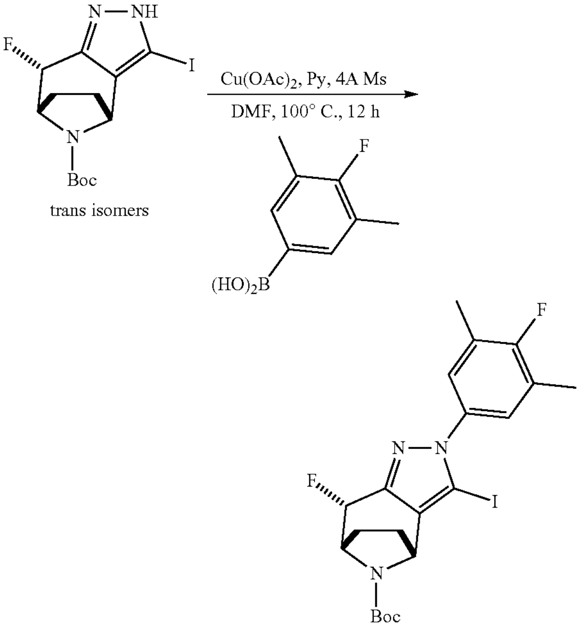

trans isomers trans isomers

To a mixture of trans-tert-butyl-8-fluoro-3-iodo-2,4,5,6,7,8-hexahydro-4,7-epiminocyclohepta [c]pyrazole-9-carboxylate (2.00 g, 4.53 mmol, 1 eq) and (4-fluoro-3,5-dimethylphenyl) boronic acid (1.52 g, 9.05 mmol, 2 eq) in DMF (20 mL) was added Py (1.43 g, 18.11 mmol, 4 eq), 4A MS (2 g) and $Cu(OAc)_2$ (164.45 mg, 905.40 μmol, 0.2 eq) in one portion at 100° C. under $O_2$ (15 Psi). The mixture was stirred at 100° C. for 12 hours. The residue was poured into saturated EDTA (50 mL), ethyl acetate (50 mL) and stirred for 60 mins. LCMS showed the reaction was completed. The residue was poured into water (50 mL). The aqueous phase was extracted with ethyl acetate (25 mL*3). The combined organic phase was washed with saturated brine (75 mL), dried with anhydrous $Na_2SO_4$, filtered and concentrated in vacuo. The residue was purified by column chromatography ($SiO_2$, hexanes:ethyl acetate=100/0 to 98/2) to give trans-tert-butyl-8-fluoro-2-(4-fluoro-3,5-dimethylphenyl)-3-iodo-2,4,5,6,7,8-hexahydro-4,7-epiminocyclohepta [c]pyrazole-9-carboxylate (650 mg, 1.06 mmol, 23.40% yield). LC-MS (ES+, m/z): 516.0 [(M+H)$^+$]; Rt=1.613 min.

Step 3: trans-tert-butyl-3-((diphenylmethylene) amino)-8-fluoro-2-(4-fluoro-3,5-dimethylphenyl)-2, 4,5,6,7,8-hexahydro-4,7-epiminocyclohepta [c]pyrazole-9-carboxylate

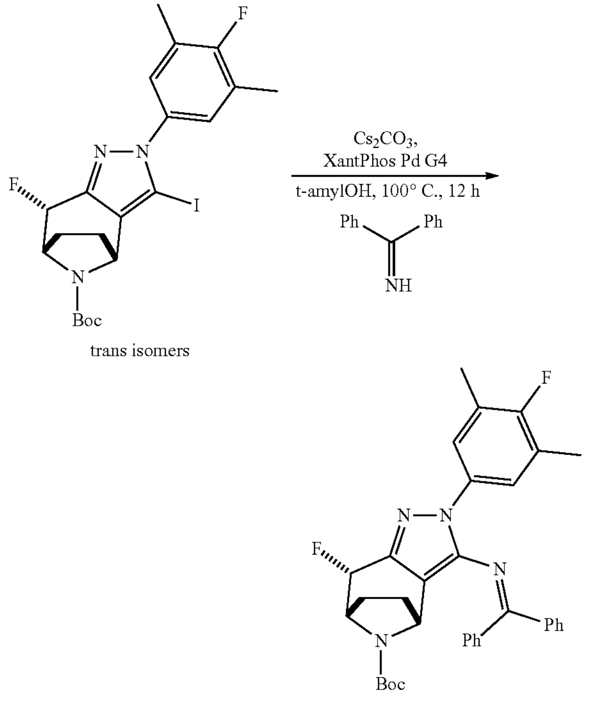

trans isomers trans isomers

To a mixture of trans-tert-butyl-8-fluoro-2-(4-fluoro-3,5-dimethylphenyl)-3-iodo-2,4,5,6,7,8-hexahydro-4,7-epiminocyclohepta [c]pyrazole-9-carboxylate (650 mg, 1.06 mmol, 1 eq) and diphenylmethanimine (576.05 mg, 3.18 mmol, 3 eq) in t-amylOH (6.5 mL) was added $Cs_2CO_3$ (690.42 mg, 2.12 mmol, 2 eq) and XantPhos Pd G4 (203.93 mg, 211.90 µmol, 0.2 eq) under $N_2$. The mixture was stirred at 100° C. for 12 hours. LCMS showed the reaction was completed. The residue was poured into saturated EDTA (20 mL), ethyl acetate (20 mL) and stirred for 60 mins. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by column chromatography ($SiO_2$, hexanes:ethyl acetate=20/1 to 5/1) to give trans-tert-butyl-3-((diphenylmethylene)amino)-8-fluoro-2-(4-fluoro-3,5-dimethylphenyl)-2,4,5,6,7,8-hexahydro-4,7-epiminocyclohepta [c]pyrazole-9-carboxylate (600 mg, 854.65 µmol, 80.66% yield). LC-MS (ES+, m/z): 569.3 [(M+H)$^+$]; Rt=0.746 min.

Step 4: trans-tert-butyl-3-amino-8-fluoro-2-(4-fluoro-3,5-dimethylphenyl)-2,4,5,6,7,8-hexahydro-4, 7-epiminocyclohepta [c]pyrazole-9-carboxylate

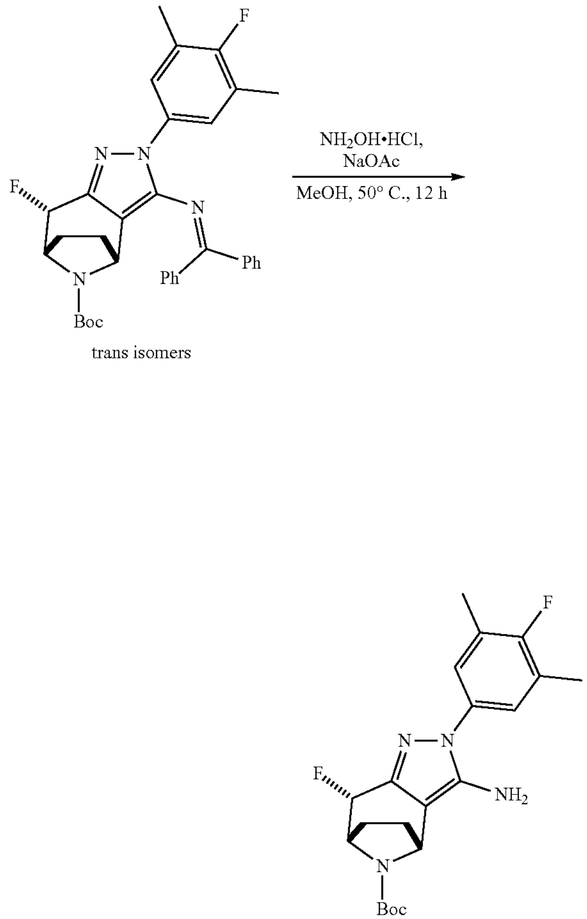

trans isomers trans isomers

To a mixture of trans-tert-butyl-3-((diphenylmethylene) amino)-8-fluoro-2-(4-fluoro-3,5-dimethylphenyl)-2,4,5,6,7,8-hexahydro-4,7-epiminocyclohepta [c]pyrazole-9-carboxylate (600 mg, 854.65 µmol, 1 eq) in MeOH (6 mL) was added $NH_2OH$·HCl (118.78 mg, 1.71 mmol, 2 eq) and NaOAc (210.32 mg, 2.56 mmol, 3 eq) in one portion at 50° C. under $N_2$. The mixture was stirred at 50° C. for 12 hours. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by column chromatography ($SiO_2$, hexanes:ethyl acetate=20/1 to 1/1) to give trans-tert-butyl-3-amino-8-fluoro-2-(4-fluoro-3,5-dimethylphenyl)-2,4,5,6,7,8-hexahydro-4,7-epiminocyclohepta [c]pyrazole-9-carboxylate (300 mg, 704.66 µmol, 82.45% yield). LC-MS (ES+, m/z): 405.1 [(M+H)$^+$]; Rt=1.343 min.

Step 5: trans-tert-butyl-3-(3-(2,2-dimethoxyethyl) ureido)-8-fluoro-2-(4-fluoro-3,5-dimethylphenyl)-2, 4,5,6,7,8-hexahydro-4,7-epiminocyclohepta [c]pyrazole-9-carboxylate

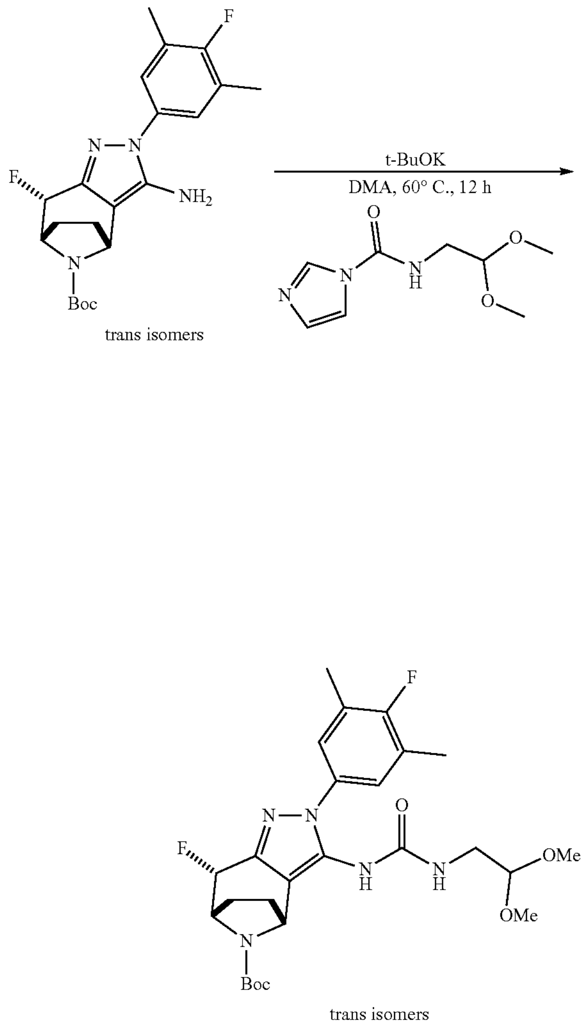

To a mixture of trans-tert-butyl-3-amino-8-fluoro-2-(4-fluoro-3,5-dimethylphenyl)-2,4,5,6,7,8-hexahydro-4,7-epiminocyclohepta [c]pyrazole-9-carboxylate (150.00 mg, 352.33 μmol, 1 eq) and N-(2,2-dimethoxyethyl)-1H-imidazole-1-carboxamide (280.74 mg, 1.41 mmol, 4 eq) in DMA (1.5 mL) was added t-BuOK (197.68 mg, 1.76 mmol, 5 eq) in one portion at 60° C. under $N_2$. The mixture was stirred at 60° C. for 12 hours (Two batches in parallel). LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by column chromatography ($SiO_2$, hexanes: ethyl acetate=20/1 to 1/1) to give trans-tert-butyl-3-(3-(2,2-dimethoxyethyl) ureido)-8-fluoro-2-(4-fluoro-3,5-dimethylphenyl)-2,4,5,6,7,8-hexahydro-4,7-epiminocyclohepta [c]pyrazole-9-carboxylate (250 mg, 448.11 μmol, 63.59% yield). LC-MS (ES+, m/z): 536.3 [$(M+H)^+$]; Rt=1.318 min.

Step 6: trans-tert-butyl-8-fluoro-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate

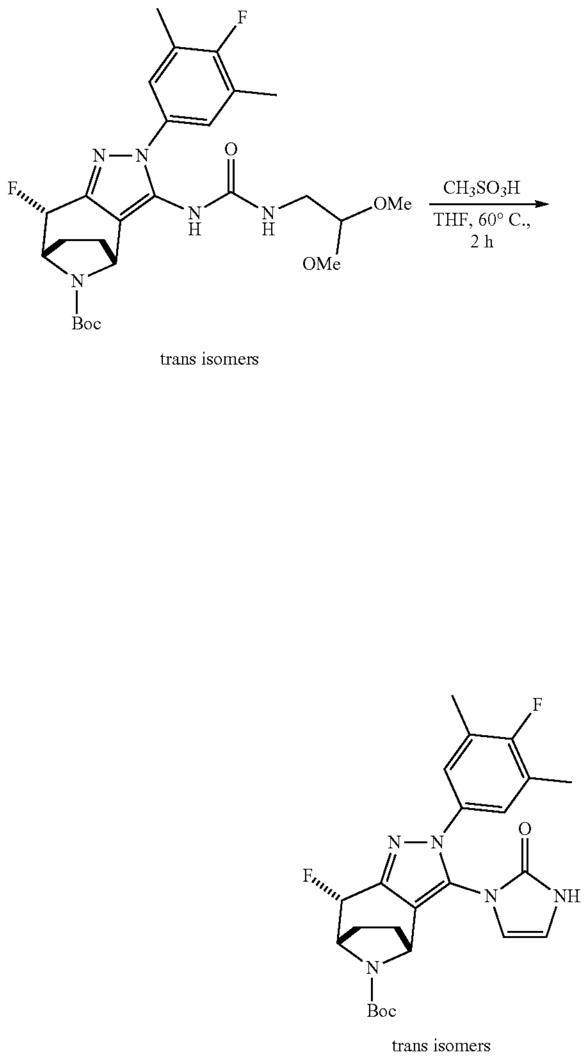

To a mixture of trans-tert-butyl-3-(3-(2,2-dimethoxyethyl) ureido)-8-fluoro-2-(4-fluoro-3,5-dimethylphenyl)-2, 4,5,6,7,8-hexahydro-4,7-epiminocyclohepta [c]pyrazole-9-carboxylate (250.00 mg, 448.11 μmol, 1 eq) in THF (2.5 mL) was added $CH_3SO_3H$ (47.37 mg, 492.92 μmol, 1.1 eq) in one portion at 60° C. under $N_2$. The mixture was stirred at 60° C. for 2 hours. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by prep-TLC ($SiO_2$, hexanes:ethyl acetate=1:1) to give trans-tert-butyl-8-fluoro-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (150 mg, 302.23 μmol, 67.44% yield). LC-MS (ES+, m/z): 472.3 [$(M+H)^+$]; Rt=1.871 min.

Step 7: trans-tert-butyl-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate

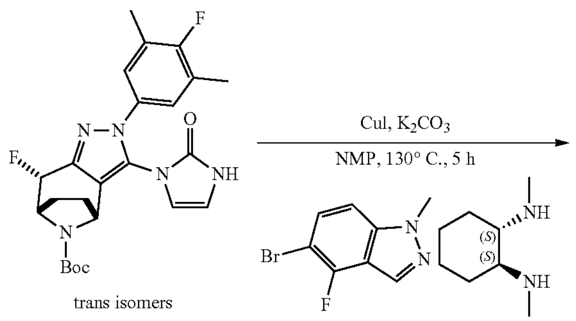

trans isomers

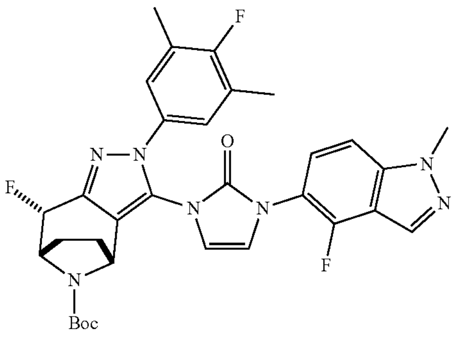

trans isomers

To a mixture of trans-tert-butyl-8-fluoro-2-(4-fluoro-3,5-dimethylphenyl)-3-(2-oxo-2,3-dihydro-1H-imidazol-1-yl)-2,4,5,6,7,8-hexahydro-4,7-epiminocyclohepta [c]pyrazole-9-carboxylate (150.00 mg, 302.23 μmol, 1 eq) and 5-bromo-4-fluoro-1-methyl-1H-indazole (138.45 mg, 604.46 μmol, 2 eq), ((1S,2S)—$N^1$,$N^2$-dimethylcyclohexane-1,2-diamine (128.97 mg, 906.68 μmol, 3 eq) in NMP (1.5 mL) was added $K_2CO_3$ (83.54 mg, 604.46 μmol, 2 eq) and CuI (115.12 mg, 604.46 μmol, 2 eq) in one portion at 130° C. under $N_2$. The mixture was stirred at 130° C. for 5 hours. LCMS showed the reaction was completed. The residue was poured into saturated EDTA (20 mL), ethyl acetate (20 mL) and stirred for 60 mins. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by column chromatography ($SiO_2$, hexanes:ethyl acetate=20/1 to 1/1) to give trans-tert-butyl-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (140 mg, 221.42 μmol, 73.26% yield, 98% purity). LC-MS (ES+, m/z): 620.2 [$(M+H)^+$]; Rt=1.402 min.

Step 8: trans-1-(4-fluoro-1-methyl-1H-indazol-5-yl)-3-(8-fluoro-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one

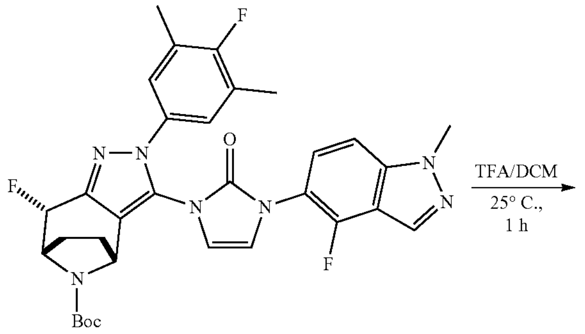

trans isomers

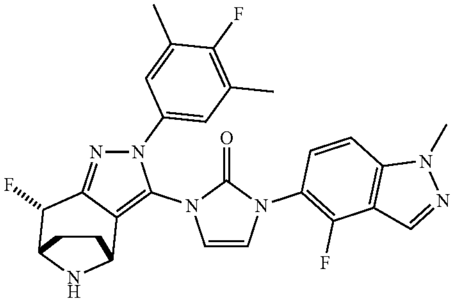

trans isomers

To a mixture of trans-tert-butyl-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carboxylate (140.00 mg, 221.42 μmol, 1 eq) in DCM (1.2 mL) was added TFA (0.2 mL) in one portion at 25° C. The mixture was stirred at 25° C. for 1 hour. LCMS showed the reaction was completed. The residue was concentrated in vacuo to give trans-1-(4-fluoro-1-methyl-1H-indazol-5-yl)-3-(8-fluoro-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (100 mg, crude). LC-MS (ES+, m/z): 520.3 [$(M+H)^+$]; Rt=1.320 min.

Step 9: trans-3-((1S,2S)-1-(5-((S)-2,2-dimethyltetrahydro-2H-pyran-4-yl)-2-(8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

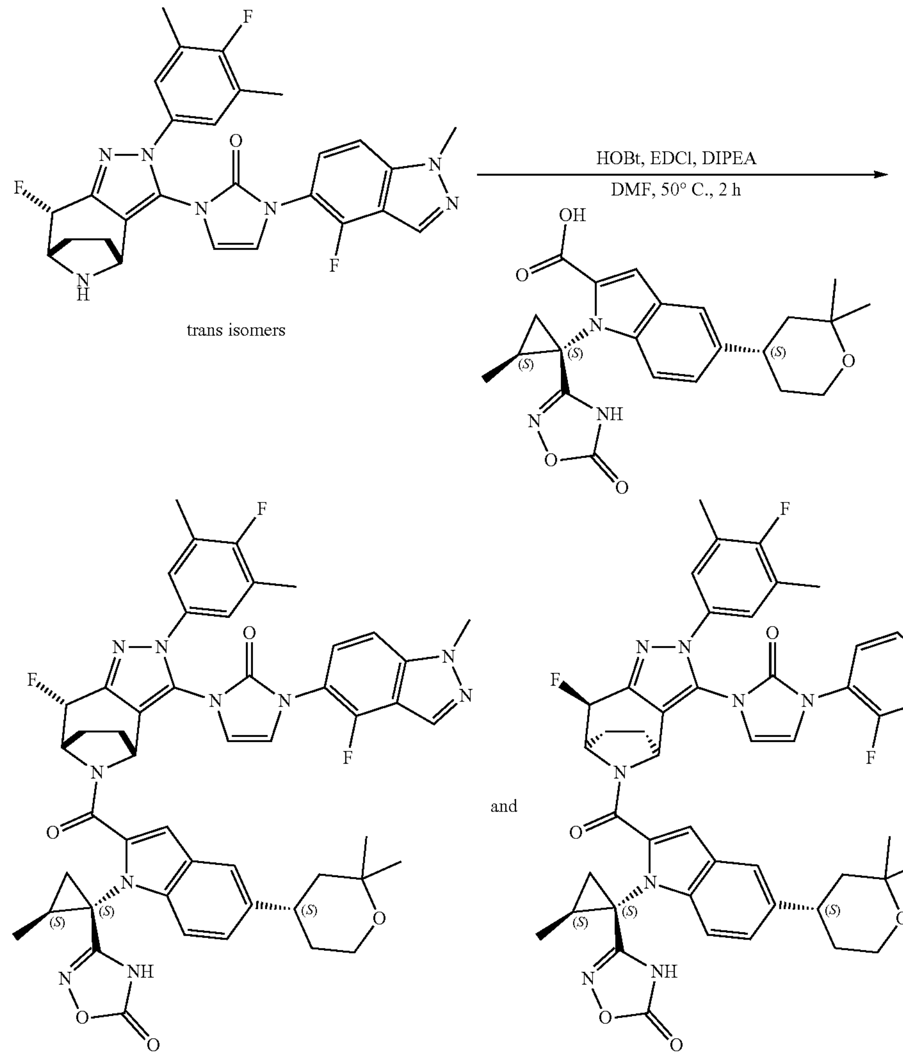

trans isomers and

To a mixture of trans-1-(4-fluoro-1-methyl-1H-indazol-5-yl)-3-(8-fluoro-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (100.00 mg, 182.86 μmol, 1 eq) and 5-((S)-2,2-dimethyltetrahydro-2H-pyran-4-yl)-1-((1S, 2S)-2-methyl-1-(5-oxo-4,5-dihydro-1,2,4-oxadiazol-3-yl) cyclopropyl)-1H-indole-2-carboxylic acid (75.24 mg, 182.86 μmol, 1 eq) in DMF (2 mL) was added DIEA (118.16 mg, 914.31 μmol, 5 eq) and HOBt (49.42 mg, 365.72 μmol, 2 eq), EDCI (70.11 mg, 365.72 μmol, 2 eq) in one portion at 50° C. under $N_2$. The mixture was stirred at 50° C. for 2 hours. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by prep-HPLC (column: Phenomenex Luna C18 75*30 mm*3 um; mobile phase: [$H_2O$ (0.1% TFA)-ACN]; gradient: 50%-80% B over 8.0 min) to give trans-3-((1,2S)-1-(5-((S)-2,2-dimethyltetrahydro-2H-pyran-4-yl)-2-((4S,7R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4, 7-epiminocyclohepta [c]pyrazole-9-carbonyl)-1H-indol-1-yl)-2-methylcyclopropyl)-1,2,4-oxadiazol-5 (4H)-one (50 mg, 54.22 μmol, 29.66% yield). $^1H$ NMR (400 MHz, DMSO-$d_6$) δ=12.22-11.58 (m, 1H), 8.37-8.21 (m, 1H), 7.68-6.74 (m, 10H), 5.66 (br s, 3H), 4.19-4.02 (m, 3H), 3.74-3.43 (m, 2H), 3.05-2.72 (m, 1H), 2.32-1.74 (m, 10H), 1.68-1.40 (m, 6H), 1.37 (br s, 10H). $^1H$ NMR (400 MHz, DMSO-$d_6$+$D_2O$) δ=8.37-8.19 (m, 1H), 7.70-6.68 (m, 10H), 5.84-5.13 (m, 3H), 4.08 (d, J=1.9 Hz, 3H), 3.74-3.64 (m, 1H), 3.58-3.41 (m, 1H), 3.10-2.71 (m, 1H), 2.31-1.77 (m, 10H), 1.69-1.40 (m, 6H), 1.34-0.84 (m, 10H) (N—H was not detected). LC-MS (ES+, m/z): 893.4 [$(M-F)^+$]; Rt=3.144 min. HRMS (EI): m/z $[M+H]^+$ found: 913.3794

Example 91 Compound 512

3-((1S,2S)-1-(5-((S)-2,2-dimethyltetrahydro-2H-pyran-4-yl)-2-((4S,7R,8R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one

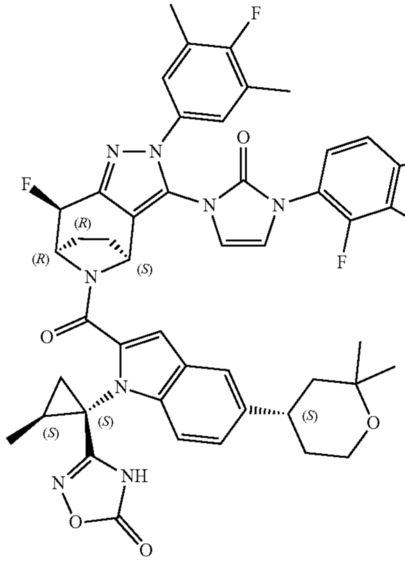

Example 92 Compound 513

3-((1S,2S)-1-(5-((S)-2,2-dimethyltetrahydro-2H-pyran-4-yl)-2-((4R,7S,8S)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5(4H)-one

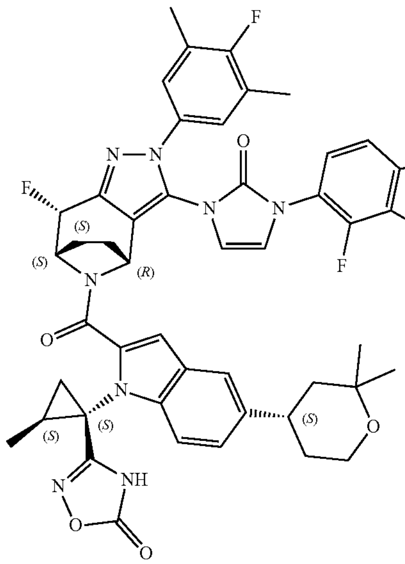

Step 1: 3-((1S,2S)-1-(5-((S)-2,2-dimethyltetrahydro-2H-pyran-4-yl)-2-((4S,7R,8R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one and 3-((1S,2S)-1-(5-((S)-2,2-dimethyltetrahydro-2H-pyran-4-yl)-2-((4R,7S,8S)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one The trans-3-((1S,2S)-1-(5-((S)-2,2-dimethyltetrahydro-2H-pyran-4-yl)-2-(-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (40 mg, 43.38 μmol, 1 eq) was separated by prep-HPLC (column: 2_Phenomenex Gemini C18 75*40 mm*5 um; mobile phase: [$H_2O$ (10 mM $NH_4HCO_3$)-ACN]; gradient: 30%-60% B over 8.0 min) to give 3-((1S,2S)-1-(5-((S)-2,2-dimethyltetrahydro-2H-pyran-4-yl)-2-((4S,7R,8R)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one (1st eluent, RT=2.971 by SFC, 10.58 mg, 11.59 μmol, 26.72% yield). $^1H$ NMR (400 MHz, DMSO-$d_6$) δ=12.44-10.91 (m, 1H), 8.55-8.25 (m, 1H), 7.77-6.68 (m, 10H), 5.94-5.16 (m, 3H), 4.14-3.98 (m, 3H), 3.84-3.43 (m, 2H), 3.10-2.70 (m, 1H), 2.31-1.78 (m, 10H), 1.68-1.42 (m, 6H), 1.35 (br s, 4H), 1.20-0.78 (m, 6H). LC-MS (ES+, m/z): 913.3 [$(M+H)^+$]; Rt=2.963 min. HRMS (EI): m/z $[M+H]^+$ found: 913.3722

And 3-((1S,2S)-1-(5-((S)-2,2-dimethyltetrahydro-2H-pyran-4-yl)-2-((4R,7S,8S)-8-fluoro-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-1H-indol-1-yl)-2-methylcyclopropyl)-1,2,4-oxadiazol-5 (4H)-one ($2^{nd}$ eluent, RT=2.580 by SFC, 10.85 mg, 11.88 μmol, 27.40% yield). $^1H$ NMR (400 MHz, DMSO-$d_6$) δ=12.27-11.51 (m, 1H), 8.30 (s, 1H), 7.67-6.78 (m, 10H), 5.87-5.06 (m, 3H), 4.10 (s, 3H), 3.79-3.50 (m, 2H), 3.10-2.74 (m, 1H), 2.32-1.74 (m, 10H), 1.69-1.43 (m, 6H), 1.40-1.20 (m, 4H), 1.17-0.84 (m, 6H). LC-MS (ES+, m/z): 913.3 [$(M+H)^+$]; Rt=3.036 min. HRMS (EI): m/z $[M+H]^+$ found: 913.3722

Example 93 Compound 516
3-((1R,2R)-1-(2-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((R)-4-oxaspiro[2.5]octan-7-yl)-1H-indol-1-yl)-2-methylcyclopropyl)-1, 2, 4-oxadiazol-5 (4H)-one
Scheme 516
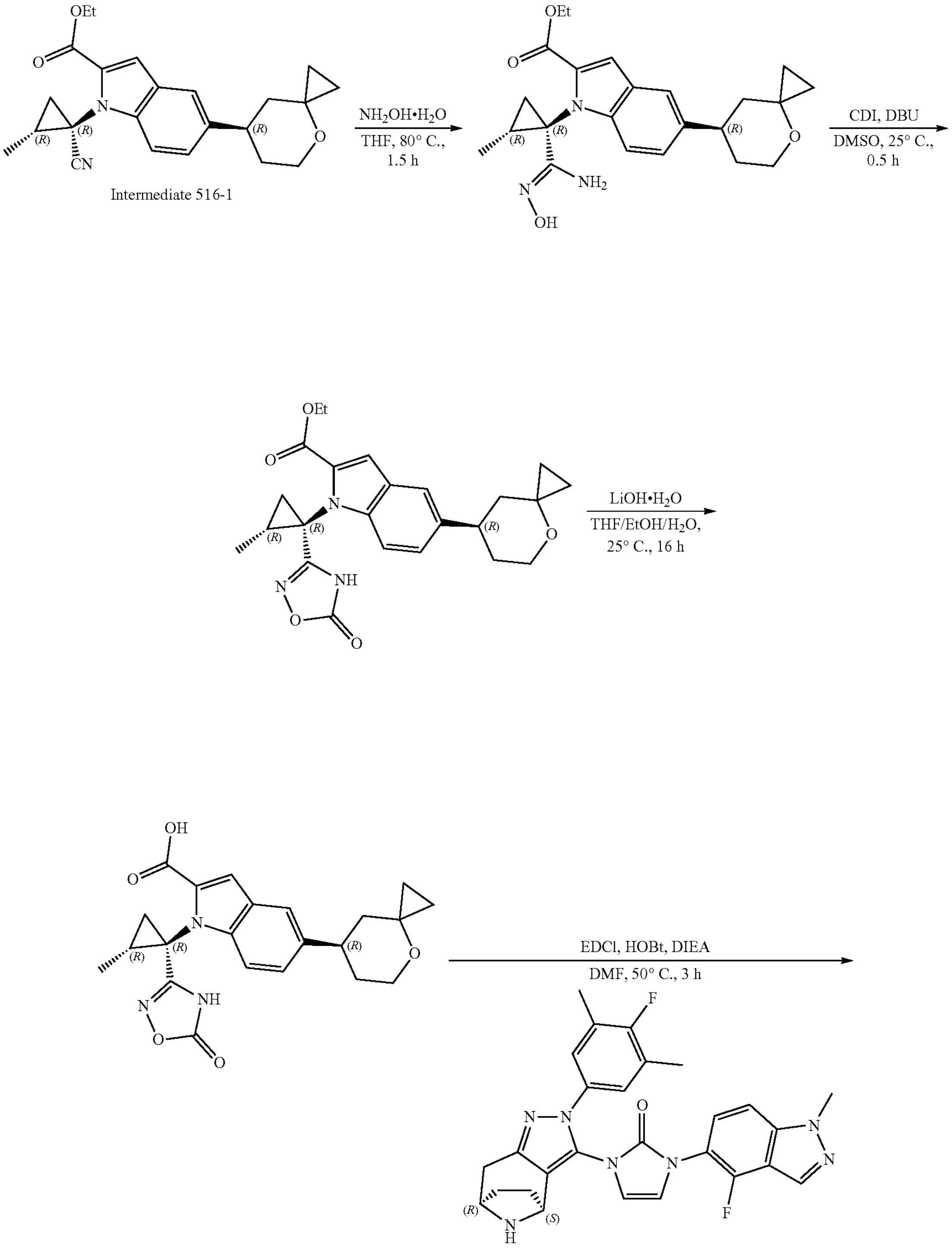

-continued

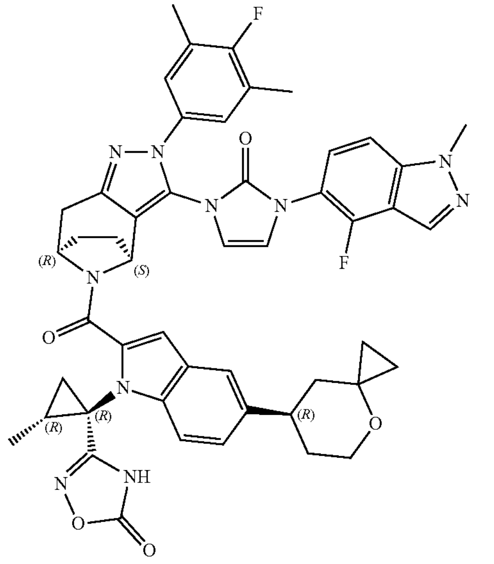

Step 1: ethyl 1-((1R,2R)-1-(N'-hydroxycarbamimidoyl)-2-methylcyclopropyl)-5-((R)-4-oxaspiro[2.5]octan-7-yl)-1H-indole-2-carboxylate

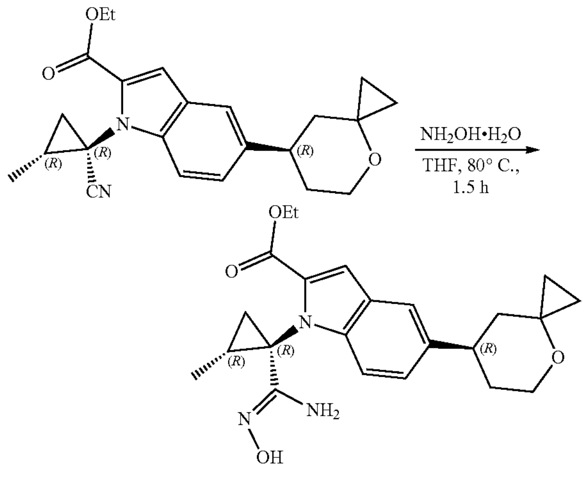

To a solution of ethyl 1-((1R,2R)-1-cyano-2-methylcyclopropyl)-5-((R)-4-oxaspiro[2.5]octan-7-yl)-1H-indole-2-carboxylate (330 mg, 871.95 μmol, 1 eq) in THF (3.3 mL) was added $NH_2OH·H_2O$ (576.01 mg, 8.72 mmol, 50% purity, 10 eq). The mixture was stirred at 80° C. for 1.5 hours under $N_2$. LCMS indicated the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated in vacuo to give ethyl 1-((1R,2R)-1-(N'-hydroxycarbamimidoyl)-2-methylcyclopropyl)-5-((R)-4-oxaspiro[2.5]octan-7-yl)-1H-indole-2-carboxylate (300 mg, crude). LC-MS (ES+, m/z): 412.2 [$(M+H)^+$]; Rt=0.483 min.

Step 2: ethyl 1-((1R,2R)-2-methyl-1-(5-oxo-4,5-dihydro-1, 2, 4-oxadiazol-3-yl)cyclopropyl)-5-((R)-4-oxaspiro[2.5]octan-7-yl)-1H-indole-2-carboxylate

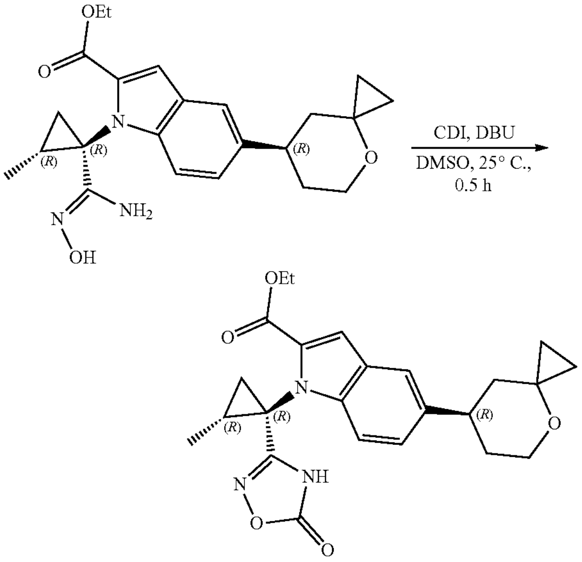

To a solution of ethyl 1-((1R,2R)-1-(N'-hydroxycarbamimidoyl)-2-methylcyclopropyl)-5-((R)-4-oxaspiro[2.5]octan-7-yl)-1H-indole-2-carboxylate (300 mg, 592.72 μmol, 1 eq) in DMSO (3 mL) was added CDI (192.22 mg, 1.19 mmol, 2 eq) and DBU (225.58 mg, 1.48 mmol, 2.5 eq). The mixture was stirred at 25° C. for 0.5 hour under $N_2$. LCMS indicated the reaction was completed. The mixture was added dropwise to $H_2O$ (20 mL) and then extracted with DCM (20 mL*3). The organic layers were combined, washed with water (50 mL), saturated brine (50 mL), dried over $Na_2SO_4$, filtered and concentrated in vacuo. The residue was purified by prep-TLC ($SiO_2$, hexanes/Ethyl acetate=1/5) to give ethyl 1-((1R,2R)-2-methyl-1-(5-oxo-4, 5-dihydro-1, 2, 4-oxadiazol-3-yl)cyclopropyl)-5-((R)-4-oxaspiro[2.5]octan-7-yl)-1H-indole-2-carboxylate (240 mg, 373.04 μmol, 62.94% yield). LC-MS (ES+, m/z): 438.2 [(M+H)+]. Rt=0.616 min.

Step 3: 1-((1R,2R)-2-methyl-1-(5-oxo-4,5-dihydro-1, 2, 4-oxadiazol-3-yl)cyclopropyl)-5-((R)-4-oxaspiro[2.5]octan-7-yl)-1H-indole-2-carboxylic acid

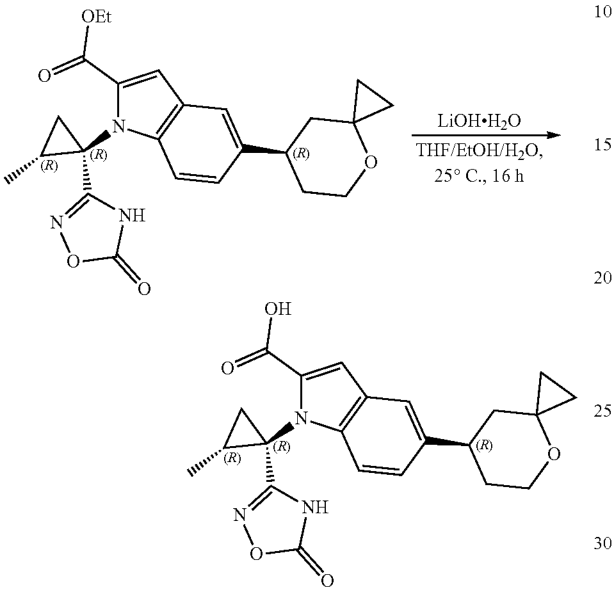

To a solution of ethyl 1-((1R,2R)-2-methyl-1-(5-oxo-4,5-dihydro-1, 2, 4-oxadiazol-3-yl) cyclopropyl)-5-((R)-4-oxaspiro[2.5]octan-7-yl)-1H-indole-2-carboxylate (240 mg, 373.04 μmol, 1 eq) in THF (0.8 mL), EtOH (0.8 mL) and $H_2O$ (0.8 mL) was added LiOH·$H_2O$ (156.54 mg, 3.73 mmol, 10 eq). The mixture was stirred at 25° C. for 16 hours under $N_2$. LCMS indicated that the reaction was completed. The mixture was concentrated in vacuo. The residue was dissolved in water (10 mL), adjusted to pH=4 with HCl (2 M), and then extracted with DCM (15 mL*3). The organic layers were combined, washed with water (50 mL), saturated brine (50 mL), dried over $Na_2SO_4$, filtered and concentrated in vacuo to give 1-((1R,2R)-2-methyl-1-(5-oxo-4, 5-dihydro-1, 2, 4-oxadiazol-3-yl)cyclopropyl)-5-((R)-4-oxaspiro[2.5]octan-7-yl)-1H-indole-2-carboxylic acid (120 mg, crude). LC-MS (ES+, m/z): 410.1 [(M+H)+]. Rt=0.520 min.

Step 4: 3-((1R,2R)-1-(2-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c] pyrazole-9-carbonyl)-5-((R)-4-oxaspiro[2.5]octan-7-yl)-1H-indol-1-yl)-2-methylcyclopropyl)-1, 2, 4-oxadiazol-5 (4H)-one

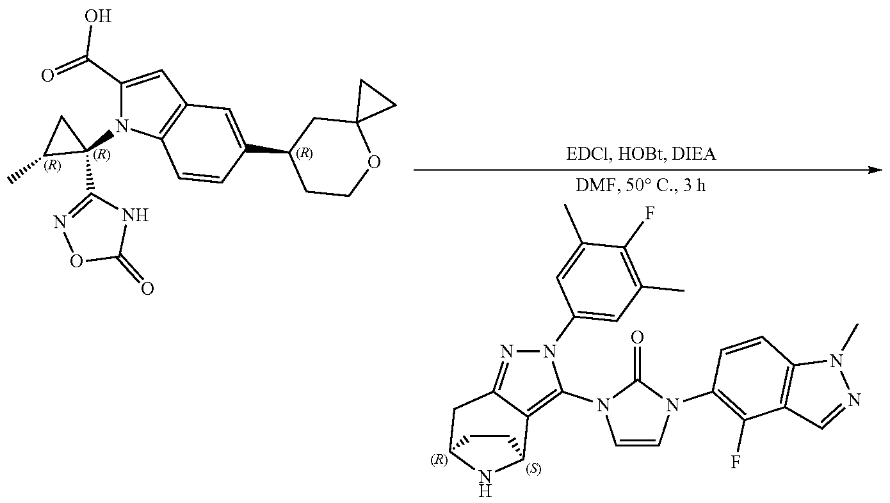

-continued

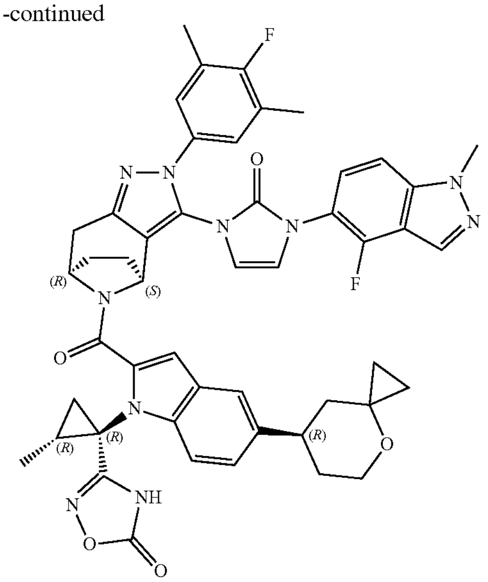

To a solution of 1-((1R,2R)-2-methyl-1-(5-oxo-4,5-dihydro-1, 2, 4-oxadiazol-3-yl) cyclopropyl)-5-((R)-4-oxaspiro[2.5]octan-7-yl)-1H-indole-2-carboxylic acid (60 mg, 138.34 μmol, 1 eq), 1-(4-fluoro-1-methyl-1H-indazol-5-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (69.38 mg, 138.34 μmol, 1 eq) and DIPEA (89.40 mg, 691.69 μmol, 5 eq) in DMF (1.2 mL) was added EDCI (34.48 mg, 179.84 μmol, 1.3 eq) and HOBt (28.04 mg, 207.51 μmol, 1.5 eq). The mixture was stirred at 50° C. for 3 hours under $N_2$. LCMS showed the reaction was completed. The mixture was filtered. The filtrate was purified by prep-HPLC (column: Phenomenex Luna C18 80*40 mm*3 um; mobile phase: [$H_2O$ (0.1% TFA)-ACN]; gradient: 50%-90% B over 10.0 min) to give 3-((1R,2R)-1-(2-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((R)-4-oxaspiro[2.5]octan-7-yl)-1H-indol-1-yl)-2-methylcyclopropyl)-1, 2, 4-oxadiazol-5 (4H)-one (24.67 mg, 27.58 μmol, 19.94% yield). $^1H$ NMR (400 MHz, DMSO-$d_6$) δ=12.39-11.68 (m, 1H), 8.52-8.27 (m, 1H), 7.81-6.65 (m, 10H), 5.61-4.91 (m, 2H), 4.20 (s, 3H), 4.04-3.81 (m, 2H), 3.55-3.29 (m, 2H), 3.12-2.93 (m, 1H), 2.39-2.21 (m, 8H), 2.11-1.68 (m, 5H), 1.64-1.12 (m, 7H), 0.93-0.38 (m, 4H). LC-MS (ES+, m/z): 893.5 [$(M+H)^+$]; Rt=3.034 min. HRMS (EI): m/z $[M+H]^+$ found: 893.3714.

Example 94 Compound 517

3-((1R,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

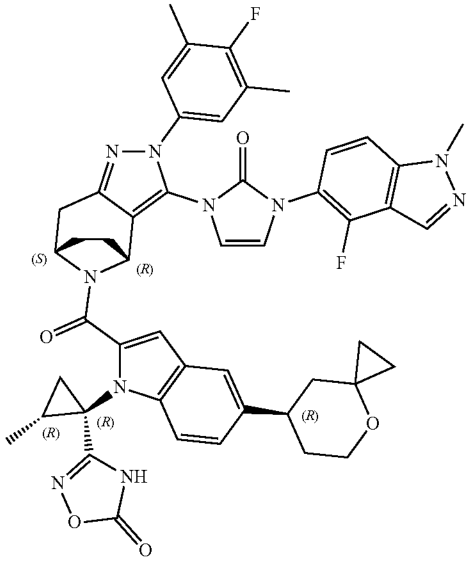

Step 1: 3-((1R,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

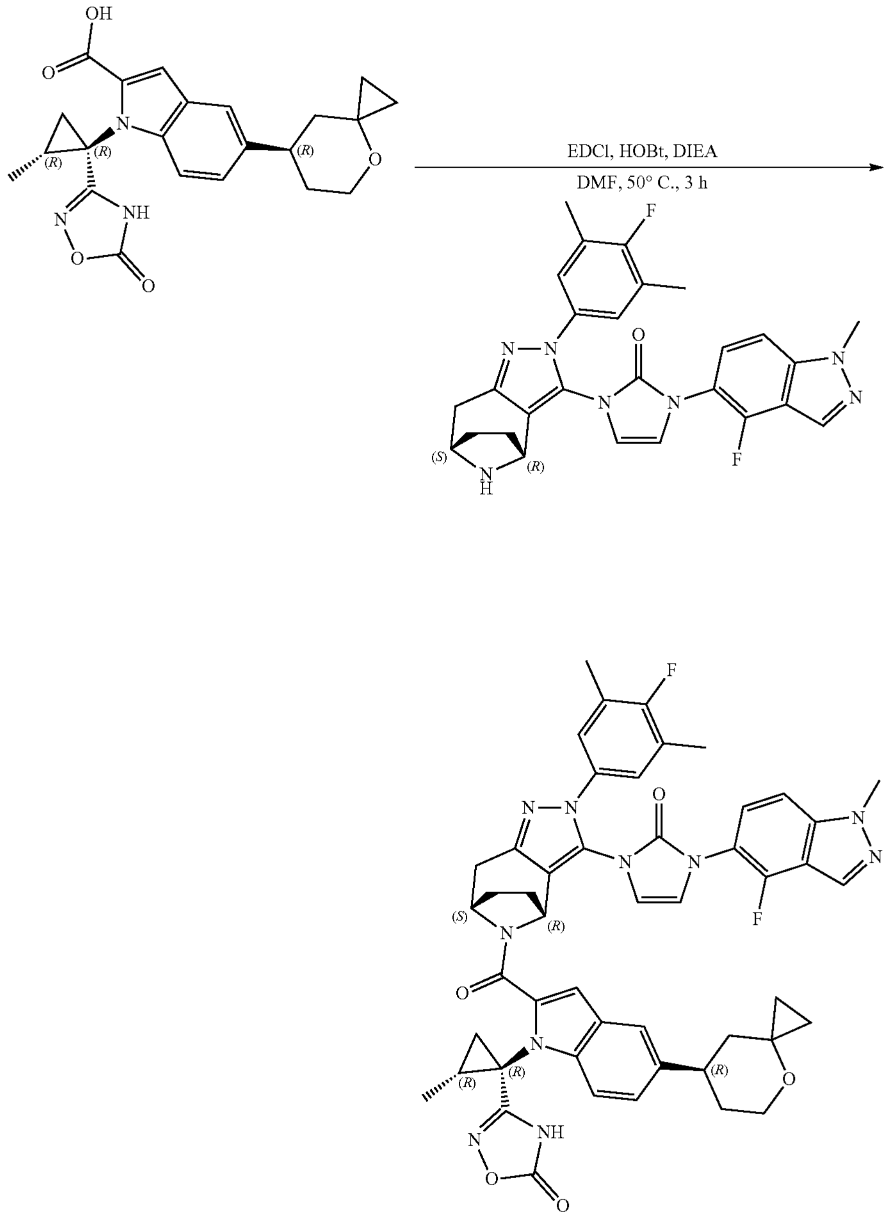

A mixture of 1-((1R,2R)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid (60 mg, 146.54 μmol, 1 eq), 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1H-imidazol-2 (3H)-one (73.47 mg, 146.49 μmol, 1 eq), EDCI (42.14 mg, 219.82 μmol, 1.5 eq), HOBt (29.70 mg, 219.82 μmol, 1.5 eq), DIPEA (94.70 mg, 732.72 μmol, 127.63 μL, 5 eq) in DMF (0.6 mL) was stirred at 50° C. for 1 hour under $N_2$. LCMS indicated the reaction was completed. The mixture was filtered. The filtrate was purified by prep-HPLC (column: Phenomenex Luna C18 80*40 mm*3 um; mobile phase: [$H_2O$ (0.1% TFA)-ACN]; gradient: 50%-90% B over 10.0 min) to give 3-((1R,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one (39.53 mg, 43.56 μmol, 29.73% yield). $^1$H NMR (400 MHz, DMSO-$d_6$) δ=12.28-11.69 (m, 1H), 8.43-8.08 (m, 1H), 7.76-6.63 (m, 10H), 5.63-4.89 (m, 2H), 4.13-4.07 (m, 3H), 3.52-3.34 (m, 2H), 3.21-2.79 (m, 3H), 2.32-2.08 (m, 9H), 1.95-1.00 (m, 11H), 0.78-0.28 (m, 4H). LC-MS (ES+, m/z): 893.4 [(M+H)$^+$]; Rt=3.184 min. HRMS (EI): m/z [M+H]$^+$ found: 893.3689.

Example 95 Compound 518
3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-1H-indol-1-yl)-2-methylcyclopropyl)-1,2,4-oxadiazol-5(4H)-one
Scheme 518
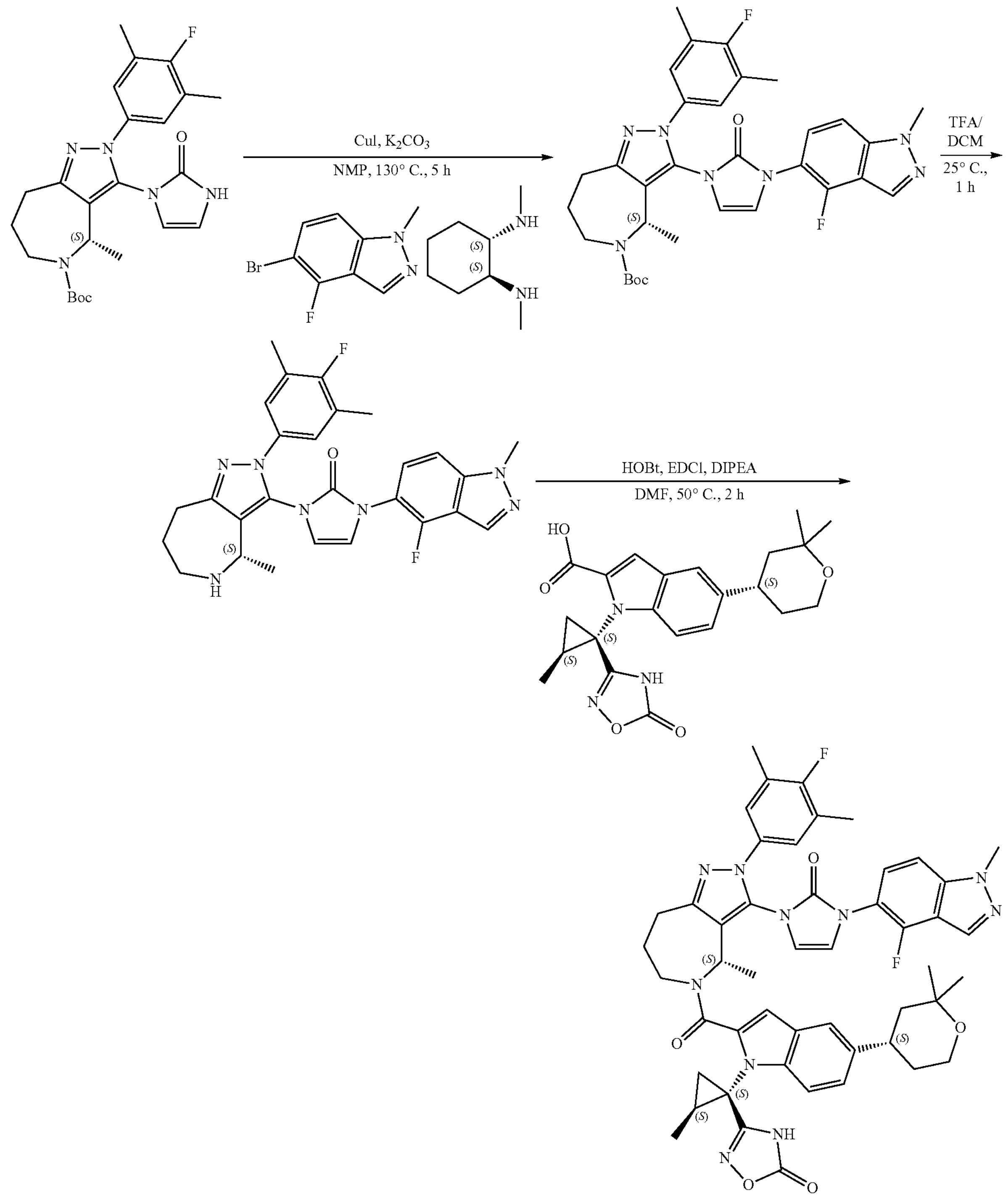

Step 1: (S)-tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,6,7,8-tetrahydropyrazolo[4,3-c]azepine-5 (2H)-carboxylate

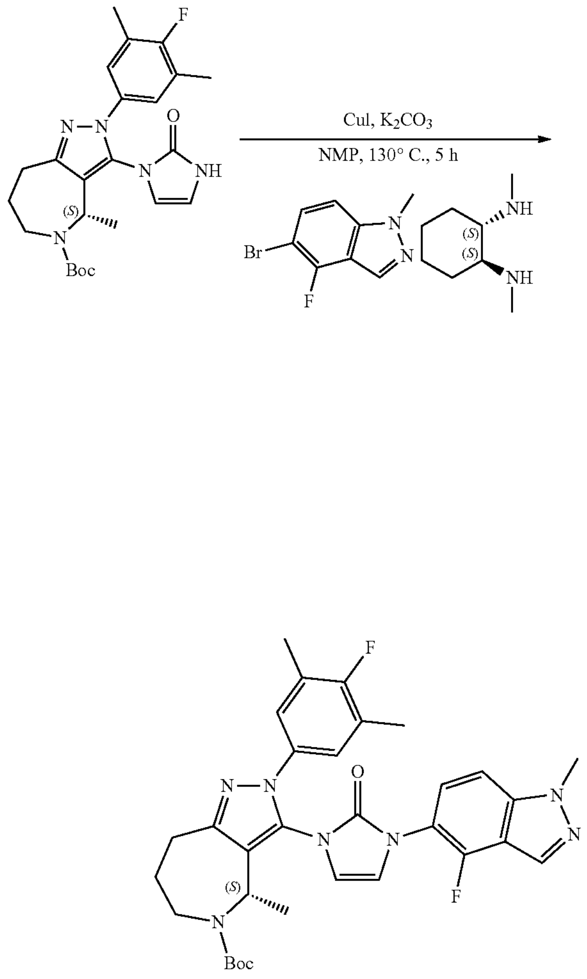

To a solution of tert-butyl (S)-2-(4-fluoro-3,5-dimethylphenyl)-4-methyl-3-(2-oxo-2,3-dihydro-1H-imidazol-1-yl)-2,6,7,8-tetrahydropyrazolo[4,3-c]azepine-5 (4H)-carboxylate (0.25 g, 521.38 μmol, 1 eq), 5-bromo-4-fluoro-1-methyl-1H-indazole (238.84 mg, 1.04 mmol, 2 eq), (1S, 2S)—$N^1$,$N^2$-dimethylcyclohexane-1,2-diamine (222.48 mg, 1.56 mmol, 3 eq) in NMP (2.5 mL) was added $K_2CO_3$ (144.11 mg, 1.04 mmol, 2 eq) and CuI (198.59 mg, 1.04 mmol, 2 eq). The mixture was stirred at 130° C. for 5 hours under $N_2$. LCMS showed the reaction was completed. The aqueous phase was extracted with ethyl acetate (20 mL*3). The combined organic phase was washed with saturated brine (20 mL*3), dried with anhydrous $Na_2SO_4$, filtered and concentrated in vacuo. The residue was purified by column chromatography ($SiO_2$, hexanes:ethyl acetate=1/1) to give tert-butyl (S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,6,7,8-tetrahydropyrazolo[4,3-c] azepine-5 (4H)-carboxylate (0.25 g, 389.29 μmol, 74.67% yield). LC-MS (ES+, m/z): 604.3 [$(M+H)^+$]; Rt=0.622 min.

Step 2: (S)-1-(4-fluoro-1-methyl-1H-indazol-5-yl)-3-(2-(4-fluoro-3,5-dimethylphenyl)-4-methyl-2,4,5,6,7,8-hexahydropyrazolo[4,3-c]azepin-3-yl)-1H-imidazol-2 (3H)-one

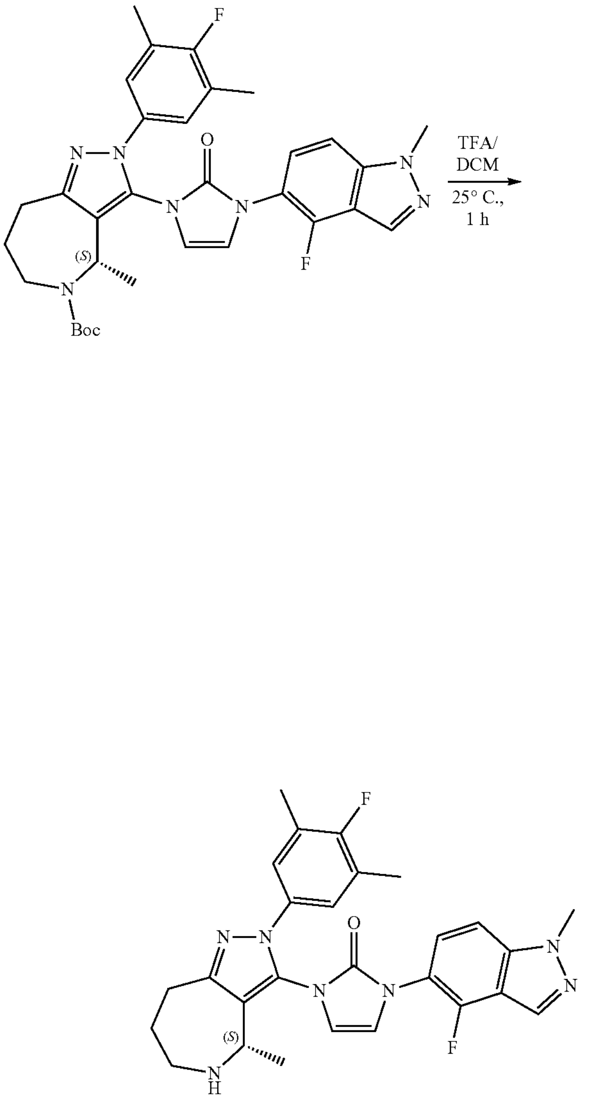

To a solution of(S)-tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-4,6,7,8-tetrahydropyrazolo[4,3-c]azepine-5 (2H)-carboxylate (0.25 g, 389.29 μmol, 1 eq) in DCM (2 mL) was added TFA (0.5 mL). The mixture was stirred at 25° C. for 1 hour. LCMS showed the reaction was completed. The residue was poured into saturated $Na_2CO_3$ (20 mL). The aqueous phase was extracted with ethyl acetate (10 mL*3). The combined organic phase was washed with saturated brine (30 mL), dried with anhydrous $Na_2SO_4$, filtered and concentrated in vacuo to give (S)-1-(4-fluoro-1-methyl-1H-indazol-5-yl)-3-(2-(4-fluoro-3,5-dimethylphenyl)-4-methyl-2,4,5,6,7,8-hexahydropyrazolo[4,3-c]azepin-3-yl)-1H-imidazol-2 (3H)-one (0.18 g, crude). LC-MS (ES+, m/z): 504.2 [$(M+H)^+$]; Rt=0.424 min.

Step 3: 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-1H-indol-1-yl)-2-methylcyclopropyl)-1,2,4-oxadiazol-5(4H)-one

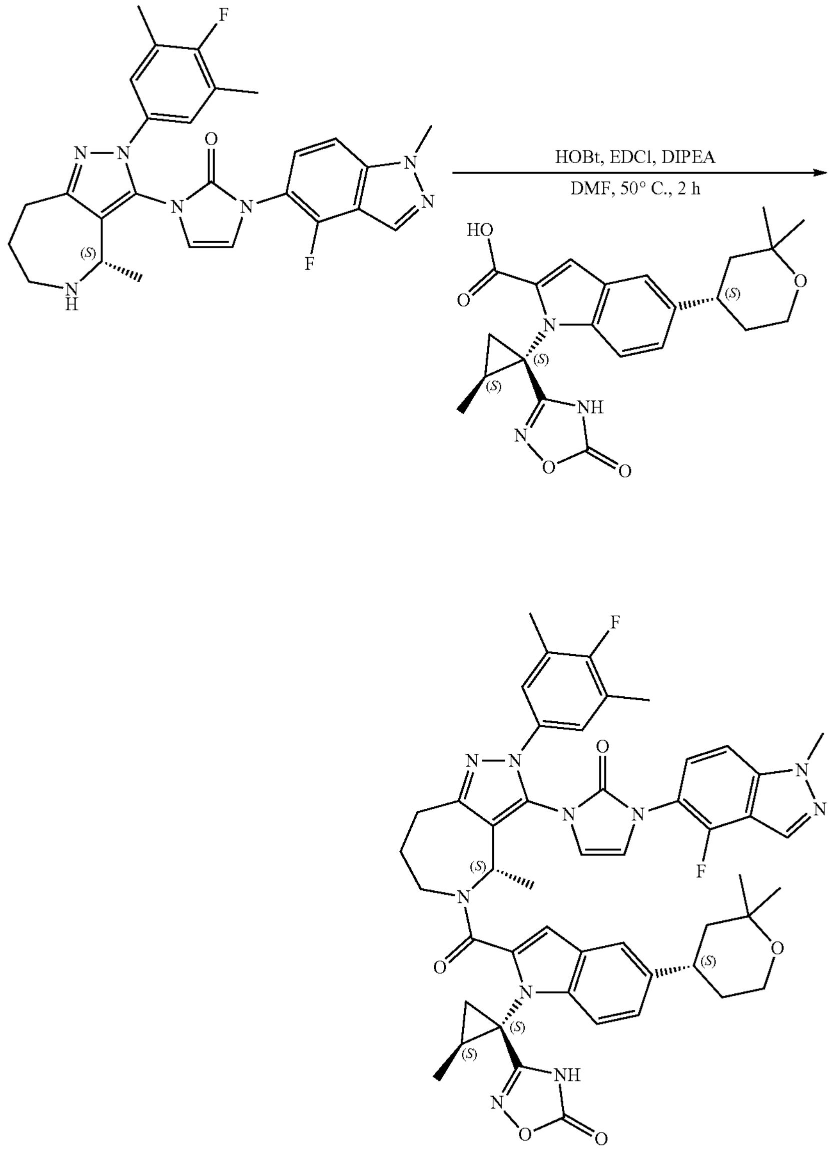

To a solution of(S)-1-(4-fluoro-1-methyl-1H-indazol-5-yl)-3-(2-(4-fluoro-3,5-dimethylphenyl)-4-methyl-2,4,5,6,7,8-hexahydropyrazolo[4,3-c]azepin-3-yl)-1H-imidazol-2(3H)-one (40 mg, 74.67 μmol, 1 eq), 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (30.72 mg, 74.67 μmol, 1 eq) in DMF (0.8 mL) was added HOBt (20.18 mg, 149.34 μmol, 2 eq), EDCI (28.63 mg, 149.34 μmol, 2 eq) and DIEA (48.25 mg, 373.35 μmol, 5 eq). The mixture was stirred at 25° C. for 16 hours under $N_2$. LCMS showed the reaction was completed. The residue was poured into water (10 mL). The aqueous phase was extracted with ethyl acetate (10 mL*3). The combined organic phase was washed with saturated brine (30 mL), dried with anhydrous $Na_2SO_4$, filtered and concentrated in vacuo. The residue was purified by prep-HPLC (TFA condition; column: Phenomenex Luna C18 75*30 mm*3 um; mobile phase: [$H_2O$ (0.1% TFA)-ACN]; gradient: 45%-75% B over 8.0 min) to give 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-1H-indol-1-yl)-2-methylcyclopropyl)-1,2,4-oxadiazol-5 (4H)-one (8.24 mg, 9.19 μmol, 12.30% yield). $^1H$ NMR (400 MHz, DMSO-$d_6$) δ=12.65-11.30 (m, 1H), 8.51-8.06 (m, 1H), 7.75-5.24 (m, 11H), 4.86-4.16 (m, 1H), 4.09 (s, 3H), 3.76-3.58 (m, 3H), 3.14-2.88 (m, 3H), 2.29-2.04 (m, 7H), 1.83-0.88 (m, 20H) $^1H$ NMR (400 MHz, DMSO-$d_6$+$D_2O$) δ=8.46-7.97 (m, 1H), 7.74-5.23 (m, 11H), 4.85-4.41 (m, 1H), 4.02 (br s, 3H), 3.78-3.27 (m, 3H), 2.99 (br s, 3H), 2.28-1.93 (m, 7H), 1.91-0.41 (m, 20H). LC-MS (ES+, m/z): 897.4 [$(M+H)^+$]; Rt=3.174 min. HRMS (EI): m/z $[M+H]^+$ found: 897.3966.

Example 96 Compound 519
3-((1R,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one
Scheme 519
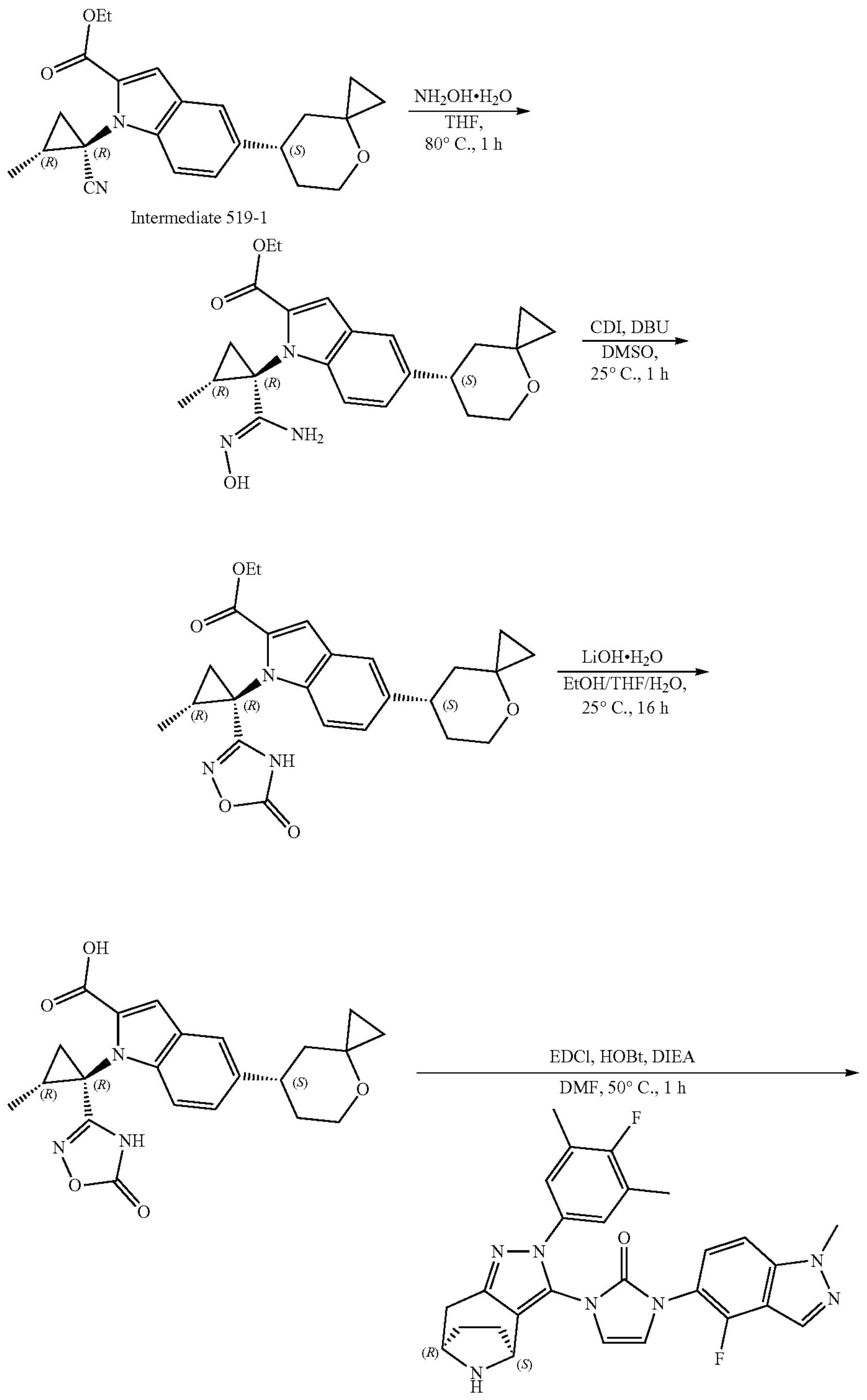

-continued

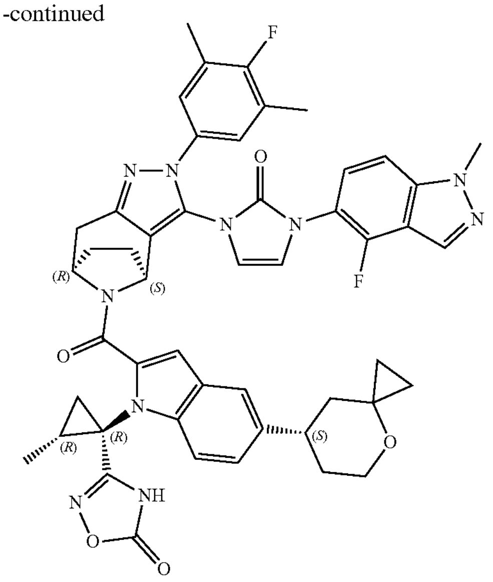

Step 1: ethyl 1-((1R,2R)-1-(N'-hydroxycarbamimidoyl)-2-methylcyclopropyl)-5-((S)-4-oxaspiro[2.5]octan-7-yl)-1H-indole-2-carboxylate

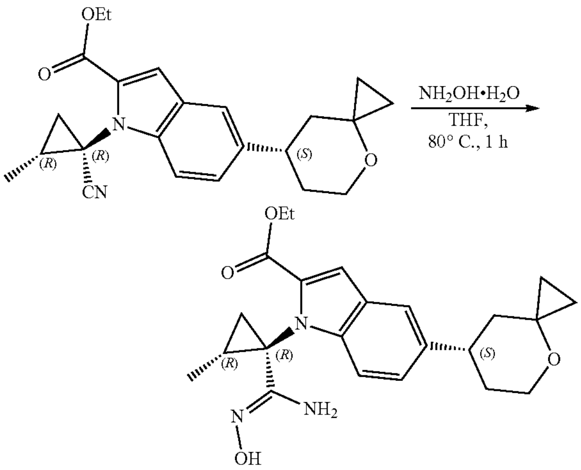

To a solution of ethyl 1-((1R,2R)-1-cyano-2-methylcyclopropyl)-5-((S)-4-oxaspiro[2.5]octan-7-yl)-1H-indole-2-carboxylate (400 mg, 1.06 mmol, 1 eq) in THF (4 mL) was added hydroxylamine (698.19 mg, 10.57 mmol, 26.42 μL, 50% purity, 10 eq). The mixture was stirred at 80° C. for 1 hour under $N_2$. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure to give ethyl 1-((1R,2R)-1-(N'-hydroxycarbamimidoyl)-2-methylcyclopropyl)-5-((S)-4-oxaspiro[2.5]octan-7-yl)-1H-indole-2-carboxylate (380 mg, crude). LC-MS (ES+, m/z): 412.3 [$(M+H)^+$]; Rt=1.484 min.

Step 2: ethyl 1-((1R,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate

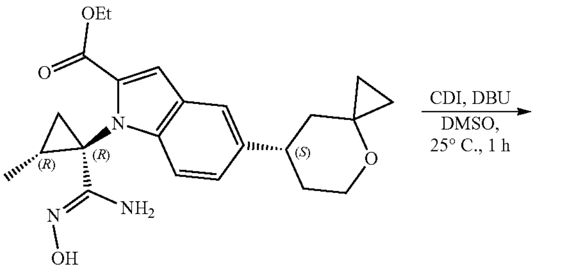

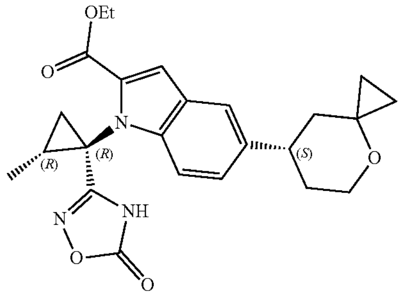

To a solution of ethyl 1-((1R,2R)-1-(N'-hydroxycarbamimidoyl)-2-methylcyclopropyl)-5-((S)-4-oxaspiro[2.5]octan-7-yl)-1H-indole-2-carboxylate (380 mg, 795.10 μmol, 1 eq) in DMSO (4 mL) was added DBU (302.62 mg, 1.99 mmol, 299.62 μL, 2.5 eq) and CDI (257.85 mg, 1.59 mmol, 2 eq). The mixture was stirred at 25° C. for 1 hour under $N_2$. LCMS showed the reaction was completed. The reaction mixture was poured into water (150 mL), then extracted with ethyl acetate (80 mL*3). The combined organic layers were washed with saturated brine (80 mL), dried over anhydrous $Na_2SO_4$, filtered and concentrated under reduced pressure. The residue was purified by column chromatography ($SiO_2$, hexanes: Ethyl acetate-3:1) to give ethyl 1-((1R,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylate (300 mg, 637.73 μmol, 80.21% yield). LC-MS (ES+, m/z): 438.1 [(M+H)$^+$]; Rt=0.623 min.

Step 3: 1-((1R,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid

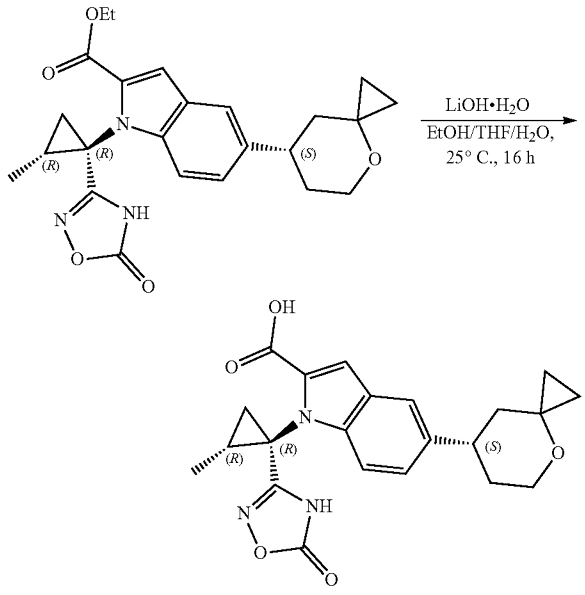

To a solution of ethyl 1-((1R,2R)-2-methyl-1-(5-oxo-4,5-dihydro-1,2,4-oxadiazol-3-yl) cyclopropyl)-5-((S)-4-oxaspiro[2.5]octan-7-yl)-1H-indole-2-carboxylate (300 mg, 637.73 μmol, 1 eq) in THF (1 mL) and $H_2O$ (1 mL), EtOH (1 mL) was added LiOH·$H_2O$ (267.59 mg, 6.38 mmol, 10 eq). The mixture was stirred at 25° C. for 16 hours under $N_2$. LCMS showed the reaction was completed. The reaction mixture was poured into water (150 mL) and adjust to pH=4 for HCl (2 M, 30 mL), then extracted with ethyl acetate (80 mL*3). The combined organic layers were washed with saturated brine (80 mL), dried over anhydrous $Na_2SO_4$, filtered and concentrated under reduced pressure to give 1-((1R,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (160 mg, 367.34 μmol, 57.60% yield). LC-MS (ES+, m/z): 410.1 [(M+H)$^+$]; Rt=0.520 min.

Step 4: 3-((1R,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-5-((S)-4-oxaspiro[2.5]octan-7-yl)-1H-indol-1-yl)-2-methylcyclopropyl)-1,2,4-oxadiazol-5(4H)-one

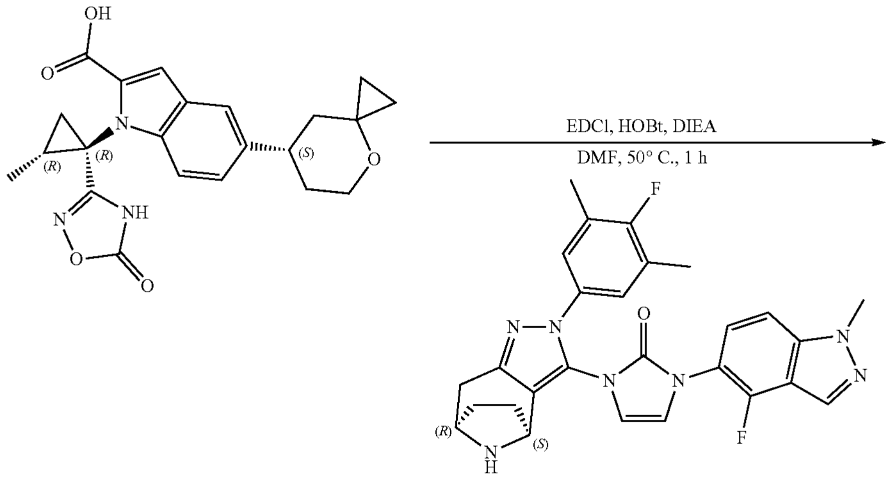

-continued

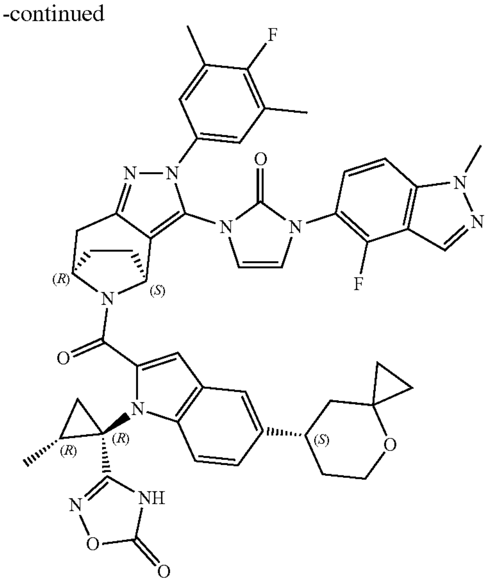

To a solution of 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (117.59 mg, 234.47 μmol, 1.2 eq) and 1-((1R,2R)-2-methyl-1-(5-oxo-4,5-dihydro-1,2,4-oxadiazol-3-yl) cyclopropyl)-5-((S)-4-oxaspiro[2.5]octan-7-yl)-1H-indole-2-carboxylic acid (80 mg, 195.39 μmol, 1 eq) in DMF (2 mL) was added EDCI (74.91 mg, 390.78 μmol, 2 eq) and DIEA (126.26 mg, 976.96 μmol, 170.16 μL, 5 eq), HOBt (52.80 mg, 390.78 μmol, 2 eq). The mixture was stirred at 50° C. for 1 hour under $N_2$. LCMS showed the reaction was completed. The reaction mixture was poured into water (50 mL), then extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (column: Phenomenex Luna 80*30 mm*3 um; mobile phase: [$H_2O$ (0.1% TFA)-ACN]; gradient: 50%-80% B over 8.0 min) to give 3-((1R,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (42.46 mg, 47.07 μmol, 24.09% yield, 99% purity). $^1$H NMR (400 MHz, DMSO-$d_6$) δ=12.28-11.61 (m, 1H), 8.31 (s, 1H), 7.72-6.70 (m, 10H), 5.53-4.80 (m, 2H), 4.10 (s, 3H), 3.43-3.24 (m, 3H), 3.05-2.79 (m, 2H), 2.32-2.07 (m; 9H), 2.01-1.58 (m, 5H), 1.51-1.04 (m, 6H), 0.80-0.28 (m, 4H). LC-MS (ES+, m/z): 893.4 [$(M+H)^+$]; Rt=3.037 min. HRMS (EI): m/z $[M+H]^+$ found: 893.3701.

Example 97 Compound 520

3-((1R,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

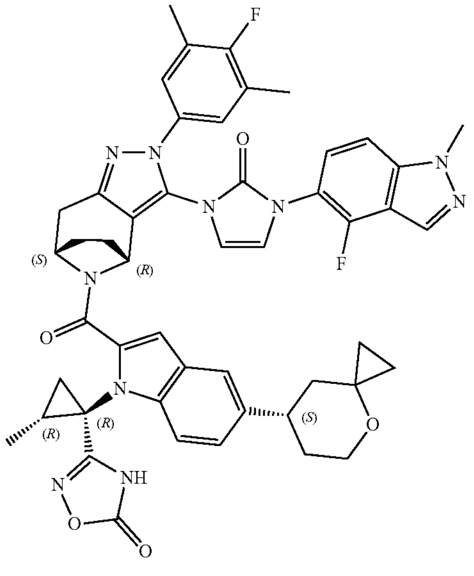

Step 1: 3-((1R,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

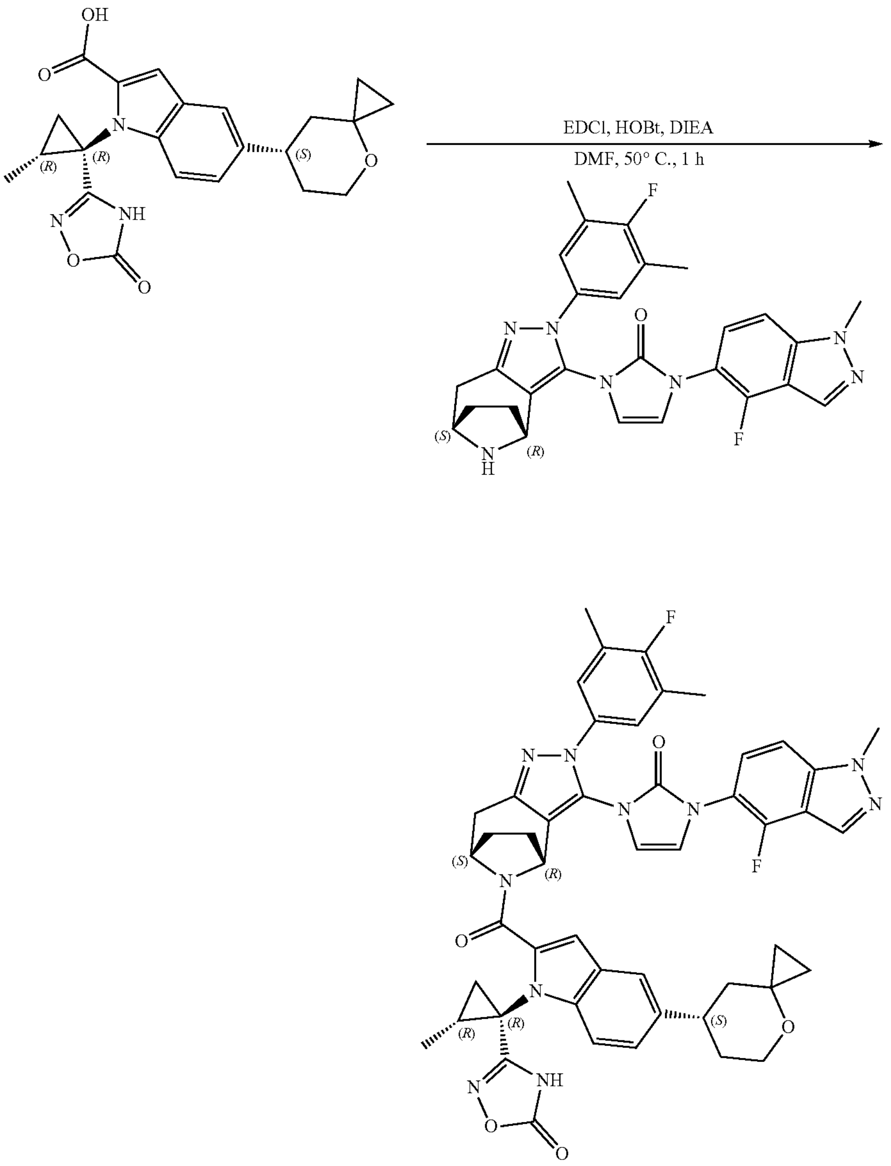

To a solution of 1-((1R,2R)-2-methyl-1-(5-oxo-4,5-dihydro-1,2,4-oxadiazol-3-yl)cyclopropyl)-5-((S)-4-oxaspiro [2.5]octan-7-yl)-1H-indole-2-carboxylic acid (80 mg, 195.39 μmol, 1 eq) and 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1H-imidazol-2 (3H)-one (146.99 mg, 293.09 μmol, 1.5 eq) in DMF (2 mL) was added HOBt (52.80 mg, 390.78 μmol, 2 eq), EDCI (74.91 mg, 390.78 μmol, 2 eq) and DIEA (126.26 mg, 976.96 μmol, 170.16 μL, 5 eq). The mixture was stirred at 50° C. for 1 hour under $N_2$. LC-MS showed the reaction was completed. The reaction mixture was diluted with water (50 mL) and stirred for 1 hour, extracted with ethyl acetate (50 mL*3). The combined organic layers were washed with saturated brine (50 mL*2), dried over $Na_2SO_4$, filtered and concentrated in vacuum. The residue was purified by prep-HPLC (TFA condition, column: 3_Phenomenex Luna C18 75*30 mm*3 um; mobile phase: [$H_2O$ (0.1% TFA)-ACN]; gradient: 50%-80% B over 8.0 min) to give 3-((1R,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (56.09 mg, 62.81 μmol, 32.15% yield). $^1H$ NMR (400 MHz, DMSO-$d_6$) δ=12.33-11.55 (m, 1H), 8.41-8.10 (m, 1H), 7.72-6.58 (m, 10H), 5.68-4.93 (m, 2H), 4.12-4.06 (m, 3H), 2.82 (br d, J=16.1 Hz, SH), 2.31-2.09 (m, 8H), 2.06-1.47 (m, 7H), 1.45-0.24 (m, 9H). LC-MS (ES+, m/z): 893.4 [$(M+H)^+$]; Rt=3.016 min. HRMS (EI): m/z $[M+H]^+$ found: 893.3701.

Example 98 Compound 521
3-((1S,2S)-1-(5-((S)-2,2-dimethyltetrahydro-2H-pyran-4-yl)-2-(2-(4-fluoro-3,5-dimethylphenyl)-3-(3-(5-fluorophthalazin-6-yl)-2-oxo-2,3-dihydro-1H-imidazol-1-yl)-2,4,5,6,7,8-hexahydropyrazolo[4,3-c]azepine-5-carbonyl)-1H-indol-1-yl)-2-methylcyclopropyl)-1,2,4-oxadiazol-5 (4H)-one
Scheme 521
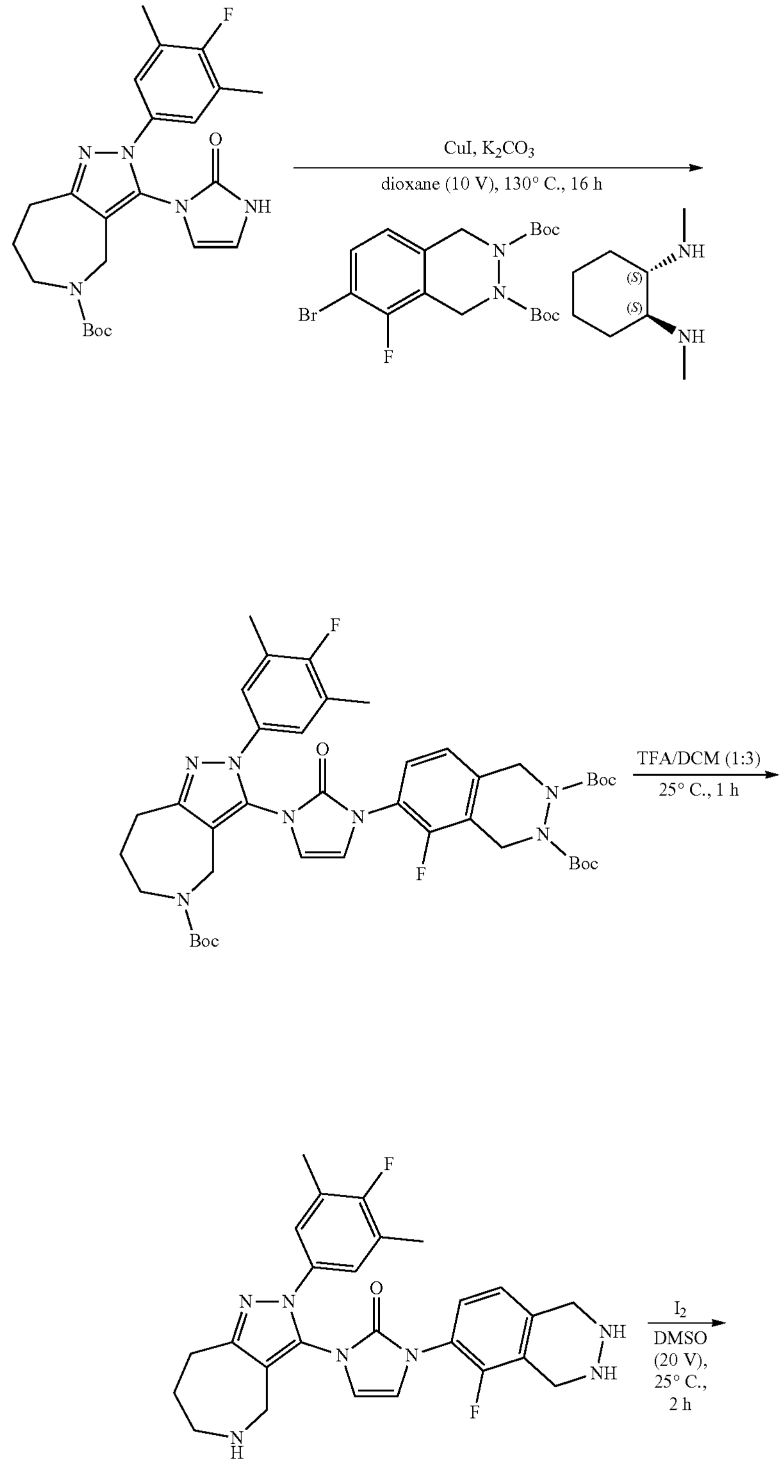

-continued

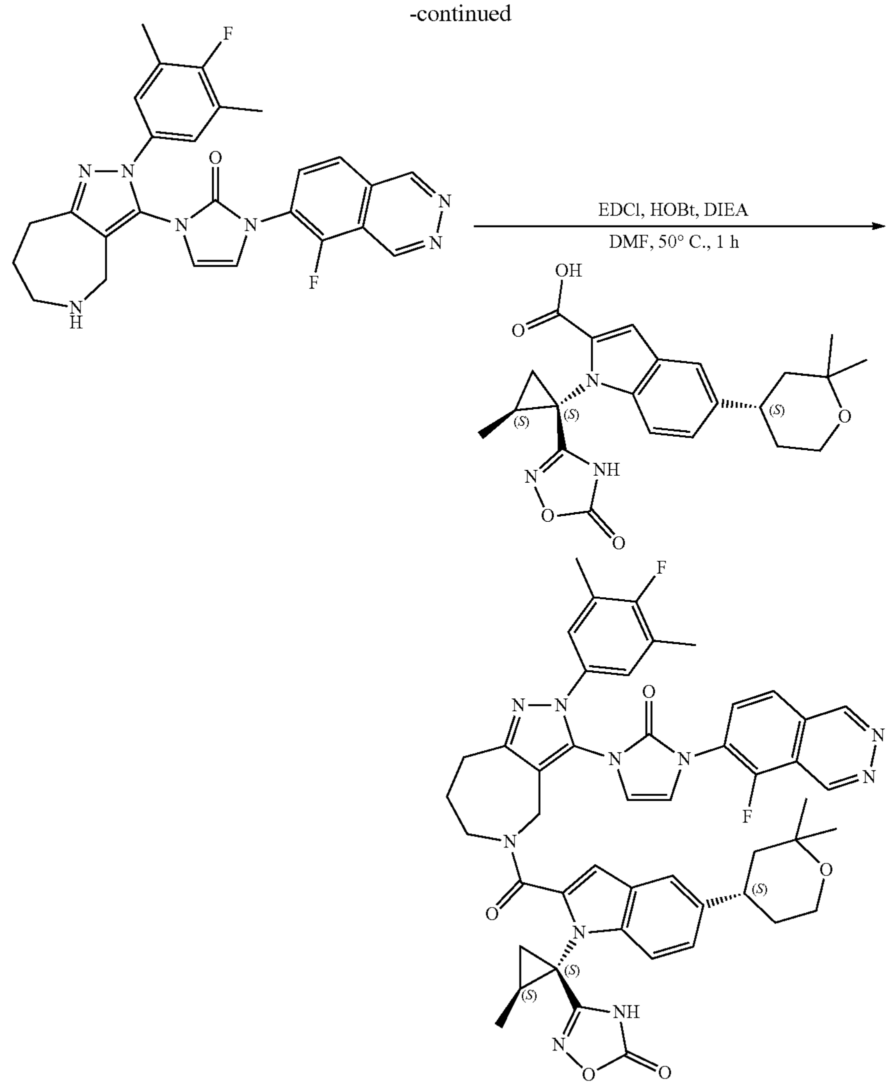

Step 1: di-tert-butyl 6-(3-(5-(tert-butoxycarbonyl)-2-(4-fluoro-3,5-dimethylphenyl)-2,4,5,6,7,8-hexahydropyrazolo[4,3-c]azepin-3-yl)-2-oxo-2,3-dihydro-1H-imidazol-1-yl)-5-fluoro-1,4-dihydrophthalazine-2,3-dicarboxylate

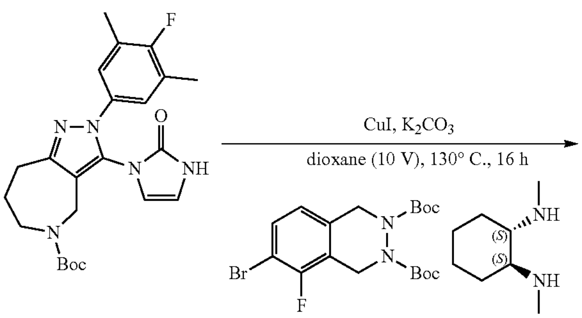

-continued

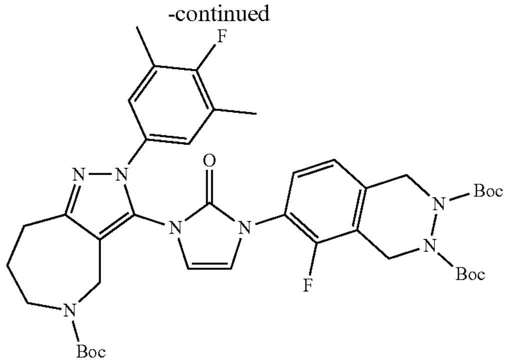

To a solution of tert-butyl 2-(4-fluoro-3,5-dimethylphenyl)-3-(2-oxo-2,3-dihydro-1H-imidazol-1-yl)-2,6,7,8-tetrahydropyrazolo[4,3-c]azepine-5 (4H)-carboxylate (200 mg, 453.00 μmol, 1 eq) and di-tert-butyl 6-bromo-5-fluoro-1,4-dihydrophthalazine-2,3-dicarboxylate (390.76 mg, 906.01 μmol, 2 eq) in NMP (2 mL) was added CuI (172.55 mg, 906.01 μmol, 2 eq), (1S,2S)—$N^1$,$N^2$-dimethylcyclohexane-1,2-diamine (128.87 mg, 906.01 μmol, 2 eq) and $K_2CO_3$ (187.83 mg, 1.36 mmol, 3 eq). The mixture was stirred at 130° C. for 16 hours under $N_2$. LCMS indicated the reaction was completed. The residue was poured into saturated EDTA solution (10 mL) and ethyl acetate (20 mL) stirred for 0.5 hour, and then extracted with ethyl acetate (20 mL*2). The organic layers were combined and washed with water (30 mL*2), saturated brine (20 mL*2), dried over $Na_2SO_4$, filtered, concentrated in vacuo. The residue was purified by prep-TLC ($SiO_2$, Commercial hexanes/ethyl acetate=1:1) to give di-tert-butyl 6-(3-(5-(tert-butoxycarbonyl)-2-(4-fluoro-3,5-dimethylphenyl)-2,4,5,6,7,8-hexahydropyrazolo[4,3-c]azepin-3-yl)-2-oxo-2,3-dihydro-1H-imidazol-1-yl)-5-fluoro-1,4-dihydrophthalazine-2,3-dicarboxylate (200 mg, 202.30 μmol, 44.66% yield). LC-MS (ES+, m/z): 792.3 [(M+H)$^+$]. Rt=0.740 min.

The reaction was repeated with tert-butyl 2-(4-fluoro-3,5-dimethylphenyl)-3-(2-oxo-2,3-dihydro-1H-imidazol-1-yl)-2,6,7,8-tetrahydropyrazolo[4,3-c]azepine-5 (4H)-carboxylate (700 mg, 1.59 mmol) to give di-tert-butyl 6-(3-(5-(tert-butoxycarbonyl)-2-(4-fluoro-3,5-dimethylphenyl)-2,4,5,6,7,8-hexahydropyrazolo[4,3-c]azepin-3-yl)-2-oxo-2,3-dihydro-1H-imidazol-1-yl)-5-fluoro-1,4-dihydrophthalazine-2,3-dicarboxylate (700 mg, 708.06 μmol, 44.66% yield). LC-MS (ES+, m/z): 792.4 [(M+H)$^+$]. Rt=0.721 min.

Step 2: 1-(5-fluoro-1,2,3,4-tetrahydrophthalazin-6-yl)-3-(2-(4-fluoro-3,5-dimethylphenyl)-2,4,5,6,7,8-hexahydropyrazolo[4,3-c]azepin-3-yl)-1,3-dihydro-2H-imidazol-2-one

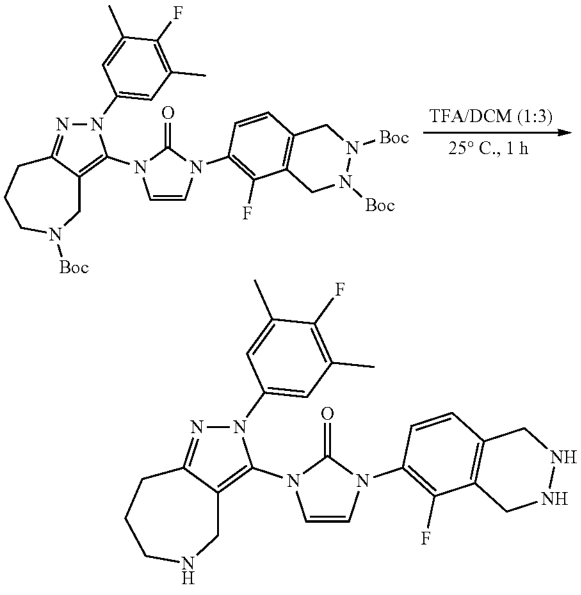

To a solution of di-tert-butyl 6-(3-(5-(tert-butoxycarbonyl)-2-(4-fluoro-3,5-dimethylphenyl)-2,4,5,6,7,8-hexahydropyrazolo[4,3-c]azepin-3-yl)-2-oxo-2,3-dihydro-1H-imidazol-1-yl)-5-fluoro-1,4-dihydrophthalazine-2,3-dicarboxylate (900 mg, 1.14 mmol, 1 eq) in DCM (9 mL) was added TFA (4.61 g, 40.39 mmol, 3 mL, 35.53 eq). The mixture was stirred at 25° C. for 1 hour under $N_2$. LCMS indicated the reaction was completed. The reaction mixture was removed TFA and DCM and adjusted to pH=7 with saturated $NaHCO_3$ (10 mL), and then extracted with DCM (20 mL*3). The organic layers were combined and washed with water (10 mL*2), saturated brine (10 mL*2), dried over $Na_2SO_4$, filtered, concentrated in vacuo to give 1-(5-fluoro-1,2,3,4-tetrahydrophthalazin-6-yl)-3-(2-(4-fluoro-3,5-dimethylphenyl)-2,4,5,6,7,8-hexahydropyrazolo[4,3-c]azepin-3-yl)-1,3-dihydro-2H-imidazol-2-one (570 mg, crude). LC-MS (ES+, m/z): 492.2 [(M+H)$^+$]. Rt=0.356 min.

Step 3: 1-(2-(4-fluoro-3,5-dimethylphenyl)-2,4,5,6,7,8-hexahydropyrazolo[4,3-c]azepin-3-yl)-3-(5-fluorophthalazin-6-yl)-1,3-dihydro-2H-imidazol-2-one

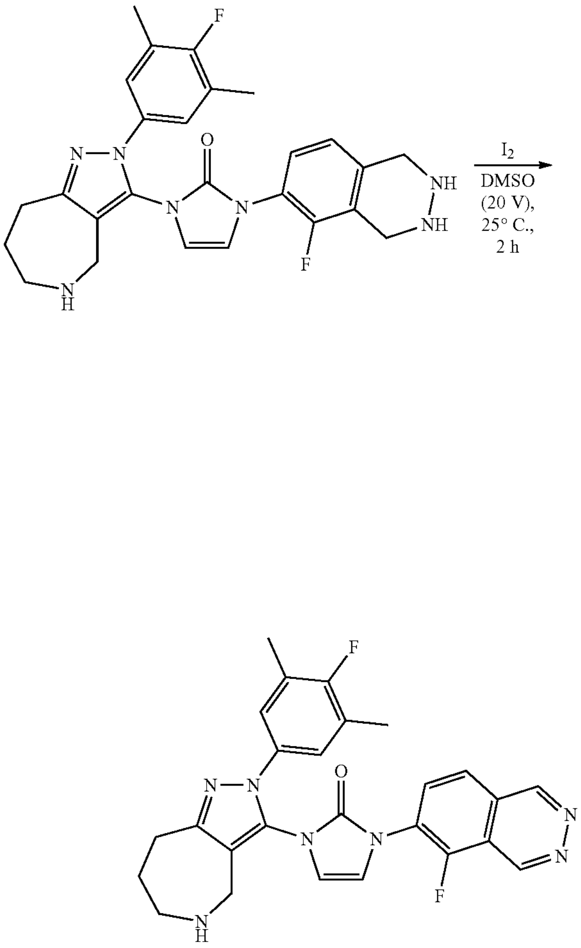

To a solution of 1-(5-fluoro-1,2,3,4-tetrahydrophthalazin-6-yl)-3-(2-(4-fluoro-3,5-dimethylphenyl)-2,4,5,6,7,8-hexahydropyrazolo[4,3-c]azepin-3-yl)-1,3-dihydro-2H-imidazol-2-one (100 mg, 203.44 μmol, 1 eq) in DMSO (2 mL) was added $I_2$ (103.27 mg, 406.89 μmol, 81.96 μL, 2 eq). The mixture was stirred at 25° C. for 2 hours under $N_2$. LCMS indicated the reaction was completed. The reaction mixture was filtered to give a residue. The residue was purified by prep-HPLC (column: 3_Phenomenex Luna C18 75*30 mm*3 um; mobile phase: [$H_2O$ (0.1% TFA)-ACN]; gradient: 5%-35% B over 8.0 min) to give 1-(2-(4-fluoro-3,5-dimethylphenyl)-2,4,5,6,7,8-hexahydropyrazolo[4,3-c]azepin-3-yl)-3-(5-fluorophthalazin-6-yl)-1,3-dihydro-2H-imidazol-2-one (20 mg, 38.97 μmol, 19.16% yield). LC-MS (ES+, m/z): 488.3 [(M+H)$^+$]. Rt=1.129 min.

Step 4: 3-((1S,2S)-1-(5-((S)-2,2-dimethyltetrahydro-2H-pyran-4-yl)-2-(2-(4-fluoro-3,5-dimethylphenyl)-3-(3-(5-fluorophthalazin-6-yl)-2-oxo-2,3-dihydro-1H-imidazol-1-yl)-2,4,5,6,7,8-hexahydropyrazolo[4,3-c] azepine-5-carbonyl)-1H-indol-1-yl)-2-methylcyclopropyl)-1,2,4-oxadiazol-5 (4H)-one

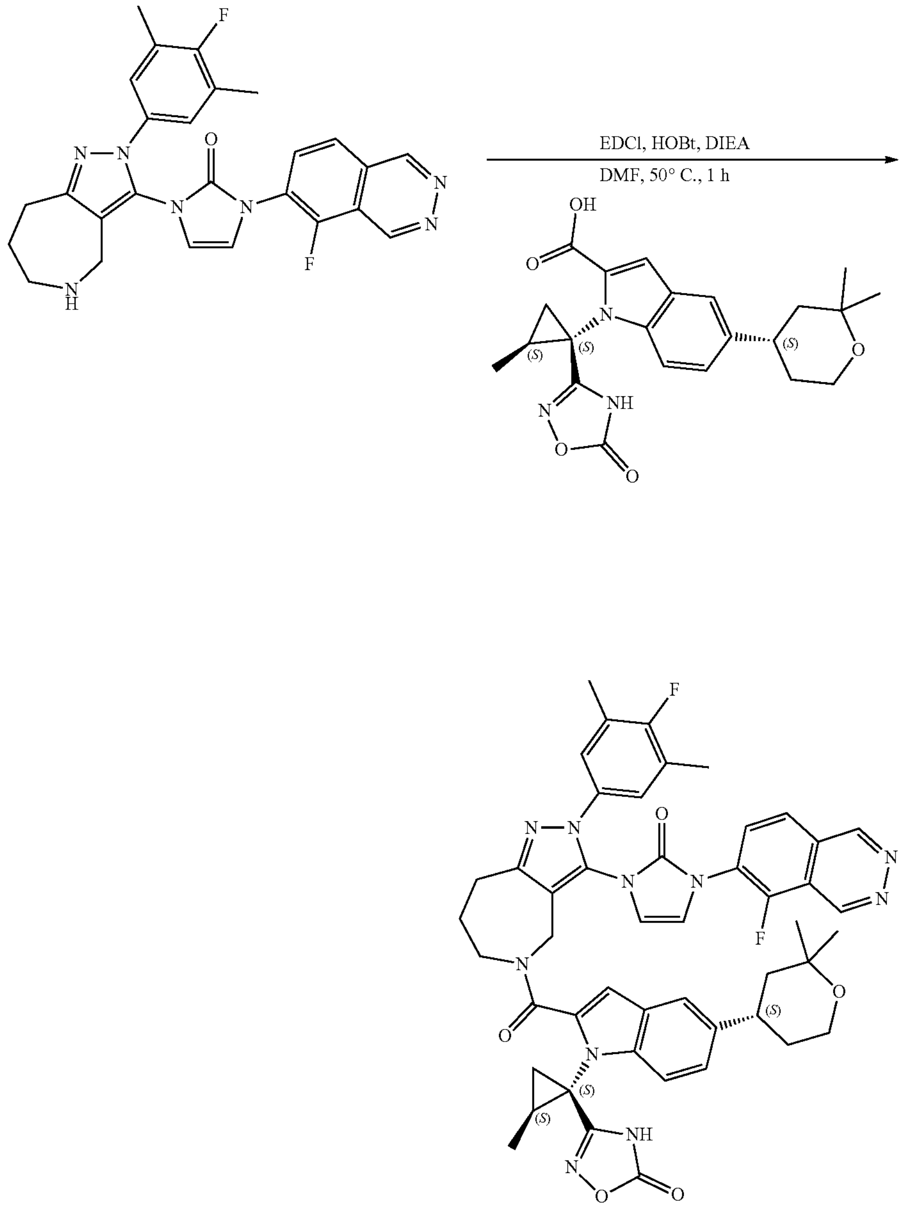

To a solution of 1-(2-(4-fluoro-3,5-dimethylphenyl)-2,4,5,6,7,8-hexahydropyrazolo[4,3-c]azepin-3-yl)-3-(5-fluorophthalazin-6-yl)-1,3-dihydro-2H-imidazol-2-one (20 mg, 41.03 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (20.26 mg, 49.23 μmol, 1.2 eq) in DMF (0.4 mL) was added DIEA (26.51 mg, 205.13 μmol, 35.73 L, 5 eq), EDCI (10.22 mg, 53.33 μmol, 1.3 eq) and HOBt (8.32 mg, 61.54 μmol, 1.5 eq). The mixture was stirred at 50° C. for 1 hour under $N_2$. LCMS indicated the reaction was completed. The mixture was added dropwise to $H_2O$ (3 mL), and then extracted with ethyl acetate (5 mL*3). The organic layers were combined, washed with water (5 mL), saturated brine (5 mL), dried over $Na_2SO_4$, filtered and concentrated in vacuo. The residue was purified by prep-HPLC (column: 3_Phenomenex Luna C18 75*30 mm*3 um; mobile phase: [$H_2O$ (0.1% TFA)-ACN]; gradient: 35%-65% B over 8.0 min) to give 3-((1S,2S)-1-(5-((S)-2,2-dimethyltetrahydro-2H-pyran-4-yl)-2-(2-(4-fluoro-3,5-dimethylphenyl)-3-(3-(5-fluorophthalazin-6-yl)-2-oxo-2,3-dihydro-1H-imidazol-1-yl)-2,4,5,6,7,8-hexahydropyrazolo[4,3-c]azepine-5-carbonyl)-1H-indol-1-yl)-2-methylcyclopropyl)-1,2,4-oxadiazol-5 (4H)-one (8.02 mg, 8.97 μmol, 21.86% yield). $^1H$ NMR (400 MHz, DMSO-$d_6$) δ=12.28-11.58 (m, 1H), 9.98-9.64 (m, 2H), 8.35-6.11 (m, 10H), 5.27-4.52 (m, 2H), 3.69-3.28 (m, 4H), 3.20-2.82 (m, 3H), 2.27-2.11 (m, 6H), 2.08-1.91 (m, 2H), 1.66-0.87 (m, 16H). LC-MS (ES+, m/z): 881.4 [(M+H)$^+$]; Rt=2.893 min. HRMS (EI): m/z [M+H]$^+$ found: 881.3705.

Example 99 Compound 525
3-((1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1,2,4-oxadiazol-5 (4H)-one
Scheme 525
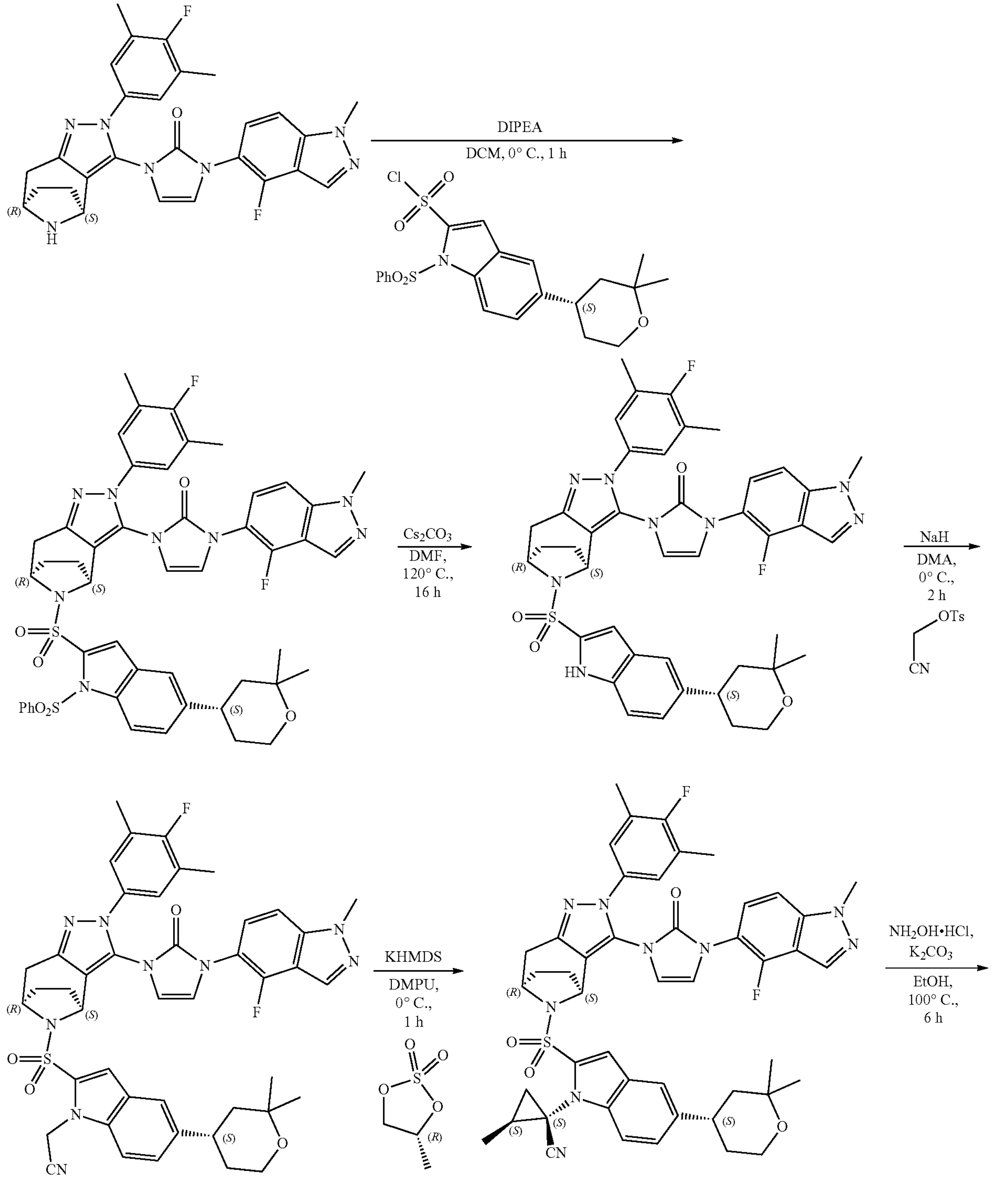

-continued
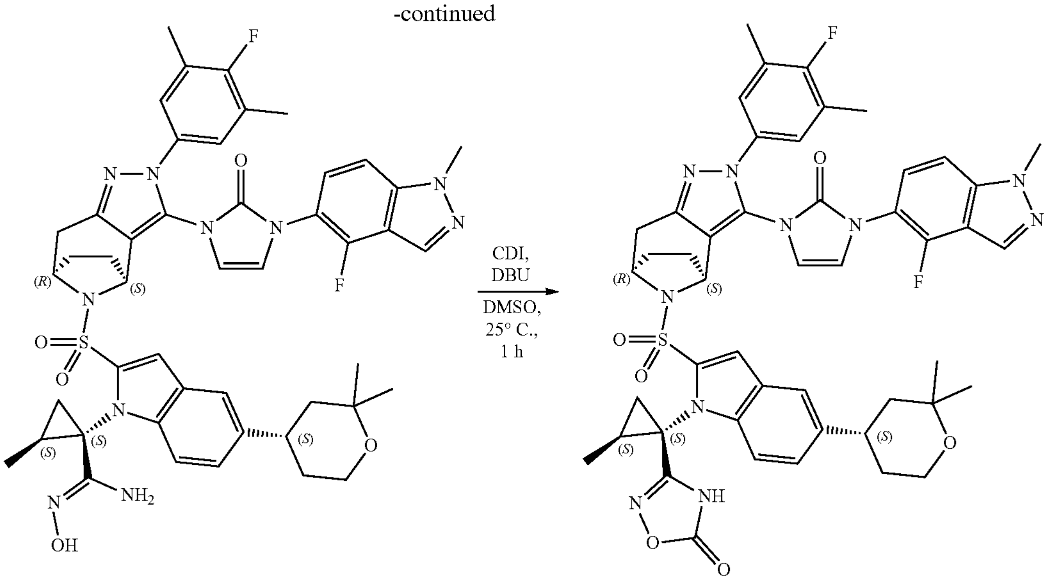
Step 1: 1-((4S,7R)-9-((5-((S)-2, 2-dimethyltetrahydro-2H-pyran-4-yl)-1-(phenylsulfonyl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one
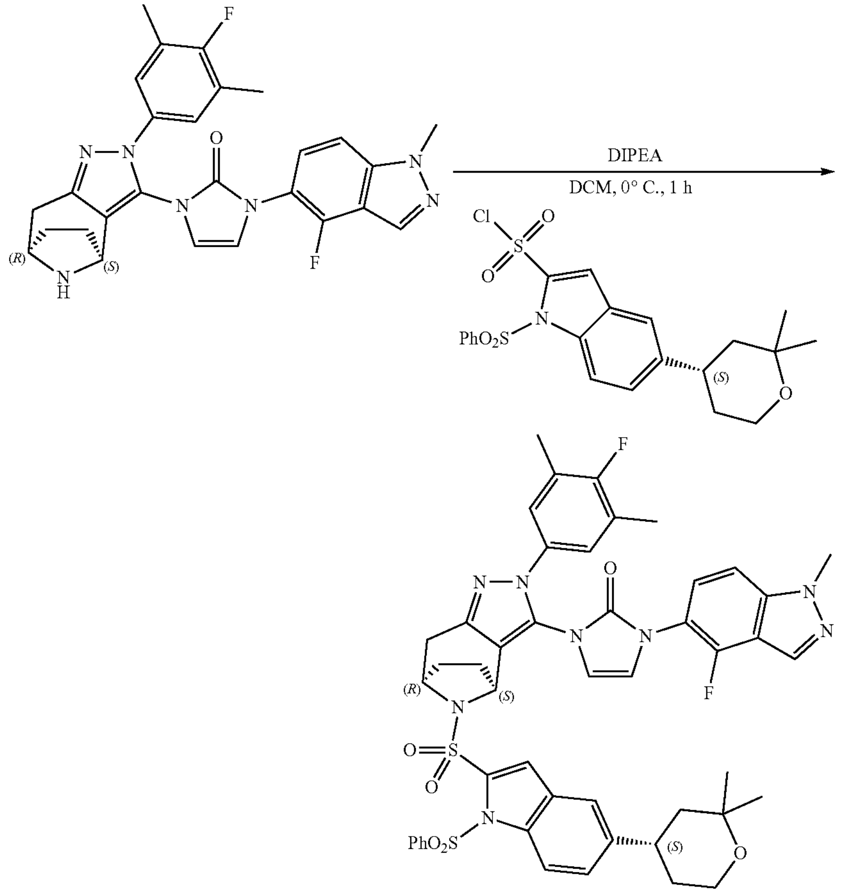

To a solution of(S)-5-(2, 2-dimethyltetrahydro-2H-pyran-4-yl)-1-(phenylsulfonyl)-1H-indole-2-sulfonyl chloride (3.00 g, 6.41 mmol, 1 eq) and 1-(4-fluoro-1-methyl-1H-indazol-5-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (3.22 g, 6.41 mmol, 1 eq) in DCM (30 mL) was added DIPEA (2.49 g, 19.23 mmol, 3 eq) at 0° C. under $N_2$. The mixture was stirred at 0° C. for 1 hour under $N_2$. LCMS showed the reaction was completed. The mixture was added dropwise to $H_2O$ (50 mL) and then extracted with DCM (50 mL*3). The organic layers were combined, washed with water (150 mL), saturated brine (150 mL), dried over $Na_2SO_4$, filtered and concentrated in vacuo. The crude product was purified by chromatography on silica gel (Commercial hexanes:ethyl acetate=3/1-1/2) to give 1-((4S,7R)-9-((5-((S)-2, 2-dimethyltetrahydro-2H-pyran-4-yl)-1-(phenylsulfonyl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (3 g, 2.92 mmol, 45.59% yield). LC-MS (ES+, m/z): 933.3 [(M+H)$^+$]; Rt=0.698 min.

Step 2: 1-((4S,7R)-9-((5-((S)-2, 2-dimethyltetrahydro-2H-pyran-4-yl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one To a solution of 1-((4S,7R)-9-((5-((S)-2, 2-dimethyltetrahydro-2H-pyran-4-yl)-1-(phenylsulfonyl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (3.9 g, 4.18 mmol, 1 eq) in DMF (39 mL) was added $Cs_2CO_3$ (6.81 g, 20.90 mmol, 5 eq). The mixture was stirred at 120° C. for 16 hours under $N_2$. LCMS showed the reaction was completed. The mixture was added dropwise to $H_2O$ (50 mL), and then extracted with DCM (50 mL*3). The organic layers were combined, washed with water (150 mL), saturated brine (150 mL), dried over $Na_2SO_4$, filtered and concentrated in vacuo. The crude product was purified by chromatography on silica gel (hexanes:ethyl acetate=2/1-1/2) to give 1-((4S,7R)-9-((5-((S)-2, 2-dimethyltetrahydro-2H-pyran-4-yl)-1H-indol-2-yl) sulfonyl)-2-(4-fluoro-3, 5-dimethylphenyl)-2, 4, 5, 6, 7, 8-hexahydro-4, 7-epiminocyclohepta [c] pyrazol-3-yl)-3-(4-fluoro-1-methyl-1H-indazol-5-yl)-1, 3-dihydro-2H-imidazol-2-one (800 mg, 761.77 μmol, 18.22% yield). LC-MS (ES+, m/z): 793.2 [(M+H)$^+$]; Rt=0.622 min.

Step 3: 2-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl) acetonitrile

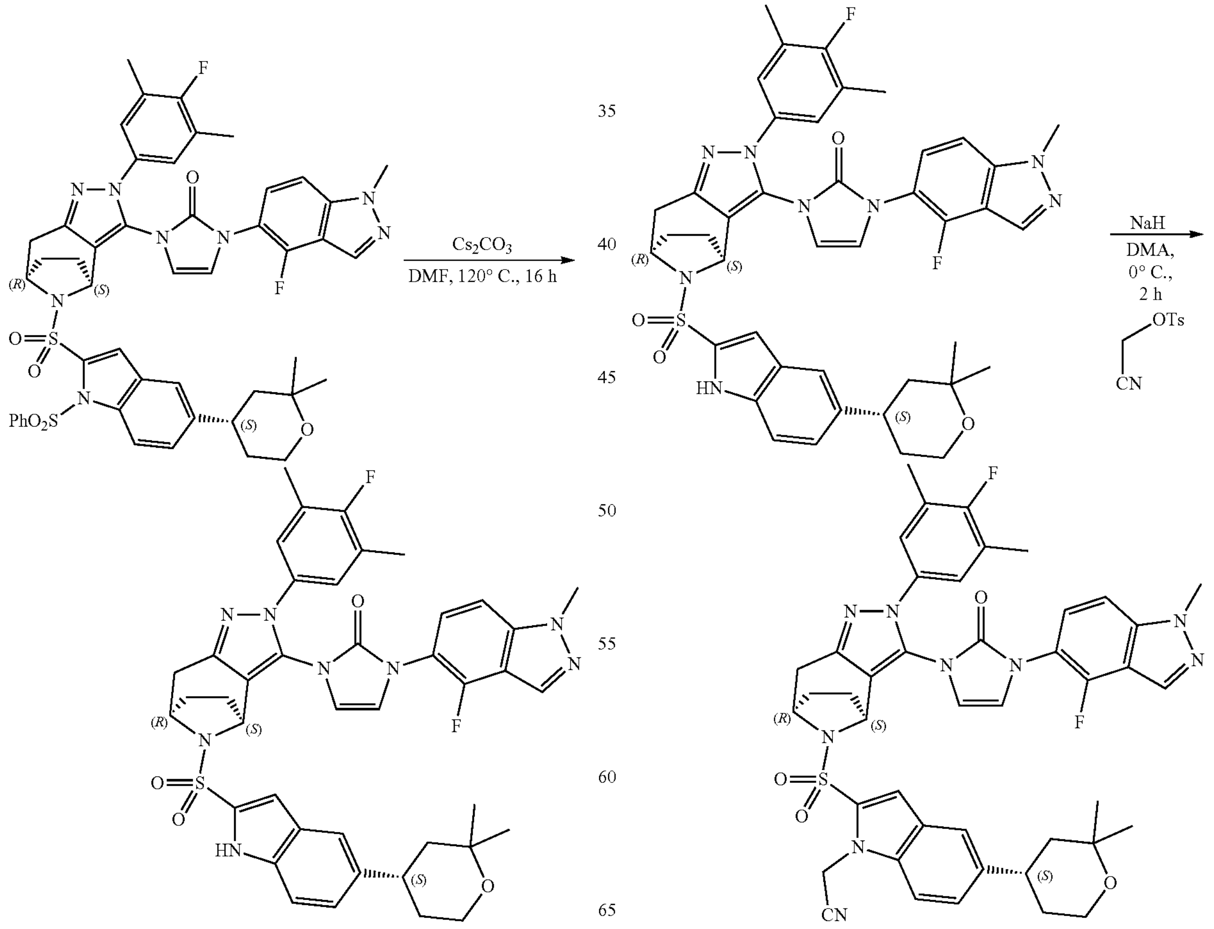

To a solution of 1-((4S,7R)-9-((5-((S)-2, 2-dimethyltetrahydro-2H-pyran-4-yl)-1H-indol-2-yl) sulfonyl)-2-(4-fluoro-3, 5-dimethylphenyl)-2, 4, 5, 6, 7, 8-hexahydro-4, 7-epiminocyclohepta [c]pyrazol-3-yl)-3-(4-fluoro-1-methyl-1H-indazol-5-yl)-1, 3-dihydro-2H-imidazol-2-one (800.00 mg, 761.77 μmol, 1 eq) in DMF (8 mL) was added NaH (152.34 mg, 3.81 mmol, 60% purity, 5 eq) at 0° C. under $N_2$. The mixture was stirred at 0° C. for 1 hour under $N_2$. Cyanomethyl 4-methylbenzenesulfonate (482.74 mg, 2.29 mmol, 3 eq) was then added. The mixture was stirred at 0° C. for 1 hour under $N_2$. LCMS showed the reaction was completed. The mixture was added dropwise to $H_2O$ (20 mL), and then extracted with DCM (20 mL*3). The organic layers were combined, washed with water (50 mL), saturated brine (50 mL), dried over $Na_2SO_4$, filtered and concentrated in vacuo. The residue was purified by prep-TLC ($SiO_2$, hexanes/ethyl acetate=1/5) to give 2-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl) acetonitrile (700 mg, 619.28 μmol, 81.30% yield). LC-MS (ES+, m/z): 832.2 [(M+H)$^+$]; Rt=0.641 min.

Step 4: (1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile

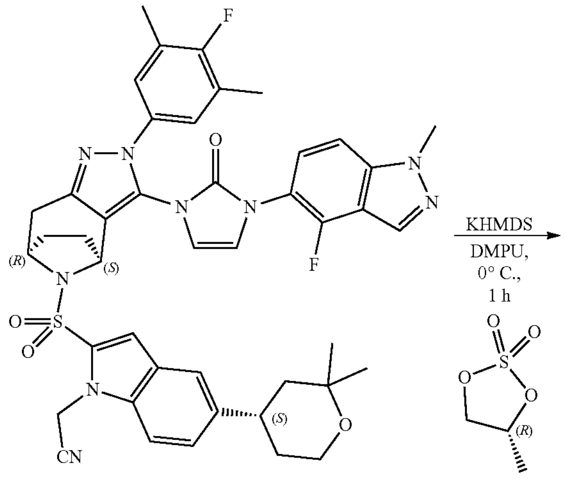

-continued

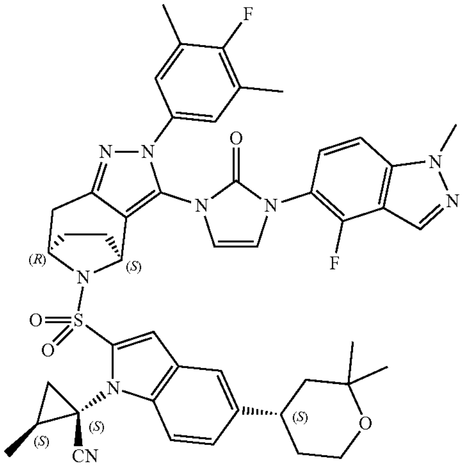

To a solution of 2-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl) acetonitrile (600 mg, 530.81 μmol, 1 eq) and (R)-4-methyl-1, 3, 2-dioxathiolane 2, 2-dioxide (219.98 mg, 1.59 mmol, 3 eq) in DMPU (6 mL) was added KHMDS (1 M, 2.12 mL, 4 eq) at 0° C. under $N_2$. The mixture was stirred at 0° C. for 1 hour under $N_2$. LCMS showed the reaction was completed. The mixture was added dropwise to $NH_4Cl$ (20 mL), and then extracted with ethyl acetate (20 mL*3). The organic layers were combined, washed with water (50 mL), saturated brine (50 mL), dried over $Na_2SO_4$, filtered and concentrated in vacuo. The crude product was purified by prep-HPLC (column: Phenomenex luna C18 250*50 mm*15 um; mobile phase: [$H_2O$ (0.1% TFA)-ACN]; gradient: 60%-90% B over 10.0 min) to give (1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile (200 mg, 214.91 μmol, 40.49% yield). LC-MS (ES+, m/z): 872.2 [(M+H)$^+$]; Rt=2.173 min.

Step 5: (1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide

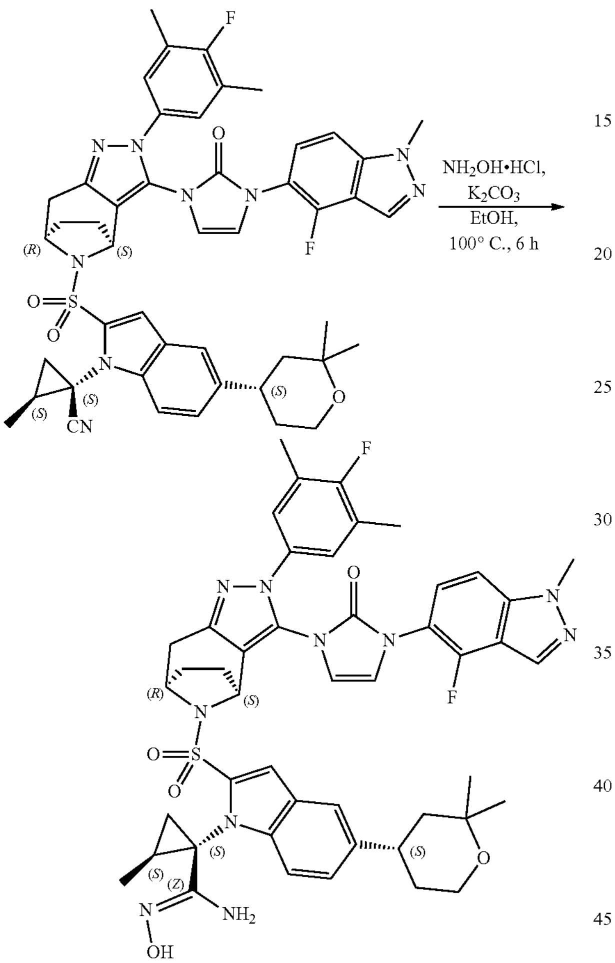

To a solution of (1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropane-1-carbonitrile (200 mg, 229.36 μmol, 1 eq) in EtOH (4 mL) was added $NH_2OH$·HCl (79.69 mg, 1.15 mmol, 5 eq) and $K_2CO_3$ (174.34 mg, 1.26 mmol, 5.5 eq). The mixture was stirred at 100° C. for 6 hours under $N_2$. LCMS showed the reaction was completed. The mixture was added dropwise to $H_2O$ (10 mL), and then extracted with DCM (10 mL*3). The organic layers were combined, washed with water (30 mL), saturated brine (30 mL), dried over $Na_2SO_4$, filtered and concentrated in vacuo to give (1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide (150 mg, crude). LC-MS (ES+, m/z): 905.3 [(M+H)+]; Rt=0.573 min.

Step 6: 3-((1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one

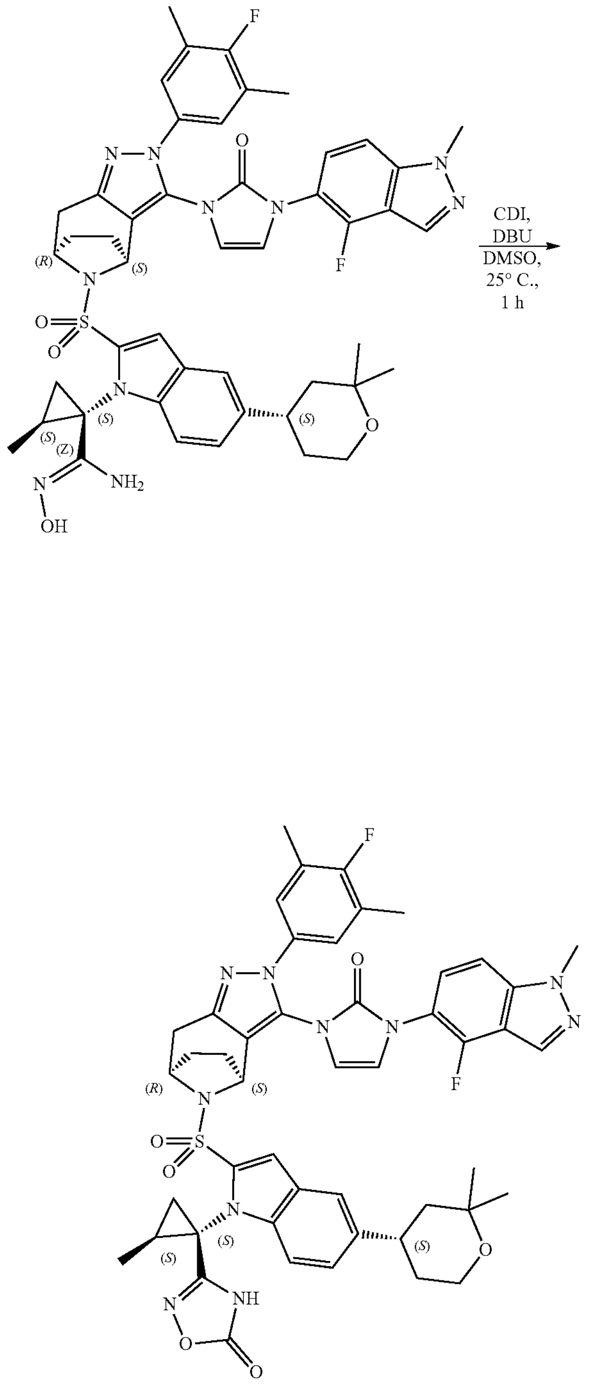

To a solution of (1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-N'-hydroxy-2-methylcyclopropane-1-carboximidamide (150 mg, 165.74 μmol, 1 eq) in DMSO (3 mL) was added CDI (53.75 mg, 331.48 μmol, 2 eq) and DBU (63.08 mg, 414.35 μmol, 2.5 eq). The mixture was stirred at 25° C. for 1 hour under $N_2$. LCMS showed the reaction was completed. The mixture was filtered. The filtrate was purified by prep-HPLC (column: WePure Biotech XP tC18 100*30*7 um; mobile phase: [$H_2O$ (10 mM $NH_4HCO_3$)-ACN]; gradient: 40%-70% B over 8.0 min) to give 3-((1S,2S)-1-(5-((S)-2, 2-dimethyltetrahydro-2H-pyran-4-yl)-2-(((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazol-9-yl) sulfonyl)-1H-indol-1-yl)-2-methylcyclopropyl)-1, 2, 4-oxadiazol-5 (4H)-one (17.25 mg, 18.14 μmol, 10.94% yield). $^1H$ NMR (400 MHz, DMSO-$d_6$) δ=12.47 (s, 1H), 8.35-8.26 (m, 1H), 7.69-7.47 (m, 3H), 7.45 (s, 3H), 7.17-7.10 (m, 2H), 7.05-6.98 (m, 1H), 6.77-6.70 (m, 1H), 5.08-4.44 (m, 2H), 4.17-4.06 (m, 3H), 3.76-3.64 (m, 2H), 3.18-2.94 (m, 2H), 2.78-2.68 (m, 1H), 2.25-2.04 (m, 10H), 1.83-1.46 (m, 7H), 1.41-1.33 (m, 3H), 1.29-1.24 (m, 3H), 1.20-1.15 (m, 3H). LC-MS (ES+, m/z): 931.4 [$(M+H)^+$]; Rt=2.944 min. HRMS (EI): m/z $[M+H]^+$ found: 931.3555.

Example 100 Compound 528

3-((1R,2S)-1-(2-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one

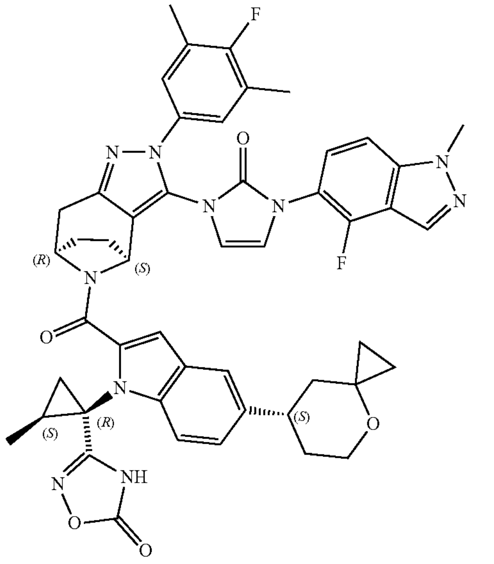

Step 1: 3-((1R,2S)-1-(2-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one

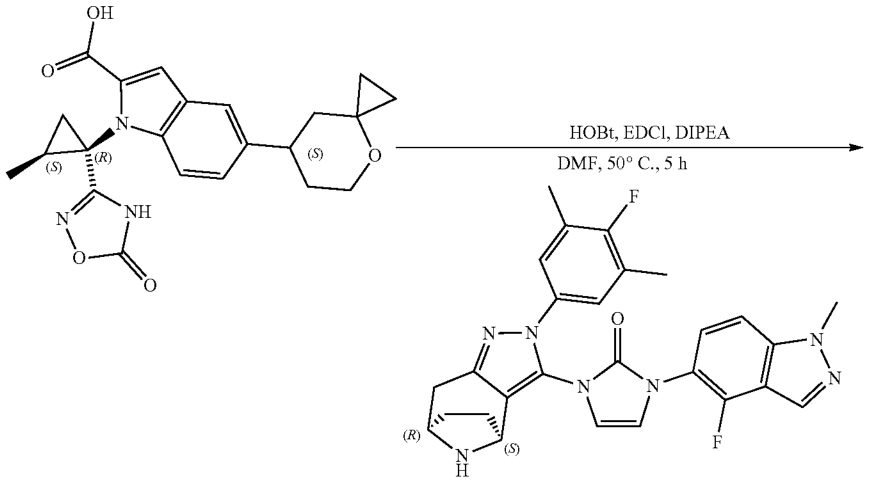

-continued

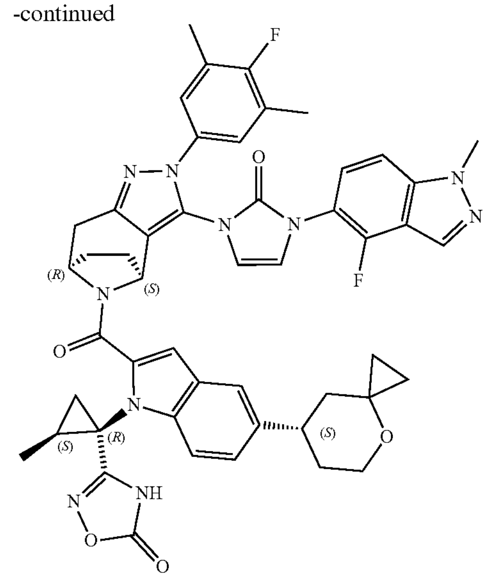

To a solution of 1-((1R,2S)-2-methyl-1-(5-oxo-4,5-dihydro-1, 2, 4-oxadiazol-3-yl) cyclopropyl)-5-((S)-4-oxaspiro[2.5]octan-7-yl)-1H-indole-2-carboxylic acid (90.00 mg, 209.26 μmol, 1 eq), 1-(4-fluoro-1-methyl-1H-indazol-5-yl)-3-((4S,7R)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (157.43 mg, 313.90 μmol, 1.5 eq) and DIPEA (135.23 mg, 1.05 mmol, 5 eq) in DMF (1.8 mL) was added EDCI (80.23 mg, 418.53 μmol, 2 eq) and HOBt (56.55 mg, 418.53 μmol, 2 eq). The mixture was stirred at 50° C. for 5 hours under $N_2$. LCMS showed the reaction was completed. The mixture was filtered. The filtrate was purified by prep-HPLC column: Phenomenex Luna C18 80*40 mm*3 um; mobile phase: [$H_2O$ (0.1% TFA)-ACN]; gradient: 50%-90% B over 10.0 min) to give 3-((1R,2S)-1-(2-((4S,7R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one (43.61 mg, 48.74 μmol, 23.29% yield). $^1H$ NMR (400 MHz, DMSO-$d_6$) δ=12.17-11.80 (m, 1H), 8.45-8.14 (m, 1H), 7.83-6.72 (m, 10H), 5.63-5.06 (m, 2H), 4.14-4.07 (m, 3H), 3.59-3.42 (m, 2H), 3.25-3.10 (m, 1H), 2.89-2.77 (m, 2H), 2.30-1.78 (m, 12H), 1.58-0.24 (m, 12H). LC-MS (ES+, m/z): 893.4 [$(M+H)^+$]; Rt=3.144 min. HRMS (EI): m/z $[M+H]^+$ found: 893.3661.

Example 101 Compound 529

3-((1R,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

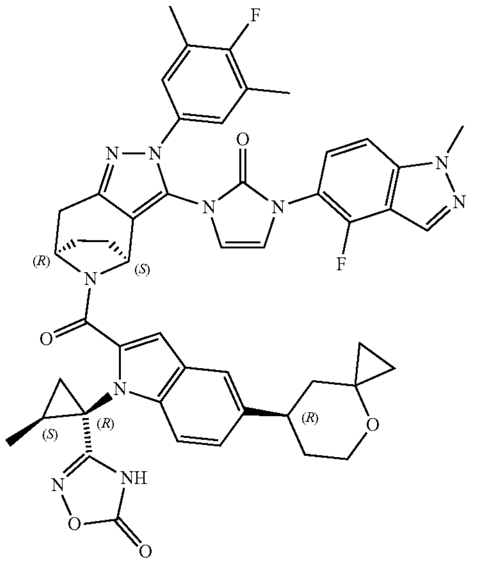

Step 1: 3-((1R,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

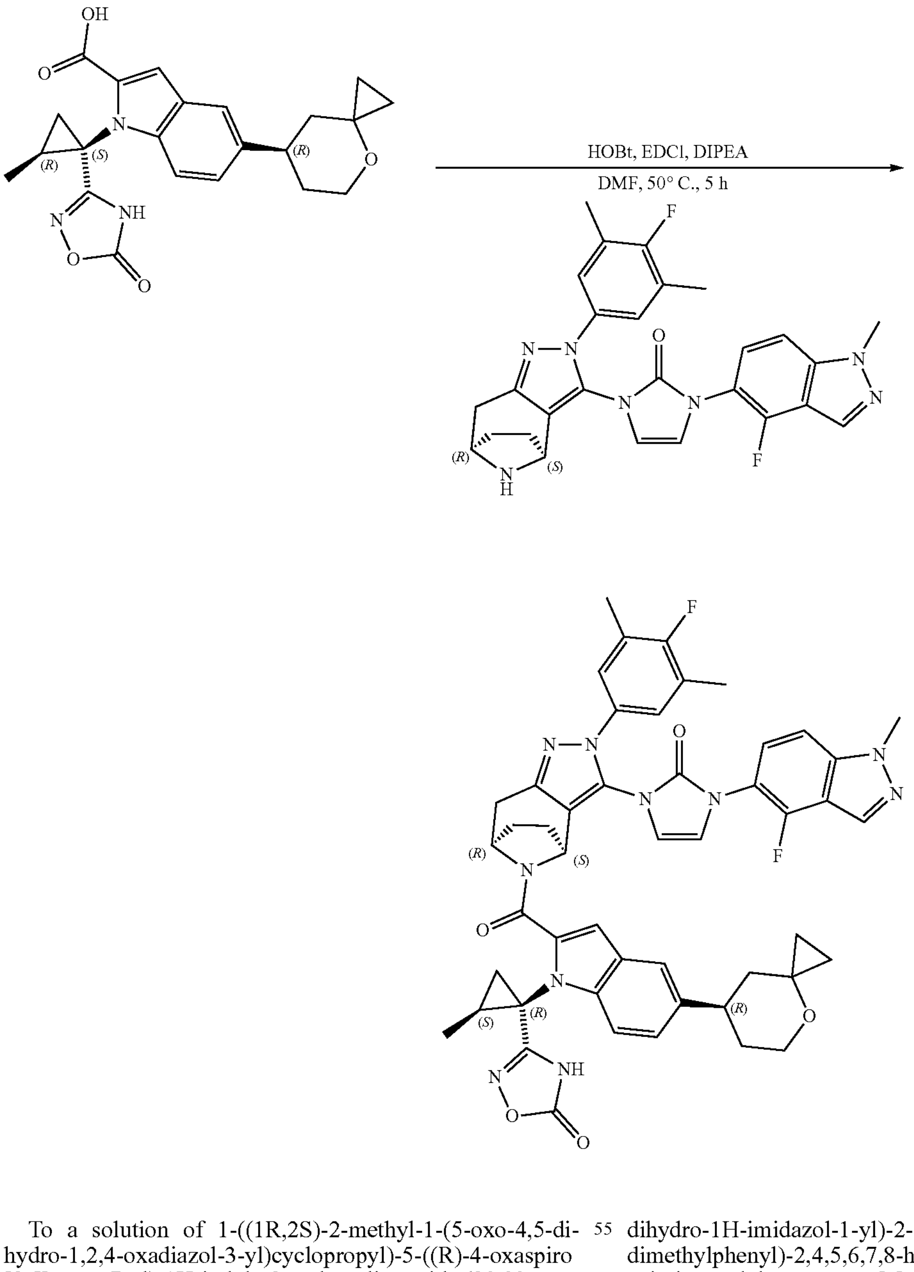

To a solution of 1-((1R,2S)-2-methyl-1-(5-oxo-4,5-dihydro-1,2,4-oxadiazol-3-yl)cyclopropyl)-5-((R)-4-oxaspiro [2.5]octan-7-yl)-1H-indole-2-carboxylic acid (80.00 mg, 195.39 μmol, 1 eq) and 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (146.99 mg, 293.09 μmol, 1.5 eq) in DMF (2 mL) was added DIPEA (252.52 mg, 1.95 mmol, 340.33 μL, 10 eq), EDCI (74.91 mg, 390.78 μmol, 2 eq) and HOBt (52.80 mg, 390.78 μmol, 2 eq). The mixture was stirred at 50° C. for 5 hours under $N_2$. LCMS indicated the reaction was completed. The mixture was added dropwise to $H_2O$ (10 mL) and then extracted with ethyl acetate (20 mL*3). The organic layers were combined, washed with water (20 mL), saturated brine (20 mL), dried over $Na_2SO_4$, filtered and concentrated in vacuo. The residue was purified by prep-HPLC (column: Phenomenex Luna C18 75*30 mm*3 um; mobile phase: [$H_2O$ (0.1% TFA)-ACN]; gradient: 50%-80% B over 8.0 min) to give 3-((1R,2S)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one (74.93 mg, 83.91 μmol, 42.95% yield). $^1H$ NMR (400 MHz, DMSO-$d_6$) δ=12.12-11.87 (m, 1H), 8.37-8.17 (m, 1H), 7.74-6.35 (m, 10H), 5.44-4.89 (m, 2H), 3.93 (br s, 3H), 3.75-3.61 (m, 1H), 3.46-3.33 (m, 1H), 3.22-3.09 (m, 1H), 2.91-2.79 (m, 1H), 2.77-2.65 (m, 1H), 2.30-1.72 (m, 13H), 1.64-1.21 (m, 3H), 1.14-1.03 (m, 1H), 0.99-0.30 (m, 7H). LC-MS (ES+, m/z): 893.4 [$(M+H)^+$]; Rt=3.144 min. HRMS (EI): m/z $[M+H]^+$ found: 893.3661.

Example 102 Compound 530

3-((1R,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5(4H)-one

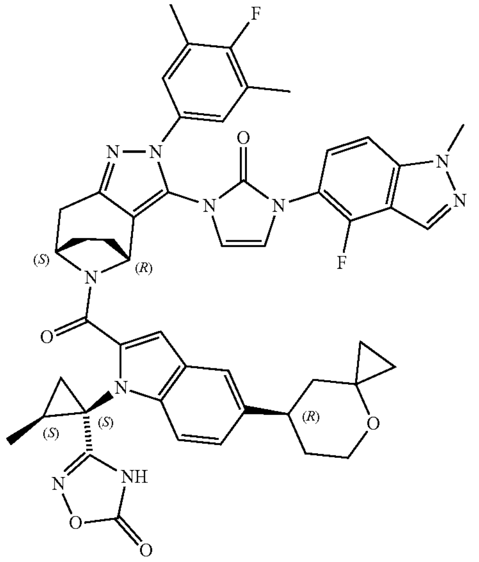

Step 1: 3-((1R,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-5-((R)-4-oxaspiro[2.5]octan-7-yl)-1H-indol-1-yl)-2-methylcyclopropyl)-1,2,4-oxadiazol-5(4H)-one

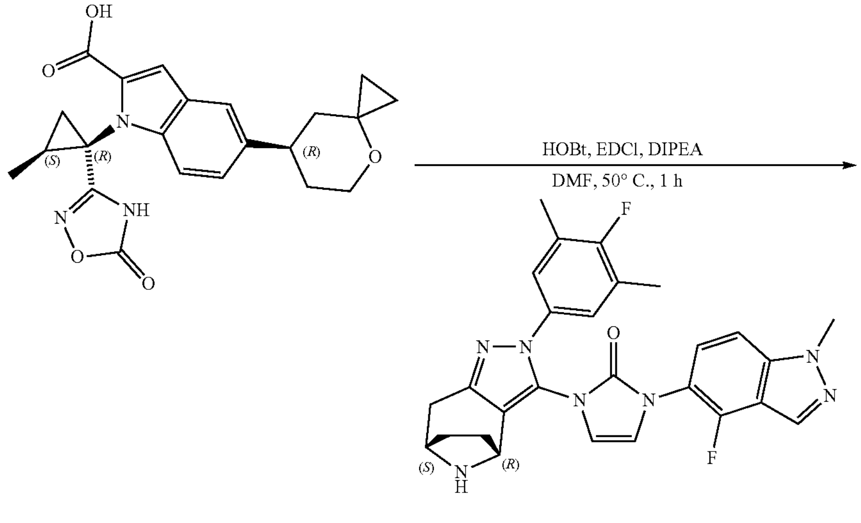

-continued

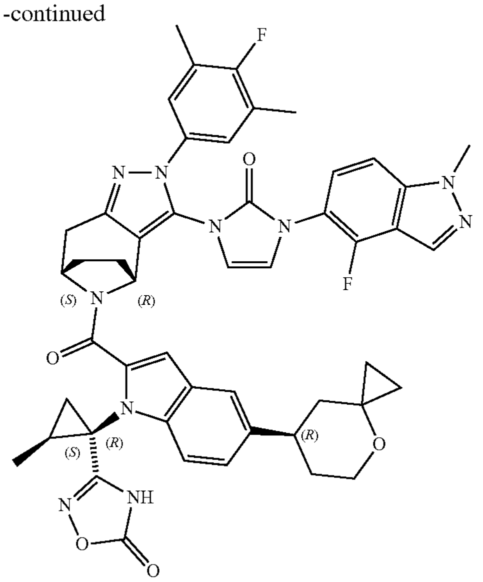

To a solution of 1-((1R,2S)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid (80.00 mg, 195.39 μmol, 1 eq) in DMF (2 mL) was added HOBt (52.80 mg, 390.78 μmol, 2 eq) and EDCI (74.91 mg, 390.78 μmol, 2 eq) and DIEA (75.76 mg, 586.17 μmol, 102.10 μL, 3 eq) followed by 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1H-imidazol-2 (3H)-one (146.99 mg, 293.09 μmol, 1.5 eq). The mixture was stirred at 50° C. for 1 hour under $N_2$. LC-MS showed the reaction was completed. The reaction mixture was diluted with water (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuo. The residue was purified by prep-HPLC (TFA condition) column: Welch Ultimate C18 120*30 mm*5 um; mobile phase: [$H_2O$ (0.1% TFA)-ACN]; gradient: 50%-80% B over 8.0 min to give 3-((1R,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one (60.11 mg, 67.32 μmol, 34.45% yield). $^1$H NMR (400 MHz, DMSO-$d_6$) δ=11.94 (br s, 1H), 8.30 (s, 1H), 7.75-6.75 (m, 10H), 5.54-5.39 (m, 1H), 5.19-4.95 (m, 1H), 4.10 (s, 3H), 3.96-3.37 (m, 3H), 3.22-2.79 (m, 2H), 2.31-1.91 (m, 11H), 1.85-1.04 (m, 6H), 0.91-0.26 (m, 7H). LC-MS (ES+, m/z): 893.5 [$(M+H)^+$]; Rt=2.924 min. HRMS (EI): m/z $[M+H]^+$ found: 893.3729.

Example 103 Compound 531

3-((1R,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

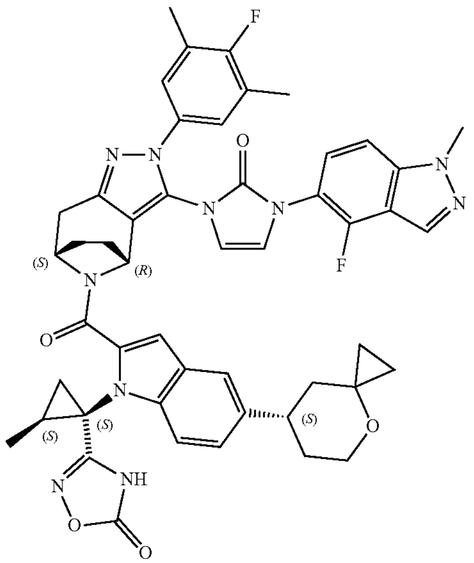

Step 1: 3-((1R,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

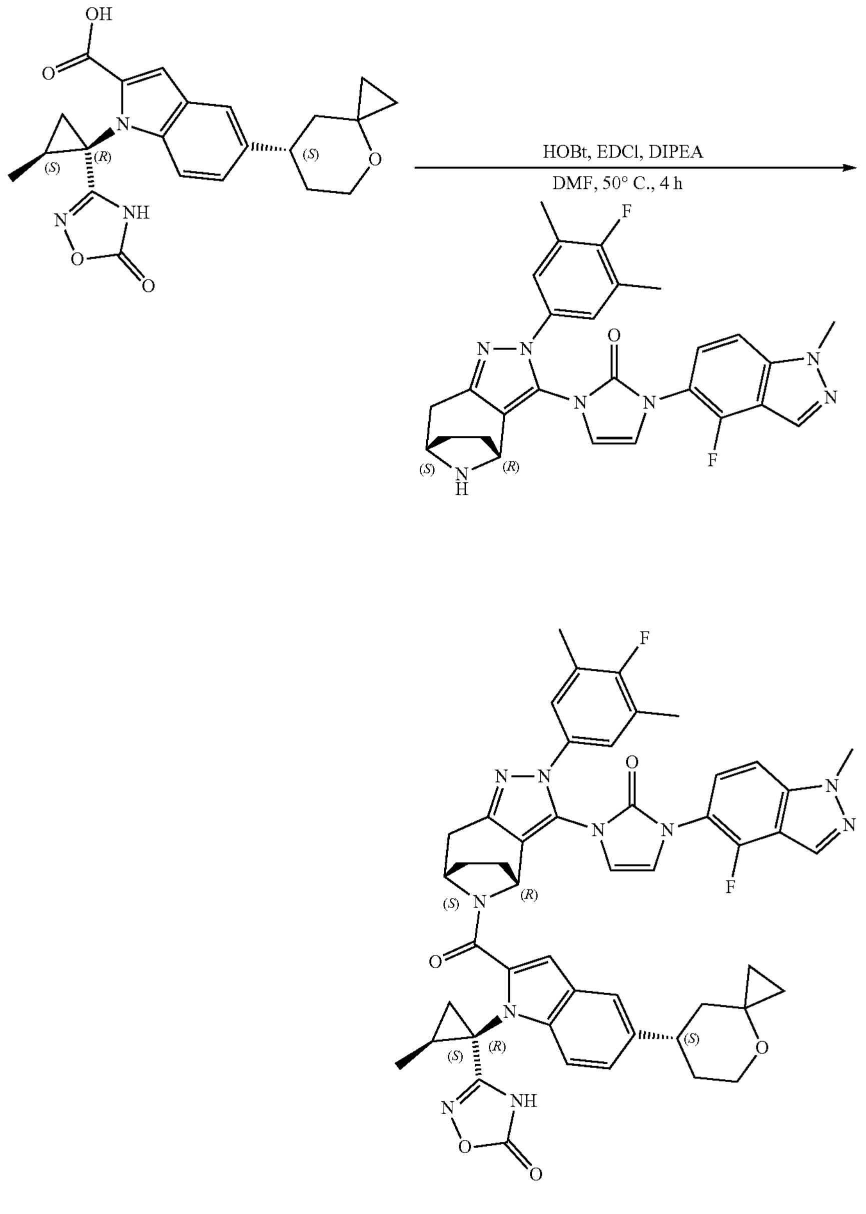

A mixture of 1-((1R,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (90.00 mg, 200.47 μmol, 1 eq), 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1H-imidazol-2 (3H)-one (150.81 mg, 300.71 μmol, 1.5 eq), EDCI (76.86 mg, 400.94 μmol, 2 eq), HOBt (54.18 mg, 400.94 μmol, 2 eq) and DIEA (259.09 mg, 2.00 mmol, 349.18 μL, 10 eq) in DMF (0.9 mL) was stirred at 50° C. for 4 hours under $N_2$ atmosphere. LCMS showed reaction was completed. The reaction mixture was quenched by addition $H_2O$ (25 mL), extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (TFA condition column: 3_Phenomenex Luna C18 75*30 mm*3 um; mobile phase: [$H_2O$ (0.1% TFA)-ACN]; gradient: 45%-75% B over 8.0 min) to give 3-((1R,2S)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (61.82 mg, 69.23 μmol, 34.53% yield). $^1H$ NMR (400 MHz, DMSO-$d_6$) δ=12.13-11.92 (m, 1H), 8.36-8.15 (m, 1H), 7.65-6.48 (m, 10H), 5.53 (br s, 1H), 5.00 (br s, 1H), 4.14-4.07 (m, 3H), 3.87-3.44 (m, 2H), 3.22-2.68 (m, 3H), 2.42-1.66 (m, 14H), 1.65-0.99 (m, 3H), 0.98-0.20 (m, 7H). LC-MS (ES+, m/z): 893.4 [$(M+H)^+$]; Rt=3.122 min. HRMS (EI): m/z $[M+H]^+$ found: 893.3729.

Example 104 Compound 536

3-((1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-2-methylcyclopropyl)-1,2,4-oxadiazol-5 (4H)-one Scheme 536

Step 1: 1-((4R,8S)-10-((5-((S)-2,2-dimethyltetrahydro-2H-pyran-4-yl)-1-(phenylsulfonyl)-1H-indol-2-yl) sulfonyl)-2-(4-fluoro-3,5-dimethylphenyl)-2,4,5,7,8,9-hexahydro-4,8-epiminooxocino [5,4-c] pyrazol-3-yl)-3-(4-fluoro-1-methyl-1H-indazol-5-yl)-1,3-dihydro-2H-imidazol-2-one To a mixture of 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (900 mg, 1.74 mmol, 1 eq) and (S)-5-(2,2-dimethyltetrahydro-2H-pyran-4-yl)-1-(phenylsulfonyl)-1H-indole-2-sulfonyl chloride (813.84 mg, 1.74 mmol, 1 eq) in DCM (9 mL) was added DIEA (674.27 mg, 5.22 mmol, 3 eq) under $N_2$. The mixture was stirred at 30° C. for 16 hours. LCMS showed the reaction was completed. The residue was poured into water (100 mL). The aqueous phase was extracted with ethyl acetate (50 mL*3). The combined organic phase was washed with saturated brine (150 mL), dried with anhydrous $Na_2SO_4$, filtered and concentrated in vacuo. The residue was purified by column chromatography ($SiO_2$, hexanes:ethyl acetate=20/1 to 1/1) to give 1-((4R,8S)-10-((5-((S)-2,2-dimethyltetrahydro-2H-pyran-4-yl)-1-(phenylsulfonyl)-1H-indol-2-yl) sulfonyl)-2-(4-fluoro-3,5-dimethylphenyl)-2,4,5,7,8,9-hexahydro-4,8-epiminooxocino [5,4-c]pyrazol-3-yl)-3-(4-fluoro-1-methyl-1H-indazol-5-yl)-1,3-dihydro-2H-imidazol-2-one (800 mg, 767.08 μmol, 44.11% yield). LC-MS (ES+, m/z): 949.3 [$(M+H)^+$]; Rt=0.673 min.

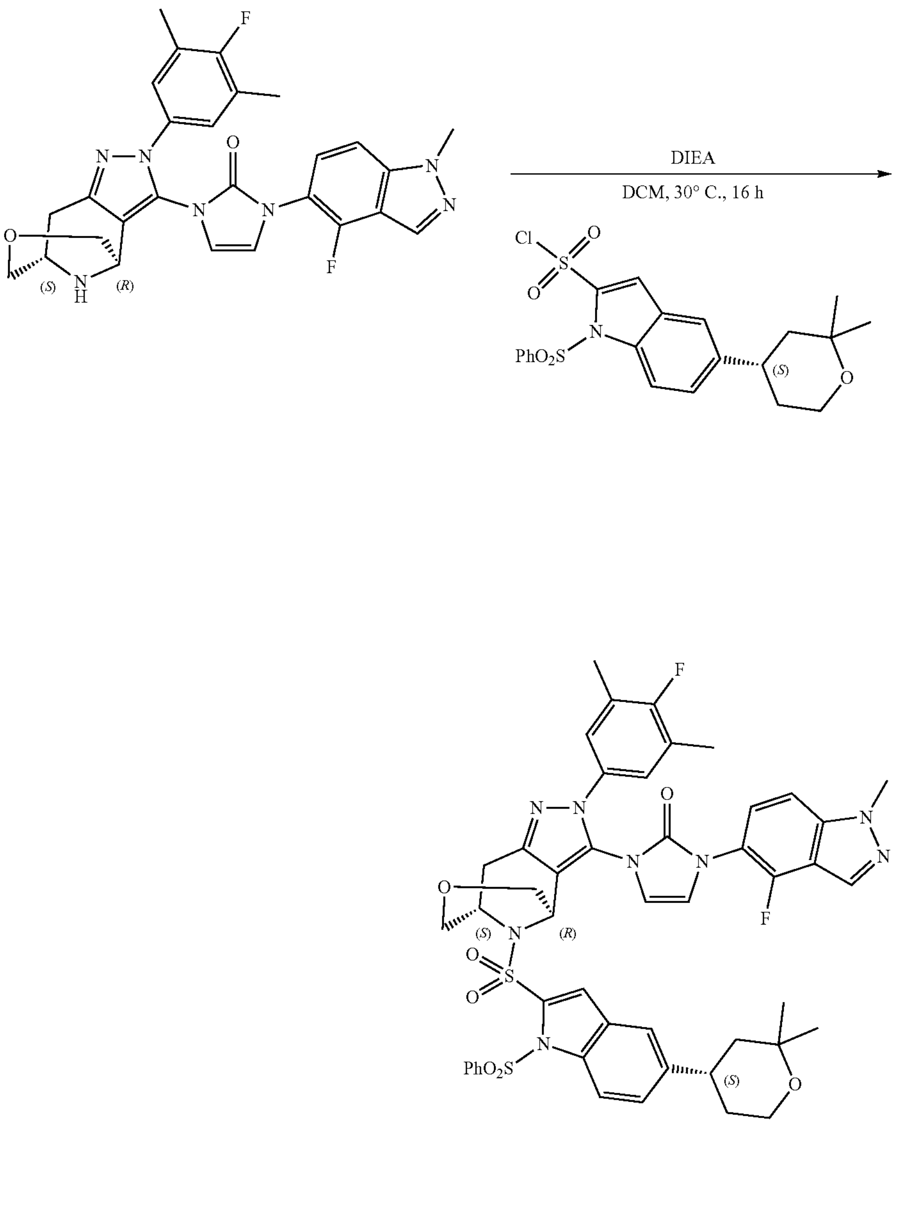

Step 2: 1-((4R,8S)-10-((5-((S)-2,2-dimethyltetrahydro-2H-pyran-4-yl)-1H-indol-2-yl) sulfonyl)-2-(4-fluoro-3,5-dimethylphenyl)-2,4,5,7,8,9-hexahydro-4,8-epiminooxocino [5,4-c]pyrazol-3-yl)-3-(4-fluoro-1-methyl-1H-indazol-5-yl)-1,3-dihydro-2H-imidazol-2-one

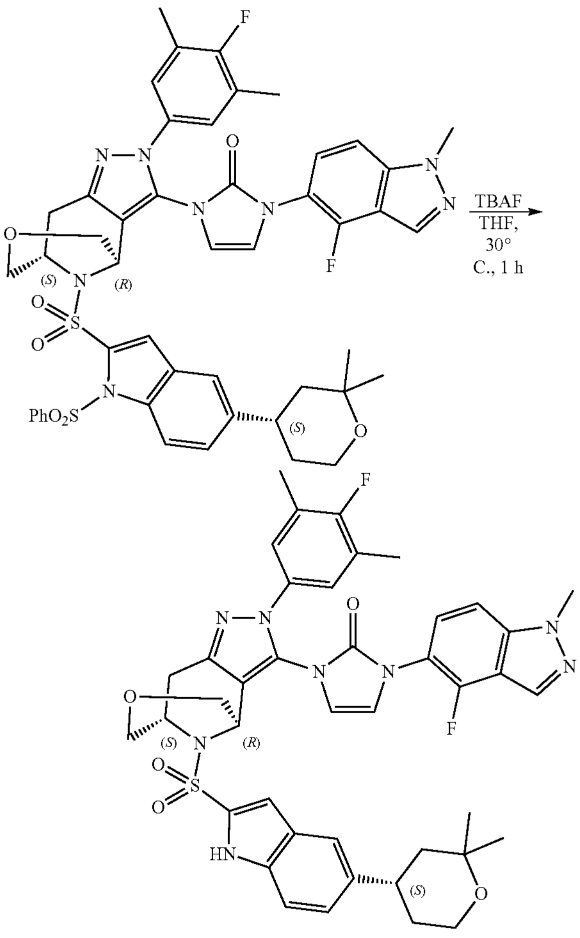

To a mixture of 1-((4R,8S)-10-((5-((S)-2,2-dimethyltetrahydro-2H-pyran-4-yl)-1-(phenylsulfonyl)-1H-indol-2-yl) sulfonyl)-2-(4-fluoro-3,5-dimethylphenyl)-2,4,5,7,8,9-hexahydro-4,8-epiminooxocino [5,4-c]pyrazol-3-yl)-3-(4-fluoro-1-methyl-1H-indazol-5-yl)-1,3-dihydro-2H-imidazol-2-one (700 mg, 671.20 μmol, 1 eq) in THF (7 mL) was added TBAF (1 M, 2 mL, 3 eq) in one portion at 30° C. under $N_2$. The mixture was stirred at 30° C. for 1 hour. LCMS showed the reaction was completed. The residue was poured into water (100 mL). The aqueous phase was extracted with ethyl acetate (50 mL*3). The combined organic phase was washed with saturated brine (150 mL), dried with anhydrous $Na_2SO_4$, filtered and concentrated in vacuo. The crude product was triturated with hexanes:ethyl acetate (24:1, 50 mL) at 20° C. for 5 minutes to give 1-((4R,8S)-10-((5-((S)-2,2-dimethyltetrahydro-2H-pyran-4-yl)-1H-indol-2-yl) sulfonyl)-2-(4-fluoro-3,5-dimethylphenyl)-2,4,5,7,8,9-hexahydro-4,8-epiminooxocino [5,4-c] pyrazol-3-yl)-3-(4-fluoro-1-methyl-1H-indazol-5-yl)-1,3-dihydro-2H-imidazol-2-one (550 mg, 598.35 μmol, 89.15% yield). LC-MS (ES+, m/z): 809.3 [$(M+H)^+$]; Rt=0.611 min.

Step 3: 2-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl) acetonitrile

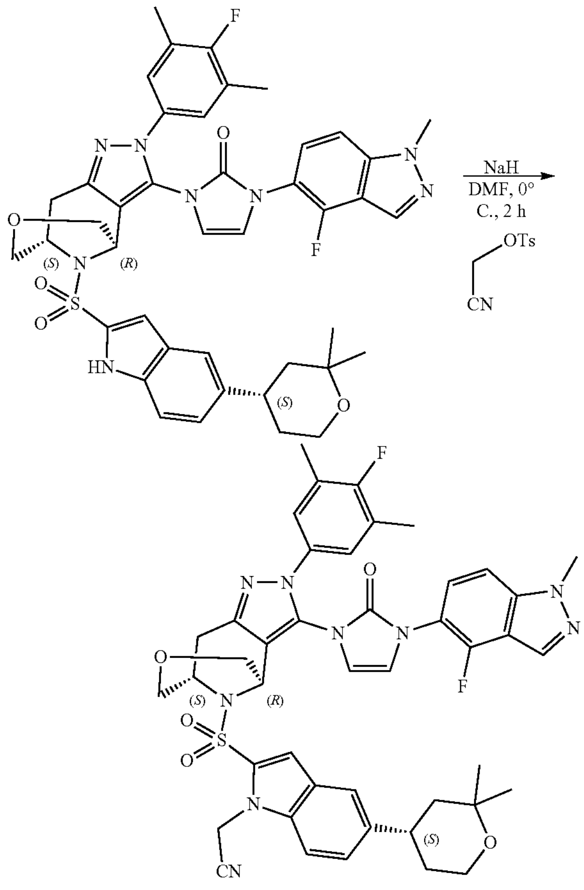

To a mixture of 1-((4R,8S)-10-((5-((S)-2,2-dimethyltetrahydro-2H-pyran-4-yl)-1H-indol-2-yl) sulfonyl)-2-(4-fluoro-3,5-dimethylphenyl)-2,4,5,7,8,9-hexahydro-4,8-epiminooxocino [5,4-c]pyrazol-3-yl)-3-(4-fluoro-1-methyl-1H-indazol-5-yl)-1,3-dihydro-2H-imidazol-2-one (500 mg, 618.13 μmol, 1 eq) in DMF (10 mL) was added NaH (123.61 mg, 3.09 mmol, 60% purity, 5 eq) in one portion at 0° C. under $N_2$. The mixture was stirred at 0° C. for 0.5 hour, cyanomethyl 4-methylbenzenesulfonate (391.72 mg, 1.85 mmol, 3 eq) was then added in one portion at 0° C. under $N_2$. The mixture was stirred at 0° C. for 1.5 hours. LCMS showed the reaction was completed. The reaction mixture was cooled to 0° C., and was poured into saturated $NH_4Cl$ solution (30 mL) at 0° C. The aqueous phase was extracted with dichloromethane (15 mL*3). The combined organic layers were washed with saturated brine (45 mL), dried over anhydrous $Na_2SO_4$, filtered and concentrated in vacuo. The residue was purified by prep-TLC ($SiO_2$, hexanes:ethyl acetate=0:1) to give 2-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol- 1-yl) acetonitrile (400 mg, 429.28 μmol, 69.45% yield). LC-MS (ES+, m/z): 848.4 [(M+H)$^+$]; Rt=0.606 min.

Step 4: (1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-2-methylcyclopropane-1-carbonitrile

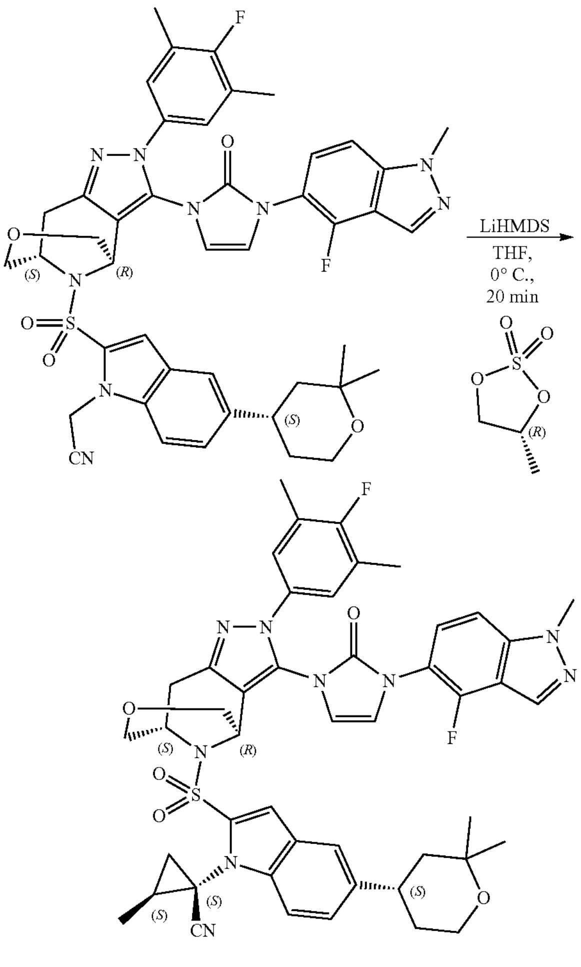

To a mixture of 2-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl) acetonitrile (100 mg, 107.32 μmol, 1 eq) and (R)-4-methyl-1,3,2-dioxathiolane 2,2-dioxide (44.48 mg, 321.96 μmol, 3 eq) in THF (2 mL) was added LiHMDS (1 M, 0.4 mL, 4 eq) in one portion at 0° C. under $N_2$. The mixture was stirred at 0° C. for 20 minutes (3 parallel reaction). LCMS showed the reaction was completed. The reaction mixture was quenched by addition $NH_4Cl$ (10 mL) at 0° C. The aqueous phase was extracted with ethyl acetate (5 mL*3). The combined organic phase was washed with saturated brine (15 mL), dried with anhydrous $Na_2SO_4$, filtered and concentrated in vacuo. The residue was purified by prep-TLC ($SiO_2$, hexanes:ethyl acetate=0:1) to give (1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-2-methylcyclopropane-1-carbonitrile (120 mg, 118.92 μmol, 36.94% yield). LC-MS (ES+, m/z): 888.4 [(M+H)$^+$]; Rt=0.639 min.

Step 5: (1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-N'-hydroxy-2-methylcyclopropane-1-carboximidamide

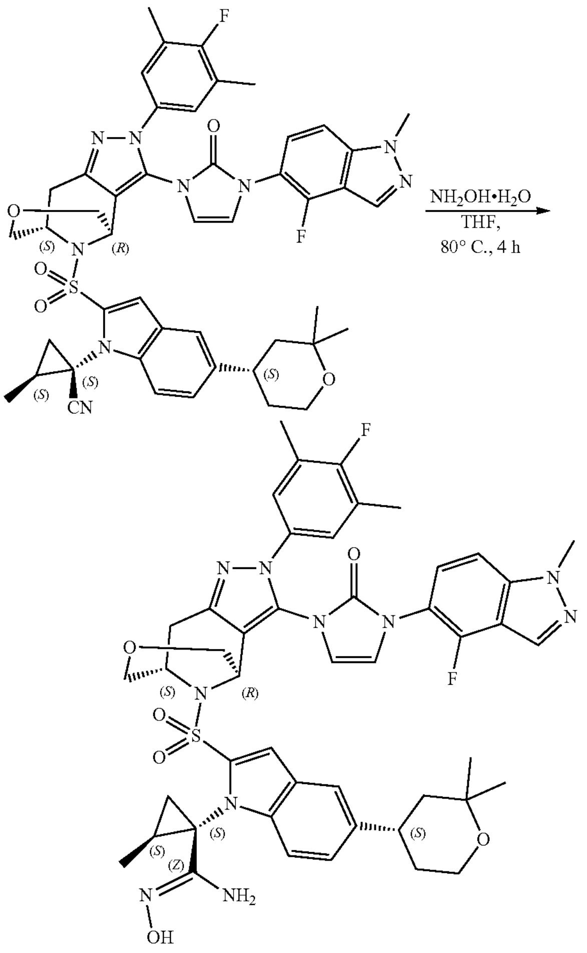

To a mixture of (1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-2-methylcyclopropane-1-carbonitrile (100 mg, 112.61 μmol, 1 eq) in THF (3 mL) was added hydroxylamine (148.78 mg, 2.25 mmol, 50% purity, 20 eq) in one portion under $N_2$. The mixture was stirred at 80° C. for 4 hours. LCMS showed the reaction was completed. The residue was poured into water (20 mL). The aqueous phase was extracted with ethyl acetate (30 mL). The combined organic phase was washed with saturated brine (30 mL), dried with anhydrous $Na_2SO_4$, filtered and concentrated in vacuo to give (1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-M-hydroxy-2-methylcyclopropane-1-carboximidamide (100 mg, crude). LC-MS (ES+, m/z): 921.4 [(M+H)$^+$]; Rt=0.555 min.

Step 6: 3-((1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-2-methylcyclopropyl)-1,2,4-oxadiazol-5(4H)-one

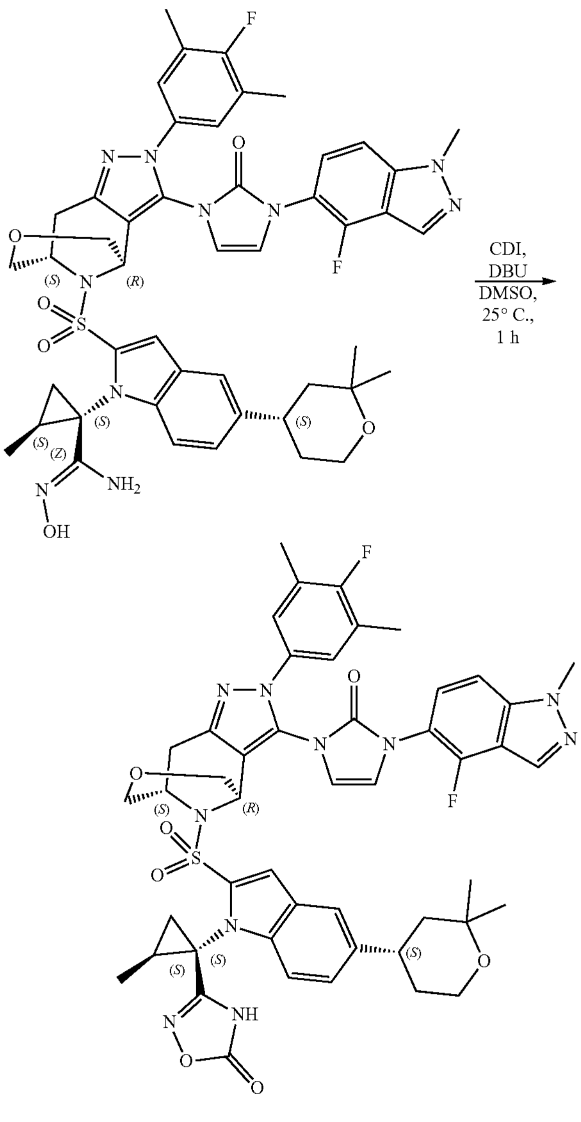

To a mixture of (1S,2S)-1-(5-((S)-2,2-dimethyltetrahydro-2H-pyran-4-yl)-2-(((4R,8S)-3-(3-(4-fluoro-1-methyl- 1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-N-hydroxy-2-methylcyclopropane-1-carboximidamide (100 mg, 108.57 μmol, 1 eq) in DMSO (1 mL) was added CDI (35.21 mg, 217.15 μmol, 2 eq) and finally added DBU (41.32 mg, 271.44 μmol, 2.5 eq) in one portion at 25° C. under $N_2$. The mixture was stirred at 25° C. for 1 hour. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated. The residue was purified by prep-HPLC (column: WePure Biotech XP tC18 150*40*7 um; mobile phase: [$H_2O$ (10 mM $NH_4HCO_3$)-ACN]; gradient: 45%-75% B over 8.0 min) and then further purified by SFC (column: DAICEL CHIRALPAK IG (250 mm*30 mm, 10 um); mobile phase: [$CO_2$-EtOH:ACN=1:1 (0.1% $NH_3H_2O$)]; B %: 50%, isocratic elution mode) to give 3-((1S,2S)-1-(5-((S)-2,2-dimethyltetrahydro-2H-pyran-4-yl)-2-(((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazol-10-yl) sulfonyl)-1H-indol-1-yl)-2-methylcyclopropyl)-1,2,4-oxadiazol-5 (4H)-one (18.28 mg, 19.26 μmol, 17.74% yield). $^1H$ NMR (400 MHz, DMSO-$d_6$) δ=12.49-11.80 (m, 1H), 8.30-8.28 (m, 1H), 7.64-7.61 (m, 1H), 7.52-7.40 (m, 2H), 7.40-7.22 (m, 3H), 7.18-7.11 (m, 2H), 7.04-6.98 (m, 1H), 6.76-6.68 (m, 1H), 5.11-4.77 (m, 1H), 4.39-4.08 (m, 4H), 4.01-3.85 (m, 2H), 3.70 (br d, J=8.0 Hz, 4H), 3.26-3.00 (m, 2H), 2.96-2.82 (m, 1H), 2.26-2.23 (m, 6H), 1.99 (br s, 1H), 1.75 (s, 2H), 1.67-1.61 (m, 2H), 1.58-1.46 (m, 2H), 1.39-1.31 (m, 3H), 1.27-1.24 (m, 3H), 1.18-1.15 (m, 3H). LC-MS (ES+, m/z): 947.3 [(M+H)$^+$]; Rt=3.001 min. HRMS (EI): m/z [M+H]$^+$ found: 947.3458.

Example 105 Compound 539

3-((1S,2R)-1-(2-((4R,7S)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one

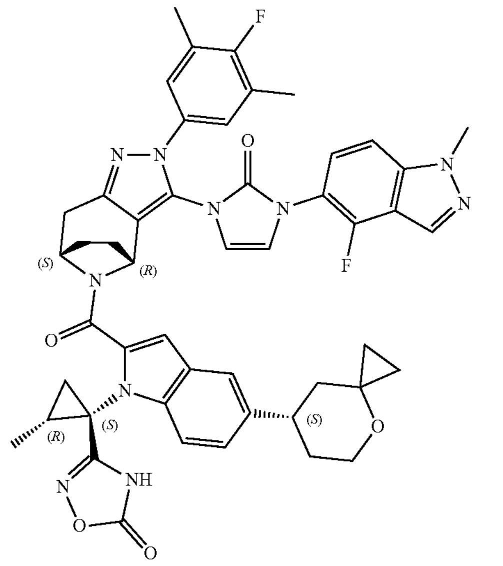

Step 1: 3-((1S,2R)-1-(2-((4R,7S)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c] pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one

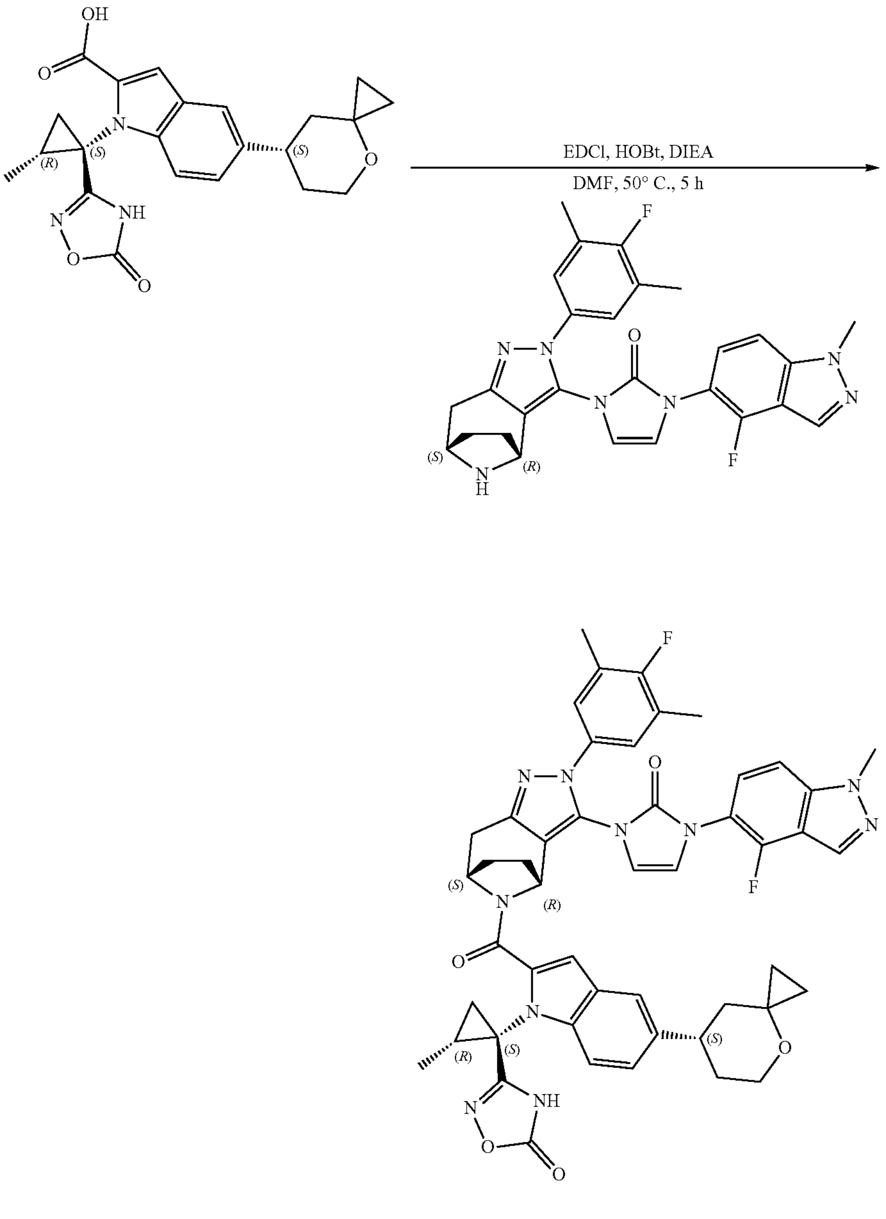

To a solution of 1-((1S,2R)-2-methyl-1-(5-oxo-4,5-dihydro-1, 2, 4-oxadiazol-3-yl) cyclopropyl)-5-((S)-4-oxaspiro[2.5]octan-7-yl)-1H-indole-2-carboxylic acid (70.00 mg, 170.97 μmol, 1 eq), 1-(4-fluoro-1-methyl-1H-indazol-5-yl)-3-((4R,7S)-2-(4-fluoro-3, 5-dimethylphenyl)-2, 4, 5, 6, 7, 8-hexahydro-4, 7-epiminocyclohepta [c]pyrazol-3-yl)-1, 3-dihydro-2H-imidazol-2-one (128.62 mg, 256.45 μmol, 1.5 eq) and DIPEA (110.48 mg, 854.84 μmol, 148.90 μL, 5 eq) in DMF (1.4 mL) was added HOBt (46.20 mg, 341.94 μmol, 2 eq) and EDCI (65.55 mg, 341.94 μmol, 2 eq). The mixture was stirred at 50° C. for 5 hours under $N_2$. LCMS showed the reaction was completed. The residue was added to $H_2O$ (10 mL) and then extracted with ethyl acetate (10 mL*3). The organic layers were combined, washed with water (30 mL), saturated brine (30 mL), dried over $Na_2SO_4$, filtered and concentrated in vacuo. The crude product was purified by prep-HPLC column: Phenomenex Luna C18 75*30 mm*3 um; mobile phase: [$H_2O$ (0.1% TFA)-ACN]; gradient: 55%-85% B over 8.0 min) to give 3-((1S,2R)-1-(2-((4R,7S)-3-(3-(4-fluoro-1-methyl-1H-indazol-5-yl)-2-oxo-2, 3-dihydro-1H-imidazol-1-yl)-2-(4-fluoro-3, 5-dimethylphenyl)-2, 4, 5, 6, 7, 8-hexahydro-4, 7-epiminocyclohepta [c]pyrazole-9-carbonyl)-5-((S)-4-oxaspiro[2.5]octan-7-yl)-1H-indol-1-yl)-2-methylcyclopropyl)-1, 2, 4-oxadiazol-5 (4H)-one (54.65 mg, 61.20 μmol, 35.80% yield). $^1$H NMR (400 MHz, DMSO-$d_6$) δ=12.16-11.82 (m, 1H), 8.45-8.12 (m, 1H), 7.79-6.75 (m, 10H), 5.57-5.11 (m, 2H), 4.12 (s, 3H), 3.69 (br d, J=10.4 Hz, 1H), 3.46-3.35 (m, 1H), 3.23-3.11 (m, 1H), 2.92-2.69 (m, 2H), 2.30-1.75 (m, 13H), 1.57-0.29 (m, 11H). LC-MS (ES+, m/z): 893.4 [$(M+H)^+$]; Rt=3.128 min. HRMS (EI): m/z $[M+H]^+$ found: 893.3709.

Example 106 Compound 540

3-((1S,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

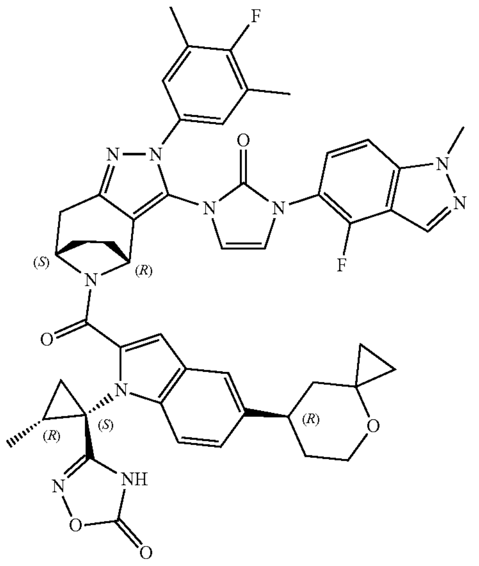

Step 1: 3-((1S,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

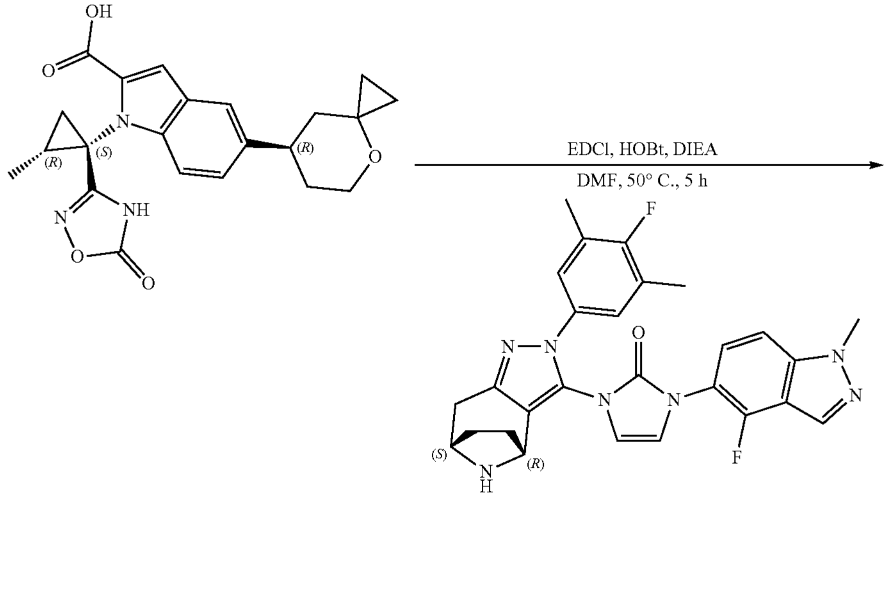

-continued

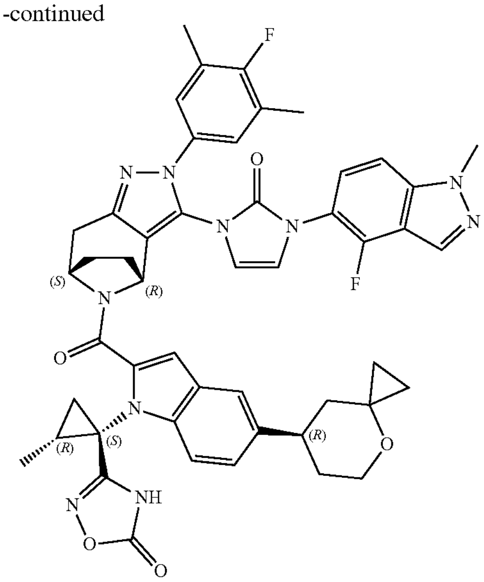

To a solution of 1-((1S,2R)-2-methyl-1-(5-oxo-4,5-dihydro-1,2,4-oxadiazol-3-yl)cyclopropyl)-5-((R)-4-oxaspiro [2.5]octan-7-yl)-1H-indole-2-carboxylic acid (100.00 mg, 244.24 μmol, 1 eq) and 1-(4-fluoro-1-methyl-1H-indazol-5-yl)-3-((4R,7S)-2-(4-fluoro-3,5-dimethylphenyl)-2,4,5,6,7,8-hexahydro-4,7-epiminocyclohepta [c]pyrazol-3-yl)-1,3-dihydro-2H-imidazol-2-one (183.74 mg, 366.36 μmol, 1.5 eq) in DMF (2 mL) was added DIPEA (157.83 mg, 1.22 mmol, 212.71 μL, 5 eq), EDCI (93.64 mg, 488.48 μmol, 2 eq) and HOBt (66.00 mg, 488.48 μmol, 2 eq). The mixture was stirred at 50° C. for 5 hours under $N_2$. LCMS indicated the reaction was completed. The mixture was added dropwise to $H_2O$ (10 mL) and then extracted with ethyl acetate (20 mL*3). The organic layers were combined, washed with water (20 mL), saturated brine (20 mL), dried over $Na_2SO_4$, filtered and concentrated in vacuo. The residue was purified by prep-HPLC (column: Phenomenex Luna C18 75*30 mm*3 um; mobile phase: [$H_2O$ (0.1% TFA)-ACN]; gradient: 55%-85% B over 8.0 min). Compound 3-((1S,2R)-1-(2-((4R,7S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one (53.32 mg, 59.71 μmol, 24.45% yield). $^1$H NMR (400 MHz, DMSO-$d_6$) δ=12.18-11.75 (m, 1H), 8.38-8.17 (m, 1H), 7.72-6.36 (m, 10H), 5.50-4.89 (m, 2H), 4.07 (br s, 3H), 3.63-3.53 (m, 1H), 3.47-3.37 (m, 1H), 3.24-3.05 (m, 1H), 2.98-2.74 (m, 2H), 2.29-1.63 (m, 13H), 1.60-1.11 (m, 3H), 1.11-1.02 (m, 1H), 0.96-0.25 (m, 7H). LC-MS (ES+, m/z): 893.4 [(M+H)$^+$]; Rt=3.130 min; HRMS (EI): m/z [M+H]$^+$ found: 893.3709.

Example 107 Compound 541

3-((1S,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one

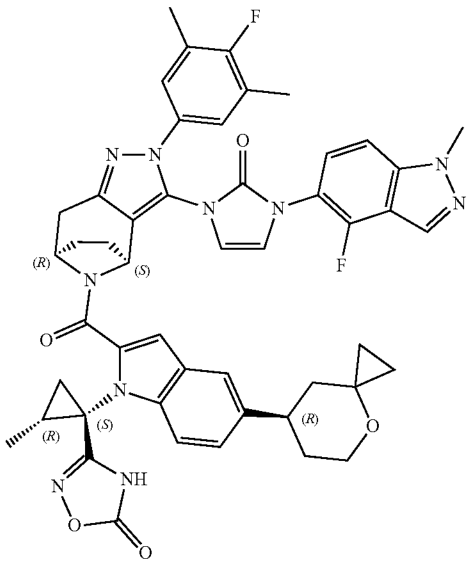

Step 7: 3-((1S,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta[c]pyrazole-9-carbonyl)-5-((R)-4-oxaspiro[2.5]octan-7-yl)-1H-indol-1-yl)-2-methylcyclopropyl)-1,2,4-oxadiazol-5(4H)-one

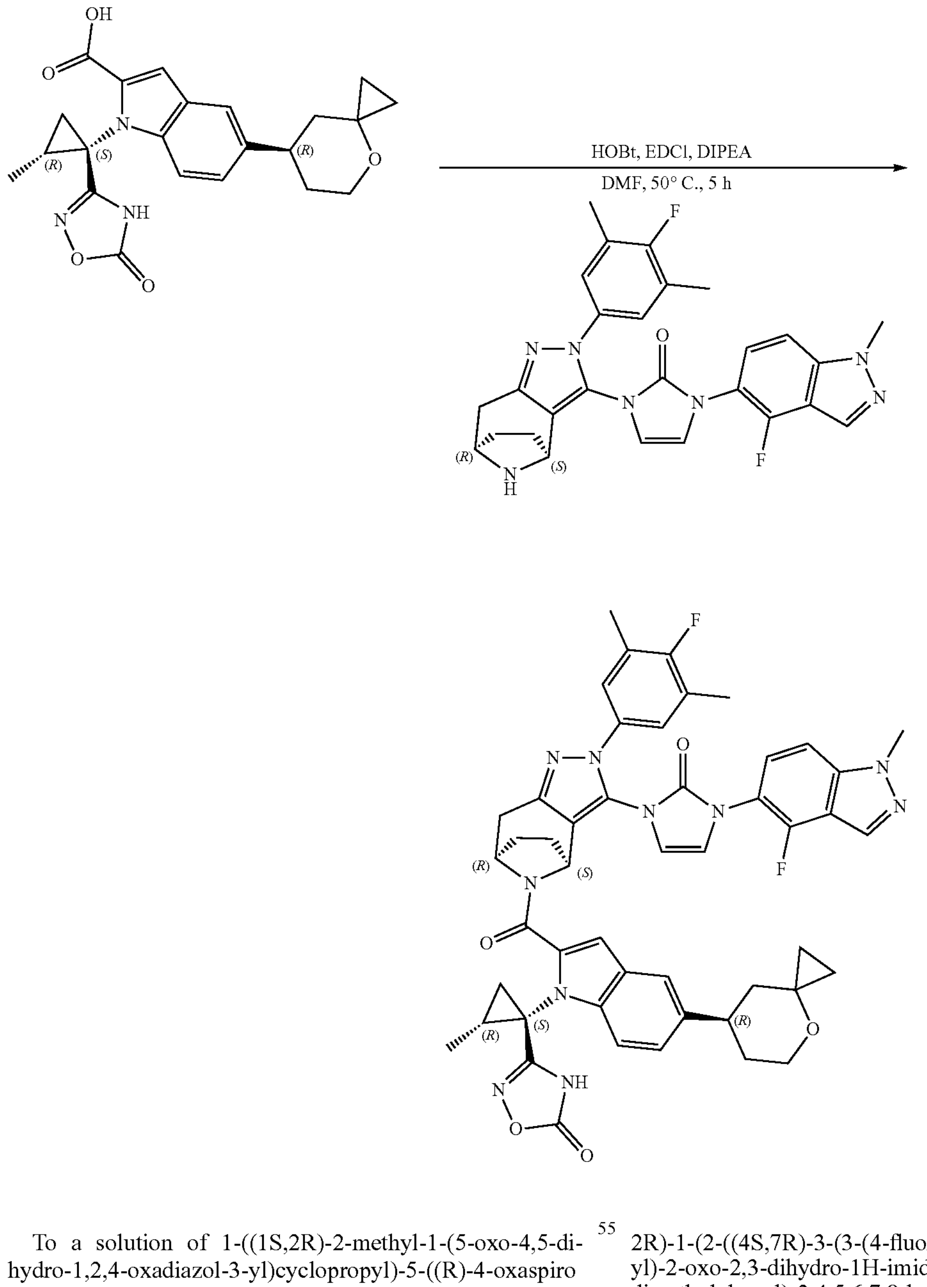

To a solution of 1-((1S,2R)-2-methyl-1-(5-oxo-4,5-dihydro-1,2,4-oxadiazol-3-yl)cyclopropyl)-5-((R)-4-oxaspiro[2.5]octan-7-yl)-1H-indole-2-carboxylic acid (100.00 mg, 244.24 μmol, 1 eq) in DMF (2 mL) was added HOBt (66.00 mg, 488.48 μmol, 2 eq) and EDCI (93.64 mg, 488.48 μmol, 2 eq) and DIEA (94.70 mg, 732.72 μmol, 127.62 μL, 3 eq). 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (183.74 mg, 366.36 μmol, 1.5 eq) was then added. The mixture was stirred at 50° C. for 5 hours under $N_2$. LC-MS showed the reaction was completed. The reaction mixture was diluted with water (50 mL) and extracted with ethyl acetate (50 mL*3). The combined organic layers were washed with saturated brine (50 mL*2), dried over $Na_2SO_4$, filtered and concentrated in vacuo. The residue was purified by prep-HPLC (TFA condition) column: Welch Ultimate C18 120*30 mm*5 um; mobile phase: [$H_2O$ (0.1% TFA)-ACN]; gradient: 50%-80% B over 8.0 min to give 3-((1S,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((R)-4-oxaspiro[2.5]octan-7-yl)-1H-indol-1-yl)-2-methylcyclopropyl)-1,2,4-oxadiazol-5 (4H)-one (82.76 mg, 92.68 μmol, 37.95% yield). $^1$H NMR (400 MHz, DMSO-$d_6$) δ=11.94 (br s, 1H), 8.30 (s, 1H), 7.68-7.29 (m, 4H), 7.28-7.02 (m, 5H), 6.89-6.80 (m, 1H), 5.57-4.90 (m, 2H), 4.10 (s, 3H), 3.89-3.16 (m, 3H), 3.04-2.72 (m, 2H), 2.30-1.68 (m, 14H), 1.63-1.08 (m, 3H), 0.90-0.28 (m, 7H). LC-MS (ES+, m/z): 893.4 [(M+H)$^+$]; Rt=2.919 min. HRMS (EI): m/z [M+H]$^+$ found: 893.3709.

Example 108 Compound 542

3-((1S,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

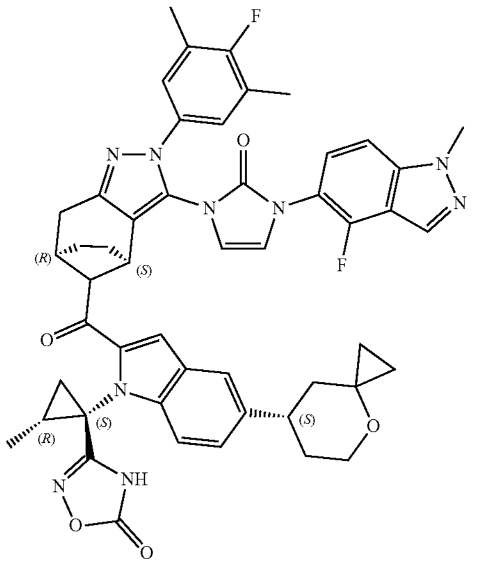

Step 1: 3-((1S,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one

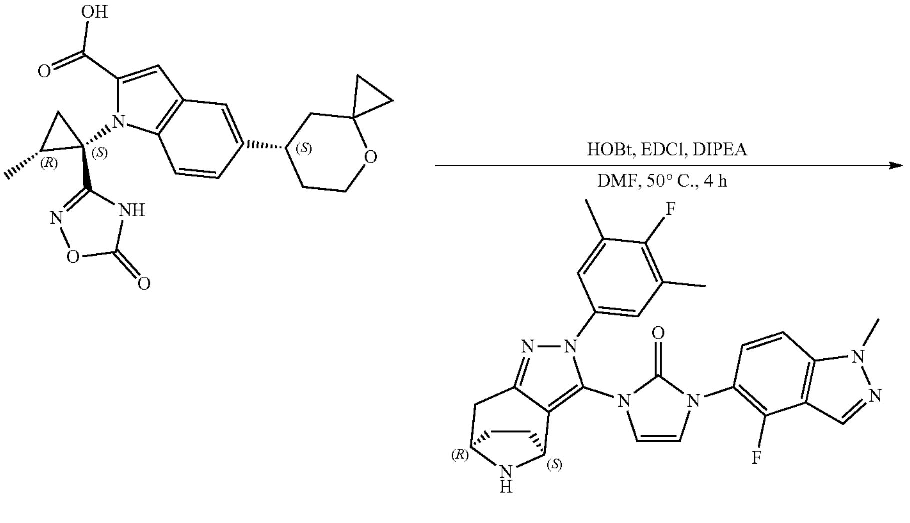

-continued

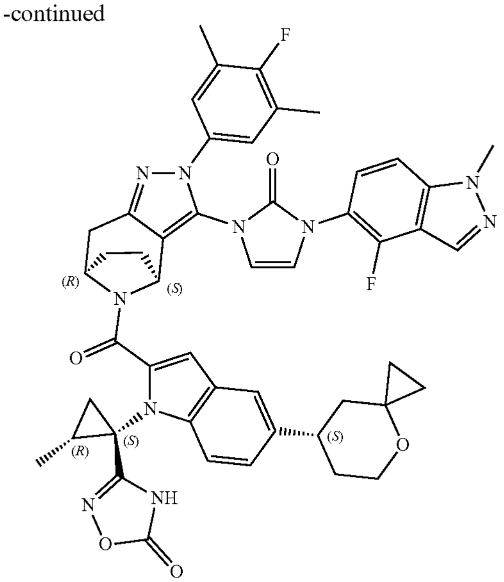

A mixture of 1-((1S,2R)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (70.00 mg, 154.04 μmol, 1 eq), 1-(4-fluoro-1-methyl-1H-indazol-5-yl)-3-((4S,7R)-2-(4-fluoro-3,5-dimethylphenyl)-2,4,5,6,7,8-hexahydro-4,7-epiminocyclohepta [c]pyrazol-3-yl)-1H-imidazol-2 (3H)-one (100.43 mg, 200.25 μmol, 1.3 eq), HOBt (41.63 mg, 308.08 μmol, 2 eq), EDCI (59.06 mg, 308.08 μmol, 2 eq) and DIEA (199.09 mg, 1.54 mmol, 268.31 μL, 10 eq) in DMF (1.4 mL) was degassed and purged with $N_2$ for 3 times. The mixture was stirred at 50° C. for 4 hours under $N_2$ atmosphere. LCMS showed the reaction was completed. The reaction mixture was poured into water (30 mL), then extracted with ethyl acetate (20 mL*3). The combined organic layers were washed with saturated brine (50 mL), dried over anhydrous $Na_2SO_4$, filtered and concentrated under reduced pressure. The residue was purified by prep-HPLC (TFA condition column: 3_Phenomenex Luna C18 75*30 mm*3 um; mobile phase: [$H_2O$ (0.1% TFA)-ACN]; gradient: 45%-75% B over 8.0 min) to give 3-((1S,2R)-1-(2-((4S,7R)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,6,7,8-hexahydro-4,7-epiminocyclohepta [c]pyrazole-9-carbonyl)-5-((S)-4-oxaspiro[2.5]octan-7-yl)-1H-indol-1-yl)-2-methylcyclopropyl)-1,2,4-oxadiazol-5 (4H)-one (73.26 mg, 82.04 μmol, 53.26% yield). $^1$H NMR (400 MHz, DMSO-$d_6$) δ=12.20-11.91 (m, 1H), 8.40-8.21 (m, 1H), 7.72-6.48 (m, 10H), 5.55-4.97 (m, 2H), 4.14-4.06 (m, 3H), 3.90-3.35 (m, 3H), 3.21-2.82 (m, 2H), 2.31-1.63 (m, 14H), 1.56-1.07 (m, 3H), 0.92-0.31 (m, 7H). LC-MS (ES+, m/z): 893.4 [$(M+H)^+$]; Rt=2.3.108 min. HRMS (EI): m/z $[M+H]^+$ found: 893.3709.

Example 109, Compound 606

3-((1S,2S)-1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-5-((S)-4-oxaspiro[2.5]octan-7-yl)-1H-indol-1-yl)-2-methylcyclopropyl)-1,2,4-oxadiazol-5 (4H)-one

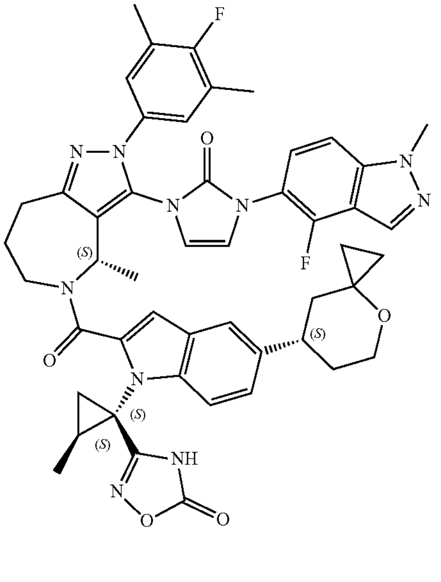

Step 1: 3-((1S,2S)-1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-5-((S)-4-oxaspiro[2.5]octan-7-yl)-1H-indol-1-yl)-2-methylcyclopropyl)-1,2,4-oxadiazol-5 (4H)-one

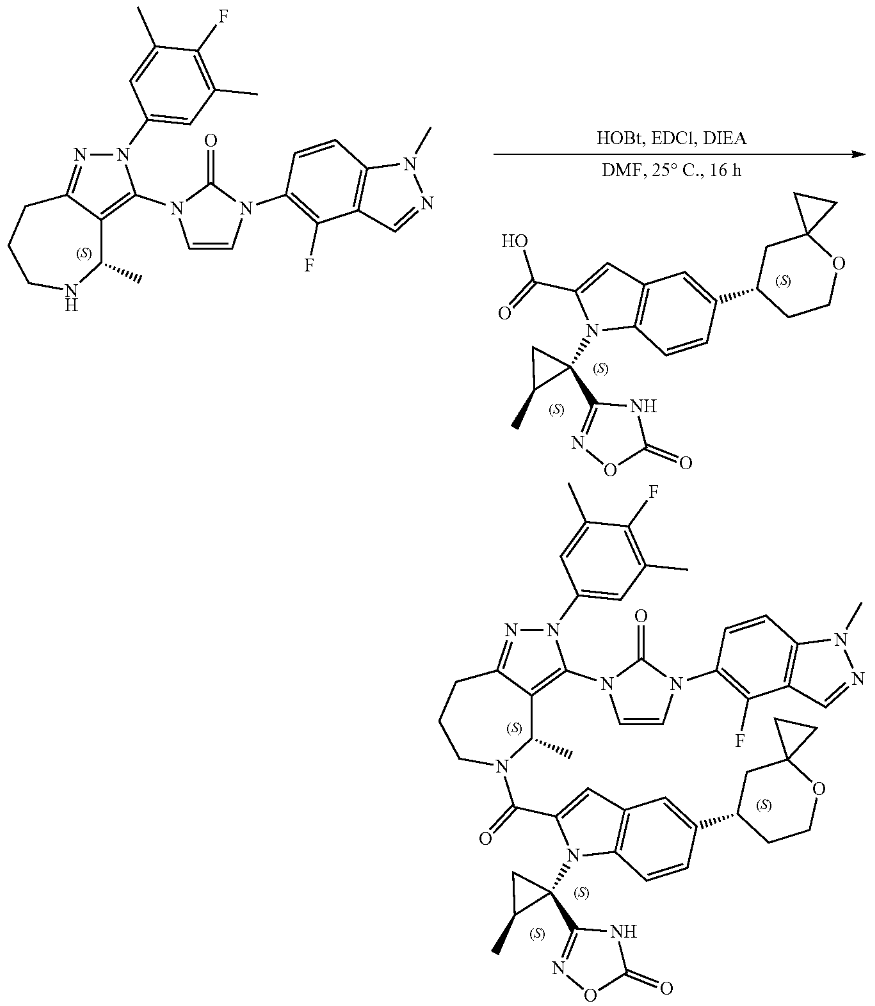

To a solution of 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-1H-indol-1-yl)-2-methylcyclopropyl)-1,2,4-oxadiazol-5 (4H)-one (40 mg, 63.55 μmol, 1 eq), 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (26.02 mg, 63.55 μmol, 1 eq) in DMF (0.8 mL) was added DIEA (41.07 mg, 317.75 μmol, 5 eq), HOBt (17.17 mg, 127.10 μmol, 2 eq) and EDCI (24.36 mg, 127.10 μmol, 2 eq). The mixture was stirred at 25° C. for 16 hours under $N_2$. LCMS showed the reaction was completed. The residue was poured into water (10 mL). The aqueous phase was extracted with ethyl acetate (20 mL*3). The combined organic phase was washed with saturated brine (30 mL), dried with anhydrous $Na_2SO_4$, filtered and concentrated in vacuo. The residue was purified by prep-HPLC (TFA condition; column: Phenomenex Luna C18 75*30 mm*3 um; mobile phase: [$H_2O$ (0.1% TFA)-ACN]; gradient: 55%-85% B over 8.0 min) to give 3-((1S,2S)-1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-5-((S)-4-oxaspiro[2.5]octan-7-yl)-1H-indol-1-yl)-2-methylcyclopropyl)-1,2,4-oxadiazol-5 (4H)-one (9.41 mg, 10.51 μmol, 16.55% yield). $^1H$ NMR (400 MHz, DMSO-$d_6$) δ=12.34-11.52 (m, 1H), 8.24 (br s, 1H), 7.73-5.31 (m, 11H), 4.53 (br s, 1H), 4.15-4.03 (m, 3H), 3.41 (br d, J=11.0 Hz, 3H), 3.12-2.95 (m, 3H), 2.33-2.04 (m, 7H), 1.98--0.03 (m, 18H). $^1H$ NMR (400 MHz, DMSO-$d_6$+$D_2O$) δ=8.38-7.90 (m, 1H), 7.71-5.87 (m, 10H), 5.82-4.37 (m, 2H), 4.02 (br s, 3H), 3.70-3.22 (m, 3H), 3.15-2.81 (m, 3H), 2.23-2.08 (m, 7H), 1.73-0.83 (m, 15H), 0.59-0.23 (m, 3H). $^1H$ NMR (400 MHz, $CD_3CN$) δ=11.88-11.19 (m, 1H), 8.28-7.84 (m, 1H), 7.61-5.55 (m, 11H), 4.82-4.16 (m, 1H), 4.07 (br s, 3H), 3.91-3.51 (m, 3H), 3.13-2.95 (m, 3H), 2.29-2.19 (m, 7H), 1.75-0.97 (m, 15H), 0.66-0.32 (m, 3H). LC-MS (ES+, m/z): 895.4 [$(M+H)^+$]; Rt=3.314 min. HRMS (EI): m/z $[M+H]^+$ found: 895.3825

Example 110, Compound 607

3-((1S,2S)-1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-5-(tetrahydro-2H-pyran-4-yl)-1H-indol-1-yl)-2-methylcyclopropyl)-1,2,4-oxadiazol-5 (4H)-one

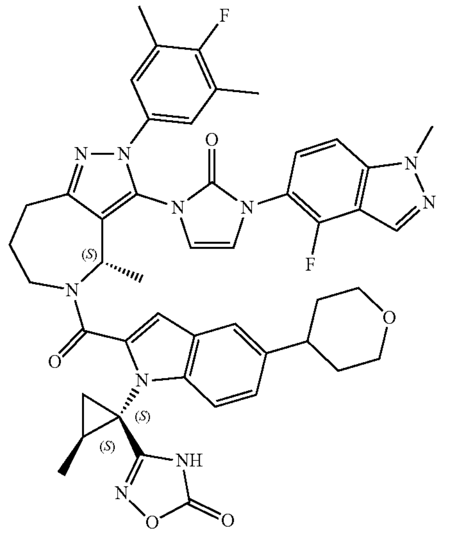

Step 1: 3-((1S,2S)-1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-5-(tetrahydro-2H-pyran-4-yl)-1H-indol-1-yl)-2-methylcyclopropyl)-1,2,4-oxadiazol-5 (4H)-one

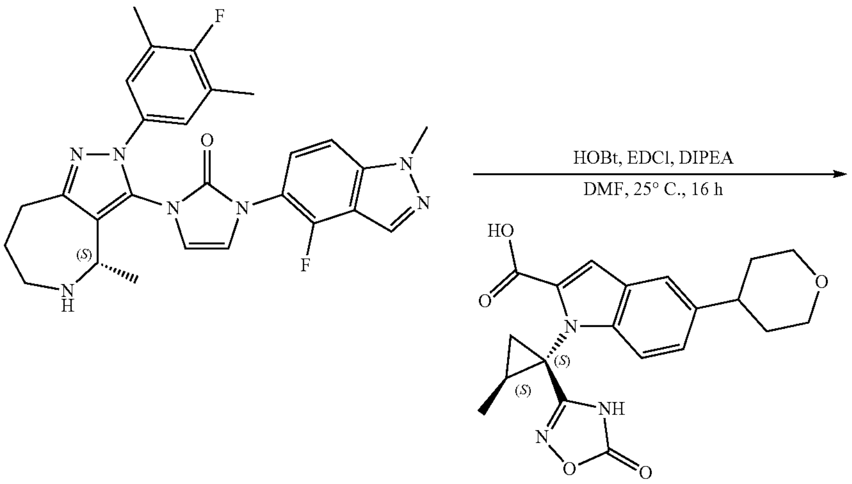

-continued

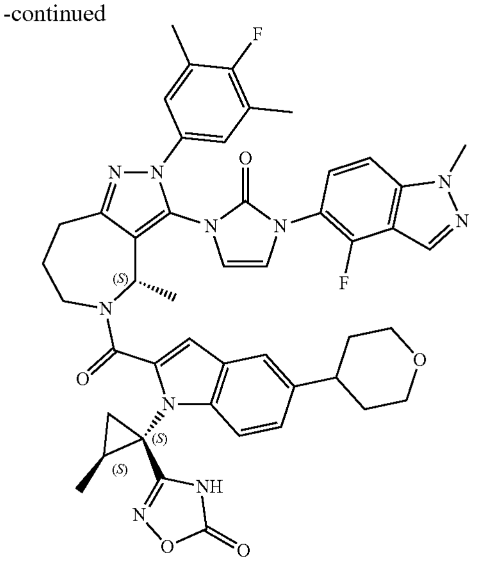

To a solution of 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-1H-indol-1-yl)-2-methylcyclopropyl)-1,2,4-oxadiazol-5 (4H)-one (40 mg, 63.55 μmol, 1 eq), 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (25.92 mg, 63.55 μmol, 1 eq) in DMF (0.8 mL) was added DIEA (41.07 mg, 317.75 μmol, 5 eq), HOBt (25.76 mg, 190.65 μmol, 3 eq) and EDCI (36.55 mg, 190.65 μmol, 3 eq). The mixture was stirred at 25° C. for 16 hours under $N_2$. LCMS showed the reaction was completed. The residue was poured into water (10 mL). The aqueous phase was extracted with ethyl acetate (20 mL*3). The combined organic phase was washed with saturated brine (30 mL), dried with anhydrous $Na_2SO_4$, filtered and concentrated in vacuo. The residue was purified by prep-HPLC (TFA condition; column: Phenomenex Luna C18 75*30 mm*3 um; mobile phase: [$H_2O$ (0.1% TFA)-ACN]; gradient: 50%-80% B over 8.0 min) to give 3-((1S,2S)-1-(2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-2,4,5,6,7,8-hexahydropyrazolo[4,3-c]azepine-5-carbonyl)-5-(tetrahydro-2H-pyran-4-yl)-1H-indol-1-yl)-2-methylcyclopropyl)-1,2,4-oxadiazol-5 (4H)-one (10.18 mg, 11.72 μmol, 18.44% yield). $^1H$ NMR (400 MHz, DMSO-$d_6$) δ=12.42-11.53 (m, 1H), 8.43-7.98 (m, 1H), 7.74-5.46 (m, 11H), 4.55 (br dd, J=4.4, 9.9 Hz, 1H), 4.10-3.93 (m, 4H), 3.71-3.42 (m, 3H), 3.06-2.81 (m, 4H), 2.29-2.00 (m, 7H), 1.95-0.80 (m, 14H). $^1H$ NMR (400 MHz, DMSO-$d_6$+$D_2O$) δ=8.38-7.87 (m, 1H), 7.83-4.42 (m, 12H), 4.06 (br s, 3H), 3.95-3.89 (m, 1H), 3.64-3.31 (m, 3H), 3.09-2.78 (m, 4H), 2.24-2.06 (m, 7H), 1.72-0.93 (m, 14H). LC-MS (ES+, m/z): 869.4 [$(M+H)^+$]; Rt=3.194 min. HRMS (EI): m/z $[M+H]^+$ found: 869.3713

Example 111 Compound 610

3-((1S,2S)-1-(2-((4S,8R)-2-(4-fluoro-3,5-dimethylphenyl)-3-(3-(8-fluoroisoquinolin-7-yl)-2-oxo-2,3-dihydro-1H-imidazol-1-yl)-4,5,6,7,8,9-hexahydro-2H-4,8-epiminocycloocta [c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one

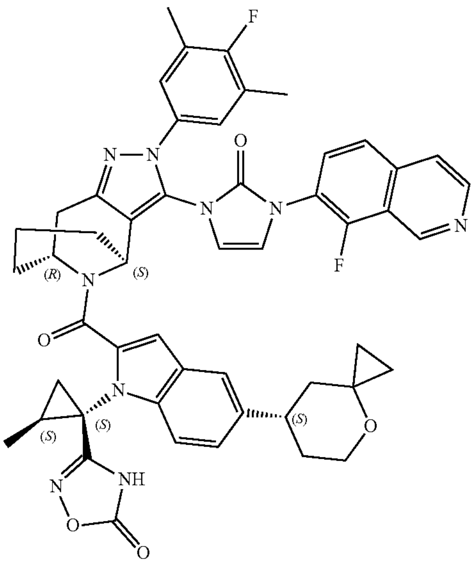

Scheme 610
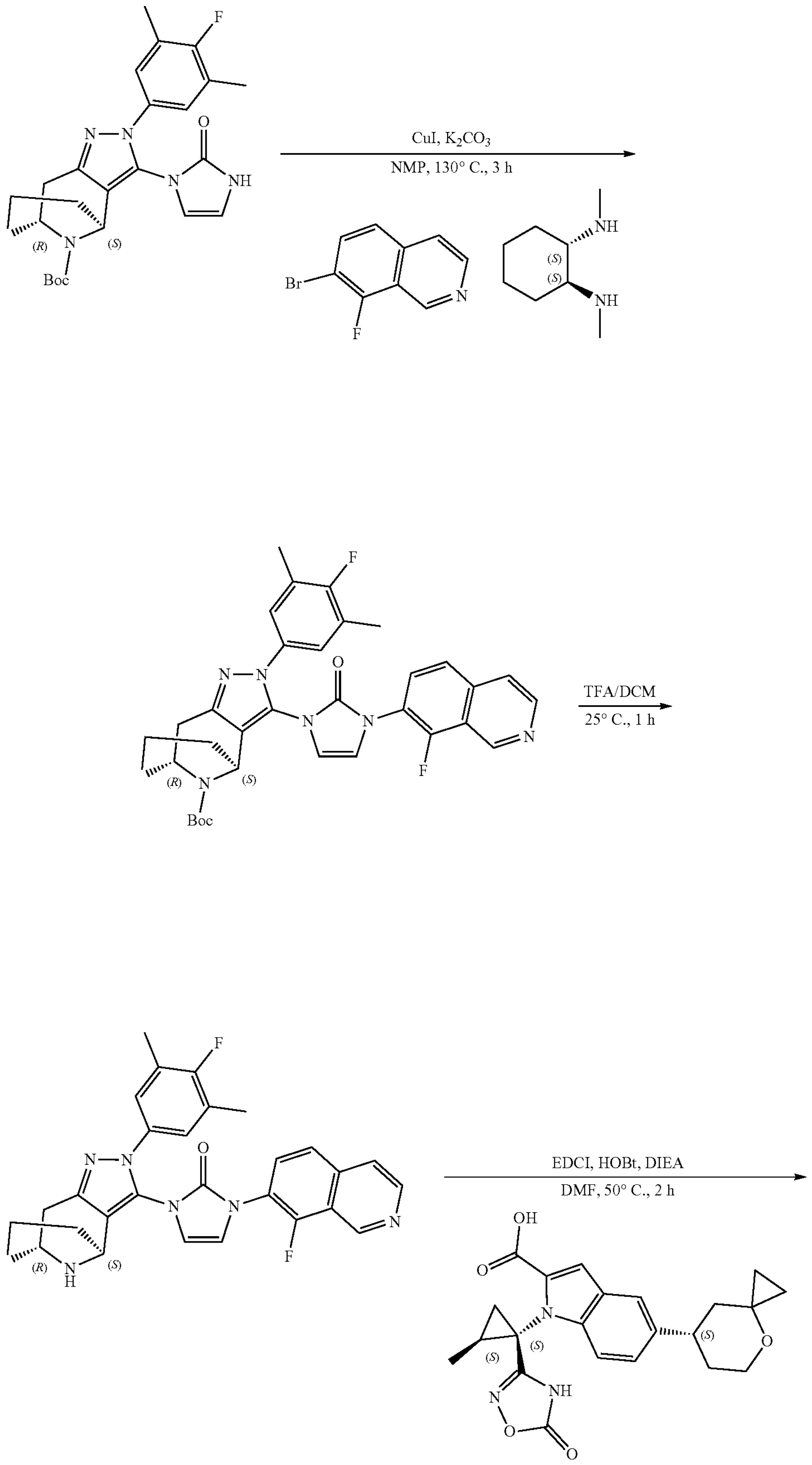

-continued

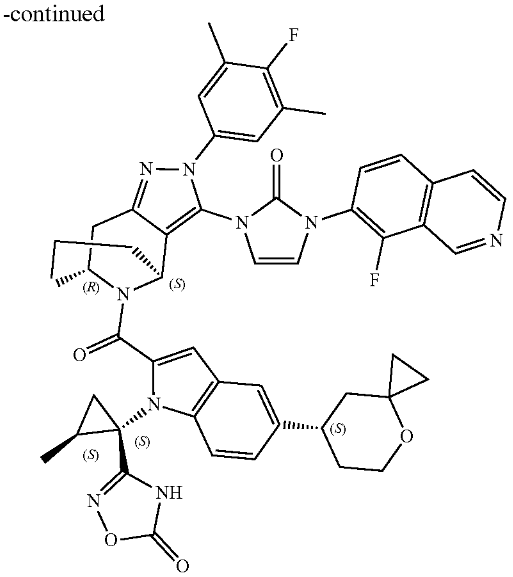

Step 1: tert-butyl (4S,8R)-2-(4-fluoro-3,5-dimethylphenyl)-3-(3-(8-fluoroisoquinolin-7-yl)-2-oxo-2,3-dihydro-1H-imidazol-1-yl)-4,5,6,7,8,9-hexahydro-2H-4,8-epiminocycloocta [c]pyrazole-10-carboxylate

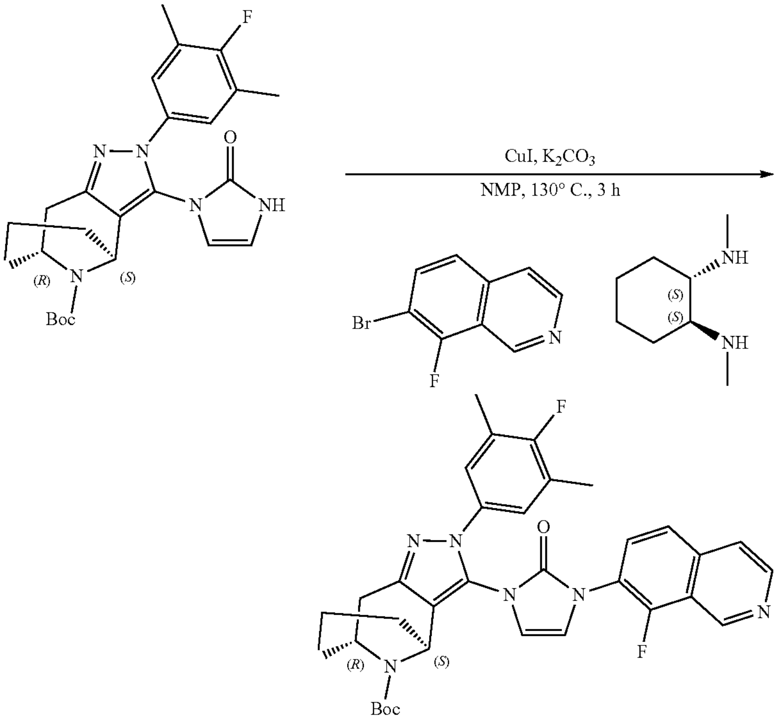

To a mixture of tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (150 mg, 320.83 μmol, 1 eq) and 7-bromo-8-fluoroisoquinoline (145.04 mg, 641.66 μmol, 2 eq), (1S,2S)—$N^1$,$N^2$-dimethylcyclohexane-1,2-diamine (136.91 mg, 962.50 μmol, 3 eq) in NMP (3 mL) was added $K_2CO_3$ (133.02 mg, 962.50 μmol, 3 eq) followed by CuI (122.20 mg, 641.66 μmol, 2 eq) in one portion under $N_2$. The mixture was stirred at 130° C. for 3 hours under $N_2$. LCMS showed the reaction was completed. The residue was poured into saturated EDTA solution (20 mL) and ethyl acetate (20 mL) stirred for 0.5 hour. The aqueous phase was extracted with ethyl acetate (20 mL*3). The combined organic phase was washed with saturated brine (30 mL), dried with anhydrous $Na_2SO_4$, filtered and concentrated in vacuum. The residue was purified by column chromatography ($SiO_2$, Commercial hexanes:ethyl acetate=20/1 to 2/1) to give tert-butyl (4S,8R)-2-(4-fluoro-3,5-dimethylphenyl)-3-(3-(8-fluoroisoquinolinnolin-7-yl)-2-oxo-2,3-dihydro-1H-imidazol-1-yl)-4,5,6,7,8,9-hexahydro-2H-4,8-epiminocycloocta [c]pyrazole-10-carboxylate (140 mg, 205.66 μmol, 64.10% yield). LC-MS (ES+, m/z): 613.4 [(M+H)$^+$]; Rt=0.552 min.

Step 2: 1-((4S,8R)-2-(4-fluoro-3,5-dimethylphenyl)-4,5,6,7,8,9-hexahydro-2H-4,8-epiminocycloocta [c]pyrazol-3-yl)-3-(8-fluoroisoquinolin-7-yl)-1,3-dihydro-2H-imidazol-2-one

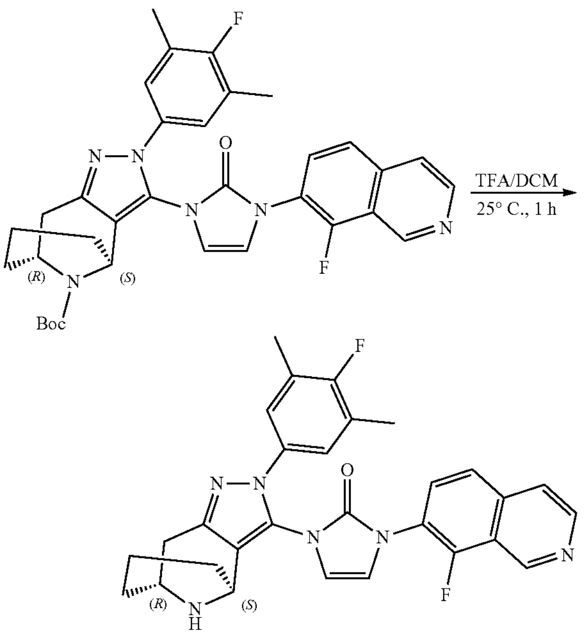

To a mixture of tert-butyl (4S,8R)-2-(4-fluoro-3,5-dimethylphenyl)-3-(3-(8-fluoroisoquinolin-7-yl)-2-oxo-2,3-dihydro-1H-imidazol-1-yl)-4,5,6,7,8,9-hexahydro-2H-4,8-epiminocycloocta [c]pyrazole-10-carboxylate (70 mg, 102.83 μmol, 1 eq) in DCM (1 mL) was added TFA (0.4 mL) in one portion at 25° C. The mixture was stirred at 25° C. for 1 hour. LCMS showed the reaction was completed. The residue poured into saturated $NaHCO_3$ (20 mL). The aqueous phase was extracted with ethyl acetate (10 mL*3). The combined organic phase was washed with saturated brine (30 mL), dried with anhydrous $Na_2SO_4$, filtered and concentrated in vacuo to give 1-((4S,8R)-2-(4-fluoro-3,5-dimethylphenyl)-4,5,6,7,8,9-hexahydro-2H-4,8-epiminocycloocta [c]pyrazol-3-yl)-3-(8-fluoroisoquinolin-7-yl)-1,3-dihydro-2H-imidazol-2-one (50 mg, crude). LC-MS (ES+, m/z): 513.3 [(M+H)$^+$]; Rt=0.397 min.

Step 3: 3-((1S,2S)-1-(2-((4S,8R)-2-(4-fluoro-3,5-dimethylphenyl)-3-(3-(8-fluoroisoquinolin-7-yl)-2-oxo-2,3-dihydro-1H-imidazol-1-yl)-4,5,6,7,8,9-hexahydro-2H-4,8-epiminocycloocta [c]pyrazole-10-carbonyl)-5-((S)-4-oxaspiro[2.5]octan-7-yl)-1H-indol-1-yl)-2-methylcyclopropyl)-1,2,4-oxadiazol-5(4H)-one

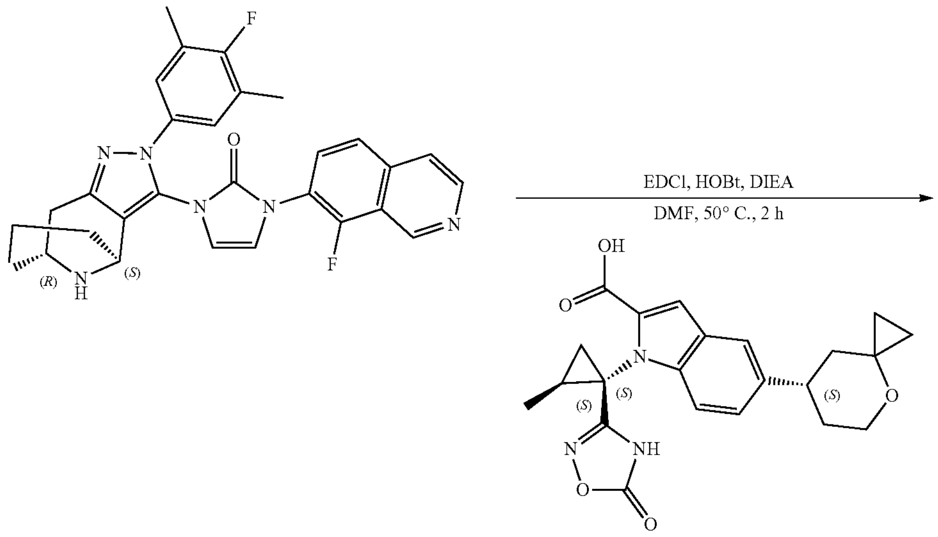

-continued

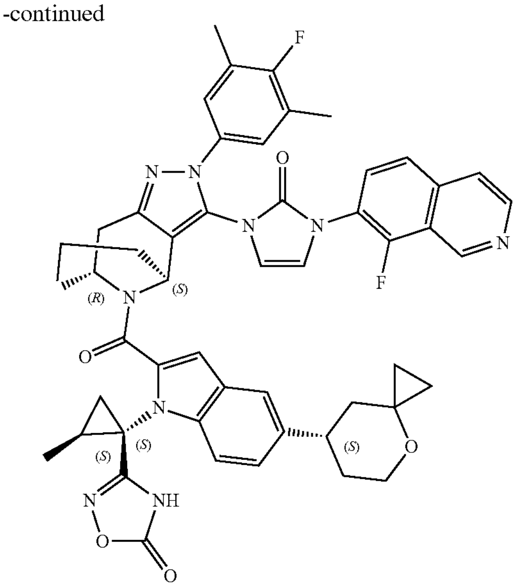

To a mixture of 1-((4S,8R)-2-(4-fluoro-3,5-dimethylphenyl)-4,5,6,7,8,9-hexahydro-2H-4,8-epiminocycloocta[c]pyrazol-3-yl)-3-(8-fluoroisoquinolin-7-yl)-1,3-dihydro-2H-imidazol-2-one (50 mg, 97.55 μmol, 1 eq) and 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (39.94 mg, 97.55 μmol, 1 eq) in DMF (1 mL) was added DIEA (63.04 mg, 487.76 μmol, 5 eq), HOBt (19.77 mg, 146.33 μmol, 1.5 eq), and EDCI (24.31 mg, 126.82 μmol, 1.3 eq) in one portion. The mixture was stirred at 50° C. for 2 hours. LCMS showed the reaction was completed. The residue was poured into water (20 mL). The aqueous phase was extracted with chloroform:isopropanol=3:1 (10 mL*3). The combined organic phase was washed with saturated brine (30 mL), dried with anhydrous $Na_2SO_4$, filtered and concentrated in vacuo. The residue was purified by prep-HPLC (column: WePure Biotech XP tC18 150*40*7 um; mobile phase: [$H_2O$ (10 mM $NH_4HCO_3$)-ACN]; gradient: 40%-70% B over 8.0 min) to give 3-((1S,2S)-1-(2-((4S,8R)-2-(4-fluoro-3,5-dimethylphenyl)-3-(3-(8-fluoroisoquinolin-7-yl)-2-oxo-2,3-dihydro-1H-imidazol-1-yl)-4,5,6,7,8,9-hexahydro-2H-4,8-epiminocycloocta[c]pyrazole-10-carbonyl)-5-((S)-4-oxaspiro[2.5]octan-7-yl)-1H-indol-1-yl)-2-methylcyclopropyl)-1,2,4-oxadiazol-5(4H)-one (20.69 mg, 22.89 μmol, 23.46% yield). $^1H$ NMR (400 MHz, DMSO-$d_6$) δ=12.30-11.65 (m, 1H), 9.72-9.24 (m, 1H), 8.73-8.60 (m, 1H), 7.99-7.85 (m, 2H), 7.65-7.47 (m, 1H), 7.45-7.06 (m, 6H), 7.03-6.66 (m, 2H), 5.85-4.94 (m, 2H), 3.80 (br s, 1H), 3.59-3.53 (m, 1H), 3.26-2.71 (m, 3H), 2.28-2.16 (m, 7H), 2.01-1.86 (m, 2H), 1.77-1.49 (m, 8H), 1.36-0.92 (m, 5H), 0.79-0.68 (m, 1H), 0.62-0.32 (m, 3H). LC-MS (ES+, m/z): 904.5 [$(M+H)^+$]; Rt=2.959 min. HRMS (EI): m/z $[M+H]^+$ found: 904.3762.

Example 112, Compound 611

2-(4-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta[c]pyrazol-3-yl)-2-oxo-2,3-dihydro-1H-imidazol-1-yl)-2-fluorophenyl)-N-methylacetamide Scheme 611

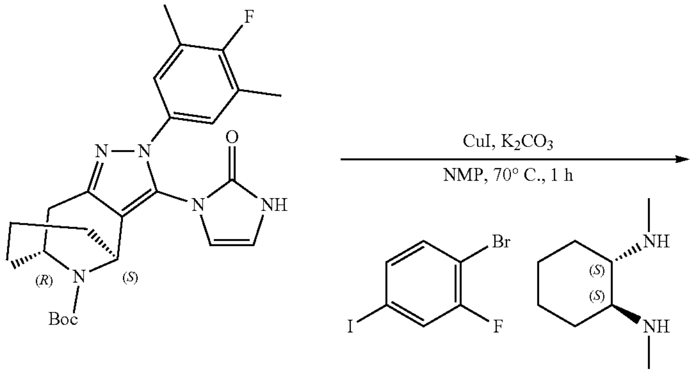

-continued
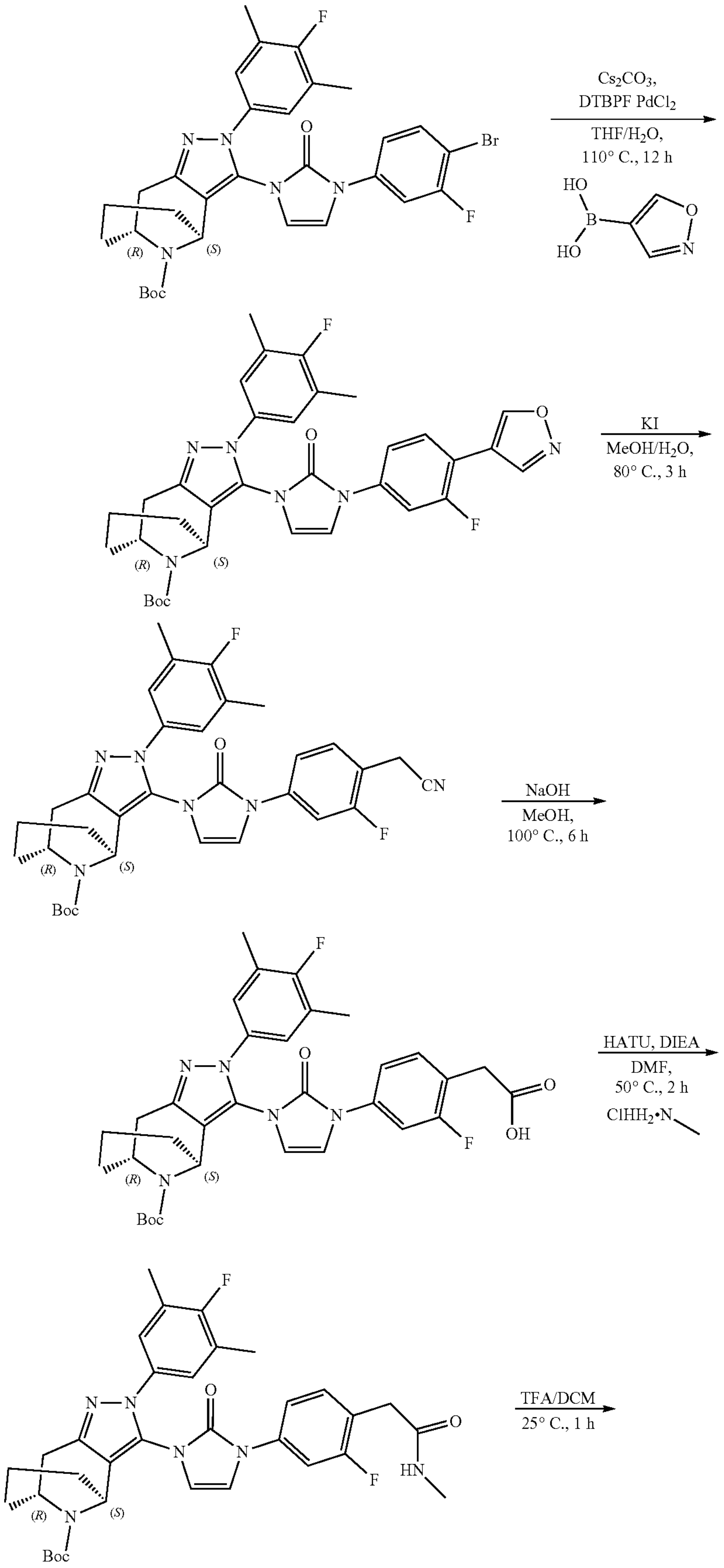

-continued

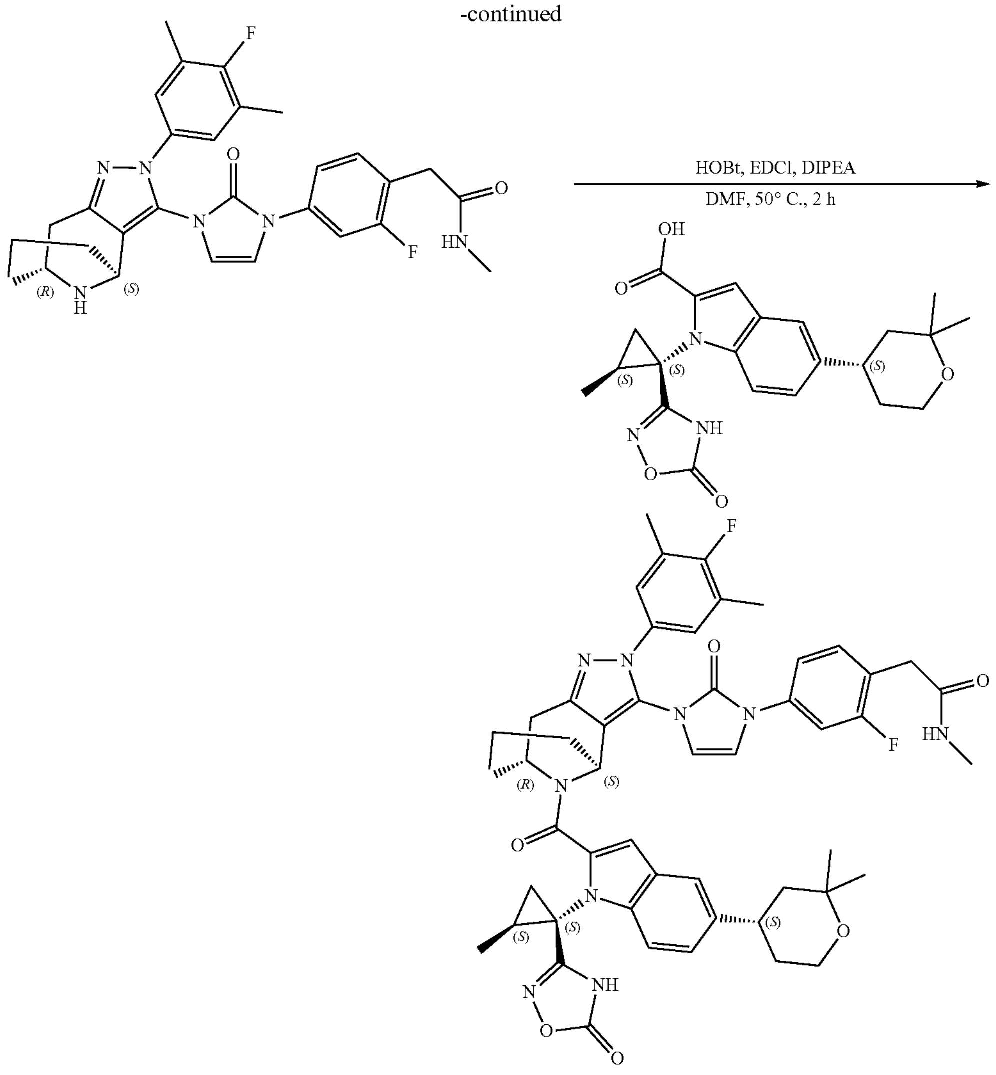

Step 1: tert-butyl (4S,8R)-3-(3-(4-bromo-3-fluorophenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate

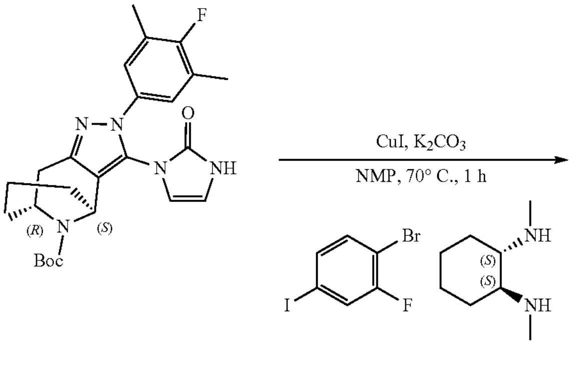

-continued

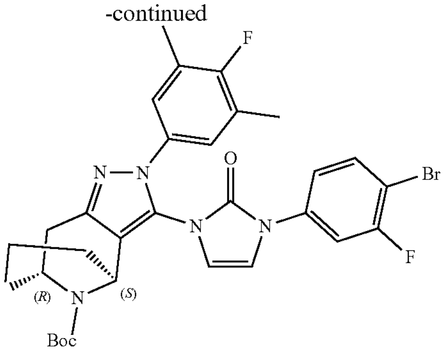

To a mixture of tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (500 mg, 1.07 mmol, 1 eq) and 1-bromo-2-fluoro-4-iodobenzene (643.58 mg, 2.14 mmol, 2 eq), (1S, 2S)—$N^1$,$N^2$-dimethylcyclohexane-1,2-diamine (456.36 mg, 3.21 mmol, 3 eq) in NMP (10 mL) was added $K_2CO_3$ (295.61 mg, 2.14 mmol, 2 eq) followed by CuI (407.35 mg, 2.14 mmol, 2 eq) in one portion under $N_2$. The mixture was stirred at 70° C. for 1 hour under $N_2$. LCMS showed the reaction was completed. The residue was poured into saturated EDTA solution (50 mL) and ethyl acetate (50 mL) stirred for 0.5 hour. The aqueous phase was extracted with ethyl acetate (25 mL*3). The combined organic phase was washed with saturated brine (75 mL), dried with anhydrous $Na_2SO_4$, filtered and concentrated in vacuo. The residue was purified by prep-TLC ($SiO_2$, Commercial hexanes:ethyl acetate=1:1) to give tert-butyl (4S,8R)-3-(3-(4-bromo-3-fluorophenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (500 mg, 671.33 μmol, 62.77% yield). LC-MS (ES+, m/z): 640.2 [$(M+H)^+$]; Rt=2.272 min.

Step 2: tert-butyl (4S,8R)-2-(4-fluoro-3,5-dimethylphenyl)-3-(3-(3-fluoro-4-(isoxazol-4-yl)phenyl)-2-oxo-2,3-dihydro-1H-imidazol-1-yl)-4,5,6,7,8,9-hexahydro-2H-4,8-epiminocycloocta [c]pyrazole-10-carboxylate

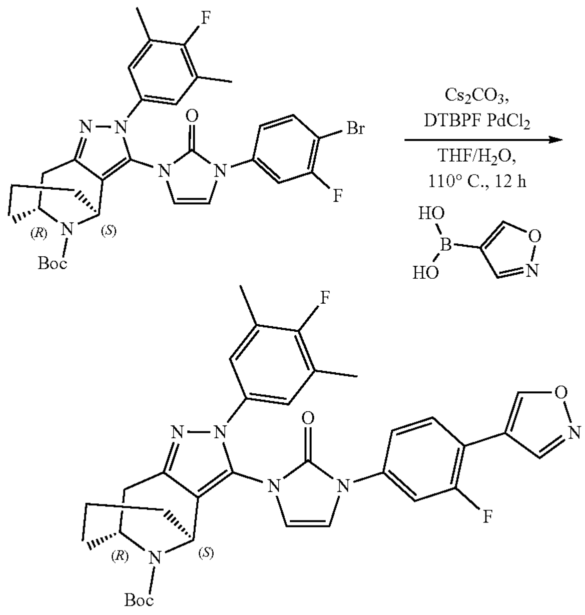

To a mixture of tert-butyl (4S,8R)-3-(3-(4-bromo-3-fluorophenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (200 mg, 268.53 μmol, 1 eq) and isoxazol-4-ylboronic acid (90.94 mg, 805.60 μmol, 3 eq) in THF (4 mL) and $H_2O$ (0.4 mL) was added $Cs_2CO_3$ (874.93 mg, 2.69 mmol, 10 eq) followed by DTBPF $PdCl_2$ (17.50 mg, 26.85 μmol, 0.1 eq) in one portion under $N_2$. The mixture was stirred at 110° C. for 12 hours. LCMS showed the reaction was completed. Two Batches were performed in parallel and then combined for work up. The residue was poured into saturated EDTA solution (30 mL) and ethyl acetate (30 mL) stirred for 0.5 hour under $N_2$. The aqueous phase was extracted with ethyl acetate (15 mL*3). The combined organic phase was washed with saturated brine (45 mL), dried with anhydrous $Na_2SO_4$, filtered and concentrated in vacuo. The residue was purified by column chromatography ($SiO_2$, Commercial hexanes: ethyl acetate-0:1) to give tert-butyl (4S,8R)-2-(4-fluoro-3,5-dimethylphenyl)-3-(3-(3-fluoro-4-(isoxazol-4-yl)phenyl)-2-oxo-2,3-dihydro-1H-imidazol-1-yl)-4,5,6,7,8,9-hexahydro-2H-4,8-epiminocycloocta [c]pyrazole-10-carboxylate (370 mg, 517.92 μmol, 96.44% yield). LC-MS (ES+, m/z): 629.3 [$(M+H)^+$]; Rt=1.950 min.

Step 3: tert-butyl (4S,8R)-3-(3-(4-(cyanomethyl)-3-fluorophenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate

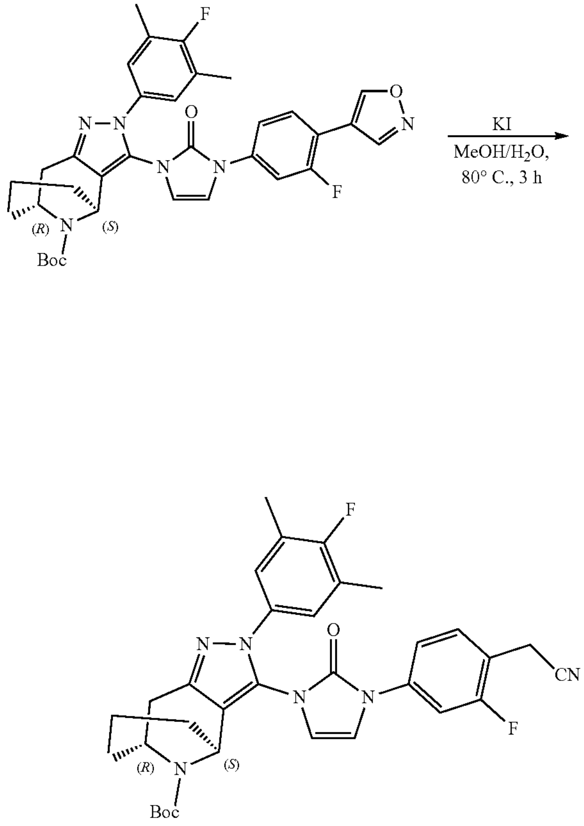

To a mixture of tert-butyl (4S,8R)-2-(4-fluoro-3,5-dimethylphenyl)-3-(3-(3-fluoro-4-(isoxazol-4-yl)phenyl)-2-oxo-2,3-dihydro-1H-imidazol-1-yl)-4,5,6,7,8,9-hexahydro-2H-4,8-epiminocycloocta [c]pyrazole-10-carboxylate (350 mg, 489.93 μmol, 1 eq) in $H_2O$ (1.4 mL) and MeOH (5.6 mL), was added KI (813.29 mg, 4.90 mmol, 10 eq) in one portion under $N_2$. The mixture was stirred at 80° C. for 3 hours. LCMS showed the reaction was completed. The residue was poured into water (30 mL). The aqueous phase was extracted with ethyl acetate (15 mL*3). The combined organic phase was washed with saturated brine (45 mL), dried with anhydrous $Na_2SO_4$, filtered and concentrated in vacuo. The residue was purified by column chromatography ($SiO_2$, Commercial hexanes:ethyl acetate=0:1) to give tert-butyl (4S,8R)-3-(3-(4-(cyanomethyl)-3-fluorophenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (250 mg, 382.91 μmol, 78.16% yield). LC-MS (ES+, m/z): 601.3 [$(M+H)^+$]; Rt=1.970 min.

Step 4: 2-(4-(3-((4S,8R)-10-(tert-butoxycarbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-2-fluorophenyl) acetic acid

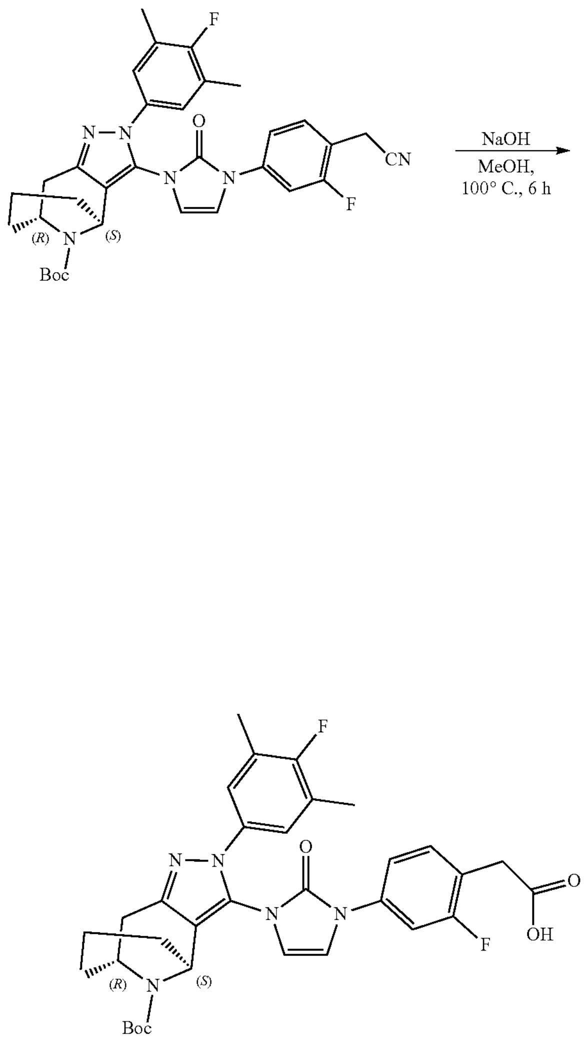

To a mixture of tert-butyl (4S,8R)-3-(3-(4-(cyanomethyl)-3-fluorophenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (200 mg, 306.33 μmol, 1 eq) in MeOH (4 mL) was added NaOH (122.52 mg, 3.06 mmol, 10 eq) in one portion under $N_2$. The mixture was stirred at 100° C. for 6 hours under $N_2$. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo to give 2-(4-(3-((4S,8R)-10-(tert-butoxycarbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-2-fluorophenyl) acetic acid (140 mg, crude). LC-MS (ES+, m/z): 620.4 [(M+H)$^+$]; Rt=0.579 min.

Step 5: tert-butyl (4S,8R)-2-(4-fluoro-3,5-dimethylphenyl)-3-(3-(3-fluoro-4-(2-(methylamino)-2-oxoethyl)phenyl)-2-oxo-2,3-dihydro-1H-imidazol-1-yl)-4,5,6,7,8,9-hexahydro-2H-4,8-epiminocycloocta [c]pyrazole-10-carboxylate

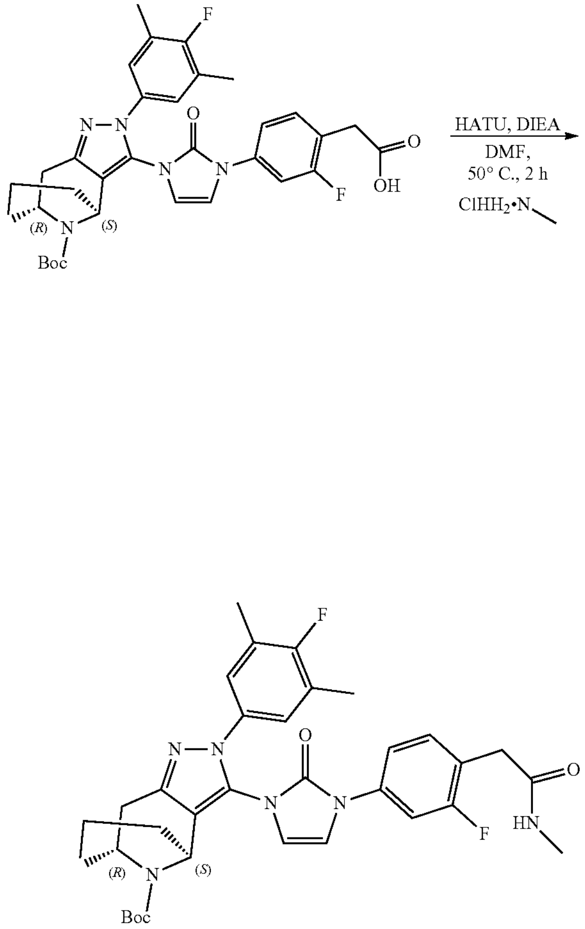

To a mixture of 2-(4-(3-((4S,8R)-10-(tert-butoxycarbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-2-fluorophenyl) acetic acid (140 mg, 203.34 μmol, 1 eq) and methanamine hydrochloride (137.29 mg, 2.03 mmol, 10 eq) in DMF (1.4 mL) was added DIEA (262.80 mg, 2.03 mmol, 10 eq) and then HATU (115.97 mg, 305.01 μmol, 1.5 eq) in one portion under $N_2$. The mixture was stirred at 50° C. for 2 hours. LCMS showed the reaction was completed. The residue was poured into water (20 mL). The aqueous phase was extracted with ethyl acetate (20 mL*3). The combined organic phase was washed with saturated brine (30 mL), dried with anhydrous $Na_2SO_4$, filtered and concentrated in vacuo. The residue was purified by prep-TLC ($SiO_2$, Commercial hexanes:ethyl acetate=1:1) to give tert-butyl (4S,8R)-2-(4-fluoro-3,5-dimethylphenyl)-3-(3-(3-fluoro-4-(2-(methylamino)-2-oxoethyl)phenyl)-2-oxo-2,3-dihydro-1H-imidazol-1-yl)-4,5,6,7,8,9-hexahydro-2H-4,8-epiminocycloocta [c]pyrazole-10-carboxylate (80 mg, 122.65 μmol, 60.32% yield). LC-MS (ES+, m/z): 633.4 [(M+H)$^+$]; Rt=1.837 min.

Step 6: 2-(2-fluoro-4-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylacetamide

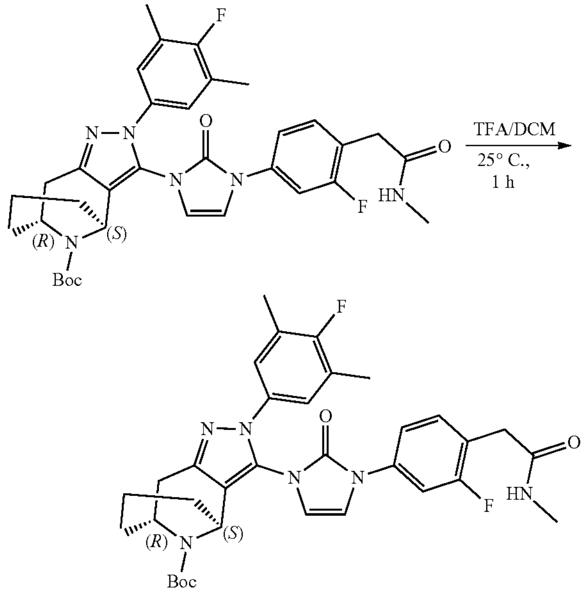

To a mixture of tert-butyl (4S,8R)-2-(4-fluoro-3,5-dimethylphenyl)-3-(3-(3-fluoro-4-(2-(methylamino)-2-oxoethyl)phenyl)-2-oxo-2,3-dihydro-1H-imidazol-1-yl)-4,5,6,7,8,9-hexahydro-2H-4,8-epiminocycloocta [c]pyrazole-10-carboxylate (40 mg, 61.32 μmol, 1 eq) in DCM (0.6 mL) was added TFA (0.2 mL). The mixture was stirred at 25° C. for 1 hour. LCMS showed the reaction was completed. The residue was poured into saturated $NaHCO_3$ (10 mL). The aqueous phase was extracted with ethyl acetate (15 mL*3). The combined organic phase was washed with saturated brine (15 mL), dried with anhydrous $Na_2SO_4$, filtered and concentrated in vacuo to give 2-(2-fluoro-4-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylacetamide (30 mg, crude). LC-MS (ES+, m/z): 533.3 [$(M+H)^+$]; Rt=1.205 min.

Step 7: 2-(4-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-2-fluorophenyl)-N-methylacetamide

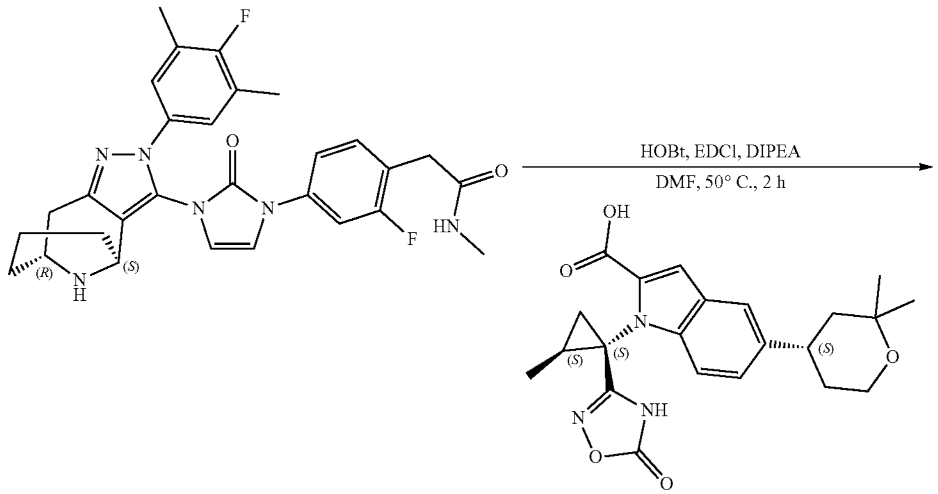

-continued

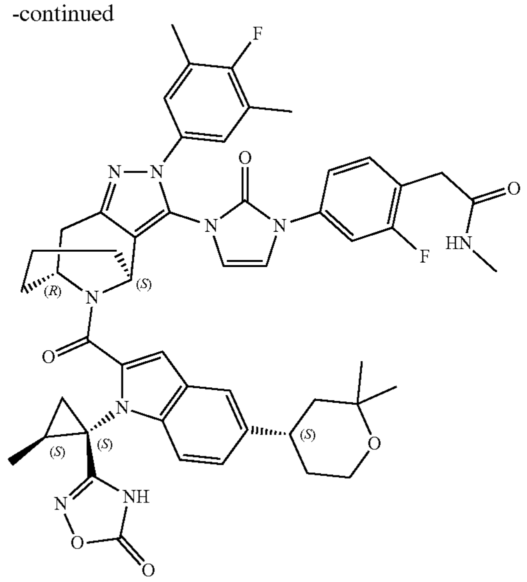

To a mixture of 2-(2-fluoro-4-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylacetamide (30 mg, 56.33 μmol, 1 eq) and 5-((S)-2,2-dimethyltetrahydro-2H-pyran-4-yl)-1-((1,2S)-2-methyl-1-(5-oxo-4,5-dihydro-1,2,4-oxadiazol-3-yl)cyclopropyl)-1H-indole-2-carboxylic acid (23.18 mg, 56.33 μmol, 1 eq) in DMF (0.6 mL) was added DIEA (36.40 mg, 281.65 μmol, 5 eq), HOBt (11.42 mg, 84.49 μmol, 1.5 eq) and EDCI (14.04 mg, 73.23 μmol, 1.3 eq) in one portion under $N_2$. The mixture was stirred at 50° C. for 2 hours. LCMS showed the reaction was completed. The residue was poured into water (20 mL). The aqueous phase was extracted with chloroform:isopropanol=3:1 (20 mL*3). The combined organic phase was washed with saturated brine (30 mL), dried with anhydrous $Na_2SO_4$, filtered and concentrated in vacuo. The residue was purified by prep-HPLC (column: Phenomenex Luna C18 75*30 mm*3 um; mobile phase: [$H_2O$ (0.1% TFA)-ACN]; gradient: 45%-75% B over 8.0 min) to give 2-(4-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-2-fluorophenyl)-N-methylacetamide (18.21 mg, 19.41 μmol, 34.46% yield). $^1$H NMR (400 MHz, DMSO-$d_6$) δ=12.36-11.63 (m, 1H), 8.05-7.85 (m, 1H), 7.74-7.47 (m, 2H), 7.45-7.29 (m, 3H), 7.28-7.08 (m, 3H), 7.05 (s, 3H), 5.85 (br d, J=16.5 Hz, 1H), 5.28-5.11 (m, 1H), 3.74-3.63 (m, 2H), 3.38 (s, 2H), 3.15 (br dd, J=7.5, 17.0 Hz, 1H), 3.03-2.72 (m, 2H), 2.58 (t, J=4.8 Hz, 3H), 2.24-2.14 (m, 6H), 1.65 (br d, J=4.9 Hz, 13H), 1.33 (br d, J=6.3 Hz, 1H), 1.28-1.23 (m, 3H), 1.22-0.89 (m, 5H). $^1$H NMR (400 MHz, DMSO+$D_2O$-$d_6$) δ=7.62-7.42 (m, 2H), 7.41-7.25 (m, 3H), 7.24-6.98 (m, 4H), 6.97-6.61 (m, 2H), 5.84-4.87 (m, 2H), 3.72-3.64 (m, 2H), 3.47-3.35 (m, 2H), 3.34-3.04 (m, 1H), 3.02-2.74 (m, 2H), 2.59-2.54 (m, 3H), 2.21-2.12 (m, 6H), 2.02-1.41 (m, 13H), 1.31 (br d, J=6.3 Hz, 1H), 1.26-1.21 (m, 3H), 1.18-0.87 (m, 5H). LC-MS (ES+, m/z): 926.4 [(M+H)$^+$]; Rt=3.248 min. HRMS (EI): m/z [M+H]$^+$ found: 926.4187.

Example 113, Compound 612

N-(2-chloro-4-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylcyclopropanecarboxamide Scheme 612

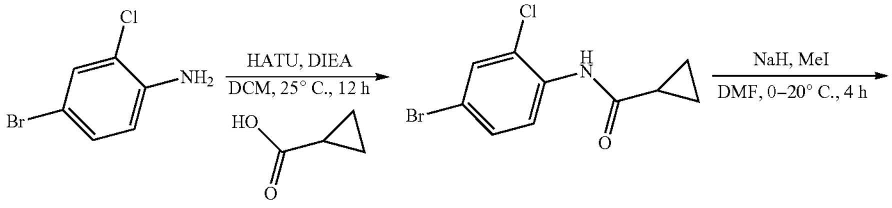

-continued
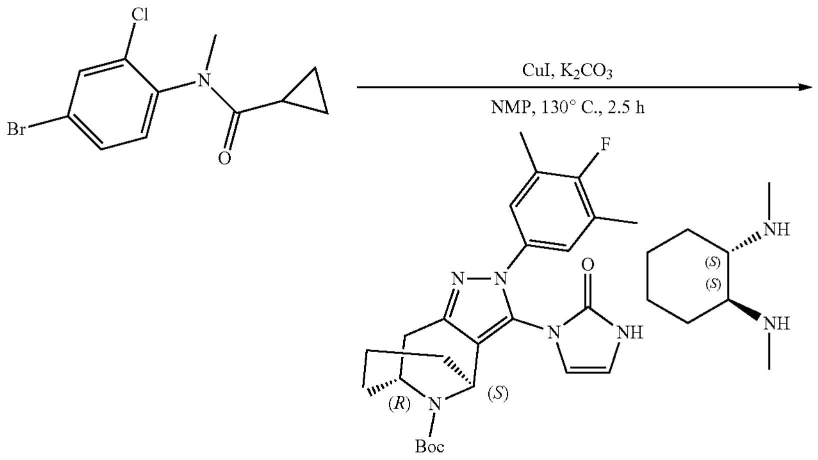
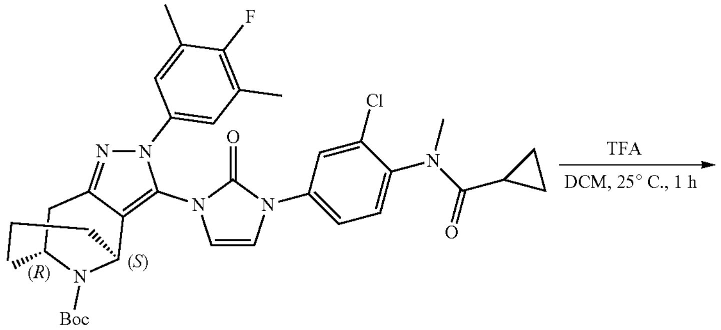
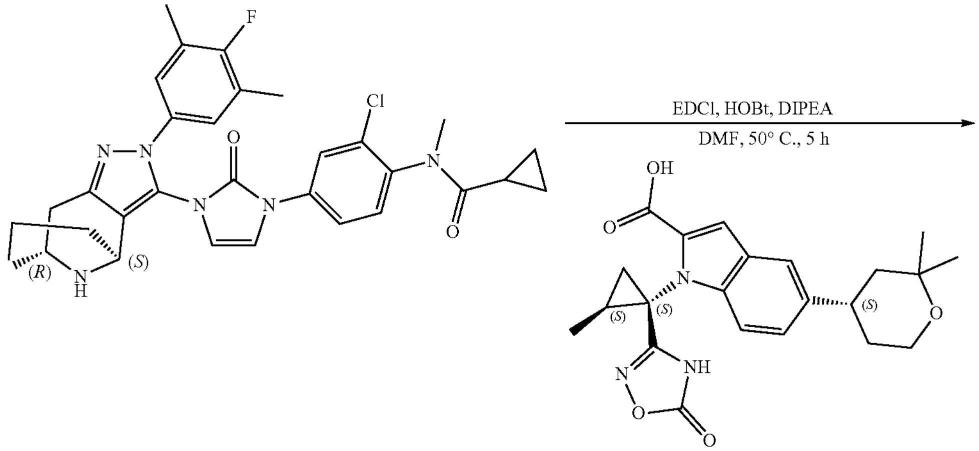

-continued

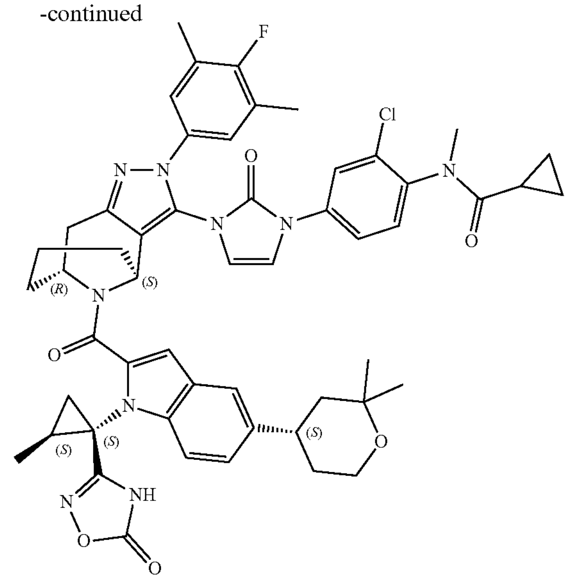

Step 1: N-(4-bromo-2-chlorophenyl)cyclopropanecarboxamide

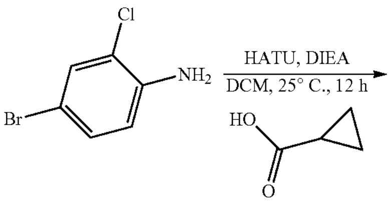

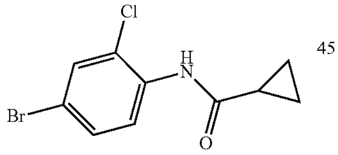

To a solution of 4-bromo-2-chloroaniline (1 g, 4.84 mmol, 1 eq) and cyclopropanecarboxylic acid (625.44 mg, 7.27 mmol, 574.86 μL, 1.5 eq) in DCM (10 mL) was added DIPEA (3.13 g, 24.22 mmol, 4.22 mL, 5 eq) and HATU (2.76 g, 7.27 mmol, 1.5 eq). The mixture was stirred at 25° C. for 12 hours under $N_2$. LCMS indicated the reaction was completed. The mixture was added dropwise to $H_2O$ (20 mL) and then extracted with DCM (30 mL*3). The organic layers were combined, washed with water (20 mL), saturated brine (20 mL), dried over $Na_2SO_4$, filtered and concentrated in vacuo. The residue was purified by prep-HPLC (column: Welch Xtimate C18 250*100 mm #10 um; mobile phase: [$H_2O$ (0.1% TFA)-ACN]; gradient: 35%-65% B over 20.0 min) to give N-(4-bromo-2-chlorophenyl) cyclopropanecarboxamide (650 mg, 2.32 mmol, 47.86% yield). LC-MS (ES+, m/z): 274.1 [$(M+H)^+$]. Rt=1.477 min.

Step 2: N-(4-bromo-2-chlorophenyl)-N-methylcyclopropanecarboxamide

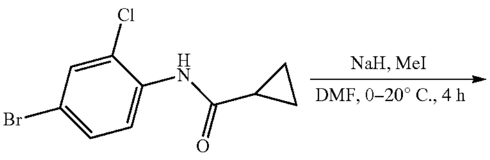

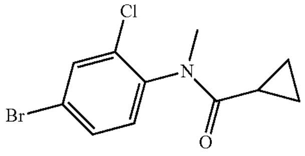

To a solution of N-(4-bromo-2-chlorophenyl)cyclopropanecarboxamide (600 mg, 2.19 mmol, 1 eq) in DMF (12 mL) was added NaH (131.12 mg, 3.28 mmol, 60% purity, 1.5 eq) at 0° C. for 0.5 hours. MeI (620.40 mg, 4.37 mmol, 272.11 μL, 2 eq) was then added at 0° C. The mixture was allowed to warm to 20° C. for 3.5 hours under $N_2$. LCMS indicated the reaction was completed. The reaction mixture was poured into saturated $NH_4Cl$ (20 mL) at 0° C. The aqueous phase was extracted with ethyl acetate (30 mL*3). The combined organic layers were washed with saturated brine (20 mL*3), dried over anhydrous $Na_2SO_4$, filtered and concentrated under reduced pressure. The residue was purified by prep-TLC ($SiO_2$, hexanes:ethyl acetate=3:1) to give N-(4-bromo-2-chlorophenyl)-N-methylcyclopropanecarboxamide (540 mg, 1.87 mmol, 85.45% yield). LC-MS (ES+, m/z): 288.1 [$(M+H)^+$]. Rt=1.547 min.

Step 3: tert-butyl (4S,8R)-3-(3-(3-chloro-4-(N-methylcyclopropanecarboxamido)phenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate

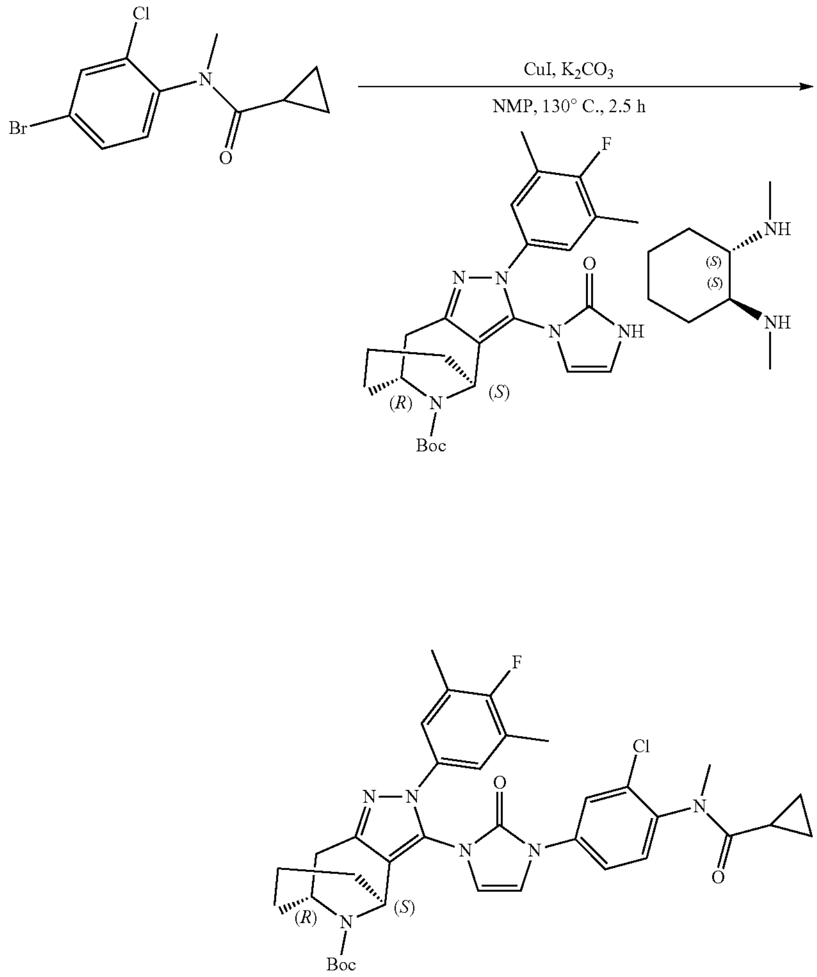

To a solution of tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (185 mg, 395.69 μmol, 1 eq) and N-(4-bromo-2-chlorophenyl)-N-methylcyclopropanecarboxamide (342.55 mg, 1.19 mmol, 3 eq) in NMP (4 mL) was added (1S,2S)—$N^1$,$N^2$-dimethylcyclohexane-1,2-diamine (112.57 mg, 791.39 μmol, 2 eq), CuI (150.72 mg, 791.39 μmol, 2 eq) and $K_2CO_3$ (164.06 mg, 1.19 mmol, 3 eq). The mixture was stirred at 130° C. for 2.5 hours under $N_2$. LCMS indicated the reaction was completed. The residue was poured into saturated EDTA solution (10 mL) and ethyl acetate (15 mL) stirred for 0.5 hour and then extracted with ethyl acetate (15 mL*2). The organic layers were washed with water (10 mL*2), saturated brine (10 mL*2), dried over $Na_2SO_4$, filtered, concentrated under reduced pressure. The residue was purified by prep-TLC ($SiO_2$, hexanes:ethyl acetate=1:1) to give tert-butyl (4S,8R)-3-(3-(3-chloro-4-(N-methylcyclopropanecarboxamido) phenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (220 mg, 307.59 μmol, 77.73% yield). $^1$H NMR (400 MHz, DMSO-$d_6$) δ=8.11-8.04 (m, 1H), 7.87-7.79 (m, 1H), 7.71-7.64 (m, 1H), 7.48-7.41 (m, 1H), 7.17-7.08 (m, 2H), 7.04-6.99 (m, 1H), 5.22-4.97 (m, 1H), 4.70-4.52 (m, 1H), 3.12-3.08 (m, 3H), 3.06-3.00 (m, 1H), 2.74-2.65 (m, 1H), 2.21-2.17 (m, 6H), 1.74-1.36 (m, 16H), 0.81-0.74 (m, 2H), 0.66-0.55 (m, 2H). LC-MS (ES+, m/z): 675.3 [(M+H)$^+$]; Rt=2.048 min.

Step 4: N-(2-chloro-4-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylcyclopropanecarboxamide

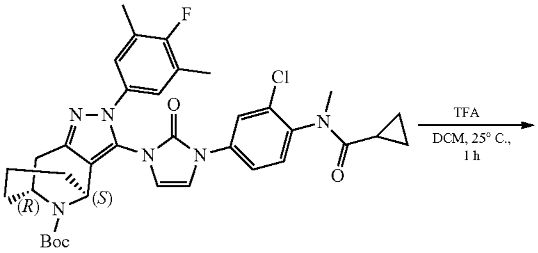

-continued

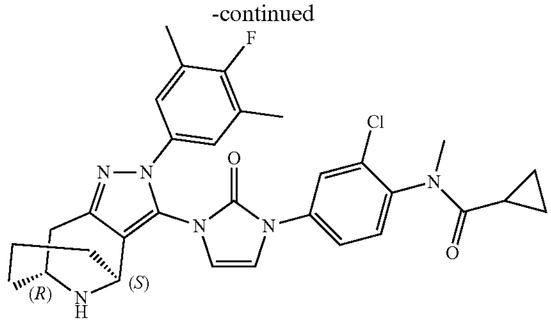

To a solution of tert-butyl (45,8R)-3-(3-(3-chloro-4-(N-methylcyclopropanecarboxamido) phenyl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carboxylate (100 mg, 148.11 μmol, 1 eq) in DCM (1 mL) was added TFA (767.50 mg, 6.73 mmol, 0.5 mL, 45.45 eq). The mixture was stirred at 25° C. for 1 hour under $N_2$. LCMS indicated the reaction was completed. The reaction mixture was removed TFA and DCM, and adjusted to pH=7 with saturated $NaHCO_3$ (10 mL), and then extracted with DCM (10 mL*3). The organic layers were combined and washed with water (10 mL*2), saturated brine (10 mL*2), dried over $Na_2SO_4$, filtered, concentrated under reduced pressure to give N-(2-chloro-4-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylcyclopropanecarboxamide (85 mg, crude). LC-MS (ES+, m/z): 575.4 [(M+H)$^+$]. Rt=0.455 min.

Step 5: N-(2-chloro-4-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl) cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylcyclopropanecarboxamide

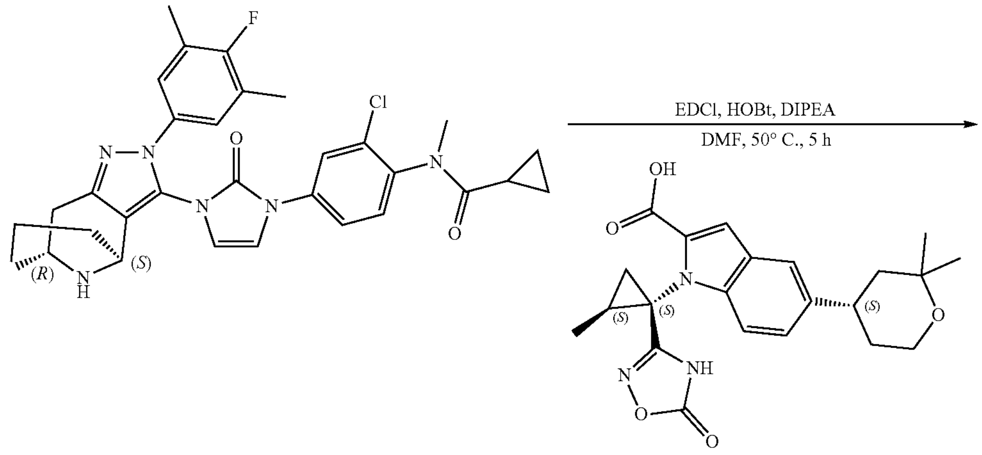

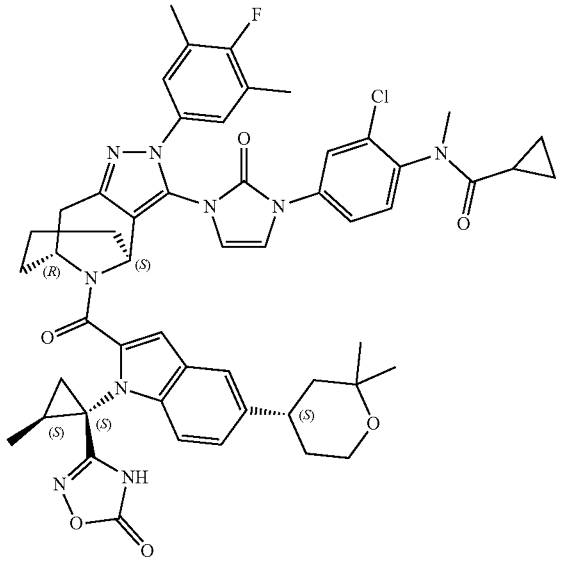

To a solution of N-(2-chloro-4-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylcyclopropanecarboxamide (40 mg, 69.56 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (34.34 mg, 83.47 μmol, 1.2 eq) in DMF (0.8 mL) was added DIPEA (44.95 mg, 347.78 μmol, 60.58 μL, 5 eq), EDCI (17.33 mg, 90.42 μmol, 1.3 eq) and HOBt (14.10 mg, 104.33 μmol, 1.5 eq). The mixture was stirred at 50° C. for 5 hours under $N_2$. LCMS indicated the reaction was completed. The mixture was added dropwise to $H_2O$ (10 mL) and then extracted with ethyl acetate (20 mL*3). The organic layers were combined, washed with water (20 mL), saturated brine (20 mL), dried over $Na_2SO_4$, filtered and concentrated in vacuo. The residue was purified by prep-HPLC (column: 3_Phenomenex Luna C18 75*30 mm*3 um; mobile phase: [$H_2O$ (0.1% TFA)-ACN]; gradient: 55%-85% B over 8.0 min) to give N-(2-chloro-4-(3-((45,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)phenyl)-N-methylcyclopropanecarboxamide (11.21 mg, 11.57 μmol, 16.64% yield). $^1$H NMR (400 MHz, DMSO-$d_6$) δ=12.28-11.66 (m, 1H), 8.13-6.65 (m, 11H), 5.80-4.89 (m, 2H), 3.55-2.86 (m, 8H), 2.24-2.16 (m, 6H), 1.90-1.15 (m, 22H), 1.01-0.88 (m, 1H), 0.81-0.50 (m, 4H). LC-MS (ES+, m/z): 968.4 [(M+H)$^+$]; Rt=3.248 min. HRMS (EI): m/z [M+H]$^+$ found: 968.3987.

Example 114, Compound 614

3-((1S,2S)-1-(2-((4S,8R)-2-(4-fluoro-3,5-dimethylphenyl)-3-(3-(5-fluoroisoquinolin-6-yl)-2-oxo-2,3-dihydro-1H-imidazol-1-yl)-4,5,6,7,8,9-hexahydro-2H-4,8-epiminocycloocta [c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one Scheme 614

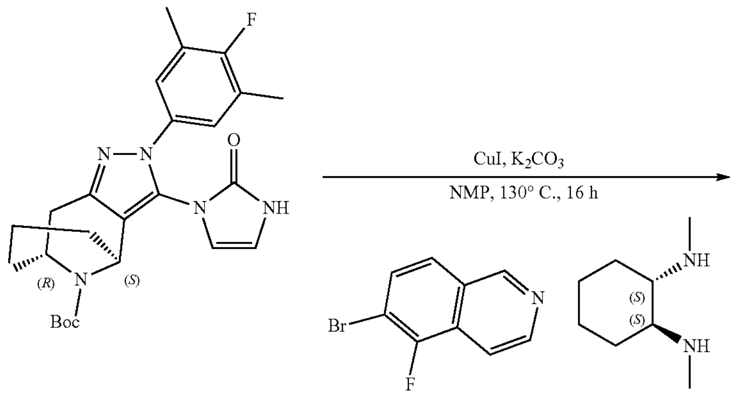

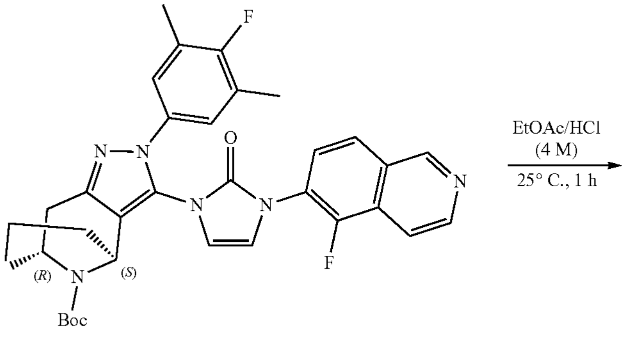

-continued
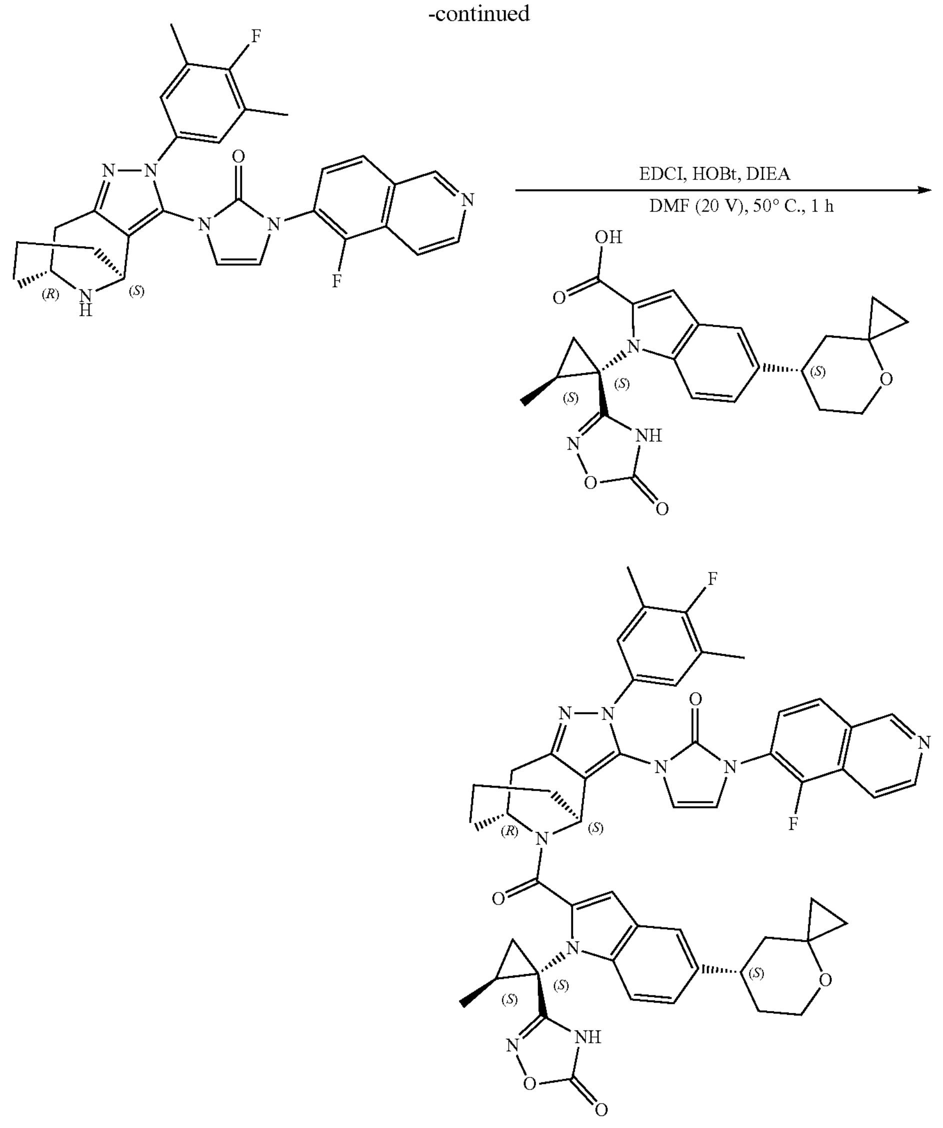
Step 1: (4S,8R)-tert-butyl 2-(4-fluoro-3,5-dimethylphenyl)-3-(3-(5-fluoroisoquinolin-6-yl)-2-oxo-2,3-dihydro-1H-imidazol-1-yl)-4,5,6,7,8,9-hexahydro-2H-4,8-epiminocycloocta [c]pyrazole-10-carboxylate
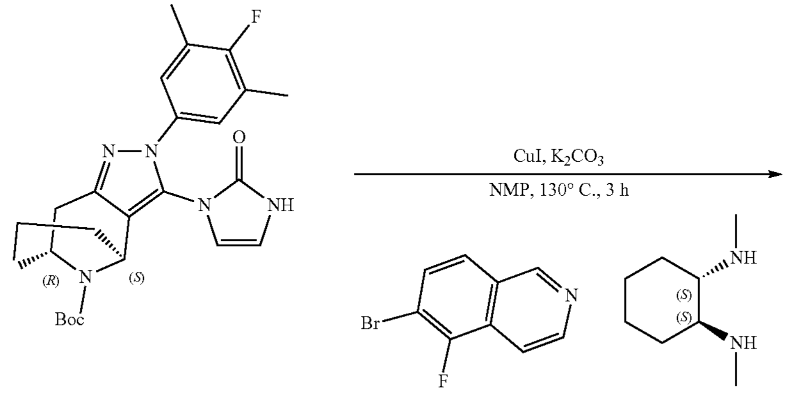

-continued

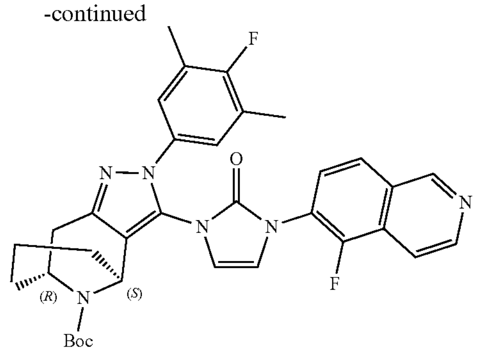

A mixture of (4S,8R)-tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (150 mg, 320.83 μmol, 1 eq), 6-bromo-5-fluoroisoquinoline (145.04 mg, 641.66 μmol, 2 eq), $K_2CO_3$ (88.68 mg, 641.66 μmol, 2 eq), CuI (122.20 mg, 641.66 μmol, 2 eq) and (1S,2S)—N1,N2-dimethylcyclohexane-1,2-diamine (45.64 mg, 320.83 μmol, 1 eq) in NMP (3 mL) was degassed and purged with $N_2$ for 3 times, and then the mixture was stirred at 130° C. for 16 hours under $N_2$ atmosphere. LCMS indicated the reaction was completed. The reaction mixture was quenched by addition saturated EDTA solution (50 mL) and ethyl acetate 50 mL, stirred for 0.5 hour, extracted with ethyl acetate (50 mL*3). The combined organic layers were washed with saturated brine (30 mL), dried over anhydrous $Na_2SO_4$, filtered and concentrated under reduced pressure. The residue was purified by prep-TLC ($SiO_2$, Commercial hexanes:ethyl acetate=1:1) to give (4S,8R)-tert-butyl 2-(4-fluoro-3,5-dimethylphenyl)-3-(3-(5-fluoroisoquinolin-6-yl)-2-oxo-2,3-dihydro-1H-imidazol-1-yl)-4,5,6,7,8,9-hexahydro-2H-4,8-epiminocycloocta [c]pyrazole-10-carboxylate (120 mg, 180.39 μmol, 56.23% yield) as yellow solid. LC-MS (ES+, m/z): 613.4 $[(M+H)^+]$; Rt=0.543 min.

Step 2: 1-((4S,8R)-2-(4-fluoro-3,5-dimethylphenyl)-4,5,6,7,8,9-hexahydro-2H-4,8-epiminocycloocta [c]pyrazol-3-yl)-3-(5-fluoroisoquinolin-6-yl)-1H-imidazol-2 (3H)-one

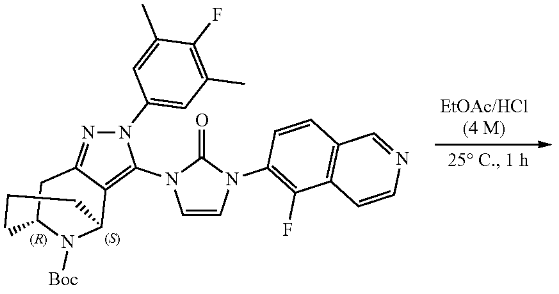

-continued

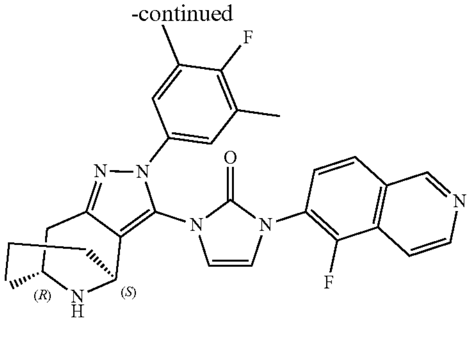

A mixture of (4S,8R)-tert-butyl 2-(4-fluoro-3,5-dimethylphenyl)-3-(3-(5-fluoroisoquinolin-6-yl)-2-oxo-2,3-dihydro-1H-imidazol-1-yl)-4,5,6,7,8,9-hexahydro-2H-4,8-epiminocycloocta [c]pyrazole-10-carboxylate (120 mg, 180.39 μmol, 1 eq) in HC/EtOAc (2.4 mL) was stirred at 25° C. for 1 hour under $N_2$. LCMS indicated the reaction was completed. The reaction mixture was concentrated under reduced pressure. The residue was purified by prep-HPLC (neutral condition column: WePure Biotech XP tC18 150*40*5 um; mobile phase: [$H_2O$ (0.05% $NH_3H_2O$+10 mM $NH_4HCO_3$)-ACN]; gradient: 20%-50% B over 8.0 min) to give 1-((4S,8R)-2-(4-fluoro-3,5-dimethylphenyl)-4,5,6,7,8,9-hexahydro-2H-4,8-epiminocycloocta [c]pyrazol-3-yl)-3-(5-fluoroisoquinolin-6-yl)-1H-imidazol-2 (3H)-one (70 mg, 129.06 μmol, 71.54% yield). LC-MS (ES+, m/z): 513.4 $[(M+H)^+]$; Rt=0.387 min.

Step 3: 3-((1S,2S)-1-(2-((4S,8R)-2-(4-fluoro-3,5-dimethylphenyl)-3-(3-(5-fluoroisoquinolin-6-yl)-2-oxo-2,3-dihydro-1H-imidazol-1-yl)-4,5,6,7,8,9-hexahydro-2H-4,8-epiminocycloocta [c]pyrazole-10-carbonyl)-5-((S)-4-oxaspiro[2.5]octan-7-yl)-1H-indol-1-yl)-2-methylcyclopropyl)-1,2,4-oxadiazol-5 (4H)-one

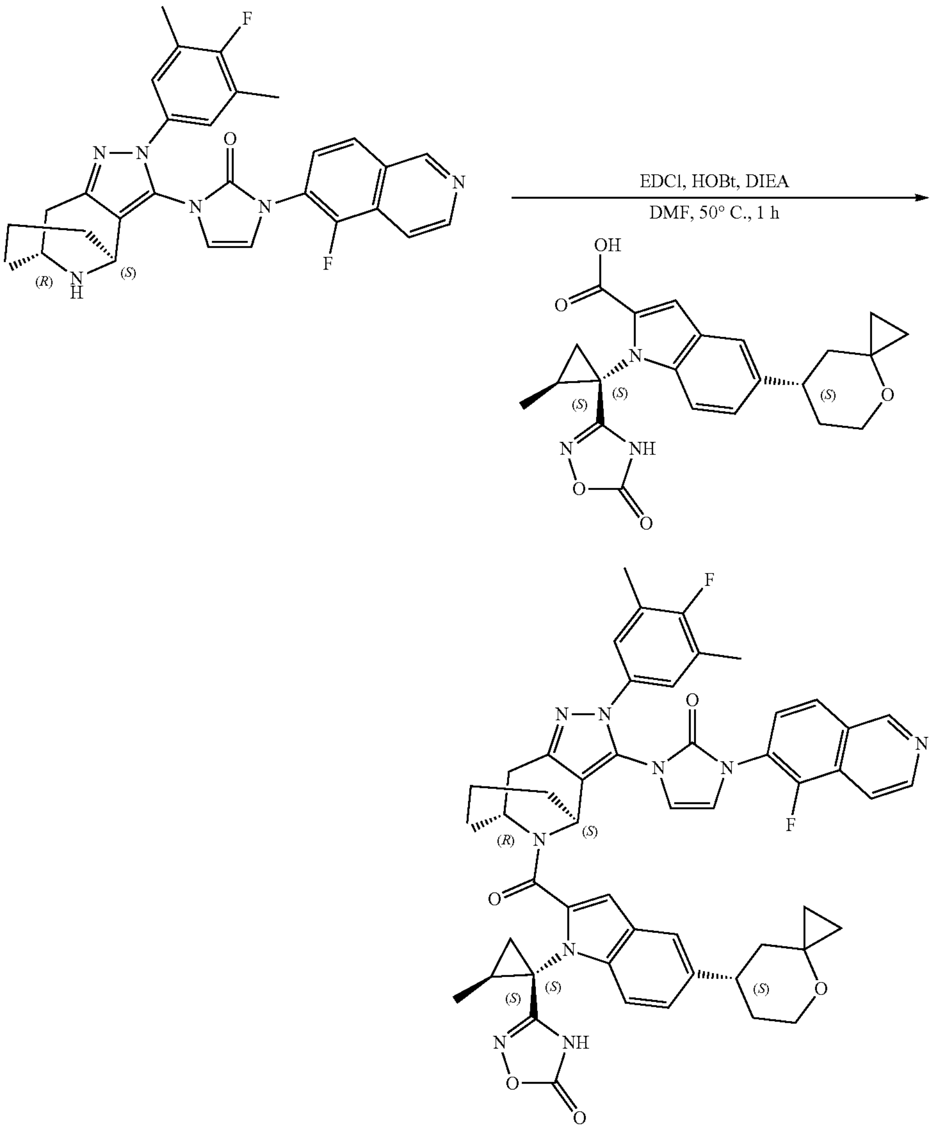

A mixture of 1-((4S,8R)-2-(4-fluoro-3,5-dimethylphenyl)-4,5,6,7,8,9-hexahydro-2H-4,8-epiminocycloocta [c]pyrazol-3-yl)-3-(5-fluoroisoquinolin-6-yl)-1H-imidazol-2 (3H)-one (35 mg, 64.53 μmol, 1 eq), 1-((1S,2S)-2-methyl-1-(5-oxo-4,5-dihydro-1,2,4-oxadiazol-3-yl)cyclopropyl)-5-((S)-4-oxaspiro[2.5]octan-7-yl)-1H-indole-2-carboxylic acid (52.84 mg, 129.06 μmol, 2 eq), HOBt (21.80 mg, 161.33 μmol, 2.5 eq), EDCI (30.93 mg, 161.33 μmol, 2.5 eq) and DIEA (83.40 mg, 645.30 μmol, 112.40 μL, 10 eq) in DMF (0.7 mL) was stirred at 50° C. for 1 hour under $N_2$ atmosphere. LCMS indicated the reaction was completed. The reaction mixture was quenched by addition $H_2O$ (20 mL) at 0° C., extracted with ethyl acetate (10 mL*3). The combined organic layers were washed with saturated brine (10 mL), dried over anhydrous $Na_2SO_4$, filtered and concentrated under reduced pressure. The residue was purified by prep-HPLC (TFA condition column: 3_Phenomenex Luna C18 75*30 mm*3 um; mobile phase: [$H_2O$ (0.1% TFA)-ACN]; gradient: 45%-75% B over 8.0 min) to give 3 3-((1S,2S)-1-(2-((4S,8R)-2-(4-fluoro-3,5-dimethylphenyl)-3-(3-(5-fluoroisoquinolin-6-yl)-2-oxo-2,3-dihydro-1H-imidazol-1-yl)-4,5,6,7,8,9-hexahydro-2H-4,8-epiminocycloocta [c]pyrazole-10-carbonyl)-5-((S)-4-oxaspiro[2.5] octan-7-yl)-1H-indol-1-yl)-2-methylcyclopropyl)-1,2,4-oxadiazol-5 (4H)-one (14.28 mg, 15.41 μmol, 23.88% yield, 97.56% purity). $^1$H NMR (400 MHz, DMSO-$d_6$) δ=12.19-11.74 (m, 1H), 9.60-9.31 (m, 1H), 8.80-8.56 (m, 1H), 8.19-8.07 (m, 1H), 7.94-7.79 (m, 1H), 7.56-6.64 (m, 9H), 5.80 (m, 1H), 5.28-4.97 (m, 1H), 3.87 (br d, J=10.3 Hz, 1H), 3.57-3.52 (m, 1H), 3.38-2.89 (m, 3H), 2.10 (m, 8H), 1.95-1.59 (m, 10H), 1.33-0.94 (m, 4H), 0.74-0.29 (m, 4H). LC-MS (ES+, m/z): 904.4 [$(M+H)^+$]; Rt=2.946 min. HRMS (EI): m/z $[M+H]^+$ found: 904.3738.

Example 115, Compound 615

3-((1S,2S)-1-(5-(2, 2-dimethyltetrahydro-2H-pyran-4-yl)-7-fluoro-2-((4S,8R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-4, 5, 6, 7, 8, 9-hexahydro-2H-4, 8-epiminocycloocta [c]pyrazole-10-carbonyl)-1H-indol-1-yl)-2-methylcyclopropyl)-1, 2, 4-oxadiazol-5 (4H)-one

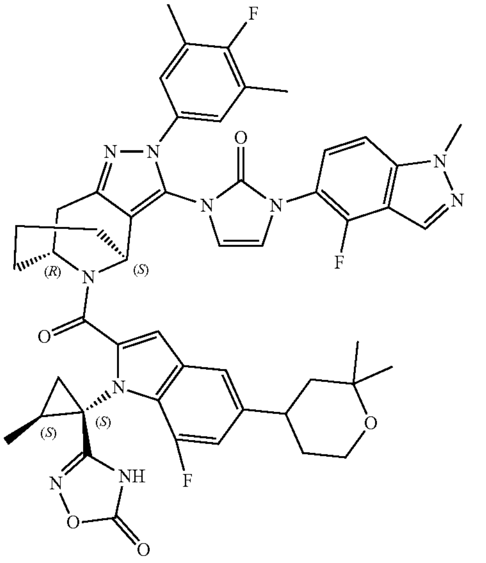

Step 1: 3-((1S,2S)-1-(5-(2, 2-dimethyltetrahydro-2H-pyran-4-yl)-7-fluoro-2-((4S,8R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-4, 5, 6, 7, 8, 9-hexahydro-2H-4, 8-epiminocycloocta [c]pyrazole-10-carbonyl)-1H-indol-1-yl)-2-methylcyclopropyl)-1, 2, 4-oxadiazol-5 (4H)-one

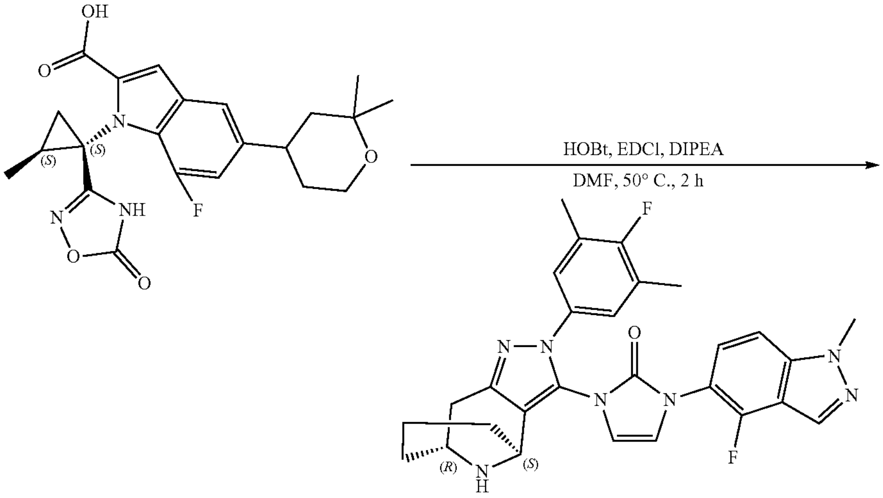

-continued

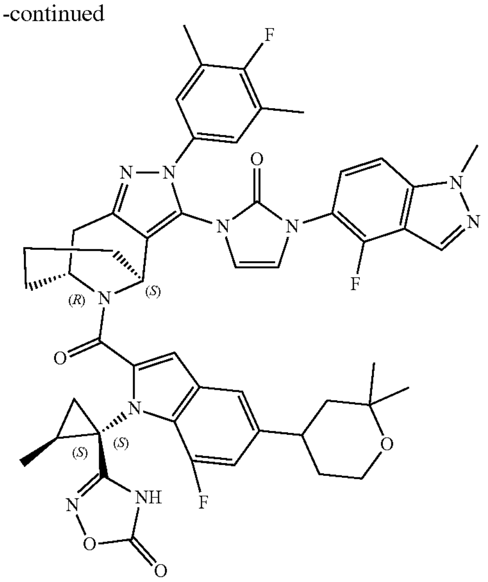

To a solution of 5-(2, 2-dimethyltetrahydro-2H-pyran-4-yl)-7-fluoro-1-((1S,2S)-2-methyl-1-(5-oxo-4,5-dihydro-1, 2, 4-oxadiazol-3-yl)cyclopropyl)-1H-indole-2-carboxylic acid (40 mg, 93.14 μmol, 1 eq), 1-(4-fluoro-1-methyl-1H-indazol-5-yl)-3-((4S,8R)-2-(4-fluoro-3, 5-dimethylphenyl)-4, 5, 6, 7, 8, 9-hexahydro-2H-4, 8-epiminocycloocta [c]pyrazol-3-yl)-1, 3-dihydro-2H-imidazol-2-one (57.63 mg, 111.77 μmol, 1.2 eq) and DIPEA (60.19 mg, 465.72 μmol, 5 eq) in DMF (0.8 mL) was added EDCI (35.71 mg, 186.29 μmol, 2 eq) and HOBt (25.17 mg, 186.29 μmol, 2 eq). The mixture was stirred at 50° C. for 2 hours under $N_2$. LCMS indicated the reaction was completed. The mixture was filtered. The filtrate was purified by prep-HPLC column: Phenomenex Luna C18 100*30 mm*5 um; mobile phase: [$H_2O$ (0.1% TFA)-ACN]; gradient: 50%-80% B over 8.0 min) to give 3-((1S,2S)-1-(5-(2, 2-dimethyltetrahydro-2H-pyran-4-yl)-7-fluoro-2-((4S,8R)-3-(3-(4-fluoro-1-methyl-1H-indazol-5-yl)-2-oxo-2, 3-dihydro-1H-imidazol-1-yl)-2-(4-fluoro-3, 5-dimethylphenyl)-4, 5, 6, 7, 8, 9-hexahydro-2H-4, 8-epiminocycloocta [c]pyrazole-10-carbonyl)-1H-indol-1-yl)-2-methylcyclopropyl)-1, 2, 4-oxadiazol-5 (4H)-one (17.29 mg, 18.60 μmol, 19.96% yield). $^1$H NMR (400 MHz, DMSO-$d_6$) δ=12.39-11.80 (m, 1H), 8.38-8.09 (m, 1H), 7.74-6.58 (m, 9H), 5.74-4.95 (m, 2H), 4.09 (br d, J=9.1 Hz, 3H), 3.71-3.53 (m, 2H), 3.22-2.71 (m, 3H), 2.32-2.16 (m, 6H), 2.02-1.45 (m, 12H), 1.32-0.89 (m, 10H). $^1$H NMR (400 MHz, DMSO-$d_6$+$D_2O$) δ=8.36-7.97 (m, 1H), 7.74-6.50 (m, 9H), 5.86-4.71 (m, 2H), 4.14-3.96 (m, 3H), 3.70-2.83 (m, 5H), 2.27-2.15 (m, 6H), 1.98-1.39 (m, 12H), 1.26-0.85 (m, 10H). LC-MS (ES+, m/z): 927.5 [$(M+H)^+$]; Rt=3.115 min. HRMS (EI): m/z $[M+H]^+$ found: 927.3951.

Example 116, Compound 617

3-((1S,2S)-1-(2-((4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((S)-2,2-dimethyltetrahydro-2H-pyran-4-yl)-1H-indol-1-yl)-2-methylcyclopropyl)-1,2,4-oxadiazol-5 (4H)-one Scheme 617

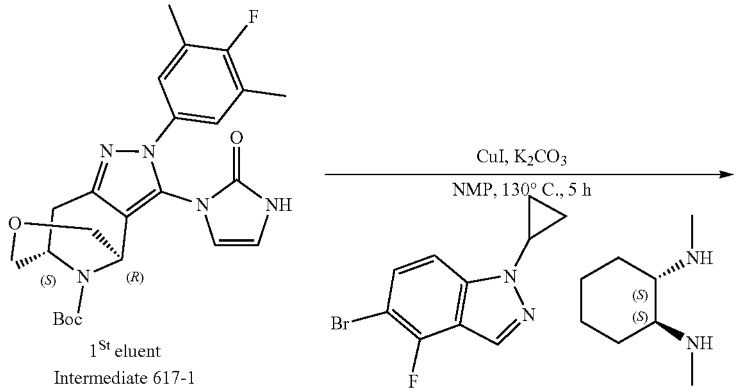

-continued
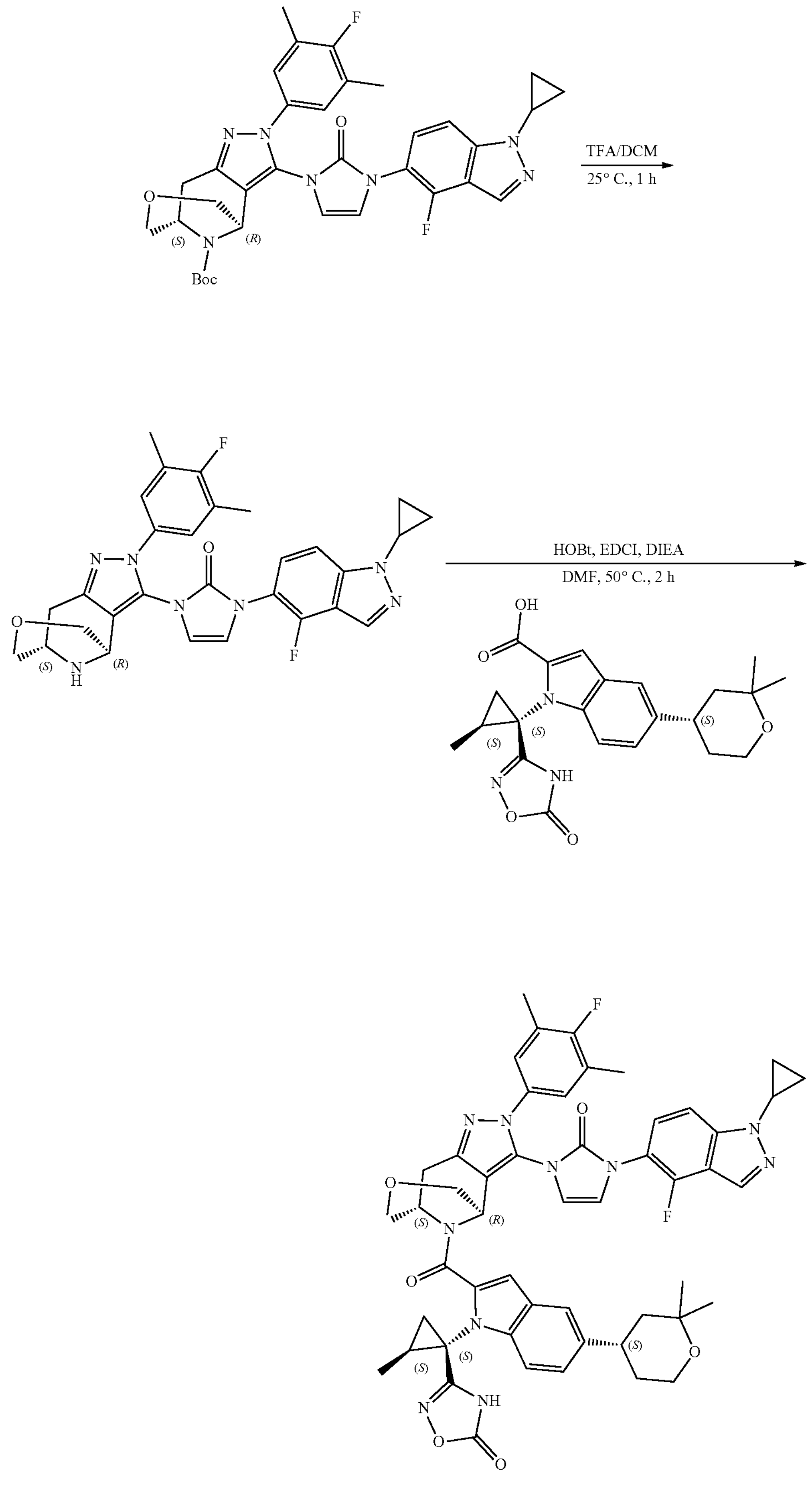

Step 1: tert-butyl (4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate

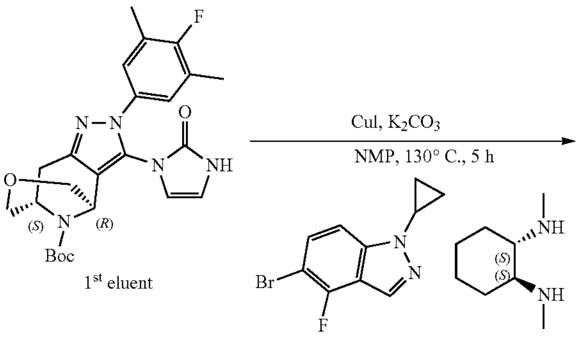

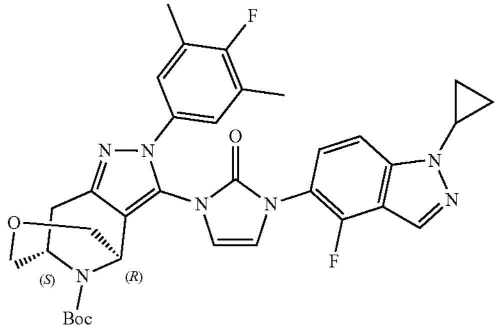

To a mixture of tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (130 mg, 263.04 μmol, 1 eq) and 5-bromo-1-cyclopropyl-4-fluoro-1H-indazole (73.81 mg, 289.35 μmol, 1.1 eq), (1S,2S)—$N^1$,$N^2$-dimethylcyclohexane-1,2-diamine (112.25 mg, 789.12 μmol, 3 eq) in NMP (1.3 mL) was added $K_2CO_3$ (109.06 mg, 789.12 μmol, 3 eq) and CuI (100.19 mg, 526.08 μmol, 2 eq) under $N_2$. The mixture was stirred at 130° C. for 5 hours under $N_2$. LCMS showed the reaction was completed. The residue was poured into saturated EDTA solution (20 mL) and ethyl acetate (20 mL) stirred for 0.5 hour. The aqueous phase was extracted with ethyl acetate (20 mL*3). The combined organic phase was washed with saturated brine (30 mL), dried with anhydrous $Na_2SO_4$, filtered and concentrated in vacuo. The residue was purified by column chromatography ($SiO_2$, hexanes:ethyl acetate=1:1) to give tert-butyl (4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (90 mg, 134.23 μmol, 51.03% yield). LC-MS (ES+, m/z): 644.3 $[(M+H)^+]$; Rt=1.950 min.

Step 2: 1-(1-cyclopropyl-4-fluoro-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one

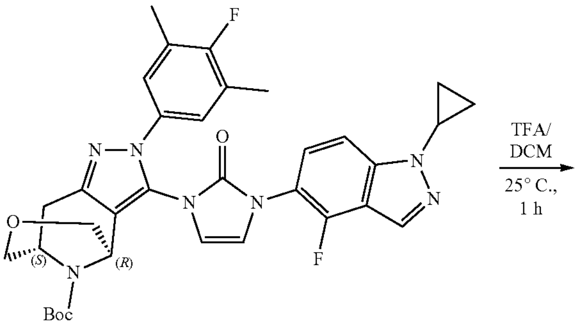

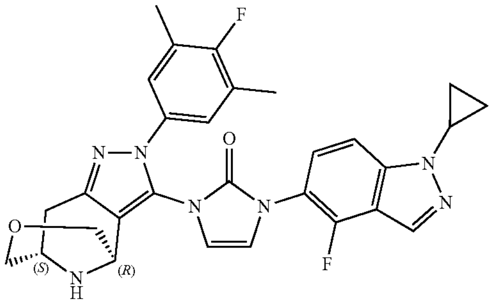

To a mixture of tert-butyl (4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (40 mg, 62.14 μmol, 1 eq) in DCM (0.6 mL) was added TFA (0.2 mL) in one portion at 25° C. The mixture was stirred at 25° C. for 1 hour. LCMS showed the reaction was completed. The residue was poured into saturated $NaHCO_3$ (10 mL). The aqueous phase was extracted with ethyl acetate (10 mL*3). The combined organic phase was washed with saturated brine (15 mL), dried with anhydrous $Na_2SO_4$, filtered and concentrated in vacuo to give 1-(1-cyclopropyl-4-fluoro-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (40 mg, crude). LC-MS (ES+, m/z): 544.2 $[(M+H)^+]$; Rt=1.263 min.

Step 3: 3-((1S,2S)-1-(2-((4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-((S)-2,2-dimethyltetrahydro-2H-pyran-4-yl)-1H-indol-1-yl)-2-methylcyclopropyl)-1,2,4-oxadiazol-5 (4H)-one

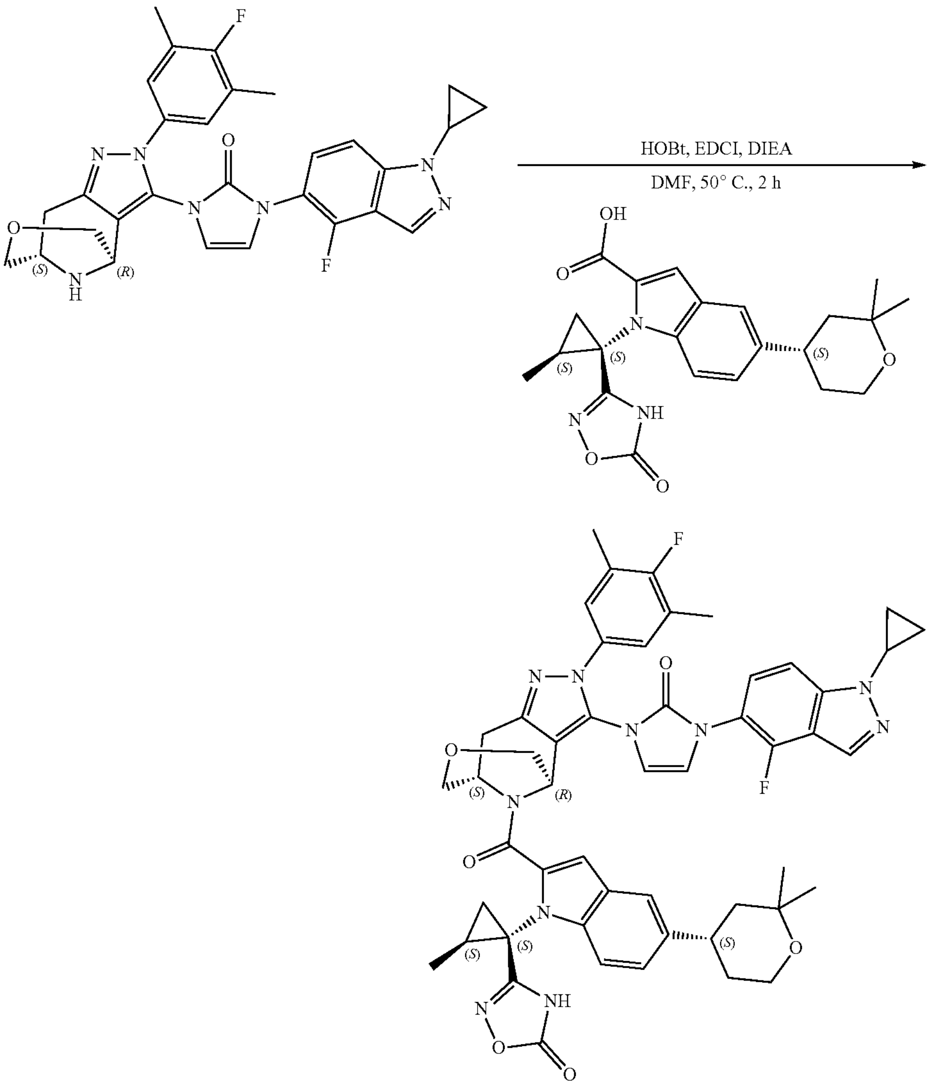

To a mixture of 1-(1-cyclopropyl-4-fluoro-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (40 mg, 73.59 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (30.28 mg, 73.59 μmol, 1 eq) in DMF (0.8 mL) was added DIEA (47.55 mg, 367.94 μmol, 5 eq), HOBt (14.92 mg, 110.38 μmol, 1.5 eq), and EDCI (18.34 mg, 95.66 μmol, 1.3 eq) under $N_2$. The mixture was stirred at 50° C. for 2 hours. LCMS showed the reaction was completed. The residue was poured into water (20 mL). The aqueous phase was extracted with chloroform: isopropanol=3:1 (10 mL*3). The combined organic phase was washed with saturated brine (30 mL), dried with anhydrous $Na_2SO_4$, filtered and concentrated in vacuo. The residue was purified by prep-HPLC (neutral condition, column: WePure Biotech XP tC18 150*40*7 um; mobile phase: [$H_2O$ (10 mM $NH_4HCO_3$)-ACN]; gradient: 40%-70% B over 8.0 min) to give 3-((1S,2S)-1-(2-((4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-((S)-2,2-dimethyltetrahydro-2H-pyran-4-yl)-1H-indol-1-yl)-2-methylcyclopropyl)-1,2,4-oxadiazol-5 (4H)-one (20.04 mg, 20.75 μmol, 28.19% yield). $^1H$ NMR (400 MHz, DMSO-$d_6$) δ=12.61-11.32 (m, 1H), 8.36-8.07 (m, 1H), 7.82-7.45 (m, 2H), 7.43-7.27 (m, 2H), 7.26-6.98 (m, 4H), 6.94-6.62 (m, 2H), 5.75-5.26 (m, 1H), 5.07-4.72 (m, 1H), 4.24-4.04 (m, 1H), 3.99-3.80 (m, 2H), 3.76-3.62 (m, 3H), 3.57-3.40 (m, 1H), 3.22-2.79 (m, 3H), 2.35-2.15 (m, 6H), 2.08-1.85 (m, 1H), 1.77-1.59 (m, 3H), 1.55-1.42 (m, 2H), 1.39-1.30 (m, 2H), 1.26 (br d, J=9.4 Hz, 3H), 1.22-1.08 (m, 7H), 1.07-0.87 (m, 2H). LC-MS (ES+, m/z): 937.4 [$(M+H)^+$]; Rt=3.319 min. HRMS (EI): m/z $[M+H]^+$ found: 937.3937.

Example 117, Compound 619

3-((1S,2S)-1-(5-(2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5(4H)-one

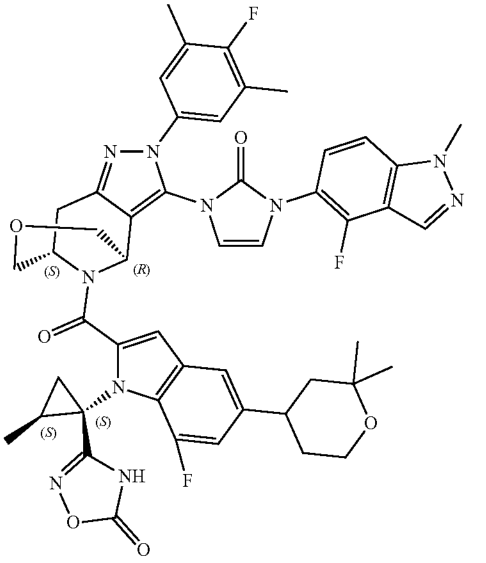

Step 1: 3-((1S,2S)-1-(5-(2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-1H-indol-1-yl)-2-methylcyclopropyl)-1,2,4-oxadiazol-5 (4H)-one

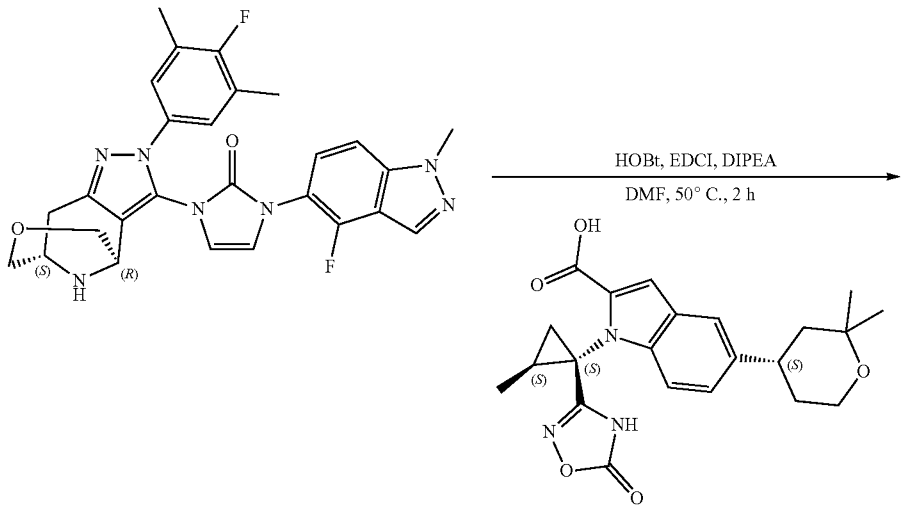

-continued

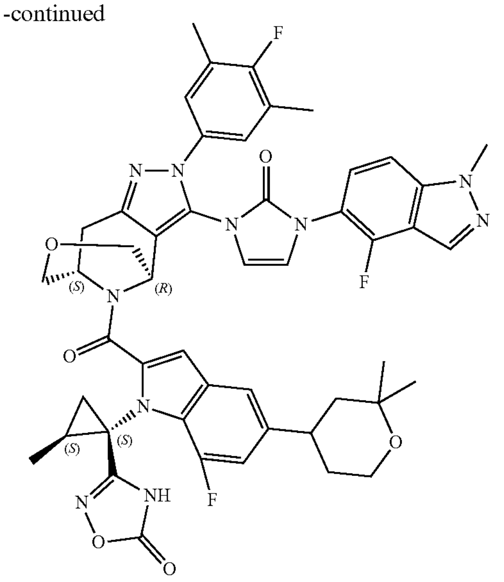

To a solution of 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (57.85 mg, 111.77 μmol, 1.2 eq) and 5-(2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (40 mg, 93.14 μmol, 1 eq) in DMF (0.8 mL) was added DIPEA (60.19 mg, 465.72 μmol, 81.12 μL, 5 eq), EDCI (23.21 mg, 121.09 μmol, 1.3 eq) and HOBt (18.88 mg, 139.72 μmol, 1.5 eq). The mixture was stirred at 50° C. for 2 hours under $N_2$. LCMS indicated the reaction was completed. The mixture was added to $H_2O$ (10 mL) and then extracted with ethyl acetate (15 mL*3). The organic layers were combined, washed with water (10 mL*2), saturated brine (10 mL), dried over $Na_2SO_4$, filtered and concentrated in vacuo. The residue was purified by prep-HPLC (column: 3_Phenomenex Luna C18 75*30 mm*3 um; mobile phase: [$H_2O$ (0.1% TFA)-ACN]; gradient: 50%-80% B over 8.0 min) to give 3-((1S,2S)-1-(5-(2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (23.17 mg, 24.92 μmol, 26.75% yield). $^1H$ NMR (400 MHz, DMSO-$d_6$) δ=12.42-11.85 (m, 1H), 8.17 (s, 1H), 7.80-6.63 (m, 9H), 5.27 (br s, 1H), 5.02-4.77 (m, 1H), 4.19-4.05 (m, 4H), 4.01 (br s, 1H), 3.80-3.30 (m, 5H), 3.17-2.85 (m, 2H), 2.32 (br d, J=1.6 Hz, 6H), 2.09-1.56 (m, 4H), 1.52-1.37 (m, 2H), 1.31-1.13 (m, 7H), 1.12-0.90 (m, 3H). LC-MS (ES+, m/z): 929.4 [(M+H)$^+$]; Rt=2.988 min. HRMS (EI): m/z [M+H]$^+$ found: 929.3734.

Example 118, Compound 701

3-((1S,2S)-1-(5-((R)-2,2-dimethyltetrahydro-2H-pyran-4-yl)-7-fluoro-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one

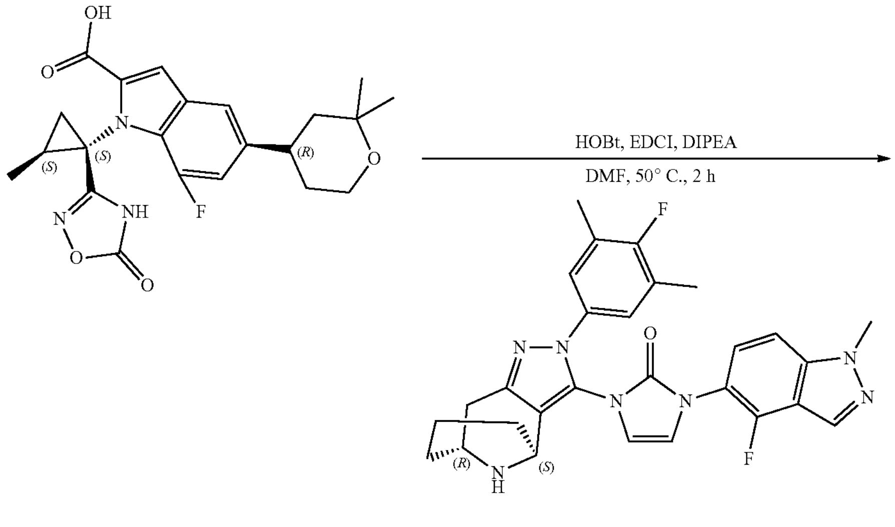

-continued

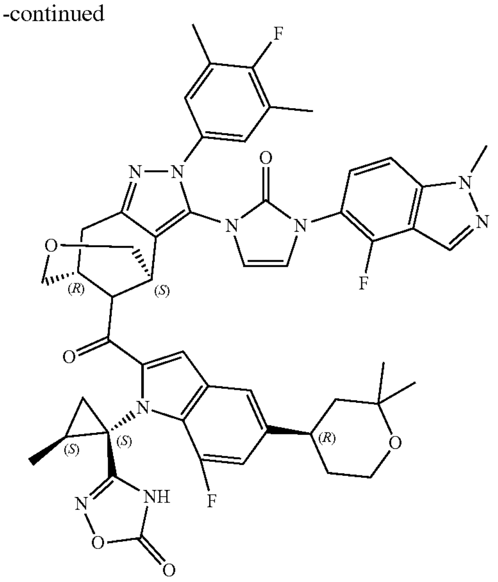

To a solution of 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (40 mg, 93.14 μmol, 1 eq), 1-(4-fluoro-1-methyl-1H-indazol-5-yl)-3-((4S,8R)-2-(4-fluoro-3, 5-dimethylphenyl)-4, 5, 6, 7, 8, 9-hexahydro-2H-4, 8-epiminocycloocta [c]pyrazol-3-yl)-1, 3-dihydro-2H-imidazol-2-one (57.63 mg, 111.77 μmol, 1.2 eq) and DIPEA (60.19 mg, 465.72 μmol, 5 eq) in DMF (0.8 mL) was added EDCI (35.71 mg, 186.29 μmol, 2 eq) and HOBt (25.17 mg, 186.29 μmol, 2 eq). The mixture was stirred at 50° C. for 2 hours under $N_2$. LCMS indicated the reaction was completed. The mixture was filtered. The filtrate was purified by prep-HPLC (column: Phenomenex Luna C18 100*30 mm*5 um; mobile phase: [$H_2O$ (0.1% TFA)-ACN]; gradient: 55%-85% B over 8.0 min) to give 3-((1S,2S)-1-(5-((R)-2,2-dimethyltetrahydro-2H-pyran-4-yl)-7-fluoro-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one (18.44 mg, 19.89 μmol, 21.36% yield). $^1$H NMR (400 MHz, DMSO-$d_6$) δ=12.36-11.84 (m, 1H), 8.39-8.09 (m, 1H), 7.74-6.59 (m, 9H), 5.73-4.96 (m, 2H), 4.13-4.07 (m, 3H), 3.72-3.54 (m, 2H), 3.34-2.70 (m, 3H), 2.31-2.13 (m, 6H), 2.01-1.40 (m, 12H), 0.92 (br d, J=5.5 Hz, 10H). LC-MS (ES+, m/z): 927.5 [(M+H)$^+$]; Rt=3.124 min. HRMS (EI): m/z [M+H]$^+$ found: 927.3914.

Example 119, Compound 702

3-((1S,2S)-1-(5-((S)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-5,6,7,8-tetrahydro-4H-pyrazolo[1,5-a][1,4]diazepine-5-carbonyl)-1H-indol-1-yl)-2-methylcyclopropyl)-1,2,4-oxadiazol-5 (4H)-one

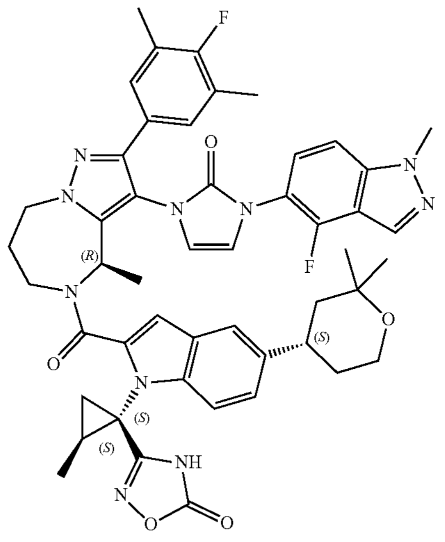

And
Compound 703
3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-5,6,7,8-tetrahydro-4H-pyrazolo[1,5-a][1,4]diazepine-5-carbonyl)-1H-indol-1-yl)-2-methylcyclopropyl)-1,2,4-oxadiazol-5 (4H)-one
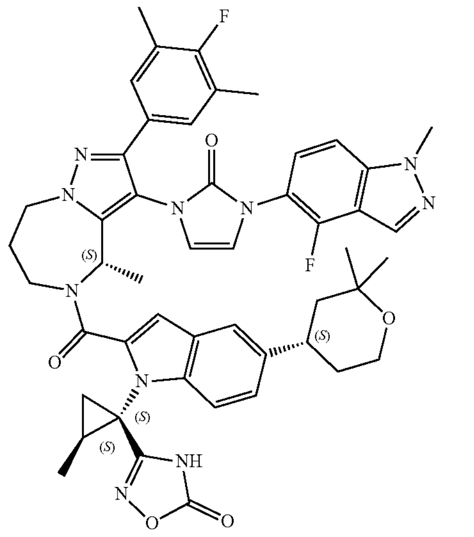
Scheme 702
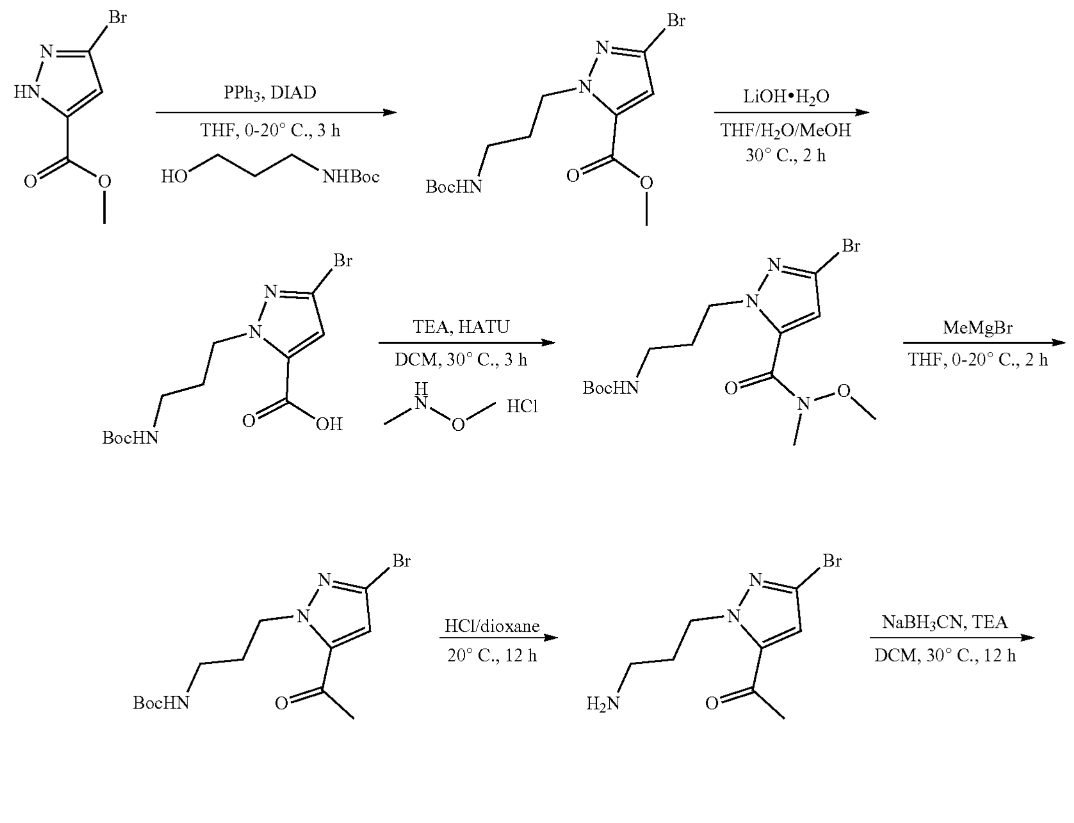

-continued
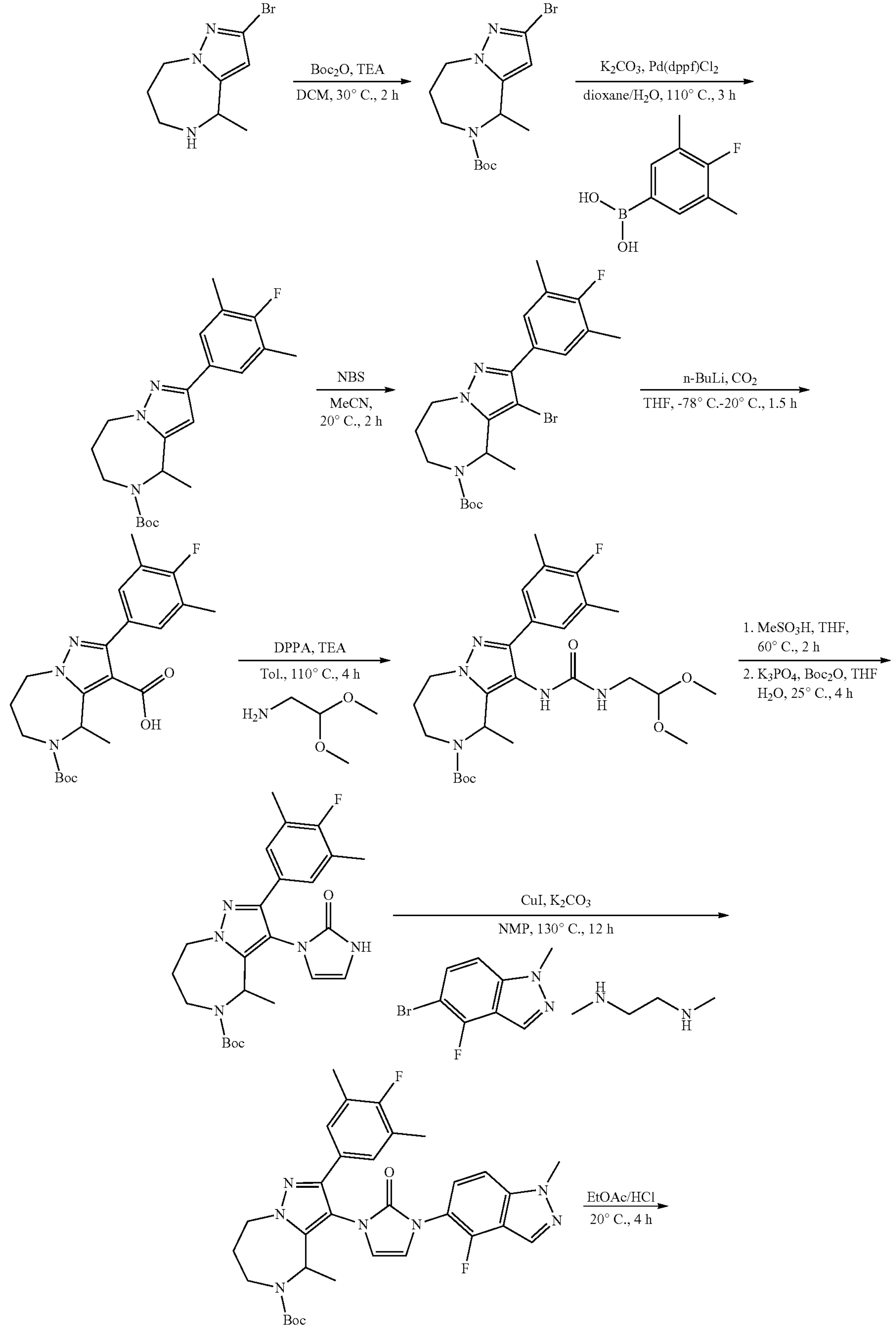

-continued

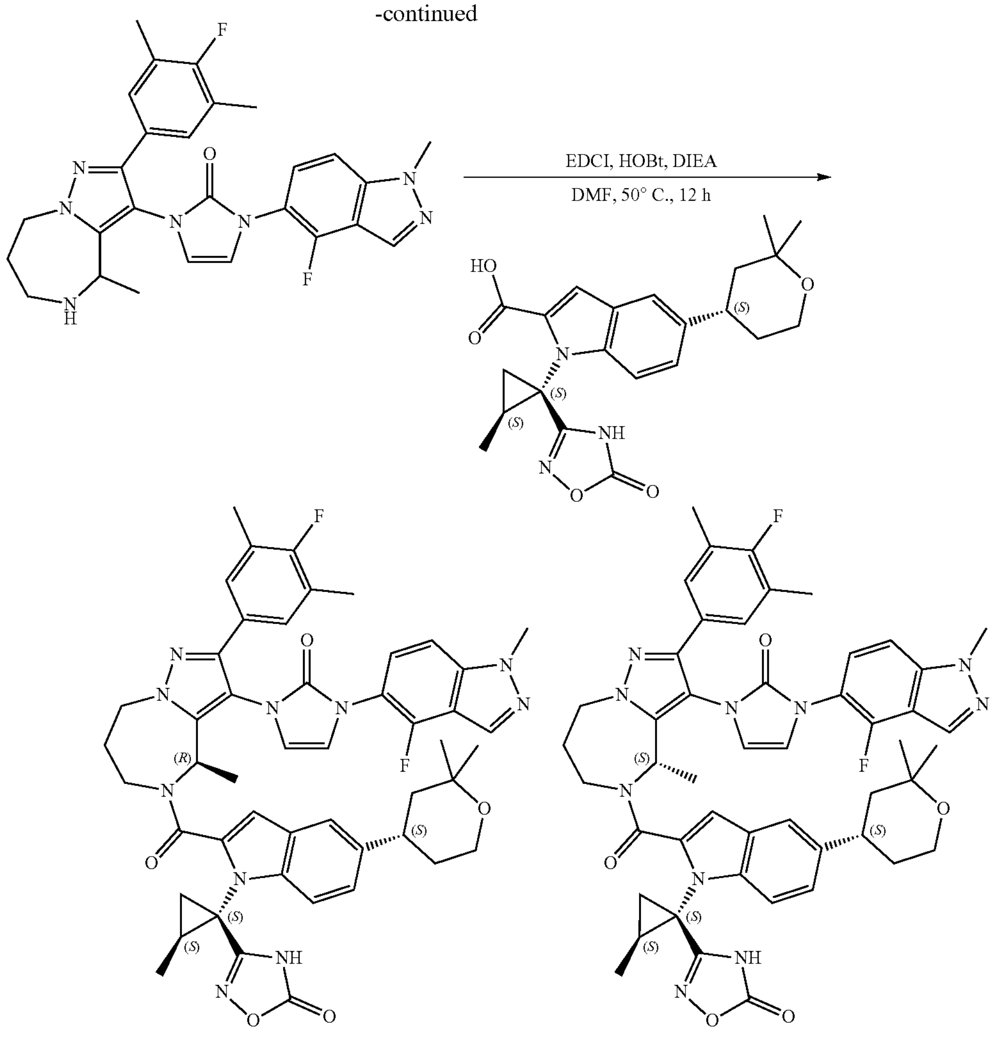

1st eluent

2nd eluent

Step 1: methyl 3-bromo-1-(3-((tert-butoxycarbonyl) amino) propyl)-1H-pyrazole-5-carboxylate

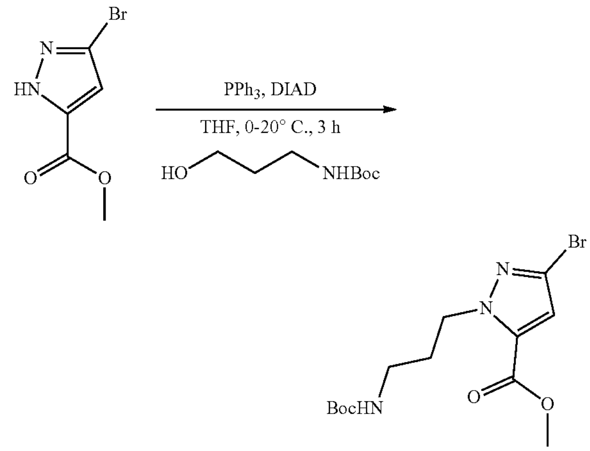

To a mixture of methyl 3-bromo-1H-pyrazole-5-carboxylate (10 g, 48.78 mmol, 1 eq) and tert-butyl (3-hydroxypropyl) carbamate (11.11 g, 63.41 mmol, 10.84 mL, 1.3 eq) in THF (100 mL) was added $PPh_3$ (16.63 g, 63.41 mmol, 1.3 eq). The suspension was degassed under vacuum and purged with $N_2$ several times. The mixture was cooled to 0° C. DIAD (19.73 g, 97.56 mmol, 18.91 mL, 2 eq) was then added dropwise to the mixture at 20° C. The mixture was stirred at 20° C. for 3 hours (10 parallel reaction). LCMS showed the reaction was completed. The reaction mixture was poured into $H_2O$ (1000 mL), then extracted with ethyl acetate (500 mL*3). The combined organic layers were washed with saturated brine (800 mL), dried over anhydrous $Na_2SO_4$, filtered and concentrated under reduced pressure. The residue was purified by silica gel chromatography (hexanes:ethyl acetate=10:1) to give methyl 3-bromo-1-(3-((tert-butoxycarbonyl)amino) propyl)-1H-pyrazole-5-carboxylate (150 g, 376.84 mmol, 77.26% yield). $^1H$ NMR (400 MHz, $CDCl_3$) δ=6.80 (s, 1H), 4.89 (br s, 1H), 4.58 (t, J=6.79 Hz, 2H), 3.88 (s, 3H), 3.09 (q, J=6.03 Hz, 2H), 1.98-2.05 (m, 2H), 1.43 (s, 9H). LC-MS (ES+, m/z): 362.0 $[(M+H)^+]$; Rt=0.581 min.

Step 2: 3-bromo-1-(3-((tert-butoxycarbonyl)amino) propyl)-1H-pyrazole-5-carboxylic acid

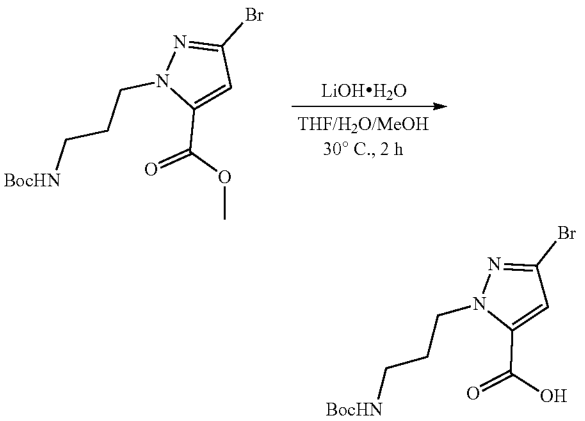

To a mixture of methyl 3-bromo-1-(3-((tert-butoxycarbonyl)amino) propyl)-1H-pyrazole-5-carboxylate (50 g, 138.04 mmol, 1 eq) in THF (500 mL), MeOH (500 mL) and $H_2O$ (500 mL) was added $LiOH{\cdot}H_2O$ (17.38 g, 414.11 mmol, 3 eq). The mixture was stirred at 30° C. for 2 hours (3 parallel reaction). LCMS showed the reaction was completed. The mixture was concentrated in vacuo. The residue was diluted with water (1000 mL). The mixture was adjusted to pH=1-2 with aqueous HCl (1 N). The mixture was extracted with ethyl acetate (800 mL*3). The combined organic phase was washed with brine (1000 mL), dried with anhydrous $Na_2SO_4$, filtered and concentrated in vacuo to give 3-bromo-1-(3-((tert-butoxycarbonyl)amino) propyl)-1H-pyrazole-5-carboxylic acid (140 g, 373.93 mmol, 90.30% yield). LC-MS (ES+, m/z): 347.9 $[(M+H)^+]$; Rt=0.385 min.

Step 3: tert-butyl (3-(3-bromo-5-(methoxy(methyl) carbamoyl)-1H-pyrazol-1-yl) propyl) carbamate

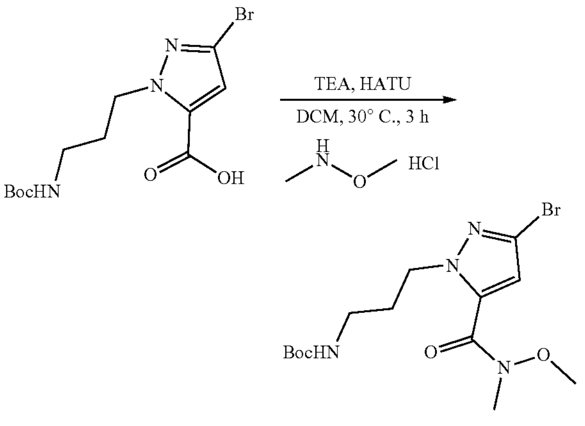

To a mixture of 3-bromo-1-(3-((tert-butoxycarbonyl) amino) propyl)-1H-pyrazole-5-carboxylic acid (35 g, 100.52 mmol, 1 eq) in DCM (350 mL) was added N, O-dimethylhydroxylamine hydrochloride (11.77 g, 120.62 mmol, 1.2 eq) and TEA (30.51 g, 301.56 mmol, 41.97 mL, 3 eq). HATU (49.69 g, 130.67 mmol, 1.3 eq) was then added to the mixture. The mixture was stirred at 30° C. for 3 hours (4 parallel reaction). LCMS showed the reaction was completed. The mixture was concentrated in vacuo. The product was purified by silica gel chromatography (hexanes:ethyl acetate=2:1) to give tert-butyl (3-(3-bromo-5-(methoxy (methyl) carbamoyl)-1H-pyrazol-1-yl) propyl) carbamate (81 g, 200.81 mmol, 52.38% yield). $^1H$ NMR (400 MHz, $CDCl_3$) δ=6.73 (s, 1H), 5.13 (br s, 1H), 4.46 (t, J-6.57 Hz, 2H), 3.65 (s, 3H), 3.35 (s, 3H), 3.07 (q, J=5.88 Hz, 2H), 2.00-2.04 (m, 2H), 1.43 (s, 9H). LC-MS (ES−, m/z): 389.0 $[(M-H)]^-$; Rt=0.528 min.

Step 4: tert-butyl (3-(5-acetyl-3-bromo-1H-pyrazol-1-yl) propyl) carbamate

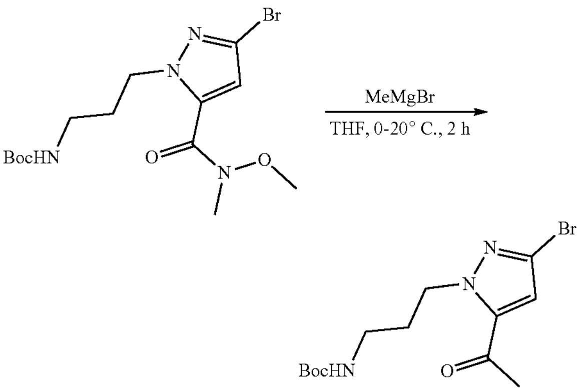

A mixture of tert-butyl (3-(3-bromo-5-(methoxy(methyl) carbamoyl)-1H-pyrazol-1-yl) propyl) carbamate (81 g, 204.95 mmol, 1 eq) in THF (800 mL) was cooled to 0° C. The suspension was degassed under vacuum and purged with $N_2$ several times. MeMgBr (3 M, 170.79 mL, 2.5 eq) was added dropwise to the mixture. The mixture was stirred at 20° C. for 2 hours under $N_2$. LCMS showed the reaction was completed. The reaction mixture was transferred dropwise to $H_2O$ (1000 mL) under $N_2$ and then extracted with ethyl acetate (500 mL*3). The combined organic layers were washed with saturated brine (1500 mL), dried over anhydrous $Na_2SO_4$, filtered and concentrated under reduced pressure to give tert-butyl (3-(5-acetyl-3-bromo-1H-pyrazol-1-yl) propyl) carbamate (69 g, 173.39 mmol, 84.60% yield). LC-MS (ES+, m/z): 346.0 $[(M+H)^+]$; Rt=0.538 min.

Step 5: 1-(1-(3-aminopropyl)-3-bromo-1H-pyrazol-5-yl) ethan-1-one

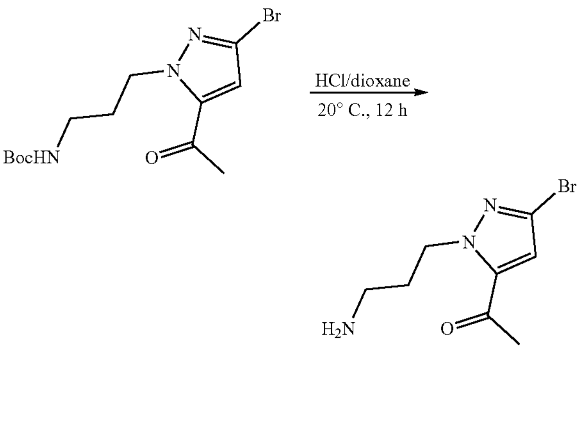

A mixture of tert-butyl (3-(5-acetyl-3-bromo-1H-pyrazol-1-yl) propyl) carbamate (23 g, 66.43 mmol, 1 eq) in HCl/dioxane (4M, 230 mL) was stirred for 12 hours at 20° C. (3 parallel reaction). LCMS showed the reaction was completed. The mixture was concentrated in vacuo to give 1-(1-(3-aminopropyl)-3-bromo-1H-pyrazol-5-yl) ethan-1-one (53 g, crude, HCl). $^1$H NMR (400 MHz, DMSO-$d_6$) δ=8.20-8.35 (m, 2H), 7.35 (s, 1H), 4.47 (br t, J-6.68 Hz, 2H), 2.72 (br s, 2H), 2.50 (s, 3H), 1.99-2.10 (m, 2H).

Step 6: 2-bromo-4-methyl-5,6,7,8-tetrahydro-4H-pyrazolo[1,5-a][1,4]diazepine

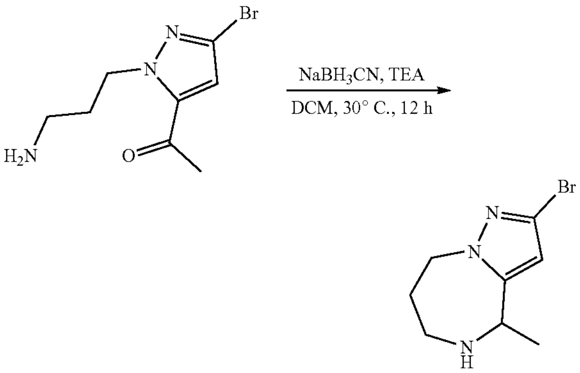

To a mixture of 1-(1-(3-aminopropyl)-3-bromo-1H-pyrazol-5-yl) ethan-1-one (53 g, 187.57 mmol, 1 eq, HCl) in DCM (1500 mL) was added TEA (189.80 g, 1.88 mol, 261.07 mL, 10 eq) and $NaBH_3CN$ (35.36 g, 562.70 mmol, 3 eq). The mixture was stirred at 30° C. for 12 hours. LCMS showed the reaction was completed. The reaction mixture was added to $NaHCO_3$ saturated aqueous solution (1000 mL). Then extracted with dichloromethane (500 mL*3). The combined organic layers were washed with saturated brine (1500 mL), dried over anhydrous $Na_2SO_4$, filtered and concentrated under reduced pressure to give 2-bromo-4-methyl-5,6,7,8-tetrahydro-4H-pyrazolo[1,5-a][1,4]diazepine (32 g, 102.91 mmol, 54.87% yield). LC-MS (ES+, m/z): 229.9 [(M+H)$^+$]; Rt=0.382 min.

Step 7: tert-butyl 2-bromo-4-methyl-7,8-dihydro-4H-pyrazolo[1,5-a][1,4]diazepine-5 (6H)-carboxylate

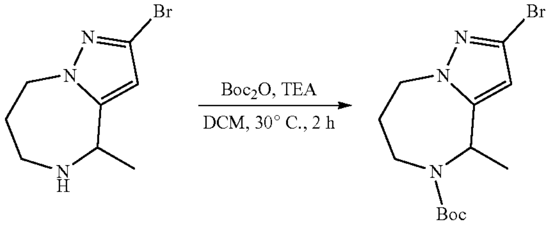 [SMILES: CC1NCCCn2nc(Br)cc21 ; "Boc2O, TEA" ; CC1c2cc(Br)nn2CCCN1C(=O)OC(C)(C)C]

To a mixture of 2-bromo-4-methyl-5,6,7,8-tetrahydro-4H-pyrazolo[1,5-a][1,4]diazepine (32 g, 139.07 mmol, 1 eq) and $Boc_2O$ (60.70 g, 278.13 mmol, 63.90 mL, 2 eq) in DCM (400 mL) was added TEA (42.22 g, 417.20 mmol, 58.07 mL, 3 eq). The reaction was stirred at 30° C. for 2 hours. LCMS showed the reaction was completed. The mixture was concentrated in vacuo. The residue was purified by silica gel chromatography (hexanes:ethyl acetate-9:1) to give tert-butyl 2-bromo-4-methyl-7,8-dihydro-4H-pyrazolo[1,5-a][1,4]diazepine-5 (6H)-carboxylate (42 g, 114.47 mmol, 82.31% yield). LC-MS (ES+, m/z): 329.9 [(M+H)$^+$]; Rt=0.567 min.

Step 8: tert-butyl 2-(4-fluoro-3,5-dimethylphenyl)-4-methyl-7,8-dihydro-4H-pyrazolo[1,5-a][1,4] diazepine-5 (6H)-carboxylate

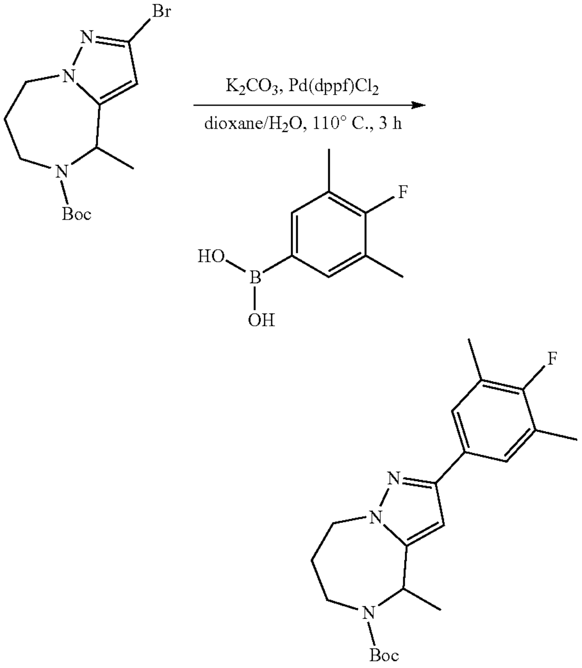

To a mixture of tert-butyl 2-bromo-4-methyl-7,8-dihydro-4H-pyrazolo[1,5-a][1,4]diazepine-5 (6H)-carboxylate (21 g, 63.59 mmol, 1 eq) and (4-fluoro-3,5-dimethylphenyl) boronic acid (11.75 g, 69.95 mmol, 1.1 eq) in dioxane (220 mL) and $H_2O$ (22 mL) was added $K_2CO_3$ (26.37 g, 190.78 mmol, 3 eq). The suspension was degassed under vacuum and purged with $N_2$ several times. Pd(dppf)$Cl_2$ (4.65 g, 6.36 mmol, 0.1 eq) was added and the mixture was stirred at 110° C. for 3 hours (2 parallel reaction) under $N_2$. LCMS showed the reaction was completed. The reaction mixture was poured into saturated EDTA (200 mL) and ethyl acetate (100 mL) stirred for 1 hour, then extracted with ethyl acetate (100 mL*3). The combined organic layers were washed with saturated brine (300 mL), dried over anhydrous $Na_2SO_4$, filtered and concentrated under reduced pressure. 2 batches of the reaction were carried out in parallel. The residue was purified by silica gel chromatography (hexanes:ethyl acetate=91:9) to give tert-butyl 2-(4-fluoro-3,5-dimethylphenyl)-4-methyl-7,8-dihydro-4H-pyrazolo[1,5-a][1,4]diazepine-5 (6H)-carboxylate (38 g, 94.63 mmol, 74.40% yield). LC-MS (ES+, m/z): 374.1 [(M+H)$^+$]; Rt=0.676 min.

Step 9: tert-butyl 3-bromo-2-(4-fluoro-3,5-dimethylphenyl)-4-methyl-7,8-dihydro-4H-pyrazolo[1,5-a][1,4] diazepine-5 (6H)-carboxylate

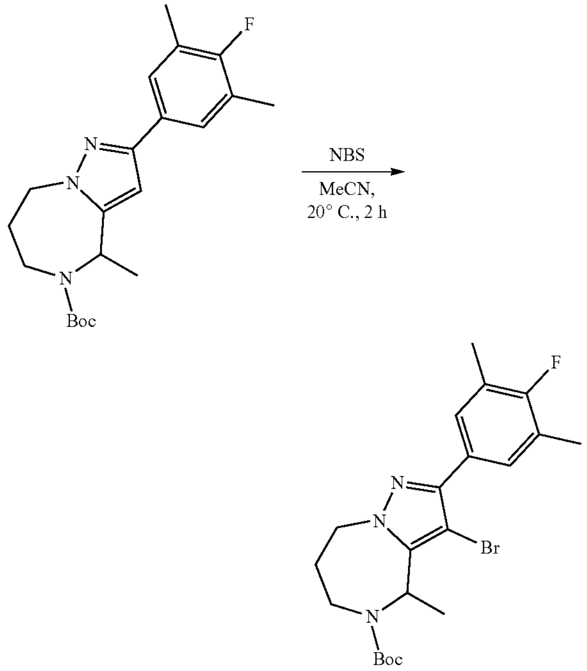

To a mixture of tert-butyl 2-(4-fluoro-3,5-dimethylphenyl)-4-methyl-7,8-dihydro-4H-pyrazolo[1,5-a][1,4]diazepine-5 (6H)-carboxylate (38 g, 101.75 mmol, 1 eq) in ACN (360 mL) was added NBS (19.92 g, 111.93 mmol, 1.1 eq) under $N_2$. The mixture was stirred at 20° C. for 2 hours. LCMS showed the reaction was completed. The mixture was concentrated in vacuo. The residue was purified by silica gel chromatography (hexanes:ethyl acetate=9:1) to give tert-butyl 3-bromo-2-(4-fluoro-3,5-dimethylphenyl)-4-methyl-7,8-dihydro-4H-pyrazolo[1,5-a][1,4]diazepine-5 (6H)-carboxylate (34 g, 69.90 mmol, 68.70% yield). LC-MS (ES+, m/z): 452.1 [(M+H)$^+$]; Rt=0.720 min.

Step 10:5-(tert-butoxycarbonyl)-2-(4-fluoro-3,5-dimethylphenyl)-4-methyl-5,6,7,8-tetrahydro-4H-pyrazolo[1,5-a][1,4]diazepine-3-carboxylic acid

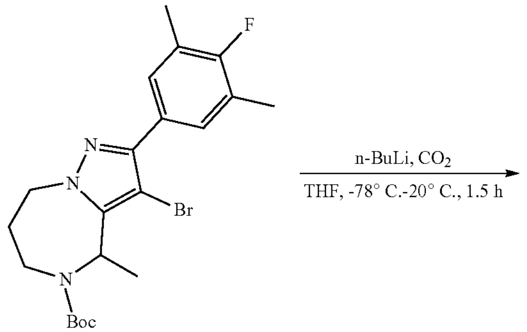

-continued

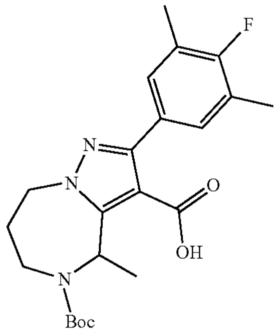

Tert-butyl 3-bromo-2-(4-fluoro-3,5-dimethylphenyl)-4-methyl-7,8-dihydro-4H-pyrazolo[1,5-a][1,4] diazepine-5 (6H)-carboxylate (18 g, 39.79 mmol, 1 eq) was dissolved in THF (720 mL). The suspension was degassed under vacuum and purged with $N_2$ several times. The mixture was cooled to −78° C. n-BuLi (2.5 M, 31.83 mL, 2 eq) was then added dropwise. The mixture was stirred for 30 min at −78° C. The reaction mixture was warmed up to 20° C. and stirred for 1 hour under $CO_2$ (15 psi). LCMS showed the reaction was completed. The reaction mixture was poured into saturated $NH_4Cl$ (1000 mL), then extracted with ethyl acetate (300 mL*3). The combined organic layers were washed with saturated brine (500 mL), dried over anhydrous $Na_2SO_4$, filtered and concentrated under reduced pressure. The residue was purified by silica gel chromatography (hexanes: ethyl acetate=1:4) to give 5-(tert-butoxycarbonyl)-2-(4-fluoro-3,5-dimethylphenyl)-4-methyl-5,6,7,8-tetrahydro-4H-pyrazolo[1,5-a][1,4]diazepine-3-carboxylic acid (9 g, 21.34 mmol, 53.64% yield). LC-MS (ES+, m/z): 418.1 [(M+H)$^+$]; Rt=0.438 min.

Step 11: tert-butyl 3-(3-(2,2-dimethoxyethyl) ureido)-2-(4-fluoro-3,5-dimethylphenyl)-4-methyl-7,8-dihydro-4H-pyrazolo[1,5-a][1,4]diazepine-5 (6H)-carboxylate

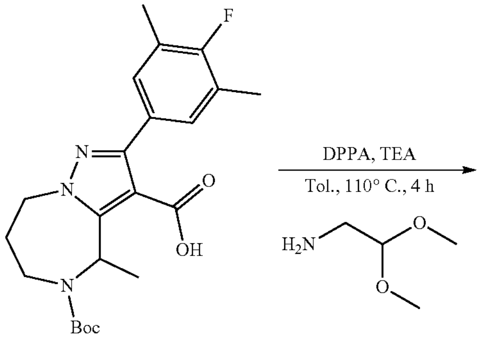

-continued

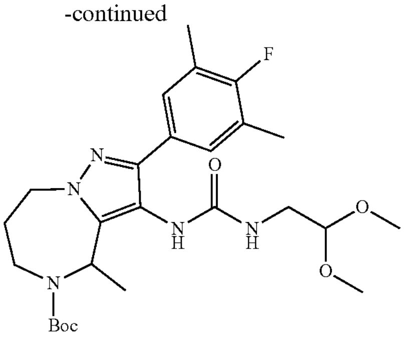

To a mixture of 5-(tert-butoxycarbonyl)-2-(4-fluoro-3,5-dimethylphenyl)-4-methyl-5,6,7,8-tetrahydro-4H-pyrazolo[1,5-a][1,4]diazepine-3-carboxylic acid (9 g, 21.56 mmol, 1 eq) in Tol. (90 mL) was added DPPA (11.87 g, 43.12 mmol, 9.31 mL, 2 eq) and TEA (6.54 g, 64.67 mmol, 9.00 mL, 3 eq). The suspension was degassed under vacuum and purged with $N_2$ several times. The mixture was stirred at 110° C. for 3 hours under $N_2$. 2,2-dimethoxyethan-1-amine (3.40 g, 32.34 mmol, 3.52 mL, 1.5 eq) was then added. The mixture was stirred at 110° C. for 1 hour under $N_2$. LCMS showed the reaction was completed. The reaction mixture was poured into $H_2O$ (200 mL), then extracted with ethyl acetate (100 mL*3). The combined organic layers were washed with saturated brine (300 mL), dried over anhydrous $Na_2SO_4$, filtered and concentrated under reduced pressure. The residue was purified by silica gel chromatography (hexanes: ethyl acetate-3:7) to give tert-butyl 3-(3-(2,2-dimethoxyethyl) ureido)-2-(4-fluoro-3,5-dimethylphenyl)-4-methyl-7,8-dihydro-4H-pyrazolo[1,5-a][1,4]diazepine-5 (6H)-carboxylate (6.2 g, 9.78 mmol, 45.39% yield). LC-MS (ES+, m/z): 520.2 [(M+H)+]; Rt=0.543 min.

Step 12: tert-butyl 2-(4-fluoro-3,5-dimethylphenyl)-4-methyl-3-(2-oxo-2,3-dihydro-1H-imidazol-1-yl)-7,8-dihydro-4H-pyrazolo[1,5-a][1,4]diazepine-5 (6H)-carboxylate

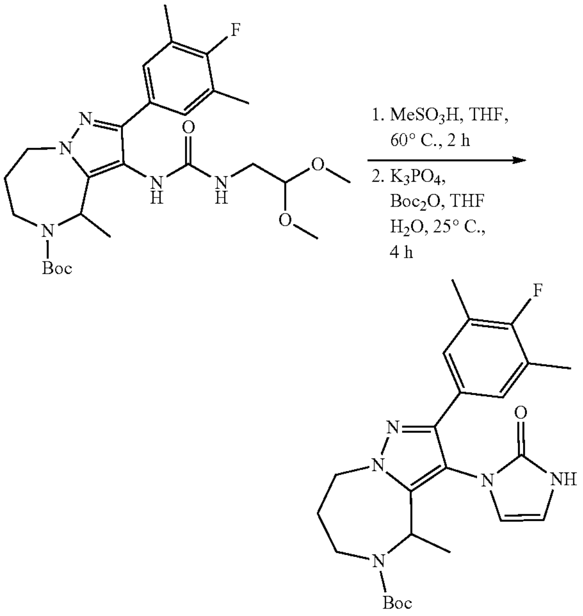

To a mixture of tert-butyl 3-(3-(2,2-dimethoxyethyl) ureido)-2-(4-fluoro-3,5-dimethylphenyl)-4-methyl-7,8-dihydro-4H-pyrazolo[1,5-a][1,4]diazepine-5 (6H)-carboxylate (6.2 g, 11.93 mmol, 1 eq) in THF (62 mL) was added methanesulfonic acid (1.72 g, 17.90 mmol, 1.28 mL, 1.5 eq). The mixture was stirred at 60° C. for 2 hours. $K_3PO_4$ (7.60 g, 35.80 mmol, 3 eq) in $H_2O$ (20 mL) was then added to the reaction to keep pH>8. $Boc_2O$ (2.60 g, 11.93 mmol, 2.74 mL, 1 eq) was added to the reaction. The mixture was stirred at 25° C. for 4 hours. LCMS showed the reaction was completed. The reaction mixture was poured into $H_2O$ (200 mL), then extracted with ethyl acetate (100 mL*3). The combined organic layers were washed with saturated brine (300 mL), dried over anhydrous $Na_2SO_4$, filtered and concentrated under reduced pressure. The residue was purified by silica gel chromatography (hexanes:ethyl acetate=3:7) and then the product was triturated with MTBE (30 mL) at 20° C. for 12 hours to give tert-butyl 2-(4-fluoro-3,5-dimethylphenyl)-4-methyl-3-(2-oxo-2,3-dihydro-1H-imidazol-1-yl)-7,8-dihydro-4H-pyrazolo[1,5-a][1,4]diazepine-5 (6H)-carboxylate (1.5 g, 3.23 mmol, 27.05% yield). LC-MS (ES+, m/z): 456.2 [(M+H)+]; Rt=0.544 min.

Step 13: tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-7,8-dihydro-4H-pyrazolo[1,5-a][1,4]diazepine-5 (6H)-carboxylate

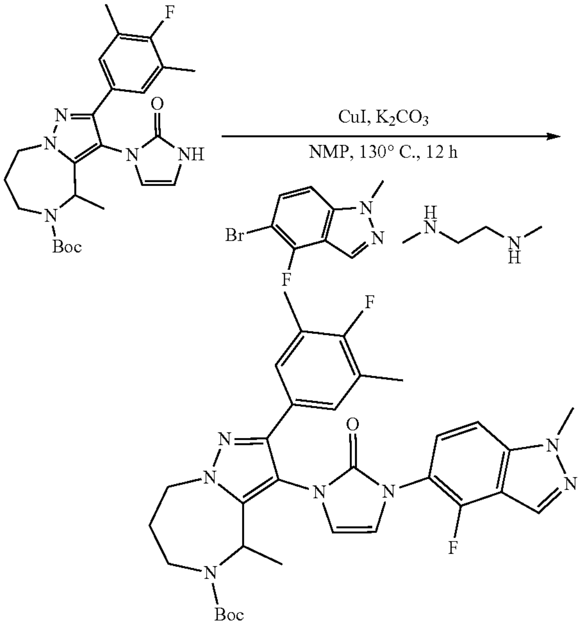

To a mixture of tert-butyl 2-(4-fluoro-3,5-dimethylphenyl)-4-methyl-3-(2-oxo-2,3-dihydro-1H-imidazol-1-yl)-7,8-dihydro-4H-pyrazolo[1,5-a][1,4]diazepine-5 (6H)-carboxylate (1.4 g, 3.07 mmol, 1 eq) and 5-bromo-4-fluoro-1-methyl-1H-indazole (774.35 mg, 3.38 mmol, 1.1 eq) in DMF (28 mL) was added $K_2CO_3$ (1.27 g, 9.22 mmol, 3 eq) and N1,N2-dimethylethane-1,2-diamine (135.46 mg, 1.54 mmol, 165.40 μL, 0.5 eq). The suspension was degassed under vacuum and purged with $N_2$ several times. CuI (117.07 mg, 614.68 μmol, 0.2 eq) was added. The mixture was stirred at 130° C. for 12 hours under $N_2$. LCMS showed the reaction was completed. The reaction mixture was poured into $H_2O$ (200 mL), then extracted with ethyl acetate (100 mL*3). The combined organic layers were washed with saturated brine (300 mL), dried over anhydrous $Na_2SO_4$, filtered and concentrated under reduced pressure. The residue was purified by silica gel chromatography (hexanes: ethyl acetate=3:7) to give tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-7,8-dihydro-4H-pyrazolo[1,5-a][1,4]diazepine-5 (6H)-carboxylate (1.05 g, 1.70 mmol, 55.46% yield). LC-MS (ES+, m/z): 604.3 [(M+H)$^+$]; Rt=0.643 min.

Step 14:1-(4-fluoro-1-methyl-1H-indazol-5-yl)-3-(2-(4-fluoro-3,5-dimethylphenyl)-4-methyl-5,6,7,8-tetrahydro-4H-pyrazolo[1,5-a][1,4]diazepin-3-yl)-1,3-dihydro-2H-imidazol-2-one

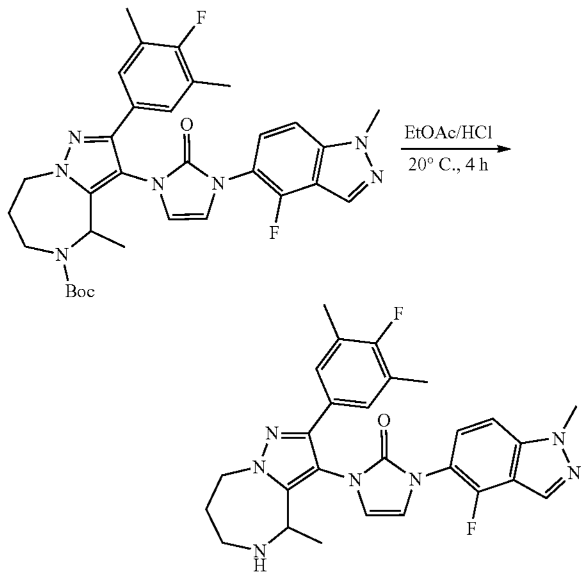

A mixture of tert-butyl 3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-7,8-dihydro-4H-pyrazolo[1,5-a][1,4]diazepine-5 (6H)-carboxylate (1.05 g, 1.74 mmol, 1 eq) in HCl/EtOAc (4 M, 10 mL, 23.00 eq) and stirred for 4 hours at 20° C. LCMS showed the reaction was completed. The mixture was filtered. The filter cake concentrated in vacuo. Then the filter cake was poured into $H_2O$ (10 mL). The aqueous layer was adjusted to pH=8-9 with saturated $NaHCO_3$ aqueous solution (30 mL). Then extracted with ethyl acetate (20 mL*3). The combined organic layers were washed with saturated brine (50 mL), dried over anhydrous $Na_2SO_4$, filtered and concentrated under reduced pressure to give 1-(4-fluoro-1-methyl-1H-indazol-5-yl)-3-(2-(4-fluoro-3,5-dimethylphenyl)-4-methyl-5,6,7,8-tetrahydro-4H-pyrazolo[1,5-a][1,4]diazepin-3-yl)-1,3-dihydro-2H-imidazol-2-one (700 mg, 1.23 mmol, 70.80% yield). LC-MS (ES+, m/z): 504.2 [(M+H)$^+$]; Rt=0.531 min.

Step 15: 3-((1S,2S)-1-(5-((S)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-5,6,7,8-tetrahydro-4H-pyrazolo[1,5-a][1,4]diazepine-5-carbonyl)-1H-indol-1-yl)-2-methylcyclopropyl)-1,2,4-oxadiazol-5 (4H)-one and 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-5,6,7,8-tetrahydro-4H-pyrazolo[1,5-a][1,4]diazepine-5-carbonyl)-1H-indol-1-yl)-2-methylcyclopropyl)-1,2,4-oxadiazol-5 (4H)-one

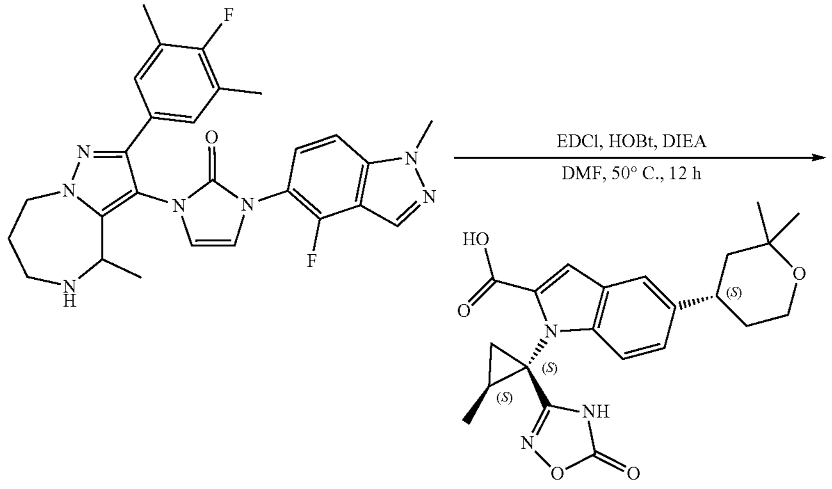

-continued

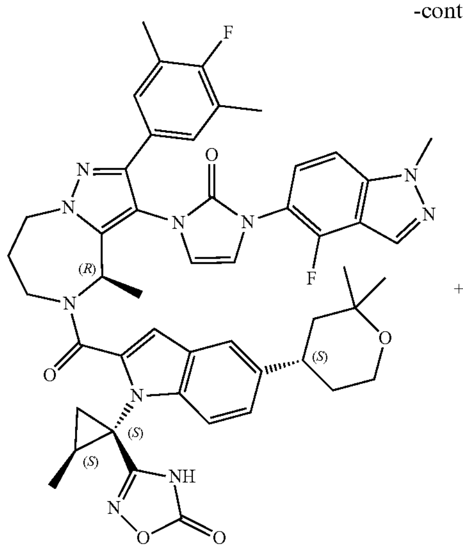

+

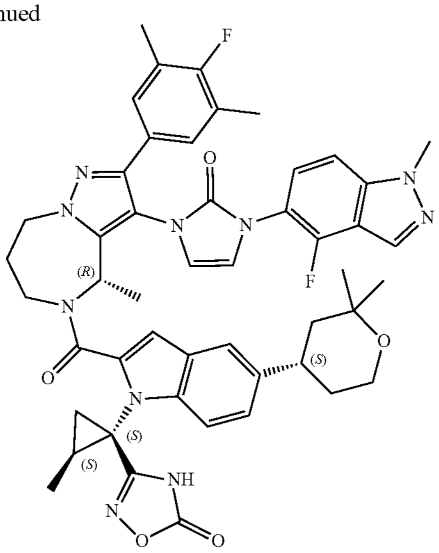

1st eluent

2nd eluent

To a mixture of 1-(4-fluoro-1-methyl-1H-indazol-5-yl)-3-(2-(4-fluoro-3,5-dimethylphenyl)-4-methyl-5,6,7,8-tetrahydro-4H-pyrazolo[1,5-a][1,4]diazepin-3-yl)-1,3-dihydro-2H-imidazol-2-one (100 mg, 198.59 μmol, 1 eq) in DMF (1 mL) was added DIEA (128.33 mg, 992.96 μmol, 172.95 μL, 5 eq), 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (81.71 mg, 198.59 μmol, 1 eq), HOBt (40.25 mg, 297.89 μmol, 1.5 eq) and EDCI (49.49 mg, 258.17 μmol, 1.3 eq). The mixture was stirred at 50° C. for 12 hours. LCMS showed the reaction was completed. The mixture was filtered. The product was purified by prep-HPLC (column: WePure Biotech XP tC18 150*40*7 um; mobile phase: [$H_2O$ (0.05% $NH_3H_2O$+10 mM $NH_4HCO_3$)-ACN]; gradient: 45%-75% B over 8.0 min) to give 3-((1S,2S)-1-(5-((S)-2,2-dimethyltetrahydro-2H-pyran-4-yl)-2-((R)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-5,6,7,8-tetrahydro-4H-pyrazolo[1,5-a][1,4]diazepine-5-carbonyl)-1H-indol-1-yl)-2-methylcyclopropyl)-1,2,4-oxadiazol-5 (4H)-one (1st eluent, RT=3.332 by prep-HPLC, 20.2 mg, 22.45 μmol, 11.31% yield). $^1$H NMR (400 MHz, DMSO-$d_6$) δ=11.75-11.23 (m, 1H), 8.20 (s, 1H), 7.59-7.24 (m, 4H), 7.24-6.97 (m, 4H), 6.70 (s, 1H), 6.01-5.90 (m, 1H), 4.71-4.51 (m, 3H), 4.10 (s, 3H), 3.74-3.55 (m, 3H), 2.94-2.78 (m, 1H), 2.20 (s, 8H), 2.05-1.95 (m, 1H), 1.88-1.79 (m, 1H), 1.76 (br d, J=7.3 Hz, 3H), 1.63-1.34 (m, 6H), 1.22-1.05 (m, 9H). $^1$H NMR (400 MHz, MeOD-$d_4$) δ=8.31-8.04 (m, 1H), 7.59-7.05 (m, 6H), 7.01-6.46 (m, 3H), 6.19-5.86 (m, 1H), 5.53-5.03 (m, 1H), 4.79-4.46 (m, 3H), 4.12 (br s, 3H), 3.95-3.46 (m, 3H), 3.11-2.52 (m, 1H), 2.44-2.03 (m, 8H), 1.99-1.52 (m, 7H), 1.50-1.17 (m, 7H), 1.16-0.95 (m, 4H), 0.94-0.77 (m, 1H). LC-MS (ES+, m/z): 897.4 [$(M+H)^+$]; Rt=2.865 min. HRMS (EI): m/z $[M+H]^+$ found: 897.4034.

And 3-((1S,2S)-1-(5-((S)-2,2-dimethyltetrahydro-2H-pyran-4-yl)-2-((S)-3-(3-(4-fluoro-1-methyl-1H-indazol-5-yl)-2-oxo-2,3-dihydro-1H-imidazol-1-yl)-2-(4-fluoro-3,5-dimethylphenyl)-4-methyl-5,6,7,8-tetrahydro-4H-pyrazolo[1,5-a][1,4]diazepine-5-carbonyl)-1H-indol-1-yl)-2-methylcyclopropyl)-1,2,4-oxadiazol-5 (4H)-one ($2^{nd}$ eluent, RT=3.511 by prep-HPLC, 14.15 mg, 15.55 μmol, 7.83% yield). $^1$H NMR (400 MHz, DMSO-$d_6$) δ=11.61-11.03 (m, 1H), 8.19 (s, 1H), 7.61-7.26 (m, 4H), 7.26-6.99 (m, 4H), 6.82-6.70 (m, 1H), 6.07-5.93 (m, 1H), 4.71-4.47 (m, 3H), 4.10 (s, 3H), 3.76-3.55 (m, 3H), 2.96-2.84 (m, 1H), 2.30-2.09 (m, 8H), 2.05-1.92 (m, 1H), 1.79 (br d, J=1.3 Hz, 3H), 1.63-1.34 (m, 7H), 1.24-1.15 (m, 4H), 1.07 (br s, 5H). $^1$H NMR (400 MHz, MeOD-$d_4$) δ=8.27-8.13 (m, 1H), 7.64-7.02 (m, 7H), 7.00-6.62 (m, 2H), 6.15 (br d, J=3.4 Hz, 1H), 5.52-5.14 (m, 1H), 4.68 (br s, 2H), 4.19-4.06 (m, 3H), 3.92-3.51 (m, 3H), 3.11-2.67 (m, 1H), 2.38-2.11 (m, 8H), 2.11-2.00 (m, 1H), 1.97 (br d, J=6.6 Hz, 2H), 1.88-1.62 (m, 3H), 1.61-1.38 (m, 3H), 1.37-1.27 (m, 2H), 1.26-1.11 (m, 4H), 1.07 (br d, J=3.9 Hz, 3H), 1.00-0.85 (m, 2H). LC-MS (ES+, m/z): 897.4 [$(M+H)^+$]; Rt=2.975 min. HRMS (EI): m/z $[M+H]^+$ found: 897.4034.

Example 120, Compound 705
3-((1S,2S)-1-(5-((S)-2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-1H-indol-1-yl)-2-methylcyclopropyl)-1,2,4-oxadiazol-5(4H)-one
Scheme 705
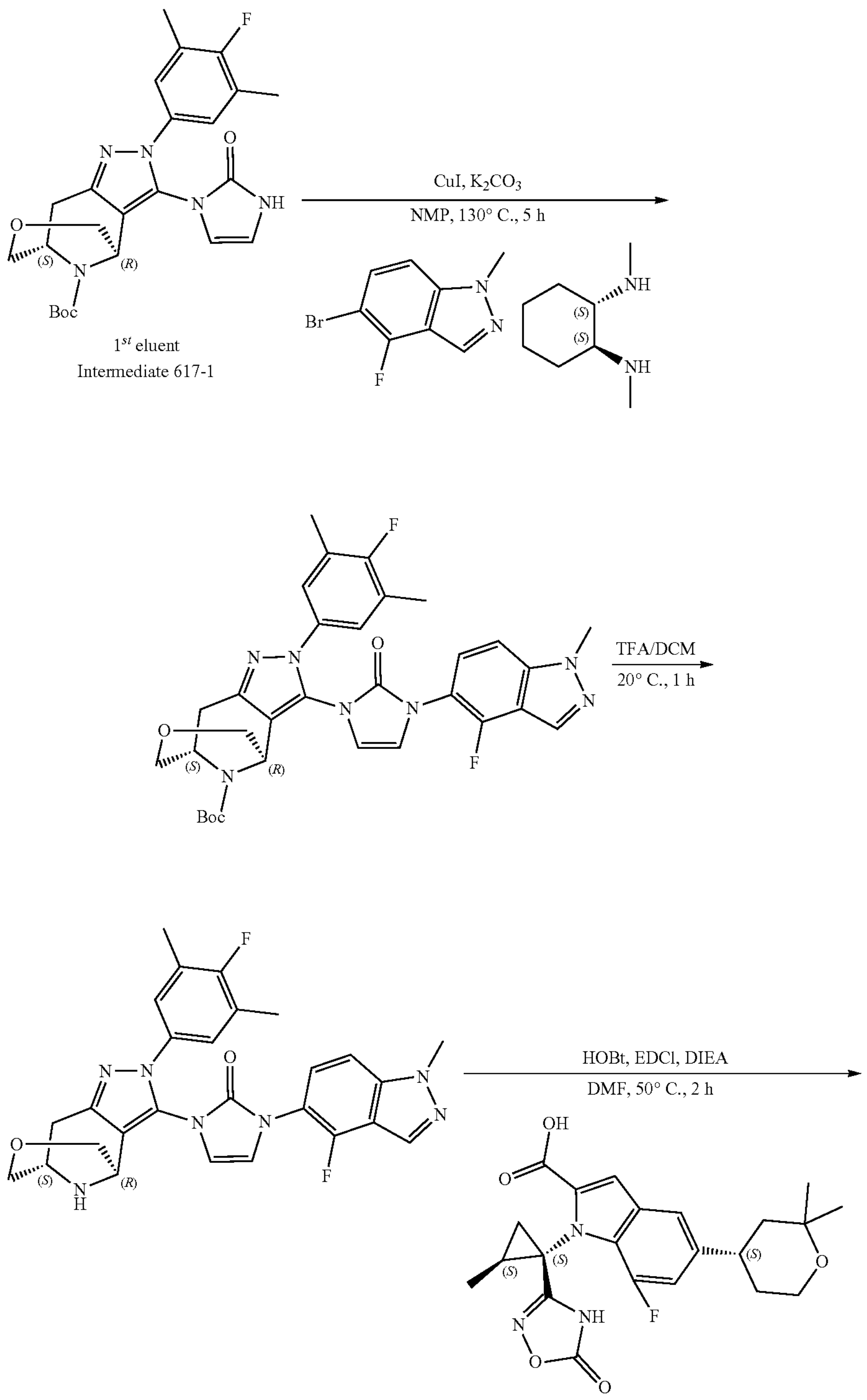

-continued

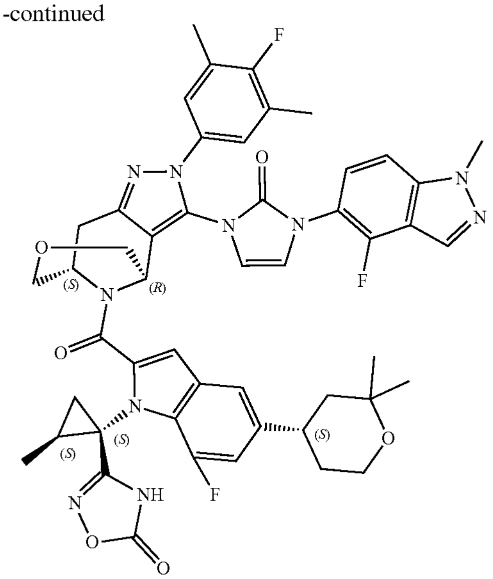

Step 1: tert-butyl (4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate

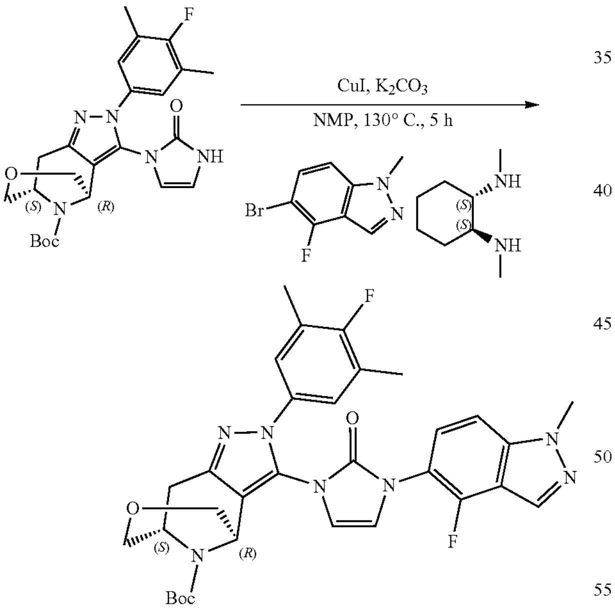

$1^{st}$ eluent
see Intermediate 617-1

To a mixture of tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (8.2 g, 17.12 mmol, 1 eq) and 5-bromo-4-fluoro-1-methyl-1H-indazole (7.84 g, 34.23 mmol, 2 eq) and (1S,2S)—$N^1$,$N^2$-dimethylcyclohexane-1,2-diamine (7.30 g, 51.35 mmol, 3 eq) in NMP (82 mL) was added $K_2CO_3$ (4.73 g, 34.23 mmol, 2 eq) and CuI (6.52 g, 34.23 mmol, 2 eq) in one portion under $N_2$. The mixture was stirred at 130° C. for 5 hours under $N_2$. LCMS showed the reaction was completed. The residue was poured into saturated EDTA (100 mL), ethyl acetate (100 mL) and stirred for 1 hour. The residue was poured into water (500 mL). The aqueous phase was extracted with ethyl acetate (250 mL*3). The combined organic phase was washed with saturated brine (750 mL), dried with anhydrous $Na_2SO_4$, filtered and concentrated in vacuo. The residue was purified by column chromatography ($SiO_2$, Petroleum ether/ethyl acetate=20/1 to 1/1) to give tert-butyl (4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (8 g, 12.18 mmol, 71.13% yield). LC-MS (ES+, m/z): 618.3 [$(M+H)^+$]. Rt=1.897 min.

Step 2: 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one

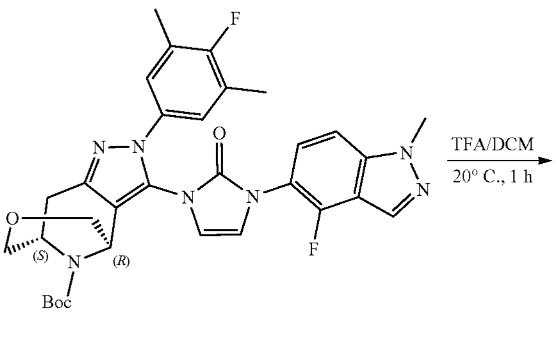

-continued

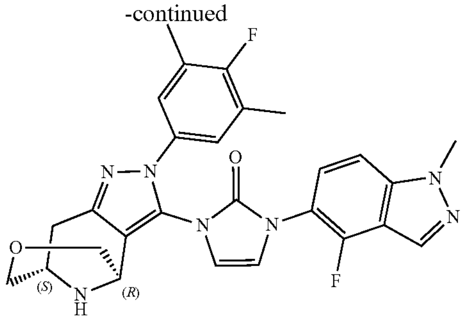

To a mixture of tert-butyl (4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (1 g, 1.62 mmol, 1 eq) in DCM (8 mL) was added TFA (2 mL) in one portion at 20° C. The mixture was stirred at 20° C. for 1 hour. TLC showed the reaction was completed. The residue was concentrated in vacuo to give 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (1 g, crude). LC-MS (ES+, m/z): 518.3 [$(M+H)^+$]; Rt=0.434 min.

Step 3: 3-((1S,2S)-1-(5-((S)-2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one

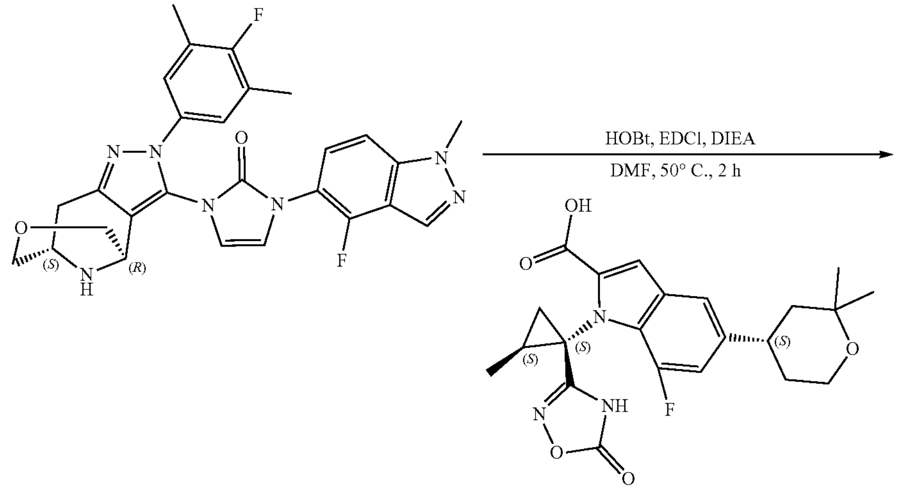

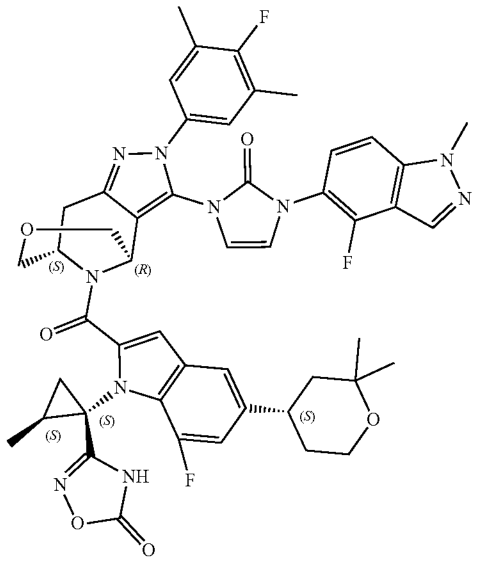

A mixture of 5-((S)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (30 mg, 69.86 μmol, 1 eq), 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1H-imidazol-2 (3H)-one (43.38 mg, 83.83 μmol, 1.2 eq), HOBt (18.88 mg, 139.72 μmol, 2 eq), EDCI (26.78 mg, 139.72 μmol, 2 eq) and DIEA (90.29 mg, 698.58 μmol, 121.68 μL, 10 eq) in DMF (0.8 mL) was stirred at 50° C. for 2 hours under $N_2$ atmosphere. LCMS indicated the reaction was completed. The reaction mixture was quenched by addition $H_2O$ (50 mL), extracted with ethyl acetate (30 mL*3). The combined organic layers were washed with saturated brine (30 mL), dried over anhydrous $Na_2SO_4$, filtered and concentrated under reduced pressure. The residue was purified by prep-HPLC (TFA condition column: 3_Phenomenex Luna C18 75*30 mm*3 um; mobile phase: [$H_2O$ (0.1% TFA)-ACN]; gradient: 50%-80% B over 8.0 min) to give 3-((1S,2S)-1-(5-((S)-2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (12.56 mg, 13.52 μmol, 19.35% yield). $^1$H NMR (400 MHz, DMSO-$d_6$) δ=12.41-11.78 (m, 1H), 8.33-8.15 (m, 1H), 7.67-6.66 (m, 9H), 5.66-5.50 (m, 1H), 5.25-5.03 (m, 1H), 4.12-4.05 (m, 3H), 4.03-3.83 (m, 1H), 3.80-3.52 (m, 4H), 3.50-3.24 (m, 1H), 3.22-2.77 (m, 3H), 2.32-2.02 (m, 6H), 1.99-1.32 (m, 6H), 1.29-0.92 (m, 10H). LC-MS (ES+, m/z): 929.4 [$(M+H)^+$]; Rt=3.003 min. HRMS (EI): m/z $[M+H]^+$ found: 929.3724.

Example 121, Compound 706

3-((1S,2S)-1-(5-((R)-2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one

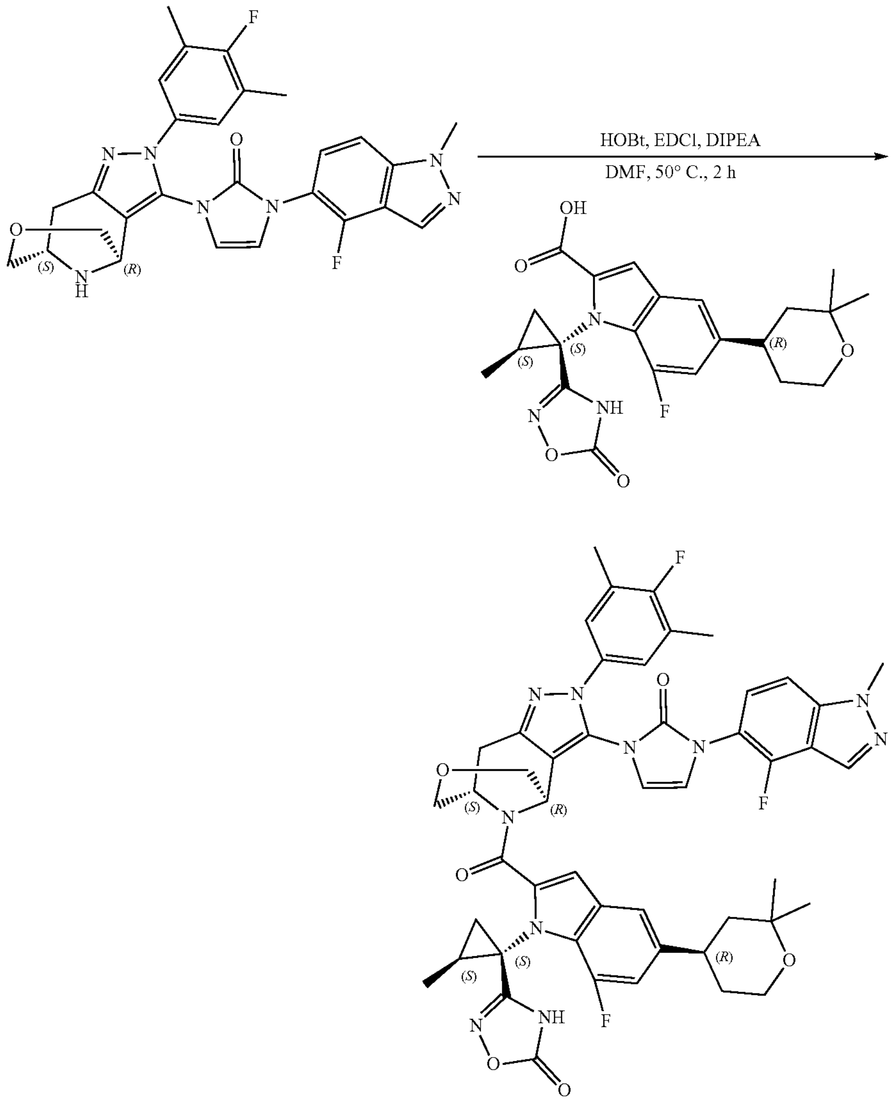

To a solution of 1-(4-fluoro-1-methyl-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (72.31 mg, 139.72 μmol, 1.2 eq) and 5-((R)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (50.00 mg, 116.43 μmol, 1 eq) in DMF (1 mL) was added DIPEA (75.24 mg, 582.15 μmol, 101.40μ, 5 eq), EDCI (29.02 mg, 151.36 μmol, 1.3 eq) and HOBt (23.60 mg, 174.65 μmol, 1.5 eq). The mixture was stirred at 50° C. for 2 hours under $N_2$. LCMS indicated the reaction was completed. The mixture was added to $H_2O$ (10 mL) and then extracted with ethyl acetate (15 mL*3). The organic layers were combined, washed with water (10 mL*2), saturated brine (10 mL), dried over $Na_2SO_4$, filtered and concentrated in vacuo. The residue was purified by prep-HPLC (column: 3_Phenomenex Luna C18 75*30 mm*3 um; mobile phase: [$H_2O$ (0.1% TFA)-ACN]; gradient: 50%-80% B over 8.0 min). Compound 3-((1S,2S)-1-(5-((R)-2,2-dimethyltetrahydro-2H-pyran-4-yl)-7-fluoro-2-((4R,8S)-3-(3-(4-fluoro-1-methyl-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-1H-indol-1-yl)-2-methylcyclopropyl)-1,2,4-oxadiazol-5 (4H)-one (28.88 mg, 31.06 μmol, 26.67% yield). $^1H$ NMR (400 MHz, DMSO-$d_6$) δ=12.39-11.82 (m, 1H), 8.35-8.11 (m, 1H), 7.71-6.69 (m, 9H), 5.55-5.26 (m, 1H), 5.00-4.82 (m, 1H), 4.18-4.03 (m, 4H), 4.02-3.83 (m, 1H), 3.79-3.31 (m, 5H), 3.18-2.93 (m, 2H), 2.32-2.15 (m, 6H), 2.10-1.55 (m, 4H), 1.52-1.38 (m, 2H), 1.32-0.89 (m, 10H). LC-MS (ES+, m/z): 929.4 [$(M+H)^+$]; Rt=2.998 min. HRMS (EI): m/z $[M+H]^+$ found: 929.3724.

Example 122, Compound 707

3-((1S,2S)-1-(5-((S)-2,2-dimethyltetrahydro-2H-pyran-4-yl)-7-fluoro-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one Scheme 707

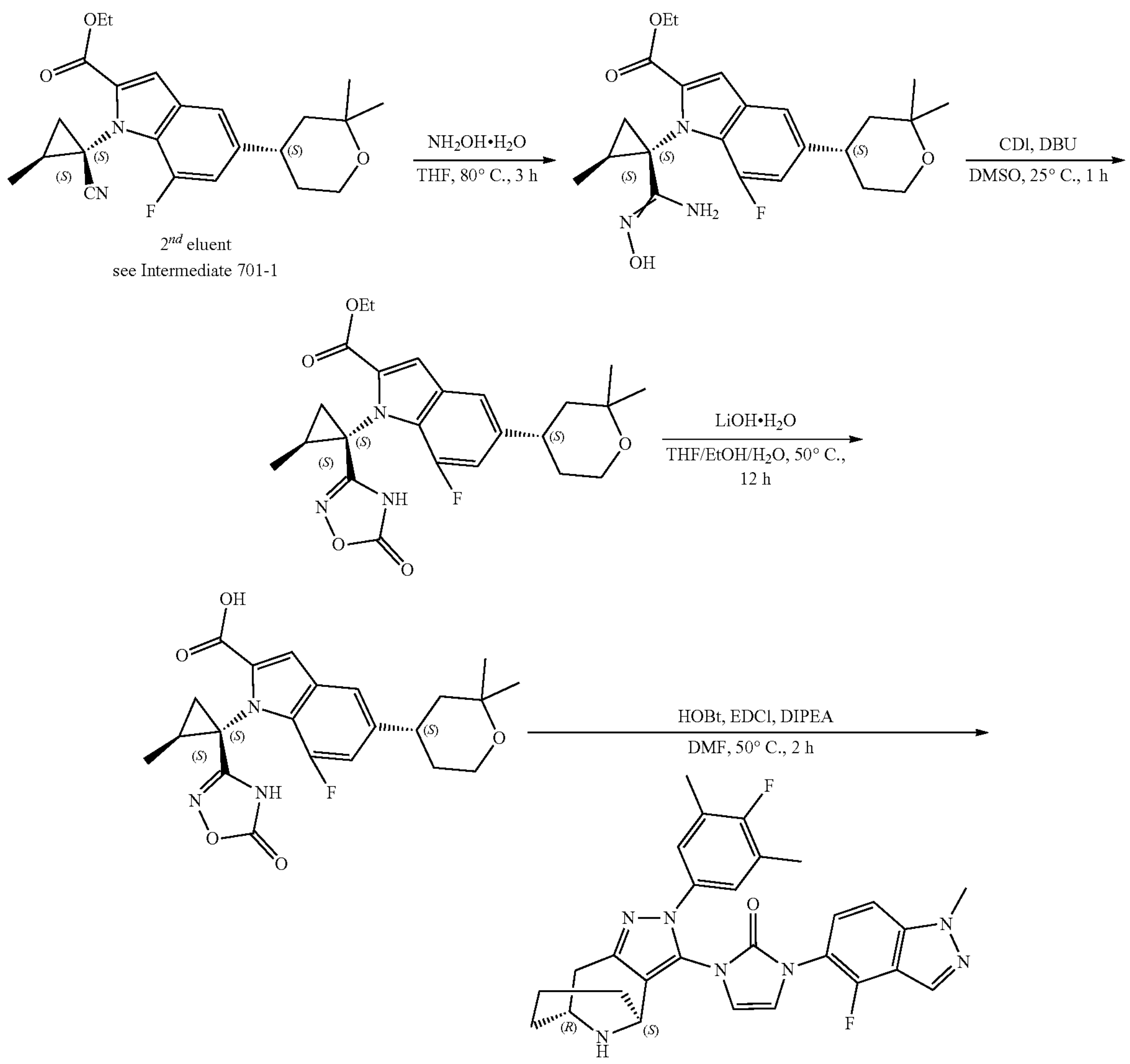

-continued

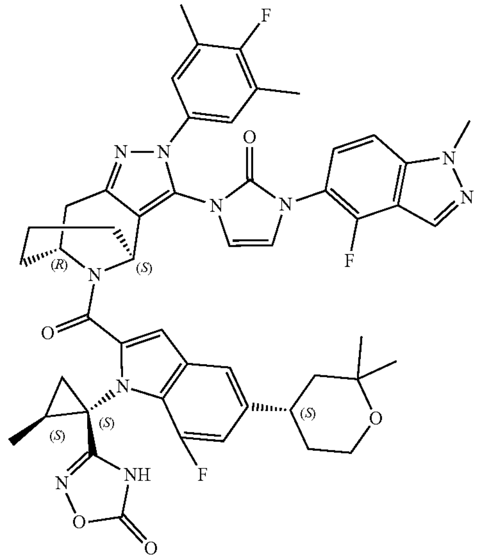

Step 1: ethyl 5-((S)-2,2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate Step 2: ethyl 5-((S)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylate

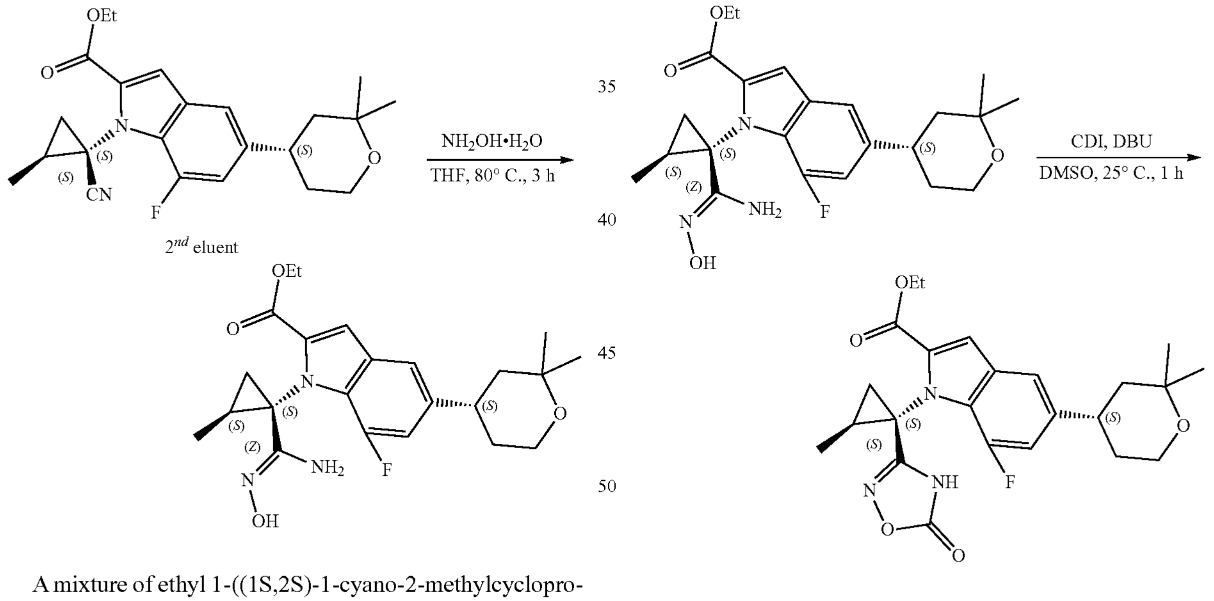

A mixture of ethyl 1-((1S,2S)-1-cyano-2-methylcyclopropyl)-5-((S)-2,2-dimethyltetrahydro-2H-pyran-4-yl)-7-fluoro-1H-indole-2-carboxylate (650 mg, 1.63 mmol, 1 eq), hydroxylamine (1.08 g, 16.31 mmol, 50% purity, 10 eq) and THF (8 mL) was stirred at 80° C. for 3 hours under $N_2$. LCMS indicated the reaction was completed. The mixture was poured into water (40 mL) and extracted with ethyl acetate (40 mL*2). The organic layers was washed with water (40 mL*2), saturated brine (40 mL*2), dried over $Na_2SO_4$, filtered, concentrated under reduced pressure to give ethyl 5-((S)-2,2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate (700 mg, crude). LC-MS (ES+, m/z): 432.2 [$(M+H)^+$]; Rt=0.459 min.

A mixture of ethyl 5-((S)-2,2-dimethyltetrahydro-2H-pyran-4-yl)-7-fluoro-1-((1S,2S)-1-(N'-hydroxycarbamimidoyl)-2-methylcyclopropyl)-1H-indole-2-carboxylate (700 mg, 1.62 mmol, 1 eq), CDI (526.10 mg, 3.24 mmol, 2 eq), DBU (740.91 mg, 4.87 mmol, 733.58 μL, 3 eq) in DMSO (10 mL) was stirred at 25° C. for 1 hour under $N_2$. LCMS indicated the reaction was completed. The mixture was poured into water (40 mL) and extracted with DCM (40 mL*2). The combined organic layers were washed with water (40 mL*2), saturated brine (40 mL*2), dried over $Na_2SO_4$, filtered, and concentrated under reduced pressure. The crude product was purified by chromatography on silica gel (hexanes: ethyl acetate=1:1) to give ethyl 5-((S)-2,2- dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylate (450 mg, 970.83 μmol, 59.84% yield). LC-MS (ES+, m/z): 458.2 [(M+H)+]; Rt=0.610 min.

Step 3: 5-((S)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid

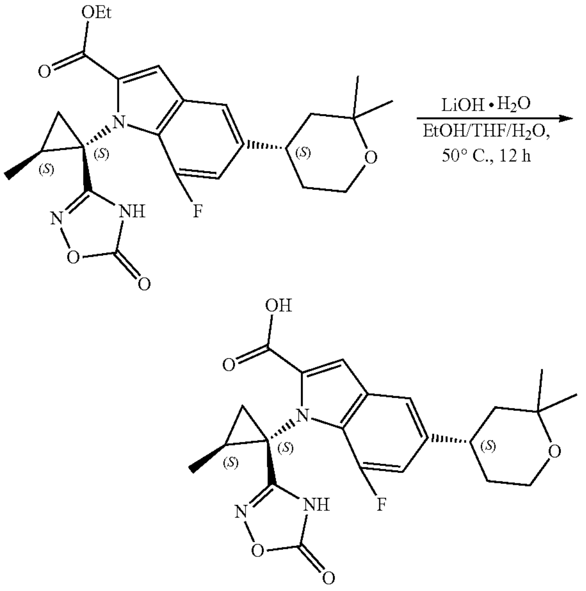

To a solution of give ethyl 5-((S)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylate (450 mg, 983.62 μmol, 1 eq) in THF (1.5 mL), EtOH (1.5 mL) $H_2O$ (1.5 mL) was added $LiOH{\cdot}H_2O$ (412.73 mg, 9.84 mmol, 10 eq). The mixture was stirred at 50° C. for 12 hours under $N_2$. LCMS indicated the reaction was completed. The crude was concentrated and adjusted to pH=2 with 1M HCl and extracted with DCM (50 mL*2). The combined organic layers were washed with $H_2O$ (50 mL), saturated brine (50 mL), filtered, and concentrated to give 5-((S)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (380 mg, crude). LC-MS (ES+, m/z): 430.2 [(M+H)+]; Rt=0.506 min.

Step 4: 3-((1S,2S)-1-(5-((S)-2,2-dimethyltetrahydro-2H-pyran-4-yl)-7-fluoro-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta[c]pyrazole-10-carbonyl)-1H-indol-1-yl)-2-methylcyclopropyl)-1,2,4-oxadiazol-5 (4H)-one

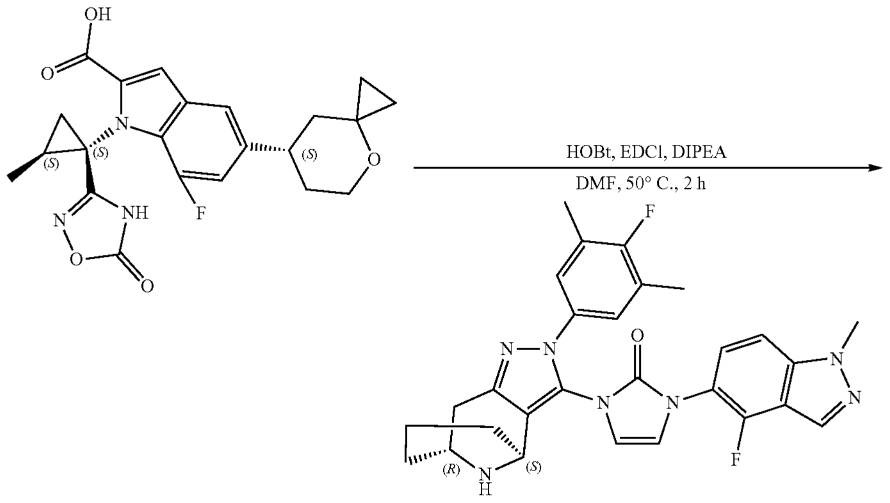

-continued

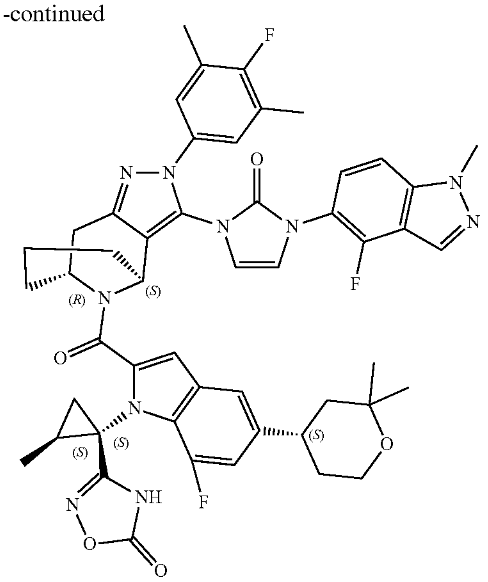

To a solution of 5-((S)-2,2-dimethyltetrahydro-2H-pyran-4-yl)-7-fluoro-1-((1S,2S)-2-methyl-1-(5-oxo-4,5-dihydro-1,2,4-oxadiazol-3-yl)cyclopropyl)-1H-indole-2-carboxylic acid (50 mg, 116.43 μmol, 1 eq), 1-(4-fluoro-1-methyl-1H-indazol-5-yl)-3-((4S,8R)-2-(4-fluoro-3,5-dimethylphenyl)-4,5,6,7,8,9-hexahydro-2H-4,8-epiminocycloocta [c]pyrazol-3-yl)-1,3-dihydro-2H-imidazol-2-one (72.03 mg, 139.72 μmol, 1.2 eq), DIPEA (75.24 mg, 582.15 μmol, 101.40 μL, 5 eq) in DMF (0.5 mL) was added EDCI (44.64 mg, 232.86 μmol, 2 eq) and HOBt (31.46 mg, 232.86 μmol, 2 eq). The mixture was stirred at 50° C. 2 hours under $N_2$. LCMS indicated the reaction was completed. The mixture was poured into water (40 mL) and extracted with DCM (40 mL*2). The combined organic layers were washed with water (40 mL*2), saturated brine (40 mL*2), dried over $Na_2SO_4$, filtered, concentrated under reduced pressure. The crude product was purified by prep-HPLC (column: Phenomenex Luna C18100*30 mm*5 um; mobile phase: [$H_2O$ (0.1% TFA) ACN]; gradient: 55%-85% B over 8.0 min) to give 3-((1S,2S)-1-(5-((S)-2,2-dimethyltetrahydro-2H-pyran-4-yl)-7-fluoro-2-((4S,8R)-3-(3-(4-fluoro-1-methyl-1H-indazol-5-yl)-2-oxo-2,3-dihydro-1H-imidazol-1-yl)-2-(4-fluoro-3,5-dimethylphenyl)-4,5,6,7,8,9-hexahydro-2H-4,8-epiminocycloocta [c]pyrazole-10-carbonyl)-1H-indol-1-yl)-2-methylcyclopropyl)-1,2,4-oxadiazol-5 (4H)-one (19.24 mg, 20.71 μmol, 17.79% yield) as yellow solid. $^1H$ NMR (400 MHz, DMSO-$d_6$) δ=12.35-11.76 (m, 1H), 8.28-7.96 (m, 1H), 7.58-6.60 (m, 9H), 5.69-5.56 (m, 1H), 5.17-4.98 (m, 1H), 4.07-3.97 (m, 3H), 3.63-3.38 (m, 2H), 3.28-2.77 (m, 3H), 2.23-2.13 (m, 6H), 1.94-1.35 (m, 12H), 1.22-0.83 (m, 10H); LC-MS (ES+, m/z): 927.4 [$(M+H)^+$]; Rt=3.285 min. HRMS (EI): m/z $[M+H]^+$ found: 927.3914.

Example 123, Compound 710

6-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1-methylindoline-2,3-dione Scheme 710

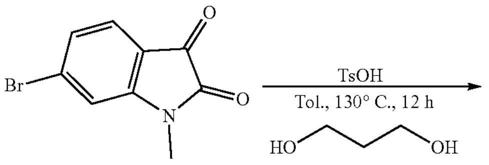

-continued
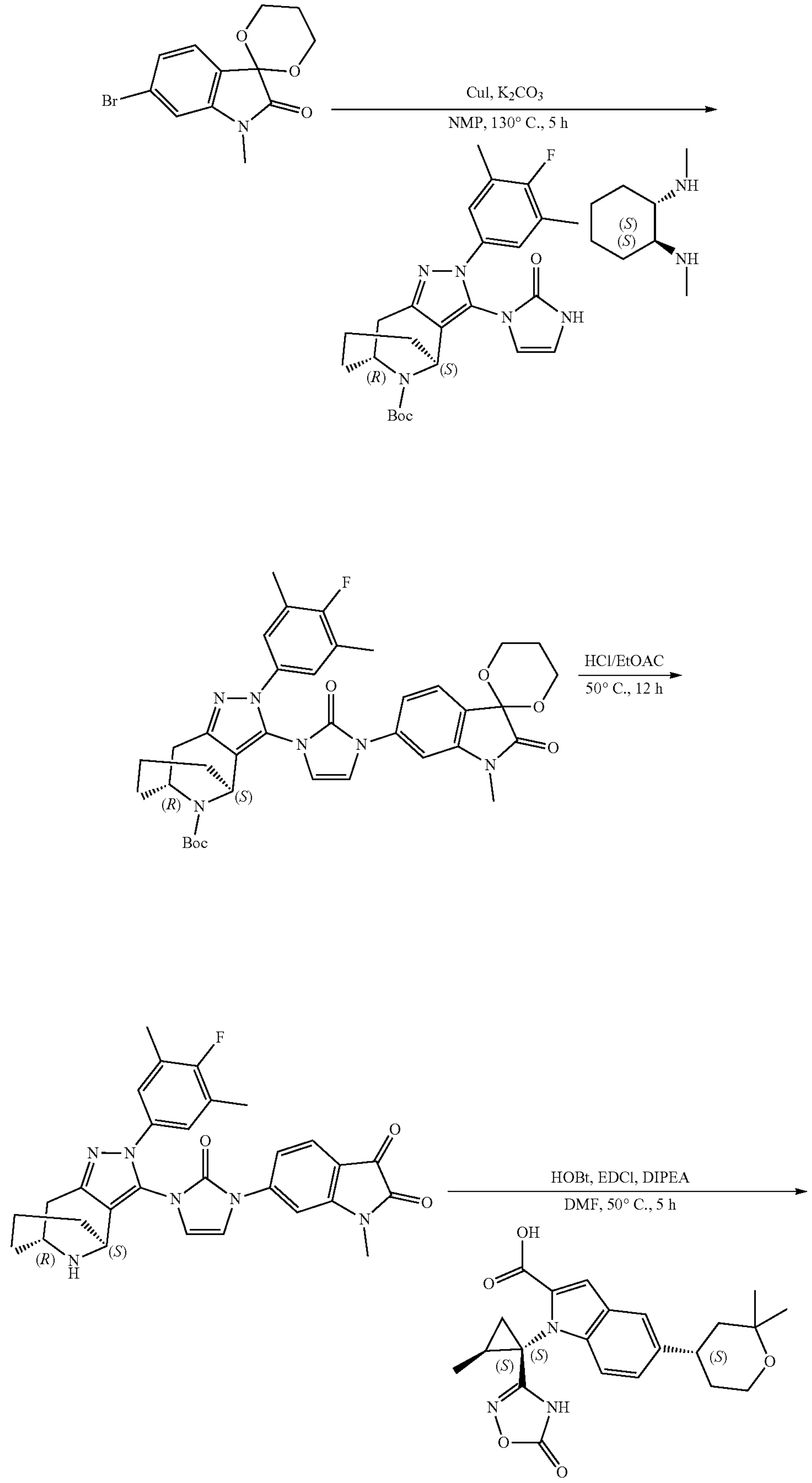

-continued

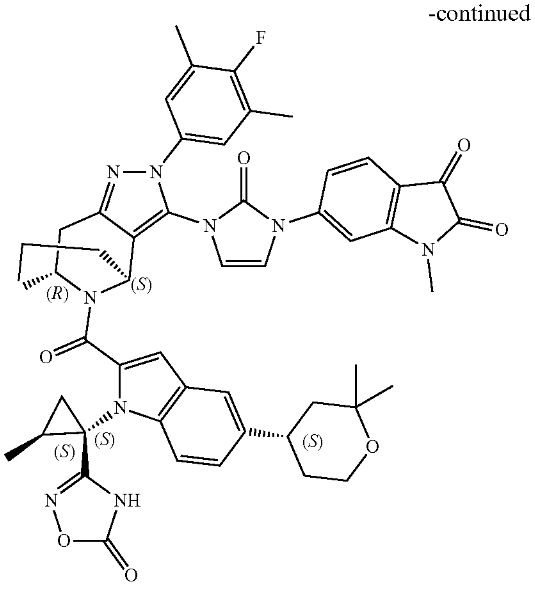

Step 1: 6-bromo-1-methylspiro[indoline-3,2'-[1,3] dioxan]-2-one

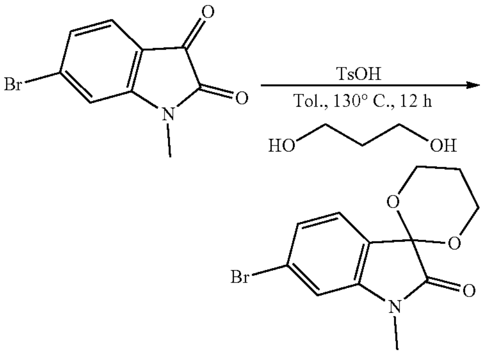

To a solution of 6-bromo-1-methyl-indoline-2,3-dione (1 g, 4.17 mmol, 1 eq) and propane-1,3-diol (1.58 g, 20.83 mmol, 1.51 mL, 5 eq) in Tol. (10 mL) was added TsOH·$H_2O$ (118.86 mg, 624.86 μmol, 0.15 eq). The mixture was stirred at 130° C. for 12 hours under $N_2$. LC-MS showed the reaction was completed. The reaction mixture was concentrated in vacuo. The reaction mixture was diluted with saturated $NaHCO_3$ (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuum. The residue was purified by column chromatography ($SiO_2$, hexanes:ethyl acetate=100/1 to 10/1) to give 6-bromo-1-methylspiro[indoline-3,2'-[1,3] dioxan]-2-one (700 mg, 2.35 mmol, 56.36% yield). LC-MS (ES+, m/z): 298.0 [$(M+H)^+$]; Rt=0.528 min.

Step 2: (4S,8R)-tert-butyl 2-(4-fluoro-3,5-dimethylphenyl)-3-(3-(1'-methyl-2'-oxospiro[[1,3] dioxane-2,3'-indolin]-6'-yl)-2-oxo-2,3-dihydro-1H-imidazol-1-yl)-4,5,6,7,8,9-hexahydro-2H-4,8-epiminocycloocta [c]pyrazole-10-carboxylate

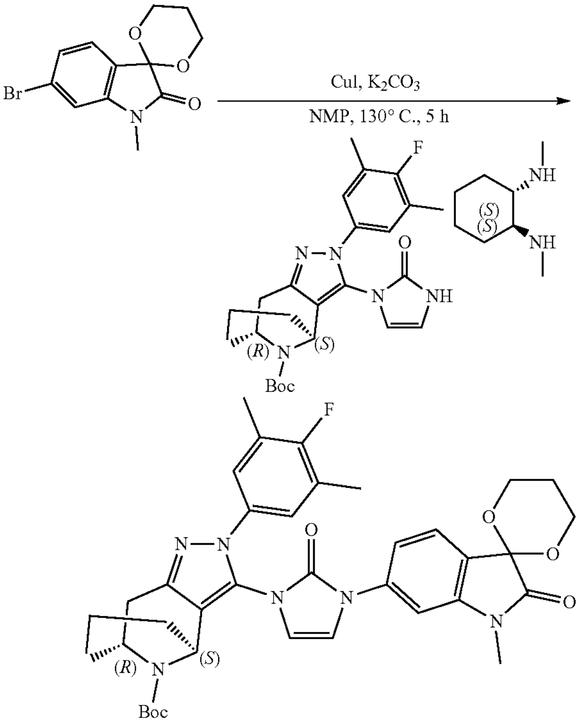

To a solution of (4S,8R)-tert-butyl 2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (0.3 g, 641.66 μmol, 1 eq) and 6'-bromo-1'-methylspiro[[1,3]dioxane-2,3'-indolin]-2'-one (191.30 mg, 641.66 μmol, 1 eq) and (1S,2S)—N1,N2-dimethylcyclohexane-1,2-diamine (182.54 mg, 1.28 mmol, 2 eq) in NMP (10 mL) was added CuI (244.41 mg, 1.28 mmol, 2 eq) and $K_2CO_3$ (266.05 mg, 1.92 mmol, 3 eq). The mixture was stirred at 130° C. for 5 hours under $N_2$. LC-MS showed the reaction was completed. The reaction mixture was diluted with saturated EDTA (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuo. The residue was purified by prep-TLC ($SiO_2$, hexanes:ethyl acetate=1:1) to give (4S,8R)-tert-butyl 2-(4-fluoro-3,5-dimethylphenyl)-3-(3-(1'-methyl-2'-oxospiro[[1,3]dioxane-2,3'-indolin]-6'-yl)-2-oxo-2,3-dihydro-1H-imidazol-1-yl)-4,5,6,7,8,9-hexahydro-2H-4,8-epiminocycloocta [c]pyrazole-10-carboxylate (420 mg, 572.69 μmol, 89.25% yield). LC-MS (ES+, m/z): 685.4 [$(M+H)^+$]; Rt=0.657 min.

Step 3: 6-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1-methylindoline-2,3-dione

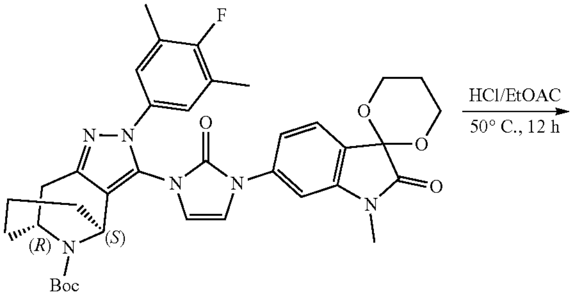

-continued

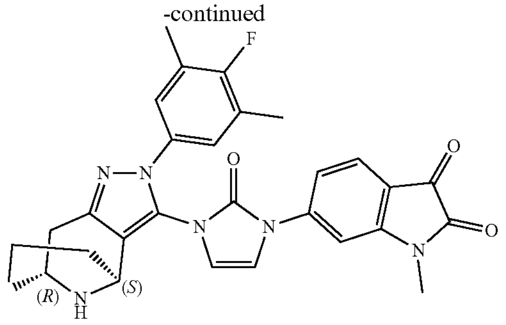

To a solution of (4S,8R)-tert-butyl 2-(4-fluoro-3,5-dimethylphenyl)-3-(3-(1'-methyl-2'-oxospiro[[1,3]dioxane-2,3'-indolin]-6'-yl)-2-oxo-2,3-dihydro-1H-imidazol-1-yl)-4,5,6,7,8,9-hexahydro-2H-4,8-epiminocycloocta [c]pyrazole-10-carboxylate (160 mg, 233.66 μmol, 1 eq) in HCl/EtOAc (4 M, 2 mL) was stirred at 50° C. for 12 hours under $N_2$. LC-MS showed the reaction was completed. The reaction mixture was concentrated in vacuo. The reaction mixture was diluted with saturated $NaHCO_3$ (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuo to give 6-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1-methylindoline-2,3-dione (120 mg, 183.20 μmol, 78.41% yield). LC-MS (ES+, m/z): 527.4 [$(M+H)^+$]; Rt=0.430 min.

Step 4: 6-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1-methylindoline-2,3-dione

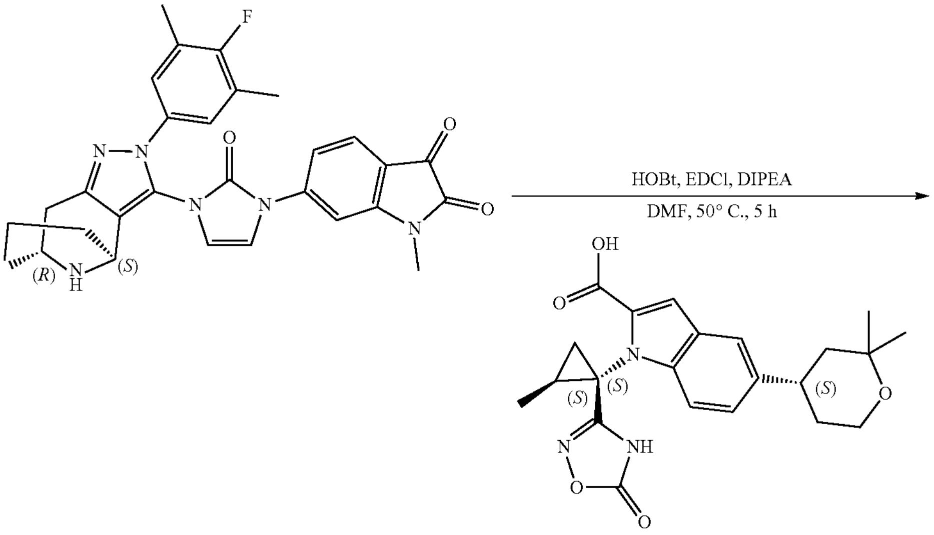

-continued

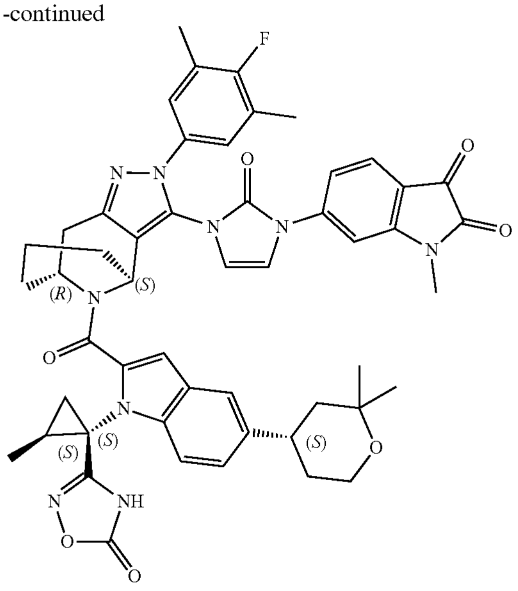

To a solution of 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (40 mg, 97.22 μmol, 1 eq) in DMF (2 mL) was added HOBt (26.27 mg, 194.43 μmol, 2 eq) and EDCI (37.27 mg, 194.43 μmol, 2 eq) and DIPEA (37.69 mg, 291.65 μmol, 50.80 μL, 3 eq). 6-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1-methylindoline-2,3-dione (66.55 mg, 126.38 μmol, 1.3 eq) was then added and the mixture was stirred at 50° C. for 5 hours under $N_2$. LC-MS showed the reaction was completed. The reaction mixture was diluted with water (50 mL) and stirred for 1 hour, extracted with ethyl acetate (50 mL*3). The combined organic layers were washed with saturated brine (50 mL*2). The combined organic layers were dried over $Na_2SO_4$, filtered and concentrated in vacuo. The residue was purified by prep-HPLC (TFA condition) column: 3_Phenomenex Luna C18 75*30 mm*3 um; mobile phase: [$H_2O$ (0.1% TFA)-ACN]; gradient: 50%-80% B over 8.0 min to give 6-(3-((4S,8R)-10-(5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carbonyl)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1-methylindoline-2,3-dione (22.34 mg, 24.21 μmol, 24.90% yield). $^1H$ NMR (400 MHz, DMSO-$d_6$) δ=12.27-11.63 (m, 1H), 7.85-6.44 (m, 11H), 5.78-4.93 (m, 2H), 3.70-3.48 (m, 3H), 3.20-2.88 (m, 5H), 2.20 (br d, J=11.8 Hz, 6H), 2.06-1.43 (m, 12H), 1.41-0.90 (m, 10H). LC-MS (ES+, m/z): 920.5 [$(M+H)^+$]; Rt=3.072 min. HRMS (EI): m/z $[M+H]^+$ found: 920.3872.

Example 124, Compound 714

3-((1S,2S)-1-(5-((S)-2,2-dimethyltetrahydro-2H-pyran-4-yl)-2-((4S,8R)-2-(4-fluoro-3,5-dimethylphenyl)-3-(3-(1'-methyl-2'-oxospiro[cyclopropane-1,3'-indolin]-5'-yl)-2-oxo-2,3-dihydro-1H-imidazol-1-yl)-4,5,6,7,8,9-hexahydro-2H-[4,8]epiminocycloocta [c]pyrazole-10-carbonyl)-1H-indol-1-yl)-2-methylcyclopropyl)-1,2,4-oxadiazol-5 (4H)-one Scheme 714

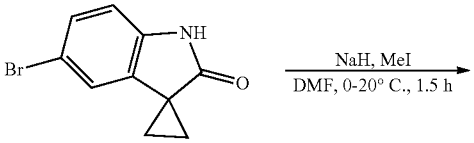

-continued
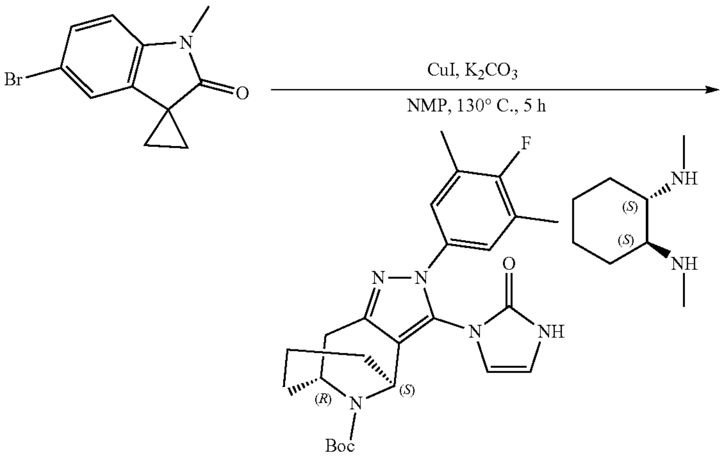
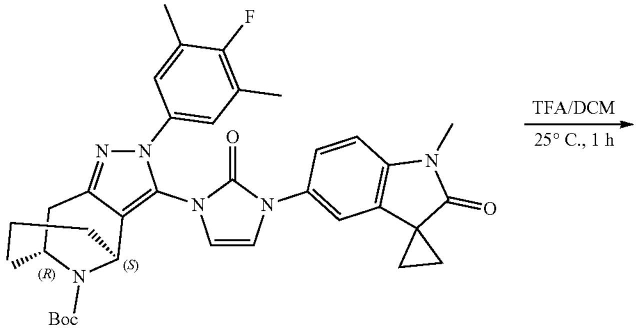
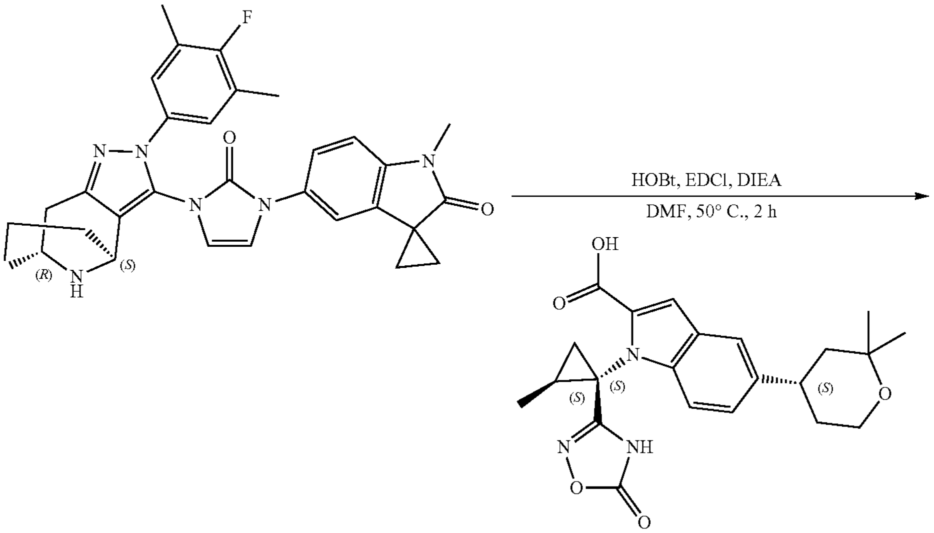

-continued

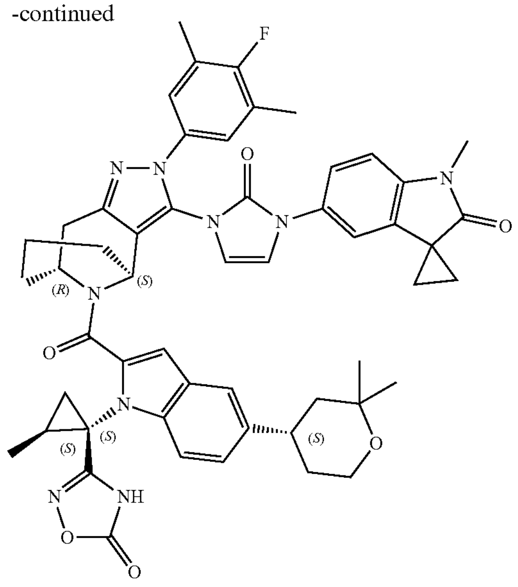

Step 1: 5'-bromo-1'-methylspiro[cyclopropane-1,3'-indolin]-2'-one

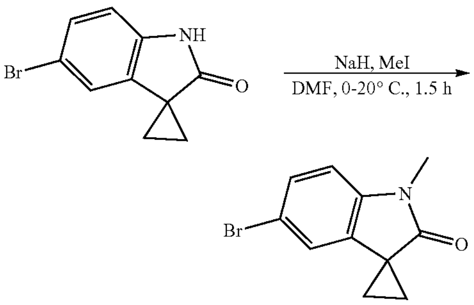

To a mixture of 5'-bromospiro[cyclopropane-1,3'-indolin]-2'-one (200 mg, 840.05 μmol, 1 eq) in DMF (2 mL) was added NaH (40.32 mg, 1.01 mmol, 60% purity, 1.2 eq) in one portion at 0° C. under $N_2$ and stirred for 30 mins. MeI (131.16 mg, 924.06 μmol, 1.1 eq) was then added in one portion at 0° C. under $N_2$. The mixture was stirred at 20° C. for 1 hour. LCMS showed the reaction was completed. The residue was poured into water (20 mL). The aqueous phase was extracted with ethyl acetate (10 mL*3). The combined organic phase was washed with saturated brine (30 mL), dried with anhydrous $Na_2SO_4$, filtered and concentrated in vacuo to give 5'-bromo-1'-methylspiro[cyclopropane-1,3'-indolin]-2'-one (170 mg, crude). $^1$H NMR (400 MHz, DMSO-$d_6$) δ=7.52-7.40 (m, 1H), 7.36-7.22 (m, 1H), 7.09-6.95 (m, 1H), 3.27-3.15 (m, 3H), 1.77-1.66 (m, 2H), 1.58-1.46 (m, 2H). LC-MS (ES+, m/z): 252.0 [(M+H)$^+$]; Rt=1.717 min. $^1$H NMR matched with literature.

Step 2: tert-butyl (4S,8R)-2-(4-fluoro-3,5-dimethylphenyl)-3-(3-(1'-methyl-2'-oxospiro[cyclopropane-1,3'-indolin]-5'-yl)-2-oxo-2,3-dihydro-1H-imidazol-1-yl)-4,5,6,7,8,9-hexahydro-2H-4,8-epiminocycloocta [c]pyrazole-10-carboxylate

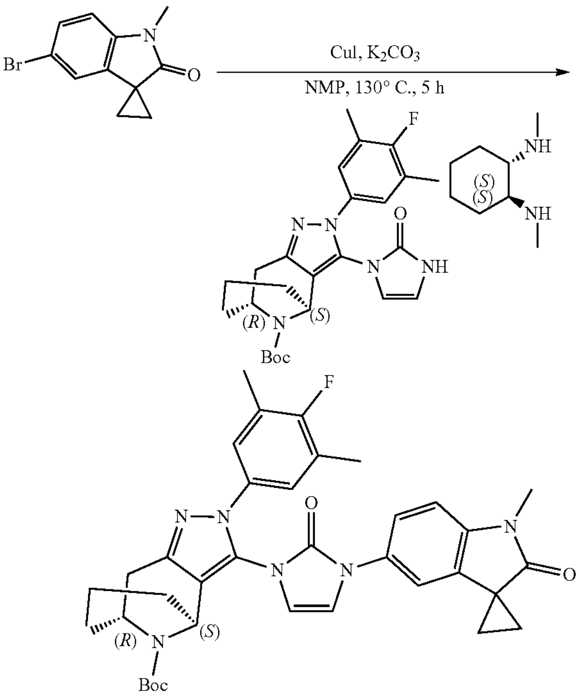

To a mixture of tert-butyl (4S,8R)-2-(4-fluoro-3,5-dimethylphenyl)-3-(2-oxo-2,3-dihydro-1H-imidazol-1-yl)-4,5,6,7,8,9-hexahydro-2H-4,8-epiminocycloocta [c]pyrazole-10-carboxylate (130 mg, 278.05 μmol, 1 eq) and 5'-bromo-1'-methylspiro[cyclopropane-1,3'-indolin]-2'-one (144.53 mg, 556.11 μmol, 2 eq) and (1S,2S)—$N^1$,$N^2$-dimethylcyclohexane-1,2-diamine (118.65 mg, 834.16 μmol, 3 eq) in NMP (1.3 mL) was added $K_2CO_3$ (115.29 mg, 834.16 μmol, 3 eq) and CuI (158.87 mg, 834.16 μmol, 3 eq) in one portion at 130° C. under $N_2$. The mixture was stirred at 130° C. for 5 hours under $N_2$. LCMS showed the reaction was completed. The residue was poured into saturated EDTA solution (20 mL) and ethyl acetate (20 mL) stirred for 0.5 hour. The aqueous phase was extracted with ethyl acetate (10 mL*3). The combined organic phase was washed with saturated brine (30 mL), dried with anhydrous $Na_2SO_4$, filtered and concentrated in vacuo. The residue was purified by column chromatography ($SiO_2$, hexanes: ethyl acetate=1:1) to give tert-butyl (4S,8R)-2-(4-fluoro-3,5-dimethylphenyl)-3-(3-(1'-methyl-2'-oxospiro[cyclopropane-1,3'-indolin]-5'-yl)-2-oxo-2,3-dihydro-1H-imidazol-1-yl)-4,5,6,7,8,9-hexahydro-2H-4,8-epiminocycloocta [c]pyrazole-10-carboxylate (120 mg, 182.24 μmol, 65.54% yield). LC-MS (ES+, m/z): 639.3 [(M+H)+]; Rt=0.632 min.

Step 3: 5'-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1'-methylspiro[cyclopropane-1,3'-indolin]-2'-one

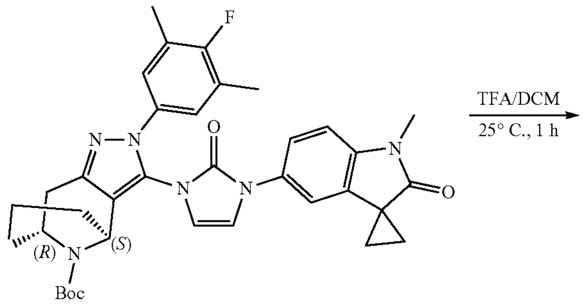

-continued

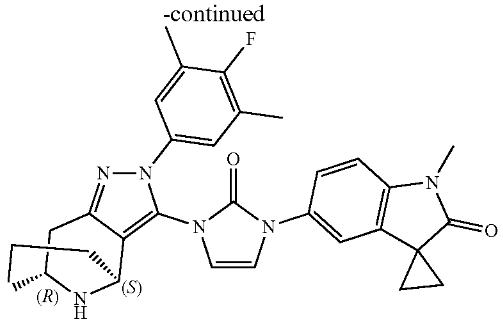

To a mixture of tert-butyl (4S,8R)-2-(4-fluoro-3,5-dimethylphenyl)-3-(3-(1'-methyl-2'-oxospiro[cyclopropane-1,3'-indolin]-5'-yl)-2-oxo-2,3-dihydro-1H-imidazol-1-yl)-4,5,6,7,8,9-hexahydro-2H-4,8-epiminocycloocta [c]pyrazole-10-carboxylate (60 mg, 91.12 μmol, 1 eq) in DCM (1 mL) was added TFA (0.2 mL). The mixture was stirred at 25° C. for 1 hour. LCMS showed the reaction was completed. The residue was poured into saturated $NaHCO_3$ (10 mL). The aqueous phase was extracted with ethyl acetate (10 mL*3). The combined organic phase was washed with saturated brine (15 mL), dried with anhydrous $Na_2SO_4$, filtered and concentrated in vacuo to give 5'-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1'-methylspiro[cyclopropane-1,3'-indolin]-2'-one (50 mg, crude). LC-MS (ES+, m/z): 539.2 [(M+H)+]; Rt=0.436 min.

Step 4: 3-((1S,2S)-1-(5-((S)-2,2-dimethyltetrahydro-2H-pyran-4-yl)-2-((4S,8R)-2-(4-fluoro-3,5-dimethylphenyl)-3-(3-(1'-methyl-2'-oxospiro[cyclopropane-1,3'-indolin]-5'-yl)-2-oxo-2,3-dihydro-1H-imidazol-1-yl)-4,5,6,7,8,9-hexahydro-2H-[4,8]epiminocycloocta [c]pyrazole-10-carbonyl)-1H-indol-1-yl)-2-methylcyclopropyl)-1,2,4-oxadiazol-5(4H)-one

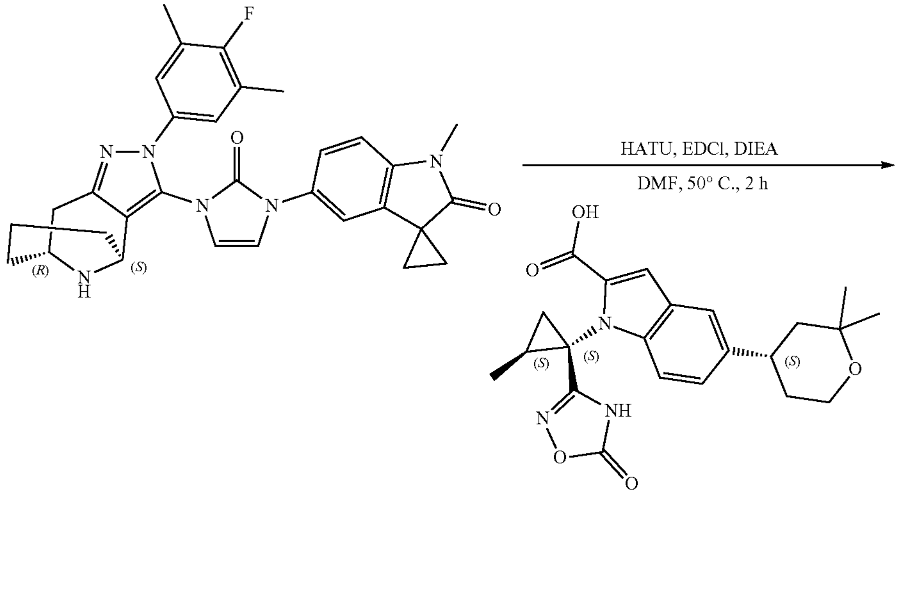

-continued

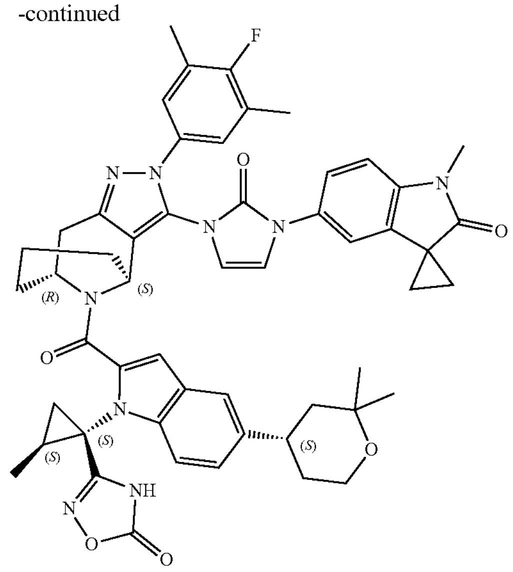

To a mixture of 5'-(3-((4S,8R)-2-(4-fluoro-3,5-dimethylphenyl)-4,5,6,7,8,9-hexahydro-2H-4,8-epiminocycloocta [c]pyrazol-3-yl)-2-oxo-2,3-dihydro-1H-imidazol-1-yl)-1'-methylspiro[cyclopropane-1,3'-indolin]-2'-one (50 mg, 92.83 μmol, 1 eq) and 5-((S)-2,2-dimethyltetrahydro-2H-pyran-4-yl)-1-((1S,2S)-2-methyl-1-(5-oxo-4,5-dihydro-1,2,4-oxadiazol-3-yl)cyclopropyl)-1H-indole-2-carboxylic acid (38.20 mg, 92.83 μmol, 1 eq) in DMF (0.5 mL) was added DIEA (59.99 mg, 464.15 μmol, 5 eq), HOBt (18.82 mg, 139.25 μmol, 1.5 eq) and EDCI (23.13 mg, 120.68 μmol, 1.3 eq) in one portion at 50° C. under $N_2$. The mixture was stirred for 2 hours at 50° C. LCMS showed the reaction was completed. The residue was poured into water (20 mL). The aqueous phase was extracted with chloroform:isopropanol=3:1 (10 mL*3). The combined organic phase was washed with saturated brine (30 mL), dried with anhydrous $Na_2SO_4$, filtered and concentrated in vacuo. The residue was purified by prep-HPLC (column: WePure Biotech XP tC18 150*40*7 um; mobile phase: [$H_2O$ (10 mM $NH_4HCO_3$)-ACN]; gradient: 40%-70% B over 8.0 min) to give 3-((1S,2S)-1-(5-((S)-2,2-dimethyltetrahydro-2H-pyran-4-yl)-2-((4S,8R)-2-(4-fluoro-3,5-dimethylphenyl)-3-(3-(1'-methyl-2'-oxospiro[cyclopropane-1,3'-indolin]-5'-yl)-2-oxo-2,3-dihydro-1H-imidazol-1-yl)-4,5,6,7,8,9-hexahydro-2H-[4,8]epiminocycloocta [c]pyrazole-10-carbonyl)-1H-indol-1-yl)-2-methylcyclopropyl)-1,2,4-oxadiazol-5 (4H)-one (20.87 mg, 21.85 μmol, 23.54% yield). JH NMR (400 MHz, DMSO-$d_6$) δ=12.37-11.56 (m, 1H), 7.71-7.49 (m, 1H), 7.46-7.33 (m, 1H), 7.33-7.13 (m, 5H), 7.13-6.61 (m, 4H), 5.80-4.84 (m, 2H), 3.72-3.50 (m, 2H), 3.27 (br s, 6H), 2.25-2.14 (m, 6H), 2.05-1.82 (m, 2H), 1.81-1.63 (m, 6H), 1.63-1.53 (m, 6H), 1.52-1.38 (m, 3H), 1.38-1.24 (m, 3H), 1.22-0.93 (m, 6H). LC-MS (ES+, m/z): 932.4 [$(M+H)^+$]; Rt=3.391 min. HRMS (EI): m/z $[M+H]^+$ found: 932.4260.

Example 125, Compound 715

3-((1S,2S)-1-(2-((4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(tetrahydro-2H-pyran-4-yl)-1H-indol-1-yl)-2-methylcyclopropyl)-1,2,4-oxadiazol-5 (4H)-one Scheme 715

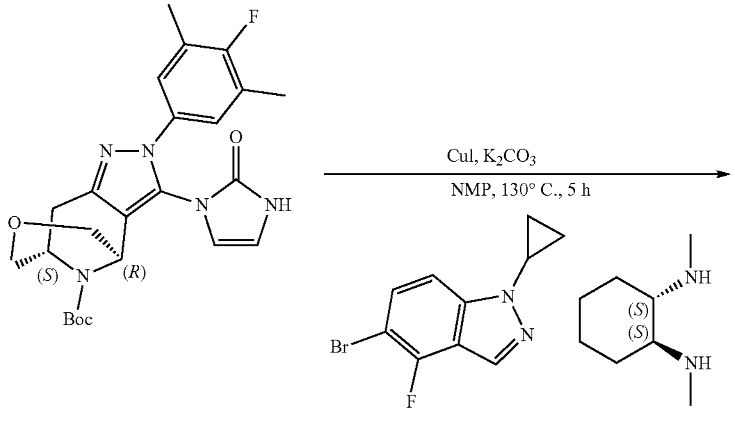

-continued
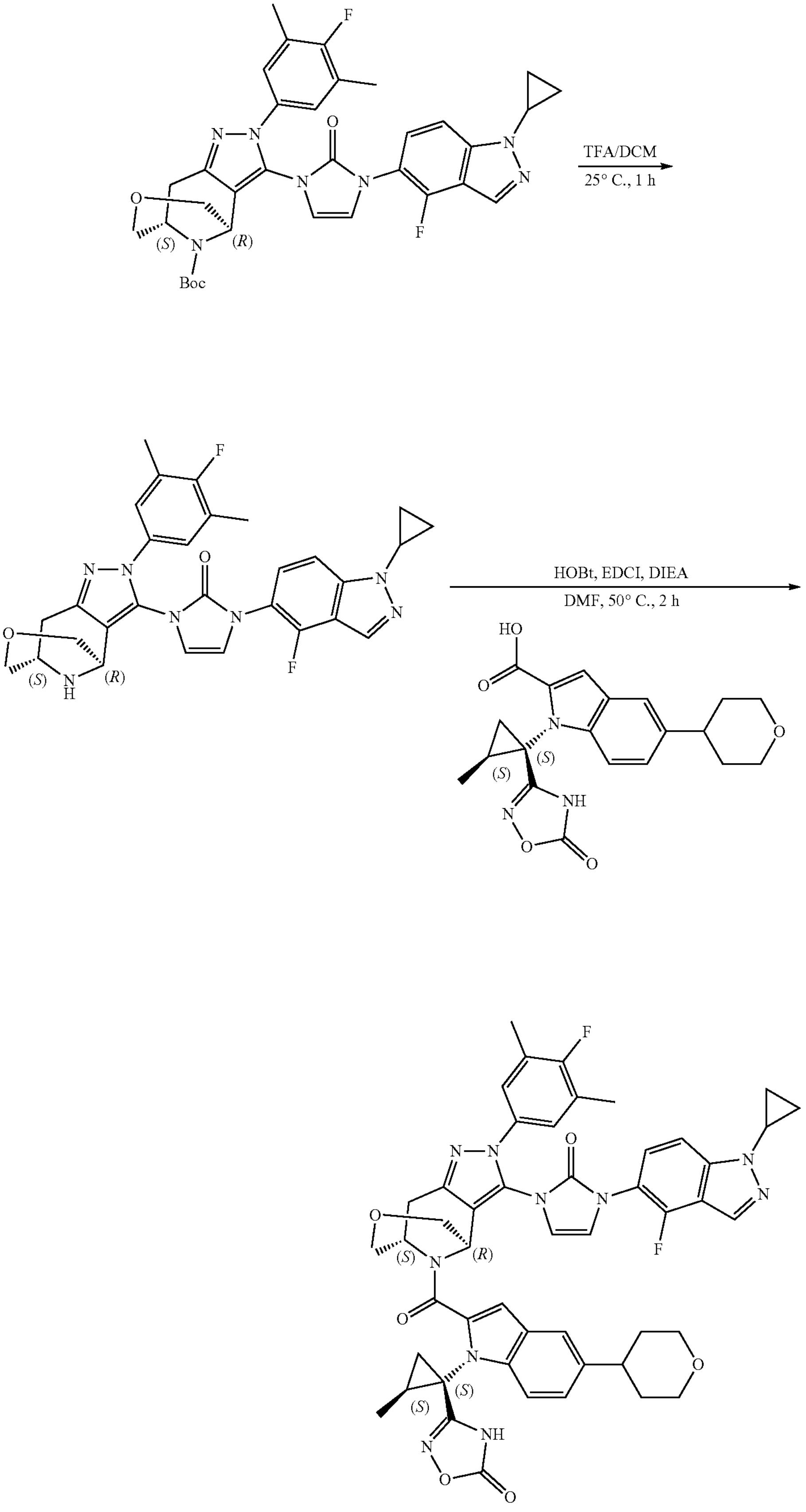

Step 1: tert-butyl (4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate

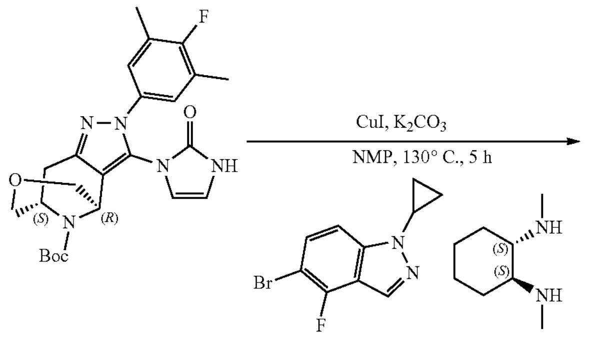

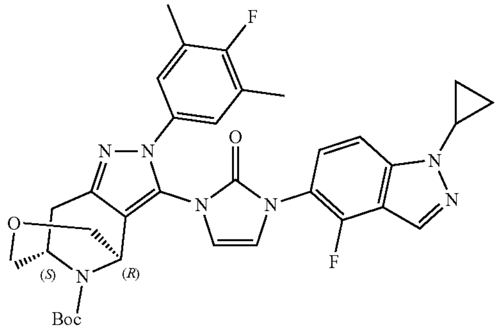

To a mixture of tert-butyl (4R,8S)-2-(4-fluoro-3,5-dimethylphenyl)-3-(2-oxo-2,3-dihydro-1H-imidazol-1-yl)-2,4,5,7,8,9-hexahydro-4,8-epiminooxocino [5,4-c]pyrazole-10-carboxylate (130 mg, 263.04 μmol, 1 eq) and 5-bromo-1-cyclopropyl-4-fluoro-1H-indazole (73.81 mg, 289.35 μmol, 1.1 eq), (1S,2S)—$N^1$,$N^2$-dimethylcyclohexane-1,2-diamine (112.25 mg, 789.12 μmol, 3 eq) in NMP (1.3 mL) was added $K_2CO_3$ (109.06 mg, 789.12 μmol, 3 eq) and CuI (100.19 mg, 526.08 μmol, 2 eq) in one portion under $N_2$. The mixture was stirred at 130° C. for 5 hours under $N_2$. LCMS showed the reaction was completed. The residue was poured into saturated EDTA solution (20 mL) and ethyl acetate (20 mL) stirred for 0.5 hour. The aqueous phase was extracted with ethyl acetate (20 mL*3). The combined organic phase was washed with saturated brine (30 mL), dried with anhydrous $Na_2SO_4$, filtered and concentrated in vacuo. The residue was purified by column chromatography ($SiO_2$, hexanes:ethyl acetate=1:1) to give tert-butyl (4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (90 mg, 134.23 μmol, 51.03% yield). LC-MS (ES+, m/z): 644.3 [(M+H)$^+$]; Rt=1.950 min.

Step 2: 1-(1-cyclopropyl-4-fluoro-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one

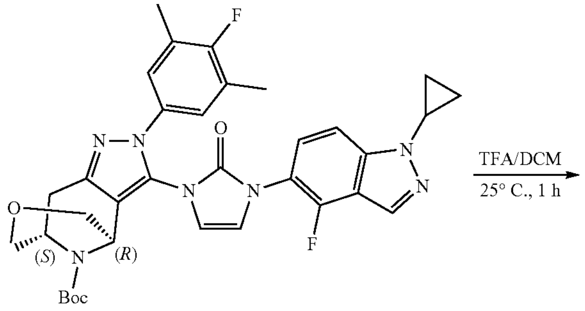

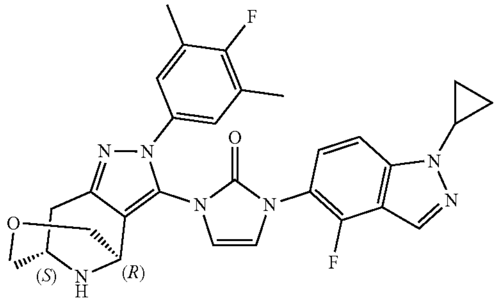

To a mixture of tert-butyl (4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carboxylate (50 mg, 74.57 μmol, 1 eq) in DCM (0.8 mL) was added TFA (0.2 mL) in one portion at 25° C. The mixture was stirred at 25° C. for 1 hour. LCMS showed the reaction was completed. The residue was poured into saturated $NaHCO_3$ (10 mL). The aqueous phase was extracted with ethyl acetate (10 mL*3). The combined organic phase was washed with saturated brine (15 mL), dried with anhydrous $Na_2SO_4$, filtered and concentrated in vacuo to give 1-(1-cyclopropyl-4-fluoro-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (30 mg, crude). LC-MS (ES+, m/z): 544.2 [(M+H)$^+$]; Rt=0.465 min.

Step 3: 3-((1S,2S)-1-(2-((4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c] pyrazole-10-carbonyl)-5-(tetrahydro-2H-pyran-4-yl)-1H-indol-1-yl)-2-methylcyclopropyl)-1,2,4-oxadiazol-5 (4H)-one

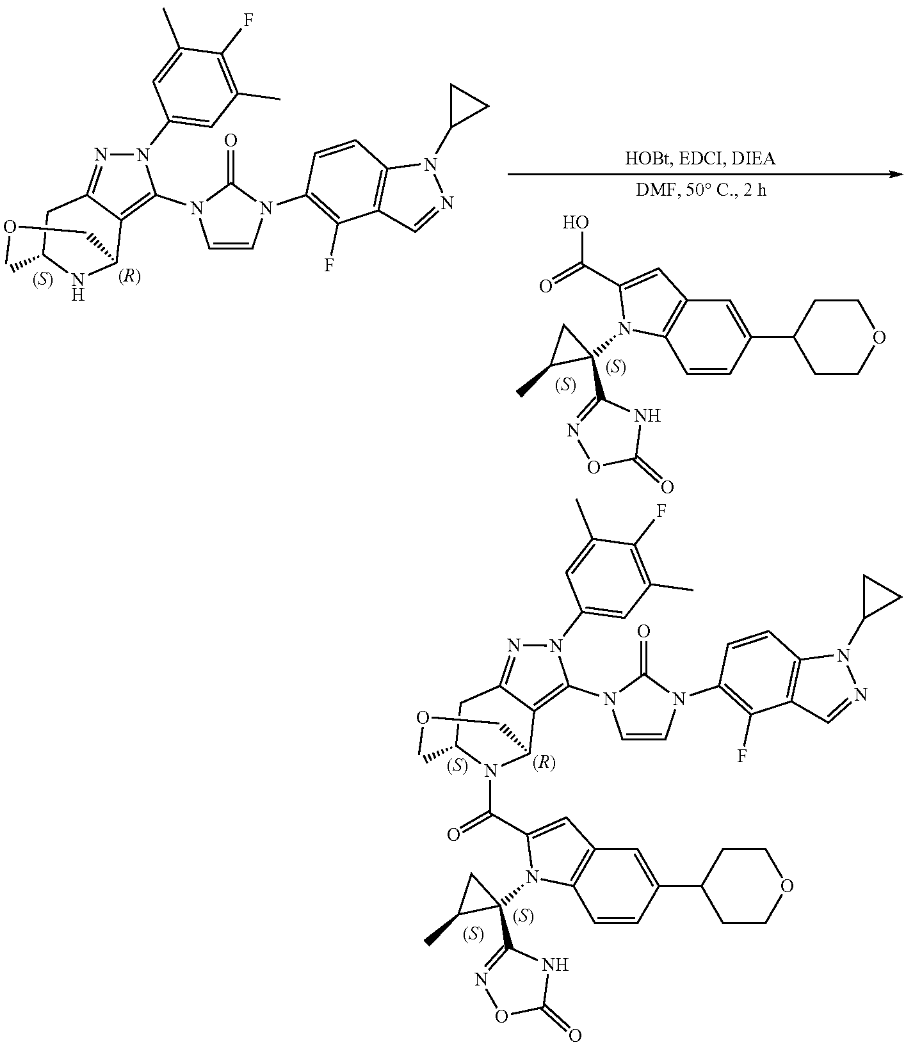

To a mixture of 1-(1-cyclopropyl-4-fluoro-1H-indazol-5-yl)-3-((4R,8S)-2-(4-fluoro-3,5-dimethylphenyl)-2,4,5,7,8,9-hexahydro-4,8-epiminooxocino [5,4-c]pyrazol-3-yl)-1,3-dihydro-2H-imidazol-2-one (30 mg, 55.19 μmol, 1 eq) and 1-((1S,2S)-2-methyl-1-(5-oxo-4,5-dihydro-1,2,4-oxadiazol-3-yl)cyclopropyl)-5-(tetrahydro-2H-pyran-4-yl)-1H-indole-2-carboxylic acid (21.16 mg, 55.19 μmol, 1 eq) in DMF (0.6 mL) was added DIEA (35.67 mg, 275.96 μmol, 5 eq), HOBt (11.19 mg, 82.79 μmol, 1.5 eq) and EDCI (13.75 mg, 71.75 μmol, 1.3 eq) in one portion at 50° C. under $N_2$. The mixture was stirred at 50° C. for 2 hours. LCMS showed the reaction was completed. The residue was poured into water (20 mL). The aqueous phase was extracted with chloroform:isopropanol=3:1 (10 mL*3). The combined organic phase was washed with saturated brine (30 mL), dried with anhydrous $Na_2SO_4$, filtered and concentrated in vacuo. The residue was purified by prep-HPLC (column: Phenomenex Luna C18 100*30 mm*5 um; mobile phase: [$H_2O$ (0.1% TFA)-ACN]; gradient: 40%-70% B over 8.0 min) to give 3-((1S,2S)-1-(2-((4R,8S)-3-(3-(1-cyclopropyl-4-fluoro-1H-indazol-5-yl)-2-oxo-2,3-dihydro-1H-imidazol-1-yl)-2-(4-fluoro-3,5-dimethylphenyl)-2,4,5,7,8,9-hexahydro-4,8-epiminooxocino [5,4-c]pyrazole-10-carbonyl)-5-(tetrahydro-2H-pyran-4-yl)-1H-indol-1-yl)-2-methylcyclopropyl)-1,2,4-oxadiazol-5 (4H)-one (14.95 mg, 16.04 μmol, 29.06% yield). $^1$H NMR (400 MHz, DMSO-$d_6$) δ=12.25-11.59 (m, 1H), 8.35-8.08 (m, 1H), 7.76-7.40 (m, 2H), 7.40-7.26 (m, 2H), 7.26-7.09 (m, 3H), 7.08-6.64 (m, 3H), 5.73-4.77 (m, 2H), 4.16-4.07 (m, 1H), 3.97-3.92 (m, 2H), 3.70-3.59 (m, 3H), 3.55-3.23 (m, 3H), 3.20-2.84 (m, 2H), 2.65-2.55 (m, 1H), 2.31-2.15 (m, 6H), 2.07-1.83 (m, 1H), 1.81-1.59 (m, 4H), 1.57-1.43 (m, 2H), 1.41-1.29 (m, 2H), 1.26-1.22 (m, 1H), 1.18-1.12 (m, 3H), 1.09-0.83 (m, 1H). $^1$H NMR (400 MHz, DMSO-$d_6$+$D_2O$) δ=8.32-8.02 (m, 1H), 7.72-7.38 (m, 2H), 7.38-7.24 (m, 2H), 7.23-7.02 (m, 3H), 7.02-6.59 (m, 3H), 5.71-4.71 (m, 2H), 4.18-4.01 (m, 1H), 3.98-3.87 (m, 2H), 3.83-3.69 (m, 3H), 3.59-3.21 (m, 3H), 3.18-2.80 (m, 2H), 2.60-2.53 (m, 1H), 2.30-2.15 (m, 6H), 2.03-1.82 (m, 1H), 1.80-1.56 (m, 4H), 1.54-1.40 (m, 2H), 1.33 (br d, J=6.3 Hz, 2H), 1.10

(br s, 4H), 1.01-0.81 (m, 1H). LC-MS (ES+, m/z): 909.3 $[(M+H)^+]$; Rt=3.173 min. HRMS (EI): m/z $[M+H]^+$ found: 909.3658.

Additional compounds listed in Table 1, including compounds ID 409-416, are or can be prepared following the synthetic methods and/or synthetic schemes as described herein and using appropriate starting materials and reagents.

Example A1

The present example identifies salts of compound 214, with promising physical stability, solubility, and/or hygroscopicity.

Compound 214 has a molecular weight of 892.97. As predicted by Marvin Sketch 24.1, the compound contains 1 acidic pKa of 6.5 and 3 weakly basic pKa(s) of 0.9, 0.6, and 0.3. Compound 214 anhydrate was used as starting material in this salt screening.

Based on the pKa(s) of compound 214, seven Class I bases, one Class II base, two Class I acids, and one Class II acid were selected as salt forming agents. Acetone, DCM, THE, EA, EtOH, and ACN/water were used as screening solvents. 1 equivalent or 0.5 equivalents of selected counter ions were applied in the screening. Slurry equilibration, cooling, slow evaporation and anti-solvent addition were used as crystallization methods. In total, 120 screening experiments were conducted.

According to the salt screening results, six amorphous salt hits were identified, including L-arginine salt amorphous form, hemi-calcium salt amorphous form, mono-potassium salt amorphous form, mono-sodium salt amorphous form, L-lysine salt amorphous form, and betaine salt amorphous form. In addition to XRPD analysis, all these salts were further characterized by mDSC, $^1$H-NMR, and IC-HPLC.

Mono-potassium salt amorphous form, was reproduced. mDSC shows a glass transition Tg of 103° C. with ΔCp of 0.1 J/g. TGA shows about 2.6% weight loss at 100° C., which should be due to the loss of water and some residual DCM, and about 2.2% weight loss from 100° C. to 200° C. HPLC shows 95.6% chemical purity. IC-HPLC shows compound 214: $K^+$ is 1:1.0. $^1$H-NMR shows 0.2 equiv. of DCM by molar ratio (1.9% by weight). Polarized light microscopy (PLM) shows the sample consists of plate-like particles with size up to 150 μm.

Mono-sodium salt amorphous form was reproduced. mDSC shows a glass transition Tg of 125° C. with ΔCp of 0.1 J/g. TGA shows about 3.7% weight loss at 100° C., which should be due to the loss of water and some residual EtOH, and about 1.8% weight loss from 100° C. to 200° C. HPLC shows 95.7% chemical purity. IC-HPLC shows compound 214: $Na^+$ is 1:1.0. $^1$H-NMR shows 0.3 equiv. of EtOH by molar ratio (1.4% by weight). PLM shows the sample consists of block-like particles with size up to 80 μm.

Hemi-calcium salt amorphous form, was reproduced. mDSC shows a glass transition Tg of 78° C. with ΔCp of 0.3 J/g. TGA shows about 2.3% weight loss at 100° C., about 4.8% weight loss from 100° C. to 200° C., and about 1.4% weight loss from 200° C. to 275° C. HPLC shows 95.4% chemical purity. IC-HPLC shows compound 214: $Ca^{2+}$ is 1:0.5. $^1$H-NMR shows 0.7 equiv. of THE by molar ratio (5.1% by weight) and 0.07 equiv. of BHT by molar ratio (1.6% by weight). PLM shows the sample consists of irregular particles with size up to 200 μm.

Solid-state stability of the free form and the three salts was investigated at 25° C./93% RH in an open container, at 40° C./75% RH in an open container, and at 60° C. in a tight container for 1 week. All these physical forms were physically and chemically stable under these conditions.

Solubility of the free form and the three salts was measured in seven aqueous pH buffers and bio-relevant fluids including pH 1.2 HCl buffer, pH 4.5 acetate buffer (50 mM), pH 6.8 phosphate buffer (50 mM), water, pH 1.6 fasted state simulated gastric fluid (FaSSGF), pH 6.5 fasted state simulated intestinal fluid v2 (FaSSIF-v2), and pH 5.8 fasted state simulated intestinal fluid v2 (FeSSIF-v2), at 37° C. for 2 hours and 24 hours. Residual solids after the solubility test were analyzed by XRPD. The solubility was also measured in FaSSIF-v2 at pH values of 7.0, 8.0, 9.0 and 10.0 for 30 min.

Figure 14:
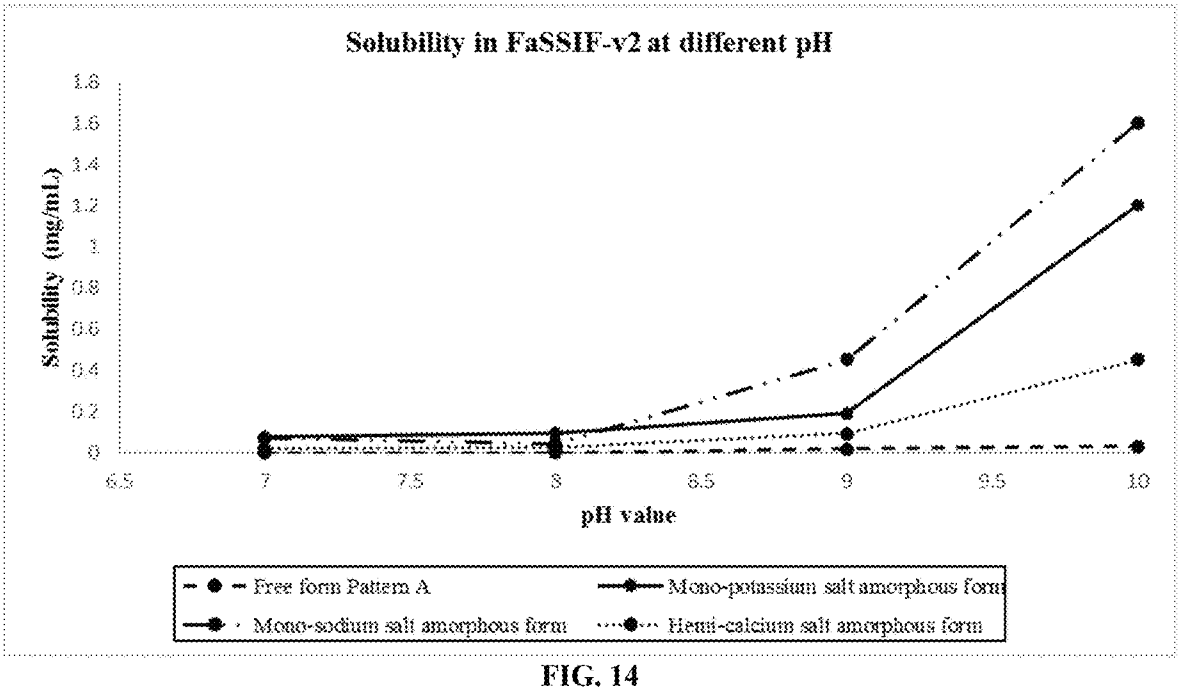
FIG. 14 depicts pH dependent solubility of Compound 214 salts.

Generally, the salt candidates and free form showed pH-dependent aqueous solubility (see, e.g., FIG. 14, FaSSIF-v2). As shown in FIG. 14, the solubility was: mono-sodium salt amorphous form >mono-potassium salt amorphous form >hemi-calcium salt amorphous form >free form. Surprisingly and unexpectedly, the sodium salt provided superior solubility, particularly in comparison to the free acid form of the compound.

Example B1a

GLP-1R CAMP Assay

Assay was carried out with HEK293 expressing human GLP-1R using HTRF assay, developed by Wuxi Apptec. The method is a competitive assay between native cAMP produced by the cells and exogenous cAMP labeled with a proprietary dye d2. The tracer binding is visualized by a mAb anti-cAMP labeled with Cryptate. The signal (i.e. energy transfer) is inversely proportional to the concentration of CAMP in either standard or experimental sample. Compounds were tested in the absence of BETP. Ten microliter of cell suspension in assay buffer (5 mM HEPES, 500 μM IBMX, 0.1% BSA) were added to each well (1,000 cells per well) in a low volume 384-well plate for the assay. Serially diluted compounds were added in 100 nL volume to duplicate wells, by Labcyte Echo. GLP-1 (7-37) was used as positive control. Assay plate was incubated for 30 minutes at room temperature. Stock of cAMP Detection Solution was prepared by mixing 38 parts of cAMP lysis buffer, 1 part of cAMP-D2, 1 part of anti-cAMP cryptate reagent (Cisbio #62AM4PEJ). Ten microliter of the cAMP Detection Solution was added to each well, and the assay plate was incubated for 1 hour at room temperature in the dark. Plates were read on Envision plate reader. The data were analyzed by ScreenUltra in Dotmatics, with % activation expressed using following formula: (Well data−negative control)/(positive control−negative control)*100. Dose response curves were plotted and $EC_{50}$ values calculated by non-linear regression using 4-parameter fit. The potency ($EC_{50}$) values for cAMP accumulation in HEK293 cells are reported in the Table 1 below (for compounds ID 1-609).

Example B1b

GLP-1R CAMP Assay

Assay was carried out with HEK293 expressing human GLP-1R using HTRF assay, developed by Wuxi Apptec. The method is a competitive assay between native cAMP produced by the cells and exogenous cAMP labeled with a proprietary dye d2. The tracer binding is visualized by a mAb anti-cAMP labeled with Cryptate. The signal (i.e. energy transfer) is inversely proportional to the concentration of CAMP in either standard or experimental sample. Compounds were tested in the absence of BETP. Ten microliter of cell suspension in assay buffer (5 mM HEPES, 500 μM IBMX, 0.1% BSA) were added to each well (1,000 cells per well) in a low volume 384-well plate for the assay. Serially diluted compounds were added in 100 nL volume to duplicate wells, by Labcyte Echo. GLP-1 (7-37) was used as positive control. Assay plate was incubated for 30 minutes at 37°. Stock of cAMP Detection Solution was prepared by mixing 38 parts of cAMP lysis buffer, 1 part of cAMP-D2, 1 part of anti-cAMP cryptate reagent (Cisbio #62AM4PEJ). Ten microliter of the cAMP Detection Solution was added to each well, and the assay plate was incubated for 1 hour at room temperature in the dark. Plates were read on Envision plate reader. The data were analyzed by ScreenUltra in Dotmatics, with % activation expressed using following formula: (Signal ratio 665 nM/620 nM*10000−negative control)/(postive control−negative control)*100. Dose response curves were plotted and $EC_{50}$ values calculated by non-linear regression using 4-parameter fit. The potency ($EC_{50}$) values for cAMP accumulation in HEK293 cells are reported in the Table 1 below (for compounds ID 610-708).

TABLE 1

Representative compounds and their $EC_{50}$ values

| Cpd ID | Structure | MW | EC50 (uM) |
| --- | --- | --- | --- |
| 1 | 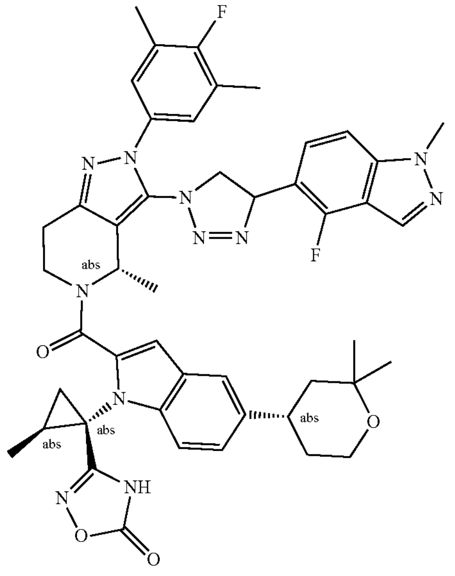 C47H47F2N11O4 | 867.96 | >10 |
| 5 | 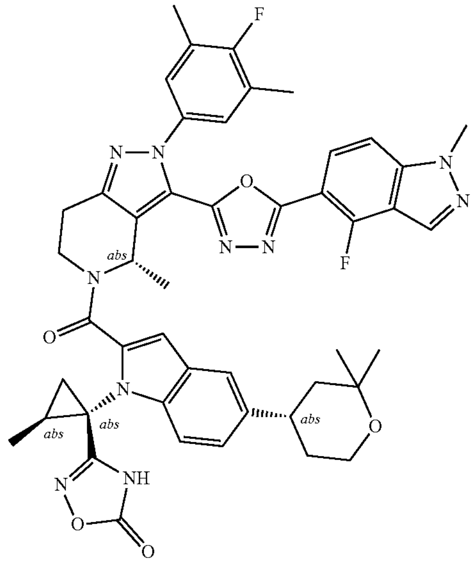 C47H46F2N10O5 | 868.95 | >10 |

TABLE 1-continued
| Representative compounds and their $EC_{50}$ values | | | |
|---|---|---|---|
| Cpd ID | Structure | MW | EC50 (uM) |
| 8 | 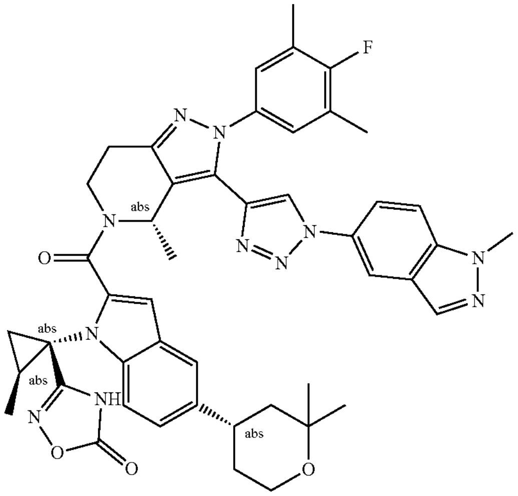 [SMILES: Cc1cc(-n2nc3c(c2-c2cn(-c4ccc5c(cnn5C)c4)nn2)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] C47H48FN11O4 | 849.97 | |
| 9 | 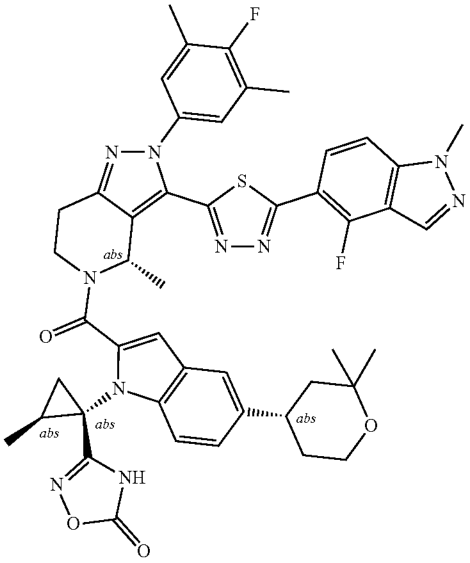 C47H46F2N10O4S | 885.01 | |

TABLE 1-continued
| Representative compounds and their $EC_{50}$ values | | | |
|---|---|---|---|
| Cpd ID | Structure | MW | EC50 (uM) |
| 11 | 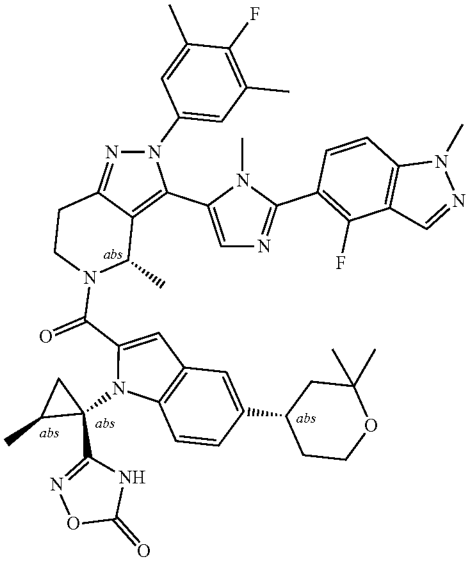 C49H50F2N10O4 | 881 | |
| 12 | 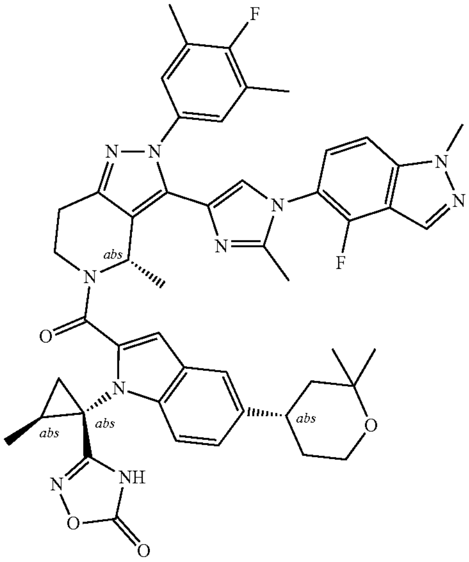 C49H50F2N10O4 | 881 | |

TABLE 1-continued
| Representative compounds and their $EC_{50}$ values | | | |
|---|---|---|---|
| Cpd ID | Structure | MW | EC50 (uM) |
| 13 | 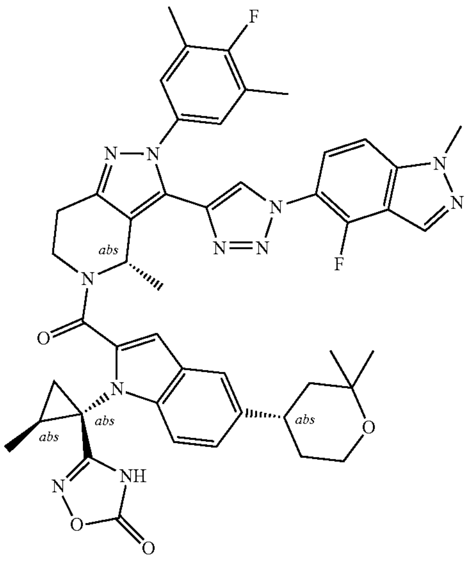 C47H47F2N11O4 | 867.96 | |
| 14 | 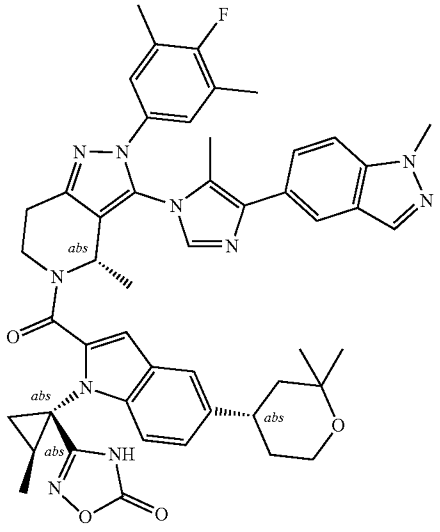 [SMILES: Cc1cc(-n2nc3c(c2-n2cnc(-c4ccc5c(cnn5C)c4)c2C)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F] C49H51FN10O4 | 863.01 | |

TABLE 1-continued
| Representative compounds and their $EC_{50}$ values | | | |
|---|---|---|---|
| Cpd ID | Structure | MW | EC50 (uM) |
| 15 | 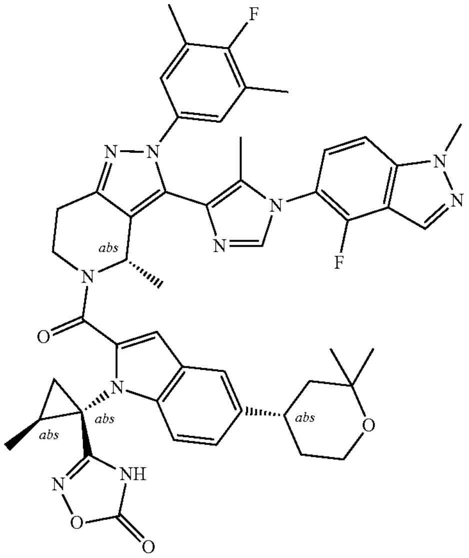 C49H50F2N10O4 | 881 | 0.584 |
| 16 | 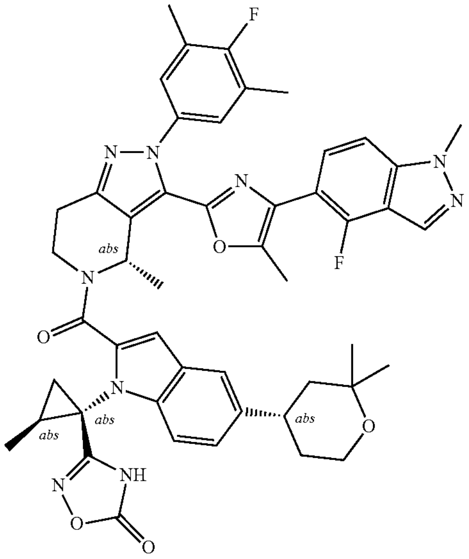 C49H49F2N9O5 | 881.99 | |

TABLE 1-continued
| Representative compounds and their $EC_{50}$ values | | | |
|---|---|---|---|
| Cpd ID | Structure | MW | EC50 (uM) |
| 17 | 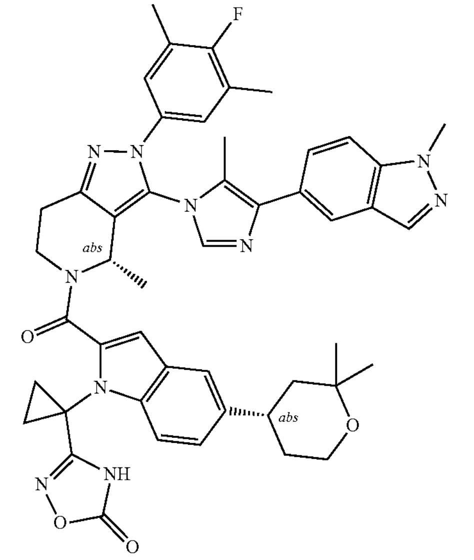 [SMILES: Cc1cc(-n2nc3c(c2-n2cnc(-c4ccc5c(cnn5C)c4)c2C)[C@H](C)N(C(=O)c2cc4cc([C@H]5CCOC(C)(C)C5)ccc4n2C2(c4noc(=O)[nH]4)CC2)CC3)cc(C)c1F] C48H49FN10O4 | 848.98 | |
| 18 | 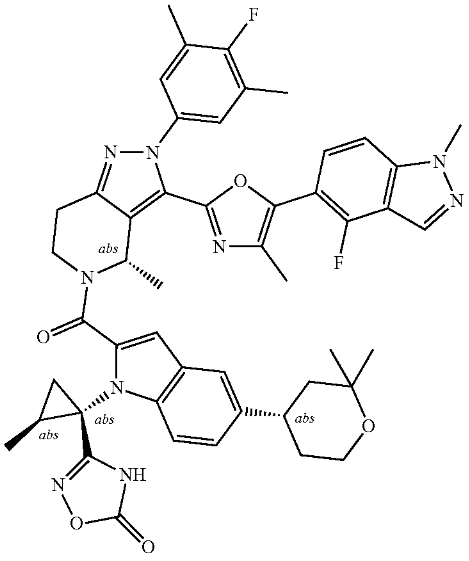 C49H49F2N9O5 | 881.99 | |

TABLE 1-continued
| Representative compounds and their $EC_{50}$ values | | | |
|---|---|---|---|
| Cpd ID | Structure | MW | EC50 (uM) |
| 20 | 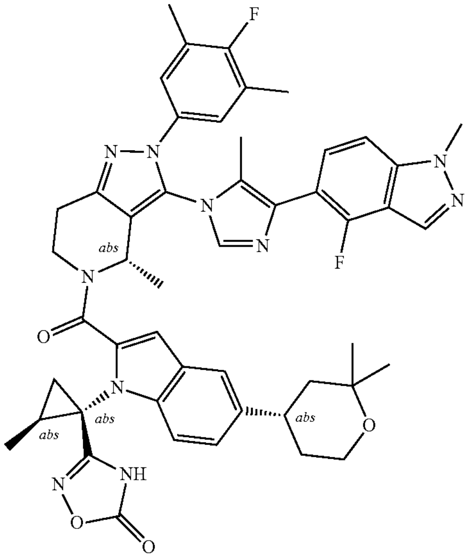 C49H50F2N10O4 | 881 | |
| 21 | 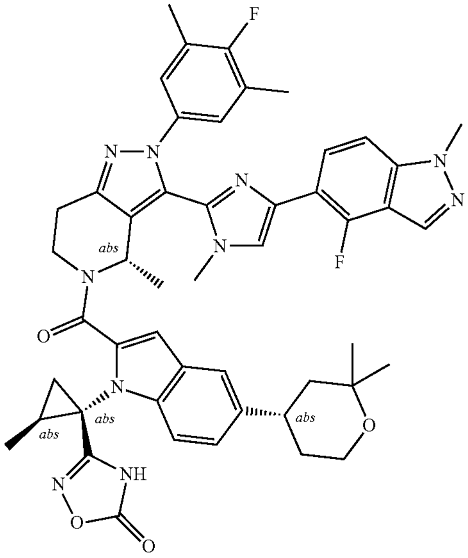 C49H50F2N10O4 | 881 | 0.591 |

TABLE 1-continued
| Representative compounds and their $EC_{50}$ values | | | |
|---|---|---|---|
| Cpd ID | Structure | MW | EC50 (uM) |
| 22 | 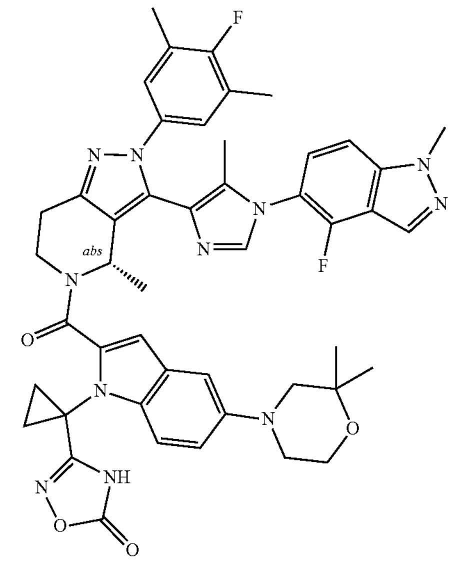 [SMILES: Cc1cc(-n2nc3c(c2-c2ncn(-c4ccc5c(cnn5C)c4F)c2C)[C@H](C)N(C(=O)c2cc4cc(N5CCOC(C)(C)C5)ccc4n2C2(c4noc(=O)[nH]4)CC2)CC3)cc(C)c1F] C47H47F2N11O4 | 867.96 | |
| 23 | 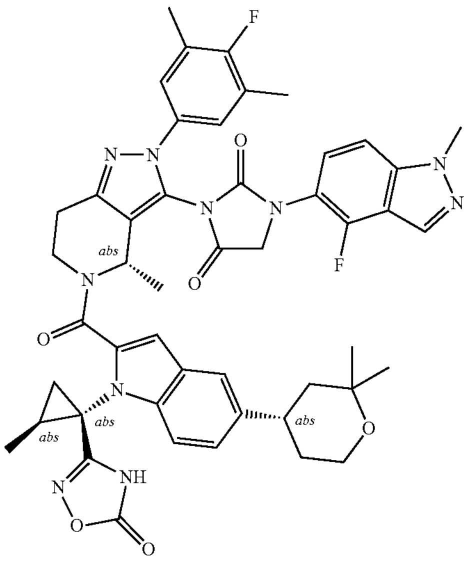 C48H48F2N10O6 | 898.97 | 0.361 |

TABLE 1-continued
| Representative compounds and their $EC_{50}$ values | | | |
|---|---|---|---|
| Cpd ID | Structure | MW | EC50 (uM) |
| 24 | 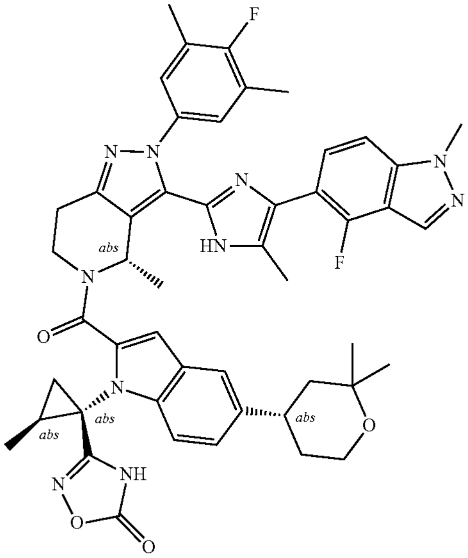 C49H50F2N10O4 | 881 | >10 |
| 26 | 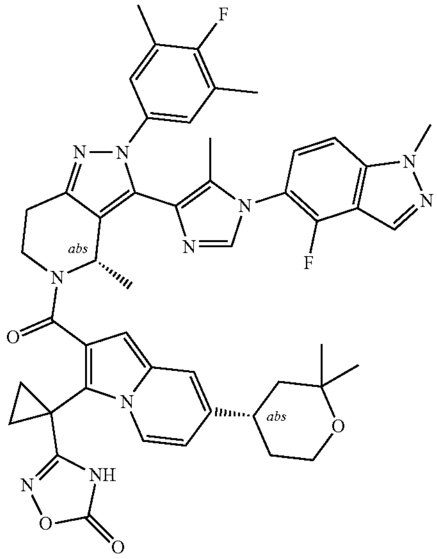 [SMILES: Cc1cc(-n2nc3c(c2-c2ncn(-c4ccc5c(cnn5C)c4F)c2C)[C@H](C)N(C(=O)c2cc4cc([C@H]5CCOC(C)(C)C5)ccn4c2C2(c4noc(=O)[nH]4)CC2)CC3)cc(C)c1F] C48H48F2N10O4 | 866.97 | |

TABLE 1-continued
| Representative compounds and their $EC_{50}$ values | | | |
|---|---|---|---|
| Cpd ID | Structure | MW | EC50 (uM) |
| 27 | 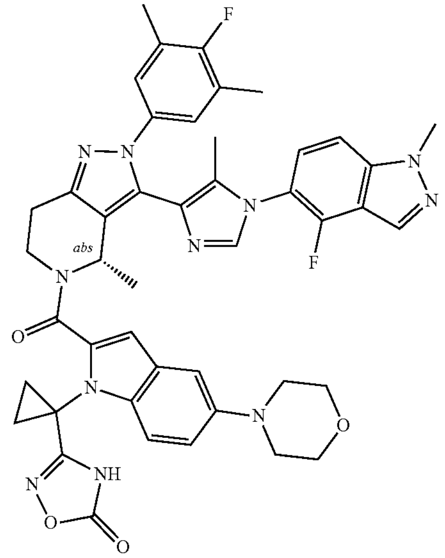 [SMILES: Cc1cc(-n2nc3c(c2-c2ncn(-c4ccc5c(cnn5C)c4F)c2C)[C@H](C)N(C(=O)c2cc4cc(N5CCOCC5)ccc4n2C2(c4noc(=O)[nH]4)CC2)CC3)cc(C)c1F] C45H43F2N11O4 | 839.91 | |
| 28 | 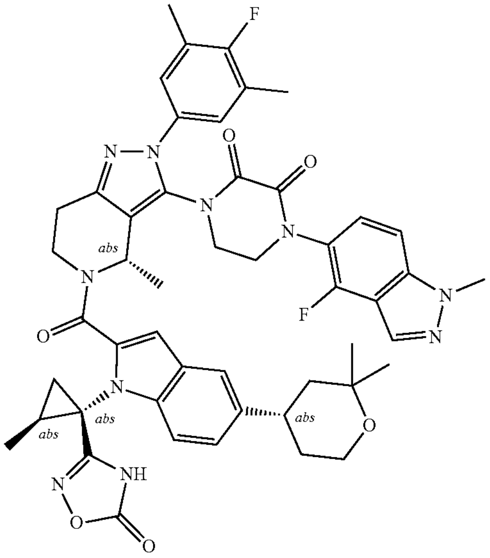 C49H50F2N10O6 | 913 | >10 |

TABLE 1-continued
| Representative compounds and their $EC_{50}$ values | | | |
|---|---|---|---|
| Cpd ID | Structure | MW | EC50 (uM) |
| 30 | 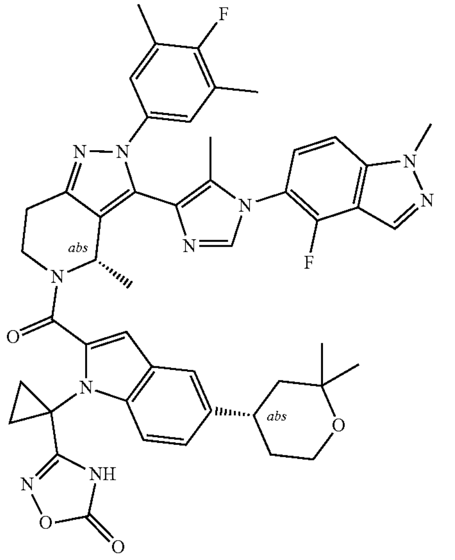 [SMILES: Cc1cc(-n2nc3c(c2-c2ncn(-c4ccc5c(cnn5C)c4F)c2C)[C@H](C)N(C(=O)c2cc4cc([C@H]5CCOC(C)(C)C5)ccc4n2C2(c4noc(=O)[nH]4)CC2)CC3)cc(C)c1F] C48H48F2N10O4 | 866.97 | >10 |
| 31 | 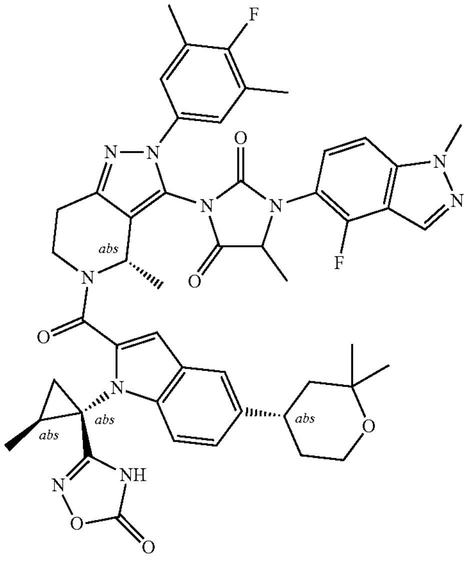 C49H50F2N10O6 | 913 | |

TABLE 1-continued
| Representative compounds and their $EC_{50}$ values | | | |
|---|---|---|---|
| Cpd ID | Structure | MW | EC50 (uM) |
| 32 | 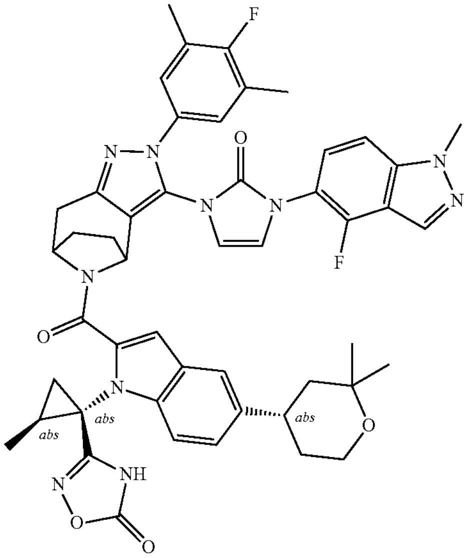 C49H48F2N10O5 | 894.98 | 0.0926 |
| 35 | 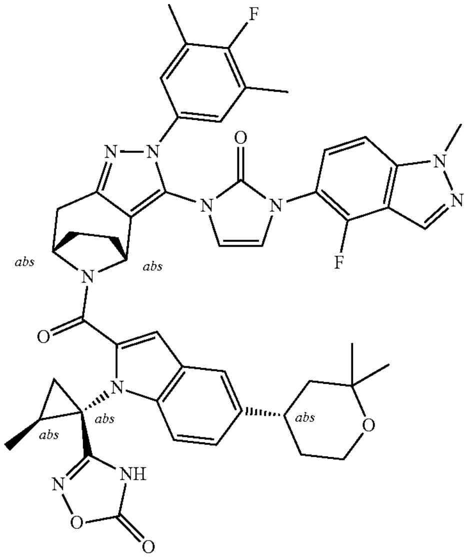 C49H48F2N10O5 | 894.98 | 100 |

TABLE 1-continued
| Representative compounds and their $EC_{50}$ values | | | |
|---|---|---|---|
| Cpd ID | Structure | MW | EC50 (uM) |
| 36 | 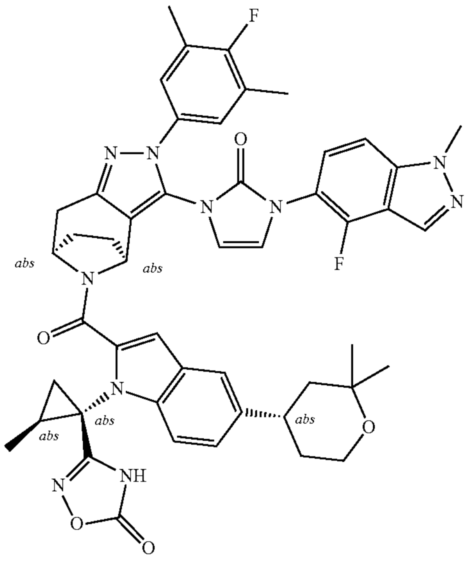 C49H48F2N10O5 | 894.98 | 0.109 |
| 37 | 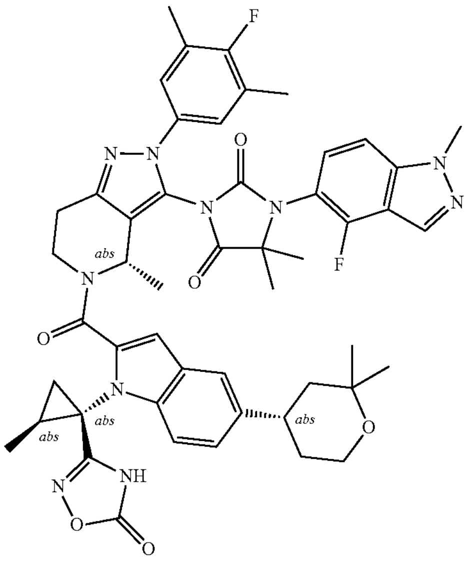 C50H52F2N10O6 | 927.03 | |

TABLE 1-continued
| Representative compounds and their $EC_{50}$ values | | | |
|---|---|---|---|
| Cpd ID | Structure | MW | EC50 (uM) |
| 105 | 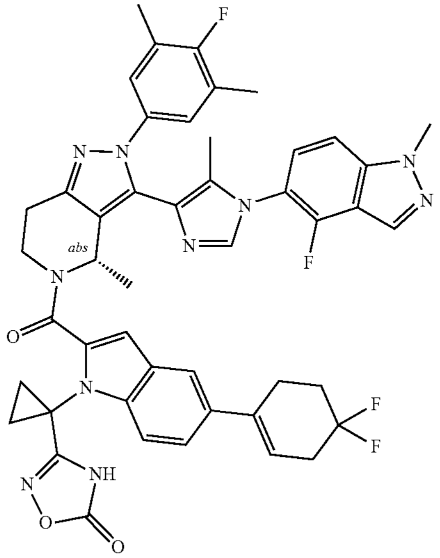 [SMILES: Cc1cc(-n2nc3c(c2-c2ncn(-c4ccc5c(cnn5C)c4F)c2C)[C@H](C)N(C(=O)c2cc4cc(C5=CCC(F)(F)CC5)ccc4n2C2(c4noc(=O)[nH]4)CC2)CC3)cc(C)c1F] C47H42F4N10O3 | 870.91 | >10 |
| 106 | 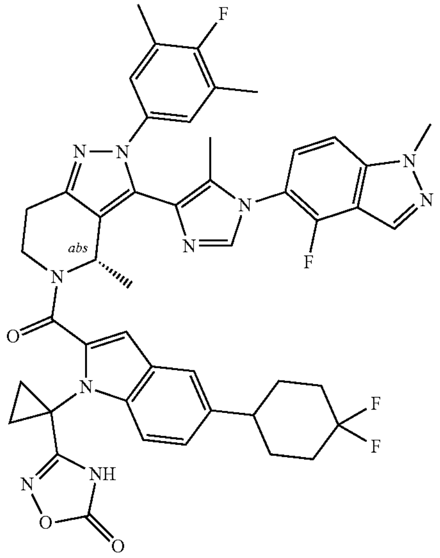 [SMILES: Cc1cc(-n2nc3c(c2-c2ncn(-c4ccc5c(cnn5C)c4F)c2C)[C@H](C)N(C(=O)c2cc4cc(C5CCC(F)(F)CC5)ccc4n2C2(c4noc(=O)[nH]4)CC2)CC3)cc(C)c1F] C47H44F4N10O3 | 872.93 | >10 |

TABLE 1-continued
| Representative compounds and their $EC_{50}$ values | | | |
|---|---|---|---|
| Cpd ID | Structure | MW | EC50 (uM) |
| 107 | 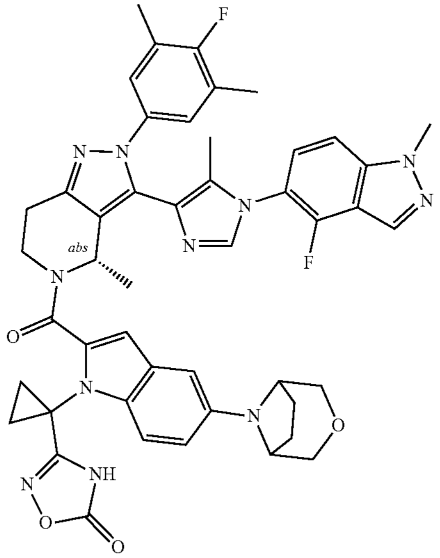 [SMILES: Cc1cc(-n2nc3c(c2-c2ncn(-c4ccc5c(cnn5C)c4F)c2C)[C@H](C)N(C(=O)c2cc4cc(N5C6CCC5COC6)ccc4n2C2(c4noc(=O)[nH]4)CC2)CC3)cc(C)c1F] C47H45F2N11O4 | 865.95 | >10 |
| 108 | 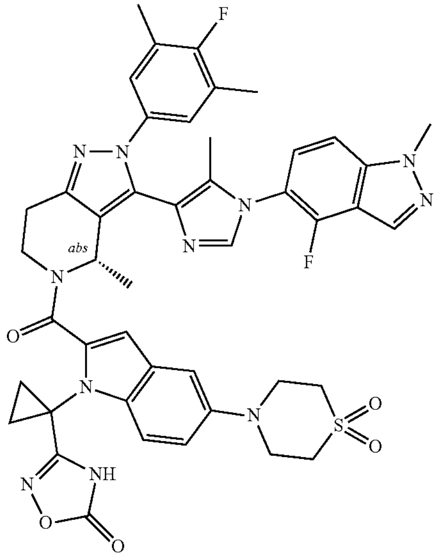 [SMILES: Cc1cc(-n2nc3c(c2-c2ncn(-c4ccc5c(cnn5C)c4F)c2C)[C@H](C)N(C(=O)c2cc4cc(N5CCS(=O)(=O)CC5)ccc4n2C2(c4noc(=O)[nH]4)CC2)CC3)cc(C)c1F] C45H43F2N11O5S | 887.97 | >10 |

TABLE 1-continued
| Representative compounds and their $EC_{50}$ values | | | |
|---|---|---|---|
| Cpd ID | Structure | MW | EC50 (uM) |
| 114 | 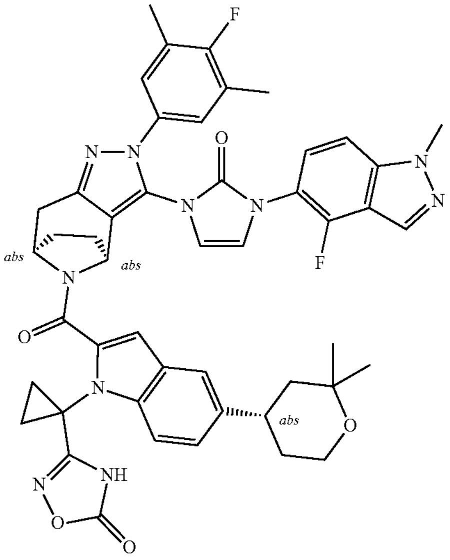 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H46F2N10O5 | 880.96 | 0.593 |
| 115 | 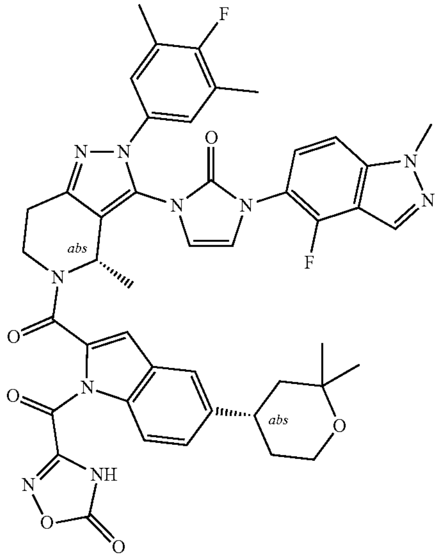 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2C(=O)c2noc(=O)[nH]2)CC3)cc(C)c1F] C45H42F2N10O6 | 856.89 | >10 |

TABLE 1-continued
| Representative compounds and their $EC_{50}$ values | | | |
|---|---|---|---|
| Cpd ID | Structure | MW | EC50 (uM) |
| 116 | 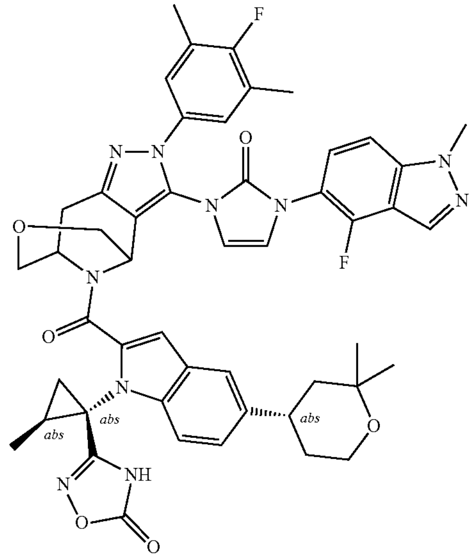 C49H48F2N10O6 | 910.98 | 0.174 |
| 117 | 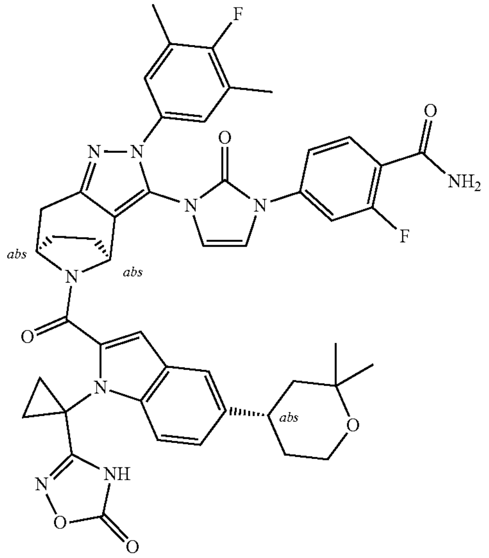 [SMILES: Cc1cc(-n2nc3c(c2-n2ccn(-c4ccc(C(N)=O)c(F)c4)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C47H45F2N9O6 | 869.93 | >10 |

TABLE 1-continued
| Representative compounds and their $EC_{50}$ values | | | |
|---|---|---|---|
| Cpd ID | Structure | MW | EC50 (uM) |
| 118 | 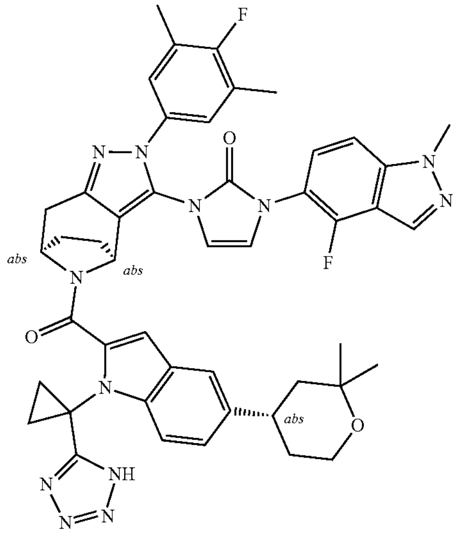 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3nnn[nH]3)CC2)cc(C)c1F] C47H46F2N12O3 | 864.96 | 0.452 |
| 119 | 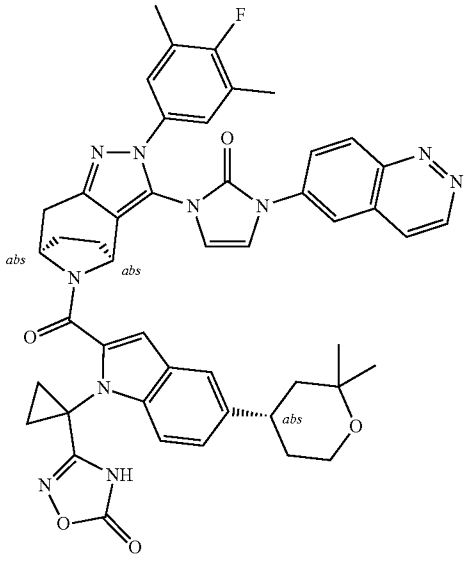 [SMILES: Cc1cc(-n2nc3c(c2-n2ccn(-c4ccc5nnccc5c4)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H45FN10O5 | 860.95 | 2.28 |

TABLE 1-continued
| Representative compounds and their $EC_{50}$ values | | | |
|---|---|---|---|
| Cpd ID | Structure | MW | EC50 (uM) |
| 120 | 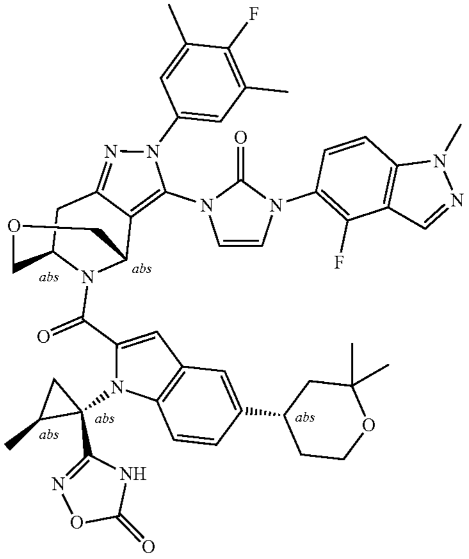 C49H48F2N10O6 | 910.98 | >10 |
| 121 | 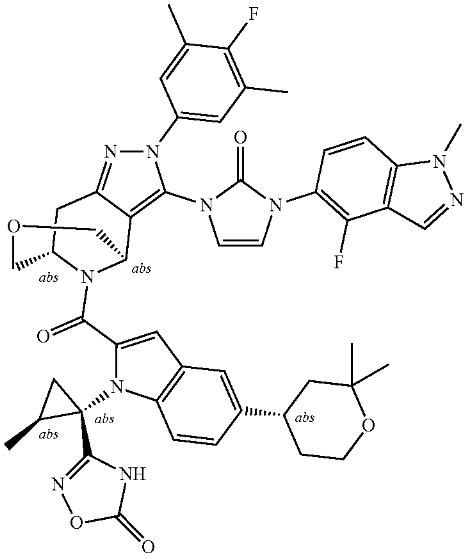 C49H48F2N10O6 | 910.98 | 0.082 |

TABLE 1-continued
| Representative compounds and their $EC_{50}$ values | | | |
|---|---|---|---|
| Cpd ID | Structure | MW | EC50 (uM) |
| 122 | 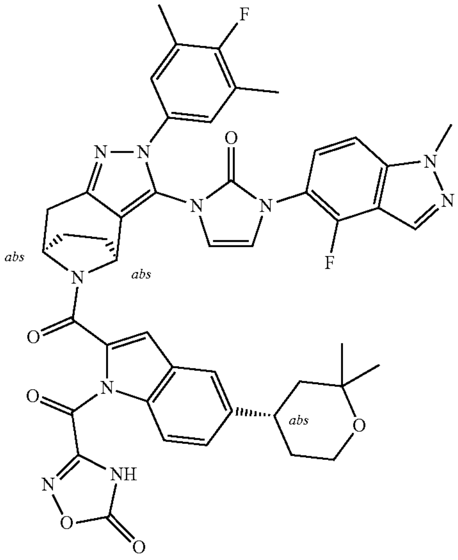 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C(=O)c2noc(=O)[nH]2)cc(C)c1F] C46H42F2N10O6 | 868.9 | >10 |
| 123 | 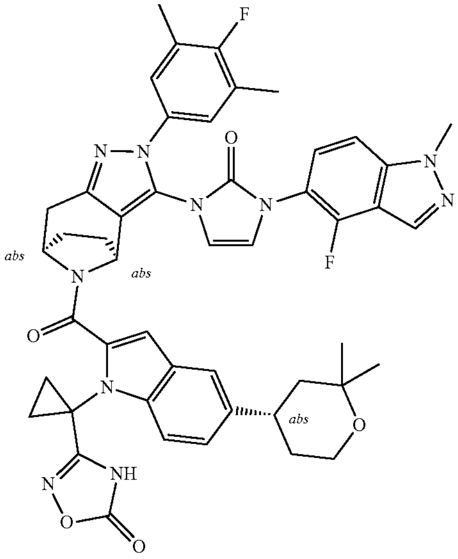 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H46F2N10O5 | 880.96 | >10 |

TABLE 1-continued
| Representative compounds and their $EC_{50}$ values | | | |
|---|---|---|---|
| Cpd ID | Structure | MW | EC50 (uM) |
| 124 | 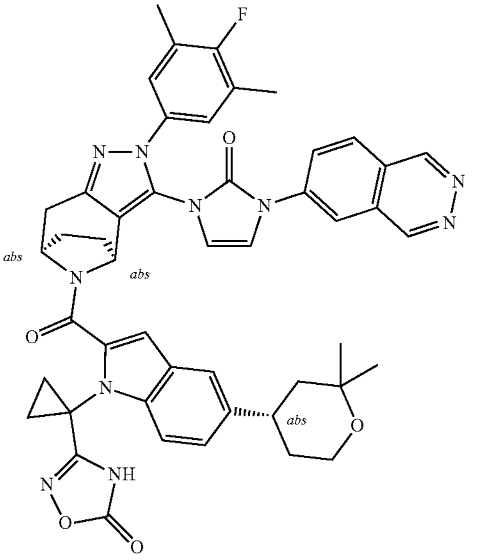 [SMILES: Cc1cc(-n2nc3c(c2-n2ccn(-c4ccc5cnncc5c4)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H45FN10O5 | 860.95 | 1.38 |
| 125 | 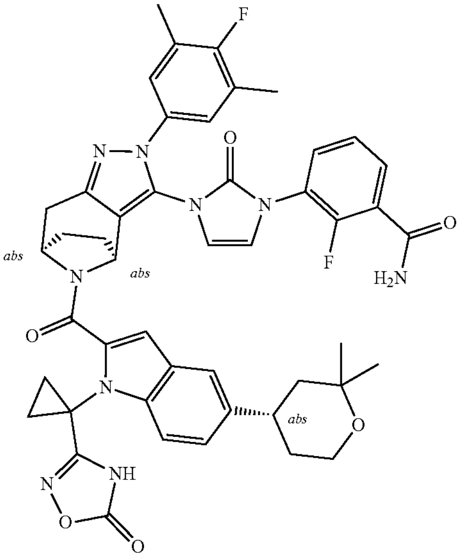 [SMILES: Cc1cc(-n2nc3c(c2-n2ccn(-c4cccc(C(N)=O)c4F)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C47H45F2N9O6 | 869.93 | >10 |

TABLE 1-continued
Representative compounds and their $EC_{50}$ values
| Cpd ID | Structure | MW | EC50 (uM) |
|---|---|---|---|
| 126 | 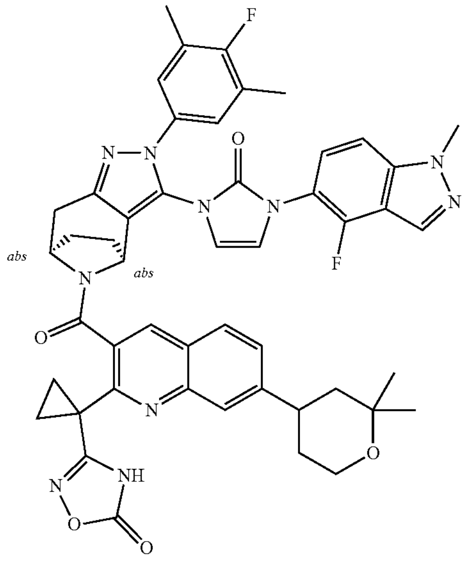 [SMILES: Cc1cc(-n2nc3c(c2-n2ccn(-c4ccc5c(cnn5C)c4F)c2=O)[C@@H]2CC[C@H](C3)N2C(=O)c2cc3ccc(C4CCOC(C)(C)C4)cc3nc2C2(c3noc(=O)[nH]3)CC2)cc(C)c1F] C49H46F2N10O5 | 892.97 | >10 |
| 127 | 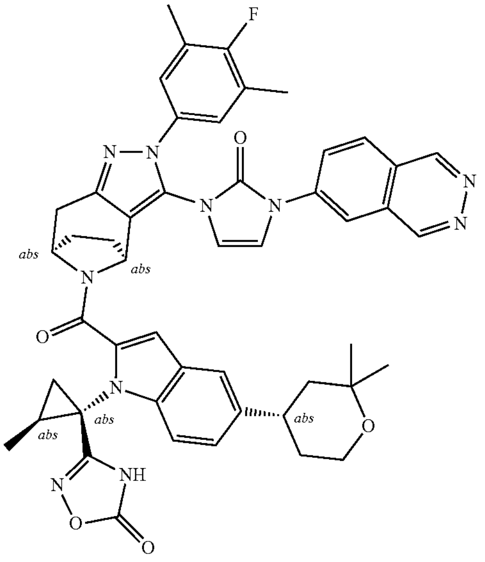 [SMILES: Cc1cc(-n2nc3c(c2-n2ccn(-c4ccc5cnncc5c4)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H47FN10O5 | 874.98 | 0.381 |

TABLE 1-continued
| Representative compounds and their $EC_{50}$ values | | | |
|---|---|---|---|
| Cpd ID | Structure | MW | EC50 (uM) |
| 128 | 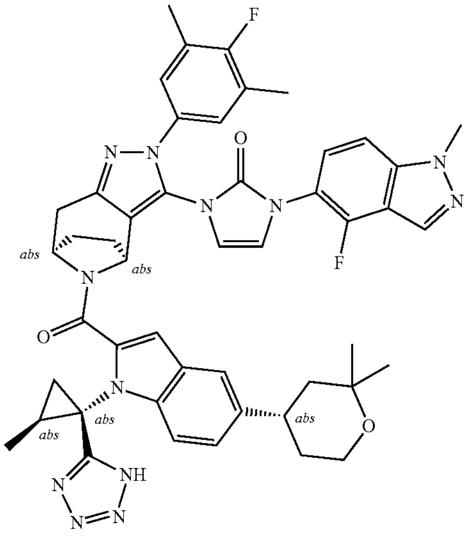 C48H48F2N12O3 | 878.99 | 0.137 |
| 129 | 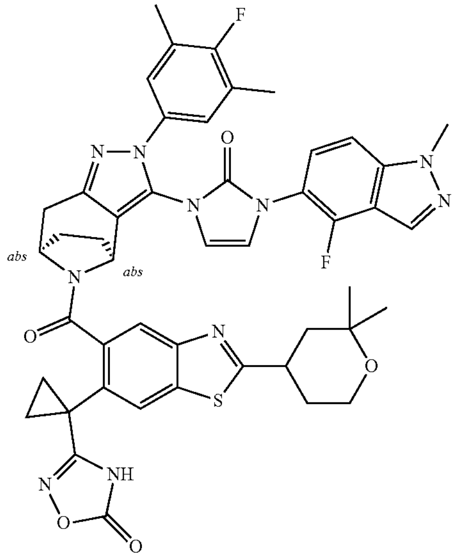 [SMILES: Cc1cc(-n2nc3c(c2-n2ccn(-c4ccc5c(cnn5C)c4F)c2=O)[C@@H]2CC[C@H](C3)N2C(=O)c2cc3nc(C4CCOC(C)(C)C4)sc3cc2C2(c3noc(=O)[nH]3)CC2)cc(C)c1F] C47H44F2N10O5S | 898.99 | >10 |

TABLE 1-continued
| Representative compounds and their $EC_{50}$ values | | | |
|---|---|---|---|
| Cpd ID | Structure | MW | EC50 (uM) |
| 130 | 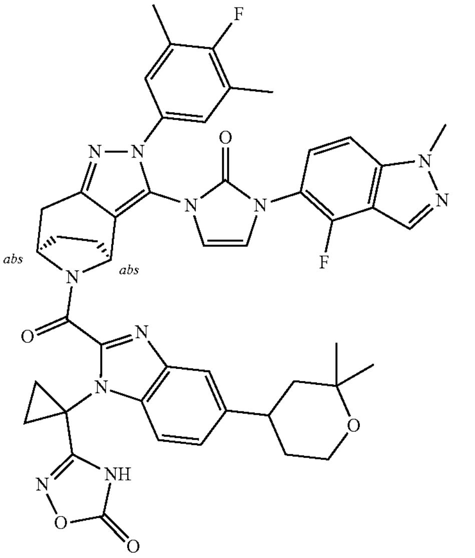 [SMILES: Cc1cc(-n2nc3c(c2-n2ccn(-c4ccc5c(cnn5C)c4F)c2=O)[C@@H]2CC[C@H](C3)N2C(=O)c2nc3cc(C4CCOC(C)(C)C4)ccc3n2C2(c3noc(=O)[nH]3)CC2)cc(C)c1F] C47H45F2N11O5 | 881.95 | >10 |
| 131 | 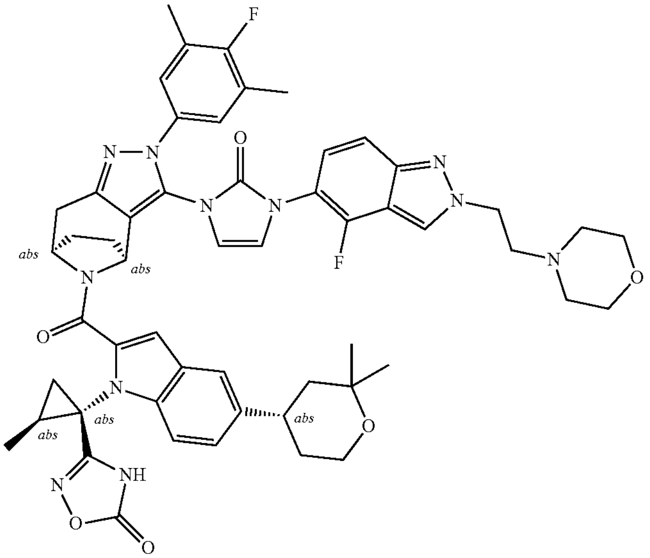 [SMILES: Cc1cc(-n2nc3c(c2-n2ccn(-c4ccc5nn(CCN6CCOCC6)cc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C54H57F2N11O6 | 994.12 | >10 |

TABLE 1-continued
| Representative compounds and their $EC_{50}$ values | | | |
|---|---|---|---|
| Cpd ID | Structure | MW | EC50 (uM) |
| 132 | 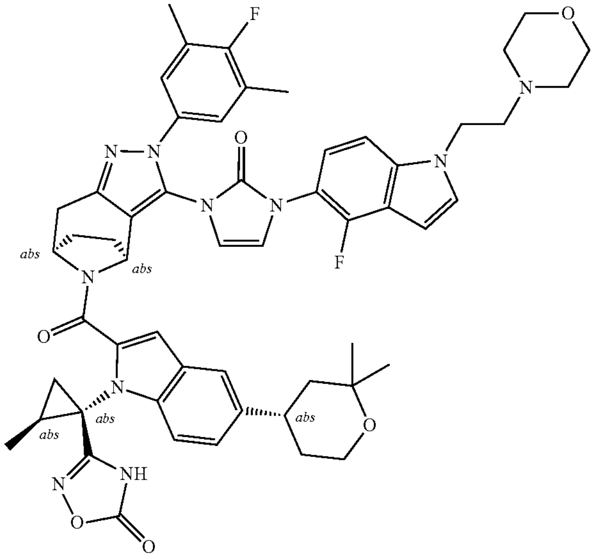 [SMILES: Cc1cc(-n2nc3c(c2-n2ccn(-c4ccc5c(ccn5CCN5CCOCC5)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C54H57F2N11O6 | 994.12 | 2.04 |
| 133 | 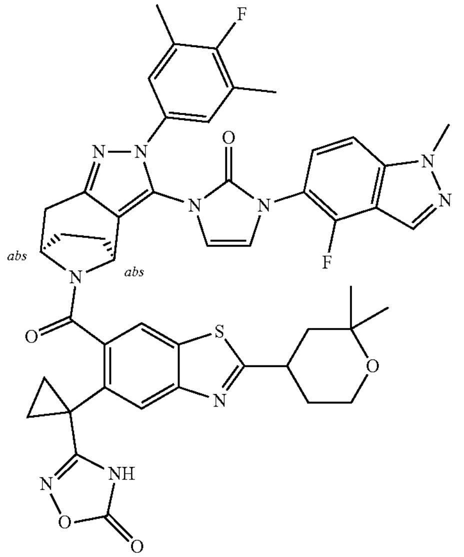 [SMILES: Cc1cc(-n2nc3c(c2-n2ccn(-c4ccc5c(cnn5C)c4F)c2=O)[C@@H]2CC[C@H](C3)N2C(=O)c2cc3sc(C4CCOC(C)(C)C4)nc3cc2C2(c3noc(=O)[nH]3)CC2)cc(C)c1F] C47H44F2N10O5S | 898.99 | >10 |

TABLE 1-continued
| Representative compounds and their $EC_{50}$ values | | | |
|---|---|---|---|
| Cpd ID | Structure | MW | EC50 (uM) |
| 134 | 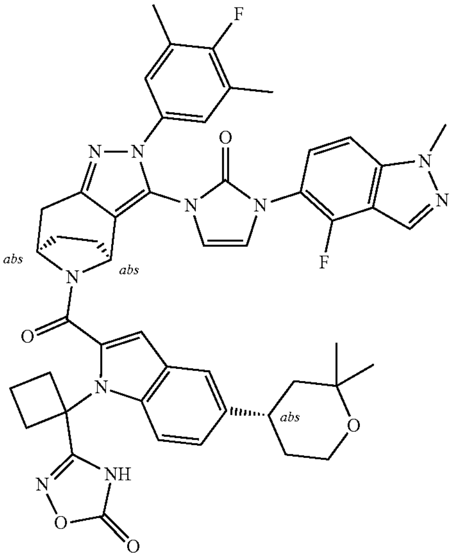 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3noc(=O)[nH]3)CCC2)cc(C)c1F] C49H48F2N10O5 | 894.98 | >10 |
| 135 | 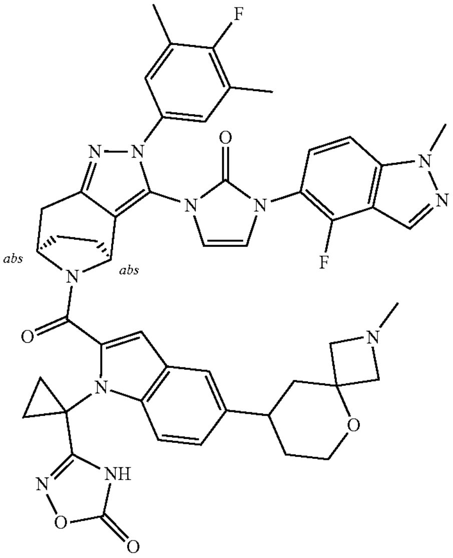 [SMILES: Cc1cc(-n2nc3c(c2-n2ccn(-c4ccc5c(cnn5C)c4F)c2=O)[C@@H]2CC[C@H](C3)N2C(=O)c2cc3cc(C4CCOC5(C4)CN(C)C5)ccc3n2C2(c3noc(=O)[nH]3)CC2)cc(C)c1F] C49H47F2N11O5 | 907.98 | >10 |

TABLE 1-continued
| Representative compounds and their $EC_{50}$ values | | | |
|---|---|---|---|
| Cpd ID | Structure | MW | EC50 (uM) |
| 136 | 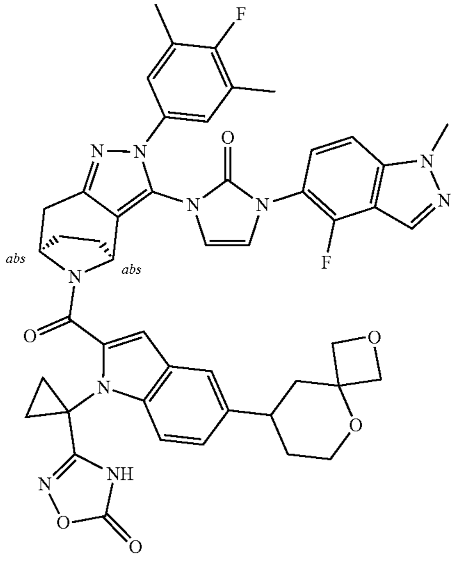 [SMILES: Cc1cc(-n2nc3c(c2-n2ccn(-c4ccc5c(cnn5C)c4F)c2=O)[C@@H]2CC[C@H](C3)N2C(=O)c2cc3cc(C4CCOC5(COC5)C4)ccc3n2C2(c3noc(=O)[nH]3)CC2)cc(C)c1F] C48H44F2N10O6 | 894.94 | >10 |
| 137 | 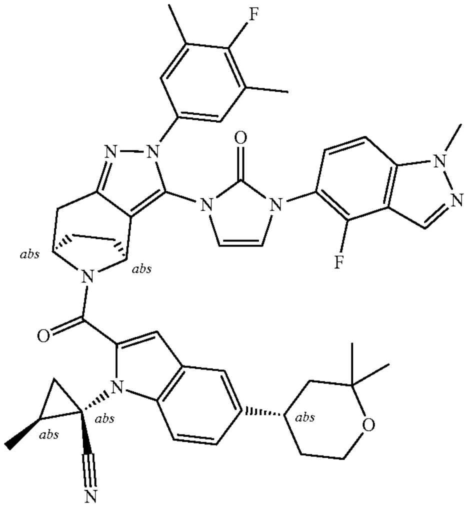 C48H47F2N9O3 | 835.96 | >10 |

TABLE 1-continued
| Representative compounds and their $EC_{50}$ values | | | |
|---|---|---|---|
| Cpd ID | Structure | MW | EC50 (uM) |
| 138 | 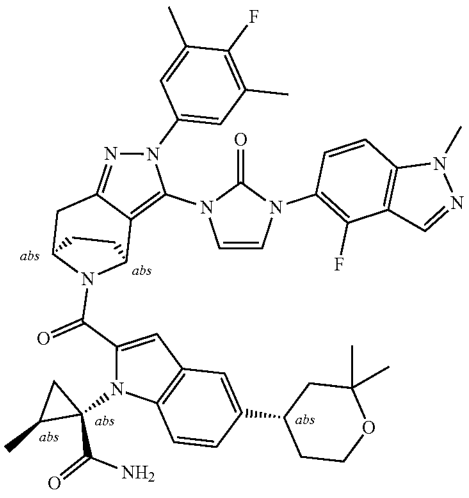 C48H49F2N9O4 | 853.98 | 1.05 |
| 139 | 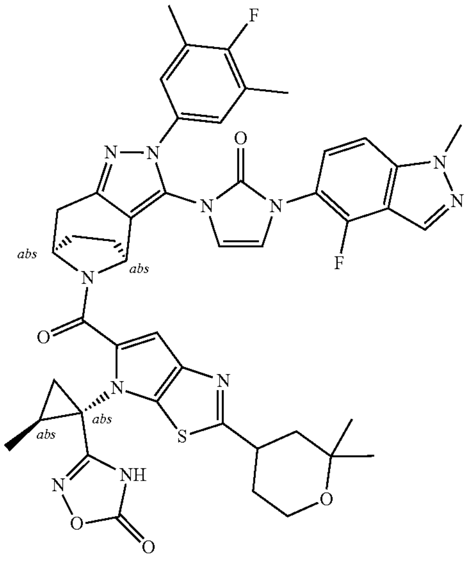 C46H45F2N11O5S | 901.99 | 3.11 |

TABLE 1-continued
| Representative compounds and their $EC_{50}$ values | | | |
|---|---|---|---|
| Cpd ID | Structure | MW | EC50 (uM) |
| 140 | 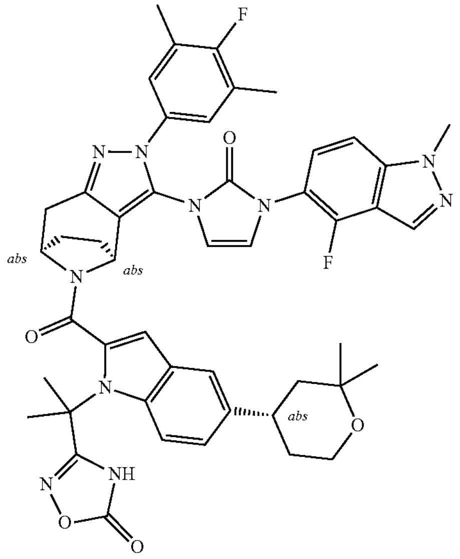 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C(C)(C)c2noc(=O)[nH]2)cc(C)c1F] C48H48F2N10O5 | 882.97 | >10 |
| 201 | 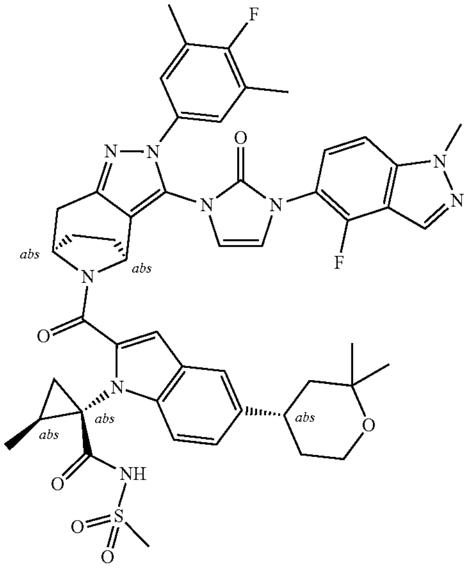 C49H51F2N9O6S | 932.06 | >10 |

TABLE 1-continued
| Representative compounds and their $EC_{50}$ values | | | |
|---|---|---|---|
| Cpd ID | Structure | MW | EC50 (uM) |
| 202 | 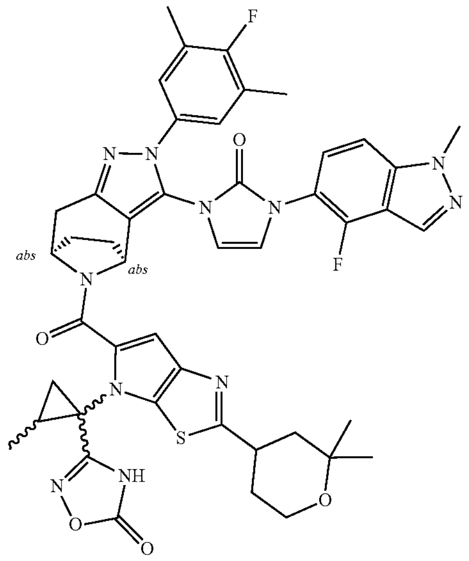 C46H45F2N11O5S | 901.99 | >10 |
| 203 | 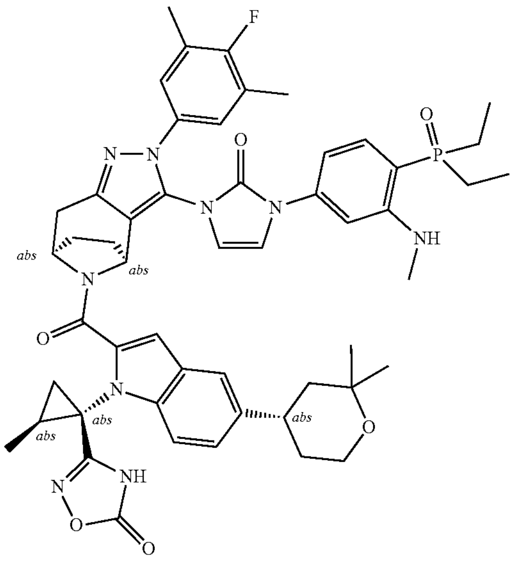 [SMILES: CCP(=O)(CC)c1ccc(-n2ccn(-c3c4c(nn3-c3cc(C)c(F)c(C)c3)C[C@H]3CC[C@@H]4N3C(=O)c3cc4cc([C@H]5CCOC(C)(C)C5)ccc4n3[C@@]3(c4noc(=O)[nH]4)C[C@@H]3C)c2=O)cc1NC] C52H59FN9O6P | 956.07 | 0.919 |

TABLE 1-continued
| Representative compounds and their $EC_{50}$ values | | | |
|---|---|---|---|
| Cpd ID | Structure | MW | EC50 (uM) |
| 204 | 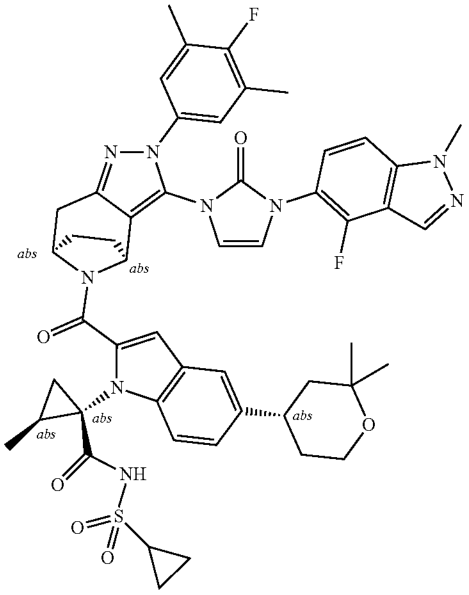 C51H53F2N9O6S | 958.1 | >10 |
| 205 | 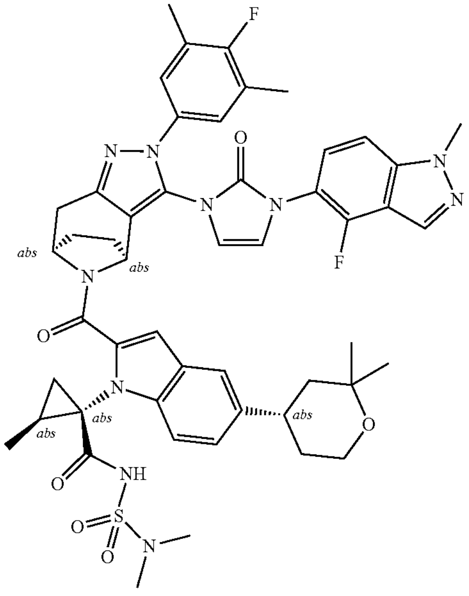 C50H54F2N10O6S | 961.1 | >10 |

TABLE 1-continued
| Representative compounds and their $EC_{50}$ values | | | |
|---|---|---|---|
| Cpd ID | Structure | MW | EC50 (uM) |
| 206 | 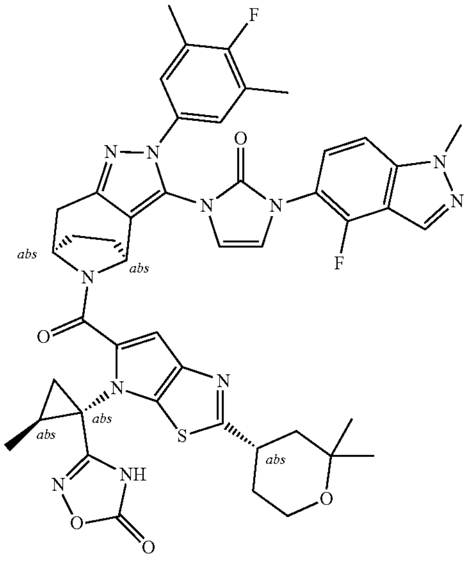 C46H45F2N11O5S | 901.99 | 1.44 |
| 207 | 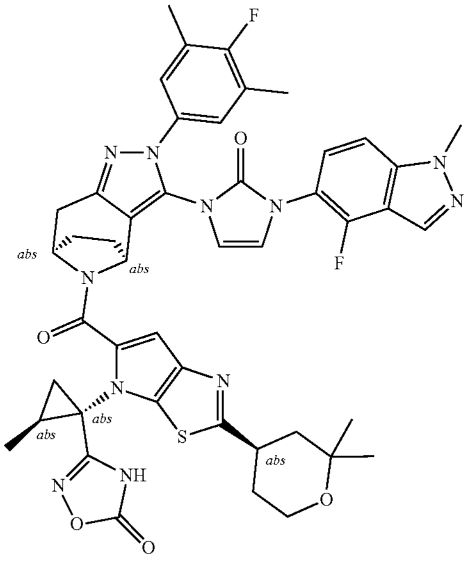 C46H45F2N11O5S | 901.99 | >10 |

TABLE 1-continued
| Representative compounds and their $EC_{50}$ values | | | |
|---|---|---|---|
| Cpd ID | Structure | MW | EC50 (uM) |
| 208 | 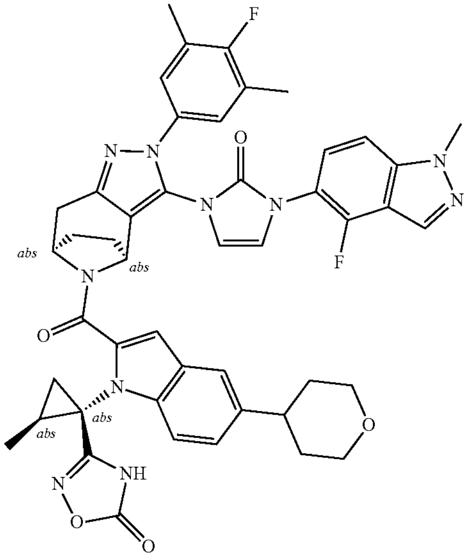 C47H44F2N10O5 | 866.93 | 0.182 |
| 209 | 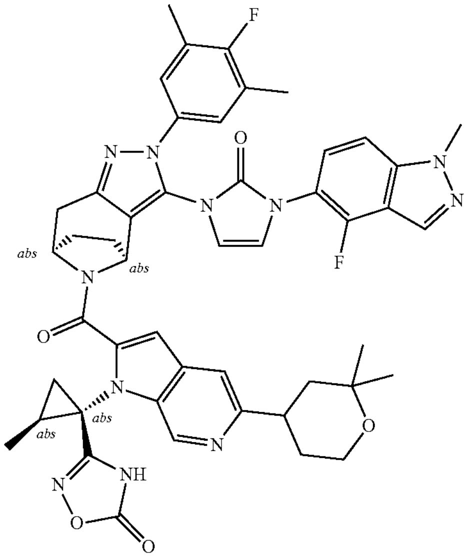 C48H47F2N11O5 | 895.97 | 0.117 |

TABLE 1-continued
| Representative compounds and their $EC_{50}$ values | | | |
|---|---|---|---|
| Cpd ID | Structure | MW | EC50 (uM) |
| 210 | 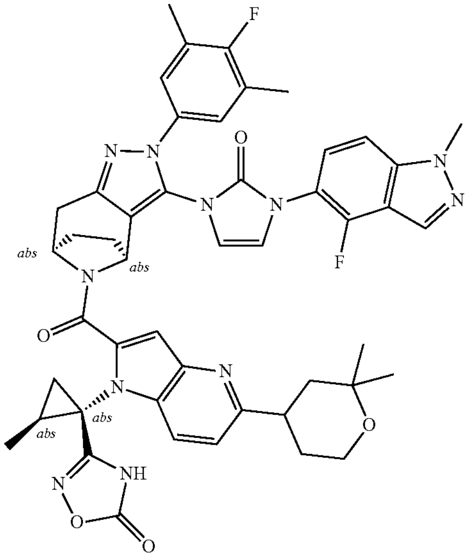 C48H47F2N11O5 | 895.97 | 0.959 |
| 211 | 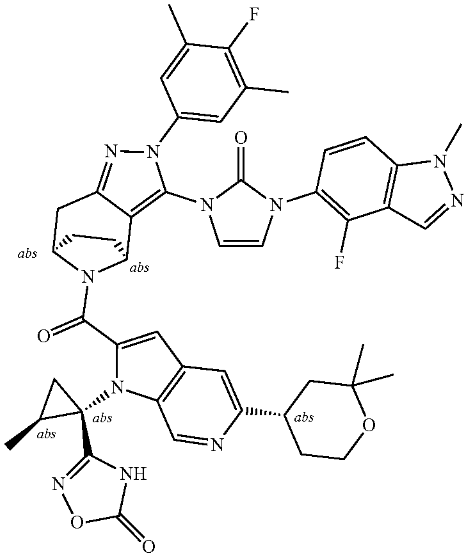 C48H47F2N11O5 | 895.97 | 0.0510 |

TABLE 1-continued
| Representative compounds and their $EC_{50}$ values | | | |
|---|---|---|---|
| Cpd ID | Structure | MW | EC50 (uM) |
| 212 | 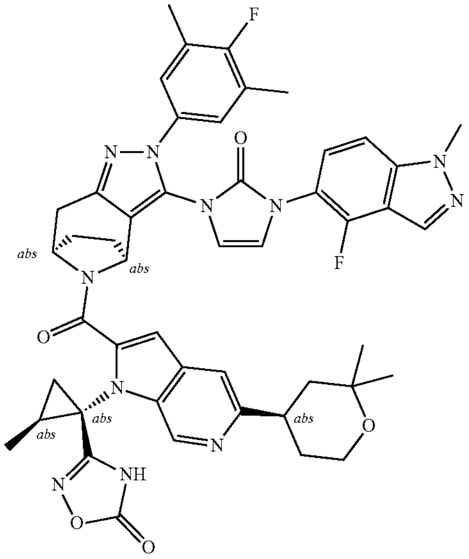 C48H47F2N11O5 | 895.97 | 0.697 |
| 213 | 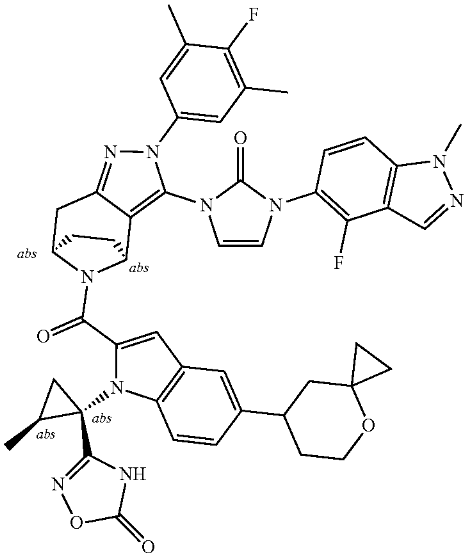 C49H46F2N10O5 | 892.97 | 0.0812 |

TABLE 1-continued
| Representative compounds and their $EC_{50}$ values | | | |
|---|---|---|---|
| Cpd ID | Structure | MW | EC50 (uM) |
| 214 | 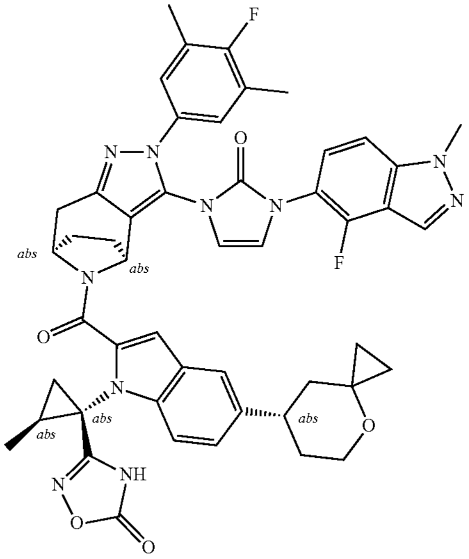 C49H46F2N10O5 | 892.97 | 0.0523 |
| 215 | 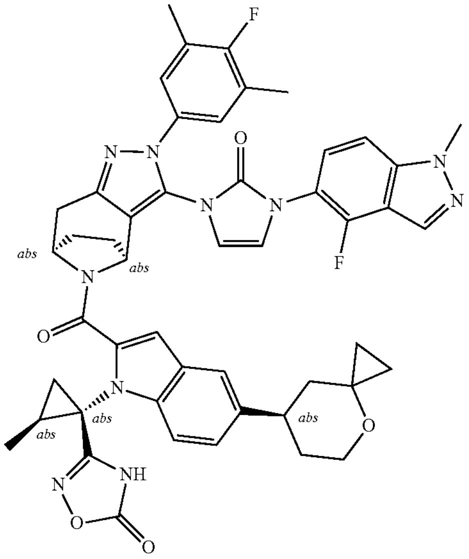 C49H46F2N10O5 | 892.97 | 4.13 |

TABLE 1-continued
| Representative compounds and their $EC_{50}$ values | | | |
|---|---|---|---|
| Cpd ID | Structure | MW | EC50 (uM) |
| 216 | 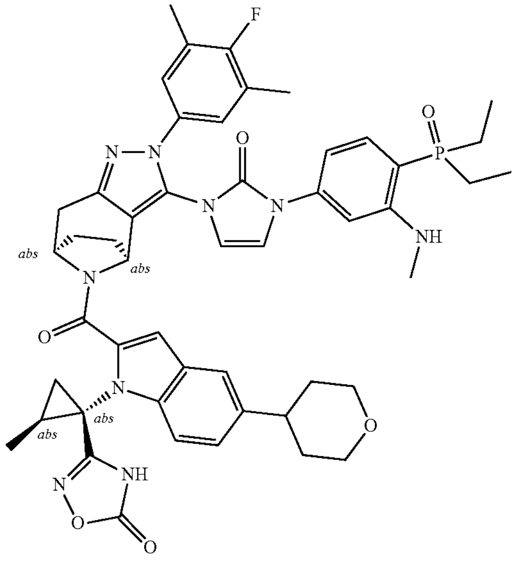 [SMILES: CCP(=O)(CC)c1ccc(-n2ccn(-c3c4c(nn3-c3cc(C)c(F)c(C)c3)C[C@H]3CC[C@@H]4N3C(=O)c3cc4cc(C5CCOCC5)ccc4n3[C@@]3(c4noc(=O)[nH]4)C[C@@H]3C)c2=O)cc1NC] C50H55FN9O6P | 928.02 | 0.233 |
| 217 | 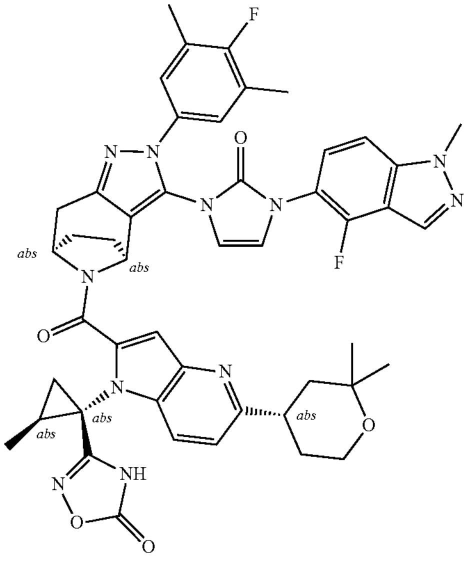 C48H47F2N11O5 | 895.97 | 0.907 |

TABLE 1-continued
| Representative compounds and their $EC_{50}$ values | | | |
|---|---|---|---|
| Cpd ID | Structure | MW | EC50 (uM) |
| 218 | 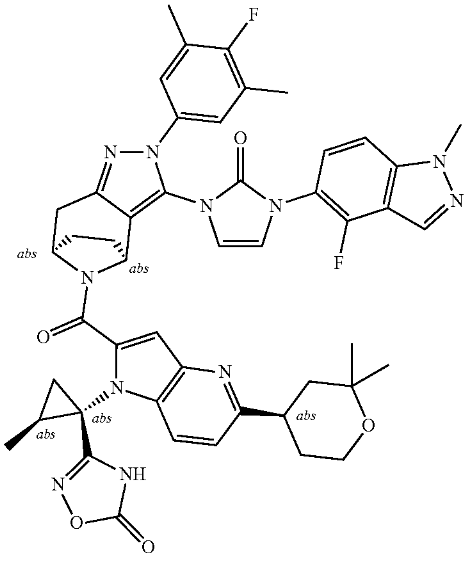 C48H47F2N11O5 | 895.97 | >10 |
| 219 | 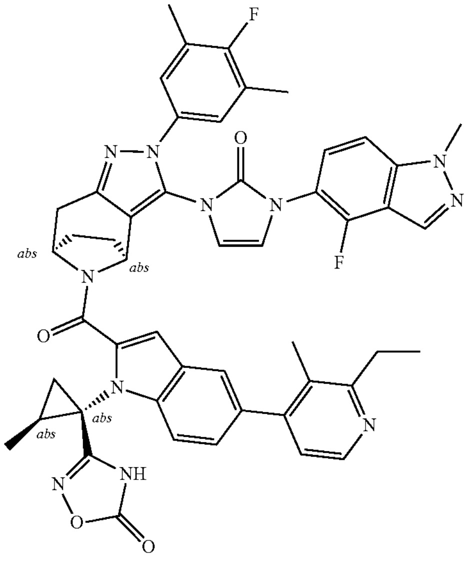 C50H45F2N11O4 | 901.98 | 0.269 |

TABLE 1-continued
| Representative compounds and their $EC_{50}$ values | | | |
|---|---|---|---|
| Cpd ID | Structure | MW | EC50 (uM) |
| 220 | 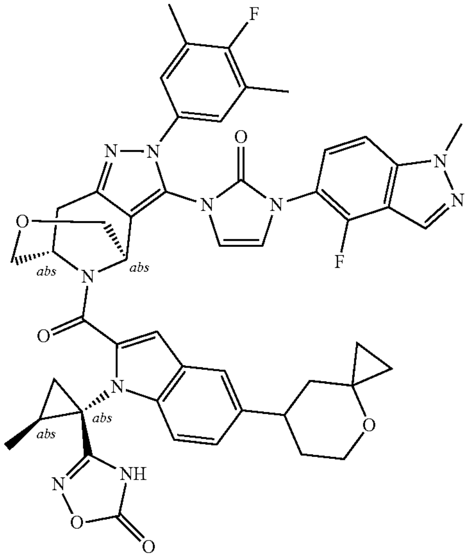 C49H46F2N10O6 | 908.97 | 0.795 |
| 221 | 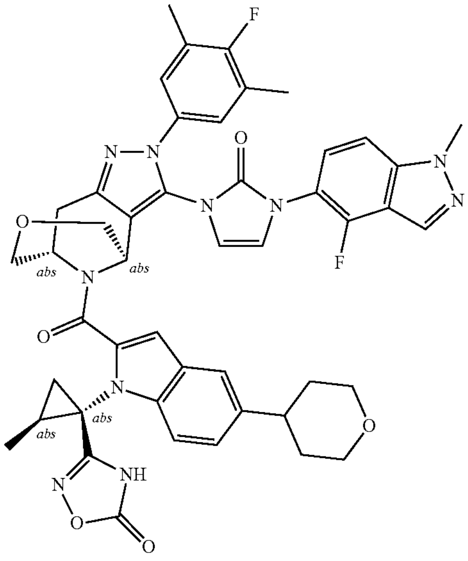 C47H44F2N10O6 | 882.93 | 0.129 |

TABLE 1-continued
| Representative compounds and their $EC_{50}$ values | | | |
|---|---|---|---|
| Cpd ID | Structure | MW | EC50 (uM) |
| 222 | 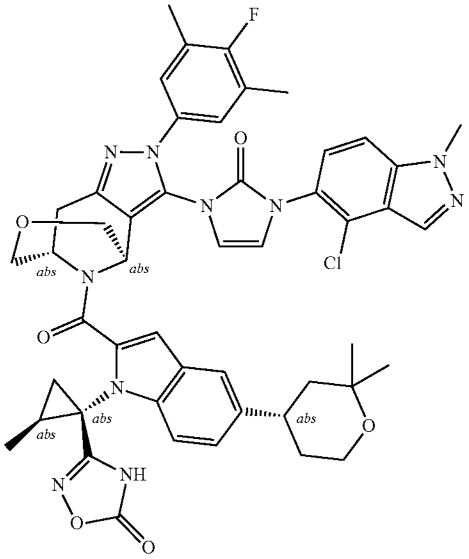 C49H48ClFN10O6 | 927.44 | 0.177 |
| 223 | 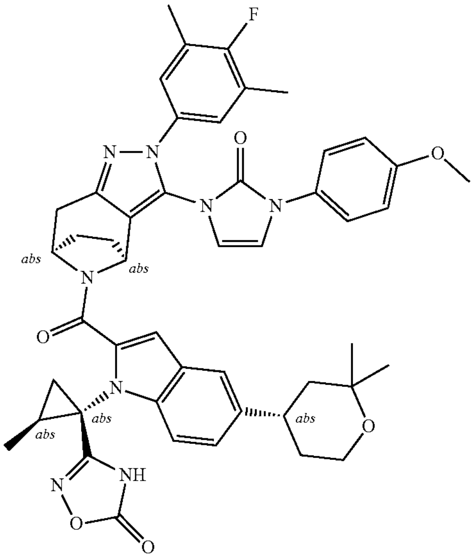 C48H49FN8O6 | 852.97 | 0.259 |

TABLE 1-continued
| Representative compounds and their $EC_{50}$ values | | | |
|---|---|---|---|
| Cpd ID | Structure | MW | EC50 (uM) |
| 224 | 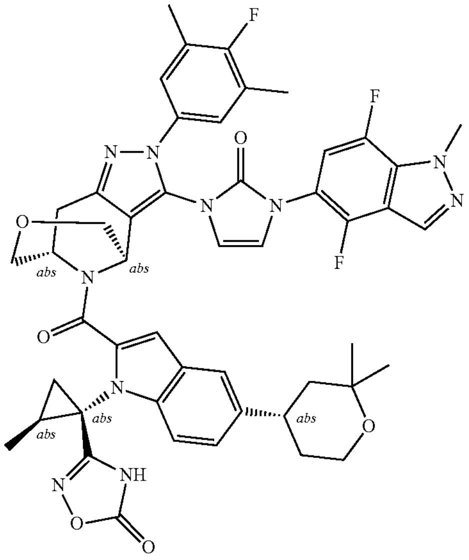 C49H47F3N10O6 | 928.97 | 0.212 |
| 225 | 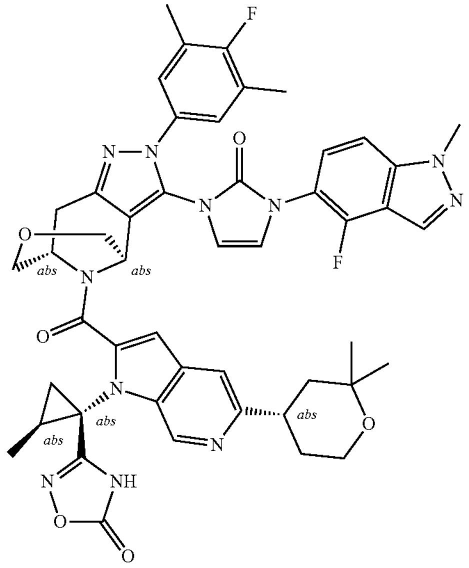 C48H47F2N11O6 | 911.97 | 0.0341 |

TABLE 1-continued
| Representative compounds and their $EC_{50}$ values | | | |
|---|---|---|---|
| Cpd ID | Structure | MW | EC50 (uM) |
| 226 | 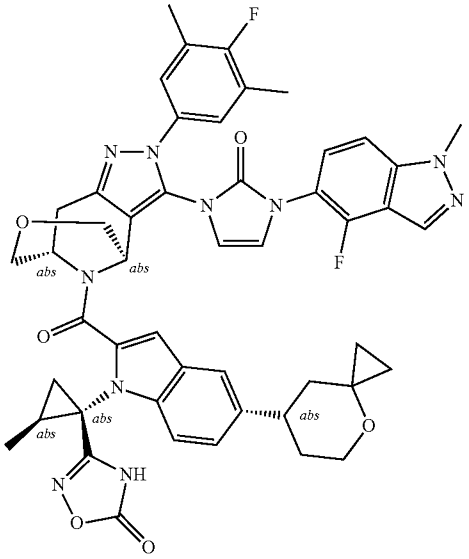 C49H46F2N10O6 | 908.97 | 0.435 |
| 227 | 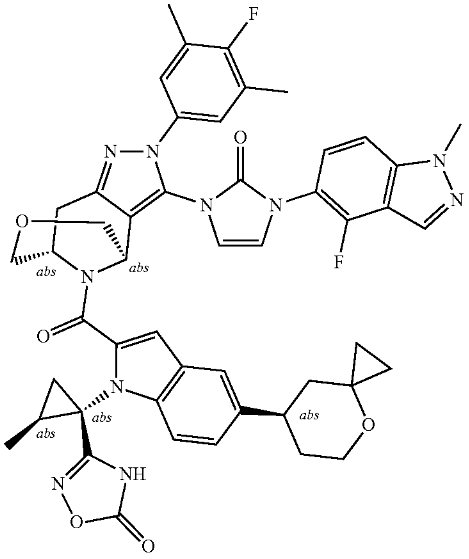 C49H46F2N10O6 | 908.97 | 0.585 |

TABLE 1-continued
| Representative compounds and their $EC_{50}$ values | | | |
|---|---|---|---|
| Cpd ID | Structure | MW | EC50 (uM) |
| 228 | 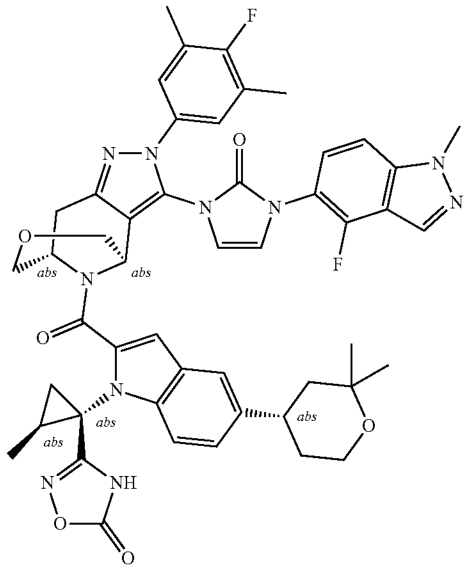 C50H51FN10O6 | 907.02 | 0.402 |
| 229 | 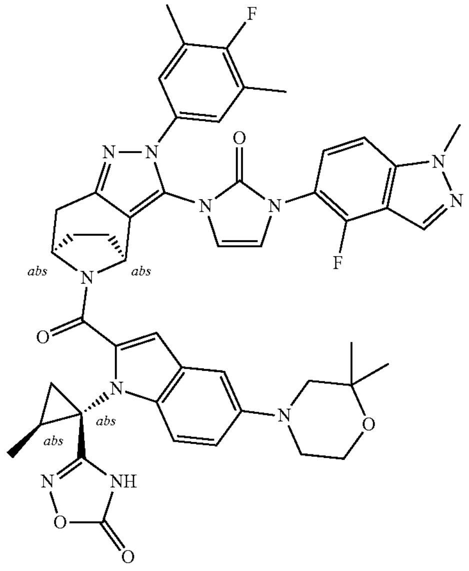 C48H47F2N11O5 | 895.97 | 0.167 |

TABLE 1-continued
| Representative compounds and their $EC_{50}$ values | | | |
|---|---|---|---|
| Cpd ID | Structure | MW | EC50 (uM) |
| 230 | 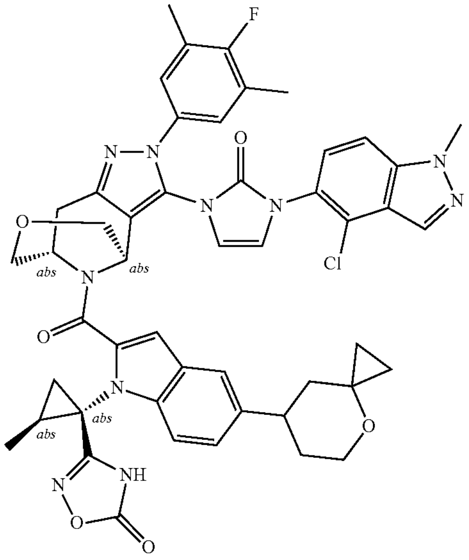 C49H46ClFN10O6 | 925.42 | 0.389 |
| 231 | 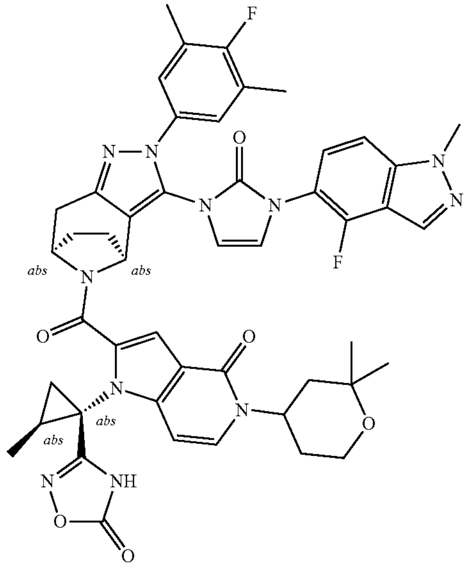 C48H47F2N11O6 | 911.97 | >10 |

TABLE 1-continued
| Representative compounds and their $EC_{50}$ values | | | |
|---|---|---|---|
| Cpd ID | Structure | MW | EC50 (uM) |
| 232 | 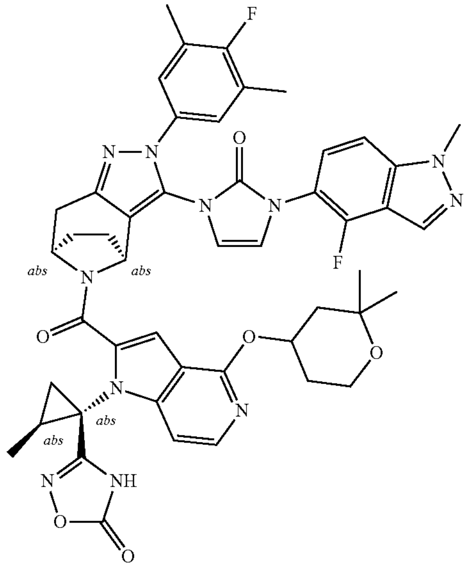 C48H47F2N11O6 | 911.97 | >10 |
| 233 | 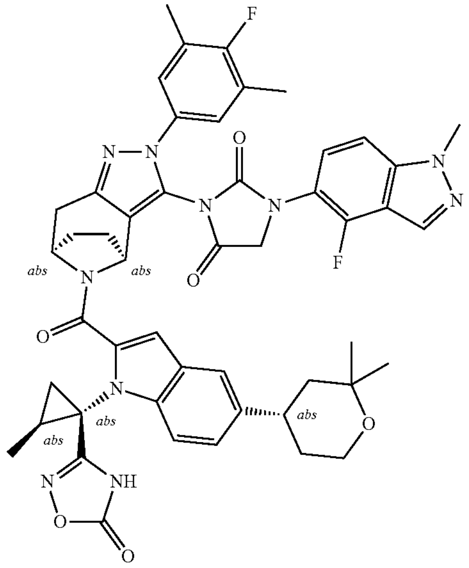 C49H48F2N10O6 | 910.98 | 149 |

TABLE 1-continued
| Representative compounds and their $EC_{50}$ values | | | |
|---|---|---|---|
| Cpd ID | Structure | MW | EC50 (uM) |
| 234 | 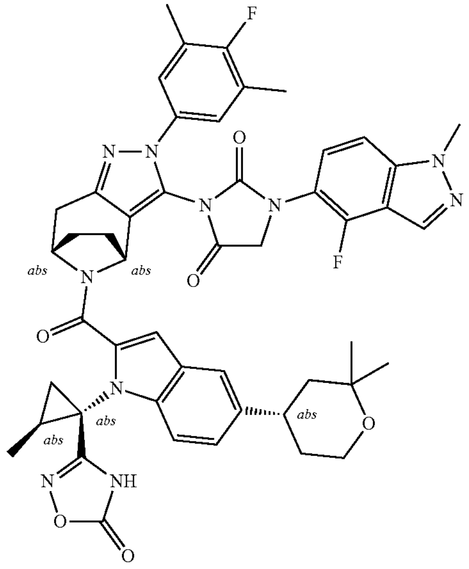 C49H48F2N10O6 | 910.98 | >10 |
| 235 | 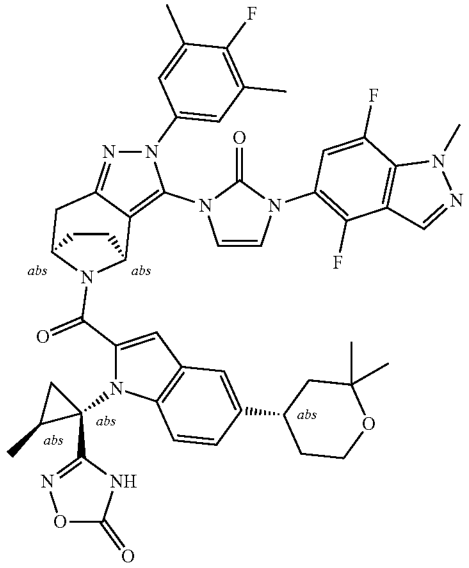 C49H47F3N10O5 | 912.98 | 0.459 |

TABLE 1-continued
| Representative compounds and their $EC_{50}$ values | | | |
|---|---|---|---|
| Cpd ID | Structure | MW | EC50 (uM) |
| 236 | 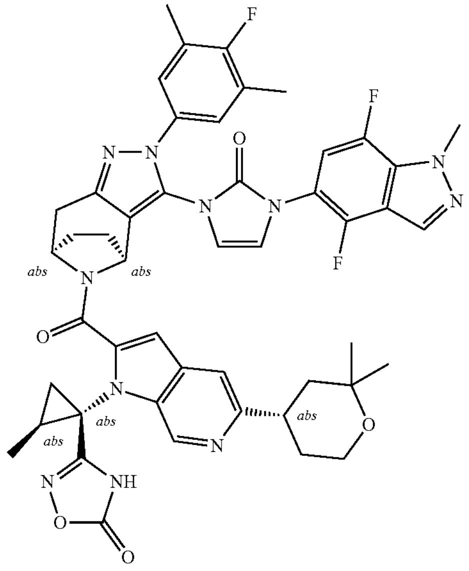 C48H46F3N11O5 | 913.96 | 0.785 |
| 237 | 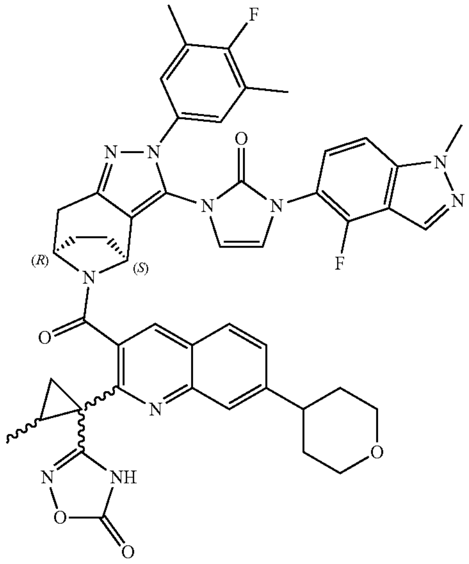 Isomer 1 C48H44F2N10O5 | 878.94 | 0.1225 |

TABLE 1-continued
| Representative compounds and their $EC_{50}$ values | | | |
|---|---|---|---|
| Cpd ID | Structure | MW | EC50 (uM) |
| 238 | 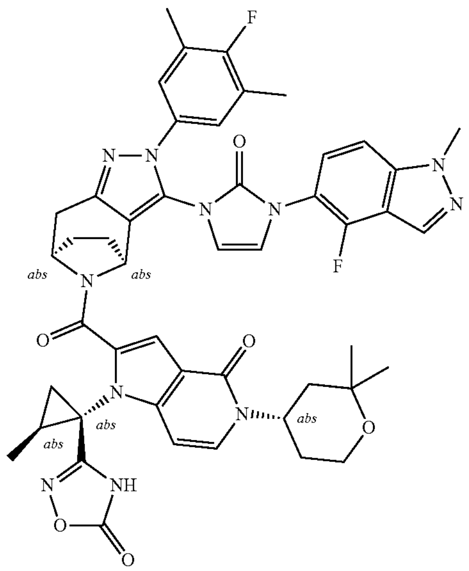 C48H47F2N11O6 | 911.97 | >10 |
| 239 | 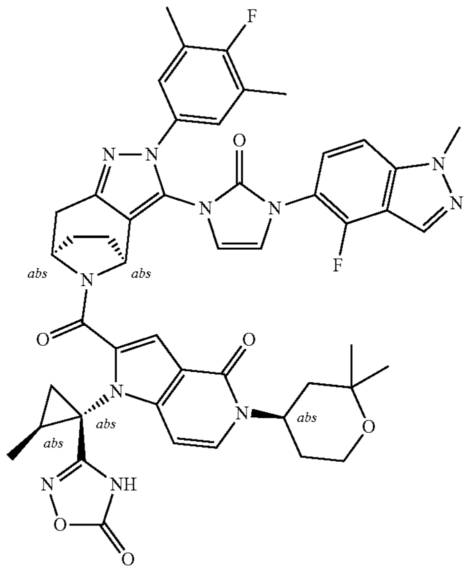 C48H47F2N11O6 | 911.97 | >10 |

TABLE 1-continued
| Representative compounds and their $EC_{50}$ values | | | |
|---|---|---|---|
| Cpd ID | Structure | MW | EC50 (uM) |
| 240 | 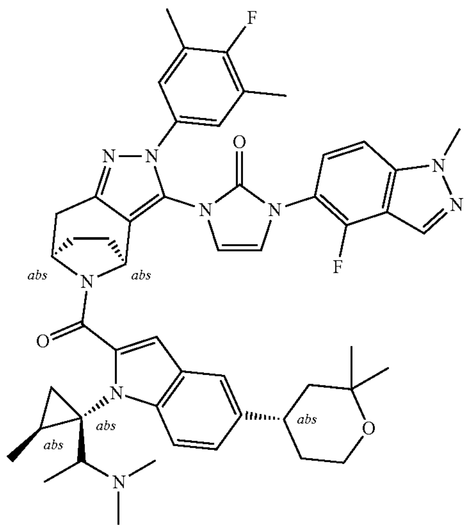 C50H53F2N9O4 | 882.03 | 0.618 |
| 241 | 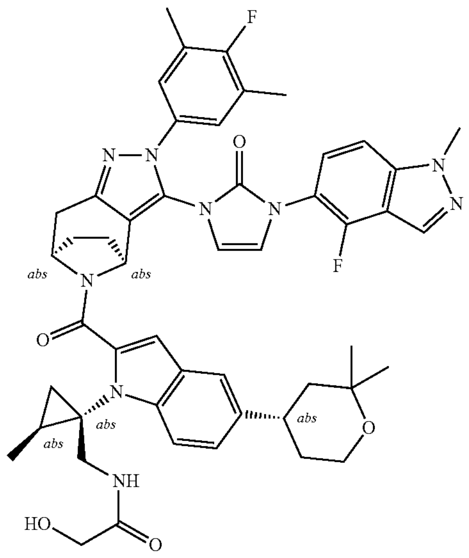 C50H53F2N9O5 | 898.03 | 0.641 |

TABLE 1-continued
| Representative compounds and their $EC_{50}$ values | | | |
|---|---|---|---|
| Cpd ID | Structure | MW | EC50 (uM) |
| 242 | 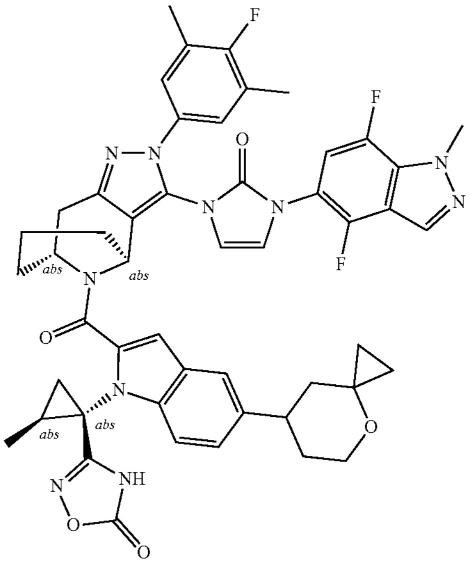 C49H45F3N10O6 | 926.96 | 0.168 |
| 243 | 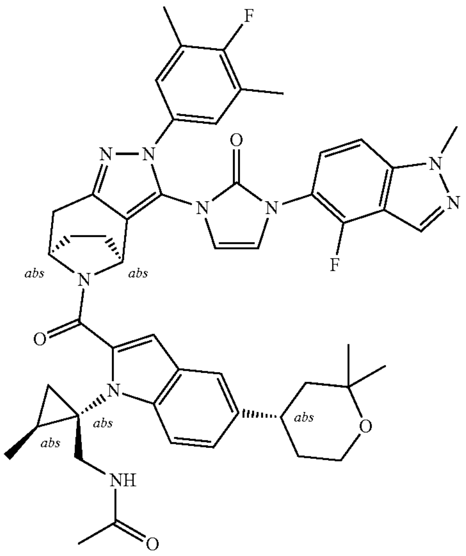 C50H53F2N9O4 | 882.03 | 0.757 |

TABLE 1-continued
| Representative compounds and their $EC_{50}$ values | | | |
|---|---|---|---|
| Cpd ID | Structure | MW | EC50 (uM) |
| 244 | 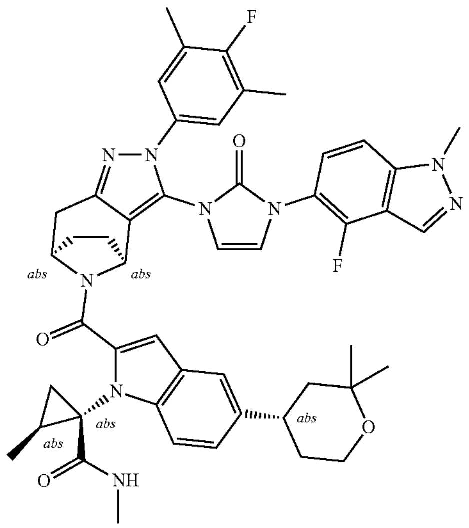 C49H51F2N9O4 | 868 | 0.390 |
| 245 | 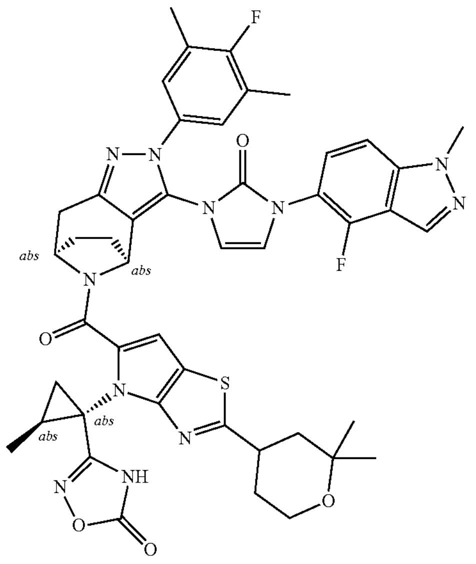 C46H45F2N11O5S | 901.99 | 5.07 |

TABLE 1-continued
| Representative compounds and their $EC_{50}$ values | | | |
|---|---|---|---|
| Cpd ID | Structure | MW | EC50 (uM) |
| 246 | 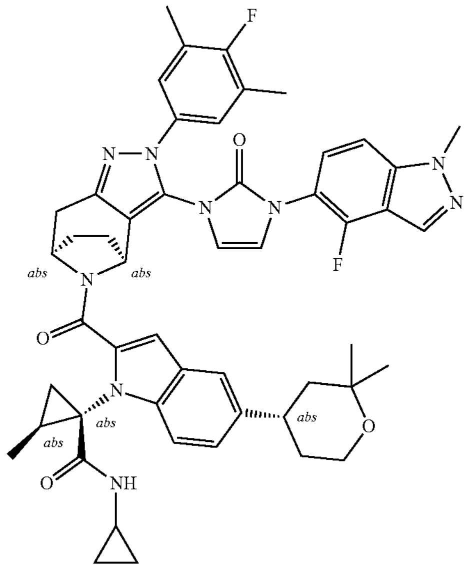 C51H53F2N9O4 | 894.04 | 0.699 |
| 301 | 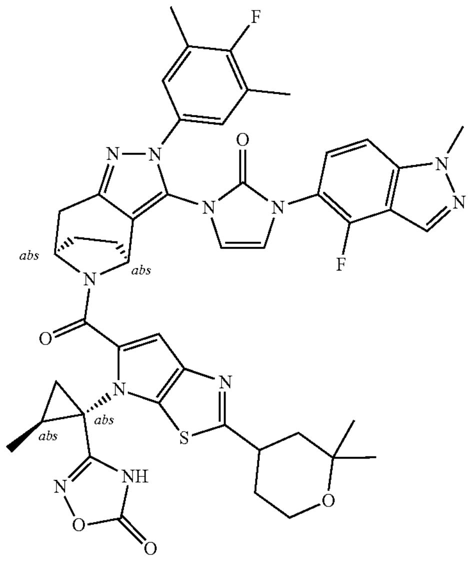 C46H45F2N11O6 | 885.93 | >10 |

TABLE 1-continued
| Representative compounds and their $EC_{50}$ values | | | |
|---|---|---|---|
| Cpd ID | Structure | MW | EC50 (uM) |
| 302 | 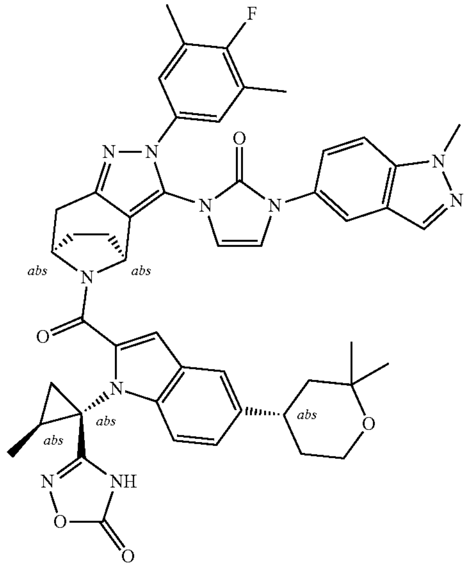 C49H49FN10O5 | 876.99 | 0.0529 |
| 303 | 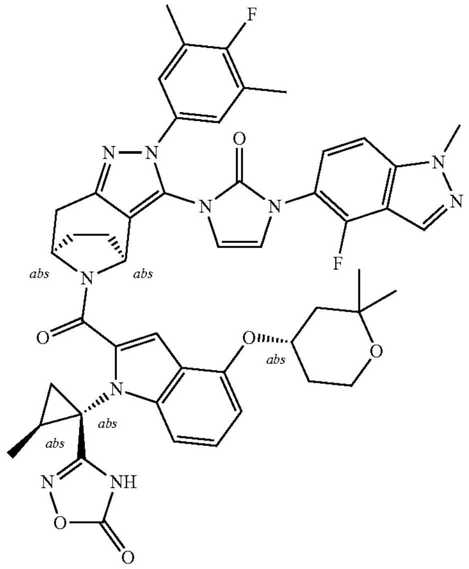 C48H47F2N11O6 | 911.97 | |

TABLE 1-continued
| Representative compounds and their $EC_{50}$ values | | | |
|---|---|---|---|
| Cpd ID | Structure | MW | EC50 (uM) |
| 304 | 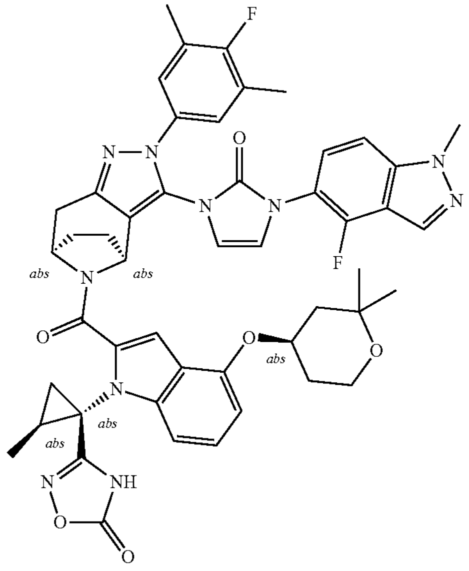 C48H47F2N11O6 | 911.97 | |
| 305 | 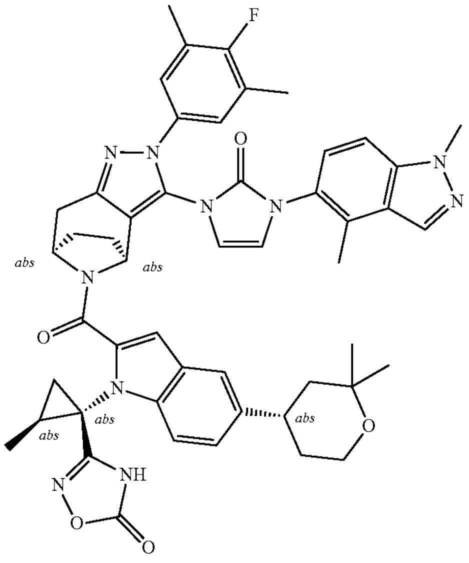 C50H51FN10O5 | 891.02 | 0.206 |

TABLE 1-continued
| Representative compounds and their $EC_{50}$ values | | | |
|---|---|---|---|
| Cpd ID | Structure | MW | EC50 (uM) |
| 306 | 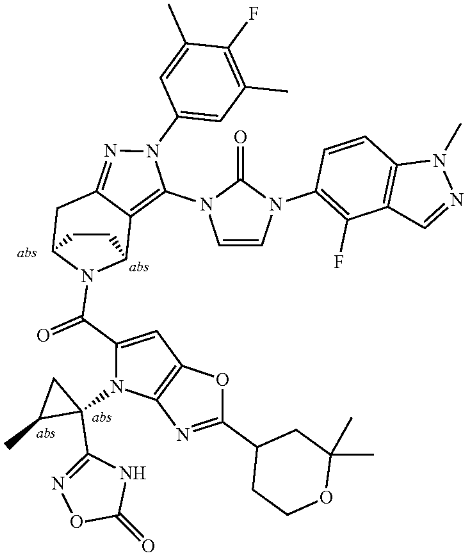 C46H45F2N11O5S | 901.99 | 2.45 |
| 307 | 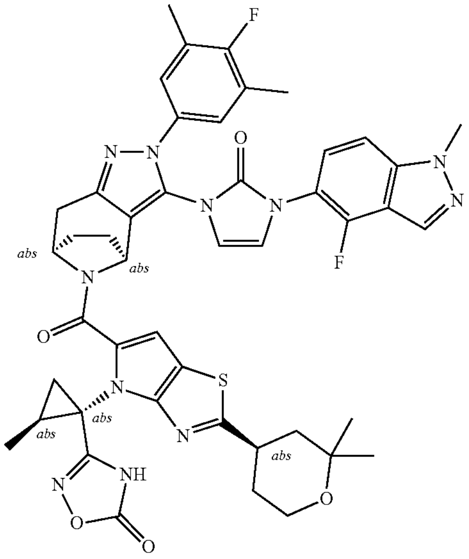 C46H45F2N11O5S | 901.99 | >10 |

TABLE 1-continued
| Representative compounds and their $EC_{50}$ values | | | |
|---|---|---|---|
| Cpd ID | Structure | MW | EC50 (uM) |
| 308 | 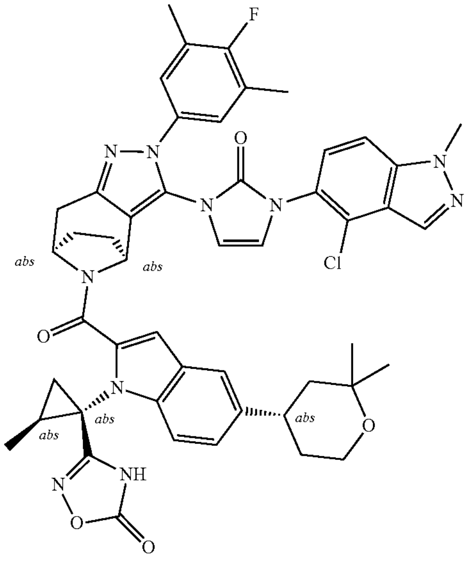 C49H48ClFN10O5 | 911.44 | 0.197 |
| 309 | 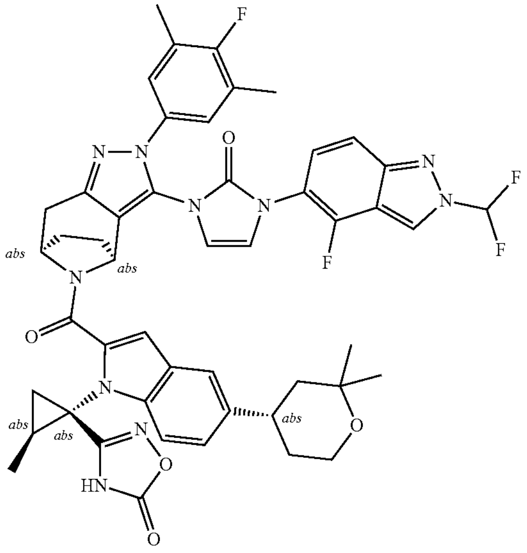 [SMILES: Cc1cc(-n2nc3c(c2-n2ccn(-c4ccc5nn(C(F)F)cc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H46F4N10O5 | 930.97 | 0.721 |

TABLE 1-continued
| Representative compounds and their $EC_{50}$ values | | | |
|---|---|---|---|
| Cpd ID | Structure | MW | EC50 (uM) |
| 310 | 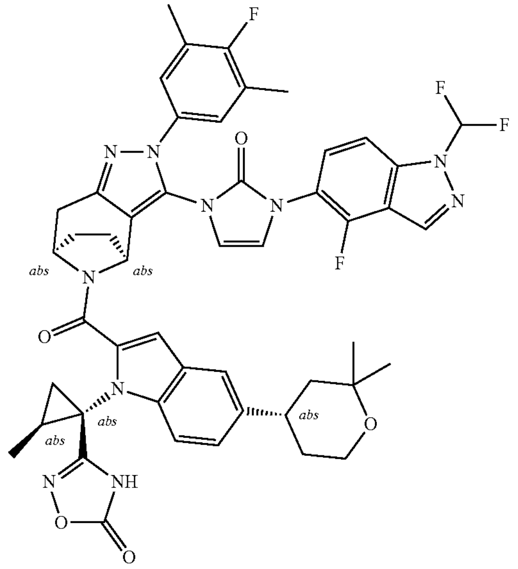 [SMILES: Cc1cc(-n2nc3c(c2-n2ccn(-c4ccc5c(cnn5C(F)F)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H46F4N10O5 | 930.97 | 0.182 |
| 311 | 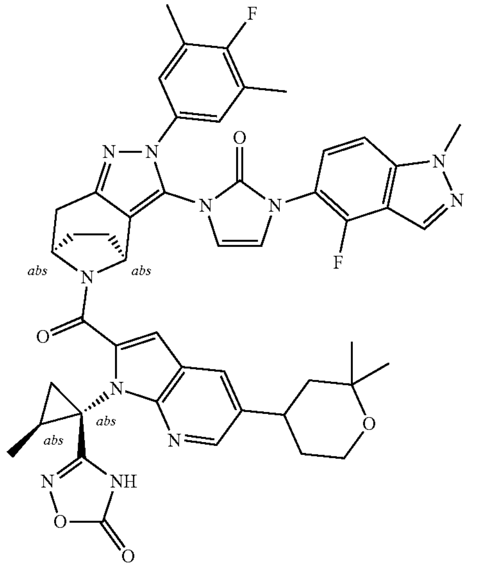 C48H47F2N11O5 | 895.97 | 0.0573 |

TABLE 1-continued
| Representative compounds and their $EC_{50}$ values | | | |
|---|---|---|---|
| Cpd ID | Structure | MW | EC50 (uM) |
| 312 | 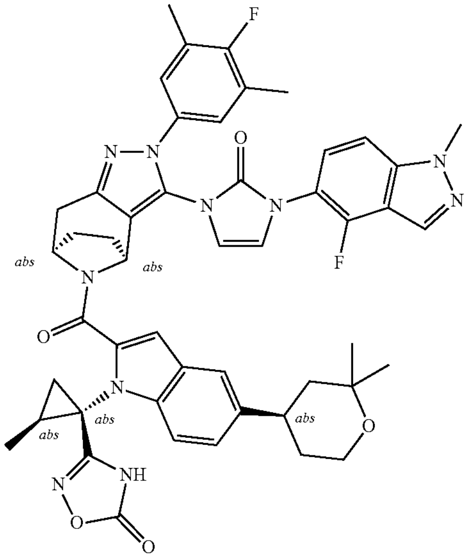 C48H47F2N11O5 | 895.97 | 1.34 |
| 313 | 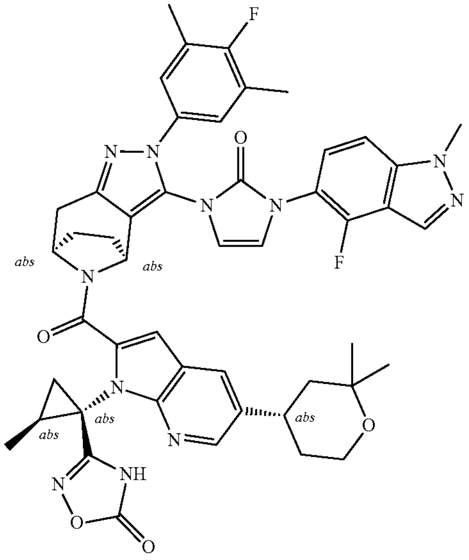 C48H47F2N11O5 | 895.97 | 0.0187 |

TABLE 1-continued
| Representative compounds and their $EC_{50}$ values | | | |
|---|---|---|---|
| Cpd ID | Structure | MW | EC50 (uM) |
| 318 | 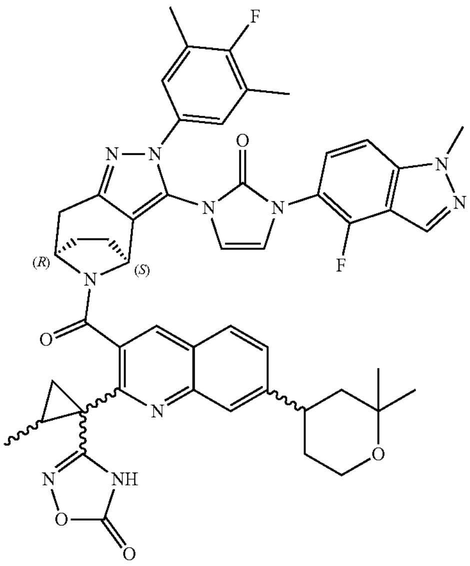 Isomer 1a C50H48F2N10O5 | 907.00 | 0.8702 |
| 319 | 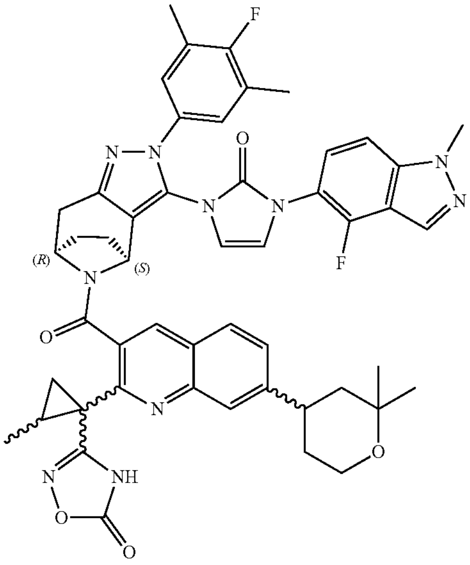 Isomer 1b C50H48F2N10O5 | 907.00 | 0.4686 |

TABLE 1-continued
| Representative compounds and their $EC_{50}$ values | | | |
|---|---|---|---|
| Cpd ID | Structure | MW | EC50 (uM) |
| 323 | 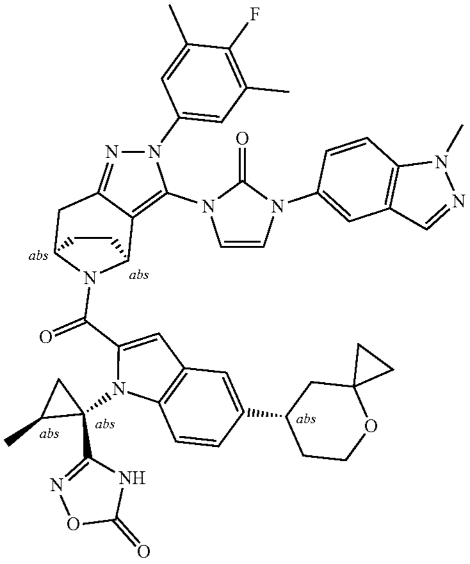 C49H47FN10O5 | 874.98 | 0.0793 |
| 324 | 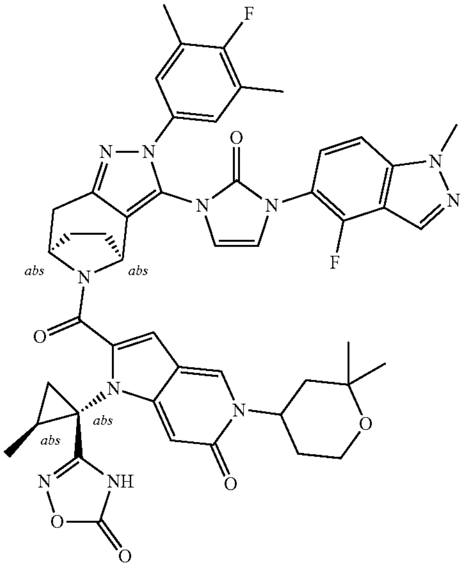 C48H47F2N11O6 | 911.97 | 0.2643 |

TABLE 1-continued
| Representative compounds and their $EC_{50}$ values | | | |
|---|---|---|---|
| Cpd ID | Structure | MW | EC50 (uM) |
| 406 | 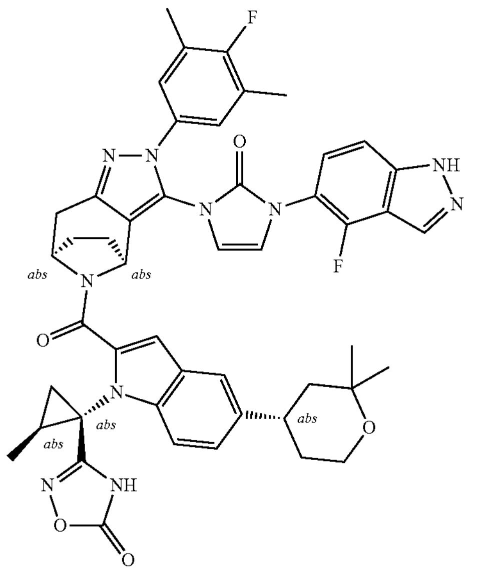 [SMILES: Cc1cc(-n2nc3c(c2-n2ccn(-c4ccc5[nH]ncc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C48H46F2N10O5 | 880.96 | 0.0184 |
| 410 | 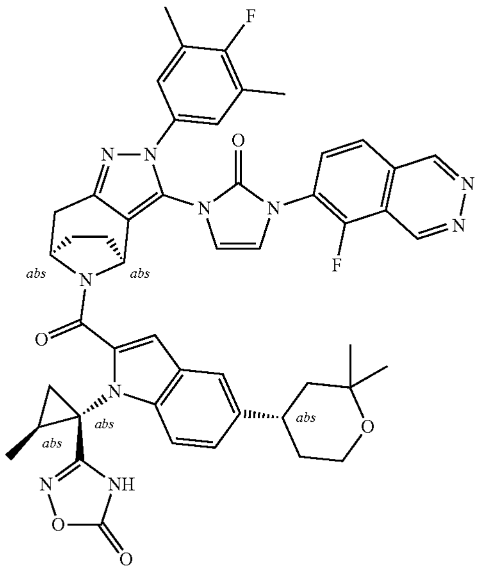 [SMILES: Cc1cc(-n2nc3c(c2-n2ccn(-c4ccc5cnncc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H46F2N10O5 | 892.97 | 0.0147 |

TABLE 1-continued
| Representative compounds and their $EC_{50}$ values | | | |
|---|---|---|---|
| Cpd ID | Structure | MW | EC50 (uM) |
| 411 | 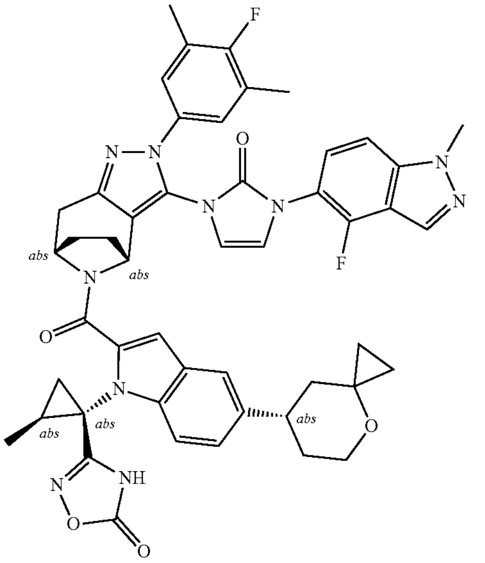 C49H46F2N10O5 | 892.97 | 0.652 |
| 412 | 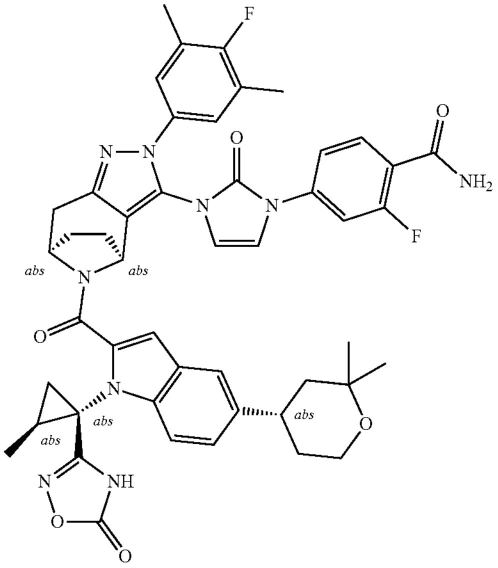 [SMILES: Cc1cc(-n2nc3c(c2-n2ccn(-c4ccc(C(N)=O)c(F)c4)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C48H47F2N9O6 | 883.96 | 0.5512 |

TABLE 1-continued
| Representative compounds and their $EC_{50}$ values | | | |
|---|---|---|---|
| Cpd ID | Structure | MW | EC50 (uM) |
| 413 | 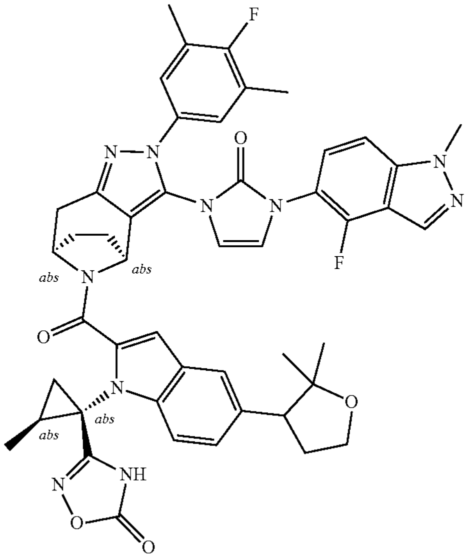 C48H46F2N10O5 | 880.96 | 1.771 |
| 414 | 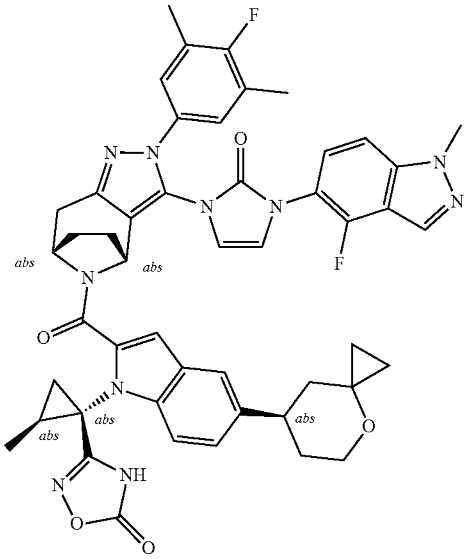 C49H46F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 415 | 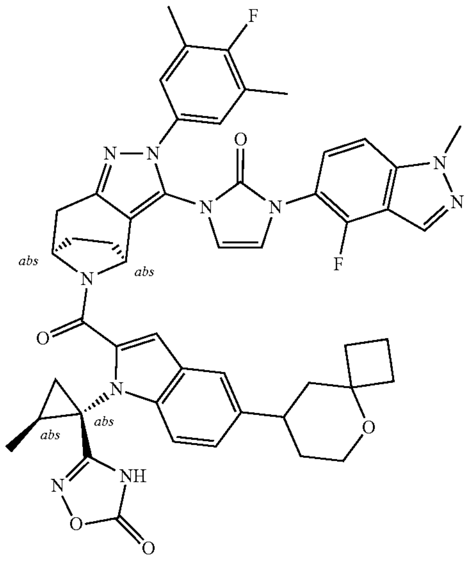 C50H48F2N10O5 | 907 | 0.3608 |
| 416 | 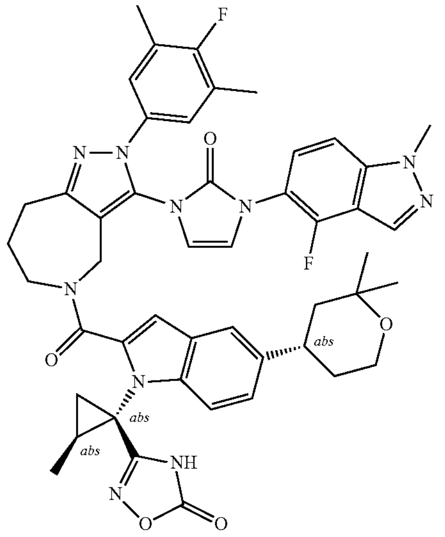 [SMILES: Cc1cc(-n2nc3c(c2-n2ccn(-c4ccc5c(cnn5C)c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C48H48F2N10O5 | 882.97 | 0.1622 |

TABLE 1-continued
| Representative compounds and their $EC_{50}$ values | | | |
|---|---|---|---|
| Cpd ID | Structure | MW | EC50 (uM) |
| 417 | 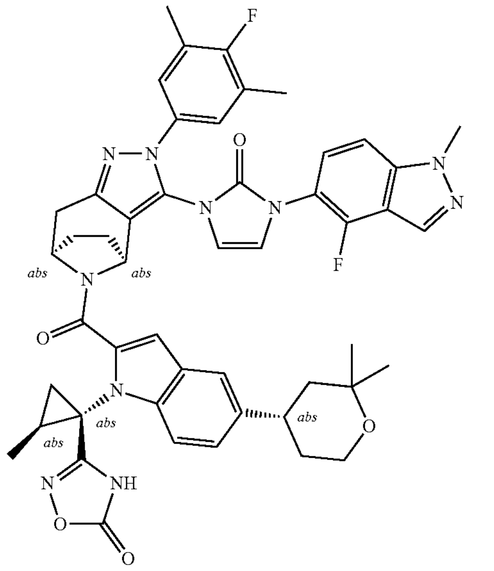 C49H50F2N10O4 | 881 | 0.11 |
| 418 | 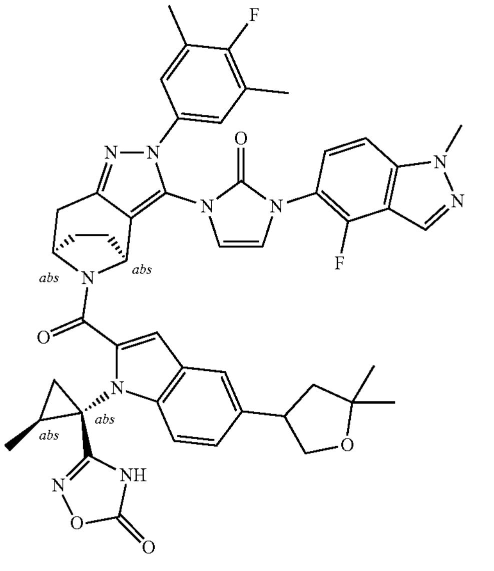 C48H46F2N10O5 | 880.96 | 0.8365 |

TABLE 1-continued
| Representative compounds and their $EC_{50}$ values | | | |
|---|---|---|---|
| Cpd ID | Structure | MW | EC50 (uM) |
| 419 | 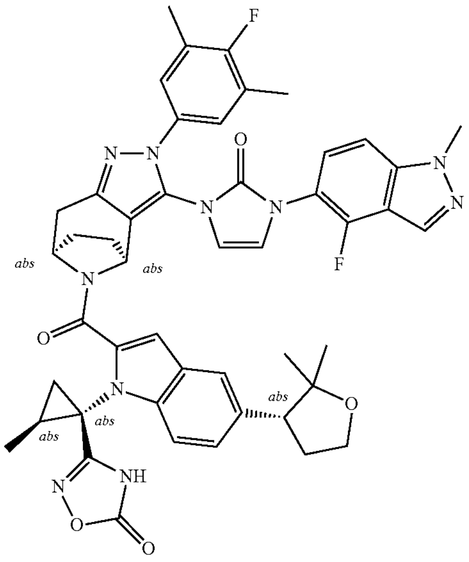 C48H46F2N10O5 | 880.96 | 10 |
| 420 | 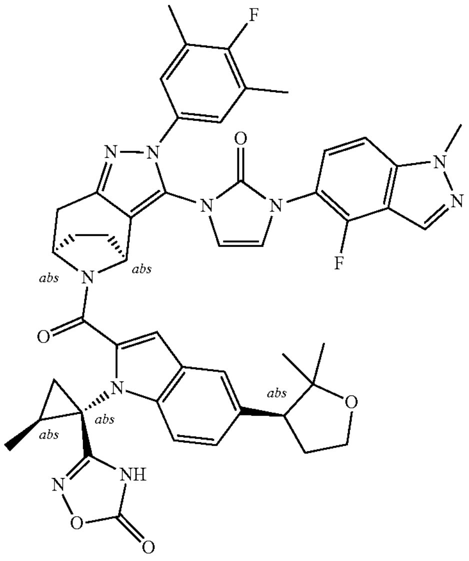 C48H46F2N10O5 | 880.96 | 0.6498 |

TABLE 1-continued
| Representative compounds and their $EC_{50}$ values | | | |
|---|---|---|---|
| Cpd ID | Structure | MW | EC50 (uM) |
| 421 | 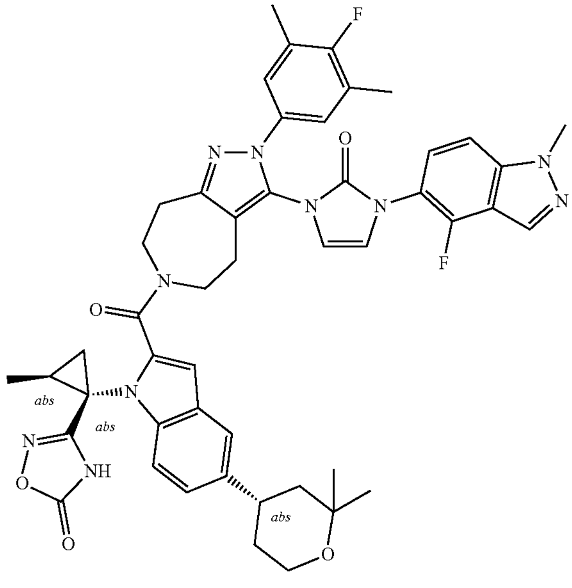 C48H48F2N10O5 | 882.97 | 10 |
| 422 | 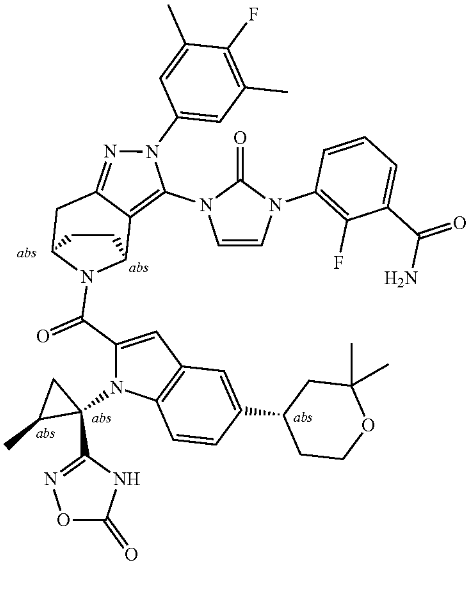 [SMILES: Cc1cc(-n2nc3c(c2-n2ccn(-c4cccc(C(N)=O)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C48H47F2N9O6 | 883.96 | 0.3029 |

TABLE 1-continued
| Representative compounds and their $EC_{50}$ values | | | |
|---|---|---|---|
| Cpd ID | Structure | MW | EC50 (uM) |
| 423 | 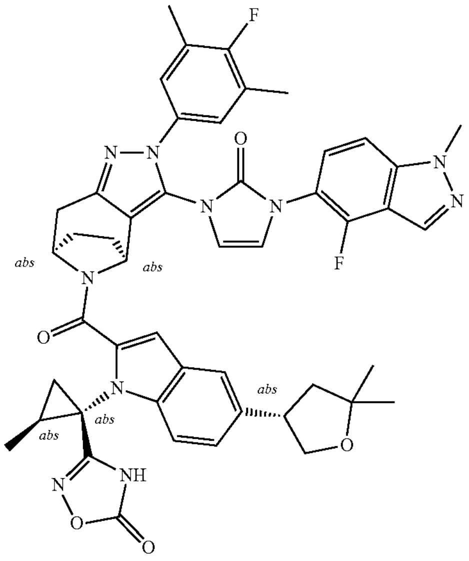 C48H46F2N10O5 | 880.96 | 2.1238 |
| 424 | 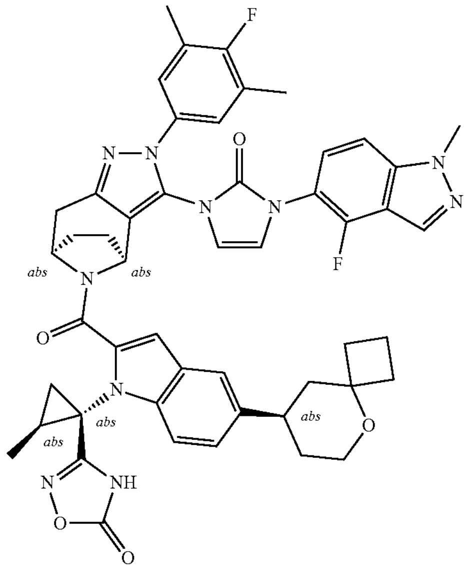 C50H48F2N10O5 | 907 | 10 |

TABLE 1-continued
| Representative compounds and their $EC_{50}$ values | | | |
|---|---|---|---|
| Cpd ID | Structure | MW | EC50 (uM) |
| 425 | 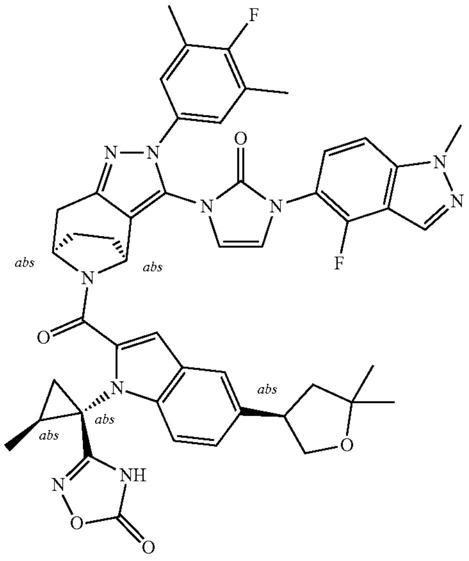 C48H46F2N10O5 | 880.96 | 0.2923 |
| 426 | 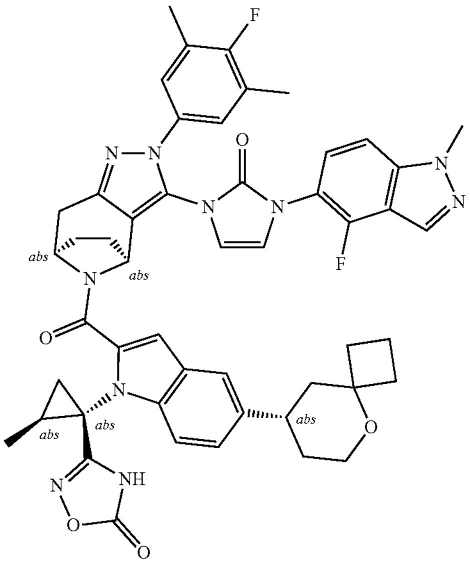 C50H48F2N10O5 | 907 | 0.1338 |

TABLE 1-continued
| Representative compounds and their $EC_{50}$ values | | | |
|---|---|---|---|
| Cpd ID | Structure | MW | EC50 (uM) |
| 427 | 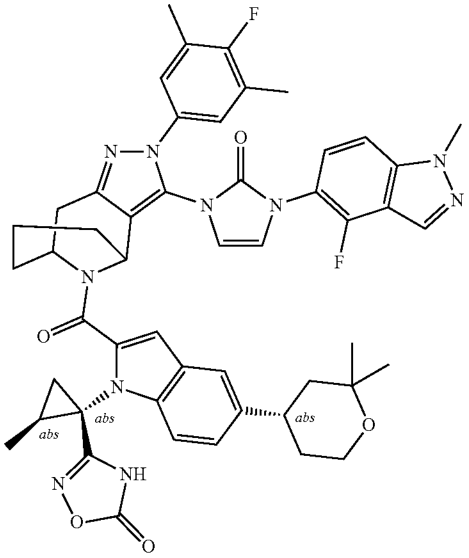 C50H50F2N10O5 | 909.01 | 0.0771 |
| 428 | 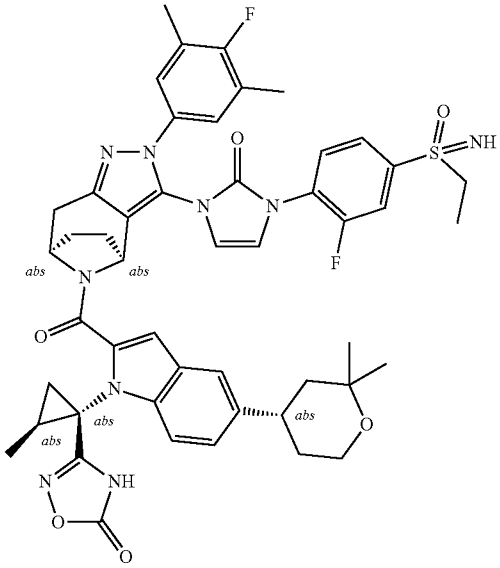 [SMILES: CCS(=N)(=O)c1ccc(-n2ccn(-c3c4c(nn3-c3cc(C)c(F)c(C)c3)C[C@H]3CC[C@@H]4N3C(=O)c3cc4cc([C@H]5CCOC(C)(C)C5)ccc4n3[C@@]3(c4noc(=O)[nH]4)C[C@@H]3C)c2=O)c(F)c1] C49H51F2N9O6S | 932.06 | 0.0948 |

TABLE 1-continued
| Representative compounds and their $EC_{50}$ values | | | |
|---|---|---|---|
| Cpd ID | Structure | MW | EC50 (uM) |
| 429 | 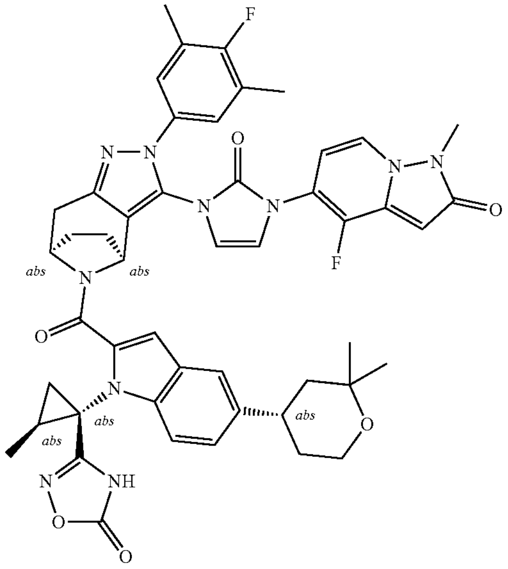 [SMILES: Cc1cc(-n2nc3c(c2-n2ccn(-c4ccn5c(cc(=O)n5C)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H48F2N10O6 | 910.98 | 0.0122 |
| 430 | 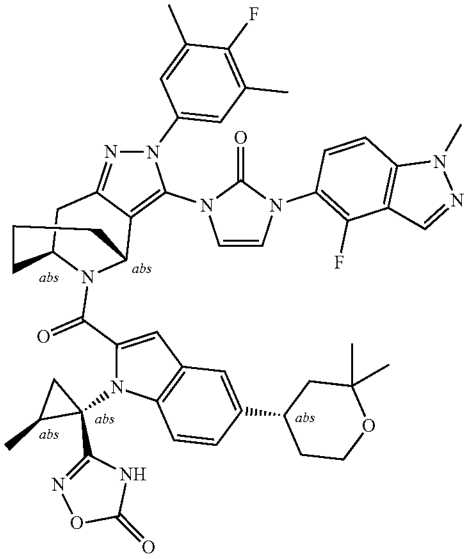 C50H50F2N10O5 | 909.01 | 10 |

TABLE 1-continued
| Representative compounds and their $EC_{50}$ values | | | |
|---|---|---|---|
| Cpd ID | Structure | MW | EC50 (uM) |
| 431 | 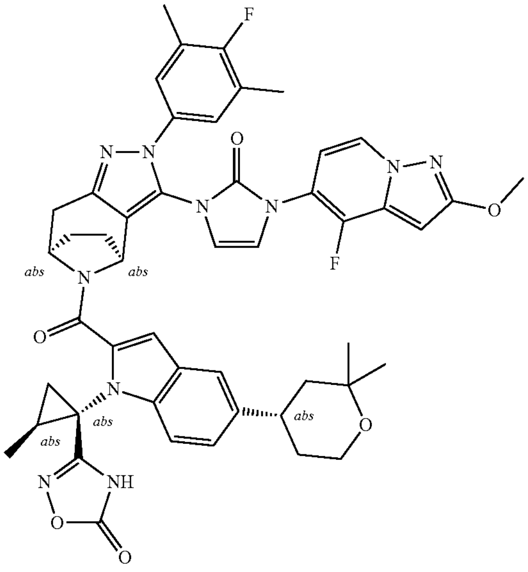 C49H48F2N10O6 | 910.98 | 0.1247 |
| 432 | 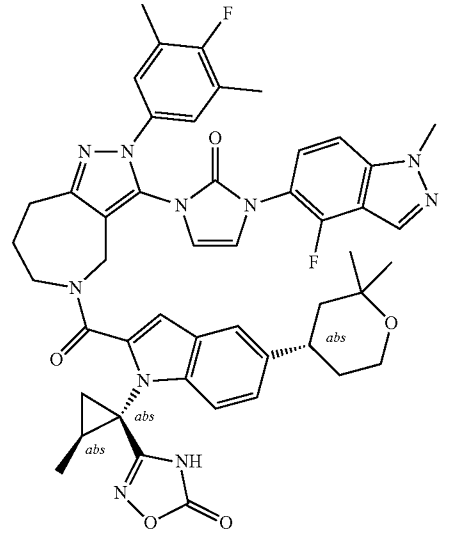 [SMILES: Cc1cc(-n2nc3c(c2-n2ccn(-c4ccc5c(cnn5C)c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C48H50F2N10O4 | 868.99 | 0.2836 |

TABLE 1-continued
| Representative compounds and their $EC_{50}$ values | | | |
|---|---|---|---|
| Cpd ID | Structure | MW | EC50 (uM) |
| 433 | 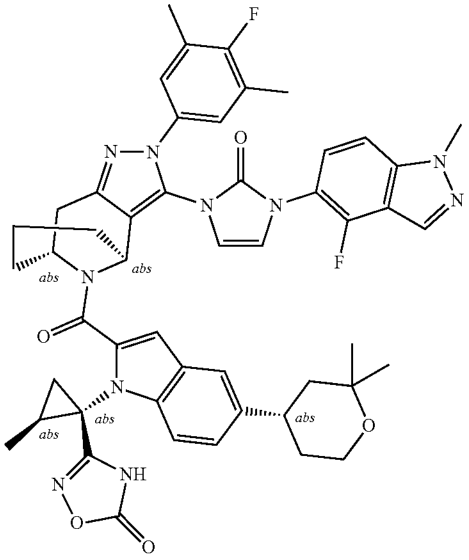 C50H50F2N10O5 | 909.01 | 0.030 |
| 434 | 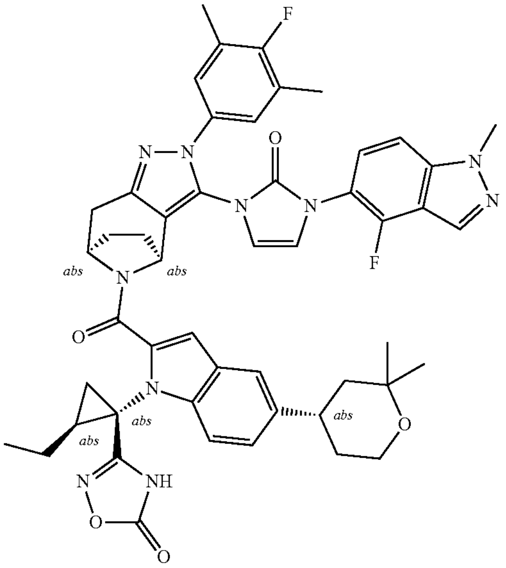 [SMILES: CC[C@H]1C[C@]1(c1noc(=O)[nH]1)n1c(C(=O)N2[C@@H]3CC[C@H]2c2c(nn(-c4cc(C)c(F)c(C)c4)c2-n2ccn(-c4ccc5c(cnn5C)c4F)c2=O)C3)cc2cc([C@H]3CCOC(C)(C)C3)ccc21] C50H50F2N10O5 | 909.01 | 0.175 |

TABLE 1-continued
| Cpd ID | Structure | MW | EC50 (uM) |
|---|---|---|---|
| 435 | 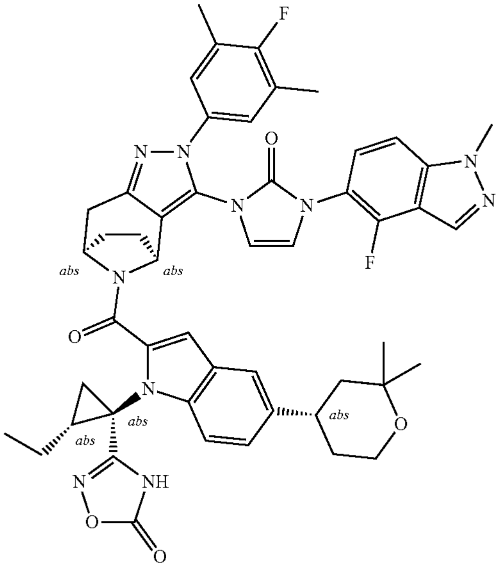 [SMILES: CC[C@@H]1C[C@@]1(c1noc(=O)[nH]1)n1c(C(=O)N2[C@@H]3CC[C@H]2c2c(nn(-c4cc(C)c(F)c(C)c4)c2-n2ccn(-c4ccc5c(cnn5C)c4F)c2=O)C3)cc2cc([C@H]3CCOC(C)(C)C3)ccc21] C50H50F2N10O5 | 909.01 | 3.87 |
| 436 | 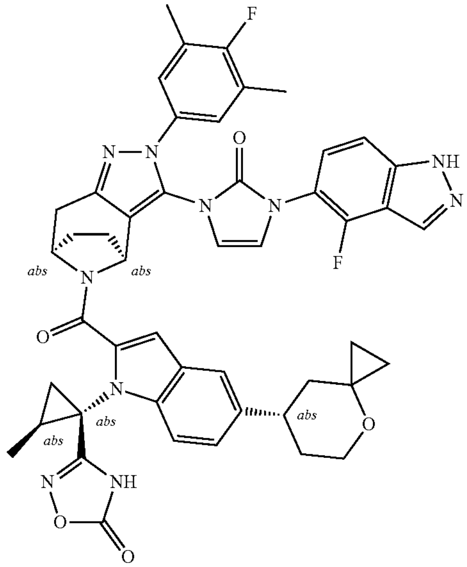 [SMILES: Cc1cc(-n2nc3c(c2-n2ccn(-c4ccc5[nH]ncc5c4F)c2=O)[C@@H]2CC[C@H](C3)N2C(=O)c2cc3cc([C@H]4CCOC5(CC5)C4)ccc3n2[C@@]2(c3noc(=O)[nH]3)C[C@@H]2C)cc(C)c1F] C48H44F2N10O5 | 878.94 | 0.07 |
Representative compounds and their $EC_{50}$ values TABLE 1-continued
Representative compounds and their $EC_{50}$ values
| Cpd ID | Structure | MW | EC50 (uM) |
|---|---|---|---|
| 437 | 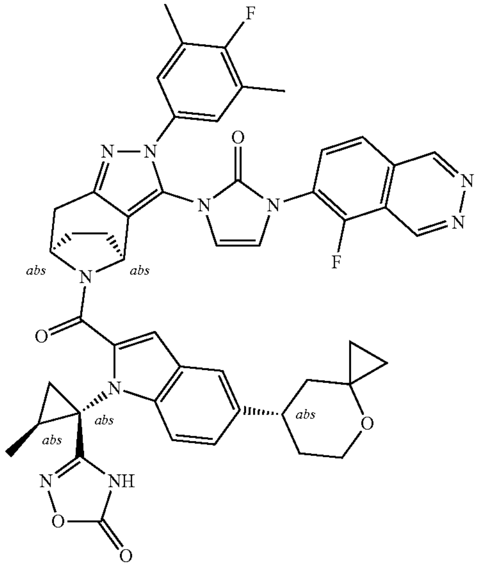 [SMILES: Cc1cc(-n2nc3c(c2-n2ccn(-c4ccc5cnncc5c4F)c2=O)[C@@H]2CC[C@H](C3)N2C(=O)c2cc3cc([C@H]4CCOC5(CC5)C4)ccc3n2[C@@]2(c3noc(=O)[nH]3)C[C@@H]2C)cc(C)c1F] C49H44F2N10O5 | 890.95 | 0.055 |
| 501 | 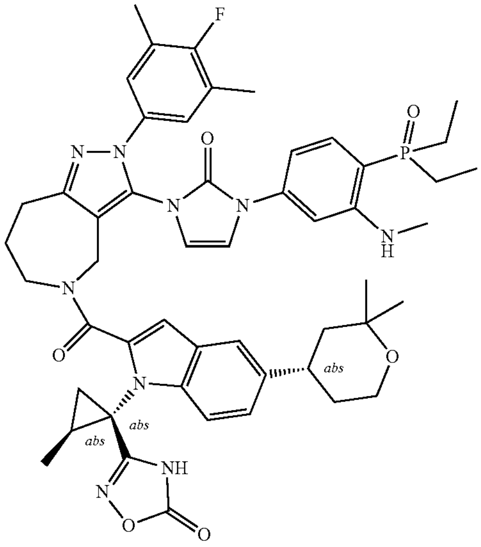 [SMILES: CCP(=O)(CC)c1ccc(-n2ccn(-c3c4c(nn3-c3cc(C)c(F)c(C)c3)CCCN(C(=O)c3cc5cc([C@H]6CCOC(C)(C)C6)ccc5n3[C@@]3(c5noc(=O)[nH]5)C[C@@H]3C)C4)c2=O)cc1NC] C51H59FN9O6P | 944.06 | |

TABLE 1-continued
| Representative compounds and their $EC_{50}$ values | | | |
|---|---|---|---|
| Cpd ID | Structure | MW | EC50 (uM) |
| 502 | 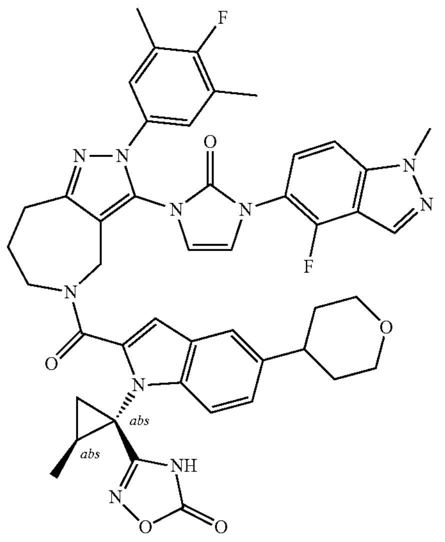 [SMILES: Cc1cc(-n2nc3c(c2-n2ccn(-c4ccc5c(cnn5C)c4F)c2=O)CN(C(=O)c2cc4cc(C5CCOCC5)ccc4n2[C@@]2(c4noc(=O)[nH]4)C[C@@H]2C)CCC3)cc(C)c1F] C46H44F2N10O5 | 854.92 | |
| 503 | 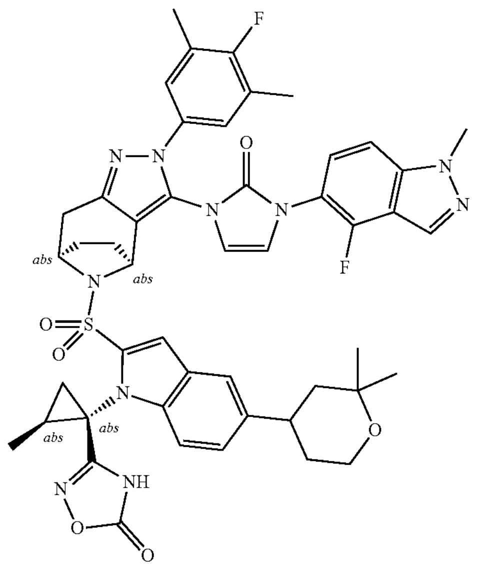 C48H48F2N10O6S | 931.03 | 0.0978 |

TABLE 1-continued
| Representative compounds and their $EC_{50}$ values | | | |
|---|---|---|---|
| Cpd ID | Structure | MW | EC50 (uM) |
| 504 | 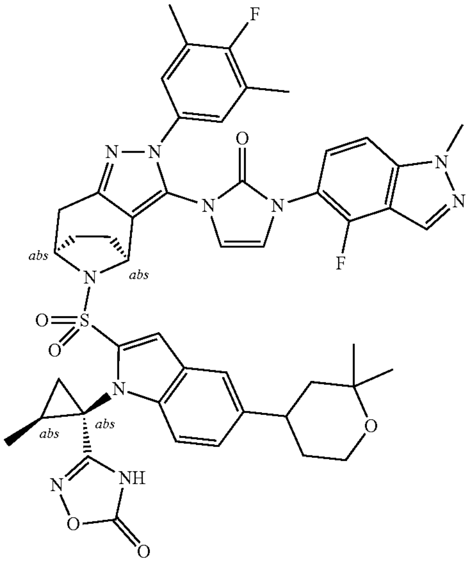 C48H48F2N10O6S | 931.03 | 1.9324 |
| 505 | 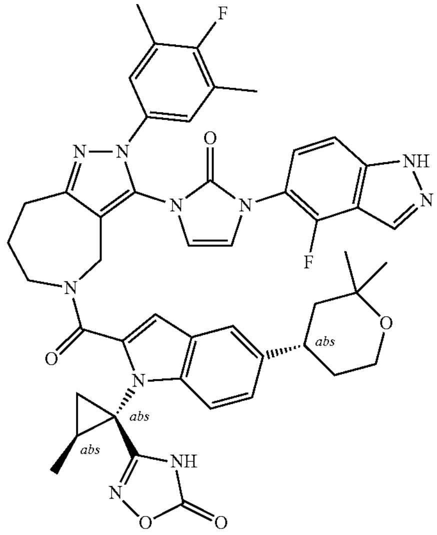 [SMILES: Cc1cc(-n2nc3c(c2-n2ccn(-c4ccc5[nH]ncc5c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C47H46F2N10O5 | 868.95 | 0.5999 |

TABLE 1-continued
| Representative compounds and their $EC_{50}$ values | | | |
|---|---|---|---|
| Cpd ID | Structure | MW | EC50 (uM) |
| 506 | 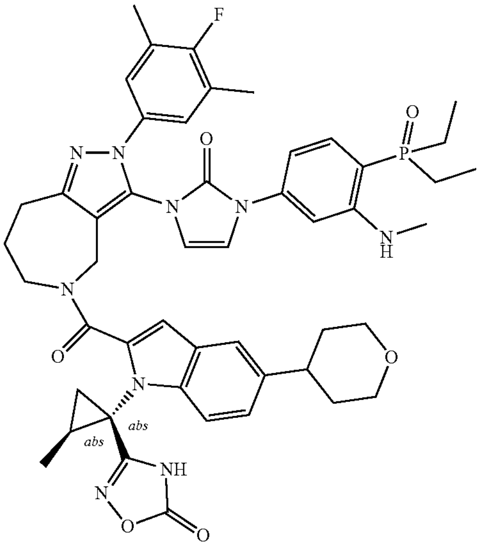 [SMILES: CCP(=O)(CC)c1ccc(-n2ccn(-c3c4c(nn3-c3cc(C)c(F)c(C)c3)CCCN(C(=O)c3cc5cc(C6CCOCC6)ccc5n3[C@@]3(c5noc(=O)[nH]5)C[C@@H]3C)C4)c2=O)cc1NC] C49H55FN9O6P | 916.01 | 0.7568 |
| 507 | 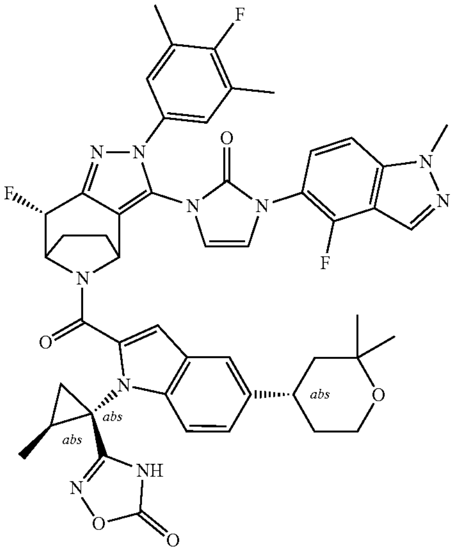 C49H47F3N10O5 | 912.98 | 0.6305 |

TABLE 1-continued
| Representative compounds and their $EC_{50}$ values | | | |
|---|---|---|---|
| Cpd ID | Structure | MW | EC50 (uM) |
| 508 | 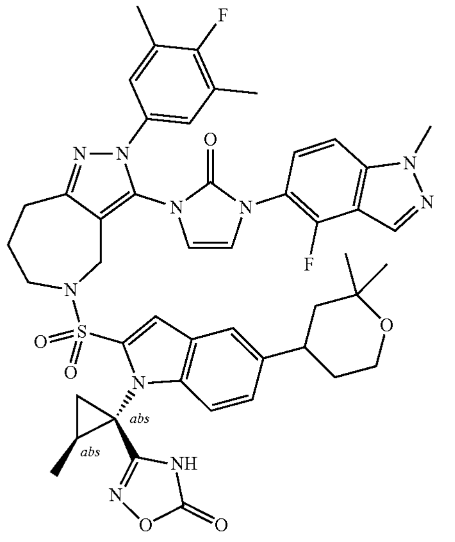 [SMILES: Cc1cc(-n2nc3c(c2-n2ccn(-c4ccc5c(cnn5C)c4F)c2=O)CN(S(=O)(=O)c2cc4cc(C5CCOC(C)(C)C5)ccc4n2[C@@]2(c4noc(=O)[nH]4)C[C@@H]2C)CCC3)cc(C)c1F] C47H48F2N10O6S | 919.02 | 10 |
| 509 | 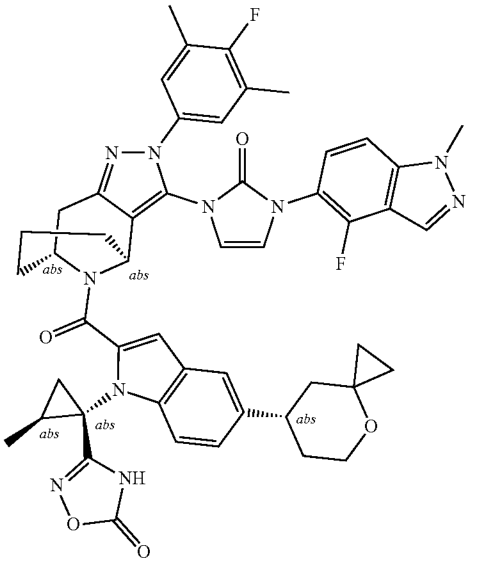 C50H48F2N10O5 | 907 | 0.1341 |

TABLE 1-continued
| Representative compounds and their $EC_{50}$ values | | | |
|---|---|---|---|
| Cpd ID | Structure | MW | EC50 (uM) |
| 510 | 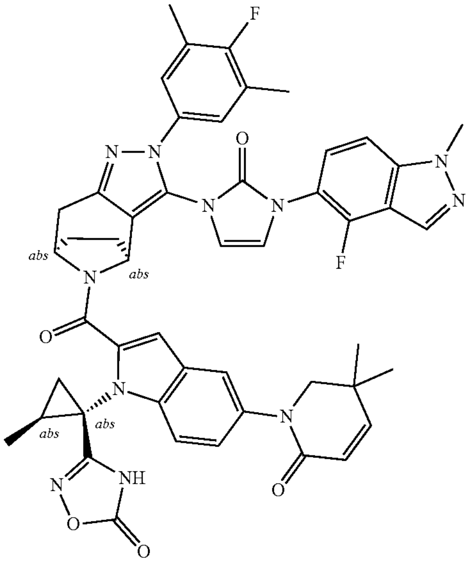 C49H45F2N11O5 | 905.97 | 10 |
| 511 | 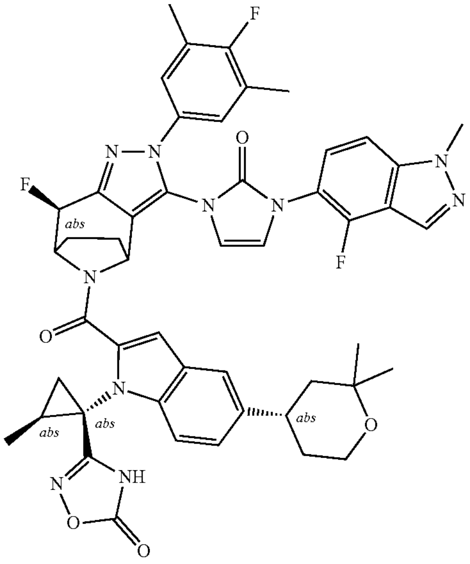 C49H47F3N10O5 | 912.98 | 0.588 |

TABLE 1-continued
| Representative compounds and their $EC_{50}$ values | | | |
|---|---|---|---|
| Cpd ID | Structure | MW | EC50 (uM) |
| 512 | 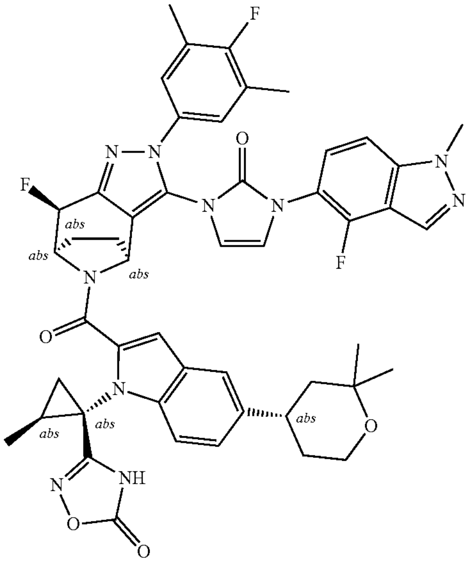 C49H47F3N10O5 | 912.98 | 0.2262 |
| 513 | 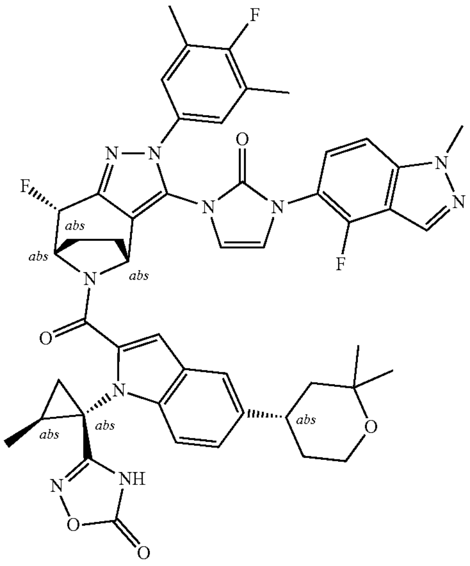 C49H47F3N10O5 | 912.98 | 10 |

TABLE 1-continued
| Representative compounds and their $EC_{50}$ values | | | |
|---|---|---|---|
| Cpd ID | Structure | MW | EC50 (uM) |
| 514 | 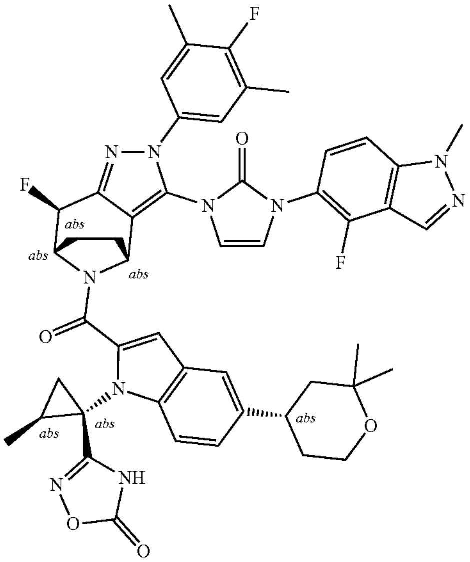 C49H47F3N10O5 | 912.98 | 10 |
| 515 | 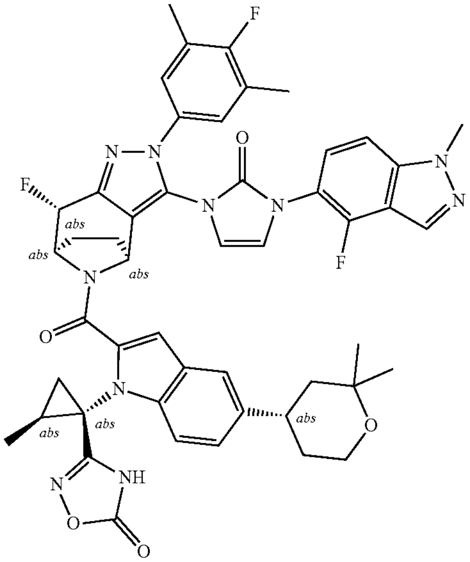 C49H47F3N10O5 | 912.98 | 0.1204 |

TABLE 1-continued
| Representative compounds and their $EC_{50}$ values | | | |
|---|---|---|---|
| Cpd ID | Structure | MW | EC50 (uM) |
| 516 | 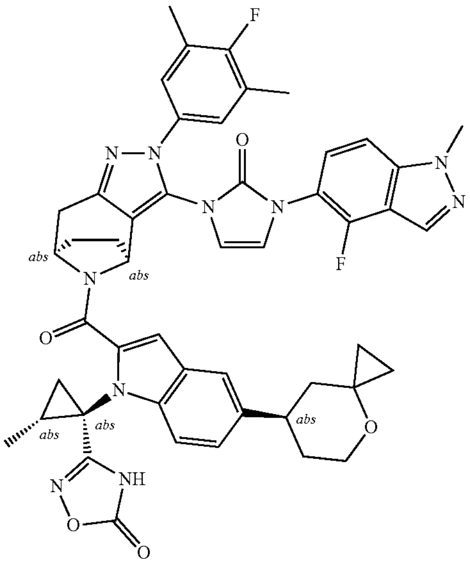 C49H46F2N10O5 | 892.97 | 10 |
| 517 | 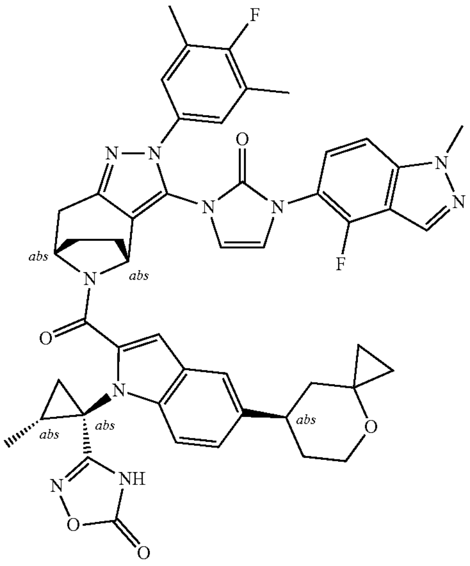 C49H64F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 518 | 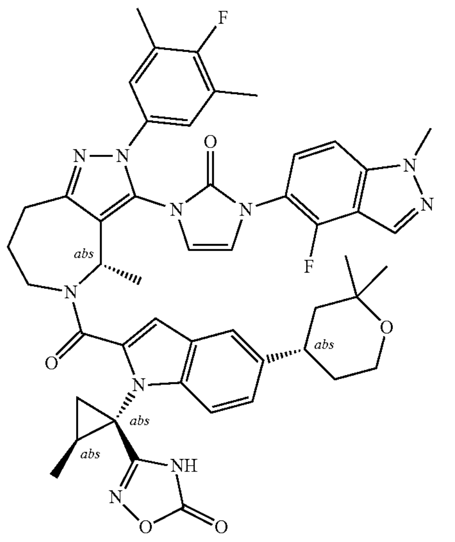 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CCC3)cc(C)c1F] C49H50F2N10O5 | 897 | 0.0735 |
| 519 | 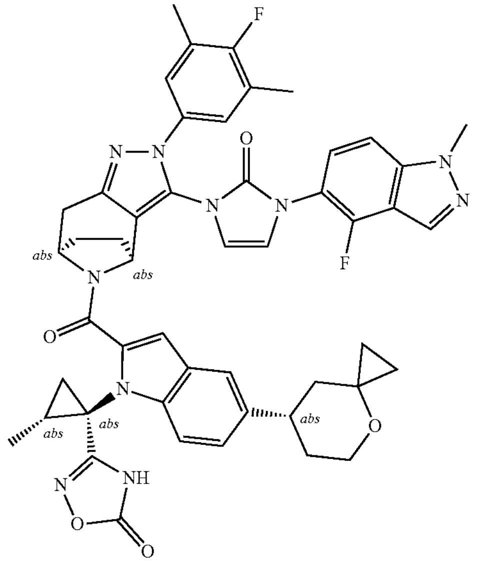 C49H46F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 520 | 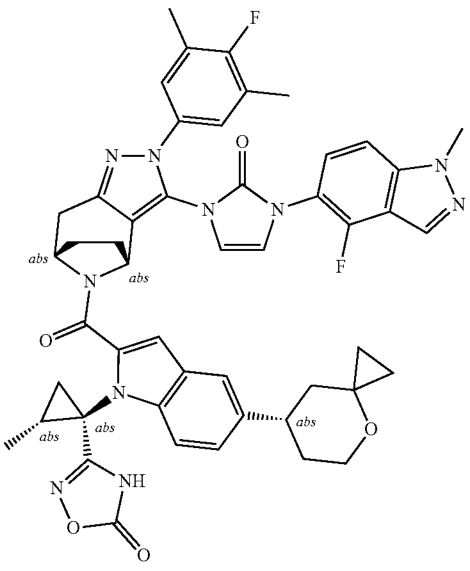 C49H46F2N10O5 | 892.97 | 10 |
| 521 | 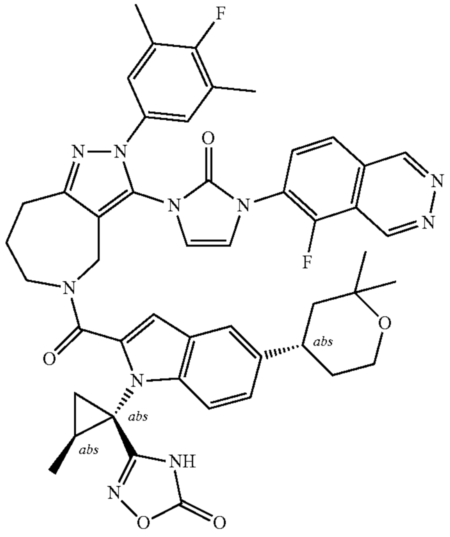 [SMILES: Cc1cc(-n2nc3c(c2-n2ccn(-c4ccc5cnncc5c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C48H46F2N10O5 | 880.96 | 0.1968 |

TABLE 1-continued
| Cpd ID | Structure | MW | EC50 (uM) |
|---|---|---|---|
| Representative compounds and their $EC_{50}$ values | | | |
| 522 | 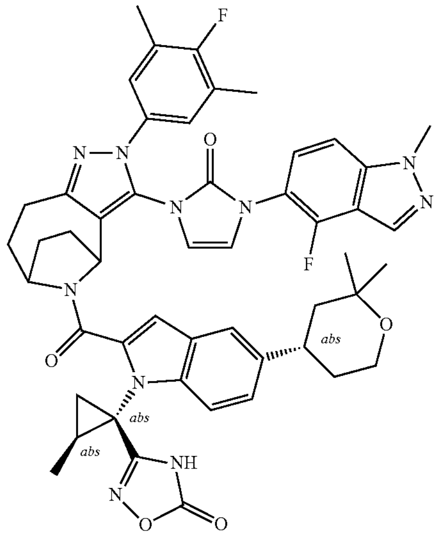 [SMILES: Cc1cc(-n2nc3c(c2-n2ccn(-c4ccc5c(cnn5C)c4F)c2=O)C2CCC(CC3)N2C(=O)c2cc3cc([C@H]4CCOC(C)(C)C4)ccc3n2[C@@]2(c3noc(=O)[nH]3)C[C@@H]2C)cc(C)c1F] C50H50F2N10O5 | 909.01 | 10 |
| 523 | 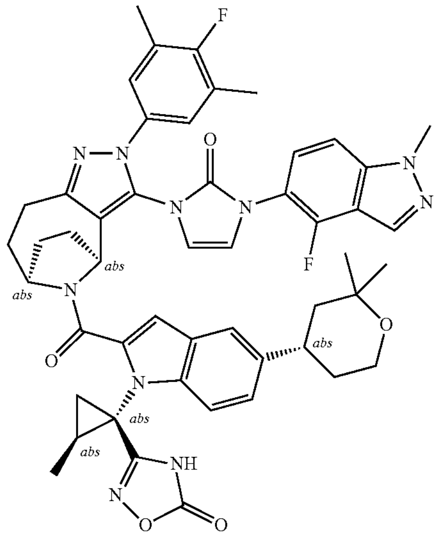 [SMILES: Cc1cc(-n2nc3c(c2-n2ccn(-c4ccc5c(cnn5C)c4F)c2=O)[C@@H]2CC[C@H](CC3)N2C(=O)c2cc3cc([C@H]4CCOC(C)(C)C4)ccc3n2[C@@]2(c3noc(=O)[nH]3)C[C@@H]2C)cc(C)c1F] C50H50F2N10O5 | 909.01 | 0.6174 |

TABLE 1-continued
| Representative compounds and their $EC_{50}$ values | | | |
|---|---|---|---|
| Cpd ID | Structure | MW | EC50 (uM) |
| 524 | 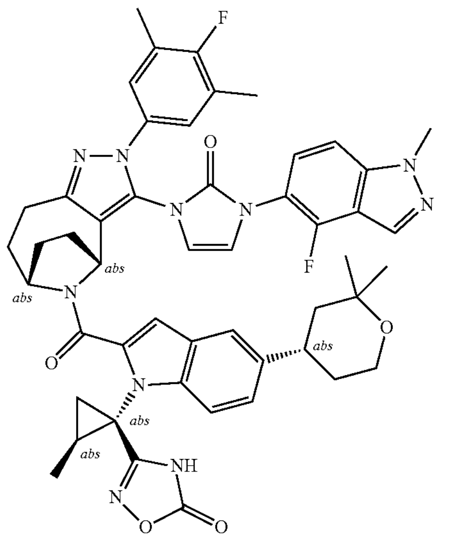 [SMILES: Cc1cc(-n2nc3c(c2-n2ccn(-c4ccc5c(cnn5C)c4F)c2=O)[C@H]2CC[C@@H](CC3)N2C(=O)c2cc3cc([C@H]4CCOC(C)(C)C4)ccc3n2[C@@]2(c3noc(=O)[nH]3)C[C@@H]2C)cc(C)c1F] C50H50F2N10O5 | 909.01 | 10 |
| 525 | 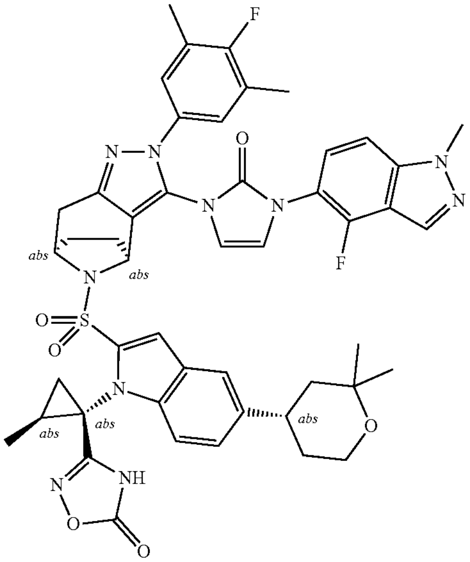 C48H48F2N10O6S | 931.03 | 0.0584 |

TABLE 1-continued
| Representative compounds and their $EC_{50}$ values | | | |
|---|---|---|---|
| Cpd ID | Structure | MW | EC50 (uM) |
| 526 | 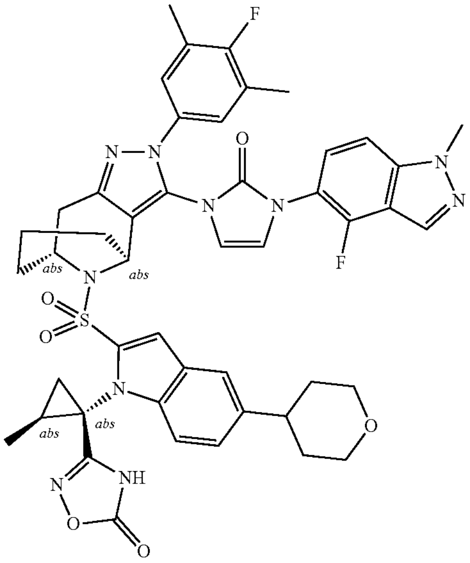 C46H44F2N10O7S | 918.98 | 1.1289 |
| 527 | 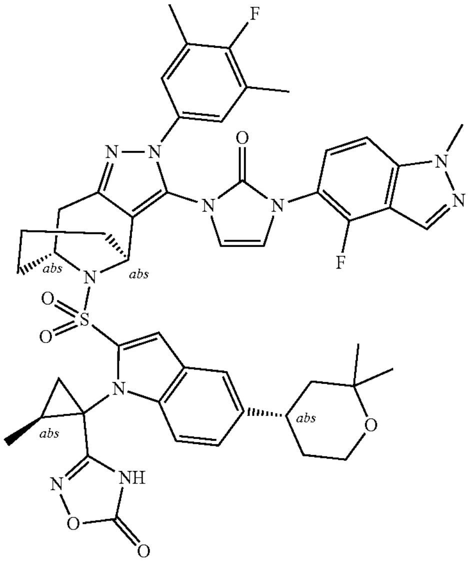 C49H50F2N10O6S | 945.06 | 0.9746 |

TABLE 1-continued
| Representative compounds and their $EC_{50}$ values | | | |
|---|---|---|---|
| Cpd ID | Structure | MW | EC50 (uM) |
| 528 | 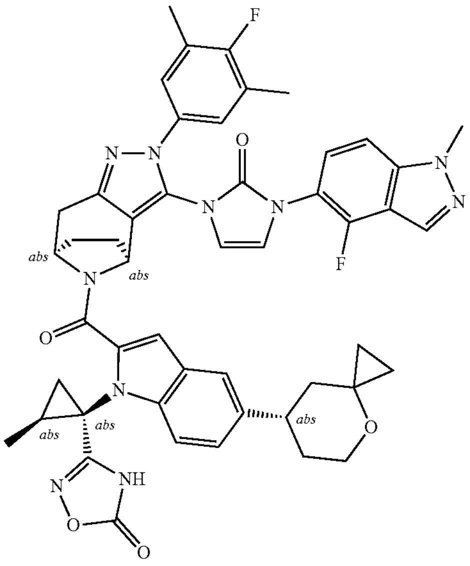 C49H46F2N10O5 | 892.97 | 1.4425 |
| 529 | 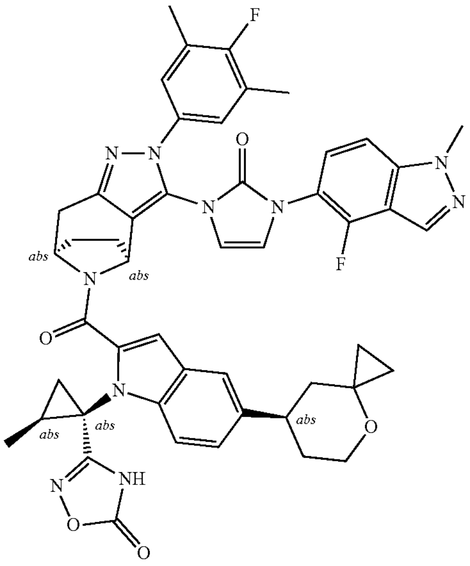 C49H46F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 530 | 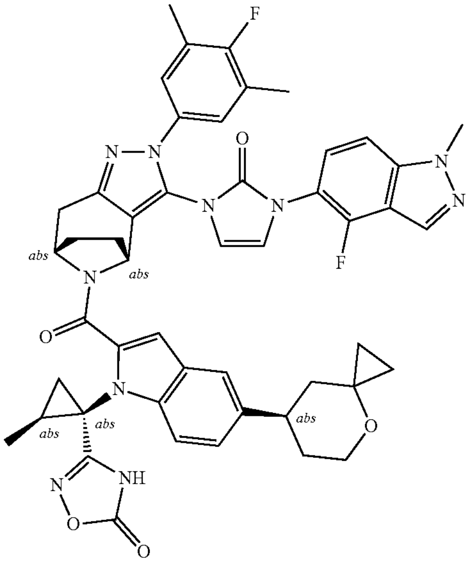 C49H46F2N10O5 | 892.97 | 10 |
| 531 | 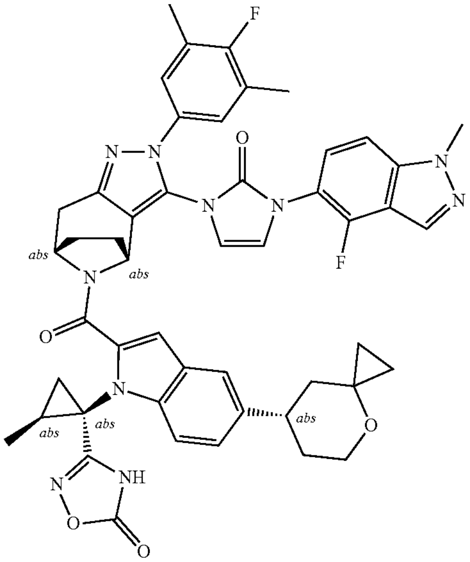 C49H46F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 532 | 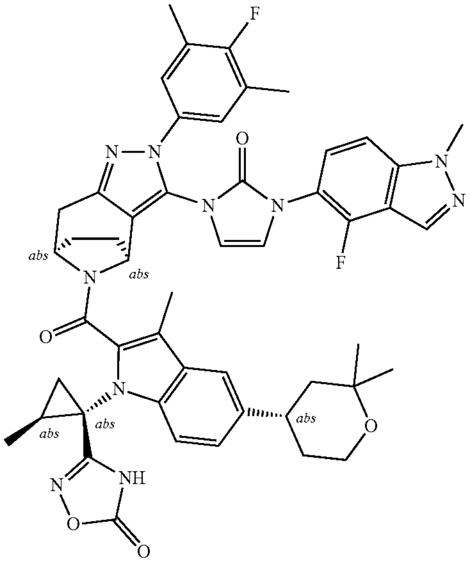 C50H50F2N10O5 | 909.01 | 0.672 |
| 533 | 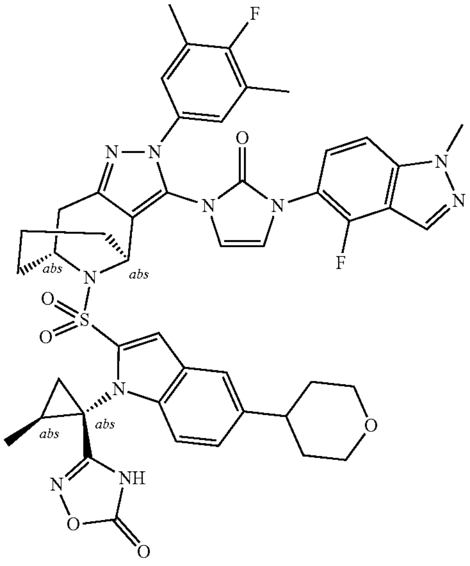 C47H46F2N10O6S | 917.01 | 10.379 |

TABLE 1-continued
| Representative compounds and their $EC_{50}$ values | | | |
|---|---|---|---|
| Cpd ID | Structure | MW | EC50 (uM) |
| 534 | 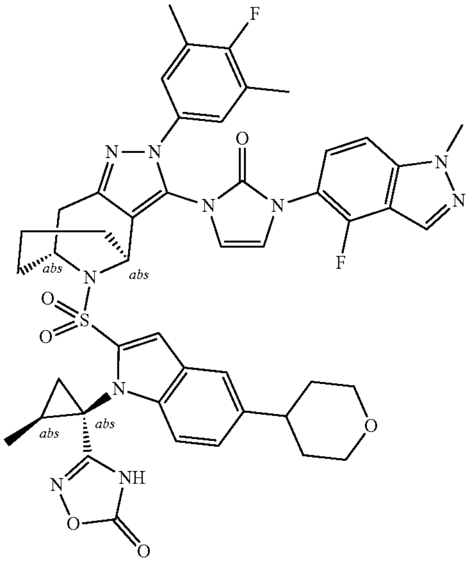 C47H46F2N10O6S | 917.01 | 10 |
| 535 | 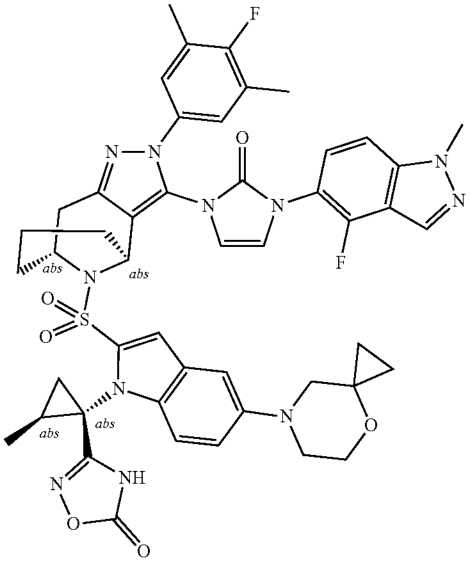 C48H47F2N11O6S | 944.03 | 1.8918 |

TABLE 1-continued
| Representative compounds and their $EC_{50}$ values | | | |
|---|---|---|---|
| Cpd ID | Structure | MW | EC50 (uM) |
| 536 | 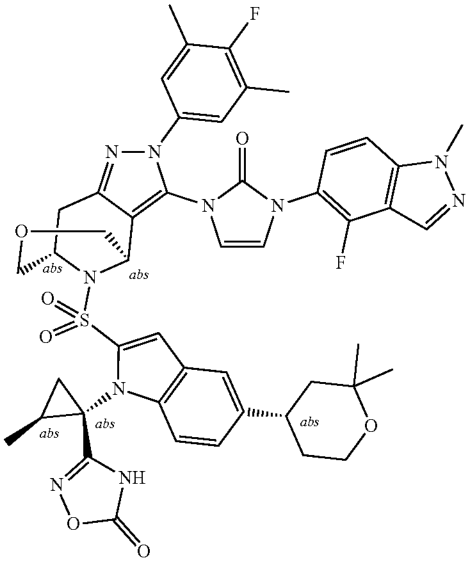 C48H48F2N10O7S | 947.03 | 0.2622 |
| 537 | 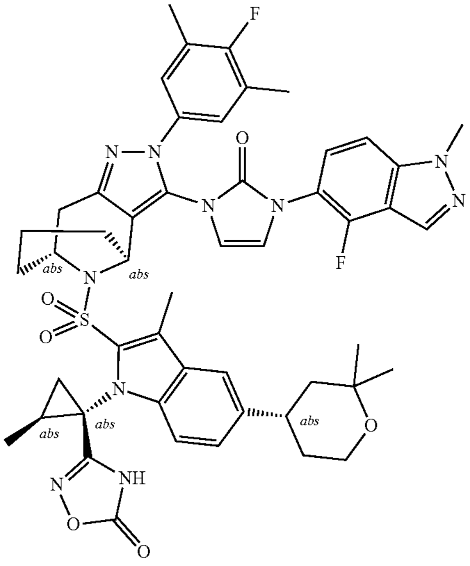 C51H52F2N10O5 | 923.04 | 1.3393 |

TABLE 1-continued
| Representative compounds and their $EC_{50}$ values | | | |
|---|---|---|---|
| Cpd ID | Structure | MW | EC50 (uM) |
| 538 | 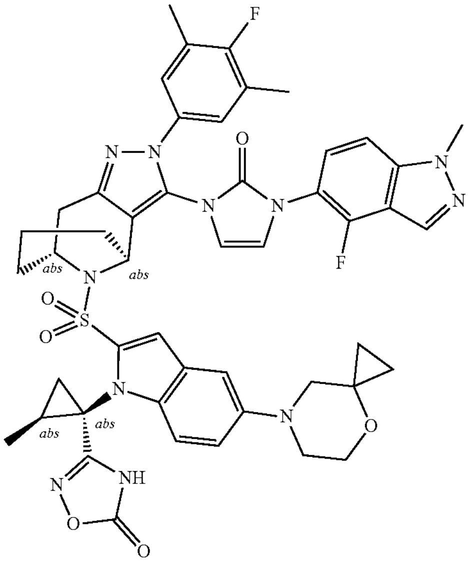 C48H47F2N11O6S | 944.03 | 10 |
| 539 | 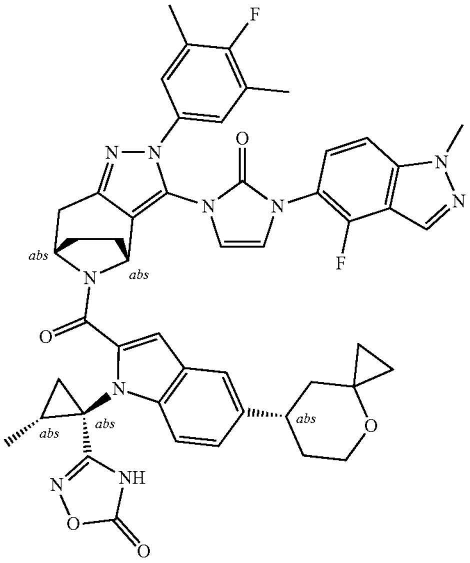 C49H46F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 540 | 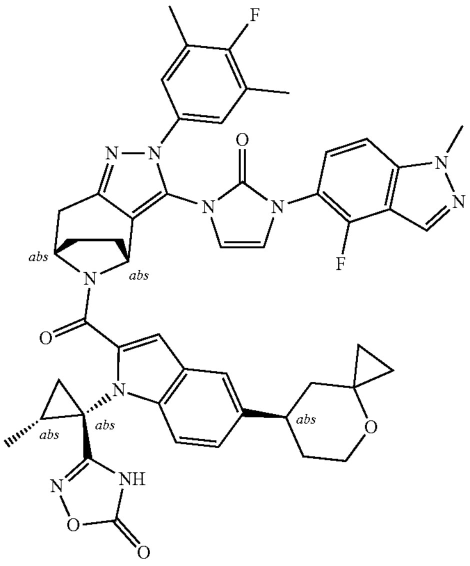 C49H64F2N10O5 | 892.97 | 10 |
| 541 | 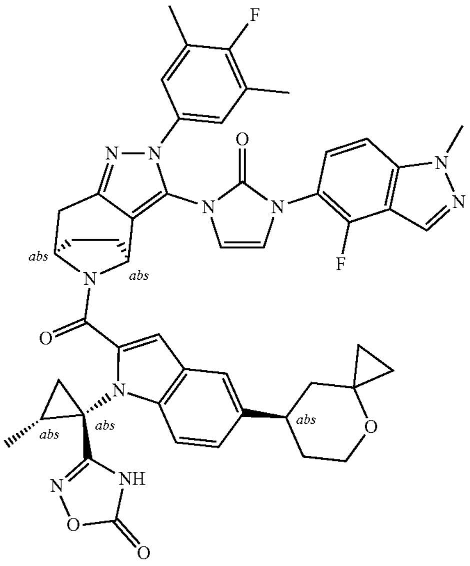 C49H46F2N10O5 | 892.97 | 10 |

TABLE 1-continued
| Representative compounds and their $EC_{50}$ values | | | |
|---|---|---|---|
| Cpd ID | Structure | MW | EC50 (uM) |
| 542 | 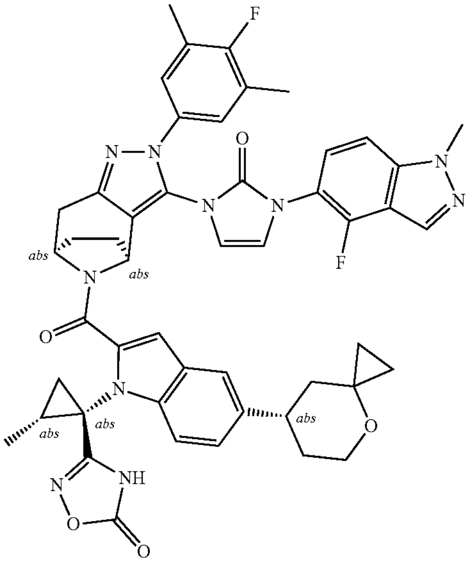 C49H46F2N10O5 | 892.97 | 1.6201 |
| 543 | 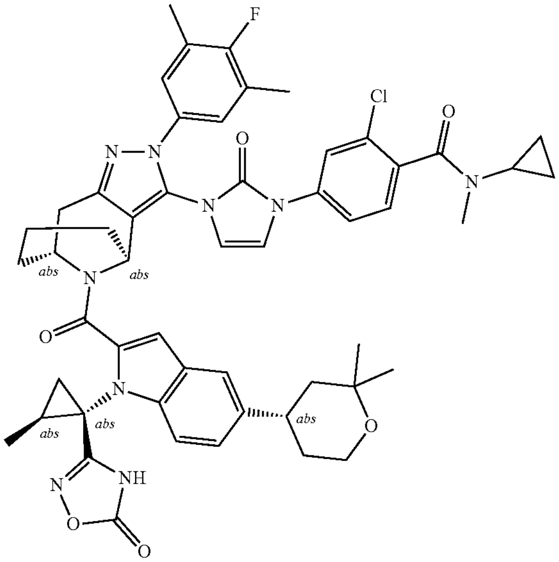 [SMILES: Cc1cc(-n2nc3c(c2-n2ccn(-c4ccc(C(=O)N(C)C5CC5)c(Cl)c4)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H55ClFN9O6 | 968.53 | 10 |

TABLE 1-continued
| Representative compounds and their $EC_{50}$ values | | | |
|---|---|---|---|
| Cpd ID | Structure | MW | EC50 (uM) |
| 544 | 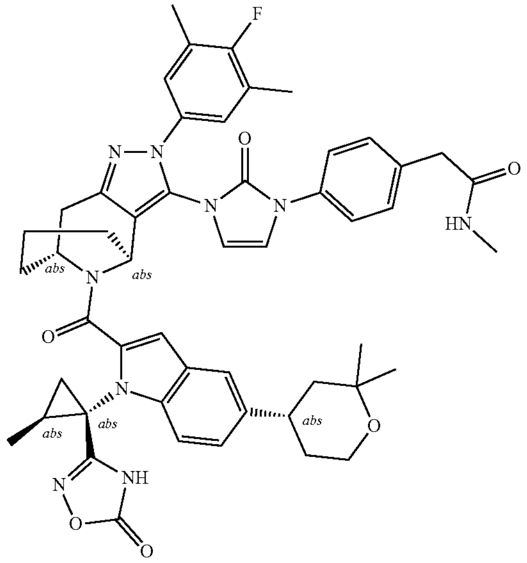 [SMILES: CNC(=O)Cc1ccc(-n2ccn(-c3c4c(nn3-c3cc(C)c(F)c(C)c3)C[C@H]3CCC[C@@H]4N3C(=O)c3cc4cc([C@H]5CCOC(C)(C)C5)ccc4n3[C@@]3(c4noc(=O)[nH]4)C[C@@H]3C)c2=O)cc1] C51H54FN9O6 | 908.05 | 10 |
| 545 | 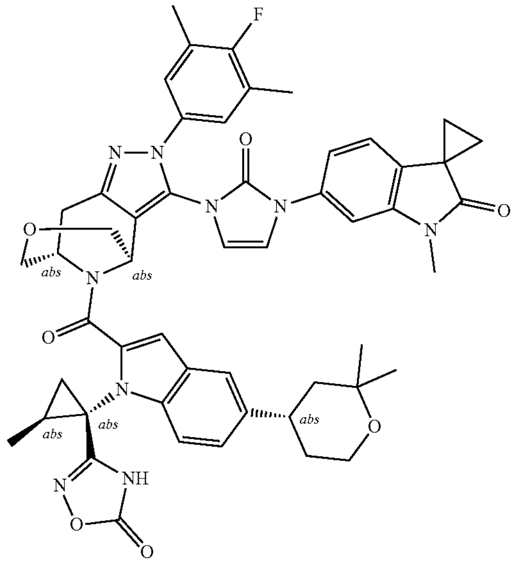 C53H54FN9O6 | 932.07 | 0.3067 |

TABLE 1-continued
| Representative compounds and their $EC_{50}$ values | | | |
|---|---|---|---|
| Cpd ID | Structure | MW | EC50 (uM) |
| 546 | 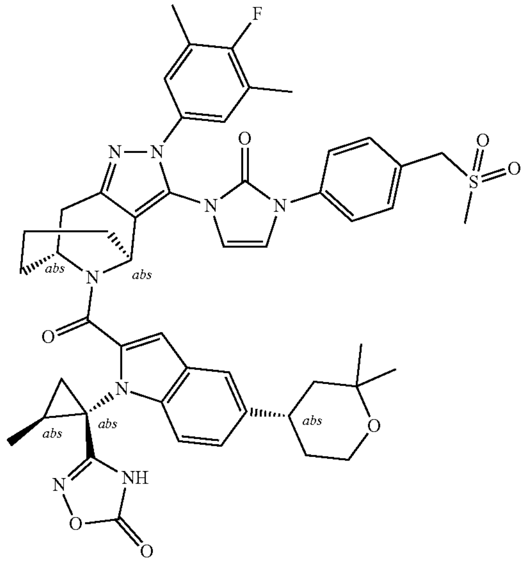 [SMILES: Cc1cc(-n2nc3c(c2-n2ccn(-c4ccc(CS(C)(=O)=O)cc4)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C50H53FN8O7S | 929.08 | 10 |
| 547 | 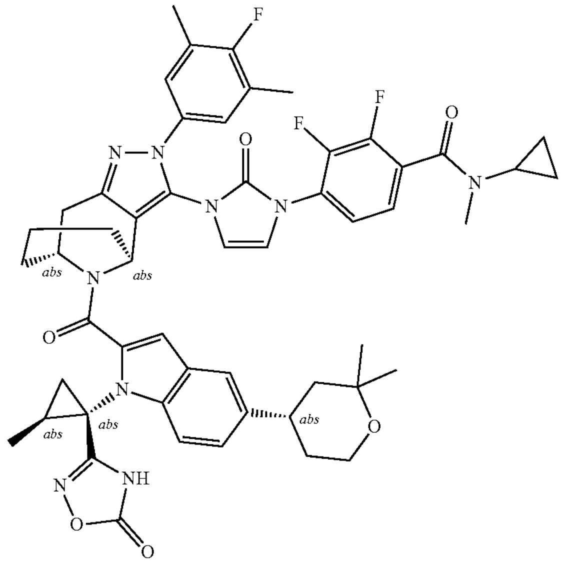 [SMILES: Cc1cc(-n2nc3c(c2-n2ccn(-c4ccc(C(=O)N(C)C5CC5)c(F)c4F)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H54F3N9O6 | 970.07 | 10 |

TABLE 1-continued
| Representative compounds and their $EC_{50}$ values | | | |
|---|---|---|---|
| Cpd ID | Structure | MW | EC50 (uM) |
| 601 | 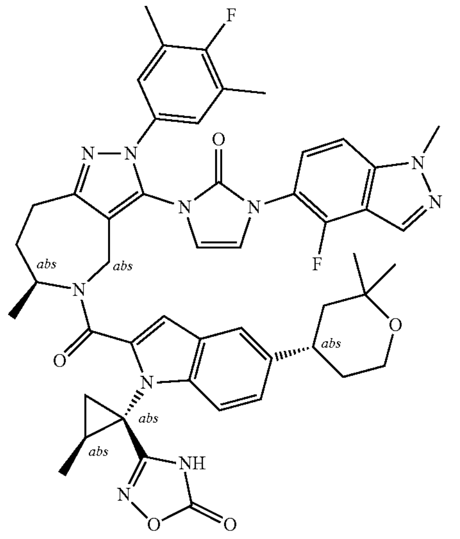 C49H50F2N10O5 | 897 | 10 |
| 602 | 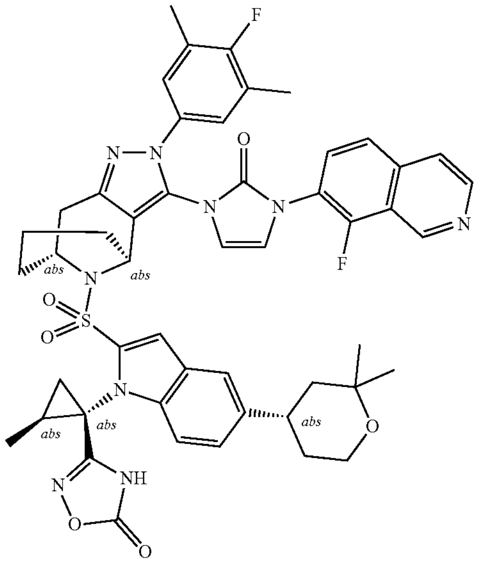 [SMILES: Cc1cc(-n2nc3c(c2-n2ccn(-c4ccc5ccncc5c4F)c2=O)[C@@H]2CCC[C@H](C3)N2S(=O)(=O)c2cc3cc([C@H]4CCOC(C)(C)C4)ccc3n2[C@@]2(c3noc(=O)[nH]3)C[C@@H]2C)cc(C)c1F] C50H49F2N9O6S | 942.06 | 1.1031 |

TABLE 1-continued
| Representative compounds and their $EC_{50}$ values | | | |
|---|---|---|---|
| Cpd ID | Structure | MW | EC50 (uM) |
| 603 | 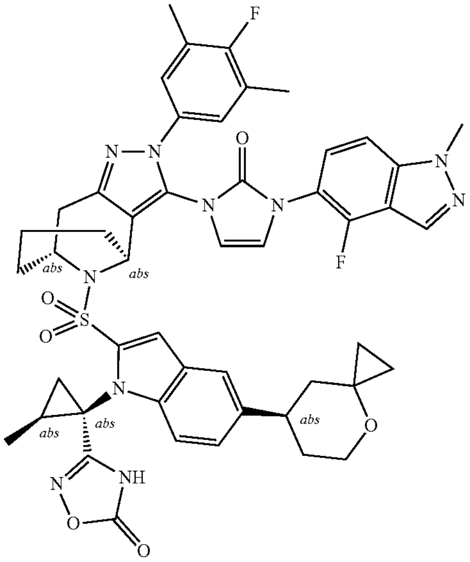 C49H48F2N10O6S | 943.04 | 10 |
| 604 | 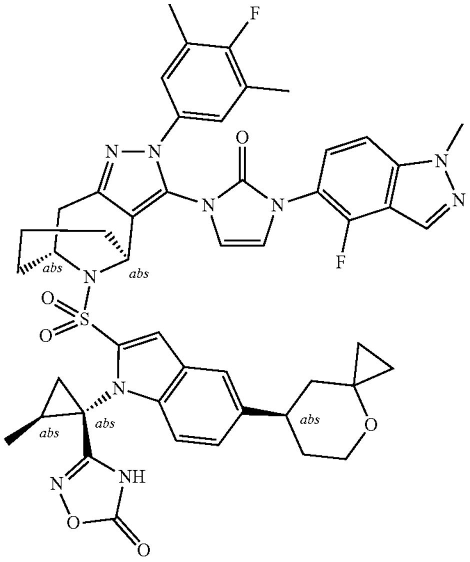 C49H48F2N10O6S | 943.04 | 0.8388 |

TABLE 1-continued
| Representative compounds and their $EC_{50}$ values | | | |
|---|---|---|---|
| Cpd ID | Structure | MW | EC50 (uM) |
| 605 | 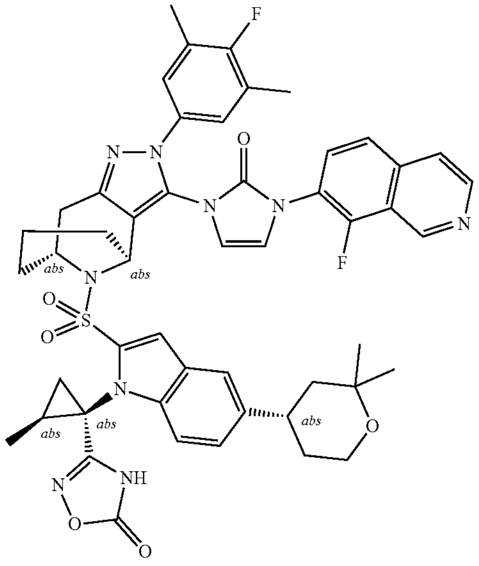 [SMILES: Cc1cc(-n2nc3c(c2-n2ccn(-c4ccc5ccncc5c4F)c2=O)[C@@H]2CCC[C@H](C3)N2S(=O)(=O)c2cc3cc([C@H]4CCOC(C)(C)C4)ccc3n2[C@]2(c3noc(=O)[nH]3)C[C@@H]2C)cc(C)c1F] C50H49F2N9O6S | 942.06 | 10 |
| 606 | 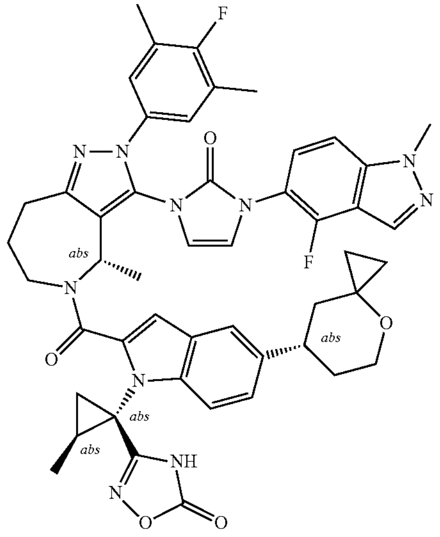 [SMILES: Cc1cc(-n2nc3c(c2-n2ccn(-c4ccc5c(cnn5C)c4F)c2=O)[C@H](C)N(C(=O)c2cc4cc([C@H]5CCOC6(CC6)C5)ccc4n2[C@@]2(c4noc(=O)[nH]4)C[C@@H]2C)CCC3)cc(C)c1F] C49H48F2N10O5 | 894.98 | 0.0804 |

TABLE 1-continued
| Representative compounds and their $EC_{50}$ values | | | |
|---|---|---|---|
| Cpd ID | Structure | MW | EC50 (uM) |
| 607 | 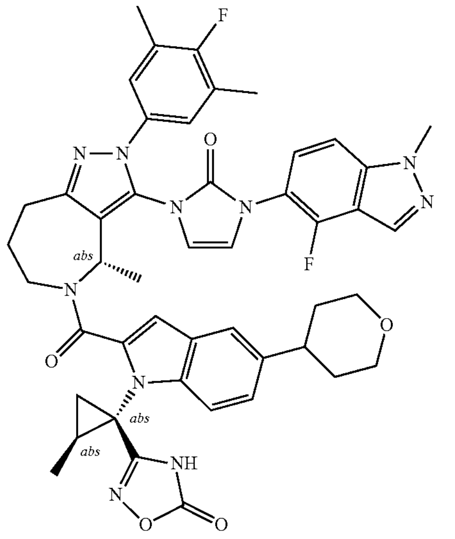 [SMILES: Cc1cc(-n2nc3c(c2-n2ccn(-c4ccc5c(cnn5C)c4F)c2=O)[C@H](C)N(C(=O)c2cc4cc(C5CCOCC5)ccc4n2[C@@]2(c4noc(=O)[nH]4)C[C@@H]2C)CCC3)cc(C)c1F] C47H46F2N10O5 | 868.95 | 0.0537 |
| 608 | 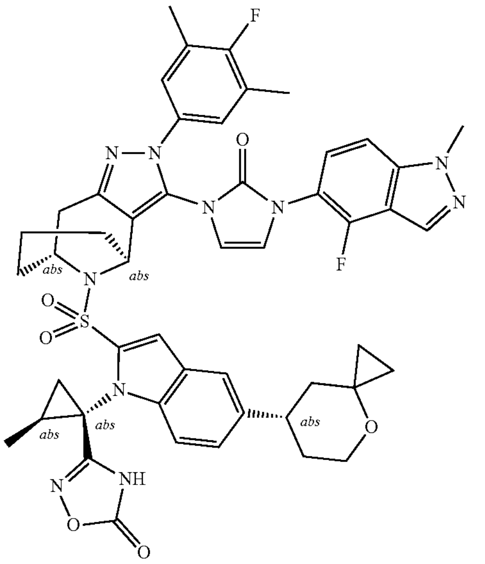 C49H48F2N10O6S | 943.04 | 10 |

TABLE 1-continued
| Representative compounds and their $EC_{50}$ values | | | |
|---|---|---|---|
| Cpd ID | Structure | MW | EC50 (uM) |
| 609 | 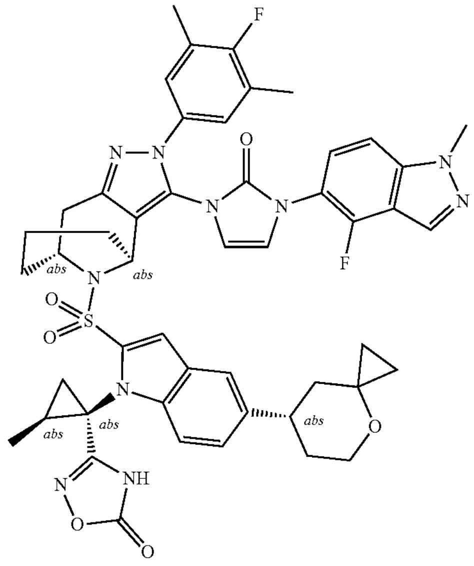 C49H48F2N10O6S | 943.04 | 10 |
| 610 | 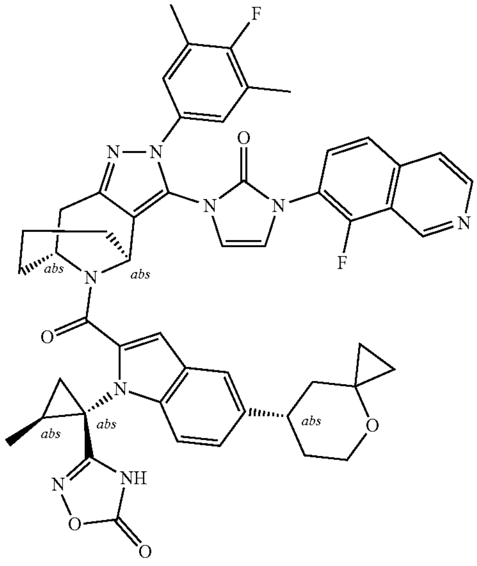 [SMILES: Cc1cc(-n2nc3c(c2-n2ccn(-c4ccc5ccncc5c4F)c2=O)[C@@H]2CCC[C@H](C3)N2C(=O)c2cc3cc([C@H]4CCOC5(CC5)C4)ccc3n2[C@@]2(c3noc(=O)[nH]3)C[C@@H]2C)cc(C)c1F] C51H47F2N9O5 | 903.99 | 0.0008 (Method B1b) |

TABLE 1-continued
| Representative compounds and their $EC_{50}$ values | | | |
|---|---|---|---|
| Cpd ID | Structure | MW | EC50 (uM) |
| 611 | 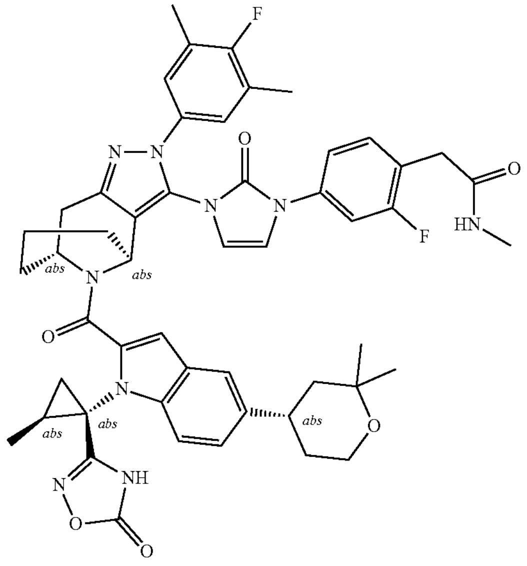 [SMILES: CNC(=O)Cc1ccc(-n2ccn(-c3c4c(nn3-c3cc(C)c(F)c(C)c3)C[C@H]3CCC[C@@H]4N3C(=O)c3cc4cc([C@H]5CCOC(C)(C)C5)ccc4n3[C@@]3(c4noc(=O)[nH]4)C[C@@H]3C)c2=O)cc1F] C51H53F2N9O6 | 926.04 | 0.0051 (Method B1b) |
| 612 | 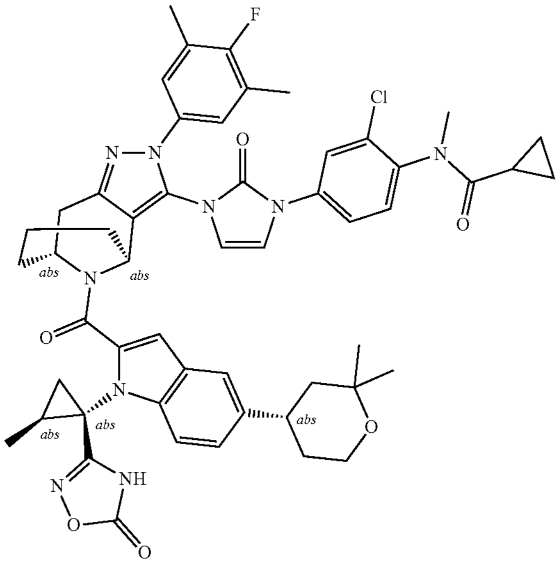 [SMILES: Cc1cc(-n2nc3c(c2-n2ccn(-c4ccc(N(C)C(=O)C5CC5)c(Cl)c4)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H55ClFN9O6 | 968.53 | 0.0019 (Method B1b) |

TABLE 1-continued
| Representative compounds and their $EC_{50}$ values | | | |
|---|---|---|---|
| Cpd ID | Structure | MW | EC50 (uM) |
| 613 | 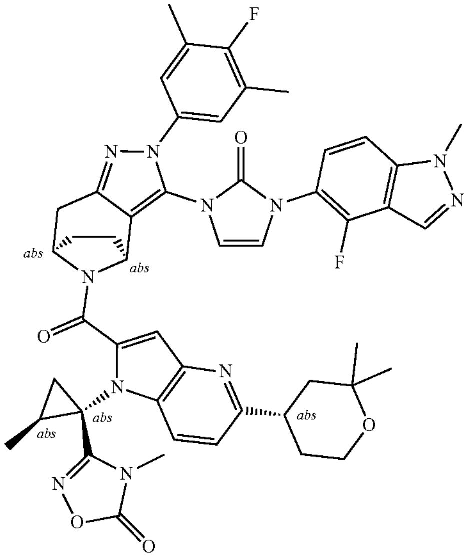 C50H50F2N10O5 | 909.01 | 0.0505 (Method B1b) |
| 614 | 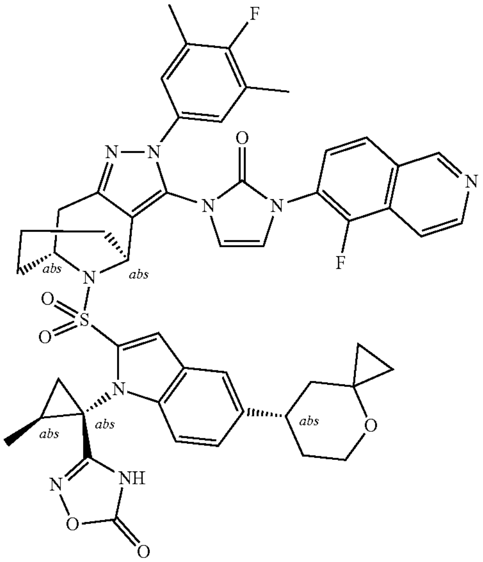 [SMILES: Cc1cc(-n2nc3c(c2-n2ccn(-c4ccc5cnccc5c4F)c2=O)[C@@H]2CCC[C@H](C3)N2S(=O)(=O)c2cc3cc([C@H]4CCOC5(CC5)C4)ccc3n2[C@@]2(c3noc(=O)[nH]3)C[C@@H]2C)cc(C)c1F] C51H47F2N9O5 | 903.99 | 0.0006 (Method B1b) |

TABLE 1-continued
| Representative compounds and their $EC_{50}$ values | | | |
|---|---|---|---|
| Cpd ID | Structure | MW | EC50 (uM) |
| 615 | 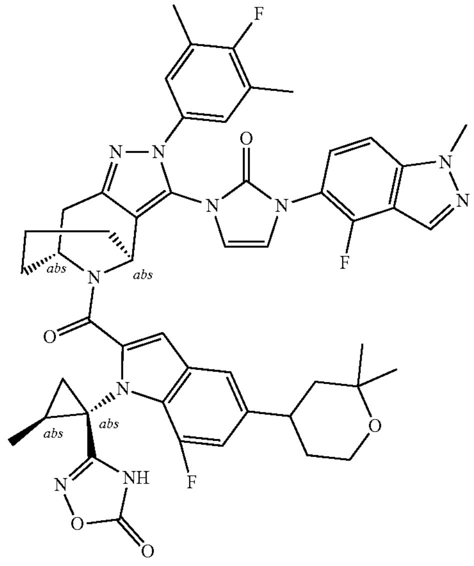 C50H49F3N10O5 | 927 | 0.0142 (Method B1b) |
| 616 | 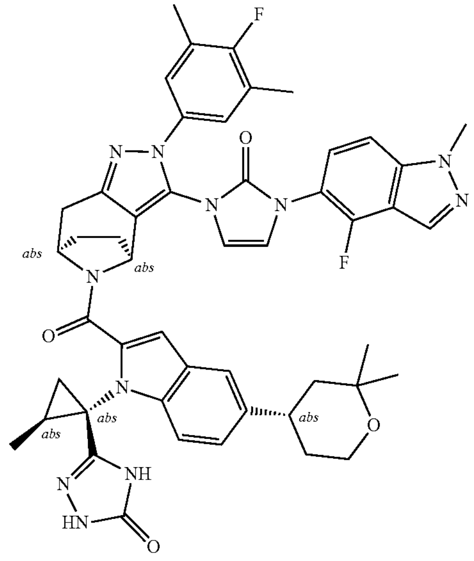 C49H49F2N11O4 | 894 | 0.100 (Method B1b) |

TABLE 1-continued
| Representative compounds and their $EC_{50}$ values | | | |
|---|---|---|---|
| Cpd ID | Structure | MW | EC50 (uM) |
| 617 | 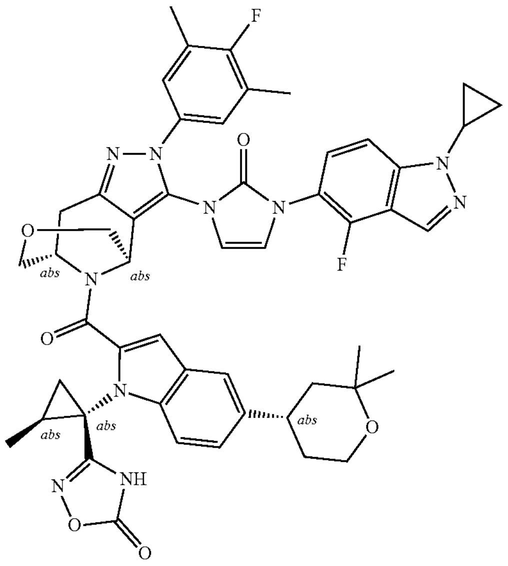 [SMILES: Cc1cc(-n2nc3c(c2-n2ccn(-c4ccc5c(cnn5C5CC5)c4F)c2=O)[C@@H]2COC[C@H](C3)N2C(=O)c2cc3cc([C@H]4CCOC(C)(C)C4)ccc3n2[C@@]2(c3noc(=O)[nH]3)C[C@@H]2C)cc(C)c1F] C51H50F2N10O6 | 937.02 | 0.0025 (Method B1b) |
| 618 | 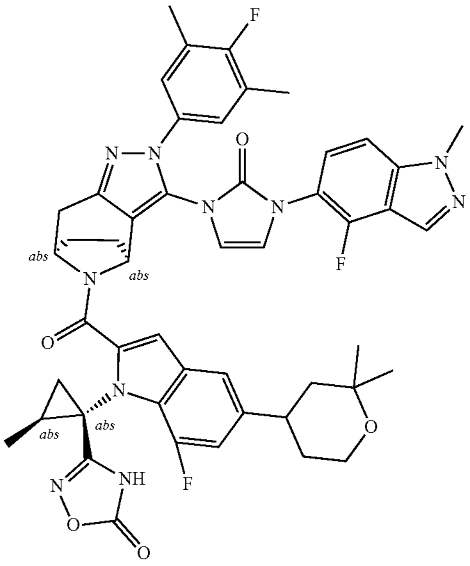 C49H47F3N10O5 | 912.98 | 0.0296 (Method B1b) |

TABLE 1-continued
| Representative compounds and their $EC_{50}$ values | | | |
|---|---|---|---|
| Cpd ID | Structure | MW | EC50 (uM) |
| 619 | 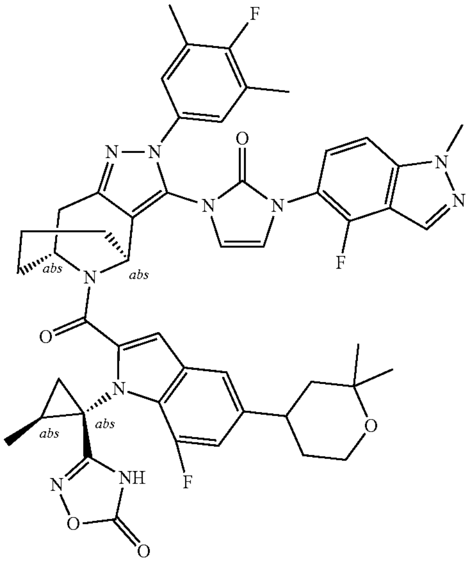 C49H47F3N10O6 | 928.97 | 0.0054 (Method B1b) |
| 701 | 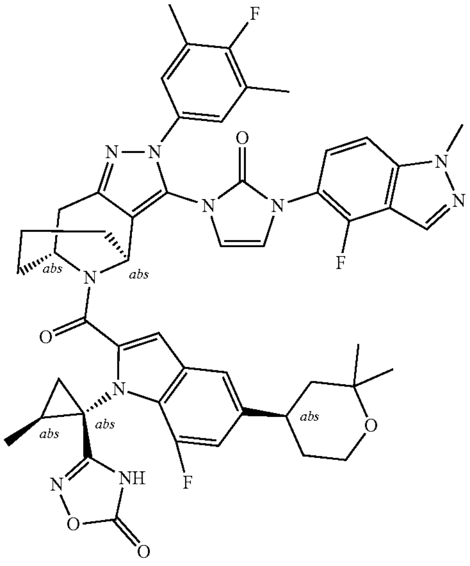 C50H49F3N10O5 | 927 | >0.100 (Method B1b) |

TABLE 1-continued
| Representative compounds and their $EC_{50}$ values | | | |
|---|---|---|---|
| Cpd ID | Structure | MW | EC50 (uM) |
| 702 | 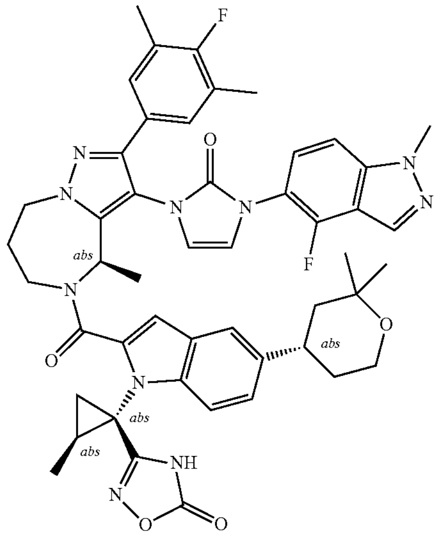 [SMILES: Cc1cc(-c2nn3c(c2-n2ccn(-c4ccc5c(cnn5C)c4F)c2=O)[C@@H](C)N(C(=O)c2cc4cc([C@H]5CCOC(C)(C)C5)ccc4n2[C@@]2(c4noc(=O)[nH]4)C[C@@H]2C)CCC3)cc(C)c1F] C49H50F2N10O5 | 897 | >0.100 (Method B1b) |
| 703 | 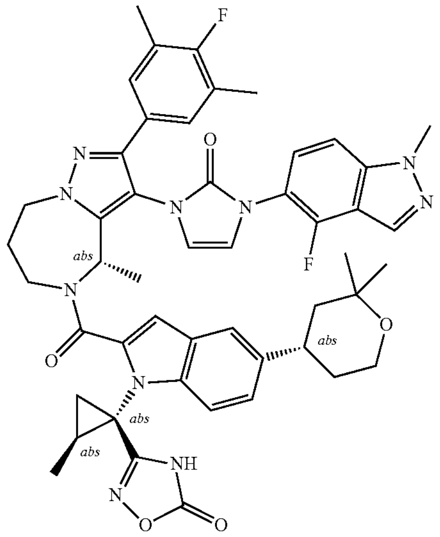 [SMILES: Cc1cc(-c2nn3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CCC3)cc(C)c1F] C49H50F2N10O5 | 897 | 0.0024 (Method B1b) |

TABLE 1-continued
| Representative compounds and their $EC_{50}$ values | | | |
|---|---|---|---|
| Cpd ID | Structure | MW | EC50 (uM) |
| 704 | 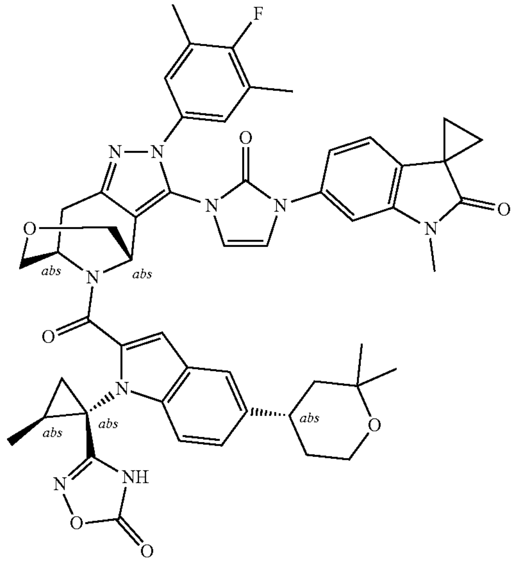 C53H54FN9O6 | 932.07 | |
| 705 | 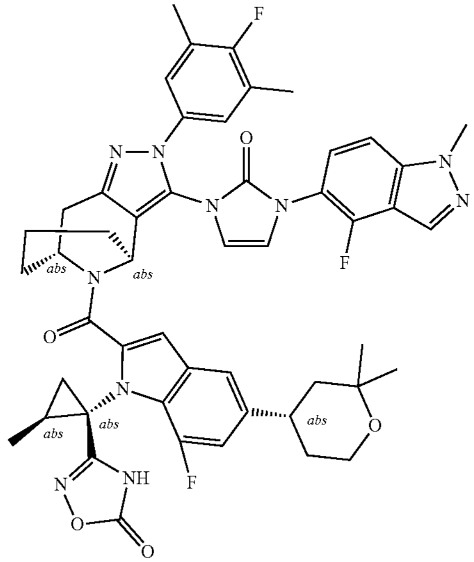 C49H47F3N10O6 | 928.97 | 0.0024 (Method B1b) |

TABLE 1-continued
| Representative compounds and their $EC_{50}$ values | | | |
|---|---|---|---|
| Cpd ID | Structure | MW | EC50 (uM) |
| 706 | 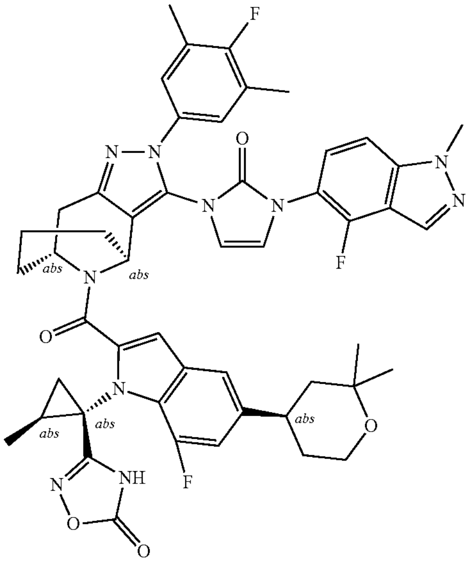 C49H47F3N10O6 | 928.97 | 0.059 (Method B1b) |
| 707 | 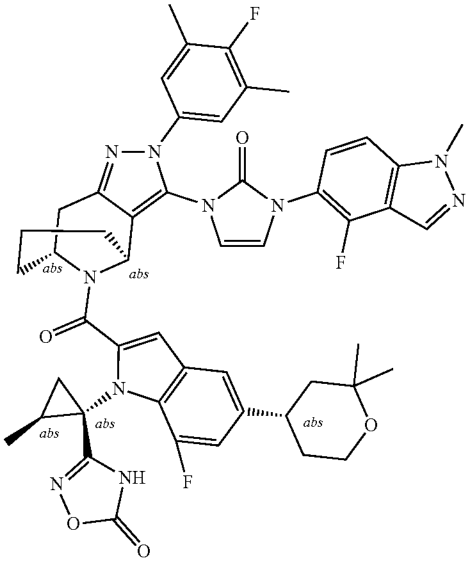 C50H49F3N10O5 | 927 | 0.0025 (Method B1b) |

TABLE 1-continued
| Representative compounds and their $EC_{50}$ values | | | |
|---|---|---|---|
| Cpd ID | Structure | MW | EC50 (uM) |
| 708 | 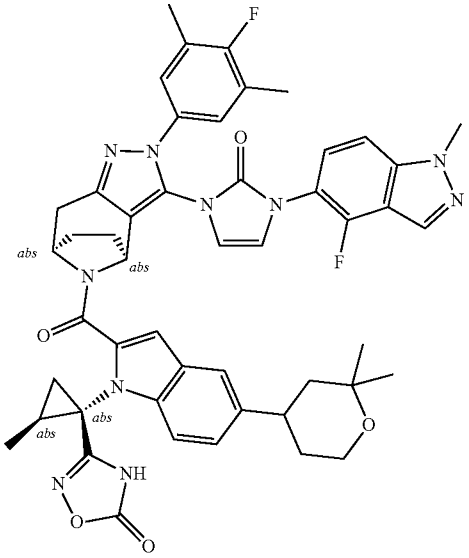 C49H47F3N10O5 | 912.98 | 0.0085 (Method B1b) |
| 709 | 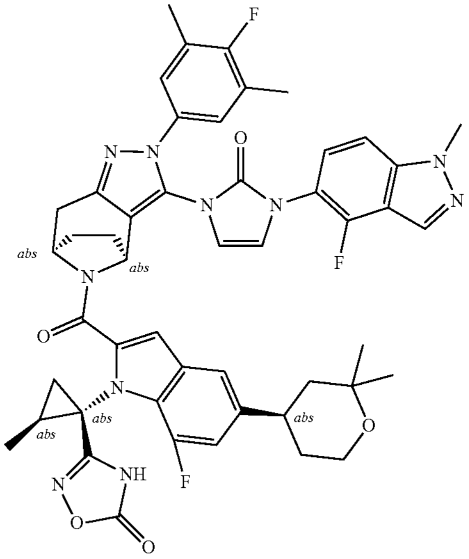 C49H47F3N10O5 | 912.98 | — |

TABLE 1-continued
| Representative compounds and their $EC_{50}$ values | | | |
|---|---|---|---|
| Cpd ID | Structure | MW | EC50 (uM) |
| 710 | 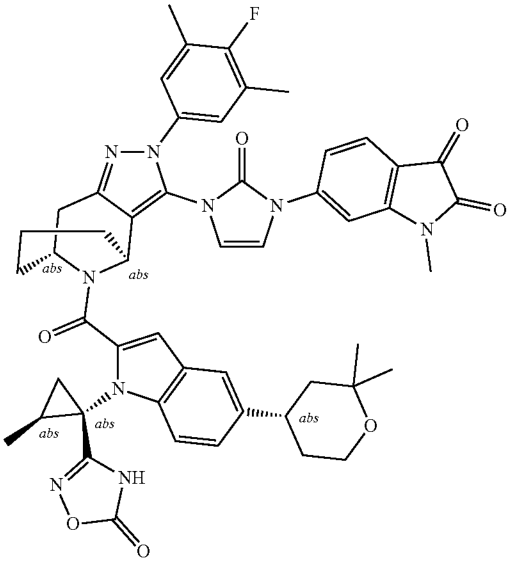 C51H50FN9O7 | 920.02 | 0.004 (Method B1b) |
| 711 | 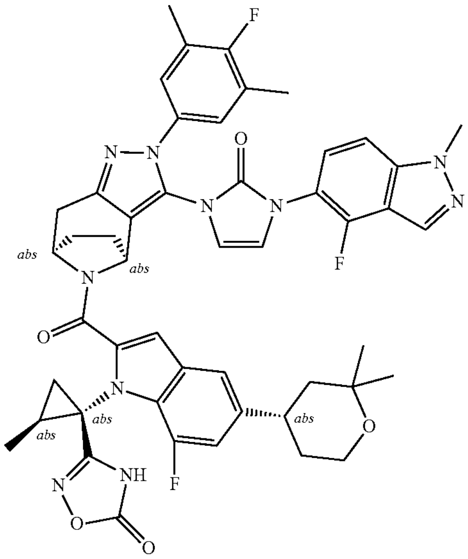 C49H47F3N10O5 | 912.98 | 0.006 (Method B1b) |

TABLE 1-continued
| Representative compounds and their $EC_{50}$ values | | | |
|---|---|---|---|
| Cpd ID | Structure | MW | EC50 (uM) |
| 712 | 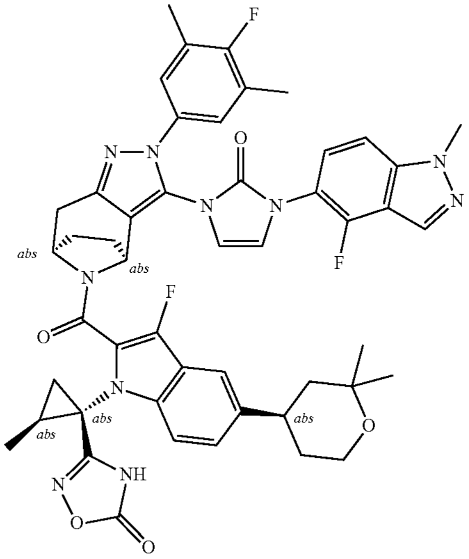 C49H47F3N10O5 | 912.98 | 0.112 (Method B1b) |
| 713 | 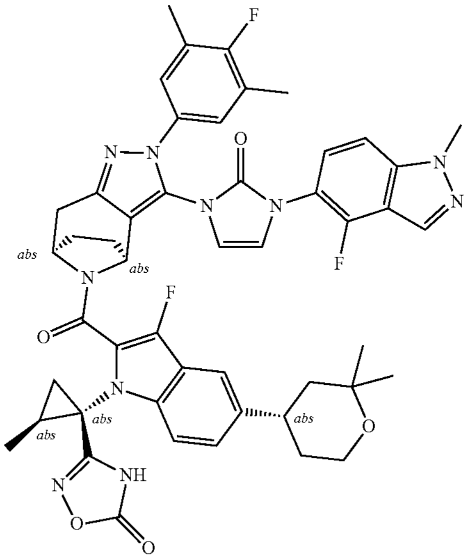 C49H47F3N10O5 | 912.98 | 0.004 (Method B1b) |

TABLE 1-continued
| Representative compounds and their $EC_{50}$ values | | | |
|---|---|---|---|
| Cpd ID | Structure | MW | EC50 (uM) |
| 714 | 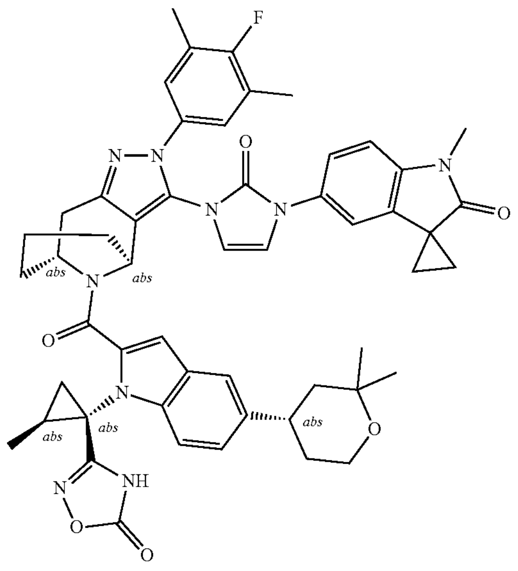 [SMILES: Cc1cc(-n2nc3c(c2-n2ccn(-c4ccc5c(c4)C4(CC4)C(=O)N5C)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H54FN9O6 | 932.07 | 0.002 (Method B1b) |
| 715 | 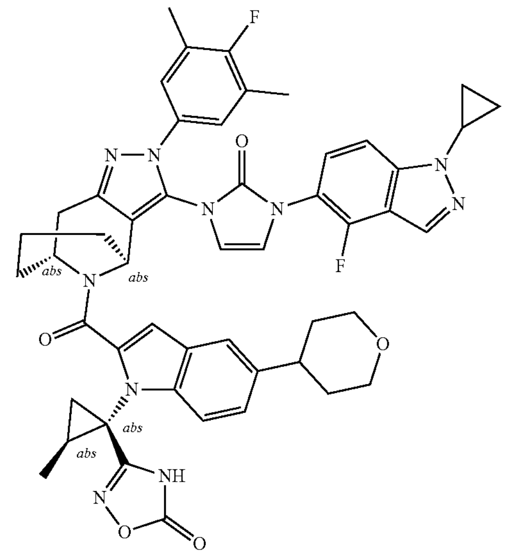 [SMILES: Cc1cc(-n2nc3c(c2-n2ccn(-c4ccc5c(cnn5C5CC5)c4F)c2=O)[C@@H]2CCC[C@H](C3)N2C(=O)c2cc3cc(C4CCOCC4)ccc3n2[C@@]2(c3noc(=O)[nH]3)C[C@@H]2C)cc(C)c1F] C49H46F2N10O6 | 908.97 | 0.004 (Method B1b) |

TABLE 1-continued
| Representative compounds and their $EC_{50}$ values | | | |
|---|---|---|---|
| Cpd ID | Structure | MW | EC50 (uM) |
| 716 | 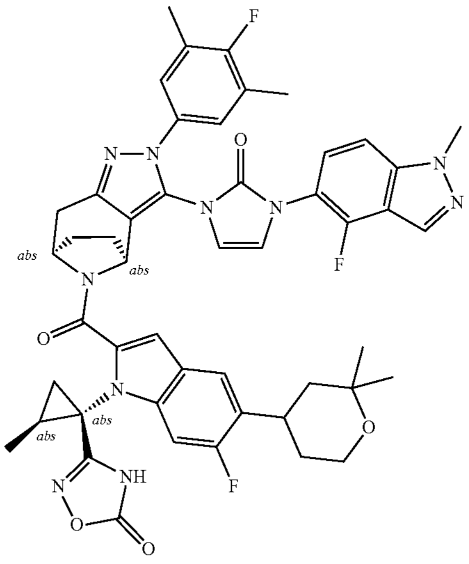 C49H47F3N10O5 | 912.98 | 0.005 (Method B1b) |
TABLE 1c
| Comparative compounds and their $EC_{50}$ values | | | | |
|---|---|---|---|---|
| Cpd ID | Structure | MW | EC50 | EC50 (uM) |
| 405 (Comparative compound) | 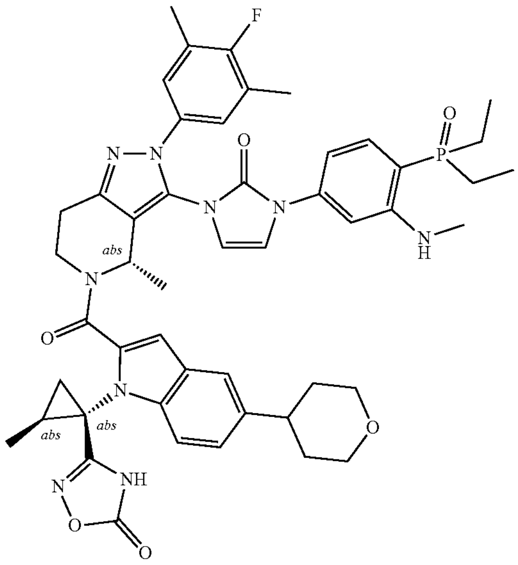 [SMILES: CCP(=O)(CC)c1ccc(-n2ccn(-c3c4c(nn3-c3cc(C)c(F)c(C)c3)CCN(C(=O)c3cc5cc(C6CCOCC6)ccc5n3[C@@]3(c5noc(=O)[nH]5)C[C@@H]3C)[C@H]4C)c2=O)cc1NC] C49H55FN9O6P | 916.01 | *** | 0.0114 |

TABLE 1d
| Cpd ID | Structure | MW | EC50 (uM) | EC50 Ratio |
|---|---|---|---|---|
| Potency comparison of stereoisomer pairs | | | | |
| 35 | 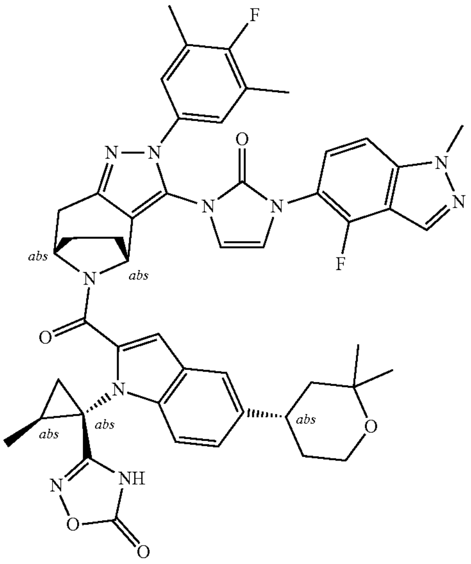 C49H48F2N10O5 | 894.98 | 100 | |
| 36 | 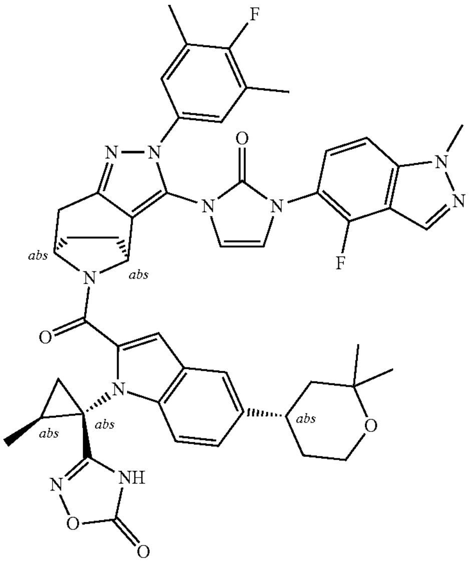 C49H48F2N10O5 | 894.98 | 0.109 | >94 |

TABLE 1d-continued
| Potency comparison of stereoisomer pairs | | | | |
|---|---|---|---|---|
| Cpd ID | Structure | MW | EC50 (uM) | EC50 Ratio |
| 120 | 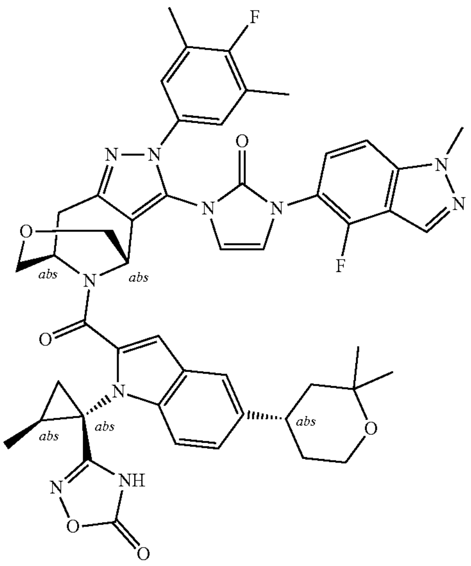 C49H48F2N10O6 | 910.98 | >10 | |
| 121 | 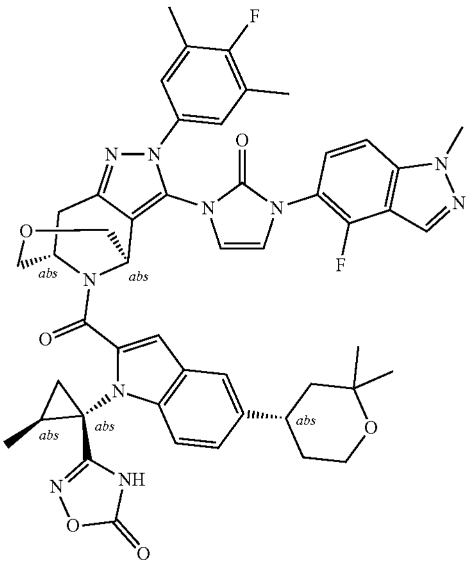 C49H48F2N10O6 | 910.98 | 0.082 | >122 |

TABLE 1d-continued
| Potency comparison of stereoisomer pairs | | | | |
|---|---|---|---|---|
| Cpd ID | Structure | MW | EC50 (uM) | EC50 Ratio |
| 411 | 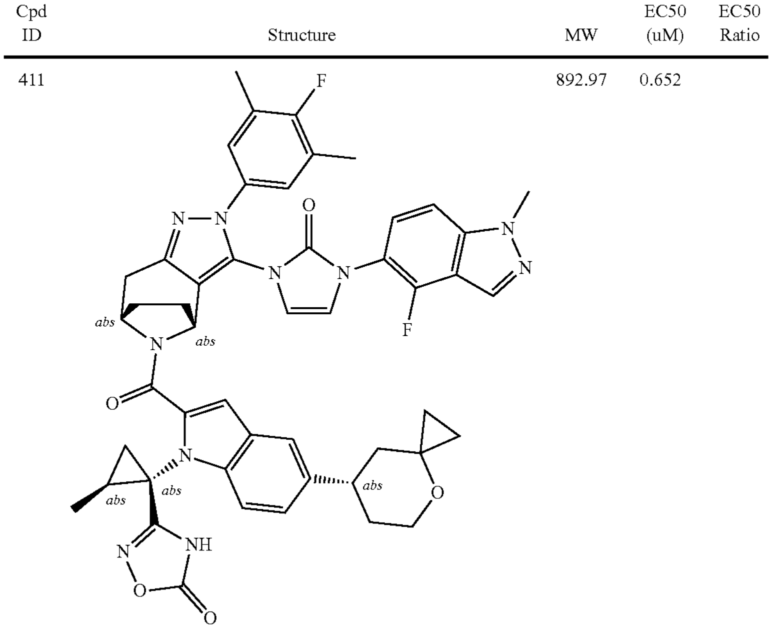 C49H46F2N10O5 | 892.97 | 0.652 | |
| 214 | 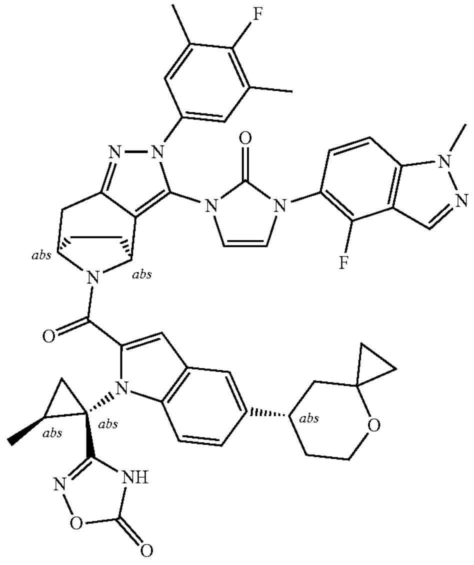 C49H46F2N10O5 | 892.97 | 0.0523 | >13 |

TABLE 1d-continued
| Potency comparison of stereoisomer pairs | | | | |
|---|---|---|---|---|
| Cpd ID | Structure | MW | EC50 (uM) | EC50 Ratio |
| 430 | 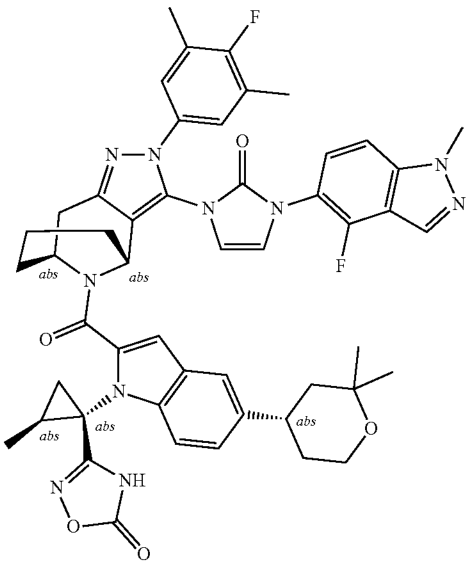 C50H50F2N10O5 | 909.01 | 10 | |
| 433 | 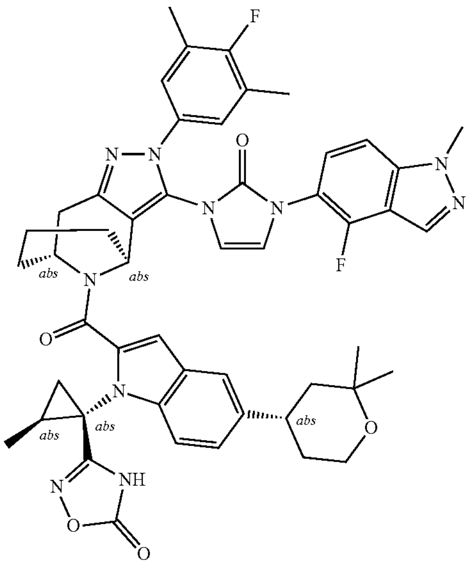 C50H50F2N10O5 | 909.01 | 0.030 | >333 |

TABLE 1d-continued
| Potency comparison of stereoisomer pairs | | | | |
|---|---|---|---|---|
| Cpd ID | Structure | MW | EC50 (uM) | EC50 Ratio |
| 514 | 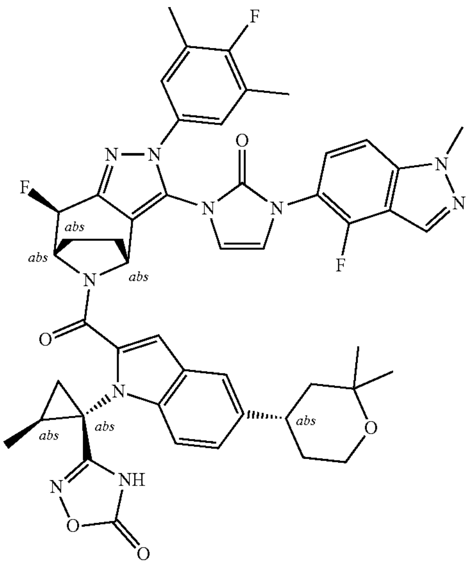 C49H47F3N10O5 | 912.98 | 10 | |
| 512 | 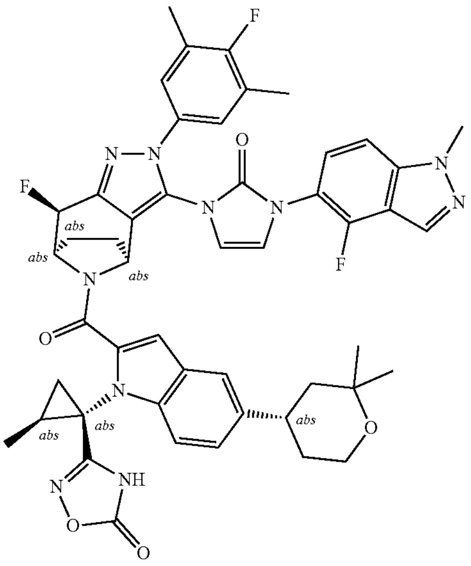 C49H47F3N10O5 | 912.98 | 0.2262 | >83 |

TABLE 1d-continued
| Potency comparison of stereoisomer pairs | | | | |
|---|---|---|---|---|
| Cpd ID | Structure | MW | EC50 (uM) | EC50 Ratio |
| 513 | 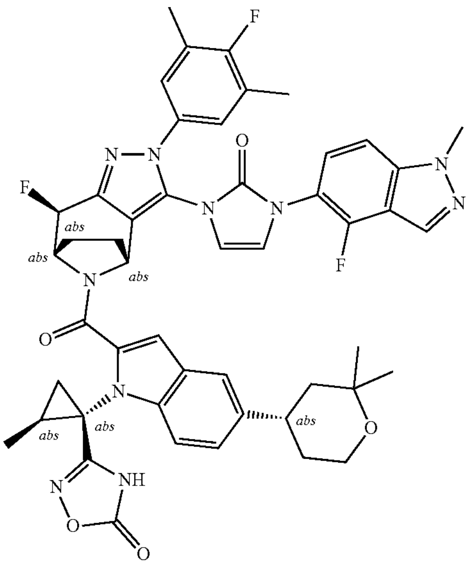 C49H47F3N10O5 | 912.98 | 10 | |
| 515 | 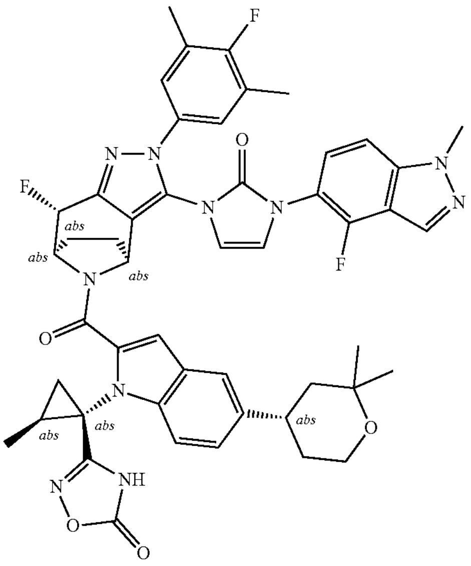 C49H47F3N10O5 | 912.98 | 0.1204 | >44 |

As shown in Table 1d, certain diastereomers show striking potency. In particular, stereochemistry at the central bridged ring can be critical for potency. When depicted as shown in Table 1d, compounds with the bridge atoms configured out of the plane or toward the reader (compounds 35, 120, 411, 430, 513, and 514) showed little or no potency, often with EC50s greater than or equal to 10 μM. In contrast, compounds with the bridge atoms configured into the plane or away from the reader (compounds 36, 121, 214, 433, 515, and 512) showed excellent potency, at less than 1 μM or even much less than 1 μM. The potency ratios were 13-fold or greater.

Example B1c

Glucose-Stimulated Insulin Secretion (GSIS) Assay

Purified islets from healthy or Type 2 diabetic donors (Prodo Laboratory, Inc., Aliso Viejo, CA) were cultured in PIM(S) media (Prodo) with 8 mM or 11 mM glucose in a 37° C. water-jacketed incubator with 5% CO2. The GSIS assay followed published procedure (Zhu et al. 2015; Ho et al. 2023). Briefly, islets were conditioned in Krebs-Ringer bicarbonate buffer (KRB, 111 mM NaCl, 4.8 mM KCl, 25 mM $NaHCO_3$, 2.3 mM $CaCl_2$, 1.2 mM $MgSO_4$, 0.15 mM $Na_2HPO_4$, 1.2 mM $KH_2PO_4$, 10 mM HEPES, 0.2% BSA) containing 2.8 mM glucose for 2 hours with 0.05% DMSO, compound 36 or orforglipron. Size-matched islets were used for each test condition. Islets were washed with KRB once and incubated in fresh KRB containing 2.8 mM glucose with 0.05% DMSO or corresponding compound for one hour to measure the basal insulin secretion in 2.8 mM glucose. Glucose concentration was increased to 11 mM and islets stimulated for one hour in the presence of 0.05% DMSO or corresponding compound to measure stimulated insulin secretion. Supernatants were harvested and insulin secreted under basal and glucose stimulated conditions were quantified using an ELISA kit (ALPCO, Salem, NH). Islets were lysed and genomic DNA was extracted using silicon spin column (Qiagen, Venlo, Netherlands). Insulin secretion was normalized to total genomic DNA.

Figure 1B:
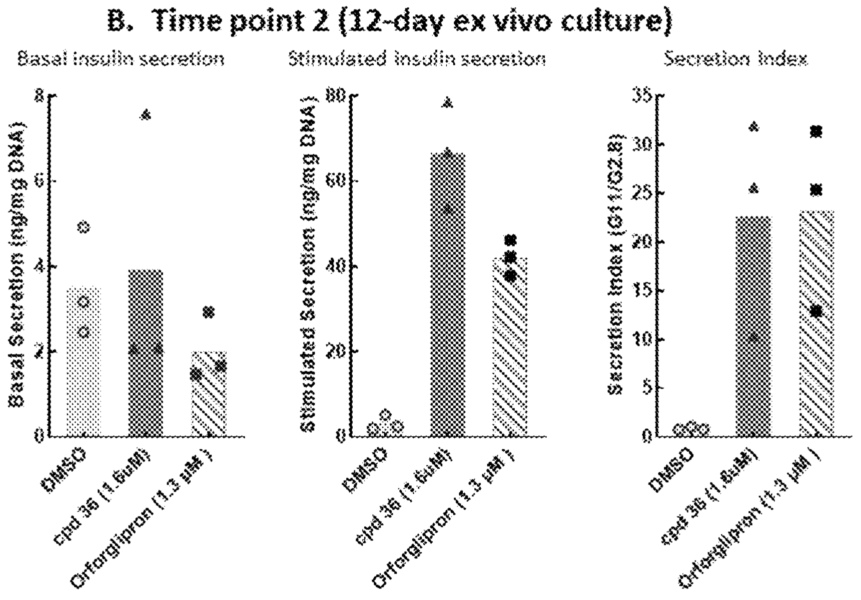
Figure 2:
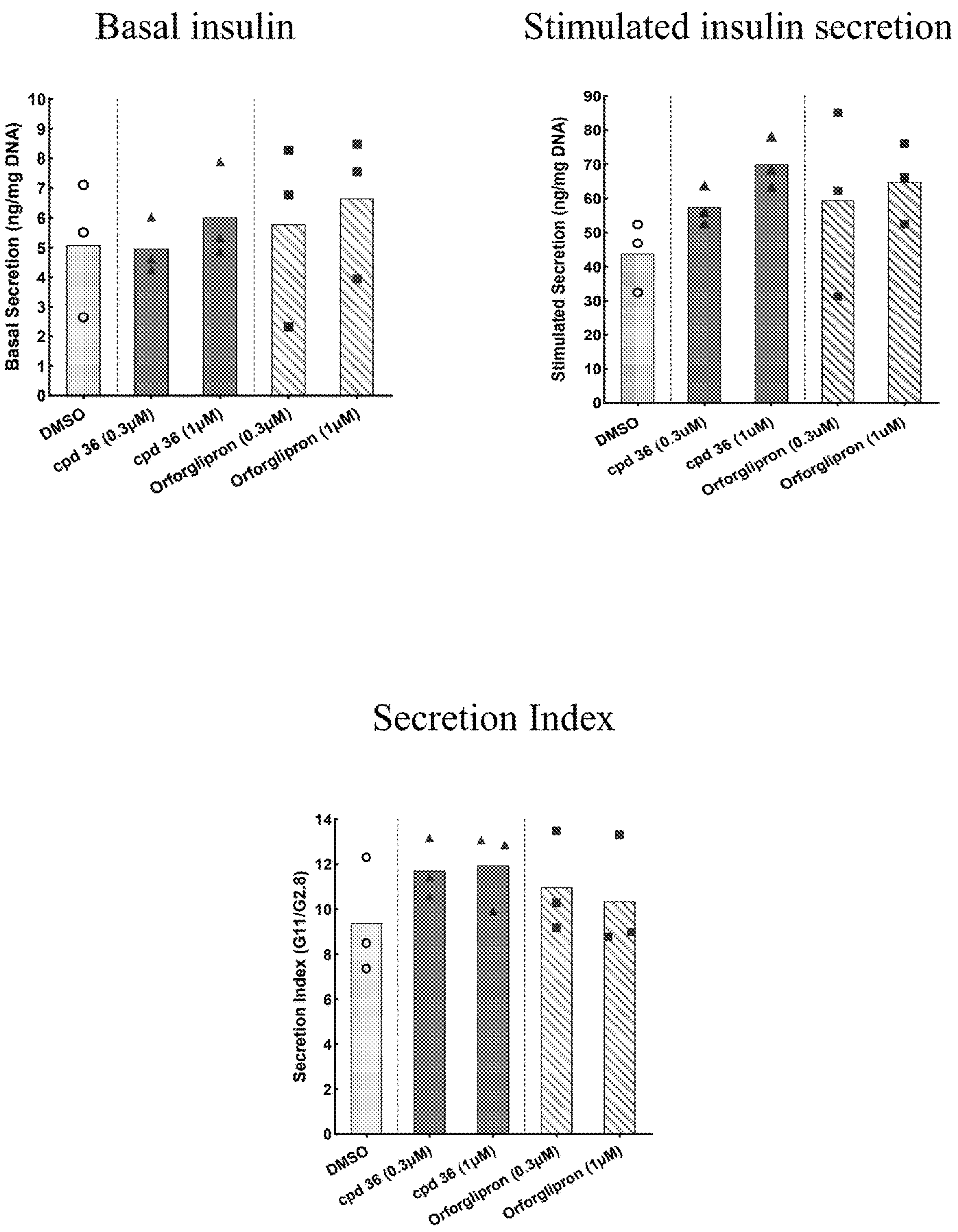
FIG. 2 depicts Compound 36 (cpd 36) increases glucose-stimulated insulin secretion in islets from a non-diabetic donor. Donor islets cultured ex vivo were assayed for GSIS in the presence of compound 36 (cpd 36), orforglipron or DMSO. Basal insulin secretion, stimulated insulin secretion and secretion index were measured.

In ex-vivo cultured islets from a T2D donor, Compound 36 potentiated GSIS (FIG. 1). Compound 36 decreased basal insulin secretion (FIG. 1A) and improved stimulated insulin as well as insulin secretion index (FIGS. 1A and B) and was overall relatively better than orforglipron. Insulin secretion index is the ratio of stimulated insulin secretion at 11 mM glucose/basal insulin secretion at 2.8 mM glucose. In ex-vivo cultured islets from a healthy donor, compound 36 potentiated islets to secrete more insulin upon glucose stimulation compared to DMSO (FIG. 2). (Ho, K. H., A. Jayathilake, Y. Mahircan, A. Nour, A. B. Osipovich, M. A. Magnuson, G. Gu, and I. Kaverina. 2023. CAMSAP2 localizes to the Golgi in islet beta-cells and facilitates Golgi-ER trafficking, *iScience,* 26:105938.Zhu X., R. Hu, M. Brissova, R. W. Stein, A. C. Powers, G. Gu, and I. Kaverina. 2015. Microtubules Negatively Regulate Insulin Secretion in Pancreatic beta Cells, Dev Cell, 34:656-68).

Orforglipron:

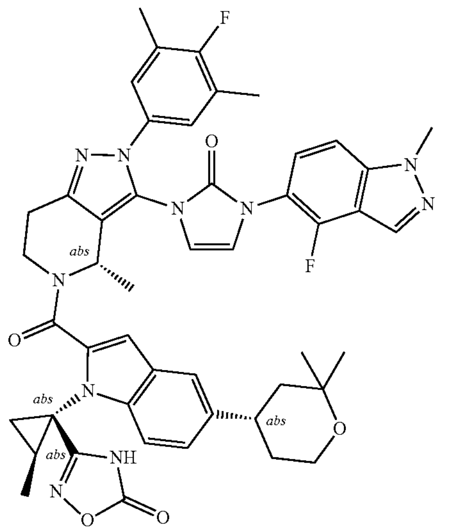 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CC3)cc(C)c1F]

Example B1d

Pharmacokinetic Analysis of the Compound 36, Compound 121, Compound 214, and Orforglipron in Cynomolgus Monkeys Non naïve male cynomolgus monkeys (n=3 monkeys/group) were fasted overnight and fed 4 hours post dose. Compounds of the present application were formulated in 10% polyethylene glycol 400/10% propylene glycol/80% glycine buffer (100 mM glycine, 64 mM NaOH, pH 10).

Figure 3A:
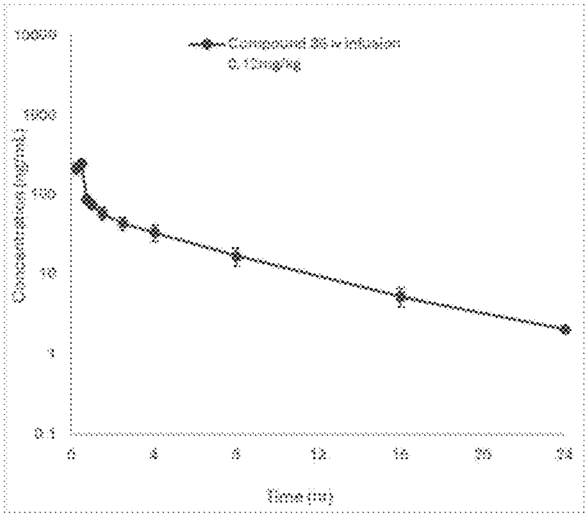
FIG. 3A, FIG. 3B, and FIG. 3C depict pharmacokinetics of Compounds 36 (FIG. 3A), 121 (FIG. 3B), and orforglipron (FIG. 3C) in cynomolgus monkeys when dosed at 0.12 mg/kg iv.
Figure 3B:
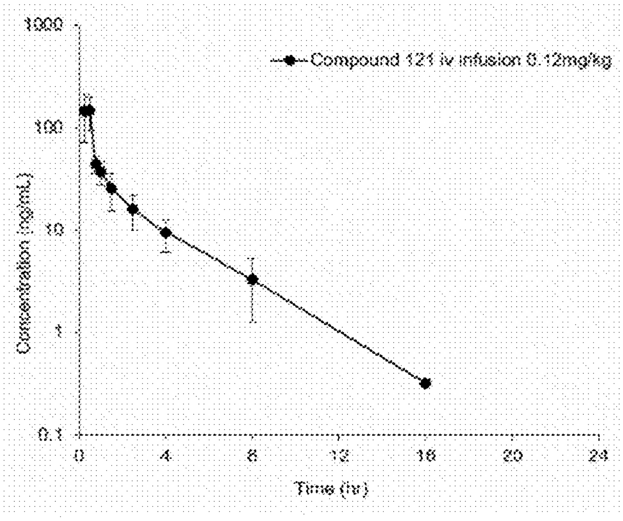
Figure 3C:
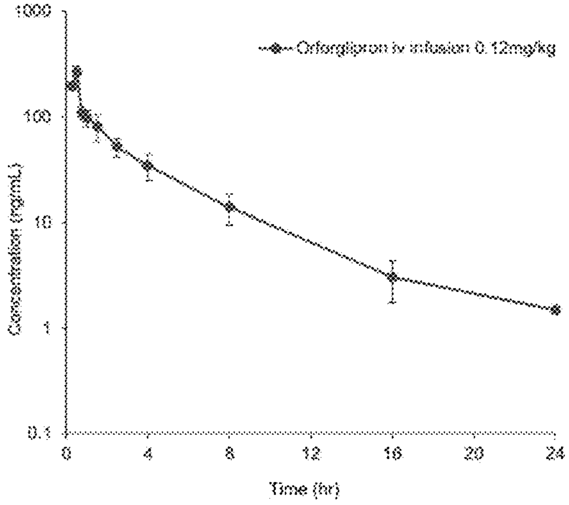
Figure 4A:
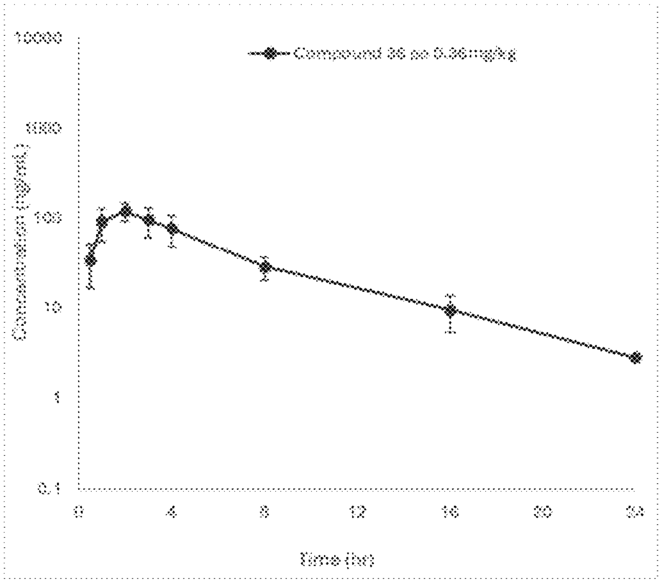
FIG. 4A, FIG. 4B, and FIG. 4C depict pharmacokinetics of Compounds 36 (FIG. 4A), 121 (FIG. 4B), and orforglipron (FIG. 4C) in cynomolgus monkeys when dosed at 0.36 mg/kg po.
Figure 4B:
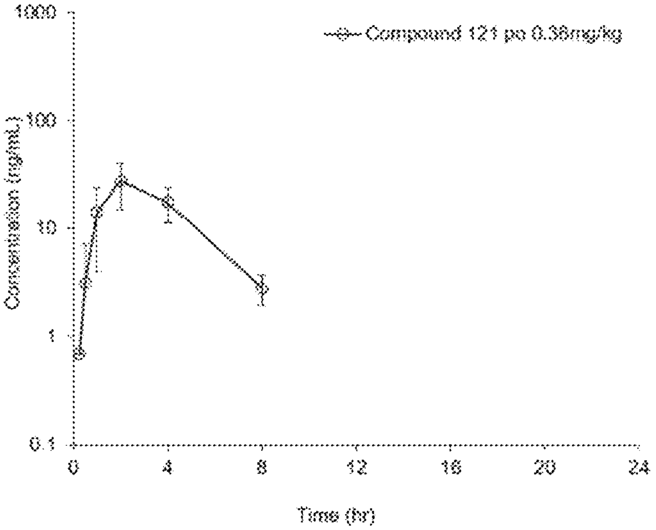
Figure 4C:
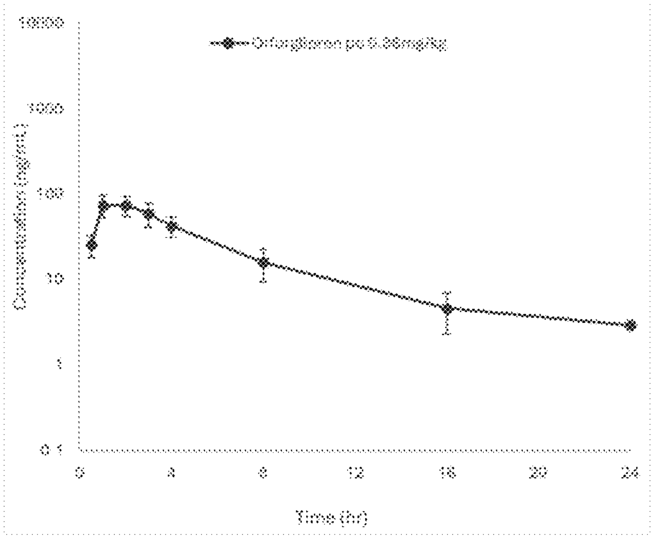
Figure 7A:
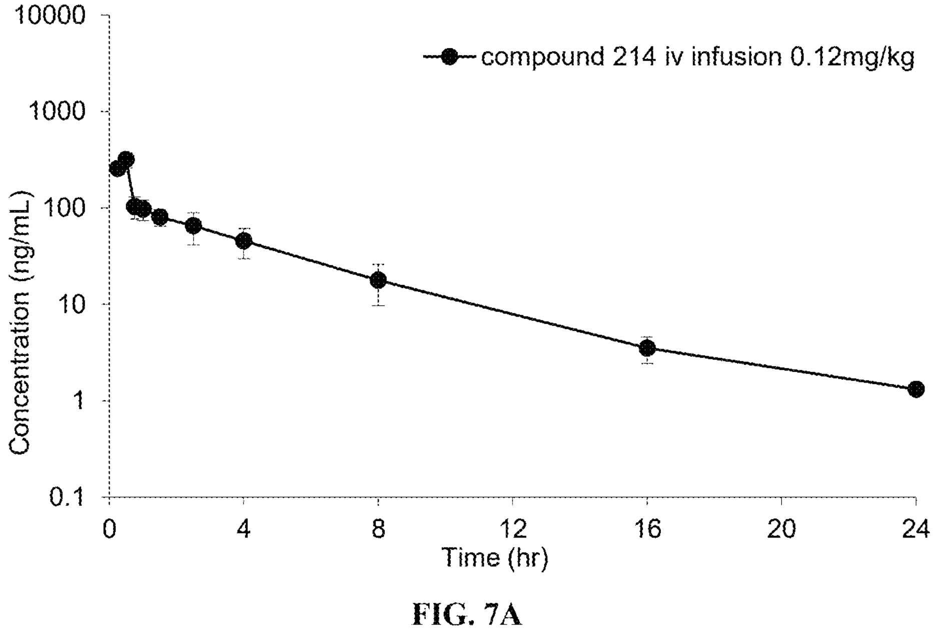
FIG. 7A and FIG. 7B depict pharmacokinetics of Compound 214 in cynomolgus monkeys when dosed at 0.12 mg/kg iv (FIG. 7A) and 0.36 mg/kg po (FIG. 7B).
Figure 7B:
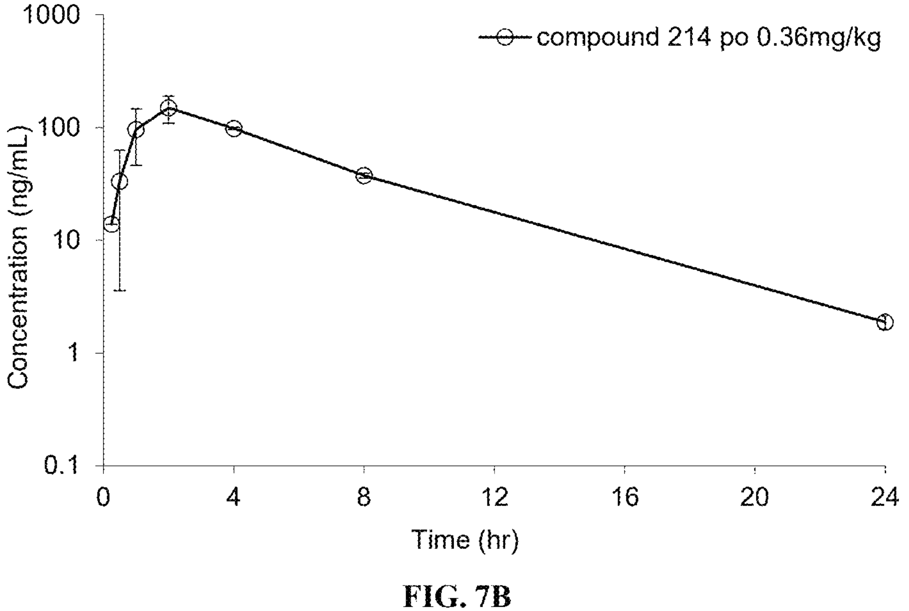

The compound was administered by i.v. infusion for 30 minutes at 0.12 mg/kg (dose volume 1 mL/kg at a speed of 2 mL/kg/h) or orally doses of 0.36 mg/kg. Blood samples were collected pre-dose and 0.25, 0.5 (just before the infusion is stopped), 0.75, 1, 1.5, 2.5, 4, 8, 16, 24 hr post dose for i.v. administration group. Blood samples were also collected pre-dose, 0.5, 1, 2, 3, 4, 8, 16 and 24 hr after administration in orally dosing group. Compound concentrations were determined by LCMS MS-31 (Triple Quad 6500+), which had a lower limit of quantification of 2 ng/mL. Pharmacokinetic parameters were estimated by non-compartmental model using WinNonlin (Phoenix 64 WinNonlin 8.2) and shown in Table B1c. The time profile of the plasma concentrations for the compounds are shown in FIGS. 3 (A, B, C, iv), 4 (A, B, C, po), and FIG. 7 (#214 A, B, iv and po). At the same doses (iv 0.12 mg/kg and po 0.36 mg/kg), compound 36 showed significantly higher exposure and better oral bioavailability than Orforglipron.

TABLE B1c

Pharmacokinetics parameters of compounds 36, 121, compound 214, and orforglipron in cynomolgus monkeys

| Compound ID | Dose (mg/kg) | Cmax (ng/mL) | Tmax (h) | AUC inf (ng*h/mL | CL (L/h/kg) | Vdss (L/kg) | $T_{1/2}$ (h) | Oral F (%) |
|---|---|---|---|---|---|---|---|---|
| 36 | 0.12 (iv) | — | — | 512 | 0.239 | 1.13 | 4.55 | — |
| 121 | 0.12 (iv) | — | — | 182 | 0.681 | 1.66 | 2.26 | — |
| 214 | 0.12 (iv) | — | — | 619 | 0.204 | 0.770 | 3.66 | — |
| Orforglipron | 0.12 (iv) | — | — | 517 | 0.239 | 0.846 | 3.70 | — |

TABLE B1c-continued

Pharmacokinetics parameters of compounds 36, 121, compound 214, and orforglipron in cynomolgus monkeys

| Compound ID | Dose (mg/kg) | Cmax (ng/mL) | Tmax (h) | AUC inf (ng*h/mL | CL (L/h/kg) | Vdss (L/kg) | $T_{1/2}$ (h) | Oral F (%) |
|---|---|---|---|---|---|---|---|---|
| 36 | 0.36 (po) | 121 | 2.00 | 771 | — | — | 4.22 | 50.2 |
| 121 | 0.36 (po) | 28.0 | 2.00 | 121 | — | — | 1.94 | 22.2 |
| 214 | 0.36 (po) | 149 | 2.00 | 1003 | — | — | 3.56 | 54.0 |
| Orforglipron | 0.36 (po) | 79.5 | 1.33 | 456 | — | — | 4.24 | 29.4 |

Example B1e

Figure 5A:
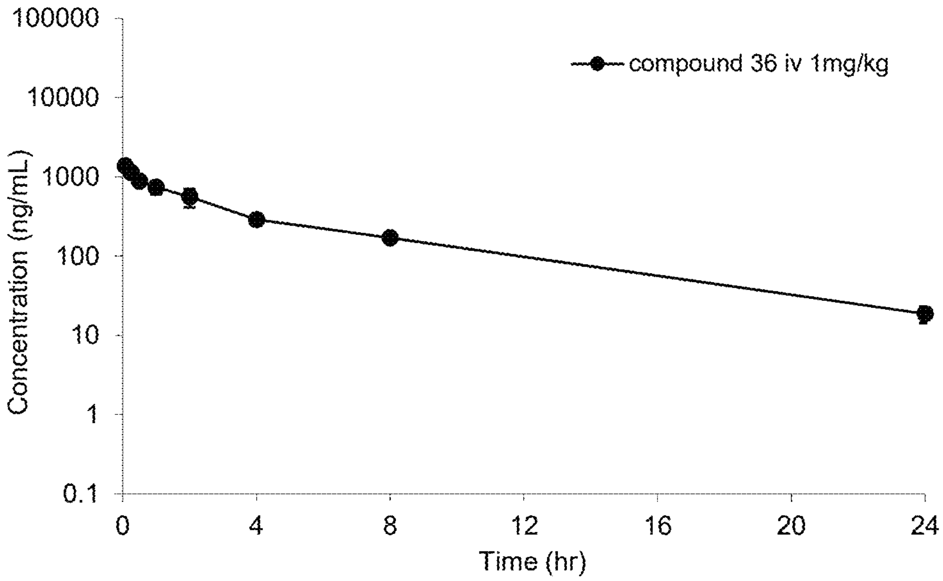
FIG. 5A, FIG. 5B, and FIG. 5C depict pharmacokinetics of Compounds 36 (FIG. 5A), 121 (FIG. 5B), and orforglipron (FIG. 5C) in male SD rats when dosed at 1 mg/kg iv.
Figure 5B:
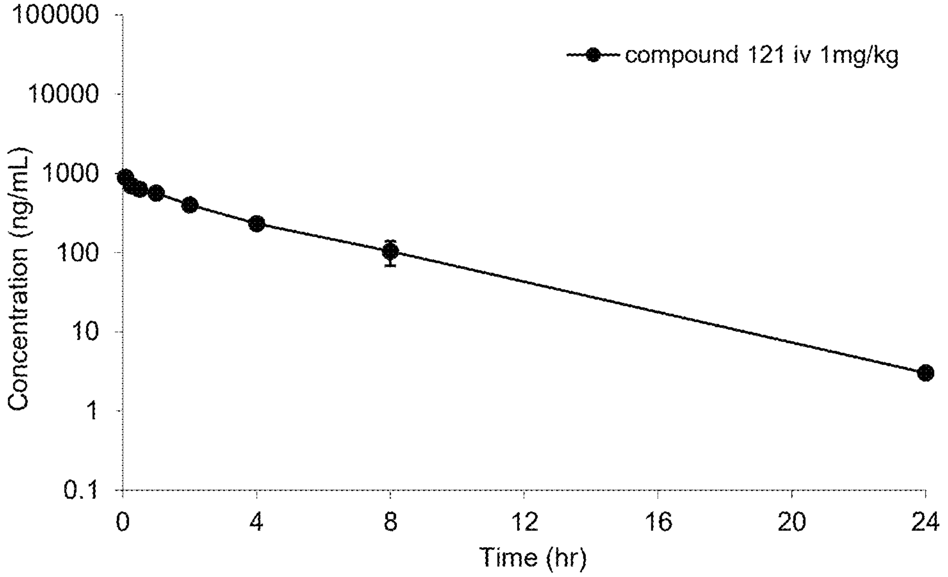
Figure 5C:
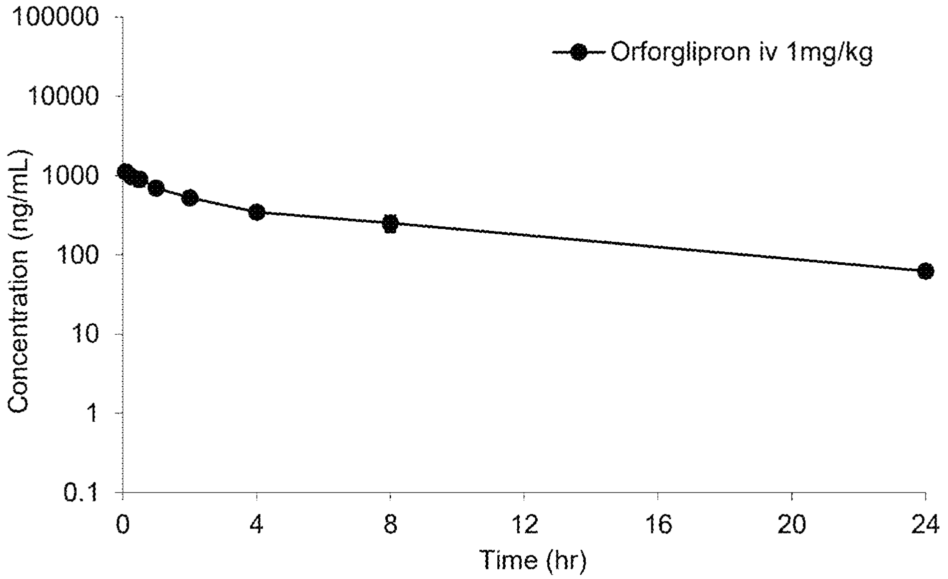
Figure 6A:
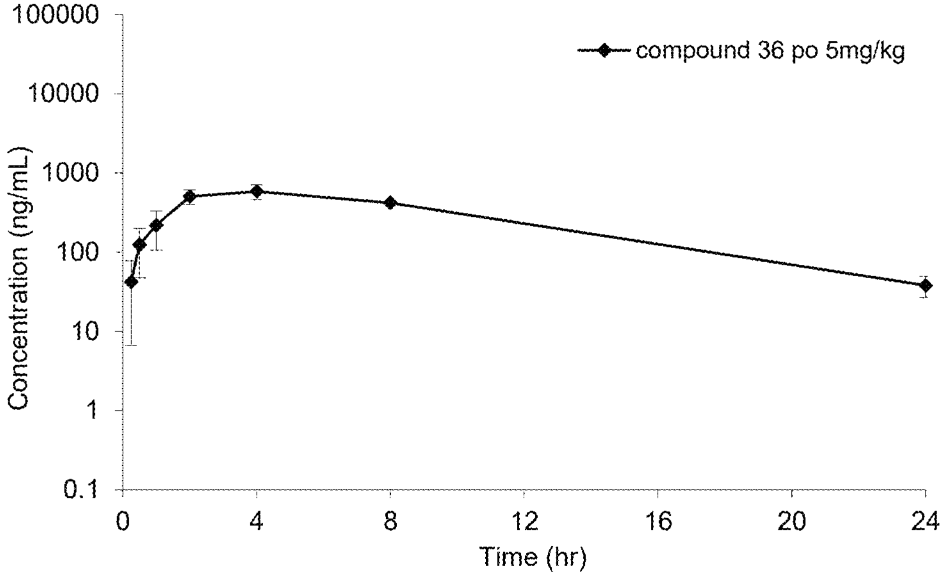
FIG. 6A, FIG. 6B, and FIG. 6C depict pharmacokinetics of Compounds 36 (FIG. 6A), 121 (FIG. 6B), and orforglipron (FIG. 6C) in male SD rats when dosed at 5 mg/kg po.
Figure 6B:
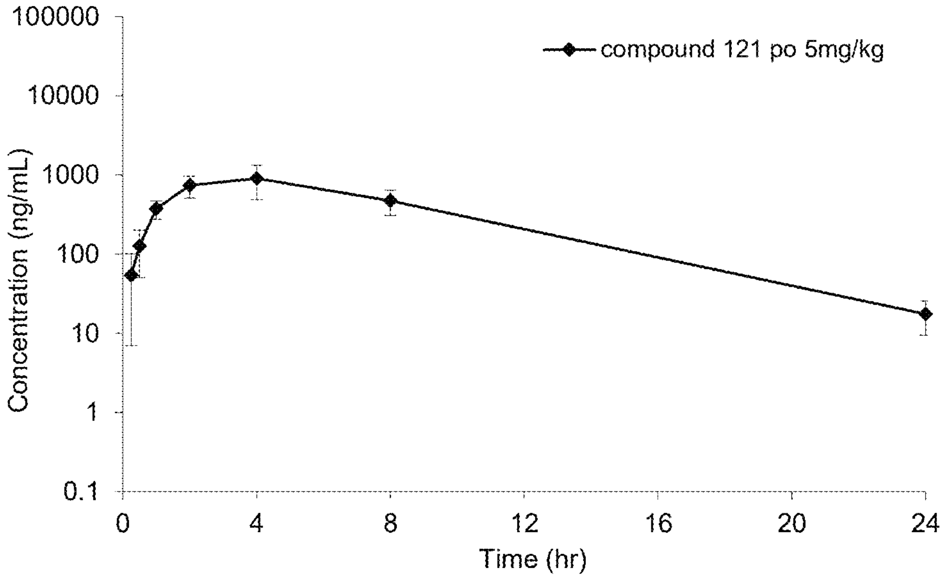
Figure 6C:
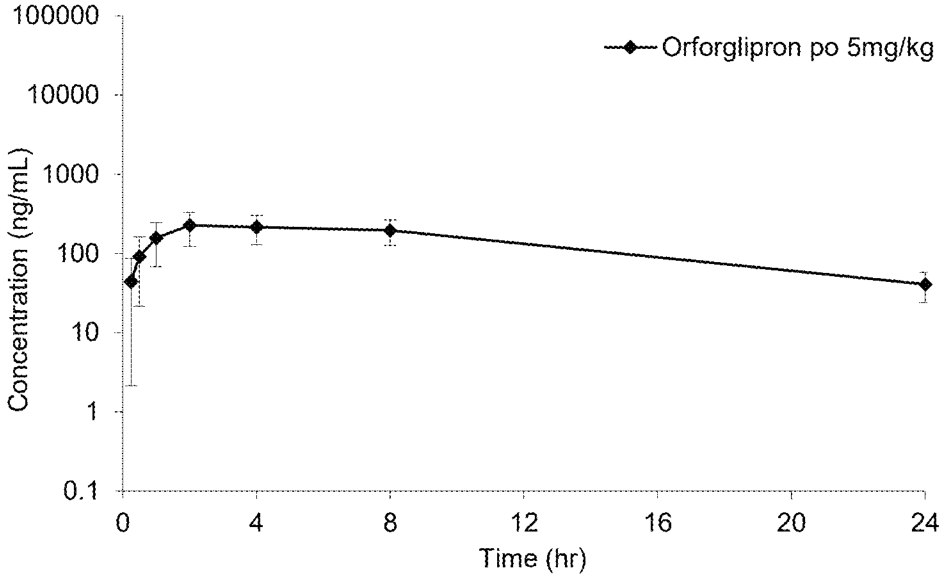
Figure 8A:
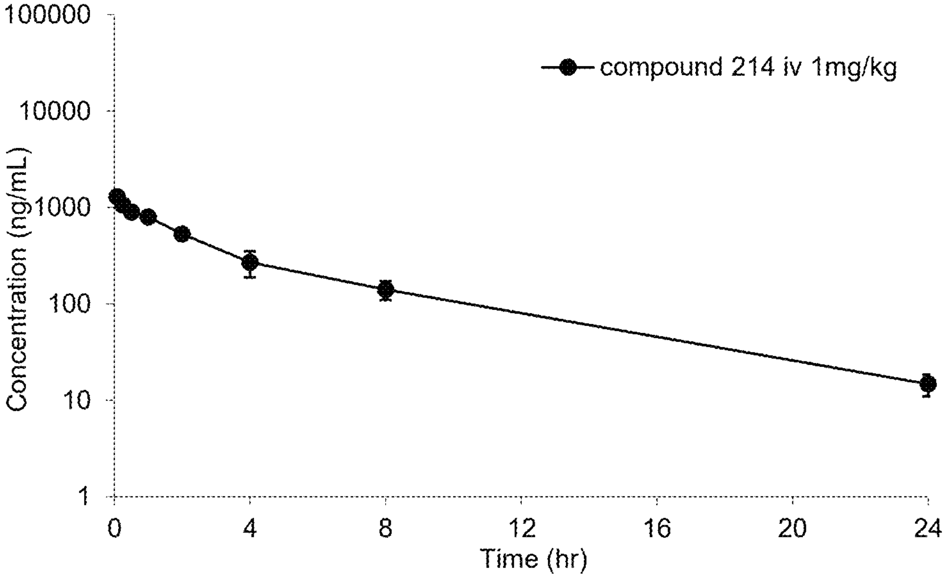
FIG. 8A and FIG. 8B depict pharmacokinetics of Compound 214 in male SD rats when dosed at 1 mg/kg iv (FIG. 8A) and 5 mg/kg po (FIG. 8B).
Figure 8B:
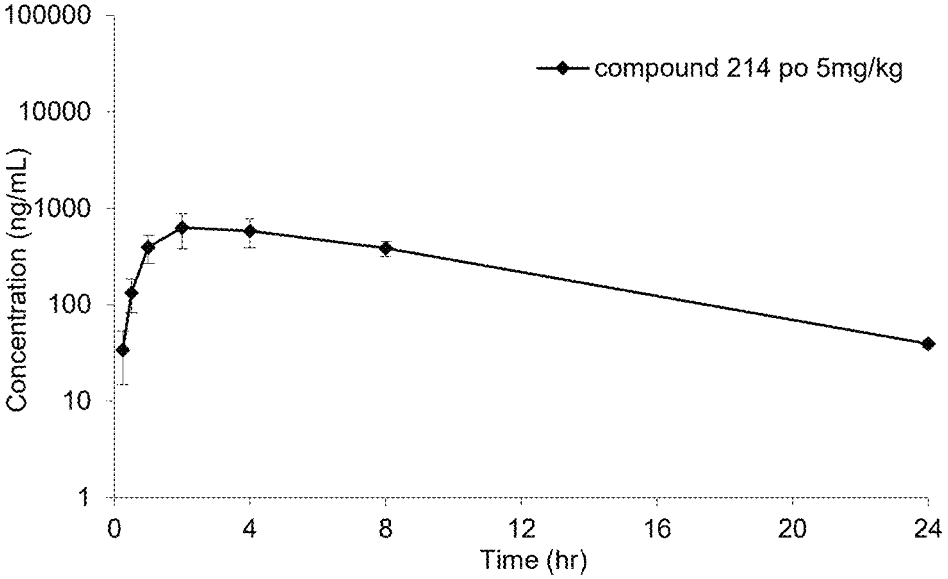

Pharmacokinetic Analysis of the Compound 36, Compound 121, Compound 214, and Orforglipron in Male SD Rats Compounds of the present application were formulated for IV (0.2 mg/mL) and PO (0.5 mg/mL) in (10% PEG400, 10% PG in 80% glycine buffer (100 mM glycine, 64 mM NaOH, pH 10)), and administered via IV (1 mg/kg) and PO (5 mg/kg) in male SD rats. The rats have free access to food and water. Blood samples were collected pre-dose and 0.083, 0.25, 0.5, 1, 2, 4, 8, 24 hours post dose for i.v. administration group. Blood samples were also collected pre-dose and 0.25, 0.5, 1, 2, 4, 8, and 24 hours after administration in orally dosing group. Compound concentrations were determined by UPLC/MS-MS-51 (Triple Quad 7500), which had a lower limit of quantification of 1 ng/mL. Pharmacokinetic parameters were estimated by non-compartmental model using WinNonlin (Phoenix 64 WinNonlin 8.2) and shown in Table Bld. The time profile of the plasma concentrations for the compounds are shown in FIG. 5 (A, B, C, iv), FIG. 6 (A, B, C, po), FIG. 8 (#214, A, B, iv and po). At the same doses (iv 1 mg/kg and po 5 mg/kg), compounds 36, 121, and 214 showed significant higher exposure and better oral bioavailability than Orforglipron.

TABLE B1d

Pharmacokinetics parameters of compound 36 in male SD rats

| Compound | Dose (mg/kg) | Cmax (ng/mL) | Tmax (h) | AUC inf (ng*h/mL | CL (L/h/kg) | Vdss (L/kg) | $T_{1/2}$ (h) | Oral F (%) |
|---|---|---|---|---|---|---|---|---|
| 36 | 1.0 (iv) | — | — | 5054 | 0.200 | 1.09 | 5.04 | — |
| 121 | 1.0 (iv) | — | — | 3334 | 0.301 | 1.24 | 3.14 | — |
| 214 | 1.0 (iv) | — | — | 4641 | 0.221 | 1.08 | 4.83 | — |
| Orforglipron | 1.0 (iv) | — | — | 6838 | 0.148 | 1.42 | 8.13 | — |
| 36 | 5.0 (po) | 610 | 3.33 | 7485 | — | — | 4.93 | 29.6 |
| 121 | 5.0 (po) | 923 | 3.33 | 9120 | — | — | 3.47 | 54.7 |
| 214 | 5.0 (po) | 640 | 2.67 | 7513 | — | — | 5.14 | 32.6 |
| Orforglipron | 5.0 (po) | 240 | 4.00 | 3416 | — | — | 7.44 | 11.2 |

Example C

X-Ray Crystallographic Analysis of Compound 36

Summary of Results

Figure 9A:
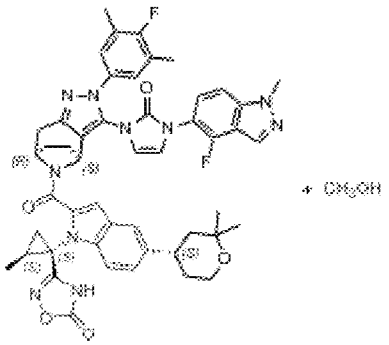
FIG. 9A and FIG. 9B depict Absolute configuration structure (FIG. 9A), and ORTEP structure (FIG. 9B) of Compound 36.
Figure 9B:
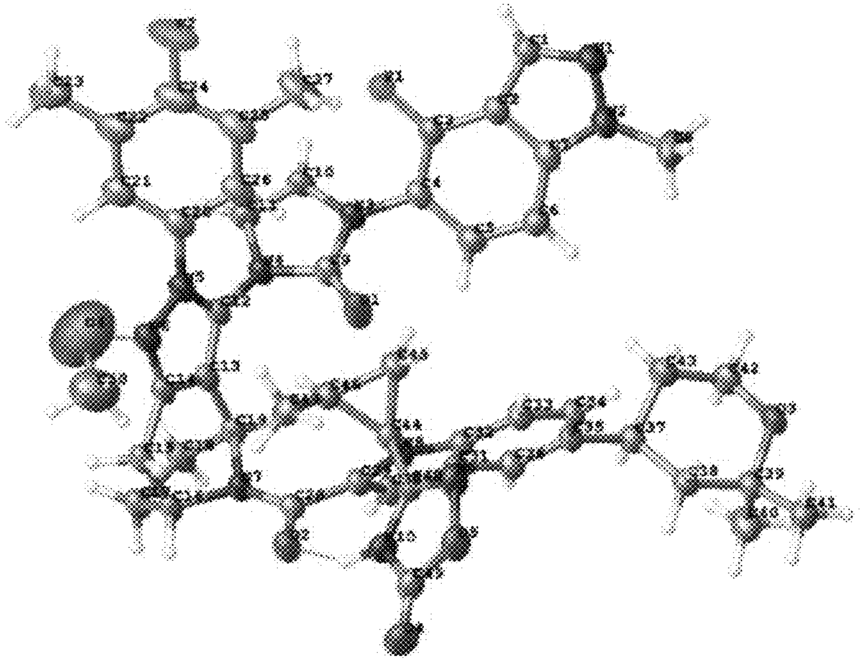

The symmetry of the crystal structure was assigned the monoclinic space group P21 with the following parameters: a=9.14578 (14) Å, b=22.7611 (3) Å, c=11.05687 (14) Å, α=90°, β=97.7848 (14)°, γ=90°, V=2280.48 (6) $Å^3$, Z=2, Dc=1.350 $g/cm^3$, μ (Cu Kα)=0.796 $mm^{-1}$, and F(000)=976.0. The absolute configuration structure is judged by the value of Flack parameter, and the structure of the tested crystal are depicted in FIG. 9.

Description of Equipment

Figure 10:
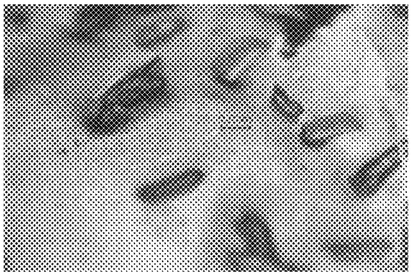
FIG. 10 depicts picture of crystals of Compound 36.
Figure 11:
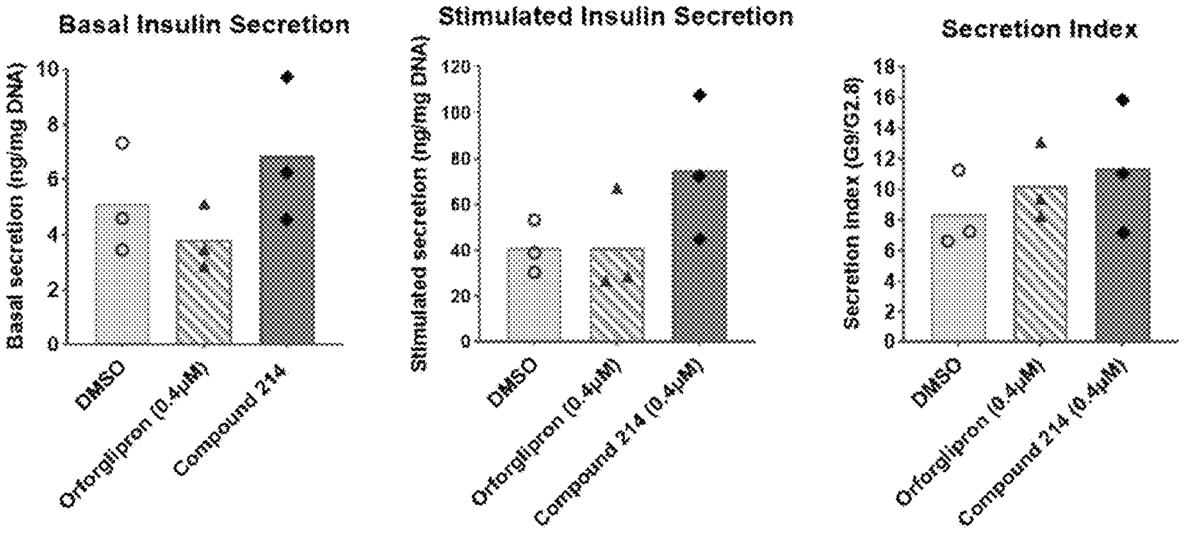
FIG. 11 panels A, B, and C provide increases in glucose-stimulated insulin secretion in islets from a non-diabetic donor with Compound 214. Donor islets cultured ex vivo were assayed for GSIS in the presence of compound 214, orforglipron or DMSO. Basal insulin secretion, stimulated insulin secretion and secretion index were measured.

Rigaku Oxford Diffraction XtaLAB Synergy-S equipped with a HyPix-6000HE area detector Cryogenic system: Oxford Cryostream 800; Cu: λ=1.54184 Å, 50W; Distance from the crystal to the CCD detector: d=35 mm Tube; Voltage: 50 kV; Tube Current: 1 mA Experimental Colorless block-shaped single crystals of compound 36 were obtained from Methanol-Dichloromethane-Water (3:1:1). A suitable crystal 0.08×0.05×0.04 $mm^3$ was selected for testing. Data collection temperature: T=150.1(3) K. Total of 39788 reflections were collected in the 2□ range from 7.768 to 133.188°. The limiting indices were: −10≤h≤10, −27≤k≤27, −13≤l≤10; which yielded 7913 unique reflections ($R_{int}$=0.0584). The structure was solved using SHELXT (Sheldrick, G. M. 2015. Acta Cryst. A71, 3-8) and refined using SHELXL (against F2) (Sheldrick, G. M. 2015. Acta Cryst. C71, 3-8). The total number of refined parameters was 625, compared with 7913 data. All reflections were included in the refinement. The goodness of fit on $F^2$ was 1.046 with a final R value for [I>=2σ(I)] $R_1$=0.0474 and $wR_2$=0.1236. The largest differential peak and hole were 0.70 and −0.55 $eÅ^{-3}$. Picture of crystals shown in FIG. 10.

Data Tables

TABLE C1

Summary of X-ray Crystallographic Data.

| | |
|---|---|
| Temperature/K | 150.1 (3) |
| Crystal system | monoclinic |
| Space group | $P2_1$ |
| a/Å | 9.14578 (14) |
| b/Å | 22.7611 (3) |
| c/Å | 11.05687 (14) |
| α/° | 90 |
| β/° | 97.7848 (14) |
| γ/° | 90 |
| Volume/$Å^3$ | 2280.48 (6) |
| Z | 2 |

TABLE C1-continued

| Summary of X-ray Crystallographic Data. | |
|---|---|
| ρcalcg/cm$^3$ | 1.350 |
| μ/mm$^{-1}$ | 0.796 |
| F(000) | 976.0 |
| Crystal size/mm$^3$ | 0.08 × 0.05 × 0.04 |
| Radiation | Cu Kα (λ = 1.54184) |
| 2Θ range for data collection/° | 7.768 to 133.188 |
| Index ranges | −10 ≤ h ≤ 10, −27 ≤ k ≤ 27, −13 ≤ 1 ≤ 10 |
| Reflections collected | 39788 |
| Independent reflections | 7913 [$R_{int}$ = 0.0584, $R_{sigma}$ = 0.0322] |
| Data/restraints/parameters | 7913/1/625 |
| Goodness-of-fit on F$^2$ | 1.046 |
| Final R indexes [I >= 2σ (I)] | $R_1$ = 0.0474, $wR_2$ = 0.1236 |
| Final R indexes [all data] | $R_1$ = 0.0506, $wR_2$ = 0.1266 |
| Largest diff. peak/hole/e Å$^{-3}$ | 0.70/−0.55 |
| Flack parameter | −0.01 (7) |

TABLE C-2

Atomic coordinates (×10$^4$) and equivalent isotropic displacement parameters (Å$^2$ × 10$^3$).

| Atom | x | y | z | U(eq) |
|---|---|---|---|---|
| F1 | 1030 (3) | 3617.5 (10) | 9750 (2) | 42.7 (5) |
| O2 | 3653 (3) | 7397.0 (12) | 6372 (2) | 39.6 (6) |
| O3 | 9340 (3) | 3430.1 (11) | 3888 (3) | 44.0 (6) |
| F2 | −3899 (3) | 4725.3 (13) | 10717 (4) | 77.5 (10) |
| N8 | 3843 (3) | 6082.8 (13) | 5950 (3) | 31.9 (6) |
| O5 | 1749 (4) | 6712.2 (14) | 2325 (2) | 48.4 (7) |
| N7 | 4139 (3) | 7131.6 (12) | 8342 (3) | 33.2 (6) |
| O1 | 2774 (4) | 5299.6 (13) | 8050 (3) | 55.4 (8) |
| O4 | 2652 (4) | 7639.7 (16) | 2435 (3) | 58.2 (8) |
| N5 | 562 (4) | 6220.9 (13) | 9836 (3) | 35.9 (7) |
| N6 | 319 (4) | 6798.2 (14) | 9534 (3) | 37.6 (7) |
| N3 | 2854 (4) | 4584.0 (13) | 9577 (3) | 34.0 (6) |
| N2 | 2747 (4) | 2608.4 (15) | 6662 (3) | 41.6 (7) |
| N1 | 1704 (4) | 2278.8 (15) | 7099 (3) | 42.6 (8) |
| N4 | 2536 (3) | 5502.4 (13) | 10079 (3) | 33.7 (6) |
| N10 | 2713 (4) | 7020.9 (15) | 4118 (3) | 39.5 (7) |
| N9 | 1621 (4) | 6244.9 (16) | 3192 (3) | 43.3 (8) |
| C13 | 2741 (4) | 6574.7 (15) | 9565 (3) | 33.6 (8) |
| C32 | 4740 (4) | 5618.9 (16) | 5689 (3) | 31.4 (7) |
| C14 | 1635 (4) | 7002.2 (15) | 9372 (3) | 34.2 (8) |
| C28 | 4088 (4) | 7020.1 (15) | 7159 (3) | 30.4 (7) |
| C11 | 2498 (4) | 5158.6 (16) | 11126 (3) | 35.7 (8) |
| C4 | 2903 (4) | 4079.9 (15) | 8815 (3) | 33.3 (7) |
| C12 | 2028 (4) | 6080.7 (15) | 9868 (3) | 34.0 (7) |
| C2 | 2000 (4) | 3126.8 (16) | 8149 (3) | 33.9 (7) |
| C29 | 4675 (4) | 6443.3 (15) | 6797 (3) | 32.3 (7) |
| C10 | 2717 (4) | 4603.7 (16) | 10817 (3) | 36.3 (8) |
| C3 | 1984 (4) | 3615.8 (16) | 8920 (3) | 33.4 (7) |
| C35 | 6970 (4) | 4817.7 (16) | 5425 (3) | 34.6 (8) |
| C44 | 2330 (4) | 6155.4 (16) | 5409 (3) | 32.2 (7) |
| C34 | 5538 (4) | 4749.3 (17) | 4794 (3) | 37.1 (8) |
| C1 | 1239 (4) | 2584.3 (17) | 7990 (3) | 37.2 (8) |
| C21 | −1497 (4) | 5987.7 (18) | 10927 (4) | 42.9 (9) |
| C49 | 2426 (5) | 7189.5 (19) | 2931 (4) | 43.9 (9) |
| C16 | 3568 (4) | 7681.2 (15) | 8833 (3) | 36.0 (8) |
| C48 | 2200 (4) | 6465.4 (17) | 4224 (3) | 34.1 (8) |
| C31 | 6144 (4) | 5696.1 (15) | 6365 (3) | 32.2 (7) |
| C7 | 2966 (4) | 3131.9 (17) | 7269 (3) | 36.4 (8) |
| C37 | 8185 (4) | 4397.7 (16) | 5194 (3) | 36.4 (8) |
| C36 | 7268 (4) | 5291.3 (16) | 6216 (3) | 34.5 (7) |
| C20 | −616 (4) | 5841.9 (17) | 10059 (3) | 38.6 (8) |
| C6 | 3903 (4) | 3607.8 (18) | 7122 (4) | 40.3 (8) |
| C18 | 5085 (5) | 7091.9 (17) | 10406 (3) | 40.9 (8) |
| C5 | 3852 (4) | 4072.2 (17) | 7901 (4) | 37.9 (8) |
| C19 | 4294 (4) | 6709.3 (16) | 9374 (3) | 34.9 (8) |
| C38 | 8481 (4) | 4443.1 (16) | 3863 (3) | 35.9 (8) |
| C30 | 6060 (4) | 6222.6 (16) | 7082 (3) | 34.0 (7) |
| C9 | 2739 (4) | 5147.3 (16) | 9103 (3) | 37.5 (8) |

TABLE C-2-continued

Atomic coordinates (×10$^4$) and equivalent isotropic displacement parameters (Å$^2$ × 10$^3$).

| Atom | x | y | z | U(eq) |
|---|---|---|---|---|
| C47 | −53 (4) | 6699.8 (19) | 5884 (4) | 41.5 (8) |
| C33 | 4414 (4) | 5145.7 (17) | 4899 (3) | 35.6 (8) |
| C22 | −2639 (5) | 5619.4 (19) | 11162 (5) | 49.8 (10) |
| C46 | 1158 (4) | 6264.0 (17) | 6232 (3) | 35.3 (8) |
| C39 | 9661 (4) | 4020.3 (16) | 3518 (4) | 38.3 (8) |
| C15 | 1917 (4) | 7612.8 (16) | 8918 (3) | 36.7 (8) |
| C43 | 7895 (5) | 3753.0 (18) | 5461 (4) | 43.6 (9) |
| C17 | 4541 (5) | 7725.0 (17) | 10080 (4) | 41.2 (9) |
| C45 | 1210 (4) | 5688.4 (17) | 5580 (4) | 37.7 (8) |
| C24 | −2800 (5) | 5100 (2) | 10480 (5) | 55.7 (12) |
| C42 | 9157 (5) | 3373.7 (19) | 5137 (4) | 47.3 (10) |
| C40 | 11212 (5) | 4202 (2) | 4068 (5) | 53.0 (11) |
| C25 | −1945 (5) | 4934.3 (19) | 9616 (5) | 50.9 (11) |
| C26 | −840 (5) | 5316.8 (18) | 9390 (4) | 43.9 (9) |
| C41 | 9548 (5) | 3992 (2) | 2138 (4) | 47.7 (10) |
| C23 | −3610 (6) | 5762 (2) | 12104 (6) | 63.3 (13) |
| C8 | 3453 (6) | 2411 (3) | 5640 (5) | 65.3 (14) |
| C27 | −2174 (6) | 4360 (2) | 8929 (6) | 66.8 (14) |
| O6 | −2396 (8) | 7354 (5) | 8857 (8) | 160 (3) |
| C50 | −2407 (11) | 7731 (4) | 7830 (8) | 108 (3) |

TABLE C-3

Bond lengths [A].

| Atom | Atom | Length/Å | Atom | Atom | Length/Å |
|---|---|---|---|---|---|
| F1 | C3 | 1.350 (4) | C11 | C10 | 1.331 (5) |
| O2 | C28 | 1.248 (4) | C4 | C3 | 1.365 (5) |
| O3 | C39 | 1.446 (5) | C4 | C5 | 1.419 (5) |
| O3 | C42 | 1.420 (5) | C2 | C3 | 1.403 (5) |
| F2 | C24 | 1.370 (5) | C2 | C1 | 1.417 (5) |
| N8 | C32 | 1.392 (5) | C2 | C7 | 1.400 (6) |
| N8 | C29 | 1.391 (5) | C29 | C30 | 1.360 (5) |
| N8 | C44 | 1.441 (5) | C35 | C34 | 1.407 (5) |
| O5 | N9 | 1.447 (5) | C35 | C37 | 1.514 (5) |
| O5 | C49 | 1.378 (5) | C35 | C36 | 1.392 (5) |
| N7 | C28 | 1.327 (4) | C44 | C48 | 1.479 (5) |
| N7 | C16 | 1.486 (4) | C44 | C46 | 1.517 (5) |
| N7 | C19 | 1.484 (4) | C44 | C45 | 1.506 (5) |
| O1 | C9 | 1.220 (5) | C34 | C33 | 1.385 (5) |
| O4 | C49 | 1.193 (5) | C21 | C20 | 1.375 (6) |
| N5 | N6 | 1.367 (4) | C21 | C22 | 1.391 (6) |
| N5 | C12 | 1.374 (5) | C16 | C15 | 1.534 (6) |
| N5 | C20 | 1.427 (5) | C16 | C17 | 1.539 (5) |
| N6 | C14 | 1.324 (5) | C31 | C36 | 1.407 (5) |
| N3 | C4 | 1.428 (5) | C31 | C30 | 1.445 (5) |
| N3 | C10 | 1.395 (5) | C7 | C6 | 1.404 (6) |
| N3 | C9 | 1.383 (5) | C37 | C38 | 1.535 (5) |
| N2 | N1 | 1.353 (5) | C37 | C43 | 1.527 (5) |
| N2 | C7 | 1.369 (5) | C20 | C26 | 1.406 (6) |
| N2 | C8 | 1.447 (6) | C6 | C5 | 1.368 (6) |
| N1 | C1 | 1.322 (5) | C18 | C19 | 1.536 (5) |
| N4 | C11 | 1.402 (5) | C18 | C17 | 1.551 (5) |
| N4 | C12 | 1.405 (5) | C38 | C39 | 1.532 (5) |
| N4 | C9 | 1.380 (5) | C47 | C46 | 1.498 (6) |
| N10 | C49 | 1.359 (5) | C22 | C24 | 1.399 (7) |
| N10 | C48 | 1.359 (5) | C22 | C23 | 1.493 (7) |
| N9 | C48 | 1.292 (5) | C46 | C45 | 1.499 (5) |
| C13 | C14 | 1.399 (5) | C39 | C40 | 1.523 (6) |
| C13 | C12 | 1.364 (5) | C39 | C41 | 1.516 (6) |
| C13 | C19 | 1.496 (6) | C43 | C42 | 1.522 (6) |
| C32 | C31 | 1.406 (5) | C24 | C25 | 1.367 (8) |
| C32 | C33 | 1.393 (5) | C25 | C26 | 1.382 (7) |
| C14 | C15 | 1.512 (5) | C25 | C27 | 1.513 (7) |
| C28 | C29 | 1.493 (5) | O6 | C50 | 1.422 (12) |

TABLE C-4

| Bond angles [deg]. | | | | | | | |
|---|---|---|---|---|---|---|---|
| Atom | Atom | Atom | Angle/° | Atom | Atom | Atom | Angle/° |
| C42 | O3 | C39 | 114.5(3) | C33 | C34 | C35 | 122.6(3) |
| C32 | N8 | C44 | 124.1(3) | N1 | C1 | C2 | 110.4(3) |
| C29 | N8 | C32 | 107.6(3) | C20 | C21 | C22 | 120.7(4) |
| C29 | N8 | C44 | 128.2(3) | O4 | C49 | O5 | 123.2(4) |
| C49 | O5 | N9 | 109.2(3) | O4 | C49 | N10 | 131.6(4) |
| C28 | N7 | C16 | 123.6(3) | N10 | C49 | O5 | 105.2(3) |
| C28 | N7 | C19 | 128.4(3) | N7 | C16 | C15 | 109.5(3) |
| C19 | N7 | C16 | 105.4(3) | N7 | C16 | C17 | 101.1(3) |
| N6 | N5 | C12 | 110.8(3) | C15 | C16 | C17 | 114.0(3) |
| N6 | N5 | C20 | 121.5(3) | N10 | C48 | C44 | 122.2(3) |
| C12 | N5 | C20 | 127.7(3) | N9 | C48 | N10 | 113.0(3) |
| C14 | N6 | N5 | 104.5(3) | N9 | C48 | C44 | 124.8(4) |
| C10 | N3 | C4 | 128.3(3) | C32 | C31 | C36 | 119.0(3) |
| C9 | N3 | C4 | 121.9(3) | C32 | C31 | C30 | 106.5(3) |
| C9 | N3 | C10 | 109.2(3) | C36 | C31 | C30 | 134.5(3) |
| N1 | N2 | C7 | 111.8(3) | N2 | C7 | C2 | 105.6(3) |
| N1 | N2 | C8 | 121.2(4) | N2 | C7 | C6 | 131.8(4) |
| C7 | N2 | C8 | 127.0(4) | C2 | C7 | C6 | 122.6(3) |
| C1 | N1 | N2 | 106.8(3) | C35 | C37 | C38 | 110.4(3) |
| C11 | N4 | C12 | 128.0(3) | C35 | C37 | C43 | 115.1(3) |
| C9 | N4 | C11 | 109.9(3) | C43 | C37 | C38 | 107.9(3) |
| C9 | N4 | C12 | 119.7(3) | C35 | C36 | C31 | 119.8(3) |
| C49 | N10 | C48 | 108.8(3) | C21 | C20 | N5 | 120.2(3) |
| C48 | N9 | O5 | 103.8(3) | C21 | C20 | C26 | 121.0(4) |
| C14 | C13 | C19 | 121.1(3) | C26 | C20 | N5 | 118.8(4) |
| C12 | C13 | C14 | 104.5(3) | C5 | C6 | C7 | 116.8(3) |
| C12 | C13 | C19 | 134.3(3) | C19 | C18 | C17 | 104.5(3) |
| N8 | C32 | C31 | 108.4(3) | C6 | C5 | C4 | 122.3(4) |
| N8 | C32 | C33 | 129.4(3) | N7 | C19 | C13 | 104.3(3) |
| C33 | C32 | C31 | 122.2(3) | N7 | C19 | C18 | 101.0(3) |
| N6 | C14 | C13 | 112.8(3) | C13 | C19 | C18 | 111.8(3) |
| N6 | C14 | C15 | 124.5(3) | C39 | C38 | C37 | 114.7(3) |

TABLE C-4-continued

| Bond angles [deg]. | | | | | | | |
|---|---|---|---|---|---|---|---|
| Atom | Atom | Atom | Angle/° | Atom | Atom | Atom | Angle/° |
| C13 | C14 | C15 | 122.5(3) | C29 | C30 | C31 | 107.2(3) |
| O2 | C28 | N7 | 121.4(3) | O1 | C9 | N3 | 127.9(3) |
| O2 | C28 | C29 | 120.6(3) | O1 | C9 | N4 | 127.1(3) |
| N7 | C28 | C29 | 117.8(3) | N4 | C9 | N3 | 105.0(3) |
| C10 | C11 | N4 | 107.2(3) | C34 | C33 | C32 | 117.3(3) |
| C3 | C4 | N3 | 120.2(3) | C21 | C22 | C24 | 115.8(4) |
| C3 | C4 | C5 | 119.6(3) | C21 | C22 | C23 | 122.1(4) |
| C5 | C4 | N3 | 120.1(3) | C24 | C22 | C23 | 122.0(4) |
| N5 | C12 | N4 | 121.4(3) | C47 | C46 | C44 | 120.7(3) |
| C13 | C12 | N5 | 107.5(3) | C47 | C46 | C45 | 121.7(3) |
| C13 | C12 | N4 | 130.9(4) | C45 | C46 | C44 | 59.9(2) |
| C3 | C2 | C1 | 136.1(4) | O3 | C39 | C38 | 109.7(3) |
| C7 | C2 | C3 | 118.4(3) | O3 | C39 | C40 | 110.6(4) |
| C7 | C2 | C1 | 105.5(3) | O3 | C39 | C41 | 104.8(3) |
| N8 | C29 | C28 | 121.0(3) | C40 | C39 | C38 | 112.3(3) |
| C30 | C29 | N8 | 110.2(3) | C41 | C39 | C38 | 108.9(3) |
| C30 | C29 | C28 | 128.3(3) | C41 | C39 | C40 | 110.2(3) |
| C11 | C10 | N3 | 108.7(3) | C14 | C15 | C16 | 109.1(3) |
| F1 | C3 | C4 | 121.2(3) | C42 | C43 | C37 | 110.0(3) |
| F1 | C3 | C2 | 118.5(3) | C16 | C17 | C18 | 106.0(3) |
| C4 | C3 | C2 | 120.3(3) | C46 | C45 | C44 | 60.6(2) |
| C34 | C35 | C37 | 120.1(3) | F2 | C24 | C22 | 116.7(5) |
| C36 | C35 | C34 | 119.2(3) | C25 | C24 | F2 | 117.8(4) |
| C36 | C35 | C37 | 120.6(3) | C25 | C24 | C22 | 125.5(4) |
| N8 | C44 | C48 | 112.3(3) | O3 | C42 | C43 | 111.8(3) |
| N8 | C44 | C46 | 119.1(3) | C24 | C25 | C26 | 117.0(4) |
| N8 | C44 | C45 | 119.9(3) | C24 | C25 | C27 | 122.4(5) |
| C48 | C44 | C46 | 118.4(3) | C26 | C25 | C27 | 120.6(5) |
| C48 | C44 | C45 | 118.3(3) | C25 | C26 | C20 | 119.9(4) |
| C45 | C44 | C46 | 59.5(2) | | | | |

TABLE C-5

| Torsion angles [deg]. | | | | | | | | | |
|---|---|---|---|---|---|---|---|---|---|
| A | B | C | D | Angle/° | A | B | C | D | Angle/° |
| O2 | C28 | C29 | N8 | −55.2(5) | C44 | N8 | C29 | C30 | 179.9(3) |
| O2 | C28 | C29 | C30 | 116.3(4) | C34 | C35 | C37 | C38 | 62.9(4) |
| F2 | C24 | C25 | C26 | −179.9(4) | C34 | C35 | C37 | C43 | −59.5(5) |
| F2 | C24 | C25 | C27 | −0.1(7) | C34 | C35 | C36 | C31 | −0.6(5) |
| N8 | C32 | C31 | C36 | −177.5(3) | C1 | C2 | C3 | F1 | −0.7(6) |
| N8 | C32 | C31 | C30 | 1.5(4) | C1 | C2 | C3 | C4 | −179.9(4) |
| N8 | C32 | C33 | C34 | 178.7(3) | C1 | C2 | C7 | N2 | −0.5(4) |
| N8 | C29 | C30 | C31 | 1.1(4) | C1 | C2 | C7 | C6 | 178.8(3) |
| N8 | C44 | C48 | N10 | −60.7(4) | C21 | C20 | C26 | C25 | −1.1(6) |
| N8 | C44 | C48 | N9 | 118.3(4) | C21 | C22 | C24 | F2 | 178.6(4) |
| N8 | C44 | C46 | C47 | 139.3(4) | C21 | C22 | C24 | C25 | −0.5(7) |
| N8 | C44 | C46 | C45 | −109.5(4) | C49 | O5 | N9 | C48 | 0.4(4) |
| N8 | C44 | C45 | C46 | 108.2(3) | C49 | N10 | C48 | N9 | 1.5(5) |
| O5 | N9 | C48 | N10 | −1.1(4) | C49 | N10 | C48 | C44 | −179.4(3) |
| O5 | N9 | C48 | C44 | 179.8(3) | C16 | N7 | C28 | O2 | 5.7(5) |
| N7 | C28 | C29 | N8 | 129.1(4) | C16 | N7 | C28 | C29 | −178.7(3) |
| N7 | C28 | C29 | C30 | −59.3(5) | C16 | N7 | C19 | C13 | 69.2(3) |
| N7 | C16 | C15 | C14 | 40.4(4) | C16 | N7 | C19 | C18 | −47.0(4) |
| N7 | C16 | C17 | C18 | −23.0(4) | C48 | N10 | C49 | O5 | −1.1(4) |
| N5 | N6 | C14 | C13 | −0.3(4) | C48 | N10 | C49 | O4 | 178.2(5) |
| N5 | N6 | C14 | C15 | 174.5(3) | C48 | C44 | C46 | C47 | −3.3(5) |
| N5 | C20 | C26 | C25 | 178.1(3) | C48 | C44 | C46 | C45 | 107.8(4) |
| N6 | N5 | C12 | N4 | −175.8(3) | C48 | C44 | C45 | C46 | −108.1(4) |
| N6 | N5 | C12 | C13 | −0.8(4) | C31 | C32 | C33 | C34 | −0.4(5) |
| N6 | N5 | C20 | C21 | −55.7(5) | C7 | N2 | N1 | C1 | 0.1(4) |
| N6 | N5 | C20 | C26 | 125.1(4) | C7 | C2 | C3 | F1 | 178.5(3) |
| N6 | C14 | C15 | C16 | −179.2(3) | C7 | C2 | C3 | C4 | −0.7(5) |
| N3 | C4 | C3 | F1 | −1.0(5) | C7 | C2 | C1 | N1 | 0.6(4) |
| N3 | C4 | C3 | C2 | 178.2(3) | C7 | C6 | C5 | C4 | −0.2(6) |
| N3 | C4 | C5 | C6 | −177.8(3) | C37 | C35 | C34 | C33 | −175.0(3) |
| N2 | N1 | C1 | C2 | −0.4(4) | C37 | C35 | C36 | C31 | 176.3(3) |
| N2 | C7 | C6 | C5 | −179.8(4) | C37 | C38 | C39 | O3 | 50.6(4) |
| N1 | N2 | C7 | C2 | 0.3(4) | C37 | C38 | C39 | C40 | −72.9(4) |
| N1 | N2 | C7 | C6 | −178.9(4) | C37 | C38 | C39 | C41 | 164.8(3) |
| N4 | C11 | C10 | N3 | −1.6(4) | C37 | C43 | C42 | O3 | −59.0(5) |

TABLE C-5-continued

Torsion angles [deg].

| A | B | C | D | Angle/° | A | B | C | D | Angle/° |
|---|---|---|---|---|---|---|---|---|---|
| N9 | O5 | C49 | O4 | −179.0(4) | C36 | C35 | C34 | C33 | 2.0(6) |
| N9 | O5 | C49 | N10 | 0.4(4) | C36 | C35 | C37 | C38 | −114.0(4) |
| C13 | C14 | C15 | C16 | −4.9(4) | C36 | C35 | C37 | C43 | 123.6(4) |
| C32 | N8 | C29 | C28 | 172.7(3) | C36 | C31 | C30 | C29 | 177.2(4) |
| C32 | N8 | C29 | C30 | −0.2(4) | C20 | N5 | N6 | C14 | −178.6(3) |
| C32 | N8 | C44 | C48 | −85.8(4) | C20 | N5 | C12 | N4 | 3.5(5) |
| C32 | N8 | C44 | C46 | 129.4(4) | C20 | N5 | C12 | C13 | 178.4(3) |
| C32 | N8 | C44 | C45 | 60.0(5) | C20 | C21 | C22 | C24 | 1.0(6) |
| C32 | C31 | C36 | C35 | −1.2(5) | C20 | C21 | C22 | C23 | 179.5(4) |
| C32 | C31 | C30 | C29 | −1.6(4) | C5 | C4 | C3 | F1 | −177.6(3) |
| C14 | C13 | C12 | N5 | 0.6(4) | C5 | C4 | C3 | C2 | 1.6(5) |
| C14 | C13 | C12 | N4 | 174.9(4) | C19 | N7 | C28 | O2 | 164.9(3) |
| C14 | C13 | C19 | N7 | −34.0(4) | C19 | N7 | C28 | C29 | −19.5(5) |
| C14 | C13 | C19 | C18 | 74.3(4) | C19 | N7 | C16 | C15 | −76.7(3) |
| C28 | N7 | C16 | C15 | 86.5(4) | C19 | N7 | C16 | C17 | 43.9(4) |
| C28 | N7 | C16 | C17 | −152.9(3) | C19 | C13 | C14 | N6 | 177.3(3) |
| C28 | N7 | C19 | C13 | −93.0(4) | C19 | C13 | C14 | C15 | 2.4(5) |
| C28 | N7 | C19 | C18 | 150.9(4) | C19 | C13 | C12 | N5 | −176.4(4) |
| C28 | C29 | C30 | C31 | −171.1(3) | C19 | C13 | C12 | N4 | −2.1(7) |
| C11 | N4 | C12 | N5 | −63.2(5) | C19 | C18 | C17 | C16 | −4.4(4) |
| C11 | N4 | C12 | C13 | 123.2(5) | C38 | C37 | C43 | C42 | 53.6(4) |
| C11 | N4 | C9 | O1 | 177.3(4) | C30 | C31 | C36 | C35 | −179.8(4) |
| C11 | N4 | C9 | N3 | −1.2(4) | C9 | N3 | C4 | C3 | −129.6(4) |
| C4 | N3 | C10 | C11 | −170.9(4) | C9 | N3 | C4 | C5 | 47.0(5) |
| C4 | N3 | C9 | O1 | −5.8(6) | C9 | N3 | C10 | C11 | 0.9(5) |
| C4 | N3 | C9 | N4 | 172.6(3) | C9 | N4 | C11 | C10 | 1.8(5) |
| C12 | N5 | N6 | C14 | 0.6(4) | C9 | N4 | C12 | N5 | 97.1(4) |
| C12 | N5 | C20 | C21 | 125.1(4) | C9 | N4 | C12 | C13 | −76.5(5) |
| C12 | N5 | C20 | C26 | −54.1(5) | C47 | C46 | C45 | C44 | 109.7(4) |
| C12 | N4 | C11 | C10 | 163.6(4) | C33 | C32 | C31 | C36 | 1.7(5) |
| C12 | N4 | C9 | 01 | 13.8(6) | C33 | C32 | C31 | C30 | −179.3(3) |
| C12 | N4 | C9 | N3 | −164.7(3) | C22 | C21 | C20 | N5 | −179.4(3) |
| C12 | C13 | C14 | N6 | −0.2(4) | C22 | C21 | C20 | C26 | −0.2(6) |
| C12 | C13 | C14 | C15 | −175.1(3) | C22 | C24 | C25 | C26 | −0.8(7) |
| C12 | C13 | C19 | N7 | 142.6(4) | C22 | C24 | C25 | C27 | 179.1(4) |
| C12 | C13 | C19 | C18 | −109.1(4) | C46 | C44 | C48 | N10 | 84.3(5) |
| C2 | C7 | C6 | C5 | 1.1(6) | C46 | C44 | C48 | N9 | −96.6(4) |
| C29 | N8 | C32 | C31 | −0.8(4) | C39 | O3 | C42 | C43 | 59.8(5) |
| C29 | N8 | C32 | C33 | −180.0(4) | C15 | C16 | C17 | C18 | 94.4(4) |
| C29 | N8 | C44 | C48 | 94.0(4) | C43 | C37 | C38 | C39 | −51.5(4) |
| C29 | N8 | C44 | C46 | −50.7(5) | C17 | C16 | C15 | C14 | −72.0(4) |
| C29 | N8 | C44 | C45 | −120.2(4) | C17 | C18 | C19 | N7 | 30.1(4) |
| C10 | N3 | C4 | C3 | 41.3(5) | C17 | C18 | C19 | C13 | −80.3(4) |
| C10 | N3 | C4 | C5 | −142.1(4) | C45 | C44 | C48 | N10 | 152.9(3) |
| C10 | N3 | C9 | O1 | −178.3(4) | C45 | C44 | C48 | N9 | −28.0(5) |
| C10 | N3 | C9 | N4 | 0.2(4) | C45 | C44 | C46 | C47 | −111.2(4) |
| C3 | C4 | C5 | C6 | −1.1(6) | C24 | C25 | C26 | C20 | 1.5(6) |
| C3 | C2 | C1 | N1 | 179.9(4) | C42 | O3 | C39 | C38 | −53.9(4) |
| C3 | C2 | C7 | N2 | −180.0(3) | C42 | O3 | C39 | C40 | 70.5(4) |
| C3 | C2 | C7 | C6 | −0.7(5) | C42 | O3 | C39 | C41 | −170.6(3) |
| C35 | C34 | C33 | C32 | −1.4(6) | C23 | C22 | C24 | F2 | 0.1(6) |
| C35 | C37 | C38 | C39 | −178.1(3) | C23 | C22 | C24 | C25 | −179.0(4) |
| C35 | C37 | C43 | C42 | 177.3(3) | C8 | N2 | N1 | C1 | −177.7(4) |
| C44 | N8 | C32 | C31 | 179.0(3) | C8 | N2 | C7 | C2 | 177.9(4) |
| C44 | N8 | C32 | C33 | −0.1(6) | C8 | N2 | C7 | C6 | −1.3(7) |
| C44 | N8 | C29 | C28 | −7.1(5) | C27 | C25 | C26 | C20 | −178.3(4) |

Example D

X-Ray Crystallographic Analysis of Compound 214

Summary of Results

Figure 12:
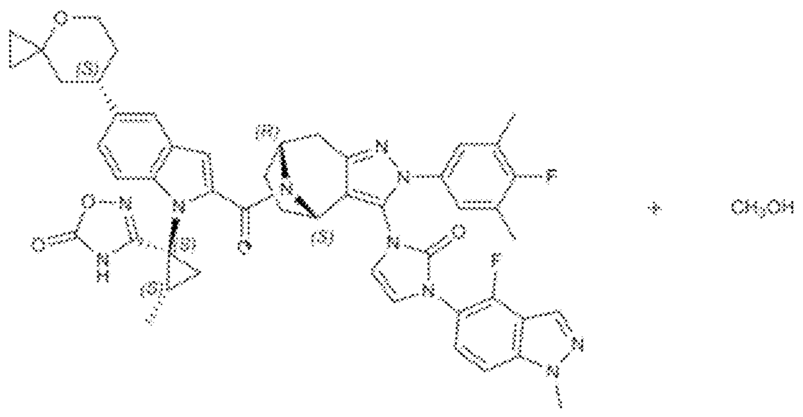
FIG. 12 depicts X-ray crystal structure of Compound 214
Figure 12:
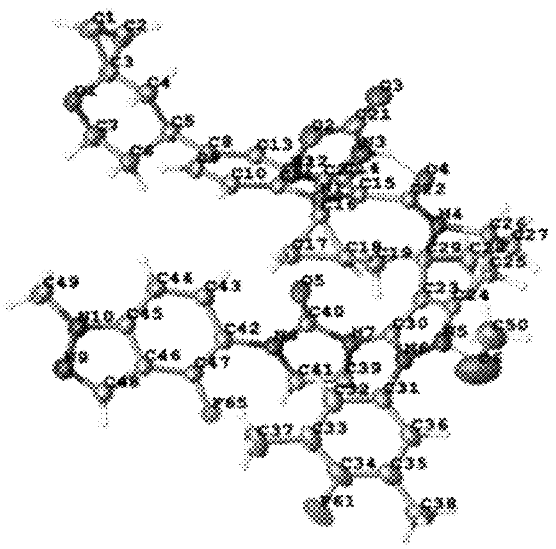

The symmetry of the crystal structure was assigned the monoclinic space group P21 with the following parameters: a=9.23300 (10) Å, b=22.5017 (3) Å, c=10.99460 (10) Å, α=90°, β=97.5050 (10), γ=90°, V=2264.65 (4) $Å^3$, Z=2, Dc=1.356 $g/cm^3$, μ(Cu Kα)=0.802 $mm^{-1}$, and F(000)=972.0. The absolute configuration structure is judged by the value of Flack parameter, and the structure of the tested crystal is determined as shown in FIG. 12.

ORTEP Structure

Description of Equipment

Rigaku Oxford Diffraction XtaLAB Synergy-S equipped with a HyPix-6000HE area detector Cryogenic system: Oxford Cryostream 800

Cu: λ=1.54184 Å, 50W

Distance from the crystal to the CCD detector: d=35 mm

Tube Voltage: 50 kV; Tube Current: 1 mA

Experimental

Colorless crystals of Compound 214 were obtained from Methanol-Methyl tert-butyl ether (1:1). A suitable crystal 0.20×0.20×0.03 $mm^3$ was selected for testing. Data collection temperature: T=149.99 (11) K. Total of 79982 reflections were collected in the 2□ range from 7.858 to 133.192°. The limiting indices were: −10≤h≤10, −26≤k≤26, −13≤l≤13; which yielded 7940 unique reflections ($R_{int}$=0.0760). The structure was solved using SHELXT (Sheldrick, G. M. 2015. Acta Cryst. A71, 3-8) and refined using SHELXL (against $F^2$) (Sheldrick, G. M. 2015. Acta Cryst. C71, 3-8). The total number of refined parameters was 619, compared with 7940 data. All reflections were included in the refinement. The goodness of fit on $F^2$ was 1.031 with a final R value for [I>=2σ(I)] $R_1$=0.0446 and $wR_2$=0.1187. The largest differential peak and hole were 0.23 and −0.49 $eÅ^{-3}$.

Figure 13:
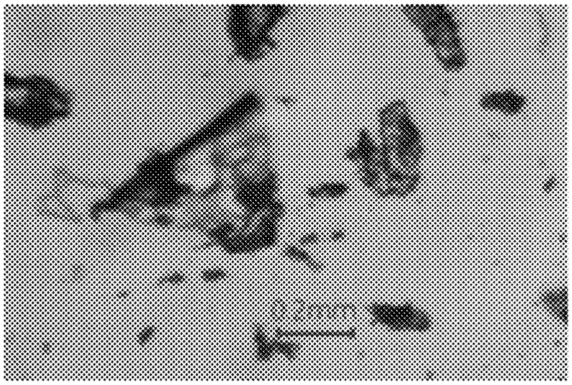
FIG. 13 depicts picture of crystals of Compound 214.

Picture of crystals depicted in FIG. 13

Data Tables

TABLE D-1

Summary of X-ray crystallographic data.

| | |
|---|---|
| Empirical formula | $C_{50}H_{50}F_2N_{10}O_6$ |
| Formula weight | 925.00 |
| Temperature/K | 149.99 (11) |
| Crystal system | monoclinic |
| Space group | $P2_1$ |
| a/Å | 9.23300 (10) |
| b/Å | 22.5017 (3) |
| c/Å | 10.99460 (10) |
| α/° | 90 |
| β/° | 97.5050 (10) |
| γ/° | 90 |
| Volume/$Å^3$ | 2264.65 (4) |
| Z | 2 |
| ρcalcg/$cm^3$ | 1.356 |
| μ/$mm^{-1}$ | 0.802 |
| F(000) | 972.0 |
| Crystal size/$mm^3$ | 0.20 × 0.20 × 0.03 |
| Radiation | Cu Kα (λ = 1.54184) |
| 2Θ range for data collection/° | 7.858 to 133.192 |
| Index ranges | −10 ≤ h ≤ 10, −26 ≤ k ≤ 26, −13 ≤ l ≤ 13 |
| Reflections collected | 79982 |
| Independent reflections | 7940 [$R_{int}$ = 0.0760, $R_{sigma}$ = 0.0291] |
| Data/restraints/parameters | 7940/1/619 |
| Goodness-of-fit on $F^2$ | 1.031 |
| Final R indexes [I >= 2σ (I)] | $R_1$ = 0.0446, $wR_2$ = 0.1187 |
| Final R indexes [all data] | $R_1$ = 0.0476, $wR_2$ = 0.1217 |
| Largest diff. peak/hole/e $Å^{-3}$ | 0.23/−0.49 |
| Flack parameter | −0.03 (8) |

TABLE D-2

Atomic coordinates (×$10^4$) and equivalent isotropic displacement parameters ($Å^2$ × $10^3$).

| Atom | x | y | z | U(eq) |
|---|---|---|---|---|
| F65 | 1128 (2) | 3613.8 (9) | 9732.2 (19) | 46.0 (5) |
| O4 | 3509 (3) | 7403.2 (10) | 6255 (2) | 41.5 (5) |
| F61 | −3826 (3) | 4677.4 (12) | 10647 (3) | 77.3 (8) |
| O2 | 1584 (3) | 6702.1 (12) | 2220 (2) | 49.5 (6) |
| O5 | 2802 (4) | 5298.9 (11) | 7970 (2) | 55.4 (7) |
| N4 | 4050 (3) | 7154.5 (11) | 8241 (2) | 36.0 (6) |
| N1 | 3727 (3) | 6074.6 (11) | 5842 (2) | 35.4 (6) |
| O1 | 9339 (3) | 3399.7 (12) | 3882 (3) | 56.6 (7) |
| N8 | 2929 (3) | 4585.7 (12) | 9533 (2) | 36.9 (6) |
| N5 | 253 (3) | 6804.4 (12) | 9409 (2) | 39.2 (6) |
| O3 | 2453 (4) | 7643.2 (14) | 2306 (3) | 60.8 (7) |
| N6 | 516 (3) | 6217.8 (12) | 9711 (2) | 37.7 (6) |
| N7 | 2511 (3) | 5511.2 (11) | 9998 (2) | 37.2 (6) |
| N3 | 2548 (3) | 7020.3 (13) | 4009 (2) | 42.4 (6) |
| N9 | 1842 (4) | 2233.9 (14) | 7138 (3) | 46.2 (7) |
| N10 | 2886 (3) | 2561.5 (13) | 6689 (3) | 44.4 (7) |

TABLE D-2-continued

Atomic coordinates (×$10^4$) and equivalent isotropic displacement parameters ($Å^2$ × $10^3$).

| Atom | x | y | z | U(eq) |
|---|---|---|---|---|
| N2 | 1476 (4) | 6229.5 (14) | 3097 (3) | 45.5 (7) |
| C24 | 1549 (4) | 7021.7 (14) | 9254 (3) | 36.5 (7) |
| C41 | 2760 (4) | 4610.1 (15) | 10773 (3) | 39.1 (7) |
| C11 | 4616 (4) | 5609.5 (14) | 5587 (3) | 35.4 (6) |
| C23 | 2670 (4) | 6595.7 (14) | 9472 (3) | 36.0 (7) |
| C16 | 2223 (4) | 6144.2 (14) | 5324 (3) | 35.7 (7) |
| C8 | 6850 (4) | 4806.7 (14) | 5311 (3) | 39.3 (7) |
| C22 | 3964 (3) | 7027.6 (14) | 7049 (3) | 33.4 (6) |
| C42 | 2993 (4) | 4074.2 (14) | 8785 (3) | 36.7 (7) |
| C47 | 2084 (4) | 3601.2 (14) | 8909 (3) | 35.8 (7) |
| C15 | 4538 (4) | 6442.9 (14) | 6703 (3) | 34.5 (7) |
| C20 | 2061 (4) | 6453.2 (15) | 4128 (3) | 37.1 (7) |
| C39 | 2481 (4) | 5172.8 (14) | 11064 (3) | 38.1 (7) |
| C30 | 1965 (4) | 6090.5 (14) | 9770 (3) | 36.3 (7) |
| C12 | 5994 (4) | 5686.9 (14) | 6270 (3) | 35.9 (7) |
| C46 | 2122 (4) | 3102.1 (14) | 8152 (3) | 36.4 (7) |
| C43 | 3950 (4) | 4055.9 (15) | 7879 (3) | 40.7 (7) |
| C40 | 2764 (4) | 5151.4 (14) | 9028 (3) | 38.5 (7) |
| C13 | 7121 (4) | 5283.6 (14) | 6116 (3) | 37.7 (7) |
| C48 | 1378 (4) | 2551.1 (15) | 8023 (3) | 41.8 (7) |
| C36 | −1554 (4) | 5983.0 (16) | 10792 (3) | 44.1 (8) |
| C26 | 3473 (4) | 7712.1 (14) | 8716 (3) | 38.3 (7) |
| C45 | 3085 (4) | 3099.2 (15) | 7279 (3) | 39.6 (7) |
| C14 | 5908 (4) | 6217.1 (14) | 6987 (3) | 36.8 (7) |
| C18 | 1076 (4) | 6248.2 (14) | 6163 (3) | 37.9 (7) |
| C5 | 8073 (4) | 4394.0 (15) | 5080 (3) | 40.4 (7) |
| C21 | 2237 (4) | 7183.2 (18) | 2809 (3) | 47.4 (8) |
| C31 | −643 (4) | 5830.4 (14) | 9937 (3) | 39.3 (7) |
| C3 | 9510 (4) | 3987.3 (17) | 3476 (4) | 47.1 (8) |
| C29 | 4205 (4) | 6735.7 (13) | 9292 (3) | 36.8 (7) |
| C44 | 4014 (4) | 3578.3 (16) | 7121 (3) | 44.5 (8) |
| C10 | 4311 (4) | 5126.1 (15) | 4791 (3) | 41.1 (7) |
| C17 | 1135 (4) | 5664.4 (15) | 5507 (3) | 41.2 (7) |
| C35 | −2656 (4) | 5601.3 (17) | 11043 (4) | 50.3 (9) |
| C28 | 4966 (4) | 7130.1 (15) | 10325 (3) | 43.3 (8) |
| C4 | 8304 (4) | 4395.5 (17) | 3719 (3) | 46.7 (8) |
| C19 | −145 (4) | 6682.7 (17) | 5837 (3) | 44.1 (8) |
| C25 | 1827 (4) | 7637.5 (14) | 8800 (3) | 39.3 (7) |
| C9 | 5430 (4) | 4732.4 (15) | 4682 (3) | 41.1 (7) |
| C27 | 4414 (4) | 7766.4 (15) | 9977 (3) | 43.7 (8) |
| C6 | 7902 (5) | 3744.3 (17) | 5454 (4) | 49.8 (9) |
| C34 | −2761 (4) | 5059.5 (17) | 10398 (4) | 56.3 (11) |
| C33 | −1875 (4) | 4892.8 (16) | 9553 (4) | 52.8 (10) |
| C32 | −803 (4) | 5289.2 (16) | 9308 (3) | 47.7 (9) |
| C2 | 11051 (5) | 4213 (2) | 3544 (4) | 59.1 (11) |
| C7 | 9214 (5) | 3389.0 (18) | 5167 (4) | 57.5 (10) |
| C38 | −3662 (5) | 5754 (2) | 11964 (5) | 62.9 (11) |
| C1 | 10187 (5) | 4038 (2) | 2338 (4) | 62.8 (11) |
| C49 | 3630 (6) | 2337 (2) | 5708 (5) | 68.8 (13) |
| C37 | −2052 (6) | 4298 (2) | 8907 (5) | 70.3 (13) |
| O6 | −2482 (5) | 7322 (3) | 8759 (5) | 117.9 (18) |
| C50 | −2548 (7) | 7724 (3) | 7783 (6) | 83.8 (15) |

TABLE D-3

Bond lengths [A].

| Atom | Atom | Length/Å | Atom | Atom | Length/Å |
|---|---|---|---|---|---|
| F65 | C47 | 1.345(4) | C16 | C18 | 1.511(5) |
| O4 | C22 | 1.248(4) | C16 | C17 | 1.506(5) |
| F61 | C34 | 1.361(5) | C8 | C13 | 1.393(4) |
| O2 | N2 | 1.447(4) | C8 | C5 | 1.509(5) |
| O2 | C21 | 1.361(5) | C8 | C9 | 1.410(5) |
| O5 | C40 | 1.214(4) | C22 | C15 | 1.487(4) |
| N4 | C22 | 1.333(4) | C42 | C47 | 1.373(5) |
| N4 | C26 | 1.485(4) | C42 | C43 | 1.417(5) |
| N4 | C29 | 1.483(4) | C47 | C46 | 1.400(4) |
| N1 | C11 | 1.381(4) | C15 | C14 | 1.361(5) |
| N1 | C16 | 1.439(4) | C12 | C13 | 1.407(5) |
| N1 | C15 | 1.399(4) | C12 | C14 | 1.438(4) |
| O1 | C3 | 1.411(5) | C46 | C48 | 1.416(5) |

TABLE D-3-continued

| Bond lengths [A]. | | | | | |
|---|---|---|---|---|---|
| Atom | Atom | Length/Å | Atom | Atom | Length/Å |
| O1 | C7 | 1.432(5) | C46 | C45 | 1.391(5) |
| N8 | C41 | 1.394(4) | C43 | C44 | 1.366(5) |
| N8 | C42 | 1.420(4) | C36 | C31 | 1.384(6) |
| N8 | C40 | 1.389(4) | C36 | C35 | 1.386(6) |
| N5 | N6 | 1.375(4) | C26 | C25 | 1.543(5) |
| N5 | C24 | 1.325(5) | C26 | C27 | 1.541(5) |
| O3 | C21 | 1.203(5) | C45 | C44 | 1.403(5) |
| N6 | C30 | 1.361(5) | C18 | C17 | 1.503(5) |
| N6 | C31 | 1.427(5) | C18 | C19 | 1.499(5) |
| N7 | C39 | 1.401(4) | C5 | C4 | 1.538(5) |
| N7 | C30 | 1.408(4) | C5 | C6 | 1.532(5) |
| N7 | C40 | 1.383(4) | C31 | C32 | 1.399(5) |
| N3 | C20 | 1.365(5) | C3 | C4 | 1.494(6) |
| N3 | C21 | 1.363(5) | C3 | C2 | 1.503(6) |
| N9 | N10 | 1.357(5) | C3 | C1 | 1.474(6) |
| N9 | C48 | 1.322(5) | C29 | C28 | 1.537(4) |
| N10 | C45 | 1.374(4) | C10 | C9 | 1.378(5) |
| N10 | C49 | 1.444(6) | C35 | C34 | 1.407(6) |
| N2 | C20 | 1.292(4) | C35 | C38 | 1.501(7) |
| C24 | C23 | 1.408(5) | C28 | C27 | 1.551(5) |
| C24 | C25 | 1.506(4) | C6 | C7 | 1.518(6) |
| C41 | C39 | 1.339(5) | C34 | C33 | 1.368(7) |
| C11 | C12 | 1.401(5) | C33 | C32 | 1.385(6) |
| C11 | C10 | 1.402(5) | C33 | C37 | 1.514(6) |
| C23 | C30 | 1.371(5) | C2 | C1 | 1.508(7) |
| C23 | C29 | 1.490(5) | O6 | C50 | 1.399(8) |
| C16 | C20 | 1.477(5) | | | |

TABLE D-4

| Bond angles [deg]. | | | | | | | |
|---|---|---|---|---|---|---|---|
| Atom | Atom | Atom | Angle/° | Atom | Atom | Atom | Angle/° |
| C21 | O2 | N2 | 109.4(2) | C11 | C12 | C14 | 106.6(3) |
| C22 | N4 | C26 | 123.3(3) | C13 | C12 | C14 | 134.1(3) |
| C22 | N4 | C29 | 128.1(3) | C47 | C46 | C48 | 135.5(3) |
| C29 | N4 | C26 | 105.4(2) | C45 | C46 | C47 | 118.8(3) |
| C11 | N1 | C16 | 124.7(3) | C45 | C46 | C48 | 105.8(3) |
| C11 | N1 | C15 | 107.9(3) | C44 | C43 | C42 | 122.2(3) |
| C15 | N1 | C16 | 127.4(3) | O5 | C40 | N8 | 128.2(3) |
| C3 | O1 | C7 | 110.8(3) | O5 | C40 | N7 | 127.4(3) |
| C41 | N8 | C42 | 128.1(3) | N7 | C40 | N8 | 104.4(3) |
| C40 | N8 | C41 | 109.6(3) | C8 | C13 | C12 | 119.9(3) |
| C40 | N8 | C42 | 121.5(3) | N9 | C48 | C46 | 110.3(3) |
| C24 | N5 | N6 | 104.6(3) | C31 | C36 | C35 | 120.6(4) |
| N5 | N6 | C31 | 121.0(3) | N4 | C26 | C25 | 109.3(3) |
| C30 | N6 | N5 | 110.8(3) | N4 | C26 | C27 | 101.4(3) |
| C30 | N6 | C31 | 128.2(3) | C27 | C26 | C25 | 113.5(3) |
| C39 | N7 | C30 | 127.3(3) | N10 | C45 | C46 | 105.8(3) |
| C40 | N7 | C39 | 110.5(3) | N10 | C45 | C44 | 131.6(3) |
| C40 | N7 | C30 | 119.9(3) | C46 | C45 | C44 | 122.6(3) |
| C21 | N3 | C20 | 108.3(3) | C15 | C14 | C12 | 107.4(3) |
| C48 | N9 | N10 | 106.8(3) | C17 | C18 | C16 | 60.0(2) |

TABLE D-4-continued

| Bond angles [deg]. | | | | | | | |
|---|---|---|---|---|---|---|---|
| Atom | Atom | Atom | Angle/° | Atom | Atom | Atom | Angle/° |
| N9 | N10 | C45 | 111.4(3) | C19 | C18 | C16 | 121.3(3) |
| N9 | N10 | C49 | 120.8(3) | C19 | C18 | C17 | 121.9(3) |
| C45 | N10 | C49 | 127.9(3) | C8 | C5 | C4 | 111.4(3) |
| C20 | N2 | O2 | 103.9(3) | C8 | C5 | C6 | 115.9(3) |
| N5 | C24 | C23 | 112.5(3) | C6 | C5 | C4 | 107.2(3) |
| N5 | C24 | C25 | 125.3(3) | O2 | C21 | N3 | 105.7(3) |
| C23 | C24 | C25 | 122.0(3) | O3 | C21 | O2 | 123.7(3) |
| C39 | C41 | N8 | 108.7(3) | O3 | C21 | N3 | 130.6(4) |
| N1 | C11 | C12 | 108.6(3) | C36 | C31 | N6 | 120.2(3) |
| N1 | C11 | C10 | 129.7(3) | C36 | C31 | C32 | 121.1(3) |
| C12 | C11 | C10 | 121.7(3) | C32 | C31 | N6 | 118.6(3) |
| C24 | C23 | C29 | 121.6(3) | O1 | C3 | C4 | 113.7(3) |
| C30 | C23 | C24 | 104.1(3) | O1 | C3 | C2 | 116.4(4) |
| C30 | C23 | C29 | 134.2(3) | O1 | C3 | C1 | 114.7(3) |
| N1 | C16 | C20 | 112.6(3) | C4 | C3 | C2 | 120.4(3) |
| N1 | C16 | C18 | 119.5(3) | C1 | C3 | C4 | 120.9(4) |
| N1 | C16 | C17 | 119.7(3) | C1 | C3 | C2 | 60.9(3) |
| C20 | C16 | C18 | 118.2(3) | N4 | C29 | C23 | 103.9(3) |
| C20 | C16 | C17 | 117.7(3) | N4 | C29 | C28 | 101.4(2) |
| C17 | C16 | C18 | 59.7(2) | C23 | C29 | C28 | 112.0(3) |
| C13 | C8 | C5 | 120.3(3) | C43 | C44 | C45 | 116.9(3) |
| C13 | C8 | C9 | 118.8(3) | C9 | C10 | C11 | 117.5(3) |
| C9 | C8 | C5 | 120.8(3) | C18 | C17 | C16 | 60.3(2) |
| O4 | C22 | N4 | 120.9(3) | C36 | C35 | C34 | 116.1(4) |
| O4 | C22 | C15 | 121.2(3) | C36 | C35 | C38 | 121.9(4) |
| N4 | C22 | C15 | 117.6(3) | C34 | C35 | C38 | 122.0(4) |
| C47 | C42 | N8 | 119.9(3) | C29 | C28 | C27 | 104.3(3) |
| C47 | C42 | C43 | 119.5(3) | C3 | C4 | C5 | 112.0(3) |
| C43 | C42 | N8 | 120.5(3) | C24 | C25 | C26 | 109.3(3) |
| F65 | C47 | C42 | 120.9(3) | C10 | C9 | C8 | 122.7(3) |
| F65 | C47 | C46 | 119.1(3) | C26 | C27 | C28 | 106.1(3) |
| C42 | C47 | C46 | 120.0(3) | C7 | C6 | C5 | 109.5(3) |
| N1 | C15 | C22 | 121.4(3) | F61 | C34 | C35 | 116.7(4) |
| C14 | C15 | N1 | 109.5(3) | F61 | C34 | C33 | 118.4(4) |
| C14 | C15 | C22 | 128.5(3) | C33 | C34 | C35 | 124.9(4) |
| N3 | C20 | C16 | 121.9(3) | C34 | C33 | C32 | 117.5(4) |
| N2 | C20 | N3 | 112.7(3) | C34 | C33 | C37 | 121.6(4) |
| N2 | C20 | C16 | 125.4(3) | C32 | C33 | C37 | 121.0(5) |
| C41 | C39 | N7 | 106.8(3) | C33 | C32 | C31 | 119.8(4) |
| N6 | C30 | N7 | 122.0(3) | C3 | C2 | C1 | 58.6(3) |
| N6 | C30 | C23 | 108.0(3) | O1 | C7 | C6 | 111.4(4) |
| C23 | C30 | N7 | 129.8(3) | C3 | C1 | C2 | 60.5(3) |
| C11 | C12 | C13 | 119.3(3) | | | | |

TABLE D-5

| Hydrogen bonds. | | | | | | |
|---|---|---|---|---|---|---|
| D | H | A | d(D − H)/Å | d(H − A)/Å | d(D − A)/Å | D − H − A/° |
| N3 | H3 | O4 | 0.88 | 1.85 | 2.656(4) | 151.2 |
| O6 | H6 | N5 | 0.84 | 1.96 | 2.788(6) | 167.2 |

TABLE D-6

| Torsion angles [deg]. | | | | | | | | | |
|---|---|---|---|---|---|---|---|---|---|
| A | B | C | D | Angle/° | A | B | C | D | Angle/° |
| F65 | C47 | C46 | C48 | −1.6(6) | C20 | C16 | C18 | C17 | 107.3(3) |
| F65 | C47 | C46 | C45 | 178.2(3) | C20 | C16 | C18 | C19 | −4.0(5) |
| O4 | C22 | C15 | N1 | −52.6(5) | C20 | C16 | C17 | C18 | −108.2(3) |
| O4 | C22 | C15 | C14 | 117.4(4) | C39 | N7 | C30 | N6 | −64.2(4) |
| F61 | C34 | C33 | C32 | 179.7(3) | C39 | N7 | C30 | C23 | 122.1(4) |
| F61 | C34 | C33 | C37 | −0.4(6) | C39 | N7 | C40 | O5 | 177.1(4) |
| O2 | N2 | C20 | N3 | −0.5(4) | C39 | N7 | C40 | N8 | −1.6(4) |
| O2 | N2 | C20 | C16 | −179.9(3) | C30 | N6 | C31 | C36 | 125.0(4) |
| N4 | C22 | C15 | N1 | 132.2(3) | C30 | N6 | C31 | C32 | −52.9(4) |
| N4 | C22 | C15 | C14 | −57.8(5) | C30 | N7 | C39 | C41 | 164.4(3) |
| N4 | C26 | C25 | C24 | 39.6(3) | C30 | N7 | C40 | O5 | 13.1(6) |

TABLE D-6-continued

| Torsion angles [deg]. | | | | | | | | | |
|---|---|---|---|---|---|---|---|---|---|
| A | B | C | D | Angle/° | A | B | C | D | Angle/° |
| N4 | C26 | C27 | C28 | −22.6(4) | C30 | N7 | C40 | N8 | −165.5(3) |
| N4 | C29 | C28 | C27 | 30.0(4) | C30 | C23 | C29 | N4 | 141.5(3) |
| N1 | C11 | C12 | C13 | −176.7(3) | C30 | C23 | C29 | C28 | −109.9(4) |
| N1 | C11 | C12 | C14 | 1.3(4) | C12 | C11 | C10 | C9 | −1.3(5) |
| N1 | C11 | C10 | C9 | 177.9(3) | C46 | C45 | C44 | C43 | 0.7(5) |
| N1 | C16 | C20 | N3 | −61.3(4) | C43 | C42 | C47 | F65 | −177.7(3) |
| N1 | C16 | C20 | N2 | 118.0(4) | C43 | C42 | C47 | C46 | 0.9(5) |
| N1 | C16 | C18 | C17 | −109.2(3) | C40 | N8 | C41 | C39 | 0.6(4) |
| N1 | C16 | C18 | C19 | 139.5(3) | C40 | N8 | C42 | C47 | −127.8(4) |
| N1 | C16 | C17 | C18 | 108.8(3) | C40 | N8 | C42 | C43 | 49.8(4) |
| N1 | C15 | C14 | C12 | 0.8(4) | C40 | N7 | C39 | C41 | 2.0(4) |
| O1 | C3 | C4 | C5 | 54.3(4) | C40 | N7 | C30 | N6 | 96.8(4) |
| O1 | C3 | C2 | C1 | 104.9(4) | C40 | N7 | C30 | C23 | −76.9(4) |
| O1 | C3 | C1 | C2 | −107.7(4) | C13 | C8 | C5 | C4 | −119.5(3) |
| N8 | C41 | C39 | N7 | −1.5(4) | C13 | C8 | C5 | C6 | 117.7(4) |
| N8 | C42 | C47 | F65 | −0.1(5) | C13 | C8 | C9 | C10 | 2.8(5) |
| N8 | C42 | C47 | C46 | 178.5(3) | C13 | C12 | C14 | C15 | 176.2(4) |
| N8 | C42 | C43 | C44 | −178.2(3) | C48 | N9 | N10 | C45 | −0.8(4) |
| N5 | N6 | C30 | N7 | −176.5(3) | C48 | N9 | N10 | C49 | 179.5(4) |
| N5 | N6 | C30 | C23 | −1.6(3) | C48 | C46 | C45 | N10 | −0.3(4) |
| N5 | N6 | C31 | C36 | −53.8(4) | C48 | C46 | C45 | C44 | 179.5(3) |
| N5 | N6 | C31 | C32 | 128.2(3) | C36 | C31 | C32 | C33 | −1.0(5) |
| N5 | C24 | C23 | C30 | 0.4(3) | C36 | C35 | C34 | F61 | 179.2(3) |
| N5 | C24 | C23 | C29 | 177.0(3) | C36 | C35 | C34 | C33 | −0.6(6) |
| N5 | C24 | C25 | C26 | −178.6(3) | C26 | N4 | C22 | O4 | 7.0(5) |
| N6 | N5 | C24 | C23 | −1.3(3) | C26 | N4 | C22 | C15 | −177.8(3) |
| N6 | N5 | C24 | C25 | 174.1(3) | C26 | N4 | C29 | C23 | 69.8(3) |
| N6 | C31 | C32 | C33 | 176.9(3) | C26 | N4 | C29 | C28 | −46.5(3) |
| N9 | N10 | C45 | C46 | 0.7(4) | C45 | C46 | C48 | N9 | −0.1(4) |
| N9 | N10 | C45 | C44 | −179.1(4) | C14 | C12 | C13 | C8 | −178.7(3) |
| N10 | N9 | C48 | C46 | 0.5(4) | C18 | C16 | C20 | N3 | 84.6(4) |
| N10 | C45 | C44 | C43 | −179.6(3) | C18 | C16 | C20 | N2 | −96.1(4) |
| N2 | O2 | C21 | O3 | −179.2(4) | C5 | C8 | C13 | C12 | 176.2(3) |
| N2 | O2 | C21 | N3 | 0.7(4) | C5 | C8 | C9 | C10 | −174.7(3) |
| C24 | N5 | N6 | C30 | 1.7(3) | C5 | C6 | C7 | O1 | −60.9(4) |
| C24 | N5 | N6 | C31 | −179.2(3) | C21 | O2 | N2 | C20 | −0.1(4) |
| C24 | C23 | C30 | N6 | 0.7(3) | C21 | N3 | C20 | N2 | 1.0(4) |
| C24 | C23 | C30 | N7 | 175.1(3) | C21 | N3 | C20 | C16 | −179.6(3) |
| C24 | C23 | C29 | N4 | −33.9(4) | C31 | N6 | C30 | N7 | 4.6(5) |
| C24 | C23 | C29 | C28 | 74.7(3) | C31 | N6 | C30 | C23 | 179.5(3) |
| C41 | N8 | C42 | C47 | 40.1(5) | C31 | C36 | C35 | C34 | 0.9(5) |
| C41 | N8 | C42 | C43 | −142.3(3) | C31 | C36 | C35 | C38 | 180.0(3) |
| C41 | N8 | C40 | O5 | −178.0(4) | C3 | O1 | C7 | C6 | 60.3(4) |
| C41 | N8 | C40 | N7 | 0.6(4) | C29 | N4 | C22 | O4 | 163.6(3) |
| C11 | N1 | C16 | C20 | −86.3(4) | C29 | N4 | C22 | C15 | −21.2(5) |
| C11 | N1 | C16 | C18 | 128.3(3) | C29 | N4 | C26 | C25 | −76.8(3) |
| C11 | N1 | C16 | C17 | 58.5(4) | C29 | N4 | C26 | C27 | 43.3(3) |
| C11 | N1 | C15 | C22 | 171.7(3) | C29 | C23 | C30 | N6 | −175.3(3) |
| C11 | N1 | C15 | C14 | 0.0(4) | C29 | C23 | C30 | N7 | −0.9(6) |
| C11 | C12 | C13 | C8 | −1.4(5) | C29 | C28 | C27 | C26 | −4.5(4) |
| C11 | C12 | C14 | C15 | −1.3(4) | C10 | C11 | C12 | C13 | 2.7(5) |
| C11 | C10 | C9 | C8 | −1.5(5) | C10 | C11 | C12 | C14 | −179.3(3) |
| C23 | C24 | C25 | C26 | −3.6(4) | C17 | C16 | C20 | N3 | 153.2(3) |
| C23 | C29 | C28 | C27 | −80.2(3) | C17 | C16 | C20 | N2 | −27.5(5) |
| C16 | N1 | C11 | C12 | −179.2(3) | C17 | C16 | C18 | C19 | −111.3(4) |
| C16 | N1 | C11 | C10 | 1.4(5) | C35 | C36 | C31 | N6 | −178.1(3) |
| C16 | N1 | C15 | C22 | −10.0(5) | C35 | C36 | C31 | C32 | −0.2(5) |
| C16 | N1 | C15 | C14 | 178.3(3) | C35 | C34 | C33 | C32 | −0.5(6) |
| C8 | C5 | C4 | C3 | −179.8(3) | C35 | C34 | C33 | C37 | 179.4(4) |
| C8 | C5 | C6 | C7 | −179.9(3) | C4 | C5 | C6 | C7 | 55.1(4) |
| C22 | N4 | C26 | C25 | 84.2(4) | C4 | C3 | C2 | C1 | −110.7(4) |
| C22 | N4 | C26 | C27 | −155.6(3) | C4 | C3 | C1 | C2 | 110.0(4) |
| C22 | N4 | C29 | C23 | −90.1(4) | C19 | C18 | C17 | C16 | 110.3(4) |
| C22 | N4 | C29 | C28 | 153.6(3) | C25 | C24 | C23 | C30 | −175.2(3) |
| C22 | C15 | C14 | C12 | −170.1(3) | C25 | C24 | C23 | C29 | 1.4(4) |
| C42 | N8 | C41 | C39 | −168.5(3) | C25 | C26 | C27 | C28 | 94.5(3) |
| C42 | N8 | C40 | O5 | −8.0(6) | C9 | C8 | C13 | C12 | −1.3(5) |
| C42 | N8 | C40 | N7 | 170.6(3) | C9 | C8 | C5 | C4 | 57.9(4) |
| C42 | C47 | C46 | C48 | 179.8(4) | C9 | C8 | C5 | C6 | −64.9(4) |
| C42 | C47 | C46 | C45 | −0.4(5) | C27 | C26 | C25 | C24 | −72.7(3) |
| C42 | C43 | C44 | C45 | −0.2(5) | C6 | C5 | C4 | C3 | −52.2(4) |
| C47 | C42 | C43 | C44 | −0.6(5) | C34 | C33 | C32 | C31 | 1.3(5) |
| C47 | C46 | C48 | N9 | 179.7(4) | C2 | C3 | C4 | C5 | −91.0(5) |
| C47 | C46 | C45 | N10 | 179.8(3) | C7 | O1 | C3 | C4 | −56.9(4) |
| C47 | C46 | C45 | C44 | −0.4(5) | C7 | O1 | C3 | C2 | 89.7(4) |
| C15 | N1 | C11 | C12 | −0.9(4) | C7 | O1 | C3 | C1 | 158.0(4) |

TABLE D-6-continued

| Torsion angles [deg]. | | | | | | | | | |
|---|---|---|---|---|---|---|---|---|---|
| A | B | C | D | Angle/° | A | B | C | D | Angle/° |
| C15 | N1 | C11 | C10 | 179.8(3) | C38 | C35 | C34 | F61 | 0.1(5) |
| C15 | N1 | C16 | C20 | 95.7(4) | C38 | C35 | C34 | C33 | −179.6(4) |
| C15 | N1 | C16 | C18 | −49.7(4) | C1 | C3 | C4 | C5 | −163.1(3) |
| C15 | N1 | C16 | C17 | −119.6(4) | C49 | N10 | C45 | C46 | −179.6(4) |
| C20 | N3 | C21 | O2 | −1.0(4) | C49 | N10 | C45 | C44 | 0.6(7) |
| C20 | N3 | C21 | O3 | 178.9(4) | C37 | C33 | C32 | C31 | −178.6(3) |

Example F: Pharmaceutical Compositions

The compositions described below are presented with a compound of Formula (I) for illustrative purposes.

Example F2a: Parenteral Composition

To prepare a parenteral pharmaceutical composition suitable for administration by injection, 100 mg of a water-soluble salt of a compound of Formula (I) is dissolved in DMSO and then mixed with 10 mL of 0.9% sterile saline. The mixture is incorporated into a dosage unit form suitable for administration by injection.

Example F2b: Oral Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example F2c: Sublingual (Hard Lozenge) Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example F2d: Inhalation Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example F2e: Rectal Gel Composition

To prepare a pharmaceutical composition for rectal delivery, 100 mg of a compound of Formula (I) is mixed with 2.5 g of methylcellulose (1500 mPa), 100 mg of methylparaben, 5 g of glycerin and 100 mL of purified water. The resulting gel mixture is then incorporated into rectal delivery units, such as syringes, which are suitable for rectal administration.

Example F2f: Topical Gel Composition

To prepare a pharmaceutical topical gel composition, 100 mg of a compound of Formula (I) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example F2g: Ophthalmic Solution Composition

To prepare a pharmaceutical ophthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

At least some of the chemical names of compounds provided herein as given and set forth in this application, may have been generated on an automated basis by use of a commercially available chemical naming software program, and have not been independently verified. In the instance where the indicated chemical name and the depicted structure differ, the depicted structure will control. In the chemical structures where a chiral center exists in a structure, but no specific stereochemistry is shown for the chiral center, both enantiomers associated with the chiral structure are encompassed by the structure.

What is claimed is:
1. A compound selected from the group consisting of:
TABLE 1'
| Compound ID | Structure |
|---|---|
| 32 | 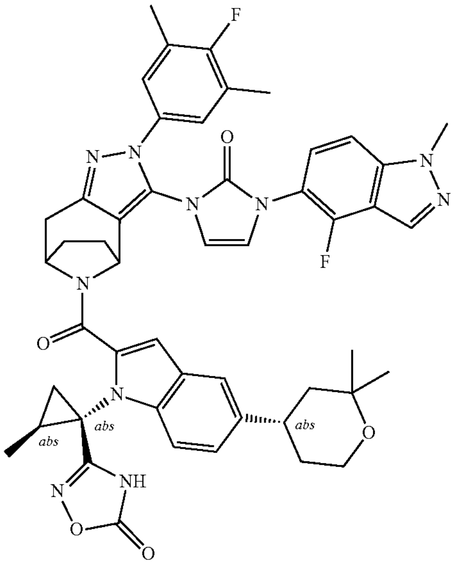<br>C49H48F2N10O5 |
| 36 | 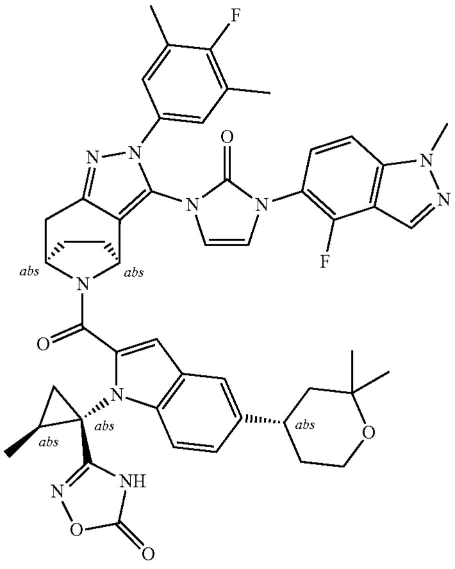<br>C49H48F2N10O5 |
TABLE 1'-continued
| Compound ID | Structure |
|---|---|
| 114 | 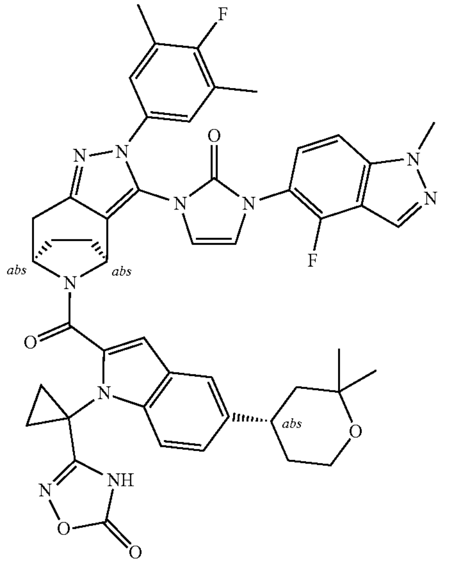 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F]<br>C48H46F2N10O5 |
| 115 | 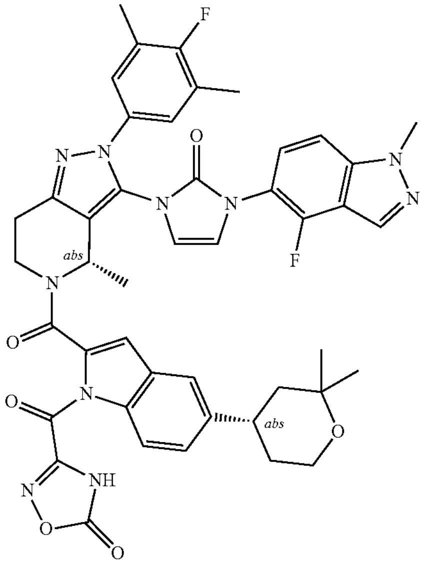 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2C(=O)c2noc(=O)[nH]2)CC3)cc(C)c1F]<br>C45H42F2N10O6 |

TABLE 1'-continued
| Compound ID | Structure |
| --- | --- |
| 116 | 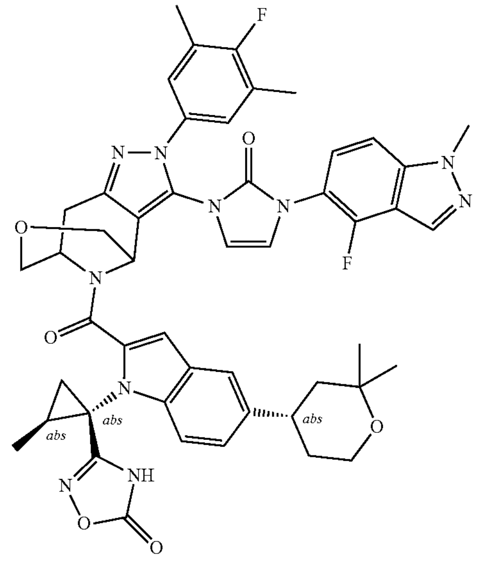 C49H48F2N10O6 |
| 117 | 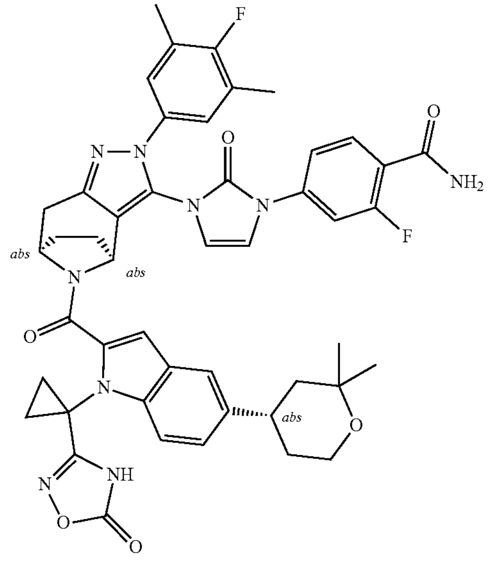 [SMILES: Cc1cc(-n2nc3c(c2-n2ccn(-c4ccc(C(N)=O)c(F)c4)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C47H45F2N9O6 |
TABLE 1'-continued
| Compound ID | Structure |
| --- | --- |
| 118 | 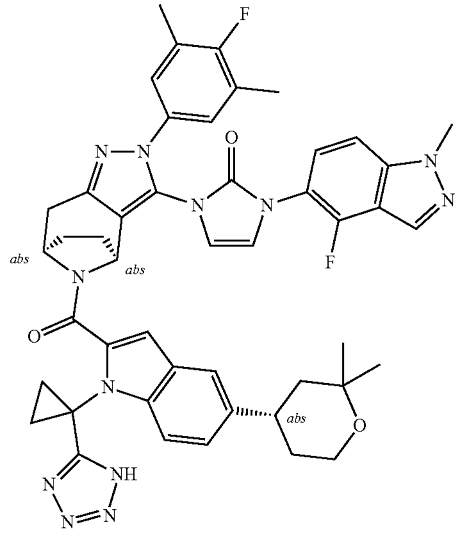 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3nnn[nH]3)CC2)cc(C)c1F] C47H46F2N12O3 |
| 119 | 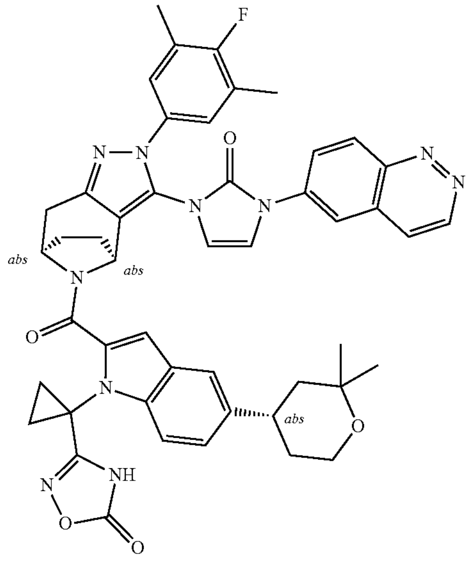 [SMILES: Cc1cc(-n2nc3c(c2-n2ccn(-c4ccc5nnccc5c4)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H45FN10O5 |

TABLE 1'-continued
| Compound ID | Structure |
|---|---|
| 121 | 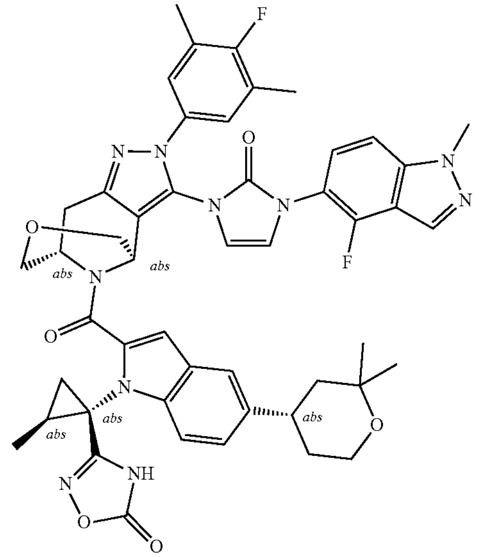 C49H48F2N10O6 |
| 122 | 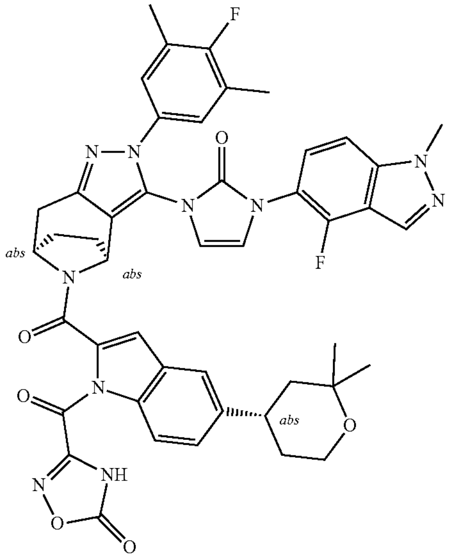 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C(=O)c2noc(=O)[nH]2)cc(C)c1F] C46H42F2N10O6 |
TABLE 1'-continued
| Compound ID | Structure |
|---|---|
| 123 | 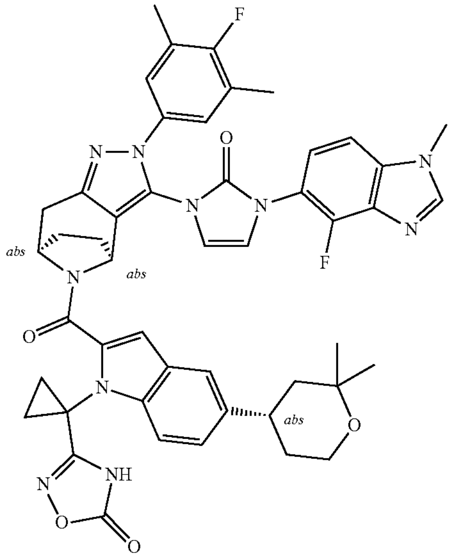 [SMILES: Cc1cc(-n2nc3c(c2-n2ccn(-c4ccc5c(ncn5C)c4F)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H46F2N10O5 |
| 124 | 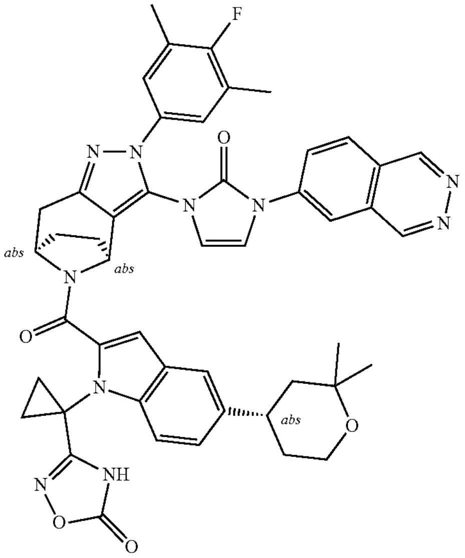 [SMILES: Cc1cc(-n2nc3c(c2-n2ccn(-c4ccc5cnncc5c4)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C48H45FN10O5 |

TABLE 1'-continued
| Compound ID | Structure |
| --- | --- |
| 125 | 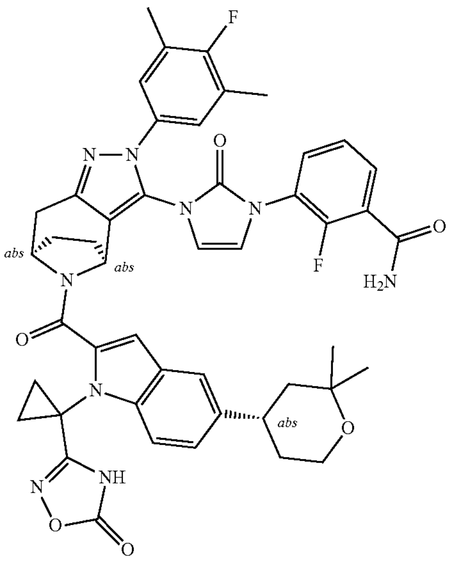 [SMILES: Cc1cc(-n2nc3c(c2-n2ccn(-c4cccc(C(N)=O)c4F)c2=O)[C@@H]2CC[C@H](C3)N2C(=O)c2cc3cc([C@H]4CCOC(C)(C)C4)ccc3n2C2(c3noc(=O)[nH]3)CC2)cc(C)c1F] C47H45F2N9O6 |
| 126 | 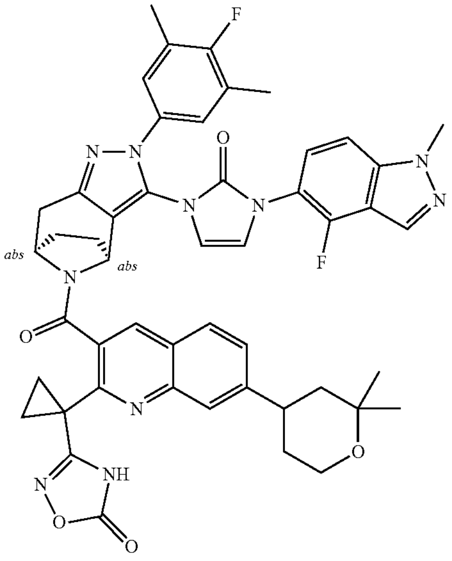 [SMILES: Cc1cc(-n2nc3c(c2-n2ccn(-c4ccc5c(cnn5C)c4F)c2=O)[C@@H]2CC[C@H](C3)N2C(=O)c2cc3ccc(C4CCOC(C)(C)C4)cc3nc2C2(c3noc(=O)[nH]3)CC2)cc(C)c1F] C49H46F2N10O5 |
TABLE 1'-continued
| Compound ID | Structure |
| --- | --- |
| 127 | 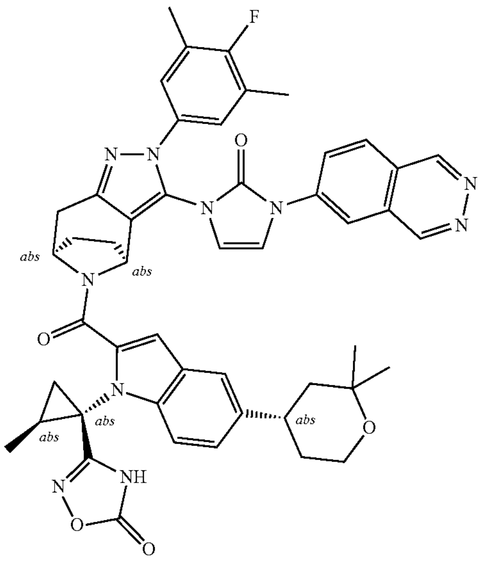 [SMILES: Cc1cc(-n2nc3c(c2-n2ccn(-c4ccc5cnncc5c4)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H47FN10O5 |
| 128 | 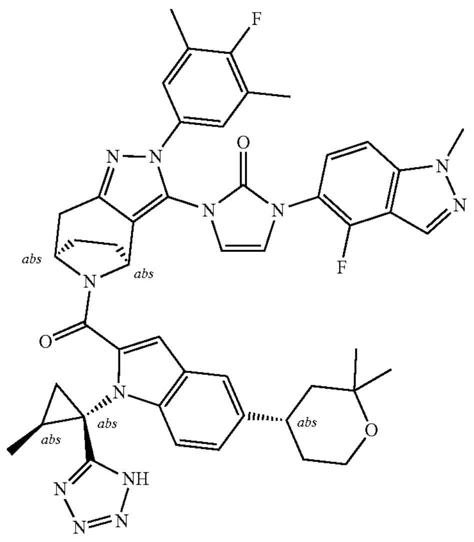 C48H48F2N12O3 |

TABLE 1'-continued
| Compound ID | Structure |
|---|---|
| 129 | 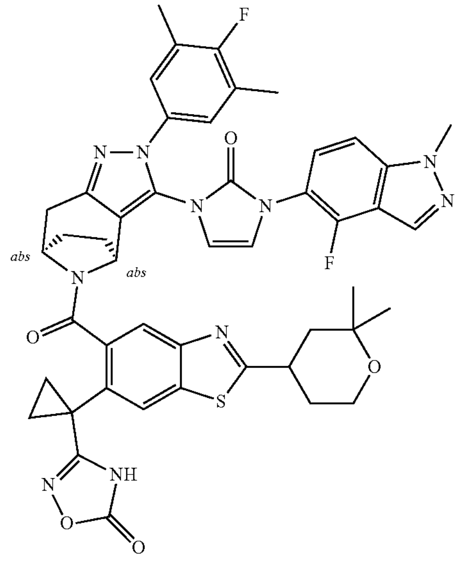 [SMILES: Cc1cc(-n2nc3c(c2-n2ccn(-c4ccc5c(cnn5C)c4F)c2=O)[C@@H]2CC[C@H](C3)N2C(=O)c2cc3nc(C4CCOC(C)(C)C4)sc3cc2C2(c3noc(=O)[nH]3)CC2)cc(C)c1F] C47H44F2N10O5S |
| 131 | 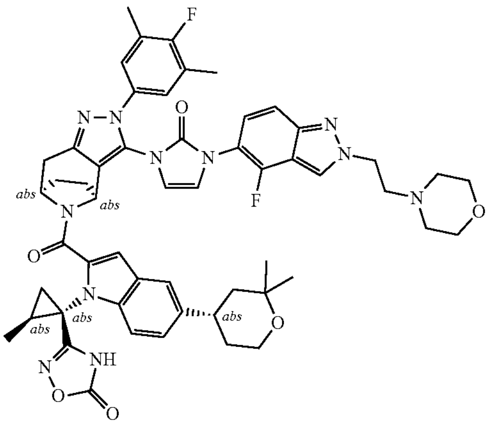 [SMILES: Cc1cc(-n2nc3c(c2-n2ccn(-c4ccc5nn(CCN6CCOCC6)cc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C54H57F2N11O6 |
| 132 | 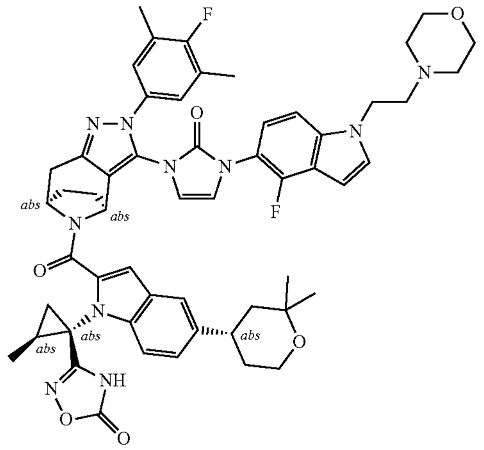 [SMILES: Cc1cc(-n2nc3c(c2-n2ccn(-c4ccc5c(ccn5CCN5CCOCC5)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C54H57F2N11O6 |
TABLE 1'-continued
| Compound ID | Structure |
|---|---|
| 134 | 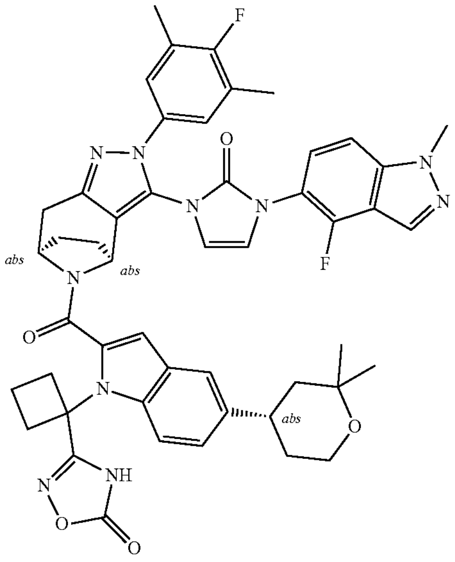 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C2(c3noc(=O)[nH]3)CCC2)cc(C)c1F] C49H48F2N10O5 |
| 135 | 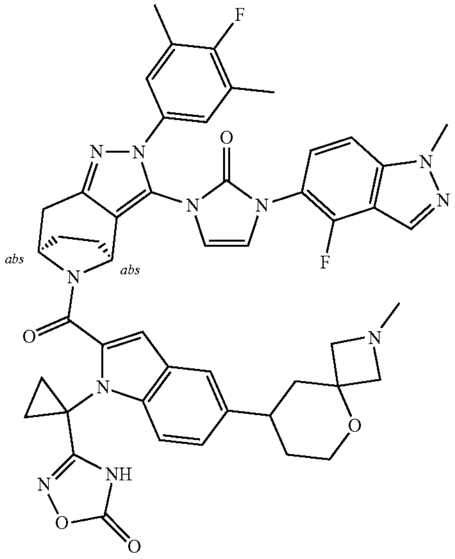 [SMILES: Cc1cc(-n2nc3c(c2-n2ccn(-c4ccc5c(cnn5C)c4F)c2=O)[C@@H]2CC[C@H](C3)N2C(=O)c2cc3cc(C4CCOC5(C4)CN(C)C5)ccc3n2C2(c3noc(=O)[nH]3)CC2)cc(C)c1F] C49H47F2N11O5 |

| Compound ID | Structure |
|---|---|
| 136 | 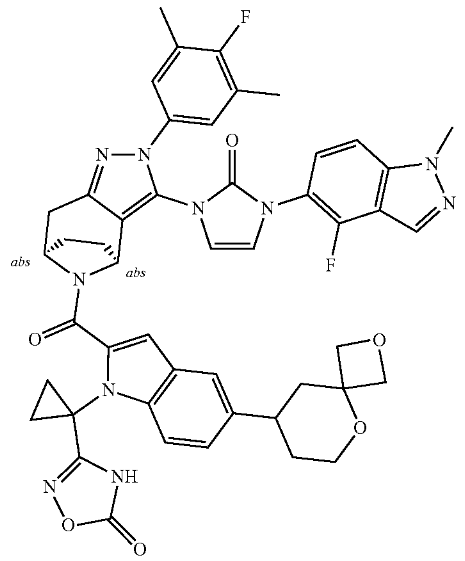 [SMILES: Cc1cc(-n2nc3c(c2-n2ccn(-c4ccc5c(cnn5C)c4F)c2=O)[C@@H]2CC[C@H](C3)N2C(=O)c2cc3cc(C4CCOC5(COC5)C4)ccc3n2C2(c3noc(=O)[nH]3)CC2)cc(C)c1F] C48H44F2N10O6 |
| 137 | 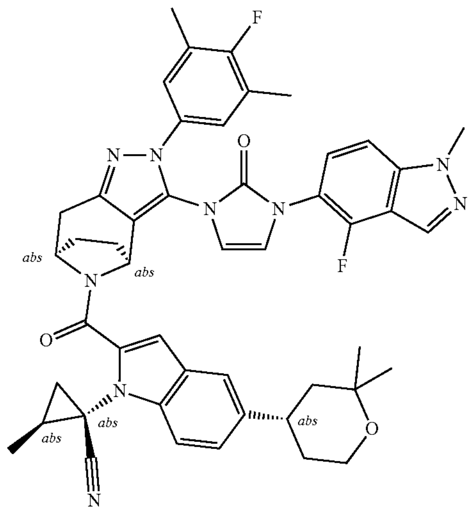 C48H47F2N9O3 |
| Compound ID | Structure |
|---|---|
| 138 | 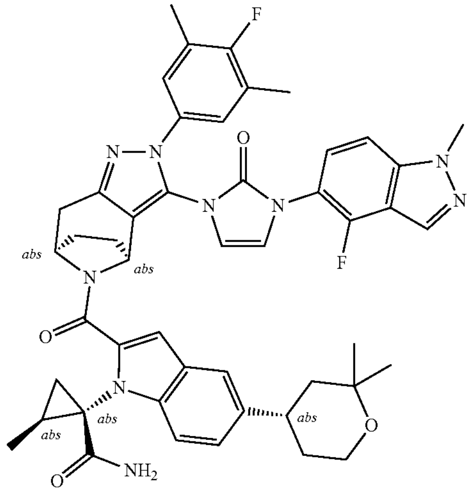 C48H49F2N9O4 |
| 139 | 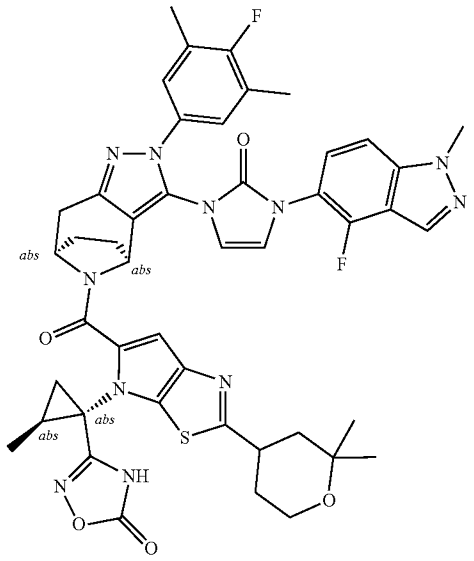 C46H45F2N11O5S |

TABLE 1'-continued
| Compound ID | Structure |
|---|---|
| 140 | 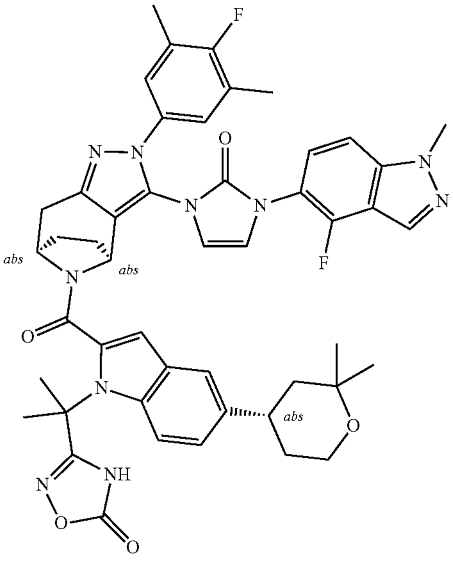 [SMILES: Cc1cc(-n2nc3c(c2-n2ccn(-c4ccc5c(cnn5C)c4F)c2=O)[C@@H]2CC[C@H](C3)N2C(=O)c2cc3cc([C@H]4CCOC(C)(C)C4)ccc3n2C(C)(C)c2noc(=O)[nH]2)cc(C)c1F] C48H48F2N10O5 |
| 201 | 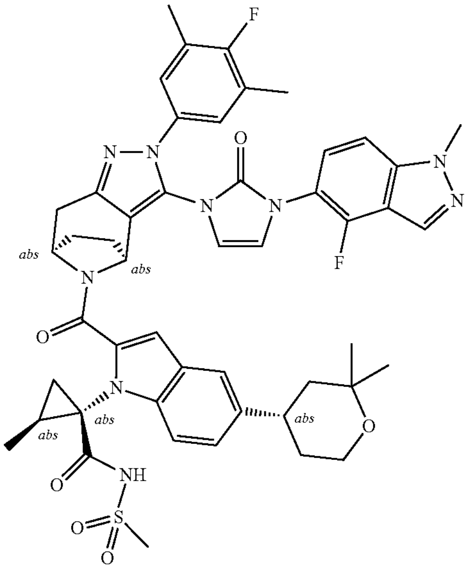 C49H51F2N9O6S |
TABLE 1'-continued
| Compound ID | Structure |
|---|---|
| 203 | 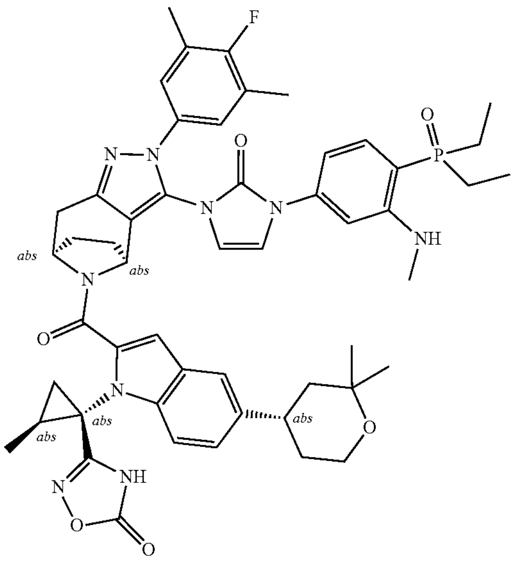 [SMILES: CCP(=O)(CC)c1ccc(-n2ccn(-c3c4c(nn3-c3cc(C)c(F)c(C)c3)C[C@H]3CC[C@@H]4N3C(=O)c3cc4cc([C@H]5CCOC(C)(C)C5)ccc4n3[C@@]3(c4noc(=O)[nH]4)C[C@@H]3C)c2=O)cc1NC] C52H59FN9O6P |
| 204 | 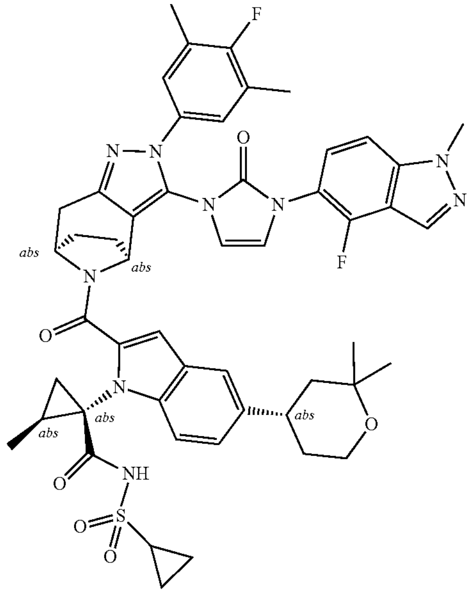 C51H53F2N9O6S |

TABLE 1'-continued
| Compound ID | Structure |
| --- | --- |
| 205 | 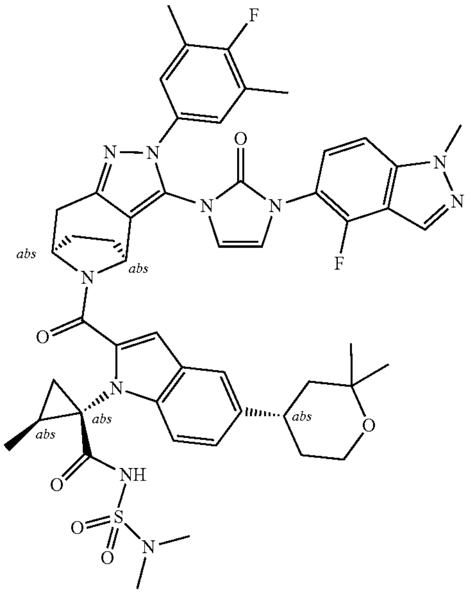 C50H54F2N10O6S |
| 206 | 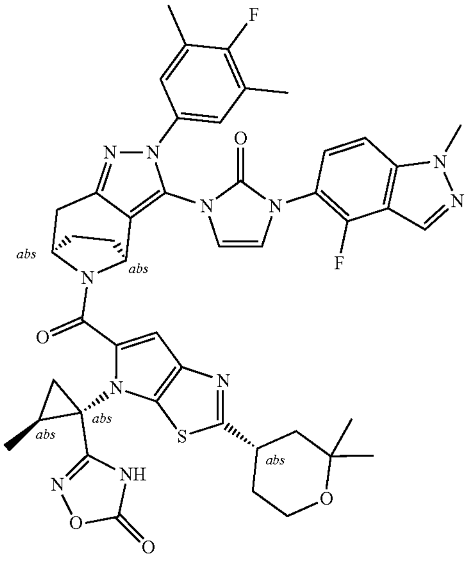 C46H45F2N11O5S |
TABLE 1'-continued
| Compound ID | Structure |
| --- | --- |
| 208 | 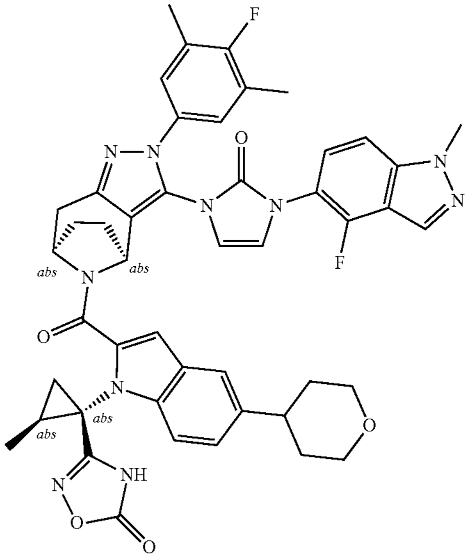 C47H44F2N10O5 |
| 209 | 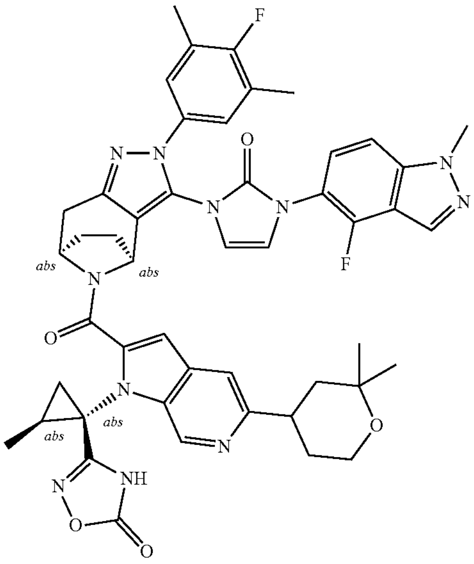 C48H47F2N11O5 |

TABLE 1'-continued
| Compound ID | Structure |
|---|---|
| 210 | 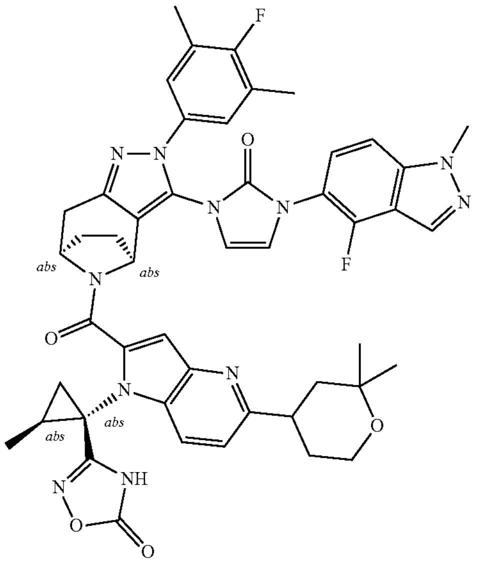 C48H47F2N11O5 |
| 211 | 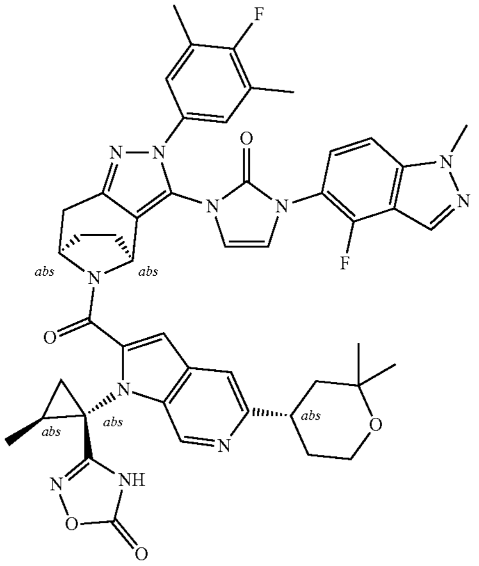 C48H47F2N11O5 |
TABLE 1'-continued
| Compound ID | Structure |
|---|---|
| 212 | 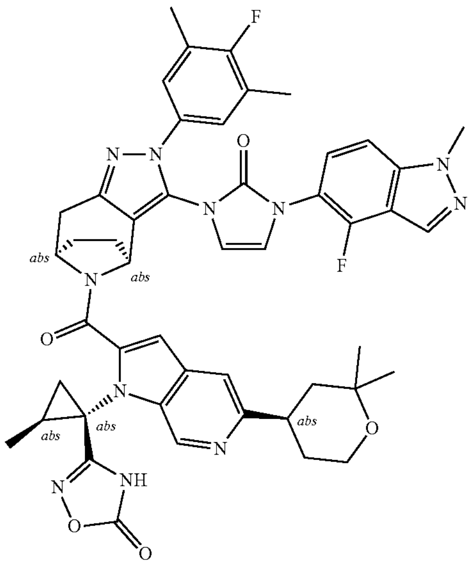 C48H47F2N11O5 |
| 213 | 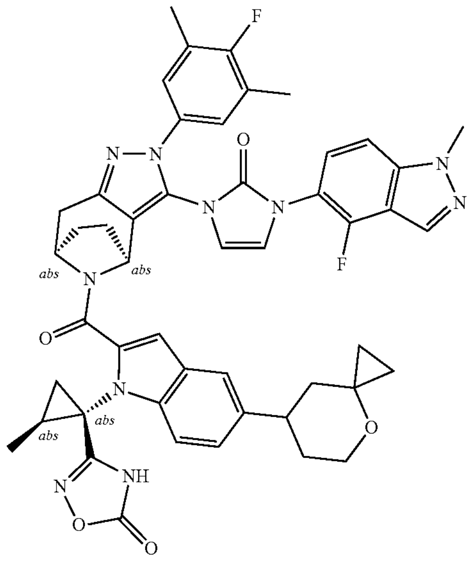 C49H46F2N10O5 |

| Compound ID | Structure |
|---|---|
| 214 | 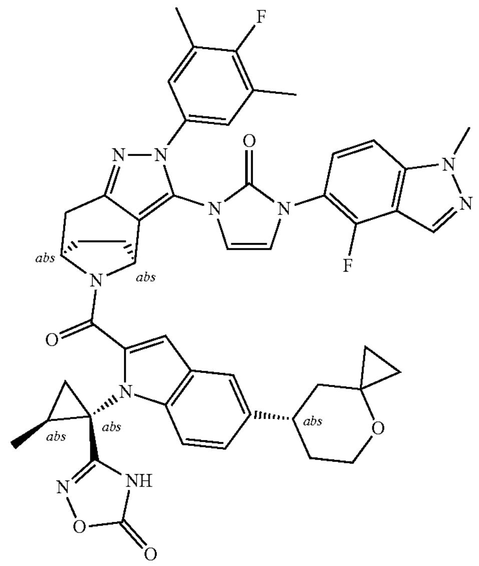 C49H46F2N10O5 |
| 215 | 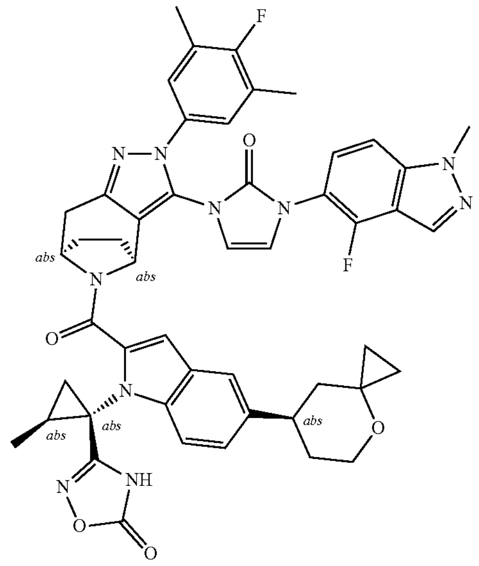 C49H46F2N10O5 |
| Compound ID | Structure |
|---|---|
| 216 | 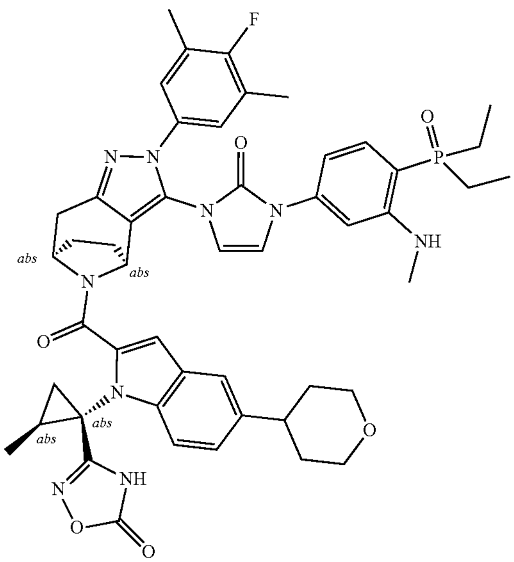 [SMILES: CCP(=O)(CC)c1ccc(-n2ccn(-c3c4c(nn3-c3cc(C)c(F)c(C)c3)C[C@H]3CC[C@@H]4N3C(=O)c3cc4cc(C5CCOCC5)ccc4n3[C@@]3(c4noc(=O)[nH]4)C[C@@H]3C)c2=O)cc1NC] C50H55FN9O6P |
| 217 | 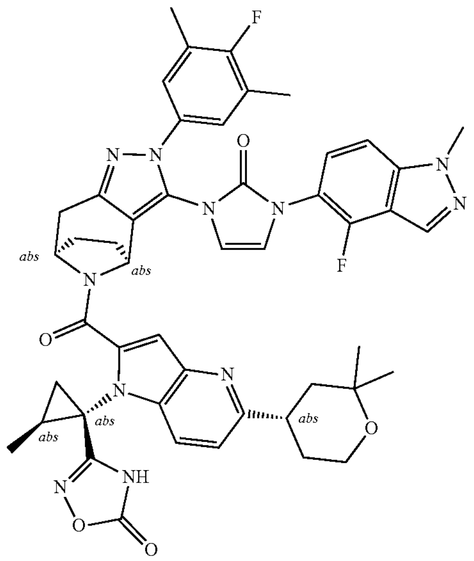 C48H47F2N11O5 |

TABLE 1'-continued
| Compound ID | Structure |
| --- | --- |
| 218 | 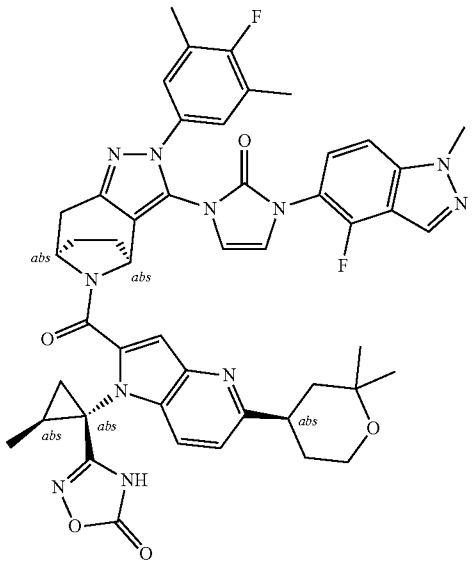 C48H47F2N11O5 |
| 219 | 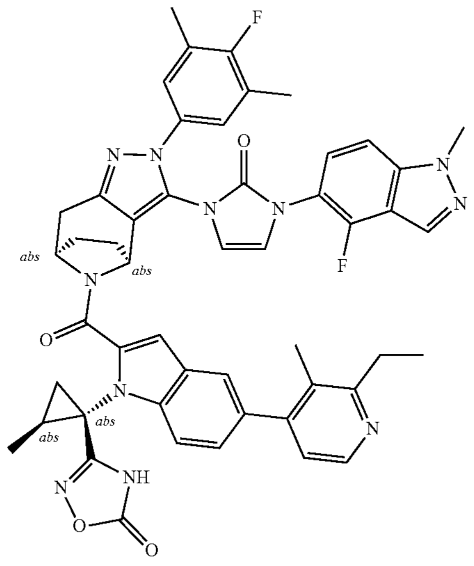 C50H45F2N11O4 |
| 220 | 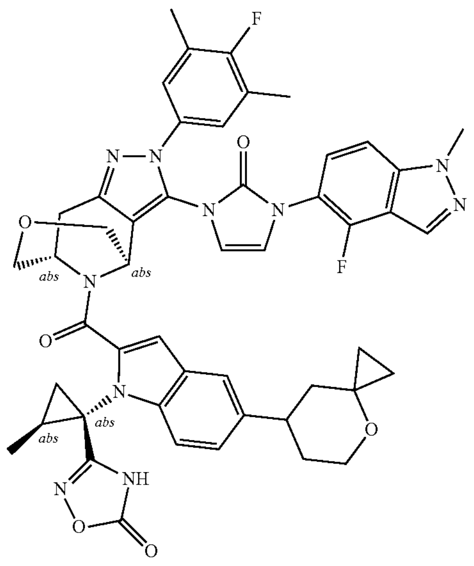 C49H46F2N10O6 |
| 221 | 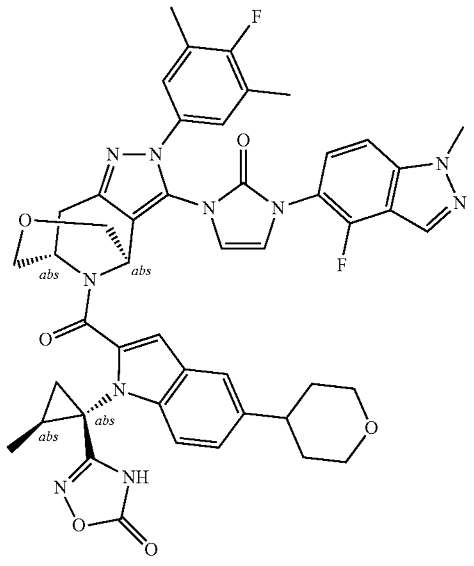 C47H44F2N10O6 |

TABLE 1'-continued
| Compound ID | Structure |
|---|---|
| 222 | 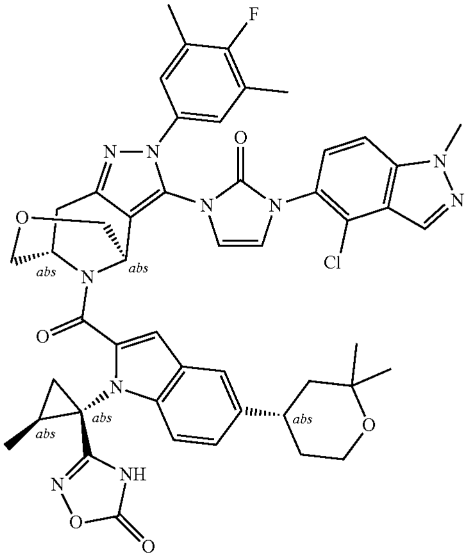 C49H48ClFN10O6 |
| 223 | 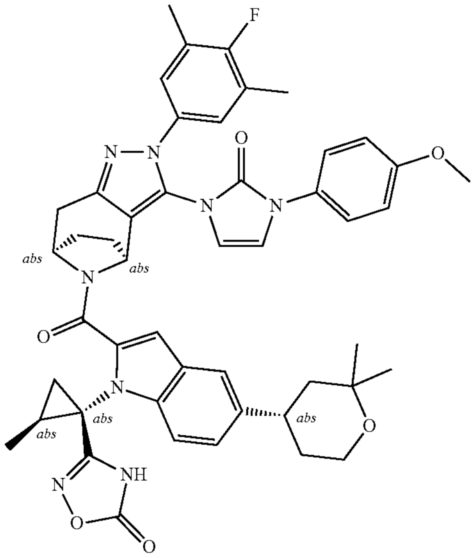 C48H49FN8O6 |
| 224 | 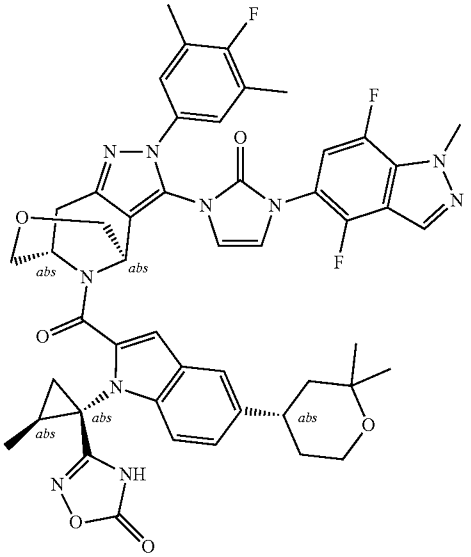 C49H47F3N10O6 |
| 225 | 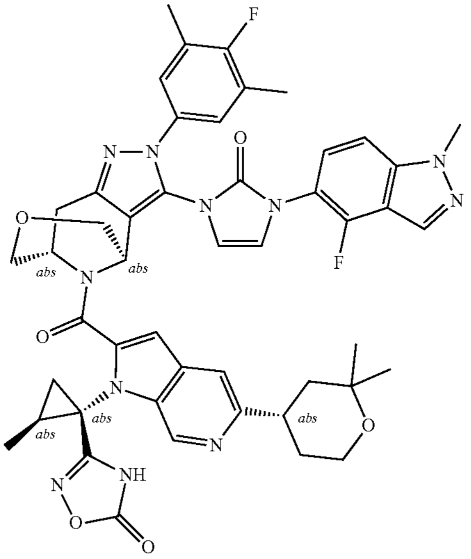 C48H47F2N11O6 |

TABLE 1'-continued
| Compound ID | Structure |
|---|---|
| 226 | 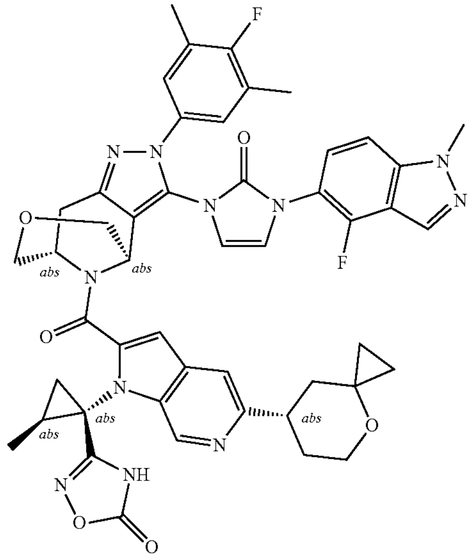 C49H46F2N10O6 |
| 227 | 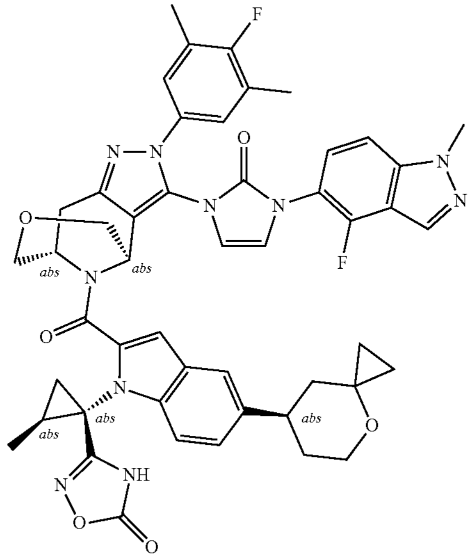 C49H46F2N10O6 |
TABLE 1'-continued
| Compound ID | Structure |
|---|---|
| 228 | 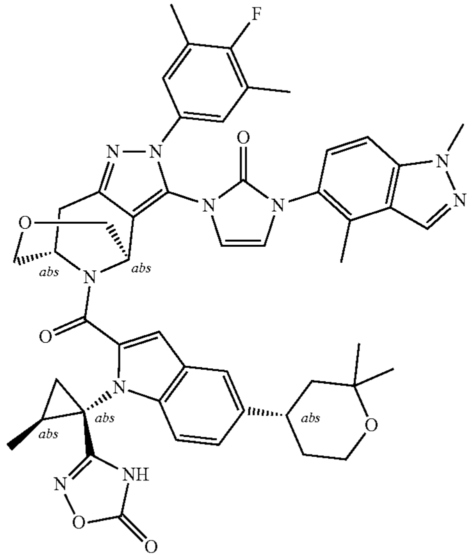 C50H51FN10O6 |
| 229 | 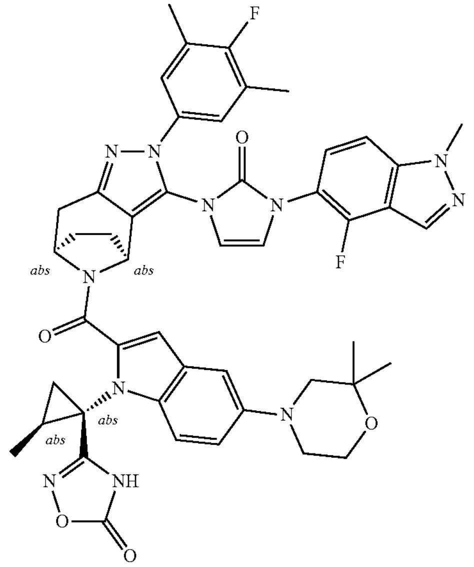 C48H47F2N11O5 |

TABLE 1'-continued
| Compound ID | Structure |
|---|---|
| 230 | 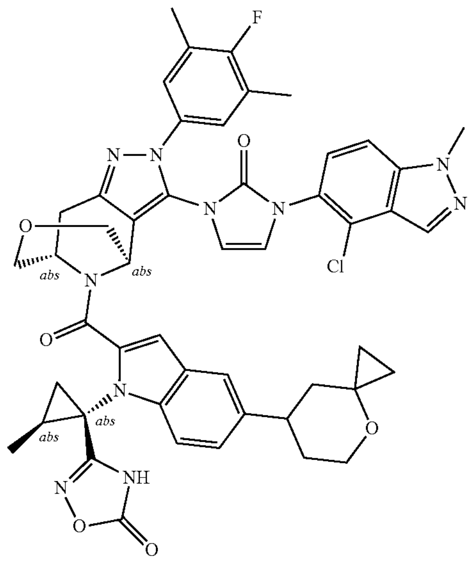 C49H46ClFN10O6 |
| 231 | 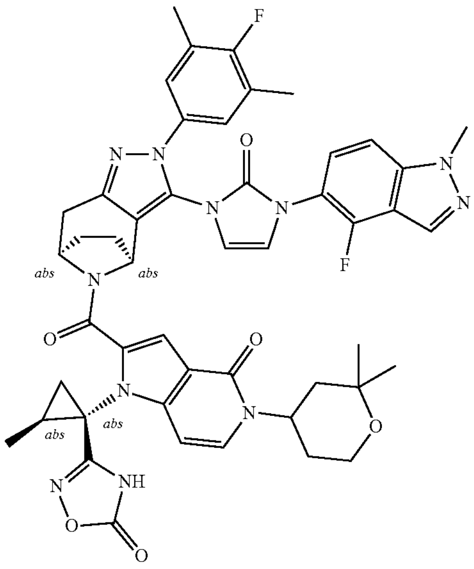 C48H47F2N11O6 |
TABLE 1'-continued
| Compound ID | Structure |
|---|---|
| 232 | 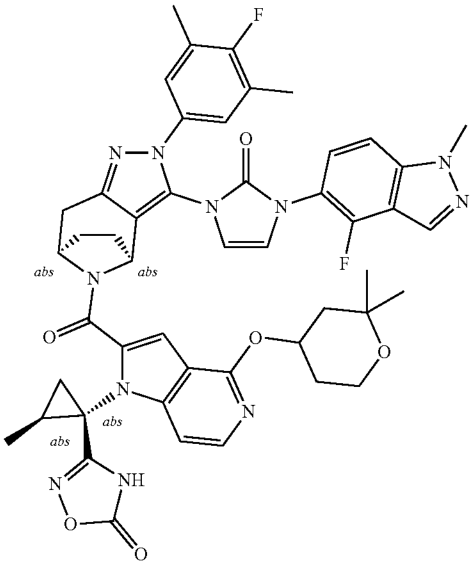 C48H47F2N11O6 |
| 233 | 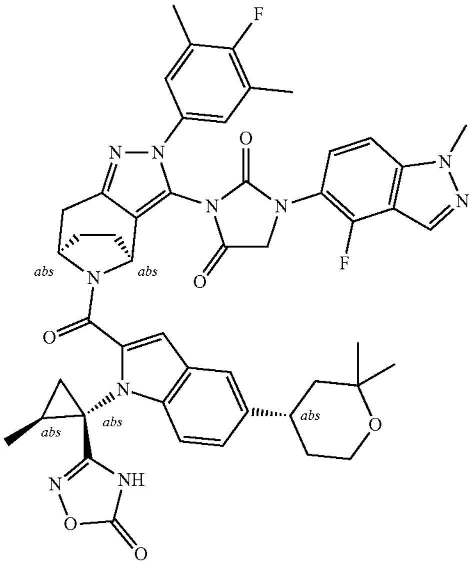 C49H48F2N10O6 |

TABLE 1'-continued
| Compound ID | Structure |
|---|---|
| 235 | 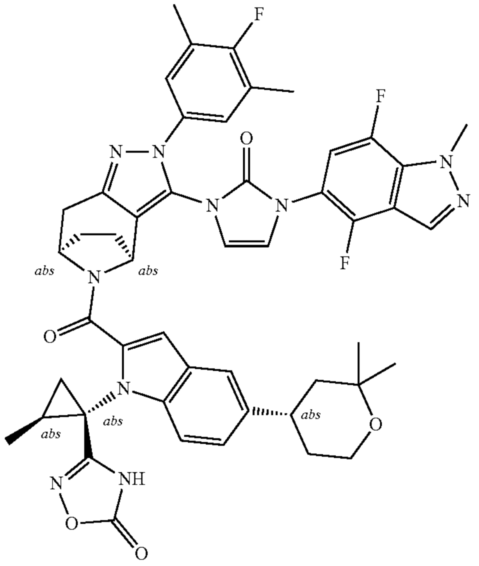<br>C49H47F3N10O5 |
| 236 | 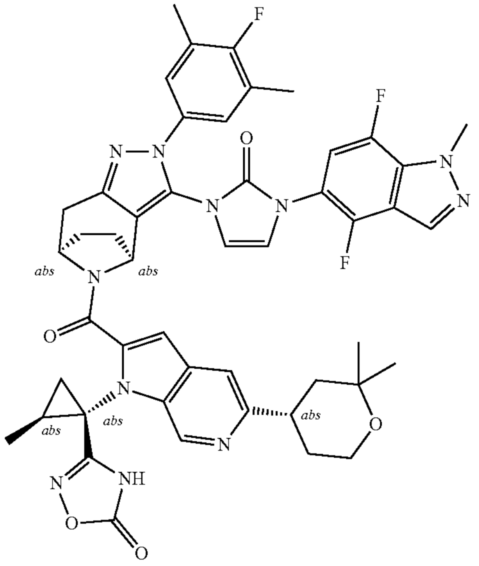<br>C48H46F3N11O5 |
TABLE 1'-continued
| Compound ID | Structure |
|---|---|
| 237 | 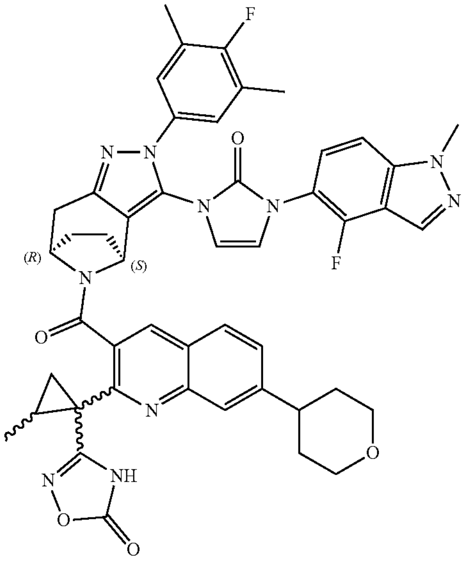<br>Isomer 1<br>C48H44F2N10O5 |
| 238 | 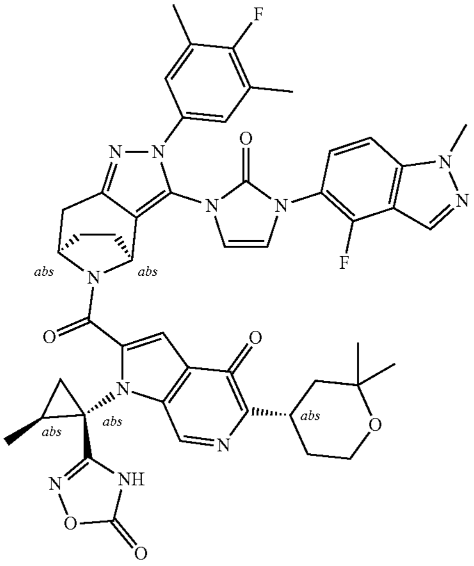<br>C48H47F2N11O6 |

TABLE 1'-continued
| Compound ID | Structure |
|---|---|
| 239 | 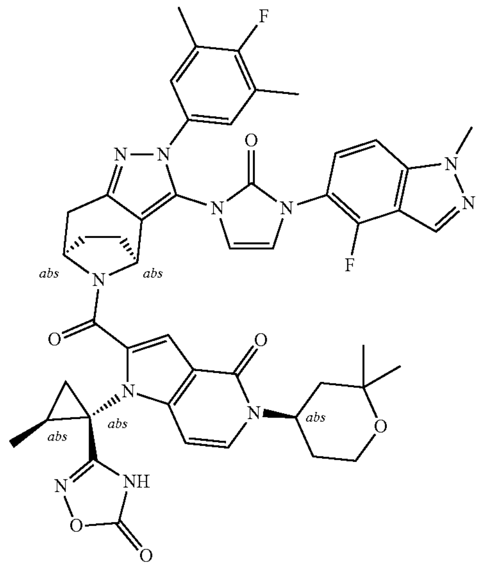 C48H47F2N11O6 |
| 240 | 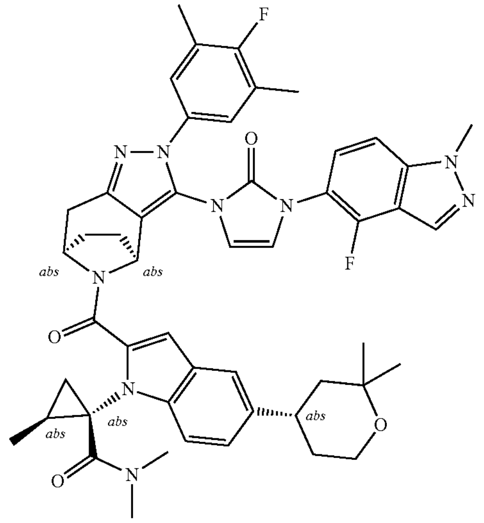 C50H53F2N9O4 |
TABLE 1'-continued
| Compound ID | Structure |
|---|---|
| 241 | 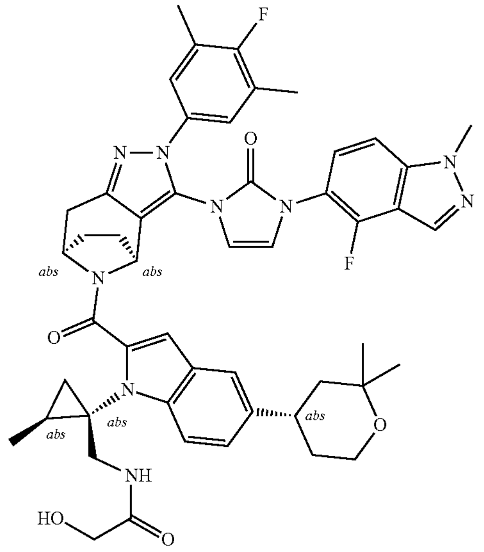 C50H53F2N9O5 |
| 242 | 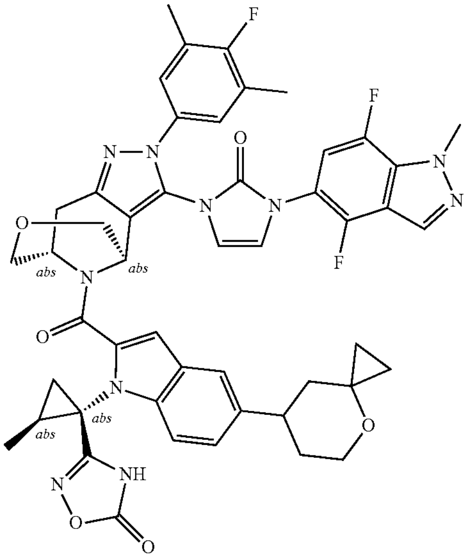 C49H45F3N10O6 |

| Compound ID | Structure |
|---|---|
| 243 | 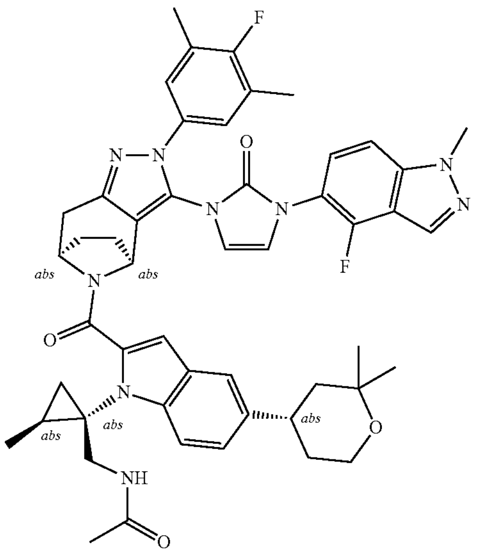 C50H53F2N9O4 |
| 244 | 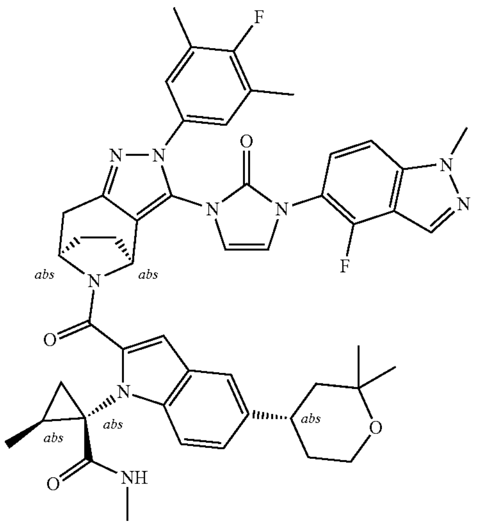 C49H51F2N9O4 |
| Compound ID | Structure |
|---|---|
| 246 | 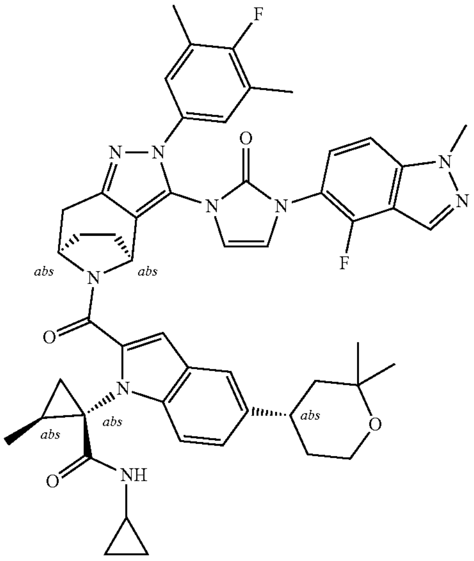 C51H53F2N9O4 |
| 302 | 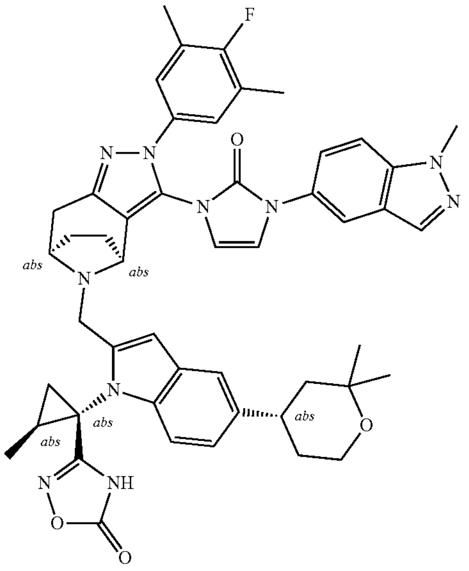 C49H49FN10O5 |

TABLE 1'-continued
| Compound ID | Structure |
| --- | --- |
| 305 | 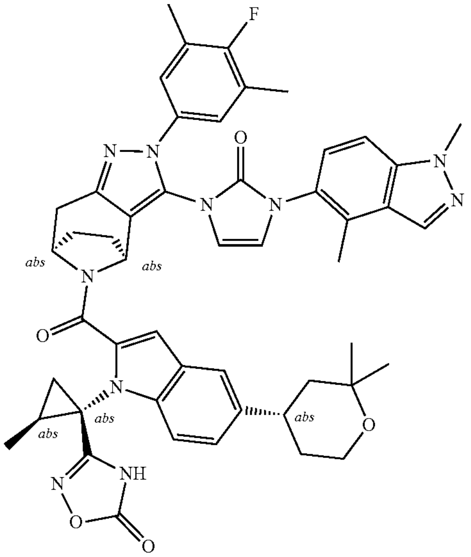 C50H51FN10O5 |
| 306 | 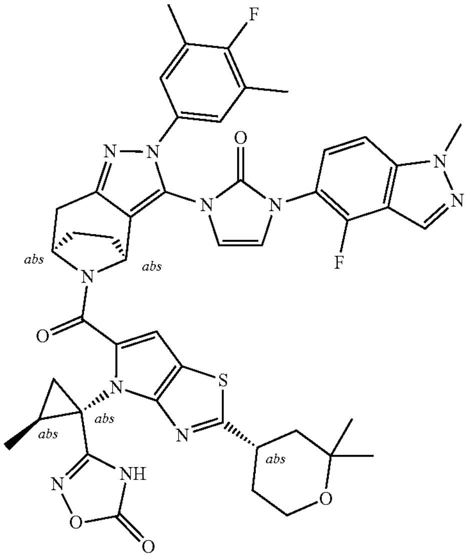 C46H45F2N11O5S |
TABLE 1'-continued
| Compound ID | Structure |
| --- | --- |
| 307 | 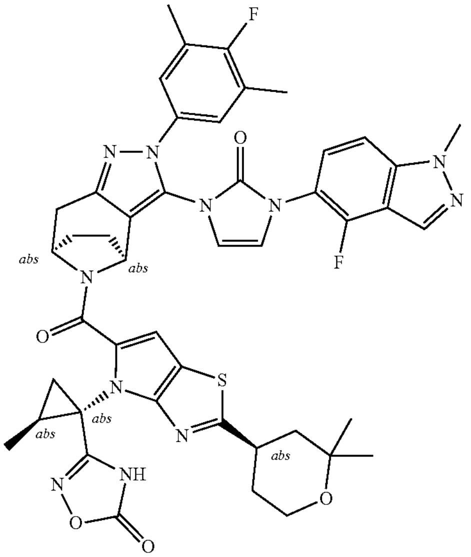 C46H45F2N11O5S |
| 308 | 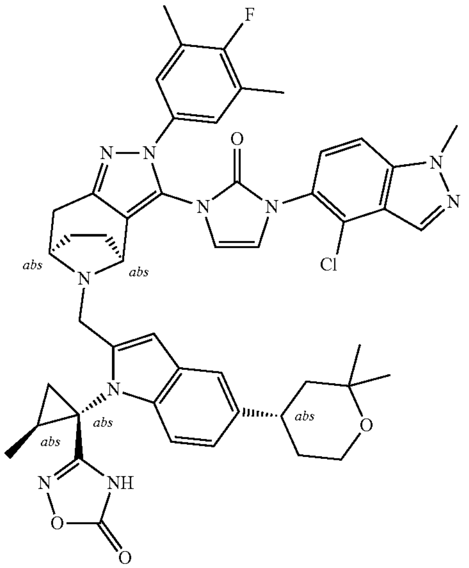 C49H48ClFN10O5 |

TABLE 1'-continued
| Compound ID | Structure |
|---|---|
| 309 | 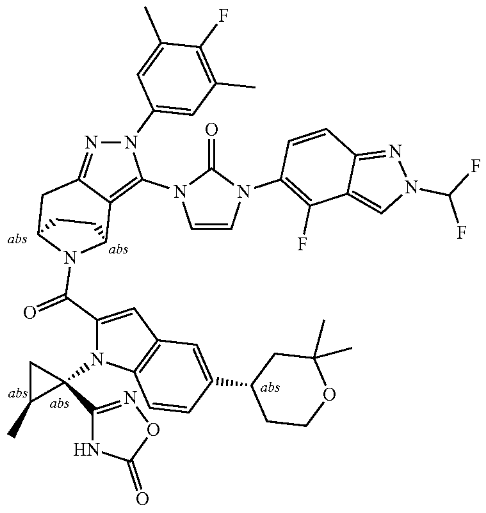 [SMILES: Cc1cc(-n2nc3c(c2-n2ccn(-c4ccc5nn(C(F)F)cc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H46F4N10O5 |
| 310 | 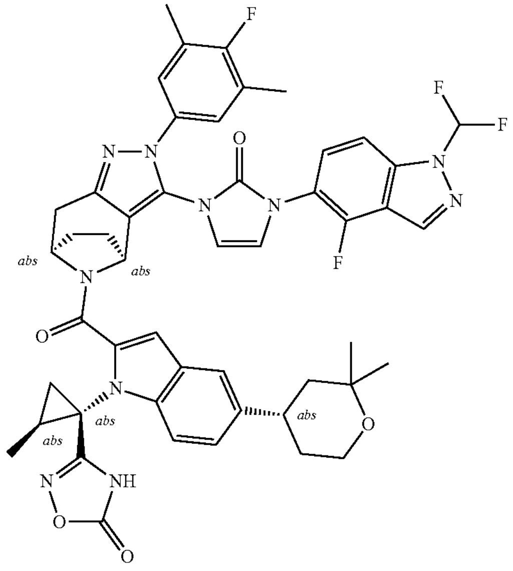 [SMILES: Cc1cc(-n2nc3c(c2-n2ccn(-c4ccc5c(cnn5C(F)F)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H46F4N10O5 |
TABLE 1'-continued
| Compound ID | Structure |
|---|---|
| 311 | 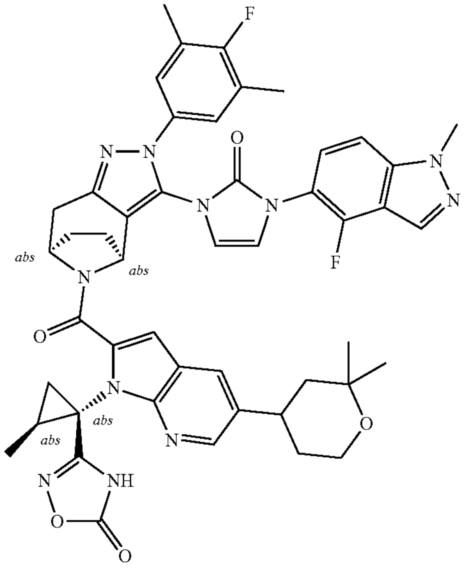 C48H47F2N11O5 |
| 312 | 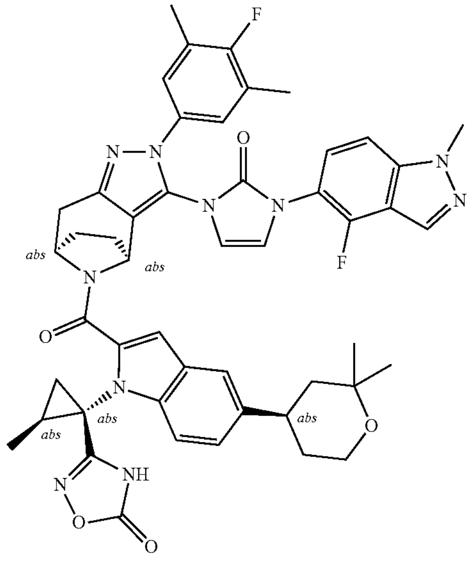 C48H47F2N11O5 |

TABLE 1'-continued
| Compound ID | Structure |
| --- | --- |
| 313 | 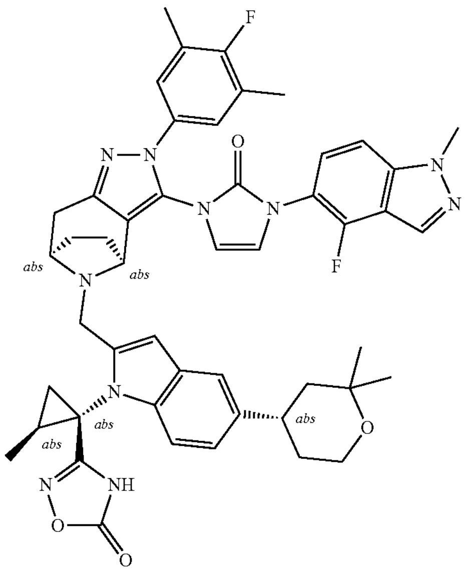<br>C48H47F2N11O5 |
| 318 | 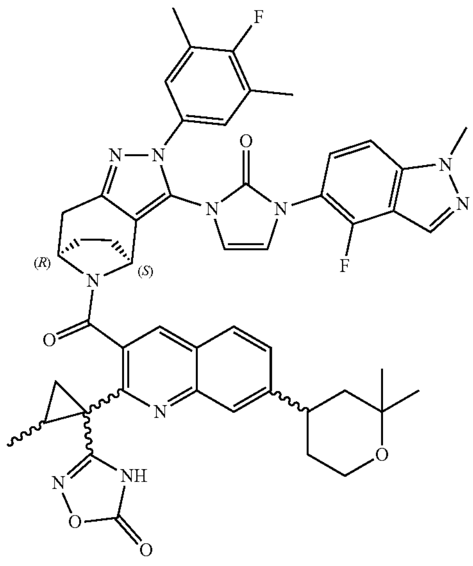<br>Isomer 1a<br>C50H48F2N10O5 |
TABLE 1'-continued
| Compound ID | Structure |
| --- | --- |
| 319 | 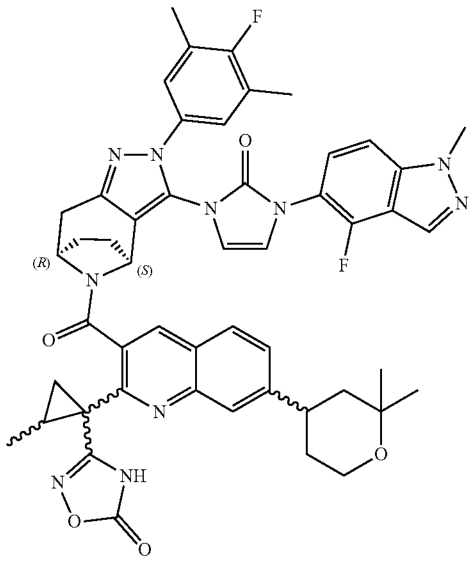<br>Isomer 1b<br>C50H48F2N10O5 |
| 323 | 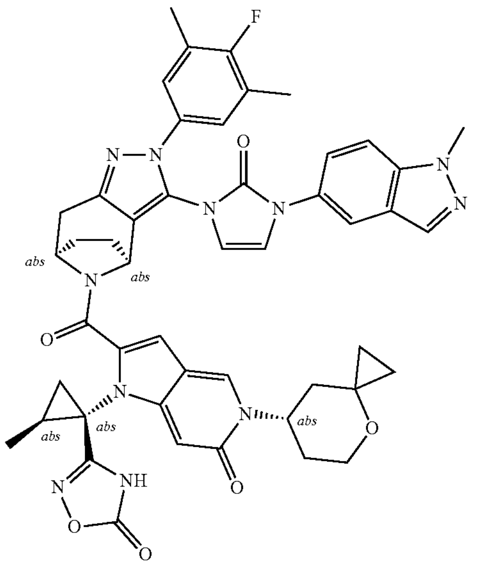<br>C49H47FN10O5 |

TABLE 1'-continued
| Compound ID | Structure |
|---|---|
| 324 | 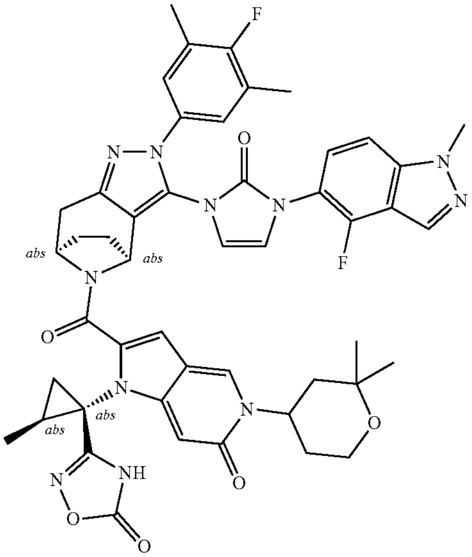 C48H47F2N11O6 |
| 406 | 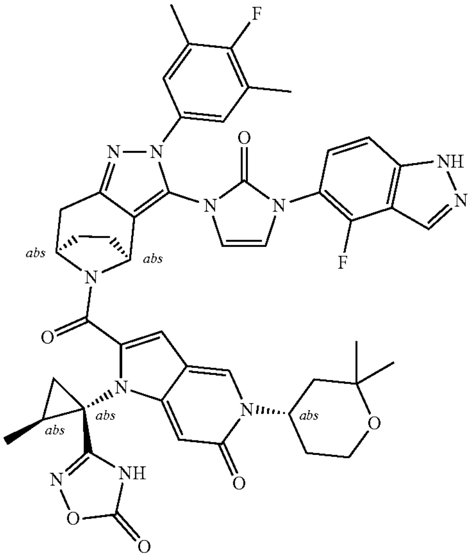 [SMILES: Cc1cc(-n2nc3c(c2-n2ccn(-c4ccc5[nH]ncc5c4F)c2=O)[C@@H]2CC[C@H](C3)N2C(=O)c2cc3cn([C@H]4CCOC(C)(C)C4)c(=O)cc3n2[C@@]2(c3noc(=O)[nH]3)C[C@@H]2C)cc(C)c1F] C48H46F2N10O5 |
TABLE 1'-continued
| Compound ID | Structure |
|---|---|
| 410 | 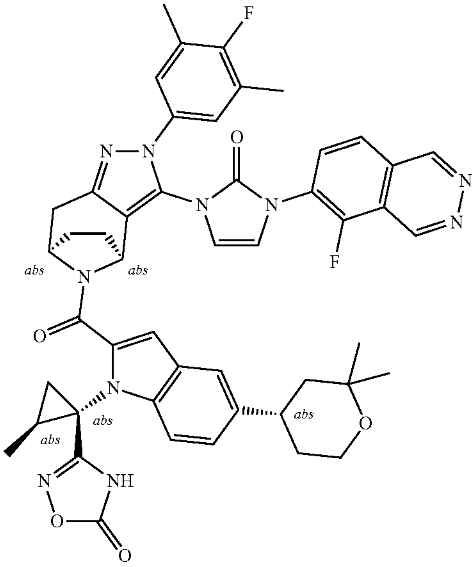 [SMILES: Cc1cc(-n2nc3c(c2-n2ccn(-c4ccc5cnncc5c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H46F2N10O5 |
| 412 | 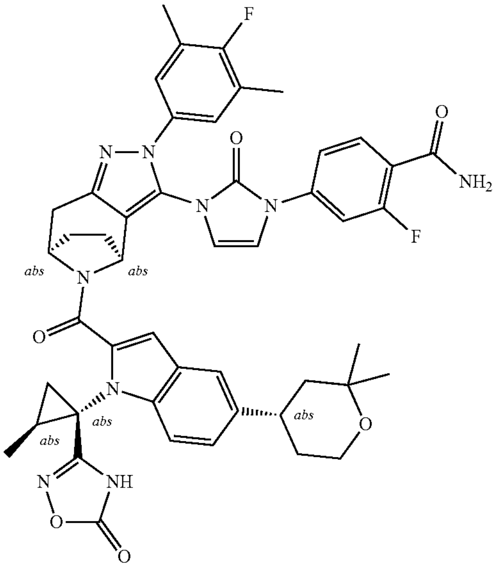 [SMILES: Cc1cc(-n2nc3c(c2-n2ccn(-c4ccc(C(N)=O)c(F)c4)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C48H47F2N9O6 |

TABLE 1'-continued
| Compound ID | Structure |
| --- | --- |
| 413 | 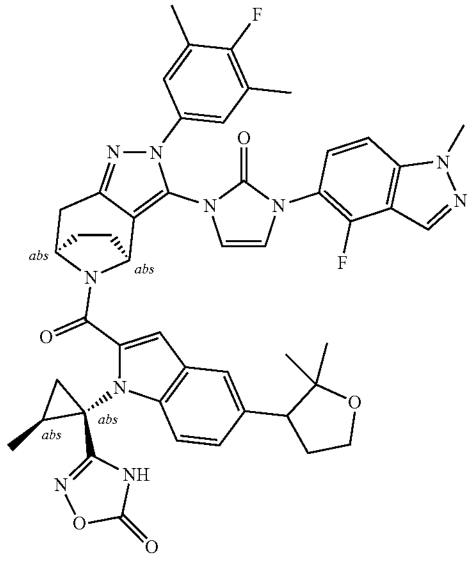 C48H46F2N10O5 |
| 415 | 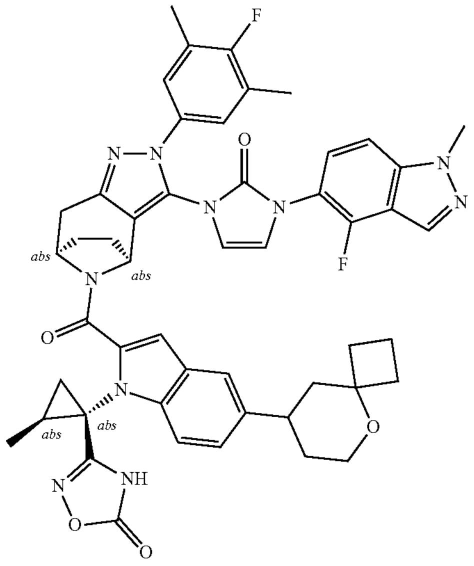 C50H48F2N10O5 |
TABLE 1'-continued
| Compound ID | Structure |
| --- | --- |
| 416 | 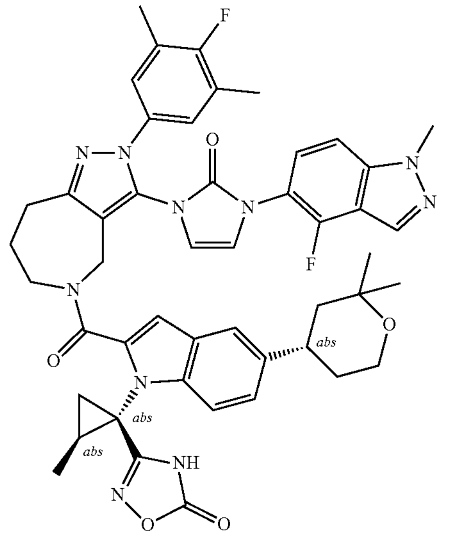 [SMILES: Cc1cc(-n2nc3c(c2-n2ccn(-c4ccc5c(cnn5C)c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C48H48F2N10O5 |
| 417 | 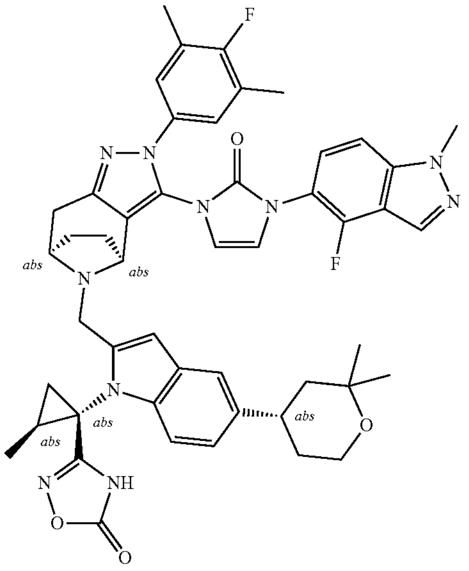 C49H50F2N10O4 |

TABLE 1'-continued
| Compound ID | Structure |
|---|---|
| 418 | 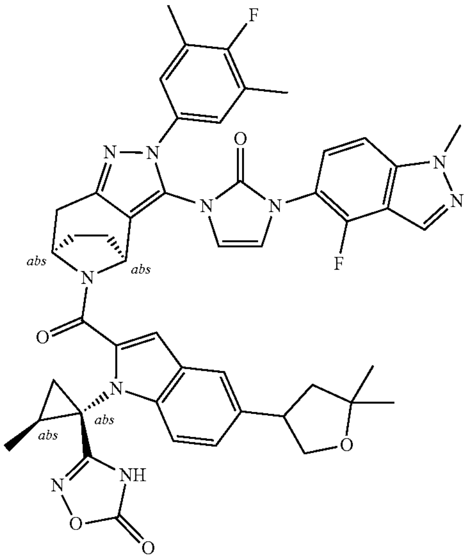 C48H46F2N10O5 |
| 419 | 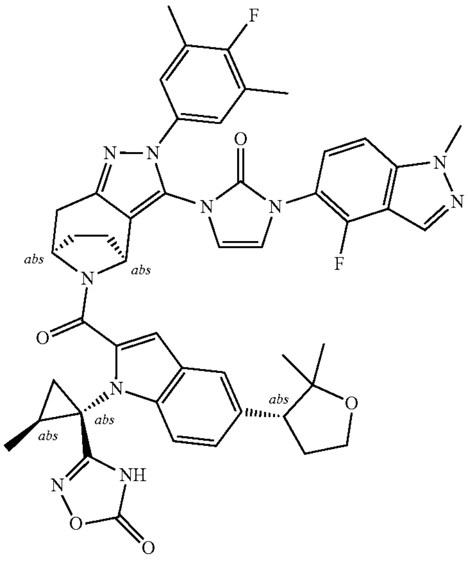 C48H46F2N10O5 |
TABLE 1'-continued
| Compound ID | Structure |
|---|---|
| 420 | 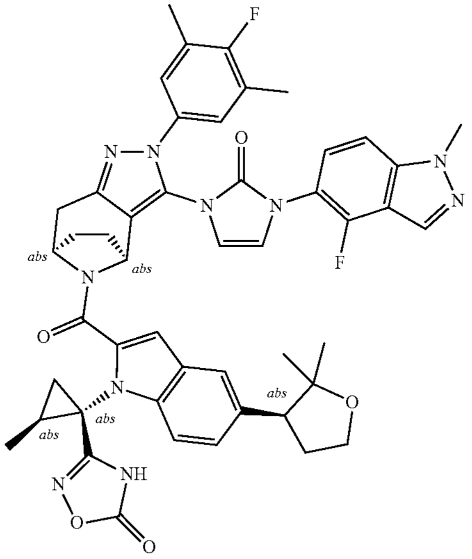 C48H46F2N10O5 |
| 421 | 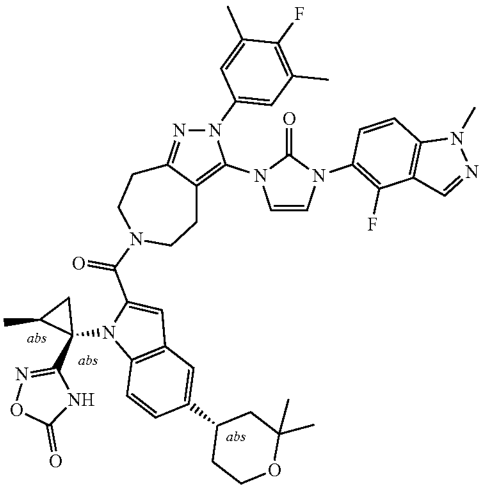 C48H48F2N10O5 |

TABLE 1'-continued
| Compound ID | Structure |
| --- | --- |
| 422 | 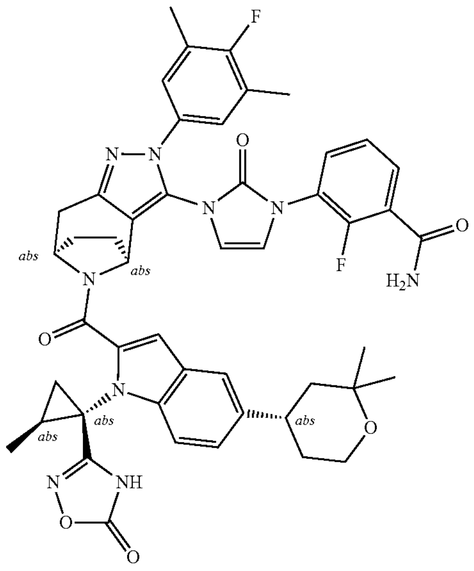 [SMILES: Cc1cc(-n2nc3c(c2-n2ccn(-c4cccc(C(N)=O)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C48H47F2N9O6 |
| 423 | 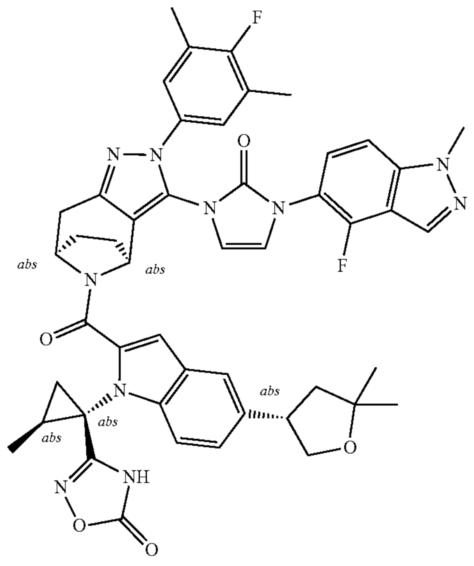 C48H46F2N10O5 |
TABLE 1'-continued
| Compound ID | Structure |
| --- | --- |
| 424 | 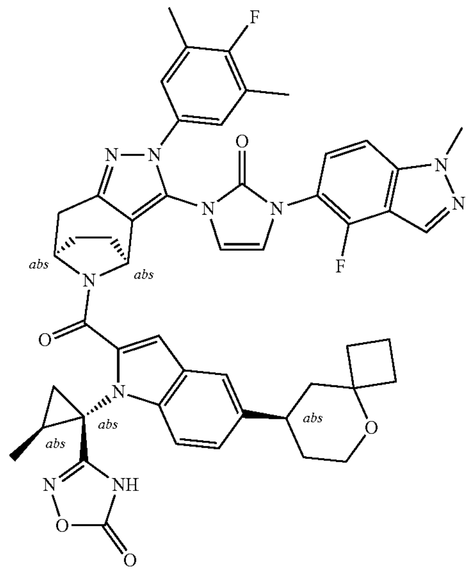 C50H48F2N10O5 |
| 425 | 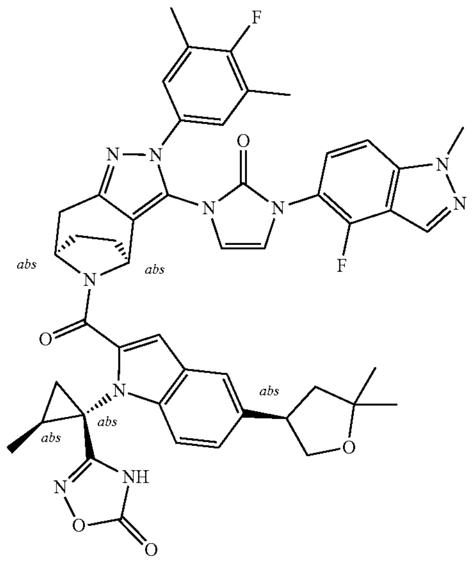 C48H46F2N10O5 |

| Compound ID | Structure |
|---|---|
| 426 | 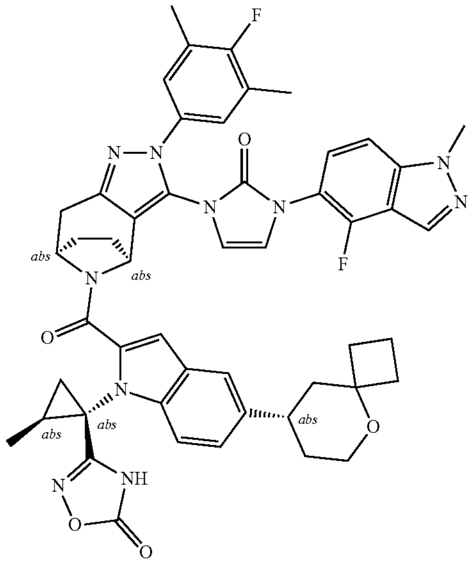 C50H48F2N10O5 |
| 427 | 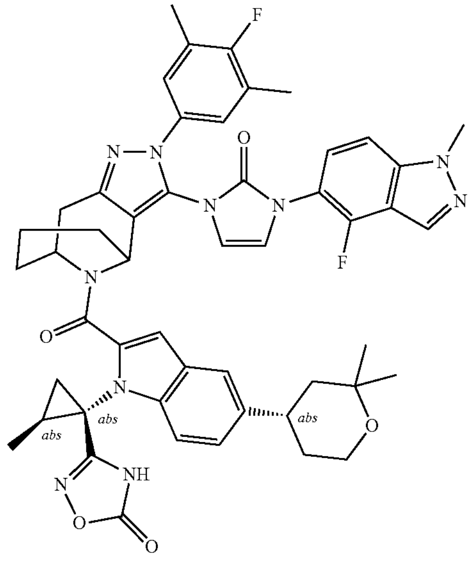 C50H50F2N10O5 |
| Compound ID | Structure |
|---|---|
| 428 | 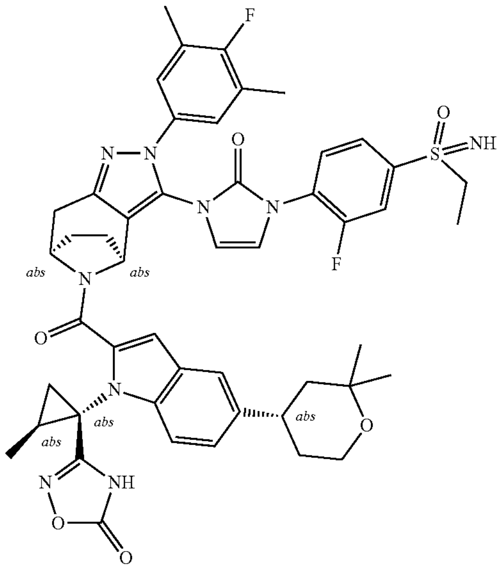 [SMILES: CCS(=N)(=O)c1ccc(-n2ccn(-c3c4c(nn3-c3cc(C)c(F)c(C)c3)C[C@H]3CC[C@@H]4N3C(=O)c3cc4cc([C@H]5CCOC(C)(C)C5)ccc4n3[C@@]3(c4noc(=O)[nH]4)C[C@@H]3C)c2=O)c(F)c1] C49H51F2N9O6S |
| 429 | 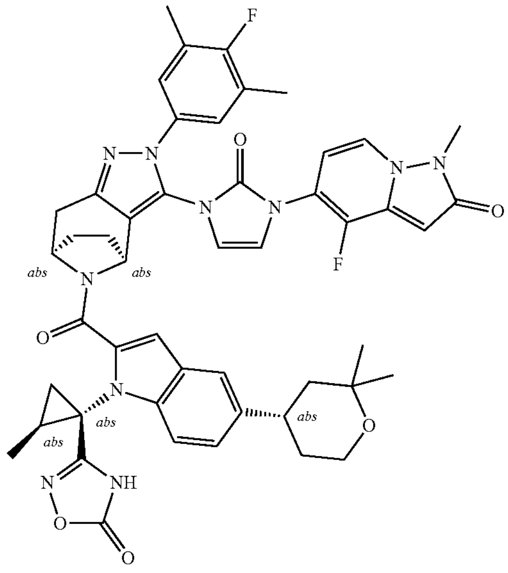 [SMILES: Cc1cc(-n2nc3c(c2-n2ccn(-c4ccn5c(cc(=O)n5C)c4F)c2=O)[C@@H]2CC[C@H](C3)N2C(=O)c2cc3cc([C@H]4CCOC(C)(C)C4)ccc3n2[C@@]2(c3noc(=O)[nH]3)C[C@@H]2C)cc(C)c1F] C49H48F2N10O6 |

TABLE 1'-continued
| Compound ID | Structure |
| --- | --- |
| 431 | 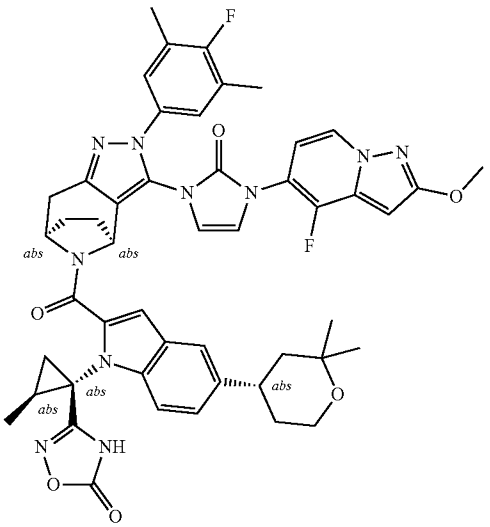 C49H48F2N10O6 |
| 432 | 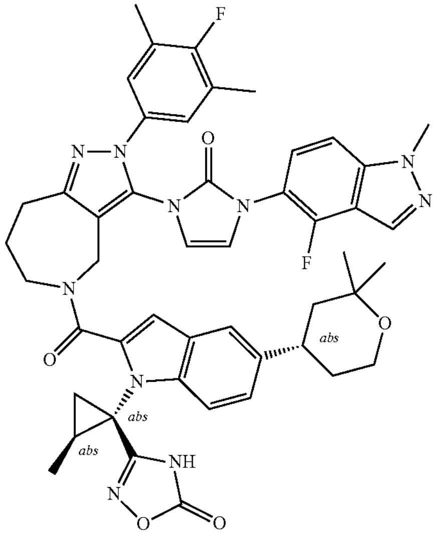 [SMILES: Cc1cc(-n2nc3c(c2-n2ccn(-c4ccc5c(cnn5C)c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C48H50F2N10O4 |
TABLE 1'-continued
| Compound ID | Structure |
| --- | --- |
| 433 | 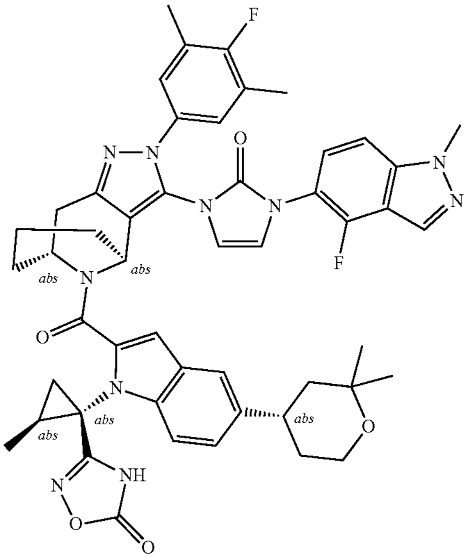 C50H50F2N10O5 |
| 434 | 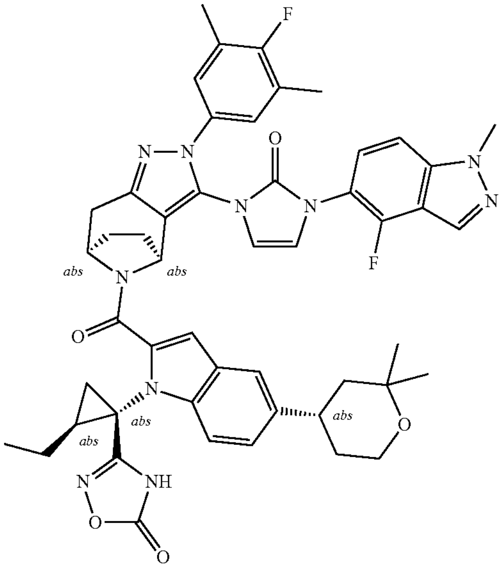 [SMILES: CC[C@H]1C[C@]1(c1noc(=O)[nH]1)n1c(C(=O)N2[C@@H]3CC[C@H]2c2c(nn(-c4cc(C)c(F)c(C)c4)c2-n2ccn(-c4ccc5c(cnn5C)c4F)c2=O)C3)cc2cc([C@H]3CCOC(C)(C)C3)ccc21] C50H50F2N10O5 |

TABLE 1'-continued
| Compound ID | Structure |
| --- | --- |
| 435 | 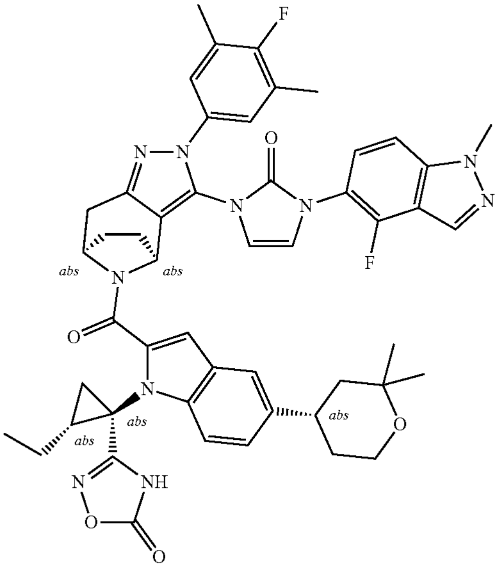 [SMILES: CC[C@@H]1C[C@@]1(c1noc(=O)[nH]1)n1c(C(=O)N2[C@@H]3CC[C@H]2c2c(nn(-c4cc(C)c(F)c(C)c4)c2-n2ccn(-c4ccc5c(cnn5C)c4F)c2=O)C3)cc2cc([C@H]3CCOC(C)(C)C3)ccc21] C50H50F2N10O5 |
| 436 | 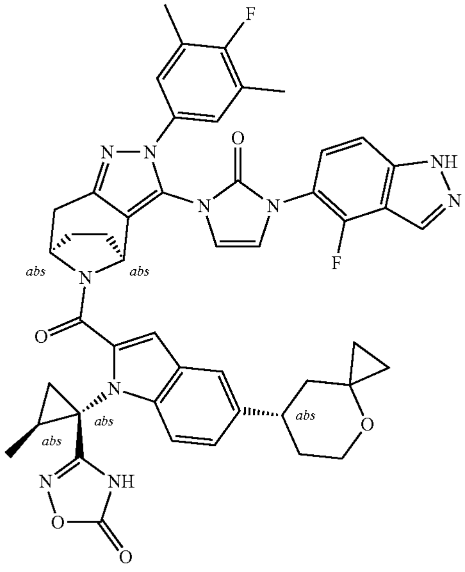 [SMILES: Cc1cc(-n2nc3c(c2-n2ccn(-c4ccc5[nH]ncc5c4F)c2=O)[C@@H]2CC[C@H](C3)N2C(=O)c2cc3cc([C@H]4CCOC5(CC5)C4)ccc3n2[C@@]2(c3noc(=O)[nH]3)C[C@@H]2C)cc(C)c1F] C48H44F2N10O5 |
TABLE 1'-continued
| Compound ID | Structure |
| --- | --- |
| 437 | 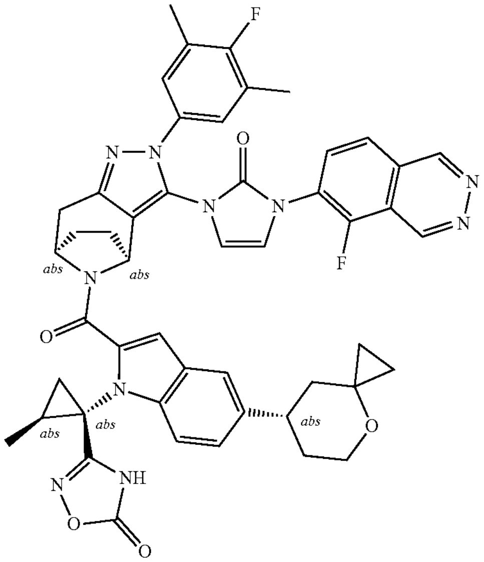 [SMILES: Cc1cc(-n2nc3c(c2-n2ccn(-c4ccc5cnncc5c4F)c2=O)[C@@H]2CC[C@H](C3)N2C(=O)c2cc3cc([C@H]4CCOC5(CC5)C4)ccc3n2[C@@]2(c3noc(=O)[nH]3)C[C@@H]2C)cc(C)c1F] C49H44F2N10O5 |
| 501 | 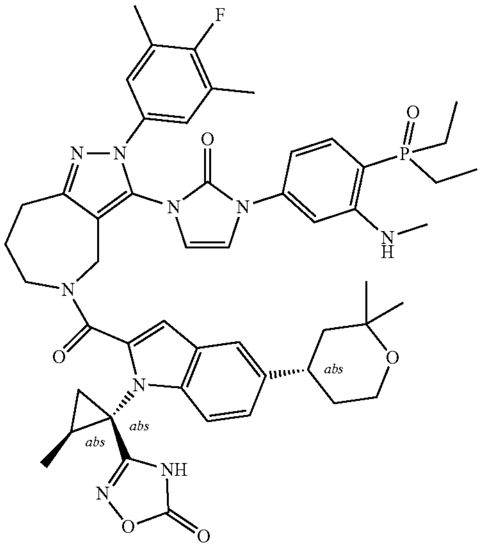 [SMILES: CCP(=O)(CC)c1ccc(-n2ccn(-c3c4c(nn3-c3cc(C)c(F)c(C)c3)CCCN(C(=O)c3cc5cc([C@H]6CCOC(C)(C)C6)ccc5n3[C@@]3(c5noc(=O)[nH]5)C[C@@H]3C)C4)c2=O)cc1NC] C51H59FN9O6P |

TABLE 1'-continued
| Compound ID | Structure |
|---|---|
| 502 | 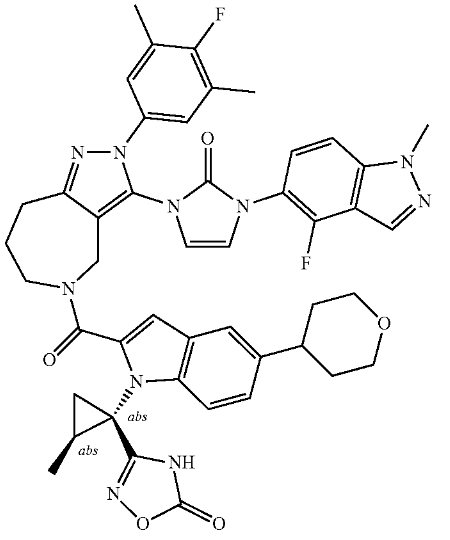 [SMILES: Cc1cc(-n2nc3c(c2-n2ccn(-c4ccc5c(cnn5C)c4F)c2=O)CN(C(=O)c2cc4cc(C5CCOCC5)ccc4n2[C@@]2(c4noc(=O)[nH]4)C[C@@H]2C)CCC3)cc(C)c1F] C46H44F2N10O5 |
| 503 | 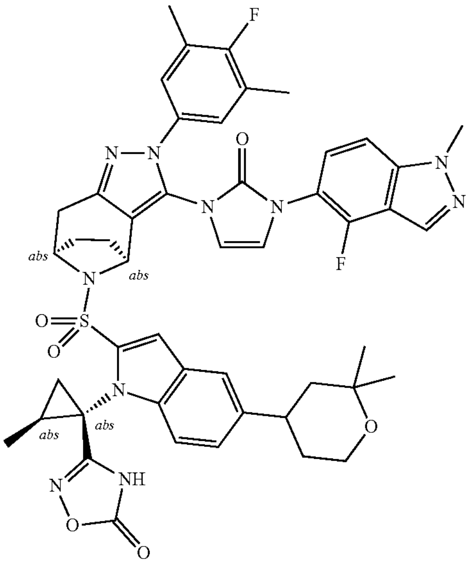 C48H48F2N10O6S |
| 504 | 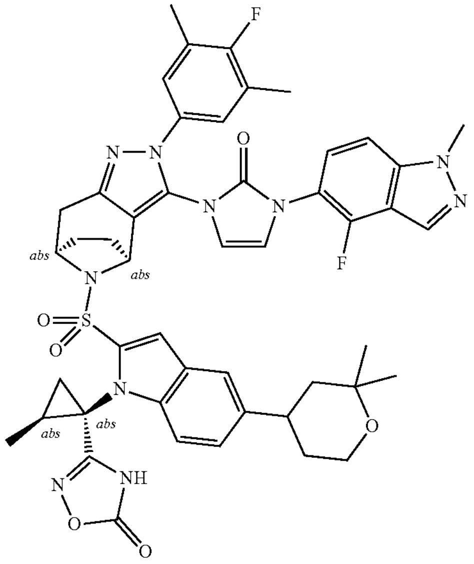 C48H48F2N10O6S |
| 505 | 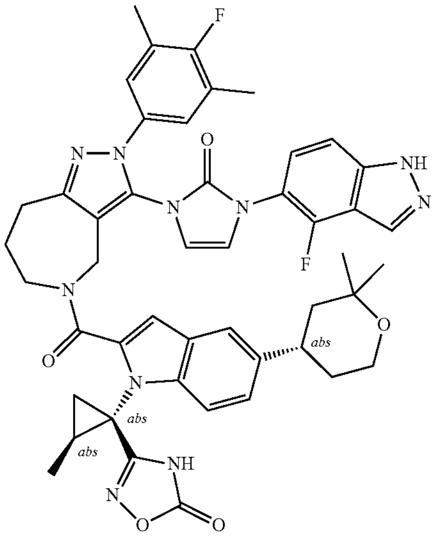 [SMILES: Cc1cc(-n2nc3c(c2-n2ccn(-c4ccc5[nH]ncc5c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C47H46F2N10O5 |

TABLE 1'-continued
| Compound ID | Structure |
| --- | --- |
| 506 | 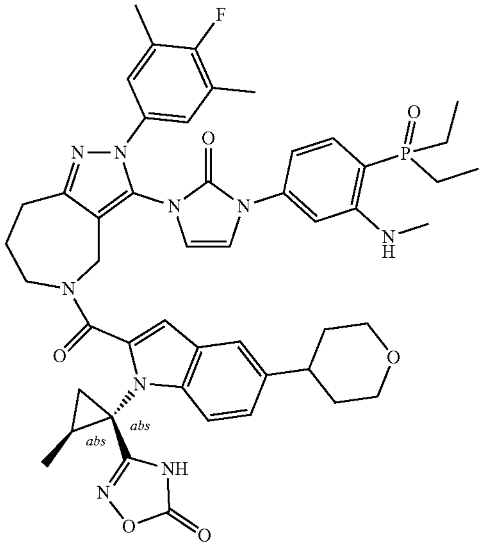 [SMILES: CCP(=O)(CC)c1ccc(-n2ccn(-c3c4c(nn3-c3cc(C)c(F)c(C)c3)CCCN(C(=O)c3cc5cc(C6CCOCC6)ccc5n3[C@@]3(c5noc(=O)[nH]5)C[C@@H]3C)C4)c2=O)cc1NC] C49H55FN9O6P |
| 507 | 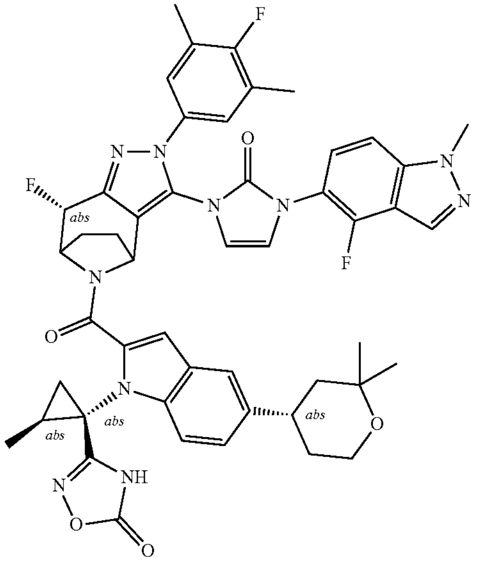 C49H47F3N10O5 |
TABLE 1'-continued
| Compound ID | Structure |
| --- | --- |
| 508 | 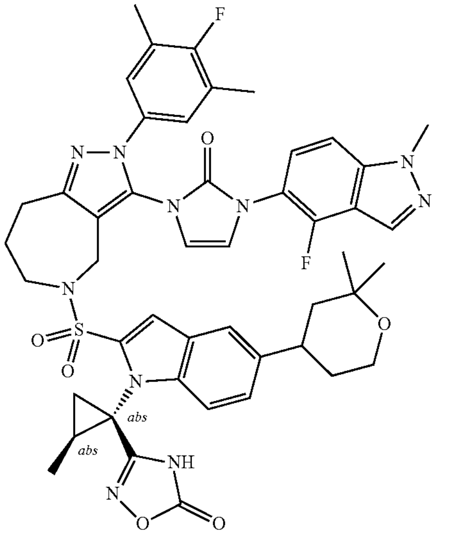 [SMILES: Cc1cc(-n2nc3c(c2-n2ccn(-c4ccc5c(cnn5C)c4F)c2=O)CN(S(=O)(=O)c2cc4cc(C5CCOC(C)(C)C5)ccc4n2[C@@]2(c4noc(=O)[nH]4)C[C@@H]2C)CCC3)cc(C)c1F] C47H48F2N10O6S |
| 509 | 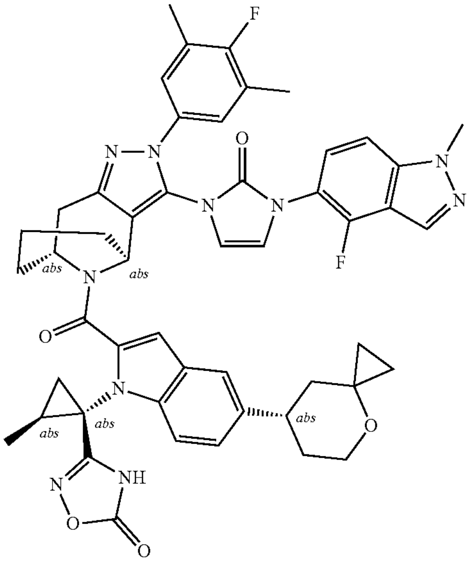 C50H48F2N10O5 |

TABLE 1'-continued
| Compound ID | Structure |
| --- | --- |
| 510 | 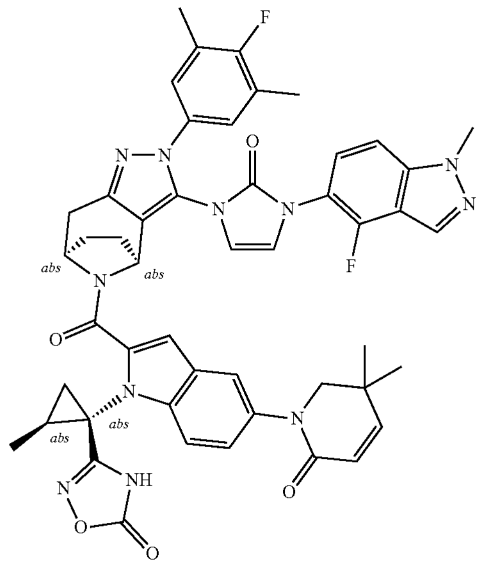 C49H45F2N11O5 |
| 511 | 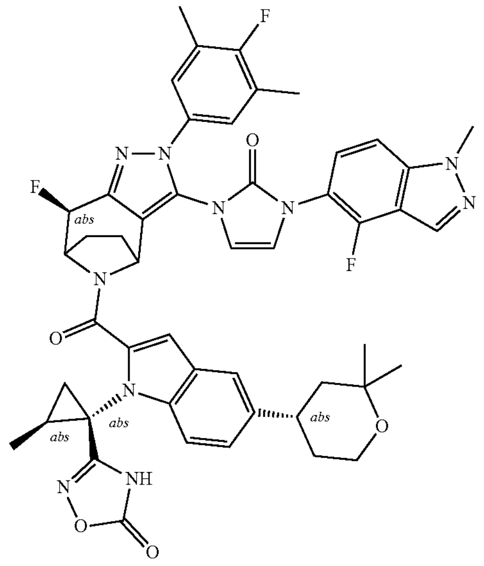 C49H47F3N10O5 |
TABLE 1'-continued
| Compound ID | Structure |
| --- | --- |
| 512 | 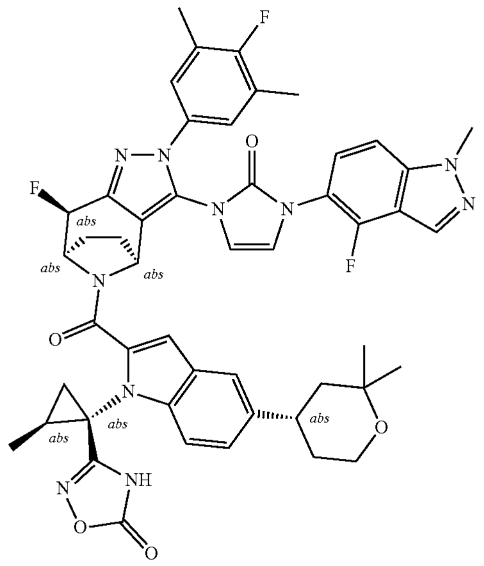 C49H47F3N10O5 |
| 515 | 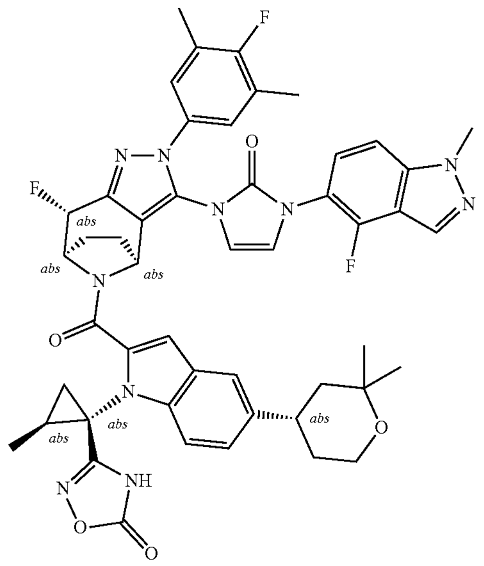 C49H47F3N10O5 |

TABLE 1'-continued
| Compound ID | Structure |
|---|---|
| 516 | 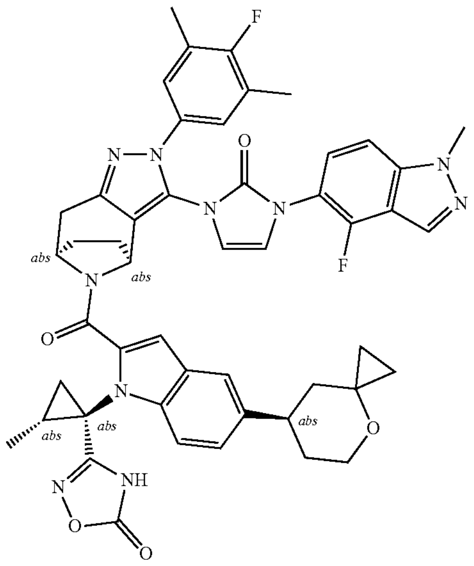 C49H46F2N10O5 |
| 518 | 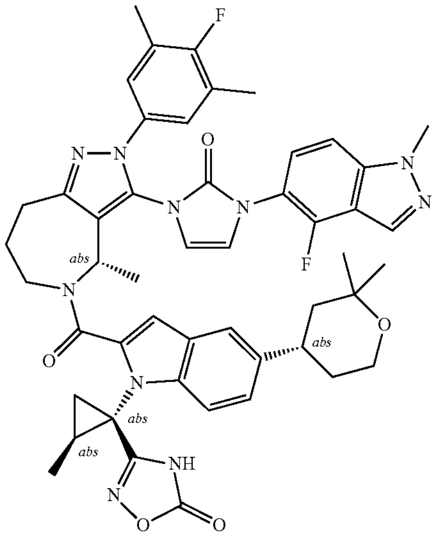 [SMILES: Cc1cc(-n2nc3c(c2-n2ccn(-c4ccc5c(cnn5C)c4F)c2=O)[C@H](C)N(C(=O)c2cc4cc([C@H]5CCOC(C)(C)C5)ccc4n2[C@@]2(c4noc(=O)[nH]4)C[C@@H]2C)CCC3)cc(C)c1F] C49H50F2N10O5 |
TABLE 1'-continued
| Compound ID | Structure |
|---|---|
| 519 | 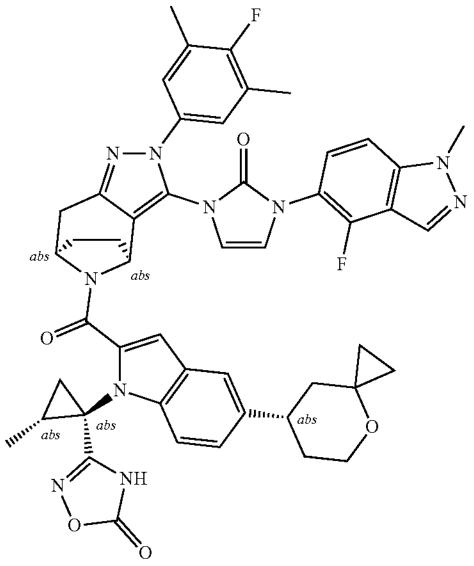 C49H46F2N10O5 C49H46F2N10O5 |
| 521 | 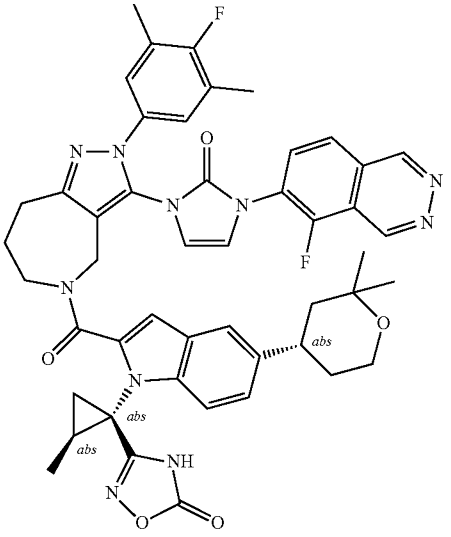 [SMILES: Cc1cc(-n2nc3c(c2-n2ccn(-c4ccc5cnncc5c4F)c2=O)CN(C(=O)c2cc4cc([C@H]5CCOC(C)(C)C5)ccc4n2[C@@]2(c4noc(=O)[nH]4)C[C@@H]2C)CCC3)cc(C)c1F] C48H46F2N10O5 |

TABLE 1'-continued
| Compound ID | Structure |
|---|---|
| 522 | 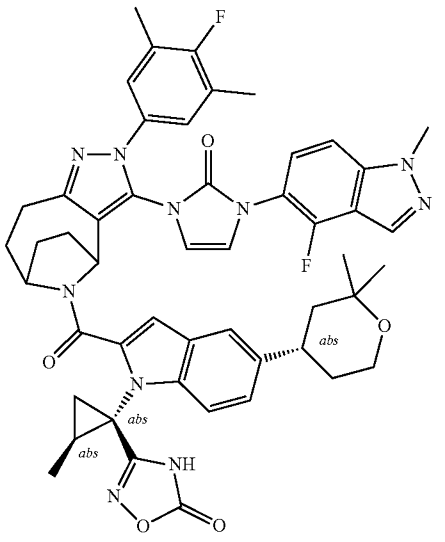 [SMILES: Cc1cc(-n2nc3c(c2-n2ccn(-c4ccc5c(cnn5C)c4F)c2=O)C2CCC(CC3)N2C(=O)c2cc3cc([C@H]4CCOC(C)(C)C4)ccc3n2[C@@]2(c3noc(=O)[nH]3)C[C@@H]2C)cc(C)c1F] C50H50F2N10O5 |
| 523 | 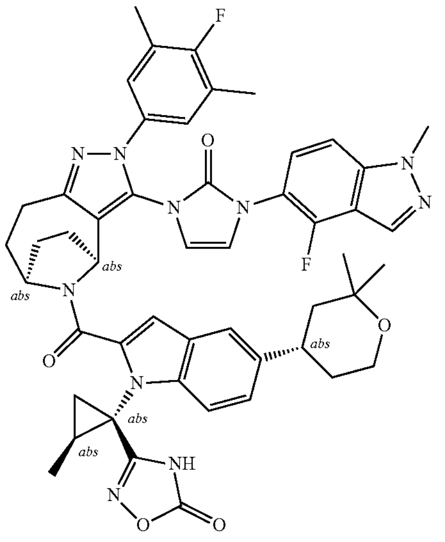 [SMILES: Cc1cc(-n2nc3c(c2-n2ccn(-c4ccc5c(cnn5C)c4F)c2=O)[C@@H]2CC[C@H](CC3)N2C(=O)c2cc3cc([C@H]4CCOC(C)(C)C4)ccc3n2[C@@]2(c3noc(=O)[nH]3)C[C@@H]2C)cc(C)c1F] C50H50F2N10O5 |
TABLE 1'-continued
| Compound ID | Structure |
|---|---|
| 525 | 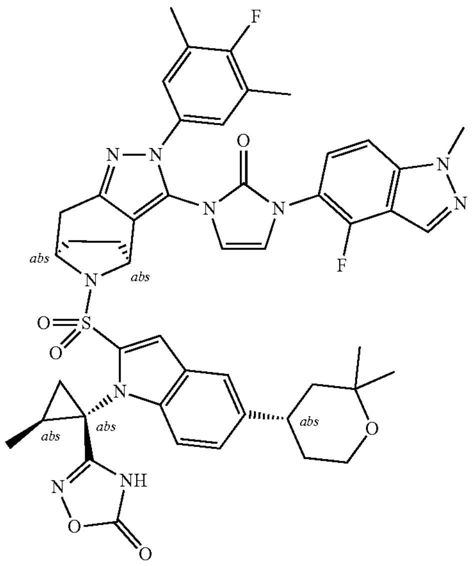 C48H48F2N10O6S |
| 526 | 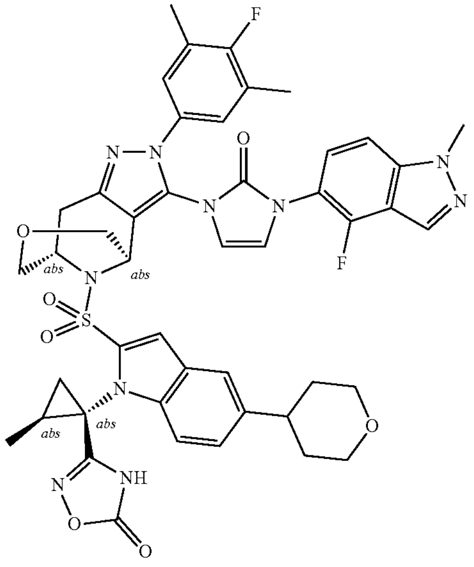 C46H44F2N10O7S |

TABLE 1'-continued
| Compound ID | Structure |
| --- | --- |
| 527 | 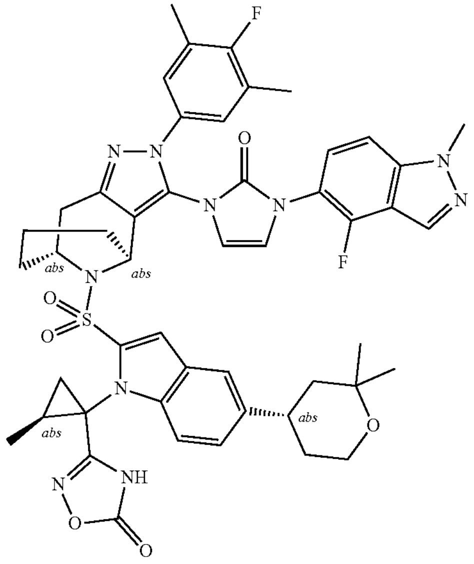 C49H50F2N10O6S |
| 528 | 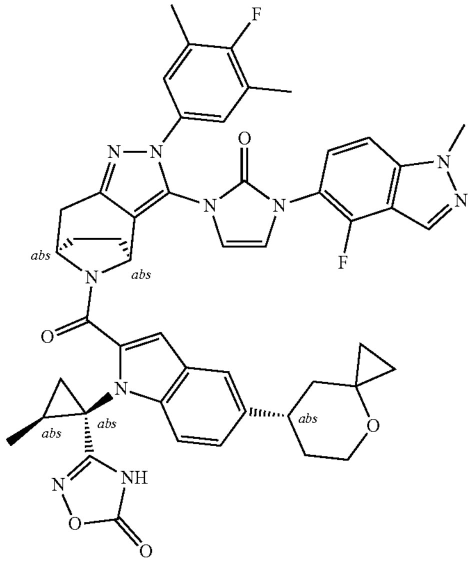 C49H46F2N10O5 |
TABLE 1'-continued
| Compound ID | Structure |
| --- | --- |
| 529 | 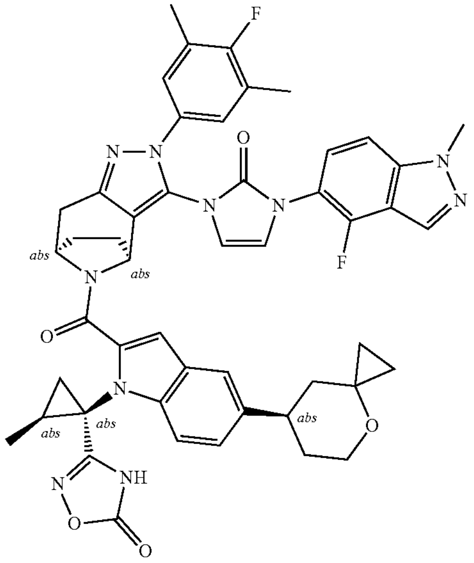 C49H46F2N10O5 |
| 532 | 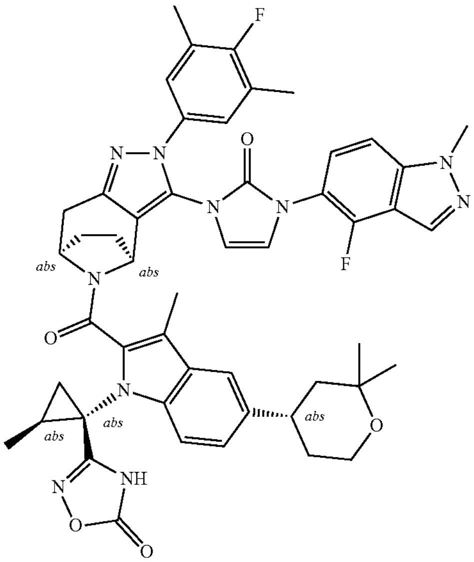 C50H50F2N10O5 |

| Compound ID | Structure |
|---|---|
| 533 | 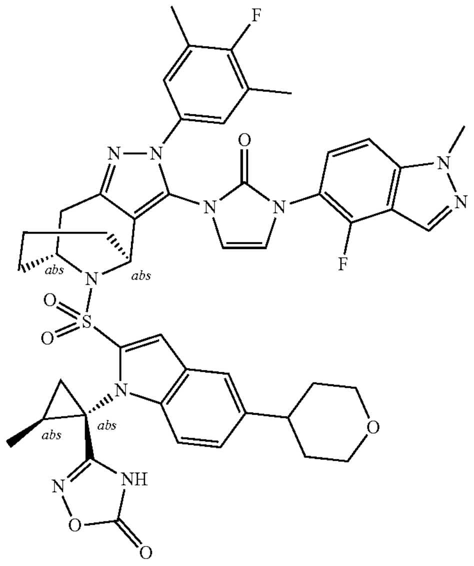 C47H46F2N10O6S |
| 534 | 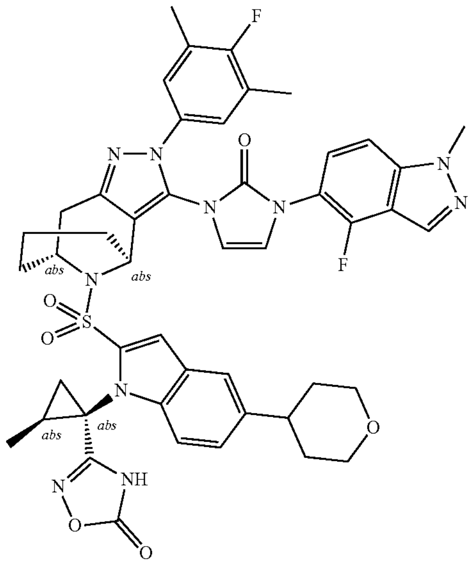 C47H46F2N10O6S |
| Compound ID | Structure |
|---|---|
| 535 | 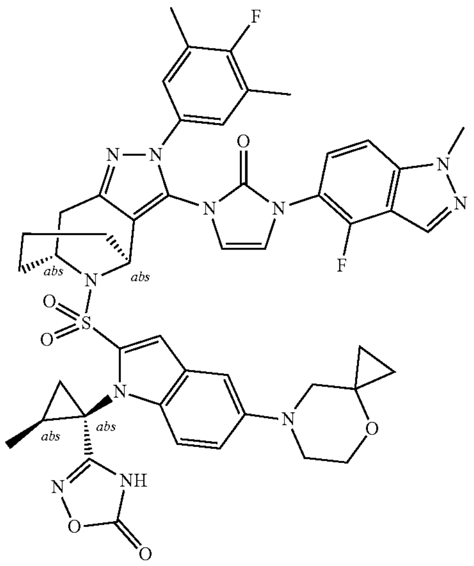 C48H47F2N11O6S |
| 536 | 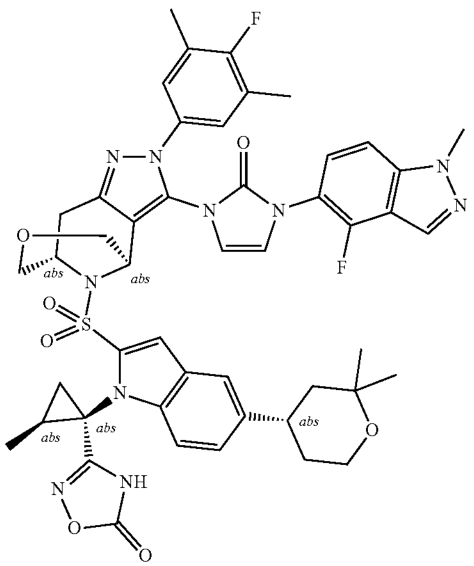 C48H48F2N10O7S |

TABLE 1'-continued
| Compound ID | Structure |
|---|---|
| 537 | 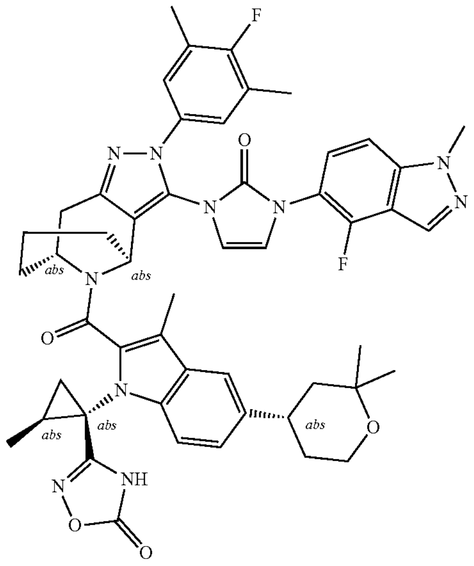 C51H52F2N10O5 |
| 542 | 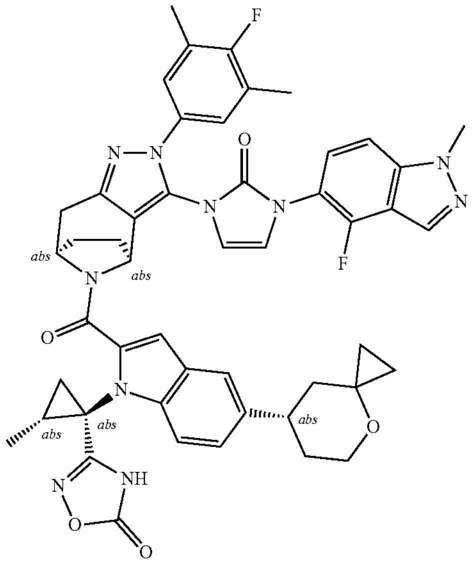 C49H46F2N10O5 |
TABLE 1'-continued
| Compound ID | Structure |
|---|---|
| 545 | 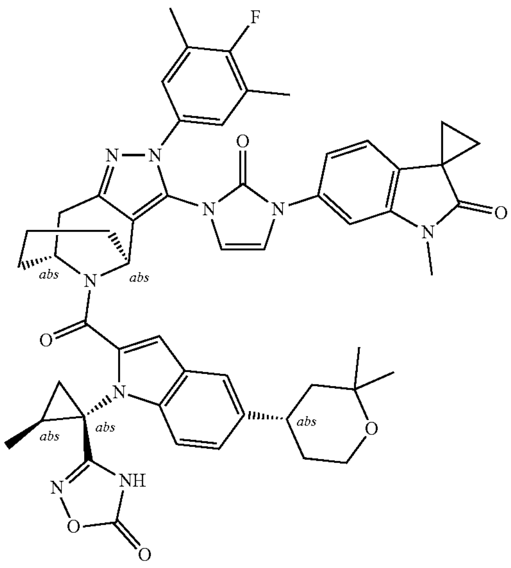 [SMILES: Cc1cc(-n2nc3c(c2-n2ccn(-c4ccc5c(c4)N(C)C(=O)C54CC4)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H54FN9O6 |
| 602 | 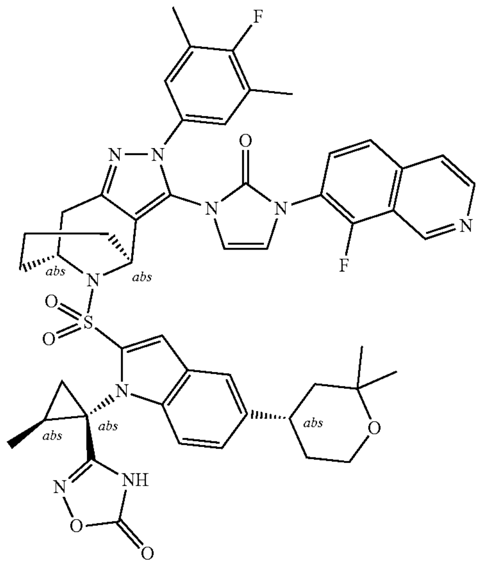 [SMILES: Cc1cc(-n2nc3c(c2-n2ccn(-c4ccc5ccncc5c4F)c2=O)[C@@H]2CCC[C@H](C3)N2S(=O)(=O)c2cc3cc([C@H]4CCOC(C)(C)C4)ccc3n2[C@@]2(c3noc(=O)[nH]3)C[C@@H]2C)cc(C)c1F] C50H49F2N9O6S |

| Compound ID | Structure |
|---|---|
| 604 | 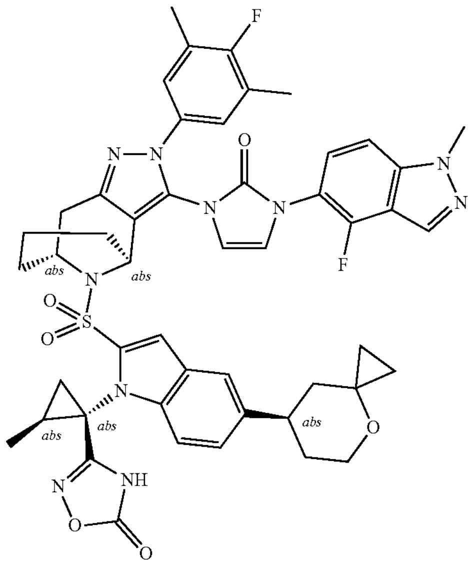 |
| | C49H48F2N10O6S |
| 605 | 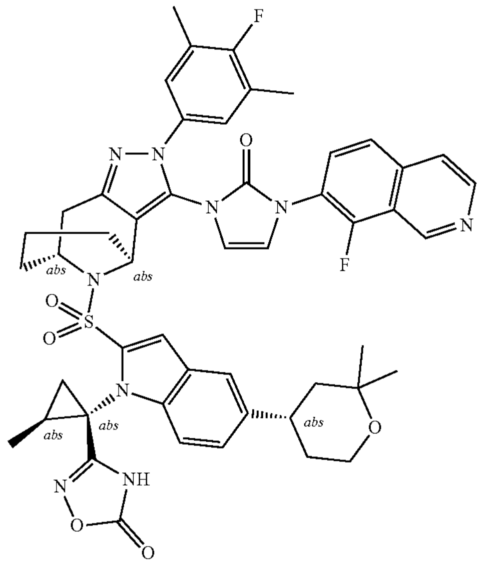 [SMILES: Cc1cc(-n2nc3c(c2-n2ccn(-c4ccc5ccncc5c4F)c2=O)[C@@H]2CCC[C@H](C3)N2S(=O)(=O)c2cc3cc([C@H]4CCOC(C)(C)C4)ccc3n2[C@@]2(c3noc(=O)[nH]3)C[C@@H]2C)cc(C)c1F] |
| | C50H49F2N9O6S |
| Compound ID | Structure |
|---|---|
| 606 | 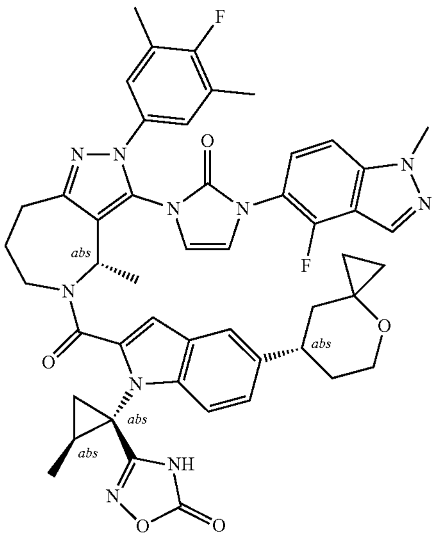 [SMILES: Cc1cc(-n2nc3c(c2-n2ccn(-c4ccc5c(cnn5C)c4F)c2=O)[C@H](C)N(C(=O)c2cc4cc([C@H]5CCOC6(CC6)C5)ccc4n2[C@@]2(c4noc(=O)[nH]4)C[C@@H]2C)CCC3)cc(C)c1F] |
| | C49H48F2N10O5 |
| 607 | 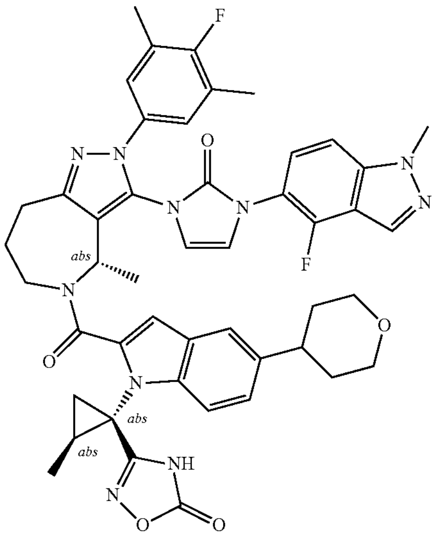 [SMILES: Cc1cc(-n2nc3c(c2-n2ccn(-c4ccc5c(cnn5C)c4F)c2=O)[C@H](C)N(C(=O)c2cc4cc(C5CCOCC5)ccc4n2[C@@]2(c4noc(=O)[nH]4)C[C@@H]2C)CCC3)cc(C)c1F] |
| | C47H46F2N10O5 |

TABLE 1'-continued
| Compound ID | Structure |
|---|---|
| 608 | 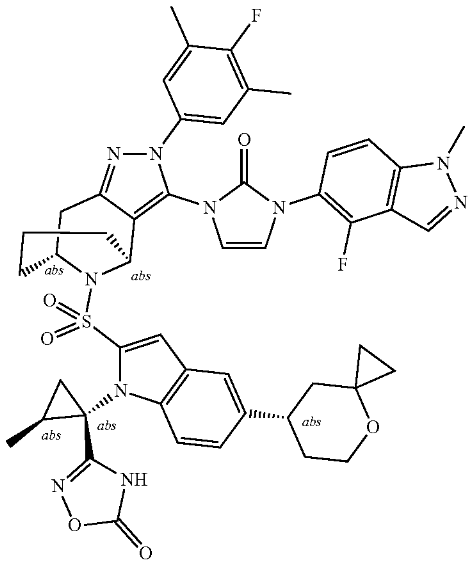<br>C49H48F2N10O6S |
| 609 | 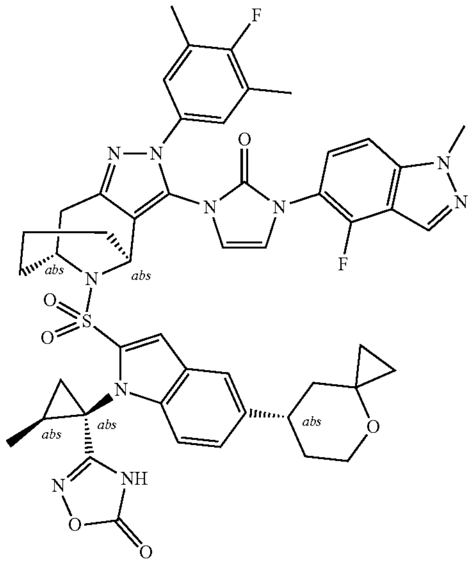<br>C49H48F2N10O6S |
TABLE 1'-continued
| Compound ID | Structure |
|---|---|
| 610 | 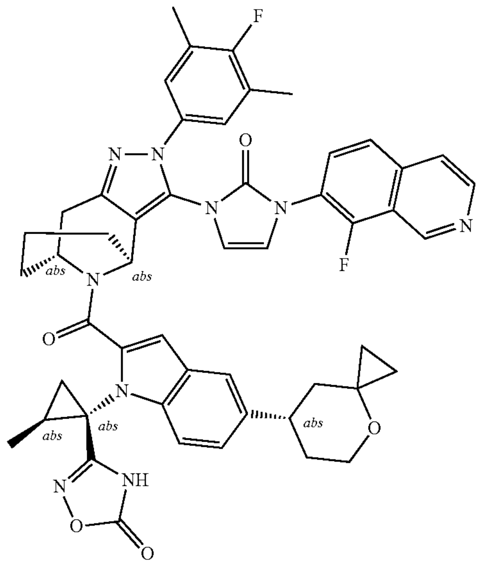 [SMILES: Cc1cc(-n2nc3c(c2-n2ccn(-c4ccc5ccncc5c4F)c2=O)[C@@H]2CCC[C@H](C3)N2C(=O)c2cc3cc([C@H]4CCOC5(CC5)C4)ccc3n2[C@@]2(c3noc(=O)[nH]3)C[C@@H]2C)cc(C)c1F]<br>C51H47F2N9O5 |
| 611 | 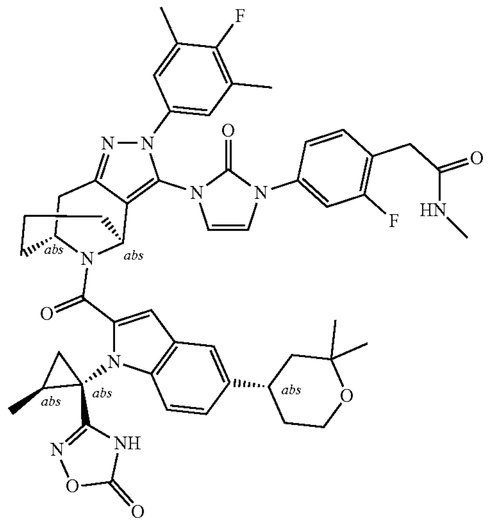 [SMILES: CNC(=O)Cc1ccc(-n2ccn(-c3c4c(nn3-c3cc(C)c(F)c(C)c3)C[C@H]3CCC[C@@H]4N3C(=O)c3cc4cc([C@H]5CCOC(C)(C)C5)ccc4n3[C@@]3(c4noc(=O)[nH]4)C[C@@H]3C)c2=O)cc1F]<br>C51H53F2N9O6 |

TABLE 1'-continued
| Compound ID | Structure |
| --- | --- |
| 612 | 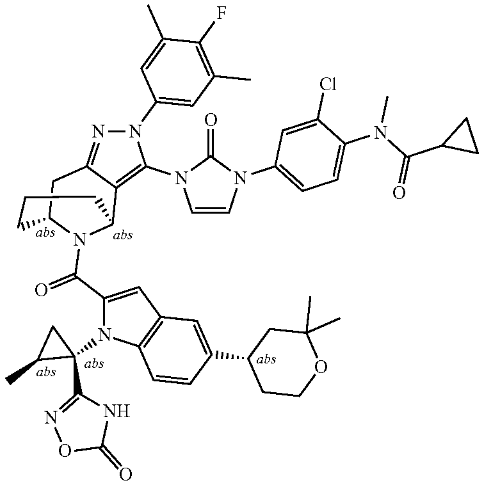 [SMILES: Cc1cc(-n2nc3c(c2-n2ccn(-c4ccc(N(C)C(=O)C5CC5)c(Cl)c4)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H55ClFN9O6 |
| 613 | 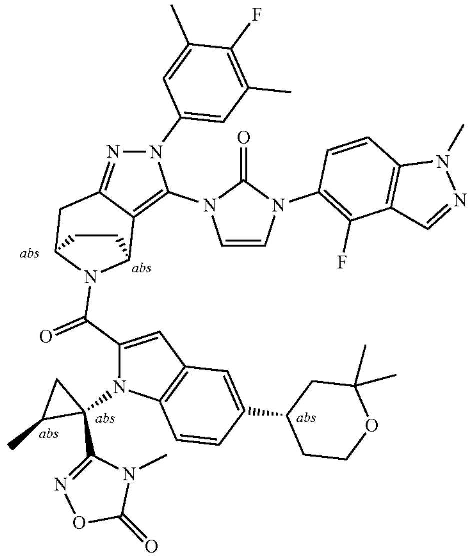 C50H50F2N10O5 |
TABLE 1'-continued
| Compound ID | Structure |
| --- | --- |
| 614 | 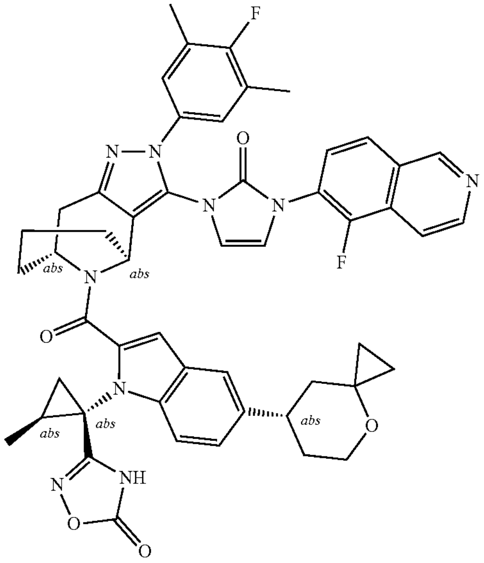 [SMILES: Cc1cc(-n2nc3c(c2-n2ccn(-c4ccc5cnccc5c4F)c2=O)[C@@H]2CCC[C@H](C3)N2C(=O)c2cc3cc([C@H]4CCOC5(CC5)C4)ccc3n2[C@@]2(c3noc(=O)[nH]3)C[C@@H]2C)cc(C)c1F] C51H47F2N9O5 |
| 615 | 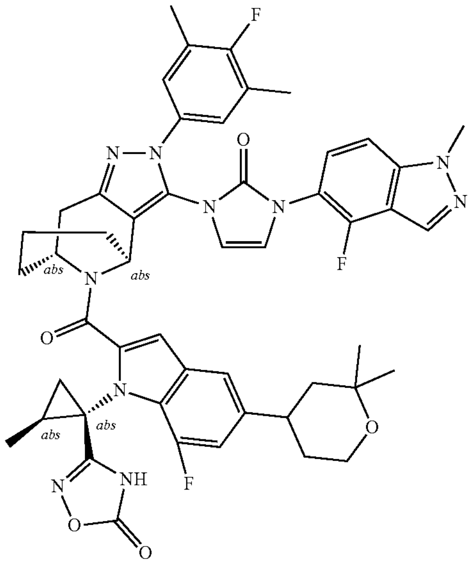 C50H49F3N10O5 |

TABLE 1'-continued
| Compound ID | Structure |
|---|---|
| 616 | 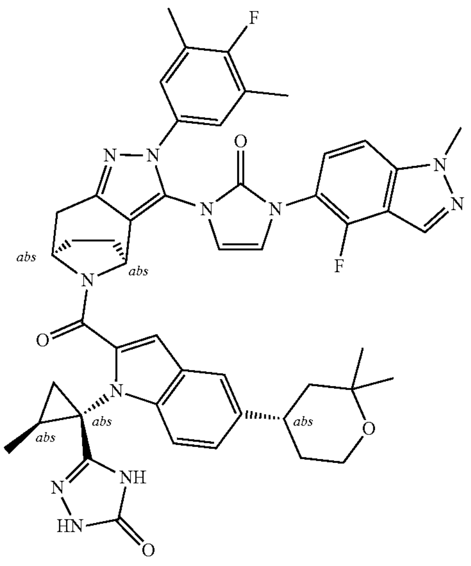<br>C49H49F2N11O4 |
| 617 | 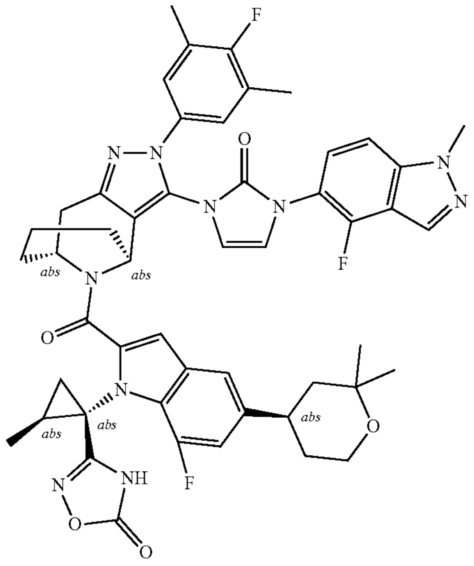<br>C51H50F2N10O6 |
TABLE 1'-continued
| Compound ID | Structure |
|---|---|
| 618 | 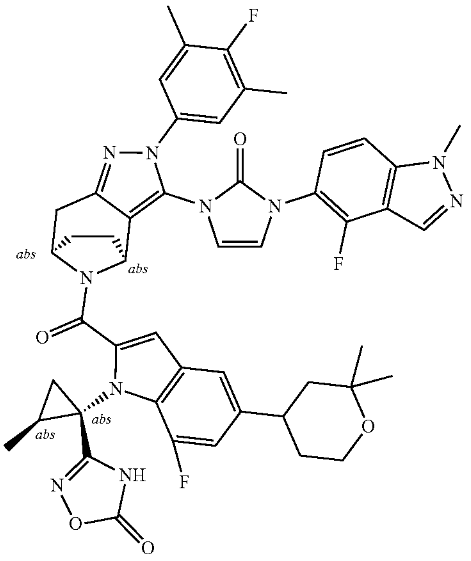<br>C49H47F3N10O5 |
| 619 | 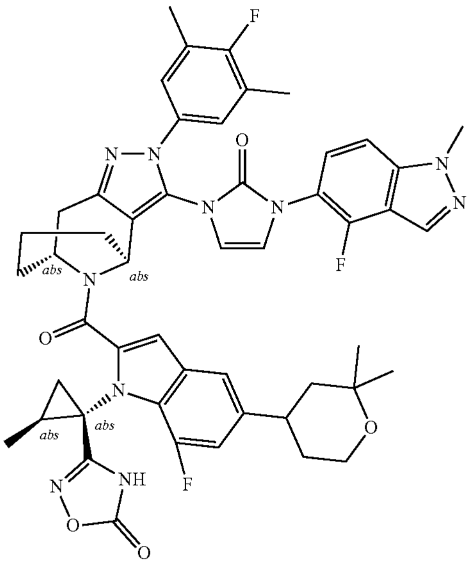<br>C49H47F3N10O6 |

TABLE 1'-continued
| Compound ID | Structure |
|---|---|
| 701 | 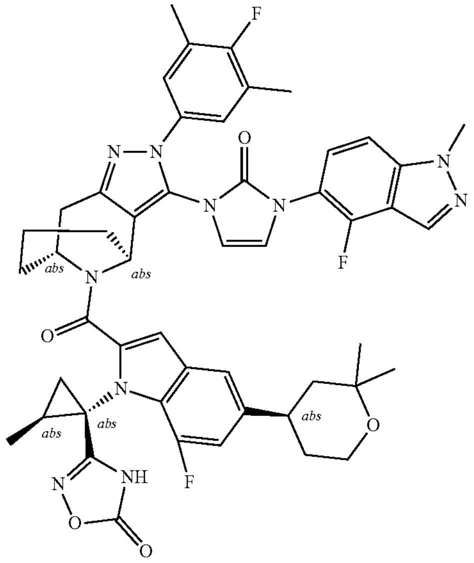 C50H49F3N10O5 |
| 702 | 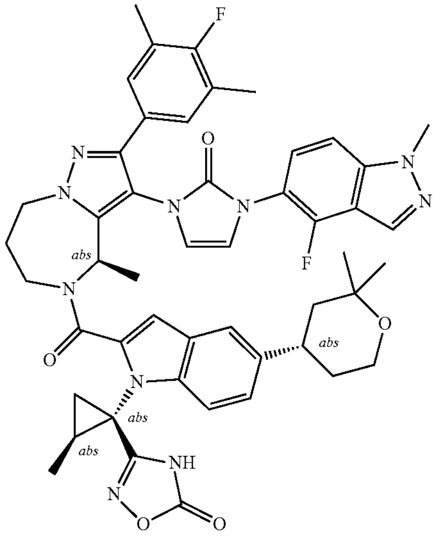 [SMILES: Cc1cc(-c2nn3c(c2-n2ccn(-c4ccc5c(cnn5C)c4F)c2=O)[C@@H](C)N(C(=O)c2cc4cc([C@H]5CCOC(C)(C)C5)ccc4n2[C@@]2(c4noc(=O)[nH]4)C[C@@H]2C)CCC3)cc(C)c1F] C49H50F2N10O5 |
| 703 | 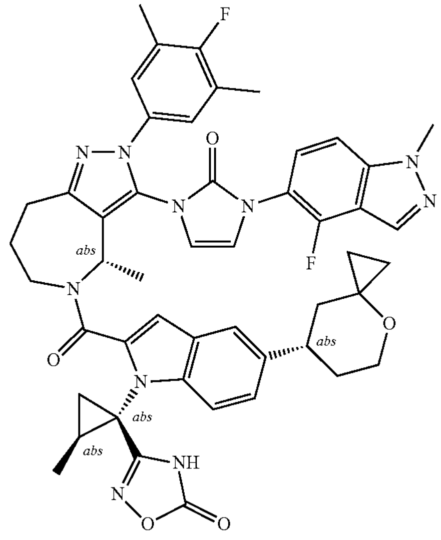 [SMILES: Cc1cc(-n2nc3c(c2-n2ccn(-c4ccc5c(cnn5C)c4F)c2=O)[C@H](C)N(C(=O)c2cc4cc([C@H]5CCOC6(CC6)C5)ccc4n2[C@@]2(c4noc(=O)[nH]4)C[C@@H]2C)CCC3)cc(C)c1F] C49H50F2N10O5 |
| 704 | 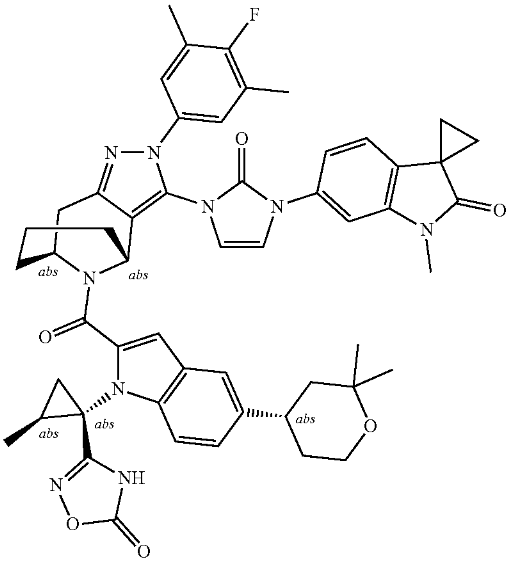 [SMILES: Cc1cc(-n2nc3c(c2-n2ccn(-c4ccc5c(c4)N(C)C(=O)C54CC4)c2=O)[C@H]2CCC[C@@H](C3)N2C(=O)c2cc3cc([C@H]4CCOC(C)(C)C4)ccc3n2[C@@]2(c3noc(=O)[nH]3)C[C@@H]2C)cc(C)c1F] C53H54FN9O6 |

TABLE 1'-continued
| Compound ID | Structure |
| --- | --- |
| 705 | 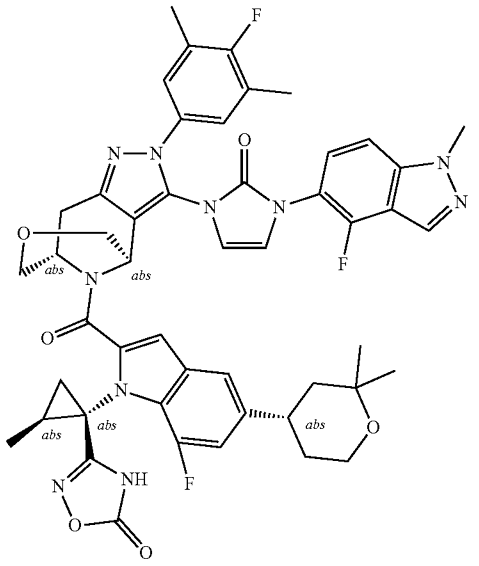 C49H47F3N10O6 |
| 706 | 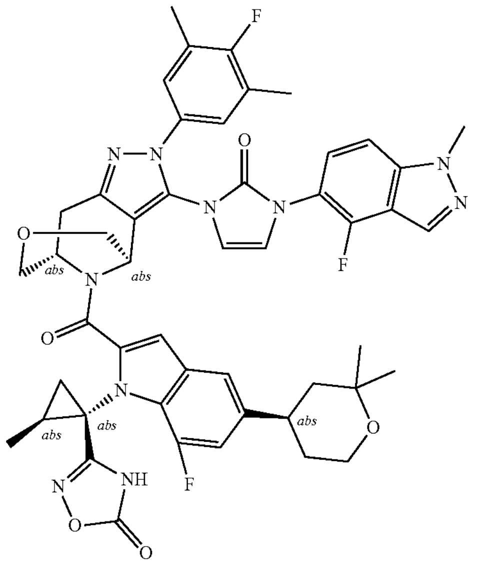 C49H47F3N10O6 |
TABLE 1'-continued
| Compound ID | Structure |
| --- | --- |
| 707 | 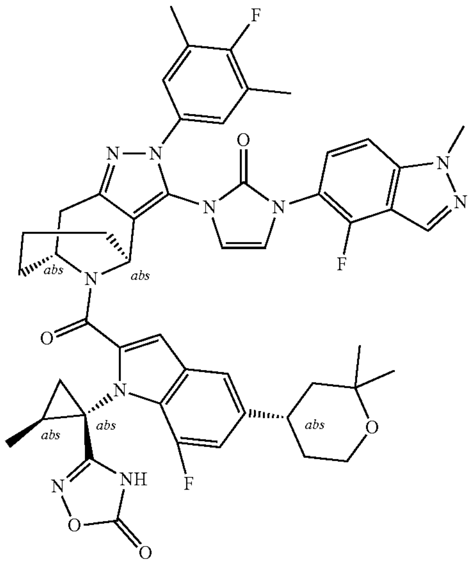 C50H49F3N10O5 |
| 708 | 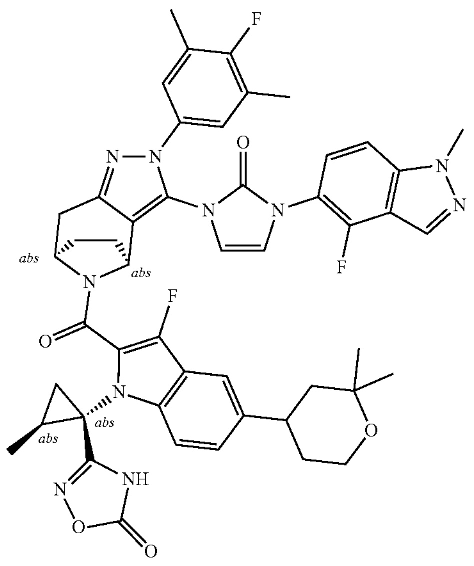 C49H47F3N10O5 |

| Compound ID | Structure |
| --- | --- |
| 709 | 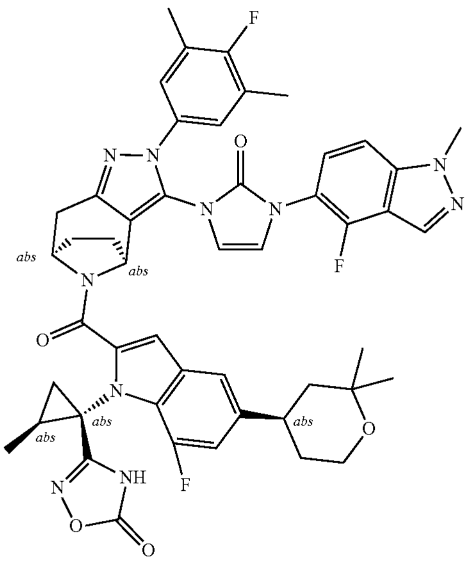 C49H47F3N10O5 |
| 710 | 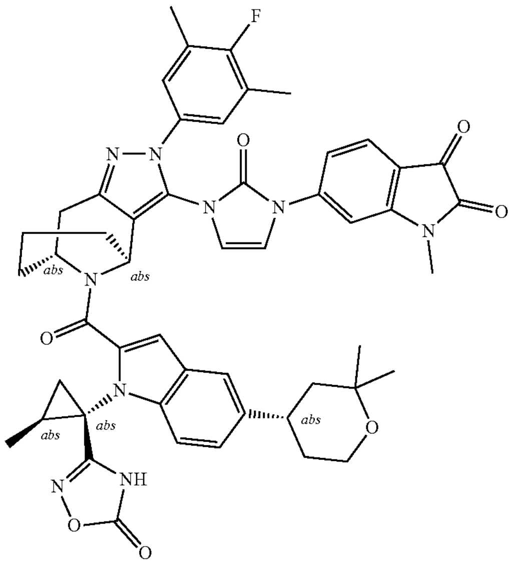 [SMILES: Cc1cc(-n2nc3c(c2-n2ccn(-c4ccc5c(c4)N(C)C(=O)C5=O)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C51H50FN9O7 |
| Compound ID | Structure |
| --- | --- |
| 711 | 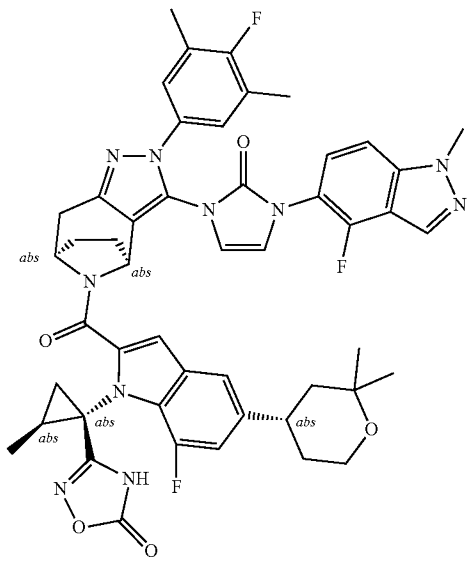 C49H47F3N10O5 |
| 712 | 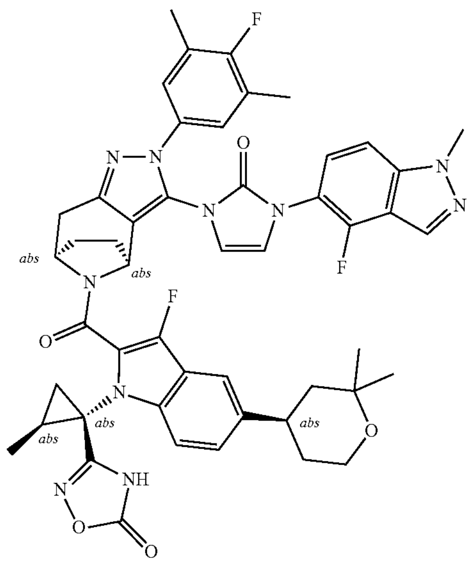 C49H47F3N10O5 |

TABLE 1'-continued

| Compound ID | Structure |
|---|---|
| 713 | 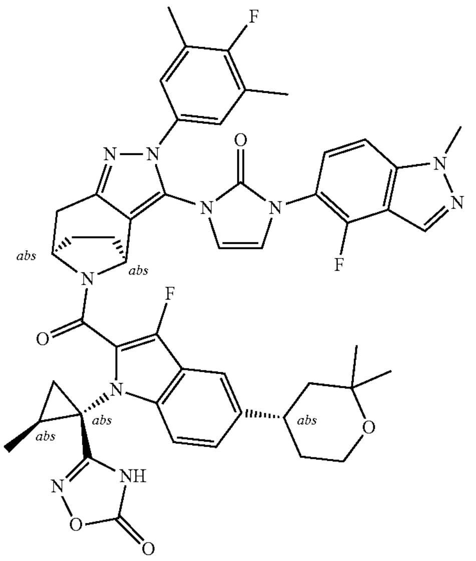 C49H47F3N10O5 |
| 714 | 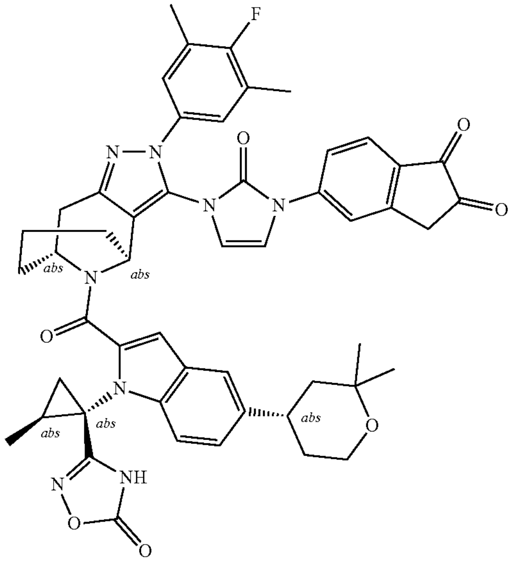 [SMILES: Cc1cc(-n2nc3c(c2-n2ccn(-c4ccc5c(c4)CC(=O)C5=O)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F] C53H54FN9O6 |
| 715 | 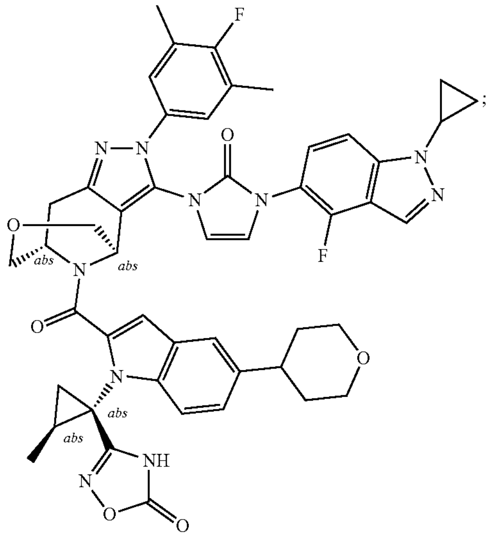 [SMILES: Cc1cc(-n2nc3c(c2-n2ccn(-c4ccc5c(cnn5C5CC5)c4F)c2=O)[C@@H]2COC[C@H](C3)N2C(=O)c2cc3cc(C4CCOCC4)ccc3n2[C@@]2(c3noc(=O)[nH]3)C[C@@H]2C)cc(C)c1F] C49H46F2N10O6 and |
| 716 | 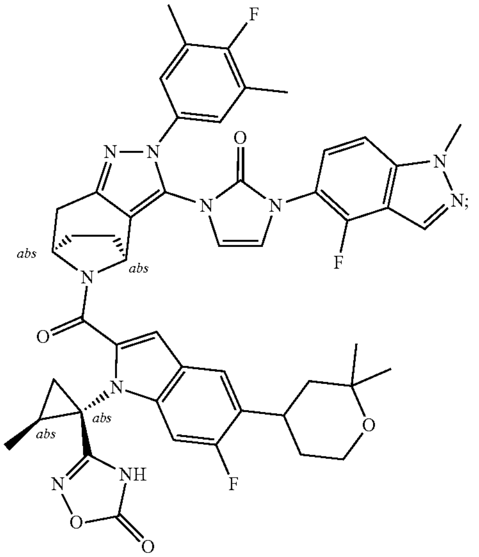 C49H47F3N10O5; |

or a pharmaceutically acceptable salt thereof.

2. The compound according to claim 1, selected from the group consisting of the compounds with ID numbers 36, 121, 128, 208, 209, 213, 214, 220, 225, 226, 302, 311, 313, 323, 406, 410, 417, 427, 428, 429, 433, 436, 437, 611-619, 703, 705-708, 710-715 and 716, or a pharmaceutically acceptable salt thereof.

3. The pharmaceutically acceptable salt of the compound of claim 1.

4. The pharmaceutically acceptable salt of claim 3, selected from L-arginine, hemi-calcium, mono-potassium, mono-sodium, L-lysine, and betaine salt forms.

5. The pharmaceutically acceptable salt of claim 3, wherein the salt is compound 214 monosodium salt or compound 36 monosodium salt.

6. The pharmaceutically acceptable salt of claim 5, wherein the salt is amorphous.

7. A pharmaceutical composition comprising the compound of claim 1, or a pharmaceutically acceptable salt thereof, and a pharmaceutically acceptable excipient.

8. A method of treating a GLP-1 related disorder in a subject in need thereof comprising administering a therapeutically effective amount of the compound according to claim 1, or a pharmaceutically acceptable salt thereof.

9. The compound according to claim 1, wherein the compound is selected from the group consisting of compounds with ID numbers 36, 121, 214, 226, 302, 323, 36, 428, 429, 433, 509, 518, 525, 606, 607, 610, 612, 614, 617, 705-708, 710-715 and 716, or a pharmaceutically acceptable salt thereof.

10. The compound according to claim 1, wherein the compound is selected from the group consisting of compounds with ID numbers 36, 121, 214, 226, 302, 323, 36, 428, 429, 433, 509, 518, 525, 606, 607, 610, 612, 614, and 617, or a pharmaceutically acceptable salt thereof.

11. The compound according to claim 1, with the ID number 36:

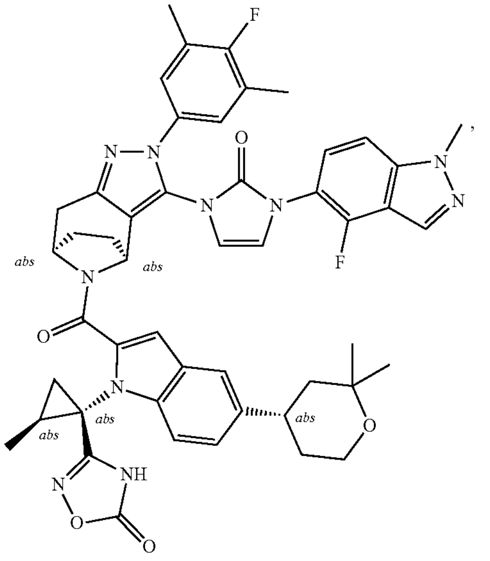

or a pharmaceutically acceptable salt thereof.

12. The compound according to claim 1, with the ID number 214:

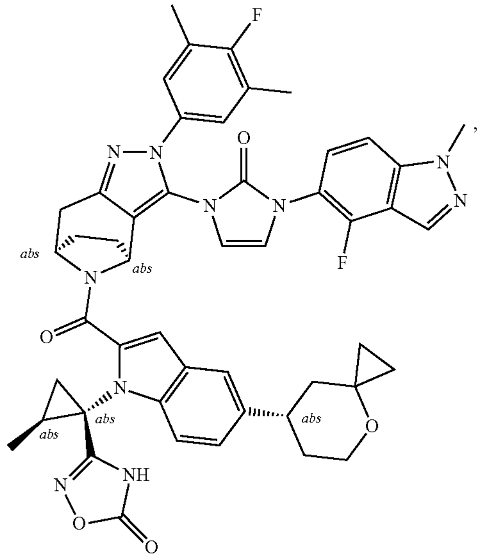

or a pharmaceutically acceptable salt thereof.

13. The compound according to claim 1, with the ID number 707:

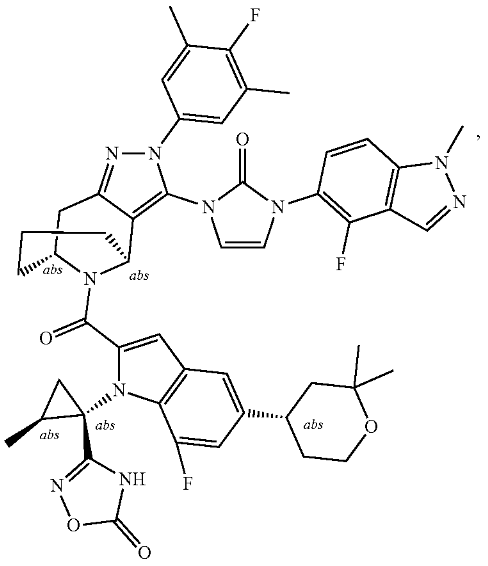

or a pharmaceutically acceptable salt thereof.

14. The compound according to claim 1, with the ID number 710:

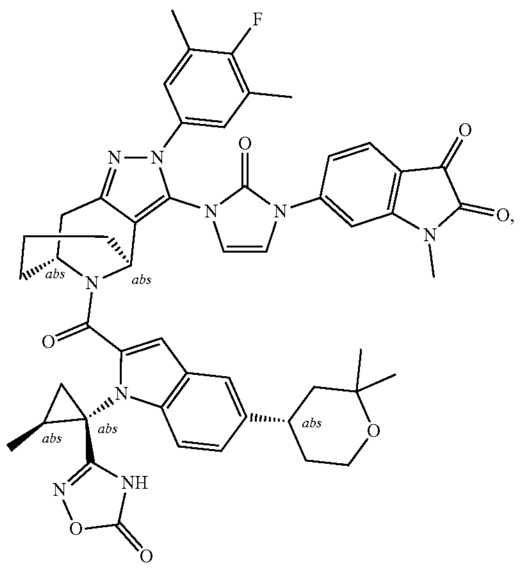 [SMILES: Cc1cc(-n2nc3c(c2-n2ccn(-c4ccc5c(c4)N(C)C(=O)C5=O)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F]

or a pharmaceutically acceptable salt thereof.

15. The compound according to claim 1, with the ID number 711:

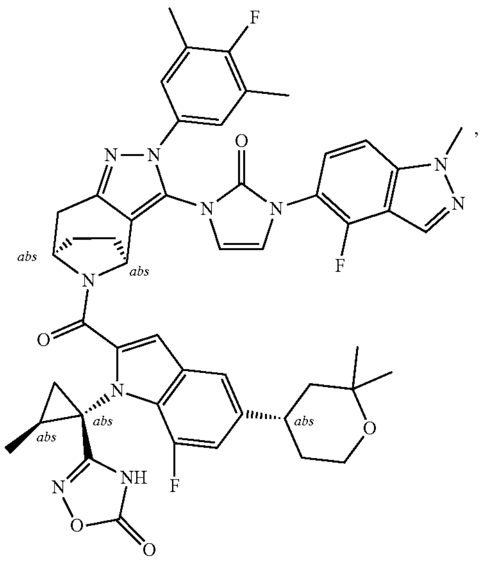

or a pharmaceutically acceptable salt thereof.

16. The compound according to claim 1, with the ID number 713:

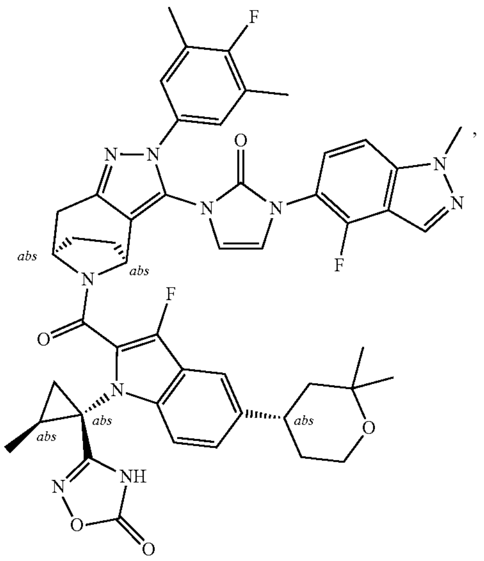

or a pharmaceutically acceptable salt thereof.

17. The compound according to claim 1, with the ID number 714:

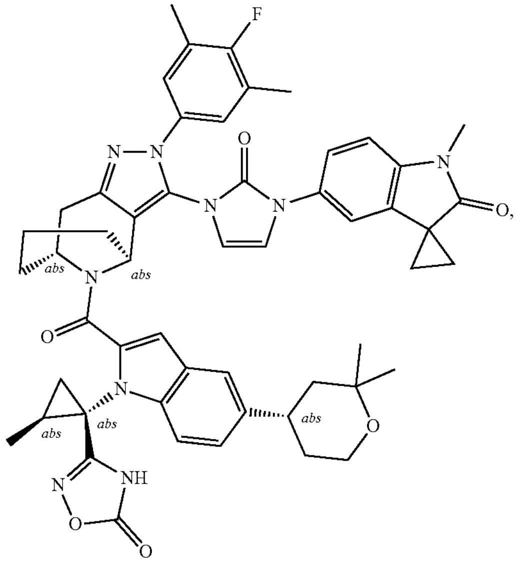 [SMILES: Cc1cc(-n2nc3c(c2-n2ccn(-c4ccc5c(c4)C4(CC4)C(=O)N5C)c2=O)[C@@H]2CCC[C@H](C3)N2C(=O)c2cc3cc([C@H]4CCOC(C)(C)C4)ccc3n2[C@@]2(c3noc(=O)[nH]3)C[C@@H]2C)cc(C)c1F]

or a pharmaceutically acceptable salt thereof.

18. The compound according to claim 1, with the ID number 225:
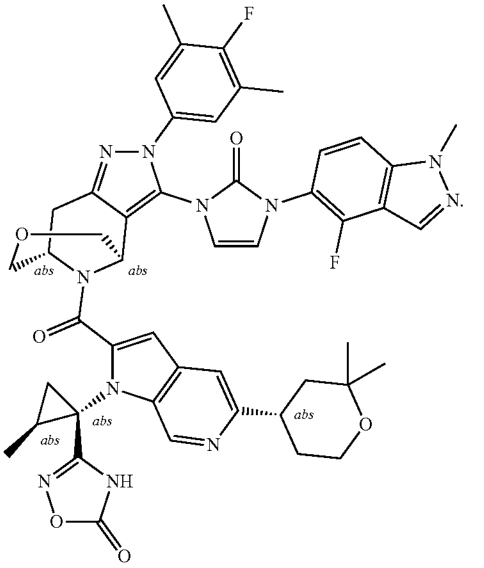
19. The compound according to claim 1, with the ID number 226:
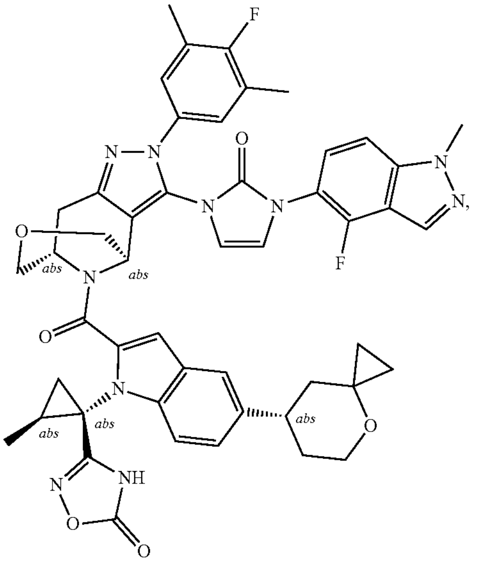
or a pharmaceutically acceptable salt thereof.
20. The pharmaceutically acceptable salt of claim 3, wherein the pharmaceutically acceptable salt is compound ID number 214 monosodium salt.
* * * * *